US012548678B2

(12) United States Patent
Owen et al.

(10) Patent No.: US 12,548,678 B2
(45) Date of Patent: Feb. 10, 2026

(54) METHODS AND SYSTEMS FOR MACHINE LEARNING ANALYSIS OF SINGLE NUCLEOTIDE POLYMORPHISMS IN LUPUS

(71) Applicant: AMPEL BioSolutions, LLC, Charlottesville, VA (US)

(72) Inventors: Katherine A. Owen, Charlottesville, VA (US); Kristy A. Bell, Charlottesville, VA (US); Jessica Kain, Charlottesville, VA (US); Amrie C. Grammer, Charlottesville, VA (US); Peter E. Lipsky, Charlottesville, VA (US)

(73) Assignee: AMPEL BioSolutions, LLC, Charlottesville, VA (US)

(*) Notice: Subject to any disclaimer, the term of this patent is extended or adjusted under 35 U.S.C. 154(b) by 259 days.

(21) Appl. No.: 17/924,955

(22) PCT Filed: May 13, 2021

(86) PCT No.: PCT/US2021/032230
§ 371 (c)(1),
(2) Date: Nov. 11, 2022

(87) PCT Pub. No.: WO2021/231713
PCT Pub. Date: Nov. 18, 2021

(65) Prior Publication Data

US 2024/0282453 A1 Aug. 22, 2024

Related U.S. Application Data

(60) Provisional application No. 63/024,730, filed on May 14, 2020.

(51) Int. Cl.

| | |
|---|---|
| ***G16H 50/30*** | (2018.01) |
| ***G16B 25/10*** | (2019.01) |
| ***G16B 40/00*** | (2019.01) |

(52) U.S. Cl.
CPC ............ *G16H 50/30* (2018.01); *G16B 25/10* (2019.02); *G16B 40/00* (2019.02)

(58) Field of Classification Search
CPC ......... G16H 50/30; G16B 25/10; G16B 40/00
See application file for complete search history.

(56) References Cited

U.S. PATENT DOCUMENTS 6,949,338 B2 9/2005 Rheins
7,991,557 B2 8/2011 Liew
(Continued)

FOREIGN PATENT DOCUMENTS

CN 111041089 A 4/2020
EP 2326731 B1 6/2011
(Continued)

OTHER PUBLICATIONS

M. K. K. Leung, A. Delong, B. Alipanahi and B. J. Frey, "Machine Learning in Genomic Medicine: A Review of Computational Problems and Data Sets," in Proceedings of the IEEE, vol. 104, No. 1, pp. 176-197, Jan. 2016, doi: 10.1109/JPROC.2015.2494198. (Year: 2016).*
(Continued)

*Primary Examiner* — Sun M Li
(74) *Attorney, Agent, or Firm* — Greenberg Traurig, LLP

(57) ABSTRACT

The present disclosure provides systems and methods for machine learning classification and assessment of disease based on gene expression data. In an aspect, a method for determining a disease state of a subject may comprise: (a) assaying a biological sample obtained or derived from the subject to produce a data set comprising gene expression measurements of the biological sample at each of a plurality of disease-associated genomic loci; (b) computer processing the data set to determine the disease state of the subject; and (c) electronically outputting a report indicative of the disease
(Continued)

state of the subject. In some embodiments, the plurality of disease-associated genomic loci comprises single nucleotide polymorphisms (SNPs). In some embodiments, the disease comprises a lupus condition. In some embodiments, the disease comprises cardiovascular disease (CVD).

20 Claims, 273 Drawing Sheets

(56) References Cited

U.S. PATENT DOCUMENTS

| | | | | |
|---|---|---|---|---|
| 8,504,343 | B2 | 8/2013 | Chawla | |
| 9,340,830 | B2 | 5/2016 | Lipson | |
| 9,822,400 | B2 | 11/2017 | Dennis, Jr. | |
| 10,978,196 | B2 | 4/2021 | Lefkofsky | |
| 11,037,685 | B2 | 6/2021 | Lefkofsky | |
| 11,195,525 | B2 | 12/2021 | Tahara | |
| 11,309,090 | B2 | 4/2022 | Lefkofsky | |
| 2003/0154032 | A1* | 8/2003 | Pittman | C07K 14/4713 702/20 |
| 2006/0257852 | A1 | 11/2006 | Rappuoli | |
| 2007/0059717 | A1 | 3/2007 | Pascual | |
| 2007/0269804 | A1 | 11/2007 | Liew | |
| 2008/0108058 | A1 | 5/2008 | Behrens | |
| 2009/0298060 | A1 | 12/2009 | Lal | |
| 2011/0118130 | A1 | 5/2011 | Loring | |
| 2011/0238319 | A1 | 9/2011 | Adamko | |
| 2011/0262485 | A1 | 10/2011 | Barber | |
| 2013/0274134 | A1 | 10/2013 | Lindstedt | |
| 2014/0135225 | A1 | 5/2014 | Crow | |
| 2015/0218640 | A1 | 8/2015 | Brandon | |
| 2015/0310163 | A1 | 10/2015 | Kingsmore | |
| 2016/0109453 | A1 | 4/2016 | Weinhausel | |
| 2016/0210403 | A1 | 7/2016 | Zhang | |
| 2017/0349950 | A1 | 12/2017 | Regev | |
| 2018/0057859 | A1 | 3/2018 | Nelson | |
| 2018/0096738 | A1 | 4/2018 | Moturu | |
| 2018/0217141 | A1 | 8/2018 | Sasso | |
| 2018/0305689 | A1 | 10/2018 | Sætrom | |
| 2018/0364229 | A1 | 12/2018 | James | |
| 2019/0065670 | A1* | 2/2019 | Yandell | G16B 20/20 |
| 2019/0080051 | A1 | 3/2019 | Menche | |
| 2019/0108912 | A1* | 4/2019 | Spurlock, III | A61P 25/28 |
| 2019/0127803 | A1 | 5/2019 | Hacohen | |
| 2019/0131016 | A1 | 5/2019 | Cohen | |
| 2019/0203298 | A1 | 7/2019 | Sandoval Del Amor | |
| 2019/0287644 | A1 | 9/2019 | Karma | |
| 2019/0292600 | A1 | 9/2019 | Spira | |
| 2019/0313920 | A1* | 10/2019 | Banerjee | A61B 5/7264 |
| 2020/0069973 | A1 | 3/2020 | Lou | |
| 2020/0143278 | A1 | 5/2020 | Narain | |
| 2020/0185063 | A1 | 6/2020 | Narain | |
| 2020/0190589 | A1 | 6/2020 | Akmaev | |
| 2020/0232046 | A1* | 7/2020 | Kennedy | G16B 25/10 |
| 2020/0342958 | A1* | 10/2020 | Mcgovern | G16B 20/20 |
| 2020/0402643 | A1 | 12/2020 | Trees | |
| 2021/0071255 | A1 | 3/2021 | Regev | |
| 2021/0098082 | A1* | 4/2021 | Udyavar | G16B 40/00 |
| 2021/0104321 | A1* | 4/2021 | Lipsky | G16H 20/10 |
| 2021/0142910 | A1 | 5/2021 | Hafez | |
| 2021/0225517 | A1 | 7/2021 | Baloglu | |
| 2021/0232934 | A1* | 7/2021 | Lai | G06N 20/00 |
| 2021/0254056 | A1 | 8/2021 | Yuting | |
| 2022/0375609 | A1* | 11/2022 | Guo | C12N 15/90 |

FOREIGN PATENT DOCUMENTS

| | | | | |
|---|---|---|---|---|
| EP | 2389582 | B1 | 11/2011 | |
| EP | 3052193 | B1 | 8/2016 | |
| EP | 3465200 | A1 | 4/2019 | |
| WO | 2002057414 | A2 | 7/2002 | |
| WO | 2006074370 | A2 | 7/2006 | |
| WO | 2008079374 | A2 | 7/2008 | |
| WO | WO-2008091708 | A2 * | 7/2008 | C12Q 1/6883 |
| WO | 2010008543 | A2 | 1/2010 | |
| WO | 2010065940 | A1 | 6/2010 | |
| WO | 2010084312 | A1 | 7/2010 | |
| WO | 2012118856 | A1 | 9/2012 | |
| WO | 2012150276 | A1 | 11/2012 | |
| WO | 2016057705 | A1 | 4/2016 | |
| WO | 2016141214 | A1 | 9/2016 | |
| WO | 2017019918 | A1 | 2/2017 | |
| WO | 2017147196 | A1 | 8/2017 | |
| WO | 2017164936 | A1 | 9/2017 | |
| WO | 2017205823 | A1 | 11/2017 | |
| WO | 2017214068 | A1 | 12/2017 | |
| WO | 2018161052 | A1 | 9/2018 | |
| WO | 2018191558 | A1 | 10/2018 | |
| WO | 2019178546 | A1 | 9/2019 | |
| WO | WO-2020014620 | A1 * | 1/2020 | C12Q 1/6883 |
| WO | 2020081204 | A1 | 4/2020 | |
| WO | 2020102043 | A1 | 5/2020 | |
| WO | 2020102519 | A1 | 5/2020 | |
| WO | 2020142551 | A1 | 7/2020 | |
| WO | 2020264426 | A1 | 12/2020 | |
| WO | 2021026097 | A1 | 2/2021 | |
| WO | 2021034712 | A1 | 2/2021 | |
| WO | 2021041726 | A1 | 3/2021 | |
| WO | 2021055742 | A1 | 3/2021 | |
| WO | 2021231713 | A2 | 11/2021 | |

OTHER PUBLICATIONS

Schrodi SJ, Mukherjee S, Shan Y, Tromp G, Sninsky JJ, Callear AP, Carter TC, Ye Z, Haines JL, Brilliant MH, Crane PK, Smelser DT, Elston RC, Weeks DE. Genetic-based prediction of disease traits: prediction is very difficult, especially about the future. Front Genet. Jun. 2, 2014;5:162. doi: 10.3389/fgen (Year: 2014).*

C. Moldovan and R. Dogaru, "Fast support vector classifier applied to microarray data," Proceedings of the 2014 6th International Conference on Electronics, Computers and Artificial Intelligence (ECAI), Bucharest, Romania, 2014, pp. 67-72, doi: 10.1109/ECAI.2014.7090167 (Year: 2014).*

Y. Li, N. Wang, E. J. Perkins and p. Gong, "Discovery of Biomarker Genes from Earthworm Microarray Data by Discriminant Analysis and Clustering," 2009 International Joint Conf on Bioinformatics, Systems Biology and Intelligent Computing, Shanghai, China, 2009, pp. 23-29, doi: 10.1109/IJCBS.2009.134 (Year: 2009).*

Abrahamowicz et al.: Development and Validation of a Novel Evidence-Based Lupus Multivariable Outcome Score for Clinical Trials. Arthritis & Rheumatology, 2018, vol. 70, No. 9, p. 1450-1458.

Banchereau et al.: Personalized immunomonitoring uncovers molecular networks that stratify lupus patients. Cell, 2016, vol. 165, No. 6, p. 551-565.

Bengtsson et al.: Role of interferons in SLE. Best Pract Res Clin Rheumatol, 2017, vol. 31, No. 3, p. 415-428.

Benjamini et al.: Controlling the false discovery rate: a practical and powerful approach to multiple testing. J R Stat Soc Series B Stat Methodol, 1995, vol. 57, No. 1, p. 289-300.

Berthier et al.: Cross-Species Transcriptional Network Analysis Defines Shared Inflammatory Responses in Murine and Human Lupus Nephritis. J. Immunol, 2012, vol. 189, No. 2, p. 988-1001.

Beyer et al.: High-resolution transcriptome of human macrophages. PLoS One, 2012, vol. 7, No. 9, e45466.

Blair et al.: Belimumab: A Review in Systemic Lupus Erythematosus. Drugs, 2018, vol. 78, No. 3, p. 355-366.

Breiman et al.: Classification and regression trees. New York: CRC Press. (1999).

Carlucci et al.: Neutrophil subsets and their gene signature associate with vascular inflammation and coronary atherosclerosis in lupus. JCI Insight, 2018, vol. 3, No. 8, e99276.

Catalina et al.: Gene expression analysis delineates the potential roles of multiple interferons in systemic lupus erythematosus. Communications Biology, 2019, vol. 2, No. 140, p. 1-13.

Catalina et al.: Gene expression analysis Demonstrates that Multiple Type 1 Interferons Are Involved in Lupus Pathogenesis [abstract]. Arthritis Rheumatol. 2017, Abstract No. 2818, access May 17, 2024.

(56) References Cited

OTHER PUBLICATIONS

Catalina. A Role for IFNB in Systemic Lupus Erythematosus (SLE) is Predicted by Analysis of Gene Expression Data Sets. Precision in Immunology FOCiS 2017 Abstract Supplement W.20. Chicago, Jun. 14-17.
Catalina. Gene Expression Analysis Delineates the Roles of Multiple Type1 Interferons in Systemic Lupus Erythematosus. FOCiS 2018 Abstract Supplement W.20. San Francisco, Jun. 20-23.
Chalmers et al.: Therapeutic targeting of macrophages in lupus nephritis. Discov Med, 2015, vol. 20, No. 108, p. 43-49.
Chiche et al.: Modular transcriptional repertoire analyses of adults with systemic lupus erythematosus reveal distinct type I and type II interferon signatures. Arthritis Rheumatol. 66(6): 1583-1595 (2014).
Clancy, RM et al. "Identification of Candidate Loci at 6p21 and 21 q22 in a Genome- Wide Association Study of Cardiac Manifestations of Neonatal Lupus", Arthritis and Rheumatism. vol. 62, No. 11, 2010, p. 3415-3424.
Cloke et al.: Characterization of a novel populations of low-density granulocytes associated with disease severity in HIV-1 infection. PLoS One, 2012, vol. 7, No. 11, e48939.
Cohen: Statistical power analysis for the behavioral sciences. 2nd ed. Hillsdale, N.J.: Lawrence Erlbaum Associates (1988), p. 1-41.
Crow et al., Microarray analysis of gene expression in lupus, Oct. 2003, Arthritis Research & Therapy, 2003, vol. 5, No. 6, p. 279-287.
Daamen, AR et al. "Molecular mechanisms governing the progression of nephritis in lupus prone mice and human lupus patients" Frontiers in Immunology, 2023, vol. 14, 17 pages.
Deng et al., "Single-cell RNA-seq reveals dynamic, random monoallelic gene expression in mammalian cells," Science, vol. 343, Jan. 10, 2014, pp. 193-196.
Deng et al.: Low-density granulocytes are elevated in mycobacterial infection and associated with the severity of tuberculosis. PLoS One, 2016, vol. 11, No. 4, e0153567.
Deng et al.: Mesenchymal stem cells promote CD206 expression and phagocytic activity of macrophages through IL-6 in systemic lupus erythematosus. Clin Immunol, 2015, vol. 161, No. 2, p. 209-216.
Denny et al.: A distinct subset of proinflammatory neutrophils isolated from patients with systemic lupus erythematosus induces vascular damage and synthesizes type I Interferons. J Immunol, 2010, vol. 184, No. 6, p. 3284-3297.
Der E., et al., "Single cell RNA Sequencing to Dissect the Molecular Heterogeneity in Lupus Nephritis," JCI Insight, May 2017, vol. 2, No. 9, p. 1-12.
DeWeerd et al.: Structural basis of a unique interferon-beta signaling axis mediated via the receptor IFNARI. Nat. Immunol., 2013, vol. 14, p. 901-907.
Fairfax, BP et al. "Genetics of gene expression in primary immune cells identifies cell type-specific master regulators and roles of HLA alleles", Nature Genetics, 2012, vol. 44, No. 5, p. 502-510.
Friedman et al.: Regularization paths for generalized linear models via coordinate descent. J Stat Softw, 2010, vol. 33, No. 1, p. 1-22.
Grammer et al.: Drug repositioning in SLE: crowd-sourcing, literature-mining and Big Data analysis. Lupus, 2016, vol. 25, No. 10, p. 1150-1170.
Hacbarth et al.: Low density neutrophils in patients with systemic lupus erythematosus, rheumatoid arthritis, and acute rheumatic fever. Arhritis Rheum, 1986, vol. 29, No. 11, p. 1334-1342.
Hanzelmann et al.: GSVA: gene set variation analysis for microarray and RNA-Seq data. BMC Bioinformatics, 2013, vol. 14, No. 7, p. 1-15.
Harris et al.: Analysis of Discoid Lupus Erythematosus (DLE) Gene Expression Reveals Dysregulation of Pathogenic Pathways Associated with Infiltrating Immune/Inflammatory Cells [abstract]. Arthritis Rheumatol. 2019; 71 (suppl 10). https://acrabstracts.org/abstracUanalysis-of-discoid-lupus-erythematosus-dle-gene-expression-reveals-dysregulation-of-pathogenic-pathways-associated-with-infiltrating-immune-inflammatory-cells/. Accessed May 20, 2024. Abstract No. 1939.
Healy et al.: Differential transcriptional response profiles in human myeloid cell populations. Clin Immunol, 2018, vol. 189, p. 63-74.
Hoffman et al.: Gene Expression and Pharmacodynamic Changes in 1,760 Systemic Lupus Erythematosus Patients From Two Phase III Trials of BAFF Blockade With Tabalumab. Arthritis & Rheumatology, 2016, vol. 69, p. 643-654.
Hornik et al., "Spherical k-Means Clustering," Journal of Statistical Software, 2012, vol. 50, Issue 10, pp. 1-22.
Hubbard et al.: Analysis of Gene Expression from Systemic Lupus Erythematosus Synovium Reveals Unique Pathogenic Mechanisms [abstract]. Arthritis Rheumatol. 2019; 71 (suppl 10). https://acrabstracts.org/abstract/analysis-of-gene-expression-from-systemic-lupus-erythematosus-synovium-reveals-unique-pathogenic-mechanisms/. Accessed May 20, 2024. Abstract No. 2022.
Hubbard et al.: Analysis of Lupus Synovitis Gene Expression Reveals Dysregulation of Pathogenic Pathways Activated within Infiltrating Immune Cells. Arthritis Rheumatol., 2018, vol. 70, suppl 10, 2018, 2 pages.
International Search Report and Written Opinion for PCT/US2019/049129, mailed Dec. 16, 2019.
International Search Report and Written Opinion for PCT/US2019/060641, mailed Mar. 9, 2020.
International Search Report and Written Opinion for PCT/US2021/031535, mailed Sep. 17, 2021.
International Search Report and Written Opinion for PCT/US2021/032230, mailed Nov. 5, 2021.
International Search Report and Written Opinion for PCT/US2021/065348, mailed Mar. 24, 2022.
International Search Report and Written Opinion for PCT/US2022/035552, mailed Dec. 8, 2022.
International Search Report and Written Opinion for PCT/US2022/046337, mailed Mar. 10, 2023.
International Search Report and Written Opinion for PCT/US2023/013173, mailed Jun. 28, 2023.
International Search Report and Written Opinion for PCT/US2023/020752, mailed Jul. 17, 2023.
International Search Report and Written Opinion for PCT/US2023/021260, mailed Oct. 18, 2023.
International Search Report and Written Opinion for PCT/US2023/027847, mailed Nov. 30, 2023.
International Search Report and Written Opinion for PCT/US2023/032946, mailed Feb. 15, 2024.
International Search Report and Written Opinion for PCT/US2023/050281, mailed Mar. 29, 2023.
Jochems et al.: Antidepressant-like properties of novel HDAC6-selective inhibitors with improved brain bioavailability. Neuropsychopharmacology, 2014, vol. 39, No. 2, p. 389-400.
Jourde-Chiche et al.: Modular transcriptional repertoire analyses identify a blood neutrophil signature as a candidate biomarker for lupus nephritis. Rheumatology (Oxford). 2017, vol. 56, No. 3, p. 477-487.
Karrar et al.: Abnormal B-cell development in systemic supus erythematosus: what the genetics tell us. Arthritis Rheumatol, 2018, vol. 70, No. 4, p. 496-507.
Kegerreis et al.: A gene expression module that identifies low-density granulocytes in the blood of patients with systemic lupus erythematosus is associated with low complement, elevated anti-dsDNA titer and both the interferon and TNF signatures. J Immunol 200, 2018, Issue 1 Supplement, 45.4.
Kegerreis et al.: A novel approach to analyze single cell RNA-SEQ data from Lupus Nephritis samples. Lupus Sci Med., 2018, Issue 5(supp 2), 2 pages.
Kegerreis et al.: Machine learning approaches to predict lupus disease activity from gene expression data. Nature Communications. Scientific Reports, 2019, vol. 9, No. 9617, p. 1-12.
Kingsmore et al.: Transcriptomic Meta-analysis of Lupus Affected Tissues Reveals Shared Immune, Metabolic, and Biochemical Dysregulation [abstract]. Arthritis Rheumatol, 2019; 71 (suppl 10). https://acrabstracts.org/abstract/transcriptomic-meta-analysis-of-lupus-affected-tissues-reveals-shared-immune-metabolic-and-biochemical-dysregulation/. Accessed May 20, 2024. Abstract No. 2899.

(56) References Cited

OTHER PUBLICATIONS

Knopf and Sangole, "Scientific Data Visualization Using Three-dimensional Self-organizing Feature Maps," 2001 IEEE International Conference on Systems, Man and Cybernetics: e-Systems and e-Man for Cybernetics in Cyberspace, Cat. No. 01 CH37236, 2002, vol. 2, p. 759-764.
Koga et al.: T cells and IL-17 in lupus nephritis. Clin Immunol., 2017, vol. 185, p. 95-99.
Kousathanas, et al., "Whole genome sequencing reveals host factors underlying critical Covid-19," Nature, 2022, vol. 607, 31 pages.
Kuhn: Building predictive models in R using the caret package. J Stat Softw., 2008, vol. 28, No. 5, p. 1-26.
Labonte et al.: Analysis of Lupus Nephritis Gene Expression Reveals Dysregulation of Pathogenic Pathways Activated Within Infiltrating Cells [abstract]. Arthritis Rheumatol. 2019; 71 (suppl 10). https://acrabstracts.org/abstract/analysis-of-lupus-nephritis-gene-expression-reveals-dysregulation-of-pathogenic-pathways-activated-within-infiltrating-cells/. Accessed May 20, 2024. Abstract No. 1930.
Labonte et al.: Identification of alterations in macrophage activation associated with disease activity in systemic lupus erythematosus. PloS one, 2018, vol. 13, No. 12, e0208132, p. 1-23.
Langefeld et al.: Transancestral mapping and genetic load in systemic lupus erythematosus. Nature Communications, 2017, p. 1-18.
Langfelder et al. WGCNA: an R package for weighted correlation network analysis. BMC Bioinformatics, 2008, vol. 9, No. 559, p. 1-13.
Li et al.: TIPE2 alleviates systemic lupus erythematosus through regulating macrophage polarization. Cell Physiol Biochem, 2016, vol. 38, No. 1, p. 330-339.
Liaw et al. Classification and regression by randomForest. R News, 2002, vol. 2, No. 3, p. 18-22.
Lood et al.: Neutrophil extracellular traps enriched in oxidized mitochondrial DNA are interferogenic and contribute to lupus-like disease. Nat Med., 2016, vol. 22, No. 2, p. 146-153.
Lugar et al.: Molecular characterization of circulating plasma cells in patients with systemic lupus erythematosus. PLoS One, 2012, vol. 7, No. 9, e44362, p. 1-15.
MARTINEZ: Macrophage activation and polarization. Front Biosci., 2008, vol. 13, p. 453-461.
Moussa et al., Single cell RNA-seq data clustering using TF-IDF based methods. BMC Genomics, 2018, vol. 19, Suppl 6, p. 31-45.
Nickles et al.: Blood RNA profiling in a large cohort of multiple sclerosis patients and healthy controls. Human Molecular Genetics, 2013, vol. 22, No. 20, p. 4194-4205.
Owen et al.: BD-01 Big Data Analyses. E-Genes identified via transancestral SNP mapping and gene expression analysis reveal novel targeted therapies for African-American and European-American SLE patients. Lupus Sci Med, 2018, Issue 5, Suppl 2, 2 pages Abstract.
Patel, Gene Expression Profiling to Understand the Alterations in the Monocyte Compartment of Pediatric Systemic Lupus Erythematosus [Dissertation], 2008, Baylor University, 24 pages.
Picard et al.: International Union of Immunological Societies: 2017 Primary Immunodeficiency Diseases Committee Report on Inborn Errors of Immunity. J Clin Immunol., 2018, vol. 38, No. 1, p. 96-128.
Plaiser et al.: Rank-rank hypergeometric overlap: identification of statistically significant overlap between gene-expression signatures. Neucleic Acids Res, 2010, vol. 38, No. 17, e169, p. 1-17.
Ritchie et al.: Limma powers differential expression analyses for RNA-sequencing and microarray studies. Nucleic Acids Res. 2015, vol. 43, No. 7, e47, p. 1-13.
Robin et al.: pROC: an open-source package for R and S+ to analyze and compare ROC curves. BMC Bioinformatics, 2011, vol. 12, No. 77, p. 1-8.
Rocha et al.: Type I interferon transcriptional signature in neutrophils and high frequency of low-density granulocytes are associated with tissue damage in malaria. Cell Rep., 2015, vol. 13, No. 12, p. 2829-2841.
Rother et al.: Disturbed T cell signaling and altered Th17 and regulatory T cell subsets in the pathogenesis of systemic lupus erythematosus. Frontiers in Immunology, 2015, vol. 6, Article 610, p. 1-10.
Scapini et al.: Human neutrophils in the saga of cellular heterogeneity: insights and open questions. Immunol Rev., 2016, vol. 273, No. 1, p. 48-60.
Schmidt et al.: Autoimmunity and primary immunodeficiency: two sides of the same coin? Nat Rev Rheumatol., 2017, vol. 14, No. 1, p. 7-18.
Schut-Bakker et al., Cluster analysis of flow cytometric list mode data on a personal computer. Cytometry, 1993, vol. 14, No. 6, p. 649-659.
She et al.: Definition, conservation and epigenetics of housekeeping and tissue-enriched genes. BMC Genomics, 2009, vol. 10, No. 269, p. 1-12.
Sun et al., IER3IP1 deficiency leads to increased 13-cell death and decreased 13-cell proliferation, Oncotarget, 2017, vol. 8, No. 34, p. 56768-56779.
Taylor et al.: Risk alleles for systemic lupus erythematosus in a large case-control collection and associations with clinical subphenotypes. PLoS Genet., 2011, vol. 7, No. 2, e1001311, p. 1-11.
Vaughn et al.: Lupus risk variants in the PXK locus alter B-cell receptor internalization. Front Genet, 2015, vol. 5, Art 450, p. 1-12.
Villanueva et al.: Netting neutrophils induced endothelial damage, infiltrate tissues, and expose immunostimulatory molecules in systemic lupus erythematosus. J Immunol., 2011, vol. 187, No. 1, p. 538-552.
Vollenhoven et al.: Efficacy and Safety of Ustekinumab, an IL-12 and IL-23 Inhibitor, in Patients with Active Systemic Lupus Erythematosus: Results of a Multicentre, Double-Blind, Phase 2, Randomised, Controlled Study. The Lancet, 2018, vol. 392, Issue 10155, p. 1330-1339.
Waddell et al.: Dissecting Interferon-Induced Transcriptional Programs in Human Peripheral Blood Cells. PLoS One, 2010, vol. 5, No. 3, e9753, 13 pages.
Wang et al., "Supramolecular Kandinsky circles with high antibacterial activity," Nature Communications, 2018, vol. 9, No. 1815, p. 1-9.
Wright et al.: Low-density granulocytes: functionally distinct, immature neutrophils in rheumatoid arthritis with altered properties and defective TNF signaling. J Leukoc Biol, 2017, vol. 101, No., p. 599-611.
Xiao et al.: Dynamic expression of microRNAs in M2b polarized macrophages associated with systemic lupus erythematosus. Gene, 2014, vol. 547, No. 2, p. 300-309.
Xu et al., "Identification of cell types from single-cell transcriptomes using a novel clustering method," Bioinformatics, 2015, vol. 31, No. 12, p. 1974-80.
Yang et al.: Oxidative stress and Treg and Th17 dysfunction in systemic lupus erythematosus. Oxid Med Cell Longev, 2016, p. 1-9.
Zheng et al., "Massively parallel digital transcriptional profiling of single cells," Nature Communications, 2017, vol. 4, p. 1-12.
Quinn et al., Prognostic Factors in a Large Cohort Patients with Early Undifferentiated Inflammatory Arthritis After Application of a Structured Management Protocol, Arthritis & Rheumatism, 2003, vol. 48, No. 11, p. 3039-3045.

* cited by examiner

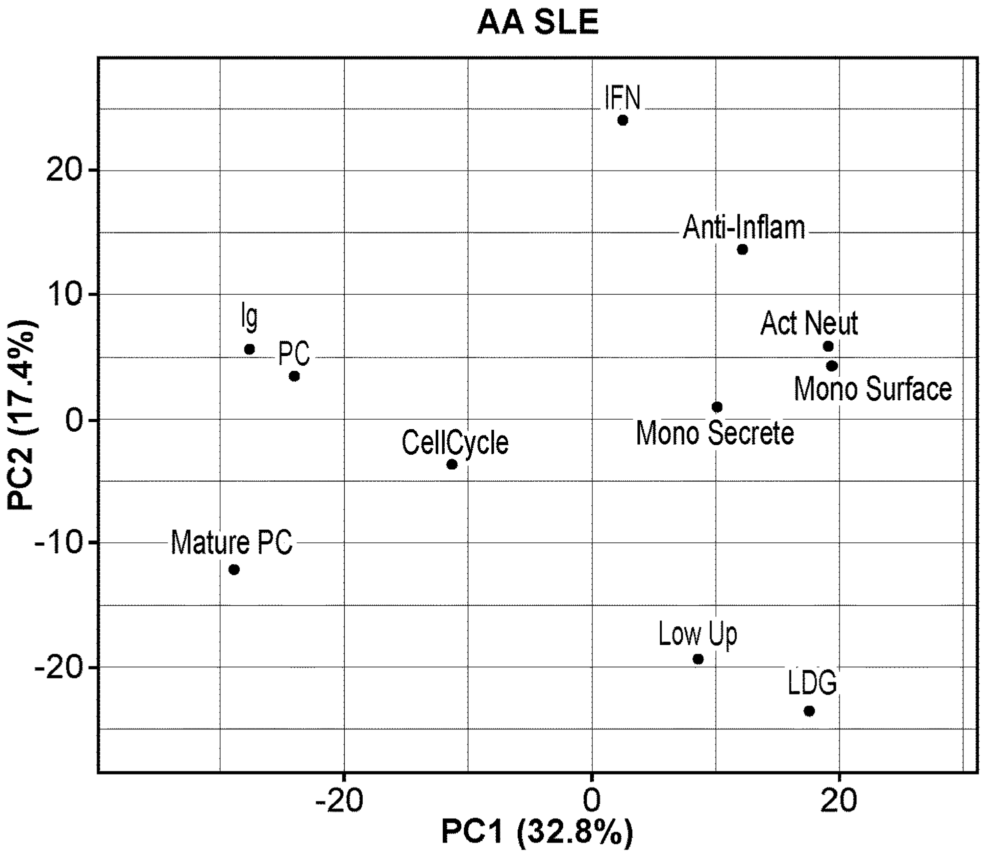
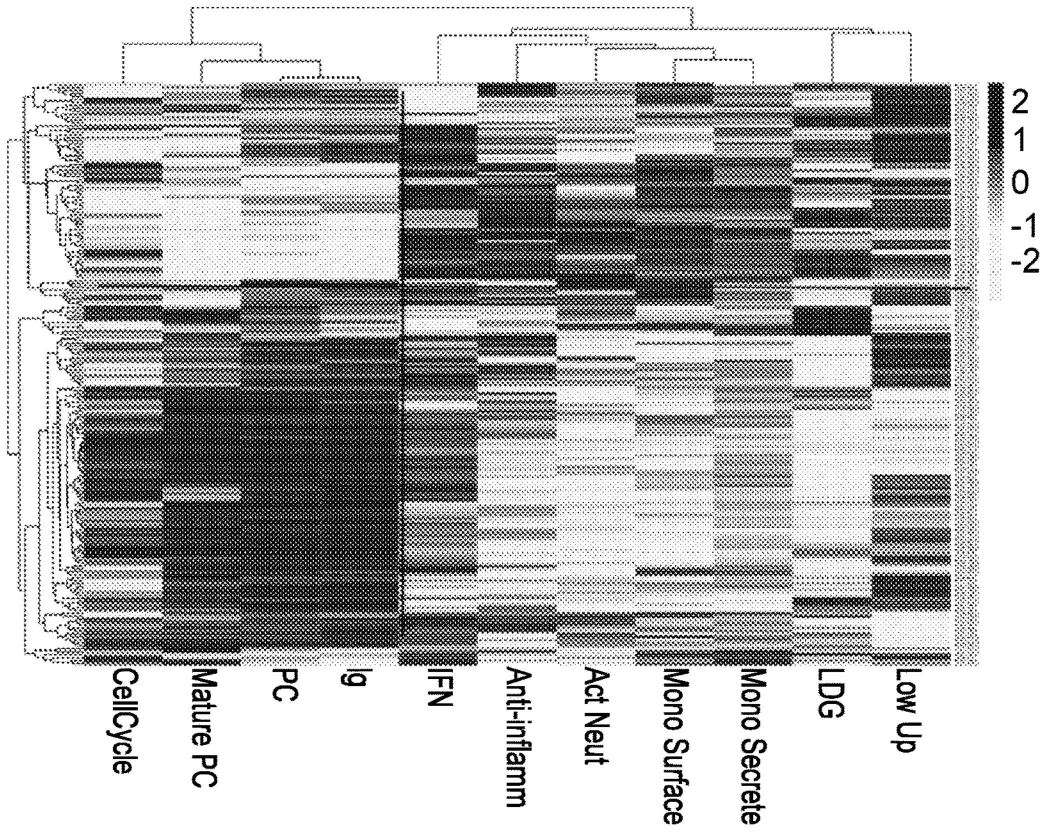
FIG. 18

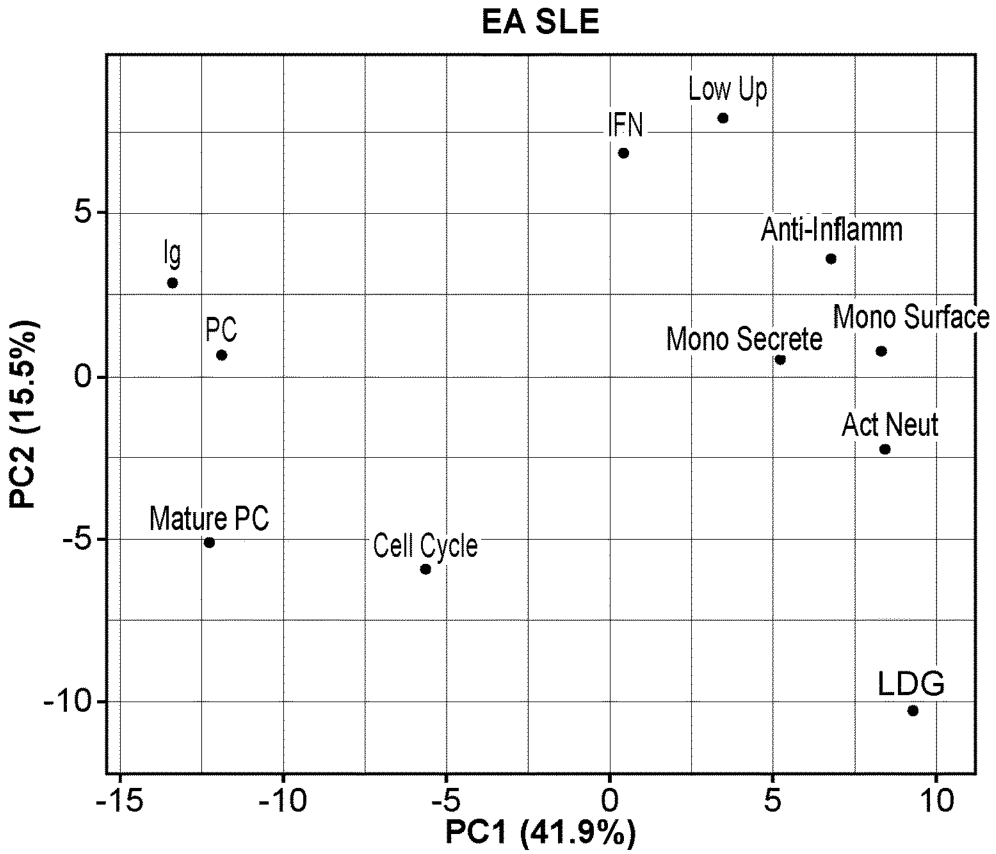
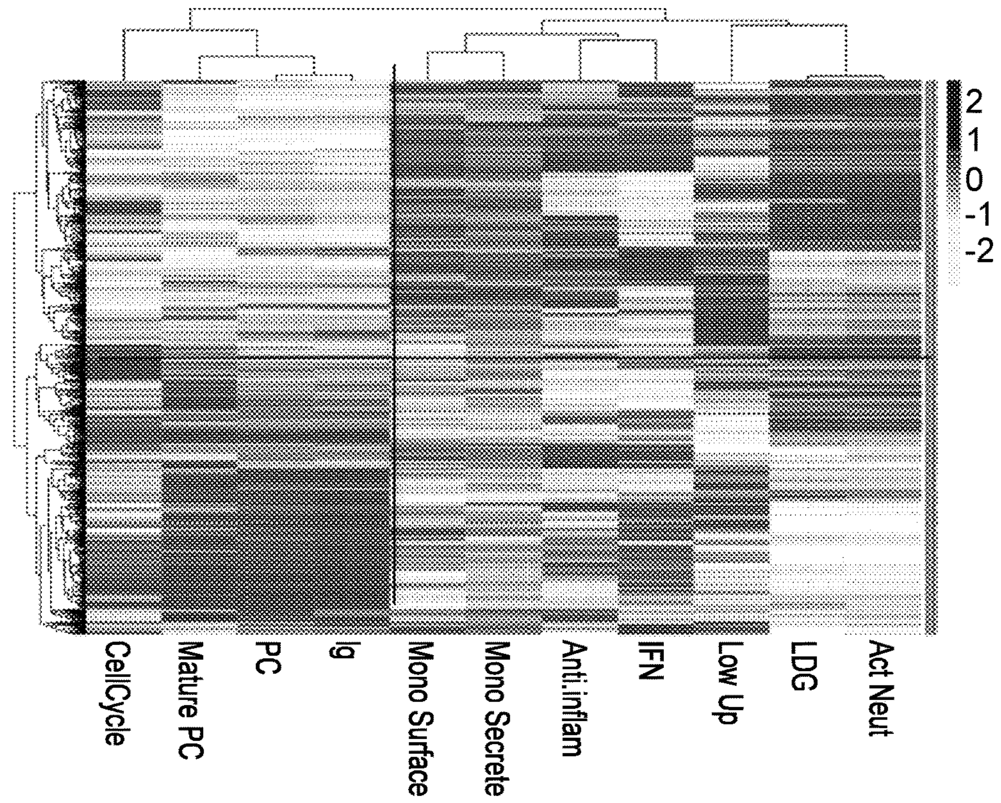
FIG. 18 (Cont. 1)

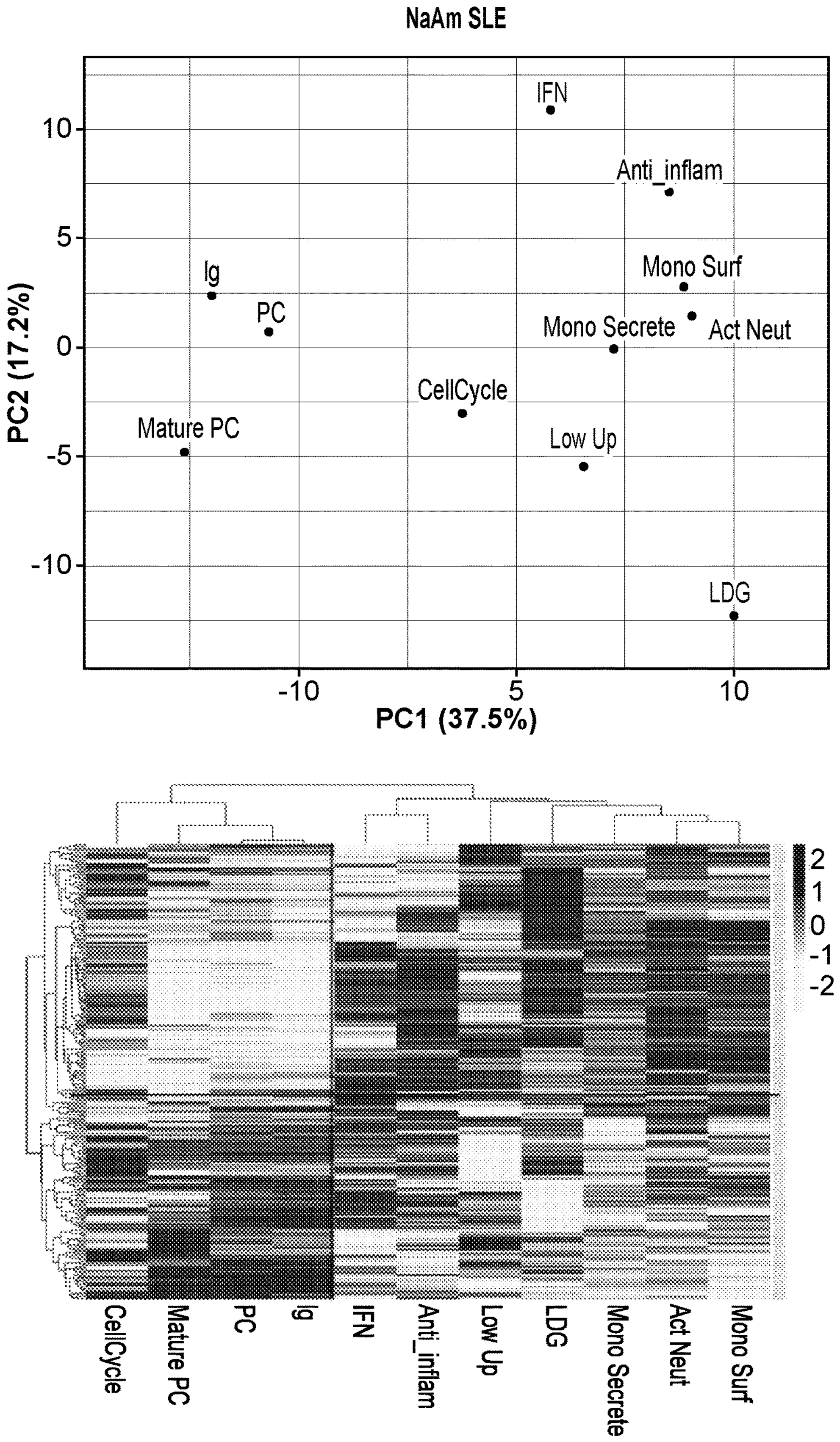
FIG. 18 (Cont. 2)

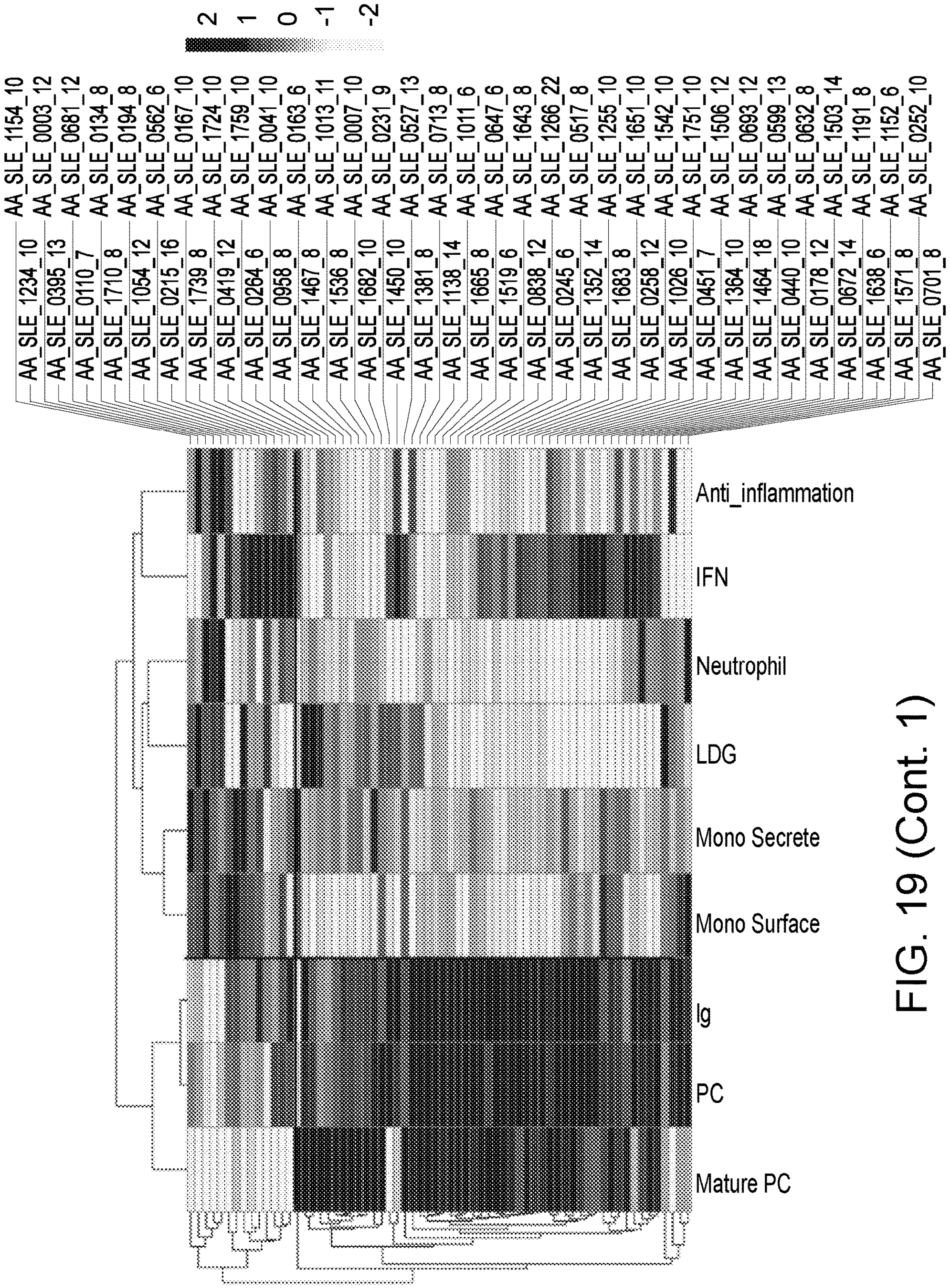
FIG. 19 (Cont. 1)

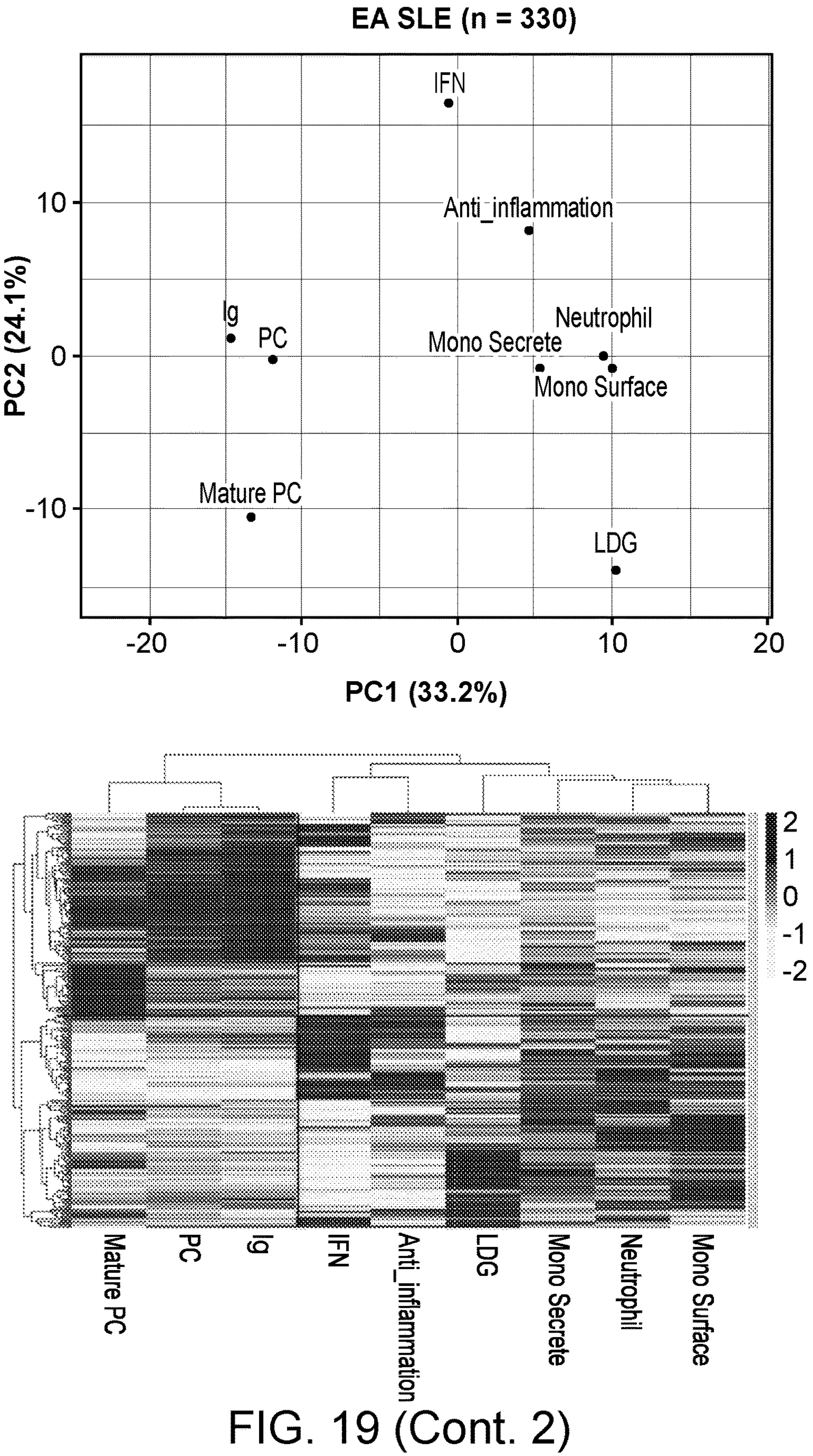
FIG. 19 (Cont. 2)

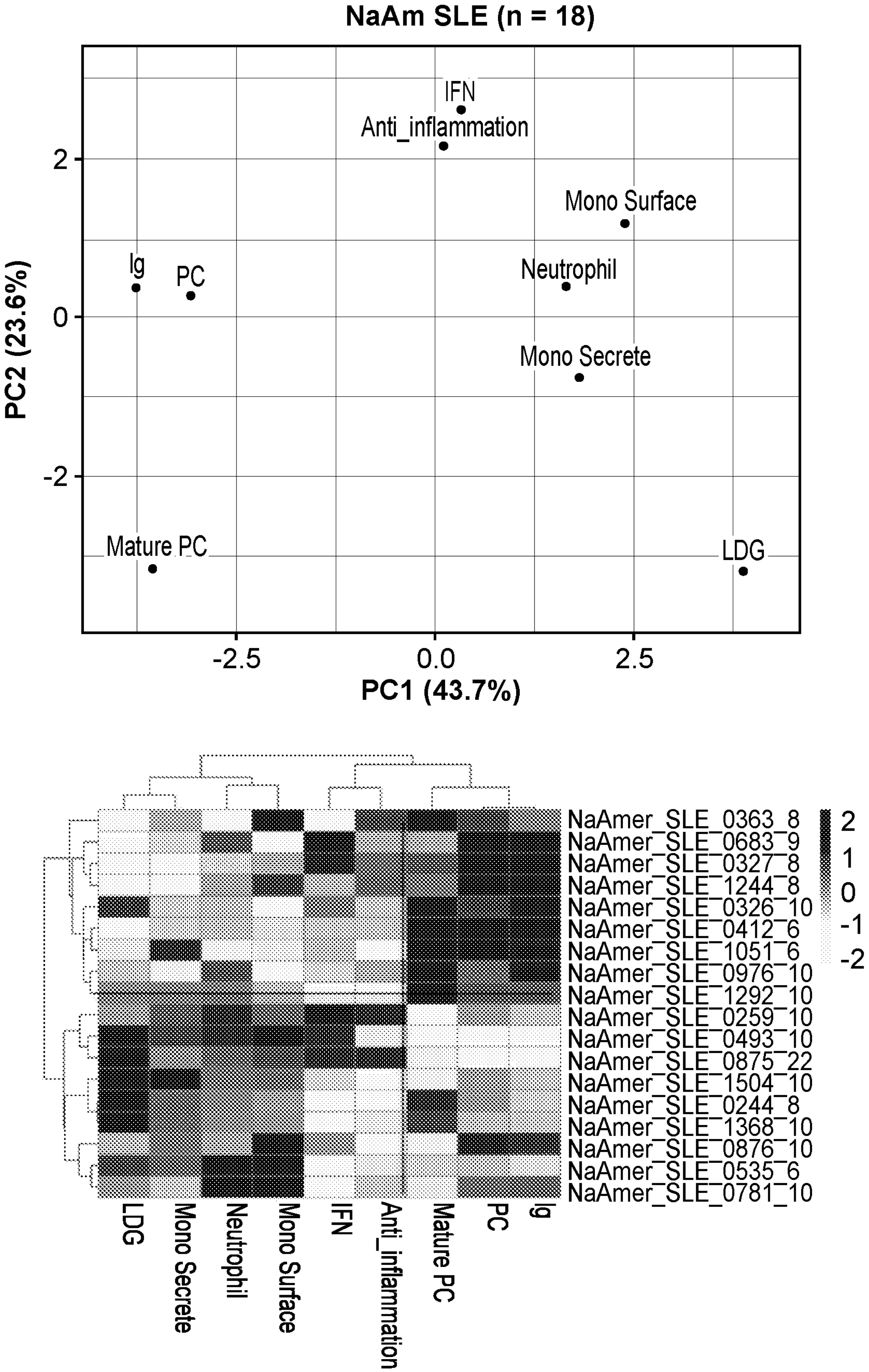
FIG. 19 (Cont. 3)

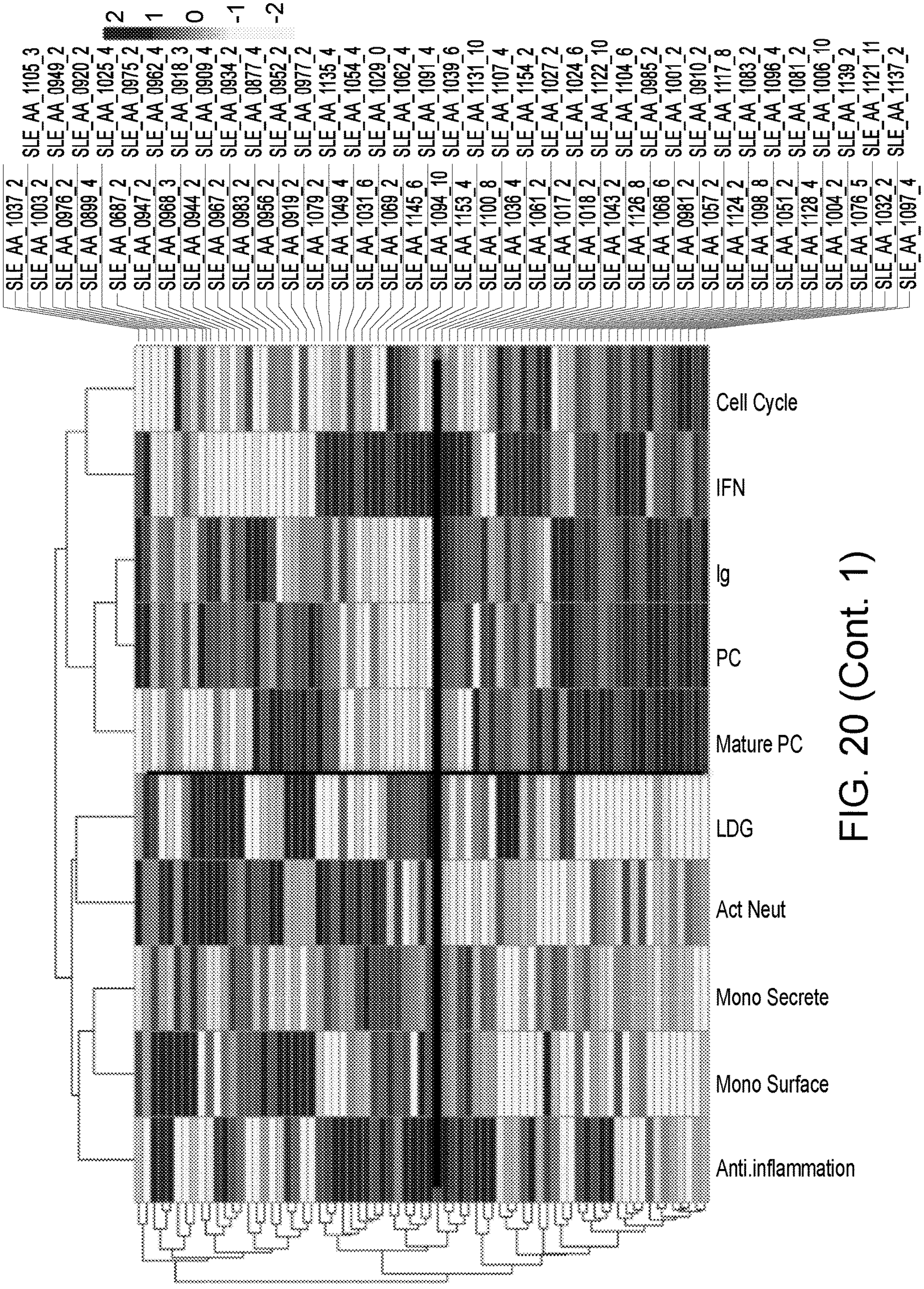
FIG. 20 (Cont. 1)

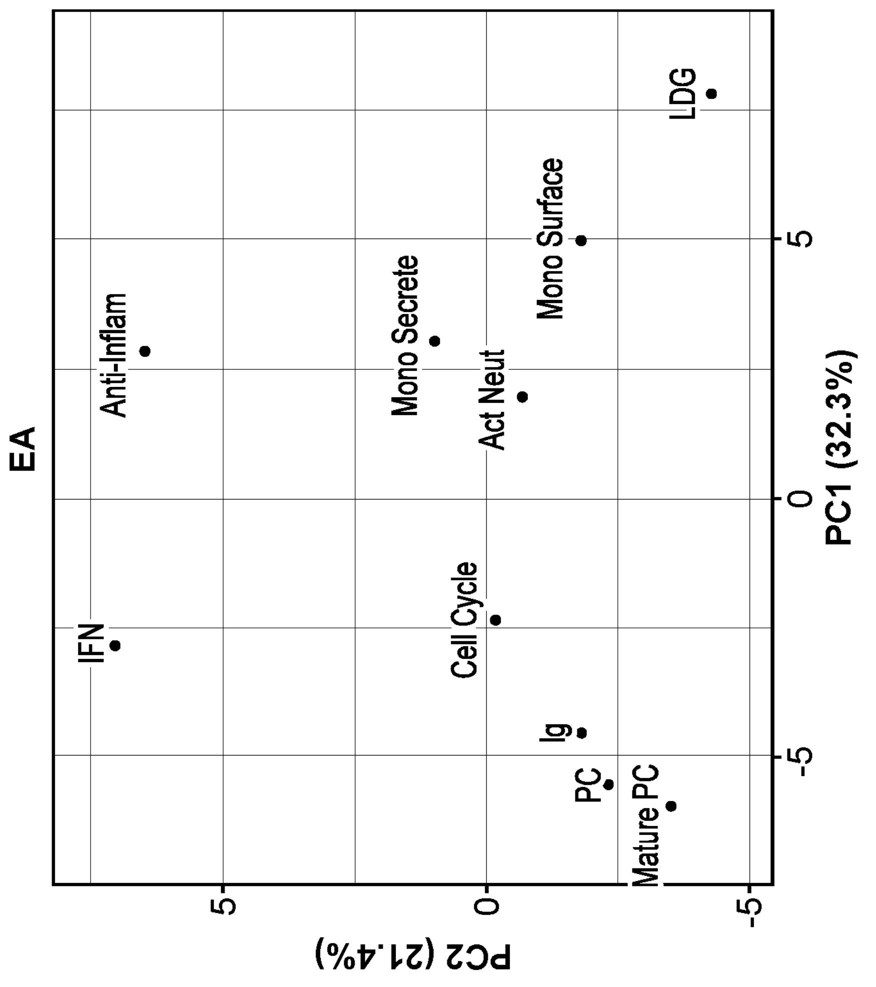
FIG. 20 (Cont. 2)

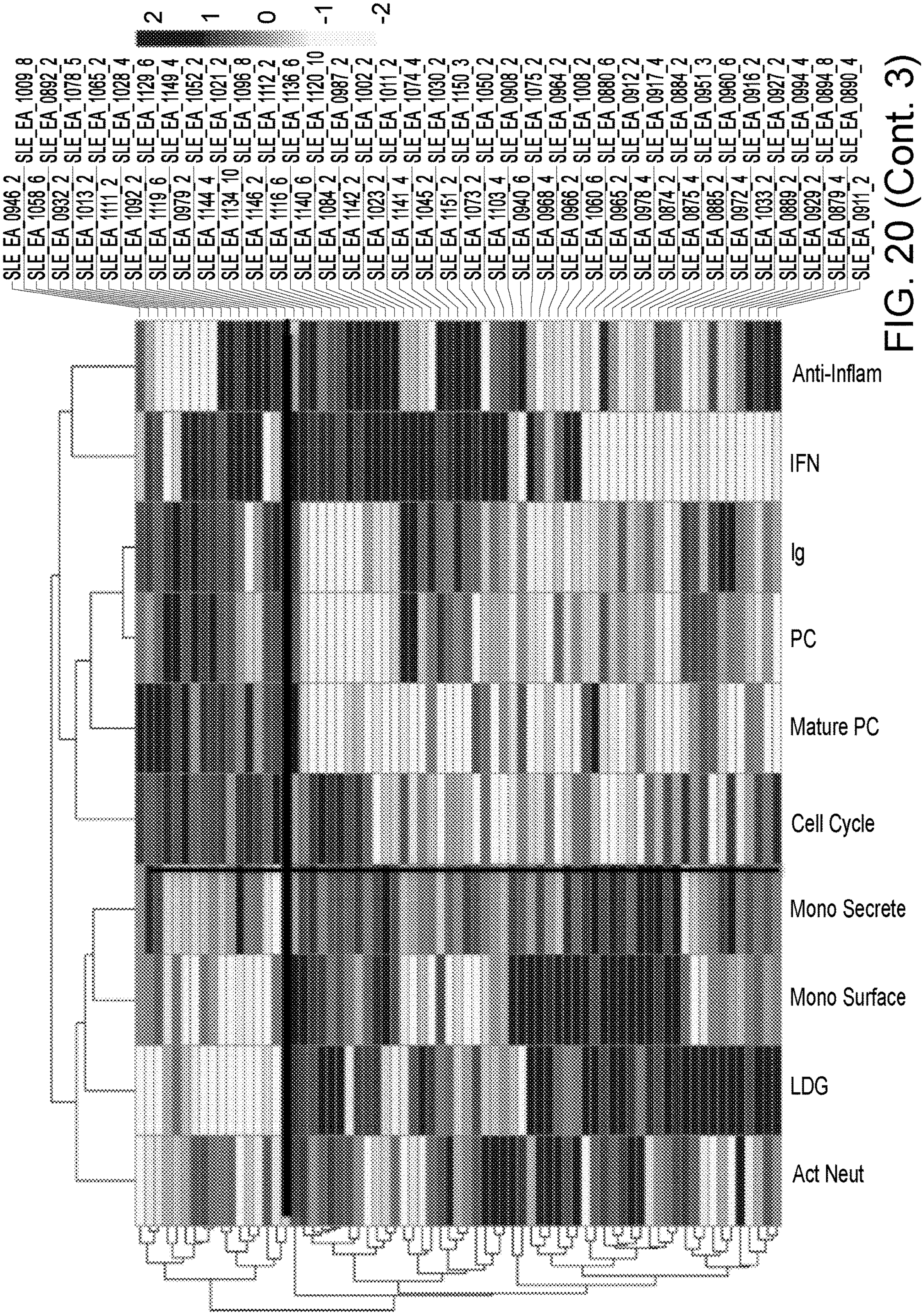
FIG. 20 (Cont. 3)

a.

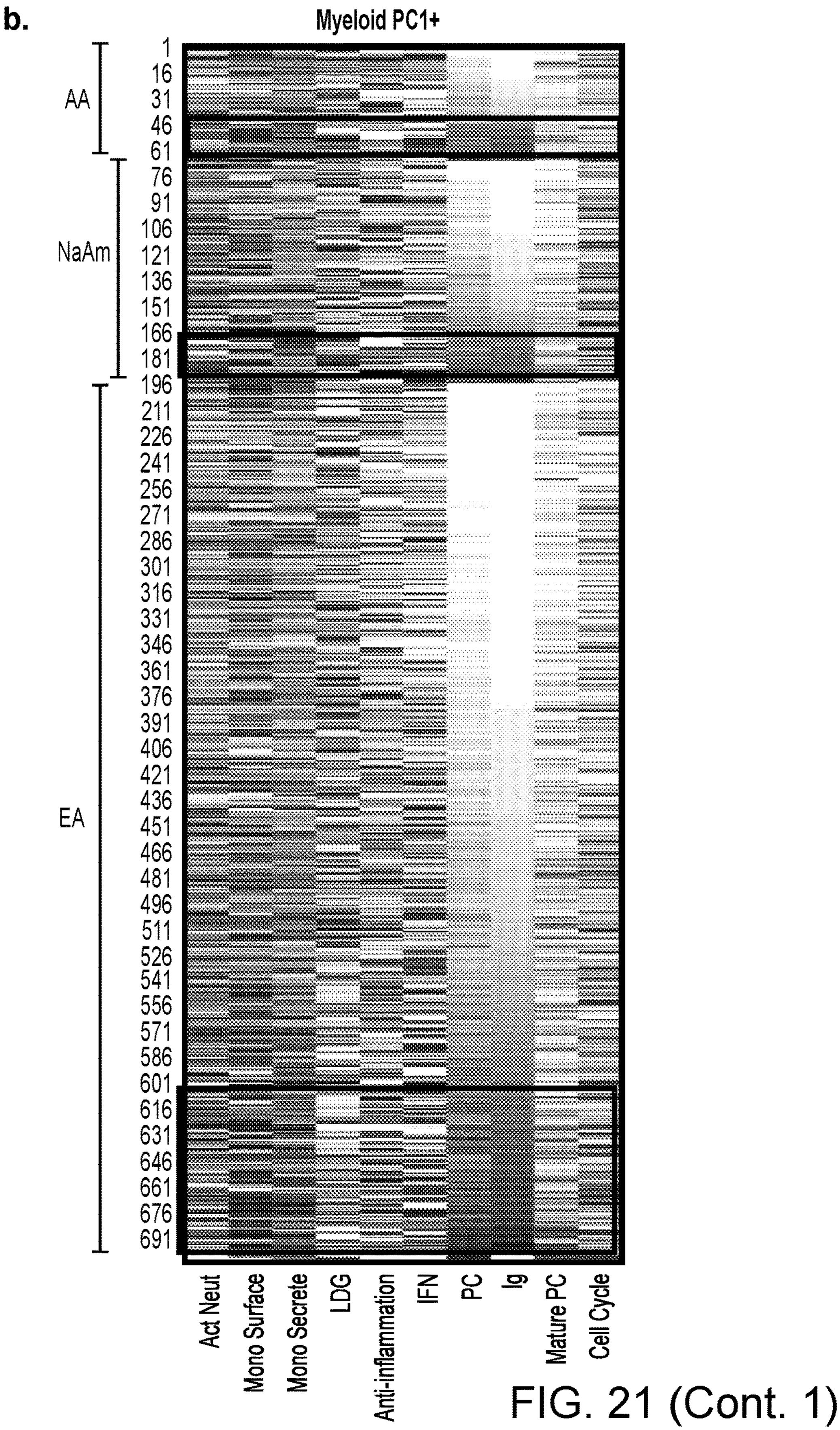
FIG. 21 (Cont. 1)

c.
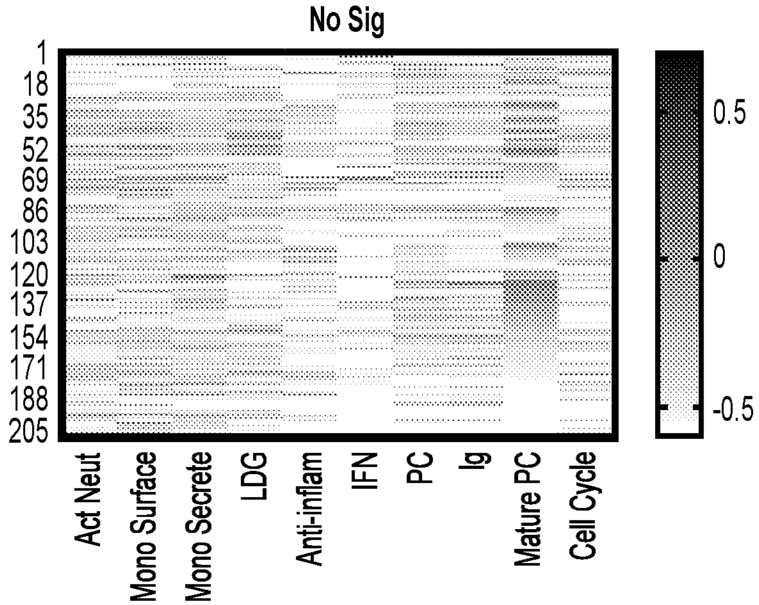
FIG. 21 (Cont. 2)

209 No Sig SLE Patients
25 AA, 23 NaAm, 161 EA

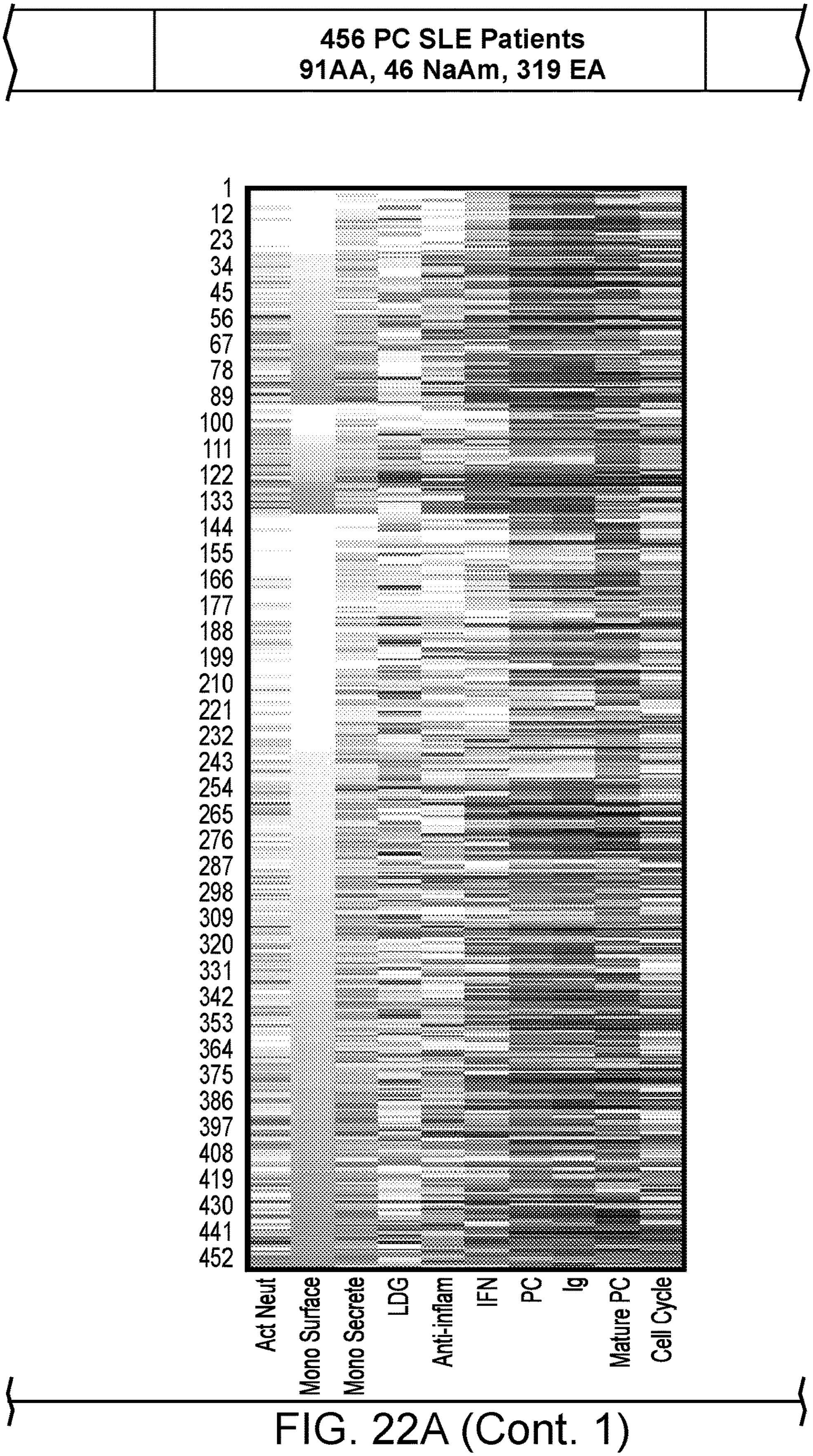
FIG. 22A (Cont. 1)

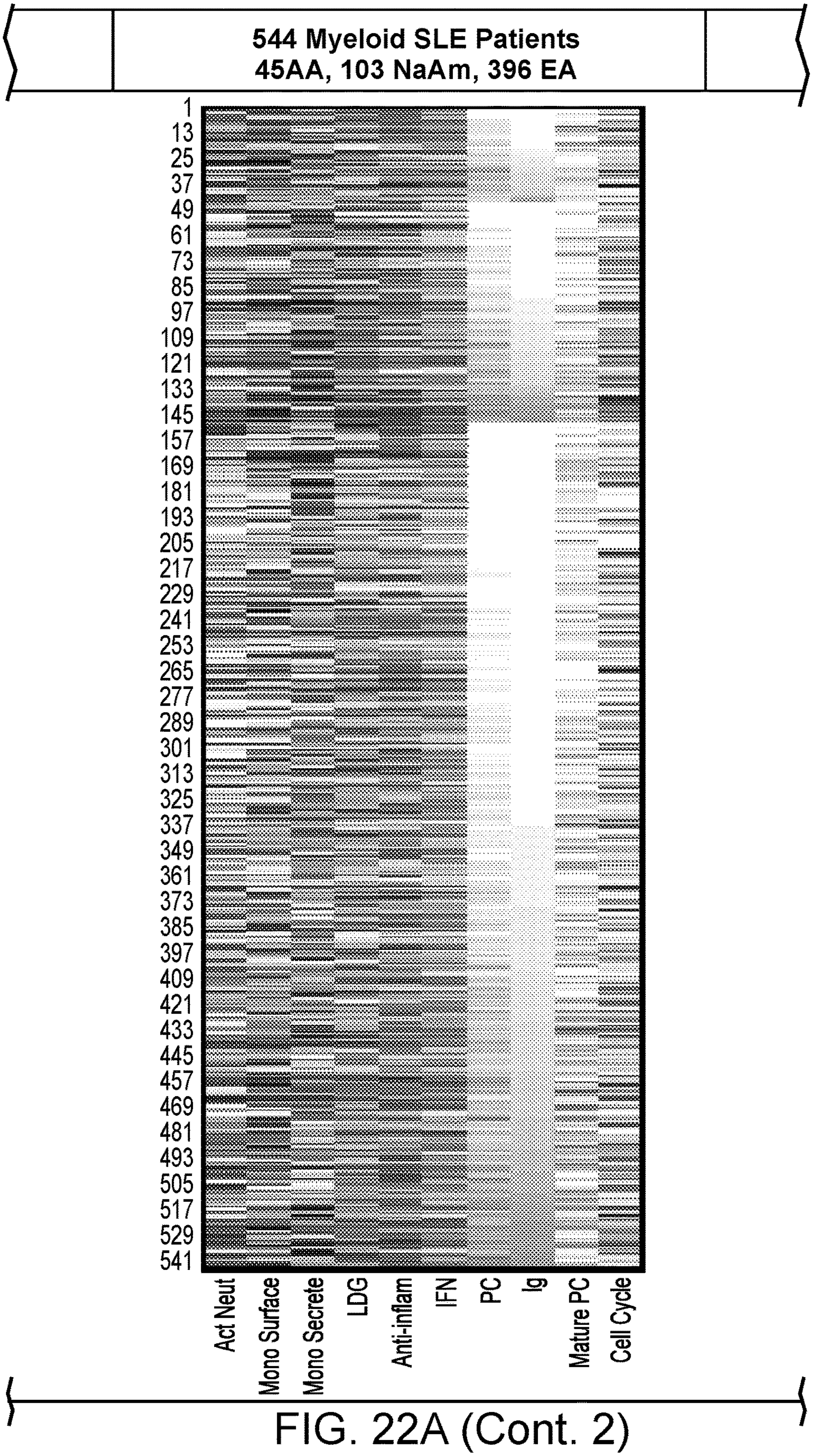
FIG. 22A (Cont. 2)

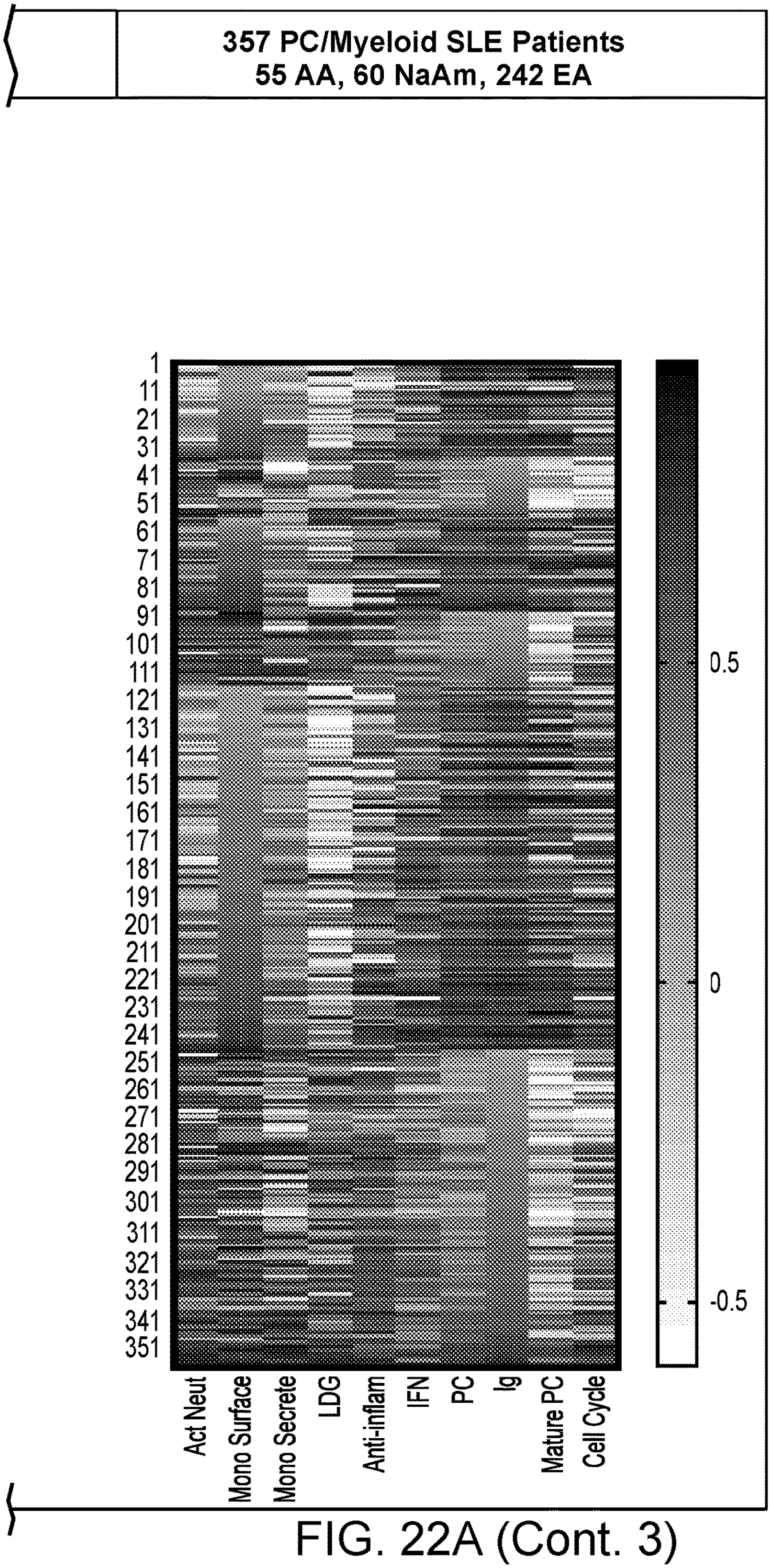
FIG. 22A (Cont. 3)

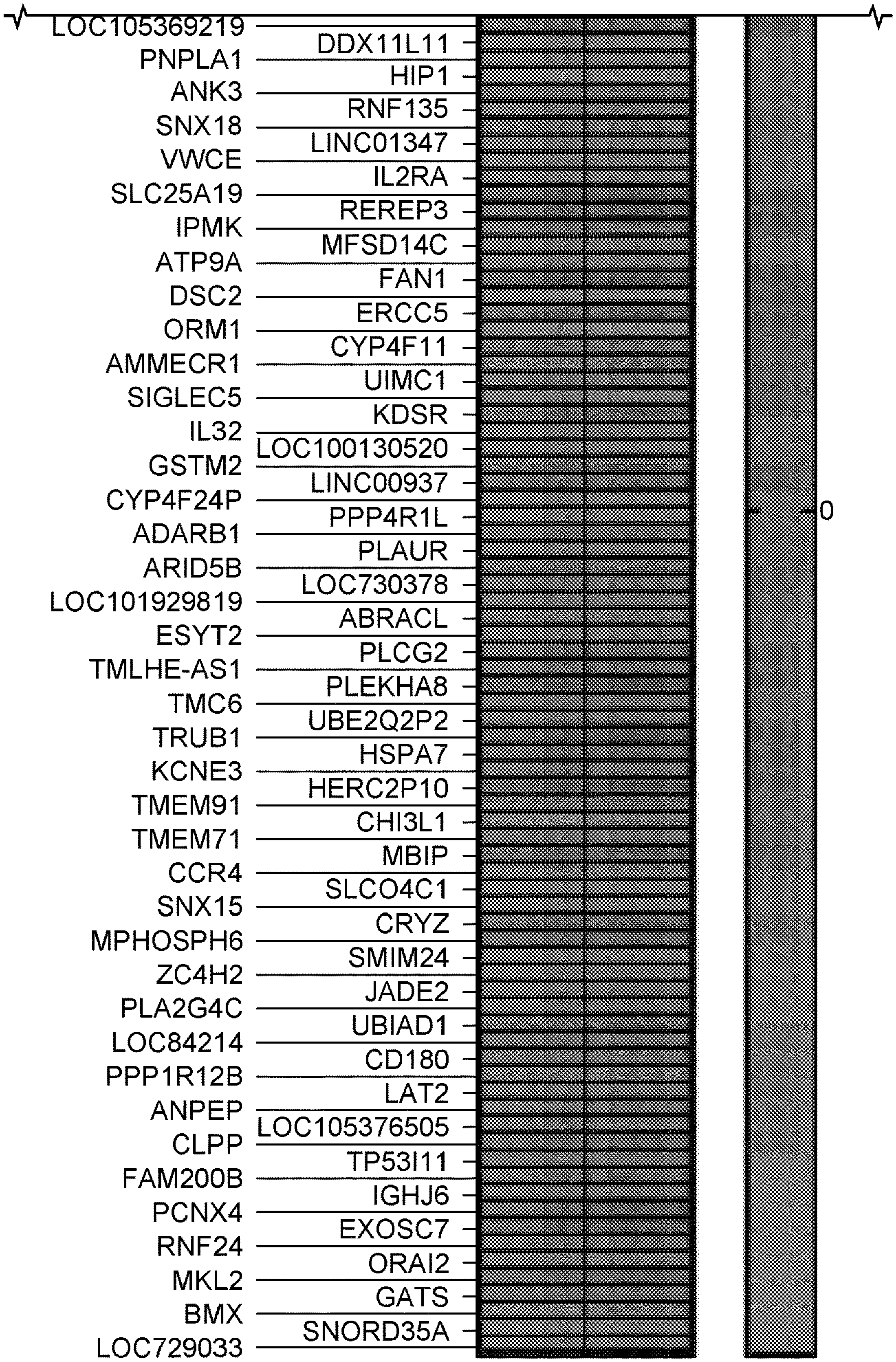
FIG. 26A (Cont. 1)

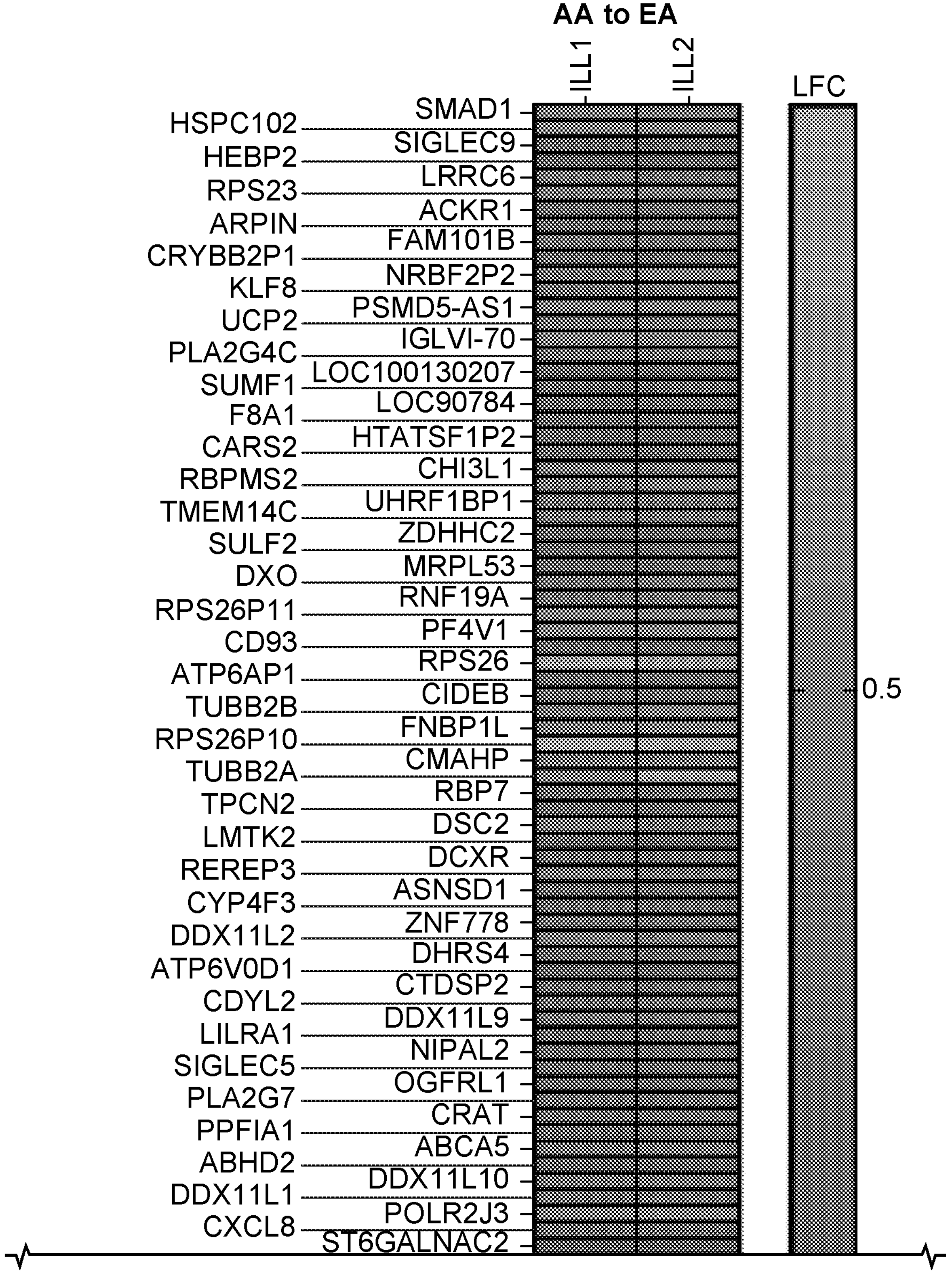
FIG. 26A (Cont. 2)

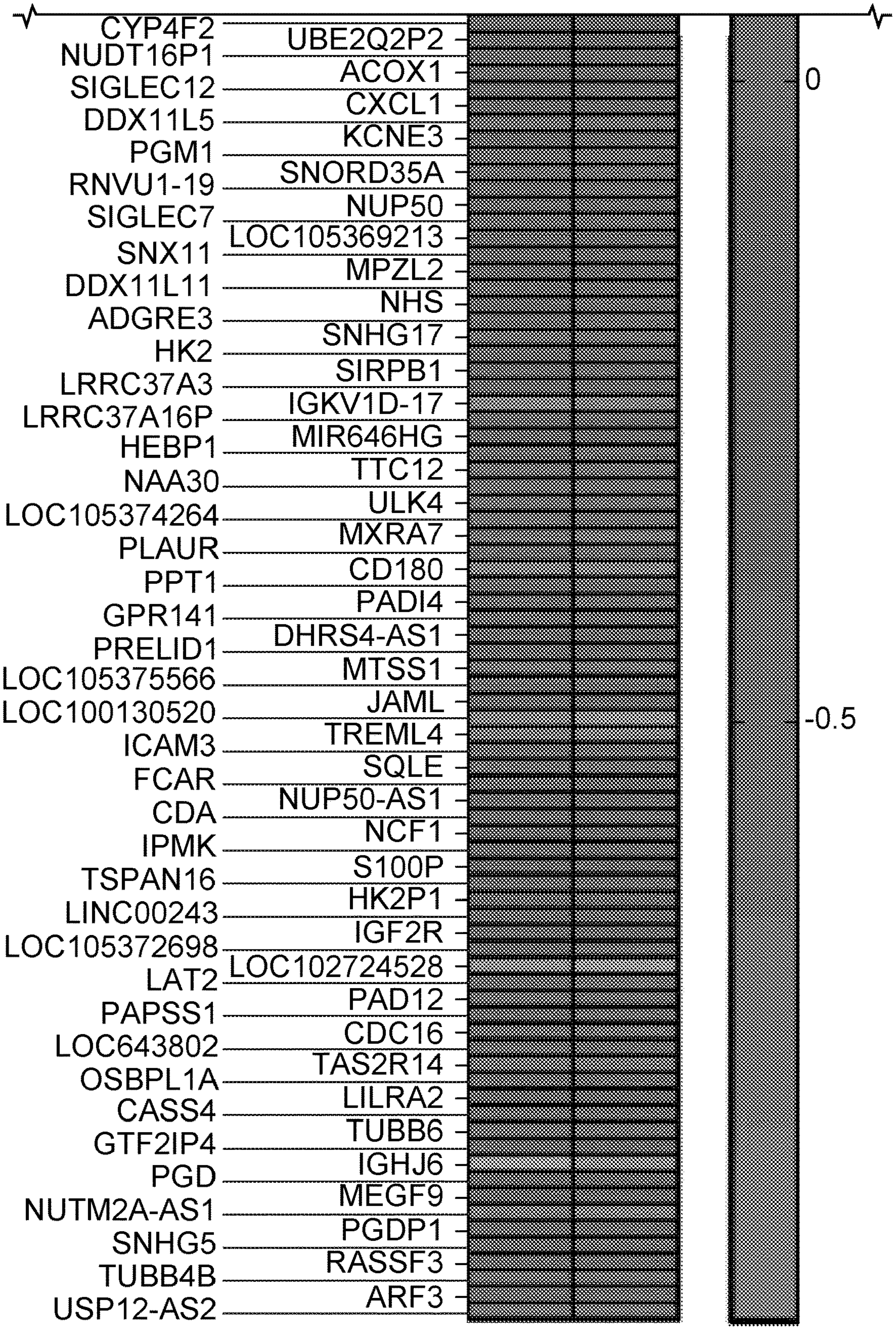
FIG. 26A (Cont. 3)

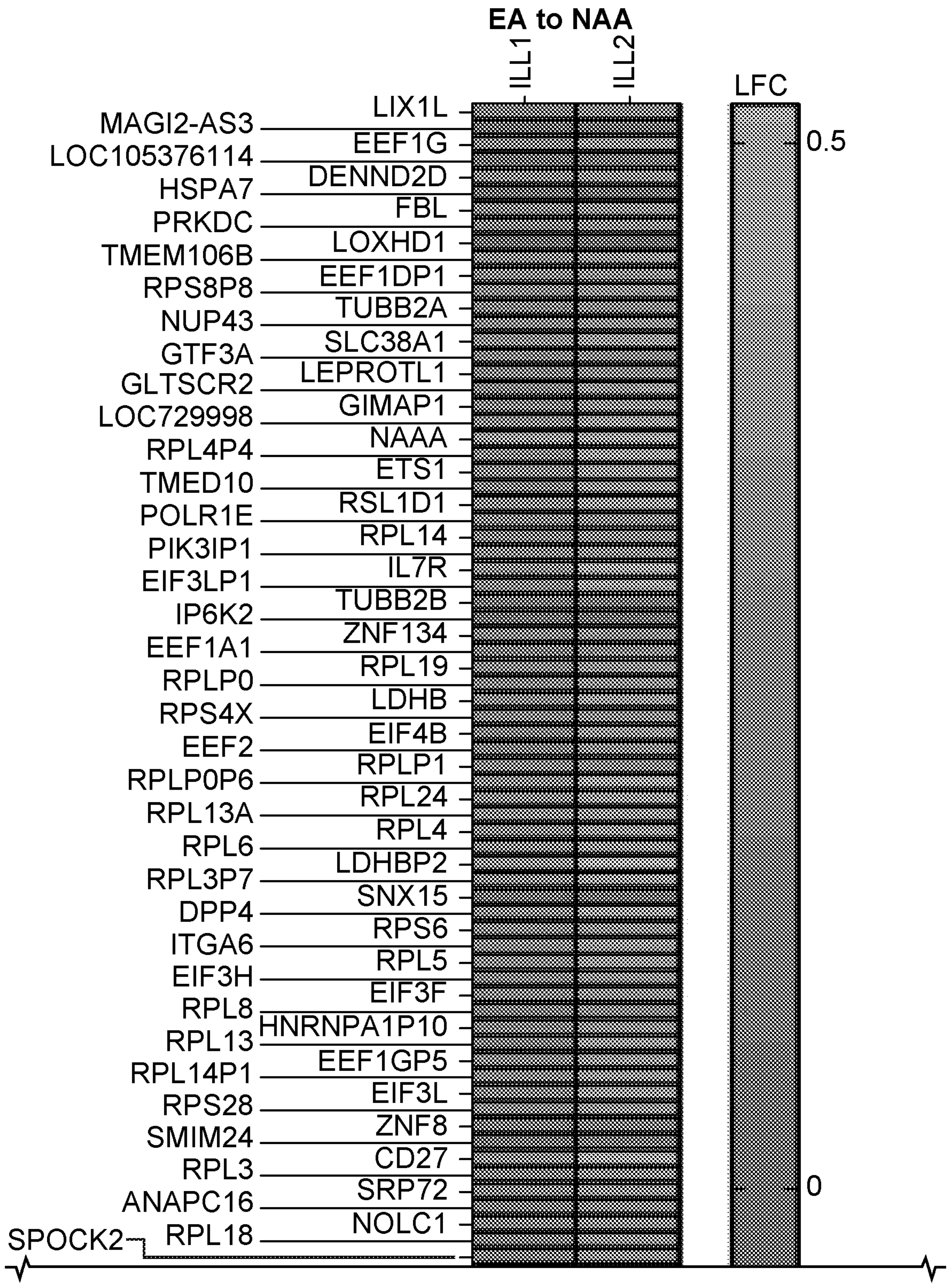
FIG. 26A (Cont. 4)

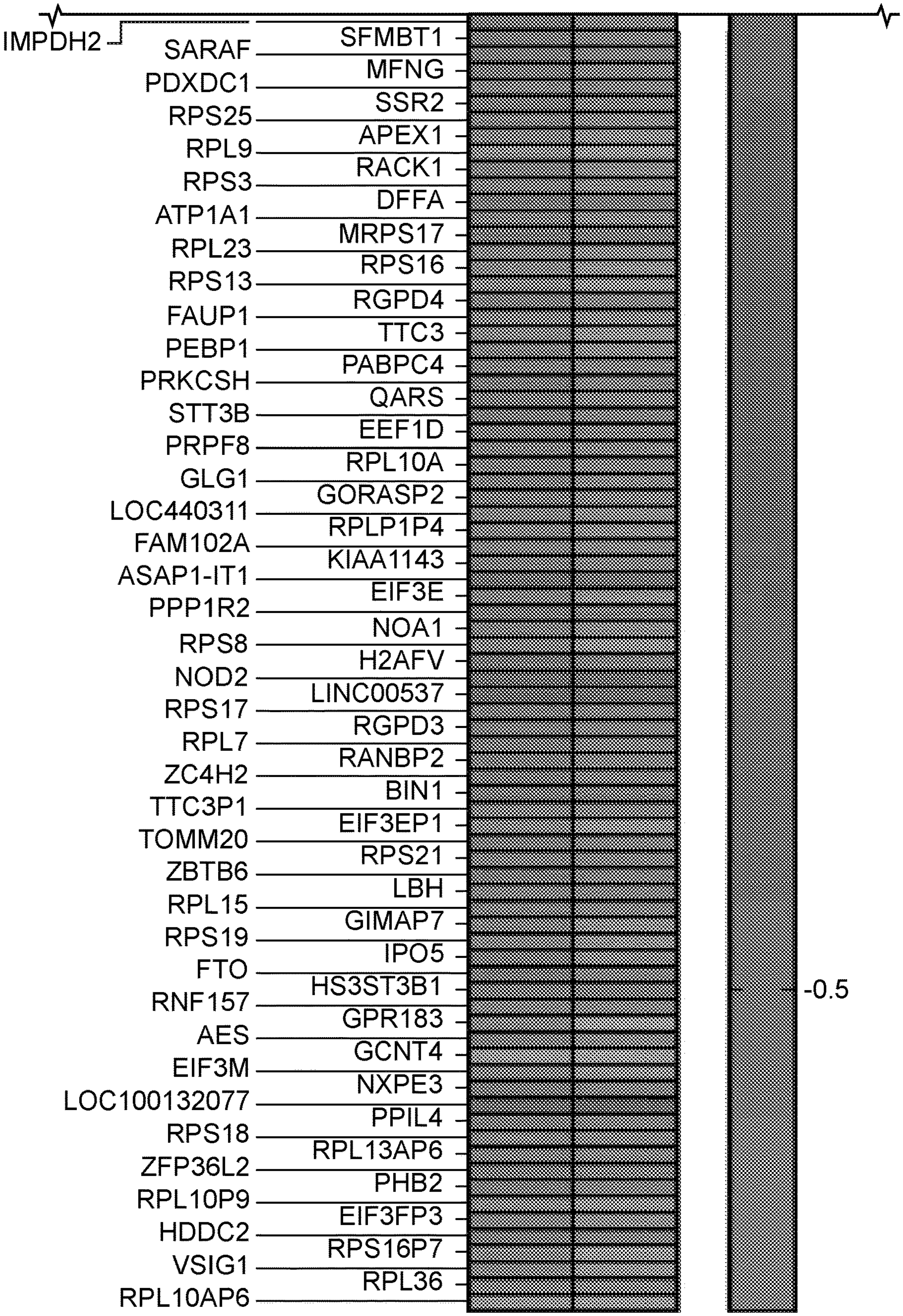
FIG. 26A (Cont. 5)

AA NAA EA

AA NAA EA

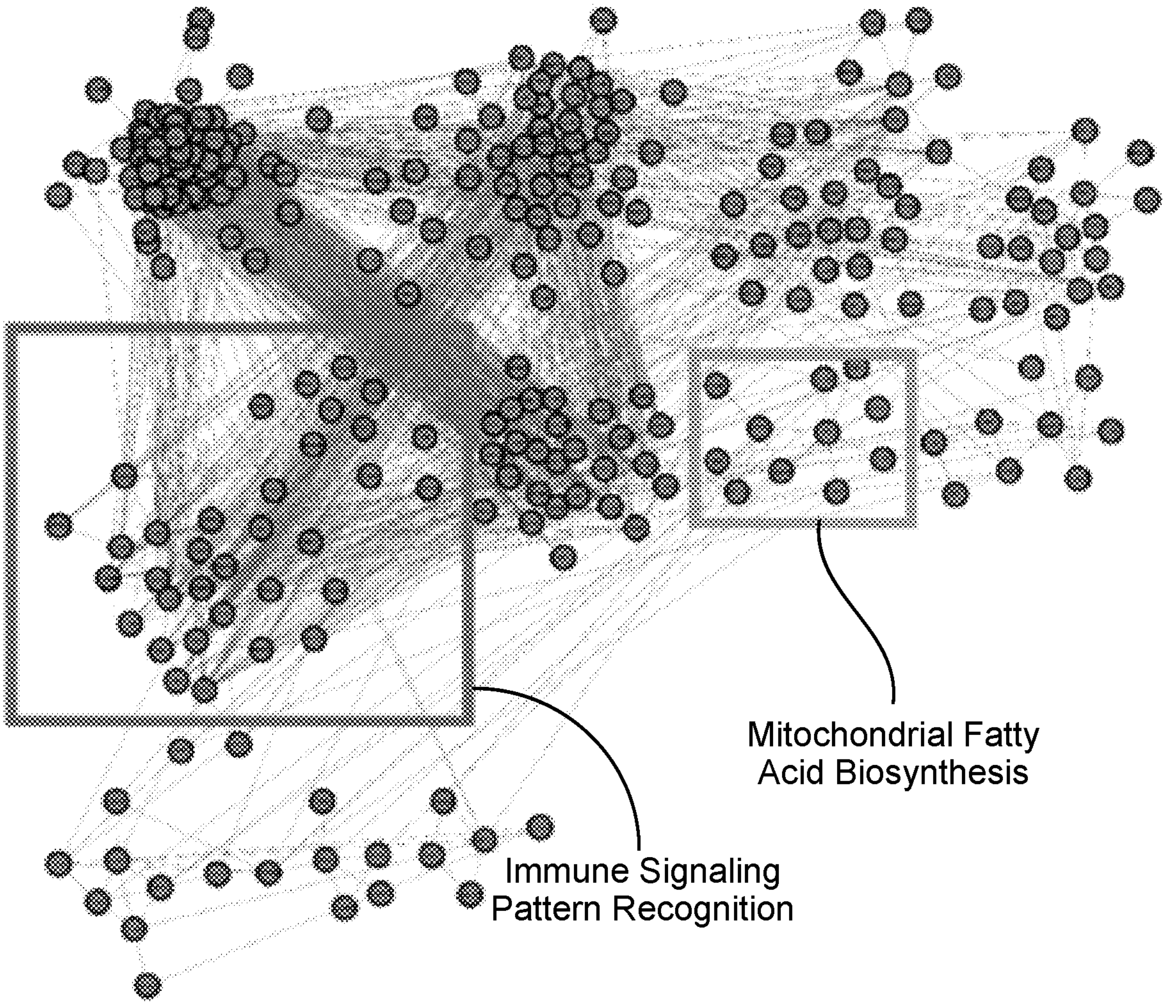
FIG. 38D (Cont. 1)

Immune Signaling Pattern Recognition
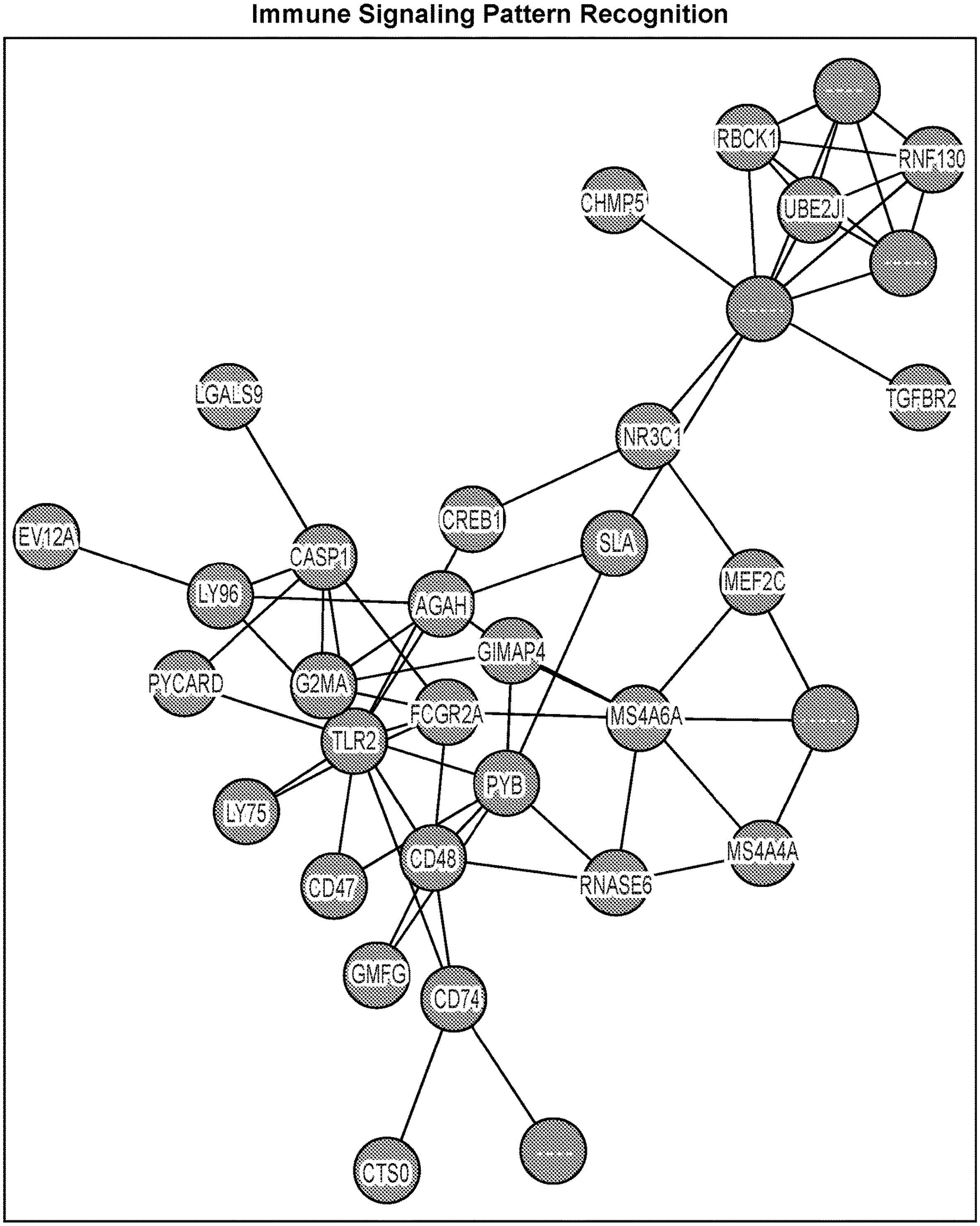
FIG. 38D (Cont. 2)

Mitochondrial Fatty Acid Biosynthesis
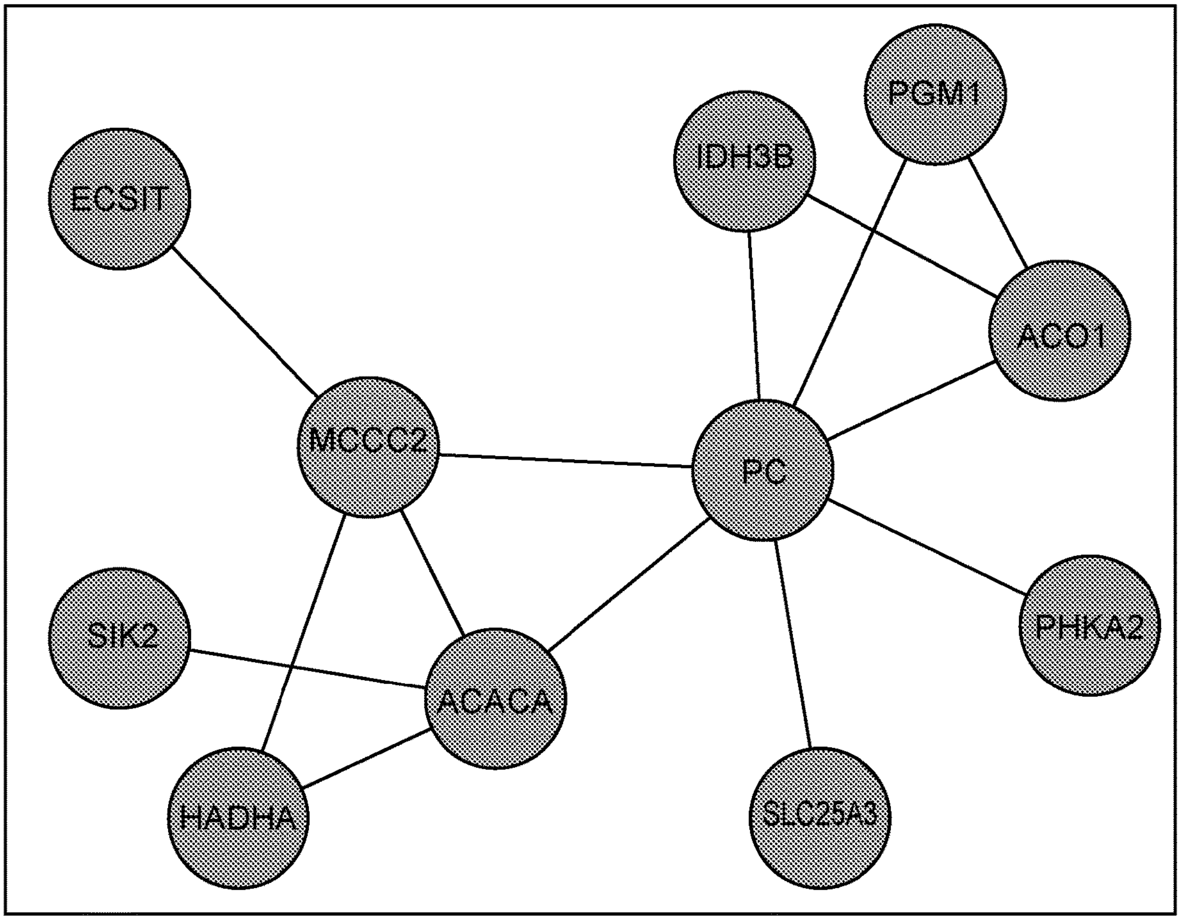
FIG. 38D (Cont. 3)

Immune and tissue cell GSVA scores for tubulointerstitium

| | Original SNPs | | eQTLs | | E-Genes | | Drugs targeting E-Genes | | Fraction of E-Genes targeted by drugs | |
|---|---|---|---|---|---|---|---|---|---|---|
| | Unfiltered | Filtered | Unfiltered | Filtered | Unfiltered | Filtered | Unfiltered | Filtered | Unfiltered | Filtered |
| AA Only | 51 | 33 | 783 | 334 | 69 | 28 | 52 | 25 | 12 | 5 |
| EA Only | 260 | 177 | 11872 | 7826 | 770 | 323 | 302 | 131 | 77 | 28 |
| Shared AA and EA | 1 | 1 | 37 | 27 | 52 | 26 | 154 | 22 | 13 | 4 |

SNP genomic functional categories

| Region | | Ancestry | | | |
|---|---|---|---|---|---|
| | | EA | | AA | |
| Coding | | SNP | % | SNP | % |
| | Exon | 7 | 2.7 | 1 | 1.9 |
| | 5' UTR | 1 | 0.4 | 0 | 0 |
| | 3' UTR | 14 | 5.4 | 4 | 7.6 |
| Non-coding | | | | | |
| | miRNA | 0 | 0 | 0 | 0 |
| | lncRNA | 8 | 3.0 | 3 | 5.7 |
| | TFBS | 4 | 1.5 | 0 | 0 |
| | Regulatory | 38 | 14.6 | 12 | 23.1 |
| | NT-R | 17 | 6.5 | 1 | 1.9 |
| | Other | 171 | 65.8 | 31 | 59.6 |
| TOTAL | | 260 | ~100 | 52 | ~100 |

NT-R = non-traditional regulatory: intronic or intergenic SNP with strong regulatory potential

FIG. 41A

Summary of eQTL analysis

| Ancestry | Original SNPs | eQTLs | E-Genes |
|---|---|---|---|
| EA | 260 | 11872 | 770 |
| AA | 52 | 783 | 69 |
| Shared | 1 | 37 | 52 |

AA GO Pathways

E-Genes

EA Pathways

| BIG-C Category | Cluster | | Canonical pathway | Predicted EA genes(s) in pathway | Pathway Drugs |
|---|---|---|---|---|---|
| Nuclear rec, trans, PRRS, Gen. transcription, Intracellular sig. | Cluster 3 | | Role of MC, FB and ECs in RA | PLCB1, PLCB2 | Dapirolizumab[8^] |
| | | | Hepatic cholestasis<br>GPCR signaling | PLCB1, PLCB2, CRHR1 | Adalimumab[4#] |
| | | | NFKB signaling | | |
| | | | Activation of IRF by cytosolic PRRS | IFIH1, ZBP1 | |
| MHC class II, Immune secreted, PRRs, WNT signaling, Immune cell surface | Cluster 1 | | Activation of IRF by cytosolic PRRs | | PF-06823859[5^] |
| | | | T cell exhaustion | TYK2 | BMS-986165[7^] |
| | | | Role of lipids in pathol. influenza | | Ruxolitinib[5#] |
| | | | Role of RIG I recpt. in antiviral immunity | TRIM25 | Rontalizumab[4^] |
| | | * | Role of WNT/GSK3B in pathol. influenza | | |
| Immune signaling, Integrin, Immune cell surface, | Cluster 5 | * | TEC kinase signaling | TEC, FCGR1B | Evobrutinib[8^] SM201[3^] |
| | | | T helper cell differentiation | IL12RB1, FCGR1B | Abatacept[8^] |
| | | | Altered T & B signaling in RA | FCGR1B | Ustekinumab[10#] |
| | | * | Cross talk between DCs & NK cells | | Dupilumab[4#] |
| | | | IL12 signaling in MC | ALOX15, IL12RB1 | Lebrikizumab[7^]<br>Fostamatnib[7^] |
| Immune signaling, Immune secreted, Immune cell surface, Intracellular signaling, | Cluster 4 | | TH1 & TH2 activation pathway | | AMG-811[8^] |
| | | | TH1 activation pathway | | BOS-161721[7^] |
| | | | T cell receptor signaling | | Theralizumab[4^] |
| | | * | PD1, PD1L cancer immunotherapy pathway | | |
| | | | CD28 signaling in TH cells | | |
| PRRs Immune secreted, Immune cell surface, Intracellular signaling, Pro-apoptosis | Cluster 7 | | NFKB signaling | TNIP1, IL1R1 | Bi655064[5^] |
| | | | Role of osteoblasts, osteoclasts & chrondrocytes in RA | | |
| | | | TLR signaling | IL1R1 | |
| | | | Role of MC, FB and ECs in RA | IL1R1 | |
| | | | IL6 signaling | IL1R1 | |

-log (pval): 25 – 2

FIG. 51B

| | | | | | |
|---|---|---|---|---|---|
| Immune secreted, Immune cell surface, Integrin, Lysosome | Cluster 2 | | Glucocorticoid signaling | | Siponimod$^{+7}$ |
| | | | Hepatic fibrosis | | |
| | | * | IL17 signaling | | |
| | | * | Angiotensin signaling | | |
| | | * | Agranulocyte adhesion & diapedesis | CXCR1, CXCL1 | |
| Immune secreted, PRRs, Pro-apoptosis Intracellular signaling | Cluster 19 | | Cardiac hypertrophy signaling | CAMK2D | Vorinostat$^{6\#}$ Everolimus$^{3\#}$ |
| | | | Role of MC, FB and ECs in RA | IL1R2 | |
| | | | NFKB signaling | MAP4K4, IL1R2 | |
| | | | Opioid signaling pathway | CAMK2D | |
| | | * | Endocannabinoid cancer inhibition pathway | | |
| miRNA processing, DNA Repair | Cl. 13 | * | MODY signaling | | |
| | | * | TGF-B signaling | | |
| | | * | AMK signaling | | |
| DNA Repair, Pro-apoptosis, Chromatin remodeling | Cl. 26 | | P53 signaling | | |
| | | | Herediatry breast cancer signaling | | |
| | | * | Ovarian cancer signaling | | |
| Immune secreted, MHC class II, Lysosome | Cl. 11 | | Autophagy | CTSH | |
| | | * | Leukotriene biosynthesis | LTA4H | |
| | | | Phagosome maturation | CTSH | |
| Immune signaling, Immune cell surface, Chromatin remodeling | Cl. 9 | | B cell receptor signaling | | |
| | | * | ERK/MAPK signaling | | |
| | | * | Ephrin signaling | | |
| Immune signaling, Transcription factors, Nuclear rec. trans | Cl. 12 | | Sirtuin signaling pathway | | |
| | | * | Cancer drug resist. by efflux | | |
| | | * | PXR/RXR | | |
| Secreted & ECM | Cl. 28 | * | Inhibition of MMPS | MMP2 | |
| | | * | Leukocyte extravasation | | |

FIG. 51B (Cont.)

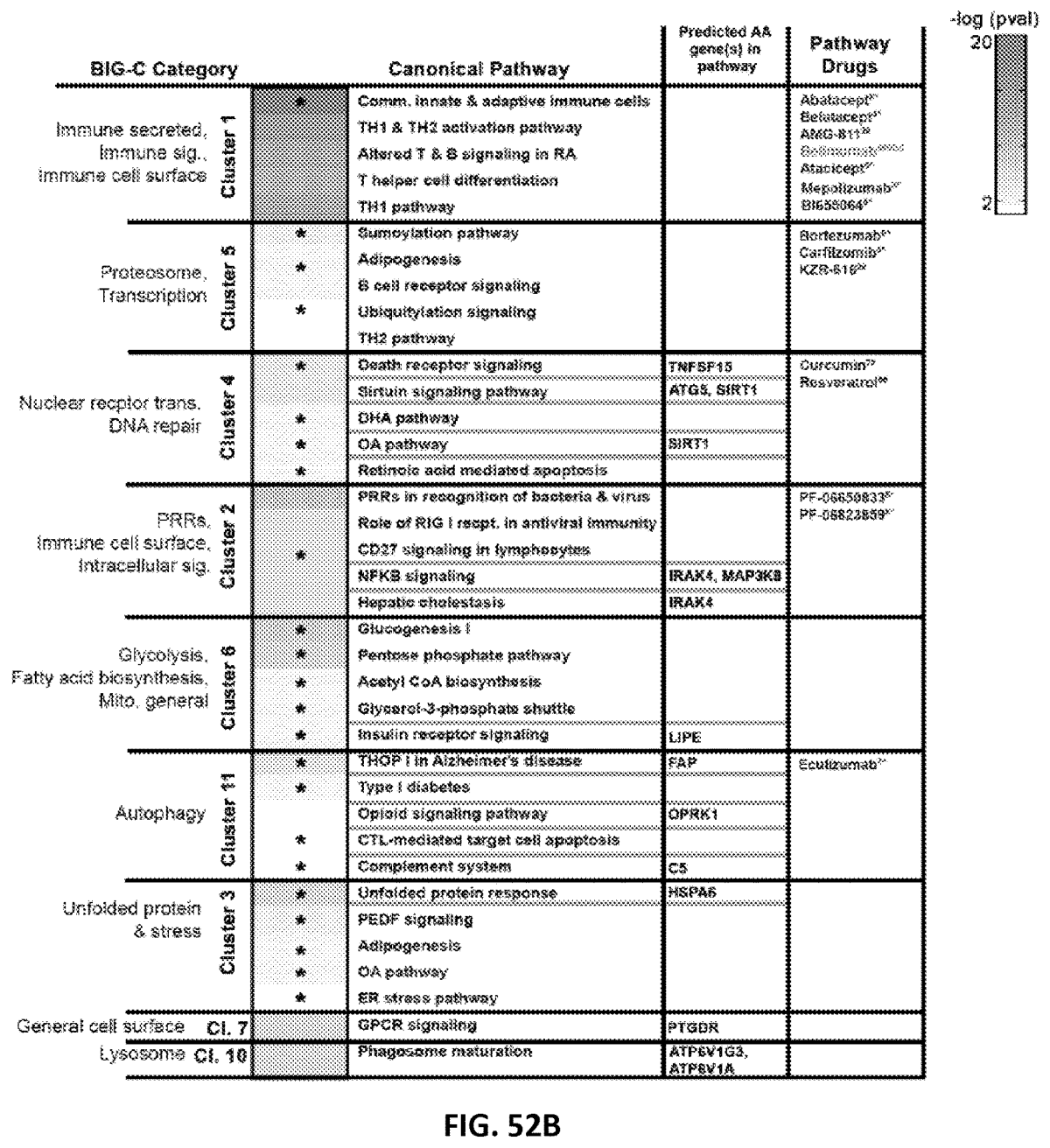

| BIG-C Category | | | Canonical Pathway | Predicted AA gene(s) in pathway | Pathway Drugs |
|---|---|---|---|---|---|
| Immune secreted, Immune sig., immune cell surface | Cluster 1 | * | Comm. innate & adaptive immune cells | | Abatacept<br>Belatacept<br>AMG-811<br>[illegible]<br>Atacicept<br>Mepolizumab<br>BI655064 |
| | | | TH1 & TH2 activation pathway | | |
| | | | Altered T & B signaling in RA | | |
| | | | T helper cell differentiation | | |
| | | | TH1 pathway | | |
| Proteosome, Transcription | Cluster 5 | * | Sumoylation pathway | | Bortezumab<br>Carfilzomib<br>KZR-616 |
| | | * | Adipogenesis | | |
| | | | B cell receptor signaling | | |
| | | * | Ubiquitylation signaling | | |
| | | | TH2 pathway | | |
| Nuclear recptor trans. DNA repair | Cluster 4 | * | Death receptor signaling | TNFSF15 | Curcumin<br>Resveratrol |
| | | | Sirtuin signaling pathway | ATG5, SIRT1 | |
| | | * | DHA pathway | | |
| | | * | OA pathway | SIRT1 | |
| | | * | Retinoic acid mediated apoptosis | | |
| PRRs, Immune cell surface, Intracellular sig. | Cluster 2 | | PRRs in recognition of bacteria & virus | | PF-06650833<br>PF-06823859 |
| | | | Role of RIG I recept. in antiviral immunity | | |
| | | * | CD27 signaling in lymphocytes | | |
| | | | NFKB signaling | IRAK4, MAP3K8 | |
| | | | Hepatic cholestasis | IRAK4 | |
| Glycolysis, Fatty acid biosynthesis, Mito. general | Cluster 6 | * | Gluconeogenesis I | | |
| | | * | Pentose phosphate pathway | | |
| | | * | Acetyl CoA biosynthesis | | |
| | | * | Glycerol-3-phosphate shuttle | | |
| | | * | Insulin receptor signaling | LIPE | |
| Autophagy | Cluster 11 | * | THOP I in Alzheimer's disease | FAP | Eculizumab |
| | | * | Type I diabetes | | |
| | | | Opioid signaling pathway | OPRK1 | |
| | | * | CTL-mediated target cell apoptosis | | |
| | | * | Complement system | C5 | |
| Unfolded protein & stress | Cluster 3 | * | Unfolded protein response | HSPA5 | |
| | | * | PEDF signaling | | |
| | | * | Adipogenesis | | |
| | | * | OA pathway | | |
| | | * | ER stress pathway | | |
| General cell surface | Cl. 7 | | GPCR signaling | PTGDR | |
| Lysosome | Cl. 10 | | Phagosome maturation | ATP6V1G3, ATP6V1A | |

-log (pval): 20 – 2

FIG. 52B

| BIG-C Category | | | Canonical pathway | Predicted shared genes(s) in pathway | Pathway Drugs |
|---|---|---|---|---|---|
| IFN stimulated genes, Immune secreted, PRRs, Intracellular signaling | Cluster 1 | | Activation of IRF by cytosolic PRRS | IRF7 | Rontalizumab[4^] Ruxolitinib[5^] PF-06823859[5^] |
| | | * | Interferon signaling | IFI6, IFI35, MX1, OAS1 | |
| | | | Role of lipids in pathol. infulenza | | |
| | | | T cell exhaustion | NFATC3 | |
| | | | Role of RIG I recpt. in antiviral immunity | IRF7 | |
| Immune secreted, Integrin, Immune signaling Intracellular signaling | Cluster 3 | * | IL-2 signaling | HRAS | Sorafenib[-3#] BOS-161721[7^] Dupilumab[4#] |
| | | * | Telomerase signaling | HRAS, ETS1 | |
| | | * | Endometrial cancer signaling | HRAS | |
| | | * | Role of JAK1 & JAK3 in cytokine sinaling | HRAS | |
| | | * | GM-CSF signaling | HRAS | |
| IFN stimulated genes, PRRs, mRNA splicing, mRNA processing, | Cluster 5 | | Role of RIG I recpt. in antiviral immunity | | Palbociclib[4#] |
| | | | Activation of IRF by cytosolic PRRS | | |
| | | | Role of PRRs in recog. bacteria & virus | | |
| | | * | Tight junction signaling | PPP2RB1 | |
| | | * | CDK5 signaling | PPP2RB1 | |
| Immune secreted, Immune signaling, Transcription factors, Intracellular signaling | Cluster 10 | * | Role of cytokines in comm. immune cells | | Vorinostat[5#] Tocilizumab[8#] AMG 811[3^] |
| | | | TH1 & TH2 activation pathway | IL6R | |
| | | | T helper cell differentiation | IL6R | |
| | | | Role of MC, FB and ECs in RA | IL6R | |
| | | | Cardiac hypertrophy signaling | IL6R | |
| miRNA processing, Pro-cell cycle, Gen. transcription, DNA rapair | Cluster 18 | * | GADD45 Signaling | BRCA1 | Palbociclib[4#] |
| | | * | DNA damage induced 14-3-3 signaling | BRCA1 | |
| | | | Sirtuin signaling pathway | | |
| | | | Hereditary breast cancer signling | BRCA1 | |
| | | * | Cell cycle DNA darnage G2/S chk. point | BRCA1 | |

-log (pval)
35
2

FIG. 53B

| | | | | | |
|---|---|---|---|---|---|
| Immune secreted, Immune cell surface, Intracellular signaling | Cluster 6 | * | TREM1 signaling | | BI 655064[5^] Ustekinumab[10#] |
| | | | TH1 & TH2 activation pathway | IL12RB2 | |
| | | | TH1 activation pathway | IL12RB2 | |
| | | | IL12 signaling in MC | IL12RB2 | |
| | | | TH2 pathway | IL12RB2 | |
| IFN stimulated genes, Nuclear rec. trans., Chromatin remodeling. Intracellular signaling | Cluster 2 | * | RAR activation | SMARCE1 | Everolimus[3#] |
| | | | Glucocorticoid signaling | SMARCE1 | |
| | | | AMK signaling | SMARCE1, RPTOR | |
| | | | Hereditary breast cancer signling | SMARCE1 | |
| | | | **Role of BRCA1 in DNA damage resp.** | SMARCE1 | |
| Proteosome, PRRs, Nuclear rec. trans., Pro-cell cycle | Cluster 7 | | NFKB signaling<br>TLR signaling<br>Altered T & B signaling in RA<br>**Role of MC, FB and ECs in RA**<br>**Role of PRRs in recog. bacteria & virus** | | Hydroxychloroquine[5#SOC] |
| Immune signaling, Immune cell surface | Cl. 23 | | T cell receptor signaling | LAT | Theralizumab[4^] |
| | | * | Role of NFAT in immune response | LAT | |
| | | | CD28 signaling in TH cells | LAT | |
| Nuclear rec. trans., Secreted & ECM | Cl. 19 | | Cardiac hypertrophy signaling | | |
| | | * | FGF signaling | | |
| | | * | Regulation of EMT | | |
| Integrin, ER | Cl. 12 | * | Coagulation system | PLAU | Natalizumab[4#] |
| | | * | Caveolar mediated endocytosis sig. | ITGAX | |
| | | * | TREM1 signaling | ITGAX | |
| Endocytosis | 22 | * | Caveolar mediated endocytosis sig. | COPA | |
| Pro-apoptosis | 21 | * | ER signaling | | |

FIG. 53B (Cont.)

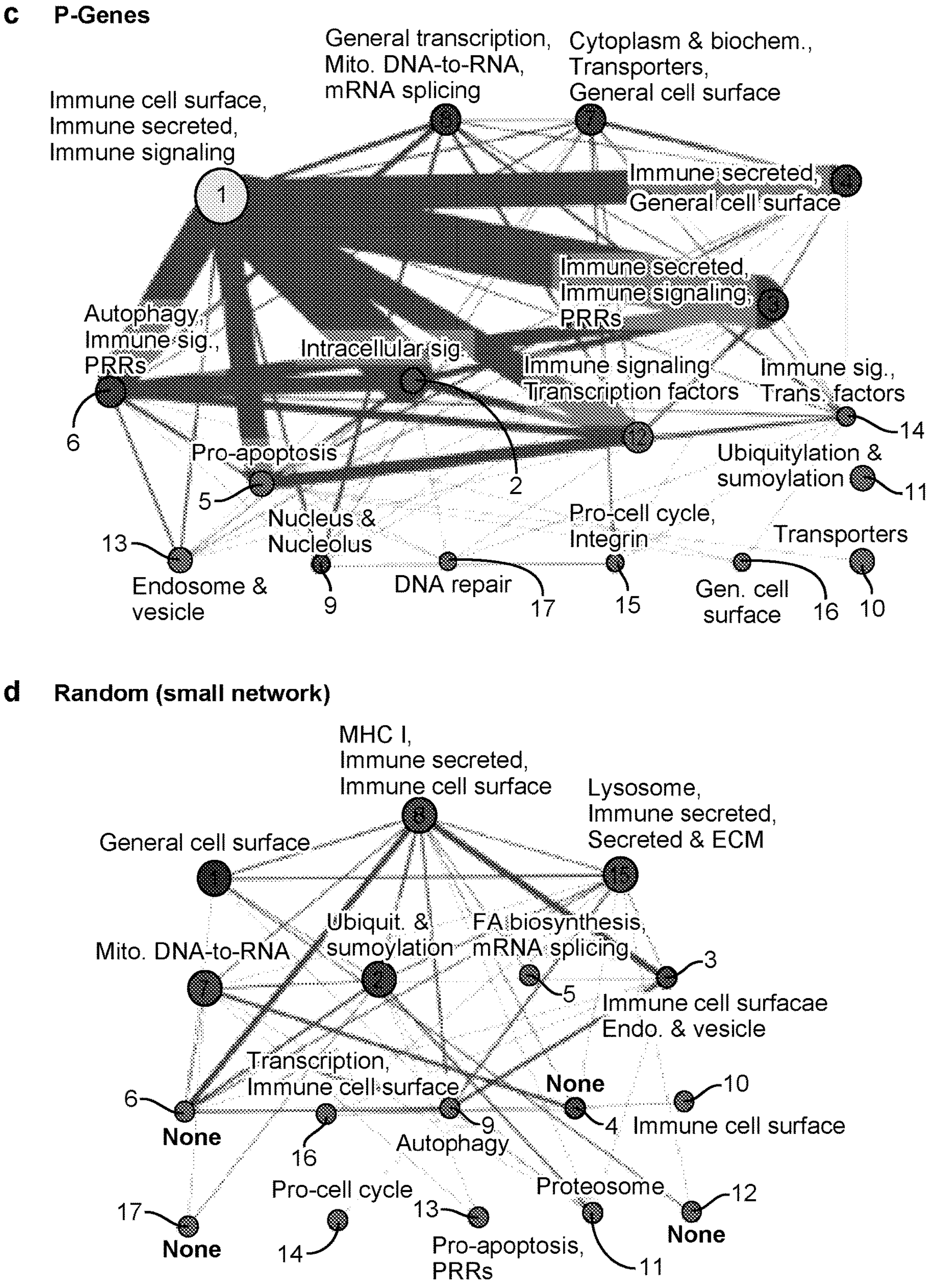
FIG. 57 (Cont. 1)

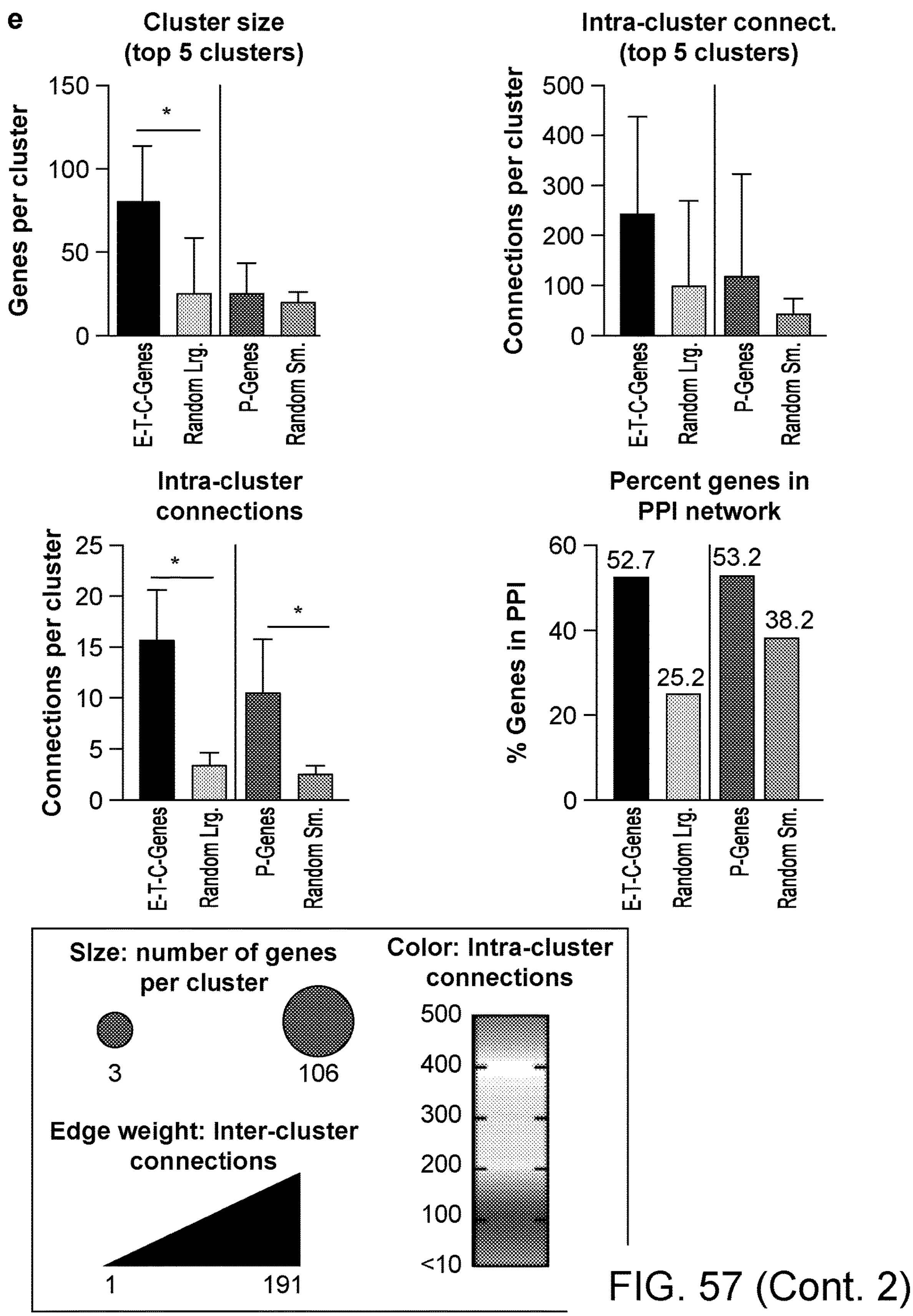
FIG. 57 (Cont. 2)

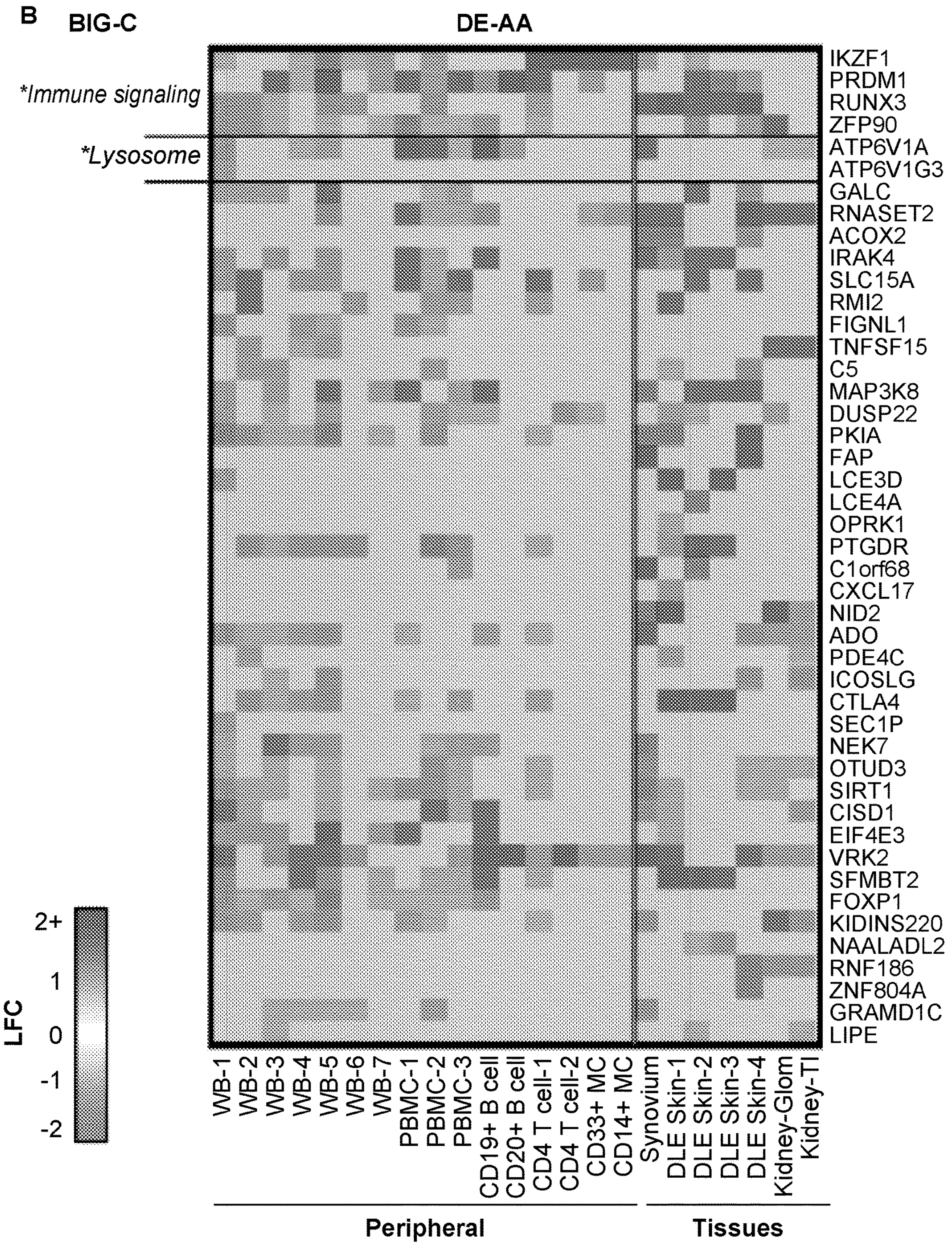
FIG. 58 (Cont. 1)

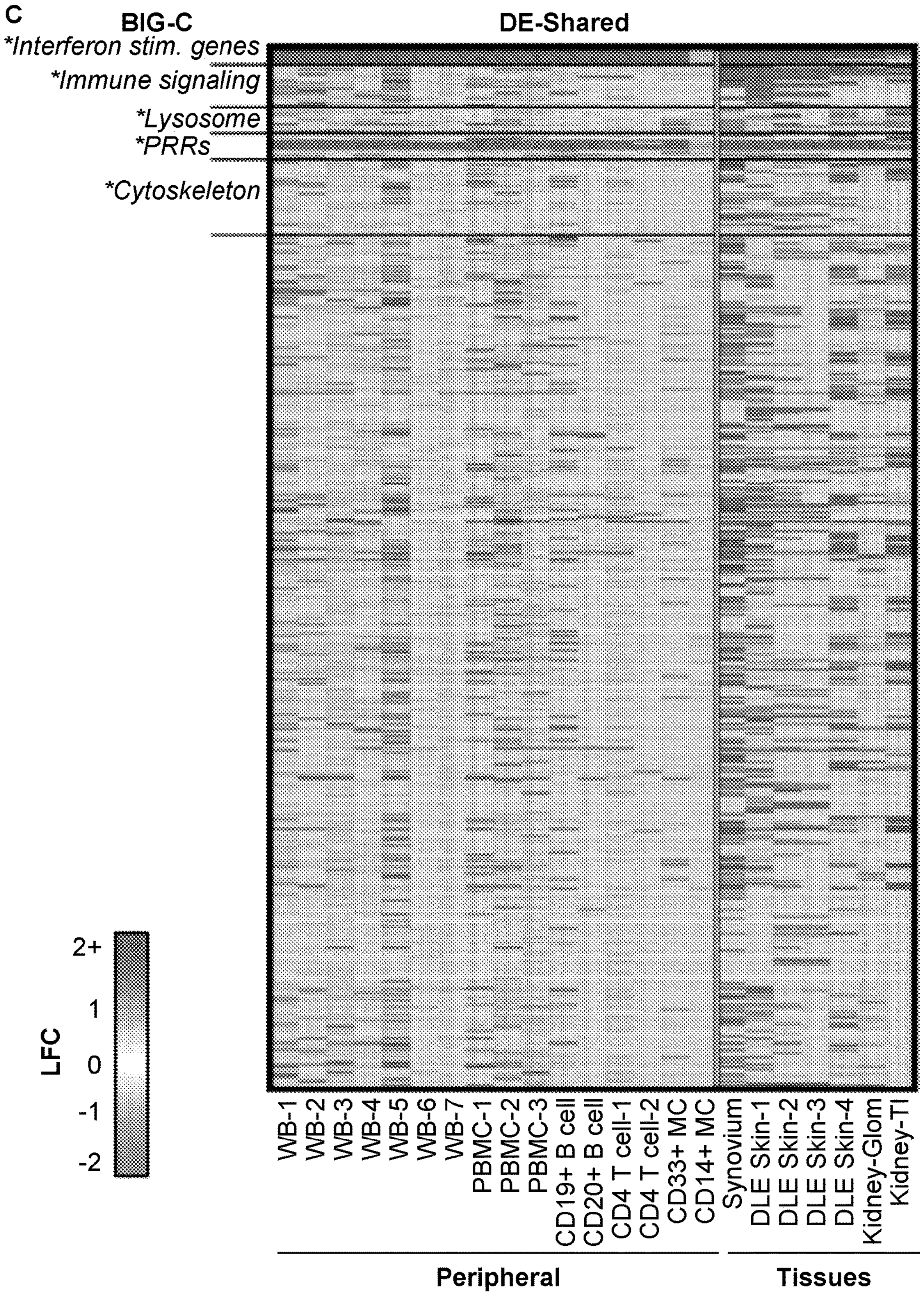
FIG. 58 (Cont. 2)

EA Pathways

| BIG-C Category | Cluster | Canonical pathway | Predicted EA genes(s) in pathway | Pathway Drugs |
|---|---|---|---|---|
| Nuclear rec. trans., PRRs, Gen. transcription, Intracellular sig. | Cluster 3 | Role of MC, FB and ECs in RA | PLCB1, PLCB2 | Dapirolizumab[8^] Adalimumab[4#] |
| | | Hepatic cholestasis GPCR signaling | PLCB1, PLCB2, CRHR1 | |
| | | NFKB signaling | | |
| | | Activation of IRF by cytosolic PRRs | IFIH1, ZBP1 | |
| MHC class II, Immune secreted, PRRs, WNT signaling. Immune cell surface | Cluster 1 | Activation of IRF by cytosolic PRRs | | PF-06823859[5^] BMS-986165[7^] Ruxolitinib[5#] Rontalizumab[4^] |
| | | T cell exhaustion | TYK2 | |
| | | Role of lipids in pathol. infulenza | | |
| | | Role of RIG I recpt. in antiviral immunity | TRIM25 | |
| | * | Role of WNT/GSK3B in pathol. influenza | | |
| Immune signaling, Integrin, Immune cell surface | Cluster 5 * | TEC kinase signaling | TEC, FCGR1B | Evobrutinib[8^] SM201[3^] Abatacept[8#] Ustekinumab[10#] Dupilumab[4#] Lebrikizumab[7^] Fostamatnib[7^] |
| | | T helper cell differentiation | IL12RB1, FCGR1B | |
| | | Altered T & B signaling in RA | FCGR1B | |
| | * | Cross talk between DCs & NK cells | | |
| | | IL12 signaling in MC | ALOX15, IL12RB1 | |
| Immune signaling. Immune secreted, Immune cell surface, Intracellular signaling | Cluster 4 * | TH1 & TH2 activation pathway TH1 activation pathway T cell receptor signaling PD1, PD1L cancer immunotherapy pathway CD28 signaling in TH cells | | AMG-811[8^] BOS-161721[7^] Theralizumab[4^] |
| PRRs, Immune secreted, Immune cell surface, Intracellular signaling, Pro-apoptosis | Cluster 7 | NFKB signaling | TNIP1, IL1R1 | Bi655064[5^] |
| | | Role of osteoblasts, osteoclasts & chrondrocytes in RA | | |
| | | TLR signaling | IL1R1 | |
| | | Role of MC, FB and ECs in RA | IL1R1 | |
| | | IL6 signaling | IL1R1 | |

-log (pval) 25 2

FIG. 59B

| | | | | | |
|---|---|---|---|---|---|
| Immune secreted, Immune cell surface, Integrin, Lysosome | Cluster 2 | | Glucocorticoid signaling | | Siponimod[+7] |
| | | | Hepatic fibrosis | | |
| | | * | IL17 signaling | | |
| | | * | Angiotensin signaling | | |
| | | * | Agranulocyte adhesion & diapedesis | CXCR1, CXCL1 | |
| Immune secreted, PRRs, Pro-apoptosis, Intracellular signaling | Cluster 19 | | Cardiac hypertrophy signaling | CAMK2D | Vorinostat[6#] Everolimus[3#] |
| | | | Role of MC, FB and ECs in RA | IL1R2 | |
| | | | NFKB signaling | MAP4K4, IL1R2 | |
| | | | Opioid signaling pathway | CAMK2D | |
| | | * | Endocannabinoid cancer inhibition pathway | | |
| miRNA processing, DNA Repair | Cl. 13 | * | MODY signaling | | |
| | | * | TGF-B signaling | | |
| | | * | AMK signaling | | |
| ,DNA Repair, Pro-apoptosis, Chromatin remodeling | Cl. 26 | | P53 Signaling | | |
| | | | Herediatry breast cancer signaling | | |
| | | * | Ovarian cancer signaling | | |
| Immune secreted, MHC class II, Lysosome | Cl. 11 | * | Autophagy | CTSH | |
| | | * | Leukotriene biosynthesis | LTA4H | |
| | | | Phagosome maturation | CTSH | |
| Immune signaling, Immune cell surface, Chromatin remodeling | Cl. 9 | | B cell receptor signaling | | |
| | | * | ERK/MAPK signaling | | |
| | | * | Ephrin signaling | | |
| Immune signaling, Transcription factors, Nuclear rec. trans. | Cl. 12 | | Sirtuin signaling pathway | | |
| | | * | Cancer drug resist. by efflux | | |
| | | * | PXR/RXR | | |
| Secreted & ECM | Cl. 28 | * | Inhibition of MMPS | MMP2 | |
| | | * | Leukocyte extravasation | | |

FIG. 59B (Cont.)

Shared Pathways

| BIG-C Category | Cluster | | Canonical pathway | Predicted shared genes(s) in pathway | Pathway Drugs |
|---|---|---|---|---|---|
| IFN stimulated genes, Immune secreted, PRRs, Intracellular signaling | Cluster 1 | | Activation of IRF by cytosolic PRRs | *IRF7* | Rontalizumab[4^] Ruxolitinib[5^] PF-06823859[5^] |
| | | * | Interferon signaling | *IFI6, IFI35, MX1, OAS1* | |
| | | | Role of lipids in pathol. infulenza | | |
| | | | T cell exhaustion | *NFATC3,* | |
| | | | Role of RIG I recpt. in antiviral immunity | *IFR7* | |
| Immune secreted, Integrin, Immune signaling Intracellular signaling | Cluster 3 | * | IL-2 signaling | *HRAS* | Sorafenib[-3#] BOS-161721[7^] Dupilumab[4#] |
| | | * | Telomerase signaling | *HRAS, ETS1* | |
| | | * | Endometrial cancer signaling | *HRAS* | |
| | | * | Role of JAK1 & JAK3 in cytokine sinaling | *HRAS* | |
| | | * | GM-CSF signaling | *HRAS, ETS1* | |
| IFN stimulated genes PRRs, mRNA splicing, mRNA processing | Cluster 5 | | Role of RIG I recpt. in antiviral immunity Activation of IRF by cytosolic PRRs Role of PRRs in recog. bacteria & virus | | Palbociclib[4#] |
| | | * | Tight junction signaling | | |
| | | * | CDK5 signaling | | |
| Immune secreted, Immune signaling, Transcription factors, Intracellular signaling | Cluster 10 | * | Role of cytokines in comm. immune cells | | Vorinostat[5#] Tocilizumab[8#] AMG 811[3^] |
| | | | TH1 & TH2 activation pathway | *IL6R* | |
| | | | T helper cell differentiation | *IL6R* | |
| | | | Role of MC, FB and ECs in RA | *IL6R* | |
| | | | Cardiac hypertrophy signaling | *IL6R* | |
| miRNA processing, Pro-cell cycle, Gen. transcription, DNA repair | Cluster 18 | * | GADD45 Signaling | *BRCA1* | Palbociclib[4#] |
| | | * | DNA damage induced 14-3-3 signaling | *BRCA1* | |
| | | | Sirtuin signaling pathway | *NDGR1* | |
| | | | Hereditary breast cancer signling | *BRCA1* | |
| | | * | Cell cycle DNA damage G2/S chk. point | *BRCA1* | |

-log (pval): 35 – 2

FIG. 61B

| | | | | | |
|---|---|---|---|---|---|
| Immune secreted, Immune cell surface, Intracellular signaling | Cluster 6 | * | TREM1 signaling | *CD40* | BI 655064$^{5\wedge}$ Ustekinumab$^{10\#}$ |
| | | | TH1 & TH2 activation pathway | *CD40, IL12RB2* | |
| | | | TH1 activation pathway | *CD40, IL12RB2* | |
| | | | IL12 signaling in MC | *CD40, IL12RB2* | |
| | | | TH2 pathway | *CD40, IL12RB2* | |
| IFN stimulated genes, Nuclear rec. trans., Chromatin remodeling. Intracellular signaling | Cluster 2 | * | RAR activation | *SMARCE1* | Everolimus$^{3\#}$ |
| | | | Glucocorticoid signaling | *SMARCE1* | |
| | | | AMK signaling | *SMARCE1, RPTOR* | |
| | | | Hereditary breast cancer signling | *SMARCE1* | |
| | | | Role of BRCA1 in DNA damage resp. | *SMARCE1* | |
| Proteosome, PRRs, Nuclear rec. trans., Pro-cell cycle | Cluster 7 | | NFKB signaling<br>TLR signaling<br>Altered T & B signaling in RA<br>Role of MC, FB and ECs in RA<br>Role of PRRs in recog. bacteria & virus | | Hydroxychloroquine$^{5\#SOC}$ |
| Immune signaling, Immune cell surface | Cl. 23 | | T cell receptor signaling | *LAT* | Theralizumab$^{4\wedge}$ |
| | | * | Role of NFAT in immune response | *LAT* | |
| | | | CD28 signaling in TH cells | *LAT* | |
| Nuclear rec. trans., Secreted & ECM | Cl. 19 | <br>*<br>* | Cardiac hypertrophy signaling<br>FGF signaling<br>Regulation of EMT | | |
| Integrin, ER | Cl. 12 | * | Coagulation system | *PLAU* | Natalizumab$^{4\#}$ |
| | | * | Caveolar mediated endocytosis sig. | *ITGAX* | |
| | | * | TREM1 signaling | *ITGAX* | |
| Endocytosis | 22 | * | Caveolar mediated endocytosis sig. | *COPA* | |
| Pro-apoptosis | 21 | * | ER signaling | | |

FIG. 61B (Cont.)

Cluster 4: Lysosome, mRNA processing, Pro-apoptosis, Pro-cell cycle, Golgi
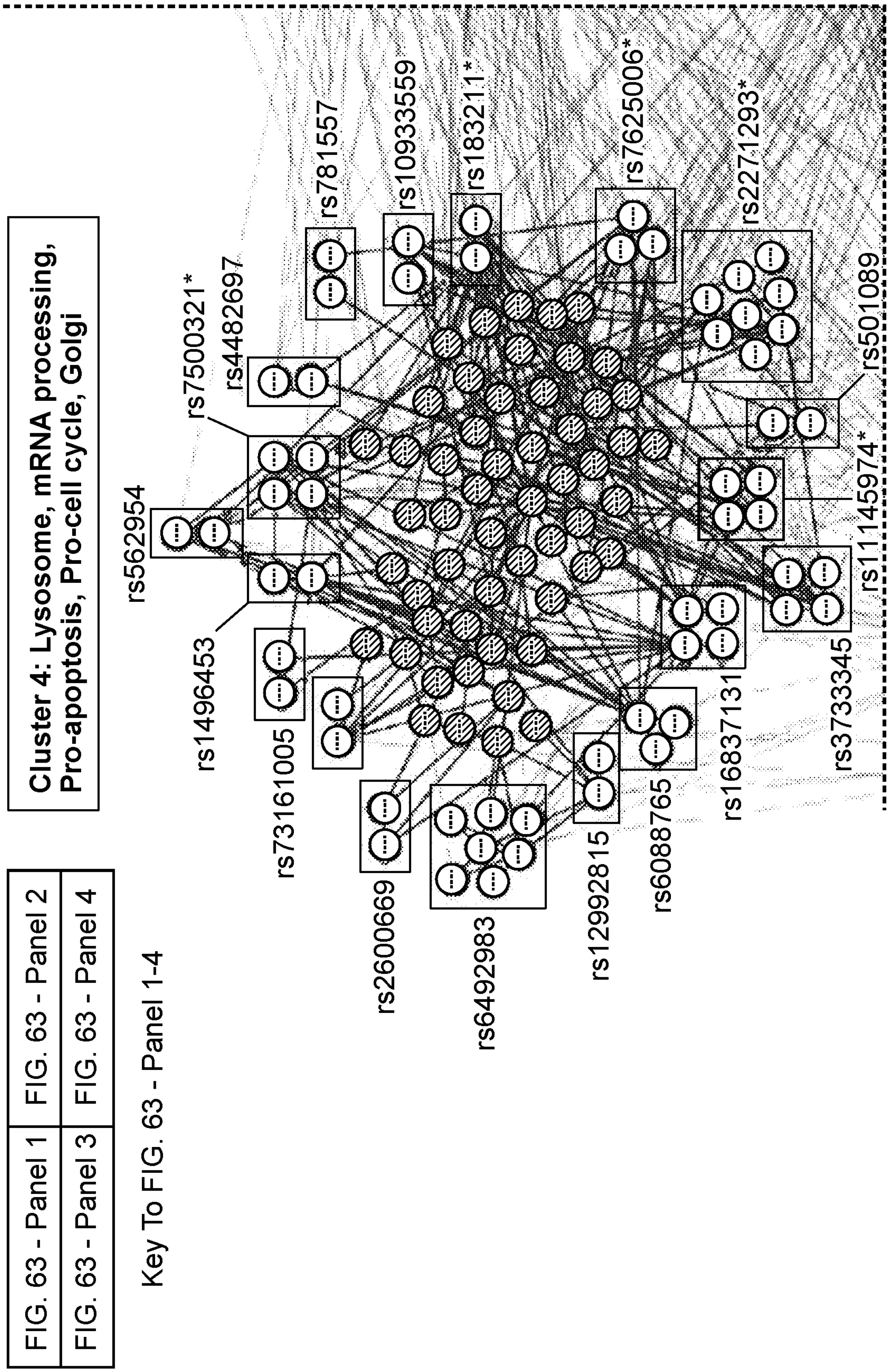
FIG. 63 - Panel 1
| | |
|---|---|
| FIG. 63 - Panel 1 | FIG. 63 - Panel 2 |
| FIG. 63 - Panel 3 | FIG. 63 - Panel 4 |
Key To FIG. 63 - Panel 1-4

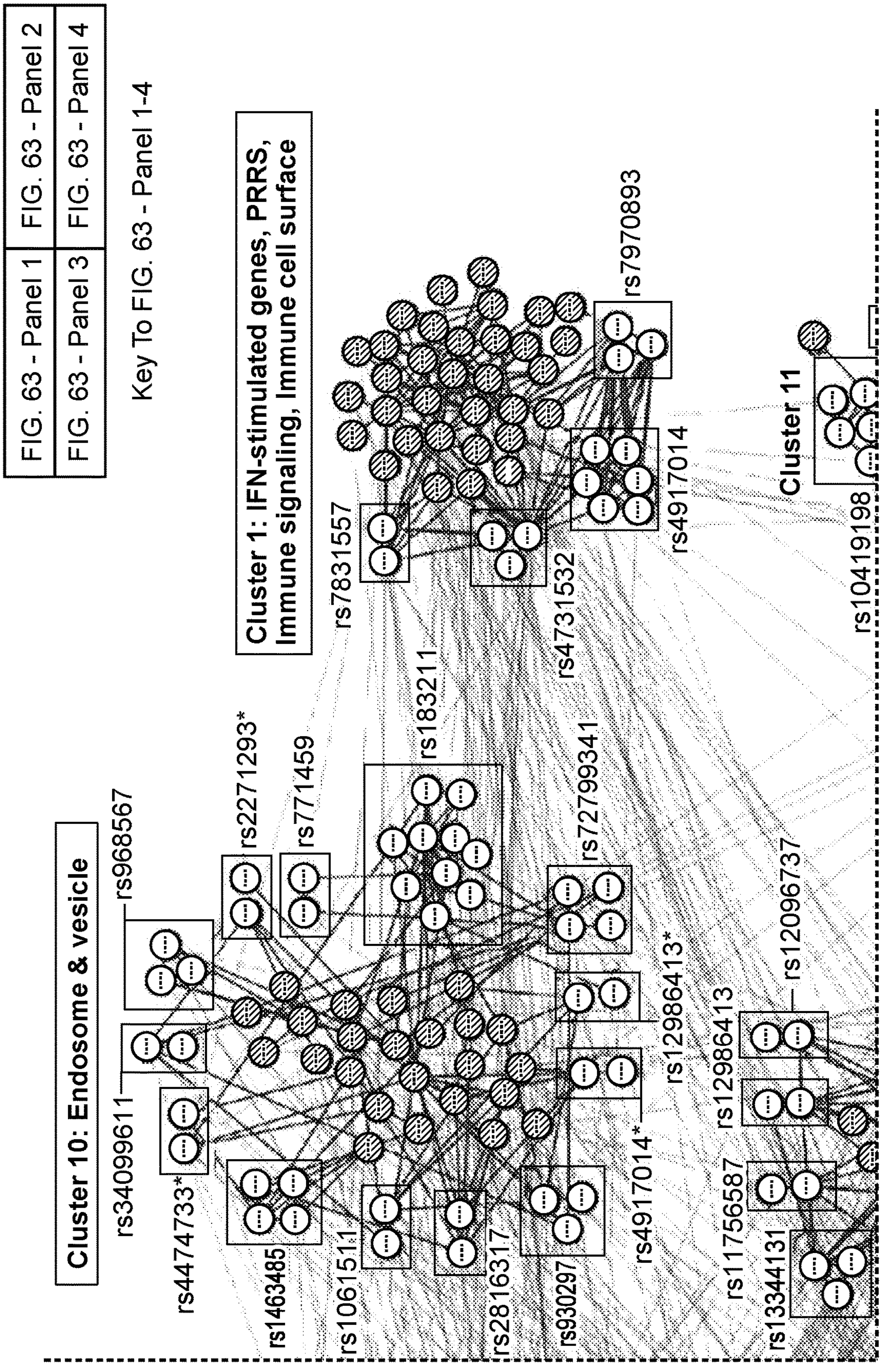
FIG. 63 - Panel 2

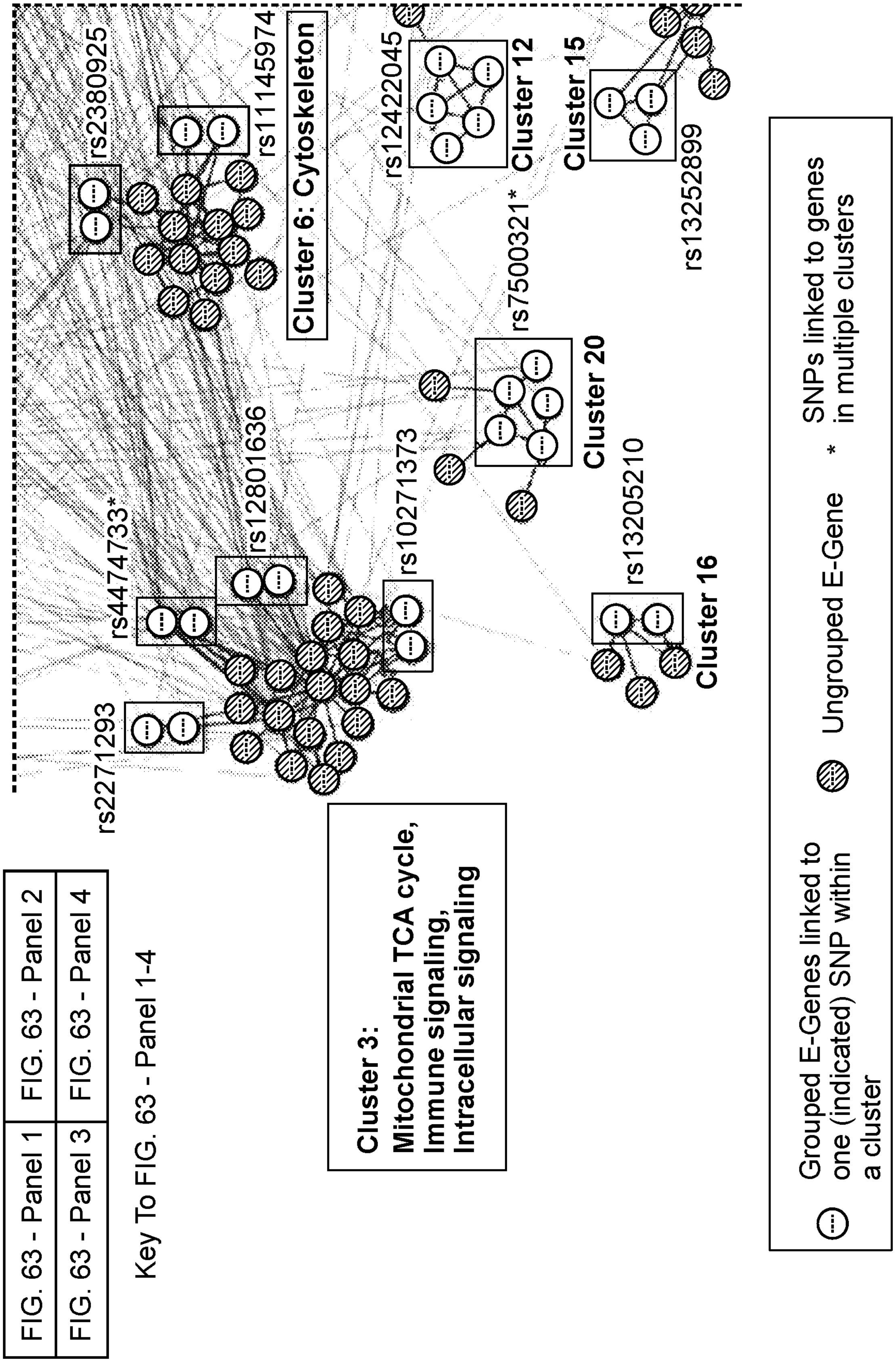
FIG. 63 - Panel 3

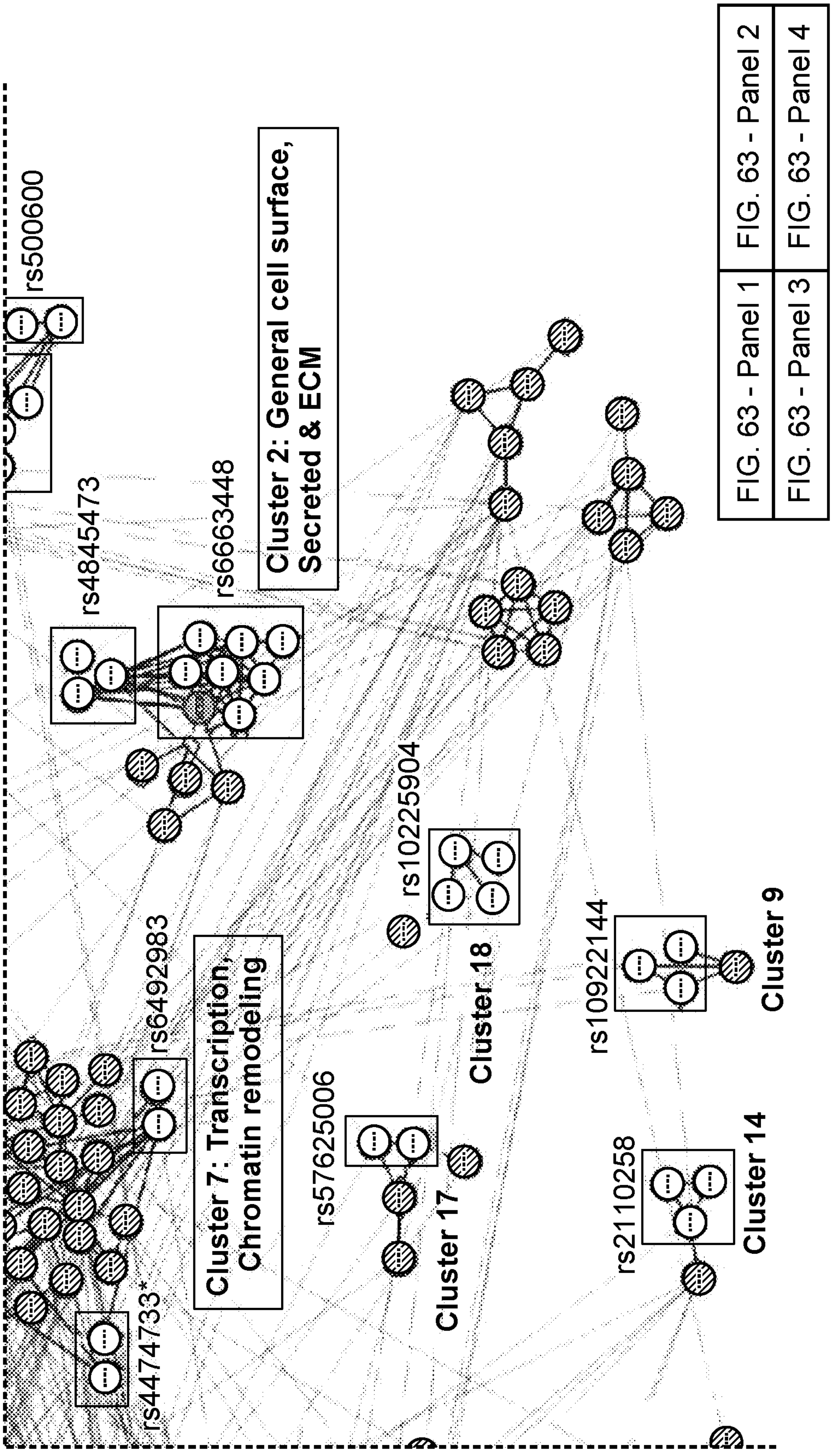
| | |
|---|---|
| FIG. 63 - Panel 1 | FIG. 63 - Panel 2 |
| FIG. 63 - Panel 3 | FIG. 63 - Panel 4 |
Key To FIG. 63 - Panel 1-4
FIG. 63 - Panel 4

EA-motivated pathways

| | BIG-C | I-Scope | | Canonical pathway |
|---|---|---|---|---|
| Cluster 6 | ***Pro-apoptosis***<br>Chromatin remodeling<br>Immune screted<br>Immune signaling<br>Intracellular signaling | ***Anergic or Act. T***<br>Myeloid | | Cardiac hypertrophy signaling<br>NFKB signaling<br>PI3K/AKT signaling<br>IL10 signaling<br>Hepatic fibrosis |
| Cluster 11 | ***Nuclear rec. trans.***<br>Immune screted<br>Immune signaling<br>Intracellular signaling<br>Transcription factors | ***T-reg***<br>Activated T<br>NK or T cells | | TH1/TH2 activation pathway<br>TH2 pathway<br>IL12 signaling & production in MC<br>TH1 pathway<br>T cell exhaustion |
| Cluster 8 | ***Immune cell surface***<br>Immune screted<br>Immune signaling<br>Intracellular signaling<br>Integrin signaling | ***T, B & myeloid***<br>T & B cells<br>T cells<br>Myeloid<br>Monocytes | | Role of JAK1/3 in cytokine signaling<br>SLE in B cell signaling pathway<br>IL15 signaling<br>STAT3 signaling<br>Cardiac hypertrophy signaling |
| Cluster 5 | ***Immune signaling***<br>PRRs<br>Immune cell surface<br>Nuclear rec. trans.<br>Pro cell cycle | ***Granulocytes***<br>T, B & myeloid<br>B cells & myeloid<br>NK cells<br>Monocytes | | ErbB2 signaling pathway<br>ICOS-ICOSL-signaling<br>FcεR signaling<br>CD28 signaling in T cells<br>ErbB2-ErbB3 signaling pathway |
| Cluster 4 | ***Immune cell surface***<br>Immune secreted<br>Immune signaling<br>Integrin signaling<br>General cell surface | ***Monocytes***<br>Granulocytes<br>T, B & myeloid | | GPCR signaling<br>Apelin endothelial signaling pathway<br>CCR5 signaling in MCs<br>P2Y purigenic receptor signaling<br>IL8 signaling |
| Cluster 23 | ***MicroRNA processing***<br>Immune secreted<br>Nuclear rec. trans.<br>DNA replication<br>Intracellular signaling | ***Myeloid*** | | Molecular mechanisms of cancer<br>p53 signaling pathway<br>PI3K/AKT signaling<br>Hepatic fibrosis<br>CHK proteins in cell cycle regulation |
| Cluster 3 | ***Interferon stim. genes***<br>Immune secreted<br>PRRs<br>mRNA splicing<br>Proteasome | ***T & B cells*** | | SLE in B cell signaling pathway<br>Altered T & B cell signaling in RA<br>EIF2 signaling<br>PRRs in the recognition of bacteria & viruses<br>Cardiac hypertrophy signaling |
| Cl. 9 | ***PRRs***<br>Immune secreted<br>Integrin signaling | ***B cells/ pDCs***<br>B cells & myeloid<br>Monocytes | | NFKB signaling<br>TLR signaling<br>Role of MC, FB and EC in RA |
| Cl. 2 | ***mRNA processing***<br>Immune secreted | | | Role of lipid rafts in pathogenesis of flu<br>Activation of IRFs by cytoplasmic PRRs<br>Role of RIG-I recept. in antiviral immunity |
| Cl. 1 | ***Ubiquit. & sumoyl.***<br>Immune secreted | | | Clathrin-mediated endocytosis<br>Protein ubiquitylation pathway<br>Iron homeostasis |
| 21 | ***Pro-apoptosis***<br>PRRs | ***B cells & myeloid*** | | TWEAK signaling<br>TLR signaling |
| 12 | ***Ubiquit. & sumoyl.***<br>General transcription | ***T cells & myeloid*** | | Nuclear excision repair pathway<br>NER pathway |
| 33 | ***MHC class II***<br>Golgi | ***APCs*** | | GABA receptor signaling<br>MIF mediated glucocorticoid rec. regulation |
| 24 | ***OXPHOS*** | | | Mitochondrial dysfunction |
| 10 | ***Immune secreted*** | ***Myeloid*** | | Histamine degradation |
| 22 | ***Cytoplasm & Biochem.*** | | | Guanosine nucleotide deg. III |
| 7 | ***General cell surface*** | | | Glucocorticoid receptor signaling |

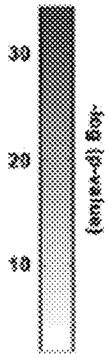

FIG. 70B

AS-motivated pathways

| | BIG-C | I-Scope | Canonical pathway |
|---|---|---|---|
| Cluster 4 | ***Chrom. remodeling***<br>DNA replication<br>mRNA splicing<br>Immune signaling<br>Immune secreted | ***Neutrophils*** | Role of BRCA1 in DNA damage response<br>Hereditary breast cancer signaling<br>EIF2 signaling<br>ATM signaling<br>NER pathway |
| Cluster 6 | ***WNT signaling***<br>Endocytosis<br>Lysosome<br>Integrin signaling<br>General cell surface<br>Immune secreted | ***Monocytes*** | SLE in B cell signaling pathway<br>Cardiac hypertrophy signaling<br>Molecular mechanisms of cancer<br>Synaptogenesis signaling pathway<br>PRRs in the recog. of bac. & viruses<br>HMGB1 signaling pathway |
| Cluster 3 | ***Secreted & ECM***<br>Intracellular signaling | | Role of Tissue Factor (TF) in cancer<br>GDNF family ligand-receptor interaction<br>Chemokine signaling<br>Ovarian cancer signaling<br>Integrin signaling |
| Cluster 19 | ***Secreted & ECM***<br>Integrin signaling | | Inhibition of MMPs<br>HOTAIR regulatory pathway<br>Granulocyte adhesion & diapedesis<br>Hepatic fibrosis<br>Agranulocyte adhesion & diapedesis |
| Cluster 1 | ***Immune Secreted***<br>Integrin pathway<br>Lysosome<br>Immune cell surface<br>General cell surface | ***Monocytes***<br>B cells/pDCs | Granulocyte adhesion & diapedesis<br>Agranulocyte adhesion & diapedesis<br>Gαi signaling<br>cAMP signaling<br>GPCR signaling |
| Cluster 2 | ***Ubiquit. & sumoyl.***<br>Peroxisomes<br>Integrin signaling<br>Secreted & ECM<br>Immune secreted | ***Monocytes*** | LXR/RXR signaling<br>Protein ubiquitylation pathway<br>Atherosclerosis signaling pathway<br>Acute phase response signaling pathway<br>Hypoxia signaling in the CV system |
| Cl. 7 | ***Chrom. remodeling***<br>General transcription<br>Transcription factors | | Glucocorticoid receptor signaling<br>ER signaling pathway<br>Hereditary breast cancer signaling |
| Cl. 13 | ***RAS superfamily***<br>Integrin<br>Immune signaling | ***NK or T cells*** | FcεR signaling<br>SLE in B cell signaling pathway<br>TEC kinase signaling |
| Cl. 15 | ***Integrin signaling***<br>Endoplasmic reticulum<br>Transcription factors | | NOTCH signaling<br>Molecular mechanisms of cancer<br>Pancreatic adenocarcinoma signaling |
| Cl. 10 | ***OXPHOS***<br>PRRs<br>Nucleus & nucleolus | ***Monocytes***<br>T, B & myeloid | TLR signaling<br>NFKB signaling<br>iNOS signaling |
| Cl. 11 | ***Proteosome***<br>mRNA processing<br>UFPR, MHC class I | | Protein ubiquitylation pathway<br>Antigen presentation pathway<br>SLE signaling pathway |
| Cl. 25 | ***Chrom. remodeling*** | | Granzyme A signaling<br>iNOS signaling<br>IL4 signaling |
| 20 | ***Nuclear rec. trans.*** | | VDR/LXR activation signaling<br>Osteoarthritis signaling |
| 14 | ***WNT signaling***<br>Secreted & ECM | | LXR/RXR activation signaling<br>FXR/RXR activation signaling |

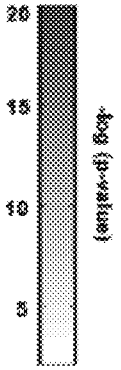

FIG. 70D

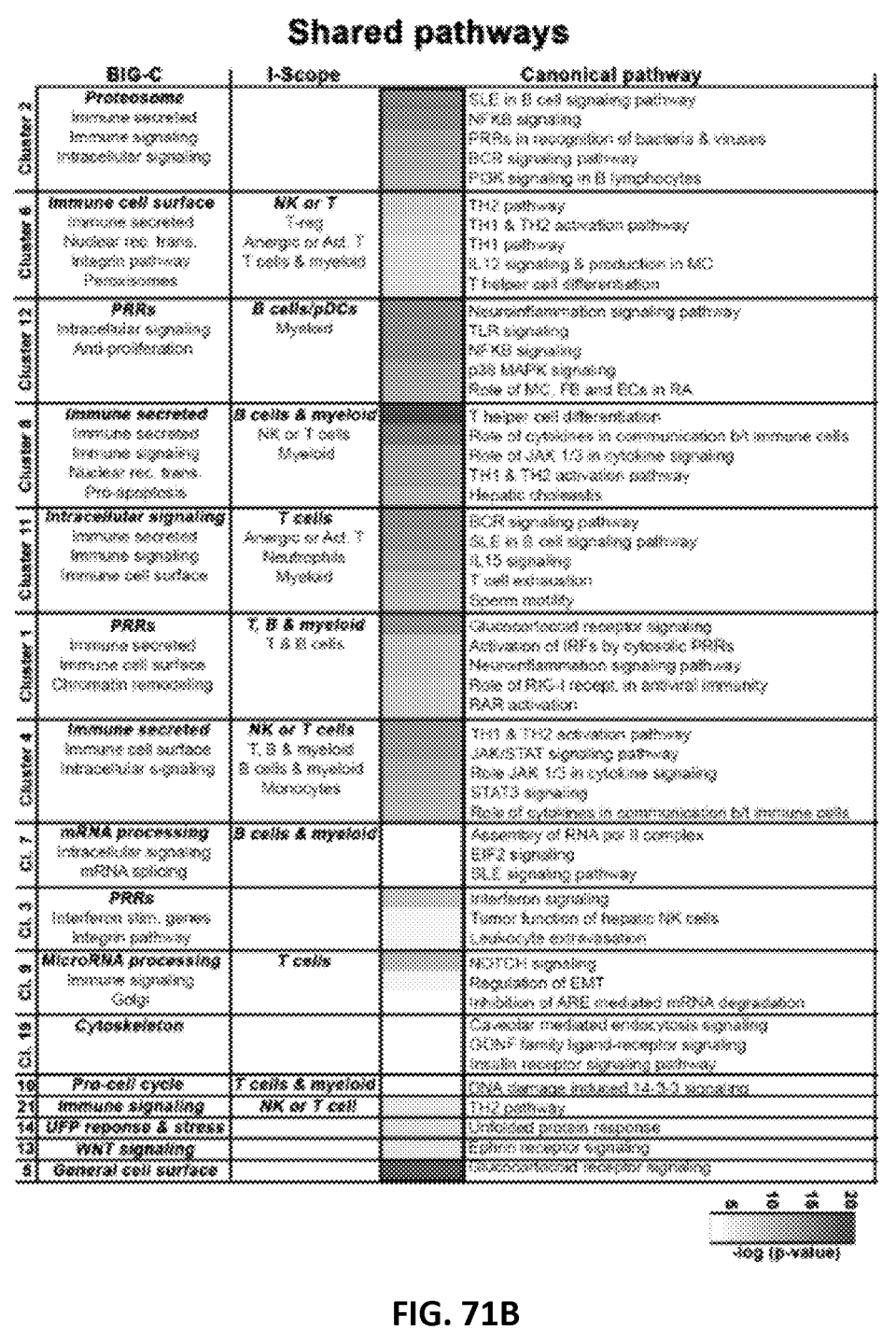

Shared pathways

| | BIG-C | I-Scope | | Canonical pathway |
|---|---|---|---|---|
| Cluster 2 | ***Proteosome***<br>Immune secreted<br>Immune signaling<br>Intracellular signaling | | | SLE in B cell signaling pathway<br>NFKB signaling<br>PRRs in recognition of bacteria & viruses<br>BCR signaling pathway<br>PI3K signaling in B lymphocytes |
| Cluster 6 | ***Immune cell surface***<br>Immune secreted<br>Nuclear rec. trans.<br>Integrin pathway<br>Peroxisomes | ***NK or T***<br>T-reg<br>Anergic or Act. T<br>T cells & myeloid | | TH2 pathway<br>TH1 & TH2 activation pathway<br>TH1 pathway<br>IL12 signaling & production in MO<br>T helper cell differentiation |
| Cluster 12 | ***PRRs***<br>Intracellular signaling<br>Anti-proliferation | ***B cells/pDCs***<br>Myeloid | | Neuroinflammation signaling pathway<br>TLR signaling<br>NFKB signaling<br>p38 MAPK signaling<br>Role of MC, FB and ECs in RA |
| Cluster 8 | ***Immune secreted***<br>Immune secreted<br>Immune signaling<br>Nuclear rec. trans.<br>Pro-apoptosis | ***B cells & myeloid***<br>NK or T cells<br>Myeloid | | T helper cell differentiation<br>Role of cytokines in communication b/t immune cells<br>Role of JAK 1/3 in cytokine signaling<br>TH1 & TH2 activation pathway<br>Hepatic cholestasis |
| Cluster 11 | ***Intracellular signaling***<br>Immune secreted<br>Immune signaling<br>Immune cell surface | ***T cells***<br>Anergic or Act. T<br>Neutrophils<br>Myeloid | | BCR signaling pathway<br>SLE in B cell signaling pathway<br>IL15 signaling<br>T cell exhaustion<br>Sperm motility |
| Cluster 1 | ***PRRs***<br>Immune secreted<br>Immune cell surface<br>Chromatin remodeling | ***T, B & myeloid***<br>T & B cells | | Glucocorticoid receptor signaling<br>Activation of IRFs by cytosolic PRRs<br>Neuroinflammation signaling pathway<br>Role of RIG-I recept. in antiviral immunity<br>RAR activation |
| Cluster 4 | ***Immune secreted***<br>Immune cell surface<br>Intracellular signaling | ***NK or T cells***<br>T, B & myeloid<br>B cells & myeloid<br>Monocytes | | TH1 & TH2 activation pathway<br>JAK/STAT signaling pathway<br>Role JAK 1/3 in cytokine signaling<br>STAT3 signaling<br>Role of cytokines in communication b/t immune cells |
| Cl. 7 | ***mRNA processing***<br>Intracellular signaling<br>mRNA splicing | ***B cells & myeloid*** | | Assembly of RNA pol II complex<br>EIF2 signaling<br>SLE signaling pathway |
| Cl. 3 | ***PRRs***<br>Interferon stim. genes<br>Integrin pathway | | | Interferon signaling<br>Tumor function of hepatic NK cells<br>Leukocyte extravasation |
| Cl. 9 | ***MicroRNA processing***<br>Immune signaling<br>Golgi | ***T cells*** | | NOTCH signaling<br>Regulation of EMT<br>Inhibition of ARE mediated mRNA degradation |
| Cl. 15 | ***Cytoskeleton*** | | | Caveolar mediated endocytosis signaling<br>GDNF family ligand-receptor signaling<br>Insulin receptor signaling pathway |
| 10 | ***Pro-cell cycle*** | ***T cells & myeloid*** | | DNA damage induced 14-3-3 signaling |
| 21 | ***Immune signaling*** | ***NK or T cell*** | | TH2 pathway |
| 14 | ***UFP reponse & stress*** | | | Unfolded protein response |
| 13 | ***WNT signaling*** | | | Ephrin receptor signaling |
| 5 | ***General cell surface*** | | | Glucocorticoid receptor signaling |

-log (p-value)

FIG. 71B

| | BIG-C | I-Scope | | Canonical pathway |
|---|---|---|---|---|
| Cluster 6 | ***Chromatin remodeling***<br>Pro-cell cycle<br>microRNA processing<br>UFP response<br>Intracellular signaling | | | Inhibition of ARE-mediated mRNA degradation<br>ERK/MAPK signaling<br>HIPPO signaling<br>PKA signaling<br>CDK5 signaling |
| Cluster 4 | ***Proteosome***<br>Endosome<br>Lysosome | ***T & B cells*** | | Inhibition of ARE-mediated mRNA degradation<br>PRRs in the recognition of bacteria & viruses<br>ErbB2 signaling pathway<br>Neuregulin signaling<br>SLE in B cell signaling |
| Cluster 2 | ***mRNA splicing***<br>mRNA processing<br>Ubiquit. & sumoyl. | | | EIF2 signaling<br>Regulation of eIF4 & p70S6K signaling<br>mTOR signaling pathway<br>SLE signaling pathway<br>Cleavage & polyaden. of pre-mRNA |
| Cl. 3 | ***mRNA splicing***<br>Nucleus & nucleolus | | **N/A** | RNA post-transcriptional modification*<br>Cellular function and maintenance*<br>Cell death and survival* |
| Cluster 9 | ***Secreted & ECM*** | ***Monocytes*** | | Extrinsic prothrombotic activation pathway<br>LXR/RXR signaling pathway<br>FXR/RXR signaling pathway<br>Reelin signaling in neurons<br>Coagulation systems |
| Cluster 1 | ***Immune cell surface***<br>General cell surface | | | Gαi signaling pathway<br>Cardiac β-adrenergic signaling pathway<br>Relaxin signaling<br>cAMP signaling<br>G protein signaling mediated by Tubby |
| Cluster 11 | ***PRRs***<br>Interferon stim. genes<br>MHC class I<br>MHC class II<br>Lysosome | ***B cells/pDCs***<br>APCs<br>NK cells | | Neuroinflammation signaling pathway<br>Role of RIG-I recept. in antiviral immunity<br>Activation of IRFs by cytosolic PRRs<br>Role of cytokines in communication b/t immune cells<br>Role of lipids/lipid rafts in pathogenesis of influenza |
| Cl. 5 | **RAS superfamily** | | | Gαq signaling pathway<br>CXCR4 signaling |
| Cl. 8 | **Peroxisomes** | | | Fatty acid b-oxidation II<br>Glutaryl-CoA degradation |
| 18 | **General cell surface** | | | Axonal guidance<br>Synaptogenesis |

FIG. 72D

Random vs SLE

Random vs CAD

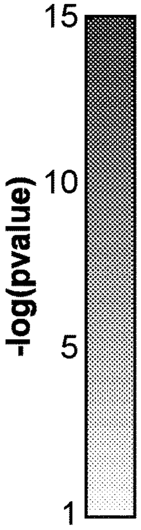

| | Functional category | Cellular category | Canonical pathway |
|---|---|---|---|
| Cluster 2 | ***IFN-stim, genes***<br>PORs<br>mRNA processing<br>Endocytosis<br>Ubiquitylation & sumo. | | Interferon signaling<br>Role of RIG-I in antiviral innate immunity<br>Activation of IRFs by cytosolic PRRs<br>Clathrin-mediated endocytosis<br>Coroncavirus pathogenesis pathway |
| Cluster 11 | ***Integrin signaling***<br>Pro-cell cycle<br>Golgi | | Kinetochore metaphase signaling<br>CTLA4 signaling in CTLs<br>COK5 signaling<br>GPS signaling pathway<br>Phagosome maturation<br>SLE in T-cell signaling pathway |
| Cluster 4 | ***mRNA splicing*** | | elf 2 signaling<br>NER pathway<br>Regulation of elf 4 and p7056K signaling<br>RAN signaling |
| Cluster 7 | **Immune signaling**<br>Immune secreted<br>Immune cell surface | ***Anergic or act. T***<br>T. B & myeloid<br>NK or T cells<br>T& myeloid<br>Myeloid | TH1 pathway<br>TH cell differentiation<br>TH1 & TH2 activation pathway<br>Role of cytokines in comm. bit immune cells<br>Oncostatin signaling |
| Cluster 17 | ***Proteasome***<br>General transcription<br>Pro-cell cycle | | Role of BRCA1 in DNA damage response<br>Protein ubiquitylation pathway<br>Adiopgenesis<br>Hereditary breast cancer signaling<br>Nucleotide excision repair pathway |
| Cl.8 | ***General transcription*** | | Spliceosomal cycle |
| Cl.3 | ***Pro-cell cycle*** | | No envrichment |
| Cl.18 | ***MHC class II*** | ***APCs*** | Leukotriene biosynthesis<br>MIF mediated glucocortocoid rec. regulation<br>Antigen presentation pathway |
| Cl.15 | ***Cytoplasm & biochem.*** | ***T & B cells*** | Quanosine nucleotide deg III<br>Urate biosynthesis |
| Cl.19 | ***Secreted & ECM*** | | Autophagy<br>Phagosome maturation |
| Cl.22 | ***General transcription*** | | Assembly of RNA pol II complex |
| Cl.14 | ***Immune cell surface*** | ***Myeloid*** | Lipid antigen presentation by CD1<br>CTL-mediated apoptosis of target cells<br>Coagulation system |
| Cl.5 | ***Cytoplasm & biochem*** | | CREB signaling in neurons<br>P2Y purigenic receptor signaling pathway |
| Cl.10 | | | Circadian rythym signaling |
| Cl.12 | ***Nuclear rec. trans.*** | | LXRVRXR activation<br>FXR/RXR activation |
| Cl.13 | ***Nuclear rec. trans.*** | | PPARaTOR activation<br>RAR/RXR activation |

FIG. 84A (Cont.)

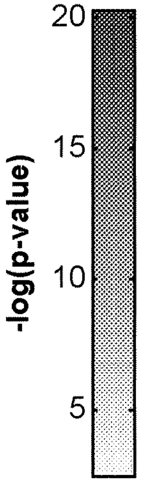

| | Functional category | Cellular category | | Canonical pathway |
|---|---|---|---|---|
| Cluster 2 | ***mRNA splicing***<br>Mito. DNA to RNA<br>Endplasmic net. | | | eIF2 signaling<br>DNA methylation & transcriptional rep. sig.<br>Regulation of eIF4 and p70S6K signaling<br>mTOR signaling<br>Transcriptional reg. network in ES cells |
| Cluster 8 | ***Proteosome***<br>Endocytosis<br>mRNA processing | ***Neutrophits*** | | Pancreatic aderocaronoma signaling<br>Erythroproetin signaling<br>TH1 pathway<br>IL23 signaling pathway<br>PRRs in the recong of bag & vinuses |
| Cluster 11 | ***PRRs***<br>Intracelluar signaling | ***Myeroid*** | | NFKB signaling<br>TLR signaling<br>Neurotinfammation pathway<br>Role of MC, FB & EC in RA<br>Infommatioma pathway |
| Cluster 6 | ***DNA repair***<br>Pro-cell cycle<br>Chromatin remodeling | | | Role of BRCA1 in DNA damage response<br>---------- BC signaling pathway<br>Role of CHK proteins in checkpoint control<br>ATM signaling<br>Cell cycle control of chromosome rep. |
| Cluster 5 | ***Integrin signaling***<br>Secreted & ECM | ***Monocytes***<br>Anergic or act. T | | Leukocyte extravasion signaling<br>Cavolin-medated endocytosis<br>NK cell signaling<br>Integrin signaling<br>Tumoricidal function of hepatic NK cells |
| Cl.1 | ***Ubiquit. & sumoyf.***<br>Proteosome | | | Protein ---------------------- pathway<br>Hypoxia signaling in CV system<br>BAG2 signaling |

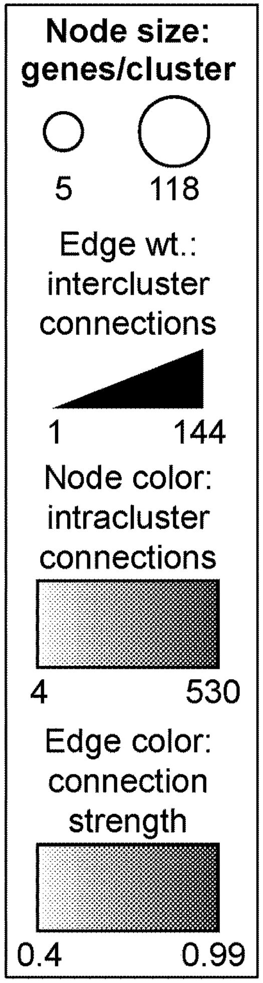

FIG. 84B (Cont. 1)

| | | | | |
|---|---|---|---|---|
| Cl.3 | ***Immune screted***<br>General cell surface | ***Monocytes***<br>GC B cells | | CREB signaling in neurosis<br>Role of PRRs in recog. bacteria & viruses |
| Cl. 19 | ***Immune screted*** | ***Monocytes*** | | Complement systems<br>cAMP mediated signaling<br>GPCR signaling |
| Cl. 33 | ***RAS superfamily***<br>Integrin | | | ------------------ guidance<br>NK cell signaling |
| Cl. 21 | ***Transposon ctl.*** | | | Telemerase signaling<br>ER-dependent breast cancer signaling |
| Cl. 4 | ***Cytoskel.*** Pro-cell cycle | | | Promotransduction pathway |
| Cl. 10 | ***OXPHOS***<br>Mito. TCA sycle | | | Microcondrial dysfunction<br>OXPHOS |
| Cl. 25 | ***Mitechandria gen.*** | | | Necroptosis signaling<br>CDP-DAG biosynthesis 1 |
| Cl. 32 | ***OXPHOS***<br>Cyto. & biochem | | | GABA receptor signaling<br>Clutamate-dep. acid resistance |
| 7 | ***Chrom, remodeling*** | | | Grantyme A signaling |
| 18 | ***DNA repair*** | | | NER signaling pathway |
| 14 | ***Cytoskeleton*** | | | Regulation of EMT |
| 26 | ***Cytoskeleton*** | | | Calcium signaling |
| 15 | **Integrin signaling** | | | Granulocyte adhesion & depedesis<br>Agranulocyte adhesion & depedesis |
| 20 | ***Integrin signaling*** | | | ER stress pathway |
| 30 | ***Gaigi*** | | | Iron homostasis |
| 12 | ***Nucleus & nuclearless*** | | | BAG2 signaling |

FIG. 84B (Cont. 2)

Shared pathways

| | Functional category | Cellular category | | Canonical pathway |
|---|---|---|---|---|
| Cluster 6 | *Immune signaling*<br>Intracellular signaling | *NK or T* | | STAT3 signaling<br>TH2 pathway<br>TH1 & TH2 activation pathway<br>Glucocortocoid receptor signaling<br>T cell exhaustion pathway |
| Cluster 2 | *Immune secreted* | *Anergic or act. T*<br>T & myeloid | | Leukocyte extravasation<br>CTLA signaling in CTLs<br>FcgR-mediated phagocytosis in MC & monocytes<br>TLR signaling<br>IL15 production |
| Cluster 8 | *mRNA processing*<br>mRNA splicing<br>General transcription | | | Spliceosomal cycle<br>Coronavirus pathogenesis pathway<br>Regulation of eIF4 and p70S6K signaling<br>mTOR signaling<br>eIF2 signaling |
| Cl. 5 | *Pro-cell cycle* | | | Mitotic roles of polo-like kinases<br>Kinetochore metaphase signaling |
| Cl. 4 | *PRRs* | | | Role of PRRs in recog. of bacteria & virus<br>IFN signaling |
| Cl. 3 | *Immune secreted* | *T, B & myeloid* | | Granulocyte adhesion & diapedesis<br>Agranulocyte adhesion & diapedesis |
| Cl. 7 | *Proteasome*<br>Anti-proliferation<br>Ubiquitylation & sumo. | | | Protein ubiquitylation pathway<br>Antiproliferative role of TOB in T cell signaling<br>Cell cycle: G2/M DNA damage checkpoint control reg. |

FIG. 85B

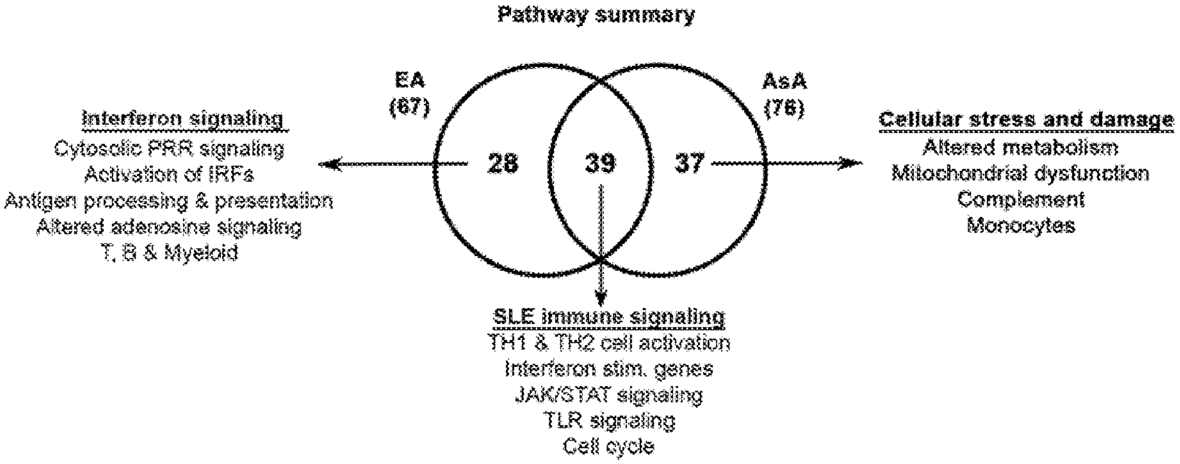

FIG. 85C

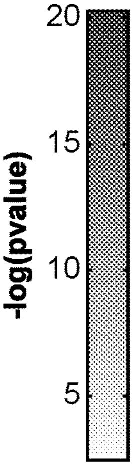

| | Functional category | Cellular category | Canonical pathway |
|---|---|---|---|
| Cluster 1 | ***Ubiquit. & sumo.*** mRNA splicing | | eIF2 signaling<br>Regulation of eIF2 and p70S6K signaling<br>mTOR signaling<br>Coronavirus pathogenesis pathway<br>Protein ubiquitination pathway |
| Cluster 3 | ***mRNA processing*** mRNA splicing | | SLE signaling pathway<br>Spliceosomal cycle<br>Assembly of RNA pol. II complex<br>Cleavage & polyadenylation of pre-mRNA<br>NER pathway |
| Cluster 9 | ***PRRs*** IFN-stimulated genes Pro-cell cycle Intracellular signaling | | Kinetochore metaphase signaling<br>HIPPO signaling<br>Cell cycle control of chromosome replication<br>ATM signaling<br>Inflammasome pathway |
| Cl.6 | ***Proteasome*** MHC class I Pro-cell cycle | | Antigen presentation pathway<br>Protein ubiquitination pathway<br>Interferon pathway |
| Cl.2 | ***Immune cell surface*** General cell surface | ***T & B cells*** | CREB signaling in neurons<br>Breast cancer regulation by strathmin 1<br>cAMP-mediated signaling |
| Cl.5 | ***Endocytosis*** Immune secreted | | Gastrin-mediated signaling<br>CREB signaling in neurons<br>Cardiac hypertrophy pathway |
| Cl.22 | ***mRNA processing*** | | |
| Cl.25 | ***Immune signaling*** | ***B cells*** pDCs | Neuroinflammation signaling pathway<br>SLE signaling pathway<br>inflammasome pathway |
| Cl.4 | ***Pro-cell cycle*** Intracellular signaling | | HIPPO signaling<br>14-3-3 mediated signaling |
| Cl.8 | ***Integrin signaling*** Secreted & ECM | ***Monocytes*** | Caveolin-mediated endocytosis signaling<br>Reg. of cellular mech by calpain proteases |
| Cl.13 | ***mRNA processing*** | | Inhibition of ARE-mdiated mRNA degradation<br>HOTAIR reg. pathway |
| Cl.21 | ***Fatty acid biosyn.*** Peroxisomes | | iNOS signaling<br>NFKB signaling |
| Cl.27 | ***Mito. TCA cycle,*** Mito. general. Peroxisomes | | Glutamine degradation I<br>Glycine cleavage complex |
| 18 | ***ROS protection*** | | Chondroitin sulfate degradation |
| 32 | ***Autophagy*** | | GABA receptor signaling |
| 33 | ***General cell surface*** | | Ga12/13 signaling<br>Signaling by RHO farmilly GTPases |
| 17 | ***Trans. factors*** | | |
| 28 | ***Glycolysis*** | | Fatty acid alpha-oxidation |
| 12 | ***Integrin signaling*** | | GP6 signaling pathway |
| 23 | ***Autophagy*** | | Superoathway of inositol phosphate compounds |
| 34 | ***Endosome & ves.*** | | Role of MAPK sig. in pathogenesis of flu |
| 24 | ***Lysosome*** | | OXPHOS<br>Mitochondrial dysfunction |
| 14 | | | Synaptogenesis |

FIG. 86 (Cont.)

Exposure: SLE GWAS (Bentham)
Outcome: CAD GWAS (UKBB)

| MR method | # of SNPs | Causal Estimate | Std. Error | P-value |
|---|---|---|---|---|
| MR Egger | 685 | 1.5E-02 | 5.9E-03 | **1.0E-02** |
| Weighted median | 685 | 5.6E-03 | 4.6E-03 | **2.2E-01** |
| Inverse variance weighted | 685 | 1.5E-02 | 4.1E-03 | **1.8E-04** |
| Robust adjusted profile score (RAPS) | 685 | 9.2E-03 | 4.3E-03 | **3.0E-02** |
| MR-PRESSO (raw) | 685 | 1.5E-02 | 4.1E-03 | **2.0E-04** |
| MR-PRESSO (outlier-corrected) | 26 outliers | 5.6E-03 | 3.4E-03 | **1.0E-01** |

Exposure: SLE Immunochip (Langefeld)
Outcome: CAD GWAS (UKBB)

| MR method | # of SNPs | Causal Estimate | Std. Error | P-value |
|---|---|---|---|---|
| MR Egger | 613 | 1.7E-02 | 8.0E-03 | **3.9E-02** |
| Weighted median | 613 | 9.1E-03 | 4.2E-03 | **3.1E-02** |
| Inverse variance weighted | 613 | 1.6E-02 | 3.6E-03 | **1.2E-05** |
| Robust adjusted profile score (RAPS) | 613 | 1.2E-02 | 3.9E-03 | **2.0E-03** |
| MR-PRESSO (raw) | 613 | 1.6E-02 | 3.6E-03 | **1.5E-05** |
| MR-PRESSO (outlier-corrected) | 24 outliers | 9.2E-03 | 3.0E-03 | **2.0E-03** |

Exposure: SLE GWAS (Bentham)
Outcome: CAD GWAS (UKBB)

| MR method | # of SNPs | Causal Estimate | Std. Error | P-value |
|---|---|---|---|---|
| MR Egger | 829 | -2.5E-02 | 3.6E-03 | **1.5E-11** |
| Weighted median | 829 | -9.1E-03 | 1.6E-03 | **4.0E-08** |
| Inverse variance weighted | 829 | -1.4E-02 | 1.6E-03 | **1.9E-20** |
| MR-RAPS | 829 | -1.1E-02 | 1.4E-03 | **6.4E-14** |

Exposure: SLE Immunochip (Langefeld)
Outcome: CAD GWAS (UKBB)

| MR method | # of SNPs | Causal Estimate | Std. Error | P-value |
|---|---|---|---|---|
| MR Egger | 829 | -1.6E-02 | 3.1E-03 | **3.5E-07** |
| Weighted median | 829 | -7.8E-03 | 1.5E-03 | **8.8E-08** |
| Inverse variance weighted | 829 | -1.2E-02 | 1.4E-03 | **1.4E-17** |
| MR-RAPS | 829 | -8.8E-03 | 1.3E-03 | **5.7E-11** |

Exposure: SLE GWAS (Bentham)
Outcome: CAD GWAS (UKBB)

| MR method | # of SNPs | Causal Estimate | Std. Error | P-value |
|---|---|---|---|---|
| MR Egger | 526 | -2.5E-03 | 4.1E-03 | 5.4E-01 |
| Weighted median | 526 | 3.7E-03 | 2.0E-03 | 6.8E-02 |
| Inverse variance weighted | 526 | 4.6E-03 | 1.6E-03 | **3.2E-03** |
| MR-RAPS | 526 | 5.4E-03 | 1.7E-03 | **1.1E-03** |
| MR-PRESSO (raw) | 526 | 4.6E-03 | 1.6E-03 | **3.3E-03** |
| MR-PRESSO (outlier-corrected) | 10 outliers | 4.9E-03 | 1.5E-03 | **9.3E-04** |

Exposure: SLE Immunochip (Langefeld)
Outcome: CAD GWAS (UKBB)

| MR method | # of SNPs | Causal Estimate | Std. Error | P-value |
|---|---|---|---|---|
| MR Egger | 526 | -4.0E-03 | 4.3E-03 | 3.5E-01 |
| Weighted median | 526 | 3.5E-03 | 2.2E-03 | 1.1E-01 |
| Inverse variance weighted | 526 | 4.8E-03 | 1.7E-03 | **5.5E-03** |
| MR-RAPS | 526 | 5.6E-03 | 1.8E-03 | **1.9E-03** |
| MR-PRESSO (raw) | 526 | 4.8E-03 | 1.7E-03 | **5.7E-03** |
| MR-PRESSO (outlier-corrected) | 11 outliers | 5.1E-03 | 1.6E-03 | **1.7E-03** |

Instrumental Variables: PhenoScanner SNPs associated with SLE
Exposure: SLE GWAS (Bentham)
Outcome: CAD GWAS (UKBB)

| MR method | # of SNPs | Causal Estimate | Std. Error | P-value |
|---|---|---|---|---|
| MR Egger | 911 | -1.9E-02 | 2.3E-03 | **4.0E-16** |
| Weighted median | 911 | -2.1E-02 | 2.0E-03 | **4.7E-26** |
| Inverse variance weighted | 911 | -1.1E-02 | 1.7E-03 | **6.3E-10** |
| MR-RAPS | 911 | -1.3E-02 | 1.7E-03 | **9.5E-15** |
| MR-PRESSO (raw) | 911 | -1.1E-02 | 1.7E-03 | **9.5E-10** |
| MR-PRESSO (outlier-corrected) | 22 outliers | -1.2E-02 | 1.4E-03 | **2.8E-16** |

Instrumental Variables: PhenoScanner non-HLA SNPs associated with SLE
Exposure: SLE GWAS (Bentham)
Outcome: CAD GWAS (UKBB)

| MR method | # of SNPs | Causal Estimate | Std. Error | P-value |
|---|---|---|---|---|
| MR Egger | 791 | 1.1E-02 | 3.6E-03 | **3.1E-03** |
| Weighted median | 791 | 3.0E-03 | 3.3E-03 | **3.7E-01** |
| Inverse variance weighted | 791 | 1.2E-02 | 2.5E-03 | **2.3E-06** |
| MR-RAPS | 791 | 1.1E-02 | 2.6E-03 | **3.0E-05** |
| MR-PRESSO (raw) | 791 | 1.2E-02 | 2.5E-03 | **2.7E-06** |
| MR-PRESSO (outlier-corrected) | 13 outliers | 7.5E-03 | 2.1E-03 | **3.6E-04** |

Exposure: SLE GWAS (Bentham)
Outcome: CAD GWAS (UKBB)

| MR method | # of SNPs | Causal Estimate | Std. Error | P-value |
|---|---|---|---|---|
| MR Egger | 317 | -6.0E-03 | 4.4E-03 | **1.7E-01** |
| Weighted median | 317 | -1.9E-02 | 1.9E-03 | **7.9E-23** |
| Inverse variance weighted | 317 | -2.6E-02 | 2.1E-03 | **1.8E-35** |

Exposure: SLE Immunochip (Langefeld)
Outcome: CAD GWAS (UKBB)

| MR method | # of SNPs | Causal Estimate | Std. Error | P-value |
|---|---|---|---|---|
| MR Egger | 317 | -2.0E-02 | 5.5E-03 | **3.2E-04** |
| Weighted median | 317 | -2.5E-02 | 2.3E-03 | **6.9E-29** |
| Inverse variance weighted | 317 | -3.3E-02 | 2.3E-03 | **1.3E-45** |

FIG. 93A

Exposure: SLE GWAS (Bentham)
Outcome: CAD GWAS (UKBB)

| MR method | # of SNPs | Causal Estimate | Std. Error | P-value |
|---|---|---|---|---|
| MR Egger | 33 | -2.4E-01 | 4.4E-02 | **6.8E-06** |
| Weighted median | 33 | -6.4E-02 | 8.1E-03 | **3.7E-15** |
| Inverse variance weighted | 33 | -5.6E-02 | 5.7E-03 | **1.6E-22** |

Exposure: SLE Immunochip (Langefeld)
Outcome: CAD GWAS (UKBB)

| MR method | # of SNPs | Causal Estimate | Std. Error | P-value |
|---|---|---|---|---|
| MR Egger | 33 | -1.3E-01 | 2.5E-02 | **9.2E-06** |
| Weighted median | 33 | -6.5E-02 | 8.0E-03 | **4.3E-16** |
| Inverse variance weighted | 33 | -6.2E-02 | 6.1E-03 | **3.2E-24** |

FIG. 93B

Exposure: SLE GWAS (Bentham)
Outcome: CAD GWAS (UKBB)

| MR method | # of SNPs | Causal Estimate | Std. Error | P-value |
|---|---|---|---|---|
| MR Egger | 103 | 8.1E-02 | 1.3E-02 | **2.9E-08** |
| Weighted median | 103 | 1.0E-02 | 4.1E-03 | **1.4E-02** |
| Inverse variance weighted | 103 | 1.7E-02 | 3.1E-03 | **7.1E-08** |

Exposure: SLE Immunochip (Langefeld)
Outcome: CAD GWAS (UKBB)

| MR method | # of SNPs | Causal Estimate | Std. Error | P-value |
|---|---|---|---|---|
| MR Egger | 103 | 1.1E-01 | 1.8E-02 | **9.5E-09** |
| Weighted median | 103 | 1.1E-02 | 4.8E-03 | **2.5E-02** |
| Inverse variance weighted | 103 | 1.9E-02 | 3.7E-03 | **1.2E-07** |

FIG. 94A

Exposure: SLE GWAS (Bentham)
Outcome: CAD GWAS (UKBB)

| MR method | # of SNPs | Causal Estimate | Std. Error | P-value |
|---|---|---|---|---|
| MR Egger | 25 | 2.4E-02 | 1.4E-02 | **9.1E-02** |
| Weighted median | 25 | 2.4E-02 | 5.8E-03 | **2.4E-05** |
| Inverse variance weighted | 25 | 2.1E-02 | 4.3E-03 | **5.0E-07** |

Exposure: SLE Immunochip (Langefeld)
Outcome: CAD GWAS (UKBB)

| MR method | # of SNPs | Causal Estimate | Std. Error | P-value |
|---|---|---|---|---|
| MR Egger | 25 | 2.9E-02 | 1.6E-02 | **8.9E-02** |
| Weighted median | 25 | 2.7E-02 | 6.6E-03 | **3.3E-05** |
| Inverse variance weighted | 25 | 2.5E-02 | 5.0E-03 | **4.9E-07** |

FIG. 94B

Exposure: SLE GWAS (Bentham)
Outcome: CAD GWAS (UKBB)

| MR method | # of SNPs | Causal Estimate | Std. Error | P-value |
|---|---|---|---|---|
| MR Egger | 60 | 6.2E-02 | 6.8E-02 | **3.7E-01** |
| Weighted median | 60 | 5.5E-02 | 6.8E-03 | **5.8E-16** |
| Inverse variance weighted | 60 | 4.5E-02 | 4.6E-03 | **2.3E-22** |

Exposure: SLE Immunochip (Langefeld)
Outcome: CAD GWAS (UKBB)

| MR method | # of SNPs | Causal Estimate | Std. Error | P-value |
|---|---|---|---|---|
| MR Egger | 60 | 1.1E-01 | 7.3E-02 | **1.3E-01** |
| Weighted median | 60 | 6.1E-02 | 7.8E-03 | **4.7E-15** |
| Inverse variance weighted | 60 | 5.0E-02 | 5.1E-03 | **1.5E-22** |

FIG. 94C

Exposure: SLE GWAS (Bentham)
Outcome: CAD GWAS (UKBB)

| MR method | # of SNPs | Causal Estimate | Std. Error | P-value |
|---|---|---|---|---|
| MR Egger | 86 | 6.5E-02 | 2.1E-02 | **3.1E-03** |
| Weighted median | 86 | 1.6E-02 | 5.3E-03 | **2.6E-03** |
| Inverse variance weighted | 86 | 1.9E-02 | 3.8E-03 | **6.7E-07** |

Exposure: SLE Immunochip (Langefeld)
Outcome: CAD GWAS (UKBB)

| MR method | # of SNPs | Causal Estimate | Std. Error | P-value |
|---|---|---|---|---|
| MR Egger | 86 | 4.3E-02 | 1.3E-02 | **1.9E-03** |
| Weighted median | 86 | 2.3E-02 | 5.6E-03 | **3.1E-05** |
| Inverse variance weighted | 86 | 2.1E-02 | 4.0E-03 | **1.5E-07** |

FIG. 94D

Instrumental Variables: SLE-associated HLA SNPs
Exposure: SLE GWAS (Bentham)
Outcome: CAD GWAS (UKBB)

| MR method | # of SNPs | Causal Estimate | Std. Error | P-value |
|---|---|---|---|---|
| MR Egger | 303 | -4.4E-03 | 4.5E-03 | **3.2E-01** |
| Weighted median | 303 | -1.9E-02 | 2.0E-03 | **4.1E-22** |
| Inverse variance weighted | 303 | -2.7E-02 | 2.1E-03 | **1.8E-35** |
| MR-RAPS | 303 | -2.1E-02 | 1.8E-03 | **1.5E-30** |

Instrumental Variables: CAD-associated HLA SNPs
Exposure: CAD GWAS (UKBB)
Outcome: SLE GWAS (Bentham)

| MR method | # of SNPs | Causal Estimate | Std. Error | P-value |
|---|---|---|---|---|
| MR Egger | 509 | 3.5E+00 | 4.0E-01 | **1.1E-16** |
| Weighted median | 509 | -5.7E-01 | 4.4E-02 | **3.8E-37** |
| Inverse variance weighted | 509 | -1.3E+00 | 9.8E-02 | **4.0E-40** |
| MR-RAPS | 509 | -7.9E-01 | 6.3E-02 | **5.0E-36** |

METHODS AND SYSTEMS FOR MACHINE LEARNING ANALYSIS OF SINGLE NUCLEOTIDE POLYMORPHISMS IN LUPUS

CROSS-REFERENCE

This application is a 371 National Phase Application of PCT/US2021/032230, filed May 13, 2021, which claims the benefit of U.S. Provisional Patent Application No. 63/024,730, filed May 14, 2020, which are incorporated by reference herein in their entirety.

BACKGROUND

Machine learning is a computational method capable of harnessing complex data from multiple sources to develop self-trained prediction and analysis tools. When applied to high-scale disease and treatment data, machine learning algorithms may quickly and effectively identify genetic and phenotypic features.

SUMMARY

In an aspect, the present disclosure provides a method of identifying one or more records having a specific phenotype, the method comprising: receiving a plurality of first records, wherein each first record is associated with one or more of a plurality of phenotypes; receiving a plurality of second records, wherein each second record is associated with one or more of the plurality of phenotypes, and wherein the plurality of second records and the plurality of first records are non-overlapping; applying a machine learning algorithm to at least one first record and at least one second record to determine a classifier; receiving a plurality of third records, wherein the third records are distinct from the plurality of first records and the plurality of second records; and applying the classifier to the plurality of third records to identify one or more third records associated with the specific phenotype.

In some embodiments, the first records and the second records comprise nucleic acid sequencing data, transcriptome data, genome data, epigenome data, proteome data, metabolome data, virome data, metabolome data, methylome data, lipidomic data, lineage-ome data, nucleosomal occupancy data, a genetic variant, a gene fusion, an insertion or deletion (indel), or any combination thereof. In some embodiments, the first records and the second records are in different formats. In some embodiments, the first records and the second records are from different sources, different studies, or both. In some embodiments, the phenotype comprises a disease state, an organ involvement, a medication response, or any combination thereof. In some embodiments, the classifier comprises an elastic generalized linear model classifier, a k-nearest neighbors classifier, a random forest classifier, or any combination thereof.

In some embodiments, the elastic generalized linear model classifier employs an elastic penalty of about 0.8 to about 1. In some embodiments, the elastic generalized linear model classifier employs an elastic penalty of at least about 0.8, about 0.825, about 0.85, about 0.875, about 0.9, about 0.925, about 0.95, about 0.975, or about 1. In some embodiments, the elastic generalized linear model classifier employs an elastic penalty of at most about 0.8, about 0.825, about 0.85, about 0.875, about 0.9, about 0.925, about 0.95, about 0.975, or about 1. In some embodiments, the elastic generalized linear model classifier employs an elastic penalty of about 0.8 to about 0.825, about 0.8 to about 0.85, about 0.8 to about 0.875, about 0.8 to about 0.9, about 0.8 to about 0.925, about 0.8 to about 0.95, about 0.8 to about 0.975, about 0.8 to about 1, about 0.825 to about 0.85, about 0.825 to about 0.875, about 0.825 to about 0.9, about 0.825 to about 0.925, about 0.825 to about 0.95, about 0.825 to about 0.975, about 0.825 to about 1, about 0.85 to about 0.875, about 0.85 to about 0.9, about 0.85 to about 0.925, about 0.85 to about 0.95, about 0.85 to about 0.975, about 0.85 to about 1, about 0.875 to about 0.9, about 0.875 to about 0.925, about 0.875 to about 0.95, about 0.875 to about 0.975, about 0.875 to about 1, about 0.9 to about 0.925, about 0.9 to about 0.95, about 0.9 to about 0.975, about 0.9 to about 1, about 0.925 to about 0.95, about 0.925 to about 0.975, about 0.925 to about 1, about 0.95 to about 0.975, about 0.95 to about 1, or about 0.975 to about 1. In some embodiments, the elastic generalized linear model classifier employs an elastic penalty of about 0.8, about 0.825, about 0.85, about 0.875, about 0.9, about 0.925, about 0.95, about 0.975, or about 1.

In some embodiments, the k-nearest neighbors classifier employs a K value of the size of the plurality of distinct first data sets, wherein k is about 1 to about 20. In some embodiments, the k-nearest neighbors classifier employs a K value of the size of the plurality of distinct first data sets, wherein k is at least about 1, about 2, about 3, about 4, about 5, about 6, about 8, about 10, about 12, about 14, about 16, or about 20. In some embodiments, the k-nearest neighbors classifier employs a K value of the size of the plurality of distinct first data sets, wherein k is at most about 1, about 2, about 3, about 4, about 5, about 6, about 8, about 10, about 12, about 14, about 16, or about 20. In some embodiments, the k-nearest neighbors classifier employs a K value of the size of the plurality of distinct first data sets, wherein k is about 1 to about 2, about 1 to about 3, about 1 to about 4, about 1 to about 5, about 1 to about 6, about 1 to about 8, about 1 to about 10, about 1 to about 12, about 1 to about 14, about 1 to about 16, about 1 to about 20, about 2 to about 3, about 2 to about 4, about 2 to about 5, about 2 to about 6, about 2 to about 8, about 2 to about 10, about 2 to about 12, about 2 to about 14, about 2 to about 16, about 2 to about 20, about 3 to about 4, about 3 to about 5, about 3 to about 6, about 3 to about 8, about 3 to about 10, about 3 to about 12, about 3 to about 14, about 3 to about 16, about 3 to about 20, about 4 to about 5, about 4 to about 6, about 4 to about 8, about 4 to about 10, about 4 to about 12, about 4 to about 14, about 4 to about 16, about 4 to about 20, about 5 to about 6, about 5 to about 8, about 5 to about 10, about 5 to about 12, about 5 to about 14, about 5 to about 16, about 5 to about 20, about 6 to about 8, about 6 to about 10, about 6 to about 12, about 6 to about 14, about 6 to about 16, about 6 to about 20, about 8 to about 10, about 8 to about 12, about 8 to about 14, about 8 to about 16, about 8 to about 20, about 10 to about 12, about 10 to about 14, about 10 to about 16, about 10 to about 20, about 12 to about 14, about 12 to about 16, about 12 to about 20, about 14 to about 16, about 14 to about 20, or about 16 to about 20. In some embodiments, the k-nearest neighbors classifier employs a K value of the size of the plurality of distinct first data sets, wherein k is about 1, about 2, about 3, about 4, about 5, about 6, about 8, about 10, about 12, about 14, about 16, or about 20.

In some embodiments, the K-value of the random forest classifier is incremented by 1 if the k-value is an even number. In some embodiments, applying a machine learning algorithm to the third data set comprises applying a machine learning algorithm to a plurality of unique third data sets.

In some embodiments, the classifier identifies said one or more third records associated with the specific phenotype with an accuracy of about 70% to about 100%. In some embodiments, the classifier identifies said one or more third records associated with the specific phenotype with an accuracy of at least about 70%, about 75%, about 80%, about 85%, about 90%, about 95%, or about 100%. In some embodiments, the classifier identifies said one or more third records associated with the specific phenotype with an accuracy of at most about 70%, about 75%, about 80%, about 85%, about 90%, about 95%, or about 100%. In some embodiments, the classifier identifies said one or more third records associated with the specific phenotype with an accuracy of about 70% to about 75%, about 70% to about 80%, about 70% to about 85%, about 70% to about 90%, about 70% to about 95%, about 70% to about 100%, about 75% to about 80%, about 75% to about 85%, about 75% to about 90%, about 75% to about 95%, about 75% to about 100%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100%. In some embodiments, the classifier identifies said one or more third records associated with the specific phenotype with an accuracy of about 70%, about 75%, about 80%, about 85%, about 90%, about 95%, or about 100%.

In some embodiments, the classifier identifies said one or more third records associated with the specific phenotype with an accuracy of about 70% to about 100%. In some embodiments, the classifier identifies said one or more third records associated with the specific phenotype with an accuracy of at least about 70%, about 75%, about 80%, about 85%, about 90%, about 95%, or about 100%. In some embodiments, the classifier identifies said one or more third records associated with the specific phenotype with an accuracy of at most about 70%, about 75%, about 80%, about 85%, about 90%, about 95%, or about 100%. In some embodiments, the classifier identifies said one or more third records associated with the specific phenotype with an accuracy of about 70% to about 75%, about 70% to about 80%, about 70% to about 85%, about 70% to about 90%, about 70% to about 95%, about 70% to about 100%, about 75% to about 80%, about 75% to about 85%, about 75% to about 90%, about 75% to about 95%, about 75% to about 100%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100%. In some embodiments, the classifier identifies said one or more third records associated with the specific phenotype with an accuracy of about 70%, about 75%, about 80%, about 85%, about 90%, about 95%, or about 100%.

In some embodiments, the classifier herein enables a specific phenotype association sensitivity of about 70% to about 100%. In some embodiments, the classifier herein enables a specific phenotype association sensitivity of at least 70%, about 75%, about 80%, about 85%, about 90%, about 95%, or about 100%. In some embodiments, the classifier herein enables a specific phenotype association sensitivity of at most 70%, about 75%, about 80%, about 85%, about 90%, about 95%, or about 100%. In some embodiments, the classifier herein enables a specific phenotype association sensitivity of about 70% to about 75%, about 70% to about 80%, about 70% to about 85%, about 70% to about 90%, about 70% to about 95%, about 70% to about 100%, about 75% to about 80%, about 75% to about 85%, about 75% to about 90%, about 75% to about 95%, about 75% to about 100%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100%. In some embodiments, the classifier herein enables a specific phenotype association sensitivity of about 70%, about 75%, about 80%, about 85%, about 90%, about 95%, or about 100%.

In some embodiments, the classifier herein enables a specific phenotype association specificity of about 70% to about 100%. In some embodiments, the classifier herein enables a specific phenotype association specificity of at least 70%, about 75%, about 80%, about 85%, about 90%, about 95%, or about 100%. In some embodiments, the classifier herein enables a specific phenotype association specificity of at most 70%, about 75%, about 80%, about 85%, about 90%, about 95%, or about 100%. In some embodiments, the classifier herein enables a specific phenotype association specificity of about 70% to about 75%, about 70% to about 80%, about 70% to about 85%, about 70% to about 90%, about 70% to about 95%, about 70% to about 100%, about 75% to about 80%, about 75% to about 85%, about 75% to about 90%, about 75% to about 95%, about 75% to about 100%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100%. In some embodiments, the classifier herein enables a specific phenotype association specificity of about 70%, about 75%, about 80%, about 85%, about 90%, about 95%, or about 100%.

In some embodiments, the method further comprises filtering the first records, the second records, or both. In some embodiments, the filtering comprises removing outliers, removing background noise, removing data without annotation data, normalizing, scaling, variance correcting, Weighted Gene Co-expression Network Analysis, enrichment analysis, dimensionality reduction, or any combination thereof. In some embodiments, the normalizing is performed by Robust Multi-Array Analysis (RMA), Guanine Cytosine Robust Multi-Array Analysis (GCRMA), Linear Models for Microarray Data, variance stabilizing transformation (VST), normal-exponential quantile correction (NEQC), or any combination thereof. In some embodiments, the variance correction comprises employing a local empirical Bayesian shrinkage, adjusting the p-values for multiple hypothesis testing using the Benjamini-Hochberg correction, and removing all data with a set false discovery rate In some embodiments, the false discovery rate is about 0.000001 to about 0.2. In some embodiments, the false discovery rate is at least about 0.000001. In some embodiments, the false discovery rate is at most about 0.2. In some embodiments, the false discovery rate is about 0.000001 to about 0.00005, about 0.000001 to about 0.00001, about 0.000001 to about 0.0005, about 0.000001 to about 0.0001, about 0.000001 to about 0.005, about 0.000001 to about 0.001, about 0.000001 to about 0.05, about 0.000001 to about 0.01, about 0.000001 to about 0.2, about 0.00005 to about 0.00001, about 0.00005 to about 0.0005, about 0.00005 to about 0.0001, about 0.00005 to about 0.005, about 0.00005 to about 0.001, about 0.00005 to about 0.05, about 0.00005 to about 0.01, about 0.00005 to about 0.2, about 0.00001 to about 0.0005, about 0.00001 to about 0.0001, about 0.00001 to about 0.005, about 0.00001 to about 0.001, about 0.00001 to about 0.05, about 0.00001 to about 0.01, about 0.00001 to about 0.2, about 0.0005 to about 0.0001, about 0.0005 to about 0.005, about 0.0005 to about 0.001, about 0.0005 to about 0.05, about 0.0005 to about 0.01, about 0.0005 to about 0.2, about 0.0001 to about 0.005, about 0.0001 to about 0.001, about 0.0001 to about 0.05, about 0.0001 to about 0.01, about 0.0001 to about 0.2, about 0.005 to about 0.001, about 0.005 to about 0.05, about 0.005 to about 0.01, about 0.005 to about 0.2, about 0.001 to about 0.05, about 0.001 to about 0.01, about 0.001 to about 0.2, about 0.05 to about 0.01, about 0.05 to about 0.2, or about 0.01 to about 0.2. In some embodiments, the false discovery rate is about 0.000001, about 0.00005, about 0.00001, about 0.0005, about 0.0001, about 0.005, about 0.001, about 0.05, about 0.01, or about 0.2.

In some embodiments, the Weighted Gene Co-expression Network Analysis comprises calculating a topology matrix, clustering the data based on the topology matrix, and correlating module eigenvalues for traits on a linear scale by Pearson correlation, for nonparametric traits by Spearman correlation, and for dichotomous traits by point-biserial correlation or t-test. The Pearson correlation or the Product Moment Correlation Coefficient (PMCC), is a number between −1 and 1 that indicates the extent to which two variables are linearly related. The Spearman correlation is a nonparametric measure of rank correlation; statistical dependence between the rankings of two variables.

In some embodiments, the one or more records having a specific phenotype correspond to one or more subjects, and the method further comprises identifying the one or more subjects as (i) having a diagnosis of a lupus condition, (ii) having a prognosis of a lupus condition, (iii) being suitable or not suitable for enrollment in a clinical trial for a lupus condition, (iv) being suitable or not suitable for being administered a therapeutic regimen configured to treat a lupus condition, (v) having an efficacy or not having an efficacy of a therapeutic regimen configured to treat a lupus condition, based at least in part on the specific phenotype corresponding to the one or more subjects.

In another aspect, the present disclosure provides a non-transitory computer-readable storage media encoded with a computer program including instructions executable by a processor to create an application for identifying one or more records having a specific phenotype, the application comprising: a first receiving module receiving a plurality of first records, wherein each first record is associated with one or more of a plurality of phenotypes; a second receiving module receiving a plurality of second records, wherein each second record is associated with one or more of the plurality of phenotypes, and wherein the plurality of second records and the plurality of first records are non-overlapping; a machine learning module applying a machine learning algorithm to at least one first record and at least one second record to determine a classifier; a third receiving module receiving a plurality of third records, wherein the third records are distinct from the plurality of first records and the plurality of second records; and a classifying module applying the classifier to the plurality of third records to identify one or more third records associated with the specific phenotype.

In some embodiments, the first records and the second records comprise nucleic acid sequencing data, transcriptome data, genome data, epigenome data, proteome data, metabolome data, virome data, metabolome data, methylome data, lipidomic data, lineage-ome data, nucleosomal occupancy data, a genetic variant, a gene fusion, an insertion or deletion (indel), or any combination thereof. In some embodiments, the first records and the second records are in different formats. In some embodiments, the first records and the second records are from different sources, different studies, or both. In some embodiments, the phenotype comprises a disease state, an organ involvement, a medication response, or any combination thereof. In some embodiments, the classifier comprises an elastic generalized linear model classifier, a k-nearest neighbors classifier, a random forest classifier, or any combination thereof. In some embodiments, the elastic generalized linear model classifier employs an elastic penalty of about 0.9. In some embodiments, the k-nearest neighbors classifier employs a K-value of about 5% of the size of the plurality of distinct first data sets. In some embodiments, the K-value of the random forest classifier is incremented by 1 if the k-value is an even number. In some embodiments, applying a machine learning algorithm to the third data set comprises applying a machine learning algorithm to a plurality of unique third data sets. In some embodiments, said classifier identifies said one or more third records associated with the specific phenotype with an accuracy of at least about 70%. In some embodiments, the method further comprises filtering the first records, the second records, or both. In some embodiments, the filtering comprises removing outliers, removing background noise, removing data without annotation data, normalizing, scaling, variance correcting, Weighted Gene Co-expression Network Analysis, enrichment analysis, dimensionality reduction, or any combination thereof. In some embodiments, the normalizing is performed by Robust Multi-Array Analysis (RMA), Guanine Cytosine Robust Multi-Array Analysis (GCRMA), Linear Models for Microarray Data, variance stabilizing transformation (VST), normal-exponential quantile correction (NEQC), or any combination thereof. In some embodiments, the variance correction comprises employing a local empirical Bayesian shrinkage, adjusting the p-values for multiple hypothesis testing using the Benjamini-Hochberg correction, and removing all data with a false discovery rate of less than 0.2. In some embodiments, the Weighted Gene Co-expression Network Analysis comprises calculating a topology matrix, clustering the data based on the topology matrix, and correlating module eigenvalues for traits on a linear scale by Pearson correlation, for nonparametric traits by Spearman correlation, and for dichotomous traits by point-biserial correlation or t-test.

In another aspect, the present disclosure provides a method for identifying a disease state or a susceptibility thereof of a subject, comprising: (a) using an assay to process a biological sample derived from the subject to generate a quantitative measure of each of a plurality of disease-associated genomic loci, wherein the plurality of disease-associated genomic loci comprises at least 5 genes associated with a module of Table 8; (b) processing the dataset to identify the disease state or the susceptibility thereof of the subject at an accuracy of at least about 70%; and (c) electronically outputting a report indicative of the disease state or the susceptibility thereof of the subject.

In some embodiments, the plurality of quantitative measures comprises gene expression measurements. In some embodiments, the disease state comprises an active lupus condition or an inactive lupus condition. In some embodiments, the lupus condition is SLE. In some embodiments, the plurality of disease-associated genomic loci comprises one or more genes selected from the group consisting of: RAB4B, ADAR, MRPL44, CDCA5, MYD88, SNN, BRD3, C7orf43, CDC20, SP1, POFUT1, SAMD4B, ATP6V1B2, TSPAN9, SP140, STK26, IRF4, LCP1, LMO2, SF3B4, HIST2H2AA3, CITED4, ADAM8, TICAM1, and HSD17B7.

In another aspect, the present disclosure provides a method for identifying an immunological state of a subject, comprising: (a) using an assay to process a biological sample derived from the subject to generate a quantitative measure of each of a plurality of genomic loci, wherein the plurality of genomic loci comprises at least 5 genes associated with a module of Table 8; (b) processing the dataset to identify the immunological state of the subject at an accuracy of at least about 70%; and (c) electronically outputting a report indicative of the immunological state of the subject.

In some embodiments, the plurality of quantitative measures comprises gene expression measurements. In some embodiments, the immunological state comprises an active or inactive state of each of one or more of the plurality of genomic loci. In some embodiments, the plurality of genomic loci comprises one or more genes selected from the group consisting of: RAB4B, ADAR, MRPL44, CDCA5, MYD88, SNN, BRD3, C7orf43, CDC20, SP1, POFUT1, SAMD4B, ATP6V1B2, TSPAN9, SP140, STK26, IRF4, LCP1, LMO2, SF3B4, HIST2H2AA3, CITED4, ADAM8, TICAM1, and HSD17B7.

In another aspect, the present disclosure provides a method for identifying a disease state or a susceptibility thereof of a subject, comprising: (a) using an assay to process a biological sample derived from the subject to generate a quantitative measure of each of a plurality of disease-associated genomic loci, wherein the plurality of disease-associated genomic loci comprises one or more genes associated with a gene cluster of Table 1 to Table 37; (b) processing the dataset to identify the disease state or the susceptibility thereof of the subject at an accuracy of at least about 70%; and (c) electronically outputting a report indicative of the disease state or the susceptibility thereof of the subject.

In some embodiments, the plurality of quantitative measures comprises gene expression measurements. In some embodiments, the disease state comprises an active lupus condition or an inactive lupus condition. In some embodiments, the lupus condition is systemic lupus erythematosus (SLE), discoid lupus erythematosus (DLE), or lupus nephritis (LN). In some embodiments, the plurality of disease-associated genomic loci comprises 5, 10, 15, 20, 25, 30, 35, 40, 45, 50, or more than 50 genes associated with the gene cluster.

In another aspect, the present disclosure provides a method for identifying an immunological state of a subject, comprising: (a) using an assay to process a biological sample derived from the subject to generate a quantitative measure of each of a plurality of disease-associated genomic loci, wherein the plurality of disease-associated genomic loci comprises one or more genes associated with a gene cluster of Table 1 to Table 37; (b) processing the dataset to identify the immunological state of the subject at an accuracy of at least about 70%; and (c) electronically outputting a report indicative of the immunological state of the subject.

In some embodiments, the plurality of quantitative measures comprises gene expression measurements. In some embodiments, the immunological state comprises an active lupus condition or an inactive lupus condition. In some embodiments, the lupus condition is systemic lupus erythematosus (SLE), discoid lupus erythematosus (DLE), or lupus nephritis (LN). In some embodiments, the plurality of disease-associated genomic loci comprises 5, 10, 15, 20, 25, 30, 35, 40, 45, 50, or more than 50 genes associated with the gene cluster.

In another aspect, the present disclosure provides a method for identifying an immunological state of a subject, comprising: (a) using an assay to process a biological sample derived from the subject to generate a quantitative measure of each of a plurality of disease-associated genomic loci, wherein the plurality of disease-associated genomic loci comprises one or more genes associated with a pathway of Table 1 to Table 37; (b) processing the dataset to identify the immunological state of the subject at an accuracy of at least about 70%; and (c) electronically outputting a report indicative of the immunological state of the subject.

In some embodiments, the plurality of quantitative measures comprises gene expression measurements. In some embodiments, the immunological state comprises an active lupus condition or an inactive lupus condition. In some embodiments, the lupus condition is systemic lupus erythematosus (SLE), discoid lupus erythematosus (DLE), or lupus nephritis (LN). In some embodiments, the plurality of disease-associated genomic loci comprises 5, 10, 15, 20, 25, 30, 35, 40, 45, 50, or more than 50 genes associated with the pathway.

Biological Data Analysis

In another aspect, the present disclosure provides a computer-implemented method for assessing a condition of a subject, comprising: (a) receiving a dataset of a biological sample of the subject; (b) selecting one or more data analysis tools, wherein the one or more data analysis tools comprise an analysis tool selected from the group consisting of: a BIG-C™ big data analysis tool, an I-Scope™ big data analysis tool, a T-Scope™ big data analysis tool, a CellScan big data analysis tool, an MS (Molecular Signature) Scoring™ analysis tool, a Gene Set Variation Analysis (GSVA) tool (e.g., P-Scope), a CoLTs® (Combined Lupus Treatment Scoring) analysis tool, and a Target Scoring analysis tool, or a combination thereof; (c) processing the dataset using the one or more data analysis tools to generate a data signature of the biological sample of the subject; and (d) based at least in part on the data signature generated in (c), assessing the condition of the subject.

In some embodiments, the dataset comprises mRNA gene expression or transcriptome data, DNA genomic data, proteomic data, metabolomic data, or a combination thereof. In some embodiments, the biological sample is selected from the group consisting of: a whole blood (WB) sample, a PBMC sample, a tissue sample, and a cell sample. In some embodiments, assessing the condition of the subject comprises identifying a disease or disorder of the subject.

In some embodiments, the method further comprises identifying a disease or disorder of the subject at a sensitivity or specificity of at least about 70%. In some embodiments, the method further comprises determining a likelihood of the identification of the disease or disorder of the subject. In some embodiments, the method further comprises providing a therapeutic intervention for the disease or disorder of the subject. In some embodiments, the method further comprises monitoring the disease or disorder of the subject, wherein the monitoring comprises assessing the disease or disorder of the subject at a plurality of time points, wherein the assessing is based at least on the disease or disorder identified at each of the plurality of time points.

In some embodiments, selecting the one or more data analysis tools comprises receiving a user selection of the one or more data analysis tools. In some embodiments, selecting the one or more data analysis tools is automatically performed by the computer without receiving a user selection of the one or more data analysis tools.

In another aspect, the present disclosure provides a computer system for assessing a condition of a subject, comprising: a database that is configured to store a dataset of a biological sample of the subject; and one or more computer processors operatively coupled to the database, wherein the one or more computer processors are individually or collectively programmed to: (i) select one or more data analysis tools, wherein the one or more data analysis tools comprise an analysis tool selected from the group consisting of: a BIG-C™ big data analysis tool, an I-Scope™ big data analysis tool, a T-Scope™ big data analysis tool, a CellScan big data analysis tool, an MS (Molecular Signature) Scoring™ analysis tool, a Gene Set Variation Analysis (GSVA) tool (e.g., P-Scope), a CoLTs® (Combined Lupus Treatment Scoring) analysis tool, and a Target Scoring analysis tool; (ii) process the dataset using the one or more data analysis tools to generate a data signature of the biological sample of the subject; and (iii) based at least in part on the data signature generated in (ii), assess the condition of the subject.

In another aspect, the present disclosure provides a non-transitory computer readable medium comprising machine-executable code that, upon execution by one or more computer processors, implements a method for assessing a condition of a subject, the method comprising: (a) receiving a dataset of a biological sample of the subject; (b) selecting one or more data analysis tools, wherein the one or more data analysis tools comprise an analysis tool selected from the group consisting of: a BIG-C™ big data analysis tool, an I-Scope™ big data analysis tool, a T-Scope™ big data analysis tool, a CellScan big data analysis tool, an MS (Molecular Signature) Scoring™ analysis tool, a Gene Set Variation Analysis (GSVA) tool (e.g., P-Scope), a CoLTs® (Combined Lupus Treatment Scoring) analysis tool, and a Target Scoring analysis tool; (c) processing the dataset using the one or more data analysis tools to generate a data signature of the biological sample of the subject; and (d) based at least in part on the data signature generated in (c), assessing the condition of the subject. In any embodiment described herein, the one or more data analysis tools can be a plurality of data analysis tools each independently selected from a BIG-C™ big data analysis tool, an I-Scope™ big data analysis tool, a T-Scope™ big data analysis tool, a CellScan big data analysis tool, an MS (Molecular Signature) Scoring™ analysis tool, a Gene Set Variation Analysis (GSVA) tool (e.g., P-Scope), a CoLTs® (Combined Lupus Treatment Scoring) analysis tool, and a Target Scoring analysis tool.

Analysis of Single Nucleotide Polymorphisms (SNPs) Associated with Lupus

In another aspect, the present disclosure provides a computer-implemented method for assessing an SLE condition of a subject, comprising: (a) receiving a dataset of a biological sample of the subject, wherein the dataset comprises quantitative measures of gene expression at each a plurality of SLE-associated genomic loci, wherein the plurality of SLE-associated genomic loci comprises (i) one or more AA-specific single nucleotide polymorphisms (SNPs) if the subject has an African-Ancestry (AA), or (ii) one or more EA-specific SNPs if the subject has a European-Ancestry (EA); (b) processing the dataset to identify one or more differentially expressed (DE) genomic loci among the plurality of SLE-associated genomic loci; and (c) based at least in part on the one or more DE genomic loci identified in (b) and whether the subject has an African-Ancestry (AA) or a European-Ancestry (EA), assessing the SLE condition of the subject.

In another aspect, the present disclosure provides a computer-implemented method for assessing an SLE condition of a subject, comprising: (a) receiving a dataset of a biological sample of the subject, wherein the dataset comprises quantitative measures of gene expression at each a plurality of systemic lupus erythematosus (SLE)-associated genomic loci, wherein the plurality of SLE-associated genomic loci comprises one or more African-Ancestry (AA)-specific single nucleotide polymorphisms (SNPs); (b) processing the dataset to identify one or more differentially expressed (DE) genomic loci among the plurality of SLE-associated genomic loci; and (c) based at least in part on the one or more DE genomic loci identified in (b) and whether the subject has an African-Ancestry (AA), assessing the SLE condition of the subject.

In another aspect, the present disclosure provides a computer-implemented method for assessing an SLE condition of a subject, comprising: (a) receiving a dataset of a biological sample of the subject, wherein the dataset comprises quantitative measures of gene expression at each a plurality of systemic lupus erythematosus (SLE)-associated genomic loci, wherein the plurality of SLE-associated genomic loci comprises one or more European-Ancestry (EA)-specific single nucleotide polymorphisms (SNPs); (b) processing the dataset to identify one or more differentially expressed (DE) genomic loci among the plurality of SLE-associated genomic loci; and (c) based at least in part on the one or more DE genomic loci identified in (b) and whether the subject has a European-Ancestry (EA), assessing the SLE condition of the subject.

In some embodiments, the dataset comprises RNA gene expression or transcriptome data, DNA genomic data, or a combination thereof. In some embodiments, the biological sample is selected from the group consisting of: a whole blood (WB) sample, a PBMC sample, a tissue sample, and a cell sample. In some embodiments, assessing the SLE condition of the subject comprises determining a diagnosis of the SLE condition, a prognosis of the SLE condition, a susceptibility of the SLE condition, a treatment for the SLE condition, or an efficacy or non-efficacy of a treatment for the SLE condition.

In some embodiments, the method further comprises determining a diagnosis of the SLE condition with a sensitivity of at least about 70%. In some embodiments, the method further comprises determining a diagnosis of the SLE condition with a specificity of at least about 70%. In some embodiments, the method further comprises determining a diagnosis of the SLE condition with a positive predictive value of at least about 70%. In some embodiments, the method further comprises determining a diagnosis of the SLE condition with a negative predictive value of at least about 70%. In some embodiments, the method further comprises determining a diagnosis of the SLE condition with an Area Under Curve (AUC) of at least about 70%. In some embodiments, the method further comprises determining a likelihood of the diagnosis of the SLE condition of the subject.

In some embodiments, the method further comprises generating a plurality of drug candidates for the SLE condition of the subject. In some embodiments, the method further comprises evaluating or predicting a relative efficacy of the plurality of drug candidates for the SLE condition of the subject. In some embodiments, the method further comprises providing a therapeutic intervention comprising one or more of the plurality of drug candidates for the SLE condition of the subject.

In some embodiments, the method further comprises selecting a treatment for the SLE condition of the subject, the treatment comprising an AA-specific drug. In some embodiments, the AA-specific drug is selected from the group consisting of: an HDAC inhibitor, a retinoid, a IRAK4-targeted drug, and a CTLA4-targeted drug. In some embodiments, the method further comprises selecting a treatment for the SLE condition of the subject, the treatment comprising an EA-specific drug. In some embodiments, the EA-specific drug is selected from the group consisting of: hydroxychloroquine, a CD40LG-targeted drug, a CXCR1-targeted drug, and a CXCR2-targeted drug. In some embodiments, the method further comprises selecting a treatment for the SLE condition of the subject, the treatment comprising a drug targeting E-Genes or pathways shared by EA and AA. In some embodiments, the drug targeting E-Genes or pathways shared by EA and AA is selected from the group consisting of: ibrutinib, ruxolitinib, and ustekinumab.

In some embodiments, the method further comprises monitoring the SLE condition of the subject, wherein the monitoring comprises assessing the SLE condition of the subject at each of a plurality of time points, and processing the plurality of assessments of the SLE condition of the subject at each of the plurality of time points.

In some embodiments, the one or more EA-specific SNPs comprise one or more SNPs of genes selected from the group listed in Table 25. In some embodiments, the one or more AA-specific SNPs comprise one or more SNPs of genes selected from the group listed in Table 26. In some embodiments, the plurality of SLE-associated genomic loci comprises one or more shared SNPs, wherein the one or more shared SNPs are common to both EA and AA. In some embodiments, the one or more shared SNPs comprise one or more SNPs of genes selected from the group listed in Table 27.

In another aspect, the present disclosure provides a computer system for assessing an SLE condition of a subject, comprising: a database that is configured to store an African-Ancestry (AA) status of the subject, a European-Ancestry (EA) status of the subject, and a dataset of a biological sample of the subject, wherein the dataset comprises quantitative measures of gene expression at each a plurality of SLE-associated genomic loci, wherein the plurality of SLE-associated genomic loci comprises (i) one or more AA-specific single nucleotide polymorphisms (SNPs) if the subject has an African-Ancestry (AA), or (ii) one or more EA-specific SNPs if the subject has a European-Ancestry (EA); and one or more computer processors operatively coupled to the database, wherein the one or more computer processors are individually or collectively programmed to: (i) process the dataset to identify one or more differentially expressed (DE) genomic loci among the plurality of SLE-associated genomic loci; and (ii) based at least in part on the one or more DE genomic loci identified in (ii), the AA status of the subject, and the EA status of the subject, assessing the SLE condition of the subject.

In another aspect, the present disclosure provides a computer system for assessing an SLE condition of a subject, comprising: a database that is configured to store an African-Ancestry (AA) status of the subject and a dataset of a biological sample of the subject, wherein the dataset comprises quantitative measures of gene expression at each a plurality of systemic lupus erythematosus (SLE)-associated genomic loci, wherein the plurality of SLE-associated genomic loci comprises one or more African-Ancestry (AA)-specific single nucleotide polymorphisms (SNPs); and one or more computer processors operatively coupled to the database, wherein the one or more computer processors are individually or collectively programmed to: (i) process the dataset to identify one or more differentially expressed (DE) genomic loci among the plurality of SLE-associated genomic loci; and (ii) based at least in part on the one or more DE genomic loci identified in (ii) and the AA status of the subject, assessing the SLE condition of the subject.

In another aspect, the present disclosure provides a computer system for assessing an SLE condition of a subject, comprising: a database that is configured to store a European-Ancestry (EA) status of the subject and a dataset of a biological sample of the subject, wherein the dataset comprises quantitative measures of gene expression at each a plurality of systemic lupus erythematosus (SLE)-associated genomic loci, wherein the plurality of SLE-associated genomic loci comprises one or more European-Ancestry (EA)-specific single nucleotide polymorphisms (SNPs); and one or more computer processors operatively coupled to the database, wherein the one or more computer processors are individually or collectively programmed to: (i) process the dataset to identify one or more differentially expressed (DE) genomic loci among the plurality of SLE-associated genomic loci; and (ii) based at least in part on the one or more DE genomic loci identified in (i) and the EA status of the subject, assess the SLE condition of the subject.

In another aspect, the present disclosure provides a non-transitory computer readable medium comprising machine-executable code that, upon execution by one or more computer processors, implements a method for assessing an SLE condition of a subject, comprising: (a) receiving a dataset of a biological sample of the subject, wherein the dataset comprises quantitative measures of gene expression at each a plurality of SLE-associated genomic loci, wherein the plurality of SLE-associated genomic loci comprises (i) one or more AA-specific single nucleotide polymorphisms (SNPs) if the subject has an African-Ancestry (AA), or (ii) one or more EA-specific SNPs if the subject has a European-Ancestry (EA); (b) processing the dataset to identify one or more differentially expressed (DE) genomic loci among the plurality of SLE-associated genomic loci; and (c) based at least in part on the one or more DE genomic loci identified in (b) and whether the subject has an African-Ancestry (AA) or a European-Ancestry (EA), assessing the SLE condition of the subject.

In another aspect, the present disclosure provides a non-transitory computer readable medium comprising machine-executable code that, upon execution by one or more computer processors, implements a method for assessing an SLE condition of a subject, comprising: (a) receiving a dataset of a biological sample of the subject, wherein the dataset comprises quantitative measures of gene expression at each a plurality of systemic lupus erythematosus (SLE)-associated genomic loci, wherein the plurality of SLE-associated genomic loci comprises one or more African-Ancestry (AA)-specific single nucleotide polymorphisms (SNPs); (b) processing the dataset to identify one or more differentially expressed (DE) genomic loci among the plurality of SLE-associated genomic loci; and (c) based at least in part on the one or more DE genomic loci identified in (b) and whether the subject has an African-Ancestry (AA), assessing the SLE condition of the subject.

In another aspect, the present disclosure provides a non-transitory computer readable medium comprising machine-executable code that, upon execution by one or more computer processors, implements a method for assessing an SLE condition of a subject, comprising: (a) receiving a dataset of a biological sample of the subject, wherein the dataset comprises quantitative measures of gene expression at each a plurality of systemic lupus erythematosus (SLE)-associated genomic loci, wherein the plurality of SLE-associated genomic loci comprises one or more European-Ancestry (EA)-specific single nucleotide polymorphisms (SNPs); (b) processing the dataset to identify one or more differentially expressed (DE) genomic loci among the plurality of SLE-associated genomic loci; and (c) based at least in part on the one or more DE genomic loci identified in (b) and whether the subject has a European-Ancestry (EA) assessing the SLE condition of the subject.

In another aspect, the present disclosure provides a method for determining a disease state of a subject, comprising: (a) assaying a biological sample obtained or derived from the subject to produce a data set comprising gene expression measurements of the biological sample at each of a plurality of disease-associated genomic loci, wherein the plurality of disease-associated genomic loci comprises at least a portion of a gene selected from the group of genes listed in Tables 1-37; (b) computer processing the data set to determine the disease state of the subject; and (c) electronically outputting a report indicative of the disease state of the subject.

In some embodiments, the plurality of disease-associated genomic loci comprises at least a portion of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 350, 400, 450, 500, 550, 600, 650, 700, 750, 800, 850, 900, 950, or 1000 genes selected from the group of genes listed in Tables 1-37.

In some embodiments, the method further comprises determining the disease state of the subject with an accuracy of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the method further comprises determining the disease state of the subject with a sensitivity of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the method further comprises determining the disease state of the subject with a specificity of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the method further comprises determining the disease state of the subject with a positive predictive value of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the method further comprises determining the disease state of the subject with a negative predictive value of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the method further comprises determining the disease state of the subject with an Area-Under-Curve (AUC) of at least about 0.50, at least about 0.55, at least about 0.60, at least about 0.65, at least about 0.70, at least about 0.75, at least about 0.80, at least about 0.85, at least about 0.90, at least about 0.91, at least about 0.92, at least about 0.93, at least about 0.94, at least about 0.95, at least about 0.96, at least about 0.97, at least about 0.98, at least about 0.99, or more than about 0.99.

In some embodiments, the subject has received a diagnosis of the disease. In some embodiments, the subject is suspected of having the disease. In some embodiments, the subject is at elevated risk of having the disease or having severe complications from the disease. In some embodiments, the subject is asymptomatic for the disease. In some embodiments, the method further comprises administering a treatment to the subject based at least in part on the determined disease state. In some embodiments, the treatment is configured to treat the disease state of the subject. In some embodiments, the treatment is configured to reduce a severity of the disease state of the subject. In some embodiments, the treatment is configured to reduce a risk of having the disease. In some embodiments, the treatment comprises a drug. In some embodiments, the drug is selected from the group listed in Tables 28-29.

In some embodiments, (b) comprises using a trained machine learning classifier to analyze the data set to determine the disease state of the subject. In some embodiments, the trained machine learning classifier is trained using gene expression data obtained by a data analysis tool selected from the group consisting of: a BIG-C™ big data analysis tool, an I-Scope™ big data analysis tool, a T-Scope™ big data analysis tool, a CellScan big data analysis tool, an MS (Molecular Signature) Scoring™ analysis tool, and a Gene Set Variation Analysis (GSVA) tool. In some embodiments, the trained machine learning classifier is selected from the group consisting of a linear regression, a logistic regression, a Ridge regression, a Lasso regression, an elastic net (EN) regression, a support vector machine (SVM), a gradient boosted machine (GBM), a k nearest neighbors (kNN), a generalized linear model (GLM), a naïve Bayes (NB) classifier, a neural network, a Random Forest (RF), a deep learning algorithm, and a combination thereof.

In some embodiments, (b) comprises comparing the data set to a reference data set. In some embodiments, the reference data set comprises gene expression measurements of reference biological samples at each of the plurality of disease-associated genomic loci. In some embodiments, the reference biological samples comprise a first plurality of biological samples obtained or derived from subjects having the disease and a second plurality of biological samples obtained or derived from subjects not having the disease.

In some embodiments, the biological sample is selected from the group consisting of: a blood sample, isolated peripheral blood mononuclear cells (PBMCs), a biopsy sample, and any derivative thereof.

In some embodiments, the method further comprises determining a likelihood of the determined disease state.

In some embodiments, the method further comprises monitoring the disease state of the subject, wherein the monitoring comprises assessing the disease state of the subject at a plurality of time points.

In some embodiments, a difference in the assessment of the disease state of the subject among the plurality of time points is indicative of one or more clinical indications selected from the group consisting of: (i) a diagnosis of the disease state of the subject, (ii) a prognosis of the disease state of the subject, and (iii) an efficacy or non-efficacy of a course of treatment for treating the disease state of the subject.

In some embodiments, the plurality of disease-associated genomic loci comprises single nucleotide polymorphisms (SNPs). In some embodiments, the SNPs comprise ancestry-specific SNPs or nonsynonymous SNPs (nsSNPs). In some embodiments, the SNPs comprise ancestry-specific SNPs. In some embodiments, the SNPs comprise nsSNPs. In some embodiments, the disease comprises a lupus condition. In some embodiments, the lupus condition is systemic lupus erythematosus (SLE), discoid lupus erythematosus (DLE), or lupus nephritis (LN). In some embodiments, the lupus condition is the SLE. In some embodiments, the disease comprises cardiovascular disease (CVD). In some embodiments, the CVD comprises coronary artery disease (CAD).

In another aspect, the present disclosure provides a computer system for determining a disease state of a subject, comprising: a database that is configured to store a dataset comprising gene expression data, wherein the gene expression data is obtained by assaying a biological sample obtained or derived from the subject to produce gene expression measurements of the biological sample at each of a plurality of disease-associated genomic loci, wherein the plurality of disease-associated genomic loci comprises at least a portion of a gene selected from the group of genes listed in Tables 1-37; and one or more computer processors operatively coupled to the database, wherein the one or more computer processors are individually or collectively programmed to: (i) computer process the data set to determine the disease state of the subject; (ii) electronically output a report indicative of the disease state of the subject.

In some embodiments, the plurality of disease-associated genomic loci comprises at least a portion of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 350, 400, 450, 500, 550, 600, 650, 700, 750, 800, 850, 900, 950, or 1000 genes selected from the group of genes listed in Tables 1-37.

In some embodiments, the one or more computer processors are individually or collectively programmed to further determine the disease state of the subject with an accuracy of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the one or more computer processors are individually or collectively programmed to further determine the disease state of the subject with a sensitivity of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the one or more computer processors are individually or collectively programmed to further determine the disease state of the subject with a specificity of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the one or more computer processors are individually or collectively programmed to further determine the disease state of the subject with a positive predictive value of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the one or more computer processors are individually or collectively programmed to further determine the disease state of the subject with a negative predictive value of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the one or more computer processors are individually or collectively programmed to further determine the disease state of the subject with an Area-Under-Curve (AUC) of at least about 0.50, at least about 0.55, at least about 0.60, at least about 0.65, at least about 0.70, at least about 0.75, at least about 0.80, at least about 0.85, at least about 0.90, at least about 0.91, at least about 0.92, at least about 0.93, at least about 0.94, at least about 0.95, at least about 0.96, at least about 0.97, at least about 0.98, at least about 0.99, or more than about 0.99.

In some embodiments, the subject has received a diagnosis of the disease. In some embodiments, the subject is suspected of having the disease. In some embodiments, the subject is at elevated risk of having the disease or having severe complications from the disease. In some embodiments, the subject is asymptomatic for the disease. In some embodiments, the one or more computer processors are individually or collectively programmed to further direct a treatment to be administered to the subject based at least in part on the determined disease state. In some embodiments, the treatment is configured to treat the disease state of the subject. In some embodiments, the treatment is configured to reduce a severity of the disease state of the subject. In some embodiments, the treatment is configured to reduce a risk of having the disease. In some embodiments, the treatment comprises a drug. In some embodiments, the drug is selected from the group listed in Tables 28-29.

In some embodiments, (i) comprises using a trained machine learning classifier to analyze the data set to determine the disease state of the subject. In some embodiments, the trained machine learning classifier is trained using gene expression data obtained by a data analysis tool selected from the group consisting of: a BIG-C™ big data analysis tool, an I-Scope™ big data analysis tool, a T-Scope™ big data analysis tool, a CellScan big data analysis tool, an MS (Molecular Signature) Scoring™ analysis tool, and a Gene Set Variation Analysis (GSVA) tool. In some embodiments, the trained machine learning classifier is selected from the group consisting of a linear regression, a logistic regression, a Ridge regression, a Lasso regression, an elastic net (EN) regression, a support vector machine (SVM), a gradient boosted machine (GBM), a k nearest neighbors (kNN), a generalized linear model (GLM), a naïve Bayes (NB) classifier, a neural network, a Random Forest (RF), a deep learning algorithm, and a combination thereof.

In some embodiments, (i) comprises comparing the data set to a reference data set. In some embodiments, the reference data set comprises gene expression measurements of reference biological samples at each of the plurality of disease-associated genomic loci. In some embodiments, the reference biological samples comprise a first plurality of biological samples obtained or derived from subjects having the disease and a second plurality of biological samples obtained or derived from subjects not having the disease.

In some embodiments, the biological sample is selected from the group consisting of: a blood sample, isolated peripheral blood mononuclear cells (PBMCs), a biopsy sample, and any derivative thereof.

In some embodiments, the one or more computer processors are individually or collectively programmed to further determine a likelihood of the determined disease state.

In some embodiments, the one or more computer processors are individually or collectively programmed to further monitor the disease state of the subject, wherein the monitoring comprises assessing the disease state of the subject at a plurality of time points.

In some embodiments, a difference in the assessment of the disease state of the subject among the plurality of time points is indicative of one or more clinical indications selected from the group consisting of: (i) a diagnosis of the disease state of the subject, (ii) a prognosis of the disease state of the subject, and (iii) an efficacy or non-efficacy of a course of treatment for treating the disease state of the subject.

In some embodiments, the plurality of disease-associated genomic loci comprises single nucleotide polymorphisms (SNPs). In some embodiments, the SNPs comprise ancestry-specific SNPs or nonsynonymous SNPs (nsSNPs). In some embodiments, the SNPs comprise ancestry-specific SNPs. In some embodiments, the SNPs comprise nsSNPs. In some embodiments, the disease comprises a lupus condition. In some embodiments, the lupus condition is systemic lupus erythematosus (SLE), discoid lupus erythematosus (DLE), or lupus nephritis (LN). In some embodiments, the lupus condition is the SLE. In some embodiments, the disease comprises cardiovascular disease (CVD). In some embodiments, the CVD comprises coronary artery disease (CAD).

In another aspect, the present disclosure provides a non-transitory computer readable medium comprising machine-executable code that, upon execution by one or more computer processors, implements a method for determining a disease state of a subject, the method comprising: (a) assaying a biological sample obtained or derived from the subject to produce a data set comprising gene expression measurements of the biological sample at each of a plurality of disease-associated genomic loci, wherein the plurality of disease-associated genomic loci comprises at least a portion of a gene selected from the group of genes listed in Tables 1-37; (b) computer processing the data set to determine the disease state of the subject; and (c) electronically outputting a report indicative of the disease state of the subject.

In some embodiments, the plurality of disease-associated genomic loci comprises at least a portion of 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 350, 400, 450, 500, 550, 600, 650, 700, 750, 800, 850, 900, 950, or 1000 genes selected from the group of genes listed in Tables 1-37.

In some embodiments, the method further comprises determining the disease state of the subject with an accuracy of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the method further comprises determining the disease state of the subject with a sensitivity of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the method further comprises determining the disease state of the subject with a specificity of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the method further comprises determining the disease state of the subject with a positive predictive value of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the method further comprises determining the disease state of the subject with a negative predictive value of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more than about 99%.

In some embodiments, the method further comprises determining the disease state of the subject with an Area-Under-Curve (AUC) of at least about 0.50, at least about 0.55, at least about 0.60, at least about 0.65, at least about 0.70, at least about 0.75, at least about 0.80, at least about 0.85, at least about 0.90, at least about 0.91, at least about 0.92, at least about 0.93, at least about 0.94, at least about 0.95, at least about 0.96, at least about 0.97, at least about 0.98, at least about 0.99, or more than about 0.99.

In some embodiments, the subject has received a diagnosis of the disease. In some embodiments, the subject is suspected of having the disease. In some embodiments, the subject is at elevated risk of having the disease or having severe complications from the disease. In some embodiments, the subject is asymptomatic for the disease. In some embodiments, the method further comprises administering a treatment to the subject based at least in part on the determined disease state. In some embodiments, the treatment is configured to treat the disease state of the subject. In some embodiments, the treatment is configured to reduce a severity of the disease state of the subject. In some embodiments, the treatment is configured to reduce a risk of having the disease. In some embodiments, the treatment comprises a drug. In some embodiments, the drug is selected from the group listed in Tables 28-29.

In some embodiments, (b) comprises using a trained machine learning classifier to analyze the data set to determine the disease state of the subject. In some embodiments, the trained machine learning classifier is trained using gene expression data obtained by a data analysis tool selected from the group consisting of: a BIG-C™ big data analysis tool, an I-Scope™ big data analysis tool, a T-Scope™ big data analysis tool, a CellScan big data analysis tool, an MS (Molecular Signature) Scoring™ analysis tool, and a Gene Set Variation Analysis (GSVA) tool. In some embodiments, the trained machine learning classifier is selected from the group consisting of a linear regression, a logistic regression, a Ridge regression, a Lasso regression, an elastic net (EN) regression, a support vector machine (SVM), a gradient boosted machine (GBM), a k nearest neighbors (kNN), a generalized linear model (GLM), a naïve Bayes (NB) classifier, a neural network, a Random Forest (RF), a deep learning algorithm, and a combination thereof.

In some embodiments, (b) comprises comparing the data set to a reference data set. In some embodiments, the reference data set comprises gene expression measurements of reference biological samples at each of the plurality of disease-associated genomic loci. In some embodiments, the reference biological samples comprise a first plurality of biological samples obtained or derived from subjects having the disease and a second plurality of biological samples obtained or derived from subjects not having the disease.

In some embodiments, the biological sample is selected from the group consisting of: a blood sample, isolated peripheral blood mononuclear cells (PBMCs), a biopsy sample, and any derivative thereof.

In some embodiments, the method further comprises determining a likelihood of the determined disease state.

In some embodiments, the method further comprises monitoring the disease state of the subject, wherein the monitoring comprises assessing the disease state of the subject at a plurality of time points.

In some embodiments, a difference in the assessment of the disease state of the subject among the plurality of time points is indicative of one or more clinical indications selected from the group consisting of: (i) a diagnosis of the disease state of the subject, (ii) a prognosis of the disease state of the subject, and (iii) an efficacy or non-efficacy of a course of treatment for treating the disease state of the subject.

In some embodiments, the plurality of disease-associated genomic loci comprises single nucleotide polymorphisms (SNPs). In some embodiments, the SNPs comprise ancestry-specific SNPs or nonsynonymous SNPs (nsSNPs). In some embodiments, the SNPs comprise ancestry-specific SNPs. In some embodiments, the SNPs comprise nsSNPs. In some embodiments, the disease comprises a lupus condition. In some embodiments, the lupus condition is systemic lupus erythematosus (SLE), discoid lupus erythematosus (DLE), or lupus nephritis (LN). In some embodiments, the lupus condition is the SLE. In some embodiments, the disease comprises cardiovascular disease (CVD). In some embodiments, the CVD comprises coronary artery disease (CAD).

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 16A shows variable importance of top 25 individual genes as determined by mean decrease in Gini impurity. FIG. 16B shows variable importance of cell modules. FIG. 16C shows that many modules shared genes, modules were de-duplicated to determine the effects on the random forest classifier. The relative importance of the full modules and de-duplicated modules was strongly correlated (Spearman's rho=0.69, p=1.94E-4). LDG: low-density granulocyte; PC: plasma cell.

FIG. 18 shows PCA and heatmap clustering of AA, EA, and NAA SLE patients for 11 GSVA enrichment modules negative in healthy controls (HC). GSVA enrichment scores were uploaded to ClustVis, and PCA plots were generated.

FIGS. 41A-41C show an example of mapping SNP associations to eQTLs and E-Genes, in accordance with disclosed embodiments. FIG. 41A shows a distribution of genomic functional categories for EA and AA SNP sets. "NT-R" is defined as Non-Traditional Regulatory: intronic or intergenic SNPs exhibiting strong regulatory potential, indicated by DNAse hypersensitivity, location within protein binding sites and evidence of epigenetic modification. "Other" non-coding regions include introns, intergenic regions, 5 kb upstream of transcription start sites and 5 kb downstream of transcription termination sites. FIG. 41B shows a summary of eQTL analysis. SLE-associated SNPs identify multiple eQTLs linked to E-Genes in the GTEx database. eQTLs and their associated E-Genes were divided into European ancestry (EA) and African ancestry (AA) groups depending on the ancestral origin of the original SLE-associated SNP. Shared E-Genes are derived from SNPs common to both EA and AA ancestries. FIG. 41C shows the number of EA and AA SNPs mapping to single E-Genes, multiple E-Genes or shared E-Genes.

FIG. 43A shows the cluster metastructure of each network and corresponding BIG-C™ categories, while FIGS. 43B-43C show the specific genes that make up each cluster.

FIG. 44A shows the fold-change variation of EA-only E-Genes. Due to the large number of DE EA E-Genes, a selection of the most highly upregulated and downregulated genes are presented. FIG. 44B shows AA-only DE E-Genes, and FIG. 44C shows DE E-Genes common to both the AA and EA gene sets. Color for all three heatmaps represents log fold change, as indicated by the legend underneath the central heatmap (FIG. 44D). Red asterisks indicate active SLEDAI datasets.

FIG. 47A shows a distribution of genomic functional categories for ancestry-specific non-HLA associated SLE SNPs (Tiers 1-3). Non-coding regions include micro (mi) RNAs, long non-coding (lnc) RNAs, introns and intergenic regions. Regulatory regions include transcription factor binding sites (TFBS), promoters, enhancers, repressors, promoter flanking regions and open chromatin. Coding regions were broken down further and include 5'UTRs, 3'UTRs, synonymous and nonsynonymous (missense and nonsense) mutations. FIG. 47B shows that functional genes predicted by SNPs are derived from 4 sources including regulatory elements (T-Genes), eQTL analysis (E-Genes), coding regions (C-Genes) and proximal gene-SNP annotation (P-Genes). FIG. 47C shows a Venn diagram depicting the overlap of all SLE-associated SNPs. FIG. 47D shows a Venn diagram depicting the overlap of and all predicted E-, T-, P-, and C-Genes.

FIG. 48A shows that ancestry-dependent and independent E-, P-, T-, and C-Genes were analyzed to determine enrichment using functional definitions from the BIG-C (Biologically Informed Gene Clustering) annotation library. Enrichment was defined as any category with an odds ratio (OR) >1 and −log 10 (p-value) >1.33. FIGS. 48B-48E shows heatmap visualizations of the top five significant IPA canonical pathways for each gene list (E-, P-, T-Genes) organized by ancestry. C-Genes were analyzed together. Top pathways with −log 10(p-value) >1.33 are listed.

FIGS. 51A-51B show that DE predicted genes and UPRs were used as input to build STRING-based PPI networks, visualized in CytoScape, and clustered with MCODE. Individual clusters were then analyzed by BIG-C and IPA to identify those molecules and pathways highly associated with disease. A total of 45 pathways were representative of EA DE genes and UPRs, with the largest clusters 3 and 1 heavily involved in pattern recognition receptor signaling (activation of IRFs by cytosolic PRRs and role of RIG-I in antiviral immunity).

FIGS. 52A-52B show that the AA network was smaller (FIG. 52A), containing fewer predicted genes and associated UPRs, yet shared multiple pathways with EA, including B cell receptor signaling, GPCR signaling, opioid signaling, phagocyte maturation and hepatic cholestasis, a pathway involved in bile acid synthesis (FIG. 52B).

FIGS. 53A-53B show that pathways exemplified by ancestry-independent genes were a blend of both EA and AA pathways. For example, common pathways included IL12 signaling and production by macrophages, TLR signaling and activation of IRFs by cytosolic PRRs, pathways that were predicted by EA genes and UPRs, as well as PRRs in the recognition of bacteria and virus, a pathway shared with AA.

FIGS. 59A-59B show key pathways determined by EA genes and upstream regulators. (a) Differentially expressed EA genes and their upstream regulators (UPRs) were used to create STRING-based PPI networks. EA genes and transcription factors identified as UPRs are indicated. Clusters were generated via CytoScape using the MCODE plugin. (b) Top IPA canonical pathways representing individual clusters and enriched (OR >1, p-value <0.05) BIG-C categories are listed; heatmap depicts the −log (p-value) for significant IPA pathways. Unique pathways are indicated by asterisks. Predicted EA genes and select drugs acting on gene targets and pathways are listed. CoLT scores (−16-+11) are in superscript; # denotes FDA-approved drugs, ^ denotes drugs in development. Standard of care (SOC).

FIGS. 61A-61B show key pathways determined by shared genes and upstream regulators. (a) Differentially expressed shared genes and their upstream regulators (UPRs) were used to create STRING-based PPI networks. DE shared genes and transcription factors identified as UPRs and indicated. Clusters were generated via CytoScape using the MCODE plugin. (b) Top IPA canonical pathways representing individual clusters and enriched (OR >1, p-value <0.05) BIG-C categories are listed; heatmap depicts the −log (p-value) for significant IPA pathways. Unique pathways are indicated by asterisks. Predicted shared genes and select drugs acting on gene targets and pathways are listed. CoLT scores (−16-+11) are in superscript; # denotes FDA-approved drugs; ^ denotes drugs in development. Standard of care (SOC).

FIG. 63 shows SNPs impact multiple E-Genes within a functional protein-interaction based molecular network. Protein-protein interaction networks and clusters were generated via CytoScape using the STRING and MCODE plugins. The network was constructed of SNP-predicted E-Genes; grouped E-Genes linked to one SNP are indicated with boxing.

FIGS. 70A-70D show examples of key pathways motivated by EA-predicted genes (FIG. 70A) and AS-predicted genes (FIG. 70C) and upstream regulators, including cluster metastructures generated based on PPI networks, clustered using MCODE and visualized in Cytoscape, where cluster size indicates the number of genes per cluster, edge weight indicates the number of inter-cluster connections, and color indicates the number of intra-cluster connections, and functional enrichment for each cluster was determined by BIG-C; and heatmap results indicating the top five canonical EA-motivated pathways (FIG. 70B) and AS-motivated pathways (FIG. 70D), respectively, representing individual clusters (−log (p-value) >1.33), where enriched BIG-C and I-Scope categories (OR >1; p-value <0.05) are listed for each cluster, and bold text indicates categories with the highest OR and lowest p-value.

FIGS. 71A-71C show examples of key pathways determined by shared genes and upstream regulators, including cluster metastructures generated based on PPI networks, clustered using MCODE, and visualized in Cytoscape, where cluster size indicates the number of genes per cluster, edge weight indicates the number of inter-cluster connections, and color indicates the number of intra-cluster connections, and functional enrichment for each cluster was determined by BIG-C (FIG. 71A); a heatmap indicating the top five canonical pathways representing individual clusters (−log (p-value) >1.33), where enriched BIG-C and I-Scope categories (OR >1; p-value <0.05) are listed for each cluster, and bold text indicates categories with the highest OR and lowest p-value (FIG. 71B); and a Venn diagram showing the number of overlapping pathways motivated by EA or AS predicted genes and their associated UPRs, where representative pathways are listed (FIG. 71C).

FIGS. 72A-72D show examples of Asian GWAS genes motivating similar pathways predicted by the AS Immunochip, including Venn diagrams depicting the ancestral overlap of all Immunochip and validation GWAS SNPs (FIG. 72A) and associated genes (FIG. 72B); key pathways determined by AS validation GWAS associated genes and upstream regulators, where cluster metastructures were generated based on PPI networks, clustered using MCODE, and visualized in Cytoscape, where cluster size indicates the number of genes per cluster, edge weight indicates the number of inter-cluster connections, and color indicates the number of intra-cluster connections (FIGS. 72C-72D). Functional enrichment for each cluster was determined by BIG-C (FIG. 72C). A heatmap indicates the top five canonical pathways representing individual clusters (−log (p-value) >1.33), where enriched BIG-C and I-Scope categories (OR >1; p-value <0.05) are listed for each cluster, and bold text indicates categories with the highest OR and lowest p-value (FIG. 72D).

(FIG. 82A) Venn diagram depicting the ancestral overlap of all SLE-associated Immunochip SNPs. (FIG. 82B) Distribution of genomic functional categories for all EA and AsA non-HLA associated SLE SNPs. (FIG. 82C) Functional SNP-associated genes are derived from 4 sources, including eQTL analysis (E-Genes), regulatory regions (T-Genes), coding regions (C-Genes) and proximal gene-SNP annotation (P-Genes). (FIGS. 82D-82E) Venn diagrams showing the overlap of all EA (FIG. 82D) and AsA (FIG. 82E) associated E-, T-, C- and P-Genes.

(FIG. 83A) Venn diagram depicting the overlap between all EA- and AsA-SNP associated genes. (FIG. 83B) Ancestry-dependent and independent SNP-associated genes were analyzed to determine enrichment using functional definitions from the BIG-C (Biologically Informed Gene Clustering) annotation library. Enrichment was defined as any category with an odds ratio (OR) >1 and a −log (p-value) >1.33. (FIG. 83C) I-Scope hematopoietic cell enrichment is defined as any category with an OR >1, left scale; indicated by the dotted line and −log (p-value) >1.33 indicated by color scale. (FIGS. 83D-83E) Heatmap visualization of the top five significant IPA canonical pathways and gene ontogeny (GO) terms for each gene list organized by ancestry. Top pathways with −log (p-value) >1.33 are listed.

FIGS. 85A-85C show key pathways determined by shared genes. (FIG. 85A) Cluster metastructures using the shared (EA and AsA) cohort of SNP-predicted genes were generated based on PPI networks, clustered using MCODE and visualized in Cytoscape. Cluster size indicates the number of genes per cluster, edge weight indicates the number of inter-cluster connections and color indicates the number of intra-cluster connections. Functional enrichment for each cluster was determined by BIG-C. (FIG. 85B) Heatmap indicates the top five canonical pathways representing individual clusters (−log (p-value) >1.33). Enriched BIG-C and I-Scope categories (OR >1; p-value <0.05) are listed for each cluster. Bold text indicates categories with the highest OR and lowest p-value. (FIG. 85C) Venn diagram showing the number of overlapping pathways motivated by EA or AsA predicted genes and their associated UPRs. Representative pathways are listed.

Figure 88A:
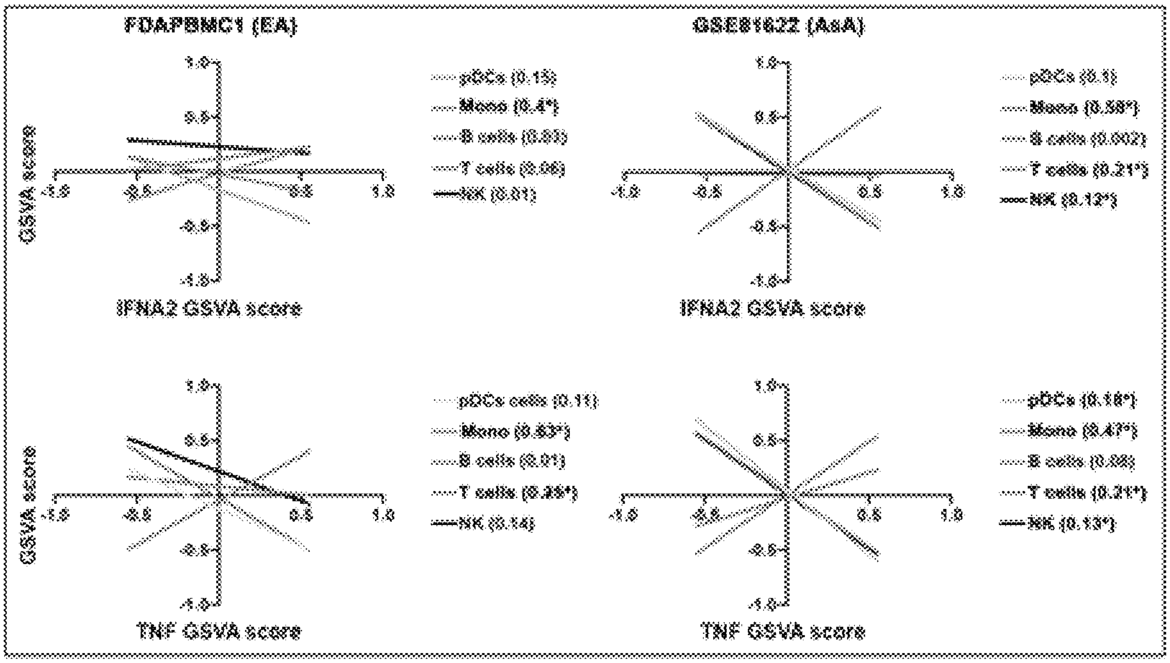
Figure 88B:
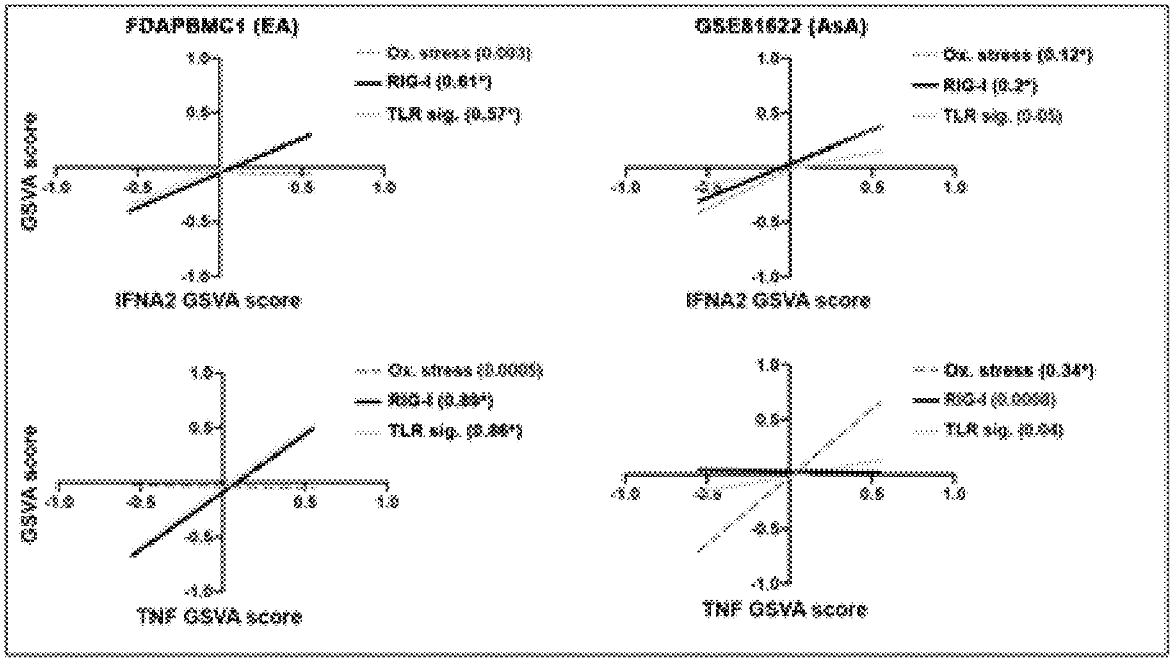
Figure 88C:
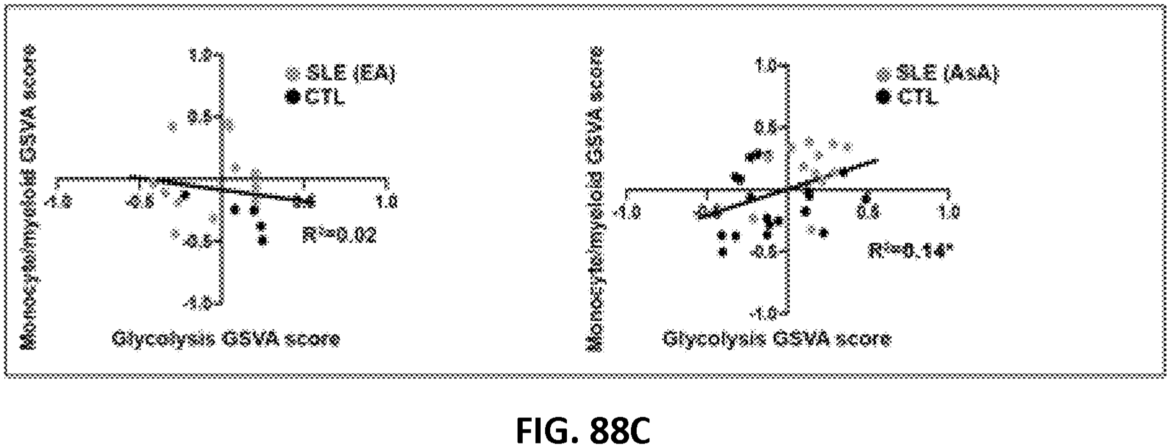

FIGS. 88A-88C show the use of linear regression to examine the relationship between cell types, processes and inflammatory cytokines. Linear regression analysis showing the relationship between GSVA scores for IFNA2 and TNF and individual cell types (pDCs, monocyte/myeloid, B cells, T cells and NK cells) (FIG. 88A) or cellular processes (oxidative stress, RIG-I and TLR signaling) (FIG. 88B) for FDAPBMC1 (EA) and GSE81622 (AsA). Transcripts overlapping both categories were removed. Categories with linear regression p values <0.05 are in bold; R2 predictive values are listed after the GSVA enrichment category. *Asterisks indicate significant relationship between categories. (FIG. 88C) Scatter plots showing the relationship between monocyte/myeloid GSVA scores and enrichment scores for glycolysis in EA and AsA. Blue; EA SLE patients, red, AsA SLE patients, black; healthy controls. Predictive R2 value is listed, *asterisks indicate significant relationships between categories.

Figure 89A:
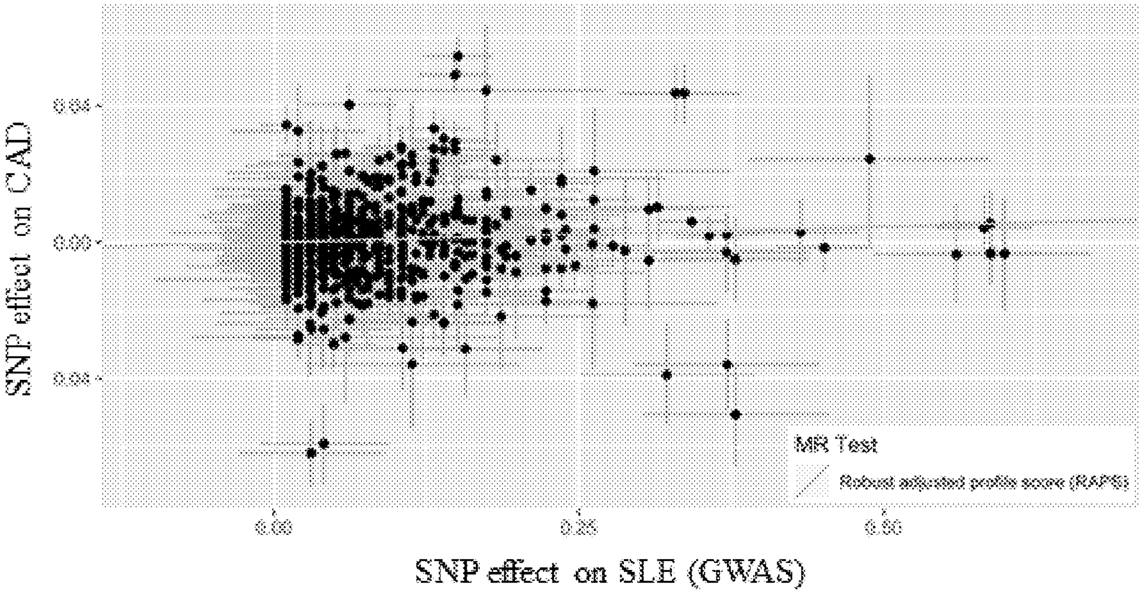
Figure 89B:
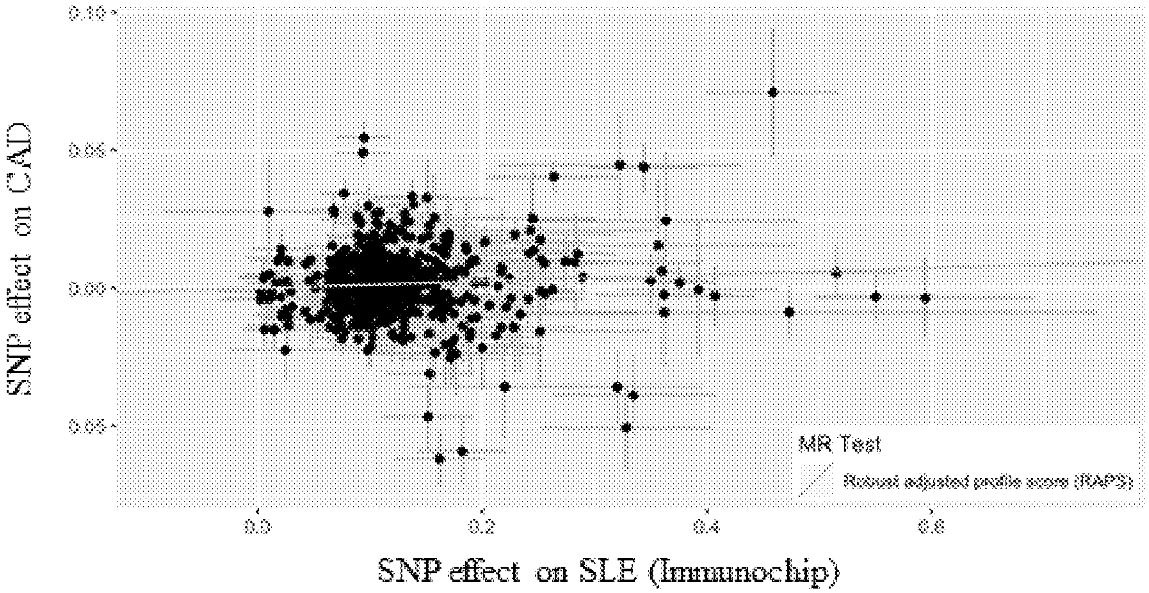

FIGS. 89A-89B show positive causal estimates of SLE on CAD by MR using 838 non-HLA SNPs from Immunochip study. MR was performed and visualized using the TwoSampleMR package in R. 838 SLE-associated non-HLA SNPs identified in a large trans-ancestral Immunochip study were used as instrumental variables for SLE. Summary statistics from the SLE GWAS (FIG. 89A) and from the SLE Immunochip study (FIG. 89B) were used for the exposure in separate analyses. Summary statistics from the UK Biobank's CAD GWAS were used for the outcome.

Figure 90A:
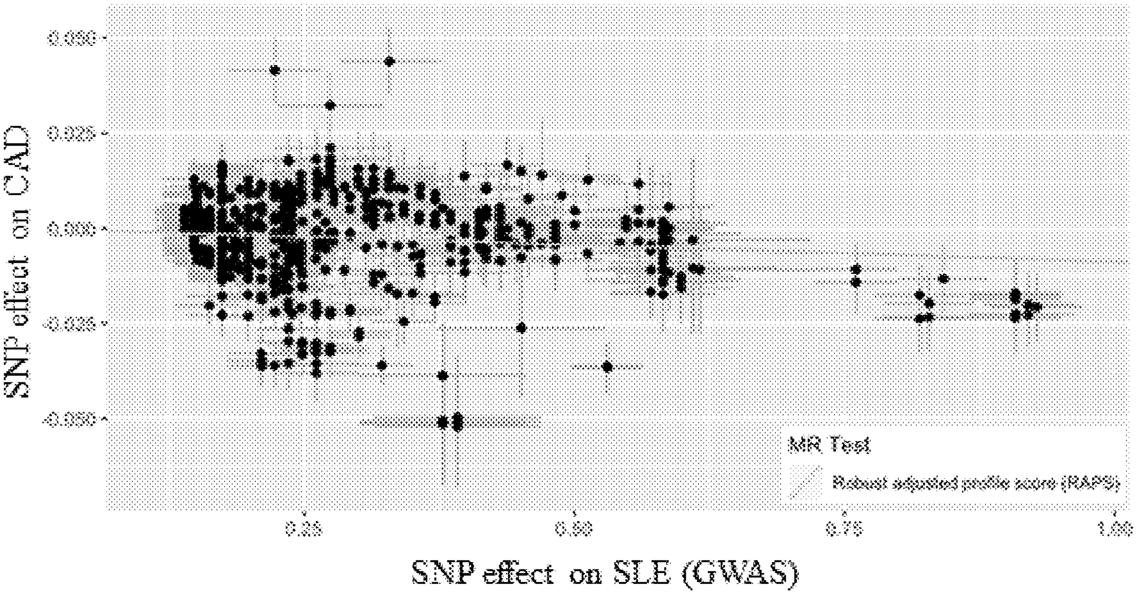
Figure 90B:
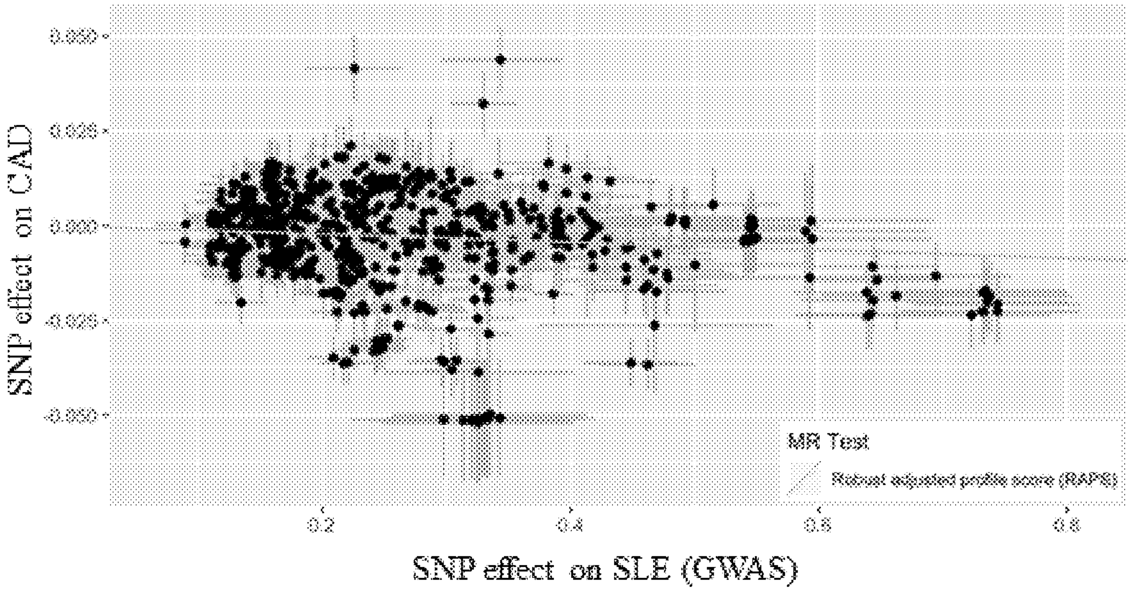

FIGS. 90A-90B show negative causal estimates of SLE on CAD by MR including HLA SNPs as instrumental variables. MR was performed and visualized using the TwoSampleMR package in R. 970 SNPs significantly (1E-6) associated with SLE in both the Immunochip and GWAS studies were used as instrumental variables for SLE. Summary statistics from the SLE GWAS (FIG. 90A) and from the SLE Immunochip study (FIG. 90B) were used for the exposure in separate analyses. Summary statistics from the UK Biobank's CAD GWAS were used for the outcome.

Figure 91A:
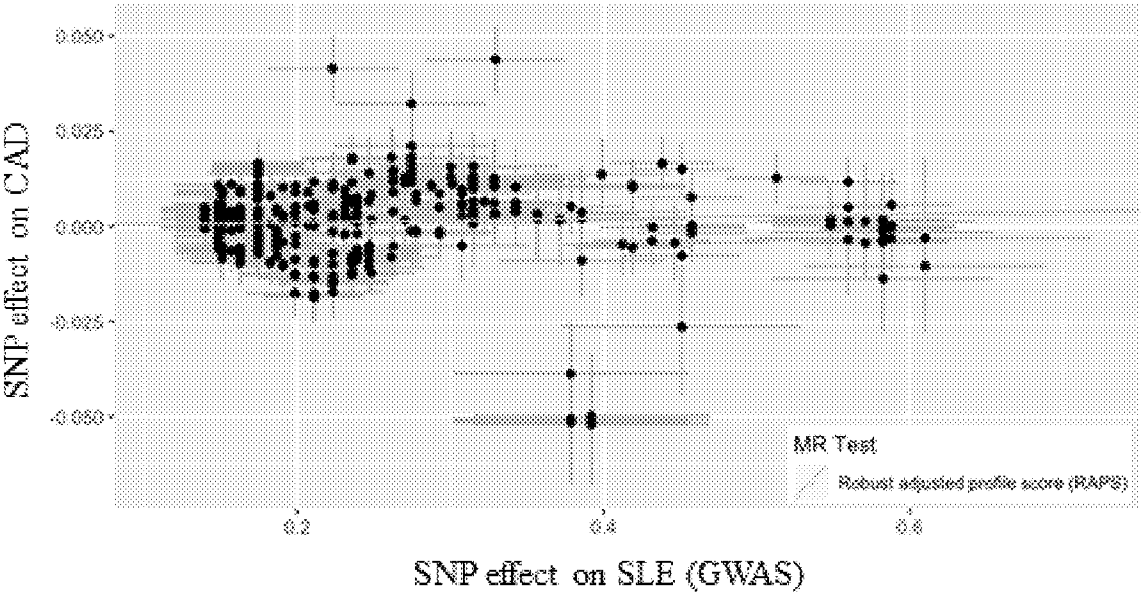
Figure 91B:
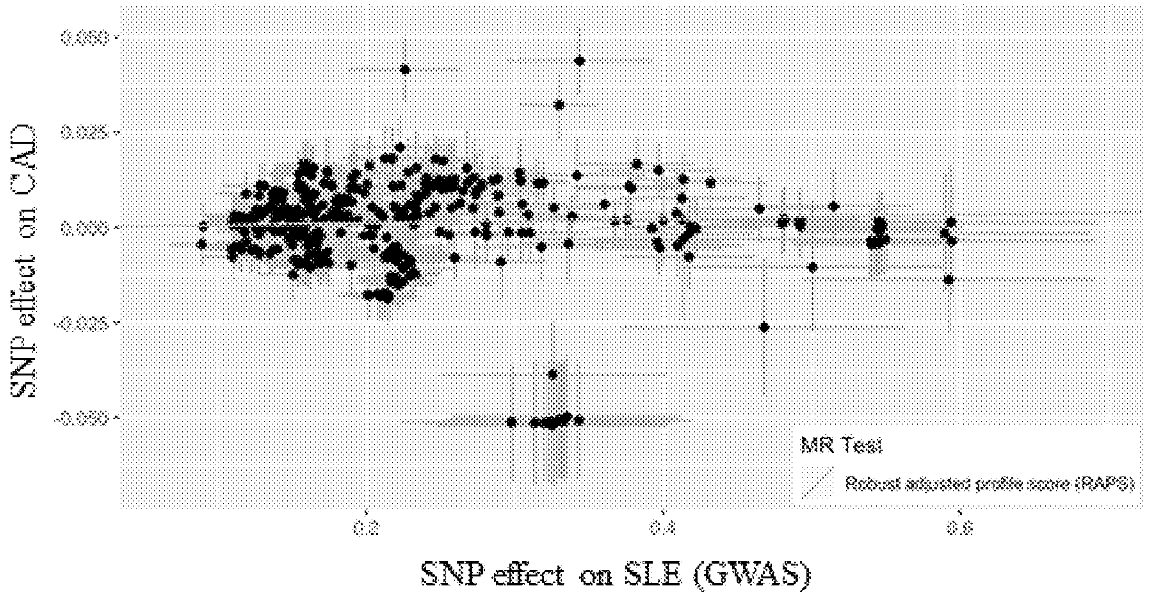

FIGS. 91A-91B show positive causal estimates of SLE on CAD by MR excluding HLA SNPs as instrumental variables. MR was performed and visualized using the TwoSampleMR package in R. 612 SNPs significantly (1E-6) associated with SLE in both the Immunochip and GWAS studies were used as instrumental variables for SLE. Summary statistics from the SLE GWAS (FIG. 91A) and from the SLE Immunochip study (FIG. 91B) were used for the exposure in separate analyses. Summary statistics from the UK Biobank's CAD GWAS were used for the outcome.

Figure 92A:
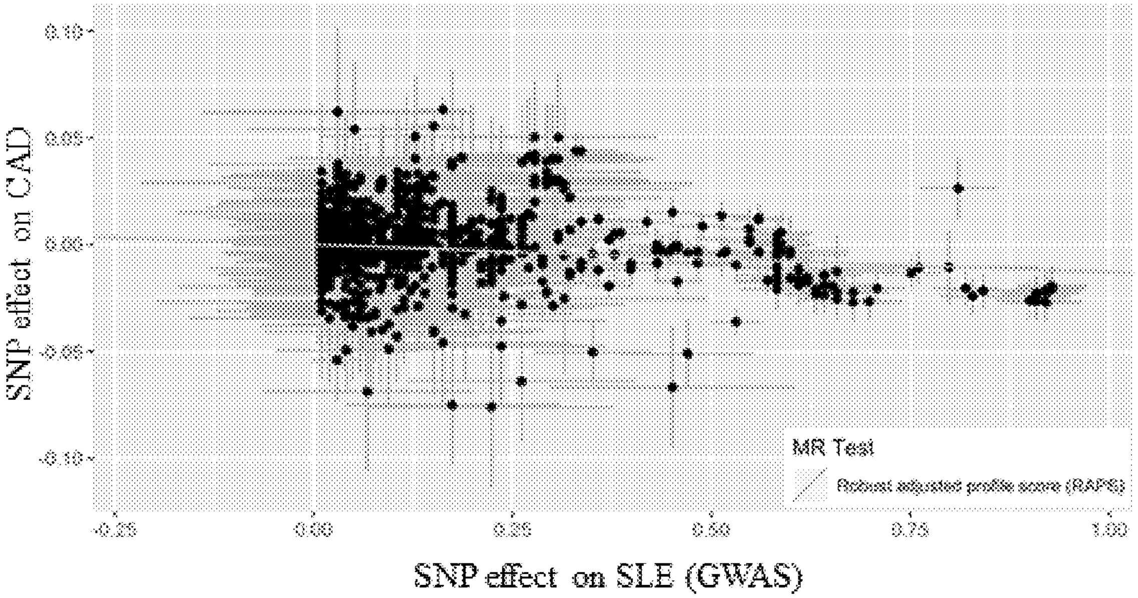
Figure 92B:
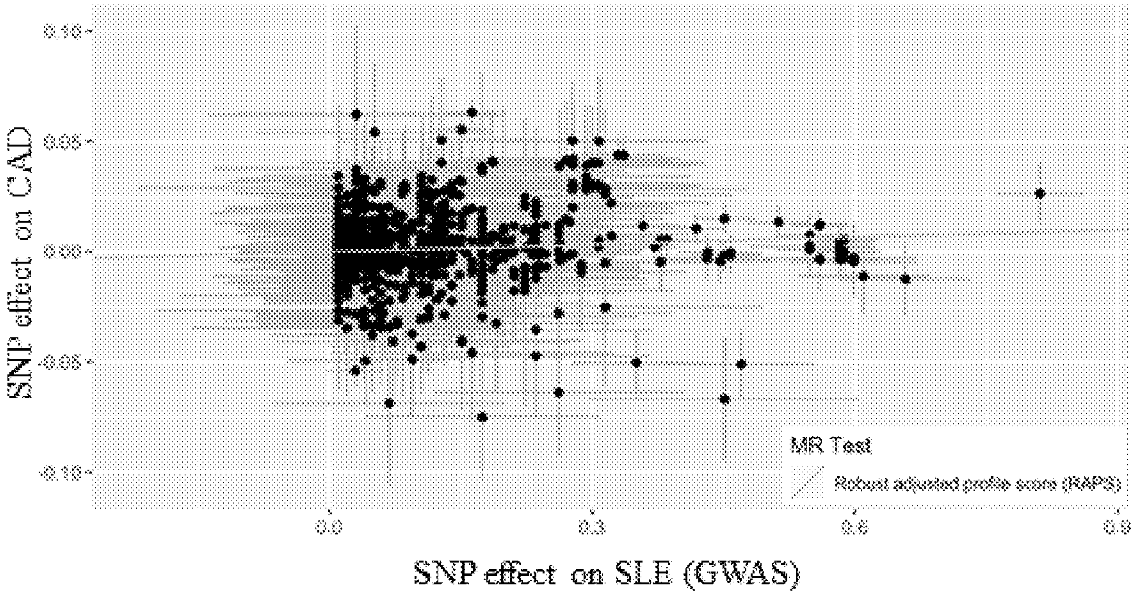

FIGS. 92A-92B show causal estimates of SLE on CAD by MR with and without SLE-associated HLA SNPs from PhenoScanner as instrumental variables. MR was performed and visualized using the TwoSampleMR package in R. SNPs significantly (1E-6) associated with SLE from the PhenoScanner database were used as instrumental variables for SLE with (FIG. 92A) and without (FIG. 92B) SNPs in the HLA region. Summary statistics from the SLE GWAS were used for the exposure and summary statistics from the UK Biobank's CAD GWAS were used for the outcome.

FIGS. 93A-93B show negative causal estimates of SLE on CAD by MR using SLE-associated SNPs by chromosome as instrumental variables. MR was performed and visualized using the TwoSampleMR package in R. 970 SNPs significantly (1E-6) associated with SLE in both the Immunochip and GWAS studies were used as instrumental variables for SLE by chromosome in separate analyses. Summary statistics from the SLE GWAS (FIGS. 93A-93B, top) and from the SLE Immunochip study (FIGS. 93A-93B, bottom) were used for the exposure in separate analyses for validation. Summary statistics from the UK Biobank's CAD GWAS were used for the outcome.

FIGS. 94A-94D show positive Causal estimates of SLE on CAD by MR using SLE-associated SNPs by chromosome as instrumental variables. MR was performed and visualized using the TwoSampleMR package in R. 970 SNPs significantly (1E-6) associated with SLE in both the Immunochip and GWAS studies were used as instrumental variables for SLE by chromosome in separate analyses. Summary statistics from the SLE GWAS (FIGS. 94A-94D, top) and from the SLE Immunochip study (FIGS. 94A-94D, bottom) were used for the exposure in separate analyses for validation. Summary statistics from the UK Biobank's CAD GWAS were used for the outcome.

Figure 95A:
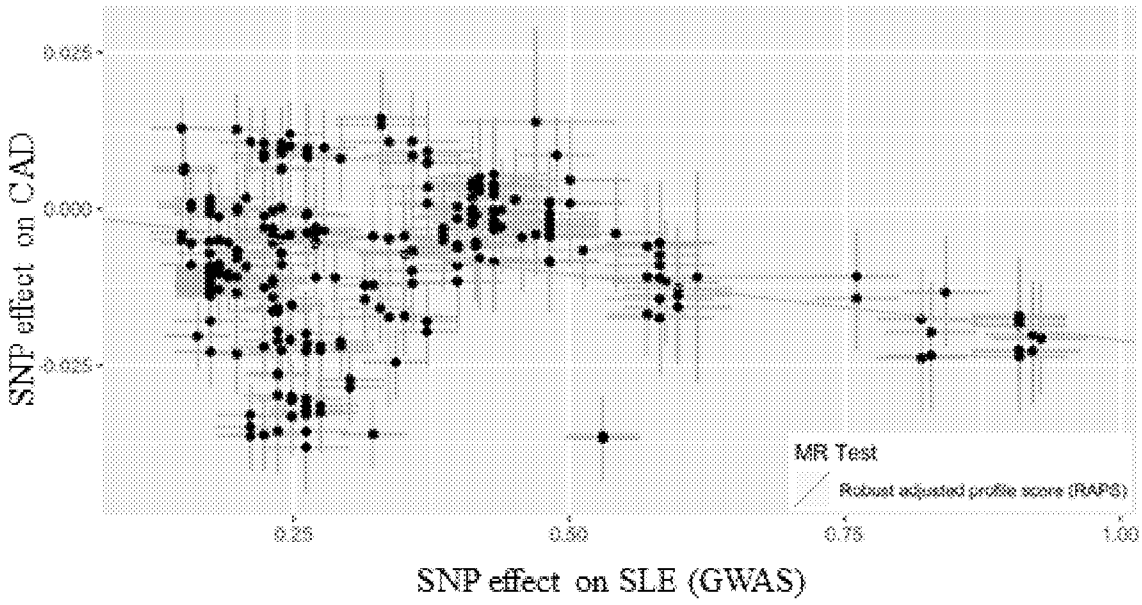
Figure 95B:
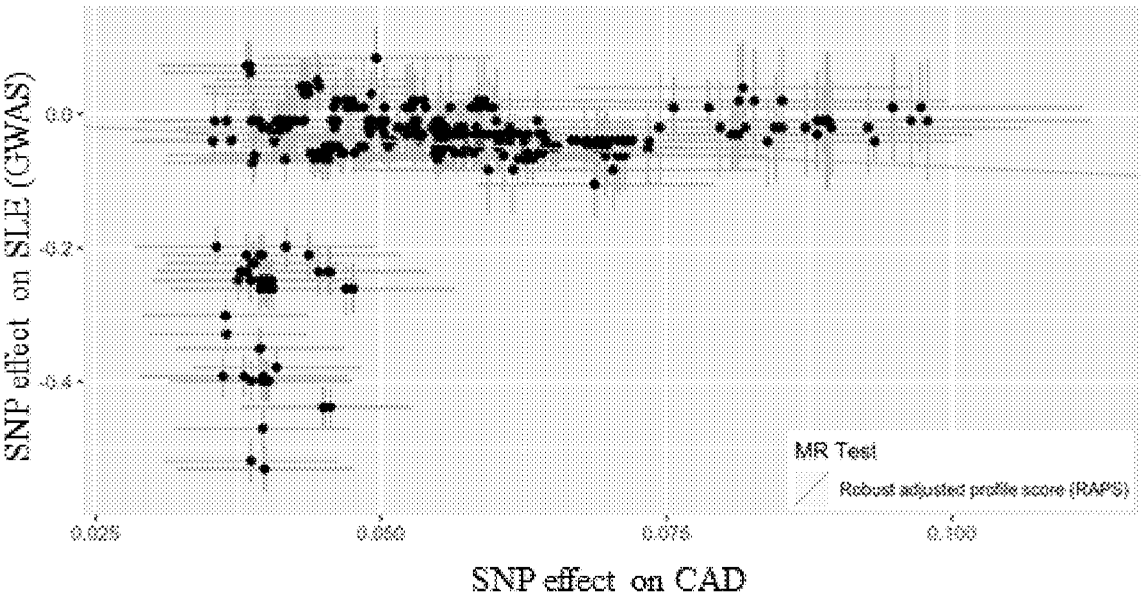

FIGS. 95A-95B show negative causal estimates of SLE-associated HLA SNPs on CAD and CAD-associated HLA SNPs on SLE by MR. MR was performed and visualized using the TwoSampleMR package in R. 970 SNPs significantly (1E-6) associated with SLE in both the Immunochip and GWAS studies were used as instrumental variables for SLE by chromosome in separate analyses. Summary statistics from the SLE GWAS (FIG. 95A) and from the SLE Immunochip study (FIG. 95B) were used for the exposure in separate analyses for validation. Summary statistics from the UK Biobank's CAD GWAS were used for the outcome.

Figure 96:
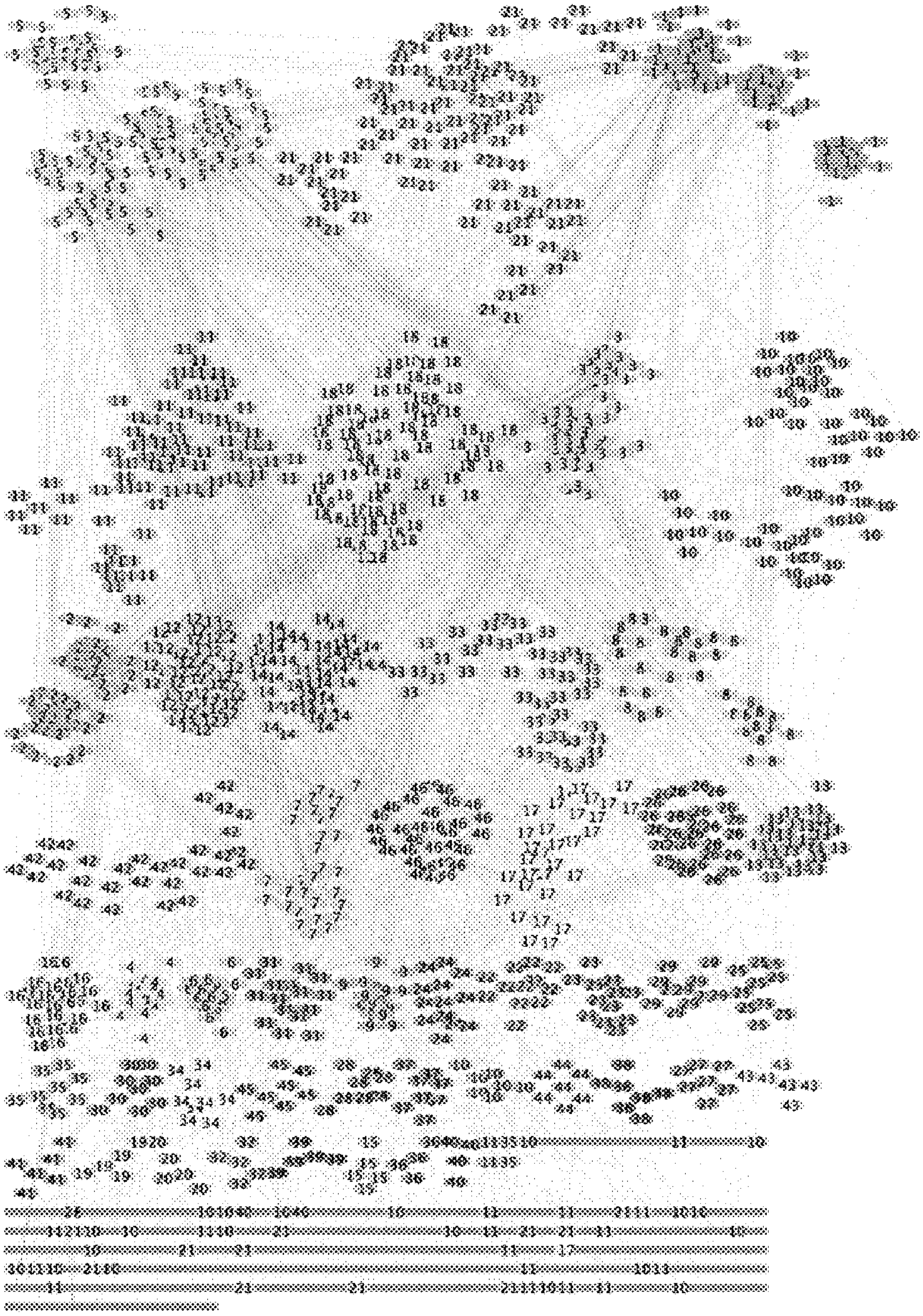

FIG. 96 shows a clustered protein-protein interaction network consisting of putative SLE genes with causal implications on CAD. Protein-protein interactions of predicted genes were obtained with STRING, visualized with Cytoscape and clustered using MCODE. Green nodes represent SNP-predicted genes; blue nodes represent UPRs.

Figure 97:
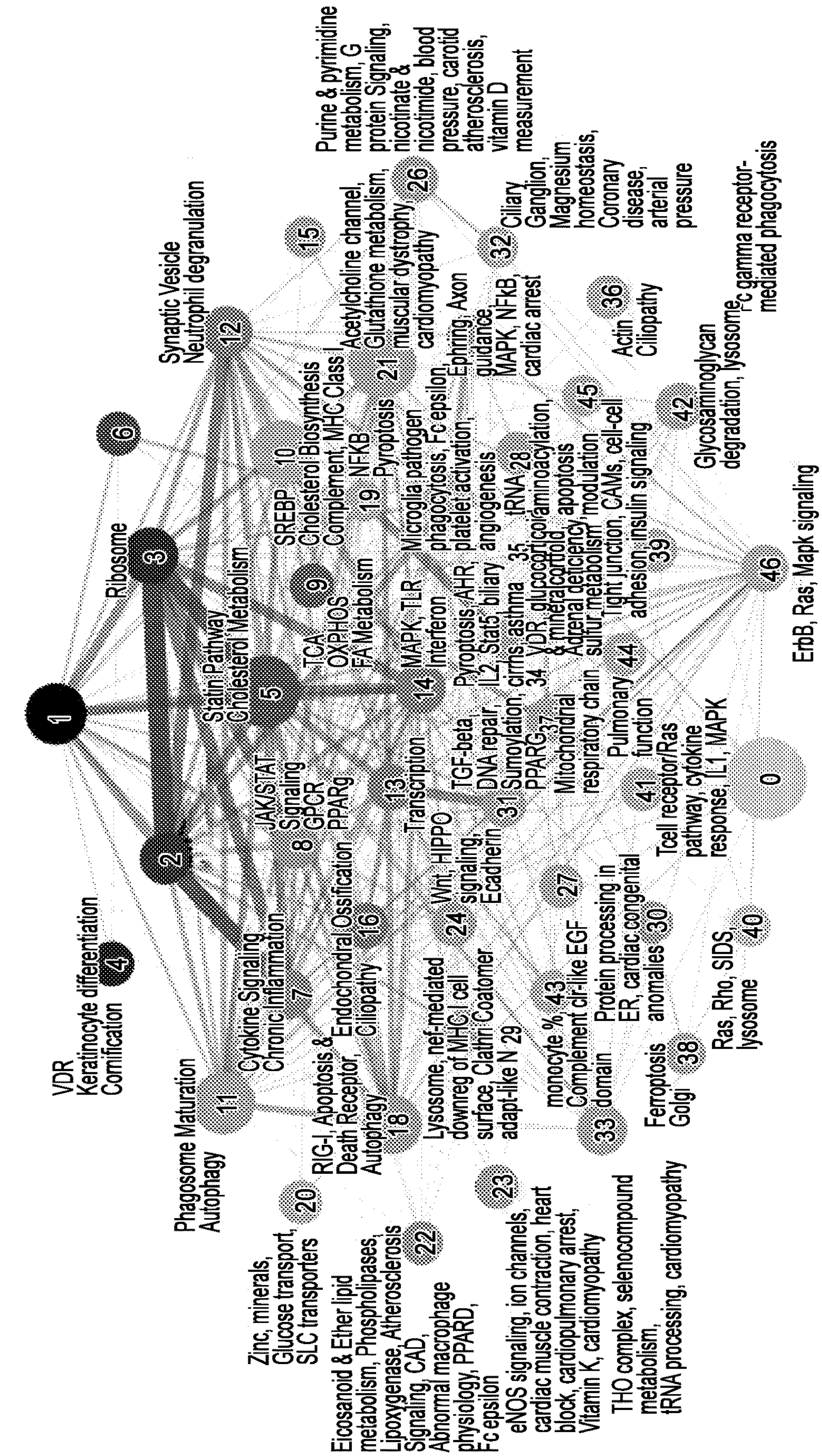

FIG. 97 shows a pathway analysis of metaclusters consisting of putative SLE genes with causal implications on CAD. MCODE clusters were further simplified into metaclusters where the size of each cluster represents the number of genes in the cluster, the shading represents the number of intra-cluster connections normalized by the number of genes in the cluster (darker colors representing higher connection/gene ratios), and the size and shading of the inter-cluster edges represents the number of inter-cluster connections normalized by the average number of genes between the two clusters.

Figure 98A:
Figure 98B:
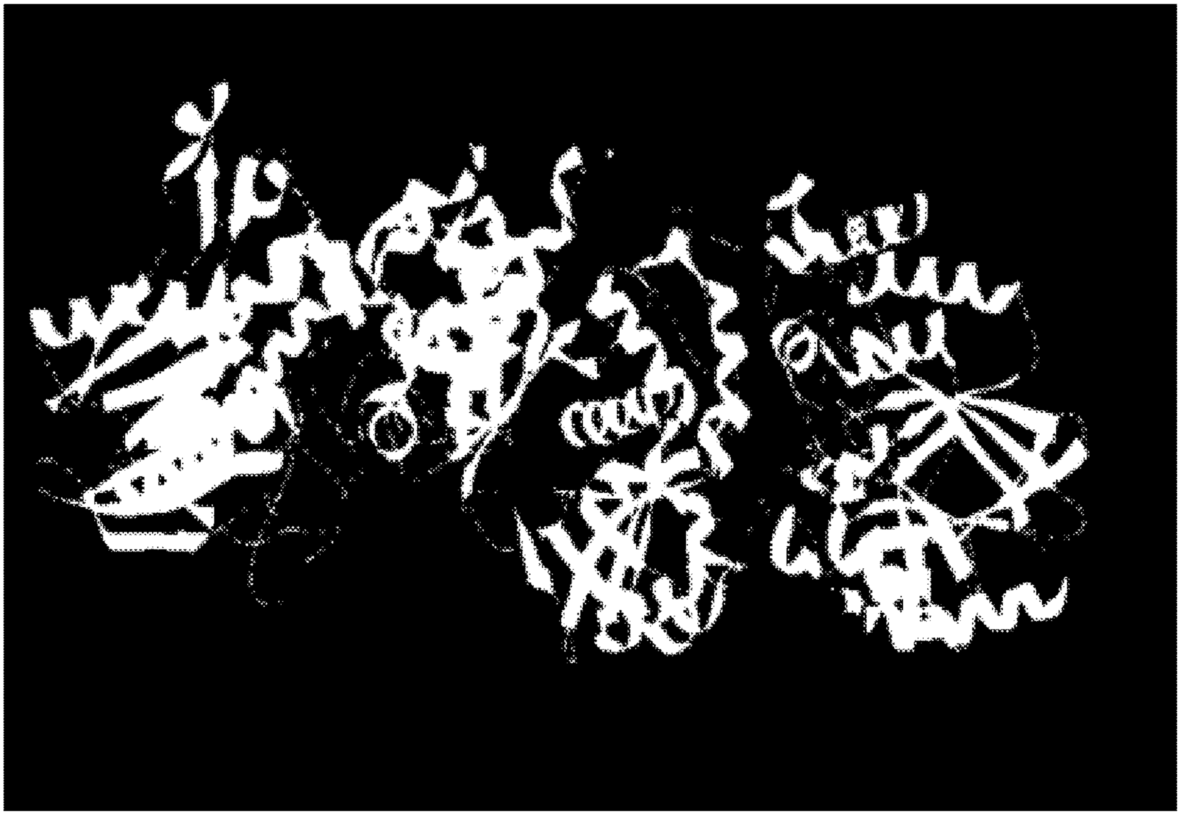

FIGS. 98A-98B show front (FIG. 98A) and side (FIG. 98B) views of NT5E showing the position of rs2225925 (arrow). Images from the PDB.

Figure 99:
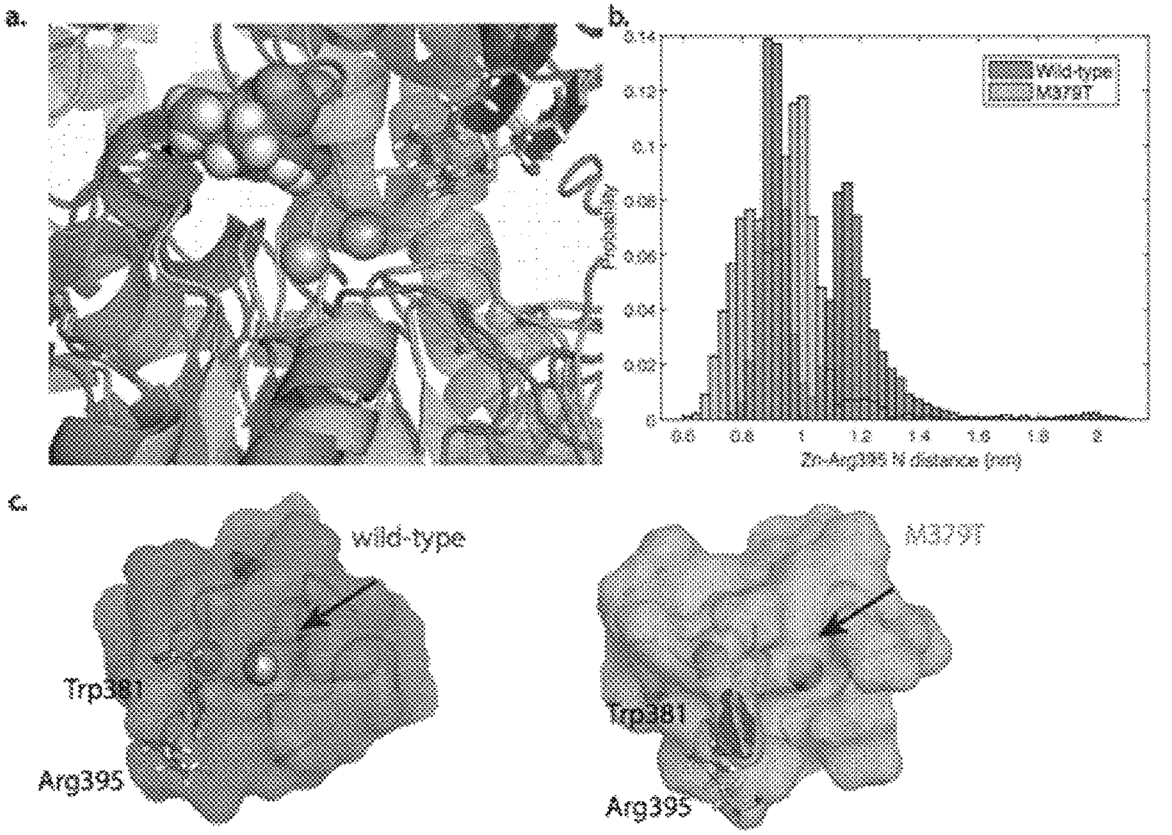

FIGS. 99A-99C show that M379T mutation decreased NT5E activity by occluding catalytic site in simulations. Molecular dynamics simulations of wild-type and M379T mutants of NT5E in the open, active state show local opening and closing of the catalytic site in the wild-type simulation but not in the mutant simulation. The mutation is rendered in FIG. 99A in spheres, with a critical Arg395 residue in sticks and the required zinc atoms in silver spheres.

FIG. 99B shows opening and closing of the binding site as measured by Arg395 nitrogen-zinc minimum distances over the simulations. FIG. 99C contrasts the binding pockets of open wild-type and locally closed mutant enzymes in the simulations. Trp381, located on the same loop as residue 379, plays a critical role in closing access to the binding site (indicated in arrows).

Figure 100:
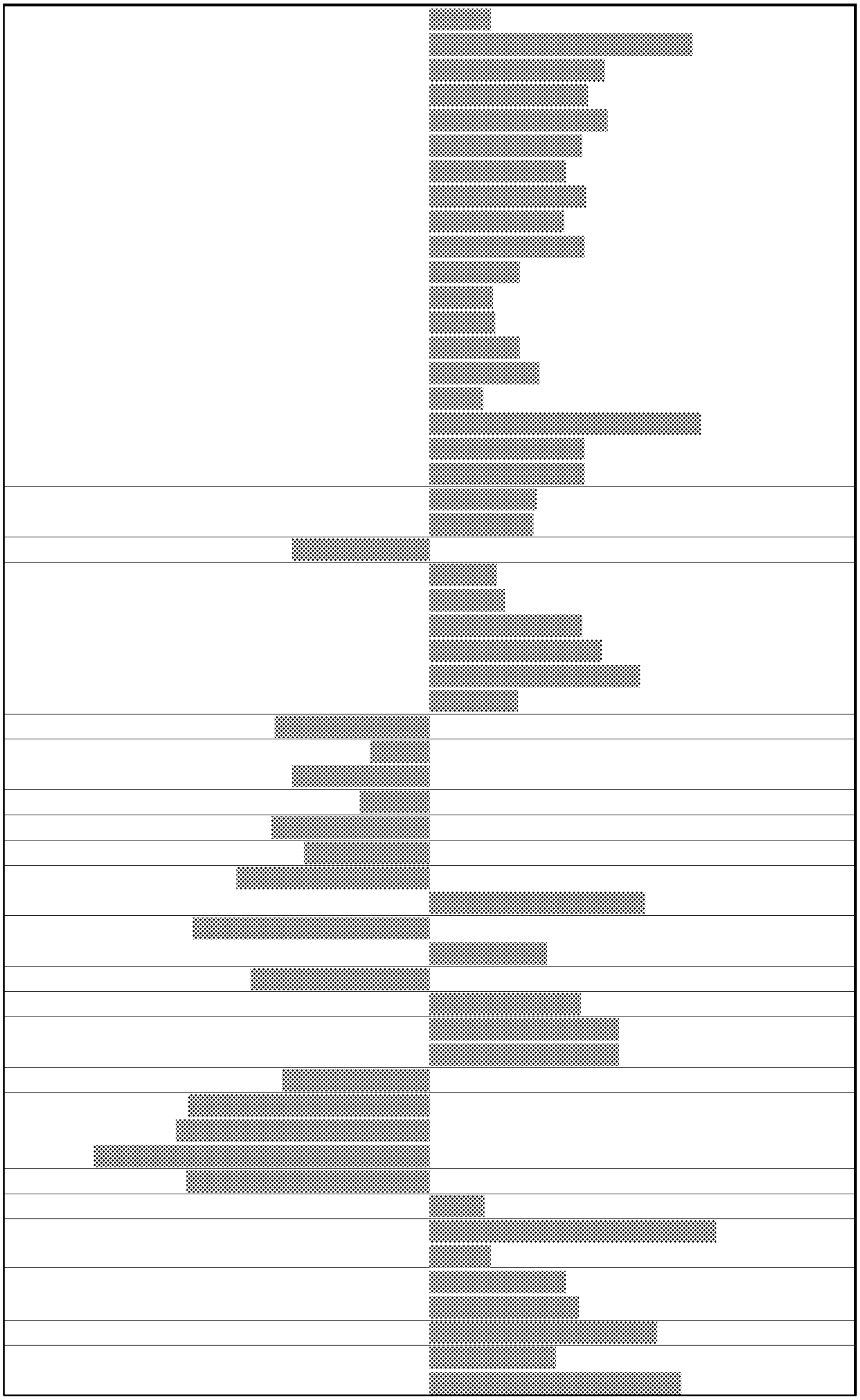

FIG. 100 shows differential expression looking at NT5E in SLE datasets.

Figure 101A:
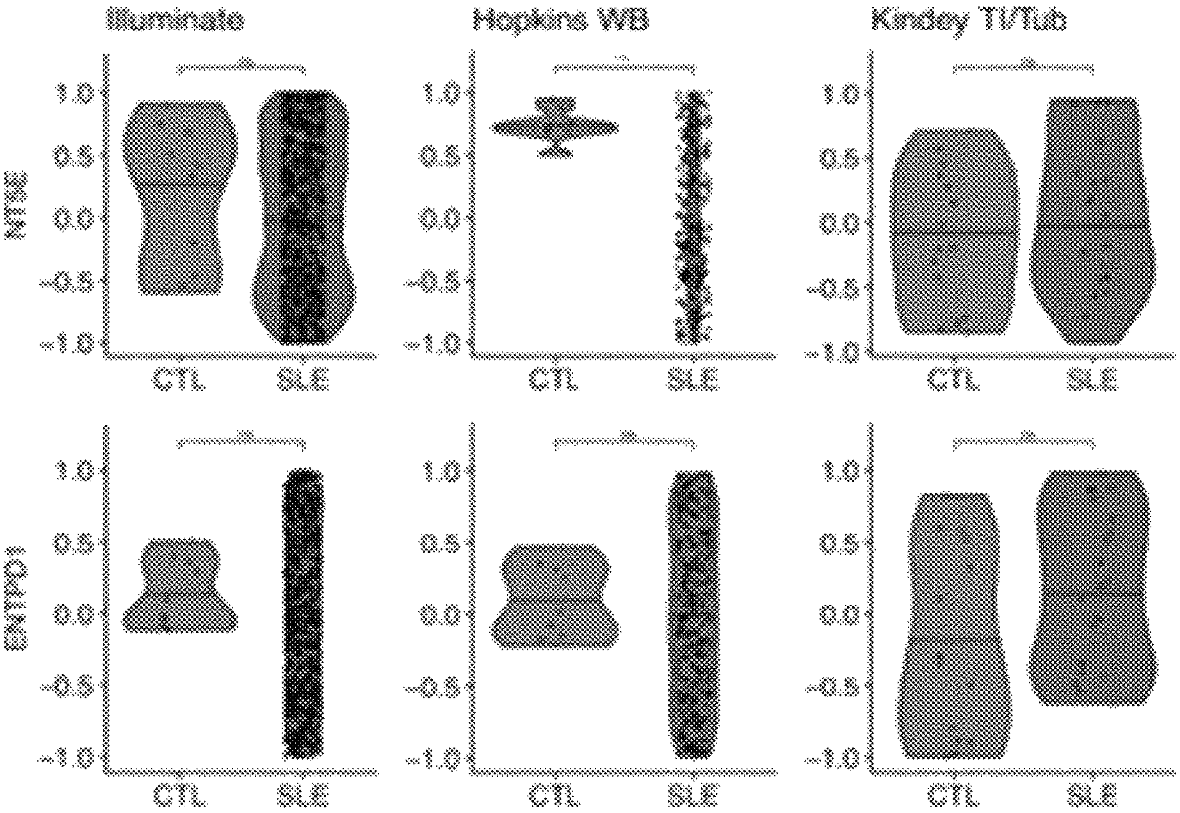
Figure 101A:
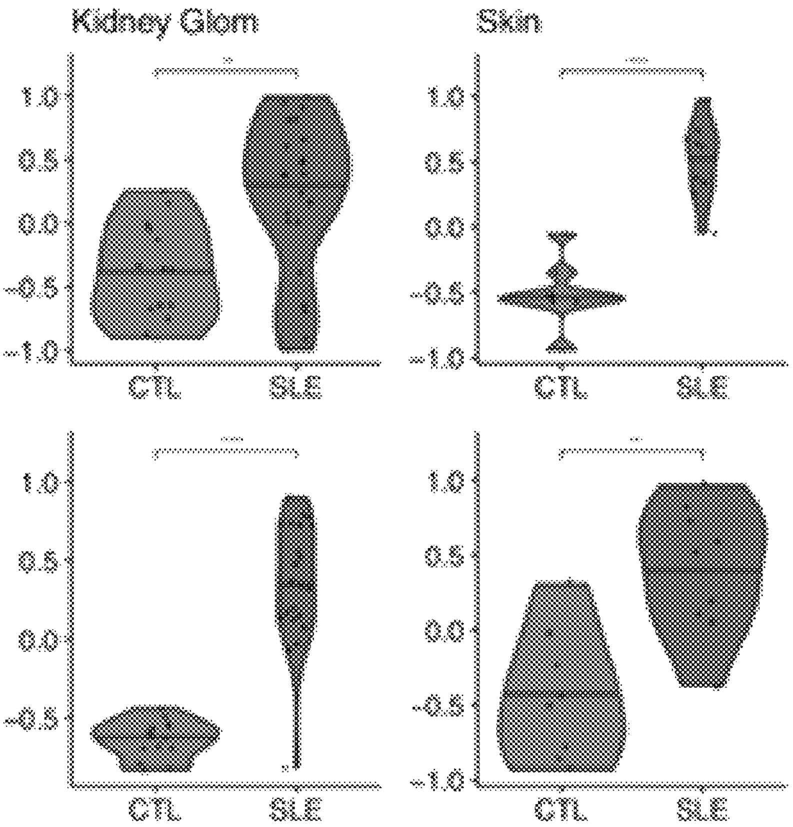
Figure 101B:
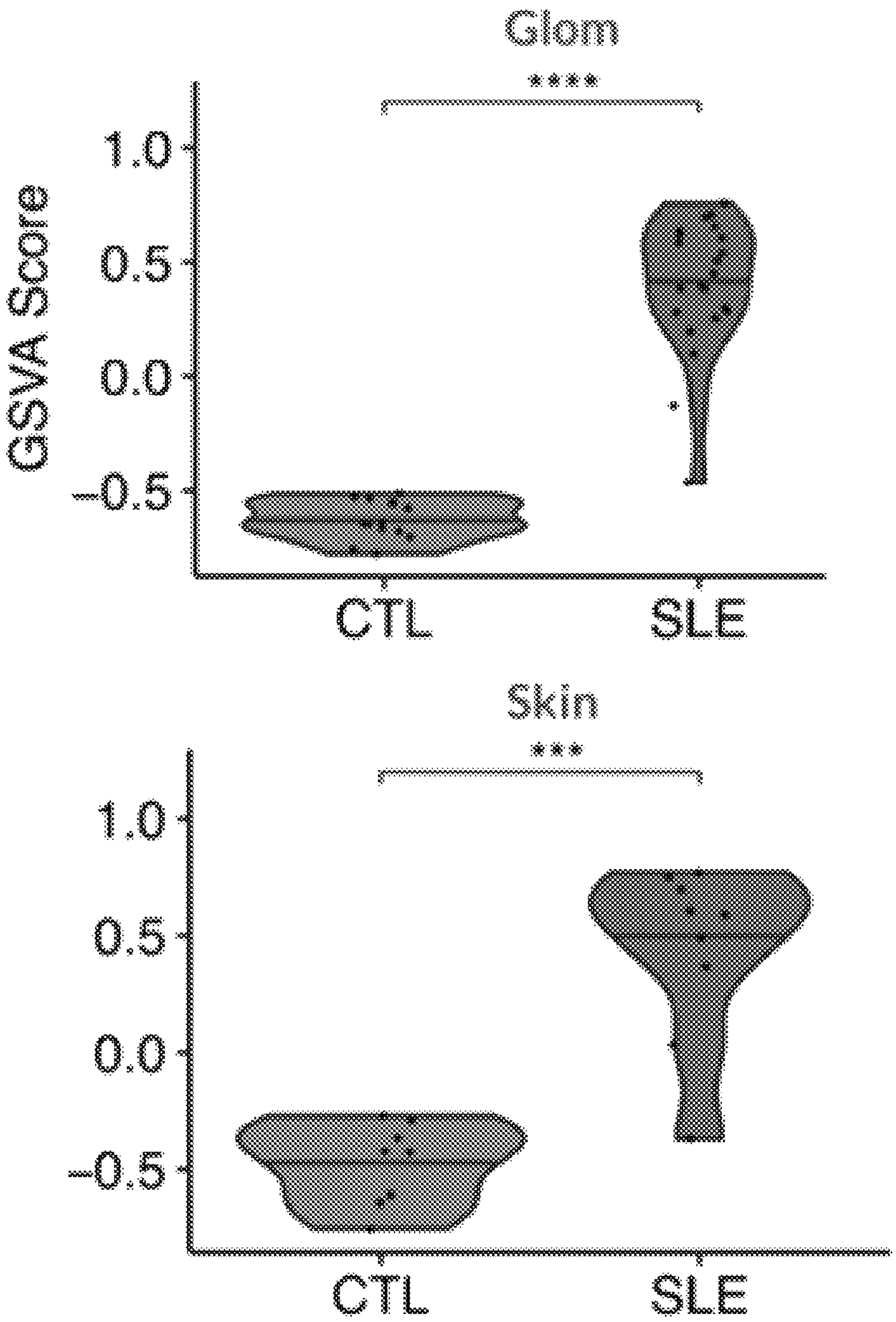

FIGS. 101A-101B show GSVA expression probing. GSVA was used to isolate datasets of interest, looking at expression of both NT5E and ENTPD1 across 5 target datasets (FIG. 101A). Once a NT5E signature was developed, GSVA was then run to compare enrichment in CTL and SLE cohorts (FIG. 101B).

Figure 102A:
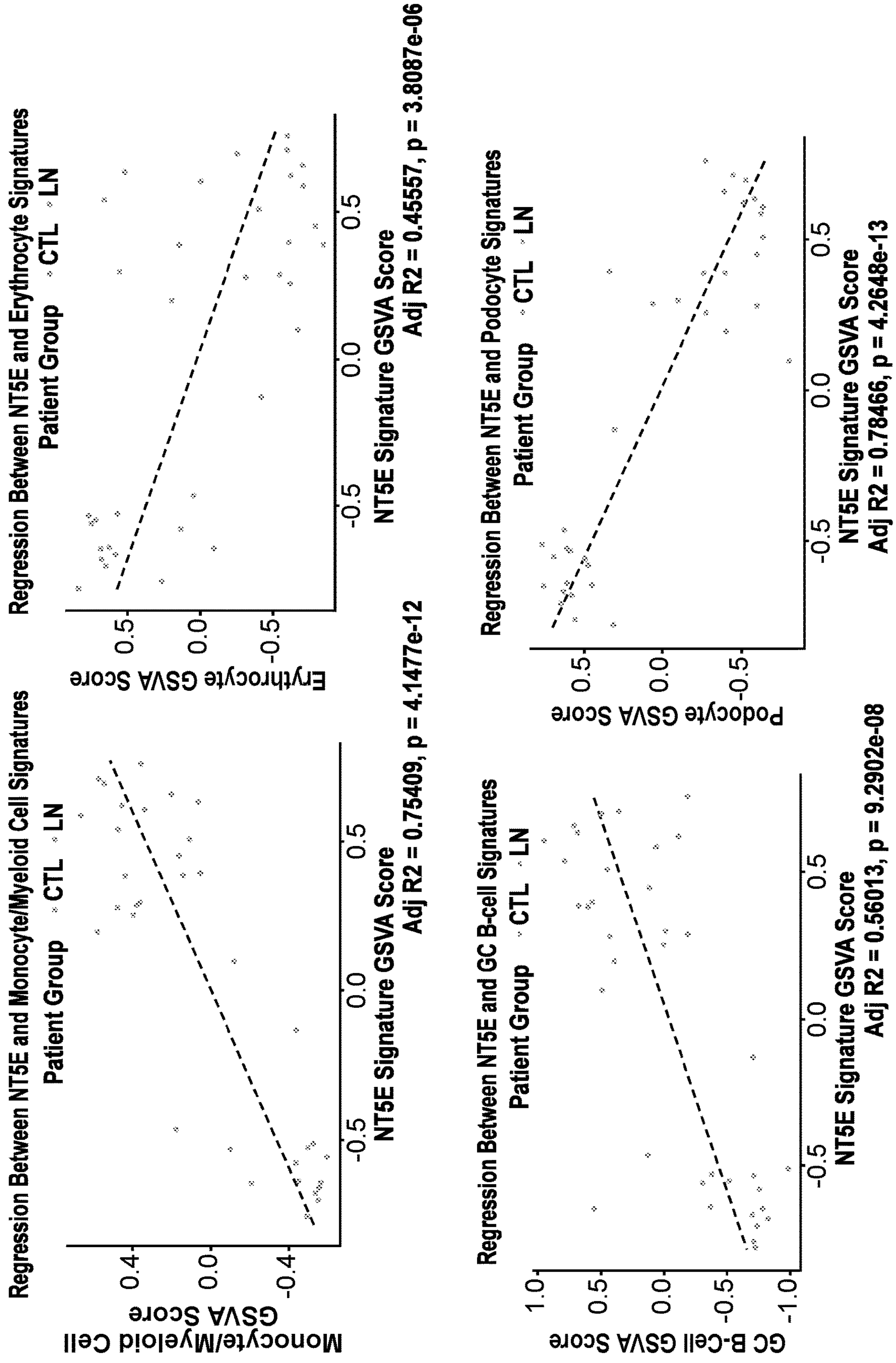
Figure 102B:
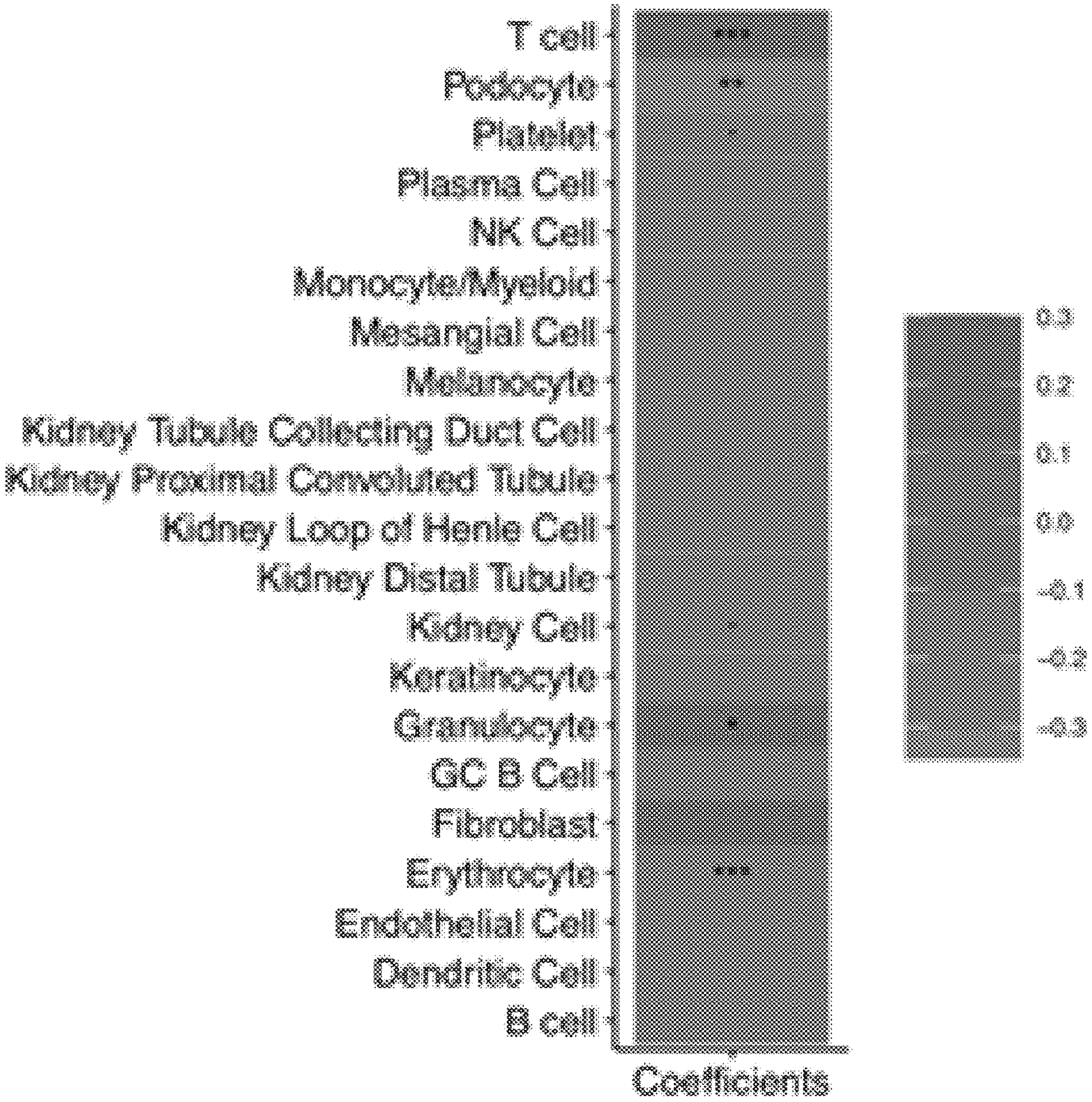

FIGS. 102A-102B show NT5E linear regression. Simple linear regression was performed between the NT5E signature GSVA scores and tissue signature GSVA scores, with the two most significant associations for positive and negative enrichment shown (FIG. 102A) Stepwise regression was then performed to highlight the relationships shown in FIG. 102A (FIG. 102B).

Figure 103A:
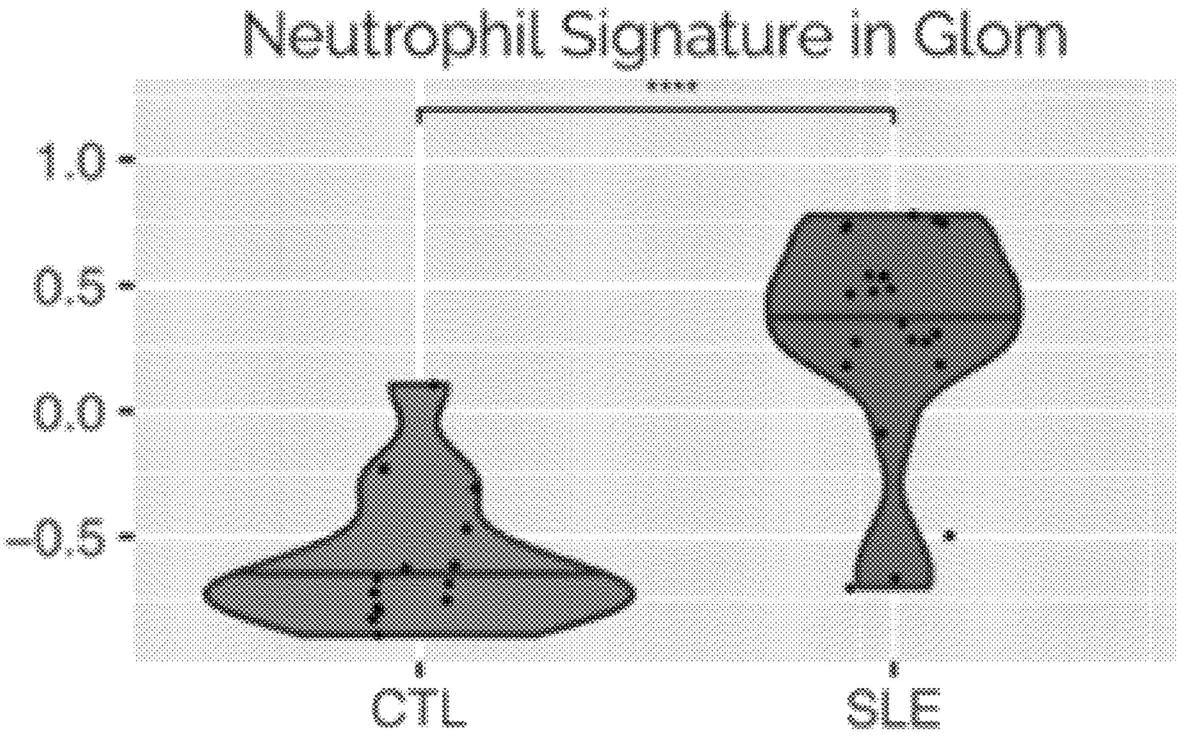
Figure 103B:
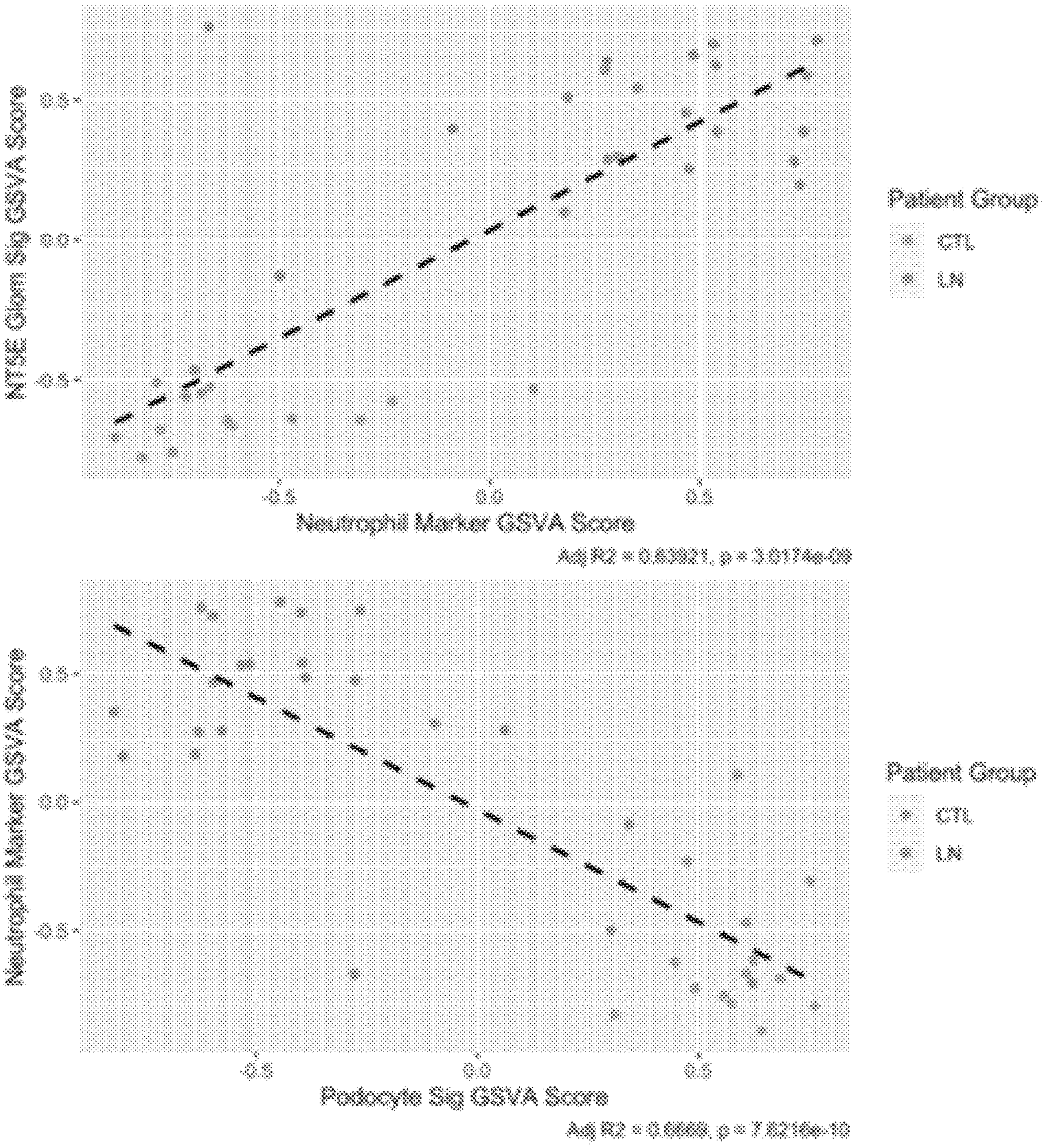

FIGS. 103A-103B show neutrophil analysis. Using known neutrophil surface markers, a neutrophil signature with good GSVA score clustering was generated (FIG. 103A). Linear regression shows that this signature is expressed in a similar manner to the NT5E signature (FIG. 103B).

Figure 104:
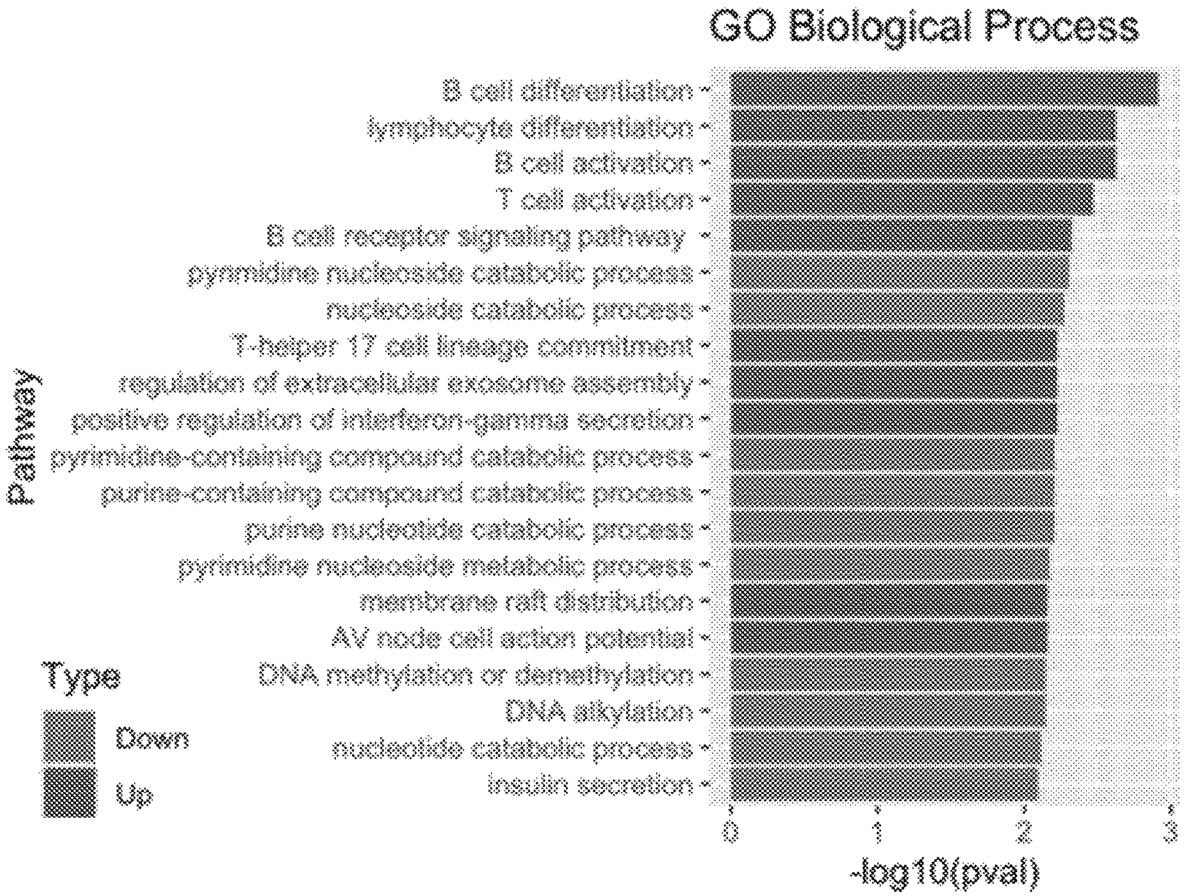

FIG. 104 shows GO enrichment analysis of CD73 KO pathways. Significant biological processes dictated by GO enrichment analysis. Gene lists separated into down and up, based on if a gene was downregulated or upregulated in CD73 KO mice relative to WT.

Figure 105:
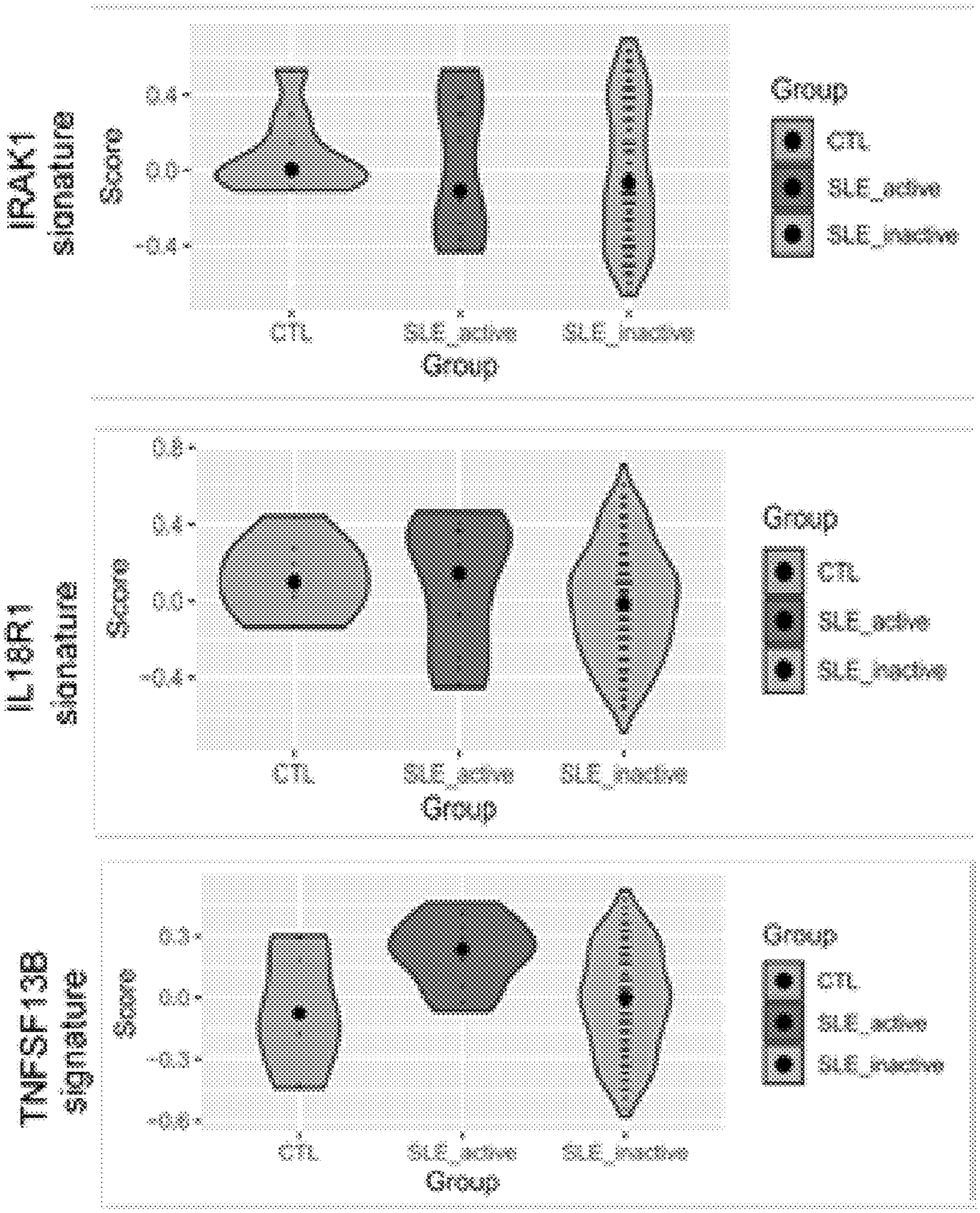

FIG. 105 shows violin plots of GSVA enrichment scores for IRAK1, IL18R1, and TNFSF13B in whole blood samples from active and inactive SLE patients and healthy controls.

Figure 106:
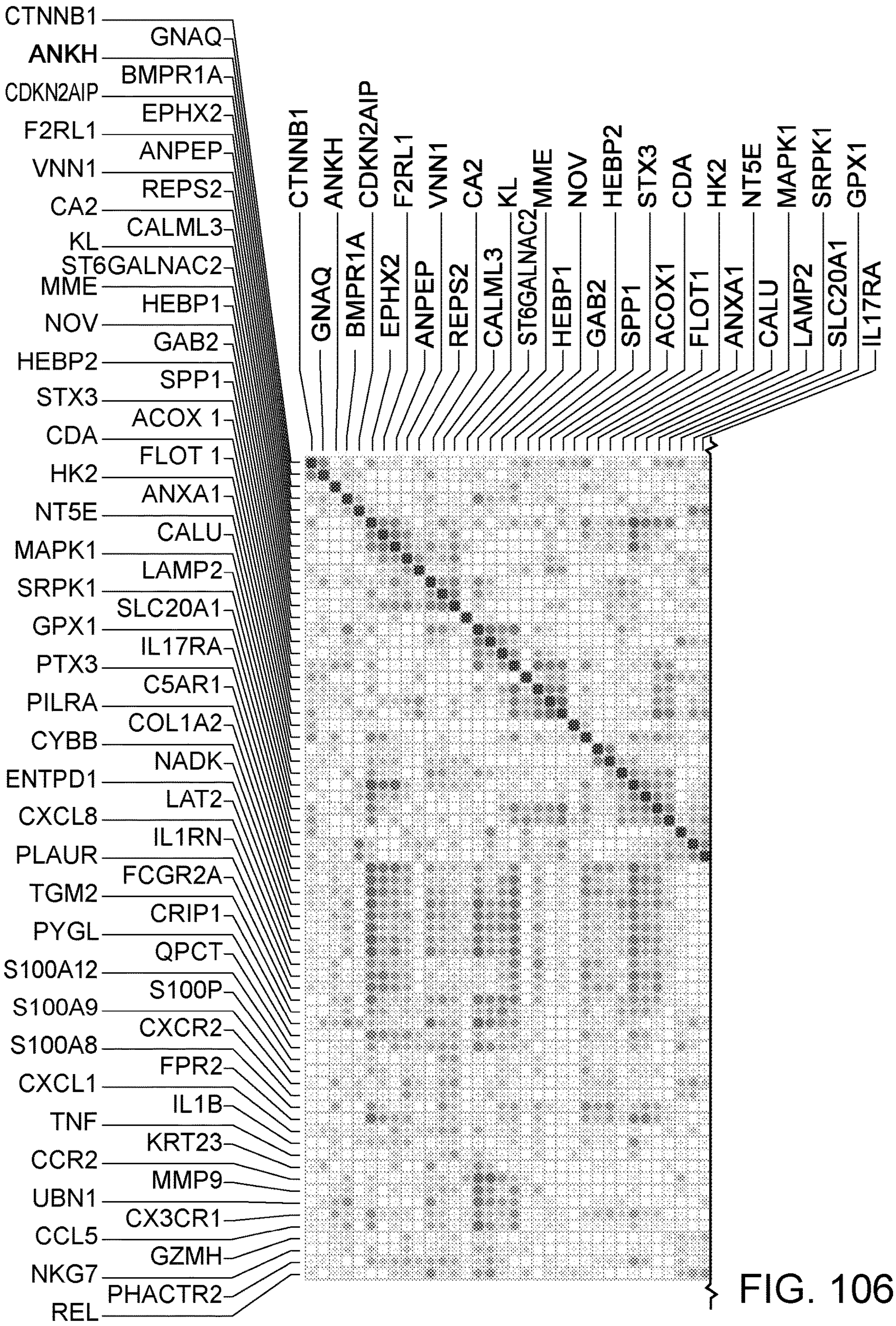
Figure 106:
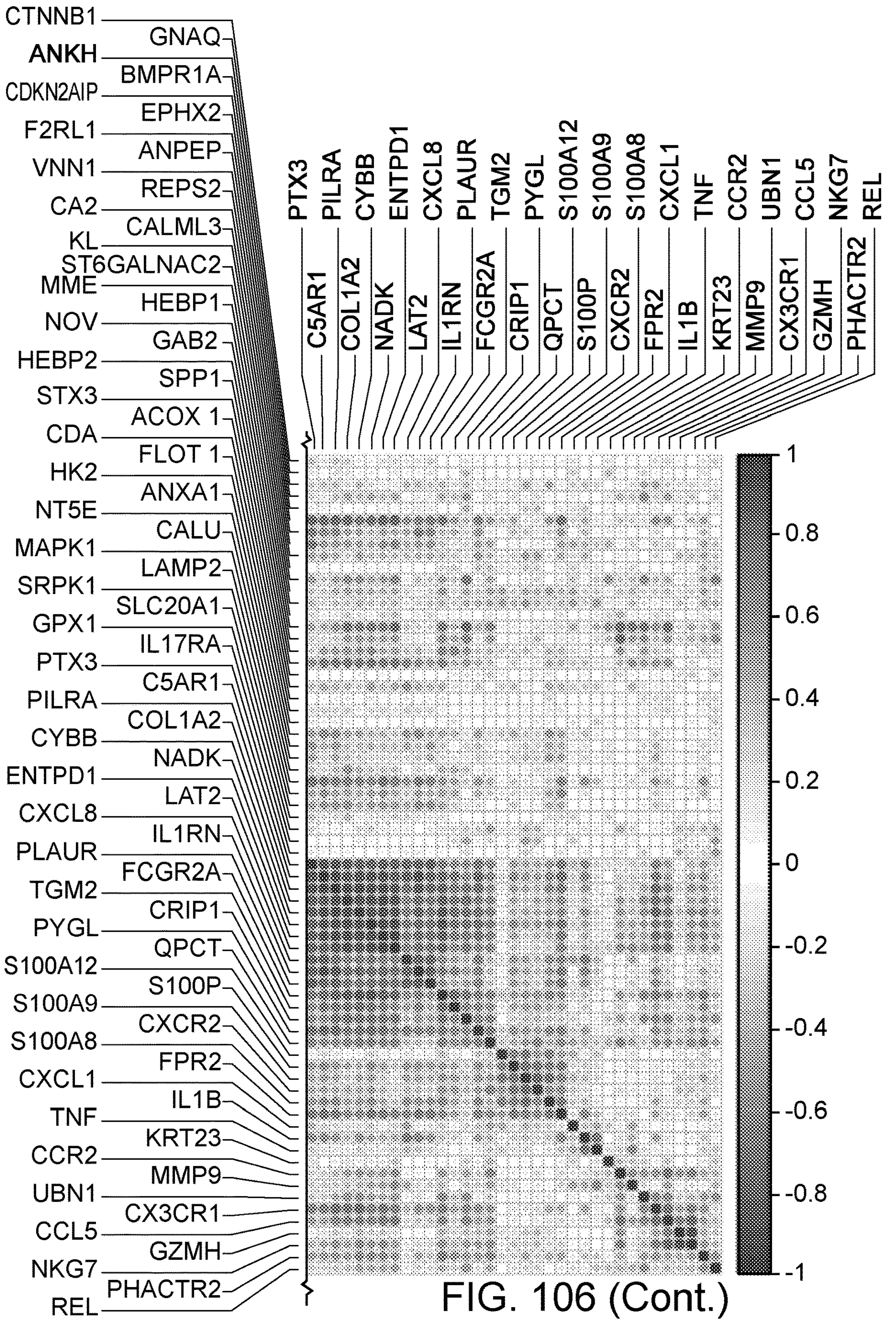

FIG. 106 shows a coexpression matrix of target genes. Genes gathered across many different literature sources were run through a coexpression matrix, in order to best generate a final NT5E gene signature.

DETAILED DESCRIPTION

Analysis by Molecular Endotyping

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by 10%, 5%, or 1%, including increments therein.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, the term "Gini impurity" refers to a measure of how often a randomly chosen element from the set may be incorrectly labeled if it is randomly labeled according to the distribution of labels in the subset.

Many complex and multi-systematic diseases and conditions currently pose major diagnostic and therapeutic challenges. Despite the wealth of records from, for example, genetic, epigenetic, and gene expression data that has emerged in the past few years, physicians often still rely on clinical evaluation and laboratory tests, including measurement of autoantibodies and complement levels.

Successful relation of records (e.g., gene expression records) to a specific disease phenotype activity has been attempted, including efforts to identify individual genes that predicted subsequent flares, and through the determination of a discrete group of differentially expressed (DE) genes that may be found in a particular record. Despite these advances, however, no such approach is available with sufficient predictive value to utilize in evaluation and treatment.

As such, there is a need for a predictive tool for evaluating patient at both the chemical and cellular levels to advance personalized treatment. Data analytical techniques such as machine learning enable proper correlation between genetic records and phenotypes.

The machine learning models tested here provide the basis of personalized medicine. Integration of the methods herein with emerging high-throughput record sampling technologies may unlock the potential to develop a simple blood test to predict phenotypic activity. The disclosures herein may be generalized to predict other manifestations, such as organ involvement. A better understanding of the cellular processes that drive pathogenesis may eventually lead to customized therapeutic strategies based on records' unique patterns of cellular activation.

Method of Identifying One or More Records Having a Specific Phenotype

Figure 1:
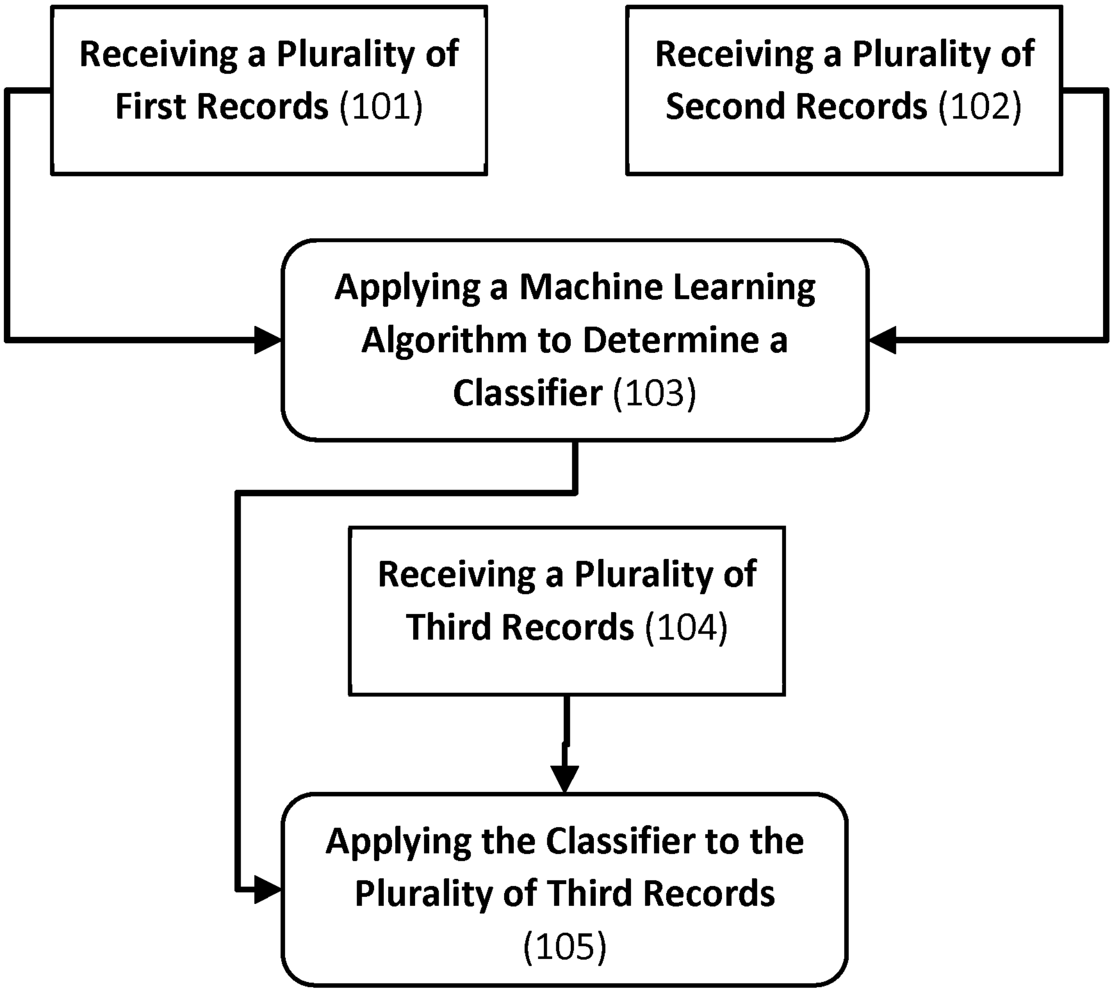
FIG. 1 shows an example of a flow chart for a method of identifying one or more records, in accordance with disclosed embodiments.

One aspect disclosed herein, per FIG. 1, is a method of identifying one or more records (e.g., raw gene expression data, whole gene expression data, blood gene expression data, or informative gene modules). The method may comprise receiving a plurality of first records 101, receiving a plurality of second records 102, receiving a plurality of third records 104, applying a machine learning algorithm to at least one first record and at least one second record to determine a classifier (e.g., a machine learning classifier) 103, and applying the classifier to the plurality of third records 105. Applying the classifier to the plurality of third records 105 may identify one or more third records associated with the specific phenotype. In some embodiments, applying a machine learning algorithm to the third data set 105 comprises applying a machine learning algorithm to a plurality of unique third data sets.

Records

The records may comprise, for example, raw gene expression data, whole gene expression data, blood gene expression data, informative gene modules, or any combination thereof. The records may be generated by Weighted Gene Co-expression Network Analysis (WGCNA). In some embodiments, at least one of the first records and the second records comprise nucleic acid sequencing data, transcriptome data, genome data, epigenome data, proteome data, metabolome data, virome data, metabolome data, methylome data, lipidomic data, lineage-ome data, nucleosomal occupancy data, a genetic variant, a gene fusion, an insertion or deletion (indel), or any combination thereof. In some embodiments, the first records and the second records are in different formats. In some embodiments, the first records and the second records are from different sources, different studies, or both.

In some embodiments each record is associated with a specific phenotype (e.g., a disease state, an organ involvement, or a medication response). Each first record may be associated with one or more of a plurality of phenotypes. The plurality of second records and the plurality of first records may be non-overlapping. The third records may be distinct from the plurality of first records, the plurality of second records, or both. The third records may comprise a plurality of unique third data sets.

The records may be received from the Gene Expression Omnibus. The records may be associated with purified cell populations, whole blood gene expression, or both. The raw Gene Expression Omnibus source may comprise GSE10325

(e.g., from www.ncbi.nlm.nih.gov/geo/query/acc.cgi?acc=GSE10325), GSE26975 (e.g., from www.ncbi.nlm.nih.gov/geo/query/acc.cgi?acc=GSE26975), GSE38351 (e.g., from www.ncbi.nlm.nih.gov/geo/query/acc.cgi?acc=GSE38351), GSE39088 (e.g., from www.ncbi.nlm.nih.gov/geo/query/acc.cgi?acc=GSE39088), GSE45291 (e.g., from www.ncbi.nlm.nih.gov/geo/query/acc.cgi?acc=GSE45291), GSE49454 (e.g., from www.ncbi.nlm.nih.gov/geo/query/acc.cgi?acc=GSE49454), or any combination thereof.

For example, as the most important genes may be involved in a number of functions other than interferon signaling, such RNA processing, ubiquitylation, and mitochondrial processes, these pathways may play important roles in directing, or at least be indicative of, phenotypic activity. CD4 T cells originally may contribute the most important modules. However, when the modules are deduplicated, CD14 monocyte-derived modules prove important as unique genes expressed by CD14 monocytes in tandem with interferon genes may be informative in the study of cell-specific methods of pathogenesis.

Phenotypes

In some embodiments, the phenotype comprises a disease state, an organ involvement a medication response, or any combination thereof. The disease state may comprise an active disease state, or an inactive disease state. At least one of the active disease state and the inactive disease state may be characterized by standard clinical composite outcome measures. The active disease state may comprise a Disease Activity Index of 6 or greater.

The disease may comprise an acute disease, a chronic disease, a clinical disease, a flare-up disease, a progressive disease, a refractory disease, a subclinical disease, or a terminal disease. The disease may comprise a localized disease, a disseminated disease, or a systemic disease. The disease may comprise an immune disease, a cancer, a genetic disease, a metabolic disease, an endocrine disease, a neurological disease, a musculoskeletal disease, or a psychiatric disease. The active disease state may comprise a Systemic Lupus Erythematosus Disease Activity Index (SLEDAI) of 6 or greater.

The organ involvement may comprise a possibly involved organ. The possibly involved organ may comprise bone, skin, hematopoietic system, spleen, liver, lung, mucosa, eye, ear, pituitary, or any combination thereof. The medication response may comprise an ultra-rapid metabolizer response, an extensive metabolizer response, an intermediate metabolizer response, or a poor metabolizer response. The ultra-rapid metabolizer response may refer to a record with substantially increased metabolic activity. The extensive metabolizer response may refer to a record with normal metabolic activity. The intermediate metabolizer response may refer to a record with reduced metabolic activity. The poor metabolizer response may refer to a record with little to no functional metabolic activity.

Machine Learning and Classifiers

The classifiers described herein may be used in machine learning algorithms. A variety of machine learning classifiers exist, wherein each classifier produces a unique machine learning process and/or output. The machine learning algorithms may comprise a biased algorithm or an unbiased algorithm. The biased algorithm may comprise Gene Set Enrichment Analysis (GSVA) enrichment of phenotype-associated cell-specific modules. The unbiased approach may employ all available phenotypic data. The machine learning algorithm may comprise an elastic generalized linear model (GLM), a k-nearest neighbors classifier (KNN), a random forest (RF) classifier, or any combination thereof. GLM, KNN, and RF machine learning algorithms may be performed using the glmnet, caret, and randomForest R packages, respectively.

The random forest classifier is able to sort through the inherent heterogeneity of the plurality of records to identify one or more third records associated with the specific phenotype. In some embodiments, the classifier identifies said one or more third records associated with the specific phenotype with an accuracy of at least about 70%. The implementation of the random forest classifier herein enable a specific phenotype association sensitivity of 85% and a specific phenotype association specificity of 83%. Further classifier optimization, however, may yield improved results.

KNN may classify unknown samples based on their proximity to a set number K of known samples. K may be 5% of the size of the pluralities of first, second, and third records. Alternatively, K may be 1%, 2%, 3%, 4%, 5%, 6%, 7%, 8%, 9%, 10%, or any increment therein. A large K value may enable more precise calculations with less overall noise. Alternatively, the k-value may be determined through cross-validation by using an independent set of records to validate the K value. If the initial value of k is even, 1 may be added in order to avoid ties. RF may generate 500 decision trees which vote on the class of each sample. The Gini impurity index, a standard measure of misclassification error, correlates to the importance of such variables. In addition, pooled predictions may be assigned based on the average class probabilities across the three classifiers.

The GLM algorithm may carry out logistic regression with a tunable elastic penalty term to find a balance between an L1 (LASSO) and an L2 (ridge), whereby penalties facilitate variable selection in order to generate sparse solutions. Least Absolute Shrinkage and Selection Operator (LASSO) is a regularization feature selection technique to reduce overfitting in regression problems. Ridge regression employs a penalty term is to shrink the LASSO coefficient values. In some embodiments, the elastic generalized linear model classifier employs an elastic penalty of about 0.9, wherein the penalty is 90% lasso and 10% ridge. The elastic penalty may be 0.1, 0.2, 0.3, 0.4, 0.5, 0.6, 0.7, 0.8, 0.9, or any increments therein.

Records may be classified as active or inactive using two different methodologies: (1) a leave-one-study-out cross-validation approach or (2) a 10-fold cross-validation approach. GLM, KNN, and RF classifiers may be tasked with identifying active and inactive state records based on whole blood (WB) gene expression data and module enrichment data.

Supervised classification approaches using elastic generalized linear modeling, k-nearest neighbors, and random forest classifiers may be implemented. The trends in performance when cross-validating by one of the pluralities of records or cross-validating 10-fold display the potential advantages and disadvantages of diagnostic tests incorporating gene expression data or module enrichment. Cross-validating by one of the pluralities of records may be used to generalize 1-fold cross validation as a suboptimal scenario, whereas a 10-fold cross-validation is in fact more optimal. Although classification of active and inactive records from the pluralities of different records with 1-fold cross-validation may be suboptimal, module enrichment may be employed to smooth out much of the technical variation between data sets. 10-fold cross-validation may enable a more standardized diagnostic test. Although the plurality of second records and the plurality of first records are non-overlapping, the test set employs overlapping records to facilitate proper classification.

Furthermore, modules that may be negatively associated with phenotypic activity may be just as important in classification as positively associated modules. Further study of underrepresented categories of transcripts may enhance understanding and correlation of phenotypic activity.

Reduction of technical noise may improve classification. For example, RNA-Seq platforms, which produce transcript count records rather than probe intensity values, may display less technical variation across records if all samples are processed in the same way.

The strong performance of the random forest classifier indicates that nonlinear, decision tree-based methods of classification may be ideal because decision trees ask questions about new records sequentially and adaptively. Random forest does not apply a one-size-fits-all approach to each of the different types of records to allow for classification of records whose expression patterns make them a minority within their phenotype. As such, active records that do not resemble the majority of active records still have a strong chance of being properly classified by random forest. By contrast other methods may approach variables from new records all at once.

Filtering

In some embodiments, the method further comprises filtering the first records, the second records, or both. In some embodiments, the filtering comprises normalizing, variance correction, removing outliers, removing background noise, removing data without annotation data, scaling, Weighted Gene Co-expression Network Analysis, enrichment analysis, dimensionality reduction, or any combination thereof.

In some embodiments, the normalizing is performed by Robust Multi-Array Analysis (RMA), Guanine Cytosine Robust Multi-Array Analysis (GCRMA), Linear Models for Microarray Data, variance stabilizing transformation (VST), normal-exponential quantile correction (NEQC), or any combination thereof. RMA may summarize the perfect matches through a median polish algorithm, quantile normalization, or both. Variance-stabilizing transformation may simplify considerations in graphical exploratory data analysis, allow the application of simple regression-based or analysis of variance techniques, or both. Normalized expression values may be variance corrected using local empirical Bayesian shrinkage, and DE may be assessed using the Linear Models for Microarray Data (LIMMA) package. Resulting p-values may be adjusted for multiple hypothesis testing using the Benjamini-Hochberg correction, which resulted in a false discovery rate (FDR). Significant genes within each study may be filtered to retain DE genes with an FDR $<0.2$, which may be considered statistically significant. The FDR may be selected a priori to diminish the number of genes that may be excluded as false negatives.

In some embodiments, the variance correction comprises employing a local empirical Bayesian shrinkage, adjusting the p-values for multiple hypothesis testing using the Benjamini-Hochberg correction, removing all data with a false discovery rate of less than 0.2, or any combination thereof. The Benjamini-Hochberg procedure may decrease the false discovery rate caused by incorrectly rejecting the true null hypotheses control for small p-values.

In some embodiments, the Weighted Gene Co-expression Network Analysis comprises calculating a topology matrix, clustering the data based on the topology matrix, correlating module eigenvalues for traits on a linear scale by Pearson correlation for nonparametric traits by Spearman correlation and for dichotomous traits by point-biserial correlation or t-test, or both. A topology matrix may specify the connections between vertices in directed multigraph.

Log 2-normalized microarray expression values from purified CD4, CD14, CD19, CD33, and low density granulocyte (LDG) populations may be used as input to WGCNA to conduct an unsupervised clustering analysis, resulting in co-expression "modules," or groups of densely interconnected genes which may correspond to comparably regulated biologic pathways. For each experiment, an approximately scale-free topology matrix (TOM) may be first calculated to encode the network strength between probes. Probes may be clustered into WGCNA modules based on TOM distances. Resultant dendrograms of correlation networks may be trimmed to isolate individual modular groups of probes by partitioning around medoids and labeled using color assignments based on module size. Expression profiles of genes within modules may be summarized by a module eigengene (ME), which may be analogous to the module's first principal component. MEs act as characteristic expression values for their respective modules and may be correlated with sample traits such as SLEDAI or cell type by Pearson correlation for continuous or semi-continuous traits and by point-biserial correlation for dichotomous traits.

WGCNA modules from CD4, CD14, CD19, and CD33 cells may be tested for correlation to SLEDAI. Plasma cell modules may be generated by differential expression analysis and not WGCNA, but may be included because of the established importance of plasma cells in SLE pathogenesis.

Removing the outliers may be performed by statistical analysis using R and relevant Bioconductor packages. Non-normalized arrays may be inspected for visual artifacts or poor hybridization using Affy QC plots. Principal Component Analysis (PCA) plots may be used to inspect the raw data files for outliers. Data sets culled of outliers may be cleaned of background noise and normalized using RMA, GCRMA, or NEQC where appropriate. Data sets may be then filtered to remove probes with low intensity values and probes without gene annotation data. WB gene expression data sets may be filtered to only include genes that passed quality control in all data sets. Differential expression (DE) analysis and WGCNA may then be carried out on data sets. WB gene expression data sets may then be further processed before machine learning analysis. WB gene expression values may be centered and scaled to have zero-mean and unit-variance within each data set and the standardized expression values from each data set may be joined for classification.

The GSVA-R package may be used as a non-parametric method for estimating the variation of pre-defined gene sets in WB gene expression data sets. Standardized expression values from WB data sets may be used to test for enrichment of cell-specific WGCNA gene modules using the Single-sample Gene Set Enrichment Analysis (ssGSEA) method, which scores single samples in isolation and may be thus shielded from technical variation within and among data sets. Statistical analysis of GSVA enrichment scores may be performed by Spearman correlation or Welch's unequal variances t-test, where appropriate. GSVA may be performed on three WB datasets using 25 WGCNA modules made from purified cells with correlation or published relationship to SLEDAI (Table 1).

Patterns of enrichment of WGCNA modules that are derived from isolated cell populations of WB that are correlated to the phenotype may be more useful than gene expression across the pluralities of records to identify active versus inactive state records. To characterize the relationships between gene signatures from various records and phenotypic activity, WGCNA may be used to generate co-expression gene modules from purified populations of cells from records with an active disease state. Such records may be subsequently tested for enrichment in whole blood of other records. WGCNA analysis of leukocyte subsets may result in several gene modules with significant Pearson correlations to SLEDAI (all $|r|>0.47$, $p<0.05$). CD4, CD14, CD19, and CD33 cells with 3, 6, 8, and 4 significant modules, respectively (Table 1). Two low-density granulocyte (LDG) modules may be created by performing WGCNA analysis of LDGs along with either neutrophils or HC neutrophils and merging the modules most strongly expressed by LDGs Two plasma cell (PC) modules may be created by using the most increased and decreased transcripts of isolated plasma cells compared to naïve and memory B cells.

TABLE 1

| Gene modules identified as correlating with SLEDAI via WGCNA analysis of leukocytes | | | | | |
|---|---|---|---|---|---|
| Cell Type | Module Name | Module Size | Correlation with SLEDAI | Top GO Biological Process | Top BIG-C Category |
| CD4 | Floralwhite | 237 | 0.81 | type I interferon signaling pathway | Interferon-Stimulated-Genes |
| | Turquoise | 805 | 0.50 | positive reg of ubiquitin-protein ligase | Proteasome |
| | Orangered4 | 237 | −0.77 | translational initiation | mRNA-Translation |
| CD14 | Plum1 | 247 | 0.47 | ubiquitin-dependent protein catabolic process | mRNA-Translation |
| | Yellow | 356 | 0.65 | type I interferon signaling pathway | Interferon-Stimulated-Genes |
| | Greenyellow | 89 | 0.49 | transcription from RNA polymerase II promoter | General-Transcription |
| | Pink | 261 | −0.77 | protein phosphorylation | Endosome-and-Vesicles |
| | Purple | 124 | 0.66 | inositol phosphate metabolic process | Fatty Acid-Biosynthesis |
| | Sienna3 | 222 | −0.64 | translational initiation | mRNA-Translation |
| CD19 | Darkolivegreen | 591 | 0.78 | cell division | Proteasome |
| | Greenyellow | 251 | 0.66 | Notch signaling pathway | mRNA-Translation |
| | Steelblue | 146 | 0.65 | gluconeogenesis | Glycolysis-Gluconeogenesis |
| | Turquoise | 572 | 0.50 | ER to Golgi vesicle-mediated transport | Unfolded-Protein-and-Stress |
| | Violet | 566 | 0.6 | mitochondrial respiratory chain complex I | Interferon-Stimulated-Genes |
| | Brown | 620 | −0.62 | regulation of transcription, DNA-templated | Chromatin-Remodeling |
| | Green | 541 | −0.49 | transcription, DNA-templated | Transcription-Factors |
| | Skyblue | 756 | −0.74 | viral transcription | mRNA-Translation |
| CD33 | Royalblue | 94 | 0.60 | positive reg of cytosolic calcium ions | Transposon-Control |
| | Sienna3 | 133 | 0.76 | type I interferon signaling pathway | Interferon-Stimulated-Genes |
| | Violet | 177 | 0.79 | defense response to virus | Interferon-Stimulated-Genes |
| | Darkmagenta | 273 | −0.49 | ubiquinone biosynthetic process | MHC-Class-TWO |
| LDG$^{+}$ | LDG_A | 334 | 0.79 | platelet degranulation | Cytoskeleton |
| | LDG_B | 92 | 0.81 | regulation of transcription | Secreted-Immune |
| PC* | PC_Up | 423 | N/A | protein N-linked glycosylation | Endoplasmic-Reticulum |
| | PC_Down | 183 | N/A | antigen processing and presentation MHC II | MHC-Class-TWO |

Gene Ontology (GO) analysis of the genes within each of the record indicates that that some processes, such as those related to interferon signaling, RNA transcription, and protein translation, may be shared among cell types, whereas other processes may be unique to certain cell types (Table 1) and may be used to better classification of records.

Figure 2A:
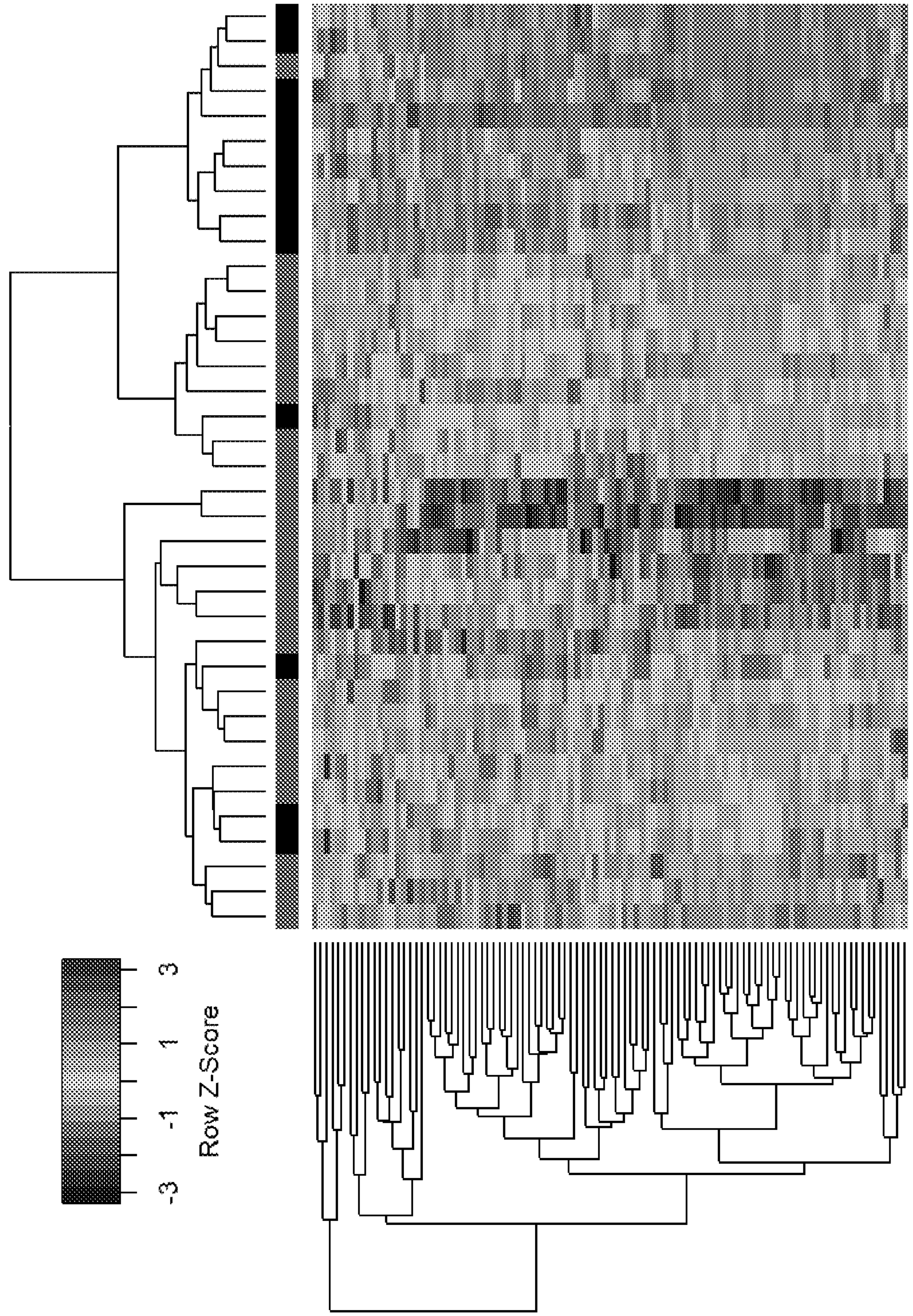
FIG. 2A shows the z-scores determined by an example of differential expression analysis of disease state compared to status of the 100 most significant records within a first plurality of records, in accordance with disclosed embodiments.
Figure 2B:
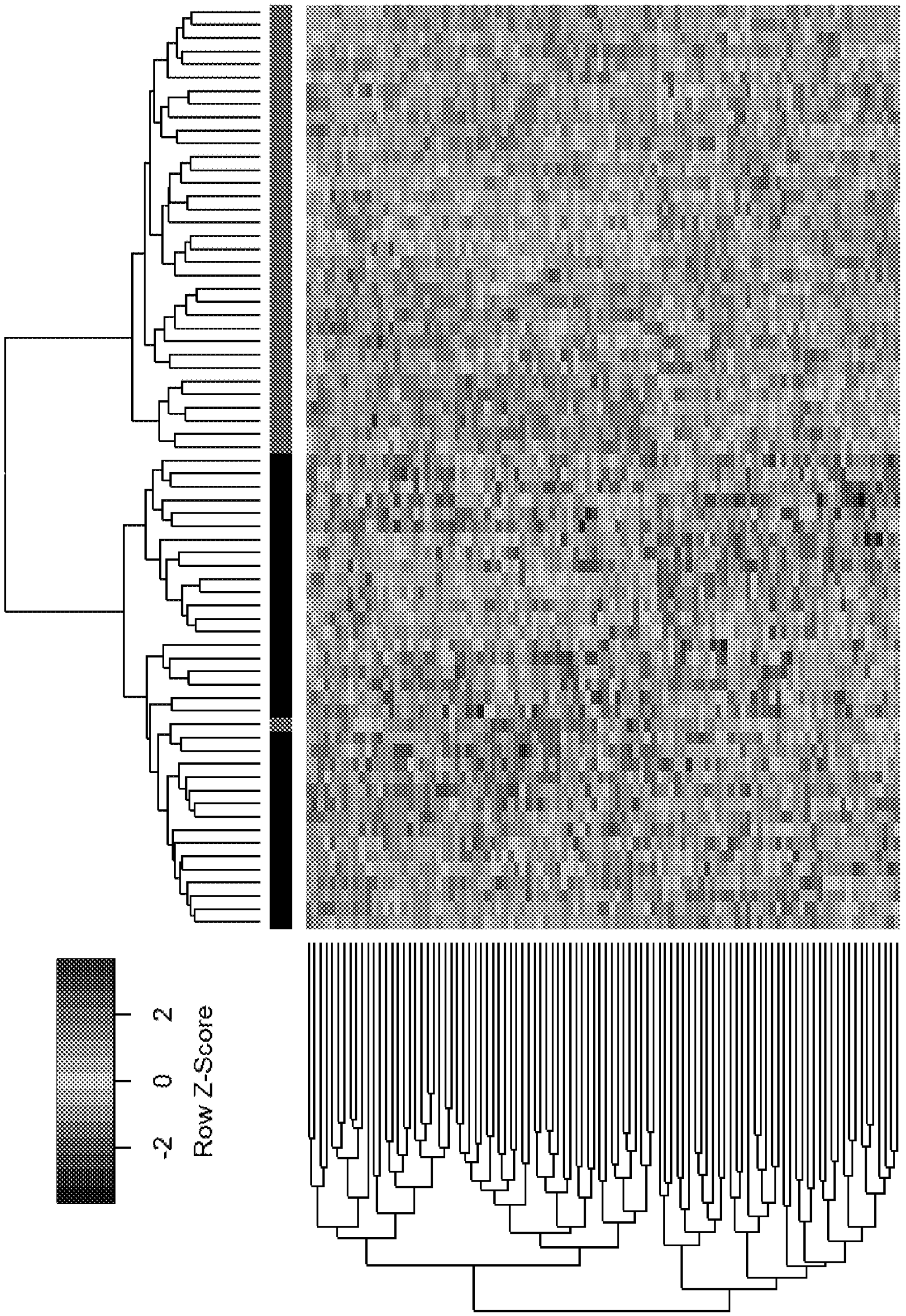
FIG. 2B shows the z-scores determined by an example of differential expression analysis of active disease state compared to status of the 100 most significant records within a second plurality of records, in accordance with disclosed embodiments.
Figure 2C:
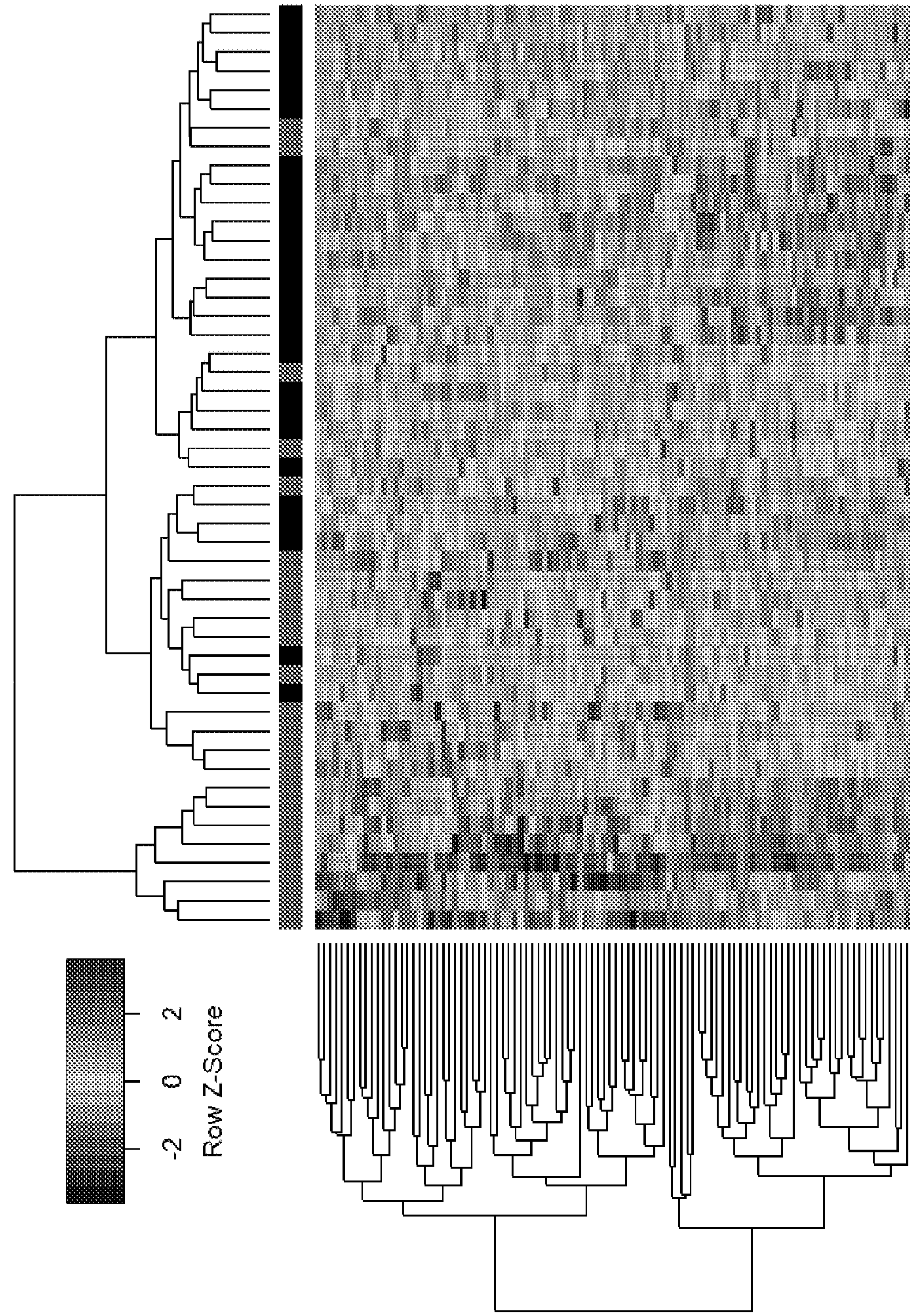
FIG. 2C shows the z-scores determined by an example of differential expression analysis of active disease state compared to status of the 100 most significant records within a third plurality of records, in accordance with disclosed embodiments.
Figure 2D:
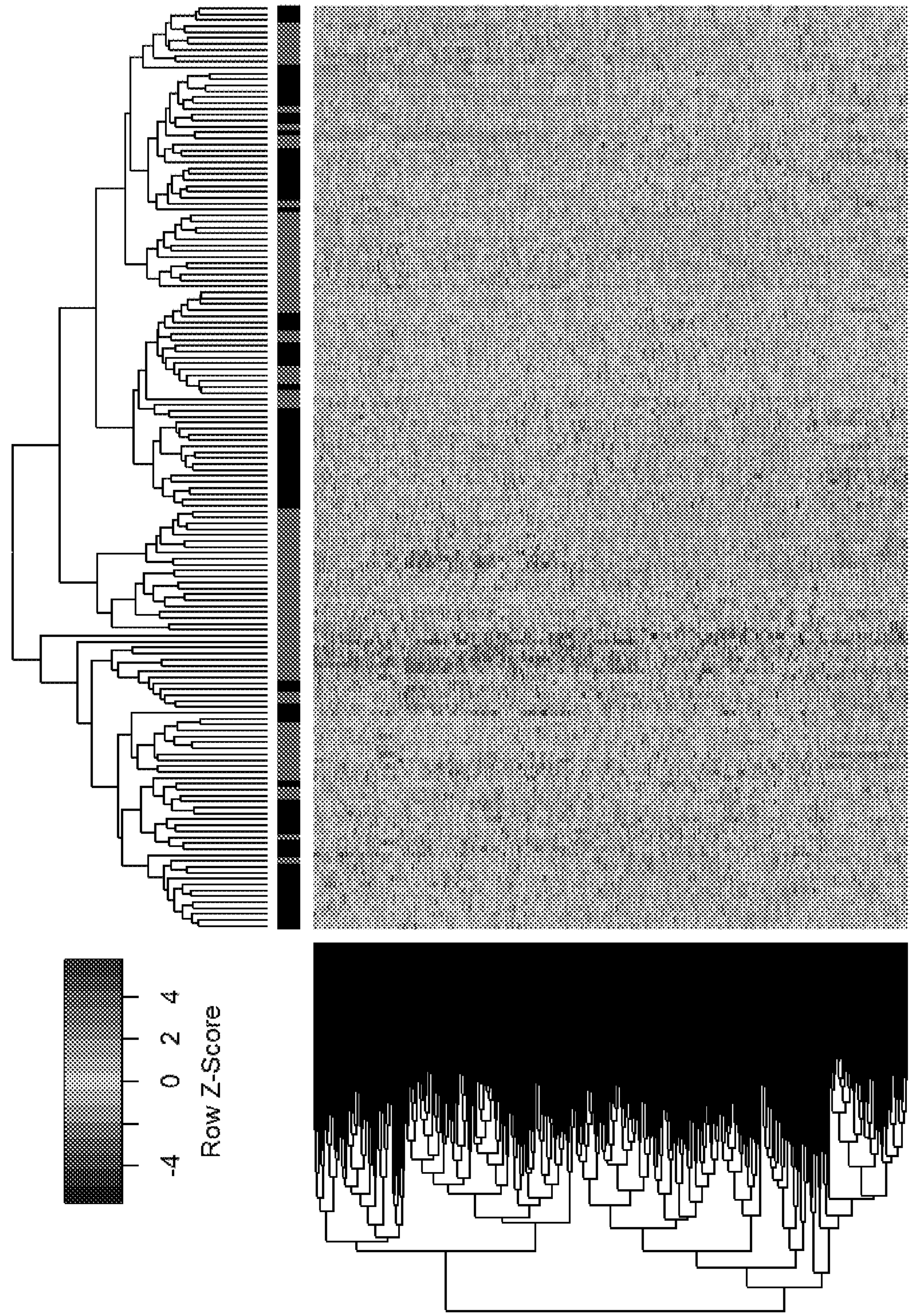
FIG. 2D shows the z-scores determined by an example of differential expression analysis of active disease state compared to the combined records within the first, second, and third pluralities of records, in accordance with disclosed embodiments.
Figure 2E:
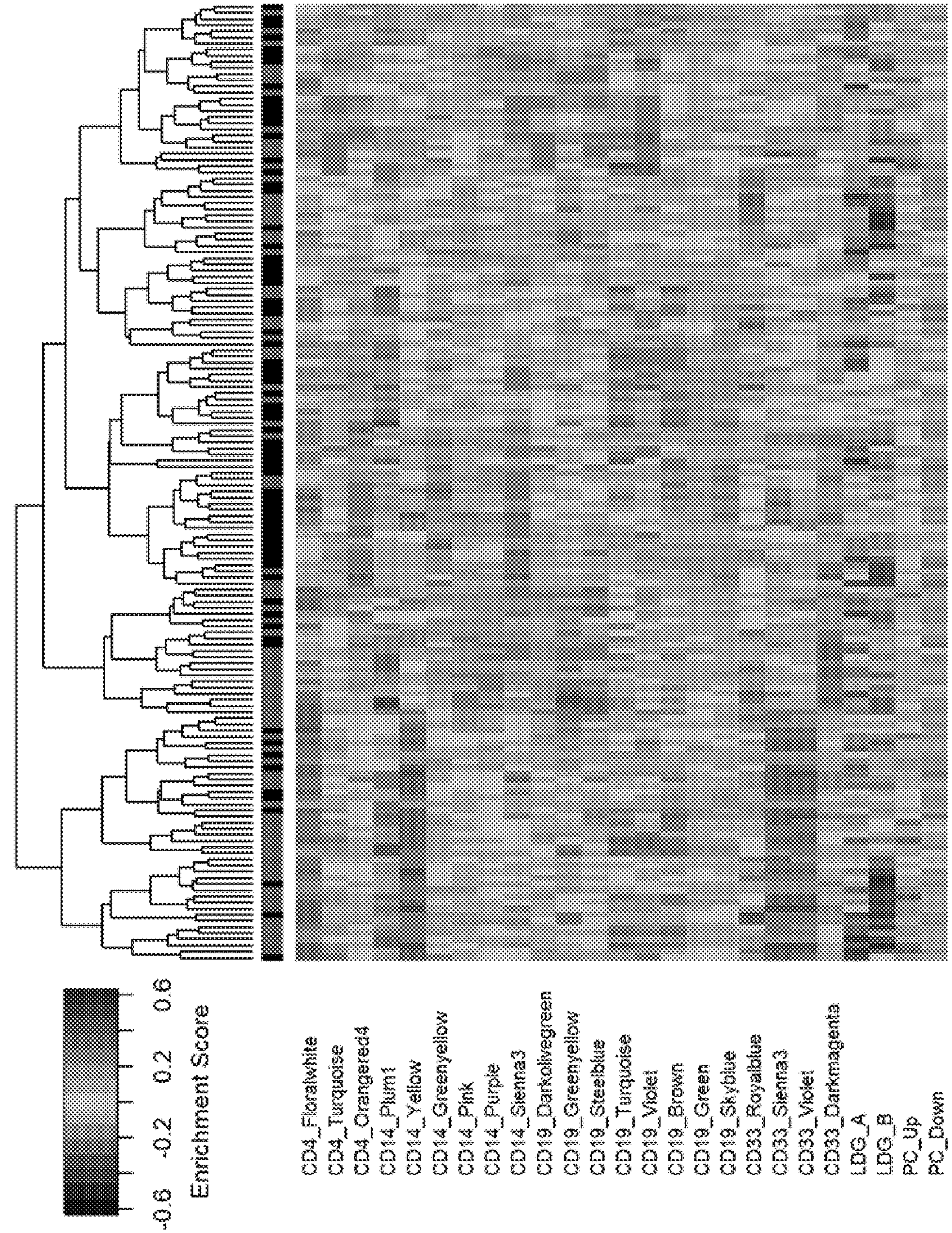
FIG. 2E shows the enrichment scores determined by an example of differential expression analysis of active disease state across a selected set of records compared to the first, second, and third pluralities of records, in accordance with disclosed embodiments.
Figure 4A:
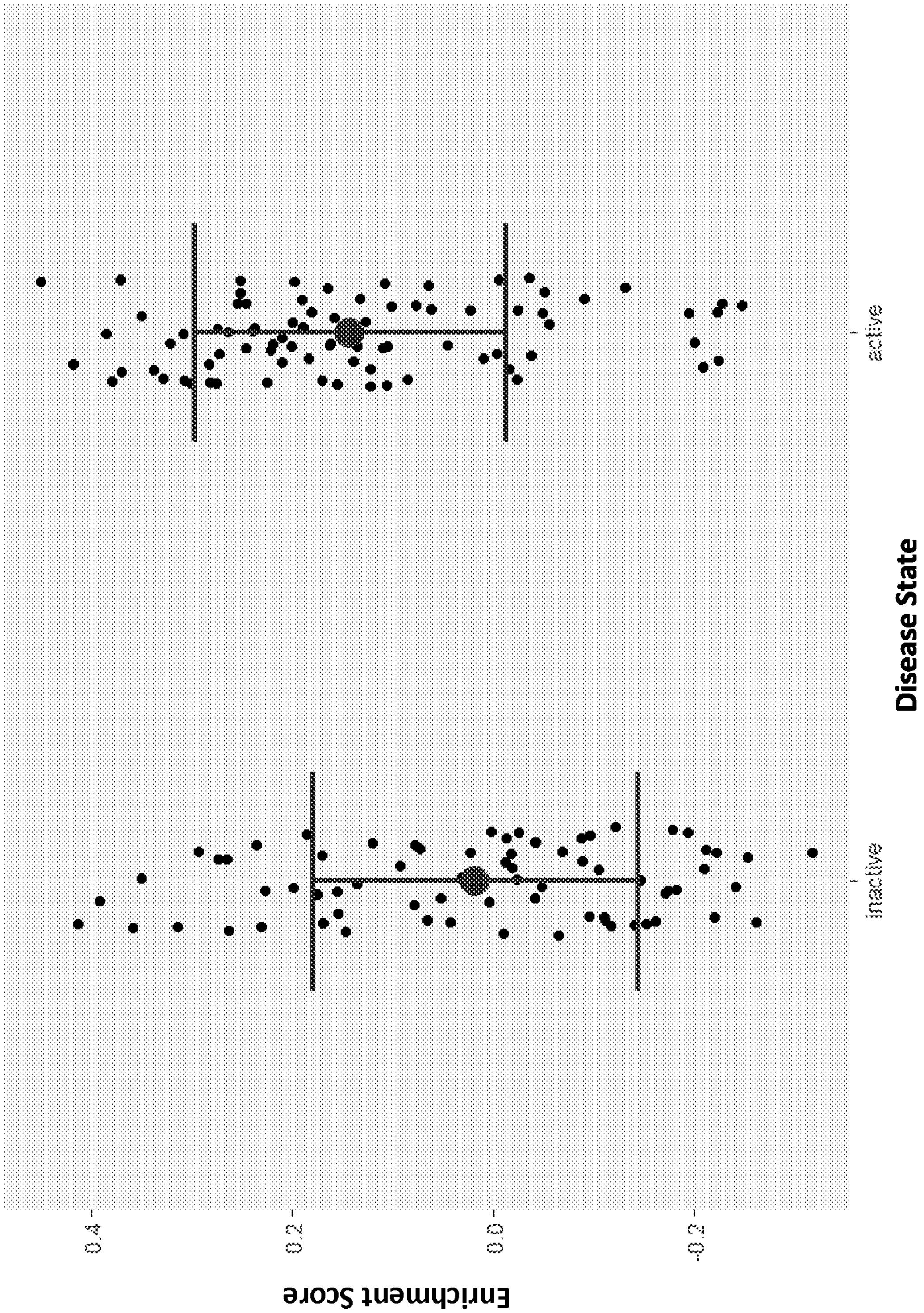
FIG. 4A shows an example of Gene Set Enrichment Analysis (GSVA) enrichment scores and standard deviations for a first plurality of records, in accordance with disclosed embodiments.
Figure 4B:
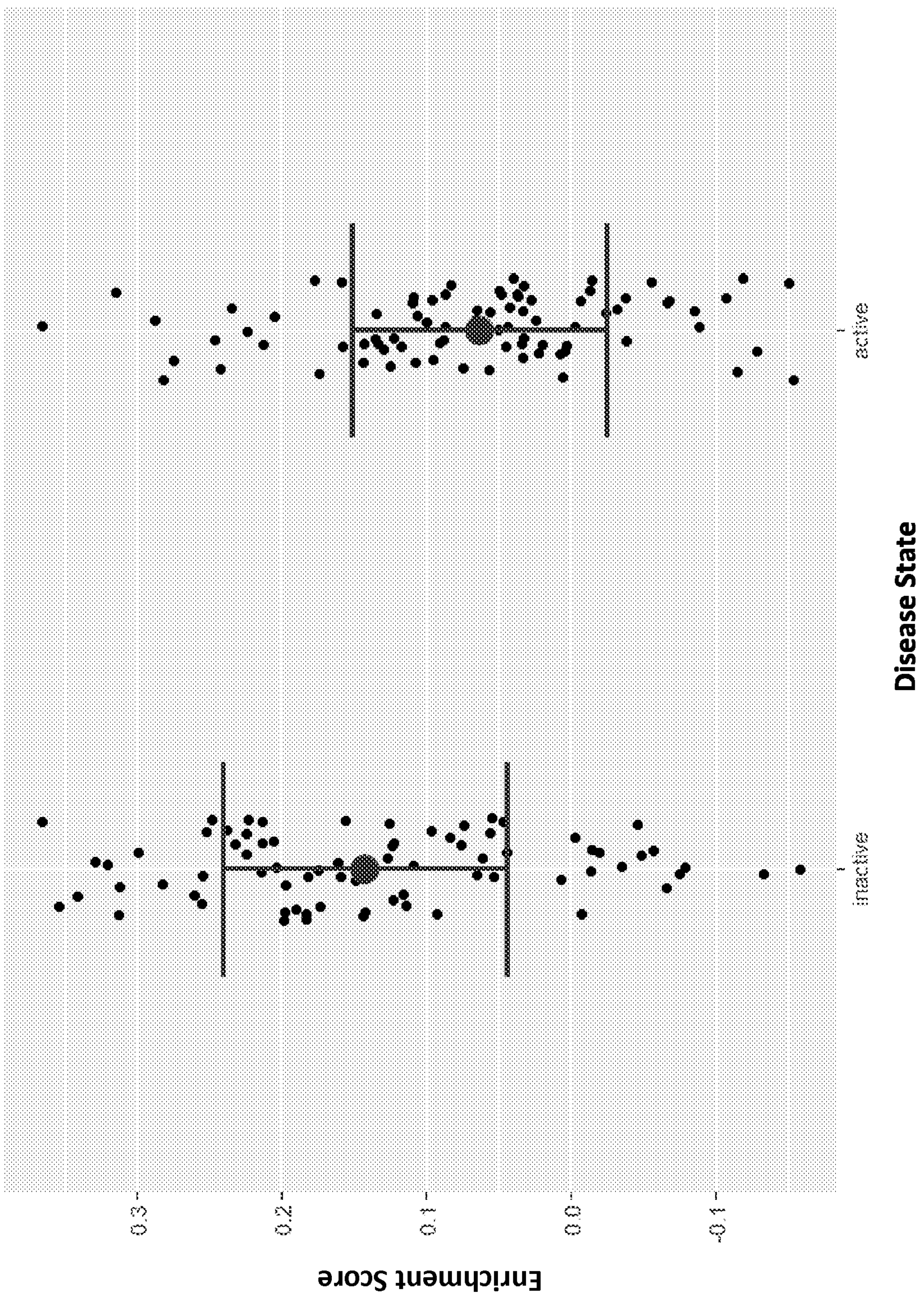
FIG. 4B shows an example of GSVA enrichment scores and standard deviations for a second plurality of records, in accordance with disclosed embodiments.

GSVA enrichment may be performed using the 25 cell-specific gene modules in WB from 156 records (82 active, 74 inactive), per Table 4 and FIG. 2E. Of the 25 cell-specific modules, 12 had enrichment scores with significant Spearman correlations to SLEDAI ($p<0.05$), and 14 had enrichment scores with significant differences between active and inactive state records by Welch's unequal variances t-test ($p<0.05$), per Table 2. Notably, each cell type produced at least one module with a significant correlation to SLEDAI in WB and at least one module with a significant difference in enrichment scores between active and inactive records, demonstrating a relationship between phenotypic activity in specific cellular subsets and overall phenotypic activity in WB. However, as the Spearman's rho values ranged from −0.40 to +0.36, no one module may have a substantial predictive value. Furthermore, the effect sizes as measured by Cohen's d when testing active versus inactive enrichment scores ranged from −0.85 to +0.79. The CD4 Floralwhite and Orangered4 modules, which had the largest positive and negative effect sizes, respectively, showed a high degree of overlap in the enrichment scores of active and inactive records, per FIGS. 4A and 4B, where error bars indicate mean±standard deviation. WB may be unable to fully separate active records from inactive records.

TABLE 2

Cell-specific modules by Spearman correlation to SLEDAI and active vs. inactive state

| | Spearman correlation to SLEDAI | | Active vs. Inactive t-test | | |
|---|---|---|---|---|---|
| | rho | p value | t statistic | p value | Cohen's d |
| CD4_Floralwhite | | 3.90E−06 | | 2.40E−06 | 0.788 |
| CD4_Turquoise | −0.044 | 0.587 | −0.93 | 0.352 | −0.149 |
| CD4_Orangered4 | −0.400 | 2.21E−07 | −5.29 | 4.35E−07 | −0.853 |
| CD14_Plum1 | 0.010 | 0.904 | −0.35 | 0.729 | −0.054 |
| CD14_Yellow | | 4.93E−06 | | 4.44E−06 | 0.761 |
| CD14_Greenyellow | −0.132 | 0.100 | −2.10 | 0.037 | −0.339 |
| CD14 Pink | −0.026 | 0.751 | 0.13 | 0.894 | 0.021 |
| CD14_Purple | −0.149 | 0.064 | −1.65 | 0.101 | −0.263 |
| CD14_Sienna3 | −0.368 | 2.27E−06 | −4.99 | 1.62E−06 | −0.799 |
| CD19_Darkolivegreen | 0.020 | 0.809 | −0.06 | 0.953 | −0.010 |
| CD19_Greenyellow | | 0.016 | | 0.012 | 0.403 |
| CD19_Steelblue | 0.016 | 0.838 | 0.55 | 0.580 | 0.089 |
| CD19_Turquoise | −0.069 | 0.393 | −0.84 | 0.403 | −0.132 |
| CD19_Violet | −0.087 | 0.282 | −1.48 | 0.141 | −0.236 |
| CD19_Brown | −0.050 | 0.537 | −1.04 | 0.301 | −0.164 |
| CD19_Green | −0.150 | 0.062 | −2.07 | 0.040 | −0.330 |
| CD19_Skyblue | −0.205 | 0.010 | −2.35 | 0.020 | −0.378 |
| CD33_Royalblue | | 8.99E−05 | | 1.03E−04 | 10.637 |
| CD33_Sienna3 | | 3.41E−06 | | 6.15E−06 | 0.753 |
| CD33_Violet | | 4.15E−05 | | 2.46E−05 | 0.696 |
| CD33_Darkmagenta | −0.216 | 6.74E−03 | −2.34 | 0.021 | −0.369 |
| LDG_A | −0.044 | 0.588 | −0.25 | 0.802 | −0.040 |
| LDG_B | | 5.71E−03 | | 0.019 | 0.377 |
| PC_Up | | 9.75E−04 | | 1.61E−03 | 0.508 |
| PC_Down | 0.022 | 0.781 | 0.80 | 0.426 | 0.129 |

Analysis of individual phenotypic activity associated peripheral cellular subset gene modules may not be sufficient to predict phenotypic activity in unrelated WB data sets, since no single module from any cell type may be able to separate active from inactive state records, per FIG. 2E. Although no single module had a sufficiently high predictive value, many cell-specific gene modules may be combined and optimized to predict phenotypes of active records.

Moreover, the results emphasized the need for more advanced analysis to employ gene expression analysis to predict phenotypic activity.

Performance and Accuracy

When training and testing sets are formed by holding out entire data sets, machine learning algorithms using raw gene expression data had an average classification accuracy of only 53 percent. However, converting this gene expression data to module enrichment improved classification accuracy to 71 percent. When training and testing sets are formed by mixing records from the three data sets, module enrichment remained at a 70 percent classification accuracy. However, classification accuracy using raw gene expression increased to a mean of 79 percent. The best overall performance came from the random forest classifier, which had a predictive accuracy of 84 percent.

The performance of each machine learning algorithm may be determined by evaluating 2 different forms of cross-validation. A random 10-fold cross-validation may randomly assign each record to one of 10 groups. A leave-one-study-out cross-validation may determine the effects of systematic technical differences among data sets on classification performance. For each pass of cross-validation, one fold or study may be held out as a test set, whereby the classifiers are trained on the remaining data. Accuracy may be assessed as the proportion of records correctly classified across all testing folds. Performance metrics such as sensitivity and specificity may be assessed after cross-validation by agglomerating class probabilities and assignments from each fold or study. Receiver Operating Characteristic (ROC) curves may be generated using the pROC R package.

Figure 5:
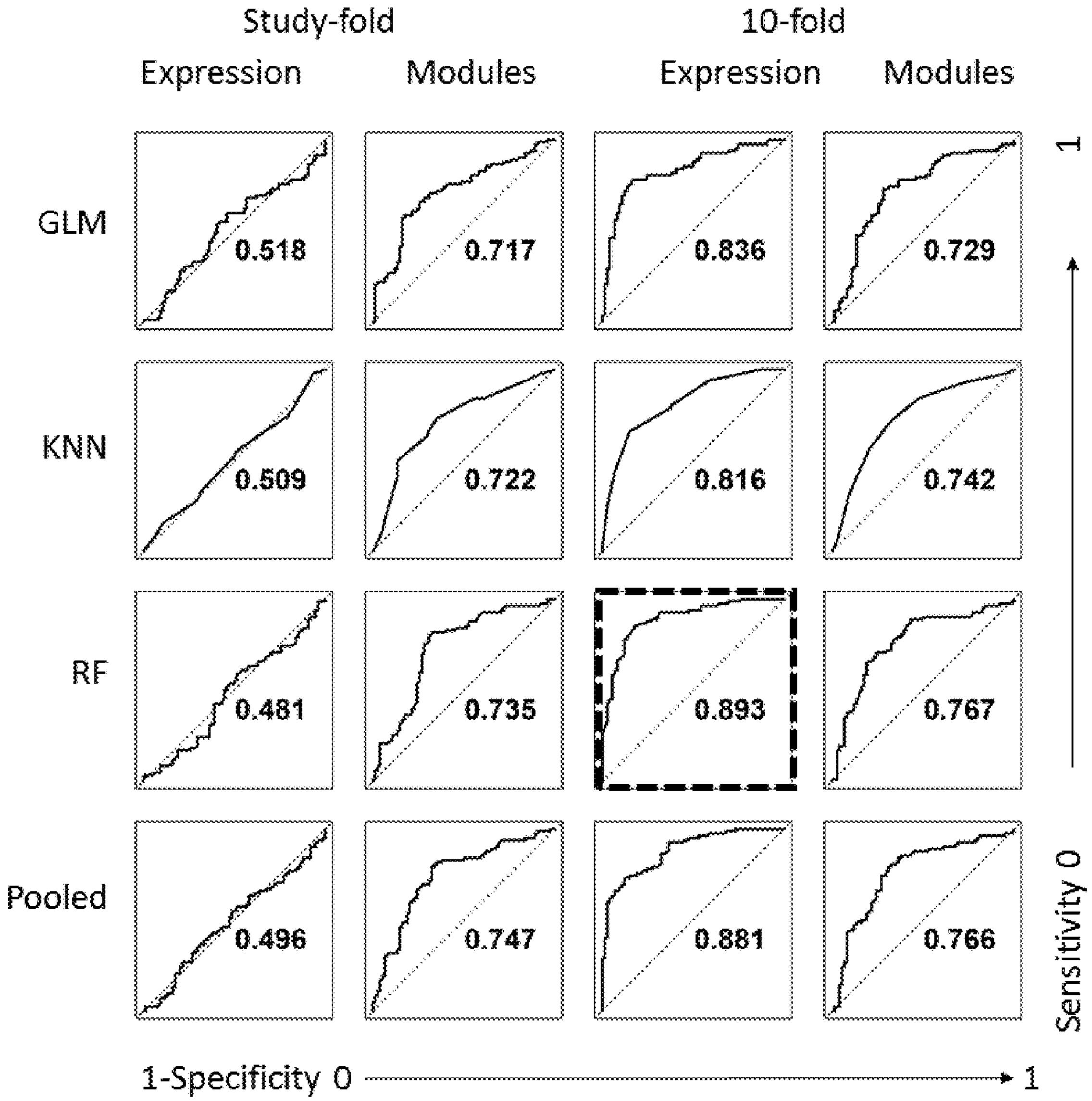
FIG. 5 shows an example of Receiver Operating Characteristic (ROC) curves and the area under each curve for machine learning classifiers under different test conditions, in accordance with disclosed embodiments.

The performance of each classifier in each situation is shown in Table 3, and corresponding ROC curves are shown in FIG. 5, whereas the area under each ROC curve is displayed. In almost all cases, the random forest classifier outperformed the GLM and KNN classifiers, although the results may be not significantly different when assessed by testing for equality of proportions ($p>0.05$). Pooled predictions based on the class probabilities from the three classifiers may not improve overall performance.

pared to the leave-one-study-out cross-validation. This increase in performance may be attributed to the presence of records from all plurality of first, second, and third records in both the training and test sets. In this case, the classifiers may learn patterns inherent to each set of records. In this circumstance, the random forest classifier may be the strongest performer with 84% accuracy (85% sensitivity, 83% specificity), whereby the ROC curve demonstrates an excellent tradeoff between recall and fall-out. The performance of module enrichment, however may not be substantially different between 10-fold cross-validation and leave-one-study-out cross-validation.

Overall, in a study-by-study approach (leave-one-study-out cross-validation), module enrichment may be more successful than raw gene expression. Importantly, when using the 10-fold cross-validation approach, raw gene expression may outperform module enrichment. Thus, phenotypic activity classification based on raw gene expression may be sensitive to technical variability, whereas classification based on module enrichment may cope better with variation among data sets.

The variable importance of Random forest provides insight into directors of the identification of phenotypic activity, random forest classifiers may be trained on all records from each of the plurality of records in order to identify the most important genes and modules as determined by mean decrease in the Gini impurity, a measure of misclassification error.

Figure 6A:
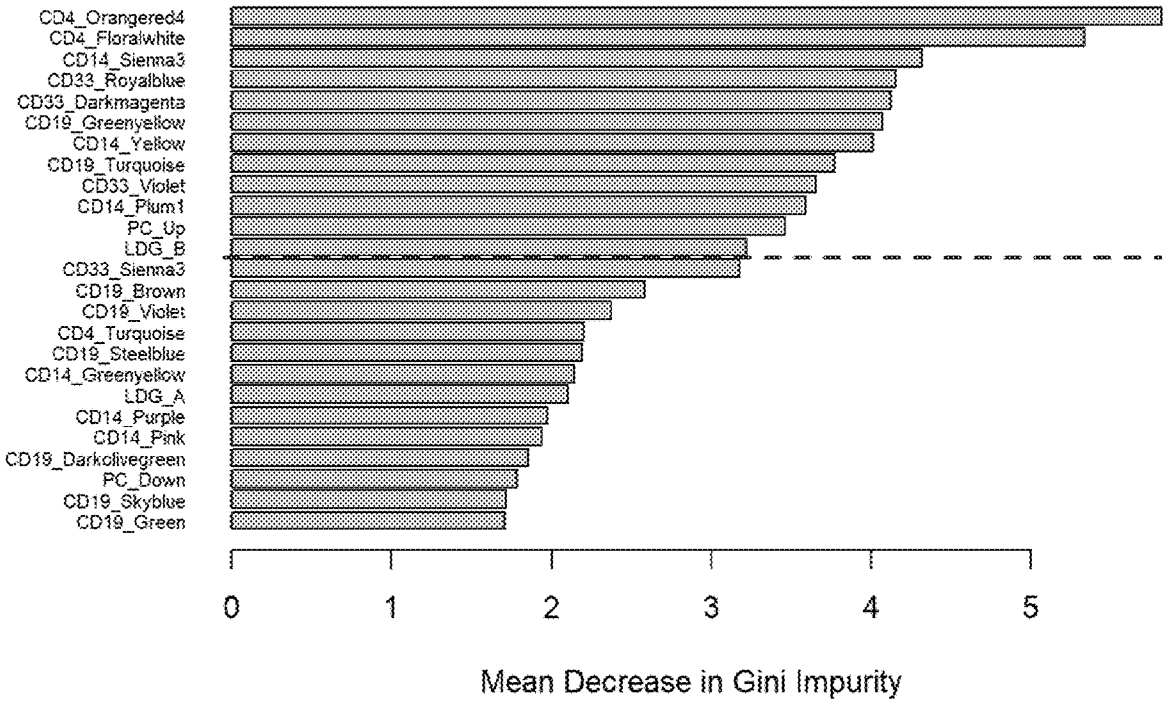
FIG. 6A shows an example of variable importance values of records as determined by mean decrease in Gini impurity, in accordance with disclosed embodiments.
Figure 6B:
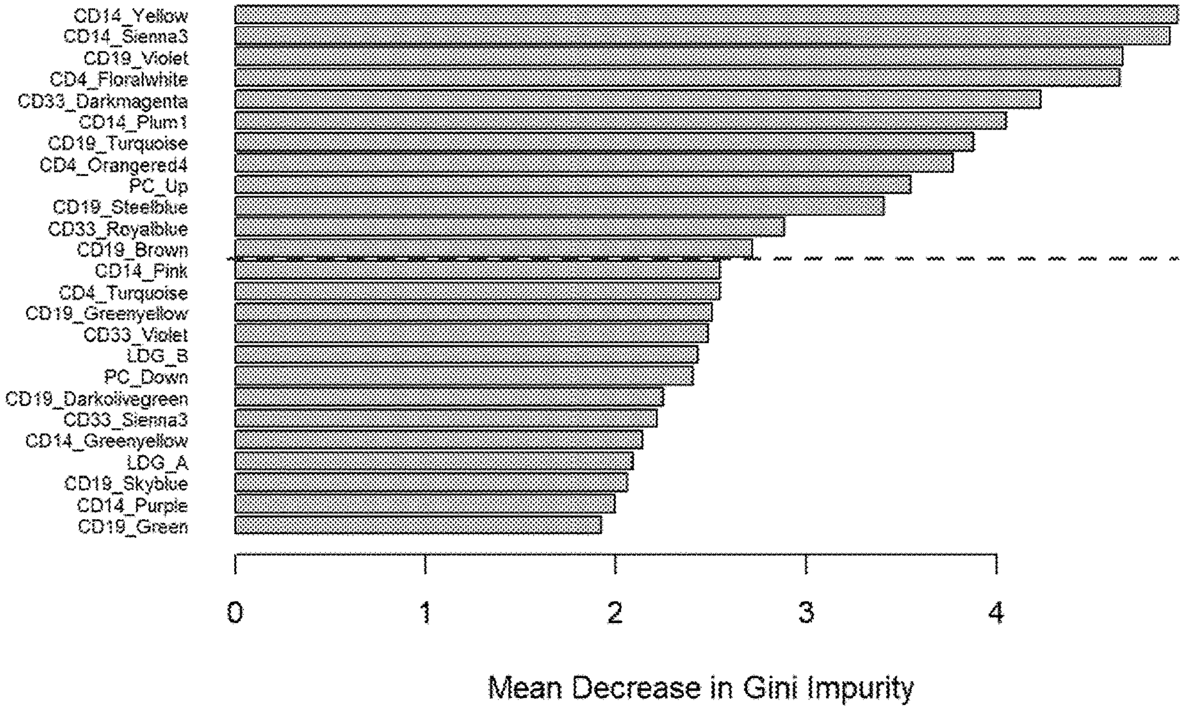
FIG. 6B shows an example of variable importance values of de-duplicated records as determined by mean decrease in Gini impurity, in accordance with disclosed embodiments.
Figure 6C:
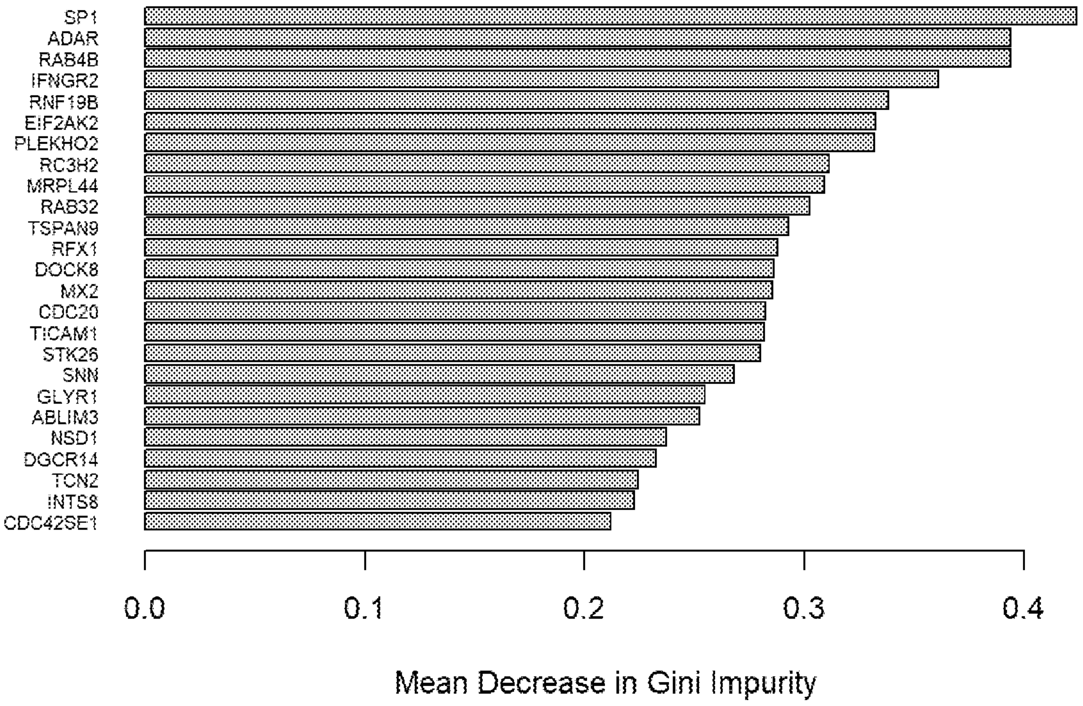
FIG. 6C shows an example of variable importance values of the top 25 individual genes determined by mean decrease in Gini impurity, in accordance with disclosed embodiments.

As shown in FIGS. 6A-6C, the most important genes and modules identified a wide array of cell types and biological functions. The most important genes encompass such diverse functions as interferon signaling, pattern recognition receptor signaling, and control of survival and proliferation, per FIG. 6C. Notably, the most influential modules may be skewed away from B cell-derived modules and towards T cell- and myeloid cell-derived modules, per FIG. 6A. As some of these modules had overlapping genes, the variable importance experiment may be repeated with modules that may be first scrubbed of any genes that appeared in more than one module before GSVA enrichment scoring. The relative variable importance scores of the de-duplicated modules correlated strongly with those of the original modules (Spearman's rho=0.73, p=5.18E-5), indicating that module behavior may be partly driven by the overlapping genes but strongly driven by unique genes, per FIG. 6A. Variable importance of top 25 individual genes. LDG: low-density granulocyte; PC: plasma cell.

TABLE 3

Cross-validation of gene expression and cell modules

| | Study-fold Cross-Validation | | 10-fold Cross-Validation | |
|---|---|---|---|---|
| | Gene Expression | Cell Modules | Gene Expression | Cell Modules |
| GLM | 0.56 | 0.68 | 0.80 | 0.72 |
| KNN | 0.48 | 0.68 | 0.75 | 0.7 |
| RF | 0.54 | 0.74 | 0.84 | 0.72 |
| Pooled | 0.53 | 0.71 | 0.78 | 0.73 |
| Mean (SD) | 0.53 (0.03) | 0.70 (0.03) | 0.79 (0.04) | 0.72 (0.01) |

When cross-validating by study, the use of expression values may achieve an accuracy of only 53 percent, per Table 3, which is consistent with the findings shown in FIGS. 2A-2D that gene expression values may provide less value towards classifying unfamiliar records. When the training records and test records are greatly heterogeneous, the classifiers learning patterns may be less helpful for classifying test records. Remarkably, the use of module enrichment scores improved accuracy to approximately 70 percent.

Per Table 3, the 10-fold cross-validation with raw gene expression values may result in better performance com- CD4_Floralwhite and CD14_Yellow, two interferon-related modules which maintained high importance after deduplication, may be further analyzed to study the effect of unique genes on module importance. Gene lists may be tested for statistical overrepresentation of Gene Ontology biological process terms with FDR correction on pantherdb.org. CD4_Floralwhite did not show any significant enrichment, but CD14_Yellow, which had the highest importance after deduplication, may be highly enriched for genes with the "Immune Effector Process" designation (26/77 genes, FDR=9.38E-11 by Fisher's exact test). This suggests that CD14+ monocytes express unique genes that may play important roles in the initiation of phenotypic activity.

Several important findings on the topic of gene expression heterogeneity within and across data sets have been elucidated by this study. First, DE analysis of active vs inactive records may be insufficient for proper classification of phenotypic activity, as systematic differences between data sets render conventional bioinformatics techniques largely non-generalizable.

Further, WGCNA modules created from the cellular components of WB and correlated to SLEDAI phenotypic activity may improve classification of phenotypic activity in records. The use of cell-specific gene modules based on a priori knowledge about their relevance to disease fared slightly better than raw gene expression, as it generated informative enrichment patterns, and many of the modules maintained significant correlations with SLEDAI in WB. However, these enrichment scores failed to completely separate active records from inactive records by hierarchical clustering.

Method Characterization

Conventional bioinformatics approaches do not satisfactorily identify one or more records having a specific phenotype. DE analysis of a plurality of first records, a plurality of second records, and a plurality of third records having an active disease state and a non-active disease state, per FIGS. 2A-2D displayed the major differences and heterogeneity. First, the 100 most significant DE genes by FDR in the plurality of first, second, and third records may be used to carry out hierarchical clustering of active and inactive disease state records, per FIGS. 2A-C. Active disease state records are clearly separated from inactive records, per FIG. 2B, but only partially separated from inactive records, per FIGS. 2A and 2C.

Figure 3:
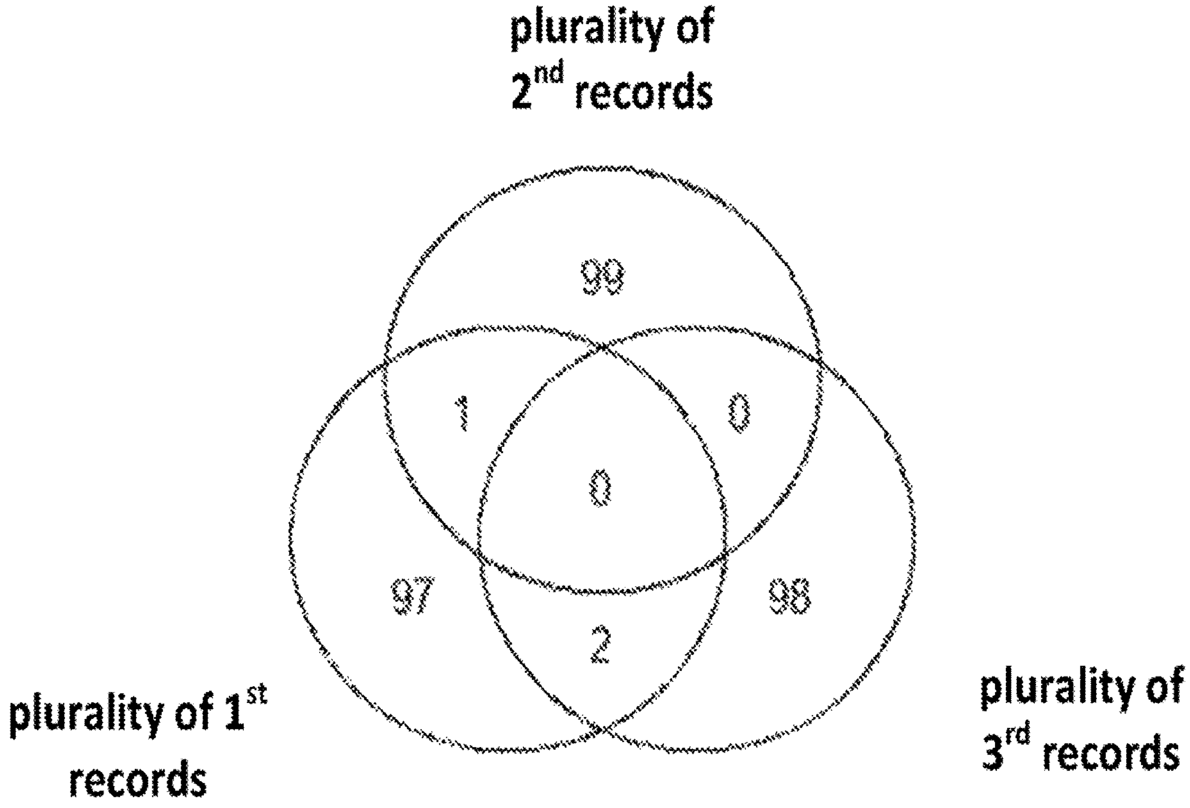
FIG. 3 shows an example of a Venn diagram of the top 100 records within each of the first, second, and third pluralities of records, in accordance with disclosed embodiments.

Out of 6,640 unique DE genes from the three pluralities of records, 5,170 genes are unique to one of the plurality of records, 1,234 are shared by two of the plurality of records, and 36 are shared by all three of the plurality of records. Per FIG. 3 there is minimal overlap of the 100 most significant genes by FDR in each of the pluralities of records. The only overlaps among the top 100 DE genes in each study by FDR are: TWY3 and EHBP1, shared between the plurality of first records and the plurality of third records; and LZIC, shared between the plurality of first records and plurality of second records. Furthermore, the fold change distributions of the 100 most significant DE genes in each of the pluralities of records varied considerably. In the plurality of first records, 94 of the 100 most significant genes are downregulated in active disease state records; in the plurality of second records, all of the top 100 genes are upregulated in active disease state records; and in the plurality of third records, the top 100 genes are more evenly distributed (41 up, 59 down). Per FIG. 3 orange bars denote active state records, wherein black bars denote inactive state records.

The plurality of first, second, and third records may represent different populations and may be collected on different microarray platforms per Table 4 below. The lack of commonality among the genes most descriptive of active state records and inactive state records in each of the pluralities of records casts doubt on whether active and inactive states from the different pluralities of records may be easily determined using conventional techniques.

TABLE 4

Accession of records by microarray platform, number of active and inactive records, SLEDAI range, and SLEADAI mean

| Accession | Microarray Platform | N Active | N Inactive | SLEDAI Range | SLEDAI Mean (SD) |
|---|---|---|---|---|---|
| Plurality of First Records | GPL570 (Affymetrix HG-U133 + 2.0) | 24 | 13 | 2-12 | 6.8 (2.7) |
| Plurality of Second Records | GPL13158 (Affymetrix HG-U133 + PM) | 35 | 35 | 0-11 | 4.3 (3.5) |

Records from the pluralities of first, second, and third records may then be joined to evaluate whether unsupervised techniques may separate active state records from inactive state records. Hierarchical clustering on the 297 unique most significant DE genes by FDR showed considerable heterogeneity, and active records and inactive records did not consistently separate, per the heat map of the top 100 DE genes by FDR from each of the pluralities of records (combined total of 297 unique genes from the plurality of first, second, and third records) expressed in all records in FIG. 2D. As such, conventional techniques failed to identify active records, highlighting the need for more advanced algorithms.

Digital Processing Device

In some embodiments, the platforms, systems, media, and methods described herein include a digital processing device, or use of the same. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing-based storage. In further embodiments, the storage and/or memory device is a combination of devices such as those disclosed herein.

In some embodiments, the digital processing device includes a display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the digital processing device, such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

Figure 7:
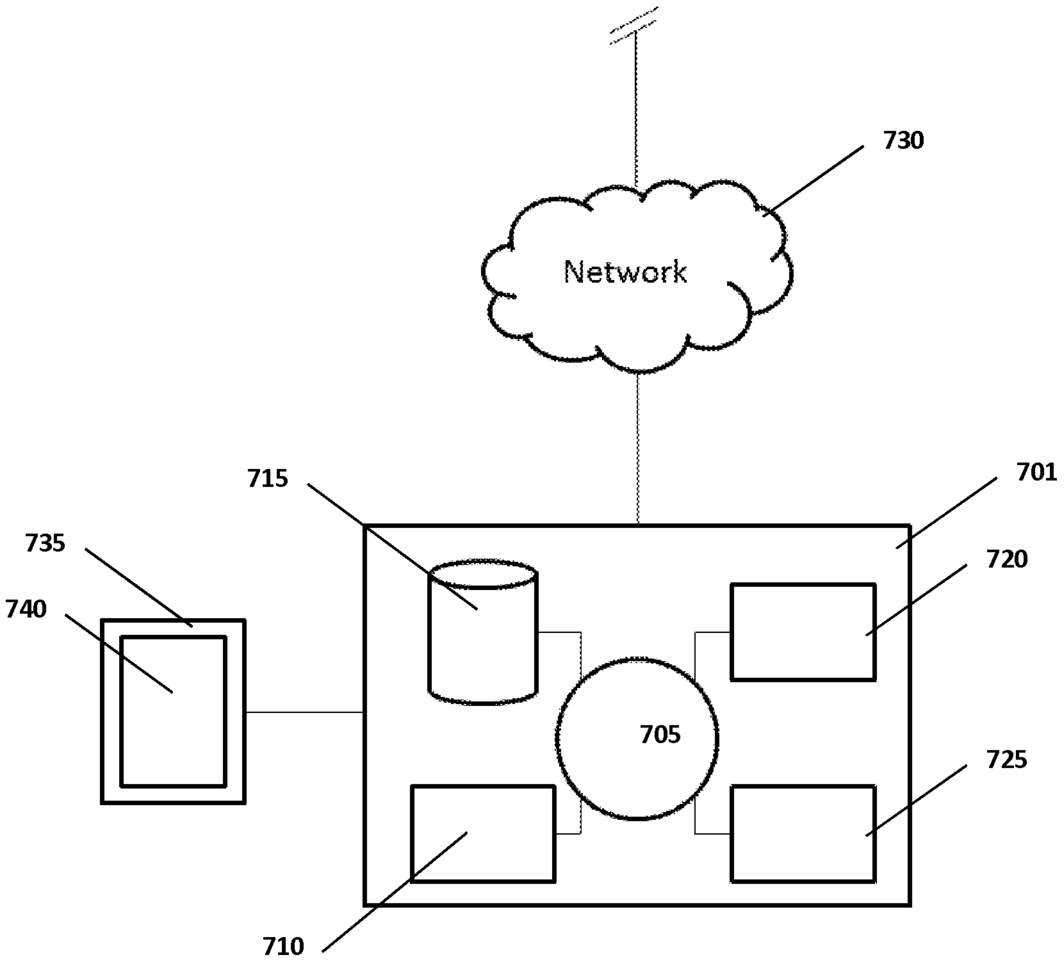
FIG. 7 shows a non-limiting schematic diagram of a digital processing device; in this case, a device with one or more CPUs, a memory, a communication interface, and a display.

Referring to FIG. 7, in a particular embodiment, a digital processing device 701 is programmed or otherwise configured to identify one or more records having a specific phenotype. The device 701 is programmed or otherwise configured to identify one or more records having a specific phenotype. In this embodiment, the digital processing device 701 includes a central processing unit (CPU, also "processor" and "computer processor" herein) 705, which is optionally a single core, a multi core processor, or a plurality of processors for parallel processing. The digital processing device 701 also includes memory or memory location 710 (e.g., random-access memory, read-only memory, flash memory), electronic storage unit 715 (e.g., hard disk), communication interface 720 (e.g., network adapter) for communicating with one or more other systems, and peripheral devices 725, such as cache, other memory, data storage and/or electronic display adapters. The memory 710, storage unit 715, interface 720 and peripheral devices 725 are in communication with the CPU 705 through a communication bus (solid lines), such as a motherboard. The storage unit 715 comprises a data storage unit (or data repository) for storing data. The digital processing device 701 is optionally operatively coupled to a computer network ("network") 730 with the aid of the communication interface 720. The network 730, in various cases, is the internet, an internet, and/or extranet, or an intranet and/or extranet that is in communication with the internet. The network 730, in some cases, is a telecommunication and/or data network. The network 730 optionally includes one or more computer servers, which enable distributed computing, such as cloud computing. The network 730, in some cases, with the aid of the device 701, implements a peer-to-peer network, which enables devices coupled to the device 701 to behave as a client or a server.

Continuing to refer to FIG. 7, the CPU 705 is configured to execute a sequence of machine-readable instructions, embodied in a program, application, and/or software. The instructions are optionally stored in a memory location, such as the memory 710. The instructions are directed to the CPU 705, which subsequently program or otherwise configure the CPU 705 to implement methods of the present disclosure. Examples of operations performed by the CPU 705 include fetch, decode, execute, and write back. The CPU 705 is, in some cases, part of a circuit, such as an integrated circuit. One or more other components of the device 701 are optionally included in the circuit. In some cases, the circuit is an application specific integrated circuit (ASIC) or a field programmable gate array (FPGA).

Continuing to refer to FIG. 7, the storage unit 715 optionally stores files, such as drivers, libraries and saved programs. The storage unit 715 optionally stores user data, e.g., user preferences and user programs. The digital processing device 701, in some cases, includes one or more additional data storage units that are external, such as located on a remote server that is in communication through an intranet or the internet.

Continuing to refer to FIG. 7, the digital processing device 701 optionally communicates with one or more remote computer systems through the network 730. For instance, the device 701 optionally communicates with a remote computer system of a user. Examples of remote computer systems include personal computers (e.g., portable PC), slate or tablet PCs (e.g., Apple® iPad, Samsung® Galaxy Tab, etc.), smartphones (e.g., Apple® iPhone, Android-enabled device, Blackberry®, etc.), or personal digital assistants.

Methods as described herein are optionally implemented by way of machine (e.g., computer processor) executable code stored on an electronic storage location of the digital processing device 701, such as, for example, on the memory 710 or electronic storage unit 715. The machine executable or machine readable code is optionally provided in the form of software. During use, the code is executed by the processor 705. In some cases, the code is retrieved from the storage unit 715 and stored on the memory 710 for ready access by the processor 705. In some situations, the electronic storage unit 715 is precluded, and machine-executable instructions are stored on the memory 710.

Non-Transitory Computer Readable Storage Medium

In some embodiments, the platforms, systems, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or extensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion® Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Figure 8:
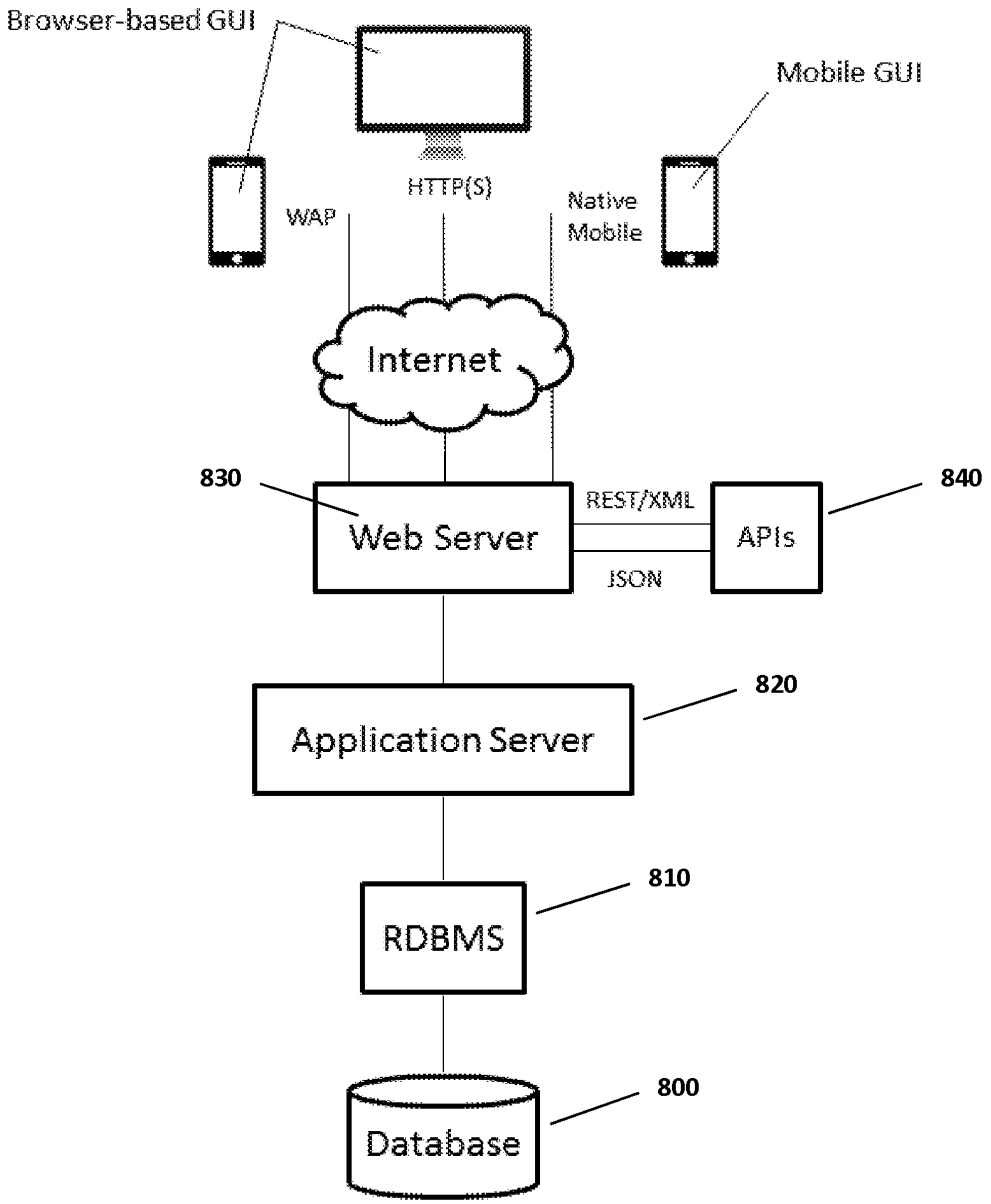
FIG. 8 shows a non-limiting schematic diagram of a web/mobile application provision system; in this case, a system providing browser-based and/or native mobile user interfaces.

Referring to FIG. 8, in a particular embodiment, an application provision system comprises one or more databases 800 accessed by a relational database management system (RDBMS) 810. Suitable RDBMSs include Firebird, MySQL, PostgreSQL, SQLite, Oracle Database, Microsoft SQL Server, IBM DB2, IBM Informix, SAP Sybase, SAP Sybase, Teradata, and the like. In this embodiment, the application provision system further comprises one or more application severs 820 (such as Java servers, .NET servers, PHP servers, and the like) and one or more web servers 830 (such as Apache, IIS, GWS and the like). The web server(s) optionally expose one or more web services via app application programming interfaces (APIs) 840. Via a network, such as the internet, the system provides browser-based and/or mobile native user interfaces.

Figure 9:
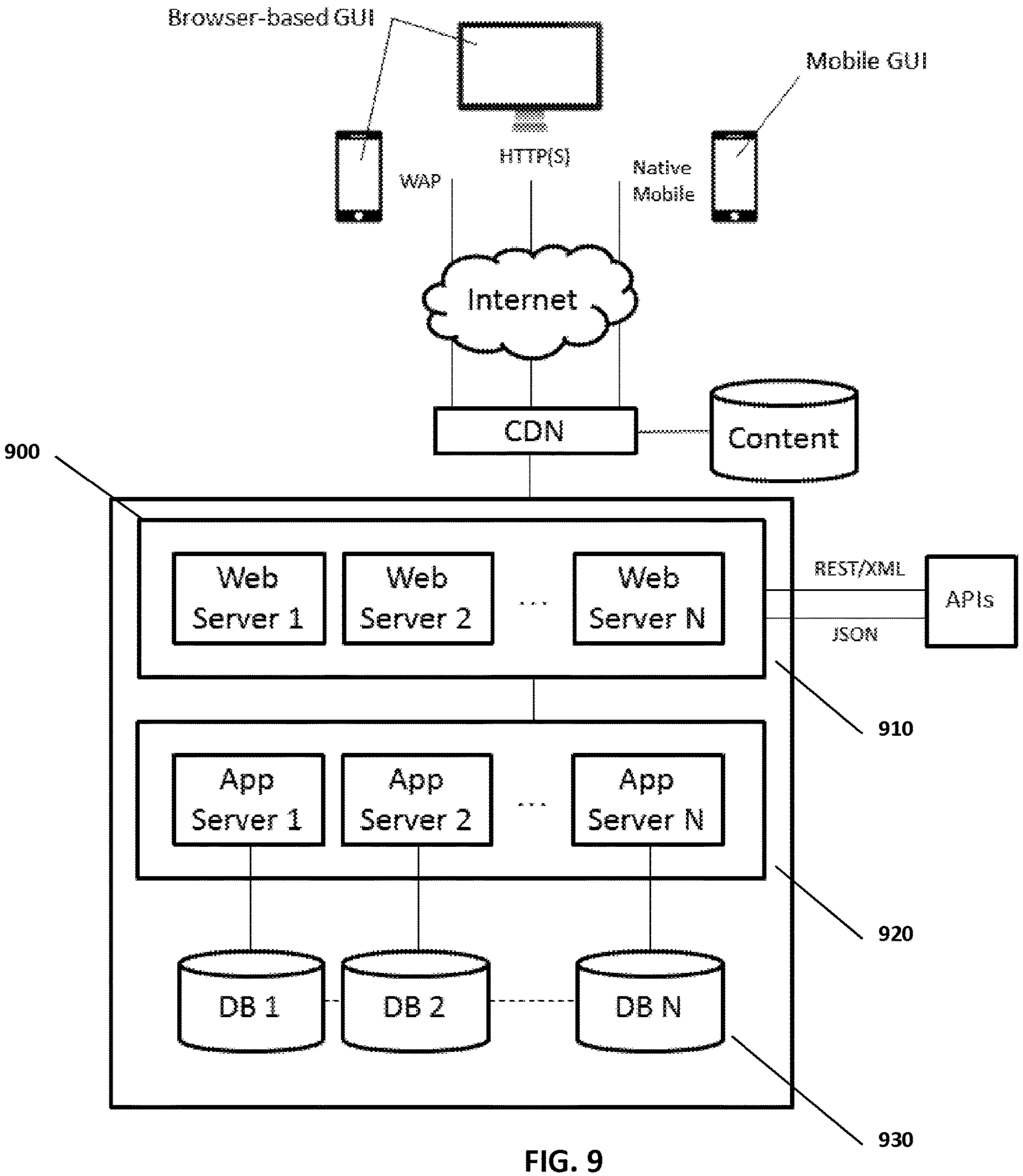
FIG. 9 shows a non-limiting schematic diagram of a cloud-based web/mobile application provision system; in this case, a system comprising an elastically load balanced, auto-scaling web server and application server resources as well synchronously replicated databases.

Referring to FIG. 9, in a particular embodiment, an application provision system alternatively has a distributed, cloud-based architecture 900 and comprises elastically load balanced, auto-scaling web server resources 910 and application server resources 920 as well synchronously replicated databases 930.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-in

In some embodiments, the computer program includes a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM Blackberry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for identifying one or more records having a specific phenotype. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

Biological Data Analysis

The present disclosure provides systems and methods to perform data analysis using drug or target scoring algorithms and/or big data analysis tools. In various aspects, such drug or target scoring algorithms and/or big data analysis tools may be used to perform analysis of data sets including, for example, mRNA gene expression or transcriptome data, DNA genomic data, proteomic data, metabolomic data, other types of "-omic" data, or a combination thereof.

In an aspect, the present disclosure provides a computer-implemented method for assessing a condition of a subject, comprising: (a) receiving a dataset of a biological sample of the subject; (b) selecting one or more data analysis tools, wherein the one or more data analysis tools comprise an analysis tool selected from the group consisting of: a BIG-C™ big data analysis tool, an I-Scope™ big data analysis tool, a T-Scope™ big data analysis tool, a CellScan big data analysis tool, an MS (Molecular Signature) Scoring™ analysis tool, a Gene Set Variation Analysis (GSVA) tool (e.g., P-Scope), a CoLTs® (Combined Lupus Treatment Scoring) analysis tool, and a Target Scoring analysis tool; (c) processing the dataset using the one or more data analysis tools to generate a data signature of the biological sample of the subject; and (d) based at least in part on the data signature generated in (c), assessing the condition of the subject.

In some embodiments, the dataset comprises mRNA gene expression or transcriptome data, DNA genomic data, proteomic data, metabolomic data, or a combination thereof. In some embodiments, the biological sample is selected from the group consisting of: a whole blood (WB) sample, a PBMC sample, a tissue sample, and a cell sample. In some embodiments, assessing the condition of the subject comprises identifying a disease or disorder of the subject.

In some embodiments, the method further comprises identifying a disease or disorder of the subject at a sensitivity or specificity of at least about 70%. In some embodiments, the method further comprises determining a likelihood of the identification of the disease or disorder of the subject. In some embodiments, the method further comprises providing a therapeutic intervention for the disease or disorder of the subject. In some embodiments, the method further comprises monitoring the disease or disorder of the subject, wherein the monitoring comprises assessing the disease or disorder of the subject at a plurality of time points, wherein the assessing is based at least on the disease or disorder identified at each of the plurality of time points.

In some embodiments, selecting the one or more data analysis tools comprises receiving a user selection of the one or more data analysis tools. In some embodiments, selecting the one or more data analysis tools is automatically performed by the computer without receiving a user selection of the one or more data analysis tools.

In another aspect, the present disclosure provides a computer system for assessing a condition of a subject, comprising: a database that is configured to store a dataset of a biological sample of the subject; and one or more computer processors operatively coupled to the database, wherein the one or more computer processors are individually or collectively programmed to: (i) select one or more data analysis tools comprising: a BIG-C™ big data analysis tool, an I-Scope™ big data analysis tool, a T-Scope™ big data analysis tool, a CellScan big data analysis tool, an MS (Molecular Signature) Scoring™ analysis tool, a Gene Set Variation Analysis (GSVA) tool (e.g., P-Scope), a CoLTs® (Combined Lupus Treatment Scoring) analysis tool, a Target Scoring analysis tool, or a combination thereof; (ii) process the dataset using the one or more data analysis tools to generate a data signature of the biological sample of the subject; and (iii) based at least in part on the data signature generated in (ii), assess the condition of the subject.

In another aspect, the present disclosure provides a non-transitory computer readable medium comprising machine-executable code that, upon execution by one or more computer processors, implements a method for assessing a condition of a subject, the method comprising: (a) receiving a dataset of a biological sample of the subject; (b) selecting one or more data analysis tools, wherein the one or more data analysis tools comprise an analysis tool selected from the group consisting of: a BIG-C™ big data analysis tool, an I-Scope™ big data analysis tool, a T-Scope™ big data analysis tool, a CellScan big data analysis tool, an MS (Molecular Signature) Scoring™ analysis tool, a Gene Set Variation Analysis (GSVA) tool (e.g., P-Scope), a CoLTs® (Combined Lupus Treatment Scoring) analysis tool, and a Target Scoring analysis tool; (c) processing the dataset using the one or more data analysis tools to generate a data signature of the biological sample of the subject; and (d) based at least in part on the data signature generated in (c), assessing the condition of the subject. In any embodiment described herein, the one or more data analysis tools can be a plurality of data analysis tools each independently selected from a BIG-C™ big data analysis tool, an I-Scope™ big data analysis tool, a T-Scope™ big data analysis tool, a CellScan big data analysis tool, an MS (Molecular Signature) Scoring™ analysis tool, a Gene Set Variation Analysis (GSVA) tool (e.g., P-Scope), a CoLTs® (Combined Lupus Treatment Scoring) analysis tool, and a Target Scoring analysis tool.

To obtain a blood sample, various techniques may be used, e.g., a syringe or other vacuum suction device. A blood sample can be optionally pre-treated or processed prior to use. A sample, such as a blood sample, may be analyzed under any of the methods and systems herein within 4 weeks, 2 weeks, 1 week, 6 days, 5 days, 4 days, 3 days, 2 days, 1 day, 12 hr, 6 hr, 3 hr, 2 hr, or 1 hr from the time the sample is obtained, or longer if frozen. When obtaining a sample from a subject (e.g., blood sample), the amount can vary depending upon subject size and the condition being screened. In some embodiments, at least 10 mL, 5 mL, 1 mL, 0.5 mL, 250, 200, 150, 100, 50, 40, 30, 20, 10, 9, 8, 7, 6, 5, 4, 3, 2, or 1 μL of a sample is obtained. In some embodiments, 1-50, 2-40, 3-30, or 4-20 μL of sample is obtained. In some embodiments, more than 5, 10, 15, 20, 25, 30, 35, 40, 45, 50, 55, 60, 65, 70, 75, 80, 85, 90, 95 or 100 μL of a sample is obtained.

The sample may be taken before and/or after treatment of a subject with a disease or disorder. Samples may be obtained from a subject during a treatment or a treatment regime. Multiple samples may be obtained from a subject to monitor the effects of the treatment over time. The sample may be taken from a subject known or suspected of having a disease or disorder for which a definitive positive or negative diagnosis is not available via clinical tests. The sample may be taken from a subject suspected of having a disease or disorder. The sample may be taken from a subject experiencing unexplained symptoms, such as fatigue, nausea, weight loss, aches and pains, weakness, or bleeding. The sample may be taken from a subject having explained symptoms. The sample may be taken from a subject at risk of developing a disease or disorder due to factors such as familial history, age, hypertension or pre-hypertension, diabetes or pre-diabetes, overweight or obesity, environmental exposure, lifestyle risk factors (e.g., smoking, alcohol consumption, or drug use), or presence of other risk factors.

In some embodiments, a sample can be taken at a first time point and assayed, and then another sample can be taken at a subsequent time point and assayed. Such methods can be used, for example, for longitudinal monitoring purposes to track the development or progression of a disease. In some embodiments, the progression of a disease can be tracked before treatment, after treatment, or during the course of treatment, to determine the treatment's effectiveness. For example, a method as described herein can be performed on a subject prior to, and after, treatment with a lupus condition therapy to measure the disease's progression or regression in response to the lupus condition therapy.

After obtaining a sample from the subject, the sample may be processed to generate datasets indicative of a disease or disorder of the subject. For example, a presence, absence, or quantitative assessment of nucleic acid molecules of the sample at a panel of condition-associated genomic loci or may be indicative of a lupus condition of the subject. Processing the sample obtained from the subject may comprise (i) subjecting the sample to conditions that are sufficient to isolate, enrich, or extract a plurality of nucleic acid molecules, and (ii) assaying the plurality of nucleic acid molecules to generate the dataset (e.g., microarray data, nucleic acid sequences, or quantitative polymerase chain reaction (qPCR) data). Methods of assaying may include any assay known in the art or described in the literature, for example, a microarray assay, a sequencing assay (e.g., DNA sequencing, RNA sequencing, or RNA-Seq), or a quantitative polymerase chain reaction (qPCR) assay.

In some embodiments, a plurality of nucleic acid molecules is extracted from the sample and subjected to sequencing to generate a plurality of sequencing reads. The nucleic acid molecules may comprise ribonucleic acid (RNA) or deoxyribonucleic acid (DNA). The extraction method may extract all RNA or DNA molecules from a sample. Alternatively, the extraction method may selectively extract a portion of RNA or DNA molecules from a sample. Extracted RNA molecules from a sample may be converted to cDNA molecules by reverse transcription (RT).

The sample may be processed without any nucleic acid extraction. For example, the disease or disorder may be identified or monitored in the subject by using probes configured to selectively enrich nucleic acid (e.g., RNA or DNA) molecules corresponding to a panel of condition-associated genomic loci. The probes may be nucleic acid primers. The probes may have sequence complementarity with nucleic acid sequences from one or more of the panel of condition-associated genomic loci. The panel of condition-associated genomic loci may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, or more condition-associated genomic loci.

The probes may be nucleic acid molecules (e.g., RNA or DNA) having sequence complementarity with nucleic acid sequences (e.g., RNA or DNA) of one or more genomic loci (e.g., condition-associated genomic loci). These nucleic acid molecules may be primers or enrichment sequences. The assaying of the sample using probes that are selective for the one or more genomic loci (e.g., condition-associated genomic loci) may comprise use of array hybridization, polymerase chain reaction (PCR), or nucleic acid sequencing (e.g., RNA sequencing or DNA sequencing, such as RNA-Seq).

The assay readouts may be quantified at one or more genomic loci (e.g., condition-associated genomic loci) to generate the data indicative of the disease or disorder. For example, quantification of array hybridization or polymerase chain reaction (PCR) corresponding to a plurality of genomic loci (e.g., condition-associated genomic loci) may generate data indicative of the disease or disorder. Assay readouts may comprise quantitative PCR (qPCR) values, digital PCR (dPCR) values, digital droplet PCR (ddPCR) values, fluorescence values, etc., or normalized values thereof.

Big Data Analysis Tools and Drug/Target Scoring Algorithms

The present disclosure provides systems and methods to perform data analysis using drug or target scoring algorithms and/or big data analysis tools. In various aspects, such drug or target scoring algorithms and/or big data analysis tools may be used to perform analysis of data sets including, for example, mRNA gene expression or transcriptome data, DNA genomic data, proteomic data, metabolomic data, other types of "-omic" data, or a combination thereof. Systems and methods of the present disclosure may use one or more of the following: a BIG-C™ big data analysis tool, an I-Scope™ big data analysis tool, a T-Scope™ big data analysis tool, a CellScan big data analysis tool, an MS (Molecular Signature) Scoring™ analysis tool, a Gene Set Variation Analysis (GSVA) tool (e.g., P-Scope), a CoLTs® (Combined Lupus Treatment Scoring) analysis tool, and a Target Scoring analysis tool.

A non-limiting example of a workflow of a method to assess a condition of a subject using one or more data analysis tools and/or algorithms may comprise receiving a dataset of a biological sample of a subject. Next, the method may comprise selecting one or more data analysis tools and/or algorithms. For example, the data analysis tools and/or algorithms may comprise a BIG-C™ big data analysis tool, an I-Scope™ big data analysis tool, a T-Scope™ big data analysis tool, a CellScan big data analysis tool, an MS (Molecular Signature) Scoring™ analysis tool, a Gene Set Variation Analysis (GSVA) tool (e.g., P-Scope), a CoLTs® (Combined Lupus Treatment Scoring) analysis tool, a Target Scoring analysis tool, or a combination thereof. Next, the method may comprise processing the dataset using selected data analysis tools and/or algorithms to generate a data signature of the biological sample of the subject. Next, the method may comprise assessing the condition of the subject based on the data signature.

The BIG-C (Biologically Informed Gene Clustering) tool may be configured to sort large groups of genes into a set of functional groups (e.g., 53 functional groups). The functional groups are created utilizing publicly available information from online tools and databases including UniProtKB/Swiss-Prot, GO Terms, KEGG pathways, NCBI PubMed, and the Interactome. The functional groups may include one or more of: Active RNA, Anti-apoptosis, anti-proliferation, autophagy, chromatin remodeling, cytoplasm and biochemistry, cytoskeleton, DNA repair, endocytosis, endoplasmic reticulum, endosome and vesicles, fatty acid biosynthesis, cell surface, transcription, glycolysis and gluconeogenesis, golgi, immune cell surface, immune secreted, immune signaling, integrin pathway, interferon stimulated genes, intracellular signaling, lysosome, melanosome, MHC class I, MHC class II, microRNA processing, microRNA, mitochondrial transcription, mitochondria, mitochondria oxidative phosphorylation, mitochondrial TCA cycle, mRNA processing, mRNA splicing, non-coding RNA, nuclear receptor, nucleus and nucleolus, palmitoylation, pattern recognition receptors, peroxisomes, pro-apoptosis, pro-cell cycle, proteasome, pseudogenes, RAS superfamily, reactive oxygen species protection, secreted and extracellular matrix, transcription factors, transporters, transposon control, ubiquitylation and sumoylation, unfolded protein and stress, and unknown. Enrichment scores for each group are calculated based on an overlap p value to determine the functional groups over or under-expressed in the gene expression dataset. The BIG-C may be configured such that each gene is sorted into only one of the 53 functional groups, allowing for a quick and relatively simple understanding of types of genes enriched and co-expressed in a big dataset.

The I-Scope™ tool may be configured to identify immune infiltrates. Hematopoietic cells are unique in that they move throughout the body patrolling for threats to the host, and may infiltrate tissue sites not normally home to immune cells. I-Scope™ may be configured to identify hematopoietic cells through an iterative search of more than 17,000 genes identified in more than 50 microarray datasets. From this search, 1226 candidate genes are identified and researched for restriction in hematopoietic cells as determined by the HPA, GTEx and FANTOM5 datasets (e.g., available at proteinatlas.org). 926 genes meet the criteria for being mainly restricted to hematopoietic lineages (brain, reproductive organ exclusions were permitted). These genes are researched for immune cell specific expression in 27 hematopoietic sub-categories: alpha beta T cell, T cell, regulatory T Cell, activated T cell, anergic T cell, gamma delta T cells, CD8 T, NK/NKT cell, NK cell, T & B cells, B cells, germinal center B cells, B cell and plasmacytoid dendritic cell, T &B & myeloid, B & myeloid, T & myeloid, MHC Class II expressing cell, monocyte, dendritic cell, plasmacytoid dendritic cells, myeloid cell, plasma cell, erythrocyte, neutrophil, low density granulocyte, granulocyte, and platelet. Transcripts are entered into I-Scope™ and the number of transcripts in each category determined. Odd's ratios are calculated with confidence intervals using the Fisher's exact test in R.

The T-Scope™ tool may be configured to help identify types of non-hematopoietic cells in gene expression datasets. T-Scope™ may be configured by downloading approximately 10,000 tissue enriched and 8,000 cell line enriched genes from the human protein atlas along with their tissue or cell line designation (e.g., available at proteinatlas.org). Genes found in more than four tissues are eliminated. Housekeeping genes described in the gene expression study by She et al. are also removed (e.g., as described by She et al., "Definition, conservation and epigenetics of housekeeping and tissue-enriched genes," BMC Genomics 2009, 10:269, which is incorporated herein by reference in its entirety). This list is further curated by removing genes differentially expressed in 34 hematopoietic cell gene expression datasets and adding kidney specific genes from datasets downloaded from the GEO repository and processed by Ampel BioSolutions. The resulting categories of genes represent genes enriched in the following 42 tissue/cell specific categories: adrenal gland, breast, cartilage, cerebral cortex, uterine cervix, chondrocyte, colon, duodenum, endometrium, epididymis, esophagus fallopian tube, esophagus, fibroblast, heart muscle, keratinocyte, kidney, liver, lung, melanocyte, ovary pancreas, parathyroid gland, placenta, podocyte, prostrate, rectum, salivary gland, seminal vesicle, skeletal muscle, skin, small intestine, smooth muscle, stomach, synoviocyte, testis, kidney loop of henle, kidney proximal tubule, kidney distal tubule, and kidney collecting duct.

The CellScan tool may be a combination of I-Scope™ and T-Scope™, and may be configured to analyse tissues with suspected immune infiltrations that should also have tissue specific genes. CellScan may potentially be more stringent than either I-Scope™ or T-Scope™ because it may be used to distinguish resident tissue cells from non-resident hematopoietic cells.

The MS (Molecular Signature) Scoring tool may be configured to assess specific pathways in a disease state. Information on genes that encode for proteins that participate in a specific signaling pathway, and whether the gene product promotes or inhibits the pathway, are compiled and curated through literature mining. Curated pathways presented by the company include CD40-CD40ligand, IL-6, IL-12/23, TNF, IL-17, IL-21, S1P1, IL-13 and PDE4, but this method may be used for any known signaling pathway with available data. To determine if a signaling pathway is over or under-expressed in a microarray dataset, the gene list for each signaling pathway may be queried against the limma differentially expressed genes from a disease state compared to healthy controls, and the differentially expressed genes in the signaling pathway may be identified for each set. The fold changes for genes that promoted the pathway may be added together and the fold changes for genes that inhibited the pathway may be subtracted from the score. This total score may be normalized based on the number of genes that could be detected on the specific microarray platform used for the experiment. Activation scores of −100 to +100 may be determined using this method with negative scores indicating an inhibition of the specific pathway in the disease state and positive scores indicating an up-regulation of a specific pathway in the disease state. The Fischer's exact test may be performed to determine if there was sufficient overlap of genes between the experimental differentially expressed genes and the genes in the signaling pathway.

Gene Set Variation Analysis (GSVA) may be performed (for example, as described in Catalina et al. (2019, Communications Biology, "Gene expression analysis delineates the potential roles of multiple interferons in systemic lupus erythematosus", which is incorporated herein by reference in its entirety) to determine enrichment of signaling pathways in individual patient samples. Gene set variation analysis may be performed using an open source software package for the coding language R available at the R Bioconductor (bioconductor.org), e.g., as described by Hanzelman et al., ("GSVA: gene set variation analysis for microarray and RNA-Seq data," BMC Bioinformatics, 2013, which is incorporated herein by reference in its entirety). The modules of genes to interrogate the datasets may be developed. Modules of genes determined to represent a specific signaling pathway or process may be identified (e.g., using publicly available datasets). For example, the IFNB1 signaling pathway is taken from a publicly available gene expression dataset of peripheral blood cells treated with IFNB1 in vitro. Genes co-expressed in this dataset (genes either all increased or decreased compared to control treated peripheral blood) are used to create modules of genes representing the IFNB1 signaling pathway, and GSVA is used to determine the enrichment of this set of genes and hence the IFNB1 signaling pathway in individual patient and control samples.

The CoLTs®, or Combined Lupus Treatment Scoring, may be configured to rank identified drugs or therapies by a number of essential characteristics, including scientific rationale, experience in lupus mice/human cells (preclinical), previous clinical experience in autoimmunity, drug properties, and safety profile, including adverse events. Face and test validities may be established by scoring SOC medications and confirming the scores with a panel of lupus clinicians. The final result may be the CoLTs® score. A CoLTs® algorithm may also be configured for drugs in development (DID), which typically do not have drug metabolism and adverse event information available.

The target scoring algorithm may be configured to prioritize a specific gene or protein that is potentially a good choice to target with a drug in lupus patients. It may be utilized even if there is currently no drug available to the target gene or protein. The algorithm may be based on the addition of 18 data based determinations plus the overall scientific rationale and generates scores from −13 (not a good target in SLE) to 27 (very promising target in SLE).

Big-C™ Big Data Analysis Tool

BIG-C® is a fast and efficient cloud-based tool to functionally categorize gene products. With coverage of over 80% of the genome, BIG-C® leverages publicly available databases such as UniProtKB/Swiss-Prot, GO terms, KEGG pathways, NCBI PubMed and Interactome to place genes into 53 functional categories. The sorting into only one of 53 functional groups allows for a quick and relatively simple understanding of types of genes enriched and co-expressed in a big dataset. This assists in deriving further insights from genes expressed for a given disease state in human or pre-clinical mouse models.

BIG-C® can be used to functionally categorize immunological genes that are not covered in cancer databases such as GO and KEGG (e.g., as described by Grammer et al. 2016, "Drug repositioning in SLE: crowd-sourcing, literature-mining and Big Data analysis," Lupus, 25(10), 1150-1170, which is incorporated herein by reference in its entirety). Using a knowledge base of over 5000 patients with systemic lupus erythematosus (SLE), over 16432 genes are each placed into one of 53 BIG-C® functional categories, and statistical analysis is performed to identify enriched categories. BIG-C® categories are cross-examined with the GO and KEGG terms to obtain additional information and insights.

A sample BIG-C® workflow may comprise the following steps. First, SLE genomic datasets are derived from whole blood, peripheral blood mononuclear cells, affected tissues, and purified immune cells. Second, datasets are analyzed using DE analysis (as shown by a differential expression heatmap) or Weighted Gene Coexpression Network Analysis (WGCNA) (as shown by a gene coexpression plot). Third, expressed genes are annotated using publicly available databases (e.g., UniProtKB/Swiss-Prot database, Human Immunodeficiencies database, Mouse MGI database, Entrez Molecular Sequence database, PubMed, and the Human Tissue Atlas). Fourth, signatures are cross-referenced with purified single-cell microarray datasets and RNAseq experiments. Fifth, BIG-C® is leveraged to separate the individual annotated genes into one of 53 functional categories shown in Table 19 (e.g., as described by Labonte et al. 2018, "Identification of alterations in macrophage activation associated with disease activity in systemic lupus erythematosus," PloS one, 13(12), e0208132, which is incorporated herein by reference in its entirety). Sixth, chi-squared analysis is used to determine enriched categories of interest from overlap p-values. Seventh, enriched categories are cross-examined with GO and KEGG terms to derive key insights for further analysis.

TABLE 19

BIG-C Categories

| Immune Cell Surface | General Cell Surface | Immune Signaling | Intracellular Signaling | MHC Class I | MHC Class II | Secreted Immune | Secreted ECM | Pat. Recog. Receptors |
|---|---|---|---|---|---|---|---|---|
| Interferon Gene Sig | PRO-Cell Cycle | Anti-Cell Cycle | PRO Apoptosis | Anti Apoptosis | Unfold Prot. Stress | Proteasome | Autophagy | Ubiquitylation |
| General Transcript. | Transcript. Factors | Nuc. Horm. Receptors | Chromatin Remodel | DNA Repair | mRNA Translation | mRNA Splicing | MicroRNA Processing | Cytoskeleton |
| Integrin Pathway | RAS Superfamily | WNT Signaling | Lysosome | Endocytosis | Endosome & Vesicles | Endoplas. Retic. | Oxidative Phosphor. | TCA Cycle |
| Mito. DNA to RNA | Mito | FA Biosynth | Transporters | Cytoplasm Biochem | Peroxisomes | ROS Protection | Nuclear & Nucleolus | ActiveRNA |
| Micro RNA | Melanosome | Unknown | Pseudogenes | Transposon Control | Golgi | Glycolysis | Palmitoylation | |

I-Scope™ Big Data Analysis Tool

I-Scope™ may be a tool configured for cross-examining the presence and activity of varying types of immune cell infiltrates with observed gene expression patterns. It may take annotated gene expression data and analyze it for hematopoietic cell lineage. I-Scope™ can be used downstream of the BIG-C® (Biologically Informed Gene-Clustering) tool in that it helps to provide even more insight into the nature of the genes being expressed after categorization.

I-Scope™ addresses the need to understand the involvement of specific cells for a given disease state. While it is helpful to understand the relative up-regulation and down-regulation at the gene expression level, it is even more informative to understand specifically in which cells this is occurring. I-Scope™ may be configured to identify hematopoietic cells through an iterative search of more than 17,000 genes identified in more than 50 microarray datasets (e.g., as described by Hubbard et al., "Analysis of Lupus Synovitis Gene Expression Reveals Dysregulation of Pathogenic Pathways Activated within Infiltrating Immune Cells," Arthritis Rheumatol, 2018; 70 (suppl 10), which is incorporated herein by reference in its entirety). I-Scope™ may function by restricting the analysis to genes of hematopoietic cell heritage and allow for cross-checking against purified single-cell experiments or datasets. The cross-check confirms and categorizes specific transcript signatures to the 28 hematopoietic cell sub-categories shown in Table 20, ultimately allowing for cellular activity analysis across multiple samples and disease states. When combined with BIG-C® categories, the cellular activity can be correlated to specific functions within a given cell type.

TABLE 20

| I-Scope ™ Cell Sub-Categories | | | | | | |
|---|---|---|---|---|---|---|
| Monos/Macs | Plasma Cells | T-Cells | B-Cells | Dendritic | T&B Cells | CD8 T |
| Myeloid Cells | Tact | LDG | Hematopoietic | Neutrophil | Ag Presentation | Granulocytes |
| Platelets | pDC | T, B, Mono | Langerhans | Bact | Mono and B | Erythrocytes |
| Mast Cell | T reg | Gd T | T anergic | FDC | CD4T | T/NK/NKT Cells |

A sample I-Scope™ workflow may comprise the following steps. First, candidate genes are identified from SLE (systemic lupus erythematosus) datasets potentially associated with immune cell expression. Second, using HPA, GTEx, and FANTOM5 datasets, expression signatures associated with hematopoietic cell lineage are identified. Third, signatures are cross-referenced with purified single-cell microarray datasets and RNAseq experiments. Fourth, transcripts are categorized into 28 hematopoietic cell sub-categories and assess cellular expression across different samples and disease states. Odd's ratios are calculated with confidence intervals using the Fisher's exact test in R. An I-Scope™ signature analysis for a given sample may lead to the I-Scope™ signature analysis across multiple samples and disease states.

down-regulation at the gene expression level, it is even more informative to understand specifically in which cells this is occurring. T-Scope™ may be configured by downloading a set of approximately 10,000 tissue enriched and 8,000 cell line enriched genes from the Human Protein Atlas along with their tissue or cell line designation. Genes differentially expressed in hematopoietic cell datasets are removed and kidney specific genes are added from the GEO repository. T-Scope™ may function by restricting the analysis to genes of known tissue cell heritage and allow for cross-checking against purified single-cell experiments or datasets. The cross-check confirms and categorizes specific transcript signatures to the 45 tissue cell sub-categories (as shown in Table 21), ultimately allowing for cellular activity analysis across multiple samples and disease states. When combined with BIG-C® categories, the cellular activity can be correlated to specific functions within a given tissue cell type.

TABLE 21

| T-Scope ™ 45 Categories of Tissue Cells | | | | | | | | |
|---|---|---|---|---|---|---|---|---|
| Adipose Tissue | Adrenal Gland | Breast | Cartilage | Cerebral Cortex | Cervix, Uterine | Chondrocyte | Colon | Dendritic |
| Duodenum | Endometrium | Endothelial | Epididymis | Erythrocytes | Esophagus | Fallopian Tube | Fibroblast | Gallbaldder |
| Heart Muscle | Keratinocyte | Keratinocyte Skin | Kidney | Kidney Distal Tubules | Kidney Loop | Kidney Proximal Tubules | Kidney Tubule Duct | Kidney Tubule |
| Langherhans | Liver | Lung | Melanocyte | Podocyte | Prostate | Rectum | Salivary Gland | Seminal Vesicle |
| Skeletal Muscle | Skin | Small Intenstine | Smooth Muscle | Stomach | Synoviocyte | Testis | Thyroid Gland | Urinary Bladder |

T-Scope™ Big Data Analysis Tool

The T-Scope™ tool may be configured for cross-examining gene expression signatures of a given sample with a database of non-hematopoietic cell types (e.g., as described by Hubbard et al., "Analysis of Gene Expression from Systemic Lupus Erythematosus Synovium Reveals Unique Pathogenic Mechanisms [Abstract], Annual Meeting of the American College of Rheumatology; June 2019; Chicago, IL, which is incorporated herein by reference in its entirety). T-Scope™ may comprise a database of 704 transcripts allocated to 45 independent categories. Transcripts detected in the sample are matched to one of the cellular categories within the T-Scope™ tool to derive further insights on tissue cell activity. T-Scope™ can be used downstream of the BIG-C® (Biologically Informed Gene-Clustering) tool to understand which tissue cell types are present. In conjunction with I-Scope™ (which provides information related to immune cells), T-Scope™ can be performed to provide a complete view of all possible cell activity in a given sample.

T-Scope™ addresses the need to understand the involvement of specific tissue cells for a given disease state. While it is helpful to understand the relative up-regulation and A sample T-Scope™ workflow may comprise the following steps. First, candidate genes are identified from SLE (systemic lupus erythematosus) differential expression datasets potentially associated with tissue cell expression. Second, using publicly available databases, expression signatures associated with potential tissue cell activity are identified. Third, signatures are cross-referenced with microarray, scRNAseq or RNAseq experiments. Fourth, transcripts are categorized into 45 tissue cell sub-categories and cellular expression is assessed across different samples and disease states. Results may be obtained using T-Scope™ in combination with I-Scope™ for identification of cells post-DE-analysis.

CellScan Big Data Analysis Tool

A cloud-based genomic platform may be configured to provide users with access to CellScan™, which comprises a suite of tools for the identification, analysis, and prioritization of targets for drug development and/or repositioning. This platform is powered by a database containing the genomic information gathered from 5000+ autoimmune patients. The cloud-based genomic platform may leverage results from RNAseq and microarray experiments in conjunction with clinical information, such as medication and lab tests, to provide previously undiscovered insights.

CellScan™ may go beyond typical 'omics analysis by performing one or more of the following: functionally categorizing genes and their products (e.g., using BIG-C®); deconvolving gene expression data to identify unique immunological cell types from blood or biopsy samples (e.g., using I-Scope™); identifying tissue specific cell from biopsy samples (e.g., using T-Scope™); identifying receptor-ligand interactions and subsequent signaling pathways (e.g., using MS-Scoring™); ranking genes and their products for targeting by drugs and miRNA mimetics (e.g., using Target-Scoring™); and prioritizing FDA-approved drugs and drugs-in-development for treatment in patients or preclinical models (e.g., using CoLTs®).

CellScan™ applications may include one or more of: Biomarker Discovery, Disease Mechanisms, Drug Mechanism of Action, Drug Mechanism of Toxicity, and Target Identification and Validation. Experimental approaches supported by CellScan™ may include one or more of: lncRNA, Metabolomics, MicroArray, miRNA, mRNA, qPCR, Proteomics, and RNAseq.

Data analysis and interpretation with CellScan™ may build on comprehensive, manually curated content of a knowledge base. Powerful, quick, and efficient tools may be used to perform deep analysis of NGS and miRNA data to identify gene function, immunological and tissue cell type, pathways, and target/drug appropriate for a specific disease state.

CellScan™ features may be configured to optimize or maximize the impact of information that surfaces in an analysis so that interpretation of a dataset is comprehensive and elucidates actionable insights. These features may include one or more of: NGS RNAseq data analysis, biomarker scoring, and prioritizing targets and drugs for human clinical trials and/or pre-clinical models. The NGS RNAseq data analysis may comprise interrogating RNA and miRNA data for function, cell-type (immunological or tissue) and pathways. The biomarker scoring may comprise using a knowledge base and gene expression data to assess and prioritize biomarkers associated with a target disease or phenotype. The target/drug prioritization may comprise leveraging objective scoring of targets and drugs based on parameters such as scientific rationale, evidence in mouse/human cells, prior clinical data, overall drug properties, and the risk of adverse events.

The knowledge base may be a repository created from millions of individual pieces of information gathered about genes, cells, tissues, drugs, and diseases, and manually reviewed for accuracy and includes rich contextual details and links to original publications. The knowledge base may enable access to relevant and substantiated knowledge from primary literature as well as public and private databases for comprehensive interpretation of NGS/RNAseq data elucidating function/pathways and prioritize targets/drugs for given disease states. Table 22 shows an example list of reference databases for the content in CellScan™, with both human and mouse species-specific identifiers supported.

TABLE 22

Reference Databases for Content in CellScan ™

| Affymetrix | Entrez Gene | HPA | scRNAseq |
|---|---|---|---|
| Agilent | FANTOM5 | Illumina | STITCH |
| BrainArray | GenBank | Interactome | Mouse Genome Database (MGD) |
| CAS Registry Number | Gene Symbol—human (Hugo/HGNC) | KEGG | UCSC (hg18) |
| Clinicaltrials.gov | Gene Symbol—mouse (Entrez Gene) | LINCS/CLUE | UCSC (hg19) |
| CodeLink | GNF Tissue Expression Body Atlas | Mosby's Drug Consult | Unigene |
| DrugBank | GO terms | NCBI PubMed | Uniprot/Swiss-Prot Accession |
| Drugs@FDA | Goodman & Gilman's Pharmacological Basis of Therapeutics | NCI-60 Cell Line Expression Atlas | |
| Ensembl | GTEx | Refseq | |

MS (Molecular Signature) Scoring™ Analysis Tool

MS-Scoring™ may be configured to identify receptor-ligand interactions and predict ongoing signaling pathways. In addition, MS-Scoring™ may be used to validate molecular pathways as potential targets for new or repurposed drug therapies. The specificity of next-generation drug therapies requires a way to understand the potential of a given therapy to act on the intended biochemical target. Moreover, a potential application of this is the repositioning of drug therapies that may have the correct biochemical targeting to address multiple clinical needs beyond the initial intended therapeutic value.

MS-Scoring™ may be specifically developed to address gaps in the QIAGEN IPA® (Ingenuity Pathway Analysis) tool that does not contain many immunologically relevant pathways. Similar to IPA®, MS-Scoring™ 1 may use log-fold change information to score the target and its signaling pathway to verify the viability of the targets. If the fold-change of the genes of a signaling pathway appears to be upregulated or inhibitors appear to be downregulated, MS-Scoring™ 1 may provide a score of +1. Conversely if the genes of a signaling pathway appear downregulated or the inhibitors upregulated, MS-Scoring™ 1 may provide a score of −1. A score of zero may be provided if no fold-change is observed. The scores may then be summed and normalized across the entire pathway to yield a final % score between −100 (inhibition) and +100 (up-regulation). Higher absolute magnitude scores, scores that are close to −100 or +100, may indicate a high potential for therapeutic targeting. The Fischer's exact test may be performed to determine if there is sufficient overlap of genes between the experimental differentially expressed genes and the genes in the signaling pathway.

A sample MS-Scoring™ 1 workflow may comprise the following steps. First, potential drugs and pathways are identified by LINCS (Library of Integrated Network-Based Cellular Signatures) as candidates for therapeutic intervention. Second, MS-Scoring™ 1 is used to evaluate individual transcript elements of the target pathway. Third, signatures are cross-referenced with purified single-cell microarray datasets and RNAseq experiments. Fourth, scores are compiled and normalized to provide an overall % score for the pathway and higher absolute magnitude scores indicate a higher potential for therapeutic targeting.

MS-Scoring™ 1 may be performed of IL-12 and IL-23 related pathways for targeting using ustekinumab for SLE (systemic lupus erythematosus) drug repositioning (e.g., as described by Grammer et al., 2016, "Drug repositioning in SLE: crowd-sourcing, literature-mining and Big Data analysis," Lupus, 25(10), 1150-1170, which is incorporated herein by reference in its entirety).

MS-Scoring™ 2 may utilize custom-defined gene modules that represent a signaling pathway or process and is particularly useful for gene expression datasets from microarray or RNAseq. The MS-Scoring™ 2 tool may be configured to take a deeper look at signaling pathways analyzed using the MS-Scoring™ 1. The tool may analyze raw gene expression data and assess enrichment by the Gene Set Variation Analysis (as described herein), which assigns an indexed score to the individual co-expressed pathways between −1 and +1 indicating levels of down-regulation and up-regulation respectively.

A sample MS-Scoring™ 2 workflow may comprise the following steps. First, a signaling pathway of interest is selected from the MS-Scoring™ 2 menu. Second, a raw gene expression data is inputted into the MS-Scoring™ 2 tool. Third, enrichment of signaling pathway(s) is assessed on a patient by patient basis. Fourth, the data can then be used to drive insight for the target signaling pathways in individual patient samples.

Results from GSVA Analysis on SLE (systemic lupus erythematosus) signaling pathways may be, e.g., as described by Hänzelmann et al., "GSVA: Gene Set Variation Analysis for Microarray and RNA-Seq Data," BMC Bioinformatics, vol. 14, no. 1, 2013, p. 7, which is incorporated herein by reference in its entirety.

COLTs® (Combined Lupus Treatment Scoring) Analysis Tool

A scoring method called CoLTs®, or Combined Lupus Treatment Scoring, may be configured to assessing and prioritizing the repositioning potential of drug therapies. COLTs® may rank identified drugs/therapies by a number of essential characteristics, including scientific rationale, experience in lupus mice/human cells (preclinical), previous clinical experience in autoimmunity, drug properties, and safety profile, including adverse events. Face and test validities may be established by scoring standard of care (SOC) medications and confirming the scores with a panel of lupus clinicians. The final result may be the CoLTs® score. A COLTs® algorithm may also be configured for drugs in development (DID) since they typically do not have drug metabolism and adverse event information available. The algorithms for COLTs® scoring are shown in Table 23.

TABLE 23

Algorithms for CoLTs ® Scoring

| Score Category | CoLTs FDA-Approved Algorithm Points | Question | CoLTs DID Algorithm Points |
|---|---|---|---|
| Rationale | 0 to +3 | Does the mechanism have a role in lupus pathogenesis? (0) No Role in lupus, (+1) possible role in lupus, (+2) likely role in lupus, (+3) demonstrated role in lupus | 0 to +3 |
| Lupus Mice | −1 to +1 | Has the drug been used to treat lupus in mice? (−1) no benefit, (0) not tried/conflicting results, (+1) efficacious in lupus mice | −1 to +1 |
| Lupus Cells in vitro | −1 to +1 | Has the drug been used in in vitro experiments with human cells? (−1) no benefit, (0) not studied/conflicting results, (+1) reduced lupus abnormalities in vitro with lupus derived cells | −1 to +1 |
| Lupus Abnormalities | −1 to +1 | Is the target of the drug abnormal in lupus? (−1) studied but not present, (0) not studied/conflicting results, (+1) drug target is active and/or present in lupus | −1 to +1 |
| Drug Clinical Experience in Autoimmunity | −1 to +1 | Has the drug been used to treat autoimmune disease? (−1) tried but not benefit, (0) not tried, (+1) trial or case report with benefit | −1 to +1 |
| Drug Clinical Experience in Lupus | −1 to +1 | Has the drug been used to treat lupus? (−1) Tried but no benefit - failed primary endpoint in Phase 2b, (0) not tried/ongoing/failed primary Phase 2b endpoint with some positive result, (+1) trial with benefit in Phase 2b clinical trials | −1 to +1 |
| Drug Properties | −3 to +3 | Does the drug interact with current SLE drugs? (−1) if it interacts with corticosteroids, NSAIDs, MMF, MTX, AZA, statins, chloroquines, cyclophsphamide, ACE inhibitors). Is binding reversible? (−1) covalent inhibition, (0) noncovalent inhibition. How the drug is administered? (+1) SC, (0) IV. How frequently is the drug administered? (1) by mouth once daily, (0) more than one time per day. Is the drug a human/humanized anitbody? (+1) human/humanized, (0) not/chimeric. Is this drug specific? (+1) one target.specific, (0) effective but not targeted, i.e. downstream, (−1) many targets/nonspecific | N/A |

TABLE 23-continued

| Algorithms for CoLTs ® Scoring | | | |
|---|---|---|---|
| Score Category | CoLTs FDA-Approved Algorithm Points | Question | CoLTs DID Algorithm Points |
| Induces Lupus | −1 to 0 | Does the drug induce lupus? (−1) Induces lupus, no reports of drug induced lupus (0) | N/A |
| Drug Metabolism | −2 to 0 | Is the drug metabolized using p450 and/or through the kidneys? (−2) If p450 and kidney excretion >20%, (−1) If p450 issues or kidney excretion >20%, (0) If neither | N/A |
| Adverse Events | −5 to 0 | Reported adverse events and Black Box Warnings from Medscape and DailyMed for each for drug are compared to the 150 scored adverse events (each event is scored from −1 to −5 based upon severity). The individual adverse events scores for each drug are summed to create the tox score, which is multiplied by the number of adverse events to create the tox product. Then tox product is then normalized to produce a score ranging from −5 to 0. | N/A |
| Range | −16 to 11 | | −5 to +8 |

CoLTs® may be configured to perform objective scoring of drug molecules based on a hypothesis-based literature search of publicly available databases. The tool has the ability to rank drug molecules from both FDA-approved and non-approved classes and ranked based upon parameters such as scientific rationale, evidence in mouse/human cells, prior clinical data, overall drug properties, and the risk of adverse events. The parameters are used within five independent drug therapy categories: small molecules, biologics, complementary and alternative therapies, and drugs in development.

CoLTs® may address the need for a systematic and objective way to evaluate the potential of drug therapies to be repositioned for treatment of autoimmune diseases, initially within SLE (systemic lupus erythematosus). The composite score may embody all the accessible information in literature databases, inclusive of efficacy and adverse reactions, to be able to assist in the prioritization of drug development. While the composite score takes into account many aspects of a drug, it may heavily weigh the risk of adverse events and ranges from −16 to +11. CoLT Scoring® may be validated through repeated scoring of 215 potential therapies using a total of over 5000 reference data points as well as by clinicians specializing in the field of rheumatology. Specifically, CoLTs®' prediction of Stelara/Ustekinumab to be a top priority biologic for lupus drug repositioning is validated by a successful Phase 2 clinical trial (e.g., as described by Vollenhoven et al., "Efficacy and Safety of Ustekinumab, an IL-12 and IL-23 Inhibitor, in Patients with Active Systemic Lupus Erythematosus: Results of a Multicentre, Double-Blind, Phase 2, Randomised, Controlled Study." The Lancet, vol. 392, no. 10155, 2018, pp. 1330-1339, which is incorporated herein by reference in its entirety). CoLTs® may be calibrated on SoC (Standard of Care) therapies for the individual autoimmune disease being assessed.

Within the ten major categories, rationale ranges from 0 to +3, mouse/human in vitro experience ranges from −1 to +1, clinical properties are on a scale of −3 to +3, the adverse effect of inducing lupus ranges from −1 to 0, metabolic properties range from −2 to 0, and finally adverse events (such as toxicity, infection, carcinogenic, etc.) were given a score of −5 to 0 (e.g., as described by Grammer et al., 2016, "Drug repositioning in SLE: crowd-sourcing, literature-mining and Big Data analysis," Lupus, 25(10), 1150-1170, which is incorporated herein by reference in its entirety). For example, CoLT Scoring® of SOC Therapies in Lupus (Belimumab, HCQ, and Rituximab) may be performed.

Target Scoring Analysis Tool

The Target scoring algorithm may be configured to prioritize a specific gene or protein that would potentially be a good choice to target with a drug in lupus patients. It may be utilized even if there is currently no drug available to the target gene or protein. The algorithm may be based on the addition of 18 data based determinations plus the overall scientific rationale and generates scores from −13 (not a good target in SLE) to 27 (very promising target in SLE). The scoring system is shown in Table 24.

TABLE 24

| Target Scoring Algorithm | | |
|---|---|---|
| Scoring Category | Points | Question |
| Genetically Alt Mice | −1 to 3 | Has the gene been studied in genetically altered mice (−1 to 3) (−1 not viable, 0 no mouse; +1 immunological phenotype, +2 immunological phenotype with autoimmunity, +3 immunological phenotype w lupus) |
| Human Deletion | 0 to 2 | Is the gene associated with a human gentic deficiency? (0 to 2) (0 none, +2 immunological/inflammatory/immunodeficiency disease) |
| Lupus Mouse Express | −1 to 1 | Do lupus mice have mRNA or Protein expression (−1 to +1) |

TABLE 24-continued

Target Scoring Algorithm

| Scoring Category | Points | Question |
|---|---|---|
| Gene Cross Lupus Mice | −1 to 1 | Lupus mice genetic (cross into lupus strain) (−1 to +1): no known genetic component or makes lupus mouse worse (−1); 0, no involvement or no impact) to known genetic component or genetic manipulation makes lupus mouse better (+1) |
| Assoc Func PW in Mice | −1 to 1 | Does the gene associate with a functional pathway known to be abnormal in lupus mice? (−1 to +1) |
| Assoc Func PW in Humans | −1 to 1 | Does the gene associate with a functional pathway known to be abnormal in human SLE? (−1 to +1) |
| GWAS | 0 to 1 | Indentified as associated with lupus by GWAS or deep sequencing: (0 = no, 1 = yes) |
| Gene Methylation | −1 to 1 | Identified as associated with lupus by Methylation Data (0 = no, 1 = yes) |
| In vitro data | −1 to 1 | Gene is implicated in in vitro experiments upus cellis in vitro (−1 to +1) |
| Change afer human SOC | −1 to 1 | Protein or mRNA (or pathway) changed in lupus mouse by treating w a drug (−1 to +1)? |
| Drug to target in lupus mouse | −1 to 1 | Protein or mRNA (or pathway) changed in lupus mouse by treating w a drug (−1 to +1)? |
| CLUE | −1 to 1 | Does CLUE analysis support the pathway as potentially involved in lupus (−1 to +1)? |
| Lupus Biomarker | | Can the target be used as a biomarker in lupus? (0 = no, 1 = yes) |
| Redundancy | −3 to 1 | Is the target non-redudant, no multiple ligand receptor interactions? −3 to 1 |
| WGCNA | 0 to 3 | Is the gene associated with one disease parameter (+1), two (+2), or three (+3)? |
| Tissue Consensus | 0 to 2 | In the gene Overexposed in SLE tissues? 0 for none, 1 for 1 tissue, 2 for two or more SLE tissues |
| Upstrean Regulator | 0 to 1 | Is the gene an UPR in IPA with a significant z-score (>3)? 0 = no, +1 = yes |
| Hematopioetic Restricted | 0 to 1 | Is the gene hematopoetically restricted? 0 = no, +1 = yes |
| Bilogic Rationale | 0 to 3 | Rationale/Mechanism: no role (or no information) to demonstrated role in lupus pathogenesis (0 to +3) |
| Target Data Score | −13 to 27 | |

Target-Scoring™ may be configured to assessing and prioritizing the potential of molecular targets for further development of drug therapies. The Target-Scoring™ tool is very similar to CoLTs® except it approaches the need for new SLE therapies from a different angle. Target Scoring may be configured to perform an objective assessment of molecular targets for the development of new or repurposed drug therapies. Like CoLTs®, it also derives data from a hypothesis-based literature search and generates a composite score based on the publicly available information. Leveraging the composite score, researchers can better prioritize the development of novel drug therapies addressing the assessed targets of interest.

Target-Scoring™ may utilize 19 different scoring categories to derive a composite score that ranges from −13 to +27 for the suitability of a gene target for SLE therapy development. Target-Scoring™ may be validated through repeated scoring of potential therapies as well as by clinicians (e.g., clinicians specializing in the field of immunology).

Classifiers

In some embodiments, the present disclosure provides a system, method, or kit having data analysis realized in software application, computing hardware, or both. In various embodiments, the analysis application or system includes at least a data receiving module, a data pre-processing module, a data analysis module, a data interpretation module, or a data visualization module. In one embodiment, the data receiving module can comprise computer systems that connect laboratory hardware or instrumentation with computer systems that process laboratory data. In one embodiment, the data pre-processing module can comprise hardware systems or computer software that performs operations on the data in preparation for analysis. Examples of operations that can be applied to the data in the pre-processing module include affine transformations, denoising operations, data cleaning, reformatting, or sub-sampling. A data analysis module, which can be specialized for analyzing genomic data from one or more genomic materials, can, for example, take assembled genomic sequences and perform probabilistic and statistical analysis to identify abnormal patterns related to a disease, pathology, state, risk, condition, or phenotype. A data interpretation module can use analysis methods, for example, drawn from statistics, mathematics, or biology, to support understanding of the relation between the identified abnormal patterns and health conditions, functional states, prognoses, or risks. A data visualization module can use methods of mathematical modeling, computer graphics, or rendering to create visual representations of data that can facilitate the understanding or interpretation of results.

Feature sets may be generated from datasets obtained using one or more assays of a biological sample obtained or derived from a subject, and a trained algorithm may be used to process one or more of the feature sets to identify or assess a condition (e.g., a disease or disorder, such as a lupus condition) of a subject. For example, the trained algorithm may be used to apply a machine learning classifier to a plurality of condition-associated genomic loci that are associated with two or more classes of individuals inputted into a machine learning model, in order to classify a subject into one of the two or more classes of individuals. For example, the trained algorithm may be used to apply a machine learning classifier to a plurality of condition-associated that are associated with individuals with known conditions (e.g., a disease or disorder, such as a lupus condition) and individuals not having the condition (e.g., healthy individuals, or individuals who do not have a lupus condition), in order to classify a subject as having the condition (e.g., positive test outcome) or not having the condition (e.g., negative test outcome).

The trained algorithm may be configured to identify the presence (e.g., positive test result) or absence (e.g., negative test result) of one or more conditions (e.g., a disease or disorder, such as a lupus condition) with an accuracy of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more than 99%. This accuracy may be achieved for a set of at least about 25, at least about 50, at least about 100, at least about 150, at least about 200, at least about 250, at least about 300, at least about 350, at least about 400, at least about 450, at least about 500, at least about 1,000, or more than about 1,000 independent samples.

The trained algorithm may comprise a machine learning algorithm, such as a supervised machine learning algorithm. The supervised machine learning algorithm may comprise, for example, a Random Forest, a support vector machine (SVM), a neural network, or a deep learning algorithm. The trained algorithm may comprise a classification and regression tree (CART) algorithm. The trained algorithm may comprise an unsupervised machine learning algorithm.

The trained algorithm may comprise a classifier configured to accept as input a plurality of input variables or features (e.g., condition-associated genomic loci) and to produce or output one or more output values based on the plurality of input variables or features (e.g., condition-associated genomic loci). The plurality of input variables or features may comprise one or more datasets indicative of the presence (e.g., positive test result) or absence (e.g., negative test result) of one or more conditions (e.g., a disease or disorder, such as a lupus condition). For example, an input variable or feature may comprise a number of sequences corresponding to or aligning to each of the plurality of condition-associated genomic loci.

The plurality of input variables or features may also include clinical information of a subject, such as health data. For example, the health data of a subject may comprise one or more of: a diagnosis of one or more conditions (e.g., a disease or disorder, such as a lupus condition), a prognosis of one or more conditions (e.g., a disease or disorder, such as a lupus condition), a risk of having one or more conditions (e.g., a disease or disorder, such as a lupus condition), a treatment history of one or more conditions (e.g., a disease or disorder, such as a lupus condition), a history of previous treatment for one or more conditions (e.g., a disease or disorder, such as a lupus condition), a history of prescribed medications, a history of prescribed medical devices, age, height, weight, sex, smoking status, and one or more symptoms of the subject.

For example, the disease or disorder may comprise one or more of: systemic lupus erythematosus (SLE), discoid lupus erythematosus (DLE), and lupus nephritis (LN). As another example, the symptoms may include one or more of: alopecia, anti-dsDNA seropositivity, arthritis, fever, hematuria, leukopenia, low serum complement, mucosal ulcer, myositis, pericarditis, pleurisy, proteinuria, pyuria, rash, thrombocytopenia, urinary cast, vasculitis, visual disturbance, or a combination thereof. As another example, the prescribed medications or drugs may include one or more of: antimalarials, corticosteroids, immunosuppressants, and nonsteroidal anti-inflammatory drugs (NSAIDs).

The trained algorithm may comprise a classifier, such that each of the one or more output values comprises one of a fixed number of possible values (e.g., a linear classifier, a logistic regression classifier, etc.) indicating a classification of the sample by the classifier. The trained algorithm may comprise a binary classifier, such that each of the one or more output values comprises one of two values (e.g., {0, 1}, {positive, negative}, or {high-risk, low-risk}) indicating a classification of the sample by the classifier. The trained algorithm may be another type of classifier, such that each of the one or more output values comprises one of more than two values (e.g., {0, 1, 2}, {positive, negative, or indeterminate}, or {high-risk, intermediate-risk, or low-risk}) indicating a classification of the sample by the classifier.

The classifier may be configured to classify samples by assigning output values, which may comprise descriptive labels, numerical values, or a combination thereof. Some of the output values may comprise descriptive labels. Such descriptive labels may provide an identification or indication of the presence (e.g., positive test result) or absence (e.g., negative test result) of one or more conditions (e.g., a disease or disorder, such as a lupus condition) of the subject, and may comprise, for example, positive, negative, high-risk, intermediate-risk, low-risk, or indeterminate. Such descriptive labels may provide an identification of a treatment for the one or more conditions of the subject, and may comprise, for example, a therapeutic intervention, a duration of the therapeutic intervention, and/or a dosage of the therapeutic intervention suitable to treat the one or more conditions of the subject. Such descriptive labels may provide an identification of secondary clinical tests that may be appropriate to perform on the subject, and may comprise, for example, an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof. For example, such descriptive labels may provide a prognosis of the one or more conditions of the subject. As another example, such descriptive labels may provide a relative assessment of the one or more conditions of the subject. Some descriptive labels may be mapped to numerical values, for example, by mapping “positive” to 1 and “negative” to 0.

The classifier may be configured to classify samples by assigning output values that comprise numerical values, such as binary, integer, or continuous values. Such binary output values may comprise, for example, {0, 1}, {positive, negative}, or {high-risk, low-risk}. Such integer output values may comprise, for example, {0, 1, 2}. Such continuous output values may comprise, for example, a probability value of at least 0 and no more than 1. Such continuous output values may comprise, for example, an un-normalized probability value of at least 0. Such continuous output values may indicate a prognosis of the one or more conditions (e.g., a disease or disorder, such as a lupus condition) of the subject. Some numerical values may be mapped to descriptive labels, for example, by mapping 1 to “positive” and 0 to “negative.”

The classifier may be configured to classify samples by assigning output values based on one or more cutoff values. For example, a binary classification of samples may assign an output value of “positive” or 1 if the sample indicates that the subject has at least a 50% probability of having one or more conditions (e.g., a disease or disorder, such as a lupus condition), thereby assigning the subject to a class of individuals receiving a positive test result. As another example, a binary classification of samples may assign an output value of "negative" or 0 if the sample indicates that the subject has less than a 50% probability of having one or more conditions (e.g., a disease or disorder), thereby assigning the subject to a class of individuals receiving a negative test result. In this case, a single cutoff value of 50% is used to classify samples into one of the two possible binary output values or classes of individuals (e.g., those receiving a positive test result and those receiving a negative test result). Examples of single cutoff values may include about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, and about 99%.

As another example, the classifier may be configured to classify samples by assigning an output value of "positive" or 1 if the sample indicates that the subject has a probability of having one or more conditions (e.g., a disease or disorder, such as a lupus condition) of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more. The classification of samples may assign an output value of "positive" or 1 if the sample indicates that the subject has a probability of having one or more conditions (e.g., a disease or disorder, such as a lupus condition) of more than about 50%, more than about 55%, more than about 60%, more than about 65%, more than about 70%, more than about 75%, more than about 80%, more than about 85%, more than about 90%, more than about 91%, more than about 92%, more than about 93%, more than about 94%, more than about 95%, more than about 96%, more than about 97%, more than about 98%, or more than about 99%.

The classifier may be configured to classify samples by assigning an output value of "negative" or 0 if the sample indicates that the subject has a probability of having one or more conditions (e.g., a disease or disorder, such as a lupus condition) of less than about 50%, less than about 45%, less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%. The classification of samples may assign an output value of "negative" or 0 if the sample indicates that the subject has a probability of having one or more conditions (e.g., a disease or disorder, such as a lupus condition) of no more than about 50%, no more than about 45%, no more than about 40%, no more than about 35%, no more than about 30%, no more than about 25%, no more than about 20%, no more than about 15%, no more than about 10%, no more than about 9%, no more than about 8%, no more than about 7%, no more than about 6%, no more than about 5%, no more than about 4%, no more than about 3%, no more than about 2%, or no more than about 1%.

The classifier may be configured to classify samples by assigning an output value of "indeterminate" or 2 if the sample is not classified as "positive", "negative", 1, or 0. In this case, a set of two cutoff values is used to classify samples into one of the three possible output values or classes of individuals (e.g., corresponding to outcome groups of individuals having "low risk," "intermediate risk," and "high risk" of having one or more conditions, such as a disease or disorder). Examples of sets of cutoff values may include {1%, 99%}, {2%, 98%}, {5%, 95%}, {10%, 90%}, {15%, 85%}, {20%, 80%}, {25%, 75%}, {30%, 70%}, {35%, 65%}, {40%, 60%}, and {45%, 55%}. Similarly, sets of n cutoff values may be used to classify samples into one of n+1 possible output values or classes of individuals, where n is any positive integer.

The trained algorithm may be trained with a plurality of independent training samples. Each of the independent training samples may comprise a sample from a subject, associated datasets obtained by assaying the sample (as described elsewhere herein), and one or more known output values or classes of individuals corresponding to the sample (e.g., a clinical diagnosis, prognosis, absence, or treatment efficacy of a condition of the subject). Independent training samples may comprise samples and associated datasets and outputs obtained or derived from a plurality of different subjects. Independent training samples may comprise samples and associated datasets and outputs obtained at a plurality of different time points from the same subject (e.g., on a regular basis such as weekly, biweekly, or monthly), as part of a longitudinal monitoring of a subject before, during, and after a course of treatment for one or more conditions of the subject. Independent training samples may be associated with presence of the condition (e.g., training samples comprising samples and associated datasets and outputs obtained or derived from a plurality of subjects known to have the condition). Independent training samples may be associated with absence of the condition (e.g., training samples comprising samples and associated datasets and outputs obtained or derived from a plurality of subjects who are known to not have a previous diagnosis of the condition or who have received a negative test result for the condition).

The trained algorithm may be trained with at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The independent training samples may comprise samples associated with presence of the condition and/or samples associated with absence of the condition. The trained algorithm may be trained with no more than about 500, no more than about 450, no more than about 400, no more than about 350, no more than about 300, no more than about 250, no more than about 200, no more than about 150, no more than about 100, or no more than about 50 independent training samples associated with presence of the condition (e.g., a disease or disorder, such as a lupus condition). The trained algorithm may be trained with no more than about 500, no more than about 450, no more than about 400, no more than about 350, no more than about 300, no more than about 250, no more than about 200, no more than about 150, no more than about 100, or no more than about 50 independent training samples associated with absence of the condition (e.g., a disease or disorder, such as a lupus condition). In some embodiments, the sample is independent of samples used to train the trained algorithm.

The trained algorithm may be trained with a first number of independent training samples associated with a presence of the condition (e.g., a disease or disorder, such as a lupus condition) and a second number of independent training samples associated with an absence of the condition (e.g., a disease or disorder, such as a lupus condition). The first number of independent training samples associated with presence of the condition (e.g., a disease or disorder, such as a lupus condition) may be no more than the second number of independent training samples associated with absence of the condition (e.g., a disease or disorder, such as a lupus condition). The first number of independent training samples associated with a presence of the condition (e.g., a disease or disorder) may be equal to the second number of independent training samples associated with an absence of the condition (e.g., a disease or disorder, such as a lupus condition). The first number of independent training samples associated with a presence of the condition (e.g., a disease or disorder, such as a lupus condition) may be greater than the second number of independent training samples associated with an absence of the condition (e.g., a disease or disorder, such as a lupus condition).

The trained algorithm may comprise a classifier configured to identify the presence (e.g., positive test result) or absence (e.g., negative test result) of one or more conditions (e.g., a disease or disorder, such as a lupus condition) at an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more; for at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The accuracy of identifying the presence (e.g., positive test result) or absence (e.g., negative test result) of the one or more conditions by the trained algorithm may be calculated as the percentage of independent test samples (e.g., subjects known to have the condition or subjects with negative clinical test results for the condition) that are correctly identified or classified as having or not having the condition.

The trained algorithm may comprise a classifier configured to identify one or more conditions (e.g., a disease or disorder, such as a lupus condition) with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the condition using the trained algorithm may be calculated as the percentage of samples identified or classified as having the condition that correspond to subjects that truly have the condition.

The trained algorithm may comprise a classifier configured to identify one or more conditions (e.g., a disease or disorder, such as a lupus condition) with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the condition using the trained algorithm may be calculated as the percentage of samples identified or classified as not having the condition that correspond to subjects that truly do not have the condition.

The trained algorithm may comprise a classifier configured to identify one or more conditions (e.g., a disease or disorder, such as a lupus condition) with a clinical sensitivity at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the condition using the trained algorithm may be calculated as the percentage of independent test samples associated with presence of the condition (e.g., subjects known to have the condition) that are correctly identified or classified as having the condition.

The trained algorithm may comprise a classifier configured to identify one or more conditions (e.g., a disease or disorder, such as a lupus condition) with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the condition using the trained algorithm may be calculated as the percentage of independent test samples associated with absence of the condition (e.g., subjects with negative clinical test results for the condition) that are correctly identified or classified as not having the condition.

The trained algorithm may comprise a classifier configured to identify the presence (e.g., positive test result) or absence (e.g., negative test result) of one or more conditions (e.g., a disease or disorder, such as a lupus condition) with an Area-Under-Curve (AUC) of at least about 0.50, at least about 0.55, at least about 0.60, at least about 0.65, at least about 0.70, at least about 0.75, at least about 0.80, at least about 0.81, at least about 0.82, at least about 0.83, at least about 0.84, at least about 0.85, at least about 0.86, at least about 0.87, at least about 0.88, at least about 0.89, at least about 0.90, at least about 0.91, at least about 0.92, at least about 0.93, at least about 0.94, at least about 0.95, at least about 0.96, at least about 0.97, at least about 0.98, at least about 0.99, or more. The AUC may be calculated as an integral of the Receiver Operator Characteristic (ROC) curve (e.g., the area under the ROC curve) associated with the trained algorithm in classifying samples as having or not having the condition.

Classifiers of the trained algorithm may be adjusted or tuned to improve or optimize one or more performance metrics, such as accuracy, PPV, NPV, clinical sensitivity, clinical specificity, AUC, or a combination thereof (e.g., a performance index incorporating a plurality of such performance metrics, such as by calculating a weight sum therefrom), of identifying the presence (e.g., positive test result) or absence (e.g., negative test result) of the condition. The classifiers may be adjusted or tuned by adjusting parameters of the classifiers (e.g., a set of cutoff values used to classify a sample as described elsewhere herein, or weights of a neural network) to improve or optimize the performance metrics. The one or more classifiers may be adjusted or tuned so as to reduce an overall classification error (e.g., an "out-of-bag" or oob error rate for a Random Forest classifier). The one or more classifiers may be adjusted or tuned continuously during the training process (e.g., as sample datasets are added to the training set) or after the training process has completed.

The trained algorithm may comprise a plurality of classifiers (e.g., an ensemble) such that the plurality of classifications or outcome values of the plurality of classifiers may be combined to produce a single classification or outcome value for the sample. For example, a sum or a weighted sum of the plurality of classifications or outcome values of the plurality of classifiers may be calculated to produce a single classification or outcome value for the sample. As another example, a majority vote of the plurality of classifications or outcome values of the plurality of classifiers may be identified to produce a single classification or outcome value for the sample. In this manner, a single classification or outcome value may be produced for the sample having greater confidence or statistical significance than the individual classifications or outcome values produced by each of the plurality of classifiers.

After the trained algorithm is initially trained, a subset of the inputs may be identified as most influential or most important to be included for making high-quality classifications (e.g., having highest permutation feature importance). For example, a subset of the panel of condition-associated genomic loci may be identified as most influential or most important to be included for making high-quality classifications or identifications of conditions (or sub-types of conditions). The panel of condition-associated genomic loci, or a subset thereof, may be ranked based on classification metrics indicative of each influence or importance of each individual condition-associated genomic locus toward making high-quality classifications or identifications of conditions (or sub-types of conditions). Such metrics may be used to reduce, in some cases significantly, the number of input variables (e.g., predictor variables) that may be used to train the one or more classifiers of the trained algorithm to a desired performance level (e.g., based on a desired minimum accuracy, PPV, NPV, clinical sensitivity, clinical specificity, AUC, or a combination thereof).

For example, if training a classifier of the trained algorithm with a plurality comprising several dozen or hundreds of input variables to the classifier results in an accuracy of classification of more than 99%, then training the classifier of the trained algorithm instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality can yield decreased but still acceptable accuracy of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%).

As another example, if training a classifier of the trained algorithm with a plurality comprising several dozen or hundreds of input variables to the classifier results in a sensitivity or specificity of classification of more than 99%, then training the classifier of the trained algorithm instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality can yield decreased but still acceptable sensitivity or specificity of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%).

The subset of the plurality of input variables (e.g., the panel of condition-associated genomic loci) to the classifier of the trained algorithm may be selected by rank-ordering the entire plurality of input variables and selecting a predetermined number (e.g., no more than about 5, no more than about 10, no more than about 15, no more than about 20, no more than about 25, no more than about 30, no more than about 35, no more than about 40, no more than about 45, no more than about 50, or no more than about 100) of input variables with the best classification metrics (e.g., permutation feature importance).

Upon identifying the subject as having one or more conditions (e.g., a disease or disorder, such as a lupus condition), the subject may be optionally provided with a therapeutic intervention (e.g., prescribing an appropriate course of treatment to treat the one or more conditions of the subject). The therapeutic intervention may comprise a prescription of an effective dose of a drug, a further testing or evaluation of the condition, a further monitoring of the condition, or a combination thereof. If the subject is currently being treated for the condition with a course of treatment, the therapeutic intervention may comprise a subsequent different course of treatment (e.g., to increase treatment efficacy due to non-efficacy of the current course of treatment).

The therapeutic intervention may include prescribed medications or drugs, which may include one or more of: antimalarials, corticosteroids, immunosuppressants, and nonsteroidal anti-inflammatory drugs (NSAIDs). The therapeutic intervention may be effective to alleviate or decrease one or more symptoms, which may include one or more of: alopecia, anti-dsDNA seropositivity, arthritis, fever, hematuria, leukopenia, low serum complement, mucosal ulcer, myositis, pericarditis, pleurisy, proteinuria, pyuria, rash, thrombocytopenia, urinary cast, vasculitis, visual disturbance, or a combination thereof.

The therapeutic intervention may comprise recommending the subject for a secondary clinical test to confirm a diagnosis of the condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

The feature sets (e.g., comprising quantitative measures of a panel of condition-associated genomic loci) may be analyzed and assessed (e.g., using a trained algorithm comprising one or more classifiers) over a duration of time to monitor a patient (e.g., subject who has a condition or who is being treated for a condition). In such cases, the feature sets of the patient may change during the course of treatment. For example, the quantitative measures of the feature sets of a patient with decreasing risk of the condition due to an effective treatment may shift toward the profile or distribution of a healthy subject (e.g., a subject without the condition). Conversely, for example, the quantitative measures of the feature sets of a patient with increasing risk of the condition due to an ineffective treatment may shift toward the profile or distribution of a subject with higher risk of the condition or a more advanced stage or severity of the condition.

The condition of the subject may be monitored by monitoring a course of treatment for treating the condition of the subject. The monitoring may comprise assessing the condition of the subject at two or more time points. The assessing may be based at least on the feature sets (e.g., quantitative measures of a panel of condition-associated genomic loci) determined at each of the two or more time points. The therapeutic intervention may include prescribed medications or drugs, which may include one or more of: antimalarials, corticosteroids, immunosuppressants, and nonsteroidal anti-inflammatory drugs (NSAIDs). The therapeutic intervention may be effective to alleviate or decrease one or more symptoms, which may include one or more of: alopecia, anti-dsDNA seropositivity, arthritis, fever, hematuria, leukopenia, low serum complement, mucosal ulcer, myositis, pericarditis, pleurisy, proteinuria, pyuria, rash, thrombocytopenia, urinary cast, vasculitis, visual disturbance, or a combination thereof. The assessing may be based at least on the presence, absence, or severity of one or more symptoms, such as alopecia, anti-dsDNA seropositivity, arthritis, fever, hematuria, leukopenia, low serum complement, mucosal ulcer, myositis, pericarditis, pleurisy, proteinuria, pyuria, rash, thrombocytopenia, urinary cast, vasculitis, visual disturbance, or a combination thereof.

In some embodiments, a difference in the feature sets (e.g., quantitative measures of a panel of condition-associated genomic loci) determined between the two or more time points may be indicative of one or more clinical indications, such as (i) a diagnosis of the condition of the subject, (ii) a prognosis of the condition of the subject, (iii) an increased risk of the condition of the subject, (iv) a decreased risk of the condition of the subject, (v) an efficacy of the course of treatment for treating the condition of the subject, and (vi) a non-efficacy of the course of treatment for treating the condition of the subject.

In some embodiments, a difference in the feature sets (e.g., quantitative measures of a panel of condition-associated genomic loci) determined between the two or more time points may be indicative of a diagnosis of the condition of the subject. For example, if the condition was not detected in the subject at an earlier time point but was detected in the subject at a later time point, then the difference is indicative of a diagnosis of the condition of the subject. A clinical action or decision may be made based on this indication of diagnosis of the condition of the subject, such as, for example, prescribing a new therapeutic intervention for the subject. The clinical action or decision may comprise recommending the subject for a secondary clinical test to confirm the diagnosis of the condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the feature sets (e.g., quantitative measures of a panel of condition-associated genomic loci) determined between the two or more time points may be indicative of a prognosis of the condition of the subject.

In some embodiments, a difference in the feature sets (e.g., quantitative measures of a panel of condition-associated genomic loci) determined between the two or more time points may be indicative of the subject having an increased risk of the condition. For example, if the condition was detected in the subject both at an earlier time point and at a later time point, and if the difference is a negative difference (e.g., the quantitative measures of a panel of condition-associated genomic loci increased from the earlier time point to the later time point), then the difference may be indicative of the subject having an increased risk of the condition. A clinical action or decision may be made based on this indication of the increased risk of the condition, e.g., prescribing a new therapeutic intervention or switching therapeutic interventions (e.g., ending a current treatment and prescribing a new treatment) for the subject. The clinical action or decision may comprise recommending the subject for a secondary clinical test to confirm the increased risk of the condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the feature sets (e.g., quantitative measures of a panel of condition-associated genomic loci) determined between the two or more time points may be indicative of the subject having a decreased risk of the condition. For example, if the condition was detected in the subject both at an earlier time point and at a later time point, and if the difference is a positive difference (e.g., the quantitative measures of a panel of condition-associated genomic loci decreased from the earlier time point to the later time point), then the difference may be indicative of the subject having a decreased risk of the condition. A clinical action or decision may be made based on this indication of the decreased risk of the condition (e.g., continuing or ending a current therapeutic intervention) for the subject. The clinical action or decision may comprise recommending the subject for a secondary clinical test to confirm the decreased risk of the condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the feature sets (e.g., quantitative measures of a panel of condition-associated genomic loci) determined between the two or more time points may be indicative of an efficacy of the course of treatment for treating the condition of the subject. For example, if the condition was detected in the subject at an earlier time point but was not detected in the subject at a later time point, then the difference may be indicative of an efficacy of the course of treatment for treating the condition of the subject. A clinical action or decision may be made based on this indication of the efficacy of the course of treatment for treating the condition of the subject, e.g., continuing or ending a current therapeutic intervention for the subject. The clinical action or decision may comprise recommending the subject for a secondary clinical test to confirm the efficacy of the course of treatment for treating the condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the feature sets (e.g., quantitative measures of a panel of condition-associated genomic loci) determined between the two or more time points may be indicative of a non-efficacy of the course of treatment for treating the condition of the subject. For example, if the condition was detected in the subject both at an earlier time point and at a later time point, and if the difference is a negative or zero difference (e.g., the quantitative measures of a panel of condition-associated genomic loci increased or remained at a constant level from the earlier time point to the later time point), and if an efficacious treatment was indicated at an earlier time point, then the difference may be indicative of a non-efficacy of the course of treatment for treating the condition of the subject. A clinical action or decision may be made based on this indication of the non-efficacy of the course of treatment for treating the condition of the subject, e.g., ending a current therapeutic intervention and/or switching to (e.g., prescribing) a different new therapeutic intervention for the subject. The clinical action or decision may comprise recommending the subject for a secondary clinical test to confirm the non-efficacy of the course of treatment for treating the condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In various embodiments, machine learning methods are applied to distinguish samples in a population of samples. In one embodiment, machine learning methods are applied to distinguish samples between healthy and diseased (e.g., a lupus condition such as SLE or DLE) samples.

Kits

The present disclosure provides kits for identifying or monitoring a disease or disorder (e.g., a lupus condition) of a subject. A kit may comprise probes for identifying a quantitative measure (e.g., indicative of a presence, absence, or relative amount) of sequences at each of a panel of condition-associated genomic loci in a sample of the subject. A quantitative measure (e.g., indicative of a presence, absence, or relative amount) of sequences at each of a panel of condition-associated genomic loci in the sample may be indicative of the disease or disorder (e.g., a lupus condition) of the subject. The probes may be selective for the sequences at the panel of condition-associated genomic loci in the sample. A kit may comprise instructions for using the probes to process the sample to generate datasets indicative of a quantitative measure (e.g., indicative of a presence, absence, or relative amount) of sequences at each of the panel of condition-associated genomic loci in a sample of the subject.

The probes in the kit may be selective for the sequences at the panel of condition-associated genomic loci in the sample. The probes in the kit may be configured to selectively enrich nucleic acid (e.g., RNA or DNA) molecules corresponding to the panel of condition-associated genomic loci. The probes in the kit may be nucleic acid primers. The probes in the kit may have sequence complementarity with nucleic acid sequences from one or more of the panel of condition-associated genomic loci. The panel of condition-associated genomic loci or genomic regions may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more distinct condition-associated genomic loci.

The instructions in the kit may comprise instructions to assay the sample using the probes that are selective for the sequences at the panel of condition-associated genomic loci in the cell-free biological sample. These probes may be nucleic acid molecules (e.g., RNA or DNA) having sequence complementarity with nucleic acid sequences (e.g., RNA or DNA) from one or more of the plurality of panel of condition-associated genomic loci. These nucleic acid molecules may be primers or enrichment sequences. The instructions to assay the cell-free biological sample may comprise introductions to perform array hybridization, polymerase chain reaction (PCR), or nucleic acid sequencing (e.g., DNA sequencing or RNA sequencing) to process the sample to generate datasets indicative of a quantitative measure (e.g., indicative of a presence, absence, or relative amount) of sequences at each of the panel of condition-associated genomic loci in the sample. A quantitative measure (e.g., indicative of a presence, absence, or relative amount) of sequences at each of a panel of condition-associated genomic loci in the sample may be indicative of a disease or disorder (e.g., a lupus condition).

The instructions in the kit may comprise instructions to measure and interpret assay readouts, which may be quantified at one or more of the panel of condition-associated genomic loci to generate the datasets indicative of a quantitative measure (e.g., indicative of a presence, absence, or relative amount) of sequences at each of the panel of condition-associated genomic loci in the sample. For example, quantification of array hybridization or polymerase chain reaction (PCR) corresponding to the panel of condition-associated genomic loci may generate the datasets indicative of a quantitative measure (e.g., indicative of a presence, absence, or relative amount) of sequences at each of the panel of condition-associated genomic loci in the sample. Assay readouts may comprise quantitative PCR (qPCR) values, digital PCR (dPCR) values, digital droplet PCR (ddPCR) values, fluorescence values, etc., or normalized values thereof.

Analysis of Single Nucleotide Polymorphisms (SNPs) Associated with Lupus

Systemic lupus erythematosus (SLE) is a heterogeneous autoimmune disease that disproportionately affects subjects (e.g., women) of African-Ancestry (AA) compared to their European-Ancestral (EA) counterparts. This disparity may be further complicated by the fact that FDA-approved treatments for SLE, such as belimumab, may not provide a significant therapeutic benefit in SLE-affected AA subjects (e.g., women).

The present disclosure provides systems and methods to assess an SLE condition of a subject via analysis of data sets based on one or more ancestral groups of the subject. In various aspects, such systems and methods may be used to perform analysis of data sets including, for example, RNA gene expression or transcriptome data, or DNA genomic data.

In an aspect, the present disclosure provides a computer-implemented method for assessing an SLE condition of a subject, comprising: (a) receiving a dataset of a biological sample of the subject, wherein the dataset comprises quantitative measures of gene expression at each a plurality of SLE-associated genomic loci, wherein the plurality of SLE-associated genomic loci comprises (i) one or more AA-specific single nucleotide polymorphisms (SNPs) if the subject has an African-Ancestry (AA), or (ii) one or more EA-specific SNPs if the subject has a European-Ancestry (EA); (b) processing the dataset to identify one or more differentially expressed (DE) genomic loci among the plurality of SLE-associated genomic loci; and (c) based at least in part on the one or more DE genomic loci identified in (b) and whether the subject has an African-Ancestry (AA) or a European-Ancestry (EA), assessing the SLE condition of the subject.

In another aspect, the present disclosure provides a computer-implemented method for assessing an SLE condition of a subject, comprising: (a) receiving a dataset of a biological sample of the subject, wherein the dataset comprises quantitative measures of gene expression at each a plurality of systemic lupus erythematosus (SLE)-associated genomic loci, wherein the plurality of SLE-associated genomic loci comprises one or more African-Ancestry (AA)-specific single nucleotide polymorphisms (SNPs); (b) processing the dataset to identify one or more differentially expressed (DE) genomic loci among the plurality of SLE-associated genomic loci; and (c) based at least in part on the one or more DE genomic loci identified in (b) and whether the subject has an African-Ancestry (AA), assessing the SLE condition of the subject.

In another aspect, the present disclosure provides a computer-implemented method for assessing an SLE condition of a subject, comprising: (a) receiving a dataset of a biological sample of the subject, wherein the dataset comprises quantitative measures of gene expression at each a plurality of systemic lupus erythematosus (SLE)-associated genomic loci, wherein the plurality of SLE-associated genomic loci comprises one or more European-Ancestry (EA)-specific single nucleotide polymorphisms (SNPs); (b) processing the dataset to identify one or more differentially expressed (DE) genomic loci among the plurality of SLE-associated genomic loci; and (c) based at least in part on the one or more DE genomic loci identified in (b) and whether the subject has a European-Ancestry (EA), assessing the SLE condition of the subject.

In some embodiments, the dataset comprises RNA gene expression or transcriptome data, DNA genomic data, or a combination thereof. In some embodiments, the biological sample is selected from the group consisting of: a whole blood (WB) sample, a PBMC sample, a tissue sample, and a cell sample. In some embodiments, assessing the SLE condition of the subject comprises determining a diagnosis of the SLE condition, a prognosis of the SLE condition, a susceptibility of the SLE condition, a treatment for the SLE condition, or an efficacy or non-efficacy of a treatment for the SLE condition.

In some embodiments, the method further comprises determining a diagnosis of the SLE condition with a sensitivity of at least about 70%. In some embodiments, the method further comprises determining a diagnosis of the SLE condition with a specificity of at least about 70%. In some embodiments, the method further comprises determining a diagnosis of the SLE condition with a positive predictive value of at least about 70%. In some embodiments, the method further comprises determining a diagnosis of the SLE condition with a negative predictive value of at least about 70%. In some embodiments, the method further comprises determining a diagnosis of the SLE condition with an Area Under Curve (AUC) of at least about 70%. In some embodiments, the method further comprises determining a likelihood of the diagnosis of the SLE condition of the subject.

In some embodiments, the method further comprises generating a plurality of drug candidates for the SLE condition of the subject. In some embodiments, the method further comprises evaluating or predicting a relative efficacy of the plurality of drug candidates for the SLE condition of the subject. In some embodiments, the method further comprises providing a therapeutic intervention comprising one or more of the plurality of drug candidates for the SLE condition of the subject.

In some embodiments, the method further comprises selecting a treatment for the SLE condition of the subject, the treatment comprising an AA-specific drug. In some embodiments, the AA-specific drug is selected from the group consisting of: an HDAC inhibitor, a retinoid, a IRAK4-targeted drug, and a CTLA4-targeted drug. In some embodiments, the method further comprises selecting a treatment for the SLE condition of the subject, the treatment comprising an EA-specific drug. In some embodiments, the EA-specific drug is selected from the group consisting of: hydroxychloroquine, a CD40LG-targeted drug, a CXCR1-targeted drug, and a CXCR2-targeted drug. In some embodiments, the method further comprises selecting a treatment for the SLE condition of the subject, the treatment comprising a drug targeting E-Genes or pathways shared by EA and AA. In some embodiments, the drug targeting E-Genes or pathways shared by EA and AA is selected from the group consisting of: ibrutinib, ruxolitinib, and ustekinumab.

In some embodiments, the method further comprises monitoring the SLE condition of the subject, wherein the monitoring comprises assessing the SLE condition of the subject at each of a plurality of time points, and processing the plurality of assessments of the SLE condition of the subject at each of the plurality of time points.

In some embodiments, the one or more EA-specific SNPs comprise one or more SNPs of genes selected from the group listed in Table 25. In some embodiments, the one or more AA-specific SNPs comprise one or more SNPs of genes selected from the group listed in Table 26. In some embodiments, the plurality of SLE-associated genomic loci comprises one or more shared SNPs, wherein the one or more shared SNPs are common to both EA and AA. In some embodiments, the one or more shared SNPs comprise one or more SNPs of genes selected from the group listed in Table 27.

In another aspect, the present disclosure provides a computer system for assessing an SLE condition of a subject, comprising: a database that is configured to store an African-Ancestry (AA) status of the subject, a European-Ancestry (EA) status of the subject, and a dataset of a biological sample of the subject, wherein the dataset comprises quantitative measures of gene expression at each a plurality of SLE-associated genomic loci, wherein the plurality of SLE-associated genomic loci comprises (i) one or more AA-specific single nucleotide polymorphisms (SNPs) if the subject has an African-Ancestry (AA), or (ii) one or more EA-specific SNPs if the subject has a European-Ancestry (EA); and one or more computer processors operatively coupled to the database, wherein the one or more computer processors are individually or collectively programmed to: (i) process the dataset to identify one or more differentially expressed (DE) genomic loci among the plurality of SLE-associated genomic loci; and (ii) based at least in part on the one or more DE genomic loci identified in (ii), the AA status of the subject, and the EA status of the subject, assessing the SLE condition of the subject.

In another aspect, the present disclosure provides a computer system for assessing an SLE condition of a subject, comprising: a database that is configured to store an African-Ancestry (AA) status of the subject and a dataset of a biological sample of the subject, wherein the dataset comprises quantitative measures of gene expression at each a plurality of systemic lupus erythematosus (SLE)-associated genomic loci, wherein the plurality of SLE-associated genomic loci comprises one or more African-Ancestry (AA)-specific single nucleotide polymorphisms (SNPs); and one or more computer processors operatively coupled to the database, wherein the one or more computer processors are individually or collectively programmed to: (i) process the dataset to identify one or more differentially expressed (DE) genomic loci among the plurality of SLE-associated genomic loci; and (ii) based at least in part on the one or more DE genomic loci identified in (ii) and the AA status of the subject, assessing the SLE condition of the subject.

In another aspect, the present disclosure provides a computer system for assessing an SLE condition of a subject, comprising: a database that is configured to store a European-Ancestry (EA) status of the subject and a dataset of a biological sample of the subject, wherein the dataset comprises quantitative measures of gene expression at each a plurality of systemic lupus erythematosus (SLE)-associated genomic loci, wherein the plurality of SLE-associated genomic loci comprises one or more European-Ancestry (EA)-specific single nucleotide polymorphisms (SNPs); and one or more computer processors operatively coupled to the database, wherein the one or more computer processors are individually or collectively programmed to: (i) process the dataset to identify one or more differentially expressed (DE) genomic loci among the plurality of SLE-associated genomic loci; and (ii) based at least in part on the one or more DE genomic loci identified in (i) and the EA status of the subject, assess the SLE condition of the subject.

In another aspect, the present disclosure provides a non-transitory computer readable medium comprising machine-executable code that, upon execution by one or more computer processors, implements a method for assessing an SLE condition of a subject, comprising: (a) receiving a dataset of a biological sample of the subject, wherein the dataset comprises quantitative measures of gene expression at each a plurality of SLE-associated genomic loci, wherein the plurality of SLE-associated genomic loci comprises (i) one or more AA-specific single nucleotide polymorphisms (SNPs) if the subject has an African-Ancestry (AA), or (ii) one or more EA-specific SNPs if the subject has a European-Ancestry (EA); (b) processing the dataset to identify one or more differentially expressed (DE) genomic loci among the plurality of SLE-associated genomic loci; and (c) based at least in part on the one or more DE genomic loci identified in (b) and whether the subject has an African-Ancestry (AA) or a European-Ancestry (EA), assessing the SLE condition of the subject.

In another aspect, the present disclosure provides a non-transitory computer readable medium comprising machine-executable code that, upon execution by one or more computer processors, implements a method for assessing an SLE condition of a subject, comprising: (a) receiving a dataset of a biological sample of the subject, wherein the dataset comprises quantitative measures of gene expression at each a plurality of systemic lupus erythematosus (SLE)-associated genomic loci, wherein the plurality of SLE-associated genomic loci comprises one or more African-Ancestry (AA)-specific single nucleotide polymorphisms (SNPs); (b) processing the dataset to identify one or more differentially expressed (DE) genomic loci among the plurality of SLE-associated genomic loci; and (c) based at least in part on the one or more DE genomic loci identified in (b) and whether the subject has an African-Ancestry (AA), assessing the SLE condition of the subject.

In another aspect, the present disclosure provides a non-transitory computer readable medium comprising machine-executable code that, upon execution by one or more computer processors, implements a method for assessing an SLE condition of a subject, comprising: (a) receiving a dataset of a biological sample of the subject, wherein the dataset comprises quantitative measures of gene expression at each a plurality of systemic lupus erythematosus (SLE)-associated genomic loci, wherein the plurality of SLE-associated genomic loci comprises one or more European-Ancestry (EA)-specific single nucleotide polymorphisms (SNPs); (b) processing the dataset to identify one or more differentially expressed (DE) genomic loci among the plurality of SLE-associated genomic loci; and (c) based at least in part on the one or more DE genomic loci identified in (b) and whether the subject has a European-Ancestry (EA) assessing the SLE condition of the subject.

Assessment of SLE Conditions

A non-limiting example of a method to assess an SLE condition of a subject may comprise one or more of the following operations. A dataset of a biological sample of a subject is received. The dataset may comprise quantitative measures of gene expression at each of a plurality of SLE-associated genomic loci. The plurality of SLE-associated genomic loci may comprise (i) SNPs specific to African-Ancestry (AA) if the subject has an African ancestry, or (ii) SNPs specific to European-Ancestry (EA) if the subject has a European ancestry. The dataset is processed to identify one or more differentially expressed (DE) genomic loci among the plurality of SLE-associated genomic loci. The SLE condition of the subject is assessed based on the DE genomic loci and whether the subject has an African ancestry or a European ancestry.

To obtain a blood sample, various techniques may be used, e.g., a syringe or other vacuum suction device. A blood sample can be optionally pre-treated or processed prior to use. A sample, such as a blood sample, may be analyzed under any of the methods and systems herein within 4 weeks, 2 weeks, 1 week, 6 days, 5 days, 4 days, 3 days, 2 days, 1 day, 12 hr, 6 hr, 3 hr, 2 hr, or 1 hr from the time the sample is obtained, or longer if frozen. When obtaining a sample from a subject (e.g., blood sample), the amount can vary depending upon subject size and the condition being screened. In some embodiments, at least 10 mL, 5 mL, 1 mL, 0.5 mL, 250, 200, 150, 100, 50, 40, 30, 20, 10, 9, 8, 7, 6, 5, 4, 3, 2, or 1 µL of a sample is obtained. In some embodiments, 1-50, 2-40, 3-30, or 4-20 µL of sample is obtained. In some embodiments, more than 5, 10, 15, 20, 25, 30, 35, 40, 45, 50, 55, 60, 65, 70, 75, 80, 85, 90, 95 or 100 µL of a sample is obtained.

The sample may be taken before and/or after treatment of a subject with a disease or disorder. Samples may be obtained from a subject during a treatment or a treatment regime. Multiple samples may be obtained from a subject to monitor the effects of the treatment over time. The sample may be taken from a subject known or suspected of having a disease or disorder for which a definitive positive or negative diagnosis is not available via clinical tests. The sample may be taken from a subject suspected of having a disease or disorder. The sample may be taken from a subject experiencing unexplained symptoms, such as fatigue, nausea, weight loss, aches and pains, weakness, or bleeding. The sample may be taken from a subject having explained symptoms. The sample may be taken from a subject at risk of developing a disease or disorder due to factors such as familial history, age, hypertension or pre-hypertension, diabetes or pre-diabetes, overweight or obesity, environmental exposure, lifestyle risk factors (e.g., smoking, alcohol consumption, or drug use), or presence of other risk factors.

In some embodiments, a sample can be taken at a first time point and assayed, and then another sample can be taken at a subsequent time point and assayed. Such methods can be used, for example, for longitudinal monitoring purposes to track the development or progression of a disease or disorder (e.g., an SLE condition). In some embodiments, the progression of a disease can be tracked before treatment, after treatment, or during the course of treatment, to determine the treatment's effectiveness. For example, a method as described herein can be performed on a subject prior to, and after, treatment with an SLE therapy to measure the disease's progression or regression in response to the SLE therapy.

After obtaining a sample from the subject, the sample may be processed to generate datasets indicative of a condition (e.g., an SLE condition) of the subject. For example, a presence, absence, or quantitative assessment of nucleic acid molecules of the sample at a panel of condition-associated (e.g., SLE-associated) genomic loci or may be indicative of a condition (e.g., an SLE condition) of the subject. Processing the sample obtained from the subject may comprise (i) subjecting the sample to conditions that are sufficient to isolate, enrich, or extract a plurality of nucleic acid molecules, and (ii) assaying the plurality of nucleic acid molecules to generate the dataset (e.g., microarray data, nucleic acid sequences, or quantitative polymerase chain reaction (qPCR) data). Methods of assaying may include any assay known in the art or described in the literature, for example, a microarray assay, a sequencing assay (e.g., DNA sequencing, RNA sequencing, or RNA-Seq), or a quantitative polymerase chain reaction (qPCR) assay.

In some embodiments, a plurality of nucleic acid molecules is extracted from the sample and subjected to sequencing to generate a plurality of sequencing reads. The nucleic acid molecules may comprise ribonucleic acid (RNA) or deoxyribonucleic acid (DNA). The extraction method may extract all RNA or DNA molecules from a sample. Alternatively, the extraction method may selectively extract a portion of RNA or DNA molecules from a sample. Extracted RNA molecules from a sample may be converted to cDNA molecules by reverse transcription (RT).

The sample may be processed without any nucleic acid extraction. For example, the disease or disorder may be identified or monitored in the subject by using probes configured to selectively enrich nucleic acid (e.g., RNA or DNA) molecules corresponding to a panel of SLE-associated genomic loci. The probes may be nucleic acid primers. The probes may have sequence complementarity with nucleic acid sequences from one or more of the panel of condition-associated (e.g., SLE-associated) genomic loci. The panel of condition-associated genomic loci may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, or more condition-associated genomic loci.

The probes may be nucleic acid molecules (e.g., RNA or DNA) having sequence complementarity with nucleic acid sequences (e.g., RNA or DNA) of one or more genomic loci (e.g., condition-associated genomic loci). These nucleic acid molecules may be primers or enrichment sequences. The assaying of the sample using probes that are selective for the one or more genomic loci (e.g., condition-associated genomic loci) may comprise use of array hybridization, polymerase chain reaction (PCR), or nucleic acid sequencing (e.g., RNA sequencing or DNA sequencing, such as RNA-Seq).

The assay readouts may be quantified at one or more genomic loci (e.g., condition-associated genomic loci) to generate the data indicative of the disease or disorder. For example, quantification of array hybridization or polymerase chain reaction (PCR) corresponding to a plurality of genomic loci (e.g., condition-associated genomic loci) may generate data indicative of the disease or disorder. Assay readouts may comprise quantitative PCR (qPCR) values, digital PCR (dPCR) values, digital droplet PCR (ddPCR) values, fluorescence values, etc., or normalized values thereof.

Classifiers

In some embodiments, the present disclosure provides a system, method, or kit having data analysis realized in software application, computing hardware, or both. In various embodiments, the analysis application or system includes at least a data receiving module, a data preprocessing module, a data analysis module, a data interpretation module, or a data visualization module. In one embodiment, the data receiving module can comprise computer systems that connect laboratory hardware or instrumentation with computer systems that process laboratory data. In one embodiment, the data pre-processing module can comprise hardware systems or computer software that performs operations on the data in preparation for analysis. Examples of operations that can be applied to the data in the pre-processing module include affine transformations, denoising operations, data cleaning, reformatting, or subsampling. A data analysis module, which can be specialized for analyzing genomic data from one or more genomic materials, can, for example, take assembled genomic sequences and perform probabilistic and statistical analysis to identify abnormal patterns related to a disease, pathology, state, risk, condition, or phenotype. A data interpretation module can use analysis methods, for example, drawn from statistics, mathematics, or biology, to support understanding of the relation between the identified abnormal patterns and health conditions, functional states, prognoses, or risks. A data visualization module can use methods of mathematical modeling, computer graphics, or rendering to create visual representations of data that can facilitate the understanding or interpretation of results.

Feature sets may be generated from datasets obtained using one or more assays of a biological sample obtained or derived from a subject, and a trained algorithm may be used to process one or more of the feature sets to identify or assess a condition (e.g., a disease or disorder, such as an SLE condition) of a subject. For example, the trained algorithm may be used to apply a machine learning classifier to a plurality of condition-associated genomic loci that are associated with two or more classes of individuals inputted into a machine learning model, in order to classify a subject into one of the two or more classes of individuals. For example, the trained algorithm may be used to apply a machine learning classifier to a plurality of condition-associated (e.g., SLE-associated) that are associated with individuals with known conditions (e.g., a disease or disorder, such as an SLE condition) and individuals not having the condition (e.g., healthy individuals, or individuals who do not have an SLE condition), in order to classify a subject as having the condition (e.g., positive test outcome) or not having the condition (e.g., negative test outcome).

The trained algorithm may be configured to identify the presence (e.g., positive test result) or absence (e.g., negative test result) of one or more conditions (e.g., a disease or disorder, such as an SLE condition) with an accuracy of at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or more than 99%. This accuracy may be achieved for a set of at least about 25, at least about 50, at least about 100, at least about 150, at least about 200, at least about 250, at least about 300, at least about 350, at least about 400, at least about 450, at least about 500, at least about 1,000, or more than about 1,000 independent samples.

The trained algorithm may comprise a machine learning algorithm, such as a supervised machine learning algorithm. The supervised machine learning algorithm may comprise, for example, a Random Forest, a support vector machine (SVM), a neural network, or a deep learning algorithm. The trained algorithm may comprise a classification and regression tree (CART) algorithm. The trained algorithm may comprise an unsupervised machine learning algorithm.

The trained algorithm may comprise a classifier configured to accept as input a plurality of input variables or features (e.g., condition-associated (e.g., SLE-associated) genomic loci) and to produce or output one or more output values based on the plurality of input variables or features (e.g., condition-associated genomic loci). The plurality of input variables or features may comprise one or more datasets indicative of the presence (e.g., positive test result) or absence (e.g., negative test result) of one or more conditions (e.g., a disease or disorder, such as an SLE condition). For example, an input variable or feature may comprise a number of sequences corresponding to or aligning to each of the plurality of condition-associated genomic loci.

The plurality of input variables or features may also include clinical information of a subject, such as health data. For example, the health data of a subject may comprise one or more of: a diagnosis of one or more conditions (e.g., a disease or disorder, such as an SLE condition), a prognosis of one or more conditions (e.g., a disease or disorder, such as an SLE condition), a risk of having one or more conditions (e.g., a disease or disorder, such as an SLE condition), a treatment history of one or more conditions (e.g., a disease or disorder, such as an SLE condition), a history of previous treatment for one or more conditions (e.g., a disease or disorder, such as an SLE condition), a history of prescribed medications, a history of prescribed medical devices, smoking status, age, height, weight, sex, race, ethnicity, nationality, African-Ancestry (AA) status, European-Ancestry (EA) status, and one or more symptoms of the subject.

For example, the disease or disorder may comprise one or more of: systemic lupus erythematosus (SLE), discoid lupus erythematosus (DLE), and lupus nephritis (LN). As another example, the symptoms may include one or more of: alopecia, anti-dsDNA seropositivity, arthritis, fever, hematuria, leukopenia, low serum complement, mucosal ulcer, myositis, pericarditis, pleurisy, proteinuria, pyuria, rash, thrombocytopenia, urinary cast, vasculitis, visual disturbance, or a combination thereof. As another example, the prescribed medications or drugs may include one or more of: antimalarials, corticosteroids, immunosuppressants, and nonsteroidal anti-inflammatory drugs (NSAIDs).

The trained algorithm may comprise a classifier, such that each of the one or more output values comprises one of a fixed number of possible values (e.g., a linear classifier, a logistic regression classifier, etc.) indicating a classification of the sample by the classifier. The trained algorithm may comprise a binary classifier, such that each of the one or more output values comprises one of two values (e.g., {0, 1}, {positive, negative}, or {high-risk, low-risk}) indicating a classification of the sample by the classifier. The trained algorithm may be another type of classifier, such that each of the one or more output values comprises one of more than two values (e.g., {0, 1, 2}, {positive, negative, or indeterminate}, or {high-risk, intermediate-risk, or low-risk}) indicating a classification of the sample by the classifier.

The classifier may be configured to classify samples by assigning output values, which may comprise descriptive labels, numerical values, or a combination thereof. Some of the output values may comprise descriptive labels. Such descriptive labels may provide an identification or indication of the presence (e.g., positive test result) or absence (e.g., negative test result) of one or more conditions (e.g., a disease or disorder, such as an SLE condition) of the subject, and may comprise, for example, positive, negative, high-risk, intermediate-risk, low-risk, or indeterminate. Such descriptive labels may provide an identification of a treatment for the one or more conditions of the subject, and may comprise, for example, a therapeutic intervention, a duration of the therapeutic intervention, and/or a dosage of the therapeutic intervention suitable to treat the one or more conditions of the subject. Such descriptive labels may provide an identification of secondary clinical tests that may be appropriate to perform on the subject, and may comprise, for example, an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof. For example, such descriptive labels may provide a prognosis of the one or more conditions of the subject. As another example, such descriptive labels may provide a relative assessment of the one or more conditions of the subject. Some descriptive labels may be mapped to numerical values, for example, by mapping "positive" to 1 and "negative" to 0.

The classifier may be configured to classify samples by assigning output values that comprise numerical values, such as binary, integer, or continuous values. Such binary output values may comprise, for example, {0, 1}, {positive, negative}, or {high-risk, low-risk}. Such integer output values may comprise, for example, {0, 1, 2}. Such continuous output values may comprise, for example, a probability value of at least 0 and no more than 1. Such continuous output values may comprise, for example, an un-normalized probability value of at least 0. Such continuous output values may indicate a prognosis of the one or more conditions (e.g., a disease or disorder, such as an SLE condition) of the subject. Some numerical values may be mapped to descriptive labels, for example, by mapping 1 to "positive" and 0 to "negative."

The classifier may be configured to classify samples by assigning output values based on one or more cutoff values. For example, a binary classification of samples may assign an output value of "positive" or 1 if the sample indicates that the subject has at least a 50% probability of having one or more conditions (e.g., a disease or disorder, such as an SLE condition), thereby assigning the subject to a class of individuals receiving a positive test result. As another example, a binary classification of samples may assign an output value of "negative" or 0 if the sample indicates that the subject has less than a 50% probability of having one or more conditions (e.g., a disease or disorder), thereby assigning the subject to a class of individuals receiving a negative test result. In this case, a single cutoff value of 50% is used to classify samples into one of the two possible binary output values or classes of individuals (e.g., those receiving a positive test result and those receiving a negative test result). Examples of single cutoff values may include about 1%, about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, and about 99%.

As another example, the classifier may be configured to classify samples by assigning an output value of "positive" or 1 if the sample indicates that the subject has a probability of having one or more conditions (e.g., a disease or disorder, such as an SLE condition) of at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more. The classification of samples may assign an output value of "positive" or 1 if the sample indicates that the subject has a probability of having one or more conditions (e.g., a disease or disorder, such as an SLE condition) of more than about 50%, more than about 55%, more than about 60%, more than about 65%, more than about 70%, more than about 75%, more than about 80%, more than about 85%, more than about 90%, more than about 91%, more than about 92%, more than about 93%, more than about 94%, more than about 95%, more than about 96%, more than about 97%, more than about 98%, or more than about 99%.

The classifier may be configured to classify samples by assigning an output value of "negative" or 0 if the sample indicates that the subject has a probability of having one or more conditions (e.g., a disease or disorder, such as an SLE condition) of less than about 50%, less than about 45%, less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, or less than about 1%. The classification of samples may assign an output value of "negative" or 0 if the sample indicates that the subject has a probability of having one or more conditions (e.g., a disease or disorder, such as an SLE condition) of no more than about 50%, no more than about 45%, no more than about 40%, no more than about 35%, no more than about 30%, no more than about 25%, no more than about 20%, no more than about 15%, no more than about 10%, no more than about 9%, no more than about 8%, no more than about 7%, no more than about 6%, no more than about 5%, no more than about 4%, no more than about 3%, no more than about 2%, or no more than about 1%.

The classifier may be configured to classify samples by assigning an output value of "indeterminate" or 2 if the sample is not classified as "positive", "negative", 1, or 0. In this case, a set of two cutoff values is used to classify samples into one of the three possible output values or classes of individuals (e.g., corresponding to outcome groups of individuals having "low risk," "intermediate risk," and "high risk" of having one or more conditions, such as a disease or disorder). Examples of sets of cutoff values may include {1%, 99%}, {2%, 98%}, {5%, 95%}, {10%, 90%}, {15%, 85%}, {20%, 80%}, {25%, 75%}, {30%, 70%}, {35%, 65%}, {40%, 60%}, and {45%, 55%}. Similarly, sets of n cutoff values may be used to classify samples into one of n+1 possible output values or classes of individuals, where n is any positive integer.

The trained algorithm may be trained with a plurality of independent training samples. Each of the independent training samples may comprise a sample from a subject, associated datasets obtained by assaying the sample (as described elsewhere herein), and one or more known output values or classes of individuals corresponding to the sample (e.g., a clinical diagnosis, prognosis, absence, or treatment efficacy of a condition of the subject). Independent training samples may comprise samples and associated datasets and outputs obtained or derived from a plurality of different subjects. Independent training samples may comprise samples and associated datasets and outputs obtained at a plurality of different time points from the same subject (e.g., on a regular basis such as weekly, biweekly, or monthly), as part of a longitudinal monitoring of a subject before, during, and after a course of treatment for one or more conditions of the subject. Independent training samples may be associated with presence of the condition (e.g., training samples comprising samples and associated datasets and outputs obtained or derived from a plurality of subjects known to have the condition). Independent training samples may be associated with absence of the condition (e.g., training samples comprising samples and associated datasets and outputs obtained or derived from a plurality of subjects who are known to not have a previous diagnosis of the condition or who have received a negative test result for the condition).

The trained algorithm may be trained with at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The independent training samples may comprise samples associated with presence of the condition and/or samples associated with absence of the condition. The trained algorithm may be trained with no more than about 500, no more than about 450, no more than about 400, no more than about 350, no more than about 300, no more than about 250, no more than about 200, no more than about 150, no more than about 100, or no more than about 50 independent training samples associated with presence of the condition (e.g., a disease or disorder, such as an SLE condition). The trained algorithm may be trained with no more than about 500, no more than about 450, no more than about 400, no more than about 350, no more than about 300, no more than about 250, no more than about 200, no more than about 150, no more than about 100, or no more than about 50 independent training samples associated with absence of the condition (e.g., a disease or disorder, such as an SLE condition). In some embodiments, the sample is independent of samples used to train the trained algorithm.

The trained algorithm may be trained with a first number of independent training samples associated with a presence of the condition (e.g., a disease or disorder, such as an SLE condition) and a second number of independent training samples associated with an absence of the condition (e.g., a disease or disorder, such as an SLE condition). The first number of independent training samples associated with presence of the condition (e.g., a disease or disorder, such as an SLE condition) may be no more than the second number of independent training samples associated with absence of the condition (e.g., a disease or disorder, such as an SLE condition). The first number of independent training samples associated with a presence of the condition (e.g., a disease or disorder) may be equal to the second number of independent training samples associated with an absence of the condition (e.g., a disease or disorder, such as an SLE condition). The first number of independent training samples associated with a presence of the condition (e.g., a disease or disorder, such as an SLE condition) may be greater than the second number of independent training samples associated with an absence of the condition (e.g., a disease or disorder, such as an SLE condition).

The trained algorithm may comprise a classifier configured to identify the presence (e.g., positive test result) or absence (e.g., negative test result) of one or more conditions (e.g., a disease or disorder, such as an SLE condition) with an accuracy of at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more; for at least about 5, at least about 10, at least about 15, at least about 20, at least about 25, at least about 30, at least about 35, at least about 40, at least about 45, at least about 50, at least about 100, at least about 150, at least about 200, at least about 250, at least about 300, at least about 350, at least about 400, at least about 450, or at least about 500 independent training samples. The accuracy of identifying the presence (e.g., positive test result) or absence (e.g., negative test result) of the one or more conditions by the trained algorithm may be calculated as the percentage of independent test samples (e.g., subjects known to have the condition or subjects with negative clinical test results for the condition) that are correctly identified or classified as having or not having the condition.

The trained algorithm may comprise a classifier configured to identify one or more conditions (e.g., a disease or disorder, such as an SLE condition) with a positive predictive value (PPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The PPV of identifying the condition using the trained algorithm may be calculated as the percentage of samples identified or classified as having the condition that correspond to subjects that truly have the condition.

The trained algorithm may comprise a classifier configured to identify one or more conditions (e.g., a disease or disorder, such as an SLE condition) with a negative predictive value (NPV) of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more. The NPV of identifying the condition using the trained algorithm may be calculated as the percentage of samples identified or classified as not having the condition that correspond to subjects that truly do not have the condition.

The trained algorithm may comprise a classifier configured to identify one or more conditions (e.g., a disease or disorder, such as an SLE condition) with a clinical sensitivity at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical sensitivity of identifying the condition using the trained algorithm may be calculated as the percentage of independent test samples associated with presence of the condition (e.g., subjects known to have the condition) that are correctly identified or classified as having the condition.

The trained algorithm may comprise a classifier configured to identify one or more conditions (e.g., a disease or disorder, such as an SLE condition) with a clinical specificity of at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, at least about 99.1%, at least about 99.2%, at least about 99.3%, at least about 99.4%, at least about 99.5%, at least about 99.6%, at least about 99.7%, at least about 99.8%, at least about 99.9%, at least about 99.99%, at least about 99.999%, or more. The clinical specificity of identifying the condition using the trained algorithm may be calculated as the percentage of independent test samples associated with absence of the condition (e.g., subjects with negative clinical test results for the condition) that are correctly identified or classified as not having the condition.

The trained algorithm may comprise a classifier configured to identify the presence (e.g., positive test result) or absence (e.g., negative test result) of one or more conditions (e.g., a disease or disorder, such as an SLE condition) with an Area-Under-Curve (AUC) of at least about 0.50, at least about 0.55, at least about 0.60, at least about 0.65, at least about 0.70, at least about 0.75, at least about 0.80, at least about 0.81, at least about 0.82, at least about 0.83, at least about 0.84, at least about 0.85, at least about 0.86, at least about 0.87, at least about 0.88, at least about 0.89, at least about 0.90, at least about 0.91, at least about 0.92, at least about 0.93, at least about 0.94, at least about 0.95, at least about 0.96, at least about 0.97, at least about 0.98, at least about 0.99, or more. The AUC may be calculated as an integral of the Receiver Operator Characteristic (ROC) curve (e.g., the area under the ROC curve) associated with the trained algorithm in classifying samples as having or not having the condition.

Classifiers of the trained algorithm may be adjusted or tuned to improve or optimize one or more performance metrics, such as accuracy, PPV, NPV, clinical sensitivity, clinical specificity, AUC, or a combination thereof (e.g., a performance index incorporating a plurality of such performance metrics, such as by calculating a weight sum therefrom), of identifying the presence (e.g., positive test result) or absence (e.g., negative test result) of the condition. The classifiers may be adjusted or tuned by adjusting parameters of the classifiers (e.g., a set of cutoff values used to classify a sample as described elsewhere herein, or weights of a neural network) to improve or optimize the performance metrics. The one or more classifiers may be adjusted or tuned so as to reduce an overall classification error (e.g., an "out-of-bag" or oob error rate for a Random Forest classifier). The one or more classifiers may be adjusted or tuned continuously during the training process (e.g., as sample datasets are added to the training set) or after the training process has completed.

The trained algorithm may comprise a plurality of classifiers (e.g., an ensemble) such that the plurality of classifications or outcome values of the plurality of classifiers may be combined to produce a single classification or outcome value for the sample. For example, a sum or a weighted sum of the plurality of classifications or outcome values of the plurality of classifiers may be calculated to produce a single classification or outcome value for the sample. As another example, a majority vote of the plurality of classifications or outcome values of the plurality of classifiers may be identified to produce a single classification or outcome value for the sample. In this manner, a single classification or outcome value may be produced for the sample having greater confidence or statistical significance than the individual classifications or outcome values produced by each of the plurality of classifiers.

After the trained algorithm is initially trained, a subset of the inputs may be identified as most influential or most important to be included for making high-quality classifications (e.g., having highest permutation feature importance). For example, a subset of the panel of condition-associated genomic loci may be identified as most influential or most important to be included for making high-quality classifications or identifications of conditions (or sub-types of conditions). The panel of condition-associated genomic loci, or a subset thereof, may be ranked based on classification metrics indicative of each influence or importance of each individual condition-associated genomic locus toward making high-quality classifications or identifications of conditions (or sub-types of conditions). Such metrics may be used to reduce, in some cases significantly, the number of input variables (e.g., predictor variables) that may be used to train the one or more classifiers of the trained algorithm to a desired performance level (e.g., based on a desired minimum accuracy, PPV, NPV, clinical sensitivity, clinical specificity, AUC, or a combination thereof).

For example, if training a classifier of the trained algorithm with a plurality comprising several dozen or hundreds of input variables to the classifier results in an accuracy of classification of more than 99%, then training the classifier of the trained algorithm instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality can yield decreased but still acceptable accuracy of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%).

As another example, if training a classifier of the trained algorithm with a plurality comprising several dozen or hundreds of input variables to the classifier results in a sensitivity or specificity of classification of more than 99%, then training the classifier of the trained algorithm instead with only a selected subset of no more than about 5, no more than about 10, no more than about 15, no more than about 20, no more than about 25, no more than about 30, no more than about 35, no more than about 40, no more than about 45, no more than about 50, or no more than about 100 such most influential or most important input variables among the plurality can yield decreased but still acceptable sensitivity or specificity of classification (e.g., at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%).

The subset of the plurality of input variables (e.g., the panel of condition-associated genomic loci) to the classifier of the trained algorithm may be selected by rank-ordering the entire plurality of input variables and selecting a predetermined number (e.g., no more than about 5, no more than about 10, no more than about 15, no more than about 20, no more than about 25, no more than about 30, no more than about 35, no more than about 40, no more than about 45, no more than about 50, or no more than about 100) of input variables with the best classification metrics (e.g., permutation feature importance).

Upon identifying the subject as having one or more conditions (e.g., a disease or disorder, such as an SLE condition), the subject may be optionally provided with a therapeutic intervention (e.g., prescribing an appropriate course of treatment to treat the one or more conditions of the subject). The therapeutic intervention may comprise a prescription of an effective dose of a drug, a further testing or evaluation of the condition, a further monitoring of the condition, or a combination thereof. If the subject is currently being treated for the condition with a course of treatment, the therapeutic intervention may comprise a subsequent different course of treatment (e.g., to increase treatment efficacy due to non-efficacy of the current course of treatment).

The therapeutic intervention may include prescribed medications or drugs, which may include one or more of: antimalarials, corticosteroids, immunosuppressants, and nonsteroidal anti-inflammatory drugs (NSAIDs). The therapeutic intervention may be effective to alleviate or decrease one or more symptoms, which may include one or more of: alopecia, anti-dsDNA seropositivity, arthritis, fever, hematuria, leukopenia, low serum complement, mucosal ulcer, myositis, pericarditis, pleurisy, proteinuria, pyuria, rash, thrombocytopenia, urinary cast, vasculitis, visual disturbance, or a combination thereof.

The therapeutic intervention may comprise recommending the subject for a secondary clinical test to confirm a diagnosis of the condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

The feature sets (e.g., comprising quantitative measures of a panel of condition-associated genomic loci) may be analyzed and assessed (e.g., using a trained algorithm comprising one or more classifiers) over a duration of time to monitor a patient (e.g., subject who has a condition or who is being treated for a condition). In such cases, the feature sets of the patient may change during the course of treatment. For example, the quantitative measures of the feature sets of a patient with decreasing risk of the condition due to an effective treatment may shift toward the profile or distribution of a healthy subject (e.g., a subject without the condition). Conversely, for example, the quantitative measures of the feature sets of a patient with increasing risk of the condition due to an ineffective treatment may shift toward the profile or distribution of a subject with higher risk of the condition or a more advanced stage or severity of the condition.

The condition of the subject may be monitored by monitoring a course of treatment for treating the condition of the subject. The monitoring may comprise assessing the condition of the subject at two or more time points. The assessing may be based at least on the feature sets (e.g., quantitative measures of a panel of condition-associated genomic loci) determined at each of the two or more time points. The therapeutic intervention may include prescribed medications or drugs, which may include one or more of: antimalarials, corticosteroids, immunosuppressants, and nonsteroidal anti-inflammatory drugs (NSAIDs). The therapeutic intervention may be effective to alleviate or decrease one or more symptoms, which may include one or more of: alopecia, anti-dsDNA seropositivity, arthritis, fever, hematuria, leukopenia, low serum complement, mucosal ulcer, myositis, pericarditis, pleurisy, proteinuria, pyuria, rash, thrombocytopenia, urinary cast, vasculitis, visual disturbance, or a combination thereof. The assessing may be based at least on the presence, absence, or severity of one or more symptoms, such as alopecia, anti-dsDNA seropositivity, arthritis, fever, hematuria, leukopenia, low serum complement, mucosal ulcer, myositis, pericarditis, pleurisy, proteinuria, pyuria, rash, thrombocytopenia, urinary cast, vasculitis, visual disturbance, or a combination thereof.

In some embodiments, a difference in the feature sets (e.g., quantitative measures of a panel of condition-associated genomic loci) determined between the two or more time points may be indicative of one or more clinical indications, such as (i) a diagnosis of the condition of the subject, (ii) a prognosis of the condition of the subject, (iii) an increased risk of the condition of the subject, (iv) a decreased risk of the condition of the subject, (v) an efficacy of the course of treatment for treating the condition of the subject, and (vi) a non-efficacy of the course of treatment for treating the condition of the subject.

In some embodiments, a difference in the feature sets (e.g., quantitative measures of a panel of condition-associated genomic loci) determined between the two or more time points may be indicative of a diagnosis of the condition of the subject. For example, if the condition was not detected in the subject at an earlier time point but was detected in the subject at a later time point, then the difference is indicative of a diagnosis of the condition of the subject. A clinical action or decision may be made based on this indication of diagnosis of the condition of the subject, such as, for example, prescribing a new therapeutic intervention for the subject. The clinical action or decision may comprise recommending the subject for a secondary clinical test to confirm the diagnosis of the condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the feature sets (e.g., quantitative measures of a panel of condition-associated genomic loci) determined between the two or more time points may be indicative of a prognosis of the condition of the subject.

In some embodiments, a difference in the feature sets (e.g., quantitative measures of a panel of condition-associated genomic loci) determined between the two or more time points may be indicative of the subject having an increased risk of the condition. For example, if the condition was detected in the subject both at an earlier time point and at a later time point, and if the difference is a negative difference (e.g., the quantitative measures of a panel of condition-associated genomic loci increased from the earlier time point to the later time point), then the difference may be indicative of the subject having an increased risk of the condition. A clinical action or decision may be made based on this indication of the increased risk of the condition, e.g., prescribing a new therapeutic intervention or switching therapeutic interventions (e.g., ending a current treatment and prescribing a new treatment) for the subject. The clinical action or decision may comprise recommending the subject for a secondary clinical test to confirm the increased risk of the condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the feature sets (e.g., quantitative measures of a panel of condition-associated genomic loci) determined between the two or more time points may be indicative of the subject having a decreased risk of the condition. For example, if the condition was detected in the subject both at an earlier time point and at a later time point, and if the difference is a positive difference (e.g., the quantitative measures of a panel of condition-associated genomic loci decreased from the earlier time point to the later time point), then the difference may be indicative of the subject having a decreased risk of the condition. A clinical action or decision may be made based on this indication of the decreased risk of the condition (e.g., continuing or ending a current therapeutic intervention) for the subject. The clinical action or decision may comprise recommending the subject for a secondary clinical test to confirm the decreased risk of the condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the feature sets (e.g., quantitative measures of a panel of condition-associated genomic loci) determined between the two or more time points may be indicative of an efficacy of the course of treatment for treating the condition of the subject. For example, if the condition was detected in the subject at an earlier time point but was not detected in the subject at a later time point, then the difference may be indicative of an efficacy of the course of treatment for treating the condition of the subject. A clinical action or decision may be made based on this indication of the efficacy of the course of treatment for treating the condition of the subject, e.g., continuing or ending a current therapeutic intervention for the subject. The clinical action or decision may comprise recommending the subject for a secondary clinical test to confirm the efficacy of the course of treatment for treating the condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In some embodiments, a difference in the feature sets (e.g., quantitative measures of a panel of condition-associated genomic loci) determined between the two or more time points may be indicative of a non-efficacy of the course of treatment for treating the condition of the subject. For example, if the condition was detected in the subject both at an earlier time point and at a later time point, and if the difference is a negative or zero difference (e.g., the quantitative measures of a panel of condition-associated genomic loci increased or remained at a constant level from the earlier time point to the later time point), and if an efficacious treatment was indicated at an earlier time point, then the difference may be indicative of a non-efficacy of the course of treatment for treating the condition of the subject. A clinical action or decision may be made based on this indication of the non-efficacy of the course of treatment for treating the condition of the subject, e.g., ending a current therapeutic intervention and/or switching to (e.g., prescribing) a different new therapeutic intervention for the subject. The clinical action or decision may comprise recommending the subject for a secondary clinical test to confirm the non-efficacy of the course of treatment for treating the condition. This secondary clinical test may comprise an imaging test, a blood test, a computed tomography (CT) scan, a magnetic resonance imaging (MRI) scan, an ultrasound scan, a chest X-ray, a positron emission tomography (PET) scan, a PET-CT scan, or any combination thereof.

In various embodiments, machine learning methods are applied to distinguish samples in a population of samples. In one embodiment, machine learning methods are applied to distinguish samples between healthy and diseased (e.g., an SLE condition such as SLE or DLE) samples.

Kits

The present disclosure provides kits for identifying or monitoring a disease or disorder (e.g., an SLE condition) of a subject. A kit may comprise probes for identifying a quantitative measure (e.g., indicative of a presence, absence, or relative amount) of sequences at each of a panel of condition-associated (e.g., SLE-associated) genomic loci in a sample of the subject. A quantitative measure (e.g., indicative of a presence, absence, or relative amount) of sequences at each of a panel of condition-associated genomic loci in the sample may be indicative of the disease or disorder (e.g., an SLE condition) of the subject. The probes may be selective for the sequences at the panel of condition-associated genomic loci in the sample. A kit may comprise instructions for using the probes to process the sample to generate datasets indicative of a quantitative measure (e.g., indicative of a presence, absence, or relative amount) of sequences at each of the panel of condition-associated genomic loci in a sample of the subject.

The probes in the kit may be selective for the sequences at the panel of condition-associated (e.g., SLE-associated) genomic loci in the sample. The probes in the kit may be configured to selectively enrich nucleic acid (e.g., RNA or DNA) molecules corresponding to the panel of condition-associated genomic loci. The probes in the kit may be nucleic acid primers. The probes in the kit may have sequence complementarity with nucleic acid sequences from one or more of the panel of condition-associated genomic loci. The panel of condition-associated genomic loci or genomic regions may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or more distinct condition-associated genomic loci.

The instructions in the kit may comprise instructions to assay the sample using the probes that are selective for the sequences at the panel of condition-associated (e.g., SLE-associated) genomic loci in the cell-free biological sample. These probes may be nucleic acid molecules (e.g., RNA or DNA) having sequence complementarity with nucleic acid sequences (e.g., RNA or DNA) from one or more of the plurality of panel of condition-associated genomic loci. These nucleic acid molecules may be primers or enrichment sequences. The instructions to assay the cell-free biological sample may comprise introductions to perform array hybridization, polymerase chain reaction (PCR), or nucleic acid sequencing (e.g., DNA sequencing or RNA sequencing) to process the sample to generate datasets indicative of a quantitative measure (e.g., indicative of a presence, absence, or relative amount) of sequences at each of the panel of condition-associated genomic loci in the sample. A quantitative measure (e.g., indicative of a presence, absence, or relative amount) of sequences at each of a panel of condition-associated genomic loci in the sample may be indicative of a disease or disorder (e.g., an SLE condition).

The instructions in the kit may comprise instructions to measure and interpret assay readouts, which may be quantified at one or more of the panel of condition-associated genomic loci to generate the datasets indicative of a quantitative measure (e.g., indicative of a presence, absence, or relative amount) of sequences at each of the panel of condition-associated genomic loci in the sample. For example, quantification of array hybridization or polymerase chain reaction (PCR) corresponding to the panel of condition-associated genomic loci may generate the datasets indicative of a quantitative measure (e.g., indicative of a presence, absence, or relative amount) of sequences at each of the panel of condition-associated genomic loci in the sample. Assay readouts may comprise quantitative PCR (qPCR) values, digital PCR (dPCR) values, digital droplet PCR (ddPCR) values, fluorescence values, etc., or normalized values thereof.

EXAMPLES

The following illustrative examples are representative of embodiments of the software applications, systems, and methods described herein and are not meant to be limiting in any way.

Example 1: Identification of Active Vs. Inactive SLE by Applying a Random Forest Classifier to SLE Gene Expression Data Random forest, a high-performing classifier, may be used to perform analysis to sort through the inherent heterogeneity in raw SLE gene expression data and may be able to identify records with active versus inactive disease with a sensitivity of 85 percent and a specificity of 83 percent. Fine tuning the algorithms may be able to generate sufficient accuracy to be informative as a stand-alone estimate of disease activity. Accuracy may be assessed as the proportion of patients correctly classified across all testing folds.

SLE is a complex, multisystem autoimmune disease that continues to be a major diagnostic as well as therapeutic challenge. There are no definitive diagnostic tools available to determine whether a patient has SLE, and diagnostic approaches in SLE have not changed in decades. Physicians still rely on clinical evaluation and a few laboratory tests, including measurement of autoantibodies and complement levels. Despite the wealth of genetic, epigenetic, and gene expression data that has emerged in the past few years at both the patient and cellular levels, none has been integrated to produce a predictive tool that can be used to evaluate an individual SLE patient.

In SLE, defects in central and peripheral tolerance allow for activation of self-reactive B cell clones and differentiation into plasmablasts/plasma cells (PCs) that secrete autoantibodies, which in turn mediate tissue damage. Genome wide association studies (GWAS) have identified numerous polymorphisms in regions encoding genes or regulatory regions that may influence B cell function, suggesting that a general state of B cell hyper-responsiveness may contribute to SLE pathogenesis. Autoantibody-containing immune complexes stimulate production of type 1 interferon, a hallmark of infection that is also observed in SLE patients, regardless of disease activity. In addition to B cells and PCs, various T cell populations also exert differential effects on SLE pathogenesis. T follicular helper cell subsets contribute to B cell activation and differentiation, and abnormal T cell receptor signaling is also thought to lead to hyper-responsive autoreactive T cell activity. Furthermore, defects in regulatory T cells, partially secondary to deficient IL-2 production, result in faulty modulation of immune activity and inflammation.

Myeloid cells (MC) also play a role in SLE pathogenesis. Factors present in the local microenvironment may cause macrophages (Mϕ) to undergo extreme changes in transcriptional regulation in a process called Mϕ polarization Overabundance of proinflammatory M1 Mϕ and decreased expression of markers for anti-inflammatory M2 Mϕ are detected in both lupus-prone mice and SLE patients, and therapeutic stimulation of M2 polarization significantly decreases disease severity in murine SLE. Experimental intervention in M2 polarization as well as microRNA array profiling suggest that abnormalities in M2 Mϕ may contribute to SLE severity. Low-density granulocytes (LDGs) are abnormal neutrophil-like cells that appear in the blood of lupus patients as well as in many other disease states. Although their involvement in SLE has not been studied as extensively as that of other cell types, LDGs have already been linked to kidney disease, vascular disease, and other manifestations in lupus patients. LDG modules may be generated by WGCNA meta-analysis (manuscript in preparation), and r values indicate separation from control and SLE neutrophils.

To date, however, it has been difficult to relate gene expression profiles to SLE disease activity successfully. Many attempts have been made to characterize SLE patients by gene expression, including efforts to identify individual genes that predicted subsequent flares, and the determination of a discrete group of differentially expressed (DE) genes that may be found in subjects with SLE renal disease. extensively analyzed pediatric lupus samples and attempted to associate modules of expressed genes with disease manifestations in children. Despite these advances, none of the data has yet provided an approach with sufficient predictive value to utilize in decision making about individual subjects with SLE, nor has any cellular phenotype been independently verified to be able to distinguish a patient with active SLE from one with inactive disease. This distinction is critical both for patient evaluation and for clinical trials, as most SLE trials are aimed at controlling disease activity.

Therefore, in order to advance personalized treatment of SLE patients, the use of big data analytical techniques, including machine learning, may be useful to understand the relationships between cell subsets, gene expression, and disease activity. Machine learning describes a wide range of computational methods which allow researchers to harness complex data and develop self-trained strategies to predict the characteristics of new samples, such as whether a given SLE patient has active or inactive disease. When applied to high-throughput bioinformatics data, machine learning algorithms may identify the gene expression features with the most utility for the task at hand and may thereby provide insights into disease pathogenesis.

Conventional bioinformatics methods in conjunction with unsupervised and supervised machine learning techniques to: (1) test the potential of raw gene expression data and modules of genes to classify subjects with active and inactive SLE, (2) determine the optimum classifier or classifiers, and (3) understand the combinations of variables that best facilitate classification.

Provided herein are machine learning approaches to integrate gene expression data from multiple SLE data sets and used it to predict active disease. Both raw whole blood gene expression data and informative gene modules generated by Weighted Gene Co-expression Network Analysis from purified leukocyte populations are employed by classification algorithms. SLE whole blood gene expression data from 156 patients across three data sets are used to classify patients as having active or inactive disease as characterized by standard clinical composite outcome measures. When training and testing sets are formed by holding out entire data sets, machine learning algorithms using raw gene expression data had an average classification accuracy of only 53 percent. However, converting this gene expression data to module enrichment improved classification accuracy to 71 percent. When training and testing sets are formed by mixing patients from the three data sets, module enrichment remained at a 70 percent classification accuracy. However, classification accuracy using raw gene expression increased to a mean of 79 percent. The best overall performance came from the random forest classifier, which had a predictive accuracy of 84 percent.

Gene expression data may be compiled as follows. Publicly available gene expression data and corresponding phenotypic data may be mined from the Gene Expression Omnibus. Raw data sources for purified cell populations are as follows: GSE10325 (CD4: 8 SLE, 9 HC; CD19: 10 SLE, 8 HC; CD33: 9 SLE, 9 HC); GSE26975 (10 SLE LDG, 10 SLE Neutrophil, 9 HC Neutrophil); GSE38351 (CD14: 8 SLE, 12 HC). Raw data sources for SLE whole blood gene expression are as follows: GSE39088 (24 active, 13 inactive); GSE45291 (35 active, 257 inactive); GSE49454 (23 active, 26 inactive). 35 randomly sampled inactive patients may be taken from GSE45291 to avoid a major imbalance between active and inactive SLE patients. Active SLE may be defined as having an SLE Disease Activity Index (SLEDAI) of 6 or greater.

Quality control and normalization may be performed as follows. Statistical analysis may be conducted using R and relevant Bioconductor packages. Non-normalized arrays may be inspected for visual artifacts or poor hybridization using Affy QC plots. PCA plots may be used to inspect the raw data files for outliers. Data sets culled of outliers may be cleaned of background noise and normalized using RMA, GCRMA, or NEQC where appropriate. Data sets may be then filtered to remove probes with low intensity values and probes without gene annotation data. WB gene expression data sets may be filtered to only include genes that passed quality control in all data sets. At this juncture, differential expression (DE) analysis and Weighted Gene Co-expression Network Analysis (WGCNA) may be carried out on data sets. WB gene expression data sets may be then further processed before machine learning analysis. WB gene expression values may be centered and scaled to have zero-mean and unit-variance within each data set, and the standardized expression values from each data set may be joined for classification.

Differential expression (DE) analysis may be performed as follows. Normalized expression values may be variance corrected using local empirical Bayesian shrinkage, and DE may be assessed using the LIMMA package. Resulting p-values may be adjusted for multiple hypothesis testing using the Benjamini-Hochberg correction, which resulted in a false discovery rate (FDR). Significant genes within each study may be filtered to retain DE genes with an FDR $<0.2$, which may be considered statistically significant. The FDR may be selected a priori to diminish the number of genes that may be excluded as false negatives.

Weighted Gene Co-expression Network Analysis (WGCNA) may be performed as follows. Log 2-normalized microarray expression values from purified CD4, CD14, CD19, CD33, and low density granulocyte (LDG) populations may be used as input to WGCNA to conduct an unsupervised clustering analysis, resulting in co-expression "modules," or groups of densely interconnected genes which may correspond to comparably regulated biologic pathways. For each experiment, an approximately scale-free topology matrix (TOM) may be first calculated to encode the network strength between probes. Probes may be clustered into WGCNA modules based on TOM distances. Resultant dendrograms of correlation networks may be trimmed to isolate individual modular groups of probes by partitioning around medoids and labeled using color assignments based on module size. Expression profiles of genes within modules may be summarized by a module eigengene (ME), which is analogous to the module's first principal component. MEs act as characteristic expression values for their respective modules and may be correlated with sample traits such as SLEDAI or cell type. This may be done by Pearson correlation for continuous or semi-continuous traits and by point-biserial correlation for dichotomous traits.

WGCNA modules from CD4, CD14, CD19, and CD33 cells may be tested for correlation to SLEDAI. SLEDAI information may be not available for the LDG modules, so the two modules provided are descriptive of LDGs compared to SLE neutrophils and HC neutrophils. Plasma cell modules may be generated by differential expression analysis and not WGCNA, but may be included because of the established importance of plasma cells in SLE pathogenesis.

Gene Set Variation Analysis (GSVA)-based enrichment of expression data may be performed as follows. The GSVA R package may be used as a non-parametric method for estimating the variation of pre-defined gene sets in SLE WB gene expression data sets. Standardized expression values from WB data sets may be used to test for enrichment of cell-specific WGCNA gene modules using the Single-sample Gene Set Enrichment Analysis (ssGSEA) method, which scores single samples in isolation and is thus shielded from technical variation within and among data sets. Statistical analysis of GSVA enrichment scores may be done by Spearman correlation or Welch's unequal variances t-test, where appropriate. GSVA may be performed on three SLE WB datasets using 25 WGCNA modules made from purified SLE cells with correlation or published relationship to SLEDAI, per Table 1. In the top line, orange: active patient; black: inactive patient. LDG: low-density granulocyte; PC: plasma cell.

Machine learning algorithms and parameters may be developed as follows. Three distinct machine learning algorithms may be employed to test biased and unbiased approaches to microarray data analysis. The biased approach involved GSVA enrichment of disease-associated, cell-specific modules, and the unbiased approach employed all available gene expression data in the WB. An elastic generalized linear model (GLM), k-nearest neighbors classifier (KNN), and random forest (RF) classifier may be deployed to classify active and inactive SLE patients and determine whether gene expression may serve as a general predictor of disease activity. GLM, KNN, and RF may be deployed using the glmnet, caret, and randomForest R packages, respectively.

GLM carries out logistic regression with a tunable elastic penalty term to find a balance between the L1 (lasso) and L2 (ridge) penalties and thereby facilitate variable selection. For our predictions, the elastic penalty may be set to 0.9, specifying a penalty that is 90% lasso and 10% ridge in order to generate sparse solutions. KNN classifies unknown samples based on their proximity to a set number k of known samples. K may be set to 5% of the size of the training set. If the initial value of k is even, 1 may be added in order to avoid ties. RF generates 500 decision trees which vote on the class of each sample. The Gini impurity index, a measure of misclassification error, may be used to evaluate the importance of variables. In addition to these three approaches, pooled predictions may be assigned based on the average class probabilities across the three classifiers.

Validation approaches may be performed as follows. The performance of each machine learning algorithm may be evaluated by 2 different forms of cross-validation. First, a random 10-fold cross-validation may be carried out by randomly assigning each patient to one of 10 groups. Next, as the data came from three separate studies, leave-one-study-out cross-validation may be also done to determine the effects of systematic technical differences among data sets on classification performance. For each pass of cross-validation, one fold or study may be held out as a test set, and the classifiers may be trained on the remaining data. Accuracy may be assessed as the proportion of patients correctly classified across all testing folds. Performance metrics such as sensitivity and specificity may be assessed after cross-validation by agglomerating class probabilities and assignments from each fold or study. Receiver Operating Characteristic (ROC) curves may be generated using the pROC R package.

Gene expression results may be obtained and analyzed as follows. Before employing machine learning techniques, it may be necessary to first assess whether conventional bioinformatics approaches may satisfactorily separate active SLE patient samples from those from inactive patients. DE analysis of active patient samples versus inactive patients in each whole blood study revealed major differences among data sets and considerable heterogeneity within data sets. First, the 100 most significant DE genes by FDR in each study may be used to carry out hierarchical clustering of active and inactive patient samples. Active patients separated from inactive patients in GSE45291, but separated with mixed results in GSE39088 and GSE49454.

Next, the lists of genes may be compared for commonalities. Out of 6,640 unique DE genes from the three studies, 5,170 genes are unique to one study, 1,234 are shared by two studies, and 36 are shared by all three studies, with a minimal overlap of the 100 most significant genes by FDR in each study. The only overlaps among the top 100 DE genes in each study by FDR are: TWY3 and EHBP1, shared between GSE39088 and GSE49454; and LZIC, shared between GSE39088 and GSE45291.

Furthermore, the fold change distributions of the 100 most significant DE genes in each study varied considerably. In GSE39088, 94 of the 100 most significant genes may be downregulated in active patients; in GSE45291, all of the top 100 genes may be upregulated in active patients; and in GSE49454, the top 100 genes may be more evenly distributed (41 up, 59 down). The three data sets are comprised of different patient populations and may be collected on different microarray platforms per Table 4. Still, the heterogeneity is striking. The lack of commonality among the genes most descriptive of active and inactive patients in each data set already casts doubt on whether active and inactive patients from different data sets may separate cleanly.

Patients from each study may be then joined to evaluate whether unsupervised techniques may separate active patients from inactive patients. Hierarchical clustering on the 297 unique most significant DE genes by FDR showed considerable heterogeneity, and active patients and inactive patients did not consistently separate, per the map of the top 100 DE genes by FDR from each study (combined total of 297 unique genes from the three studies) expressed in all patients. If gene expression has the potential to identify active SLE patients, conventional bioinformatics techniques failed to harness that, highlighting the need for more advanced algorithms.

Patterns of enrichment of WGCNA modules may be derived from isolated cell populations of WB that are correlated to the SLEDAI disease activity measure may be more useful than gene expression across studies to identify active versus inactive lupus patients. To characterize the relationships between SLE gene signatures from various peripheral cellular subsets and disease activity, WGCNA may be used to generate co-expression gene modules from purified populations of cells from subjects with active SLE, which may subsequently be tested for enrichment in whole blood of other SLE subjects. WGCNA analysis of leukocyte subsets resulted in several gene modules with significant Pearson correlations to SLEDAI (all $|r| > 0.47$, $p < 0.05$). CD4, CD14, CD19, and CD33 cells had 3, 6, 8, and 4 significant modules, respectively, per Table 1. Two low-density granulocyte (LDG) modules may be created by performing WGCNA analysis of LDGs along with either SLE neutrophils or HC neutrophils and merging the modules most strongly expressed by LDGs Two plasma cell (PC) modules may be created by using the most increased and decreased transcripts of isolated SLE plasma cells compared to SLE naïve and memory B cells.

Gene Ontology (GO) analysis of the genes within each module showed that some processes, such as those related to interferon signaling, RNA transcription, and protein translation, are shared among cell types, whereas other processes may be unique to certain cell types (Table 1) and may be used to better classify patients.

To characterize the relationships between SLE gene modules from cell subsets and disease activity in greater detail, GSVA enrichment may be performed using the 25 cell-specific gene modules in WB from 156 SLE patients (82 active, 74 inactive), per Table 4. Of the 25 cell-specific modules, 12 had enrichment scores with significant Spearman correlations to SLEDAI ($p < 0.05$), and 14 had enrichment scores with significant differences between active and inactive patients by Welch's unequal variances t-test ($p < 0.05$) (Table 2). Notably, each cell type produced at least one module with a significant correlation to SLEDAI in WB and at least one module with a significant difference in enrichment scores between active and inactive patients, demonstrating a relationship between disease activity in specific cellular subsets and overall disease activity in WB. However, the Spearman's rho values ranged from −0.40 to +0.36, suggesting that no one module had substantial predictive value. Furthermore, the effect sizes as measured by Cohen's d when testing active versus inactive enrichment scores ranged from −0.85 to +0.79. The CD4 Floralwhite and Orangered4 modules, which had the largest positive and negative effect sizes, respectively, showed a high degree of overlap in the enrichment scores of active and inactive patients, whereas error bars indicate mean±standard deviation. WB may be unable to fully separate active patients from inactive patients.

Analysis of individual disease activity-associated peripheral cellular subset gene modules may be not sufficient to predict disease activity in unrelated WB data sets, since no single module from any cell type may be able to separate active from inactive SLE patients. Although no single module had a sufficiently high predictive value, many cell-specific gene modules may be combined and optimized to predict disease activity in SLE patients. Moreover, the results emphasized the need for more advanced analysis to employ gene expression analysis to predict disease activity.

Machine learning results may be obtained and analyzed as follows. To assess the effectiveness of either raw gene expression or module-based enrichment techniques, SLE patients may be classified as active or inactive using two different methodologies: (1) a leave-one-study-out cross-validation approach or (2) a 10-fold cross-validation approach. GLM, KNN, and RF classifiers may be tasked with identifying active and inactive SLE patients based on WB gene expression data and module enrichment data. The performance of each classifier in each situation is shown in Table 2, and corresponding ROC curves. Area under the curve is shown in each plot. In almost all cases, the random forest classifier outperformed the GLM and KNN classifiers, although the results may be not significantly different when assessed by testing for equality of proportions ($p>0.05$). Pooled predictions based on the class probabilities from the three classifiers did not improve overall performance.

When cross-validating by study, the use of expression values achieved an accuracy of only 53 percent, per Table 3. This is in line with the findings that gene expression values have little to no utility when attempting to classify unfamiliar samples. When the training data and test data show little similarity to one another (e.g., they come from different data sets), the classifiers learn patterns that are unhelpful for classifying test samples. Remarkably, the use of module enrichment scores improved accuracy to approximately 70 percent.

When doing 10-fold cross-validation (Table 3), the use of raw gene expression values resulted in better performance compared to module enrichment in contrast to leave-one-study-out cross-validation. This increase in performance may be attributed to the presence of data from all three studies in both the training and test sets. In this case, the classifiers have the opportunity to learn patterns inherent to each data set, which proves useful during testing. In this circumstance, the random forest classifier may be the strongest performer with 84% accuracy (85% sensitivity, 83% specificity). The ROC curve demonstrated an excellent tradeoff between recall and fall-out.

The performance of module enrichment may be not substantially different between 10-fold cross-validation and leave-one-study-out cross-validation.

Overall, in a study-by-study approach (leave-one-study-out cross-validation), module enrichment outperformed raw gene expression. Importantly, when using the 10-fold cross-validation approach, raw gene expression outperformed module enrichment. These results indicate that disease activity classification based on raw gene expression is sensitive to technical variability, whereas classification based on module enrichment better copes with variation among data sets.

Random forest had the highest accuracy in three out of four testing scenarios. To determine whether its assessments of variable importance may be used to gain insight into directors of the identification of SLE activity, random forest classifiers may be trained on all patients from all data sets in order to identify the most important genes and modules as determined by mean decrease in the Gini impurity, a measure of misclassification error.

The most important genes and modules identified a wide array of cell types and biological functions. The most important genes encompass such diverse functions as interferon signaling, pattern recognition receptor signaling, and control of survival and proliferation. Notably, the most influential modules skewed away from B cell-derived modules and towards T cell- and myeloid cell-derived modules. As some of these modules had overlapping genes, the variable importance experiment may be repeated with modules that may be first scrubbed of any genes that appeared in more than one module before GSVA enrichment scoring. The relative variable importance scores of the de-duplicated modules correlated strongly with those of the original modules (Spearman's rho=0.73, p=5.18E-5), indicating that module behavior may be partly driven by the overlapping genes but strongly driven by unique genes. Variable importance of top 25 individual genes. LDG: low-density granulocyte; PC: plasma cell.

CD4_Floralwhite and CD14_Yellow, two interferon-related modules which maintained high importance after deduplication, may be further analyzed to study the effect of unique genes on module importance. Gene lists may be tested for statistical overrepresentation of Gene Ontology biological process terms with FDR correction on pantherdb.org. CD4_Floralwhite did not show any significant enrichment, but CD14_Yellow, which had the highest importance after deduplication, is highly enriched for genes with the "Immune Effector Process" designation (26/77 genes, FDR=9.38E-11 by Fisher's exact test). This suggests that CD14+ monocytes express unique genes that may play important roles in the initiation of SLE activity.

Several important findings on the topic of SLE gene expression heterogeneity within and across data sets have been elucidated by this study. First, DE analysis of active vs inactive patients may be insufficient for proper classification of SLE disease activity, as systematic differences between data sets may render conventional bioinformatics techniques largely non-generalizable.

Further, WGCNA modules created from the cellular components of WB and correlated to SLEDAI disease activity may improve classification of disease activity in SLE patients. The use of cell-specific gene modules based on a priori knowledge about their relevance to disease fared slightly better than raw gene expression, as it generated informative enrichment patterns, and many of the modules maintained significant correlations with SLEDAI in WB. However, these enrichment scores failed to completely separate active patients from inactive patients by hierarchical clustering.

A comparison may be then performed between the raw expression data and the WGCNA generated modules of genes in machine learning applications. Supervised classification approaches using elastic generalized linear modeling, k-nearest neighbors, and random forest classifiers may be implemented. The trends in performance when cross-validating by study or cross-validating 10-fold speak to the potential advantages and disadvantages of diagnostic tests incorporating gene expression data or module enrichment. Cross-validating by study serves as a kind of "worst-case" scenario, whereas 10-fold cross-validation serves as a "best-case." Attempting to classify active and inactive SLE patients from different data sets and different microarray platforms during cross-validation by study may encounter challenges, but module enrichment may be able to smooth out much of the technical variation between data sets. 10-fold cross-validation simulated a more standardized diagnostic test. Although the data may be sourced from three different microarray platforms, each cohort in the test set had many similar patients in the training set to facilitate classification by gene expression. If such a test may be reliably free from technical noise, it is likely that raw gene expression may perform very well. RNA-Seq platforms, which produce transcript counts rather than probe intensity values, may display less technical variation across data sets if all samples are processed in the same way. An optimal panel of genes may be constructed that is similar to that identified by the random forest classifier, which may result in a simple, focused test to determine disease activity by gene expression data alone.

The strong performance of the random forest classifier indicates that nonlinear, decision tree-based methods of classification may be well suited to SLE diagnostics. This may be because decision trees ask questions about new samples sequentially and adaptively in contrast to other methods that approach variables from new samples all at once. Random forest is able to "understand" to an extent that different types of patients exist and that a one-size-fits-all approach may tend to misclassify those patients whose expression patterns make them a minority within their phenotype. In other words, active patients that do not resemble the majority of active patients may still have a strong chance of being properly classified by random forest.

The random forest classifier may be used to assess the importance of each gene and module in patient classification. The most important genes may be involved in a number of functions other than interferon signaling, such RNA processing, ubiquitylation, and mitochondrial processes. These pathways may play important roles in directing, or at least be indicative of, SLE disease activity. CD4 T cells originally contributed the most important modules, but when the modules may be de-duplicated, CD14 monocyte-derived modules gained importance. This suggests that unique genes expressed by CD14 monocytes in tandem with interferon genes may prove to be informative in the study of cell-specific methods of SLE pathogenesis. Furthermore, it is important to note that modules that may be negatively associated with disease activity may be just as important in classification as positively associated modules. Further study of underrepresented categories of transcripts may enhance our understanding of SLE activity.

While creating dedicated training and test sets may be preferable to cross-validation, this approach may require a large number of samples. Although there are large numbers of publicly available gene expression profiles of SLE patients, many of these profiles are not annotated with SLEDAI data. Furthermore, some data sets which include SLEDAI data show heavy class imbalance, which impedes classification. Cross-platform expression data may be integrated toward expanding the ability to classify active and inactive SLE patients.

The machine learning models developed provide the basis of personalized medicine for SLE patients. Integration of these approaches with high-throughput patient sampling technologies may unlock the potential to develop a simple blood test to predict SLE disease activity. These approaches may also be generalized to predict other SLE manifestations, such as organ involvement. A better understanding of the cellular processes that drive SLE pathogenesis may eventually lead to customized therapeutic strategies based on patients' unique patterns of cellular activation.

Example 2: Prediction of Lupus Disease Activity by Applying a Machine Learning Approaches to SLE Gene Expression Data The integration of gene expression data to predict systemic lupus erythematosus (SLE) disease activity may be a significant challenge because of the high degree of heterogeneity among patients and study cohorts, especially those collected on different microarray platforms. Machine learning approaches may be deployed to integrate gene expression data from three SLE data sets, and may be used to classify patients as having active or inactive disease (e.g., as characterized by standard clinical composite outcome measures). Both raw whole blood gene expression data and informative gene modules generated by Weighted Gene Co-expression Network Analysis from purified leukocyte populations were employed with various classification algorithms. Classifiers were evaluated by 10-fold cross-validation across three combined data sets or by training and testing in independent data sets, the latter of which amplified the effects of technical variation. A random forest classifier achieved a peak classification accuracy of 83 percent under 10-fold cross-validation, but its performance may be severely affected by technical variation among data sets. The use of gene modules rather than raw gene expression was more robust, achieving classification accuracies of approximately 70 percent regardless of how the training and testing sets were formed. Fine tuning the algorithms and parameter sets may generate sufficient accuracy to be informative as a standalone estimate of disease activity.

SLE is a complex, multisystem autoimmune disease that continues to be a major diagnostic as well as therapeutic challenge. There may be no definitive, specific diagnostic tools available to determine whether a patient has SLE, and diagnostic approaches in SLE have not changed in decades. Physicians still rely on clinical evaluation and a few laboratory tests, including measurement of autoantibodies and complement levels. Despite the wealth of genetic, epigenetic, and gene expression data that has emerged in the past few years at both the patient and cellular levels, none has been integrated to produce a predictive tool that may be used to evaluate an individual SLE patient.

In SLE, defects in central and peripheral tolerance allow for activation of self-reactive B cell clones and differentiation into plasmablasts/plasma cells (PCs) that secrete autoantibodies, which in turn mediate tissue damage. Genome wide association studies (GWAS) have identified numerous polymorphisms in regions encoding genes or regulatory regions that may influence B cell function, suggesting that a general state of B cell hyper-responsiveness may contribute to SLE pathogenesis. Autoantibody-containing immune complexes stimulate production of type 1 interferon, a hallmark of infection that is also observed in SLE patients, regardless of disease activity. In addition to B cells and PCs, various T cell populations also exert differential effects on SLE pathogenesis. T follicular helper cell subsets contribute to B cell activation and differentiation, and abnormal T cell receptor signaling is also thought to lead to hyper-responsive autoreactive T cell activity. Furthermore, defects in regulatory T cells, partially secondary to deficient IL-2 production, result in faulty modulation of immune activity and inflammation.

Myeloid cells (MC) also play a role in SLE pathogenesis. Factors present in the local microenvironment may cause macrophages (Mϕ) to undergo extreme changes in transcriptional regulation in a process called Mϕ polarization. Overabundance of proinflammatory M1 Mϕ and decreased expression of markers for anti-inflammatory M2 Mϕ are detected in both lupus-prone mice and SLE patients, and therapeutic stimulation of M2 polarization significantly decreases disease severity in murine SLE. Experimental intervention in M2 polarization as well as microRNA array profiling suggest that abnormalities in M2 Mϕ may contribute to SLE severity. Low-density granulocytes (LDGs) are abnormal neutrophil-like cells that appear in the blood of lupus patients as well as in many other disease states. Although their involvement in SLE has not been studied as extensively as that of other cell types, LDGs have already been linked to kidney disease, vascular disease, and other manifestations in lupus patients.

To date, however, it has been difficult to relate gene expression profiles to SLE disease activity successfully. Gene expression data analysis approaches may have challenges with producing sufficient predictive value to utilize in decision making about individual subjects with SLE. Furthermore, no cellular phenotype has been independently verified to be able to distinguish a patient with active SLE from one with inactive disease. This distinction is critical both for patient evaluation and for clinical trials, as most SLE trials are aimed at controlling disease activity.

Therefore, in order to advance personalized treatment of SLE patients, the use of big data analytical techniques, including machine learning, may be useful to understand the relationships between cell subsets, gene expression, and disease activity. Machine learning describes a wide range of computational methods to harness complex data and develop self-trained strategies to predict the characteristics of new samples, such as whether a given SLE patient has active or inactive disease. Machine learning techniques may be used, for example, to characterize lupus disease risk and identify new biomarkers based on genotypic data or urine tests. When applied to high-throughput transcriptomic data, machine learning algorithms may be used to identify the gene expression features with the most utility to identify subjects with higher degrees of disease activity and may also provide insights into disease pathogenesis.

Bioinformatics methods may be applied in conjunction with unsupervised and supervised machine learning techniques to: (1) test the potential of raw gene expression data and modules of genes to classify subjects with active and inactive SLE, (2) determine the optimum classifier or classifiers, and (3) understand the combinations of variables that best facilitate classification.

Gene expression data may be analyzed to assess SLE disease activity as follows. Before employing machine learning techniques, first an assessment was made regarding whether bioinformatics approaches may accurately separate active SLE patient samples from those obtained from inactive patients. First, three whole blood (WB) data sets (Table 5) were filtered to include only those genes which passed quality control and filtering in all three studies. Table 5 shows data sources for active (SLEDAI≥6) and inactive (SLEDAI<6) SLE WB gene expression. Data sets are listed by Gene Expression Omnibus (GEO) accession numbers. N Active/Inactive: number of active/inactive patients in data set. Range, mean, and standard deviation of SLEDAI values in each data set are provided.

TABLE 5

Accession of records by microarray platform, number of active and inactive records, SLEDAI range, and SLEADAI mean

| Accession | Microarray Platform | N Active | N Inactive | SLEDAI Range | SLEDAI Mean (SD) |
|---|---|---|---|---|---|
| GSE39088 | GPL570 (Affymetrix HG-U133 + 2.0) | 24 | 13 | 2-12 | 6.8 (2.7) |
| GSE45291 | GPL13158 (Affymetrix HG-U133 + PM) | 35 | 35 | 0-11 | 4.3 (3.5) |
| GSE49454 | GPL10558 (Illumina HumanHT-12 v4.0) | 23 | 26 | 0-26 | 7.7 (7.2) |

Differential expression (DE) analysis of active versus inactive patient samples with the remaining filtered 7,848 genes revealed major differences among data sets and considerable heterogeneity within data sets. GSE39088 had only 176 DE genes with a false discovery rate (FDR) less than 0.2 and none with FDR <0.05; GSE45291 had 5850 DE genes with FDR <0.2 and 4837 with FDR <0.05; GSE49454 had 1710 DE genes with FDR <0.2 and 72 with FDR <0.05 (Data S1).

Hierarchical clustering was carried out on each study with all genes, DE genes with FDR <0.2, and DE genes with FDR <0.05 to determine whether active and inactive patients may separate into two clusters. The Adjusted Rand Index (ARI) was used to compare these clusterings to the known status of the patients. When using all genes, all three studies had ARIs near zero, indicating that clustering separated active and inactive patients no better than random chance (Table 6). Table 6 shows Adjusted Rand Index of Unsupervised Hierarchical Clustering Compared to Known Disease Activity. Data sets are listed by GEO accession numbers. GSE39088 had no genes with FDR <0.05. The "Three Consistent DE Genes" are DNAJC13, IRF4, and RPL22.

TABLE 6

Adjusted Rand Index of Unsupervised Hierarchical Clustering Compared to Known Disease Activity

| | Adjusted Rand Index |
|---|---|
| GSE39088 | −0.04 |
| GSE39088; FDR < 0.2 | 0.19 |
| GSE39088; FDR < 0.05 | N/A |
| GSE45291 | 0.03 |
| GSE45291; FDR < 0.2 | −0.01 |
| GSE45291; FDR < 0.05 | 0.94 |
| GSE49454 | 0.04 |
| GSE49454; FDR < 0.2 | 0.14 |
| GSE49454; FDR < 0.05 | 0.14 |
| All Studies | 0.03 |
| All Studies; Three Consistent DE Genes | 0.05 |

GSE39088 and GSE49454 showed only mild improvement after filtering genes, whereas GSE45291 attained an ARI of 0.94 when using genes with FDR <0.05.

Figure 10A:
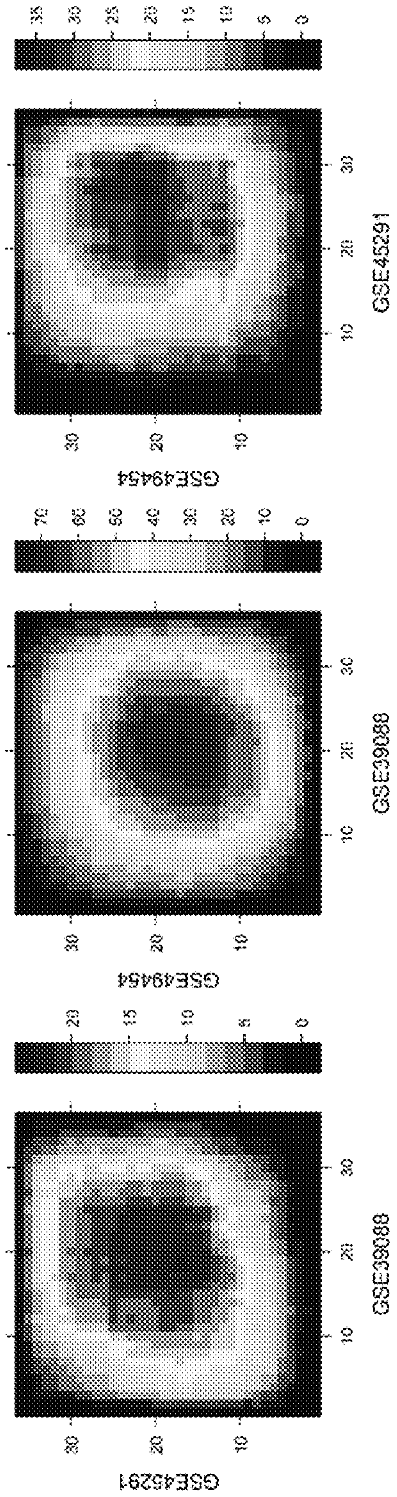
FIG. 10A shows an example of heatmaps of −log 10(overlap p values) from RRHO, in accordance with disclosed embodiments. Strongest overlaps near the center of each plot indicate weak agreement among the most significantly upregulated and downregulated genes from each data set. Strong agreement between data sets may be indicated by a diagonal from the bottom-left corner to the top-right corner.

Next, the lists of genes were compared for commonalities. Out of 6,440 unique DE genes from the three studies, 5,170 genes were unique to one study, 1,234 were shared by two studies, and 36 were shared by all three studies. Of these 36 genes, only three had consistent fold changes across all studies (DNAJC13 and IRF4 upregulated; RPL22 downregulated). Rank-rank Hypergeometric Overlap (RRHO) was next applied as a threshold-free comparison of the studies (as described by, for example, Plaisier et al., "Rank-rank hypergeometric overlap: identification of statistically significant overlap between gene-expression signatures," Nucleic Acids Res. 38, e169, which is incorporated by reference herein in its entirety). All genes that were tested for differential expression were sorted by FDR from most significantly overexpressed to most significantly underexpressed and broken into 36 groups of 218 genes each. Among the three studies, the ranked gene lists failed to demonstrate significant overlap of the most overexpressed and underexpressed genes (FIG. 10A). The three data sets were comprised of different patient populations and were collected on different microarray platforms (Table 5); still, the heterogeneity is striking. The lack of commonality among the genes most descriptive of active and inactive patients in each data set casts doubt on whether active and inactive patients from different data sets may separate cleanly.

Figure 10B:
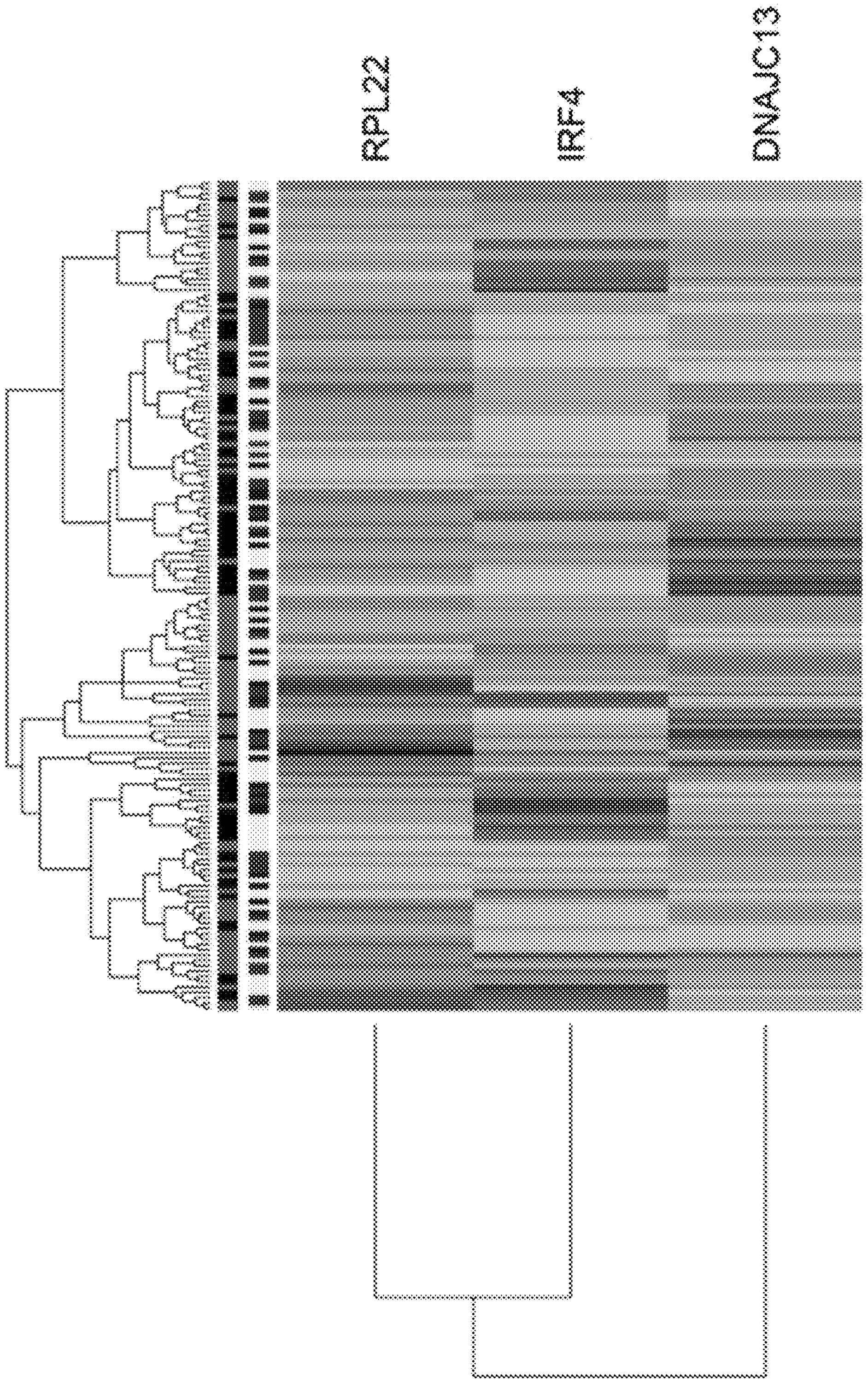
FIG. 10B shows an example of clustering all three studies on three consistent DE genes, in accordance with disclosed embodiments. DNAJC13, IRF4, and RPL22 were consistently differentially expressed in each study yet fail to fully separate active from inactive patients. Orange bars denote active patients; black bars denote inactive patients. Blue, yellow, and red bars denote patients from GSE39088, GSE45291, and GSE49454, respectively.

Patients from each study were then joined to evaluate whether unsupervised techniques may separate active patients from inactive patients. Expression profiles from each study were first normalized to have zero mean and unit variance. FIG. 10B shows that even these three genes (DNAJC13, IRF4, and RPL22) failed to separate active patients from inactive patients precisely. Hierarchical clustering on all genes had an ARI of 0.03 when compared to the known status of the patients, and clustering on the three consistent DE genes shared among the studies (DNAJC13, IRF4, and RPL22) had an ARI of 0.05 (Table 6). If gene expression has the potential to identify active SLE patients robustly, bioinformatics techniques may fail to harness that potential, thereby highlighting the need for more advanced algorithms.

Figure 11:
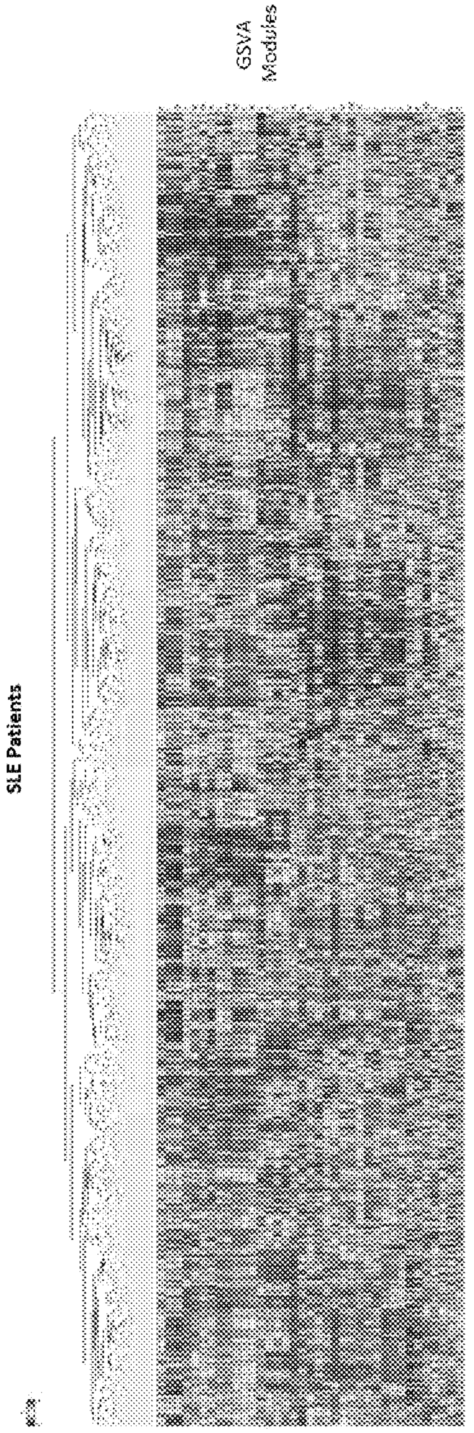
FIG. 11 shows GSVA results of a lupus Illuminate gene set, demonstrating the striking heterogeneity in SLE patient WB by showing patient specific enrichment of 27 cell and process specific modules of genes. In order to understand pathogenic mechanisms of SLE, a big data analysis approach may be used on purified cell populations implicated in SLE to help understand aberrant cellular-specific mechanisms.

Thus far, bulk analysis of many WB and PBMC datasets on multiple platforms may show increased transcripts for IFN signature genes, granulocytes, monocytes, and plasma cells and decreased lymphocytes, but may yield little information on mechanisms of pathogenesis excepting IFN and pattern recognition receptor signaling because of the commonality of many transcripts expressed by different cell populations. Patient-specific transcriptomic "fingerprints" using readily accessible WB may be advantageously generated and analyzed to determine the relative contribution of cells, therapy, and ancestral effects, thereby providing valuable information that potentially may be used in determining entry into a clinical trial or personalized medicine strategies. FIG. 11 shows GSVA results of a lupus Illuminate gene set, demonstrating the striking heterogeneity in SLE patient WB by showing patient specific enrichment of 27 cell and process specific modules of genes. Distinct groups of lupus patients defined by GSVA groups or clusters or genes can be visually identified via the GSVA analysis. In order to understand pathogenic mechanisms of SLE, a big data analysis approach may be used on purified cell populations implicated in SLE to help understand aberrant cellular-specific mechanisms.

Patterns of enrichment of Weighted Gene Co-expression Network Analysis (WGCNA) modules derived from isolated cell populations that are correlated to the SLEDAI SLE disease activity index may be more useful than gene expression across studies to identify active versus inactive lupus patients. To characterize the relationships between SLE gene signatures from various peripheral cellular subsets and disease activity, WGCNA was used to generate co-expression gene modules from purified populations of cells from subjects with active SLE, which may subsequently be tested for enrichment in whole blood of other SLE subjects. WGCNA analysis of leukocyte subsets resulted in several gene modules with significant Pearson correlations to SLEDAI (all $|r|>0.47$, $p<0.05$). CD4, CD14, CD19, and CD33 cells yielded 3, 6, 8, and 4 modules significantly correlated to disease activity, respectively (Table 7). Table 7 shows cell module correlations to disease activity and functional analysis. Information on cell modules including number of genes, Pearson correlation coefficient to SLEDAI, and functional analysis. +: LDG modules were generated by WGCNA meta-analysis, and r values indicate separation from control and SLE neutrophils as SLEDAI was unavailable. *: PC modules are based solely on differential expression. LDG: low-density granulocyte; PC: plasma cell.

Two low-density granulocyte (LDG) modules were created by performing WGCNA analysis of LDGs along with either SLE neutrophils or HC neutrophils and merging the modules most strongly expressed by LDGs. Two plasma cell (PC) modules were created by using the most increased and decreased transcripts of isolated SLE plasma cells compared to SLE naïve and memory B cells.

TABLE 7

Cell module correlations to disease activity and functional analysis

| Cell Type | Module Name | Module Size | Correlation with SLEDAI | Top GO Biological Process | Top BIG-C Category |
|---|---|---|---|---|---|
| CD4 | Floralwhite | 237 | 0.81 | type I interferon signaling pathway | Interferon-Stimulated-Genes |
| | Turquoise | 805 | 0.50 | positive reg of ubiquitin-protein ligase | Proteasome |
| | Orangered4 | 237 | −0.77 | translational initiation | mRNA-Translation |
| CD14 | Plum1 | 247 | 0.47 | ubiquitin-dependent protein catabolic process | mRNA-Translation |
| | Yellow | 356 | 0.65 | type I interferon signaling pathway | Interferon-Stimulated-Genes |
| | Greenyellow | 89 | −0.49 | transcription from RNA polymerase II promoter | General-Transcription |
| | Pink | 261 | −0.77 | protein phosphorylation | Endosome-and-Vesicles |
| | Purple | 124 | −0.66 | inositol phosphate metabolic process | Fatty-Acid-Biosynthesis |
| | Sienna3 | 222 | −0.64 | translational initiation | mRNA-Translation |

TABLE 7-continued

Cell module correlations to disease activity and functional analysis

| Cell Type | Module Name | Module Size | Correlation with SLEDAI | Top GO Biological Process | Top BIG-C Category |
|---|---|---|---|---|---|
| CD19 | Darkolivegreen | 591 | 0.78 | cell division | Proteasome |
| | Greenyellow | 251 | 0.66 | Notch signaling pathway | mRNA-Translation |
| | Steelblue | 146 | 0.65 | gluconeogenesis | Glycolysis-Gluconeogenesis |
| | Turquoise | 572 | 0.50 | ER to Golgi vesicle-mediated transport | Unfolded-Protein-and-Stress |
| | Violet | 566 | 0.61 | mitochondrial respiratory chain complex I | Interferon-Stimulated-Genes |
| | Brown | 620 | −0.62 | regulation of transcription, DNA-templated | Chromatin-Remodeling |
| | Green | 541 | −0.49 | transcription, DNA-templated | Transcription-Factors |
| | Skyblue | 756 | −0.74 | viral transcription | mRNA-Translation |
| CD33 | Royalblue | 94 | 0.60 | positive reg of cytosolic calcium ions | Transposon-Control |
| | Sienna3 | 133 | 0.76 | type I interferon signaling pathway | Interferon-Stimulated-Genes |
| | Violet | 177 | 0.79 | defense response to virus | Interferon-Stimulated-Genes |
| | Darkmagenta | 273 | −0.49 | ubiquinone biosynthetic | MHC-Class-TWO |
| $LDG^+$ | LDG_A | 334 | 0.79 | process platelet degranulation | Cytoskeleton |
| | LDG_B | 92 | 0.81 | regulation of transcription | Secreted-Immune |
| | LDG_C | 82 | −0.39 | viral process | Nucleus-and-Nucleolus |
| PC* | PC_Up | 423 | N/A | protein N-linked glycosylation | Endoplasmic-Reticulum |
| | PC_Down | 183 | N/A | antigen processing and presentation MHC II | MHC-Class-TWO |

Gene Ontology (GO) analysis of the genes within each module showed that some processes, such as those related to interferon signaling, RNA transcription, and protein translation, were shared among cell types, whereas other processes were unique to certain cell types (Table 7) and may be used to classify patients more effectively. The genes in each module are listed in Table 8.

TABLE 8

Genes in modules identified via Gene Ontology (GO) analysis

| Cell Type | Module Name | Genes |
|---|---|---|
| CD4 | Floral white | AARS, ABCA1, ABR, ADAM10, ADAR, AEN, AHR, AIMP1, ALOX5, ALOX5AP, APBA3, APOL1, ARHGEF3, ARID5B, ARMCX2, ASB6, ATG4B, ATOX1, ATP1B3, ATP5J2, ATP6V1E1, BATF, BCCIP, BCL2, C19orf66, C3orf14, CAPN2, CAPN3, CASPI, CD164, CD55, CFLAR, CGGBP1, CHMP5, CISH, CLP1, CMTR1, CNP, CREM, CYTIP, DCAF11, DDX60, DHX58, DNAJA1, DR1, DUSP5, EIF2AK2, EIF2S1, EIF3J, ELAC2, ENO1, ERCC1, ETV7, FAM13A, FAM46A, FAR2, FBXL8, FCHSD2, FEM1B, GADD45B, GALNS, GCH1, GPKOW, GPR171, GPRC5B, GSN, GTPBP1, H2BFS, HDAC9, HEMK1, HERC5, HERC6, HIST1HI1C, HIST1H2BD, HIST1H2BH, HIST1H2BK, HLA-B, HN1, ICA1, IDI1, IFI16, IFI27, IFI35, IFI44, IFI44L, IFI6, IFIH1, IFIT1, IFIT3, IFIT5, IFITM1, IGHMBP2, IKBKE, INSL3, IPO4, IPO7, IRF4, IRF7, IRS1, ISG15, ISG20, JUN, LAMP2, LAMP3, LAP3, LARP1, LARP7, LDHA, LGALS3BP, LGALS9, LIMK2, LTA, LY6E, MAP4, ME3, MRPL42, MT1E, MT1F, MT1G, MT1H, MTIHL1, MT1X, MT2A, MTM1, MTMR1, MX1, MX2, MYD88, N4BP1, NLRP2, NMI, NOP14, NPDC1, NPEPPS, NQ02, NUP188, OAS1, OAS2, OAS3, OASL, OGFOD3, P2RX5, PARP12, PARP3, PCK2, PDCD10, PDCD6, PDXK, PFKP, PGAM1, PGAP1, PHF11, PIGV, PIM1, PIP4K2C, PLSCR1, PNO1, POMP, PSMA1, PSMA5, PSMB10, PSMB9, PSME1, PSME2, PTGER2, RAB11FIP1, RASGRP3, RBCK1, RCL1, RCN1, REC8, RELB, REXO2, RMDN3, RSAD2, RTP4, RUVBL2, SAMD9, SCO2, SELP, SEMA3G, SIPA1L1, SIRT5, SLC25A15, SNRPG, SOCSI, SOCS2, SP100, SP110, SPATS2L, SPCS3, SQRDL, STAT1, STAT5A, STX17, SUB1, SUSD4, TAP1, TBK1, TDRD7, TFDP2, TLR5, TLR7, TMEM140, TMSB10, TMX2, TNIP2, TRADD, TRAFD1, TRAK2, TRANK1, TRBC1, TRIM21, TRIM22, TRIM26, TRIOBP, TSPAN13, TUBB2A, TULP4, TXNL4A, TYMP, UBAP2, UBAP2L, UBE2L6, UCHL3, UPP1, USP11, USP18, USP46, WARS, XAF1, YBX3, ZBP1, ZCCHC2, ZMIZ2, ZNF207, ZNF273 |
| CD4 | Turquoise | AAMDC, AASDHPPT, ABCC1, ABCC10, ACOT13, ACOT9, ACP1, ACSL1, ACTA2, ACTR3, ACVR1, ADIPOR2, ADK, AIFM1, AIM2, AIMP2, AKAP1, ALAS1, ANAPC5, ANP32E, ANXA2, ANXA2P2, ANXA2P3, ANXA4, APOL3, APPBP2, APTX, ARL3, ARPC1A, ARPC2, ARPC3, ARPP19, ASCC1, ATF7IP, ATG4A, ATG5, ATIC, ATMIN, ATP2C1, ATP5G1, ATP5G3, ATP5I, ATP5J, ATP5S, ATP5SL, ATP6VOE1, ATP6V1A, ATP6V1C1, ATP6V1D, ATP6V1H, ATPIF1, B3GNT2, B4GALT5, BAG1, BAG5, BAK1, BAZ1IA, BHLHE40, BID, BIRC3, BLVRA, BLZF1, BORA, BTG3, BTN2A2, BUD31, BZW2, C10orf2, C11orf48, C11orf73, C14orf159, C14orf166, C1GALT1, C1GALT1C1, C1orf50, CIQBP, C21orf59, C21orf91, C2CD3, C2orf43, C2orf44, |

TABLE 8-continued

| Genes in modules identified via Gene Ontology (GO) analysis | | |
|---|---|---|
| Cell Type | Module Name | Genes |
| | | C2orf47, C6orf106, C8orf60, CALU, CAPZA1, CARS, CASK, CASP3, CASP4, CCDC53, CCDC69, CCNA2, CCNB1IP1, CCNH, CCR5, CCT2, CCT3, CD28, CD38, CD59, CDC123, CDC27, CDC73, CDK2AP1, CDK7, CDS2, CDV3, CEACAM5, CEBPG, CHCHD3, CHMP2A, CHMP4A, CHN1, CHP1, CHST11, CHST12, CHST7, CISD1, CKS2, CLN8, CLTA, CLUAP1, CMC2, CNDP2, CNPY2, COA3, COMMD3, COPS2, COPS5, COPS6, COQ2, COX17, COX5A, COX5B, COX6B1, COX7A2, COX7B, CPSF6, CPT2, CRIPT, CSNKIAI, CSNK2A1, CSTF1, CSTF2, CSTF3, CTDSP2, CTNNBL1, CTPS1, CTSK, CUL1, CUL3, CUL5, CYB5R4, CYCS, CYLD, DBI, DCLREIA, DCPS, DCTN5, DCTN6, DCTPP1, DDB2, DDX10, DDX19A, DDX24, DDX27, DDX52, DDX54, DDX58, DECRI, DEF8, DERL2, DGCR2, DGUOK, DHTKD1, DIABLO, DIMT1, DNAJC15, DNAJC2, DNAJC9, DNPEP, DNTTIP2, DOK1, DYNC1H1, DYNC1LI1, DYNLL1, DYNLT1, EBNAIBP2, EBP, EEF1E1, EFR3A, EIF2B2, EIF2S2, EIF4A3, EIF4E2, EIF4ENIF1, EIF5B, ELOVL6, ELP3, EMC3, EMC7, EMC8, ENDOD1, ENY2, EPS8L2, ERAP2, ERO1L, ETF1, ETFB, ETNK1, ETS1, EZH2, EZR, F5, FABP5, FAM105A, FAM32A, FAM50B, FAM63B, FAM69A, FANCL, FARS2, FARSA, FAS, FASTKD5, FBX05, FBXO7, FBXW2, FDPS, FDX1, FEN1, FH, FIBP, FIG4, FLNB, FOXK2, FRAT2, GADD45A, GALK2, GARS, GART, GBP1, GBP2, GEMIN4, GEMIN6, GGCT, GGCX, GIGYF2, GLA, GLB1, GLG1, GLRX2, GLRX3, GM2A, GMFG, GMNN, GMPS, GNAI3, GNPDA1, GORASP2, GOT2, GPR107, GRAMD3, GRPEL1, GRSF1, GSTO1, GTF2A2, GTF2B, GTF2E2, GTF2H2, GTF2H5, GTPBP4, H2AFZ, HAUS7, HCCS, HCFC2, HCP5, HDGFRP3, HDHD1, HDLBP, HEATR6, HERPUD1, HEXIM1, HIF1AN, HIGD1A, HINFP, HIRIP3, HISTIH2AC, HMGB2, HMGCS1, HNRNPAB, HNRNPC, HNRNPDL, HNRNPR, HPRT1, HRSP12, HSP90AA1, HSPA4, HSPA5, HSPD1, HSPE1, HTATIP2, HTRA2, IARS, ICOS, ICT1, IDHI, IDH2, IDH3A, IDS, IER3IP1, IFT27, IL10RB, IL13RA1, IL18R1, IL27RA, IMMT, ING2, INPP1, INPP5B, INTS12, IP6K2, IPPK, ITFG1, ITGAE, ITGB1BP1, ITPA, JAK2, JAM2, JARID2, JMJD6, KATNAI, KCMF1, KCTD2, KDM5A, KEAPI, KHNYN, KIAA0040, KIAA0101, KIAA0391, KIAA0586, KIAA0922, KIF22, KLC1, KLF10, KLF12, KLHDC4, KLHL7, KPNA2, KPNA4, KPNB1, LAGE3, LAMTOR2, LAMTOR5, LARP4, LARS2, LCMTI, LDLR, LDLRAD4, LETM1, LOC100289097, LPCAT1, LRRC59, LRRC8D, LSM3, LXN, LYST, MAD2LIBP, MADD, MAF, MAGEF1, MANF, MAPK13, MAPK1IP1L, MAPK9, MAPKAPK5, MBD2, MCL1, MCM3, MCM6, MCTS1, MCUR1, MDH2, ME2, MED27, MED8, MEOX1, METTL1, METTL22, MFAP1, MFSD5, MICA, MICALL1, MICB, MIOS, MMD, MOB1A, MPC2, MPHOSPH9, MR1, MREG, MRGBP, MRPL15, MRPL17, MRPL20, MRPL22, MRPL3, MRPL33, MRPL46, MRPL57, MRPS11, MRPS14, MRPS16, MRPS17, MRPS18A, MRPS18B, MRPS28, MRPS30, MRPS33, MRPS35, MTAP, MTCH2, MTG1, MTHFD2, MTMR12, MTMR2, MTX2, MYL6, MYO5A, N4BP2L2, NAB1, NADK, NBN, NCAPD2, NCAPH2, NCF4, NCK1, NCKAP1L, NDC80, NDUFA1, NDUFA6, NDUFA8, NDUFA9, NDUFAB1, NDUFAF1, NDUFB3, NDUFB4, NDUFB7, NDUFB8, NDUFS2, NDUFS3, NDUFS6, NEU1, NFE2L1, NFIL3, NFKBIE, NGFRAP1, NIPBL, NME1, NME7, NMT1, NOD2, NOP16, NPM1, NRAS, NRBF2, NSD1, NSDHL, NSUN3, NTHL1, NUDC, NUDT21, NUP155, NUP37, NUP93, NUP98, OBFC1, ODC1, OPTN, OSBPL3, PAF1, PAFAH1B1, PAICS, PAK1IP1, PAK2, PAM, PANK2, PANX1, PARK7, PARN, PCIF1, PCMT1, PCTP, PDCD11, PDCD5, PDE4B, PDE6D, PDIA6, PDPK1, PDSS1, PEX13, PEX26, PFDN2, PGD, PGM1, PHF21A, PIGT, PIK3C3, PIK3R4, PIN4, PIP4K2A, PITPNA, PLAGL1, PLXNC1, PMAIP1, PMS2P3, POLB, POLDIP2, POLR2I, POLR3C, POLR3K, POP4, POP7, POU2AF1, PPAP2A, PPIE, PPM1G, PPP1R16B, PPP1R7, PPP2CA, PPRC1, PRDX3, PRDX4, PRIM1, PRKX, PRMT5, PRPF18, PRPS2, PSEN1, PSMA2, PSMA3, PSMA4, PSMA7, PSMB1, PSMB3, PSMB7, PSMC1, PSMC2, PSMC3IP, PSMC5, PSMD1, PSMD12, PSMD13, PSMD14, PSMD2, PSMD4, PSMD6, PSMD9, PSMG1, PTPN2, PTRH2, PTTG1, PUS1, PWP1, QKI, QRSL1, RAB22A, RAB27A, RAB29, RABGAP1L, RABGGTA, RABIF, RAC1, RACGAPI, RAD23B, RAD50, RAN, RAP1GDS1, RBX1, RER1, RFC2, RFC3, RFC4, RFK, RFX5, RGS1, RHEB, RIPKI, RITI, RMDN1, RMND5A, RNASEHI, RNASEH2B, RNF34, RNF8, RNMTL1, RPA3, RPF1, RPL26L1, RPL28, RPN2, RPP30, RPP40, RPS6KB1, RPUSD2, RRAS2, RRP12, RRP9, RRS1, RTCA, RTCB, RTFDC1, RUVBL1, RWDD2B, RYBP, SAMHD1, SAP18, SAP30, SAP30BP, SAP30L, SARIA, SAT1, SDHA, SEC11A, SEC14L1, SEC16A, SENP5, SEPHS1, SERBP1, SERPINB1, SERPINI1, SF3B3, SF3B5, SFPQ, SGK1, SH2D2A, SHFM1, SKAP2, SLBP, SLC16A1, SLC25A12, SLC25A4, SLC2A3, SLC35B1, SLC35D2, SLC35F2, SLC3A2, SLC5A6, SLC7A5, SMAD3, SMAP1, SMARCA4, SMC4, SMC6, SMCHD1, SMCO4, SMS, SNAPC3, SNF8, SNRNP25, SNRNP35, SNRPB2, SNRPC, SNRPD1, SNRPD3, SNUPN, SNW1, SNX1, SOD1, SOS1, SP140, SP140L, SPCS2, SPTLC2, SRD5A1, SR1, SRP19, SRSF4, STAM, STARD7, STAU1, STK17B, STK4, STOML1, STOML2, STRAP, STX4, STX7, STX8, SUCLG1, SUMO1, SYNCRIP, SYT11, TACO1, TAF12, TAF9, TALDOI, TARBPI, TARS, TARS2, TBCID1, TBCID22A, TBL2, TBXAS1, TCEB3, TCOF1, TDP1, TESC, TFG, TFPT, TFRC, THADA, THG1L, THOC5, TIMM23, TINF2, TIPARP, TJP2, TMCO1, TMEM11, TMEM126B, TMEM135, TMEM156, TMEM186, TMEM2, TMEM5, TMEM62, TMEM70, TMSB4X, TNFRSF1B, TNFSF10, TNFSF8, TOM1, TOX, TP53TG1, TPK1, TRAF3, TRAK1, TRAPPC12, TRIB1, TRIM14, TRIM38, TRIM5, TRIM68, TSR1, TSR3, TTC1, TTC17, TUBG1, TXN, TXNL1, TXNRD1, UBAC1, UBE2A, UBE2D1, UBE2K, UBL5, UBQLN2, UBR2, UBXN8, UCHL5, UGGTI, UMPS, UQCR10, UQCRC2, UQCRQ, USP15, USP25, USP39, UTP11L, UTP18, UTP3, VAMP4, VAV3, VCP, VDAC1, VDAC2, VOPP1, VRK1, VRK2, VTI1B, WBP1L, WDYHV1, WIPF2, WIPI1, WRAP53, WSB2, WWP2, XRCC4, YARS, YEATS2, YIPF1, YLPM1, YWHAH, YWHAQ, ZBED1, ZC2HC1A, ZDHHC4, ZMIZ1, ZNF226, ZNF536, ZNF593, ZNF710, ZPR1 |
| CD4 | Orange red4 | ABCB1, ABLIM1, ACVR1B, ADARB1, ADNP2, ALDH6A1, ALDOC, ANGEL1, ANXA1, APIS2, APBA2, APP, APRT, AQP3, ARCN1, ARL2BP, ARRB1, ASB8, ATXN2, ATXN7L3B, B4GALT4, BACH2, BAG3, BNIP3L, C12orf10, C14orf1, CACNA1A, CBX7, CCDC101, CCNG1, CCNI, CCR2, CD44, CDC37, CDIPT, CDK5R1, CERK, CHPT1, CKAP4, CMPK1, COX4I1, COX7A2L, COX7C, CRIP1, CRK, CUTA, CUX1, DDAH2, DDOST, DIAPH1, DNAJB1, DPEP2, |

TABLE 8-continued

Genes in modules identified via Gene Ontology (GO) analysis

| Cell Type | Module Name | Genes |
|---|---|---|
| | | DPH5, DVL1, EDEM1, EEF1D, EEF2, EIF2D, EIF3F, EIF3G, EIF3H, EIF3K, EIF3L, EIF4B, ENO2, EP400, EPHA1, ERN2, ESD, FAM168B, FAM20B, FAM8A1, FBL, FCGRT, FGFR1, FHL1, FOXO3, FTL, GGA1, GLO1, GLS, GPR183, GPR27, GPX4, GSS, GTF2F1, GTPBP3, HADHA, HIP1R, HLA-F-AS1, HMCES, HNRNPAO, HOPX, HSD17B11, HSD17B8, HSF2, HSPA1L, IGF2R, IGHD, IMPDH2, INPP5A, IRS2, ITFG2, ITPKB, KCNQ1, KLHDC2, KLRB1, KLRG1, KPNA1, LAIR1, LAMP1, LAPTM5, LINC00623, LITAF, LSM14A, LTA4H, MAGED2, MAN1B1, MAN1C1, MED21, METTL9, MGA, MID2, MMP24-AS1, MOB3B, NAP1L1, NCOA1, NDRG3, NFATC2IP, NPC2, ORAI2, P4HB, PABPC1, PABPC3, PABPC4, PACSIN2, PAFAH2, PCBP2, PDCD4-AS1, PEBP1, PFDN5, PIK3R1, PLEKHB1, PMM1, POLR1E, POU6F1, PPM1F, PPP1R2, PPP2R5D, PRKCA, PRKD3, PRMT2, PRNP, PRUNE, PSAP, PTDSS1, PURA, QARS, RAB11FIP3, RCC1, RCOR3, REPIN1, RGCC, RNF130, RPL11, RPL15, RPL18, RPL19, RPL22, RPL29, RPL3, RPL35, RPL35A, RPL6, RPL8, RPLP0, RPS14, RPS16, RPS19, RPS21, RPS28, RPS3, RPS5, RPS7, RPS9, RSL1D1, RUFY3, SCPEP1, SDHAF1, SEMA4C, SERINC5, SESN1, SF3A3, SGSM3, SLC25A6, SLC35C2, SND1, SORLI, SPAG8, SPOCK2, SPSB3, SRSF8, SSBP2, SSR2, SSR4, ST13, SVIL, TAF7, TBC1D5, TGFBR2, TKTL1, TMEM134, TMEM230, TOMM20, TRAPPC6A, TRIM27, TRIM44, TRMT112, TSC22D3, TSPO, TTC9, TXN2, TXNIP, UBA52, UBE2E3, UXT, VEGFB, VGLL4, VIPR1, VPS51, WDR41, YIPF2, ZBTB18, ZC3HAV1, ZFAND3, ZMAT3, ZSCAN18 |
| CD14 | Plum1 | ABCD3, ADO, AKAP7, AMD1, ANKRA2, ANP32A, ANXA1, ARAP2, ARL6IP1, ARMCX1, ARMCX3, ARPC2, ARPC3, ATP2C1, ATP6AP2, ATP6V1C1, AUH, BECN1, C1D, C5AR1, C5orf22, C6orf62, CAPZA1, CAPZA2, CBX3, CCDC91, CCNC, CD55, CD9, CDC5L, CDC73, CEBPB, CEBPD, CHMP2B, CHUK, CISH, CLIP1, CLPX, CNOT2, COMMD8, CPEB3, CSGALNACT2, CTBS, CUL2, CYB5B, CYP1B1, DEK, DENR, DERA, DNTTIP2, DRI, DRAM1, DTWD1, DUSP11, DYNLT3, E2F3, EBAG9, EDEM3, EID1, EIF3J, EIF4E, EP300, EPS15, EWSR1, FAM216A, FOXN3, FUBP3, FUCA1, GLIPR1, GLTSCRIL, GLUL, GNPTAB, GRSF1, HBS1L, HMGN4, HSD17B11, HUS1, IBTK, IMPACT, ISCA1, ITM2B, IVD, KCTD9, KIAA0226, KIN, KLHL20, KTN1, KYNU, LAMP2, LAPTM4A, LARP4, LARP4B, LEPROT, LILRB2, LIN7C, LSM5, LYN, LYPLA1, MAK16, MAP3K8, MAP4K3, MARCH7, MARS, MCM9, MEAF6, MED7, MEF2A, MFF, MICU2, MKNK2, MTHFD2, MYO5A, NAA50, NDUFA4, NDUFA5, NDUFB1, NFE2L2, NPTN, NUMB, NUP88, NXT2, OGFRL1, ORC4, PAIP1, PAK2, PCNP, PDHX, PDLIM5, PDS5A, PFDN4, PICALM, PLAA, PPMIB, PPP1CB, PPP2CB, PPP2R3C, PRNP, PRRG4, PSMD10, PSME4, PSMF1, PSPC1, PTEN, PTP4A1, QKI, RAB11FIP2, RAB27A, RAB29, RAB2A, RAB7A, RALA, RAP2C, RBMS1, RCN2, RDH11, REST, REV3L, RFK, RMND5A, RNF103, RNF11, RNF170, RP2, RPL37, RPL39, RTN4, SARIB, SARAF, SAT1, SCP2, SEC23A, SEC23B, SEMA3C, SEP15, SERBP1, SERPINB1, SHOC2, SKP1, SLC25A24, SLC35A3, SLMO2, SMA4, SNRPA1, SNTB1, SNX10, SOCS5, SP2, SRGN, SRP9, SRSF10, ST3GAL6, STXBP3, SUB1, SUCLA2, SUCLG2, SUMO1, SYPL1, TAF11, TBL2, TCEAL4, TCEB1, TERF1, THAP1, THOC7, TM2D3, TMEM115, TMEM165, TMEM70, TMSB4X, TMX1, TOB1, TRAPPC13, TRIM8, TSNAX, TSPAN31, TSPYL4, TTC37, TXNRD1, U2SURP, UBE2A, UBE2B, UBE2E1, UBE2K, UBXN8, UFM1, UHRFIBPIL, ULK2, USP16, USP4, USP8, USP9X, UTP3, VCAN, VPS54, WBP11, WIPI1, WWP1, XPOT, YTHDF3, YWHAB, YWHAQ, ZEB2, ZFAND6, ZFP36L1, ZNF292, ZNF468, ZSCAN16 |
| CD14 | Yellow | ABCA1, ACSL1, ACVR1B, ADAM17, ADAP2, ADAR, ADD3, AGRN, AIM2, AIMP1, ALAS1, ANKRD49, ARHGAP26, ARID3B, ARL4A, ATP10A, ATP11B, ATP5J, ATP6VOE1, ATP6V1E1, ATP8B4, ATXN7, B2M, B3GNTL1, BACH1, BARD1, BCAS2, BCL10, BLVRA, BST2, BTG3, C11orf24, C12orf5, C19orf66, C1GALT1C1, C1QA, C2orf47, C3AR1, CALM1, CALML4, CAPN2, CASP3, CASP7, CCR1, CD2AP, CD300A, CD38, CDC40, CHIC2, CHMP5, CHPT1, CIR1, CLN5, CMTR1, CNIH4, CNP, COAL, COX17, CREG1, CTSC, CTSL, CTSS, CUL1, CXCL10, CYLD, DAB2, DBR1, DCTN6, DDIT4, DDX58, DDX60, DECR1, DENND1B, DHRS7B, DIAPH1, DICER1, DNAJC15, DNASE2, DPM1, DRAP1, DYNLT1, DYSF, EIF2AK2, ENPP4, EPHB2, EXT1, FADD, FAM175B, FAM46A, FAM65B, FAM8A1, FAS, FCGRIB, FCGR3B, FFAR2, FKBPL, FMR1, FPR2, FYCO1, GALNT3, GBP1, GBP2, GCH1, GCLM, GCNT1, GHITM, GLRX2, GNG5, GPN2, GPR137B, GPR65, HBP1, HEG1, HELZ, HERC5, HERC6, HIST2H2BE, HLA-A, HLA-B, HLA-C, HLA-F, HLA-J, HNRNPA2B1, HPRT1, IFI16, IFI27, IFI35, IFI44, IFI44L, IFI6, IFIH1, IFIT1, IFIT2, IFIT3, IFIT5, IFITM1, IFITM2, IFITM3, IFNGR1, IL15, ILIRN, IL6ST, IQGAP2, IRF7, IRF9, ISG15, ISG20, ITFG1, JUP, KAT2B, KCNJ2, KDM5B, KDM6A, KLF9, KLHL9, KMO, LAP3, LARP7, LGALS3BP, LIPT1, LMO2, LRRFIP1, LXN, LY6E, LY96, MAFB, MAGOH, MAML1, MAP2K6, MARCKS, MBD2, MED28, MERTK, METTL 18, METTL5, MGAM, MILR1, MRPL16, MRPL18, MRPL19, MRPS14, MRPS22, MS4A4A, MSL2, MSMO1, MT1E, MT1F, MT1G, MT1H, MT1HL1, MT1X, MT2A, MX1, MX2, MYC, MYD88, MYL12A, MYL4, MYOF, N4BP1, NAB1, NAPA, NAT1, NDUFB3, NDUFSI, NECAP1, NFE2, NGRN, NMI, NPC1, NRIP1, NT5C2, OAS1, OAS2, OAS3, OASL, PANX1, PARP12, PCMT1, PELO, PER2, PFKP, PGK1, PHF11, PHF3, PHTF2, PIGB, PIK3CA, PIN4, PLAC8, PLAGL2, PLIN2, PLSCR1, PML, PNO1, POLB, PPMID, PPP2R1B, PRKAG2, PSMA4, PSMB9, PSMC2, PSMD12, PSME2, PTPN12, PTPRO, RAB11A, RAB1A, RAB8A, RAB9A, RABGAP1L, RAPGEF2, RBM7, RBX1, RC3H2, REC8, RGL1, RHEB, RHOA, RIN2, RNASE1, RNASE2, RNF122, RPP38, RPS27, RPS27L, RSAD2, RTCB, RTP4, S100A11, S100A8, SAMD9, SAMSN1, SC5D, SCFD1, SEC22B, SERPING1, SH3GLB1, SIGLEC1, SKAP2, SLA, SLC25A46, SLC30A1, SLC31A2, SLCO4C1, SMCHD1, SNRK, SNX1, SP100, SP110, SPATS2L, SPTLC2, SQLE, SRP19, SSB, ST3GAL5, STAT1, STAT2, STOM, STS, SWAP70, TANK, TAOK3, TAP1, TBK1, TCF4, TCF7L2, TCN2, TDP2, TDRD7, TFEC, TFG, TFIP11, TIMP1, TLR2, TMED5, TMEM110, TMEM123, TMEM131, TMEM255A, TMEM50A, TMPO, TNFSF10, TNS3, TOR1B, TRAF6, TRIM14, TRIM21, TRIM22, TRIM38, TSG101, TYROBP, UBE2JI, UBE2L6, UCHL3, USP18, USP25, VAV3, VDR, VEZFI, VRK2, VWASA, WDFY3, WDR41, WDR5B, WDYHV1, XAF1, YME1L1, ZBTB1, ZC3HAV1, ZCCHC2, ZNF267, ZNF322, ZNF350, ZNF443, ZNF701 |

TABLE 8-continued

| Genes in modules identified via Gene Ontology (GO) analysis | | |
|---|---|---|
| Cell Type | Module Name | Genes |
| CD14 | Green yellow | ACVR2A, AGTPBP1, APOD, APOL1, ARHGAP10, ASTE1, ASXL2, ATP5C1, BLM, BTBD7, Clorf216, CAST, CCDC51, CCL5, CD27, CD3D, CEMP1, CHD4, CROT, ENSA, EP400, EPM2AIP1, ERP44, FAM114A1, FAM208A, FBXO9, FGFRI, FLCN, FUT6, GABI, GNA11, HAP1, HYAL2, ITFG2, ITGAL, KANSL3, KIF21B, KLF12, KMT2A, KPNB1, KSR1, LMF1, LOC100272216, LOC100505915, LOC647070, LPAR1, MACF1, MASP1, MICAL2, MLH3, MMP9, MUC5AC, MYB, MYO1C, N4BP2L2, NCALD, NDST1, OCA2, PAX8, PGGTIB, POLR1C, POLR2C, PRDM14, PRODH, RNGTT, RRP15, SIPR4, SCAF4, SEPT6, SFI1, SLC12A4, SPN, STK39, SYT11, TBP, TCAF1, TMEM212, TMEM59L, TNNI3, TNPO3, TRAF3, TUG1, UNC45A, USP34, VWA9, ZHX3, ZNF665, ZNF76, ZNRF4 |
| CD14 | Pink | ACAN, ACOT11, ADGRB1, AGER, AKAP8L, AKT3, ALDH2, ALDOB, ALS2CL, AMT, ANKRD2, ARMC7, ARPP19, ATP8B2, ATXN10, BACEI, BAIAP2, BARX2, BAZ2A, BBS1, BIN3-IT1, BNIP3L, BRAP, BRE, BTNL3, C5, C9orf9, CA1, CA14, CAD, CAMK2B, CARS, CBX5, CBX6, CCDC71, CCDC86, CCDC9, CD1A, CDC42BPB, CDKN2A, CEACAM6, CHRNA2, CHRNG, CISD1, CKLF, CLTA, COA7, COL1A1, COL6A2, CPD, CREBZF, CRIP1, CSNKIG1, CTNNA1, CTSK, CYFIP2, DAXX, DGCR11, DHFR, DHX32, DNAJA3, DNPH1, DOCK1, DPH2, DST, DYRK3, DYRK4, EIF3M, ENGASE, EPHB4, EPHB6, FAM189B, FAM192A, FBXL5, FBXO42, FKBP4, FUT7, FXYD3, GABBR2, GAS8, GBF1, GCNT4, GDPD5, GIPC1, GLS, GOLGA3, GPR107, GSTA1, H2AFY2, HDAC6, HDHD1, HECTD4, HFE, HMGA1, HMGB1, HNRNPD, IKBKE, INTS5, IQCC, IQSEC2, ITPK1, JRK, KDM4C, KDM5C, KIR2DL2, KLHDC10, LAMC1, LDB3, LDLRAD4, LGALS2, LGALS8, LINC00894, LMNA, LRCH4, LRRN2, LUZP1, LYRM9, MAPK8IP2, MAPK8IP3, MARK4, MBP, MDK, MED12, MINK1, MPPE1, MPPED1, MRE11A, MTOR, MUC3B, MUTYH, MYO19, MYO7A, NAA10, NACA, NECAB3, NENF, NF2, NFATC4, NIPAL2, NKTR, NNAT, NOP14, NPEPLI, NPR2, NPTXR, NR4A1, NSUN5P1, NTM, NUP188, OCEL1, ONECUT2, OPHN1, OPN3, PAPPA2, PCYOX1L, PCYT2, PDCD4-AS1, PDCD6, PDGFB, PEAK1, PIGO, PIP4K2C, PIPOX, PKD2L1, PKM, PLA2G6, PLCB3, PLCD1, PLEKHG3, POLR1D, PPIA, PPP2R4, PPP6R2, PRAF2, PRINS, PRRC2B, PSMD4, PTCRA, PTGES, R3HDM1, RAB31, RANBP10, RAP1GAP, RAPGEF3, RBM17, REXO2, RHO, RNASEH2B, RPGR, RPH3A, RPL35A, S100A13, SAFB2, SEC31A, SERINC2, SF3A1, SFN, SFTPB, SHQ1, SIGMAR1, SLC15A2, SLC28A1, SLC44A1, SLC46A3, SLC7A6, SMARCD1, SMCIA, SMPD2, SNCA, SNX11, SNX3, SORBS3, SSBP1, SSBP3, ST6GALNAC2, STK24, SUPT20H, SUPT6H, SYT13, TARBP1, TARBP2, TBX1, TCOF1, THUMPD2, THY1, TMEM109, TMEM147-AS1, TMPRSS15, TNK1, TNS1, TOMM34, TOP3A, TOPORS-AS1, TPM1, TPT1, TRIT1, TRO, TTC17, TTLL12, UBAP2L, UBE3B, UBL3, UGDH, UNC119, UNC13A, USEI, VAC14, VPRBP, VPS13D, WDTCI, WWC3, ZBTB22, ZBTB40, ZMYM3, ZMYND11, ZNF337, ZNF592, ZNF629, ZNF839, ZSWIM8, ZZEF1 |
| CD14 | Purple | AATK, ACSL5, ADGRE3, AEBP1, AIMP2, ANXA2P1, AQP6, ARMC6, ATG4B, AVPI1, BEST1, C14orf93, C1orf54, C22orf31, C2CD2, CASP10, CBFB, CCDC130, CDX1, CEACAM3, CKAP5, COL8A2, CXorf56, DCUN1D4, DIMTI, DYNCIH1, EIF5B, EMID1, FAM102A, FAM206A, FARS2, FASTK, FXYD2, GABRR2, GALT, GLPIR, GLT8D1, GPATCH8, HEATRI, HMGXB3, HSPB6, HUWE1, IFT88, INPP5E, IPPK, ITPKC, KIAA0586, KLK3, KRT31, LAMP1, LLGL1, LMBR1L, LRRC14, MAGT1, MAP3K10, MAP3K7, MARC2, MAST2, MECP2, MLX, MTMR9, MYBL2, MYNN, MYO9A, NFATC1, NIT2, NSMAF, NTRK3, NUP210, OR2H2, OXSM, PBX2, PCDH12, PCK2, PHKA2, PHLPP2, PLCG1, PLEK2, POFUT1, POU6F1, PPIG, PPPIR26, PRCP, PRUNE, PVR, PYCR1, RAB3IL1, RAD1I, RBM19, RIN1, RMDN3, RPL38, RPS11, RRAGA, SCML2, SDHAF1, SECISBP2L, SEL1L, SLAMF8, SLCIA4, ST3GAL4, STARD8, SUPV3L1, TBX5, TCF3, THRA, TIMELESS, TMEM2, TRIM26, TRIM45, TRIO, TRMT12, TRPM6, TUB, UBAP2, UBE2D4, VAMP3, VPS33B, WDR70, WNT10B, ZC3H13, ZMIZ2, ZNF419, ZNF862 |
| CD19 | Sienna 3 | ABCC5, ACIN1, ACP1, ACYP2, AFG3L2, AHCYL1, AHNAK, AKR7A2, ALOX5, ANAPC5, AP2B1, APEX1, ARIH2, ARL1, ARMCX6, ASB8, ATIC, ATP5I, ATP5L, ATRN, AUP1, BTF3, C14orf159, C2orf68, CAMLG, CAPN3, CASC3, CCDC69, CCNB1IP1, CCT3, CD244, CDC16, CDK10, CDK19, CES2, CIITA, CKAP4, COIL, COPZ1, COX4I1, COX7C, CRTAP, CTNS, CYP27A1, DCTD, DHX9, DUS1L, DVL1, ECHS1, EEF2, EIF1, EIF2B3, EIF2B4, EIF2B5, EIF2D, EIF3A, EIF3D, EIF3E, EIF3F, EIF3H, EIF3K, EIF3L, EIF4B, EIF4EBP2, ENG, EPRS, FAM162A, FAM35A, FAM49A, FBL, FBRS, FBXO21, FCER1A, FKBP11, FLII, FOLR2, FTSJ3, FUBP1, FXN, FYN, GARS, GAS2LI, GATAD1, GLG1, GOLGB1, GOT2, GRWDI, GSS, HADHA, HDLBP, HEBP1, HEMK1, HINT1, HLA-DMA, HLA-DQA1, HNRNPA1, HNRNPDL, IARS, ILF3, IMPDH2, INTS3, IPO5, ISG20L2, ITPA, IVNSIABP, KAT2A, KATNB1, KDM6B, LASIL, LDHB, LETMD1, LRRC47, LSG1, LSM4, LY86, LYRM4, LZTFL1, MANICI, MAP4, MAP4K1, MAPK7, MBD1, MDH2, MGST2, MMS19, MPRIP, MPST, MRPS35, MXI1, NAE1, NAP1L1, NONO, NPEPPS, NPM1, NUP93, OSBP, OXA1L, PABPC4, PAM, PCBP2, PDCD11, PFKM, PHB2, PHF20, PMM2, PMS2P1, POLD2, POLR2H, POLR2I, PON2, PPOX, PRKCB, PRKDC, PSKH1, PTAFR, PTCD3, QARS, RAE1, RCC1, RCN1, REPIN1, RPA1, RPL15, RPL19, RPL22, RPL3, RPLPO, RPLP1, RPS10, RPS16, RPS17, RPS23, RPS27A, RPS3, RPS4X, RPS6, RPS7, RPS9, RRNAD1, SDR39U1, SEC11A, SET, SFPQ, SGPL1, SGSM2, SH3YL1, SIVAI, SKP2, SLC11A2, SLC25A5, SLC25A6, SLC5A3, SLC9A3R1, SND1, SORLI, SPCS2, SPG7, SPINT2, SPSB3, SRPRB, SRSF4, SRSF5, ST13, STARD7, SUGP2, SYK, TAF15, TARDBP, TBCID12, THAP11, TPCN1, TPT1P8, TSEN34, TST, TUBG1, TXN2, UBE2I, UQCRC2, VENTX, VPS4A, ZNF32, ZNF395 |
| CD14 | Dark olive green | AACS, ABCB9, ABCC4, ABCF2, ACOT7, ACOX1, ACTA2, ACTG1, ACTR1A, ADA, ADIPOR1, AEN, AGK, AGPS, AK2, AKR1A1, ALDH18A1, ALDH3A2, ANAPC15, ANG, AP2B1, AP2S1, APHIB, APIP, APOBEC3G, APOL1, APOO, AQP3, ARL3, ARPC2, ASF1B, ASPM, ATAD2, ATF6, ATOX1, ATP1B3, ATP5B, ATP5C1, ATP5G1, ATP5G3, ATP5H, ATP5J, ATP5J2, ATP8B2, AUNIP, AURKA, AURKB, B2M, B4GALT1, B9D1, BATF, BCAR3, BCCIP, BIRC5, BLMH, BMP8B, BRAP, BSG, BUB1, BUB1B, C14orf1, C15orf39, C19orf10, C1orf216, C21orf91, C22orf29, C2orf49, C3orf14, C6orf106, CADM1, CALML4, CALR, CALU, CAMKK2, CARHSP1, |

TABLE 8-continued

| Genes in modules identified via Gene Ontology (GO) analysis | | |
|---|---|---|
| Cell Type | Module Name | Genes |
| | | CAV1, CCDC51, CCNA2, CCNB2, CCND2, CCNE1, CCNE2, CCR2, CCT5, CD320, CDC20, CDC25A, CDC45, CDC6, CDCA3, CDCA4, CDCA8, CDK1, CDK2, CDK4, CDK5, CDKN2A, CDKN2C, CDKN3, CDS2, CENPA, CENPE, CENPF, CENPM, CENPN, CEP55, CFLAR, CHAF1A, CHCHD2, CHEK1, CHP1, CHST2, CINP, CKAP5, CLIC1, CLIC4, CLPB, CNIH1, CNP, CNPY2, COA4, COX6A1, COX6B1, COX7A2L, COX7B, COX8A, CRADD, CREB3, CRELD2, CSNK1E, CSNK2A1, CSRP1, CTNNAL1, CUL5, CUTA, CYC1, DARS2, DAZAP1, DCPS, DDB1, DDX19A, DESI1, DHFR, DLGAP5, DNA2, DNAAF1, DNAJC1, DNAJC15, DNAJC3, DNMT1, DONSON, DPP3, DTL, E2F8, EBP, EDC3, EDEM2, EEF1E1, EFCAB11, EIF2S1, EIF4A3, EIF4G1, EIF4H, ELAVL1, ELL, EMC1, EMC6, EMC9, ERCC6L, ERGIC2, ERO1L, ESPL1 F11R, FA2H, FADD, FANCG, FANCI, FARSA, FBXW2, FKBPIA, FKBP2, FLAD1, FOXM1, GABPA, GABPB1, GADD45A, GADD45GIP1, GALE, GALNT14, GAR1, GARS, GART, GATB, GCLM, GDE1, GEMIN4, GGCX, GINS1, GINS2, GINS3, GLRX, GLRX5, GMDS, GMPPA, GNAI3, GNAS, GNB1, GORASP2, GOSR2, GOT1, GOT2, GPN2, GRB2, GTF2A2, GTF2F2, GTPBP8, GTSE1, GUF1, H2AFV, H2AFX, HBS1L, HDLBP, HES1, HEXB, HIRIP3, HIST1H1C, HJURP, HMBS, HMGB1, HMGB3, HMMR, HMOX2, HNRNPAB, HOXB7, HSD17B10, HSF2, HSPD1, HYI, IARS, IDE, IDH2, IFNAR2, IGF1, IGF2BP3, IGHG1, IL12A, IL2RB, IL6ST, IMPADI, INPP4A, ISOC2, ITCH, ITGAX, ITGB7, KCNA3, KDM4A, KIF14, KIF15, KIF18B, KIF20A, KIF22, KIF23, KIF2C, KIF4A, KIFC1, KLHL5, KPTN, LAMP5, LANCL2, LAP3, LARP1, LDHA, LGALS1, LGALS3, LMNB1, LMNB2, LOC730101, LRRC42, LRRC59, LSM1, LSM12, LTB4R, MAGEH1, MAGT1, MAPK6, MCCC2, MCFD2, MCM10, MCM4, MCM6, MDH1, MDH2, MELK, MET, METTL1, MGATI, MGST2, MIS18A, MKI67, MMADHC, MPDU1, MRPL12, MRPL15, MRPL23, MRPL24, MRPL3, MRPL33, MRPL40, MRPL42, MRPL44, MRPS11, MRPS16, MRPS17, MRPS18B, MRPS2, MRPS34, MRPS7, MRTO4, MSRB2, MTFR1, MTRR, MTX1, MYBL2, NAA35, NAPA, NAPG, NASP, NBN, NCAPG, NCAPG2, NCAPH, NCLN, NDC1, NDUFA1, NDUFA13, NDUFA2, NDUFA4, NDUFA6, NDUFA7, NDUFA9, NDUFABI, NDUFAF3, NDUFB8, NDUFS7, NEK2, NET1, NEU1, NFE2L1, NME1, NOP10, NPM1, NRBP1, NSDHL, NTHL1, NUDT21, OGDH, OIP5, OPTN, OR7E12P, ORMDL2, OSBP, PAFAHIB3, PAGR1, PAICS, PAK1IP1, PAK2, PARP2, PARPBP, PBK, PCCB, PDE6D, PDK1, PDXK, PGD, PGM3, PGRMC1, PHB, PHGDH, PIM2, PKMYT1, PLA2G12A, PLAGL2, PLK4, PLOD1, PMM2, PNO1, PNPLA4, POLA1, POLA2, POLDIP3, POLE2, POLR2D, POMP, POP7, PPA1, PPAT, PPIA, PPIF, PPP2R1B, PPP2R2A, PPP6C, PRC1, PRCC, PRDM1, PRDX1, PRIM1, PRIM2, PRKAG1, PRMT5, PROSER1, PRRC1, PSAT1, PSMA2, PSMA5, PSMA7, PSMB1, PSMB2, PSMB5, PSMB6, PSMB8, PSMC1, PSMC3, PSMD11, PSMD12, PSMD14, PSMD8, PSMD9, PSME2, PSME3, PSMG2, PTPLAD1, PXMP2, PXMP4, R3HDMI, RAB27A, RAB2A, RAB6A, RAB8A, RABAC1, RABL6, RAD1, RAD51, RAD54B, RALA, RANBPI, RAPIA, RCC1, RECQL4, RER1, REXO2, RFC5, RFK, RGS13, RMND5A, RNASEH1, RNASEH2A, RRAGD, RRBP1, RRM1, RRS1, RUVBL1, S100A4, SAE1, SAMHD1, SBNO1, SCAMP2, SDF2L1, SDHB, SEC13, SEC23IP, SEL1L, SEPHS1, SF3B5, SFXN1, SH3GLB1, SHMT1, SIL1, SKAL, SLBP, SLC12A2, SLC16A1, SLC19A1, SLC25A11, SLC25A3, SLC25A4, SLC25A5, SLC35A2, SLC39A14, SLC39A7, SLC7A5, SLC9A3R1, SLCO3A1, SLIRP, SMC2, SMOX, SNRPC, SNRPD1, SNRPF, SNRPG, SP100, SPAG5, SPC25, SRM, SRPR, SRPRB, SRSF10, SSR3, SSSCA1, STAM2, STARD7, STIL, STIP1, STRAP, SUMO3, SUPT4H1, SZRD1, TBL2, TCEB2, TDP1, TECR, TGOLN2, THEMIS2, TIMM13, TIMM8B, TIMP2, TIPIN, TK1, TLE3, TM9SF4, TMA16, TMED9, TMEM106C, TMEM110, TMEM147, TMEM184B, TMEM194A, TMEM248, TMEM258, TMEM5, TMEM59, TMEM97, TMPO, TMSB10, TOP1, TOP2A, TPGS2, TPX2, TRAPPC2L, TRAPPC3, TRIP13, TSHR, TST, TTK, TUBB2B, TUSC2, TXLNA, TXN2, TXNL4A, UBE2C, UBE2D3, UBE2H, UBE2L3, UBE2S, UBFD1, UCHL1, UFD1L, UGGT1, UQCRC1, UQCRFS1, UQCRQ, UROS, USP14, VAPA, VKORC1, WBSCR22, WDR1, WDR12, WDR76, WHSC1, XRCC4, XRCC5, YARS, YIF1A, YKT6, ZDHHC3, ZNF207, ZNF35, ZNF593, ZNHIT1, ZWILCH, ZWINT |
| CD19 | Green yellow | ABCC1, ABHD14A, ACLY, ACO2, ACP2, ACTB, ADAP1, ADCY3, ADRA2C, AKIRIN1, ALDH3A1, ALG3, ANO10, APIS1, APEH, ARF3, ARFIP1, ARHGDIA, ARSA, ARTN, ATG13, ATP13A1, ATP6VOB, AURKAIP1, BAZ1B, BOP1, BTG2, BYSL, C11orf24, C17orf53, CAD, CCDC186, CCNF, CD99, CDK16, CHN2, CHPF, CHPF2, CLDN14, CLPP, CLSPN, CNTD2, COMMD4, COMT, COPE, CRMP1, CSNKID, CTPS2, CXCR3, CYP4F12, DBP, DCSTAMP, DCTPP1, DIAPH1, DLEC1, DNAJB12, DNASE2, DOK4, DPM2, DTX3, E2F1, EHD3, EIF2AK1, EIF3B, EIF6, ELMO1, ERLIN1, ERV9-1, EXOSC4, FAM214B, FLNB, FLNC, FN1, FOXRED2, FTSJ2, G3BP1, GANAB, GAS6, GCDH, GGA3, GNB1L, GPR144, GPR25, GRWD1, HAPLN2, HAXI, HDGF, HEATR2, HHLA3, HMOX1, HNRNPF, HOXC4, HSPA6, HSPBP1, IFRD2, IGH, IGHD, IGHM, IGK, IGLL3P, IKBKE, IL13, IL1RAPL2, INTS5, IQCE, JAG1, KATNB1, KCNN3, KCNQ4, KCTD5, KDM8, KNOP1, KPNA6, LDHC, LDLR, LEPRE1, LILRB4, LPCAT4, LRRC41, LTK, LYPLA2, MAPKAPK3, MAST2, MBDI, MCAT, MCL1, MEF2D, MEG3, MICU1, MROH7, MRPL34, MSMB, MSRB1, MST1L, MUC3A, NABP2, NDUFB2, NDUFB7, NEUROD4, NF2, NFYA, NHP2, NIPAL3, NKX3-1, NOC2L, NOL3, NOLC1, NPAS1, NQO1, NUBP2, NUCB1, OXCT2, PAFAH2, PAM16, PCDHGB6, PCYT1B, PEA15, PEPD, PEX19, PFDN1, PHTF1, PIGO, PLA2G2D, PLIN3, PLK1, PLOD3, PNMA2, POLE, POLR2L, PPIC, PPPIR14B, PPP2R3A, PPP5C, PRKCD, PRR5, PSEN2, PSENEN, PSMD3, PSMD5, PTBP1, PTGES2, PTP4A3, PTPN12, PTPN18, PTPN9, PYGB, RAB5A, RAC1, RANGAP1, RASGRF1, RBM12B, REC8, RITA1, RNF130, RRP9, RSPH6A, RXRA, SAMD14, SAP30, SARS, SARS2, SCAMP3, SEC24C, SGTA, SIGLEC6, SIVA1, SLC12A8, SLC16A6, SLC1A5, SLC35C1, SLC4A10, SLC52A2, SLC6A2, SPAG1IA, SPN, STXBP6, STYXL1, SUMO2, SYP, TADA2A, TARBP2, TCEAI, TCF25, TDRD12, TEX261, THAP3, THOC5, TIMM10, TKT, TMEM223, TMEM230, TOMM22, TOR3A, TOX4, TRIP6, TSFM, UBE2N, UBE2NL, UBE2Q1, UPF1, VAC14, VARS, VAV1, VCX2, VPREB1, WDR18, WDR62, WTAP, YIPF2, ZNF282, ZNF609 |

TABLE 8-continued

Genes in modules identified via Gene Ontology (GO) analysis

| Cell Type | Module Name | Genes |
|---|---|---|
| CD19 | Steel blue | ABCF1, ADI1, ADSL, AHCY, ALDOA, AP3D1, ATF4, ATF5, ATPIA1, ATP2C1, B4GALT5, BCKDK, BCL2L11, BID, C12orf43, C21orf59, C4orf27, CCDC86, CCT3, CCT7, CD58, CDK7, CHST11, CKLF, CLP1, COG7, COPA, CYTIP, DAP, DDX39A, DENND3, DYNLRB1, ECHS1, EDF1, EIF2B4, EIF3I, ELAC2, ENO1, ERGIC3, FAF2, FASN, FASTKD5, FTSJ1, GALNT2, GAPDH, GCN1L1, GLO1, GPAA1, GPI, GPN1, GSS, GSTO1, GSTZ1, GTPBP4, GUK1, HNRNPC, IMMT, IMP4, IPO4, IRAK1, KARS, LAGE3, LCMT1, LRP8, LRPAPI, LSM4, MAD2L1BP, MAGED1, MAPKAP1, MCM5, MCM7, MCOLN1, MECR, MIF, MPHOSPH10, MRPL11, MTMR12, NCL, NDUFS2, NDUFV2, NOL7, NQO2, NRD1, NUDC, NUDT1, NUDT15, NUP205, NUP93, ODC1, PA2G4, PARP4, PCK2, PGAM1, PGK1, PIGT, POLD3, POLDIP2, PPIH, PPP1R7, PSMA1, PSMB3, PSMB4, PSMC5, PSMD2, PSMD4, PUS3, RGCC, RHOB, RNF114, RPP30, SDF4, SF3B2, SKP2, SLC2A5, SLC38A2, SLC39A8, SLC3A2, SLC43A3, SLCO4A1, SOD1, SPTLC2, SSR2, SSRP1, ST6GALNAC4, TACO1, TBCID15, TCEB3, TDRD7, TIMM44, TNPO3, TRAP1, TSSC1, TTLL12, TUBA1B, TUBA1C, TUBB, TUBB3, TUBB4B, TUFM, UBL4A, VDAC2, WARS, WDR45, XRCC6, YBX1, ZNF410 |
| CD19 | Turquoise | AARS, AASDHPPT, ACADM, ACATI, ACSL4, ACTR2, ACVR1, ADAM10, ADSS, AKAP1, ALG5, ALG6, AMD1, ANKRD12, ANKRD17, ANKRD36, ANP32B, ANP32E, ANXA5, ANXA7, API5, APOBEC3B, ARF4, ARFGAP3, ARHGAP6, ARHGEF12, ARID3A, ARL1, ARL4C, ARL5A, ARL6IP1, ARMC1, ARMCX3, ARPP19, ASNS, ATG5, ATP2A2, ATP6AP2, ATXN1, AZIN1, B3GNT2, B4GALT3, BAG2, BARD1, BBIP1, BBS7, BCKDHB, BECN1, BIK, BRCC3, BTN1A1, BUB3, BZW1, C1D, C1orf27, C1QBP, C2orf43, C6orf62, CAAP1, CANX, CAPN2, CAPN7, CAPRIN1, CAPZA2, CASP10, CASP3, CBFB, CBX3, CBX6, CCNB1, CCNC, CCP110, CD164, CD27, CD38, CD59, CD86, CDC27, CDC42, CDK14, CDK17, CDK2AP2, CDV3, CENPQ, CENPU, CEP57, CEP97, CHST12, CHST15, CHUK, CITED2, CKAP4, CLASP2, CLCC1, CLDND1, CLINT1, CMAHP, CNKSR1, COBLL1, COL13A1, COPB1, COPG1, CORO1C, CPOX, CREB3L2, CRIP1, CSF2RB, CSNK1G3, CSPP1, CTBP1, CTBS, CUL2, CUL4B, CYB5B, DAAM1I, DAD1, DAPK1, DCTD, DCTN4, DCTN5, DDOST, DDX18, DDX3X, DENND1B, DENND5B, DERL1, DERL2, DMC1, DNAAF2, DNAJA2, DNAJB9, DNAJC10, DNM1L, DNMT3B, DSTN, DUSP5, EBAG9, ECHDC1, EDEM1, EDEM3, EED, EGLN1, EID1, EIF1AX, EIF3A, EIF3J, EIF4E, EIF5, ELL2, ENPP3, ENTPD1, EPHA4, EPRS, ERAP1, ETFA, ETNK1, ETS1, EXOC5, EZH2, FAIM, FAM114A1, FAM129A, FAM46C, FBXO46, FBXW7, FDX1, FEM1B, FEM1C, FKBP11, FLI1, FNDC3A, FNDC3B, FPGT, FUBP3, FUT6, FUT8, FXR1, G3BP2, GALK2, GALNTI, GALNT3, GBAS, GCLC, GDI2, GFPTI, GGH, GHITM, GLDC, GLE1, GLG1, GLS, GLUD1, GLUD2, GOLPH3, GOLTIB, GPNMB, GPR15, GPRC5D, GPX7, GSN, GSPT1, GUSBP11, H2AFY, HCFC2, HERPUD1, HIBCH, HIF1AN, HIGD1A, HIRA, HMGB2, HMGCR, HN1, HNRNPR, HNRNPU, HRASLS2, HS2ST1, HSD17B8, HSP90B1, HSPA13, HSPA4, HSPA5, HSPA9, HSPH1, HYOU1, IDH3A, IFT52, IGKC, IGLC1, IGLJ3, IGLV1-44, IKZF5, IL12B, IL6R, ILF2, ILF3, IMPA1, INSIG1, IPO5, IPO7, IQCB1, IQCG, IQGAP1, IQGAP2, IRF4, ISCA1, ISOC1, ITGA4, ITM2A, ITM2C, IVD, JUN, KCNJ13, KCTD3, KDELR2, KDM5A, KDM6A, KIAA0101, KIF11, KLF10, KRR1, L2HGDH, LARP4, LAX1, LIMS1, LIN7C, LINS, LITAF, LMAN1, LMAN2, LMO4, LTN1, LYPLA1, M6PR, MAD2L1, MANIA1, MANIA2, MAN2A1, MANEA, MANF, MAP2K6, MAP4K3, MAPRE1, MARCH7, MBNL2, ME2, MED13L, MED17, MFN1, MGAT2, MGLL, MLEC, MLLT10, MLX, MOB1A, MORF4L1, MORF4L2, MRPL35, MTDH, MTF2, MTHFD2, MYO1D, MZB1, NAA50, NABI, NAGA, NANS, NBR1, NCOA3, NFE2L2, NFIL3, NFX1, NMD3, NNT, NONO, NRAS, NT5DC2, NUCB2, NUDT4, NUP50, NUP98, NUS1P3, NUSAP1, NXPE3, OAT, OGT, ORC2, OSBPL3, OSBPL9, OXR1, P4HB, PABPC4, PAPOLA, PAPSS1, PAQR3, PARM1, PDIA3, PDIA4, PDIA5, PDIA6, PDLIM5, PEBP1, PELI1, PERP, PGPEP1, PHF7, PHYH, PIAS2, PICALM, PIGK, PLA2G16, PLEKHA6, PLK2, POTEKP, POU2AF1, POU4F1, PPCDC, PPIB, PPP1CB, PPPIR2, PPP3R1, PRDX3, PRDX4, PREB, PRKAG2, PRKAR1A, PRKCI, PROSC, PRPS1, PSEN1, PSMD13, PTGES3, PTP4A1, PTP4A2, PTPN11, PTPN22, PYCR1, RAB1A, RACGAP1, RAD17, RAD23B, RAP2B, RB1CC1, RBBP4, RBM3, RBM47, RCBTB2, RCN2, RDX, RECQL, REEP5, RHOA, RHOQ, RIF1, RIPK1, RNF115, RNF19A, RNPEP, ROCK1, ROCK2, RPA1, RPL36AL, RPN1, RPN2, RPRD1A, RRM2, RSRC2, RTN3, RUFY3, S100A10, SAMSN1, SCARB2, SCYL2, SEC11A, SEC14L1, SEC22B, SEC23A, SEC24A, SEC24D, SEC31A, SEC61A1, SEC61B, SEC61G, SEC63, SEL1L3, SELT, SEMA4A, SEPT2, SERBP1, SERP1, SGK1, SGPP1, SHCBP1, SLAMF7, SLC1A4, SLC25A17, SLC25A46, SLC30A5, SLC33A1, SLC35A3, SLC35B1, SLC39A6, SLC7A1, SLMO2, SMARCCI, SMC4, SMCHD1, SND1, SNX13, SNX4, SORT1, SP3, SPAG1, SPATS2, SPCS1, SPCS2, SPCS3, SPOP, SPTLC1, SPTSSA, SRGN, SRI, SRP54, SRP72, SRPK1, SRSF1, SRSF3, SS18, SSB, SSR1, SSR4, STEAP3, STK38L, STRN3, STT3A, SUB1, SUCLG2, SUMO1, SUMO4, TAF2, TES, TESC, TFAM, TFB2M, TFCP2, TFDP1, TFRC, TGDS, TLK2, TM9SF1, TM9SF2, TMBIM6, TMED10, TMED2, TMED3, TMED5, TMEM135, TMEM165, TMEM208, TMEM39A, TMEM50B, TMEM57, TMX1, TOMM70A, TOPORS, TOR1A, TOR1AIP1, TOX, TP5313, TP63, TPD52, TPP2, TRA2A, TRAMI, TRAM2, TRIB1, TRIM23, TRRAP, TSPAN31, TTC37, TUBGCP3, TWSGI, TXNDC15, TXNRD2, TYMS, U2SURP, UAPI, UBA5, UBA6, UBE2A, UBE2E1, UBE2G1, UBE2J1, UBE3A, UBE4B, UBR5, UBXN4, UCHL5, UFL1, UFM1, UGDH, URI1, USO1, USP46, USP8, VAMP3, VCP, VDAC1, VDR, VIM, VOPP1, VWA9, WDR44, WDYHV1, WIPF1, WIPI1, XAF1, XBP1, XPNPEP1, XPOT, YAF2, YIPF5, YIPF6, YTHDF2, YWHAE, YWHAH, ZBP1, ZBTB32, ZC3H13, ZDHHC13, ZFAND1, ZFR, ZNF706 |
| CD19 | Violet | ABCE1, ACAA2, ACN9, ACOT13, ACP1, ACSL1, ADAR, AGA, AGPAT4, AIFM1, AIMP2, ALG8, ALG9, ALKBHI, ANAPC5, ANXA2, ANXA2P1, ANXA2P2, APOL3, ARMCX5, ARPC5L, ASAH1, ASCC3, ASUN, ATG3, ATIC, ATP13A3, ATP1B1, ATP5A1, ATP5E, ATP5L, ATP6V1A, ATP6V1C1, AVEN, AZI2, B4GALT4, BAG1, BAK1, BLVRA, BLZF1, BORA, BPGM, BRCA1, BTG3, BZW2, C11orf48, C11orf58, C11orf73, C12orf4, C14orf166, C14orf2, C16orf62, CIGALT1, C2orf47, CACYBP, CAND1, CARS, CASPI, CASP6, CASP7, CBR1, CBX5, CCBL2, |

TABLE 8-continued

Genes in modules identified via Gene Ontology (GO) analysis

| Cell Type | Module Name | Genes |
|---|---|---|
| | | CCDC53, CCDC88C, CCNH, CCR1, CCT2, CCT4, CCT6A, CCT8, CD2AP, CDC123, CDC25B, CDC37L1, CDC5L, CDC73, CDK12, CDK2AP1, CDKN1A, CDR2, CEBPG, CEP63, CEP76, CERS6, CETN2, CHCHD3, CHMP2A, CHMP5, CIAPIN1, CKS1B, CKS2, CLCN3, CLEC2D, CLN5, CLTA, CMC2, CNIH4, CNOT6, COA3, COL9A3, COMMD3, COPS2, COPS3, COPS4, COPS6, COPS8, COX17, COX5A, COX5B, COX6C, COX7A2, CPSF6, CRIPT, CSE1L, CSTF2, CSTF3, CTPS1, CYCS, CYP11B1, DBF4, DBI, DCAF17, DCTN6, DDRGK1, DDX1, DDX10, DDX24, DDX46, DDX49, DDX60, DERA, DHRS9, DHX15, DHX29, DIABLO, DIMT1, DLAT, DLD, DLEU2, DNAJA1, DNAJC2, DNAJC9, DPM1, DR1, DRG1, DUT, DYNLT1, E2F3, EHD4, EI24, EIF2AK2, EIF2B1, EIF2B2, EIF2B3, EIF2S2, EIF4E2, EIF5B, EMC3, EMC7, EMC8, ENOPH1, ENOSF1, ENY2, ETF1, ETFDH, EXOSC2, EXOSC9, FABP5, FAHD2A, FAM206A, FAM49A, FARS2, FASTKD2, FASTKD3, FBXO5, FECH, FEN1, FGFRIOP, FGL2, FH, FOCAD, FOXK2, GALC, GBP1, GEMIN2, GIGYF2, GLA, GLMN, GLRX3, GLT8D1, GMNN, GNG5, GOLGA5, GPKOW, GPR137B, GRPELI, GRSF1, GTF2E2, GTF2H2, GTF3C3, GUSB, GYG1, H2AFZ, HADH, HADHB, HARS, HATI, HCCS, HDAC2, HDHD1, HEATRI, HEATR3, HEG1, HERC5, HERC6, HIST1H2BH, HMGXB4, HNRNPD, HPRT1, HRSP12, HSD17B12, HSP90AA1, HSPA14, HSPB11, HSPE1, HYPK, ICT1, IFI27, IFI35, IFI44, IFI44L, IFI6, IFIH1, IFIT1, IFIT3, IFIT5, IFITM1, IFT27, INPP1, INTS12, INTS6, INTS7, ISG15, ISG20, ITFG1, ITGB1BP1, ITGB3BP, JAK2, JMJD6, KEAP1, KIAA0020, KIAA0196, KIAA1279, KIF20B, KLC1, KLF12, KLHL7, KPNA2, LAMP2, LAMTOR2, LCP2, LGALS8, LSM3, LSM5, MAP2K4, MAPK1IP1L, MBIP, MCM2, MCM3, MCTS1, MCURI, MED27, MED6, MED8, METAP2, METTL22, METTL5, MICB, MIEF1, MLH1, MOSPD1, MPC1, MPC2, MPHOSPH9, MPP6, MRPL13, MRPL17, MRPL18, MRPL19, MRPL20, MRPL22, MRPL46, MRPL48, MRPL57, MRPS14, MRPS15, MRPS18A, MRPS22, MRPS27, MRPS31, MRPS33, MRPS35, MSH2, MSH6, MTIX, MTAP, MTCH2, MTHFD1, MTX2, MX1, MX2, MYO5A, NAMPT, NARS, NARS2, NCAPD2, NCBP1, NDC80, NDUFA8, NDUFAF1, NDUFAF4, NDUFB1, NDUFB3, NDUFB4, NDUFB5, NDUFB6, NDUFC1, NDUFS1, NDUFS3, NDUFS4, NDUFS5, NDUFS6, NECAP1, NFYB, NIF3L1, NINJ2, NMI, NMT1, NOD2, NPTN, NTAN1, NUP153, NUP37, NUPL1, OASI, OAS2, OAS3, OASL, OGFOD3, ORC5, OXCT1, PAAF1, PAIP1, PARK7, PAXIP1, PCMT1, PCNA, PCNX, PDCD2, PDCD5, PDHA1, PDHB, PDHX, PDS5B, PDXDC1, PELO, PFDN6, PI4K2A, PIGF, PIK3CG, PIP4K2C, PLAA, PLIN2, PLSCR1, POLE3, POLR2K, POP4, POP5, PPA2, PPID, PPM1G, PPP1CC, PPP2CB, PPP2R5C, PPT1, PRDX6, PRPF18, PRPF4, PSMA3, PSMA4, PSMB7, PSMB9, PSMC2, PSMC3IP, PSMD1, PSMD6, PSMD7, PSME1, PSMG1, PSPH, PSRC1, PTENP1, PTPN2, PTRH2, PTS, PTTG1, QDPR, QKI, RAB22A, RAB40B, RAB7A, RABEPK, RAD51API, RAD51C, RAEI, RAN, RANBP9, RBBP8, RBCK1, RBM15, RBMX2, RBX1, RCN1, RFC2, RFC3, RFC4, RHEB, RIOK2, RMDN1, RMDN3, RNF103, RNF11, RPA3, RPF1, RPL26L1, RPP40, RPS27L, RPS6KB1, RPS6KC1, RSAD2, RTF1, RTP4, RUVBL2, RWDD1, RWDD2B, SAC3D1, SAMD9, SAR1A, SAT1, SCAM1, SCFDI, SCO2, SCP2, SDHC, SEC23B, SHFM1, SLAMF1, SLC20A1, SLC25A12, SLC25A20, SLC30A9, SLC35F2, SLFN12, SMAD2, SMAP1, SMARCA4, SMARCA5, SMC3, SMCO4, SNAP29, SNF8, SNRPB2, SNRPD3, SNRPE, SOAT1, SOS1, SPATA5L1, SPATS2L, SQLE, SQRDL, SRBD1, SRP19, SRR, SSBP1, STAG1, STAT1, STAU1, STK17B, STMN1, STOM, STOML2, STX18, SUCLG1, SYNCRIP, SYT11, TAF1B, TAF5, TAF9, TALDO1, TAPI, TARS, TBCID31, TBCA, TBX21, TCEB1, TCTN3, TEX30, TFG, THG1L, THOC7, TIMM17A, TIMM23, TIMM9, TLE4, TMCO1, TMEM126B, TMEM70, TNFSF10, TPM4, TPRKB, TRDMT1, TRIM14, TRIM26, TSC22D1, TSG101, TSN, TTC1, TTF2, TUBG1, TWF1, TXN, TXNL1, TXNRD1, UBAC1, UBAP2, UBE2B, UBE2K, UBE2L6, UBE2V2, UBE3C, UBXN8, UCHL3, UFC1, UFSP2, UMPS, UQCC1, UQCR10, UQCRB, UQCRC2, USP10, USP16, USP18, UTP11L, UTP18, VDAC3, VRK2, VTI1B, WDR61, WSB2, YIPF1, YME1L1, YWHAQ, ZC3H15, ZDHHC4, ZFYVE21 |
| CD19 | Brown | ABCA1, ABCC5, ABCG1, ABI1, ACAP2, ACSL3, ACYP1, ADAM17, ADARB1, ADAT1, ADD3, ADRBK2, AGL, AGPAT5, AHCYL1, AHNAK, AIDA, AIM1, AIMP1, AKAP11, AKAP9, ALCAM, ALDH1L1, ALMS1, ALPK1, AMMECR1, ANK3, ANKRA2, ANKRD10, ANKRD10-IT1, ANKRD36B, ANXA11, AP1AR, APAF1, APOOL, APP, APPBP2, APPL1, ARFGEF2, ARGLU1, ARHGAP10, ARHGAP12, ARHGAP26, ARHGAP5, ARHGEF18, ARHGEF6, ARID1A, ARID4B, ARNT, ARNTL, ARPC1B, ASAP1, ASPH, ATAD2B, ATF7IP, ATF7IP2, ATP10D, ATP2B1, ATP8A1, ATP8B1, ATRX, ATXN10, ATXN7, AVIL, BACE2, BANK1, BAZ2B, BBS10, BICD2, BIRC3, BLCAP, BLNK, BMP2K, BRD4, BTBD1, BTN2A2, C11orf21, C11orf80, C18orf8, C5orf28, C9orf156, C9orf91, CA5B, CALCOCO1, CAPN3, CASP8AP2, CAT, CBFA2T3, CBR4, CCNG2, CCNT2, CCR6, CCSER2, CD180, CD1C, CD24, CD46, CD47, CDC40, CDC42EP3, CDK13, CEP104, CEP135, CEP83, CHD1, CHD9, CIAO1, CIR1, CLCN4, CLEC4A, CNNM3, CNOT8, COIL, COL5A3, CRI, CR2, CRBN, CREB1, CREBZF, CRK, CRY2, CRYL1, CSAD, CSNK1A1, CTAGE5, CTNNB1, CTSS, CWC25, CXorf21, CYBB, CYP2E1, DAPP1, DBT, DCK, DCLRE1C, DCP2, DCUN1D2, DCUN1D4, DDX52, DENND4A, DIAPH2, DIP2A, DIS3, DKFZP586I1420, DLG1, DLGAP4, DNAJB14, DNAJC16, DOPEY2, DSCR3, DSE, DSERG1, DSP, DUS2, DUSP22, DYM, DZANK1, E2F5, EAPP, EFR3A, EGR3, EIF3M, EIF4G3, ELOVL5, ENTPD4, EPS15, ERBB2IP, ERP44, ETAA1, EVI5, EXOSC5, EXOSC7, FAM134A, FAM13B, FAM178A, FAM179B, FAM192A, FAM49B, FAM53C, FAM63B, FAM65B, FBXO28, FBXO3, FBXO41, FBXO42, FBXW12, FCGR2B, FCGR2C, FCRL2, FGFR1, FKBP9, FLJ42627, FMR1, FOXN3, FRAT1, FUBP1, GALNT10, GALNT7, GATAD1, GFOD1, GLIPR1, GNE, GNG7, GOLGA4, GPATCH8, GPR153, GPR18, GPR183, GSTA4, GTF2H3, HAUS2, HCG26, HCK, HDAC4, HDAC9, HECTD4, HERC4, HEXA, HEXIM1, HMG20A, HMGN4, HNRNPH1, HNRNPM, HRK, ICK, IDO1, IFNGR1, IGHV5-78, IKZF1, IL13RA1, IL15, IL6, IL7, INADL, INPP5B, IRAK4, IRGQ, ITPRI, ITSN2, JADE3, JAG2, JRKL, KAT2B, KCNMB3, KDM3B, KDM4C, KIAA0040, KIAA0355, KIAA0754, KIAA1033, KIAA1109, KIAA1551, KIF16B, KLHL20, KLHL24, KMO, KMT2A, KPNA1, KPNB1, KRCC1, KRIT1, LANCL1, LAPTM4A, LARP4B, LARS, LBH, LEMD3, LIAS, LINC00597, LOC100272216, LOC100505915, |

TABLE 8-continued

| Genes in modules identified via Gene Ontology (GO) analysis | | |
|---|---|---|
| Cell Type | Module Name | Genes |
| | | LOC157562, LOC728093, LONRF1, LPGAT1, LPP, LRRFIP1, LRRFIP2, LSM14A, LUC7L3, LYN, LZTFL1, MACF1, MALT1, MAP3K5, MAP3K7, MAP3K8, MAP4, MAP4K5, MARCH1, MARCH3, MARCH6, MARCKS, MAT2B, MAVS, MBD4, MED14, MEF2A, MEF2C, METAP1, METTL3, METTL4, METTL8, MEX3C, MFSD11, MGC12488, MGEA5, MINOS1P1, MOB3B, MPZL1, MR1, MRPS30, MSANTD2, MSL2, MSL3, MTMR4, MVK, MYO1C, MYO1F, MZT2B, N4BP2L1, N4BP2L2, N4BP2L2-IT2, NAA40, NAAA, NACAP1, NCOR1, NDRG2, NDUFAF7, NEMF, NFATC2IP, NFYC, NHLRC2, NOTCH2, NOTCH2NL, NPEPPS, NR2C1, NRCAM, NSFLIC, NUP43, OPN3, OSBPL10, OSBPL8, OSGEP, OSGEPL1, OTUD4, P2RY10, PAIP2B, PARP12, PAXBP1, PCF11, PCMTD2, PDCD6, PDCL, PDLIM1, PDS5A, PEX12, PFKM, PGF, PHF2, PHF20, PHKB, PHLDA1, PHTF2, PIAS1, PIKFYVE, PITPNA, PKN2, PKNOX1, PLA2G4C, PLAGI, PLAGL1, PLEKHF2, PLEKHM1, PODNL1, POGZ, POLRIB, PPAP2A, PPFIA1, PPIP5K1, PPPIR12A, PPP3CA, PPP6R3, PRDM10, PRDX2, PREPL, PRKAA1I, PRKACB, PRKAR2A, PRKD3, PRPF39, PRPF4B, PRR11, PRRC2C, PSME4, PSMF1, PTBP2, PTEN, PTGER4, PTK2, PTPN6, PTPRC, PTPRK, PUM1, PYROXD1, QRSL1, RAB1IFIP2, RAB14, RAB3GAP1, RABGAPI, RABGAPIL, RAD52, RALB, RALGAPAI, RALGAPB, RALGPS1, RALGPS2, RAP2C, RBL2, RBM25, RBM39, RBM48, RBM5, RBMS1, REL, REPS1, REST, RFWD3, RFX5, RFX7, RGP1, RIOK3, RNF219, RNF38, RPL28, RPS15A, RPS6KA5, RRAS2, RREB1, RSF1, RSRP1, RUFY2, RUNX1-1T1, SACS, SCAF4, SCRNI, SDCCAG3, SEC24B, SECISBP2, SECISBP2L, SEH1L, SERGEF, SETBP1, SFTPB, SH3BP5, SHMT2, SHOC2, SIAH1, SIRT5, SKAP2, SLC15A2, SLC25A24, SLC2A3, SLC2A6, SLC35D2, SLC35E1, SLC35E3, SLC38A6, SLC46A3, SLC4A7, SLK, SMA4, SMARCA2, SMC6, SMYD2, SNAP23, SNAPC3, SND1-IT1, SNX10, SNX3, SPAG16, SPG11, SPG21, SPIDR, SPTBN1, SRPK2, SRSF11, ST13, ST8SIA4, STAP1I, STEAP1, STK38, STRN, STX7, SUNI, SUPT20H, SUV420H1, SWAP70, SYK, SYNRG, TAB2, TAF9B, TANK, TAOK1, TARBP1, TASP1, TBCID5, TBCID9, TCF12, TCF4, TCL1B, THAP9-AS1, THOC1, TIA1, TIPRL, TLK1, TM2D1, TMBIM4, TMCC2, TMEM168, TMEM212, TMEM41B, TMEM63A, TMEM9B, TNFAIP8, TNFRSF10C, TNKS2, TOB2, TPR, TRAPPC2, TRIB2, TRIM38, TRIM52, TRIO, TRMT13, TSC22D2, TSNAX, TSPAN13, TSPAN3, TSPYL1, TSPYL4, TSPYL5, TSR1, TTC13, TTN, TTR, UBE2D4, UBE3B, UBP1, UBQLN4, UBXN7, USP15, USP22, USP33, USP34, USP4, USP47, USP6, USP6NL, USP9X, UST, UTP6, UTRN, UVRAG, VAV3, VPS13A, VPS13B, VPS13C, WAPAL, WDR11, WDR60, WDR77, WDR82, WNK1, WWC3, WWOX, XIST, YTHDC2, YWHAB, ZBED2, ZBTB1, ZBTB20, ZBTB24, ZC3H7B, ZCCHC11, ZFC3H1, ZFX, ZKSCAN7, ZMYM6, ZMYND11, ZNF107, ZNF142, ZNF146, ZNF154, ZNF160, ZNF26, ZNF273, ZNF280D, ZNF33B, ZNF354A, ZNF43, ZNF468, ZNF506, ZNF510, ZNF518A, ZNF529, ZNF532, ZNF562, ZNF573, ZNF587, ZNF611, ZNF665, ZNF669, ZNF675, ZNF701, ZNF721, ZNF75D, ZNF764, ZNF85, ZNHIT6 |
| CD19 | Green | ABCB7, ABHD10, ABHD6, ACAA1, ACO1, ACTR3B, ACYP2, ADD2, ADIPOR2, ADK, ADO, ADPGK, ADPRM, ADRB2, AGO1, AGO4, AKAP10, AMIGO2, ANGEL2, ANKH, ANKRD26, ANKRD27, ANKRD6, AP4S1, APC, AQR, ARFGEF1, ARHGAP19, ARHGAP24, ARHGAP32, ARHGEF10, ARHGEF5, ARHGEF9, ARIH1, ARL8B, ARMCX2, ATG12, ATG7, ATP5S, ATP6VOE1, ATP6V1H, ATP7A, ATP9B, ATRN, AVL9, BAG5, BBS4, BBS9, BDH2, BPHL, BRE, BRWD1, BTBD3, BTBD7, C10orf2, C11orf30, C11orf95, C1orf109, C2CD2, C2orf42, C2orf44, C9orf78, CACFD1, CALCOCO2, CAMSAP1, CARKD, CARS2, CASP4, CBX1, CCDC25, CCDC28A, CDC16, CDYL, CELSR1, CENPI, CEP162, CEPTI, CFAP44, CFDP1, CGRRF1 CHD1L, CLNS1A, CNTNAP2, COA1, COQ7, COX11, COX7C, CPQ, CRCP, CREBL2, CRKL, CROT, CRYBG3, CRYZL1, CTNS, CTR9, CTSK, CUL3, CUL4A, CUZD1, CXorf57, CYP2C8, DAPK2, DAZAP2, DAZL, DCLK2, DDX27, DDX28, DDX42, DEGS1, DENND2D, DFNA5, DHX40, DHX57, DIEXF, DLG3, DNAJA3, DNAJC8, DNASE1L1, DOPEY1, DPF2, DPH5, DPP8, DST, DUS4L, DYNCIH1, EBLN2, EIF2B5, ENAH, ENTPD1-AS1, EPM2A, EPM2AIP1, ERCC3, ERCC5, EXOCI, EXOC2, EXT2, FAM149B1, FAM172A, FAM50A, FAM50B, FAN1, FANCF, FBXL14, FBXL4, FEZ2, FGGY, FHL1, FIG4, FKTN, FMO5, FNBP1L, FNTA, FOXJ3, FRAT2, FTH1, FTSJ3, GALNT11, GAPVD1, GAS2, GCC1, GCNT1, GGNBP2, GIN1, GLTSCR1L, GNG11, GNL3L, GNPAT, GOLGA1, GPATCH1, GPM6A, GPM6B, GPR65, GSTA1, HARS2, HAUS5, HCP5, HDDC2, HEATR6, HEMK1, HILPDA, HLCS, HMGCS1, HN1L, HNRNPH3, HOMER1, HPS1, HPS4, HS3ST1, HSD17B7, HSDL2, IDI1, IFFO1, IFNAR1, IFT74, IL18, IL24, IL27RA, IMPA2, ING1, INTS9, INVS, IP6K2, IRAK3, ITGAE, ITGB5, ITPR2, IVNSIABP, JAM3, KANSL2, KATNA1, KCTD2, KIAA0586, KIAA0753, KIDINS220, KIZ, KLF3-AS1, KLHDC10, KRT18, KYNU, L3MBTL1, LAMP1, LARGE, LARS2, LASP1, LCMT2, LEP, LETM1, LGR4, LINC00667, LMO2, LOC100129361, LOC389906, LPCAT3, LRRC1, LRRC47, LRRC8B, LSG1, LUC7L, LYRMI, MAEA, MAGEF1, MAMLD1, MAP2K1, MAP2K7, MAP3K7CL, MAP3K9, MAPK14, MARS, MAT2A, MCCC1, MCF2L, MDC1, METTL13, MICALL1, MID1, MIPEP, MKRN2, MLH3, MORC4, MPPE1, MPPED2, MRFAPIL1, MRS2, MTERF1, MTMR2, MTMR3, MTOR, MTRF1, MTUS1, MYBL1, MYH3, MYOIB, MYOIE, MYOMI, NACA, NAIP, NBEA, NCBP2, NCKAP1L, NFS1, NHP2L1, NIPBL, NKRF, NOP14-AS1, NPAT, NPC1, NPFF, NSMAF, NSMCE4A, NUBP1, NUDCD3, NUDT13, NUP160, OARD1, OCRL, OPAI, OR10H1, OSBPL2, OVGP1, PAPD7, PCM1, PCYT1A, PDCD11, PDZD8, PEX3, PEX5, PFAS, PHACTRI, PHF3, PHIP, PIAS3, PIAS4, PIGB, PIGV, PJA1, PLCXD1, PLEKHA8P1, POL1, POLR1C, POLR2J4, PON2, POU2F1, PPARD, PPARGCIA, PPCS, PPFIBP2, PPM1B, PPPIR12B, PRPF6, PRPSAP1, PRR5L, PSPC1, PTCD3, PTPRN2, PUM2, PUS1, QTRTD1, RAB9A, RABEPI, RBM41, REPS2, REV1, RFPL3S, RGS7, RHOH, RMND5B, RNASEH2B, RNFT2, RNMT, RPA4, RPL10L, RPL23AP32, RPL37, RPL37A, RPP38, RPS6KA2, RRAGB, RRN3P1, RRP12, RSLID1, RTN1, RUFY1, RWDD3, SAMM50, SAYSD1, SCAF8, SCAPER, SCD, SCN2B, SCRIB, SDHAF1, SEC14L1P1, SEC16A, SEC22A, SEC62, SEMA3F, SEPHS2, SEPT7, SERPINB6, SETD4, SETX, SF3B3, SIK2, SLA, SLC24A1, SLC25A13, SLC25A37, SLC25A38, SLC36A1, SMARCAL1, SMEK2, SMIM14, SNAPC4, SNRNP200, SNRNP35, SNX5, SOBP, SON, SP140, SPATA2, SPRY1, SRD5A1, SS18L1, ST3GAL6, ST6GAL1, STK17A, STRADA, STX12, STX2, SUPT16H, |

TABLE 8-continued

| Cell Type | Module Name | Genes |
|---|---|---|
| Genes in modules identified via Gene Ontology (GO) analysis | | |
| | | SUPT7L, SYF2, SYT17, TACC1, TBCC, TBL1X, TBRG4, TBX19, TBXA2R, TCEAL1, TCEAL4, TCF7L2, TCL6, TDRD3, TECPR2, THNSL2, THOC2, TIMM22, TIMM8A, TJAP1, TLDC1, TLE1, TLR1, TM6SF1, TMA7, TMEM127, TMEM186, TMEM231, TMEM251, TMEM62, TNFSF4, TOMM20, TOMM34, TOP2B, TOPORS-AS1, TP53TG1, TPH1, TPST1, TPT1P8, TRAF3IP3, TRAK2, TREML2, TRIM32, TSEN2, TTC19, TTLL5, TUBBP5, UBAP2L, UBE2D2, UBE4A, UCN, UGT2B28, UIMC1, UNC119B, UPF3A, URB2, URGCP, UROD, USPL1, VCL, VIPAS39, VPRBP, VPS26A, VPS33B, VPS37C, VPS41, WBPIL, WDR48, WDR73, WRAP73, WWP2, XPA, XYLT2, YARS2, YLPM1, YPEL1, YWHAZ, ZBTB3, ZCCHC24, ZCWPW1, ZFYVE26, ZHX3, ZKSCAN4, ZMYMI, ZMYND8, ZNF10, ZNF112, ZNF133, ZNF135, ZNF140, ZNF16, ZNF165, ZNF180, ZNF189, ZNF200, ZNF202, ZNF213-AS1, ZNF223, ZNF224, ZNF225, ZNF227, ZNF23, ZNF236, ZNF239, ZNF254, ZNF271, ZNF337, ZNF350, ZNF394, ZNF415, ZNF432, ZNF45, ZNF473, ZNF493, ZNF516, ZNF544, ZNF571, ZNF587B, ZNF614, ZNF623, ZNF638, ZNF671, ZNF696, ZNF7, ZNF710, ZNF74, ZNF813, ZNF93, ZSCAN26, ZSCAN9 |
| CD19 | Sky blue | ABAT, ABCA11P, ABCB4, ABCD4, ABLIM1, ACACB, ACSL5, ACTR5, ADAM28, ADAP2, ADCK2, ADCK3, ADCY7, ADD1, ADNP2, AEBP1, AGBL2, AHCYL2, AKAP8, AKR7A2, AKT3, ALAD, ALDH2, ALG13, ALOX5, AMPD3, AMT, ANKEF1, ANKMY1, ANKRD11, ANKRD49, ANKZF1, AP1S2, AP2A2, APLP2, APPL2, ARAP2, ARHGAP15, ARHGAP17, ARHGAP25, ARHGEF7, ARID5B, ARIH2, ARL4A, ARL6IP5, ASB1, ASB13, ASMTL, ASTEI, ASXL1, ATG14, ATG4B, ATM, ATXN7L3B, AUTS2, B3GALT4, B3GNTLI, BACH2, BANP, BCL2, BCL6, BCLAF1, BCORL1, BEND5, BEX4, BIN1, BNIP3L, BPTF, BRD1, BRD3, BTAF1, BTG1, BTN2A1, C10orf76, C12orf29, C14orf93, C21orf33, C2orf68, C3orf18, C5orf45, C6orf120, CAMLG, CAMTA2, CAPRIN2, CASD1, CAST, CBFA2T2, CBLB, CBLL1, CBR3, CBX7, CCBL1, CCDC101, CCDC109B, CCDC22, CCDC93, CCNB1IP1, CCNG1, CCNI, CCNL1, CCNL2, CCR7, CD1A, CD1D, CD200, CD22, CD244, CD2BP2, CD40, CD55, CD69, CD96, CDC14A, CDK10, CDK19, CDK5RAP1, CDK5RAP3, CDKN1C, CECR7, CELFI, CEP164, CEP170, CEP68, CHCHD7, CHD7, CHI3L2, CHMP1B, CHTOP, CLASRP, CLCN6, CLECIIA, CLK1, CLK4, CLMN, CMPK1, CNBP, CNOT2, CNPPD1, CNTRL, COL4A3, CREBBP, CRELD1, CRLF3, CSDE1, CSRNP2, CTDSP2, CTNNBL1, CTSB, CUX1, CXCR4, CYFIP2, CYHR1, CYLD, DAG1, DCAF10, DCAF8, DDHD2, DDX17, DEK, DENND4C, DEPDC5, DFFB, DGKD, DHRS12, DICER1, DIDO1, DIP2C, DMTF1, DMXL1, DNAJC11, DOK1, DPEP2, DPYD, DSTYK, DVL1, DYNLT3, DYRKIA, DYRK2, ECD, ECHDC2, EEF1A1, EEF1D, EFCAB14, EGRI, EIF1B, EIF3E, EIF3F, EIF3L, EIF4B, ELL3, ENGASE, EP400, EPB41L2, ESD, EVL, EXOC3, EXOSC10, EZH1, FAM111A, FAM134C, FAM160B2, FAM168A, FAM168B, FAM193A, FAM208A, FAM32A, FAM46A, FAM60A, FBXL12, FBXL15, FBXL5, FBXO11, FBXO21, FBXO9, FKBP15, FLJ10038, FNBP1, FNBP4, FOXJ2, FOXO1, FRYL, FUCAI, FYCO1, GABBR1, GCC2, GDPD3, GGA2, GGPS1, GIT2, GLOD4, GMEB2, GMFB, GNA11, GNA12, GNB5, GOLGA7, GOLGA8A, GON4L, GOSR1, GPBPIL1, GPR107, GPRASP1, GRAMD1B, GSAP, GSDMB, GSEI, GSTM4, GTF3C2, GVINP1, H2AFJ, HAGH, HBP1, HEBP1, HECA, HERC1, HFE, HIVEP2, HLA-DQB1, HLA-E, HLA-F, HLA-F-AS1, HNRNPA0, HNRNPA1, HNRNPA3, HNRNPDL, HNRNPL, HPS6, HSBP1, HSD17B11, HSPBAP1, HTATIP2, HTRA2, HUWE1, ICAM3, ID3, IER5, IFT57, IFT88, IKBKB, IL11RA, IL16, IL4R, ING4, INPP5D, IRS2, IST1, ITM2B, JADE1, JADE2, JAK1, JARID2, JMJDIC, JRK, KAT2A, KAT6A, KBTBD2, KCNQ1, KDM2A, KDM3A, KDM4B, KDM5B, KDM7A, KIAA0141, KIAA0226L, KIAA0247, KIAA0430, KIAA0907, KIAA0922, KIAA0930, KIAA1467, KLF11, KLHDC2, KLHL22, KPNA4, KRBOX4, LAIR1, LAMC1, LDOC1, LETMD1, LHFPL2, LIN37, LINC00094, LINC00341, LIPT1, LMAN2L, LMBR1L, LMF1, LOC202181, LOC647070, LOC728392, LPIN2, LRIG1, LRRC37A2, LRRC40, LTA4H, LTB, LY75, LYRM9, LYST, MADD, MAML1, MAN1B1, MAN1C1 MAN2A2, MAN2B2, MANBA, MAP2K5, MAP3K4, MAP4K4, MAPK1, MAPK9, MAPKAPK5-AS1, MAPRE2, MARCH8, MARCKSL1, MAX, MBNL1, MCM3AP, MEAF6, MECP2, MED13, MED23, METRN, METTL17, MGA, MGAT5, MIA3, MICA, MICAL3, MKKS, MKNK1, MKRN1, MLYCD, MOAP1, MPRIP, MTCH1I, MTERF4, MTF1, MTMR1, MTMR9, MYCBP2, MYL12B, MYO9A, MZF1, NADSYN1, NAPIL1, NATI0, NBPF1, NCK2, NCR3, NDRG3, NDST2, NECAP2, NEK7, NEK9, NFATCI, NFATC3, NGRN, NISCH, NKTR, NLRP1, NOD1, NR3C1, NR3C2, NREP, NRF1, NRIP1, NSUN5P1, NT5E, NUP210, NUP214, NUP88, OAZ2, OFD1, OGGI, OSER1, OTUD3, P2RX5, P2RY14, PAFAH1B1, PAN2, PANK4, PAPOLG, PARP6, PARP8, PASK, PATZ1I, PCBP2, PCGF3, PCNT, PCNXL2, PDE8A, PECAM1, PEG10, PFDN5, PGAP3, PGS1, PHC1, PHF11, PHF21A, PHKA2, PHLPP2, PIBF1, PIGA, PIGG, PIK3C2B, PIK3CD, PIK3R1, PIK3R4, PILRB, PIN4, PISD, PKI55, PKIA, PLCL2, PLEKHJ1, PNISR, PNN, PNRC1, POLG2, POLR2G, PPM1F, PPOX, PPP1R16B, PPP6R2, PRDM2, PRDM4, PRKCB, PRKCZ, PRKRIR, PRKX, PRMT2, PRNP, PRPF3, PRRC2B, PRUNE, PSIP1, PTPLB, PTPRE, PTPRO, PTTG1IP, PURA, PWP2, QRICHI, RAB33B, RANBP10, RANBP6, RASA1, RBBP6, RBM10, RBM12, RBM19, RBM4, RBM4B, RBM6, RECK, RGL2, RGS14, RIN3, RLF, RNASET2, RNF111, RNF125, RNF141, RNF41, RPARP-ASI, RPL11, RPL14, RPL18, RPL22, RPL24, RPL27, RPL31, RPL34, RPL35, RPL35A, RPL39, RPL6, RPL7, RPS12, RPS16, RPS17, RPS21, RPS23, RPS25, RPS27A, RPS28, RPS29, RPS3, RPS6, RPS6KA3, RPS7, RRAGA, RRNAD1, RSAD1, RSBN1, RXRB, RYK, S1PR1, SAFB, SAP18, SARAF, SAV1, SC5D, SDCBP, SDR39U1, SEC31B, SELL, SENP6, SEPT6, SERTAD2, SESNI, SET, SETD2, SETDB1, SF3B1, SFPQ, SFSWAP, SGPL1, SH2B3, SH3BGRL, SH3YL1, SIK3, SIN3B, SIRT1, SKP1, SLC23A2, SLC25A36, SLC25A44, SLC37A1, SLC6A16, SLC7A6, SLC9A8, SMAD3, SMARCEL, SMIM7, SNN, SNRK, SNUPN, SNX1, SNX11, SNX2, SNX27, SOCS5, SORL1, SOS2, SP140L, SPECC1L, SPG7, SPSB3, SRRM2, SRSF5, SRSF6, SRSF7, SRSF8, SSBP2, SSH1, ST3GAL1, STAG2, STAT5A, STAT5B, STK19, STK26, STX16, STX4, STX6, SUGP2, SYNE1, SYPL1, TAF1A, TAF1C, TAF1D, TAF7, TAOK3, TARDBP, TAZ, TBC1D13, TBP, TCF3, TCF7, TCTN1, TGFBR2, TGFBRAP1, TGIF1, TGIF2, TM2D3, TMCC1, TMCO6, TMEM134, TMEM164, TMEM2, TMEM243, TMF1, TMUB2, TMX4, TNFAIP3, TNFRSF10B, TNKS, TNS3, TOM1, TP73-AS1, |

TABLE 8-continued

Genes in modules identified via Gene Ontology (GO) analysis

| Cell Type | Module Name | Genes |
|---|---|---|
| | | TPCN1, TPTI, TRAF3, TRAF5, TRAK1, TRAPPC10, TRAPPC12, TRAPPC8, TRIM13, TRIM27, TRIM33, TRIM44, TRIM68, TRMT61B, TSC1, TSC22D3, TSEN34, TTC12, TTC31, TTC9, TTF1, TUBA1A, TUG1I, TXNIP, TXNL4B, UBE2G2, UBE2I, UBQLN2, UBR2, UBR4, UBXN1, UNC45A, USP12, USP24, USP7, UXS1, VAMP4, VEZF1, VILL, VPS11, VPS13D, VPS35, VPS39, WASF1, WDR19, WDR37, WDR55, WDR59, WDR5B, WIPF2, WIPI2, WSB1, XPC, XPO6, XRCC2, XYLT1, YPEL5, YTHDC1, YY1AP1, ZBED5, ZBTB11, ZBTB14, ZBTB40, ZBTB5, ZBTB7A, ZC3HAV1, ZDHHC17, ZDHHC6, ZHX2, ZKSCAN5, ZMYM4, ZMYM5, ZNF106, ZNF134, ZNF136, ZNF137P, ZNF14, ZNF195, ZNF204P, ZNF211, ZNF212, ZNF217, ZNF222, ZNF230, ZNF232, ZNF235, ZNF24, ZNF248, ZNF266, ZNF268, ZNF274, ZNF277, ZNF302, ZNF304, ZNF318, ZNF32, ZNF329, ZNF37BP, ZNF395, ZNF419, ZNF443, ZNF451, ZNF551, ZNF592, ZNF606, ZNF672, ZNF767P, ZNF83, ZNF839, ZNF84, ZRSR2, ZSCAN18, ZSCAN32, ZXDC, ZZEF1 |
| CD33 | Royal blue | ACTC1, ADAMTS2, ADD1, AGGF1, AGPAT1, ANXA9, APBB1IP, APLP2, ARHGDIA, ARHGEF11, BCL2L1, C10orf76, C1orf115, CA5BP1, CACNB2, CFAP70, CLDN4, COCH, COL8A2, CPSF6, CSNKIG1, CYB5R2, CYP1A2, DACH1, DBT, DEDD, DOCK5, DUSP7, E2F4, ECE2, EPN1, ERCC8, ERV9-1, FADS2, FAM124B, FAM13A, FASN, FUT6, GNAQ, GTPBP1, HFE, HIST1H2AM, HMGCS2, HTATSF1, IGLJ3, KCNJ3, KCNMB3, KLHL26, LDLRAD4, LPARI, MAP7, MATN1, MED14, MOB4, MVB12B, NDN, NREP, OPRLI, OR7E12P, PANK3, PDLIM7, PDX1, PEX14, PLAA, PLCE1, PLSCR2, PNPLA2, PPARG, PPP2RIB, PRKCA, PSEN2, PTCRA, PTGFR, PTK2B, PTPN1, PXMP4, RBKS, RERE, RITA1, SCN1B, SIGLEC7, SP1, SPATA2, STAP2, STRN4, STYXL1, TBCID10B, TDRD12, TMEM45A, ZHX3, ZNF155, ZNF235, ZNF536, ZNF556 |
| CD33 | Sienna 3 | ACSL1, ACVRI, ADM, AP2B1, APOL6, AQP9, ARID5B, ATP2A2, B3GALT4, BCAS2, C2, CALU, CCL2, CCR1, CD38, CD63, CDS2, CHD7, CHST11, CLIC4, CSF2RB, CSNKIAI, CUL1, CXCL8, DCTN5, DDX60, DESI1, DNASE2, DRAM1, EGR1, EMC1, EMC7, EPHB2, ERO1L, ERP44, FCAR, FCGR1B, FFAR2, FLVCR2, GALNT2, GAS7, GK, GNAI3, GNPDA1, HPSE, IER2, IFI27, IFI35, IFI6, IFIT2, IFIT3, IGSF6, IL15RA, IL1RN, IRF7, ISG20, JMJD6, JUN, KCNJ15, KHNYN, KLF9, KMO, KYNU, LAMPI, LAP3, LDHA, LDLR, LEPROT, LGALS3BP, LGALS8, LIMK2, LMNB1, LXN, MAPK1IP1L, MED6, MR1, MTIHL1, MTIX, MT2A, N4BP1, NAIP, NAMPT, NAPA, NMI, NRAS, NUDT15, OASL, PANX1, PEF1, PLIN3, PLSCR1, POP4, PPPIR2, PRPF18, PSMD12, PSMD14, QKI, RAB5A, RAB8B, RIPK2, RIT1, RNF19B, RSAD2, SC5D, SEC24A, SERPING1, SIRPA, SLC12A6, SLC2A3, SLC31A2, SLC38A2, SLC39A8, SPATS2L, SQLE, SREBF2, SRP54, STATI, SUMO3, SYNJ2, TAPI, TCEB1, TFEC, TMCO1, TMEM180, TMSB10, TNFAIP6, TOR1B, TRAFDI, TRIP4, TXN, XBP1, YME1L1, ZDHHC3 |
| CD33 | Violet | ACOT13, ACOX1, ACPP, ACTA2, ADAR, ADARB1, AIM2, APOBEC3G, ATP10A, BCL2L13, BLM, BLVRA, BLZF1, C15orf39, C19orf66, CIQA, C2orf47, CACNA1A, CBR1, CD2AP, CDK7, CEBPG, CHMP5, CHST12, CLU, CMC2, CMTR1, CNIH4, CNP, COA3, COX17, CR1, CSNK1D, CYB5A, DBI, DDA1, DDX58, DHX58, DHX8, DNAJA1, DPM1, DYNLT1, DYSF, EIF2AK2, ENOPHI, ERGIC2, ETFDH, ETNK1, EXT1, EXT2, F2RL1, FAM49A, FAM69A, FAM8A1, FAS, FKBP15, FOLR3, FXYD6, GCH1, GLE1, GMPR, GRK6, GRPEL1, GTPBP2, HERC5, HERC6, HGF, HINFP, HIST2H2BE, HSPB11, IFI44, IFI44L, IFIH1, IFIT1, IFIT5, IFITM1, IFITM3, IGJ, IGKC, IGLC1, IK, ING1, IRF2, ISG15, JUP, KEAPI, KIAA0040, KIAA0226, KLHL7, LAIR2, LARP7, LEPROTLI, LILRA2, LILRA5, LOC100996756, LY6E, LY96, MAD2LIBP, MCTSI, MICU1, MRPL22, MSRB2, MX1, MX2, NCALD, NDFIP1, NDUFS6, NFYA, NRN1, NSUN3, NUCB1, NUDT9, OAS2, OAS3, OSBPL1A, PAK2, PDK3, PGGT1B, PHF11, PML, POLB, PPP1R3D, PPP2R2A, PSMA4, PSME3, QRSL1, RBMS2, RIN2, RNF34, RPS6KC1, RTP4, SAMD4A, SAMD9, SAP30L, SCCPDH, SEC22B, SIGLEC1, SLC25A37, SMAD3, SMCHD1, SNRPG, SNTB1, SORT1, SP100, SP110, SP140, SPATA5L1, SPTLC2, SRD5A1, SRP19, STAP1, STEAP4, STX17, SULTIBI, TBPL1, TCF4, TCN2, TDRD7, TLE3, TMEM140, TMEM2, TMEM255A, TMOD3, TNFSF10, TRIM14, TRIM21, TRIM22, TROVE2, UAP1L1, UBE2K, USP18, VAMP1, VTIIB, WDFY3, WWC3, XRCC4, ZNF322 |
| CD33 | Dark magenta | ABCC4, ACTR1B, AHI1, AK1, AKAP13, AKAP8L, ALG12, ANGEL1, ANK3, ANKEF1, APOM, AQP3, ARFIP2, ARFRP1, ARHGEF16, ARRB1, ARTN, ASAP3, ATAD3A, ATNI, B3GAT1, B4GALT1, BAHD1, BATF3, BCL2, BCL7A, BIN1, BOP1, BTBD2, C10orf2, C14orfl, C16orf45, C16orf58, C5orf45, CA11, CABP1, CACNA1I, CACNA2D2, CASP10, CD5, CD74, CD79A, CDHR1, CDK16, CEP170B, CES2, CFHR2, CIC, CLEC10A, CLOCK, CLUAP1, CMTM6, CNTFR, COLIA2, COMT, COQ3, COQ4, COQ7, COX11, CRELD1, CRTAC1, CRY2, CRYGD, CRYM, CSFIR, CTSF, CWF19L1, CXADR, CYLD, DAO, DDX31, DECR2, DIEXF, DMPK, DNPEP, DNPH1, DOCK6, DOLPP1, DPH2, DSPP, DTNA, DZIP3, ECHS1, EHD2, EIF3A, EIF5A, ENPP1, EPOR, ERBB2, ESR2, EVX1, EXOSC4, FAM153A, FANCC, FBXO2, FBXO31, FCF1, FGF4, FGF6, FHL1, FKBP4, FUBP1, FZR1, GAMT, GDF5, GFER, GJB3, GLP1R, GNB1L, GOLGA2P5, GOLGA8A, GON4L, GRHL2, HABP4, HADH, HEMK1, HGH1, HIP1R, HIST1H1T, HIST3H2A, HLA-DPA1, HLA-DQB1, HMGA1, HMOX2, HNRNPAO, HRK, ICAM4, IGH, IGSF9B, IPO9, ISYNA1, IZUMO4, KCNA3, KDM8, KLF12, KLHDC3, LIMD2, LIMS2, LINC00260, LINC01278, LRRC16A, LTA, LTBP4, MACRODI, MAZ, MCM3 AP, MCM3AP-AS1, MEGF6, MGAT4B, MID2, MMP19, MRMI, MRPL12, MRTO4, MUC5AC, MUC8, MYO1C, NAA40, NECAB3, NF2, NFATC1, NFATC2IP, NIPAL3, NIPSNAPI, NPAT, NPM3, NPRL3, NPTXR, NR3C2, NRF1, NRL, NSG1, NUBPL, NUFIP1, OSBP2, PCBP4, PCYT2, PDLIM4, PGAP2, PHC1, PHGDH, PHLPP2, PIK3IP1, PLCG1, PLCH2, PLXNB2, PNPLA4, POF1B, POLD4, POLR3G, POU6F1, PPDPF, PPIP5K1, PPPIR13B, PPP2R5D, PREPL, PSAT1, PTGIR, RAB11FIP3, RAB2A, RAB40B, RBM19, RCL1, REXO4, RFTN1, RGS12, RNPS1, ROBO3, RPS12, RRPIB, SAFB2, SBF1, SEMA3G, SF3B3, SGSM2, SH2D3A, SIVA1, SLC12A2, SLC25A22, SLC25A4, SLC2A6, SLC5A5, SLC7A8, SMPD2, SNAP25, SOX12, SPDEF, SPTBN1 SREK11P1, SSBP3, STAG3, STRA13, SURF2, SYNGR3, TAC3, TCEA2, TCEB2, TCL6, TEAD3, TFAM, TJP3, TLE2, TM7SF2, TMEM177, TMEM63A, TOP3B, TPT1P8, TRAF3IP3, TRAF4, |

TABLE 8-continued

| Genes in modules identified via Gene Ontology (GO) analysis | | |
|---|---|---|
| Cell Type | Module Name | Genes |
| | | TRAK1, TRIM2, TSKU, TSPAN5, TTC28, TUBD1, TULP3, UBE2D4, UBE20, USP13, USP5, UTP20, VASH1, VPS13D, WDR59, WDR61, WDR73, WDR74, YPEL1, ZBTB38, ZFP36L2, ZNF510, ZNF76, ZSCAN18 |
| LDG | LDG_A | ABCC3, ABCC4, ABHD15, ABI2, ABLIM3, ACER3, ACRBP, ACSBG1, ACVRI, ADCY3, ADRA2A, AFAP1, AFAP1IL2, AFF3, AGBL5, AGPAT5, AIG1, AKIP1, ALDH1A1, ALOX12, ANKRD28, ANO6, APIS2, APP, AQP10, AR, ARHGAP18, ARHGAP21, ARHGAP32, ARHGAP6, ARHGEF12, ARMCX3, ASAP2, ATP5E, ATP5S, ATP9A, AVPRIA, B4GALT6, BACE1, BCL11A, BCL2L1, BCL2L2, BEND2, BET1, BEX3, BICD1, BLNK, BMP6, BMP8B, C12orf75, C12orf76, C15orf52, C15orf54, C19orf33, Clorf198, C2orf88, C7orf73, CA13, CA2, CALDI, CAMTAI, CANX, CASP6, CCDC88A, CD151, CD226, CD36, CDC14B, CDIP1, CDK2AP1, CDK6, CDKL1, CDYL, CHD9, CLCN3, CLDN5, CLECIB, CLIC4, CLU, CMTM5, CNRIP1, CNST, COMT, CPED1, CPNE5, CRAT, CRLS1, CTC-338M12.4, CTDSPL, CTTN, CXCL5, DAAM1, DAB2, DCLREIA, DDX11L2, DENND2C, DIMT1, DMTN, DNAJC6, DNM3, DPPA4, DPYSL2, DST, EGF, EGLN3, EHD3, ELOVL7, ENDOD1, ENKUR, EPB41L3, ERG, ERV3-1, ESAM, F13A1, F2R, FAM20B, FAM212B-AS1, FAM65C, FAM69B, FAM81B, FAXDC2, FHL1, FHL2, FKBPIB, FNBPIL, FRMD3, FSTLI, GADD45A, GAS2L1, GGTA1P, GLCE, GMPR, GNA12, GNAZ, GNG11, GNG8, GPIBA, GP5, GP6, GPX1, GRAP2, GRB14, GSTP1, GUCY1A3, GUCY1B3, H1F0, H2AFJ, HEMGN, HEXIM2, HGD, HIST1H2AE, HIST1H2BJ, HIST1H2BO, HIST1H41, HMGB1, HMGN1, HRASLS, IGF2BP3, IGKC, IGLC1, IRS1, ITGA2B, ITGA9, ITGB1, ITGB3, ITGB5, JAM3, KALRN, KCND3, KIF2A, KLHL5, LAPTM4B, LGALSL, LINC00853, LINC00938, LIPH, LMNA, LOC101928419, LOC105371967, LOC105377276, LOC283194, LPAR5, LRBA, LTBP1, LYPLAL1, LZTS2, MIAP, MAGI2-AS3, MAGOHB, MAP1A, MAP1B, MAP3K7CL, MAST4, MAX, MBTD1, MCM6, MCUR1, MEIS1, MEST, MFAP3L, MGLL, MINPP1, MITF, MLH3, MMD, MMRN1, MOB1B, MPL, MSANTD3, MSN, MTHFD2L, MTMR2, MTURN, MYB, MYCTI, MYL9, MYLK, MYNN, NAP1L1, NAT8B, NCAPG2, NCK1-AS1, NCKAP1, ND4, NENF, NEXN, NIPA1, NLK, NORAD, NPRL3, NREP, NRGN, NT5M, NUTM2A-AS1, OPN3, P2RY12, PANX1, PARD3, PARVB, PAWR, PBX1, PCYTIB, PDE2A, PDE3A, PDE5A, PDGFA, PDGFC, PDLIMI, PDZD2, PDZK1IIP1, PEAR1, PF4, PF4V1, PGRMC1, PITPNM2, PKHD1L1, PKIG, PLA2G12A, PLEKHA8P1, PLOD2, PNMA1, PPBP, PPM1L, PRDX6, PRG2, PRKAR2B, PROS1, PROSER2, PRTFDC1, PRUNE1, PSD3, PSPH, PTCRA, PTG1R, PTGS1, PTK2, PTPN18, PTPRS, PXDC1, PYGB, RAB13, RAB27B, RAB30, RAPIB, RAP2B, RBPMS2, RCC2, RDH11, RGS10, RHBDD1, RHOBTB1, RNF11, RNF217, RSU1, SAV1, SCFD2, SCN9A, SDC4, SDPR, SEC14L5, SEPT11, SERPINE2, SH3BGRL2, SH3TC2, SHTN1, SIAE, SLA2, SLC25A43, SLC35D2, SLC35D3, SLC44A1, SLC8A3, SMAD1, SMIM24, SMIM5, SMOX, SNAPC3, SNCA, SNPH, SOX4, SPARC, SPOCD1, SPSB1, SPX, SSX2IP, ST3GAL3, STMN1, STON2, STRADB, SYNM, SYTL4, TAL1, TARBP1, TBXA2R, TCEAL8, TCF4, TCL1A, TDRP, TEX2, TFB1M, TFPI, TGFB1I1, TGFBI, THBS1, THRB, TLK1, TLR7, TMCC2, TMEM158, TMEM40, TMEM45A, TMEM64, TNFSF4, TNIK, TNS1, TNS3, TPM1, TPSAB1, TPSB2, TPST2, TPTEP1, TRBV27, TREML1, TRIM10, TRIM13, TRIM58, TSC22D1, TSPAN18, TSPAN33, TSPAN9, TTC7B, TUBB, TUBB1, TWSGI, UBE2E2, UBE20, UBL4A, UGCG, USP12, USP31, UXSI, VCL, VEPH1, VIL1, VSIG2, VWA5A, VWF, WASF1, WASF3, WDR11-AS1, WHAMMP2, WRB, WWC1, XK, XPNPEP1, YIF1B, YWHAE, YWHAH, ZBTB16, ZC3HAV1L, ZNF175, ZNF271P, ZNF367, ZNF431, ZNF521, ZNF529-AS1, ZNF542P, ZNF677, ZNF718 |
| LDG | LDG_B | ABCA13, ARG1, ATP8B4, AZU1, CAMP, CEACAM6, CEACAM8, CHIT1, CLEC12A, CLEC5A, CPNE3, CRISP3, CTSG, CYBB, DEFA4, ELANE, HP, LCN2, LTF, MGSTI, MMP8, MPO, MS4A3, OLFM4, OLR1, RNASE3, SERPINB10, SLC2A5, STOM, TCN1, ANLN, BIRC5, BUBIB, CCNA1, CDK1, CDKN2B, DHFR, GFI1, INHBA, IQGAP3, KIAA0101, KIF11, KIF14, KNL1, MIS18BP1, NCAPG, RGCC, RRM2, SKA2, TOP2A, TYMS, AGPS, ANXA4, ATP23, BCL2L15, BEX1, CD24, CTBP2, CTC1, DCBLD2, ECRP, ERG, FBXO9, GALNT10, GCLM, GLOD5, GVINP1, HMGB2, HMGN2, KBTBD6, LINC00323, LMO4, MED7, NFYC, NUCB2, PCOLCE2, PDLIM5, PLEKHA3, PPFIA4, RPE, SCD, SENP1, SLC28A3, SMIM8, TACSTD2, TCTEX1D1, THBS4, TMEM234, TMEM50B, TMLHE, TRMT5, ZNF788 |
| PC | PC_Up | AAK1, ADA, ADCYAP1, ADGRB1, AGK, AHCYL2, ALG5, ALG9, AMOTL2, ANG, ANKSIB, APOA4, AQP3, ARF4, ARHGEF40, ARL1, ASICI, ASPM, ATF5, ATP11A, ATPIA2, ATP2A2, AURKA, B4GALT3, B9D1, BAZ1B, BCAN, BIK, BIRC5, BMP8B, BSCL2, BUB1, BUB1B, C11orf80, C1GALT1C1, C1orf27, CA6, CADM1, CADM3, CALML4, CALR, CALU, CASP3, CAV1, CCNA2, CCNB1, CCNB2, CCNC, CCND2, CCNE2, CCR10, CD27, CD300A, CD320, CD38, CD59, CD6, CDC20, CDC25A, CDC42BPA, CDC6, CDCA3, CDKN2C, CDKN3, CDR2, CENPE, CENPN, CENPU, CEP55, CEP97, CFLAR, CHAC1, CHEKI, CHPF, CHST12, CHST2, CITED2, CKAP4, CLIC3, CLINT1, CNKSR1, CNPY2, COL9A3, COPA, COPB2, COX11, COX7A2, CRB1, CRELD2, CSF2RB, CSHL1, CSNK1E, CTNNAL1, CYP11B2, CYP26A1, CYP2E1, DCPS, DDOST, DENNDIB, DERLI, DERL2, DLGAP5, DNAJCI, DNAJC3, DOK4, DRD4, DSTN, E2F8, EDEM2, EDEM3, EFS, ELL2, ERAPI, ERCC6L, ESPL1, ESRI, EXOSC4, EXT1, FAAH, FABP5, FAM149A, FAR2, FAXDC2, FBXO5, FDX1, FEN1, FKBP11, FKBP2, FNDC3B, FOLH1B, FUT8, FZD7, GAB1, GADD45A, GALNT2, GARS, GAS6, GC, GCSH, GFI1, GGH, GLRX5, GMNN, GMPPA, GMPPB, GNAS, GOLT1B, GPLD1, GPR15, GPRC5D, GRIK1, GSC2, GSPT1, H2AFX, HDLBP, HIBCH, HIST1H2AM, HIST1H2BB, HIST1H2BC, HIST1H2BG, HIST1H3D, HIST1H4B, HIST1H4L, HJURP, HMGN5, HMMR, HPGD, HPX, HRH1, HSD11B2, HSD17B8, HSP90B1, HSPA13, HSPA5, HYOU1, IDH2, IFNAR2, IGF1, IGHD, IGHG1, IGHG3, IGHM, IGK, IGKC, IGKV1-5, IGKV1D-13, IGKV1D-8, IGL, IGLJ3, IGLL1, IGLL3P, IGLV3-19, IGLV4-60, IL1R1, IL6R, IL6ST, INPP4A, IQGAP2, IQSEC2, IRF4, ITGA6, ITGB1BP1, ITM2C, JCHAIN, KCNJ5, KCNK12, KCNN3, KDELC1, KDELR2, KIAA0101, KIF20A, KIFC1, KIR2DL4, KLF10, KLK11, KLKB1, LAP3, LAX1, LDLRAD4, LGALS3, LIME1, LMAN1, LMAN2, LRRC59, LSR, LZTS1, MANIA1, MANEA, MANF, MAP2K6, MAPKAPK5, MAST1, MBNL2, |

TABLE 8-continued

| Genes in modules identified via Gene Ontology (GO) analysis | | |
|---|---|---|
| Cell Type | Module Name | Genes |
| | | MCM10, MCM3AP, MCUR1, MELK, MGAT2, MIF, MKI67, MLEC, MORF4L2, MPHOSPH9, MRPL22, MTNR1A, MTRR, MUC5B, MYCBP, MYDGF, MYOID, NANS, NAT2, NAT8, NCAPG, NCOA3, NDUFB6, NEK2, NES, NEU1, NEUROG3, NME1, NPIP, NPIPB15, NPM1, NT5DC2, NUCB2, NUSIP3, NUSAPI, OGFOD3, OGT, P4HB, PAK5, PAM, PARP2, PCDHGA3, PCSK4, PDEIA, PDIA2, PDIA4, PDIA6, PDK1, PDXK, PERP, PGM3, PHGDH, PIK3CG, PKP4, PMM2, POU6F2, PPA1, PPCDC, PPIB, PRDM1, PRDX4, PREB, PROSC, PSMA3, PSMC2, PTPRD, PTTG1, PTTG3P, PYCRI, PYCRL, R3HCC1, RAB27A, RAPGEF2, RBM47, RGS13, RGS16, RPN1, RPN2, RRBP1, RRM2, RS1, RWDD2A, SAR1A, SAR1B, SCUBE3, SDC1, SDF2L1, SEC13, SEC14L1, SEC23B, SEC24A, SEC24D, SEC61A1, SEC61B, SEC61G, SEL1L, SELPLG, SEMA4A, SEPT10, SEPT4, SERPINF1, SGK1, SIL1, SLAMF7, SLC16A1, SLC16A6, SLC19A1, SLC1A4, SLC1A7, SLC27A2, SLC31A2, SLC35B1, SLC7A11, SLC7A5, SLC9A3R1, SLCO2B1, SLCO3A1, SLCO4A1, SLFN12, SMAD6, SPATS2, SPCS1, SPCS2, SPCS3, SPINK5, SPRR1A, SRM, SRP19, SSR1, SSR3, SSR4, ST3GAL6, ST6GALNAC4, STARD5, STT3A, SULTIC2, TAZ, TBL2, TECR, TIMM17A, TIMM44, TIMM8B, TIMP2, TIMP4, TKI, TLX3, TM9SF1, TMBIM6, TMED10, TMED2, TMED5, TMEM184B, TMEM208, TMEM258, TNFRSF17, TP63, TPP2, TPST2, TRA, TRAM1, TRAM2, TRAT1, TRD, TRIB1, TRIP13, TRIP6, TSHR, TST, TUBG1, TXN, TXNDC15, TXNDC5, TYMS, UAP1, UBE2C, UCHL1, UCK2, UGGT2, UQCRB, VDR, VEGFA, WARS, WHSC1, WIPI1, XBP1, XCL1, YIPF2, ZMYM2, ZNF593, ZWINT |
| PC | PC_Down | ABLIM1, ABR, ADARB1, AKAP1, AKT3, ALOX5AP, ANKZF1, ARHGAP17, ARPC4, BANK1, BCL11A, BIN1, BLK, BMP2K, C7orf26, CACNA1A, CAPN3, CBR3, CBX7, CCND3, CCR6, CD19, CD1C, CD1D, CD22, CD37, CD72, CDK5R1, CEP170, CERS4, CIITA, CLCN4, CLIP2, CNPPD1, COAL, CPQ, CSGALNACT1, CYLD, DCUN1D4, DDX24, DDX60, DEK, DENND5A, DHX58, DPEP2, DYRK2, ELF4, FAM208A, FAM20B, FAM46A, FAM65A, FCGR2A, FCMR, FGR, FOXO4, FYN, GAS7, GCNT1, GGA1, GGA2, GPD1L, GPR18, GRAP, GSAP, HCK, HHEX, HIP1R, HLA-DMA, HLA-DMB, HLA-DOB, HLA-DPA1, HLA-DQB1, HLA-DRB1, HLA-DRB3, HS3ST1, ID3, INPP5D, IRF5, IRF8, ITPKB, KDM4B, KIAA0141, KIF21B, KLF9, KLHDC10, KMO, LAIR1, LAPTM5, LAT2, LBH, LINC00472, LIPA, LPGAT1, LYL1, LYST, MAPRE2, MFHAS1, MNDA, MS4A1, MTSS1, MZF1, NAIP, NCR3, NLRP1, NOTCH2, NOTCH2NL, NT5E, OPN3, P2RX5, PAX5, PCDH9, PDE4DIP, PDLIM2, PHC1, PIK3CD, PIKFYVE, PKIG, PLAC8, PLCB2, PLEKHA1, PLEKHO1, POLD4, PPM1F, PRPF6, PRRC2B, PTK2, PTK2B, PTPN12, PTPN6, PTPRCAP, RASGRP2, RBMS1, RIN3, RNF130, RNF141, RTL1, SAMD4A, SH3BP2, SIDT2, SIPA1L1, SLC15A3, SMG1, SNAP23, SNN, SNX1, SNX2, SNX6, SPIB, SSBP2, STAT6, STX7, SUSD5, SWAP70, SYNPO, SYPL1, TBCID22A, TBLIX, TGFBR2, TMEM127, TNFSF12, TNFSF13, TRAK1, TRAK2, TRIM34, TRIM38, TSPAN-3, TTC9, UNC119, UNKL, USF2, VAV3, VEGFB, WASF2, XIST, ZBTB18, ZEB2, ZNF236, ZNF318, ZNF395, ZNF443, ZNF83, ZSCAN18, ZXDC |

Figure 12:
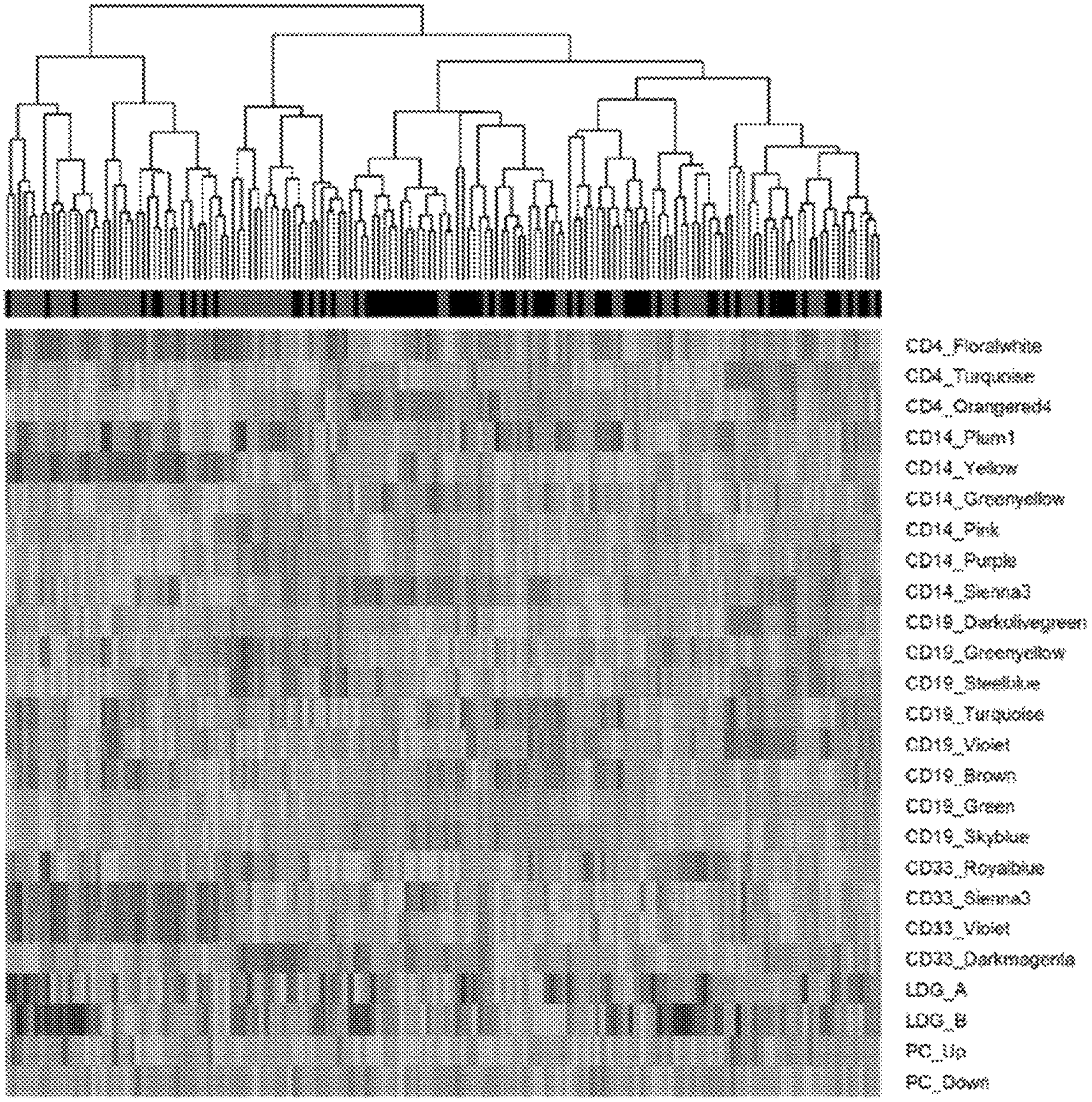
FIG. 12 shows an example of cellular gene modules providing a basis for machine learning predictions of SLE activity, in accordance with disclosed embodiments. GSVA was performed on three SLE WB datasets using 25 WGCNA modules made from purified SLE cells with correlation or published relationship to SLEDAI. Orange: active patient; black: inactive patient. LDG: low-density granulocyte; PC: plasma cell.

To characterize the relationships between SLE gene modules from cell subsets and disease activity in greater detail, Gene Set Variation Analysis (GSVA) enrichment was carried out using the 25 cell-specific gene modules (FIG. 12). Of the 25 cell-specific modules, 12 had enrichment scores with significant Spearman correlations to SLEDAI ($p<0.05$), and 14 had enrichment scores with significant differences between active and inactive patients (Welch's t-test, $p<0.05$) (Table 9). Table 9 shows assessment of WGCNA module relationships with SLE disease activity in WB, including statistics on WGCNA module relationships with SLEDAI and active disease. Correlation to SLEDAI was done by Spearman rank correlation, and the relationship with active versus inactive disease was assessed by Welch's unequal variances t-test and Cohen's d. Significant results are bolded ($p<0.05$). LDG: low-density granulocyte; PC: plasma cell.

TABLE 9

Cell-specific modules by Spearman correlation to SLEDAI and active vs. inactive state

| | Spearman correlation to SLEDAI | | Active vs. Inactive t-test | | |
|---|---|---|---|---|---|
| | rho | p value | t statistic | p value | d |
| CD4_Floralwhite | 0.360 | 3.90E−06 | 4.90 | 2.40E−06 | 0.788 |
| CD4_Turquoise | −0.044 | 0.587 | −0.93 | 0.352 | −0.149 |
| CD4_Orangered4 | −0.400 | 2.21E−07 | −5.29 | 4.35E−07 | −0.853 |
| CD14_Plum1 | 0.010 | 0.904 | −0.35 | 0.729 | −0.054 |
| CD14_Yellow | 0.356 | 4.93E−06 | 4.76 | 4.44E−06 | 0.761 |
| CD14_Greenyellow | −0.132 | 0.100 | −2.10 | 0.037 | −0.339 |
| CD14_Pink | −0.026 | 0.751 | 0.13 | 0.894 | 0.021 |
| CD14_Purple | −0.149 | 0.064 | −1.65 | 0.101 | −0.263 |
| CD14_Sienna3 | −0.368 | 2.27E−06 | −4.99 | 1.62E−06 | −0.799 |
| CD19_Darkolivegreen | 0.020 | 0.809 | −0.06 | 0.953 | −0.010 |
| CD19_Greenyellow | 0.192 | 0.016 | 2.55 | 0.012 | 0.403 |
| CD19_Steelblue | 0.016 | 0.838 | 0.55 | 0.580 | 0.089 |
| CD19_Turquoise | −0.069 | 0.393 | −0.84 | 0.403 | −0.132 |
| CD19_Violet | −0.087 | 0.282 | −1.48 | 0.141 | −0.236 |
| CD19_Brown | −0.050 | 0.537 | −1.04 | 0.301 | −0.164 |

TABLE 9-continued

| Cell-specific modules by Spearman correlation to SLEDAI and active vs. inactive state | Spearman correlation to SLEDAI | | Active vs. Inactive t-test | | |
|---|---|---|---|---|---|
| | rho | p value | t statistic | p value | d |
| CD19_Green | −0.150 | 0.062 | −2.07 | 0.040 | −0.330 |
| CD19_Skyblue | −0.205 | 0.010 | −2.35 | 0.020 | −0.378 |
| CD33_Royalblue | 0.308 | 8.99E−05 | 3.99 | 1.03E−04 | 0.637 |
| CD33_Sienna3 | 0.362 | 3.41E−06 | 4.69 | 6.15E−06 | 0.753 |
| CD33_Violet | 0.322 | 4.15E−05 | 4.35 | 2.46E−05 | 0.696 |
| CD33_Darkmagenta | −0.216 | 6.74E−03 | −2.34 | 0.021 | −0.369 |
| LDG_A | −0.044 | 0.588 | −0.25 | 0.802 | −0.040 |
| LDG_B | 0.220 | 5.71E−03 | 2.37 | 0.019 | 0.377 |
| PC_Up | 0.262 | 9.75E−04 | 3.21 | 1.61E−03 | 0.508 |
| PC_Down | 0.022 | 0.781 | 0.80 | 0.426 | 0.129 |

Notably, each cell type produced at least one module with a significant correlation to SLEDAI in WB and at least one module with a significant difference in enrichment scores between active and inactive patients, demonstrating a relationship between disease activity in specific cellular subsets and overall disease activity in WB. However, the Spearman's rho values ranged from −0.40 to +0.36, suggesting that no one module had substantial predictive value. Furthermore, the effect sizes as measured by Cohen's d when testing active versus inactive enrichment scores ranged from −0.85 to +0.79. The CD4 Floralwhite and Orangered4 modules, which had the largest positive and negative effect sizes, respectively, showed a high degree of overlap in the enrichment scores of active and inactive patients (FIG. 4).

Figure 13A:
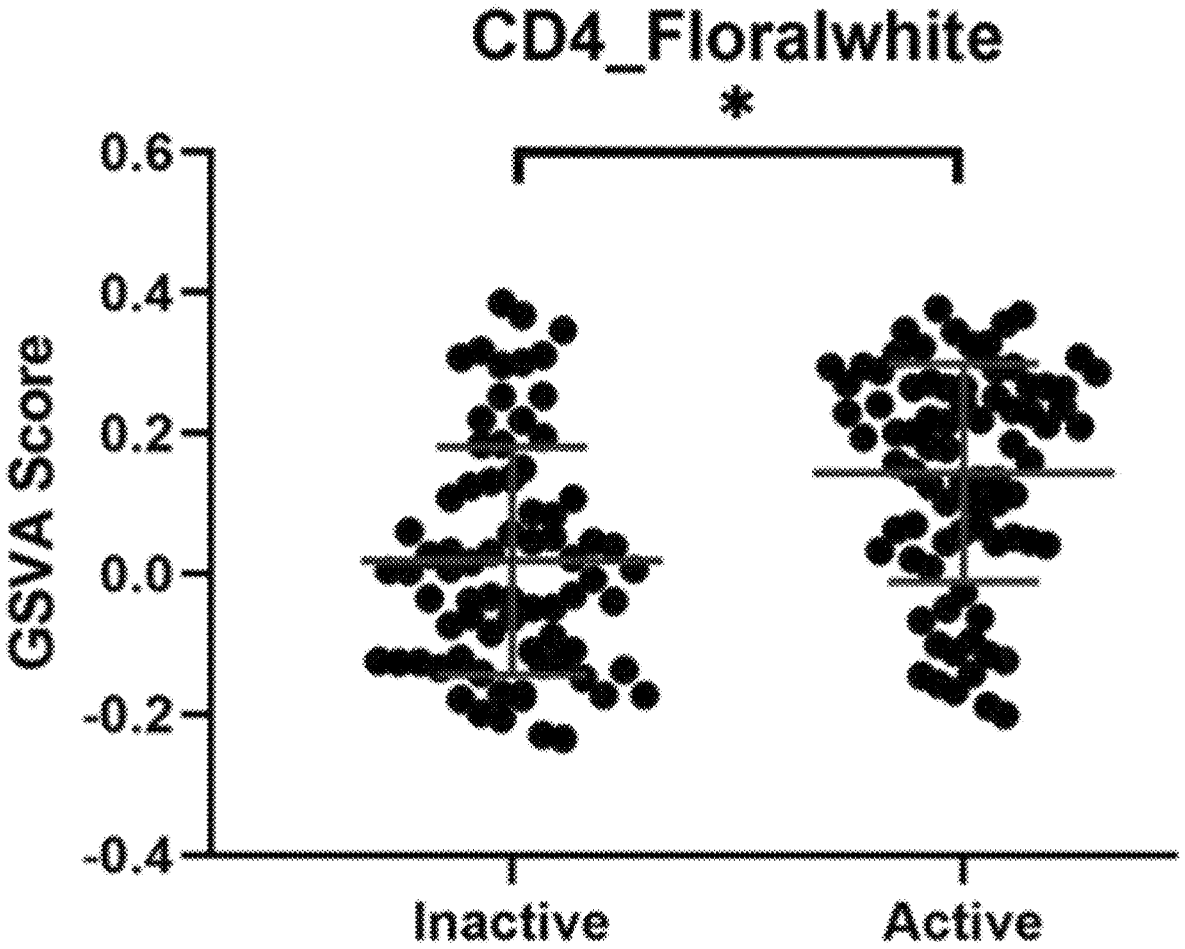
FIGS. 13A and 13B show an example of individual WGCNA modules being ineffective at separating active and inactive SLE subjects, in accordance with disclosed embodiments. GSVA enrichment scores for CD4_Floralwhite (FIG. 13A) and CD4_Orangered4 (FIG. 13B) in SLE WB are unable to fully separate active patients from inactive patients. Asterisks denote significant differences by Welch's t-test. Error bars indicate mean±standard deviation.
Figure 13B:
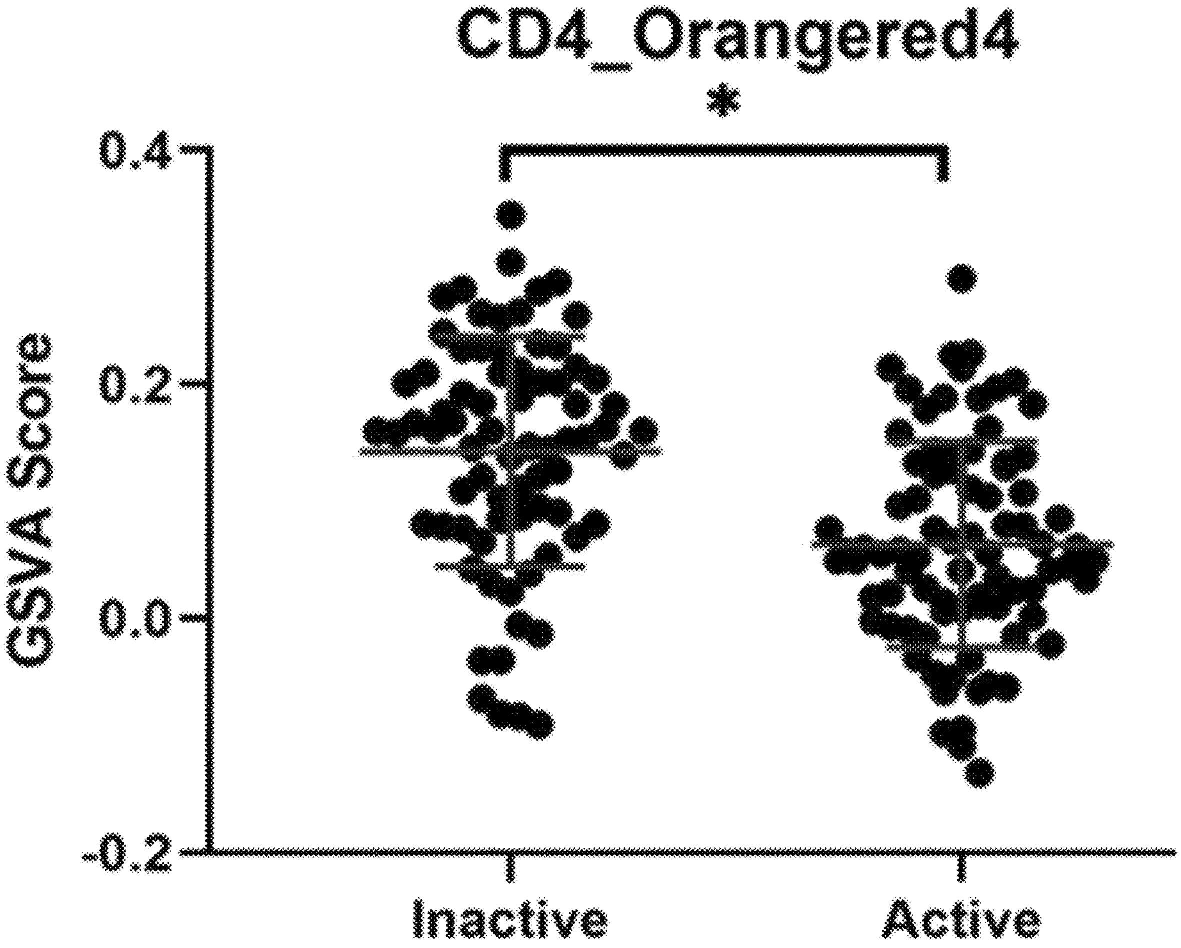

Analysis of individual disease activity-associated peripheral cellular subset gene modules was not sufficient to predict disease activity in unrelated WB data sets, since no single module from any cell type was able to separate active from inactive SLE patients (FIGS. 13A and 13B). The results emphasized the need for more advanced analysis to employ gene expression analysis to predict disease activity.

Figure 14:
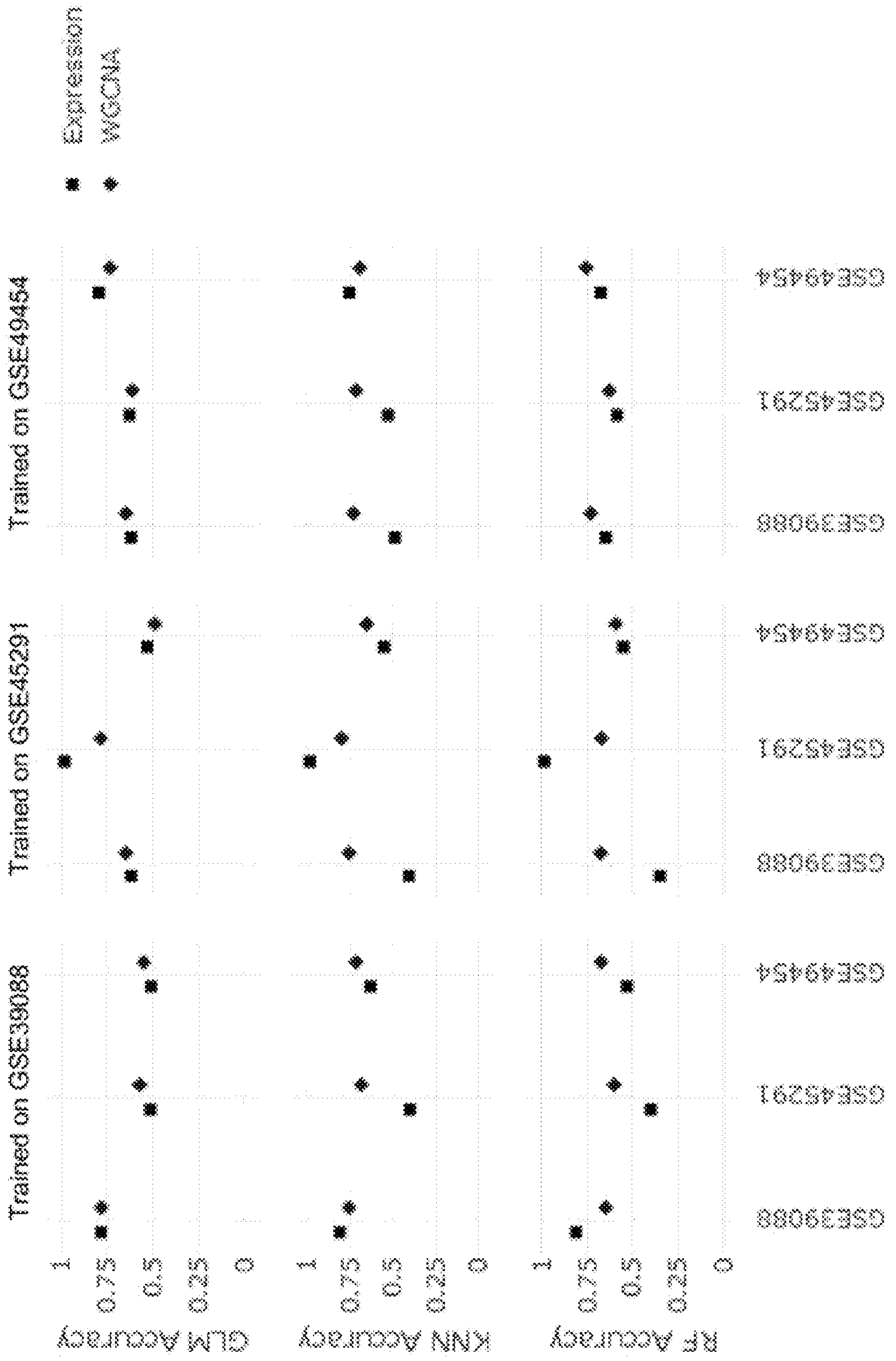
FIG. 14 shows an example of performance of machine learning classifiers across three independent data sets, in accordance with disclosed embodiments. Classifiers were trained on the data sets listed across the top and evaluated in the data sets listed across the bottom. Data sets are listed by their GEO accession numbers. Expression (black): gene expression data. WGCNA (blue): module enrichment scores.
Figure 15:
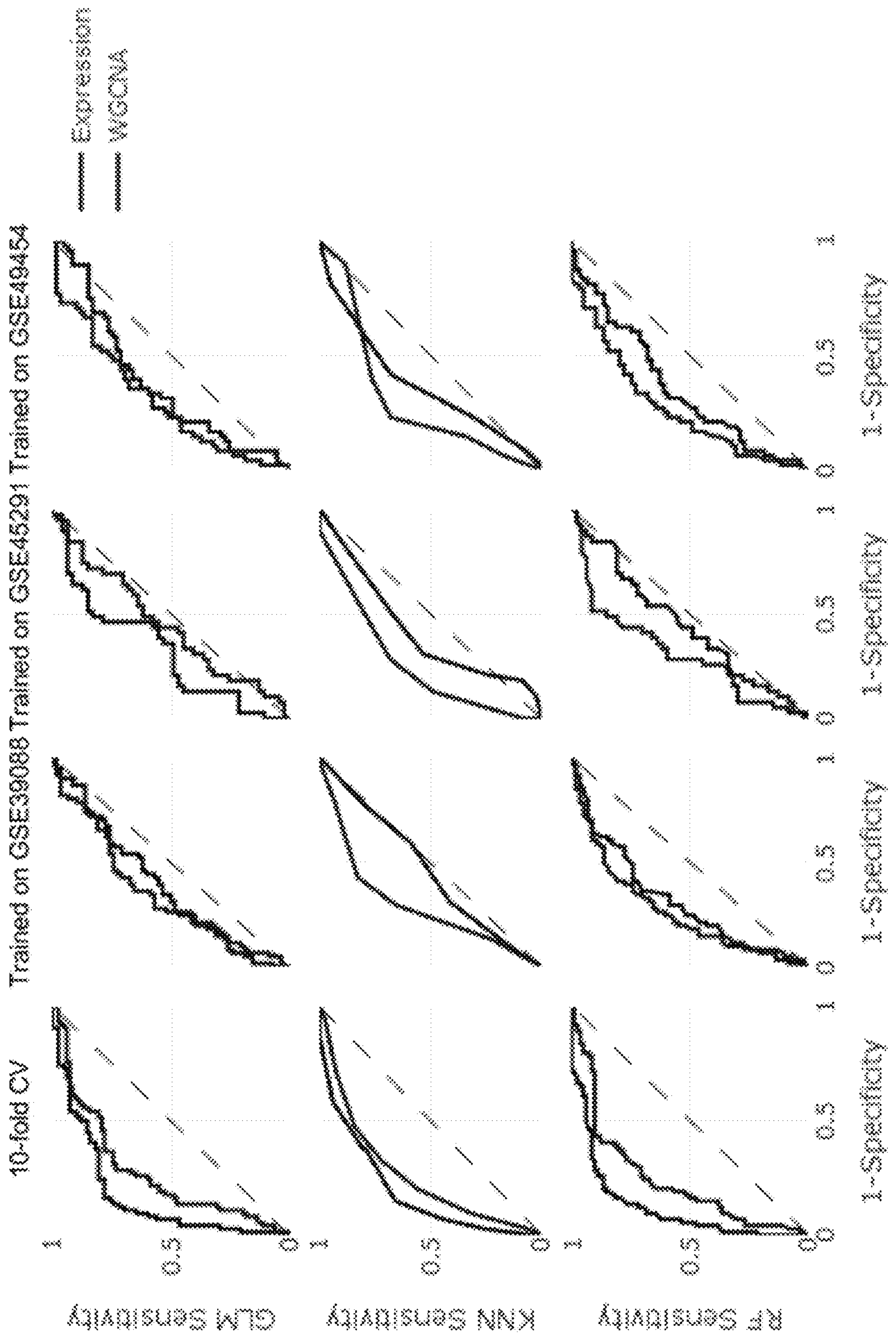
FIG. 15 shows an example of area under the ROC curve of machine learning classifiers across three independent data sets, in accordance with disclosed embodiments. Classifiers were trained on the data sets listed across the top and tested in the other two data sets. Data sets are listed by their GEO accession numbers. Expression (black): gene expression data. WGCNA (blue): module enrichment scores.

Machine learning may be applied to analyze and assess disease activity as follows. To assess the effectiveness of either raw gene expression or module-based enrichment techniques, SLE patients were classified as active or inactive using generalized linear models (GLM), k-nearest neighbors (KNN), and random forest (RF) classifiers. Classifiers were validated using two different methodologies: (1) 10-fold cross-validation or (2) study-based cross-validation, in which classifiers were trained on each data set independently and tested in the other two data sets. When evaluating the performance of classifiers on the data set on which they were trained, GLM accuracy was defined as one minus the cross-validated classification error from the cv.glmnet( ) function, and RF accuracy was determined based on out-of-bag predictions. The accuracy of each classifier trained with either gene expression or module enrichment is shown in FIG. 14, and receiver operating characteristic (ROC) curves are plotted in FIG. 15. Classification metrics for each classifier are shown in Table 10.

TABLE 10

Classification metrics for GLM, KNN, and RF classifiers

| | | 10-fold CV | | Trained on GSE39088 | | Trained on GSE45291 | | Trained on GSE49454 | |
|---|---|---|---|---|---|---|---|---|---|
| | | Expression | WGCNA | Expression | WGCNA | Expression | WGCNA | Expression | WGCNA |
| GLM | Accuracy | 0.80 | 0.72 | 0.51 | 0.56 | 0.57 | 0.56 | 0.63 | 0.63 |
| | Sensitivity | 0.78 | 0.73 | 0.86 | 0.79 | 0.51 | 0.60 | 0.54 | 0.59 |
| | Specificity | 0.82 | 0.70 | 0.18 | 0.34 | 0.64 | 0.51 | 0.73 | 0.67 |
| | AUC | 0.84 | 0.73 | 0.62 | 0.65 | 0.68 | 0.55 | 0.63 | 0.69 |
| | Kappa | 0.60 | 0.43 | 0.04 | 0.14 | 0.15 | 0.11 | 0.26 | 0.26 |
| | PPV | 0.83 | 0.73 | 0.50 | 0.53 | 0.63 | 0.60 | 0.71 | 0.69 |
| | NPV | 0.77 | 0.70 | 0.58 | 0.64 | 0.52 | 0.51 | 0.56 | 0.57 |
| KNN | Accuracy | 0.75 | 0.70 | 0.50 | 0.70 | 0.49 | 0.70 | 0.51 | 0.72 |
| | Sensitivity | 0.66 | 0.72 | 0.59 | 0.83 | 0.23 | 0.68 | 0.31 | 0.68 |
| | Specificity | 0.85 | 0.68 | 0.41 | 0.57 | 0.79 | 0.72 | 0.77 | 0.77 |
| | AUC | 0.82 | 0.74 | 0.54 | 0.71 | 0.58 | 0.75 | 0.63 | 0.70 |
| | Kappa | 0.50 | 0.40 | 0.00 | 0.40 | 0.03 | 0.40 | 0.07 | 0.44 |
| | PPV | 0.83 | 0.71 | 0.49 | 0.65 | 0.58 | 0.74 | 0.62 | 0.78 |
| | NPV | 0.69 | 0.68 | 0.51 | 0.78 | 0.46 | 0.65 | 0.47 | 0.66 |
| RF | Accuracy | 0.83 | 0.72 | 0.45 | 0.63 | 0.47 | 0.63 | 0.61 | 0.66 |
| | Sensitivity | 0.83 | 0.77 | 0.86 | 0.91 | 0.53 | 0.62 | 0.54 | 0.61 |
| | Specificity | 0.82 | 0.68 | 0.07 | 0.36 | 0.38 | 0.64 | 0.69 | 0.73 |
| | AUC | 0.89 | 0.77 | 0.69 | 0.73 | 0.58 | 0.68 | 0.65 | 0.74 |
| | Kappa | 0.65 | 0.45 | −0.07 | 0.27 | −0.08 | 0.26 | 0.22 | 0.33 |
| | PPV | 0.84 | 0.72 | 0.47 | 0.58 | 0.51 | 0.67 | 0.68 | 0.73 |
| | NPV | 0.81 | 0.72 | 0.33 | 0.81 | 0.41 | 0.58 | 0.55 | 0.60 |

When performing 10-fold cross-validation, the use of gene expression values resulted in better performance from all three classifiers compared to module enrichment scores. The random forest classifier was the strongest performer with 83 percent accuracy, and its corresponding ROC curve demonstrated an excellent tradeoff between recall and fall-out (AUC of 0.89). This high accuracy may likely be attributed to the presence of data from all three studies in both the training and test sets. In this case, the classifiers have the opportunity to learn patterns inherent to each data set, which proves useful during testing. To ensure that the classifiers were not disproportionately learning patterns from certain data sets at the expense of others, the classification results from the 10-fold cross-validation approach were subdivided by data set. All classifiers exhibited good performance with small differences between their highest and lowest accuracies in individual data sets, with the exception of the WGCNA-based KNN classifier (Table 11).

Table 11 shows classification metrics of 10-fold CV machine learning classifiers with results subdivided by data set. Data sets are listed by their GEO accession numbers. Range: difference between maximum and minimum values for each metric. Expression: gene expression data. WGCNA: module enrichment scores. AUC: area under the receiver operating characteristic curve. Kappa: Cohen's kappa coefficient. PPV: positive predictive value. NPV: negative predictive value.

when tested on unfamiliar data sets. Remarkably, the use of module enrichment scores improved RF test accuracy to approximately 65 percent and improved KNN test accuracy to approximately 70 percent.

Overall, gene expression values provide high accuracy when performing 10-fold cross-validation but are rendered nearly useless when performing study-based cross-validation. These results indicate that disease activity classification based on raw gene expression, while more accurate, is sensitive to technical variability, whereas classification based on module enrichment better copes with variation among data sets.

Random forest consistently achieved high performance, and its assessments of variable importance may be used to gain insight into directors of the identification of SLE activity. To this end, random forest classifiers were trained on all patients from all data sets in order to identify the most important genes and modules as determined by mean decrease in the Gini impurity, a measure of misclassification error. The classifier trained with gene expression data achieved an out-of-bag accuracy of 81 percent, with a sensitivity of 83 percent and a specificity of 78 percent. The classifier trained with module enrichment scores achieved an out-of-bag accuracy of 73 percent, with a sensitivity of 78 percent and a specificity of 68 percent.

Figure 16A:
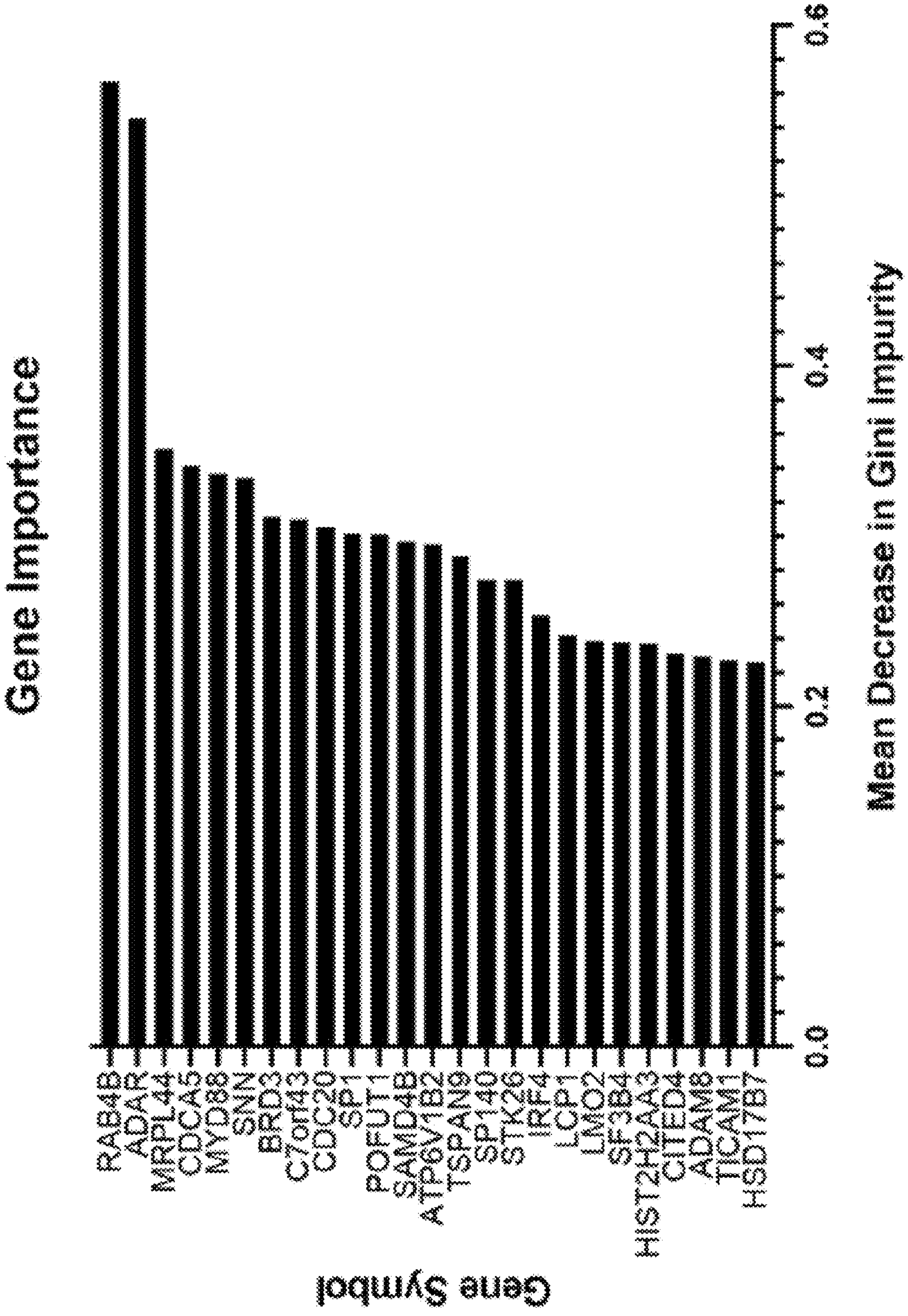
FIGS. 16A-16C show an example of random forest classifier revealing variable importance of genes and modules, in accordance with disclosed embodiments.

The most important genes and modules identified a wide array of cell types and biological functions (FIGS. 16A-

TABLE 11

Classification metrics of 10-fold CV machine learning classifiers with results subdivided by data set

| | | Subset: GSE39088 | | Subset: GSE45291 | | Subset: GSE49454 | | Range | |
|---|---|---|---|---|---|---|---|---|---|
| | | Expression | WGCNA | Expression | WGCNA | Expression | WGCNA | Expression | WGCNA |
| GLM | Accuracy | 0.81 | 0.70 | 0.83 | 0.74 | 0.76 | 0.69 | 0.07 | 0.05 |
| | Sensitivity | 0.73 | 0.73 | 0.83 | 0.71 | 0.76 | 0.76 | 0.10 | 0.05 |
| | Specificity | 0.93 | 0.67 | 0.83 | 0.77 | 0.75 | 0.63 | 0.18 | 0.14 |
| | AUC | 0.85 | 0.74 | 0.84 | 0.75 | 0.84 | 0.70 | 0.01 | 0.05 |
| | Kappa | 0.63 | 0.39 | 0.66 | 0.49 | 0.51 | 0.39 | 0.15 | 0.10 |
| | PPV | 0.94 | 0.76 | 0.83 | 0.76 | 0.76 | 0.68 | 0.18 | 0.08 |
| | NPV | 0.70 | 0.63 | 0.83 | 0.73 | 0.75 | 0.71 | 0.13 | 0.10 |
| KNN | Accuracy | 0.78 | 0.84 | 0.76 | 0.70 | 0.71 | 0.59 | 0.07 | 0.25 |
| | Sensitivity | 0.68 | 0.86 | 0.71 | 0.71 | 0.56 | 0.60 | 0.15 | 0.26 |
| | Specificity | 0.93 | 0.80 | 0.80 | 0.69 | 0.88 | 0.58 | 0.13 | 0.22 |
| | AUC | 0.85 | 0.84 | 0.79 | 0.75 | 0.84 | 0.65 | 0.06 | 0.19 |
| | Kappa | 0.58 | 0.66 | 0.51 | 0.40 | 0.43 | 0.18 | 0.15 | 0.48 |
| | PPV | 0.94 | 0.86 | 0.78 | 0.69 | 0.83 | 0.60 | 0.16 | 0.26 |
| | NPV | 0.67 | 0.80 | 0.74 | 0.71 | 0.66 | 0.58 | 0.08 | 0.22 |
| RF | Accuracy | 0.81 | 0.81 | 0.83 | 0.71 | 0.84 | 0.67 | 0.03 | 0.14 |
| | Sensitivity | 0.82 | 0.82 | 0.86 | 0.74 | 0.80 | 0.76 | 0.06 | 0.08 |
| | Specificity | 0.80 | 0.80 | 0.80 | 0.69 | 0.88 | 0.58 | 0.08 | 0.22 |
| | AUC | 0.87 | 0.86 | 0.90 | 0.78 | 0.88 | 0.72 | 0.03 | 0.14 |
| | Kappa | 0.61 | 0.61 | 0.66 | 0.43 | 0.67 | 0.34 | 0.06 | 0.27 |
| | PPV | 0.86 | 0.86 | 0.81 | 0.70 | 0.87 | 0.66 | 0.06 | 0.20 |
| | NPV | 0.75 | 0.75 | 0.85 | 0.73 | 0.81 | 0.70 | 0.10 | 0.05 |

When performing study-based cross-validation, classifiers trained on expression data performed better on their respective training sets than those trained on module enrichment scores in nearly all cases (FIG. 14). However, the accuracy of classifiers trained on expression values in the test sets was approximately 50 percent. This is in line with the findings of the initial bioinformatic analysis (Table 6), namely, that gene expression values may have little utility when attempting to classify unfamiliar samples. When the training and test data come from different data sets, the classifiers learn patterns that are unhelpful for classifying test samples. Although classifiers trained on module enrichment scores did not achieve high accuracies in their training sets, they did not experience as sharp a drop in accuracy

Figure 16B:
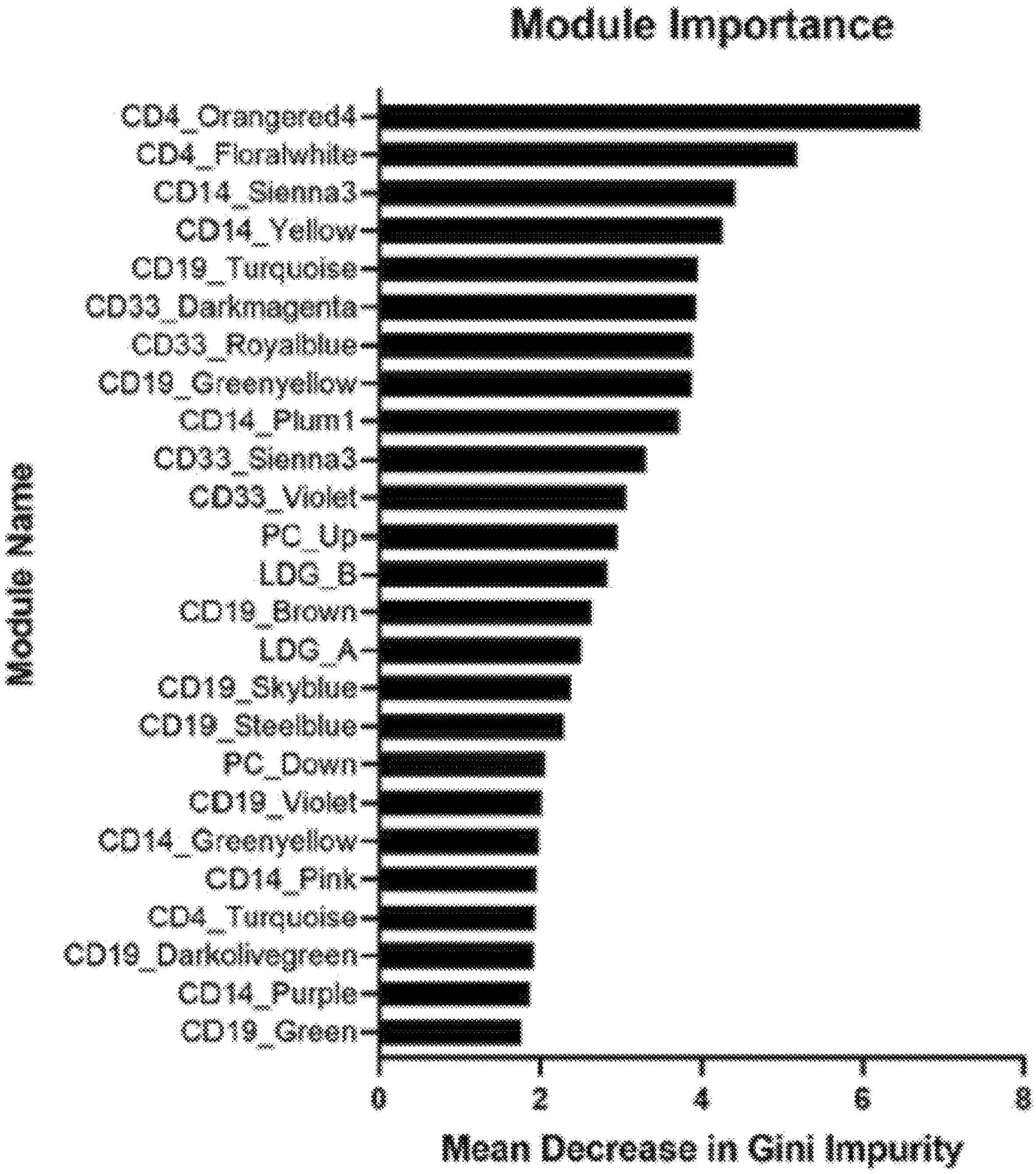
Figure 16C:
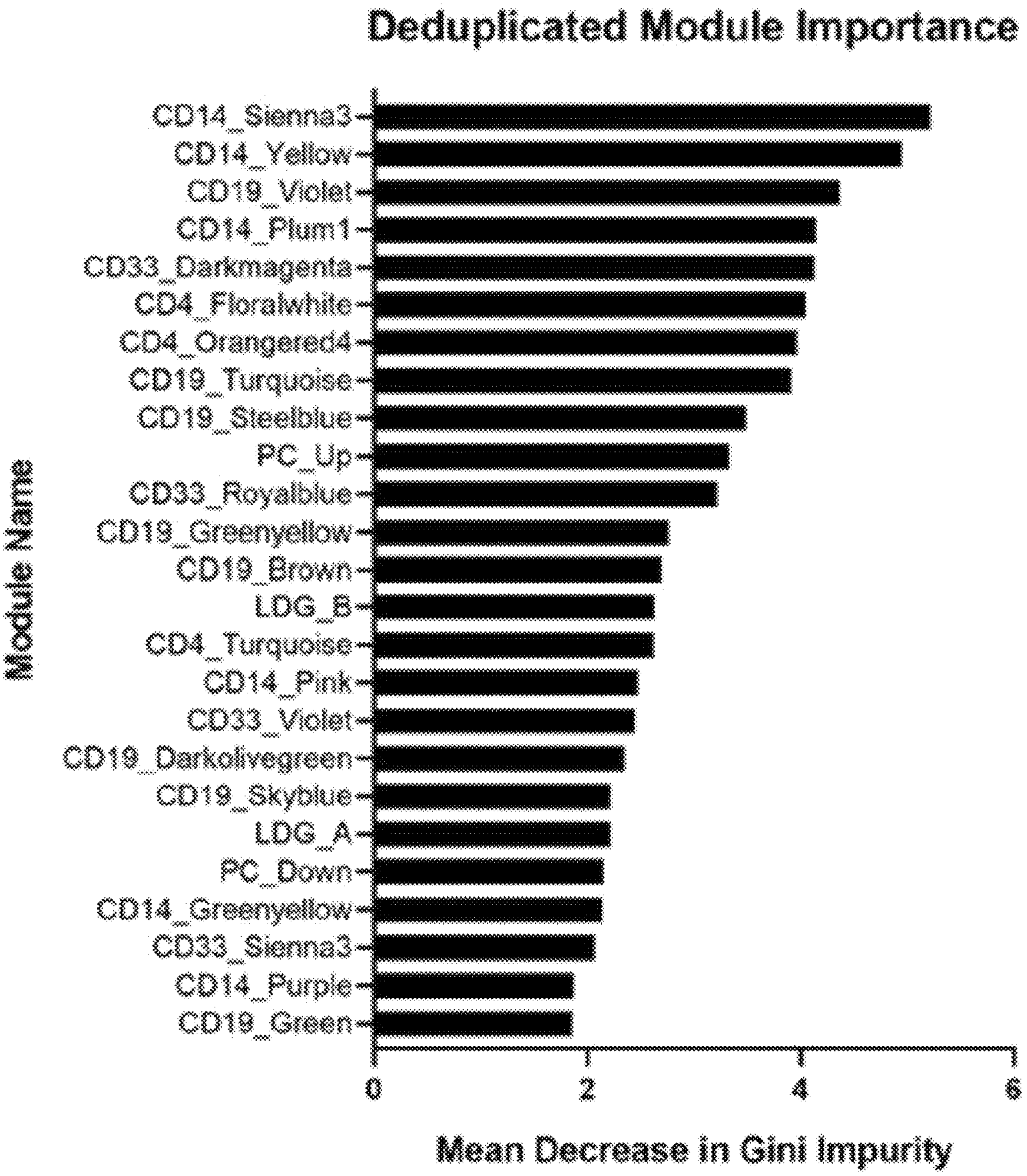

16C). The most important genes encompass such diverse functions as interferon signaling, pattern recognition receptor signaling, and control of survival and proliferation (FIG. 16A). These most important genes include RAB4B, ADAR, MRPL44, CDCA5, MYD88, SNN, BRD3, C7orf43, CDC20, SP1, POFUT1, SAMD4B, ATP6V1B2, TSPAN9, SP140, STK26, IRF4, LCP1, LMO2, SF3B4, HIST2H2AA3, CITED4, ADAM8, TICAM1, and HSD17B7. Notably, the most influential modules skewed away from B cell-derived modules and towards T cell- and myeloid cell-derived modules (FIG. 16B). As some of these modules had overlapping genes, the variable importance experiment was repeated with modules that were de-duplicated by removing any genes that appeared in more than one module before GSVA enrichment scoring. The relative variable importance scores of the de-duplicated modules correlated strongly with those of the original modules (Spearman's rho=0.69, p=1.94E-4), indicating that module behavior was partly driven by the overlapping genes but strongly driven by unique genes (FIG. 16C).

CD4_Floralwhite and CD14_Yellow, two interferon-related modules which maintained high importance after deduplication, were further analyzed to study the effect of unique genes on module importance. Gene lists were tested for statistical overrepresentation of Gene Ontology biological process terms with FDR correction on pantherdb.org. CD4_Floralwhite did not show any significant enrichment, but CD14_Yellow, which had the highest importance after deduplication, was highly enriched for genes with the "Immune Effector Process" designation (26/77 genes, FDR=9.38E-11 by Fisher's exact test). This suggests that CD14+ monocytes express unique genes that may play important roles in the initiation of SLE activity.

Several important findings related to SLE gene expression heterogeneity within and across data sets have been elucidated by this study. First, DE analysis of active vs. inactive patients may be insufficient for proper classification of SLE disease activity, as systematic differences between data sets render conventional bioinformatics techniques largely non-generalizable.

Next, it was hypothesized that WGCNA modules created from the cellular components of WB and correlated to SLEDAI disease activity may improve classification of disease activity in SLE patients. The use of cell-specific gene modules based on a priori knowledge about their relevance to disease fared slightly better than raw gene expression, as it generated informative enrichment patterns, and many of the modules maintained significant correlations with SLEDAI in WB. However, these enrichment scores failed to separate active patients from inactive patients completely by hierarchical clustering.

Raw expression data was then compared alongside the WGCNA generated modules of genes in machine learning applications. A supervised classification approach was applied using elastic generalized linear modeling, k-nearest neighbors, and random forest classifiers. The trends in performance when cross-validating by study or cross-validating 10-fold indicate the potential advantages and disadvantages of diagnostic tests incorporating gene expression data or module enrichment. Cross-validating by study serves as a kind of "worst-case" scenario, whereas 10-fold cross-validation serves as a "best-case." Attempting to classify active and inactive SLE patients from different data sets and different microarray platforms during cross-validation by study proved difficult, but module enrichment was able to smooth out much of the technical variation between data sets. 10-fold cross-validation simulated a more standardized diagnostic test. Although the data was sourced from three different microarray platforms, each cohort in the test set had many similar patients in the training set to facilitate classification by gene expression. If such a test may be reliably free from technical noise, it is likely that raw gene expression may perform very well.

RNA-Seq platforms, which produce transcript counts rather than probe intensity values, may display less technical variation across data sets because they are not dependent on the binding characteristics of pre-defined probes that differ among arrays. On the other hand, comparison of RNA-Seq and microarray samples may show that the two methods may deliver highly consistent results, so a microarray-based test may be feasible if it were only conducted on one platform. Constructing an optimal panel of genes similar to that identified by the random forest classifier may result in a simple, focused test to determine disease activity by gene expression data alone. Interestingly, module enrichment scores, which show little variation across platforms, may be used to develop diagnostic tests that leverage existing data sets, even if they are sourced from different platforms.

The strong performance of the random forest classifier indicates that nonlinear, decision tree-based methods of classification may be well suited to SLE diagnostics. This may be because decision trees ask questions about new samples sequentially and adaptively in contrast to other methods that approach variables from new samples all at once. Random forest is able to "understand" to an extent that different types of patients exist and that a one-size-fits-all approach may tend to misclassify those patients whose expression patterns make them a minority within their phenotype. To put it more simply, active patients that do not resemble the majority of active patients still have a strong chance of being properly classified by random forest.

The random forest classifier was used to assess the importance of each gene and module in patient classification. The most important genes were involved in a number of functions other than interferon signaling, such RNA processing, ubiquitylation, and mitochondrial processes. These pathways may play important roles in directing, or at least be indicative of, SLE disease activity. CD4 T cells originally contributed the most important modules, but when the modules were de-duplicated, CD14 monocyte-derived modules gained importance. This suggests that unique genes expressed by CD14 monocytes in tandem with interferon genes may prove to be informative in the study of cell-specific methods of SLE pathogenesis. Furthermore, it is important to note that modules that were negatively associated with disease activity were just as important in classification as positively associated modules. Study of under-represented categories of transcripts may enhance an understanding of SLE activity.

While creating dedicated training and test sets may be preferable to cross-validation, this approach may require a large number of samples. Although there are large numbers of publicly available gene expression profiles of SLE patients, many of these profiles are not annotated with SLEDAI data. Furthermore, some data sets which include SLEDAI data show heavy class imbalance, which impedes classification. Cross-platform expression data may be integrated toward expanding the ability to classify active and inactive SLE patients.

The machine learning models developed provide the basis of personalized medicine for SLE patients. Integration of these approaches with high-throughput patient sampling technologies may unlock the potential to develop a simple blood test to predict SLE disease activity. These approaches may also be generalized to predict other SLE manifestations, such as organ involvement. A better understanding of the cellular processes that drive SLE pathogenesis may eventually lead to customized therapeutic strategies based on patients' unique patterns of cellular activation.

Gene expression data may be compiled from SLE patients as follows. Publicly available gene expression data and corresponding phenotypic data were mined from the Gene Expression Omnibus. Raw data sources for purified cell populations are as follows: GSE10325 (CD4: 8 SLE, 9 HC; CD19: 10 SLE, 8 HC; CD33: 9 SLE, 9 HC); GSE26975 (10 SLE LDG, 10 SLE Neutrophil, 9 HC Neutrophil); GSE38351 (CD14: 8 SLE, 12 HC). Raw data sources for SLE whole blood gene expression are as follows: GSE39088

(24 active, 13 inactive); GSE45291 (35 active, 257 inactive); GSE49454 (23 active, 26 inactive). 35 randomly sampled inactive patients were taken from GSE45291 to avoid a major imbalance between active and inactive SLE patients. Active SLE was defined as having an SLE Disease Activity Index (SLEDAI) of 6 or greater.

Quality control and normalization of raw data files may be performed as follows. Statistical analysis was conducted using R and relevant Bioconductor packages. Non-normalized arrays were inspected for visual artifacts or poor hybridization using Affy QC plots. PCA plots were used to inspect the raw data files for outliers. Data sets culled of outliers were cleaned of background noise and normalized using RMA, GCRMA, or NEQC where appropriate. Data sets were then filtered to remove probes with low intensity values and probes without gene annotation data. WB gene expression data sets were filtered to only include genes that passed quality control in all data sets. At this juncture, differential expression (DE) analysis and Weighted Gene Co-expression Network Analysis (WGCNA) were carried out on data sets. WB gene expression data sets were then further processed before machine learning analysis. WB gene expression values were centered and scaled to have zero-mean and unit-variance within each data set, and the standardized expression values from each data set were joined for classification.

Differential Expression analysis may be performed as follows. Normalized expression values were variance corrected using local empirical Bayesian shrinkage, and DE was assessed using the LIMMA R package. Resulting p-values were adjusted for multiple hypothesis testing using the Benjamini-Hochberg correction, which resulted in a false discovery rate (FDR). Significant genes within each study were filtered to retain DE genes with an FDR <0.2, which were considered statistically significant. The FDR was selected a priori to diminish the number of genes that may be excluded as false negatives. Rank-rank hypergeometric overlap between data sets was assessed using the RRHO R package. Additional analyses examined differentially expressed genes with an FDR <0.05.

Weighted Gene Co-expression Network Analysis (WGCNA) of purified cell populations may be performed as follows. Log 2-normalized microarray expression values from purified CD4, CD14, CD19, CD33, and low density granulocyte (LDG) populations were used as input to WGCNA to conduct an unsupervised clustering analysis, resulting in co-expression "modules," or groups of densely interconnected genes which may correspond to comparably regulated biologic pathways. For each experiment, an approximately scale-free topology matrix (TOM) was first calculated to encode the network strength between probes. Probes were clustered into WGCNA modules based on TOM distances. Resultant dendrograms of correlation networks were trimmed to isolate individual modular groups of probes by partitioning around medoids and labeled using color assignments based on module size. Expression profiles of genes within modules were summarized by a module eigengene (ME), which is analogous to the module's first principal component. MEs act as characteristic expression values for their respective modules and may be correlated with sample traits such as SLEDAI or cell type. This was done by Pearson correlation for continuous or semi-continuous traits and by point-biserial correlation for dichotomous traits.

WGCNA modules from CD4, CD14, CD19, and CD33 cells were tested for correlation to SLEDAI. SLEDAI information was not available for the LDG modules, so the two modules provided are descriptive of LDGs compared to SLE neutrophils and HC neutrophils.

Plasma cell modules were generated by differential expression analysis and not WGCNA, but were included because of the established importance of plasma cells in SLE pathogenesis and their increase in active disease.

Gene Set Variation Analysis (GSVA)-based enrichment of expression data may be performed as follows. The GSVA R package was used as a non-parametric method for estimating the variation of pre-defined gene sets in SLE WB gene expression data sets. Standardized expression values from WB data sets were used to test for enrichment of cell-specific WGCNA gene modules using the Single-sample Gene Set Enrichment Analysis (ssGSEA) method, which scores single samples in isolation and is thus shielded from technical variation within and among data sets. Statistical analysis of GSVA enrichment scores was done bv Spearman correlation or Welch's unequal variances t-test, where appropriate. Effect sizes were assessed by Cohen's d.

Machine learning algorithms and parameters may be developed as follows. Three distinct machine learning algorithms were employed to test biased and unbiased approaches to microarray data analysis. The biased approach involved GSVA enrichment of disease-associated, cell-specific modules, and the unbiased approach employed all available gene expression data in the WB. An elastic generalized linear model (GLM), k-nearest neighbors classifier (KNN), and random forest (RF) classifier were deployed to classify active and inactive SLE patients and determine whether gene expression may serve as a general predictor of disease activity. GLM, KNN, and RF were deployed using the glmnet, caret, and randomForest R packages, respectively.

GLM carries out logistic regression with a tunable elastic penalty term to find a balance between the L1 (lasso) and L2 (ridge) penalties and thereby facilitate variable selection. For our predictions, the elastic penalty was set to 0.9, specifying a penalty that is 90% lasso and 10% ridge in order to generate sparse solutions. KNN classifies unknown samples based on their proximity to a set number k of known samples. K was set to 5% of the size of the training set. If the initial value of k was even, 1 was added in order to avoid ties. RF generates 500 decision trees which vote on the class of each sample. The Gini impurity index, a measure of misclassification error, was used to evaluate the importance of variables. In addition to these three approaches, pooled predictions were assigned based on the average class probabilities across the three classifiers.

Validation approaches may be performed as follows. The performance of each machine learning algorithm was evaluated by 2 different forms of cross-validation. First, a random 10-fold cross-validation was carried out by randomly assigning each patient to one of 10 groups. For each pass of cross-validation, one group was held out as a test set, and the classifiers were trained on the remaining data. Next, as the data came from three separate studies, study-based cross-validation was also done to determine the effects of systematic technical differences among data sets on classification performance. In this circumstance, the classifiers were trained on one data set and tested in the other two data sets. Accuracy was assessed as the proportion of patients correctly classified across all testing folds. Performance metrics such as sensitivity and specificity were assessed after cross-validation by agglomerating class probabilities and assignments from each fold or study. Receiver Operating Characteristic (ROC) curves were generated using the pROC R package.

Example 3: Molecular Endotyping Analysis for Identifying Subsets of Patients with Systemic Lupus Erythematosus Who are Candidates to be Enrolled in Clinical Trials and Have a Propensity to Respond to Specific Drugs Using methods and systems of the present disclosure, molecular endotyping analysis may be performed for identifying subsets of patients with Systemic Lupus Erythematosus who are candidates to be enrolled in clinical trials and have a propensity to respond to specific drugs. In precision medicine, identifying patients who may be appropriate candidates for entry into a clinical trial and/or who have a propensity to respond to a specific therapy is crucial, for example, to de-risk clinical trials. In trials of complex diseases, such as Systemic Lupus Erythematosus (SLE), with current approaches, it may be difficult to identify significant phenotypic and transcriptomic differences between subjects who may be responders and non-responders to specific therapies. For example, post-hoc analysis of the ILLUMINATE trials of tabalumab in SLE by Lilly was unable to identify any genes that were differentially expressed between responders and non-responders.

A hypothesis may be that SLE in particular is a common clinical manifestation of several molecular abnormalities or endotypes, each driven by a distinct combination of cell types and immune or inflammatory mechanisms. Incorporating knowledge of endotypes of individual subjects (e.g., SLE patients) may be a crucial step in the identification of subjects appropriate to enter a clinical trial and/or to benefit from a specific therapy (e.g., targeted therapy to treat SLE).

Methods and systems of the present disclosure can be used to determine whether distinct phenotypic and/or transcriptomic subsets of subjects exist and, subsequently, whether each group is likely to respond to specific therapies. The appropriate or inappropriate entry of such patients into trials may inflate or deflate the efficacy of a clinically tested treatment. Moreover, an investigational product that fails in a clinical trial may later be documented to be highly efficacious when tested on a patient subset with an appropriate molecular endotype.

Figure 17:
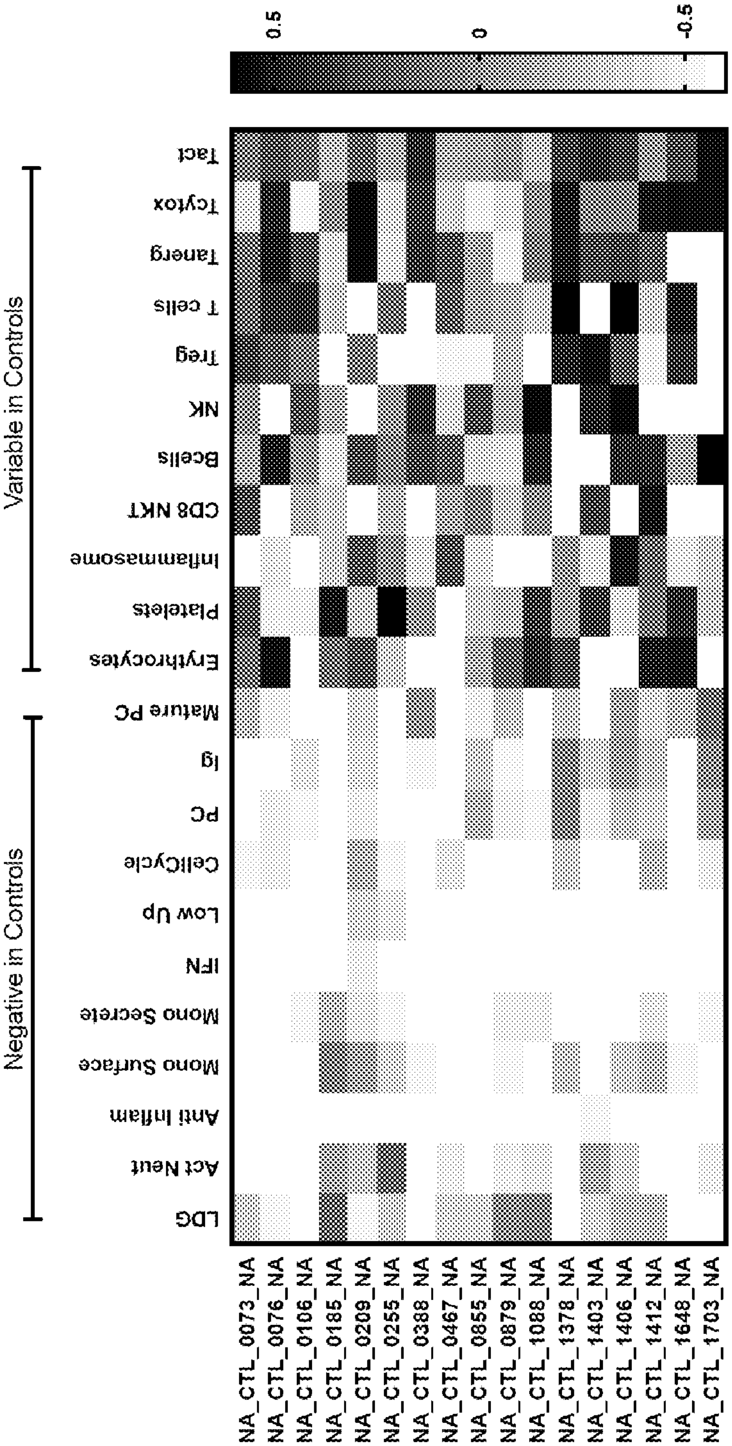
FIG. 17 shows a heat map showing the variation of gene expression in normal controls. Differentially expressed (DE) transcripts pertaining to cell type and process signatures in 10 SLE whole blood and peripheral blood mononuclear cell microarray datasets were used to create modules of genes potentially enriched in SLE patients determined by Gene Set Variation Analysis (GSVA).

The ability to stratify SLE patients into different groups associated with different types of disease or disease activity by transcriptomic signatures provides significant advantages toward determining appropriate patient care and enrollment in clinical trials. Using methods and systems disclosed herein, immunologically active SLE patients can be distinguished for entry into SLE clinical trials or to change patients to a more appropriate drug regimen. Results demonstrated that SLE patients can be grouped (e.g., clustered or distinguished) by their transcriptomic signatures. For example, FIG. 17 shows a heat map showing the variation of gene expression in normal controls. Differentially expressed (DE) transcripts pertaining to cell type and process signatures in 10 SLE whole blood and peripheral blood mononuclear cell microarray datasets were used to create modules of genes potentially enriched in SLE patients determined by Gene Set Variation Analysis (GSVA). Although significant differences in transcripts pertaining to B cells, T cells, erythrocytes, and platelets between SLE patients may be observed in SLE, it is notable that at the level of RNA transcription, these signatures may not be uniformly expressed in the healthy controls (HC) (FIG. 17) from several SLE datasets, demonstrating that the differences in these signatures are related to heterogeneity in controls unrelated to SLE.

A suite of clustering techniques may be used to partition clinical trial enrollees at baseline based on gene expression data and/or clinical parameters. These methods may be used to drastically reduce the dimensionality of transcriptomic-scale data, even for cases in which Principal Component Analysis (PCA) fails to generate an informative set of variables.

Furthermore, extensive analysis of the contribution of subject demographic and clinical variables revealed that many of the differences between datasets and patients were not related to the disease, but to the patient's ancestry, gender, or the subject's drug regimen, each of which may independently influence the transcriptomic signature. Thus, in order to determine whether there were different types of SLE molecular endotypes common amongst patients of different ancestral backgrounds, different SLE standard of care treatments and different manifestations, 11 transcriptomic signatures negative in controls were used for principal component analysis (PCA) of 1,566 female SLE patients divided into three ancestry sub-groups; African ancestry (AA, n=216), European ancestry (EA, n=1,118) and Native Southern American ancestry (NAA, n=232). An 11-dimension principal component analysis (PCA) was performed, and results established that principal component 1 (PC1) was determined by whether the patient had circulating plasma cells (PC1-) or myeloid cells (PC1+); in other words, the greatest separation between patients was affected by whether they had a plasma cell or Myeloid Cell dominated transcriptomic signature. As another example, PC2 was roughly half the contribution of PC1 and was related to the difference between the presence of a low-density granulocyte (LDG)/neutrophil signature and the interferon (IFN) signature. As shown in FIG. 17, heatmap clustering of the PCA analysis demonstrated two prominent divisions between the 11 immunologically related modules in the SLE patients. Plasma cell, Immunoglobulins, Mature PC, and cell cycle grouped together (FIG. 17, left) and all the other signatures grouped together including IFN and anti-inflammation. PCA and heatmap divisions were the same between ancestries, except that more AA SLE patients were PC1− (plasma cells) than PC1+ (myeloid) and more NAA SLE patients were PC1+ (myeloid) than PC1− (plasma cell).

FIG. 18 shows PCA and heatmap clustering of AA, EA, and NAA SLE patients for 11 GSVA enrichment modules negative in healthy controls (HC). GSVA enrichment scores were uploaded to ClustVis, and PCA plots were generated. Low Up, a signature derived from SLE patients with no enrichment for IFN, PC, or myeloid cells (FCGR1A, SNORD80, SNORD44, SNORD47, SNORD24, CEACAM1, and LGALS1) changed where it grouped depending on ancestry. Heatmaps were generated using correlation clustering distance for both rows and columns. The heatmap clustering of the 11 modules revealed a dichotomy in SLE patient transcriptomic signatures; SLE patients with strong PC signatures were less likely to have strong myeloid signatures, especially in patients of AA ancestry, and in SLE patients with strong myeloid signatures, there were fewer contributing plasma cell signatures. Interferon signatures occurred with either myeloid or plasma cell signatures but were more often paired with strong monocyte signatures. Low density granulocytes/neutrophils were associated with the myeloid signature as well. Importantly, within each ancestral background, there were both plasma cell and myeloid SLE patients (FIG. 18). Steroids may be shown to be associated with low-density granulocyte enrichment and low-density granulocytes were important in both PC1 as part of the myeloid signature and the signature dominated PC2; therefore, PCA plots and heatmaps were generated for SLE patients not taking steroids. AA SLE patients not taking steroids had few patients with myeloid SLE signatures. The proportion of EA and NAA SLE patients with myeloid signatures decreased, although since most NAA SLE patients were on steroids there were very few patients in this analysis (FIG. 19).

Figure 19:
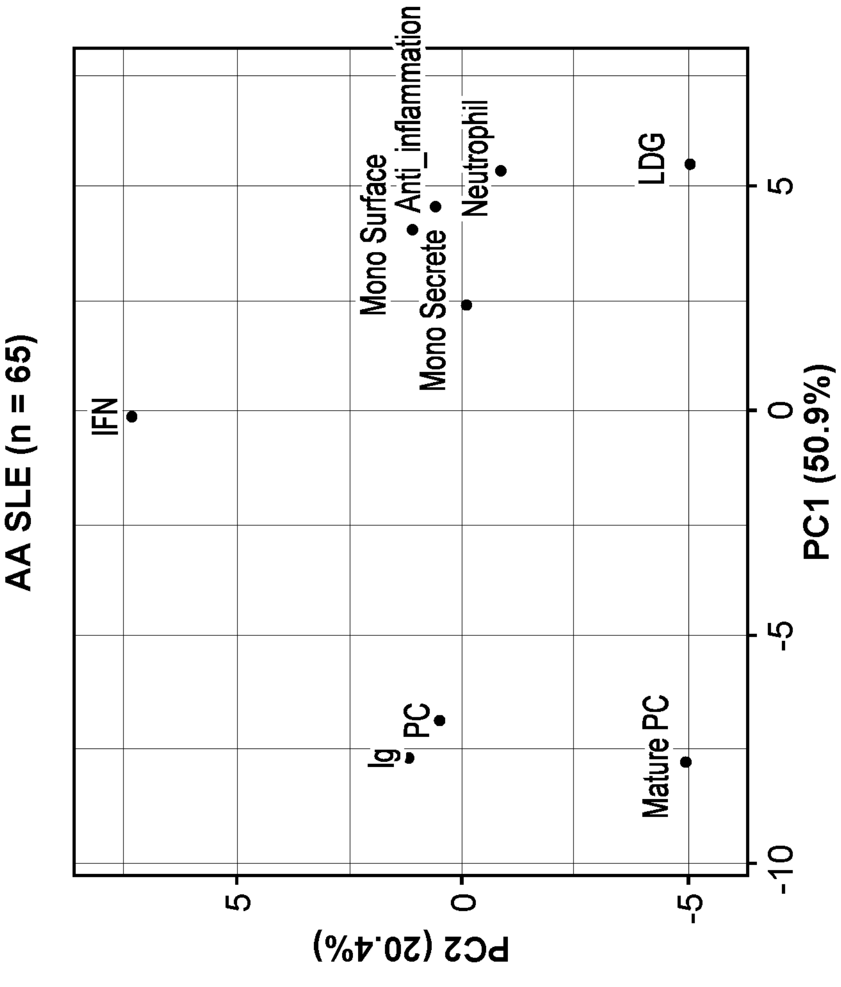
FIG. 19 shows PCA and heatmap clustering of AA, EA, and NAA SLE Patients not taking steroids for 9 GSVA enrichment modules negative in healthy controls (HC). The cell cycle and Low Up modules were removed, GSVA enrichment scores for the 9 remaining modules were uploaded to ClustVis, and PCA plots and heatmaps were generated. Heatmaps were generated using correlation clustering distance for both rows and columns.

FIG. 19 shows PCA and heatmap clustering of AA, EA, and NAA SLE Patients not taking steroids for 9 GSVA enrichment modules negative in healthy controls (HC). The cell cycle and Low Up modules were removed, GSVA enrichment scores for the 9 remaining modules were uploaded to ClustVis, and PCA plots and heatmaps were generated. Heatmaps were generated using correlation clustering distance for both rows and columns.

SLE microarray datasets have wide heterogeneity related to the disease but also because of the different platforms to measure transcripts and variability; therefore, it was important to establish that the divisions found in the 1,566 female illuminate patients (GSE88884) are applicable to SLE patients assayed on a different array platform. AA and EA SLE patients with low disease activity (SLEDAI range 2-11) from dataset GSE45291 had PC1 and PC2 components similar to GSE88884 patients and demonstrated the same dichotomy in having either a plasma cell or Myeloid cell type of SLE. As was shown for dataset GSE88884, there were a higher percentage of SLE patients with AA ancestry and plasma cell SLE, and a higher percentage of SLE patients with EA ancestry and myeloid SLE (FIG. 20).

Figure 20:
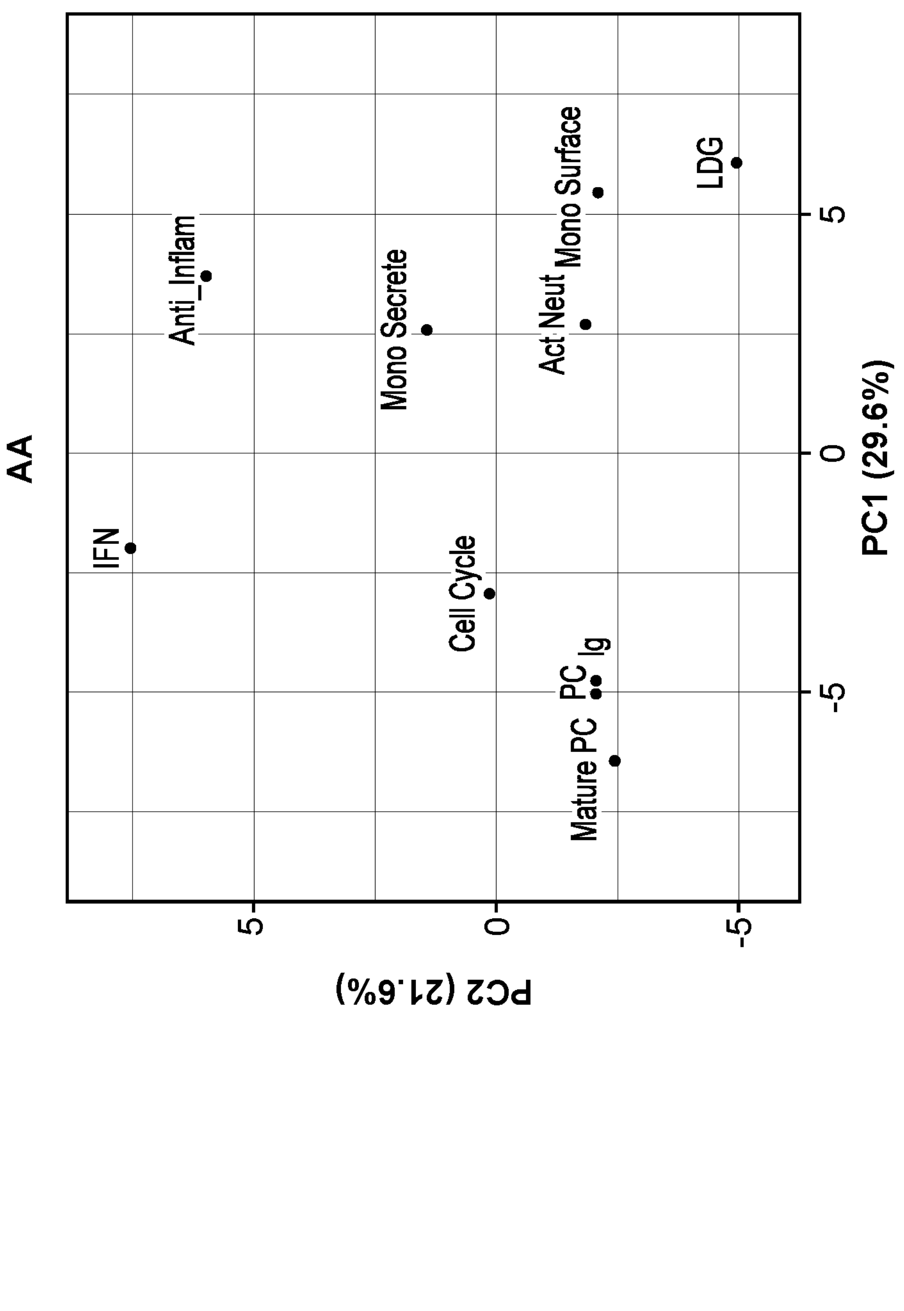
FIG. 20 shows PCA and heatmap clustering of a second, independent microarray dataset demonstrate that SLE patients divided into plasma cell or myeloid lupus. 73 AA and 71 EA patients from GSE45291 with SLEDAI in the range of 2-11 had GSVA scores calculated for 10 signatures. ClustVis was used to determine PC1 and PC2 for AA (top left) and EA (top right).

FIG. 20 shows PCA and heatmap clustering of a second, independent microarray dataset demonstrate that SLE patients divided into plasma cell or myeloid lupus. 73 AA and 71 EA patients from GSE45291 with SLEDAI in the range of 2-11 had GSVA scores calculated for 10 signatures. ClustVis was used to determine PC1 and PC2 for AA (top left) and EA (top right). Heatmaps show the patient distribution for the plasma cell related GSVA enrichment categories (Cell cycle, Mature plasma cell, plasma cell, and immunoglobulin chains) versus the myeloid cell enrichment categories (Interferon, Anti-Inflammation, Mono Surface, Mono Secrete, LDG, and Act Neut). Dataset GSE45291 was assayed on Affymetrix chip HT HG-U133+ PM which does not have probes for small nucleolar RNAs that make up most of the Low Up signature.

209 female SLE patients (13.3%) enrolled in the Illuminate clinical trial (GSE88884) had GSVA scores for the 10 immunologically related modules indistinguishable from HC (not including LowUp, which was based on patients which were difficult to distinguish from HC). These immunologically inactive SLE patients represented all three ancestry sets studied: 161 EA (14.4%), 25 AA (11.6%), and 23 NAA (10.3%); they were categorized as having no immunologically related signature (No Sig). PCA analysis was performed using the 10 immunologically related GSVA modules, and the PC1 loadings for each patient were used to determine the classification of either plasma cell or myleoid SLE based on whether they were PC1-(enriched for modules for plasma cell, Ig) or PC1+ (enriched for myeloid modules) (FIG. 21).

Figure 21:
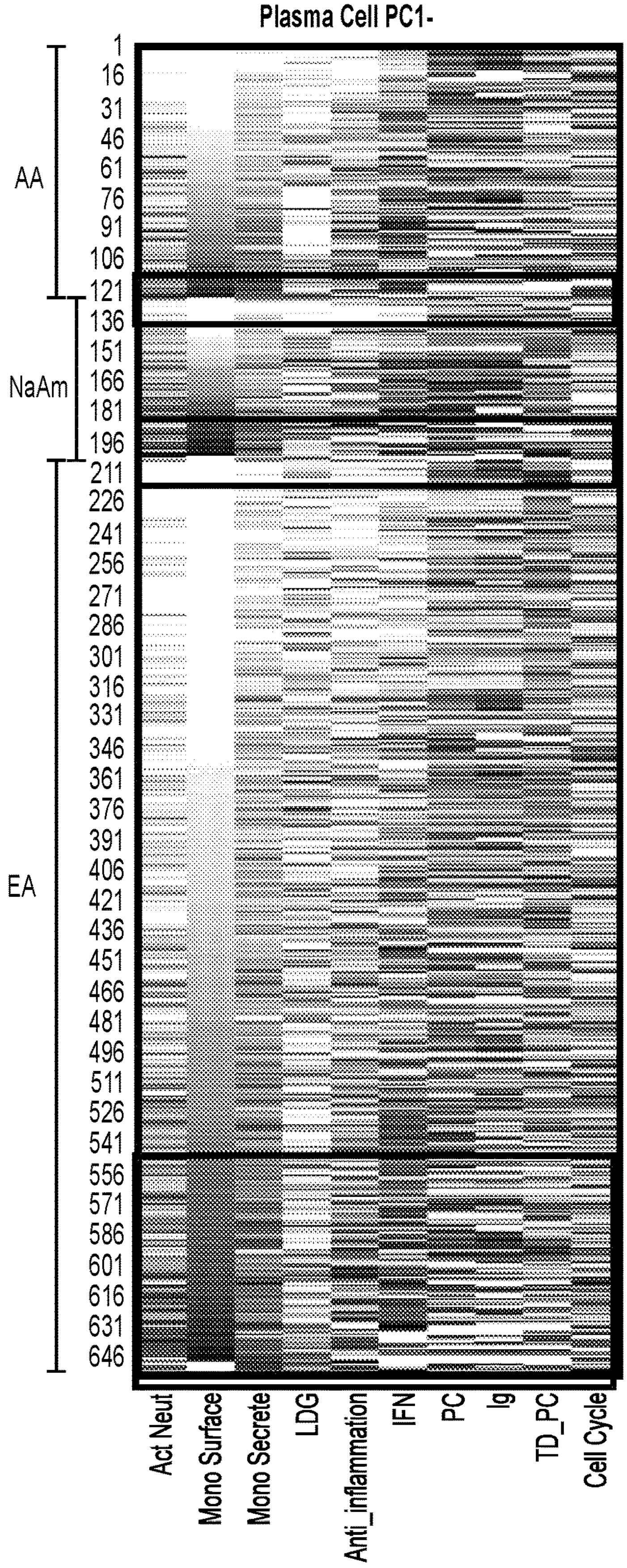
FIG. 21 shows heatmap clustering of SLE patients by enrichment of 10 immunologically related modules. SLE patients were grouped on the basis of having a negative PC1 loading score (plasma cell, left), a positive PC1 loading score (myeloid, middle), no enrichment of the 10 modules (No Sig, right). SLE patients within Plasma Cell or Myeloid that also expressed the opposite signature, as defined by either having a Mono GSVA enrichment score of at least 0.1, are identified by black boxes.

FIG. 21 shows heatmap clustering of SLE patients by enrichment of 10 immunologically related modules. SLE patients were grouped on the basis of having a negative PC1 loading score (plasma cell, left), a positive PC1 loading score (myeloid, middle), no enrichment of the 10 modules (No Sig, right). SLE patients within Plasma Cell or Myeloid that also expressed the opposite signature, as defined by either having a Mono GSVA enrichment score of at least 0.1, are identified by black boxes.

SLE disease measures were compared for each ancestry between PC1−, PC1+, and No Sig SLE patients. Although the average SLEDAI was generally higher for SLE patients expressing either PC or Myeloid modules compared to the No Sig group of patients, there was not a discernable cut-off for a SLEDAI which was suitable for defining a patient with no transcriptional sign of immunological perturbation. The mean SLEDAI was significantly higher (p<0.05 by Tukey's multiple comparisons test) for myeloid among AA patients, plasma cell and myeloid among EA patients, and plasma cell for NAA patients, as compared to the No Sig category within each ancestry. No significant difference in SLEDAI was found between SLE patients with myeloid versus plasma cell SLE. Steroid usage was significantly higher (p<0.05) for the myeloid signature for all three ancestries (Table 12).

TABLE 12

Disease differences between PC1−, PC1+, and No Sig categories

| | AA (n = 216) | | | EA (n = 1118) | | | NaAm (n = 232) | | |
|---|---|---|---|---|---|---|---|---|---|
| | PC1− | PC1+ | No Sig | PC1− | PC1+ | No Sig | PC1− | PC1+ | No Sig |
| n | 125 | 66 | 25 | 449 | 508 | 161 | 80 | 129 | 23 |
| average SLEDAI | 10.73 | 10.97^ | 8.8 | 10.74$ | 10.21$$ | 9.35 | 11.80* | 11.124 | 9.04 |
| median SLEDAI | 10 | 10 | 8 | 10 | 10 | 8 | 11 | 10 | 8 |
| mode SLEDAI | 8 | 8 | 8 | 10 | 8 | 8 | 12 | 10 | 8 |
| # Manifest | 3.6 | 3.8 | 3.2 | 3.8 | 3.6 | 3.2 | 4 | 4 | 35 |
| average steroid | 7.99 | 9.83^^ | 4.2 | 9.05$ | 9.47$$ | 4.13 | 10.76 | 12.98## | 6.52 |
| median steroid | 5 | 10 | 0 | 7.5 | 10 | 0 | 10 | 10 | 5 |
| mode steroid | 0 | 10 | 0 | 0 | 10 | 0 | 10 | 10 | 5 |
| MMF or MTX (n) | 16.8% (21) | 41% (27) | 16% (4) | 12.2% (55) | 22% (113) | 19% (31) | 24% (19) | 36% (47) | 22% (5) |
| dsDNA (n) | 40% (50) | 32% (21) | 20% (5) | 22% (98) | 20% (133) | 10% (25) | 23% (18) | 30% (39) | 17% (4) |
| lowC (n) | 3% (4) | 1 1% (7) | 0% | 8% (37) | 7% (38) | 119% (18) | 8% (6) | 8% (10) | 4% (1) |
| dsDNA + lowC (n) | 27% (34) | 24% (16) | 8% (2) | 45% (200) | 30% ( 152) | 7% (12) | 51% (41) | 28% (46) | 13% (3) |

^AA SLEDAI PC1+ 10 No sig = .05

^^AA SLEDAI PCT+ Savokf to No Sig p =. 02

ANOVA & Turkey's Multiple Comparison

#EA SLEDAI PC1− to No Sig p = .0001

EA SLEDAI PCl+ to No Sig p = .03

$EA Steroid PC1− to No Sig p < .0001

$$EA Steroid PC1+ to No Sig p < .0001

*NaAm SLEDI PC1 to No Sig p = .02

=NaAm Seroid PC1+ 1= No Sig p = .001

A heatmap visualization of the different ancestral SLE patients together as plasma cell, myeloid, or No Sig was generated; it revealed SLE patients with both plasma cell and myeloid signatures. Patients with both signatures (as determined by having a GSVA enrichment score 2 standard deviations above healthy control GSVA scores for both the myeloid and the plasma cell signatures) were combined to form a new group, "Both" (FIGS. 22A-22B).

Figure 22A:
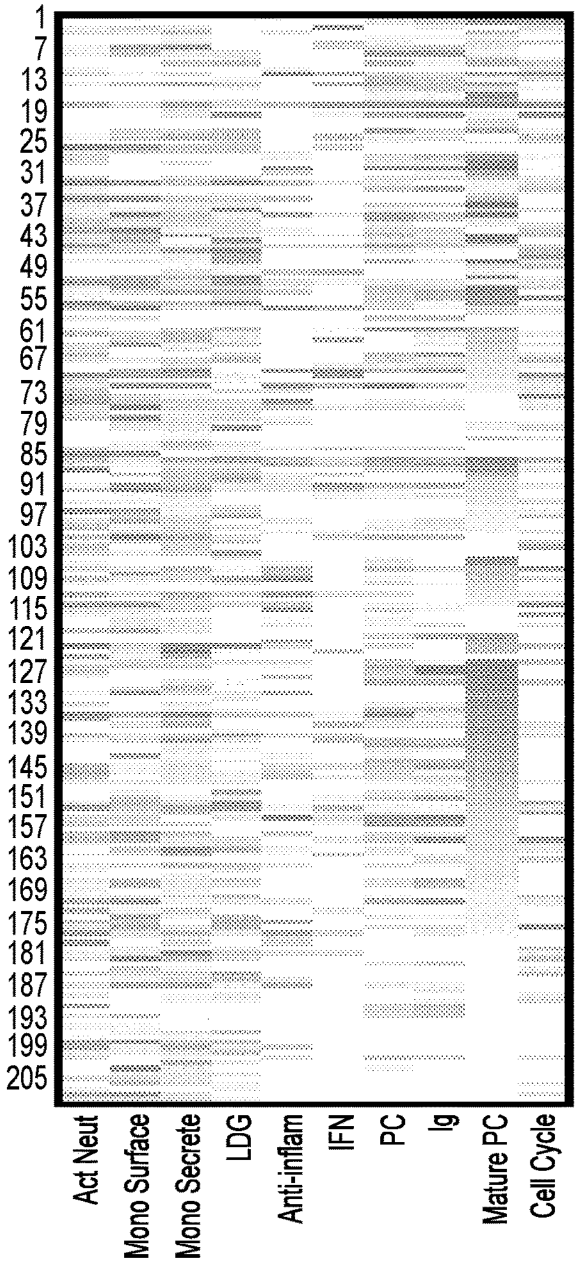
FIGS. 22A-22B show heatmap clustering of SLE patients by enrichment of 10 immunologically related modules. Four divisions were found for the 1,566 female SLE patients enrolled in the ILL clinical trials. Based on PC1 loadings for PCA of patients, PC and myeloid SLE patients were sorted by the opposite GSVA enrichment signature: monocyte cell surface for the PC signature (PCA PC1-) and Ig for the myeloid signature (PCA PC1+), and SLE patients with GSVA enrichment scores of at least 0.1 for the opposite signature were removed and reclassified as having both signatures (FIG. 22A). SLE patients of all ancestries were grouped based on the four classifications. ANOVA and Tukey's multiple comparisons test was performed between the four groupings (FIG. 22B).
Figure 22B:
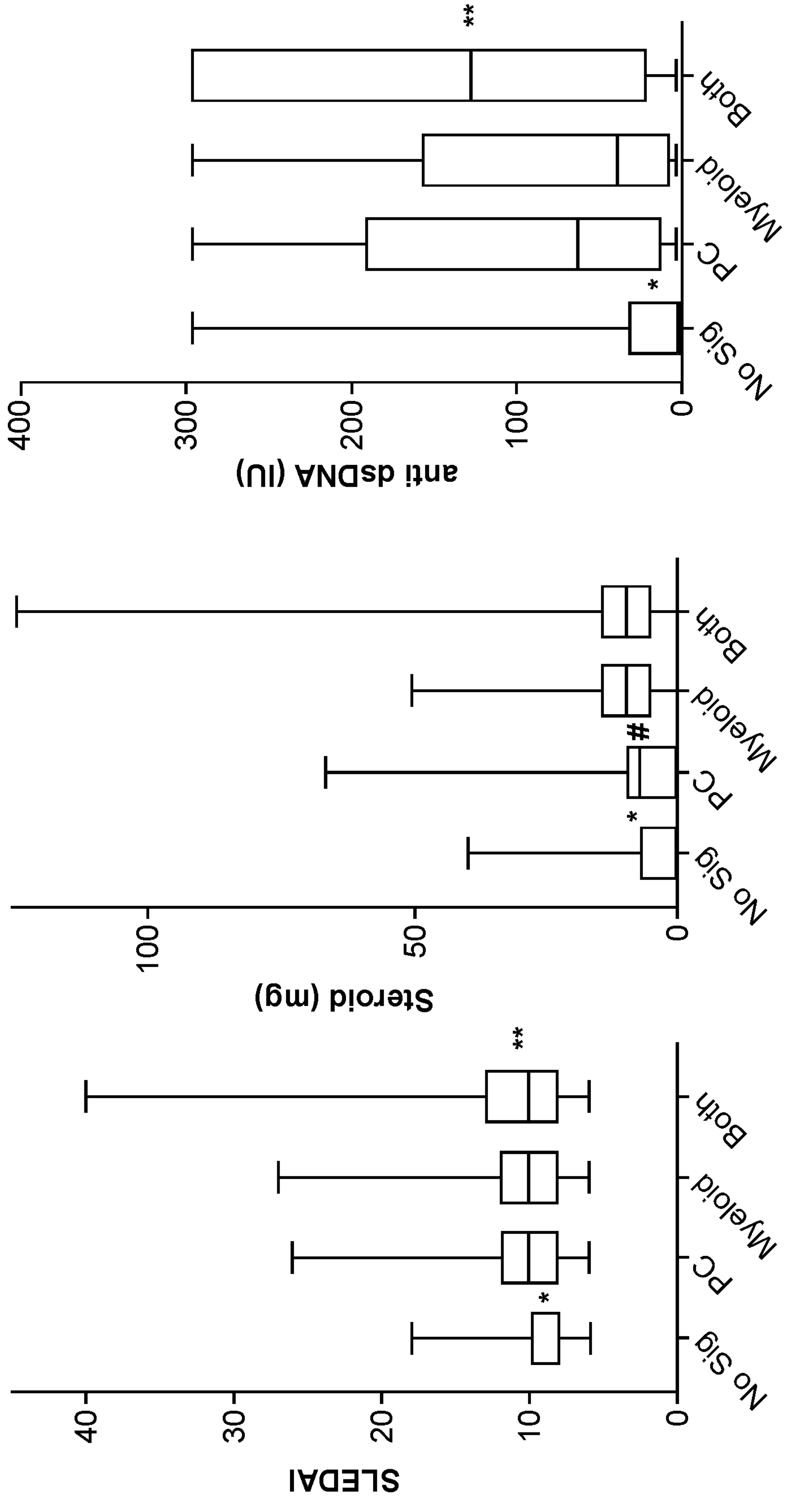
Figure 22B:
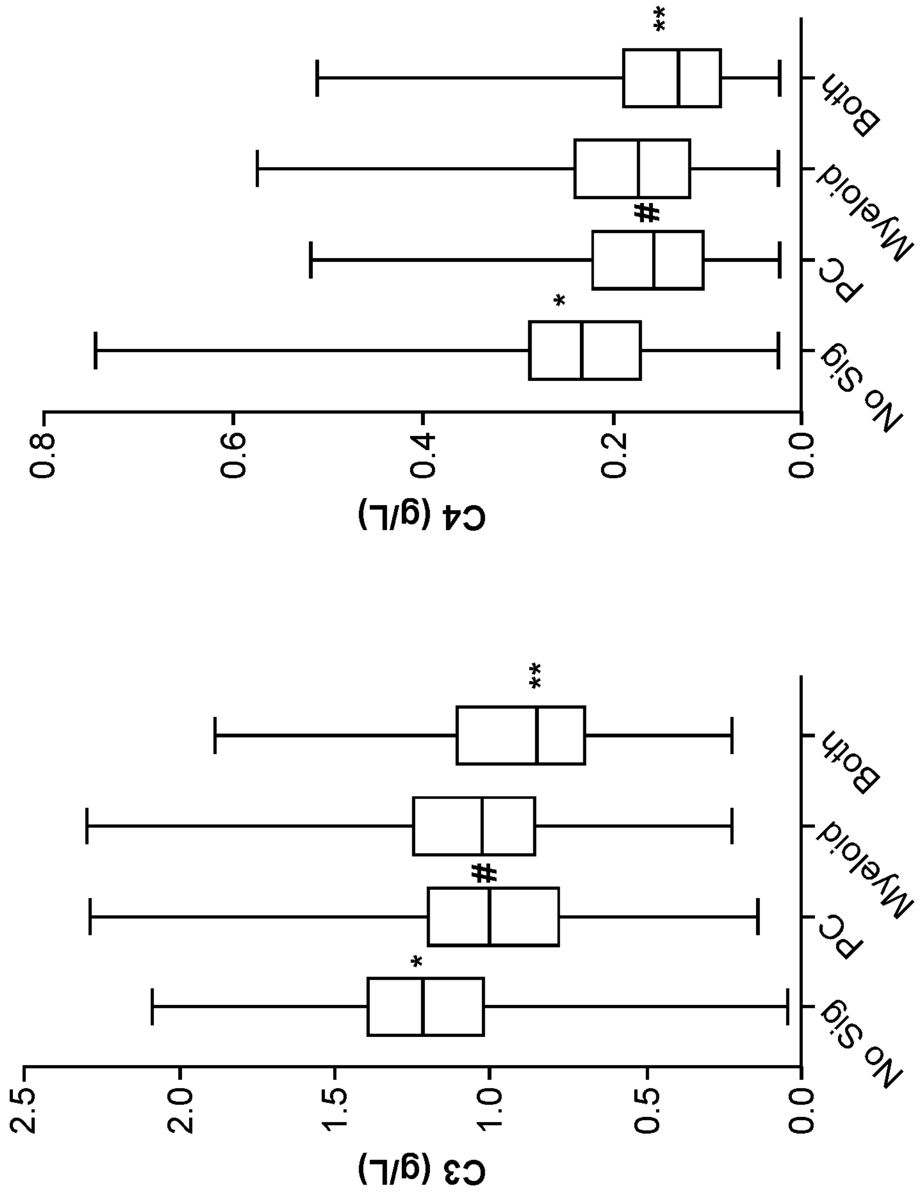
Figure 23A:
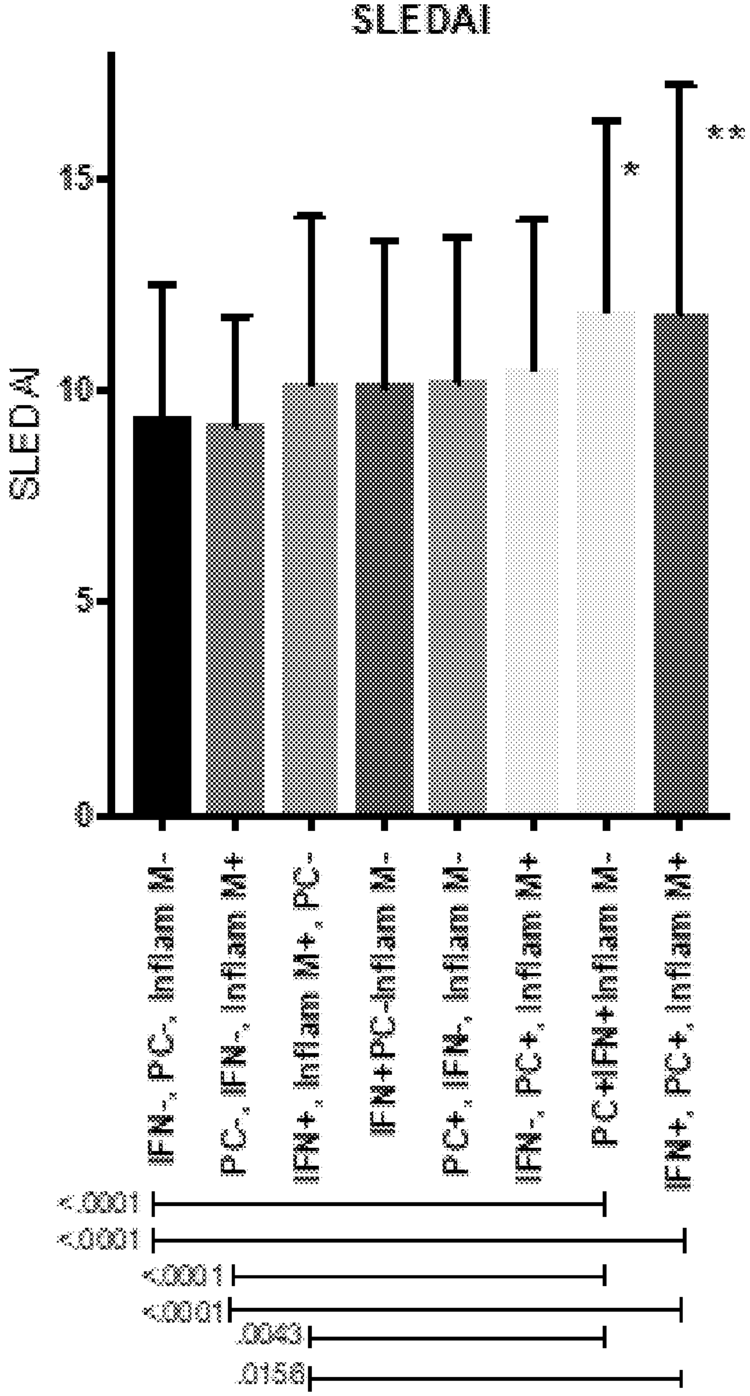
FIGS. 23A-23D show the correlation between clinical measures of disease activity and WGCNA modules. Patients were divided into sub-groups based on their expression of positive eigengenes for each category. Significant differences between clinical traits were determined between group using PRISM v7 Tukey's multiple comparison test, and p values are shown between groups when less than or equal to 0.05.
Figure 23B:
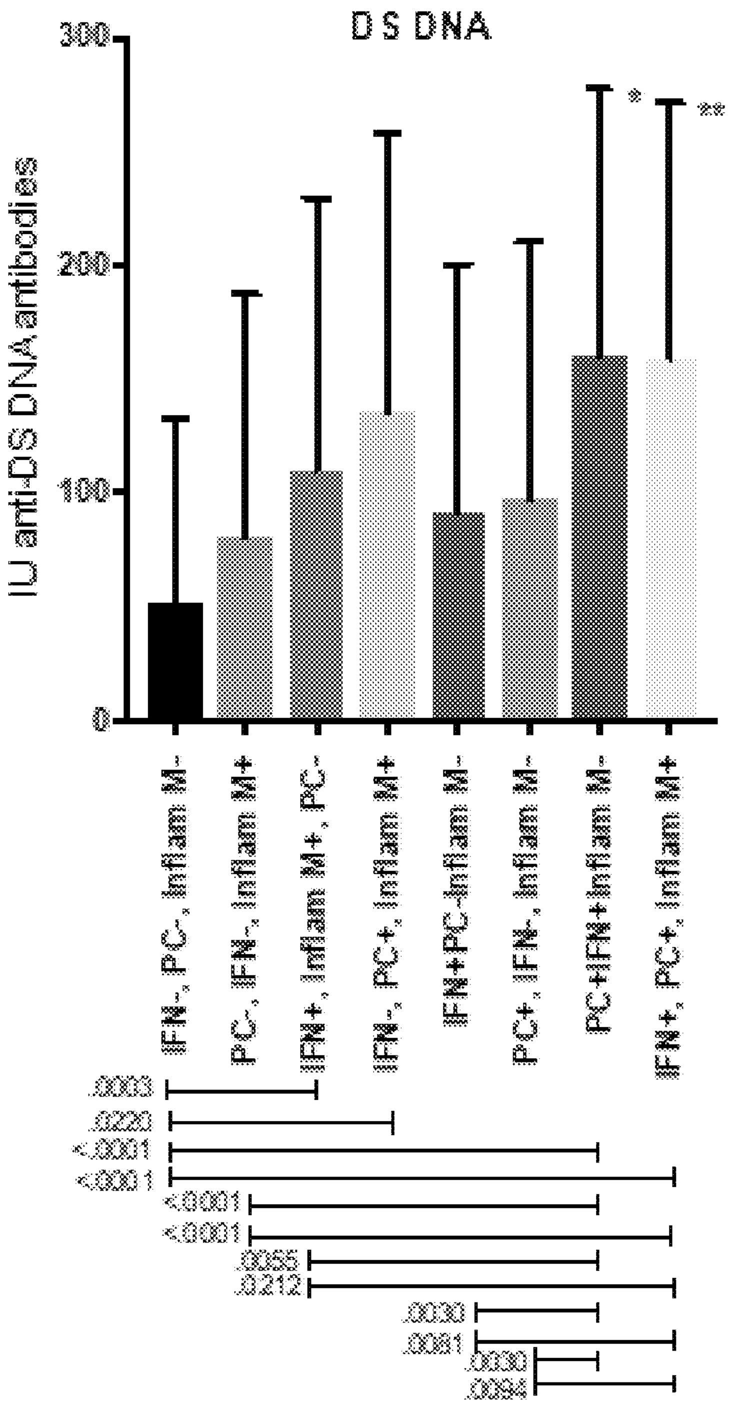
Figure 23C:
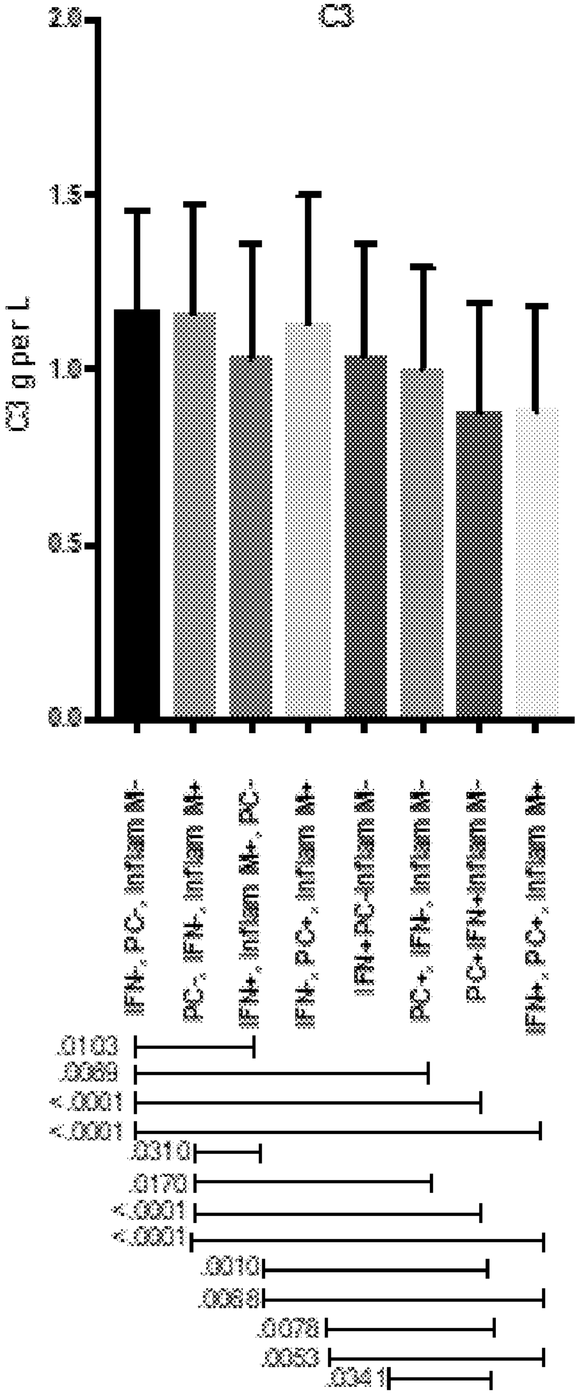
Figure 23D:
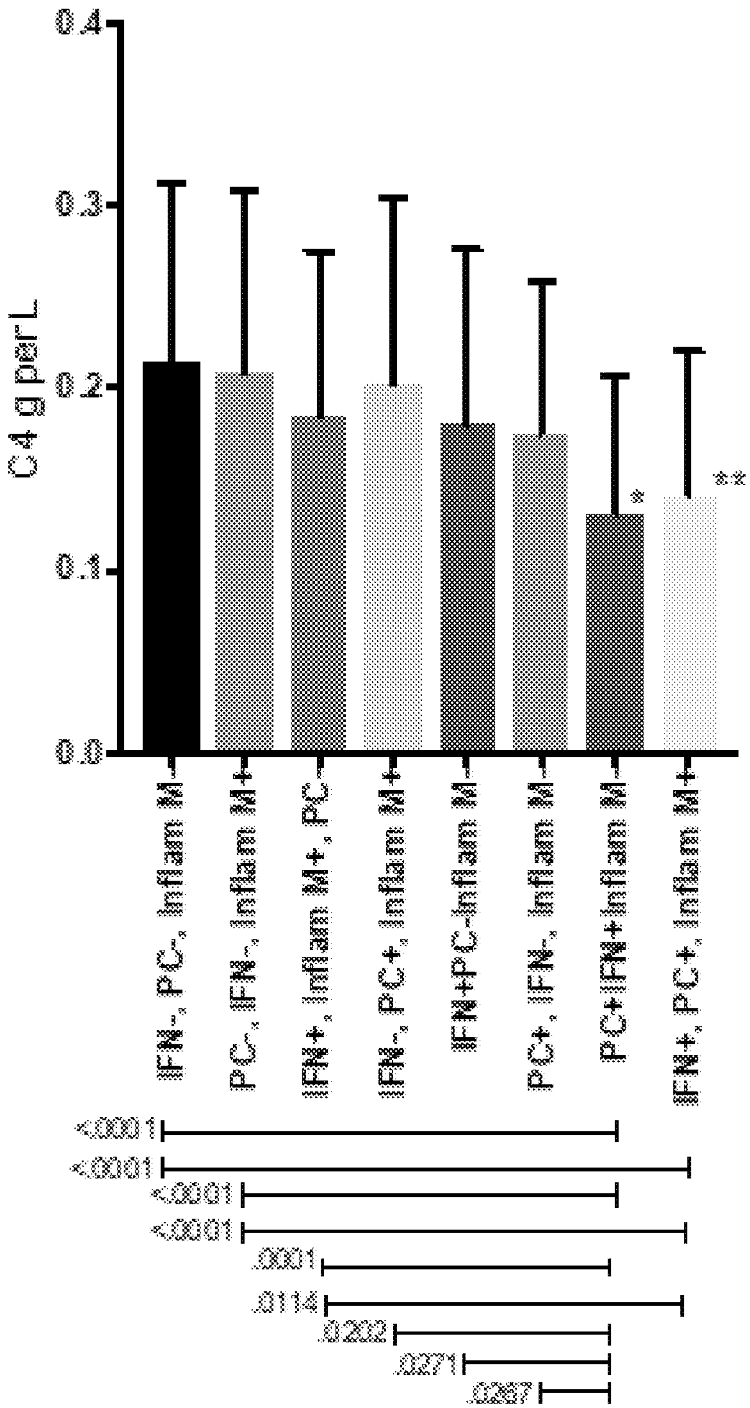

FIGS. 22A-22B show heatmap clustering of SLE patients by enrichment of 10 immunologically related modules. Four divisions were found for the 1,566 female SLE patients enrolled in the ILL clinical trials. Based on PC1 loadings for PCA of patients, PC and myeloid SLE patients were sorted by the opposite GSVA enrichment signature: monocyte cell surface for the PC signature (PCA PC1-) and Ig for the myeloid signature (PCA PC1+), and SLE patients with GSVA enrichment scores of at least 0.1 for the opposite signature were removed and reclassified as having both signatures (FIG. 22A). SLE patients of all ancestries were grouped based on the four classifications. ANOVA and Tukey's multiple comparisons test was performed between the four groupings (FIG. 22B). For SLEDAI, No sig* was significantly lower from PC, Myeloid, and Both ($p<0.05$), and Both** was significantly ($p<0.05$) higher than PC and Myeloid. For steroid usage, No sig* was significantly lower ($p<0.0001$) than all other groups. PC was significantly lower than Both ($p=0.0053$). For aDS DNA, No sig* was significantly lower ($p<0.0001$) than all other groups and Both** was significantly higher ($p<0.0001$) than all other groups. For complement C3 and C4, all groups were significantly different ($p<0.01$) from each other; No sig* had the highest values, followed by myeloid. PC had lower values than No Sig and Myeloid, but Both** had the lowest C3 and C4 values.

Heatmap clustering of the four groups demonstrated that similar percentages of AA, EA, and NAA patients were found in the No Sig (AA 12%, NAA 12%, EA 13%) and Both (AA 25%, NAA 26%, EA 22%) groups, but there were a higher percentage of AA patients in the plasma cell only ($p<0.05$, Fisher's Exact Test; AA 42%, NAA 20%, EA 29%) and NAA in myeloid only ($p<0.05$ Fisher's Exact Test; AA 21%, NaAm 44%, EA 35%) (FIG. 22A). Comparison of the SLEDAI, steroid dose, anti-double stranded DNA levels, C3, and C4 serum measurements by ANOVA revealed significant differences between the groups. The No Sig classification with no immunologic transcriptomic signatures had the lowest SLEDAI and anti-double stranded DNA levels, and the highest C3 and C4 levels. Interestingly, this group was also taking the least amount of corticosteroids. SLE patients with both a myeloid and a plasma cell transcriptomic signature had the highest SLEDAI and highest percentage of anti-double stranded DNA values, and the lowest C3 and C4 values. This group was taking similar steroids to the myeloid only group and significantly more steroids than the No Sig or plasma cell only group. The plasma cell only and myeloid only groups were similar for SLEDAI and anti-double stranded DNA levels, but the plasma cell group had significantly lower C3 and C4 levels and were taking less steroids (FIG. 22B).

The Low Up Category was derived from the highest overexpressed transcripts by log fold change ($FDR<0.05$) between patients not separated from healthy control after initial PCA analysis of all the GSE88884 dataset log 2 expression values. This signature was expressed in 30% of the No Sig SLE patients and was increased in more immunologically transcriptomic patients: plasma cell only, 39% (180/456); myeloid only, 55% (298/544); and Both, 71% (254/357).

Example 4: Molecular Endotyping Analysis for Identifying Subsets of Patients with Systemic Lupus Erythematosus Who are Candidates to be Enrolled in Clinical Trials and Have a Propensity to Respond to Specific Drugs Using methods and systems of the present disclosure, molecular endotyping analysis may be performed for identifying subsets of patients with Systemic Lupus Erythematosus who are candidates to be enrolled in clinical trials and have a propensity to respond to specific drugs.

Weighted gene co-expression network analysis (WGCNA) was performed, using a computer program in R that takes a microarray or RNAseq dataset and identifies modules (groups) of genes that are co-expressed in a similar manner in the samples and or controls. Each individual sample is designated with a positive or negative value for each module indicating whether the individual sample co-expresses the genes in the module or does not. The number of groups or modules WGCNA identifies is unbiased in that there is no preconceived number of modules in a data set. The gene expression value of a module (eigengene) is used to determine whether an individual patient expresses a module or modules, whether groups of patients can be identified who express a similar constellation of modules and, also, whether there are patterns to the groupings. This approach can also be employed to determine whether positivity of specific WGCNA modules is correlated to SLE disease measures, such as disease activity, autoantibodies, and complement abnormalities. and other confounding factors such as patient ancestry.

WGCNA was performed on a set of 810 female systemic lupus erythematosus (SLE) patients and 11 healthy control whole blood samples. Patients were mainly of European ancestry (EA), African ancestry (AA), or Southern Native American ancestry (NAA; Guatemala, Peru, Ecuador) ancestry. The WGCNA results identified 13 discrete modules. Characterization of the modules was performed using multiple programs, such as CellScan and I-scope to determine whether a module was enriched in cellular markers corresponding to a specific cell type, and BIG-C to determine whether modules were enriched in specific cellular function or process. This analysis revealed prominent signatures related to cell types and processes, IFN signaling, and MicroRNA in 12 of the 13 modules. One module, turquoise (modules are randomly designated with colors for convenience), had more than 5,000 genes and no discernable cell type or function. This module also had the lowest percentage of genes that were differentially expressed between SLE patients and controls in separate limma analysis (for example, AA to CTL only had 1.67% of the turquoise genes differentially expressed (DE) compared to CTL).

TABLE 13

WGCNA modules identified in SLE patients.

| | number of genes DE to control | Percent Positive of DE transcripts in Module IFN black | PC magenta | Lymphocytes blue | IL1, Inflamm myeloid brown | unknown turquoise | T cell, SNOR As pink | Platelets purple |
|---|---|---|---|---|---|---|---|---|
| AA to ctl | 1591 | 70.03 | 15.58 | 16.32 | 10.13 | 1.67 | 6.55 | 14.04 |
| EA to ctl | 1906 | 71.18 | 6.49 | 18.25 | 25.11 | 2.62 | 17.86 | 3.51 |
| NaAm to ctl | 6580 | 85.59 | 20.35 | 74.38 | 64.76 | 9.82 | 32.14 | 23.98 |

| | number of genes DE to control | Percent Positive of DE transcripts in Module Erythrocytes green | Micro RNA cyan | Myeloid light cyan | NKTR IL16 red | Granulocytes/ Basophils midnight blue | CD14+ TGFB1+ yellow |
|---|---|---|---|---|---|---|---|
| AA to ctl | 1591 | 6.95 | 2.8 | 4.71 | 7.79 | 7.49 | 3.56 |
| EA to ctl | 1906 | 4.63 | 0.93 | 7.58 | 15.15 | 10.08 | 3.21 |
| NaAm to ctl | 6580 | 26.77 | 37.58 | 25.42 | 45.45 | 42.64 | 25.19 |

Modules with negative eigengene values in healthy human controls were the IFN PRR module (black), plasma cell module (magenta), inflammatory myeloid module (brown), MicroRNA module (cyan) and platelet module (purple). Modules with positive expression in healthy controls were NKTR (red), lymphocytes (blue) and T cells (pink) (Table 14).

TABLE 14

WGCNA modules and their eigengene values in healthy controls

| | Decreased in Controls IFN black | Plasma Cells magenta | Inflammatory Myeloid Cells, IL1, Tons of Secreted Protein Genes brown | MicroRNA TNFSF4 cyan | Platelets purple |
|---|---|---|---|---|---|
| CTL.0073.NA | −0.06 | −0.03 | −0.07 | −0.03 | −0.01 |
| CTL.0106.NA | −0.04 | −0.02 | −0.04 | −0.02 | −0.04 |
| CTL0256.NA | −0.05 | −0.01 | −0.04 | −0.01 | 0.00 |
| CTL.0343.NA | −0.04 | −0.04 | 0.02 | 0.04 | −0.02 |
| CTL.0388.NA | −0.05 | −0.02 | −0.03 | 0.00 | −0.01 |
| CTL.0581.NA | −0.06 | −0.03 | −0.03 | −0.01 | −0.01 |
| CTL.0812.NA | −0.05 | −0.03 | 0.00 | 0.01 | 0.04 |
| CTL.0879.NA | −0.06 | −0.02 | 0.00 | 0.00 | −0.02 |
| CTL.1403.NA | −0.03 | −0.02 | −0.02 | 0.00 | 0.00 |
| CTL.1406.NA | −0.04 | −0.01 | −0.01 | 0.03 | −0.01 |
| CTL.1703.NA | −0.04 | 0.00 | −0.03 | −0.02 | 0.00 |

| | Modules with variable expression in Controls Myeloid, SELL, TBK1, CD16, SYK, TANK, IRAK4, AOAH, not activated light cyan | Basophils-VEGFA, METRNL, OSM, LCAT, LTBR, LILRB5, LCE1F, S1PR4 mignight blue | CD14 Monocytes, oxphos and tca cycle, peroxisomes, proteasome, TGFB1, TNFSF8, IK, LYZ, FCN2, HBB, HAVCR2, CCR2+, nMS4A6A, BTN3A3, yellow | Erythrocytles, GYPAE, GYPAB, KEL, RHD, BSG green | No discernable cell type or function module >5000 turquoise |
|---|---|---|---|---|---|
| CTL.0073.NA | −0.06 | 0.00 | −0.03 | 0.03 | 0.04 |
| CTL.0106.NA | −0.03 | 0.00 | −0.02 | −0.05 | 0.02 |
| CTL0256.NA | −0.04 | −0.01 | −0.01 | 0.05 | 0.01 |
| CTL.0343.NA | 0.05 | −0.03 | 0.05 | 0.01 | −0.04 |

TABLE 14-continued

| WGCNA modules and their eigengene values in healthy controls | | | | | |
|---|---|---|---|---|---|
| CTL.0388.NA | 0.01 | −0.03 | 0.03 | −0.03 | −0.01 |
| CTL.0581.NA | −0.04 | 0.00 | −0.02 | 0.06 | 0.02 |
| CTL.0812.NA | −0.01 | 0.01 | −0.02 | 0.05 | 0.03 |
| CTL.0879.NA | −0.02 | 0.02 | −0.02 | 0.03 | 0.04 |
| CTL.1403.NA | 0.00 | −0.02 | 0.01 | −0.01 | −0.01 |
| CTL.1406.NA | 0.02 | −0.03 | 0.04 | −0.02 | −0.04 |
| CTL.1703.NA | 0.00 | −0.05 | 0.04 | −0.02 | −0.02 |

| | Increased in Controls | | |
|---|---|---|---|
| | NKTR, IL16 T cell receptor J chains red | Lymphocytes, T cells, B cells blue | T cells pink |
| CTL.0073.NA | 0.02 | 0.01 | 0.05 |
| CTL.0106.NA | 0.00 | 0.02 | 0.03 |
| CTL0256.NA | 0.02 | 10.01 | 0.04 |
| CTL.0343.NA | 0.06 | 0.02 | 0.02 |
| CTL.0388.NA | 0.04 | 0.04 | 0.01 |
| CTL.0581.NA | 10.00 | 0.00 | 0.02 |
| CTL.0812.NA | −0.01 | −0.02 | 0.00 |
| CTL.0879.NA | −0.01 | 0.00 | 0.02 |
| CTL.1403.NA | 0.03 | 0.03 | 0.02 |
| CTL.1406.NA | 0.0 | 0.04 | 0.04 |
| CTL.1703.NA | 0.04 | 0.06 | 0.01 |

As shown in Table 15, WGCNA identified four modules with correlation to the presence of SLE: IFN signaling and pattern recognition receptors (black), plasma cells (magenta), inflammatory myeloid cells (brown) and T cells (pink). The IFN and plasma cell modules had a relationship to the lupus disease activity measure SLEDAI and also to anti-double stranded DNA antibodies (dsDNA) and a negative relationship to complement protein C3 and C4 levels, important serum components associated with active SLE disease. Inflammatory myeloid cells were significantly correlated to anti-double stranded DNA, but not to low complement or the SLEDAI. T cells (pink) had a negative correlation to the SLE cohort and a negative relationship to the presence of anti-double stranded DNA autoantibodies and a positive relationship to complement C3 and C4 levels.

TABLE 15

WGCNA module correlations in 810 female SLE patients

| WGNA Module Correlations . . . | assigned color | module Count | Cohort | Cohort p | SLEDAI |
|---|---|---|---|---|---|
| IFN and PRR | black | 347 | 0.16 | 3.6E−06 | 0.25 |
| Plasma Cells | magenta | 231 | 0.07 | 0.05778 | 0.22 |
| Inflammatory Myeloid Cells | brown | 908 | 0.07 | 0.03332 | 0.05 |
| Micro RNA | cyan | 322 | 0.00 | 0.9426 | 0.04 |
| Platelets | purple | 171 | 0.02 | 0.50223 | −0.03 |
| Myeloid.Not activated. | light cyan | 594 | 0.04 | 0.3008 | 0.05 |
| Basophils | midnight blue | 387 | 0.04 | 0.28478 | 0.03 |
| T cells | pink | 336 | 0.08 | 0.01916 | 0.04 |
| Lymphocytes T and B cells, mRNA translation | blue | 3365 | −0.06 | 0.06677 | −0.03 |
| NKTR, IL16 | red | 462 | −0.07 | 0.05007 | 0.01 |
| Unknown | turquoise | 5569 | −0.01 | 0.74594 | −0.04 |
| Monocyte TGFB1 CCR2+ | yellow | 1433 | −0.01 | 0.68829 | 0.05 |
| Erythrocytes | green | 691 | 0.03 | 0.4157 | −0.06 |

| WGNA Module Correlations . . . | SLEDAI.p. | dsDNAIU | dsDNAIU.p | C3 GperL |
|---|---|---|---|---|
| IFN and PRR | 9.9E−13 | 0.30 | 4.9E−19 | 0.32 |
| Plasma Cells | 9.7E−11 | 0.29 | 1.8E−17 | −0.32 |
| Inflammatory Myeloid Cells | 0.18802 | 0.10 | 0.0054 | 0.00 |
| Micro RNA | 0.20196 | 0.00 | 0.99021 | 0.10 |
| Platelets | 0.33369 | 0.02 | 0.48014 | 0.20 |

TABLE 15-continued

| WGCNA module correlations in 810 female SLE patients | | | | |
|---|---|---|---|---|
| Myeloid.Not activated. | 0.16035 | 0.10 | 0.00622 | −0.05 |
| Basophils | 0.43885 | −0.02 | 0.59274 | 0.10 |
| T cells | 0.20566 | −0.16 | 5.1E−06 | 0.18 |
| Lymphocytes T and B cells, mRNA translation | 0.39424 | −0.03 | 0.40269 | −0.08 |
| NKTR, IL16 | 0.87992 | −0.06 | 0.09848 | 10.05 |
| Unknown | 0.23356 | −0.07 | 0.03969 | 0.09 |
| Monocyte TGFB1 CCR2+ | 0.19486 | 10.07 | 0.05707 | −0.12 |
| Erythrocytes | 0.10228 | −0.11 | 0.00246 | 0.21 |

. . . WGNA Module Correlations

| | assigned color | C3 GperL.p | C4 GperL | C4 GperL.P | RaceAA |
|---|---|---|---|---|---|
| IFN and PRR | black | 2.5E−21 | −0.28 | 1.2E−16 | 0.04 |
| Plasma Cells | magenta | 1.4E−21 | −0.30 | 2E−18 | 0.12 |
| Inflammatory Myeloid Cells | brown | 0.91912 | −0.01 | 0.80436 | −0.11 |
| Micro RNA | cyan | 0.00379 | 0.09 | 0.01468 | 0.00 |
| Platelets | purple | 3.3E−09 | 0.16 | 2.8E−06 | 0.10 |
| Myeloid.Not activated. | lightcyan | 0.16016 | −0.05 | 0.14122 | −0.07 |
| Basophils | midnight blue | 0.00341 | 10.09 | 0.01196 | 0.01 |
| T cells | pink | 1.1E−0 | 0.17 | 1.5E−06 | 0.12 |
| Lymphocytes T and B cells, mRNA translation | blue | 0.0149 | −0.08 | 10.0223 | 0.03 |
| NKTR, IL16 | red | 0.17912 | 0.05 | 0.1911 | 0.06 |
| Unknown | turquoise | 0.01398 | 0.08 | 0.02564 | 0.02 |
| Monocyte TGFB1 CCR2+ | yellow | 0.00085 | −0.11 | 0.00137 | −0.01 |
| Erythrocytes | green | 8.4E−10 | 0.15 | 1E−05 | 0.06 |

. . . WGNA Module Correlations

| | RaceAA.p | RaceNaAm | Race-NaAm.p | RaceEA | RaceEA.p |
|---|---|---|---|---|---|
| IFN and PRR | 0.2396 | 0.08 | 0.03115 | −0.08 | 0.02481 |
| Plasma Cells | 0.00088 | 0.06 | 0.07102 | −0.06 | 0.10054 |
| Inflammatory Myeloid Cells | 0.00162 | 0.11 | 0.00202 | 0.02 | 0.4957 |
| Micro RNA | 0.96314 | 0.13 | 0.00022 | −0.08 | 0.02075 |
| Platelets | 0.00622 | 0.07 | 0.04613 | −0.12 | 0.0004 |
| Myeloid.Not activated. | 0.05153 | 0.01 | 0.70275 | 0.07 | 0.0369 |
| Basophils | 0.6846 | 0.17 | 9.5E−07 | −0.14 | 3.6E−05 |
| T cells | 0.0007 | 0.03 | 0.35564 | −0.11 | 0.00114 |
| Lymphocytes T and B cells, mRNA translation | 0.42534 | −0.19 | 3.4E−08 | 0.14 | 9.8E−05 |
| NKTR, IL16 | 0.08086 | −0.05 | 0.13721 | 0.01 | 0.77421 |
| Unknown | 0.55253 | 0.08 | 0.02007 | −0.09 | 0.00694 |
| Monocyte TGFB1 CCR2+ | 0.76358 | −0.11 | 0.00199 | 0.12 | 0.00077 |
| Erythrocytes | 0.08531 | 0.09 | 0.00851 | −0.12 | 0.00036 |

In order to understand whether the three modules with positive correlation to the SLE cohort were related to other modules, the categories IFN PRR (black), plasma cell (magenta), and inflammatory myeloid (brown) were investigated further. The percentage of patients with positive eigengenes for each category was determined, and whether or not patients with positive eigengenes for one of these three gene modules were also positive for the other gene modules was determined. Table 16 demonstrates that patients positive for the IFN module were evenly split with regard to positivity of all other modules, except for the (myeloid not activated) (66%) and the (CD14 monocyte, TGFB1) modules (63%). Patients with positive eigengene values for the plasma cell module were also more likely to be IFN positive (72%), (CD14 TGFB1) positive (68%) and lymphocyte module positive (72%). Patients with inflammatory myeloid cell modules were likely to have positive eigengenes for the MicroRNA module (75%), (myeloid not activated) module (78%), basophils or granulocytes (67%), and negative eigengenes for lymphocytes (35%).

had positive eigengenes for the no identity module (72%) and T cells (67%). They were also likely negative for the MicroRNA module (26%+), myeloid not activated module (12%+), and CD14+TGFB1 monocyte (30%+). Whereas plasma cell and myeloid positive eigengenes were not mutually exclusive, they were unlikely to come together without also having an IFN signature (3%) and it was more common for these signatures to be alone (plasma cell+IFN 17% of patients, myeloid+IFN 16% of patients) than together with the IFN signature (13% of patients). These three patterns of signatures comprised 46% of the total patients (Table 16).

Next, the relationship between these modules and SLE disease activity was determined. The four disease measures considered were the SLEDAI, IU of anti-double stranded autoantibodies, g per L complement C3 and C4. As shown in FIGS. 23A-23D, for all disease measures, categories with plasma cells had higher measures of disease activity (increased SLEDAI, autoantibodies, Low C3, C4) than categories without, but the highest disease measures were when patients had positive eigengene values for both PC and the IFN signature.

TABLE 16

Percentage of Patients in Each Category with Positive Eigengene Values
Percentage of patients in each category with positive eigengene values

| | n | % Patients Positive | IFN PRR | Plasma Cell | Myeloid Inflam. | Micro RNA | Platelets | Myeloid not activated | Baso-philis | CD14, TGFB1 | Eryth-rocyte | No Identity | NKT R-IL16 | Lymp-hocyte | T cells |
|---|---|---|---|---|---|---|---|---|---|---|---|---|---|---|---|
| IFN PRR Module Positive | 430 | 53% | | 57% | 55% | 53% | 47% | 66% | 48% | 63% | 40% | 37% | 53% | 54% | 39% |
| Plasma Cell module Positive | 337 | 42% | 72% | | 37% | 35% | 37% | 53% | 36% | 68% | 34% | 38% | 54% | 72% | 39% |
| Inflammatory Myeloid Module | 384 | 47% | 61% | 33% | | 75% | 57% | 78% | 67% | 53% | 53% | 41% | 50% | 35% | 44% |
| IFN Plus Myeloid Plus Plasma Cell | 104 | 13% | | | | 70% | 42% | 87% | 57% | 72% | 32% | 22% | 51% | 50% | 29% |
| IFN PRR Plus Myeloid | 132 | 16% | | | | 78% | 62% | 81% | 76% | 45% | 51% | 45% | 45% | 22% | 42% |
| IFN PRR Plus Plasma Cell | 140 | 17% | | | | 18% | 32% | 46% | 21% | 76% | 33% | 34% | 59% | 84% | 37% |
| Plasma Cell Plus Myeloid | 22 | 3% | | | | 55% | 50% | 68% | 36% | 68% | 64% | 45% | 64% | 68% | 32% |
| IFN Only | 53 | 7% | | | | 53% | 57% | 43% | 36% | 60% | 51% | 45% | 64% | 62% | 57% |
| PC Only | 71 | 9% | | | | 11% | 37% | 11% | 35% | 48% | 32% | 59% | 45% | 82% | 58% |
| Inflam Myeloid Only | 126 | 16% | | | | 80% | 63% | 68% | 72% | 44% | 71% | 48% | 52% | 31% | 60% |
| No IFN, PC or Myeloid | 162 | 20% | | | | 26% | 47% | 12% | 51% | 30% | 62% | 72% | 48% | 51% | 67% |

Further breakdown of the three categories with positive relationships to having SLE disease (versus control) demonstrated that patients who had positive eigengene values for all three categories were also likely to be positive for MicroRNA (70%), (Myeloid not activated) (87%), (CD14, TGFB1) (72%), and to have less positive eigengenes for erythrocytes (32%) and the T cell module (29%). Consideration of patients with positive eigengenes for two of the three modules showed that myeloid cells generally stayed together with the exception of the (CD14+TGFB1) module that seemed to sort with the IFN signature. Patients with positive eigengenes for inflammatory myeloid cells were generally positive for the MicroRNA signature, (myeloid not activated), basophils, and erythrocytes. Patients with positive eigengene values for plasma cells were likely to also be positive for lymphocytes (B and T cells) unless also positive for inflammatory myeloid cells. Perhaps most striking were the patients without positive eigengenes for any of the three modules positively correlated to SLE. These patients likely FIGS. 23A-23D show the correlation between clinical measures of disease activity and WGCNA modules. Patients were divided into sub-groups based on their expression of positive eigengenes for each category. Significant differences between clinical traits were determined between group using PRISM v7 Tukey's multiple comparison test, and p values are shown between groups when less than or equal to 0.05.

The pink module had a negative correlation to the SLE cohort and included many T Cell Receptor J region chains and SNORAs and SNORDs. Its negative correlation with the presence of SLE may be used to help subdivide the patients further.

WGCNA was used to divide patients into distinct subsets based on the whether they had expression of plasma cell transcripts, IFN, PRR, and myeloid transcripts, or inflammatory myeloid transcripts. It also revealed that 20% of patients were negative for these transcripts, demonstrating that a significant proportion of patients entered into this clinical trial may have a type of non-immune cell mediated lupus. For example, these patients may be eliminated or excluded from lupus clinical trials for immune modulating drugs. Additionally, WGCNA clearly identified patients with only plasma cells but no inflammatory myeloid cells, and vice versa. Both of these signatures were likely to have an IFN signature as well. These signatures or endotypes may also allow for immune modulating drugs, which target plasma cells or myeloid cells, to be properly administered to patients with the matching blood signatures.

Example 5: Molecular Endotyping Analysis for Identifying Subsets of Patients with Systemic Lupus Erythematosus Who are Candidates to be Enrolled in Clinical Trials and Have a Propensity to Respond to Specific Drugs Using methods and systems of the present disclosure, molecular endotyping analysis may be performed for identifying subsets of patients with Systemic Lupus Erythematosus who are candidates to be enrolled in clinical trials and have a propensity to respond to specific drugs.

Methods of molecular endotyping analysis may comprise performing Gene Set Variation Analysis (GSVA) on gene expression data with predefined gene sets, which may include genes descriptive of inflammatory or immune pathways or immune cell types. This yields a relatively small number of variables which are amenable to standard clustering methods such as k-means, k-medoids, or Gaussian mixture modeling (GMM). GMM may be advantageous over k-means because it considers the variance of each variable separately and is therefore less likely to be adversely affected by clusters of varying shapes and sizes. For each of these methods, clustering algorithms were applied with a range of possible numbers of clusters. Metrics such as the clustering silhouette and Bayesian Information Criterion (BIC) were used to select an optimal number of clusters. GMM analysis of GSVA scores from immunologically related modules in patients from the ILLUMINATE-1 and ILLUMINATE-2 trials indicated that the data was best fitted by four clusters.

The first cluster of patients was highly immunologically active, the second cluster was immunologically inactive, and the other two clusters displayed heterogeneous activation of immune cells and pathways. Patients in these clusters differed in their demographics, concomitant medications, and SLE manifestations. They also showed promising differences in their responses to tabalumab versus placebo. The cluster defined by myeloid cell activation showed little benefit from tabalumab, whereas the cluster defined by lymphoid cell activation trended toward a positive response to tabalumab. Interestingly, the immunologically inactive cluster also trended towards a positive response, partly because this group was the least responsive to placebo.

Figure 24:
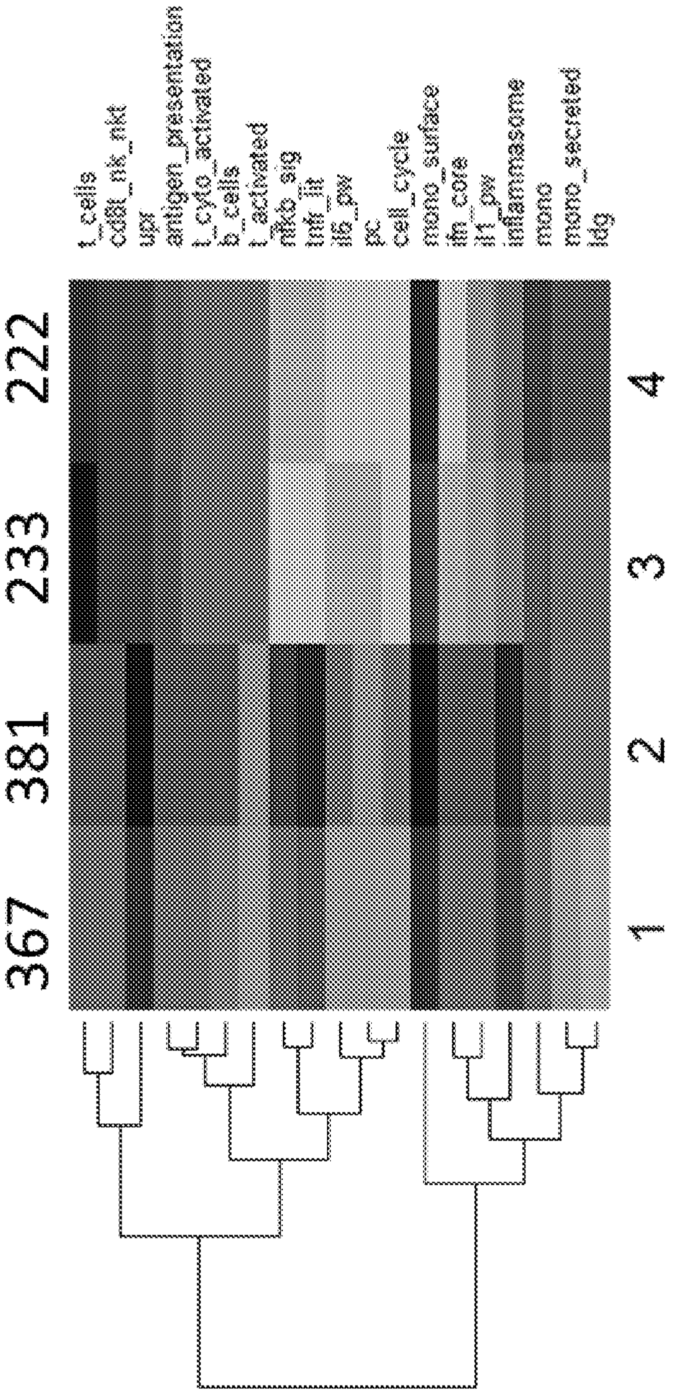
FIG. 24 shows mean GSVA scores of patients in each cluster defined by GMM. Numbers at the top denote the number of patients in each cluster.

FIG. 24 shows mean GSVA scores of patients in each cluster defined by GMM. Numbers at the top denote the number of patients in each cluster.

The unbiased gene expression methods do not take prior knowledge of gene sets into account. In some embodiments, the method comprises unsupervised clustering of gene sets generated by WGCNA, as described above. The modules generated by WGCNA can then be used to perform k-means, k-medoids, or GMM clustering of patients. In some embodiments, a search is performed for genes whose expression values are bimodally distributed (preliminary analysis of ILLUMINATE data indicates there are roughly 40 of these genes, mostly IFN-related). These genes are then investigated with clustering methods. In some embodiments, non-linear dimensionality reduction is performed on gene expression data with an autoencoder neural network, and then subjects are clustered based on the resulting latent variables. A particular kind of autoencoder, termed a Gaussian mixture variational autoencoder (GMVAE), constrains the latent variables to be generated by Gaussian mixtures. The gene expression data activates the components of the Gaussian mixtures, which in turn activate the latent variables, which are decoded to reconstruct the gene expression input. A GMM may then be fitted to the latent space to perform clustering; alternatively, subjects may be assigned to clusters based directly on the mixture probabilities.

Clustering methods based on the subjects' clinical parameters also may be used to generate meaningful subsets. Combinations of factors such as age, ancestry, SLE manifestations, and concomitant medications allow for clustering of trial subjects. Methods such as k-medoids may be applicable to categorical data sets. GMVAEs, which are often employed to cluster image data, may be used to process binary clinical variables because these variables are analogous to activated or deactivated pixels in an image.

GMVAE clustering of clinical variables from patients in the ILLUMINATE trials was performed, and five clusters of patients were identified (Table 17). A GMVAE with two latent dimensions was trained on 13 clinical variables. The model correctly reconstructed an average of 10 traits, indicating strong performance even with a relatively low number of samples by neural network standards. This approach was used to identify five patient clusters. There is a very similar cluster of young patients with aggressive disease that respond poorly to placebo (Chi-square p value=0.16).

TABLE 17

| Average patients in each cluster | | | | | | | | | | | | | |
|---|---|---|---|---|---|---|---|---|---|---|---|---|---|
| Size | SLEDAI | Age | Alopecia | Anti-dsDNA | Low Comp. | Ulcers | Antimal. | Cortico. | Immuno. | NSAID | Q2W | Q4W | Placebo |
| 218 | 11 | 42 | 62% | 67% | 35% | 35% | 65% | 82% | 39% | 30% | 41% | 44% | 38% |
| 405 | 12 | 37 | 59% | 98% | 94% | 35% | 63% | 98% | 50% | 13% | 41% | 51%* | 30% |
| 242 | 8 | 45 | 76% | 11% | 2% | 25% | 81% | 74% | 31% | 23% | 46% | 47% | 41% |
| 110 | 11 | 39 | 49% | 92% | 51% | 22% | 57% | 80% | 57% | 26% | 47% | 33% | 31% |
| 228 | 9 | 46 | 50% | 18% | 14% | 52% | 59% | 21% | 25% | 71% | 41% | 40% | 38% |

Figure 25:
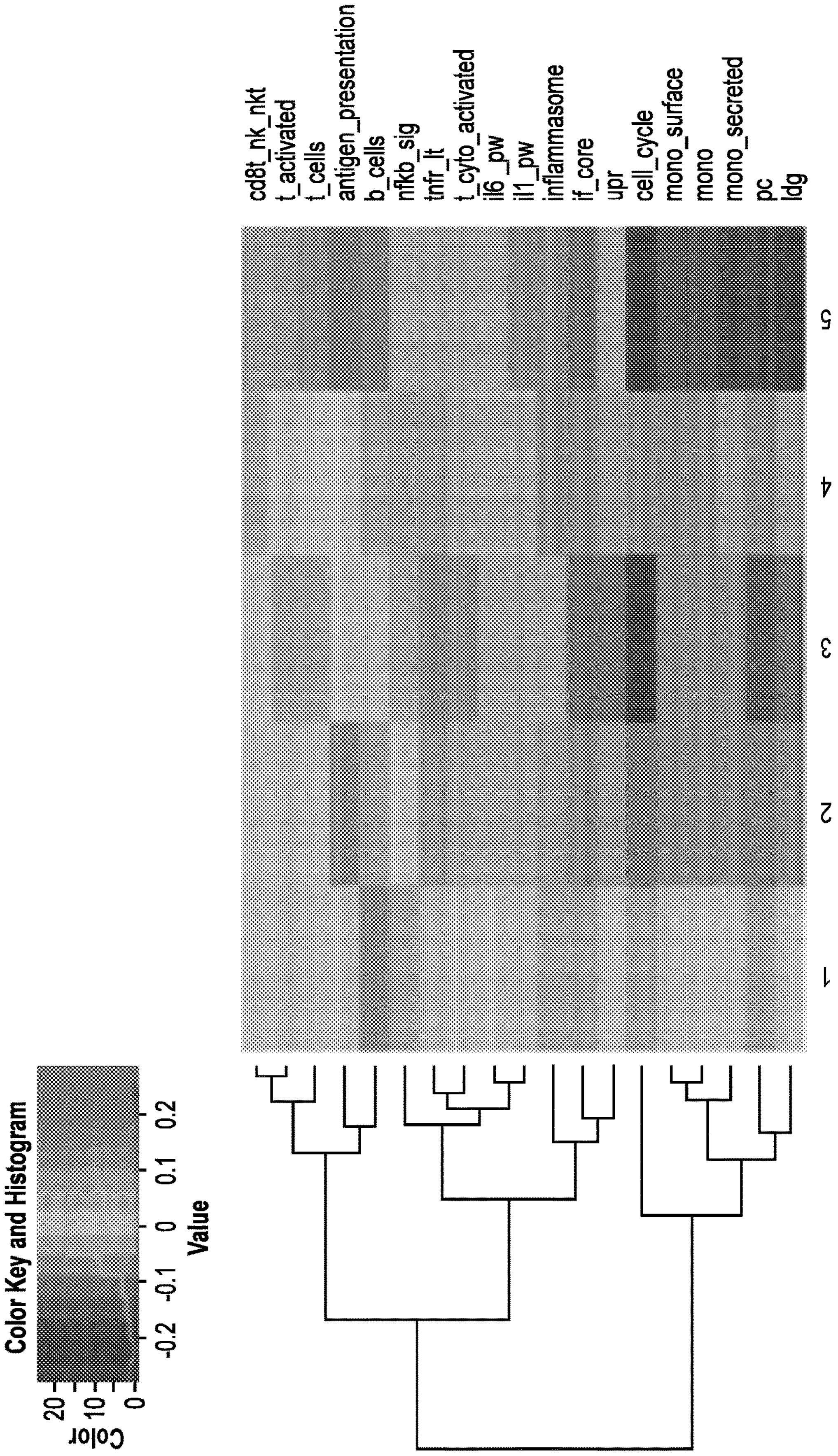
FIG. 25 shows gene expression of subjects in groups defined by GMVAE. GSVA analysis of the patients in these clusters showed that the patients without serological SLE activity (clusters 3 and 5) also did not show immunological activity by gene expression, whereas the other clusters did show immunological activity.
Figure 26A:
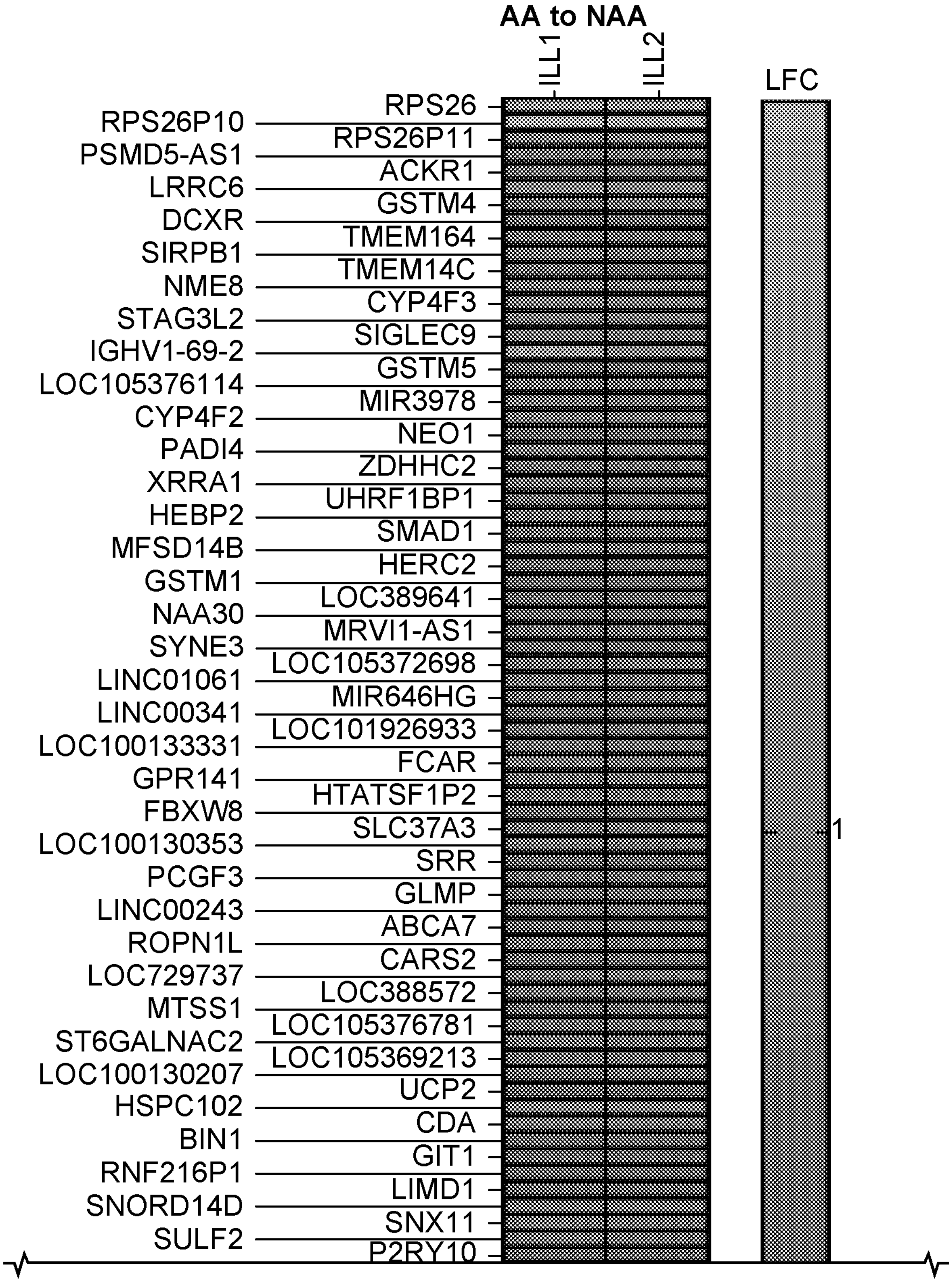
FIGS. 26A-26D show limma differential expression (DE) analysis of AA, EA, and NAA SLE patients to each other, including determining thousands of DE transcripts for each ancestry compared to the others for the ILL1 dataset.
Figure 26B:
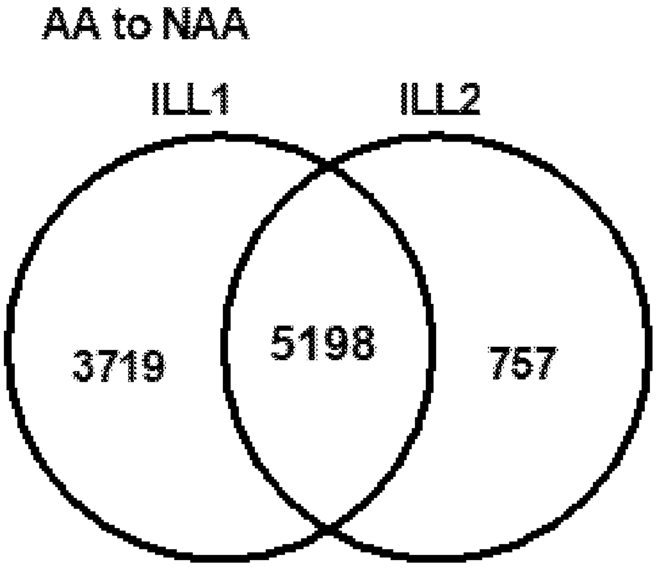
Figure 26C:
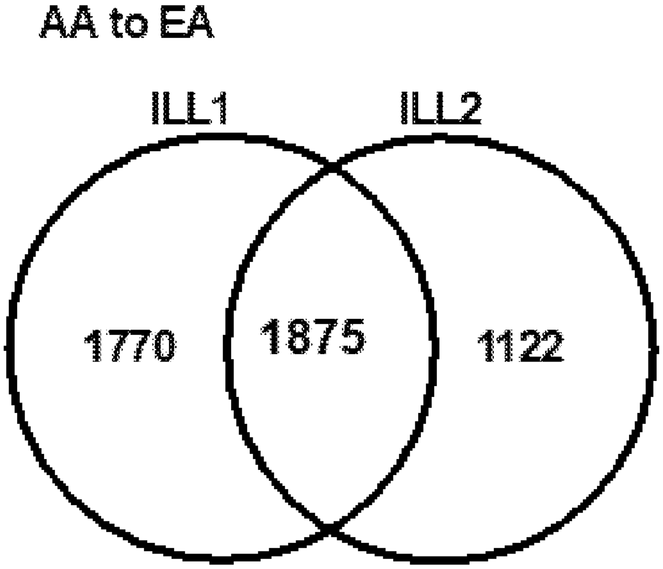
Figure 26D:
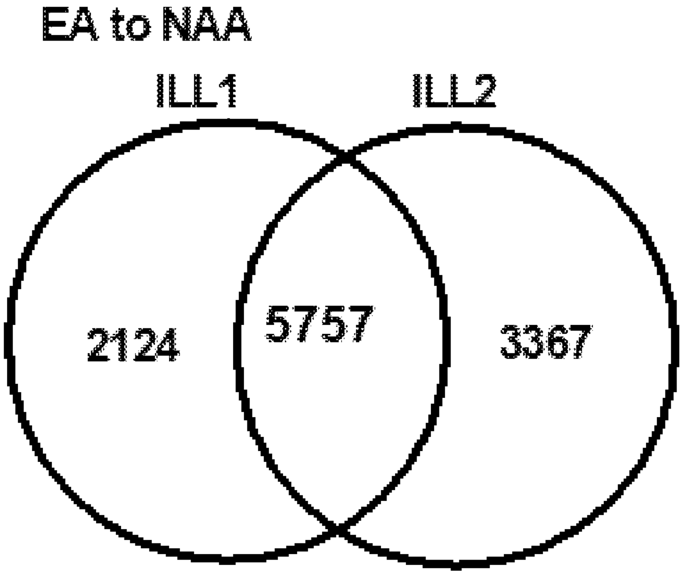

The patients in clusters 3 and 5 did not have anti-dsDNA or low complement, and were treated with antimalarials and either corticosteroids or NSAIDs. These patients did not show significant benefit from tabalumab compared to placebo. The other three clusters were more likely to have anti-dsDNA and low complement. Cluster 4, which included 171 patients treated with corticosteroids and immunosuppressives, showed a trend toward positive response to tabalumab (SRI-5 response rates: Q2W 47%, Q4W 33%, Placebo 31%). Cluster 2, which was treated with antimalarials and corticosteroids, achieved significant results (SRI-5 response rates: Q2W 41%, Q4W 51%, Placebo 30%). FIG. 25 shows gene expression of subjects in groups defined by GMVAE. GSVA analysis of the patients in these clusters showed that the patients without serological SLE activity (clusters 3 and 5) also did not show immunological activity by gene expression, whereas the other clusters did show immunological activity.

These approaches demonstrate that patients can be automatically distinguished or stratified into distinct groups, clusters, or subsets, via analysis of their gene expression data, based on factors such as whether a given clinical trial (e.g., for a lupus drug) is more or less likely to succeed for a particular patient. Certain subsets of subjects were shown to respond to treatment at substantially different rates from the other subjects in the study. However, small deviations toward better response to active treatment and worse response to placebo can be combined to produce significant results. Subsets have been successfully identified which are a fraction of the size of the original trials yet still see significant improvement from active treatment compared to placebo. Also, subsets of patients may be identified who achieve little to no benefit from active treatment and ought to be excluded from enrollment in clinical trials. In the ILLUMINATE trials, subsets were identified based on characteristics beyond those that were originally tested for an effect on the outcome. For example, it may seem intuitive to divide subjects in an anti-B-cell activating factor trial on the basis of anti-dsDNA seropositivity, but this failed to explain the failure of the trial. In the analysis results presented herein, the trial succeeded in a cluster of patients with anti-dsDNA, low complement, and concomitant corticosteroids but failed in clusters of patients that were more defined by concomitant use of immunosuppressives. These results demonstrate that complex combinations of factors may be used to more effectively and successfully subdivide patients (e.g., into responder and non-responder groups).

Example 6: Ancestry Influences the Gene Expression Profile in Systemic Lupus Erythematosus (SLE) and Contributes to Gene Expression Heterogeneity in Lupus Patients Systemic Lupus Erythematosus (SLE) generally refers to a complex autoimmune disease, which has both sex and ancestral bias in affected patients. Gene expression analysis may reveal complex heterogeneity between SLE patients, and the contribution of ancestry, drugs, and SLE manifestations to this heterogeneity were determined. Gene expression analysis between female disease-matched SLE patients of African, European, and Native American ancestry revealed thousands of differentially expressed (DE) transcripts between ancestries, but none within a single ancestry. African, European, and Native ancestry SLE patients had significantly different cellular contributions to gene expression, and these differences were found to be related to significantly different percentages of patients in each ancestry with specific signatures. Gene Set Variation Analysis (GSVA) showed an increase in plasma cells, B cells, and T cells in the majority of African ancestry patients and an increase in myeloid cell transcripts in most European and Native American ancestry patients. The treatment of SLE patients with drugs, such as corticosteroids and immunosuppressives, significantly changed their gene expression and contributed to the disparate signatures between and within ancestries. Autoantibodies and low complement, but not other clinical features of SLE, were also significantly associated with the gene expression in European and Native American ancestry SLE patients and to a lesser degree in African ancestry SLE patients. Further, differences between African and European ancestry SLE patients were found to be similar to those between healthy people of these ancestries. These ancestry-specific gene expression profiles provide a specific transcriptomic background upon which the SLE patient gene expression pattern can be built.

Systemic Lupus Erythematosus (SLE) generally refers to a complex autoimmune disease affecting mostly women (9:1) and characterized by autoantibodies to DNA and nuclear proteins leading to immune complex formation, complement deposition, and immune damage in multiple organ systems. Heterogeneity in ancestral prevalence, disease severity, organ involvement, and response to treatment can be observed; however, an explanation had not been fully delineated. Whereas the disease may be most prevalent in Asians and people of African-Ancestry (AA), a disproportionate number of clinical trials may be focused on the European Ancestry (EA) population. Further, Native people of North American ancestry may have earlier onset of disease and more organ involvement. In some cases, increased active disease, organ involvement, and autoantibody levels may be observed for AA compared to EA patients, and increased mortality may be observed for AA patients. At the cellular level, the AA population may have more activated B cells and B cell receptor signaling than the EA population. There may be differences in responses of both innate immune cells as well as lymphocytes, suggesting that ancestral differences in immune cells may contribute to the different disease course and incidence between populations. Also, there may be ancestry-related differences in response to therapy across individual patients. For example, AA SLE patients may respond better to B cell depletion therapies than Caucasian patients, but they may display lower responses to anti-BAFF treatment in Phase III clinical trials. Higher serum levels of BAFF in AA SLE patients may suggest that higher doses of the biologic may be necessary in AA patients, and that underlying genetic differences between AA and EA SLE patients may be accounted for in determining treatment decisions. There may be different genetic components contributing to disease development and progression in different ancestral populations. For example, transancestral genetic mapping may demonstrate a multigenic effect in SLE that differs according to ancestral background, suggesting a heterogeneous genetic component to disease activity. Unfortunately, many multigenic Genome Wide Association Study (GWAS) differences between AA and EA may be present in non-coding regions, thereby making extrapolation to differences in disease severity challenging.

Heterogeneity in SLE gene expression signatures may be observed for the IFN-stimulated genes. SLE patient gene expression differences may be investigated by creating modules of genes over-represented in pediatric SLE patients. Although expression of some modules may be correlated with changes in disease activity, it may be difficult to reconcile disease activity as measured by SLE Disease Activity Index (SLEDAI) and gene expression signatures in patients. For example, an attempt to group lupus patients in 158 pediatric SLE patients may suggest as many as seven different types of lupus. Increased plasmablasts may be detected in AA and increased myeloid signatures may be observed in some EA and Hispanic SLE patients, suggesting that there may be an ancestral basis to explain some of the heterogeneity in SLE gene expression signatures. The many different SLE organ manifestations may also contribute to the heterogeneity in gene expression signatures. The low-density granulocyte (LDG) signature observed in SLE PBMC may correlate with skin and vasculitis manifestations. Further, neutrophil signatures may correlate with progression to active lupus nephritis in pediatric SLE patients. An association between the IFN signature and skin involvement, anti-double-stranded DNA autoantibodies (anti-dsDNA), low complement (Low C) and musculoskeletal SLEDAI manifestations may also be observed.

Whole blood transcriptomes and gene expression analysis may be performed to assess the pattern of abnormal representation of thousands of genes simultaneously, thereby deducing the underlying abnormalities. Moreover, this approach can be used to develop an understanding of the association of ancestry, standard of care (SOC) therapy, and SLE manifestations. Here, the contribution of ancestry, SOC drug therapy, and SLE manifestations to the blood gene expression profile of subjects with SLE was determined. Although some study may assume the transcriptomic differences between SLE patients and healthy controls (HC) are related to the disease, these results provide strong evidence that much of the gene expression signature measured between SLE patients and HC is related to patient ancestry and SOC drug regimens, thereby resulting in alterations in the proportions of hematopoietic cells, cellular processes, and signaling pathways detected.

Significant Ancestral Gene Expression Differences in SLE Patients

In order to determine ancestral contributions to gene expression signatures in whole blood (WB), two large phase 3 clinical trial databases with microarray analysis at baseline were analyzed (GSE88884, as described by Hoffman, 2017, which is incorporated by reference herein in its entirety). The Illuminate 1 (ILL1) and Illuminate 2 (ILL2) clinical trials had microarray expression data for 1,566 female patients of self-described ancestry as follows: AA (n=216), EA (n=1,118), and Native American Ancestry (NAA; mostly from South America, n=232; top three countries of origin Peru (n=81), Ecuador (n=30), and Guatemala (n=27)); male patients and patients of multiple, Asian, and other ancestries were removed to avoid contributions of gender differences and low numbers of patients, respectively. Ancestral backgrounds were split evenly between the ILL1 and ILL2 datasets, allowing for a training and test set to determine bulk gene expression differences. Entry criteria for the trials required a positive anti-nuclear autoantibody (ANA) titer and a minimum disease activity of 6, as determined by the SLE Disease Activity Index (SLEDAI). Disease activity was similar among ancestries, as was percentage of patients with anti-dsDNA (Table S1). The trials excluded patients with progressive lupus nephritis and entered only one patient with central nervous system manifestations. Most female patients recruited had a mixture of six SLE manifestations: arthritis (86.4%), anti-dsDNA (57.5%), low complement (Low C, 40.0%), alopecia (58.9%), rash (68.3%), and mucosal ulcers (31.7%) (Table S2). Gene expression differences were first determined by carrying out limma differential expression (DE) analysis of AA, EA, and NAA SLE patients to each other. At a false discovery rate (FDR) of 0.05, thousands of DE transcripts were determined for each ancestry compared to the others for the ILL1 dataset (FIGS. 26A-26D). As a control, each ancestral background was randomized into two separate groups five separate times, and DE to patients of the same ancestral background was assessed. No DE transcripts were found, even at a less stringent FDR of 0.2. DE analysis of ILL2 SLE patients of AA, EA, and NAA SLE patients to each other yielded similar results to ILL1, indicating thousands of DE transcripts between ancestries at an FDR of 0.05 (FIGS. 26A-26D). Importantly, the patterns of ancestry-related DE genes were comparable in ILL1 and ILL2 (FIGS. 26A-26D).

Figure 27A:
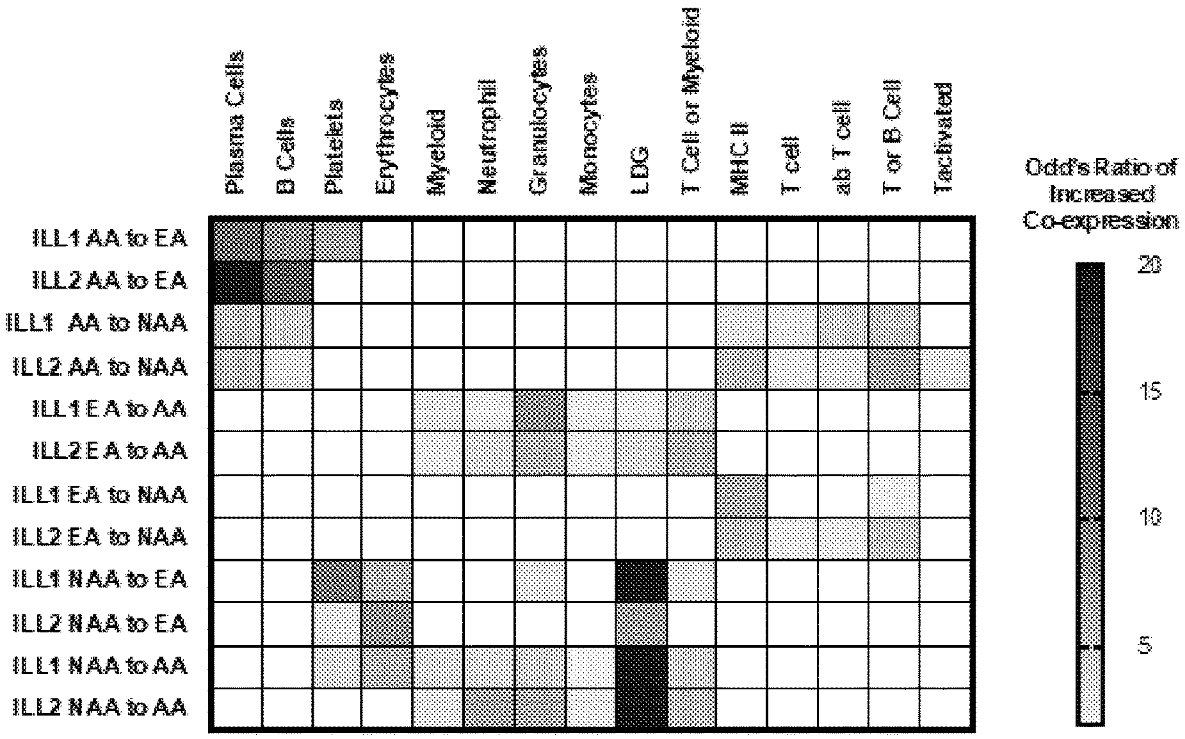
FIG. 27A shows that in EA SLE patients, transcripts for monocytes and low-density granulocytes (LDGs) were enriched in the ILL1 and ILL2 datasets compared to AA SLE patients, whereas T cell and MHC class II transcripts were enriched in EA patients compared to NAA patients. NAA patients had increased myeloid signatures, including transcripts associated with monocytes, LDGs, and neutrophils compared to both AA and EA patients.

In order to interpret the biological meaning of the ancestral gene expression differences, I-scope, a tool for determining the likely hematopoietic cell type in bulk datasets, was used to determine whether there were cellular differences between SLE patients of different ancestral backgrounds. I-Scope demonstrated a relative predominance of plasma cells and B cells in AA patients, and of myeloid cells in EA and NAA patients. In EA SLE patients, transcripts for monocytes and low-density granulocytes (LDGs) were enriched compared to AA SLE patients, whereas T cell and MHC class II transcripts were enriched in EA patients compared to NAA patients. NAA patients had increased myeloid signatures, including transcripts associated with monocytes, LDGs, and neutrophils compared to both AA and EA patients (FIG. 27A). Thus, the same ancestral-based cellular enrichments were found for the ILL1 and ILL2 dataset, and the transcripts signifying these cellular categories were remarkably similar between the ILL1 and ILL2 datasets. These results indicated a meaningful difference in gene expression profiles of SLE subjects with similar disease severity but of different ancestries.

Next, Gene ontology (GO) biological pathway and Biologically Informed Gene Clustering (BIG-C) (Labonte et al., 2018) enrichment of molecular pathways (Fisher's Exact $p<0.05$) in AA, EA, or NAA patients was performed, and results supported the conclusions of the I-scope analysis. GO biological pathways demonstrated increased innate immune response and neutrophil chemotaxis in EA and NAA SLE patients compared to AA patients, and increased immunoglobulin transcripts (in GO categories complement activation and regulation of immune response) in AA compared to EA and NAA. There were no GO biological pathways enriched in EA patients compared to both AA and NAA patients. BIG-C analysis revealed that AA patients had increased immune cell surface, immune signaling, and MHC II compared to both NAA and EA patients. AA patients also manifested increased IFN stimulated genes, chromatin remodeling, fatty acid biosynthesis, and the unfolded protein response compared to EA patients. NAA patients had increased immune cell surface, immune signaling, MHC I, autophagy, inflammasome and pattern recognition receptors, anti-apoptosis, and ROS protection compared to both AA and EA patients. NAA patients had increased IFN stimulated genes, transporters, unfolded protein response and integrin pathway compared to EA patients. Similar to GO biological pathways, there were no increased BIG-C categories for EA patients compared to both AA and NAA patients. Gene categories up-regulated in EA patients compared to AA patients included immune cell surface, autophagy, ROS protection, lysosome, and glycolysis. AA and EA patients shared increases in a number of categories compared to NAA patients indicating these processes were likely decreased in NAA patients compared to both AA and EA patients; these included mitochondrial DNA to RNA, mRNA translation, mRNA splicing, MicroRNA processing, TCA cycle, oxidative phosphorylation, and proteasome.

The 798 ILL1 and 768 ILL2 SLE patients were analyzed separately and yielded similar results, even at the individual gene level. To rule out the possibility that these findings could not be extrapolated to other SLE datasets, and to confirm the finding that ancestral differences were significantly contributing to the heterogeneity in gene expression signatures, SLE dataset GSE45291 was also analyzed. 73 AA and 71 EA SLE patients with the same range of SLEDAI scores (2-11), similar mean SLEDAI (AA 3.78+/−2.46; EA 3.53+/−2.08), and mode of SLEDAI (2), were analyzed by Linear Models for Microarray Data (limma) DE analysis, and results indicated that 859 transcripts were increased in AA patients compared to EA patients, and 955 transcripts were increased in EA patients compared to AA patients (FDR 0.05).

Figure 27B:
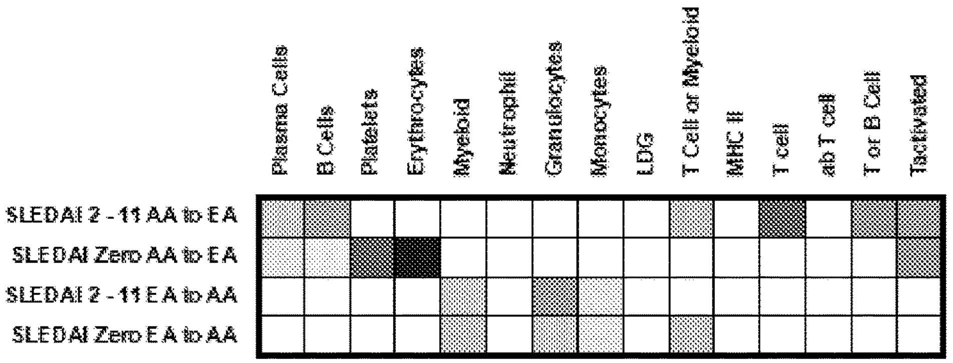
FIG. 27B shows that, similar to the results using the ILL1 and ILL2 datasets, EA SLE patients were enriched for transcripts associated with myeloid cells, and AA SLE patients were enriched for transcripts associated with plasma cells, B cells, and T cells.

Similar to the results using the ILL1 and ILL2 datasets, EA SLE patients were enriched for transcripts associated with myeloid cells (FIG. 27B), and AA SLE patients were enriched for transcripts associated with plasma cells, B cells, and T cells (FIG. 27B).

GO biological pathway analysis demonstrated increased transcripts associated with chemotaxis, TLR signaling, and proteins which may be phosphorylated in EA, and increased transcripts for regulation of immune response, translation, T cell co-stimulation, complement activation, and BCR signaling in AA SLE patients.

BIG-C analysis showed increased immune cell surface, immune signaling, oxidative phosphorylation, mRNA translation, ubiquitylation and ER in AA and increased autophagy, inflammasome, glycolysis, lysosome, endosome, immune cell surface, and intracellular signaling in EA patients. DE analysis of SLE patients with inactive disease (SLEDAI of zero), including 25 AA and 75 EA patients, also revealed significant DE transcripts: 470 increased transcripts in EA patients and 258 increased transcripts in AA SLE patients (FDR of 0.05).

I-scope analysis showed a similar pattern of increased transcripts related to myeloid cells in EA patients, including CLEC4D, CXCL1, CXCL8, FCGR3B, FGL2, LTB4R, BPI, CAMP, IL17RA, MMP9, SIGLEC9, BMX, ITGAM, FPR1, and to plasma cells and B cells in AA patients, including transcripts for IGKC, IKGV4-1, IGLC1, IGLJ3, and JAKMIP1, even though the number of these cell-specific transcripts were decreased compared to patients with higher SLEDAI values (FIGS. 27A-27B). GO biological pathway analysis demonstrated increased glucose metabolism, small GTPase signal transduction, and vesicle fusion in EA patients, and increased membrane components, heme biosynthesis, microtubule, and secreted protein transcripts in AA patients with very low disease activity. Further, BIG-C analysis demonstrated immune cell surface, cytoskeleton, MHC II, and mitochondria increased in AA patients, and TCR cycle, lysosome, endosome, and ubiquitylation upregulated in EA patients. Thus, DE analysis of 4 SLE datasets comprising 1,810 female SLE patients demonstrated significant ancestral components to the whole blood gene expression profile, and some of these gene expression differences were observed to be independent of disease activity.

Figure 28A:
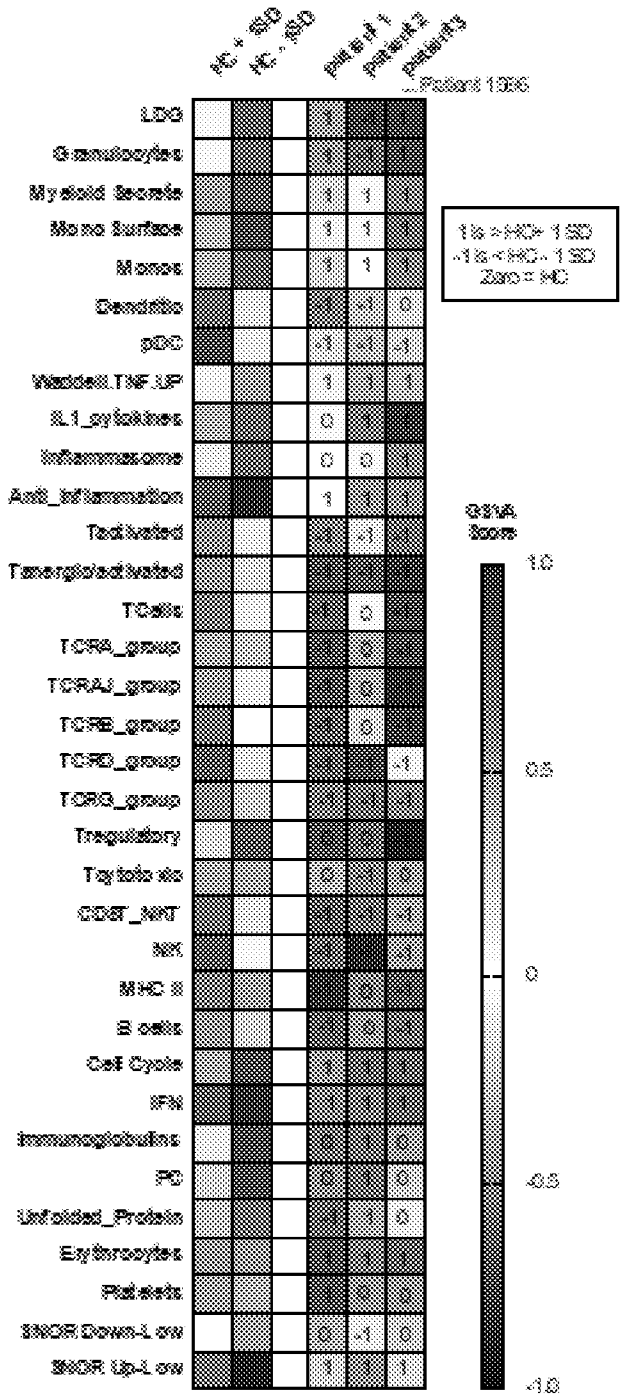
FIG. 28A shows results of gene set variation analysis (GSVA) employed to compare enrichment of 34 modules of genes corresponding to lymphocytes, myeloid cells, cellular processes, as well as groups of all the T Cell Receptor (TCR) and immunoglobulin (Ig) genes found on the Affymetrix HTA2.0 array.

Differences in Gene Expression Between Ancestries were Associated with Significantly Different Percentages of Patients with Particular Signatures Using the population gene expression analysis was useful for finding signatures that were significantly different for groups of patients of a specific ancestry. Further, a possibility that features of individual subjects, such as therapy and/or specific disease manifestations, may have contributed to such DE was ruled out, which may be important since ancestral groups may differ in these features. To address this, gene set variation analysis (GSVA) was employed to compare enrichment of 34 modules of genes corresponding to lymphocytes, myeloid cells, cellular processes, as well as groups of all the T Cell Receptor (TCR) and immunoglobulin (Ig) genes found on the Affymetrix HTA2.0 array. GSVA calculates enrichment scores using the log 2 expression values for a group of genes in each SLE patient and healthy control and normalizes these scores between −1 (no enrichment) and +1 (enriched). When many genes of a particular cell type or process are co-expressed, GSVA roughly reflects cell counts (FIG. S2). GSVA enrichment scores were calculated for the set of 1,566 female SLE patients and 17 female HC from the ILL1 and ILL2 datasets (GSE88884). The average plus or minus 1 standard deviation (SD) for the healthy controls was used to determine whether a patient had an increased, decreased, or similar signature compared to HC (FIG. 28A).

Figure 28B:
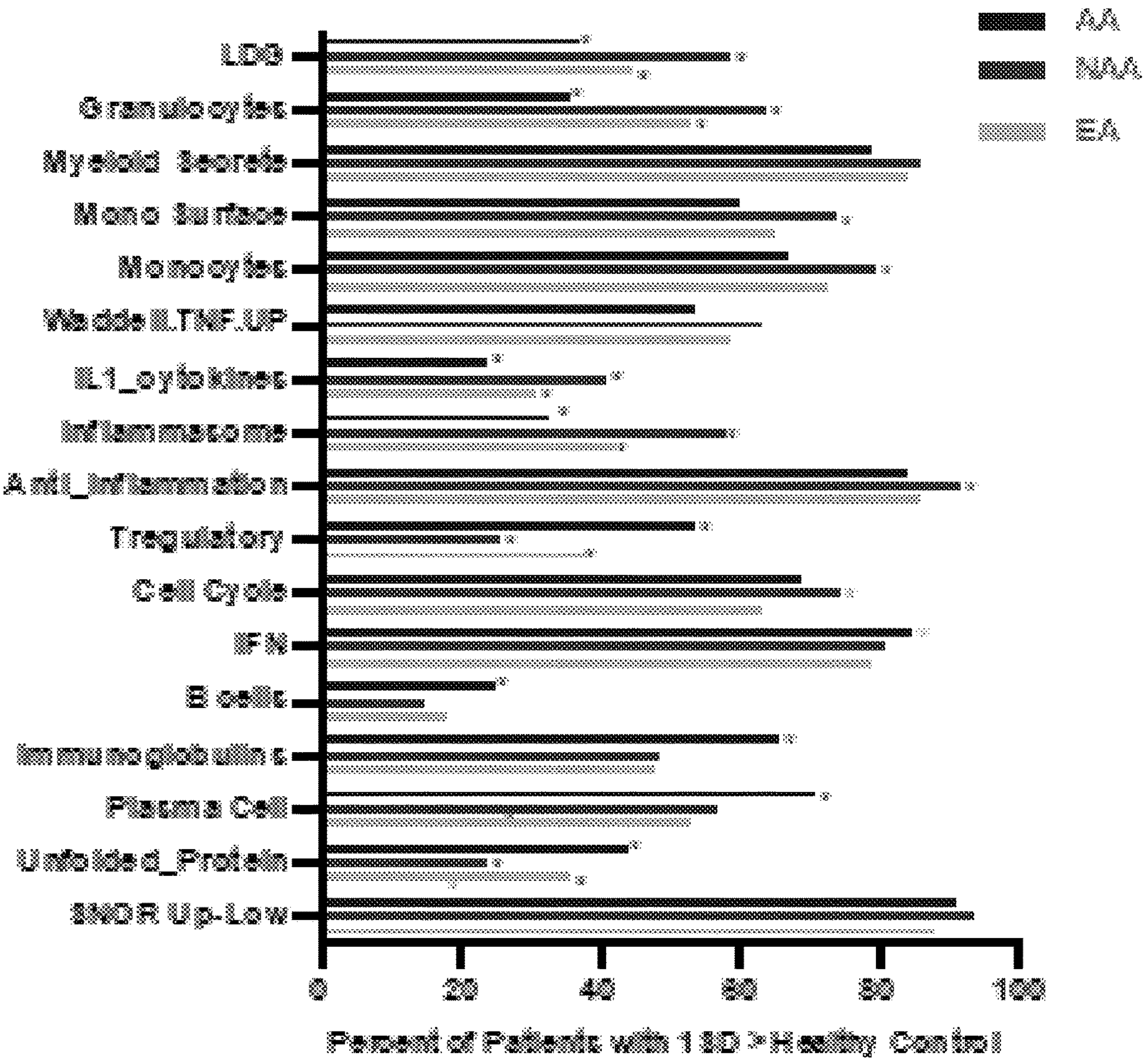
FIGS. 28B-28C show that the AA and NAA patient groups had significantly more SLE patients with platelet and erythrocyte enrichment than EA patients, and significantly fewer patients with decreased erythrocyte and platelet GSVA scores compared to EA patients.
Figure 28C:
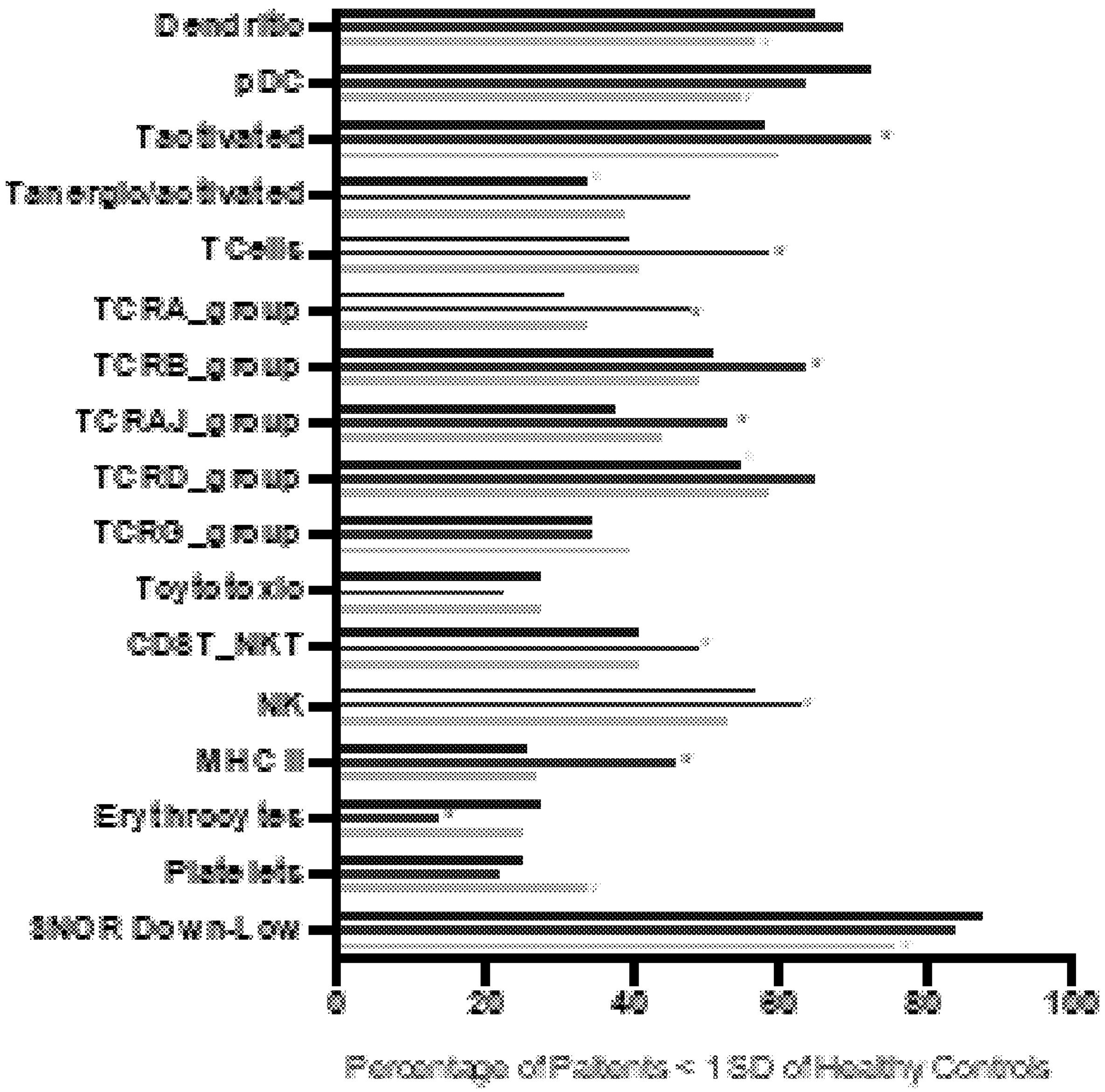

GSVA results demonstrated that the differences between the ancestry groups were related to the significantly different percentages of patients with particular signatures. All three ancestry groups had significantly different frequencies of patients ($p<0.01$, Fisher's Exact Test) with enrichment of the LDG, granulocyte, IL1 cytokine, and inflammasome signatures. NAA patients had the highest percentage of patients with these signatures, followed by EA patients, and AA patients had the lowest. NAA patients also had significantly more patients with monocyte cell surface and monocytes than AA patients; however, interestingly, signatures for myeloid secreted proteins, which included complement components, TNF, and CXCL10, were not different between the three ancestry groups. The AA patient group had significantly more patients with B cell, Ig, plasma cell, and T regulatory (IKZF2, FOXP3) signatures compared to EA and NAA patients. The NAA patient group had significantly fewer patients with T cell associated signatures compared to both EA and AA patients. The EA patient group had significantly fewer patients with dendritic and pDC signatures decreased compared to controls. The percentage of AA patients with IFN signatures was higher than that of EA patients (Fisher's exact $p=0.04$), but differences in overall percentages only ranged from 79% positive (EA) to 85% positive (AA). The AA and NAA patient groups had significantly more SLE patients with platelet and erythrocyte enrichment than EA patients, and significantly fewer patients with decreased erythrocyte and platelet GSVA scores compared to EA patients (FIGS. 28B-28C).

Figure 28D:
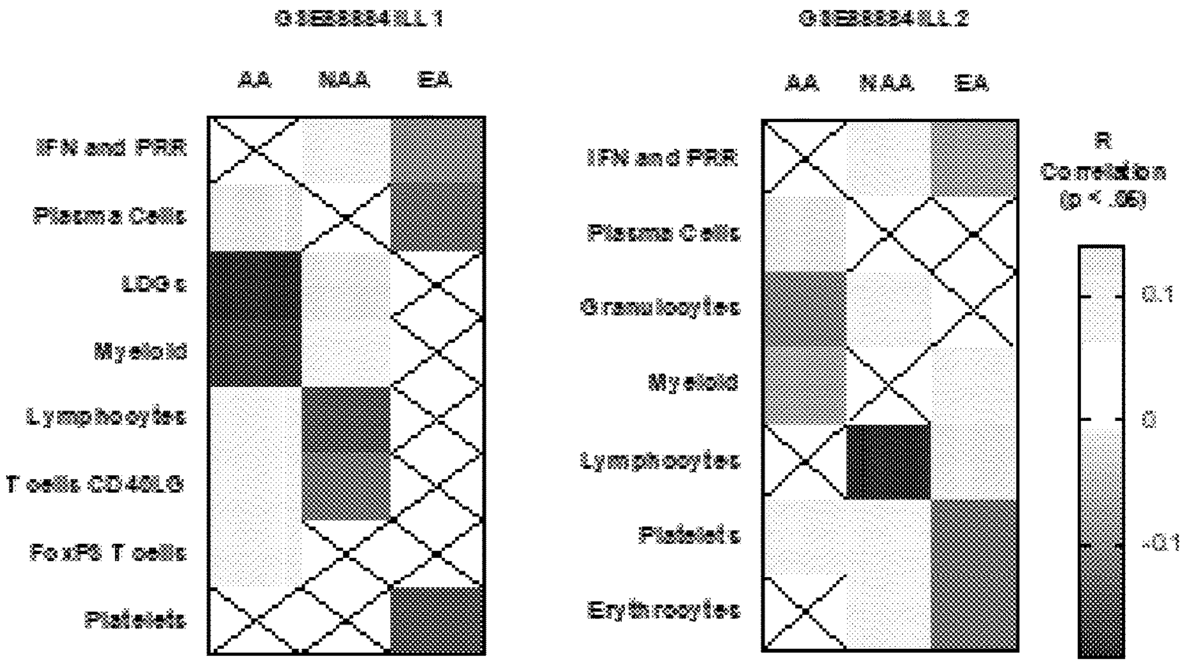
FIG. 28D shows an orthogonal approach using weighted gene co-expression network analysis (WGCNA) to confirm the association of ancestry with cellular signatures. WGCNA of GSE88884 ILL1 and ILL2 was performed separately, and results demonstrated a significant ($p<0.05$) positive association by Pearson correlation of AA ancestry to plasma cell, T cell, and FOXP3 T cell modules, as well as a significant negative correlation to granulocyte and myeloid cell WGCNA modules.

An orthogonal approach using weighted gene co-expression network analysis (WGCNA) was used to confirm the association of ancestry with cellular signatures. WGCNA of GSE88884 ILL1 and ILL2 was performed separately, and results demonstrated a significant ($p<0.05$) positive association by Pearson correlation of AA ancestry to plasma cell, T cell, and FOXP3 T cell modules, as well as a significant negative correlation to granulocyte and myeloid cell WGCNA modules. NAA ancestry had positive correlations to IFN, granulocyte, platelet, and erythrocyte modules, and negative correlations to T cell and lymphocyte modules. EA ancestry was positively correlated to one myeloid cell module and negatively correlated to IFN, plasma cell, platelet, and erythrocyte modules (FIG. 28D). These analyses confirmed the findings from the DE and GSVA analysis.

SOC Therapy is Associated with Changes in Gene Expression Profiles

Figure 29:
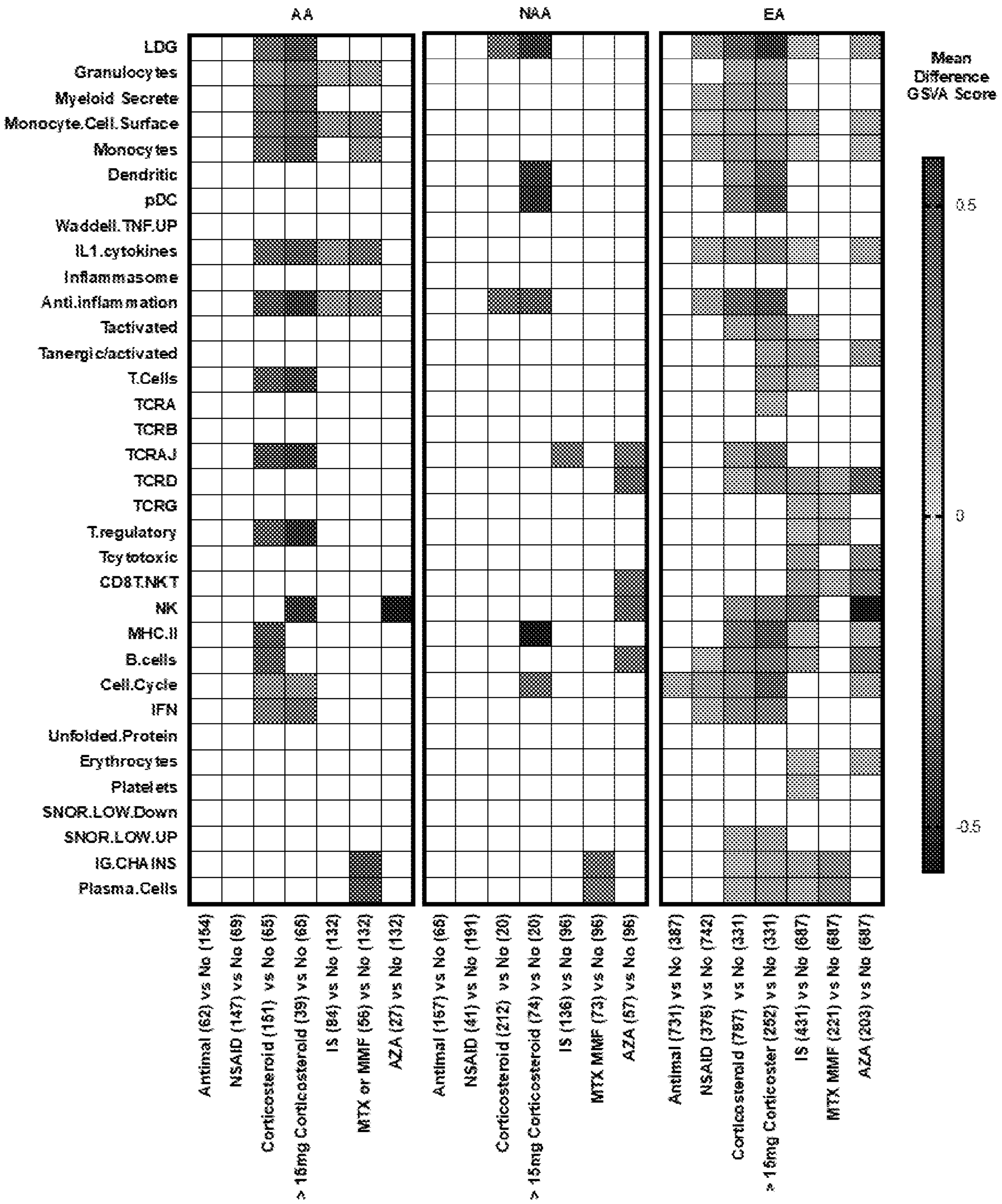
FIG. 29 shows a comparison of patients on specific therapies to patients not receiving the therapies for the 34 cell type and process modules, in order to determine the effect of SOC drugs on patient gene expression signatures.

All SLE patients in these analyses were on SOC drug therapy, and the heterogeneity observed in gene expression signatures between ancestral backgrounds may have been influenced by different drug regimens. In order to determine the effect of SOC drugs on patient gene expression signatures, patients on specific therapies were compared to patients not receiving the therapies for the 34 cell type and process modules. Within ancestral groupings, patients taking corticosteroids had significantly (Sidek's multiple comparisons test) increased LDG (AA, EA, and NAA, with p<0.0001) and anti-inflammation (AA, EA, and NAA, with p<0.0001) GSVA scores compared to patients of the same ancestry not taking the drugs, demonstrating that these signatures were strongly influenced by corticosteroid usage. Additionally, both AA and EA patients receiving corticosteroids had significant enrichment for granulocytes (AA, p=0.0009; EA, p=0.005), myeloid secreted (AA, p=0.0001; EA, p<0.0001), monocyte cell surface (AA and EA, p<0.0001), monocytes (AA and EA, p<0.0001), cell cycle (AA, p=0.04; EA, p<0.0001) and the IFN signature (AA, p=0.001; EA, p<0.0001). The effect of corticosteroids on myeloid signatures was further amplified at corticosteroid doses greater than 15 mg/day. Immunosuppressive therapy (e.g., IS, azathioprine (AZA), mycophenolate mofetil (MMF), or methotrexate (MTX)) did not have a consistent effect on all three ancestry groups. However, IS increased monocyte cell surface (EA, p=0.0013; AA, p=0.0103) and IL1 (EA, p=0.03; AA, p=0.0168) in AA and EA patients. When IS therapy was restricted to just MMF and MTX, there was a consistent decrease across all three ancestry groups in plasma cell (AA, p=0.0087; EA, p<0.0001; NAA, p=0.0130) and immunoglobulin (AA, p=0.0026; EA, p<0.0001; NAA, p=0.0168) GSVA scores. AZA treatment yielded significantly decreased NK cell GSVA scores (AA, p=0.0004; EA, p<0.0001; NAA, p=0.002) in all three ancestry groups and also significantly decreased T cytotoxic (EA and NAA, p <0.0001) and B cells (EA and NAA, p<0.0001) in NAA and EA ancestries. EA patients receiving NSAIDs compared to all other treatments had decreased LDG (p<0.0001) and anti-inflammation signatures (p=0.0053), whereas anti-malarial drugs had no significant effect on enrichment scores of the 34 cell type and process modules (FIG. 29).

Figure 30A:
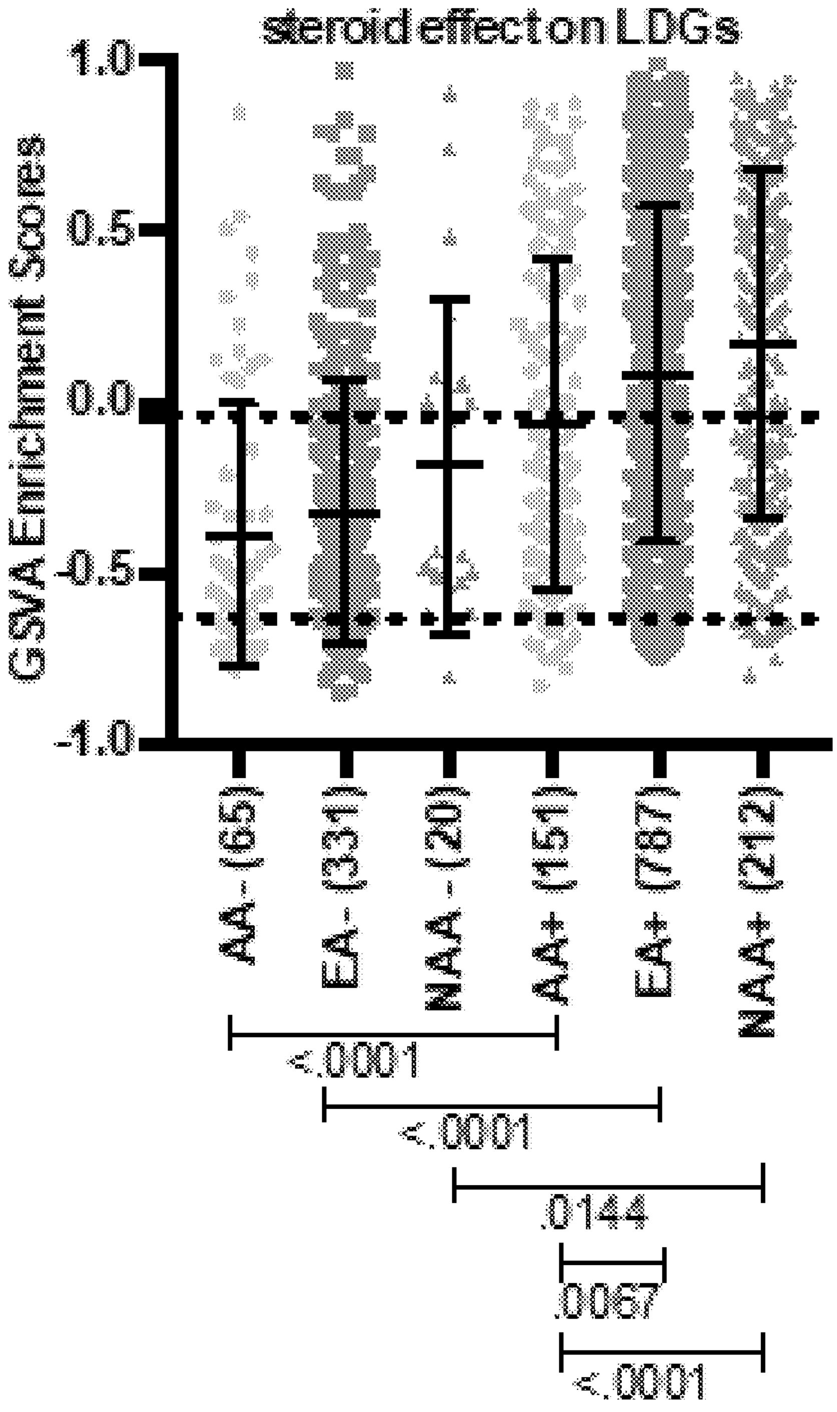
FIGS. 30A-30C show a comparison of LDG, monocyte, and T cell GSVA scores for patients with or without corticosteroids, demonstrating that the corticosteroids were the largest contributor to the differences between patient LDG, monocyte, and T cell scores, but that AA patients still had lower LDG and monocyte scores and NAA patients still had lower T cell scores in the absence of corticosteroids.
Figure 30B:
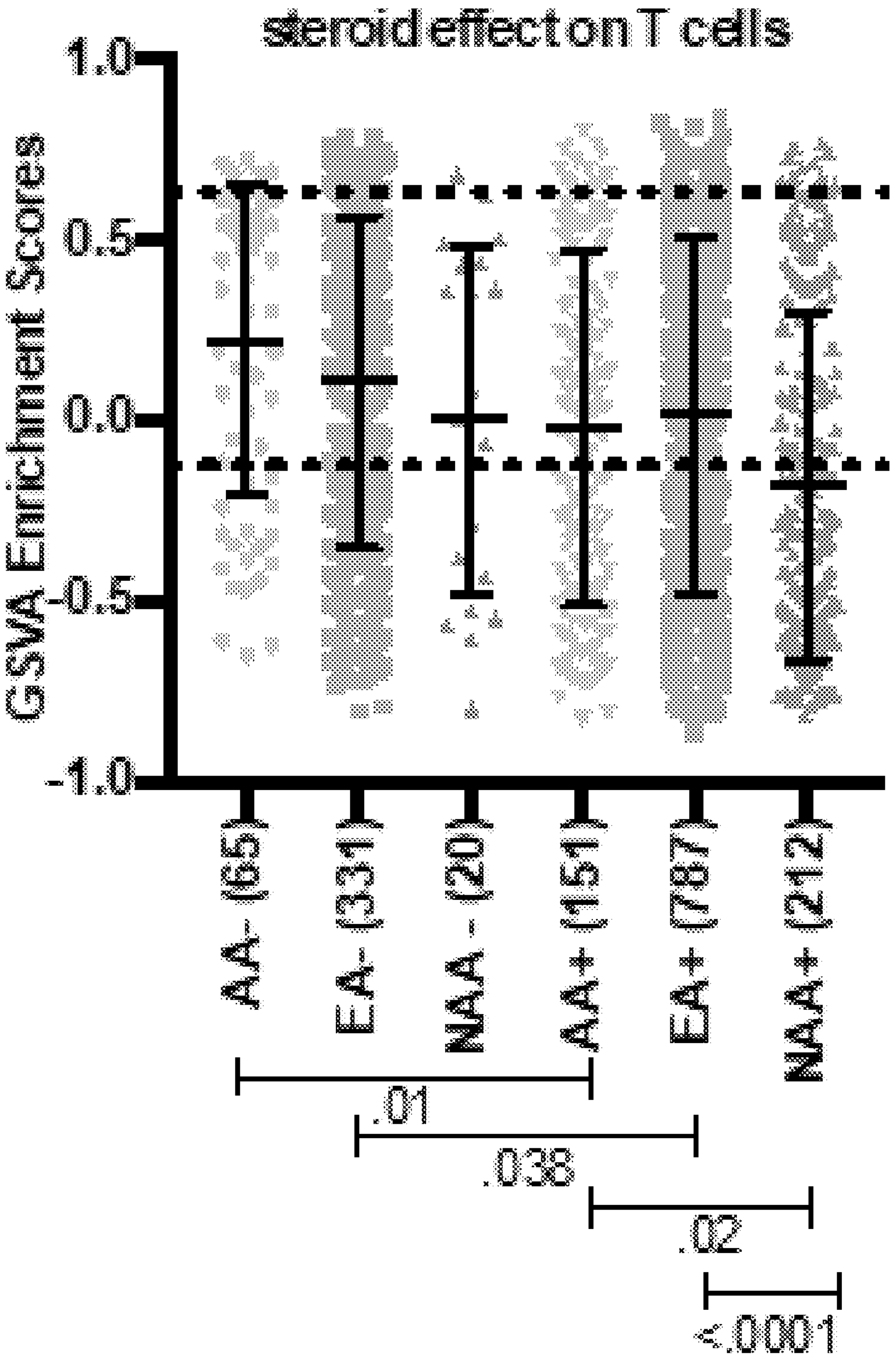
Figure 30C:
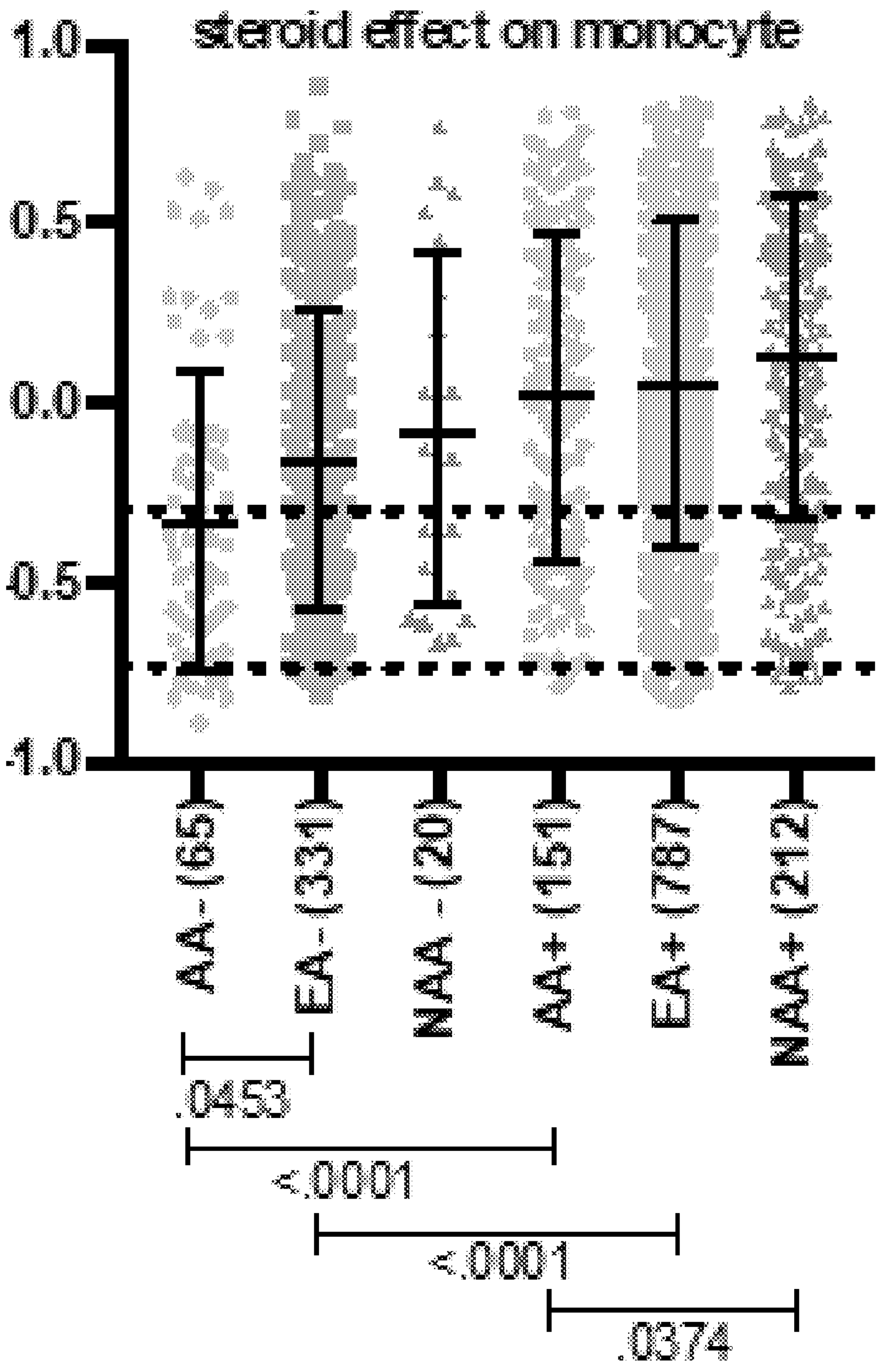
Figure 30D:
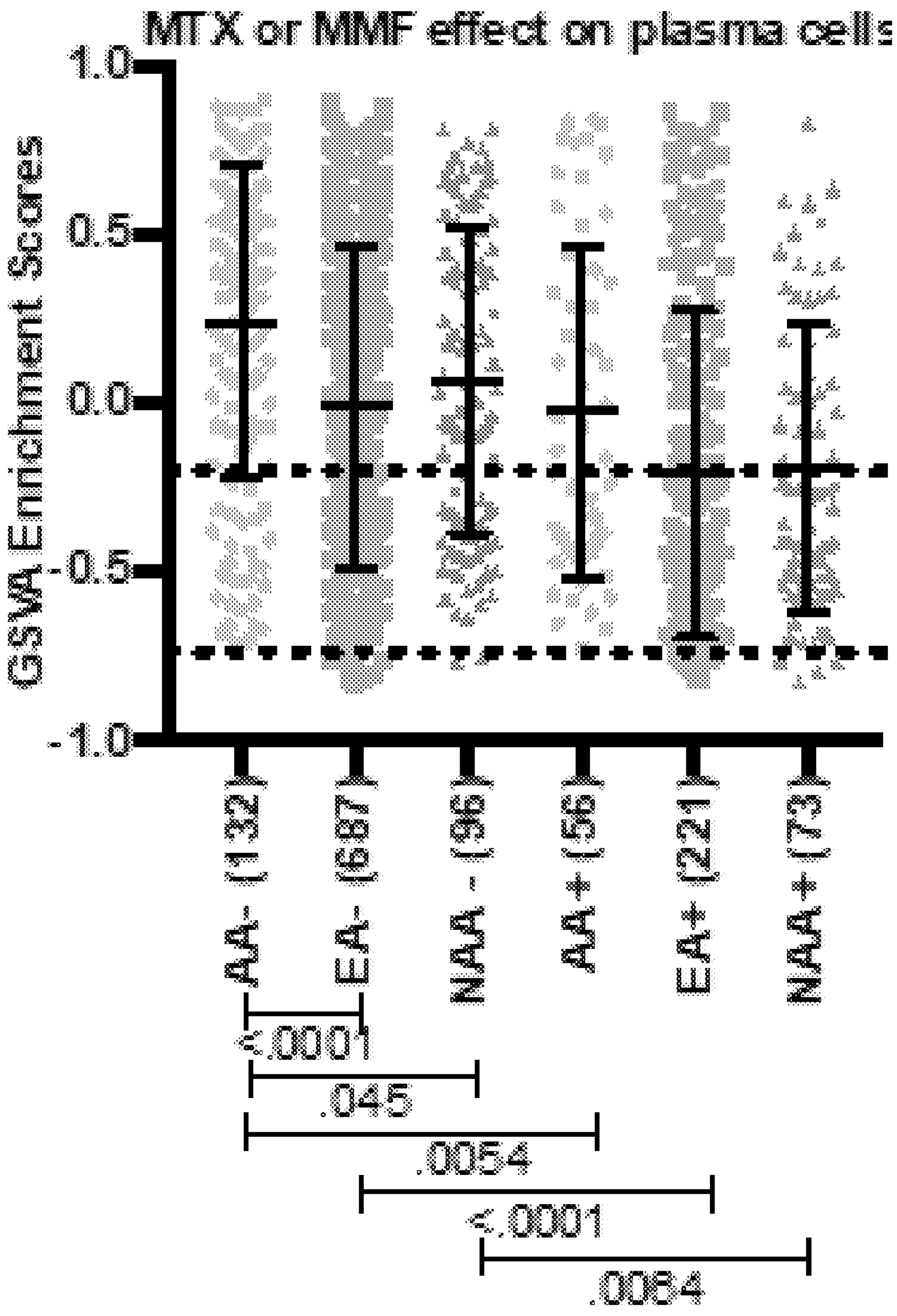
FIG. 30D shows that MTX and MMF significantly lowered plasma cell GSVA scores, but did not negate the increased plasma cells determined for AA patients versus EA and NAA patients.
Figure 30E:
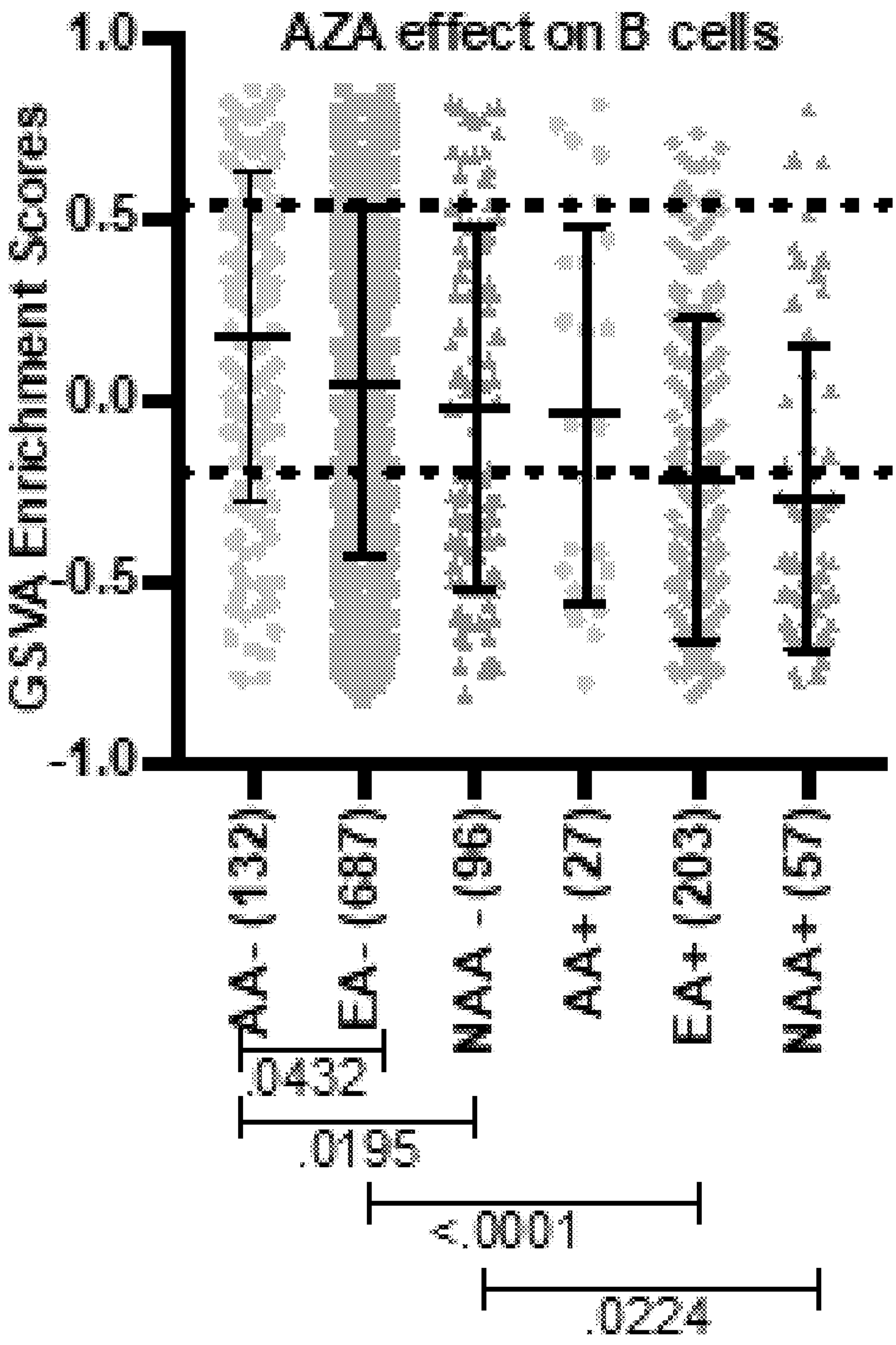
FIG. 30E shows that compensating for AZA treatment also did not offset the increased B cells in AA SLE patients.
Figure 30F:
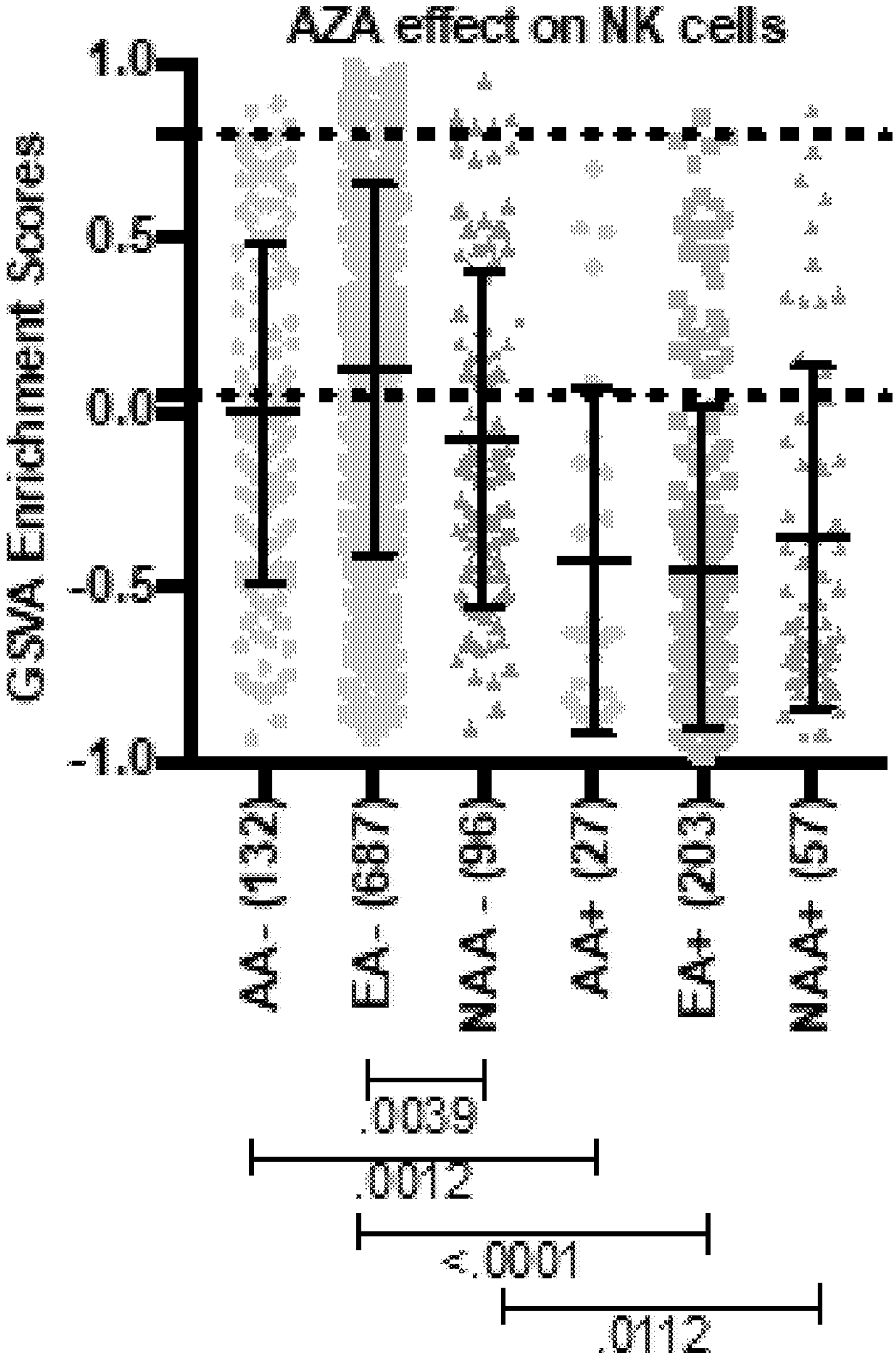
FIG. 30F shows that compensating for AZA treatment also did not offset the difference in NK cells between EA and NAA SLE patients.

To demonstrate that these treatment differences were sufficient to account for the ancestral gene expression differences, signatures were compared between patients on the same drug regimens. Almost all NAA SLE patients were receiving corticosteroids (92%; n=214/232) compared to 70% of AA (n=152 out of 216) and EA (n=787 out of 1,118) patients, and NAA patients were also more frequently taking immunosuppressive drugs (58%) compared to AA (39%) and EA (39%) patients. Comparison of LDG, monocyte, and T cell GSVA scores for patients with or without corticosteroids demonstrated that the corticosteroids were the largest contributor to the differences between patient LDG, monocyte, and T cell scores, but that AA patients still had lower LDG and monocyte scores and NAA patients still had lower T cell scores in the absence of corticosteroids (FIGS. 30A-30C). MTX and MMF significantly lowered plasma cell GSVA scores, but did not negate the increased plasma cells determined for AA patients versus EA and NAA patients (FIG. 30D). Compensating for AZA treatment also did not offset the increased B cells in AA SLE patients (FIG. 30E) or the difference in NK cells between EA and NAA SLE patients (FIG. 30F).

Dataset GSE45291 also had current drug information available for the gene expression data; therefore, GSVA enrichment scores were determined for the 34 cell and process modules, and differences between different drug treatments were determined. Corticosteroids increased LDG, monocyte, and anti-inflammation GSVA enrichment scores, MTX and MMF decreased plasma cell GSVA enrichment scores, and AZA decreased NK and B cell enrichment scores (FIG. S3), in support of the data generated from dataset GSE88884.

Figure 31A:
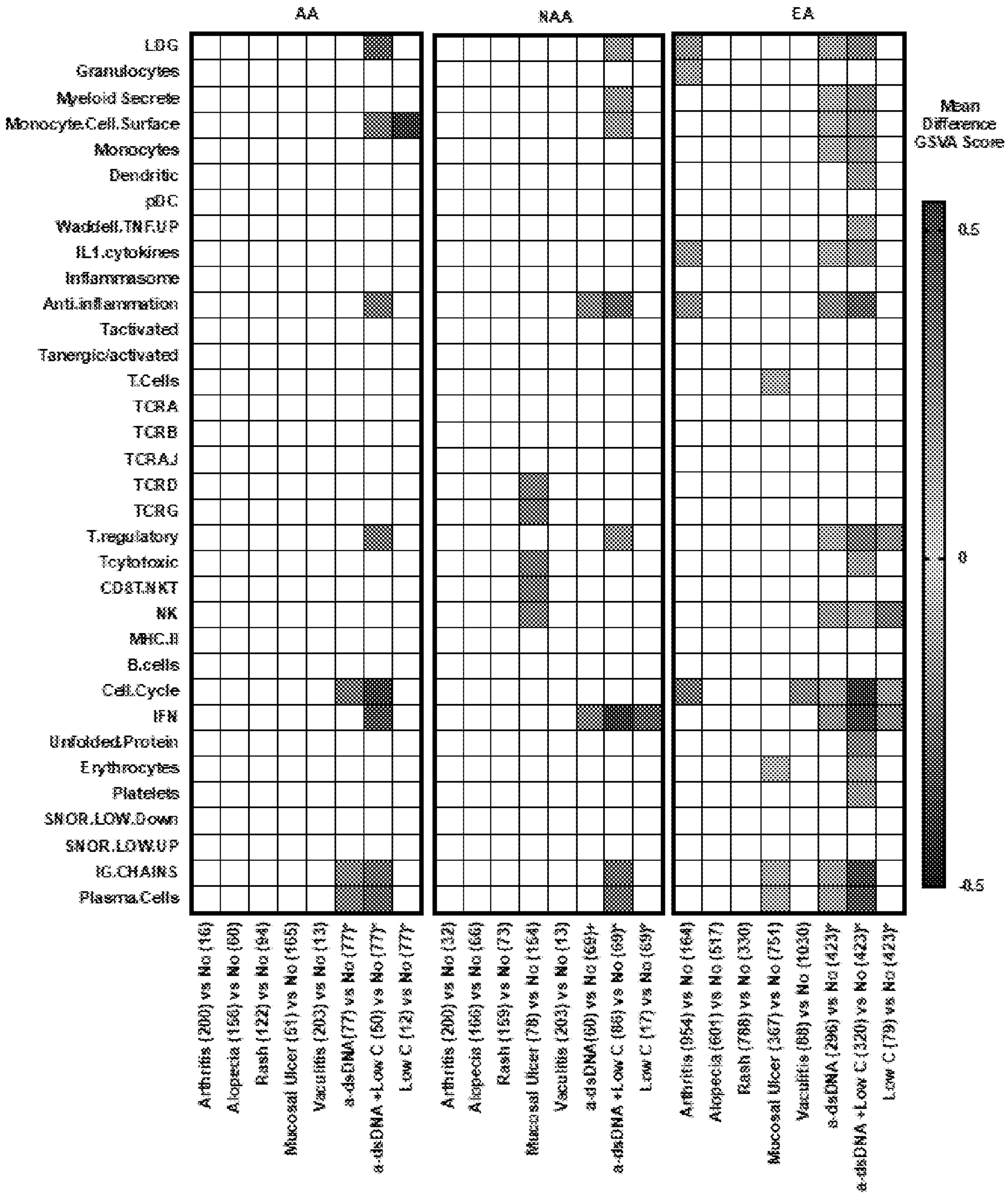
FIG. 31A shows a comparison of GSVA enrichment scores for the 34 modules for patients with each manifestation individually to all other manifestations, in order to determine the association between different SLE manifestations and gene expression profiles.

Autoantibodies and Complement Levels, but not Clinical Features were Associated with Gene Expression Profiles Variation in SLE disease manifestations may be a cause for cellular and gene expression heterogeneity in SLE WB. In order to determine the association between different SLE manifestations and gene expression profiles, GSVA enrichment scores for the 34 modules were compared for patients with each manifestation individually to all other manifestations. The presence of arthritis, rash, alopecia, mucosal ulcers, or vasculitis had no consistent differences on GSVA scores of the 34 modules across the ancestries. Patients of all ancestries with both anti-dsDNA and Low C had significantly higher (Sedak's multiple comparisons test, p<0.01) GSVA enrichment scores for anti-inflammation (AA. p=0.0277; EA and NAA, p<0.0001), IFN (AA, p<0.0001; EA and NAA, p<0.0001), plasma cells (AA, p=0.0032; EA and NAA, p <0.0001), immunoglobulins (AA, p=0.0044; EA and NAA, p<0.0001), monocyte cell surface (AA, p=0.03; EA, p<0.0001; NAA, p=0.04) and LDGs (AA, p=0.0008, EA p<0.0001; NAA, p=0.0103) compared to patients without anti-dsDNA and Low C. For AA and EA SLE patients, increased GSVA scores for plasma cells (AA, p=0.02; EA, p=0.0002) and Ig (AA, p=0.04; EA, p=0.0001) were also found for SLE patients with anti-dsDNA, but not Low C (FIG. 31A).

Figure 31B:
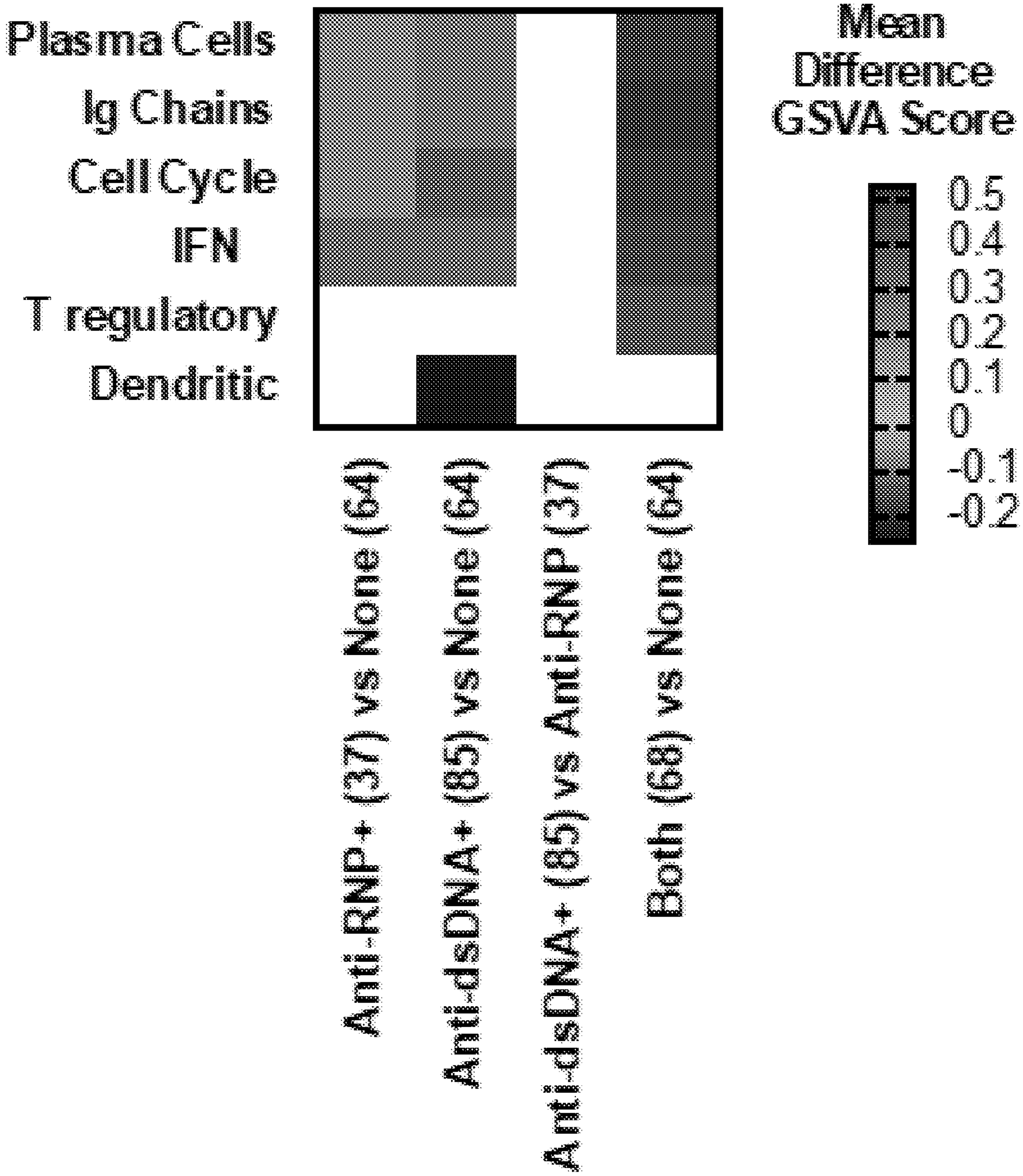
FIG. 31B shows a comparison of the change in gene expression profile for the anti-dsDNA, anti-RNP, or both, to the 64 patients in this subset without anti-RNP or anti-dsDNA autoantibodies showed significant increases in GSVA enrichment scores for IFN (anti-dsDNA, $p=0.0023$; anti-RNP, $p=0.0323$; both, $p<0.0001$), plasma cells (anti-dsDNA, $p=0.01$; anti-RNP and both, $p<0.0001$), Ig (anti-dsDNA, $p=0.0039$; anti-RNP and both, $p<0.0001$) and cell cycle (anti-dsDNA, $p=0.0003$; anti-RNP and both, $p<0.0001$).

All patients in the ILL1 and ILL2 datasets were ANA positive, and 255 SLE patients also had anti-ribonucleoprotein (RNP) autoantibody titers measured. For these 255 SLE patients (19 AA, 54 NAA, and 182 EA), 86 SLE patients were positive for anti-dsDNA, 37 were positive for anti-RNP, and 68 were positive for both. Comparison of the change in gene expression profile for the anti-dsDNA, anti-RNP, or both, to the 64 patients in this subset without anti-RNP or anti-dsDNA autoantibodies showed significant increases in GSVA enrichment scores for IFN (anti-dsDNA, p=0.0023; anti-RNP, p=0.0323; both, p<0.0001), plasma cells (anti-dsDNA, p=0.01; anti-RNP and both, p<0.0001), Ig (anti-dsDNA, p=0.0039; anti-RNP and both, p<0.0001) and cell cycle (anti-dsDNA, p=0.0003; anti-RNP and both, p<0.0001). There was a significant decrease in dendritic cells for anti-dsDNA (p=0.03) and a significant increase in T regulatory GSVA scores for both (p<0.0001) (FIG. 31B).

Figure 32A:
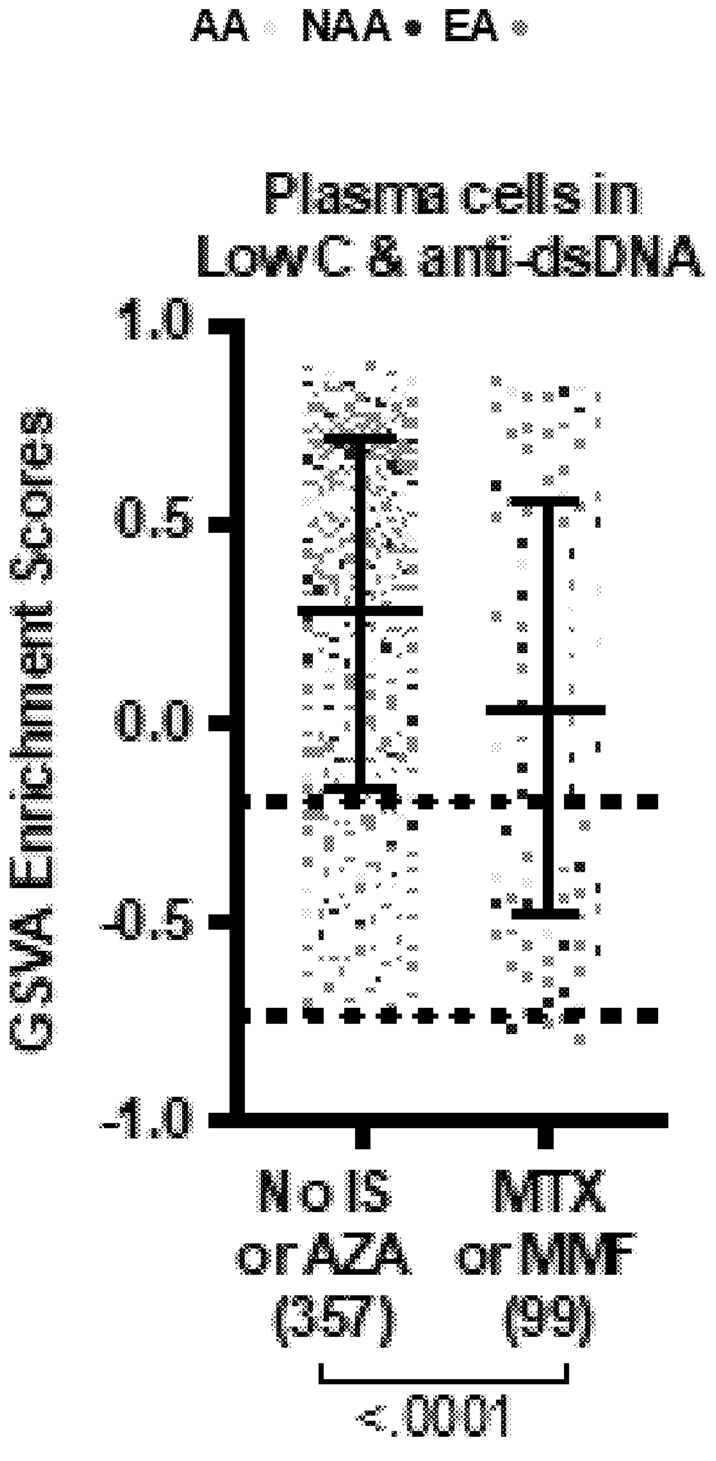
FIG. 32A shows a comparison of patients positive for both Low C and anti-dsDNA with and without specific drugs or manifestations for cell specific GSVA scores, to determine whether autoantibodies and complement levels or drugs contributed more to the relationship with specific GSVA signatures.
Figure 32B:
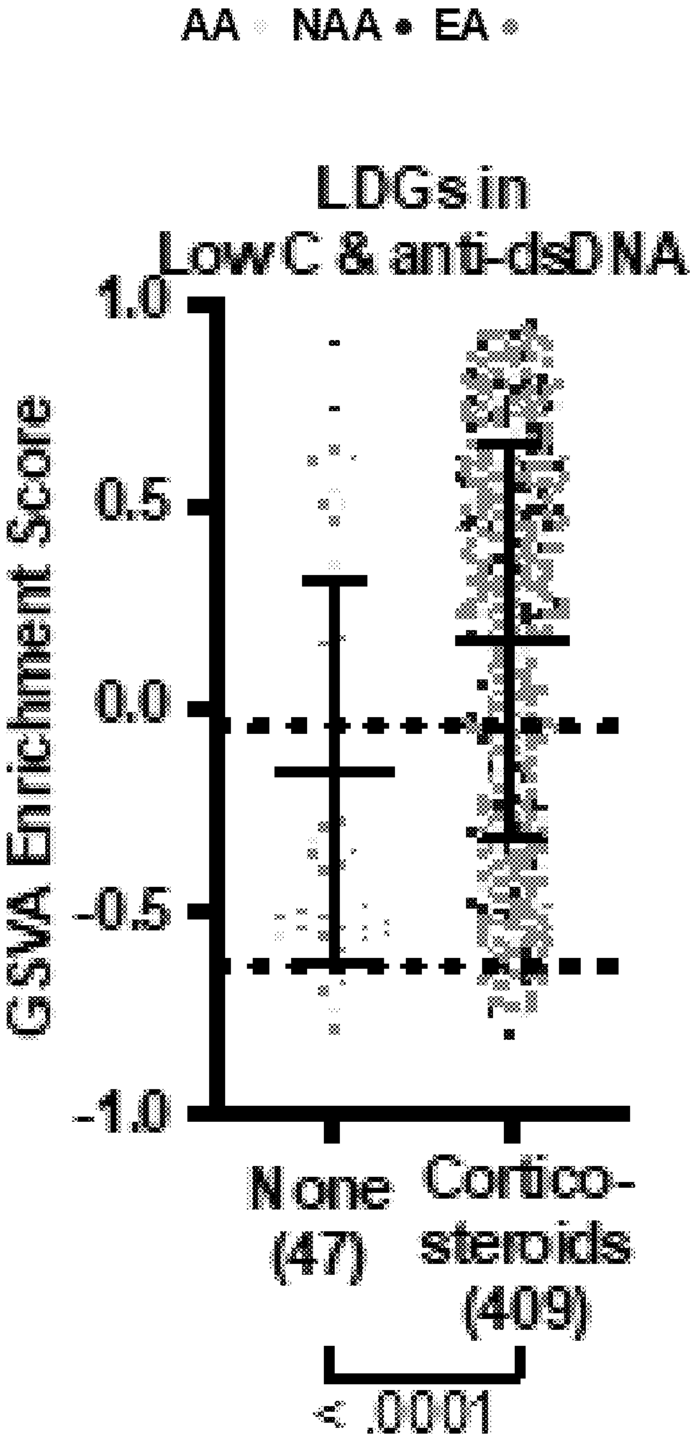
FIG. 32B shows that 90% of patients with both Low C and anti-dsDNA were also receiving corticosteroids, and patients taking corticosteroids had significantly increased LDG GSVA scores, demonstrating that the increase in LDGs observed in patients with anti-dsDNA and Low C was related to concomitant corticosteroid usage, and not the presence of anti-dsDNA and Low C.

The significant increase in plasma cell signatures detected in AA patients may not be explained by AA patients having an increased incidence of anti-dsDNA and Low C; the AA patient group had the lowest number and percentage of patients with both anti-dsDNA and Low C, 23% (n=50), whereas 29% (n=320) of EA patients and 37% (n=86) of NAA patients had both anti-dsDNA and Low C. To determine whether autoantibodies and complement levels or drugs contributed more to the relationship with specific GSVA signatures, patients positive for both Low C and anti-dsDNA were compared with and without specific drugs or manifestations for cell specific GSVA scores. Patients having both Low C and anti-dsDNA had significantly lower plasma cell GSVA scores if they were also taking either MTX or MMF (FIG. 32A). 90% of patients with both Low C and anti-dsDNA were also receiving corticosteroids, and patients taking corticosteroids had significantly increased LDG GSVA scores, demonstrating that the increase in LDGs observed in patients with anti-dsDNA and Low C was related to concomitant corticosteroid usage, and not the presence of anti-dsDNA and Low C (FIG. 32B).

Figure 32C:
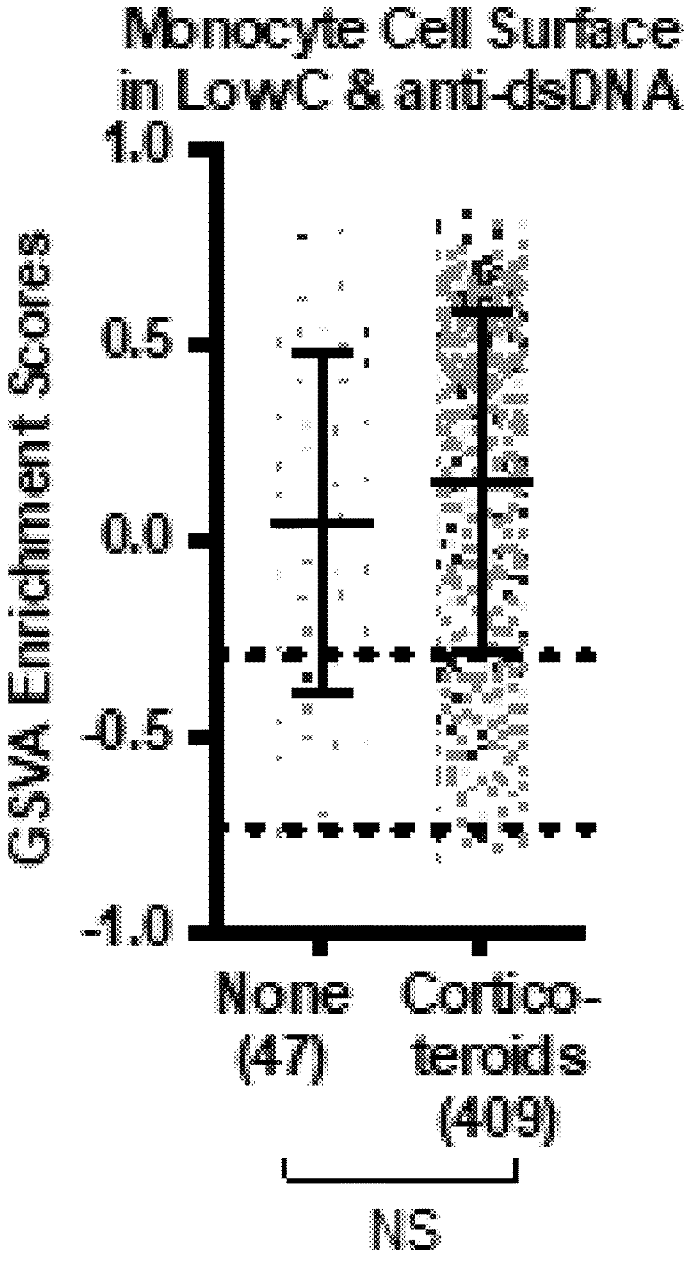
FIGS. 32C-32D show that the increase in IFN signature observed in EA and AA SLE patients on corticosteroids was related to the disproportionate numbers of patients with Low C and anti-dsDNA in the corticosteroid population, 39%, versus only 13% of the patients not taking corticosteroids who had both Low C and anti-dsDNA.
Figure 32D:
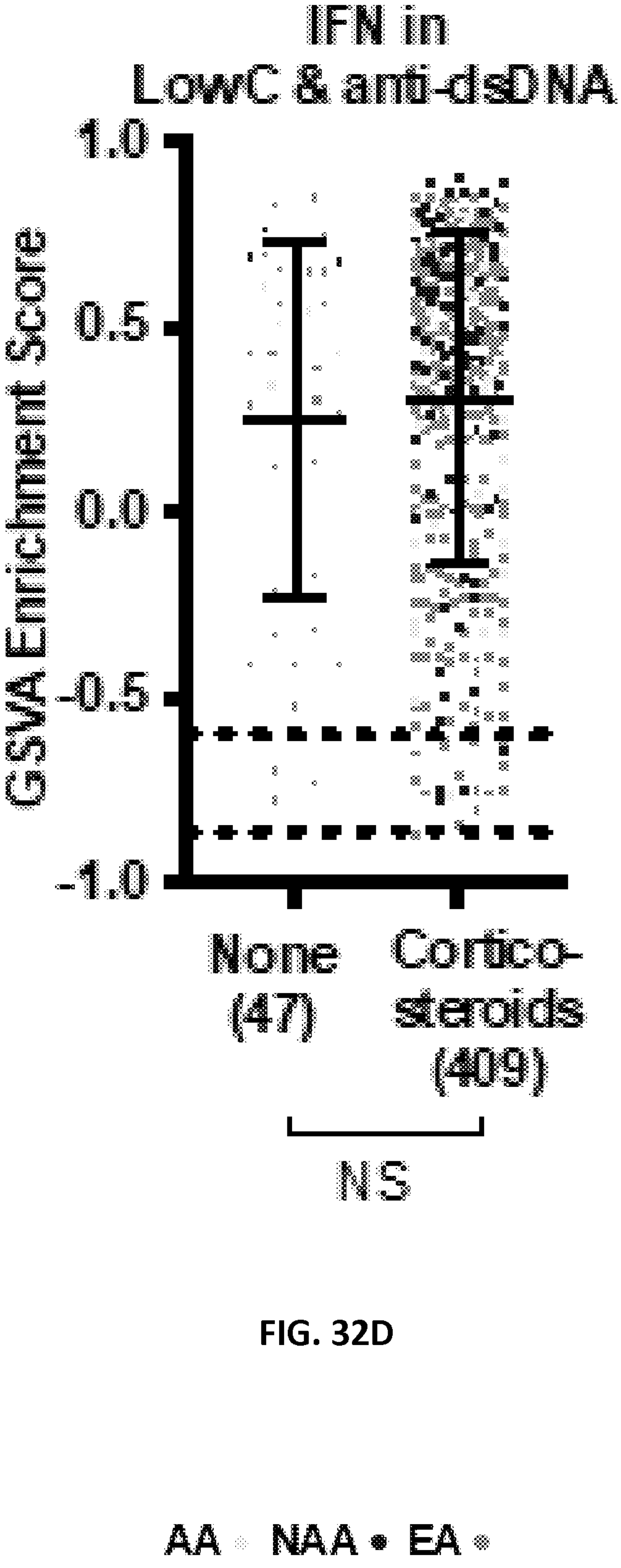
Figure 32E:
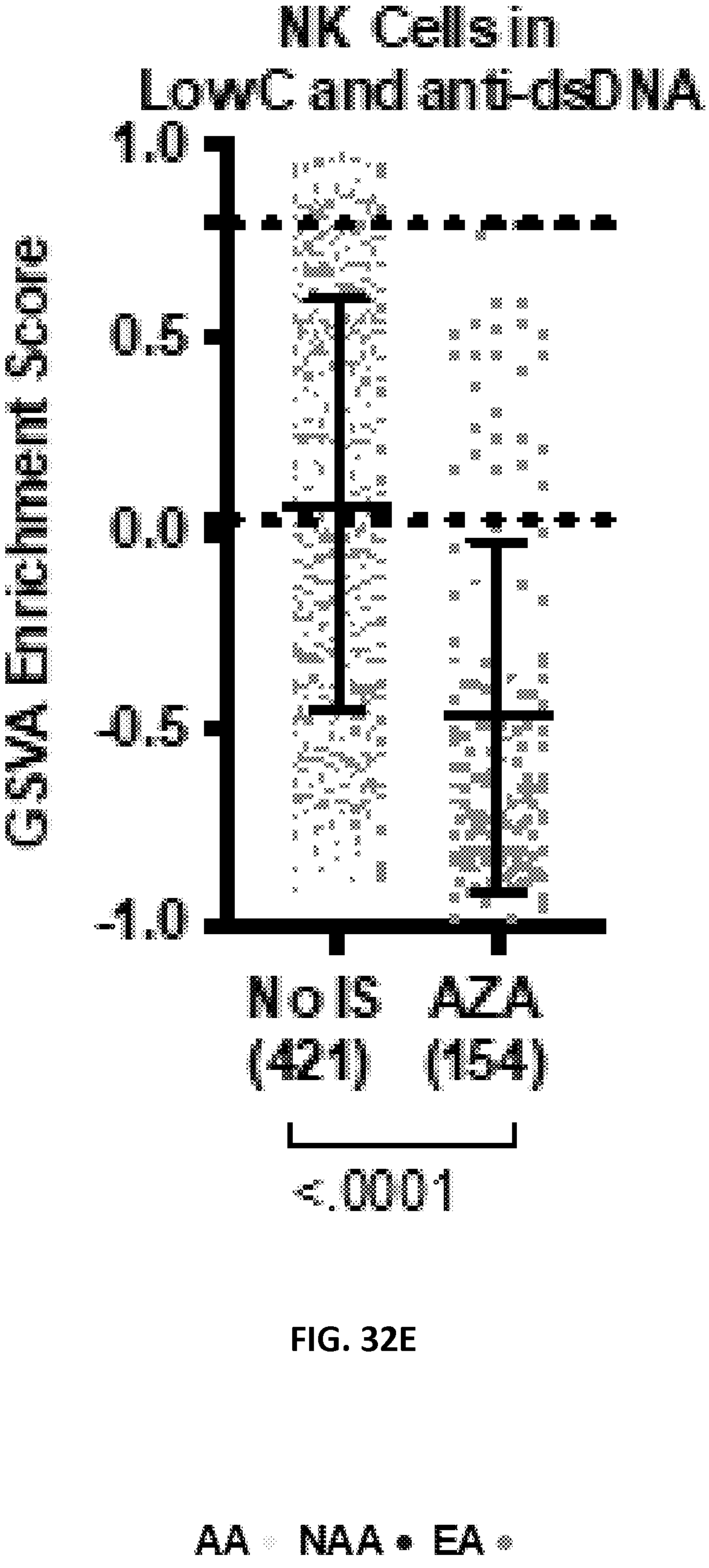
FIGS. 32E-32F show that in EA SLE patients, decreased NK cells were detected in those with anti-dsDNA or Low C. The effect was related to 23% of patients with Low C and anti-dsDNA also being on AZA (FIG. 32E) compared to only 15% of patients without low C or anti-dsDNA taking AZA (FIG. 32F) and thus not directly related to having anti-dsDNA and Low C.
Figure 32F:
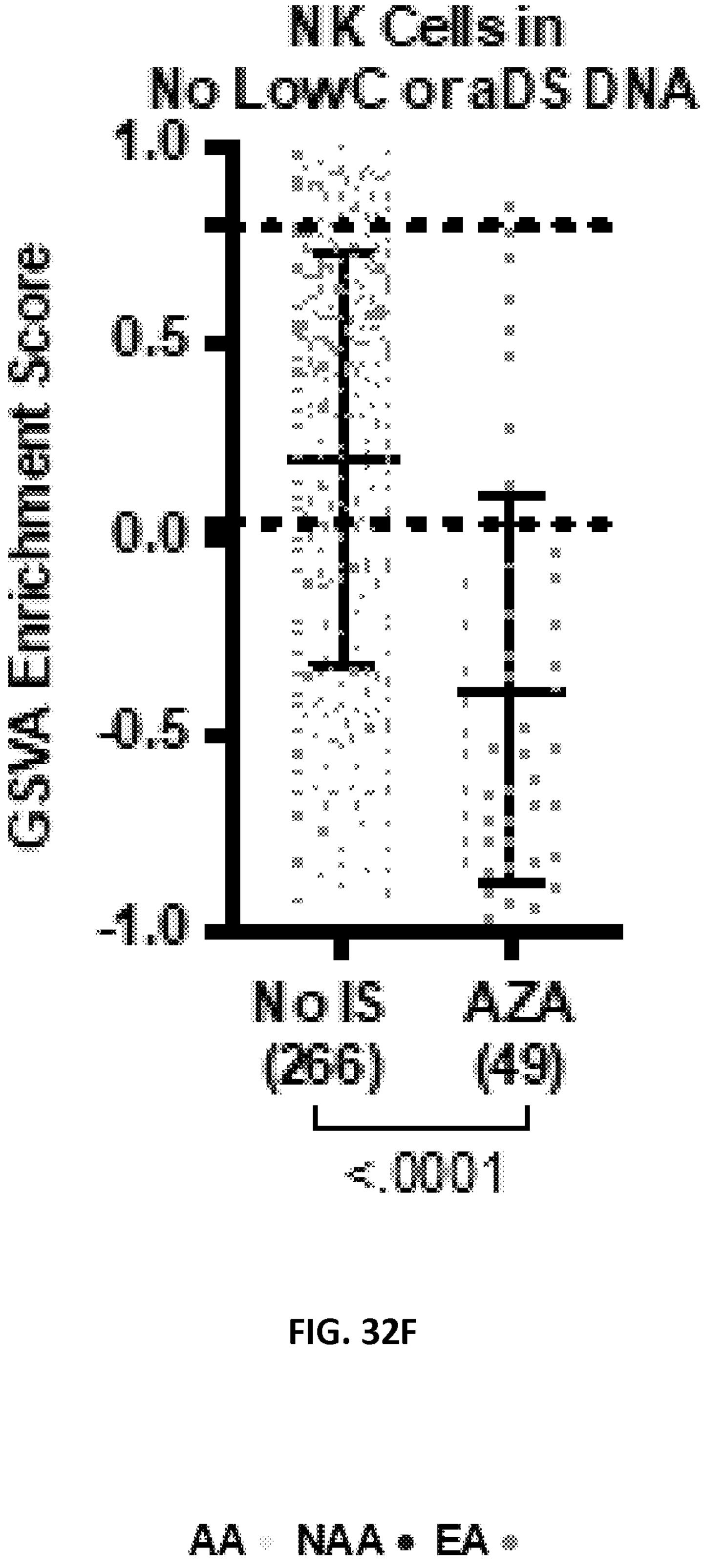
Figure 32G:
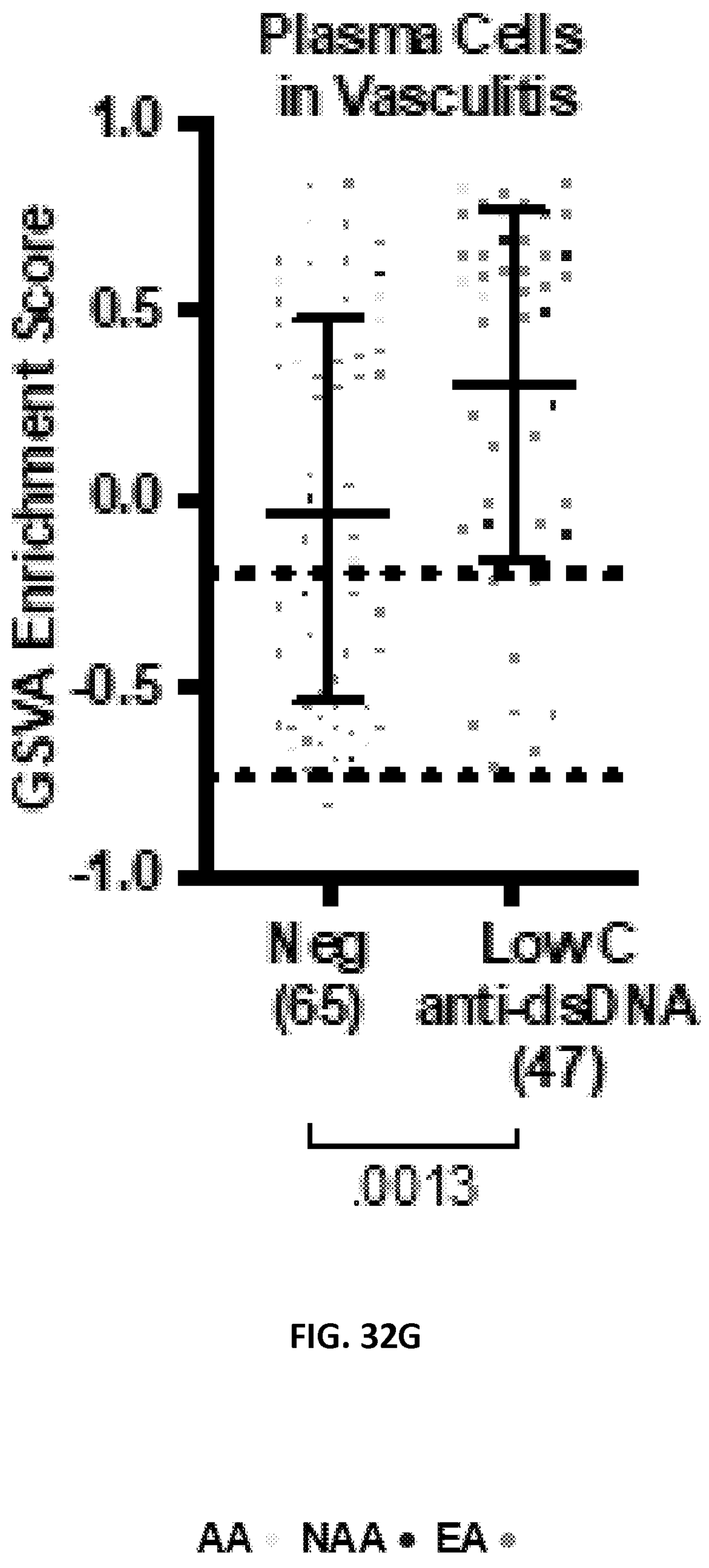
FIGS. 32G-32H show that separation of vasculitis patients by anti-dsDNA and Low C demonstrated that the significant increase in plasma cells and IFN GSVA scores were likely related to the patients also having both anti-dsDNA and Low C, as there was a significant increase in GSVA enrichment scores for IFN and plasma cells in vasculitis patients with both anti-dsDNA and Low C (plasma cell mean difference=0.2873, p=0.0013, IFN mean difference=0.3889, p<0.0001).
Figure 32H:
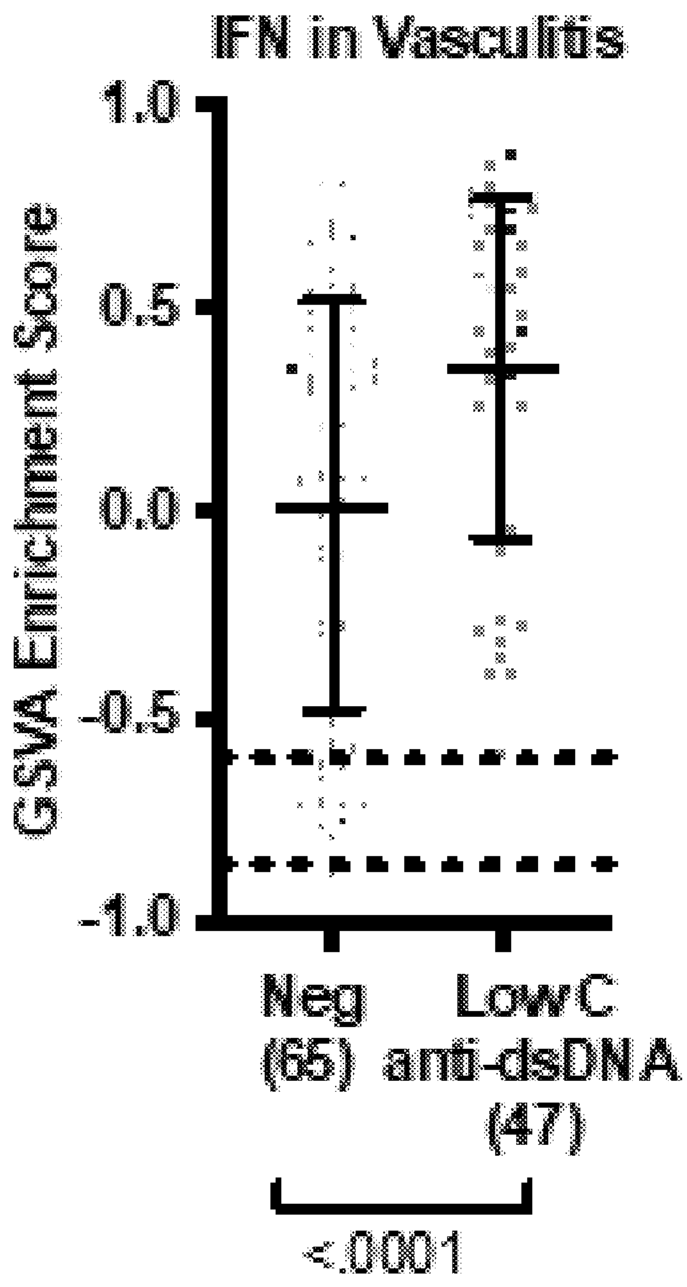

The increase in monocyte cell surface and IFN signature GSVA scores in patients with both Low C and anti-dsDNA was not explained by corticosteroid usage, as GSVA scores were similar between patients taking or not taking corticosteroids. The increase in IFN signature observed in EA and AA SLE patients on corticosteroids was related to the disproportionate numbers of patients with Low C and anti-dsDNA in the corticosteroid population, 39%, versus only 13% of the patients not taking corticosteroids who had both Low C and anti-dsDNA (FIGS. 32C-32D). In EA SLE patients, decreased NK cells were detected in those with anti-dsDNA or Low C. The effect was related to 23% of patients with Low C and anti-dsDNA also being on AZA (FIG. 32E) compared to only 15% of patients without low C or anti-dsDNA taking AZA (FIG. 32F) and thus not directly related to having anti-dsDNA and Low C. Vasculitis patients had a higher incidence of both anti-dsDNA and Low C, 41%, compared to 22% overall. Separation of vasculitis patients by anti-dsDNA and Low C demonstrated that the significant increase in plasma cells and IFN GSVA scores were likely related to the patients also having both anti-dsDNA and Low C, as there was a significant increase in GSVA enrichment scores for IFN and plasma cells in vasculitis patients with both anti-dsDNA and Low C (FIGS. 32G-32H; plasma cell mean difference=0.2873, p=0.0013, IFN mean difference=0.3889, p<0.0001). Thus, SLE serum components significantly contribute to individual gene expression signatures, but still may not explain the differences observed between AA, EA, and NAA patients.

Figure 33A:
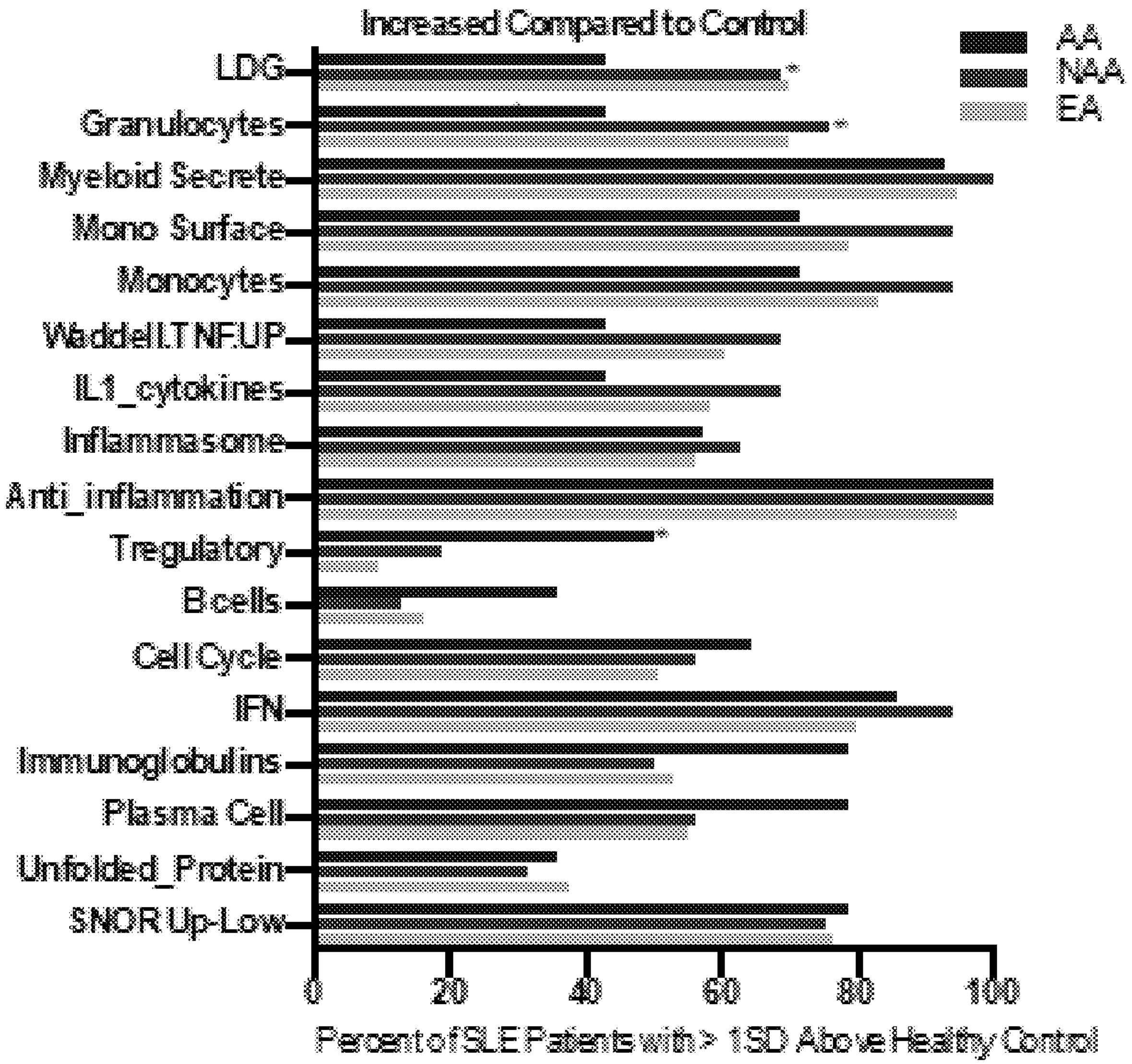
FIG. 33A shows GSVA enrichment scores calculated for the 34 cell and process modules for 14 AA, 93 EA, and 17 NAA GSE88884 ILL1 and ILL2 male patients and male HC, to determine whether ancestral differences are also observed in male lupus subjects.
Figure 33B:
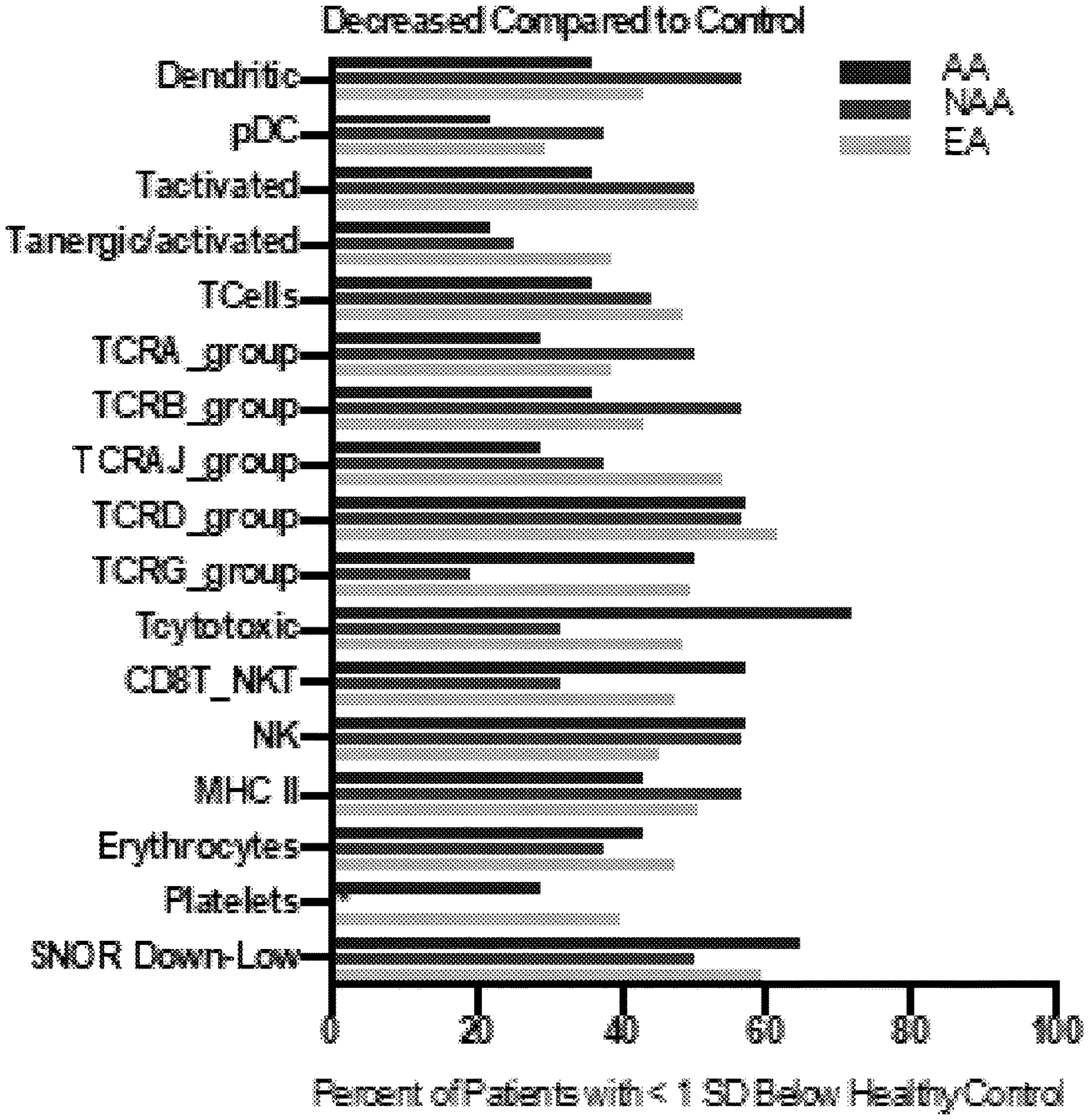
FIG. 33B shows that the combination of anti-dsDNA and Low C was associated with positive plasma cell signatures, as was detected for female SLE patients.

Male SLE Patients Demonstrated Similar Ancestral Differences as Female SLE Patients Since the frequency and severity of SLE in male and female patients with SLE is different, initially only female lupus subjects were examined. However, to determine whether ancestral differences are also observed in male lupus subjects, GSVA enrichment scores were calculated for the 34 cell and process modules for 14 AA, 93 EA, and 17 NAA GSE88884 ILL1 and ILL2 male patients and male HC. As shown in FIG. 33A, the pattern of enrichment was similar to that seen between the results obtained for female patients in FIG. 27B, with increased plasma cells, Ig, and T regulatory signatures in AA SLE patients and increased LDG and myeloid signatures in NAA and EA SLE patients. The statistical significance between the groups may not be apparent because of the low numbers of patients examined, except for the LDG and granulocyte signature in NAA compared to AA patients (p=0.0261, p=0.013), the T regulatory signature in AA compared to NAA patients (p=0.0008), and a lack of decreased platelet signatures in NAA compared to AA (p=0.0365) and EA (p=0.0001) patients. AA male patients were also less likely to have decreased TCR alpha and TCR beta signatures compared to EA (p=0.0257, p=0.0141) and NAA (p=0.0013, p=0.0017) male patients. The combination of anti-dsDNA and Low C was associated with positive plasma cell signatures, as was detected for female SLE patients (FIG. 33B).

Figure 33C:
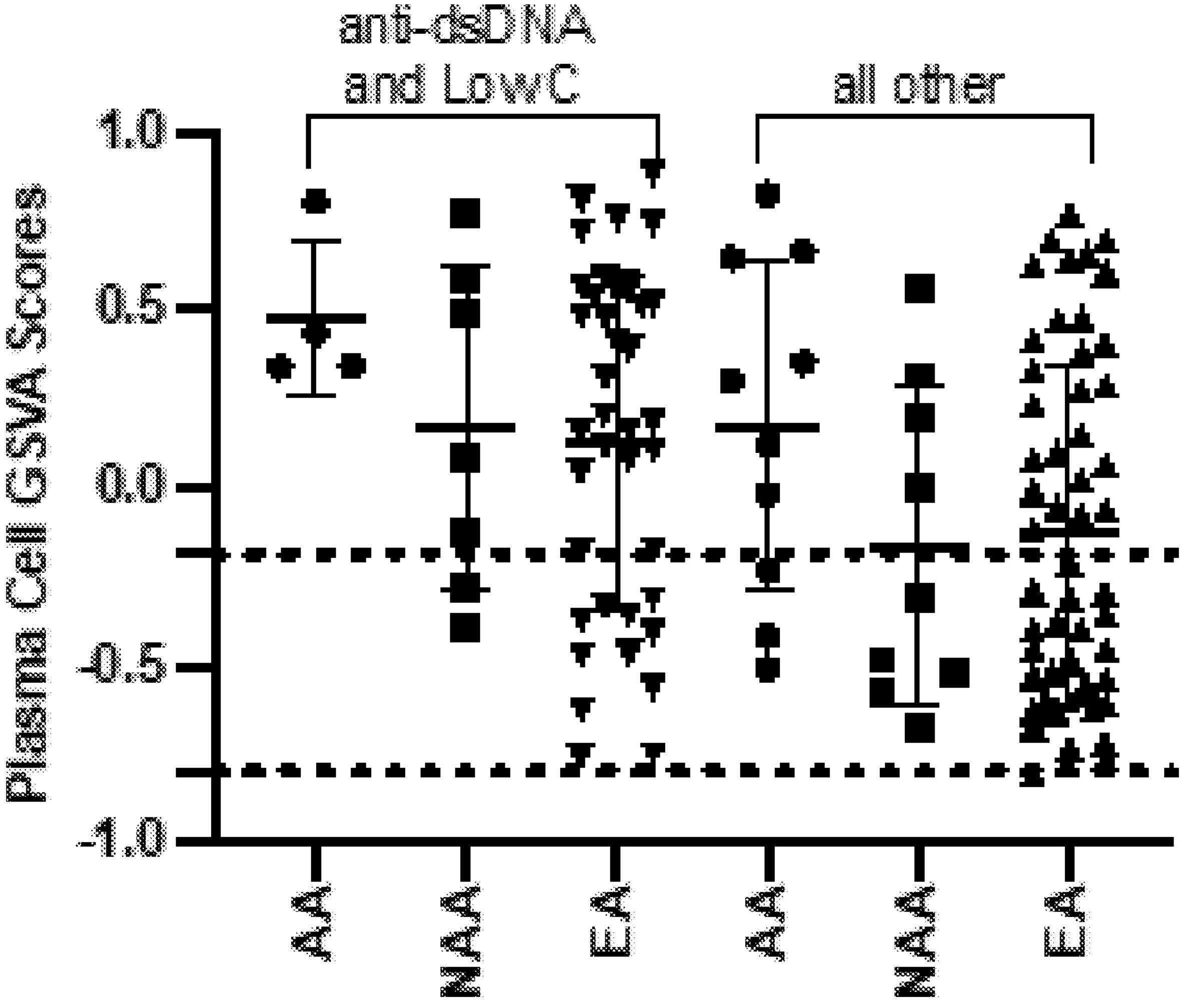
FIGS. 33C-33E show results of using EA SLE patients to determine differences between female patients and male patients with SLE. Because of the large number of female patients, the sets of female patients and male patients were able to be balanced for the percentage of patients on corticosteroids, AZA, and MTX/MMF. Further, the female patients were divided into two age groups, 25-49 years and over 50 years, because of the effects of estrogen on immune responses.
Figure 33D:
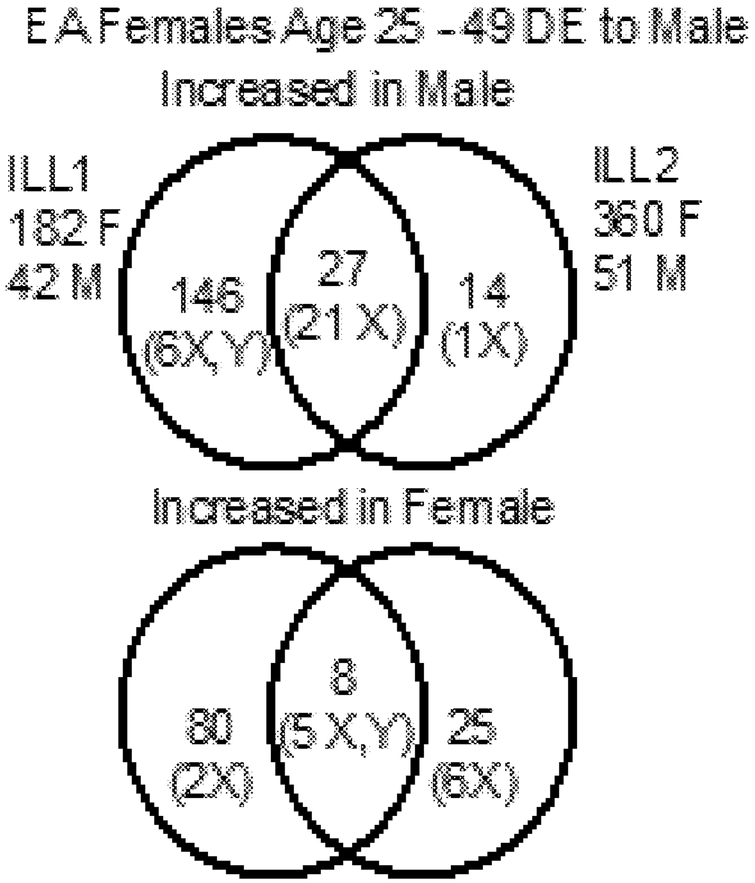
Figure 33E:
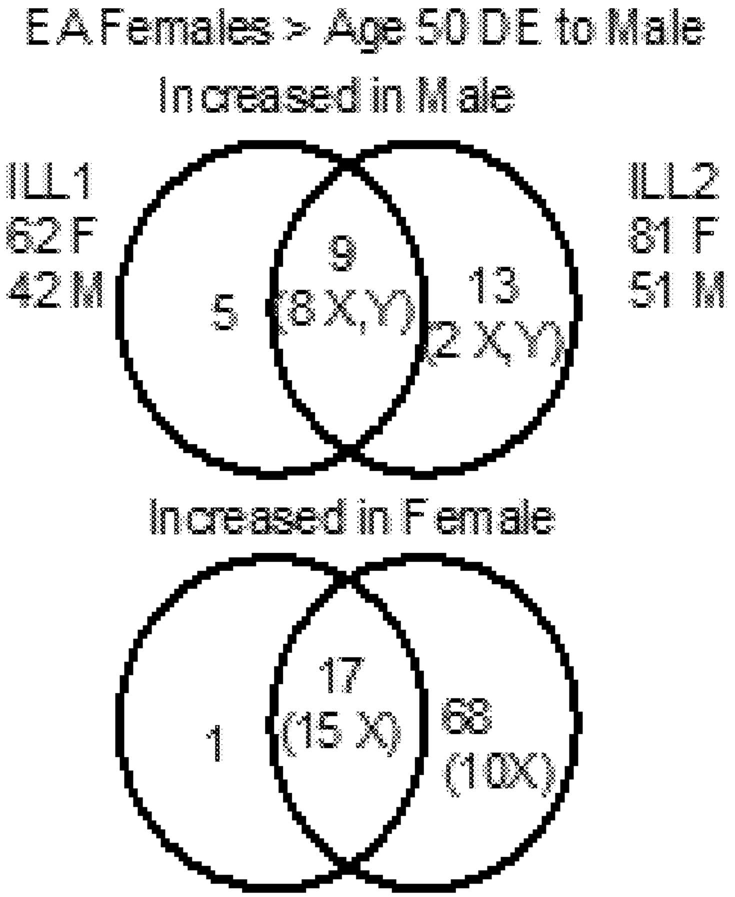

EA SLE patients were used to determine differences between female patients and male patients with SLE. Because of the large number of female patients, the sets of female patients and male patients were able to be balanced for the percentage of patients on corticosteroids, AZA, and MTX/MMF. Further, the female patients were divided into two age groups, 25-49 years and over 50 years, because of the effects of estrogen on immune responses. For comparison of females 25-49 years old to males, there were 261 DE transcripts from the ILL1 dataset and 74 DE transcripts from the ILL2 dataset (FDR=0.05); 35 of these transcripts were in common between the two datasets, and of these, 26 were encoded on the X or Y chromosome. For comparison to females over 50 years of age, there were 32 DE transcripts from ILL1 and 97 DE transcripts from ILL2; 26 of these transcripts were in common between the two datasets, and of these, 23 were encoded on the X or Y chromosome (FIGS. 33C-33E). For comparison of females age 25-49, there were several increased TCR alpha J region chains, but no increased expression of previously reported estrogen induced genes. There were no DE genes associated with plasma cells or interferon signatures. There were a few transcripts associated with granulocytes (CSF2RA, CEACAM8, DEFA4, CLEC4D, BPI) increased in ILL2 males compared to females over age 50 and ILL1 males compared to females 25-49 years, but no consistent pattern based on age of the female patients.

Figure 34A:
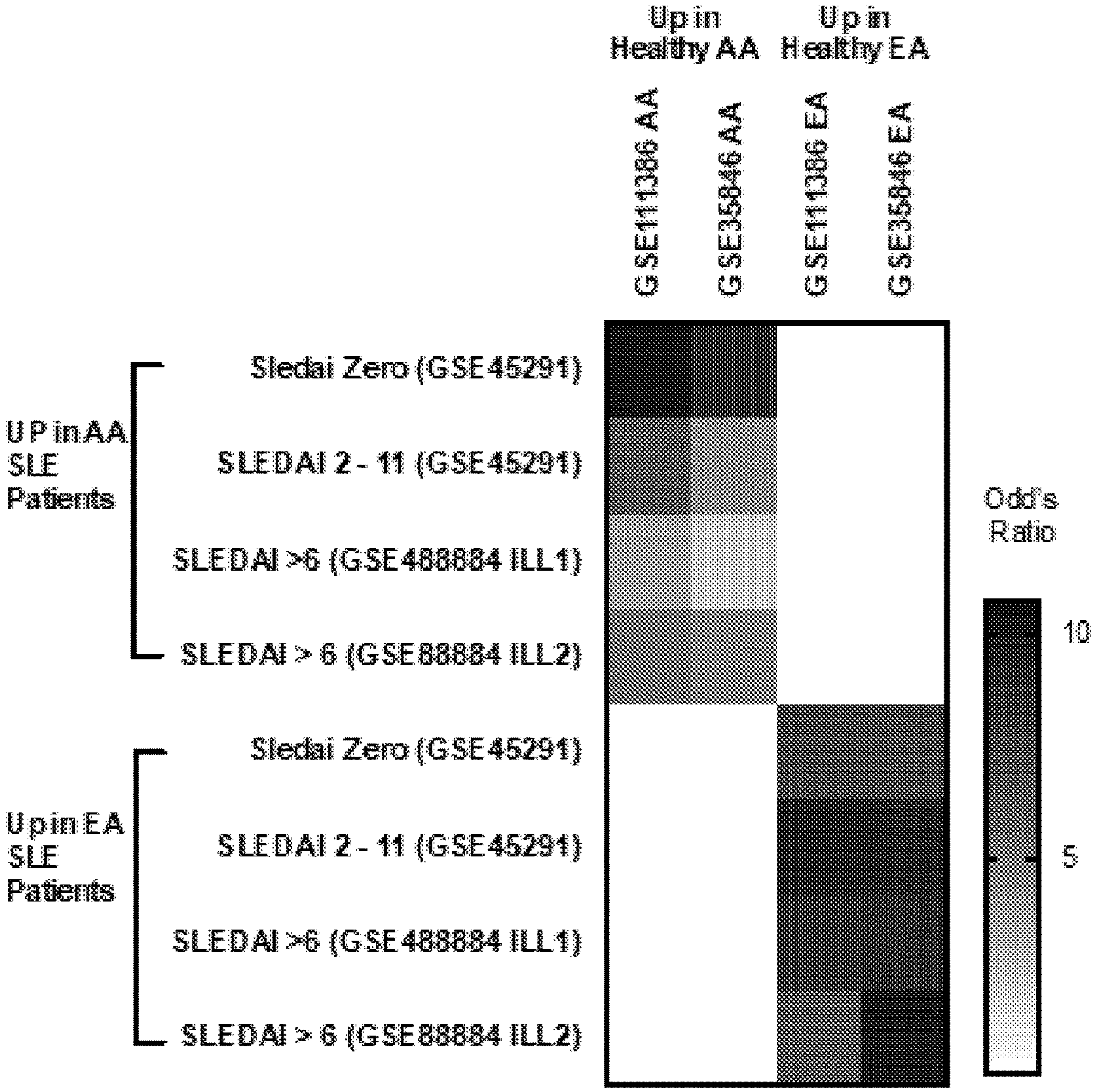
FIG. 34A shows gene expression analysis of adult, self-described AA and EA HC subjects carried out on two separate microarray datasets of normal subjects of different ancestries, in order to demonstrate that gene expression differences detected between SLE patients are related to heritable differences manifesting in expressed genes in hematopoietic cells of healthy subjects of different ancestries.

Ancestry Provides the Gene Expression Backbone, but SOC Drugs Greatly Modify Gene Expression Analyses of the DE transcripts between different ancestries have shown that EA and NAA populations overexpressed the Duffy blood group antigen ACKR1, the platelet and monocyte receptor CD36, and G6PD, in comparison to all AA populations, and that all of these genes have risk alleles resulting in decreased expression in the AA population. Therefore, gene expression differences detected between SLE patients was shown to be related to heritable differences manifesting in expressed genes in hematopoietic cells of healthy subjects of different ancestries. In order to demonstrate this, gene expression analysis of adult, self-described AA and EA HC subjects was carried out on two separate microarray datasets of normal subjects of different ancestries. Both datasets had hundreds of DE transcripts for healthy AA patients compared to healthy EA patients; GSE111386 (10 AA, 57 EA) had 3,295 DE transcripts and GSE35846 (22 AA, 55 EA) had 2,476 DE transcripts (FDR of 0.2) with 1,234 transcripts in common between the two datasets. Significant odds ratios (overlap p value <0.0001) were documented between transcripts increased in HC AA subjects compared to HC EA subjects, and transcripts increased in AA SLE patients compared to EA SLE patients in all four SLE datasets: GSE88884 ILL1, GSE88884 ILL2, GSE45291 with SLEDAI of 0, and GSE45291 with SLEDAI of 2-11) and significant odds ratios (Fisher's exact p value <0.0001) were demonstrated between transcripts increased in EA HC subjects and those increased in EA SLE patients, but no significant overlap was observed between AA HC subjects and EA SLE patients, or between EA HC subjects and AA SLE patients (FIG. 34A).

Figure 34B:
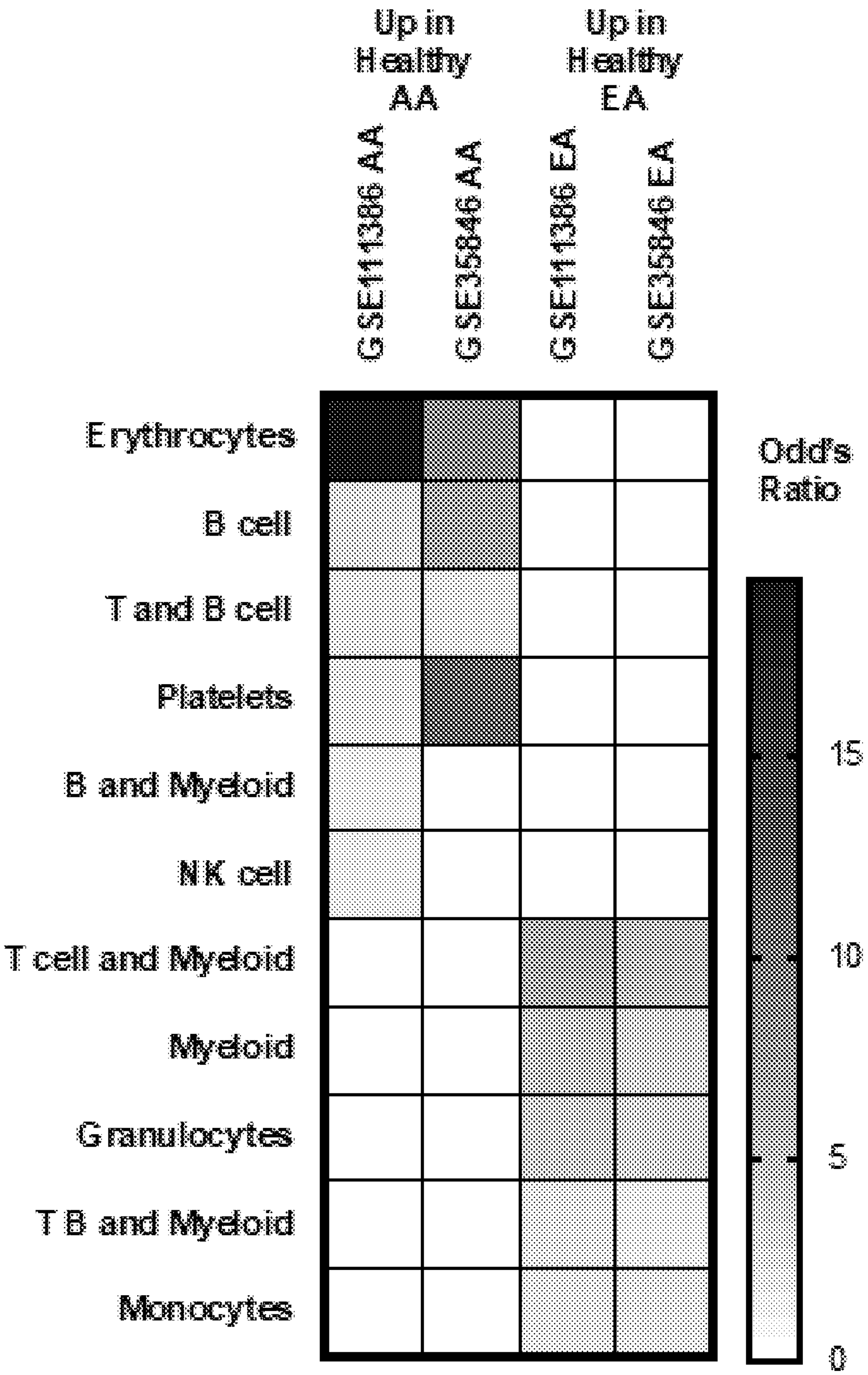
FIG. 34B shows that I-scope analysis of the transcripts increased in healthy AA patients demonstrated an increase in B cell, dendritic, erythrocyte, and platelet associated transcripts compared to EA HC subjects, and an increase in granulocyte, monocyte, and myeloid transcripts in healthy EA subjects compared to AA HC subjects.

I-scope analysis of the transcripts increased in healthy AA patients demonstrated an increase in B cell, dendritic, erythrocyte, and platelet associated transcripts compared to EA HC subjects, and an increase in granulocyte, monocyte, and myeloid transcripts in healthy EA subjects compared to AA HC subjects (FIG. 34B). IFI27, a gene commonly used to monitor the IFN signature, was increased in healthy AA subjects in both datasets, and IFITM2, another IFN signature gene, was increased in both healthy EA datasets. CXCL5, IL32, and TNFSF4 were increased in healthy AA subjects in both datasets, and CXCL8, CXCL1, GRN, MMP9, TNFSF14, and CXCL6 were increased in healthy EA subjects in both datasets. There were no genes associated with plasma cells or LDGs DE between AA and EA HC subjects, and the majority of the IFN signature genes and inflammatory secreted genes were not differentially expressed between AA and EA subjects, including IFI44, IFI44L, C1QA, C1QB, C1QC, CCL2, CXCL10, CXCL2, IL1B, TNF, and THBD.

Figure 35:
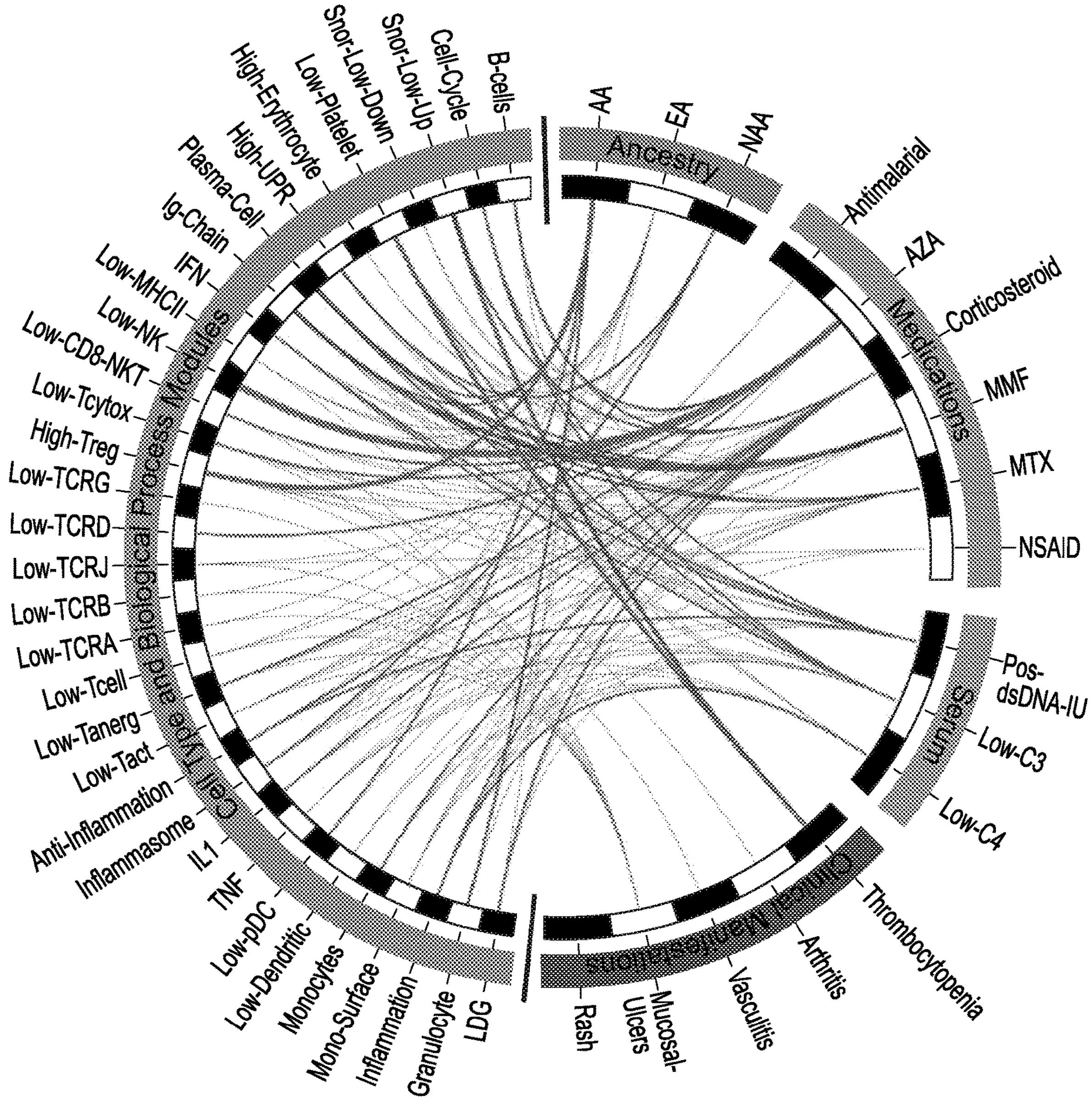
FIG. 35 shows a CIRCOS visualization of the odds ratios for each variable significantly (p<0.05) contributing to each GSVA enrichment score. Ancestry significantly influenced 21 of the 34 cell type and process module scores.

In order to determine the relative importance of ancestry, SOC drugs, and SLE manifestations to gene expression signatures, stepwise logistic regression analysis was performed for each of the 34 cell type and process signatures using the variables of ancestry (AA, EA, NAA), SOC drugs (MTX, MMF, AZA, corticosteroid drugs, NSAID drugs, and anti-malarial drugs), SLE serum components (anti-dsDNA, Low C3, Low C4) and SLE manifestations (arthritis, rash, mucosal ulcers, vasculitis, thrombocytopenia). FIG. 35 shows a CIRCOS visualization of the odds ratios for each variable significantly ($p<0.05$) contributing to each GSVA enrichment score. Ancestry significantly influenced 21 of the 34 cell type and process module scores. For AA patients, there was a negative relationship to LDG, granulocytes, IL1 cytokines, and inflammasome and a positive relationship to low pDC, Treg, IFN, plasma cells, Ig, and B cells. Low MHC II and the low SNOR up were negatively associated with NAA patients, and NAA status was positively associated with inflammasome, low T cells, and platelets. For EA patients, there was a negative association to low NK cells, granulocytes, UPR, low SNOR down, and the cell cycle and a positive association to the inflammasome, low platelets, and Treg. SLE serum components significantly influenced 19 of the 34 modules with the most significant odds ratios and confidence intervals for the IFN signature, cell cycle, plasma cells, and Ig. SLE manifestations influenced the transcriptome the least, with significant relationships to 14 signatures, but with confidence intervals very close to 1. SOC drugs influenced every cell and process module GSVA enrichment score, with the most profound effects by AZA on NK and B cells, MTX/MMF on plasma cells, Ig, and T cells, and corticosteroids on myeloid cells (based on Spearman correlation coefficients between variables, confidence intervals, p values, and odd's ratios).

Based on this data, it was hypothesized that balancing SOC drugs in SLE patients may significantly reduce the number of DE transcripts between AA and EA SLE patients. The DE analysis was repeated on GSE88884 ILL1 and ILL2 AA to EA SLE patients from FIGS. 26A-26D, but this time with selected AA and EA SLE patients of similar daily steroid usage (mean, median, and mode), no immunosuppressive drugs, and similar percentages receiving anti-malarial drugs and NSAID drugs. There were 606 DE transcripts from the ILL1 dataset AA (n=41) to EA (n=144), and 535 DE transcripts for ILL2 dataset AA (n=44) to EA (n=154) (FDR=0.05); a loss of 83 and percent 82 percent of the DE transcripts, respectively, compared to DE analysis of all ILL1 and ILL2 AA to EA SLE patients with non-matched SOC drugs in FIGS. 26A-26D. Thus, the combination of different drug regimens and ancestry significantly changed patient gene expression having profound implications for interpretation of gene expression analyses.

Discussion

The analysis and results herein provide a significant understanding of the contributions of SLE patient ancestry and SOC drugs to the subject's gene expression profile. Furthermore, the results demonstrate important ancestry-based gene expression differences present in healthy controls of AA, NAA, and EA ancestry, that serve as the background for the heterogenous transcriptomic signatures detected in SLE patients. Thousands of DE transcripts were identified when AA, EA, and NAA SLE patients were compared to each other. There were no detectable transcripts when SLE patients of the same ancestry were randomized and compared, demonstrating that the differential expression between ancestral groups was determined by genetic ancestral make-up to a significant extent.

The ancestry-related differences in gene expression profiles highlights an important issue of using appropriate numbers of controls with matching ancestry to determine meaningful changes in a disease state. A striking overlap was observed between unrelated AA HC subjects and EA DE analyses and the separate AA SLE and EA DE analyses of 1,810 patients. Somewhat surprisingly, the AA HC subjects overlapped with AA SLE patients better than the EA HC subjects to EA SLE patients, since the AA subjects may be expected to contain more admixture than the EA subjects. These data demonstrate that ancestral gene expression differences serve as a backdrop on which the transcriptomic signature is built and accounts for much of the heterogeneity in blood gene signatures. Ancestral SNPs in HC may be estimated to account for about 17-28% of variation in gene expression, and these results demonstrated these gene expression differences readily contribute to an SLE patient's transcriptomic signature. Additionally, several ancestral-related genes divergent between AA and EA populations that are also involved in immune responses were differentially expressed between SLE patients and HC subjects of different ancestries: IL8, CXCL1, CXCL5, STAT1, CEPBP, ITGAM, and CD58, demonstrating that ancestral SNPs contribute to the gene expression profile. It may be shown that AA is associated with increased responses to infection and increased expression of inflammatory response genes. While generally, an increased inflammatory response may be associated with an increase in innate immune response cells, the results actually showed a depletion, or less of an increase, in myeloid cells in AA patients compared to EA and NAA patients. Interestingly, there was no significant difference in expression of transcripts for inflammatory mediators such as complement, TNF, and CXCL10, despite the difference in detection of cell types that generally produce these inflammatory mediators. This result indicates that individual innate immune cells from AA patients produce more inflammatory mediators.

The ramifications of these results toward interpretation of gene expression analysis are important. HC of AA and EA ancestries were reproducibly shown to be disparate in transcripts for erythrocyte, platelet, B cell, T cell, NK cell, granulocytes, and monocyte transcripts; furthermore, this transcript data agrees with cell counts and genetic differences between ancestries. Platelet counts may be shown to be higher in AA than EA patients, and the Duffy Null Polymorphism (ACRK1 gene) may be shown to be a cause of decreased neutrophil counts in AA patients. CD19+ B cell counts may be shown to be increased in AA patients compared to EA patients, and CD3+ T cells may be shown to be increased in EA patients versus AA patients, although overall lymphocyte counts may not be different. The erythrocyte transcripts increased in AA patients may be related to increased reticulocytes in the circulation, and this may be explained by AA patients more frequently possessing x-linked G6PD alleles responsible for the African ancestry-associated G6PD deficiency prominent in AA males. Reticulocytosis may be augmented in AA patients with SLE, as persons with G6PD deficiency may have induced hemolysis secondary to infection and leukocyte phagocytosis. G6PD was decreased in both AA SLE patients and AA HC subjects compared to EA SLE patients and EA HC subjects. The ancestral transcriptomic backbone may be emphasized depending on HC comparators, and as a result, many DE transcripts may be inappropriately attributed to the disease instead of the ancestry, whether or not the allelic differences play an actual role in the pathogenesis of SLE. Analysis of purified cell types from AA and EA SLE patients may show only about 10% similar transcripts, indicating disparate constitutive pathways and metabolism operating in AA and EA SLE patient hematopoietic cells. Although these data and results described herein confirmed strong ancestral contributions to the SLE signature, there were patients within all ancestries with disparate signatures from the prevailing ancestral type, demonstrating that personalized medicine strategies to determine the type of lupus may be helpful, instead of relying on ancestral background or group statistics (e.g., median or mean). Additionally, drugs and their effect on cell populations and signaling pathways may be taken into account to help focus attention onto pathways and cells involved in disease and not the treatment. The IL-1, inflammasome, and LDG increased signatures detected in NAA patients appeared to be related to corticosteroid drugs. This signature may be further deciphered by performing studies of healthy NAA patients. Single-cell technology may be used to elucidate and observe effects of ancestry and SOC drugs, and to distinguish between out cell populations prominent in ancestries and induced or repressed by concomitant drugs, from cell populations actively participating in disease processes.

The results demonstrate a strong relationship between SLE serum components and circulating Ig, plasma cell, cell cycle, and IFN GSVA scores; further, this association was more pronounced in EA and NAA patients than AA patients. These data also and demonstrated that observed increases in plasma cell signatures in pediatric AA SLE patients are likely related to ancestry, and not disease activity. Increased Ig production is associated with plasma cells, and Ig genes have been used as a proxy for plasma cell measurements in microarray datasets. Both healthy control AA and EA datasets were on Illuminate chips that harbor only a few Ig genes, so although Ig genes were not detected as different between healthy AA and EA, in some cases, this signature may derive from healthy B cells, which may explain why AA plasma cell GSVA scores did not correlate as well with serum component measurements. Single-cell RNAseq analysis of isolated hematopoietic cell types in healthy subjects may demonstrate that B cells have increased Ig transcripts compared to all cell types except plasma cells. Lupus in the AA population may be strongly biased towards generation of plasma cells. Since healthy AA subjects, in two separate datasets, also showed increased transcripts associated with B cells, the increase in plasma cells may have an origin in the inherent differences in the healthy AA population.

Further, the results herein demonstrated that increased IFN signatures were associated with anti-dsDNA and Low C in all ancestry groups. AA SLE patients may be shown to be more likely to have an IFN signature than EA SLE patients; the results obtained also detected significantly more AA than EA SLE patients with an IFN signature, but the percentages of IFN-positive patients were greater than 75% for both ancestry groups and less useful for distinguishing AA from EA SLE patients. Corticosteroids may be demonstrated to decrease IFN signaling, but this effect was not seen in this study and may be a result of the large number of patients on corticosteroids also having both anti-dsDNA and Low C. In some cases, monocytes appear to retain the IFN signature in inactive lupus patients, confounding usage of this signature to determine disease activity, and the increased IFN signature in SLE patients with anti-dsDNA and Low C may be accompanied with increased signatures for monocyte cell surface transcripts.

Besides the effect of ancestry and SLE serum components, the results and data demonstrated the profound effect SOC therapies have on SLE patient gene expression profiles, and indicate a method of accounting for these effects using the change in GSVA enrichment score associated with drug administration. When the SOC drugs were matched between AA and EA SLE patients, more than 80% of the DE transcripts were lost between AA and EA SLE patients from ILL1, and this was repeated in ILL2. Patients with increased GSVA scores compared to controls for the inflammasome, IL-1, and myeloid signatures were significantly increased in the NAA population, and the number of DE transcripts between AA and EA patients was almost twice the difference between AA and EA patients, indicating at first that this population was the most different from AA and EA patients. However, further analysis determined that NAA were also receiving more corticosteroids and immunosuppressive therapy, and that this therapy was likely accounting for much of their increased myeloid and decreased lymphocyte signatures.

Further, the results showed increased signatures for myeloid cells in pediatric EA and NAA (Hispanic) SLE compared to AA patients, although this difference may be related to the benign neutropenia common in people of African ancestry, the increased corticosteroids taken by NAA patients, and not lupus related. By using more than 1,500 SLE patients, it was shown that AA SLE patients did not have significantly enriched plasma cell signatures compared to EA and NAA ancestry groups, if all patients had both anti-dsDNA and Low C, or if all patients were receiving MTX or MMF. Although AA patients also had the lowest number of patients on AZA, and AZA therapy was related to decreased B cell GSVA scores, there were not enough patients receiving this therapy for this drug to account for the differences noted between ancestry groups. In confirmation of the methodology used, AZA treatment significantly decreased NK cell GSVA scores in all three ancestry groups in the GSE88884 and GSE45291 datasets, consistent with an effect of AZA on NK cells. EA patients had significantly higher NK cell GSVA scores compared to NAA patients, when both were not receiving AZA treatment; however, there was no significant difference when both ancestry groups were receiving AZA treatment.

The association of neutrophil granule protein transcripts (LDG signature) with corticosteroid usage may be observed. Corticosteroid usage also had a significant effect on most myeloid signatures including monocyte cell surface transcripts, myeloid secreted protein transcripts, and IL1 transcripts. This may be a result of increasing this population in the periphery as steroids may be shown to increase demargination of mature neutrophils. The LDG signature was also prominently detected in EA SLE patients with SLEDAI values of zero on corticosteroids. LDGs in autoimmunity may be described as being inflammatory and contributing to SLE pathogenesis from data obtained from in vitro experiments demonstrating an increased capacity for production of inflammatory cytokines. However, corticosteroids may be demonstrated to induce human monocytes to secrete G-CSF, and G-CSF may mobilize neutrophils from the bone marrow, indicating a mechanism where chronic corticosteroid use may promote the release of immature neutrophils. G-CSF therapy for neutropenia in lupus patients may induce flares and vasculitis, indicating a pathologic role for G-CSF. G-CSF also may be shown to increase a glycosylated, membrane form of MPO on mature neutrophils and monocytes, and this form of MPO may bind to E-selectin on human endothelium and induce cytotoxicity. The strong relationship between LDGs and corticosteroid usage, and yet the presence of transcripts for granule proteins in patients reportedly not taking corticosteroids, may be indicative that there may be two or more different populations of granule expressing cell populations. The relative contribution to microarray signatures of genes related to neutrophils may be disparate between AA and other populations and may not reflect differences in lupus. Therefore, different neutrophil signatures may arise because of ancestry-related rather than lupus-related differences.

The observed lack of difference in GSVA scores for inflammatory cell populations, inflammatory cytokines, IFN signatures, and the TNF pathway for patients treated with anti-malarial drugs (e.g., hydroxychloroquine (Plaquenil), chloroquine (Aralen), and quinacrine (Atabrine)) compared to all other treatments was surprising, as chloroquine may decrease anti-inflammatory cytokine production. Experiments may demonstrate that hydroxychloroquine blocks TLR 9/7 stimulation and subsequent IFN production in vitro. As plasmacytoid dendritic cells were generally decreased in the periphery of SLE patients, perhaps the target cells for anti-malarial drugs are found in tissues, but this data demonstrated no significant changes in cell populations or processes associated with anti-malarial usage in the periphery. Surprisingly, NSAID drugs had more of an effect on gene expression profiles than anti-malarial drugs. Although commonly known as cyclooxygenase isoenzyme inhibitors, NSAID drugs may be shown to block caspases and inflammation; although the change in GSVA score was not greater than 0.2, there did appear to be a decrease in LDGs and the anti-inflammation signature, at least in EA SLE patients.

Major differences may be reported in lupus cohorts between male and female SLE patients with respect to renal involvement and serological manifestations. While renal patients were excluded from the ILL1 and ILL2 clinical trials, among patients with non-renal manifestations, there did not appear to be consistent differences in gene expression other than the expected transcripts encoded on the X and Y chromosomes. Gene expression differences attributable to estrogen in female patients under 50 may be expected; however, analysis of the DE transcripts did not reveal an obvious link to effects on the immune system. The ancestral differences between males also appeared similar to the ancestral differences between females, indicating the ancestral component to gene expression are more important to take into consideration than male-vs.-female differences.

Self-identified ancestry gave useful information for the genetic background of an individual; further, pairing studies with genetic data may be performed to determine specific ancestry admixtures. The current results provide a framework for determining the meaningful contributions to the SLE disease transcriptome and to separate these contributions from the effects of SOC therapy and ancestry.

In summary, ancestry plays an important role in the gene expression profiles of individual SLE patients and by implication contributes to the molecular pathways operative in each subject. Understanding, for example, that some self-described AA patients may have higher levels of transcripts for B cells, erythrocytes, and platelets compared to EA SLE patients may help explain differences in gene expression data that do not manifest from the SLE disease, but from the patient's ancestral background. The relationship of corticosteroid drugs to LDGs has implications against using this signature as a measure of disease severity or interpreting LDGs as playing a role in worsening disease, as worsening disease may prompt an increase in corticosteroid doses. Combinations of different ancestry, SOC therapy, and autoantibody production associated with gene expression profiles m datasets comprised of different populations from around the world difficult to compare. Understanding the contributions of the gene expression signature components may permit a better understanding and interpretation of the signatures and their relationship to disease status.

Methods

Gene expression datasets were obtained as follows. Data were derived from publicly available datasets on Gene Expression Omnibus (GEO, www.ncbi.nlm.nih.gov/geo/). Raw data sources were used as follows: GSE88884 female whole blood Illuminate 1 (ILL1; 10 female HC, 798 female SLE (540 EA, 101 AA, and 157 NAA); all with SLEDAI ≥6), GSE88884 female whole blood Illuminate 2 (ILL1; 7 female HC, 767 female SLE (577 EA, 115 AA, and 75 NAA) all with SLEDAI ≥6), GSE88884 male whole blood Illuminate 1 SLE (ILL1: 5 male HC, 59 male SLE (6 AA, 42 EA, and 11 NAA), GSE88884 male whole blood Illuminate 2 (ILL2: 4 male HC, 65 male SLE (8 AA, 51 EA, and 6 NAA); (GSE45291 whole blood (9 female HC, female SLE: 73 AA, 71 EA with SLEDAI of 2-11), GSE45291 whole blood (9 female HC, female SLE: 25 AA, 75 EA; all with SLEDAI of 0), GSE35846 whole blood from healthy females (55 EA, 22 AA), and GSE111386 whole blood from healthy females (10 AA, 57 EA). Clinical data including disease activity assessed by SLEDAI, anti-dsDNA titers, complement levels, disease manifestations, and standard of care drugs were provided by Eli Lilly (GSE88884 Illuminate I and Illuminate 2).

Quality control and normalization of raw data files were performed as follows. Statistical analysis was conducted using R and relevant Bioconductor packages. For datasets GSE88884 and GSE45291, non-normalized arrays were inspected for visual artifacts or poor RNA hybridization using Affy QC plots. To increase the probability of identifying differentially expressed genes (DEGs), analysis was conducted using normalized datasets prepared using both the native Affy chip definition files, followed by custom Brain Array Entrez CDFs maintained by the University of Michigan Molecular and Behavioral Neuroscience Institute. The Affy CDFs include multiple probes per gene and almost twice as many probes as BA CDFs. Whereas Affy chip definition files can provide the greatest amount of variance information for Bayesian fitting, the Brain Array chip definition files are used to exclude probes with known non-specific binding and those shown by quarterly BLASTs to no longer fall within the target gene. Illumina CDFs were used for the Illumina datasets (GSE35846, GSE111386).

Differential gene expression (DE) analysis was performed as follows. GCRMA normalized expression values were variance-corrected using local empirical Bayesian shrinkage, followed by calculation of DE using the ebayes function in the open source BioConductor LIMMA package (www.bioconductor.org/packages/release/bioc/html/limma.html). Resulting p-values were adjusted for multiple hypothesis testing and filtered to retain DE probes with a False Discovery Rate (FDR) of less than 0.05.

Determination of female and male controls was performed as follows. Log 2 expression values were used to determine sex of unknown healthy controls and to compute sex module scores using the formula below:

$$\text{Sex module} = XISTlog2expression + TSIXlog2expression - (UTYlog2expression + USP9Ylog2expression).$$

Female controls scored above zero and male controls scored below zero.

I-Scope

I-scope is a tool developed to identify immune infiltrates. I-scope was created through an iterative search of more than 17,000 genes identified in more than 50 microarray datasets. From this search, 1,226 candidate genes were identified and researched for restriction in hematopoietic cells as determined by the HPA, GTEx, and FANTOM5 datasets (www.proteinatlas.org). A set of 926 genes met a set of criteria for being mainly restricted to hematopoietic lineages (brain, reproductive organ exclusions were permitted). These genes were researched for immune cell specific expression in hematopoietic sub-categories: T cells, Regulatory T Cells (Treg), Activated Tcells (Tactivated), Anergic/Activated cells (Tanergic), Alpha/Beta T cells (abTcells), Gamma delta T cells (gdTcells), CD8 T, NK/NKT cells, NK cells, T or B cells, B cells, B or pDC cells, GC B cells, T or B or Myeloid cells, B or Myeloid cells, Antigen Presenting Cells or MHC Class II expressing cells (MHC II), Dendritic cells (Dendritic), Plasmacytoid dendritic cells (pDC), Myeloid cells (Myeloid), Monocytes, Plasma Cells (Plasma), Erythrocytes (Erythro), Granulocytes (Neut), Low density granulocytes (LDG), and Platelets. Transcripts are entered into I-scope, and the number of transcripts in each category were determined. Odds ratios were calculated with confidence intervals using the Fisher's exact test in R.

Gene ontology (GO) biological pathways were determined as follows. The database for annotation, visualization and integrated discovery (DAVID) (david.abcc.ncifcrf.gov/) was used to determine enriched GO biological pathways.

Gene Set Variation Analysis (GSVA) was performed as follows. The GSVA (V1.25.0) software package is an open source package available from R/Bioconductor, and was used as a non-parametric, unsupervised method for estimating the variation of pre-defined gene sets in patient and control samples of microarray expression data sets (www.bioconductor.org/packages/release/bioc/html/GSVA.html). The inputs for the GSVA algorithm were a gene expression matrix of log 2 microarray expression values (Brain Array chip definitions) for pre-defined gene sets co-expressed in SLE datasets. Enrichment scores (GSVA scores) were calculated non-parametrically using a Kolmogorov Smirnoff (KS)-like random walk statistic and a negative value for a particular sample and gene set, meaning that the gene set has a lower expression than the same gene set with a positive value. The enrichment scores (ES) were the largest positive and negative random walk deviations from zero, respectively, for a particular sample and gene set. The positive and negative ES for a particular gene set depend on the expression levels of the genes that form the pre-defined gene set.

Enrichment modules containing cell type and process-specific genes were created through an iterative process of identifying DE transcripts pertaining to a restricted profile of hematopoietic cells in 13 SLE microarray datasets, and checked for expression in purified T cells, B cells, and Monocytes to remove transcripts indicative of multiple cell types. Genes were identified through literature mining, GO biological pathways, and STRING interactome analysis as belonging to specific categories. The Low Disease (Signature) Up and Low Disease (Signature) Down are the seven most over-expressed and seven most under-expressed transcripts by log fold change for 348 female patients from dataset GSE88884 (ILL1 and ILL2) that were not separated from healthy controls by principal component analysis (PCA) compared by limma DE analysis to HC (FDR=0.05). The LDG signature was taken from purified LDGs DE to HC and SLE neutrophils, (Villaneueva, 2011) and consists mainly of neutrophil granule proteins from Module B as described in Kegerreis et al (2019). The overlap in genes between some signatures was intentional and used to check that signatures were behaving cohesively between patients.

Weighted Gene Coexpression Network Analysis (WGCNA) was performed as follows. WGCNA is an open source package for R available at horvath.genetics.ucla.edu/html/CoexpressionNetwork/Rpackages/WGCNA/.

Log 2 normalized microarray expression values for the GSE88884 ILL1 and ILL2 datasets were filtered using an IQR to remove saturated probes with low variability between samples and used as inputs to WGCNA (V1.51). Adjacency co-expression matrices for all probes in a given set were calculated by Pearson's correlation using signed network type specific formulae. Blockwise network construction was performed using soft threshold power values that were manually selected and specific to each dataset in order to preserve maximal scale free topology of the networks.

Resultant dendrograms of correlation networks were trimmed to isolate individual modular groups of probes, labeled using semi-random color assignments, based on a detection cut height of 1, with a merging cut height of 0.2, with the additional use of a partitioning around medoids function. Final membership of probes representing the same gene into modules was based on selection of greatest scale within module correlation against module eigengene (ME) values. Correlation to ancestry was performed using Pearson's r against MEs, defining modules as either positively or negatively correlated with those traits as a whole.

Gene Overlap analysis was performed as follows. Gene Overlap is an R bioconductor package (www.bioconductor.org/packages/release/bioc/html/GeneOverlap.html), which was used to test the significance of overlap between two sets of gene lists. It uses the Fisher's exact test to compute both an odd's ratio and overlap p value. For comparison of datasets on different array platforms (Illuminate versus Affymetrix), an FDR of 0.2 was used.

Logistic regression modeling was performed as follows. SAS 9.4 (Cary, NC) was used for stepwise logistic regression. GSVA enrichment scores greater or less than healthy control averages plus or minus one standard deviation were determined, and SLE patients were assigned a 1 or 0 based on having a signature greater than or less (Low) than HC, respectively. These scores were used as 34 dependent binary variables to be modeled individually as the outcome variable to 17 independent categorical (e.g., binary) variables, including ancestry (AA, EA, and NAA), drugs (corticosteroid drugs, antimalarial drugs, NSAID drugs, Azathioprine, Methotrexate, Mycophenalate mofetil), and SLE manifestations (rash, arthritis, mucosal ulcers, vasculitis, thrombocytopenia, anti-ds DNA, Low C3, and Low C4). Spearman correlation coefficients were determined between variables, followed by stepwise linear regression, in order to determine if groups were too similar to give independent information to the model. Further, odd's ratios, p values, and confidence intervals were determined. Immunosuppressive as a general category was removed since it had a Spearman correlation greater than 0.4 compared to MTX and MMF. The stepwise approach was used to produce the statistically significant model. The results of any model that violated the Hosmer Lemeshow test were discarded.

CIRCOS analysis was performed as follows. CIRCOS (V0.69.3) software was used to visualize the odd's ratios determined by stepwise logistic regression analysis. Odd's ratio values are non-negative, and a change from an odds ratio of 0.5 to 0.25 is the same relative change as that between 2.0 and 4.0. For representative visualization, odd's ratios between 0 and 1 were converted to the 1/X value, where X is an odd's ratio between 0 and 1.

Statistical analysis was performed as follows. GraphPad PRISM 7 version 7.0c was used to calculate or perform mean, median, mode, standard deviation, ANOVA, Tukey's multiple comparisons test, Sedak's multiple comparisons test, linear regression analysis, and unpaired t-test with Welch's correction. The Fisher's exact test was performed in R.

Data availability was as follows. All microarray datasets in this publication are available on the NCBI's database Gene Expression Omnibus (GEO) (www.ncbi.nlm.nih.gov/geo/).

Code availability was as follows. All software used to produce results described in this example is open source, and freely available for R. Additionally, example code used to produce results described in this example for LIMMA, GSVA and WGCNA are available at figshare (www-.figshare.com). File names are "AMPEL BioSolutions LIMMA Differential Expression Analysis Code", "AMPEL BioSolutions Gene Set Variation Analysis Code", and "AMPEL BioSolutions Weighted Correlation Network Analysis WGCNA Code".

Example 7: Ancestry Influences the Gene Expression Profile in Systemic Lupus Erythematosus (SLE) and Contributes to Gene Expression Heterogeneity in Lupus Patients Systemic Lupus Erythematosus (SLE) is a complex autoimmune disease with both sex and ancestral bias. Gene expression analysis has revealed complex heterogeneity between SLE patients, making deconvolution of the data difficult and delineation of the impact of different disease drivers uncertain. Therefore, the individual contributions of ancestry, gender, and medications to gene expression heterogeneity were assessed. Further, the association of gene expression profiles with various SLE manifestations was determined.

Bulk Differential Expression (DE) analysis and Gene Set Variation Analysis (GSVA) were carried out on 1,903 SLE patients of African (AA), European (EA), and Native American (NAA) ancestry. Modules of genes defined by co-expression in patients and representing either functional or cell specific groups were used to determine the relationship between drugs, SLE manifestations and individual patient gene expression. Logistic regression analysis was used to understand the relative contribution of ancestry, drugs and SLE manifestations to gene expression signatures.

Gene expression analysis between female disease-matched SLE patients of AA, EA, and NAA ancestry revealed thousands of DE transcripts between ancestries, but none within a single ancestry. AA, EA, and NAA SLE patients had significantly different cellular contributions to gene expression, and these differences were related to significantly different percentages of patients in each ancestry with specific signatures. GSVA showed an increase in plasma cells, B cells, and T cells in the majority of AA SLE patients, and an increase in myeloid cells in most EA and NAA SLE patients. Corticosteroid drugs and immunosuppressive drugs significantly changed gene expression and contributed to the disparate signatures between and within ancestry groups. Anti-dsDNA autoantibodies and low complement, but not other clinical features of SLE, were significantly associated with gene expression in AA, EA, and NAA SLE patients. Despite the impact of medications, ancestry made a significant contribution to gene expression profiles. Notably, Differences between AA and EA SLE patients were observed to be similar to those between healthy people of these ancestry groups, and there were fewer differences between males and females of the same ancestry, than between ancestry groups.

Figure 36:
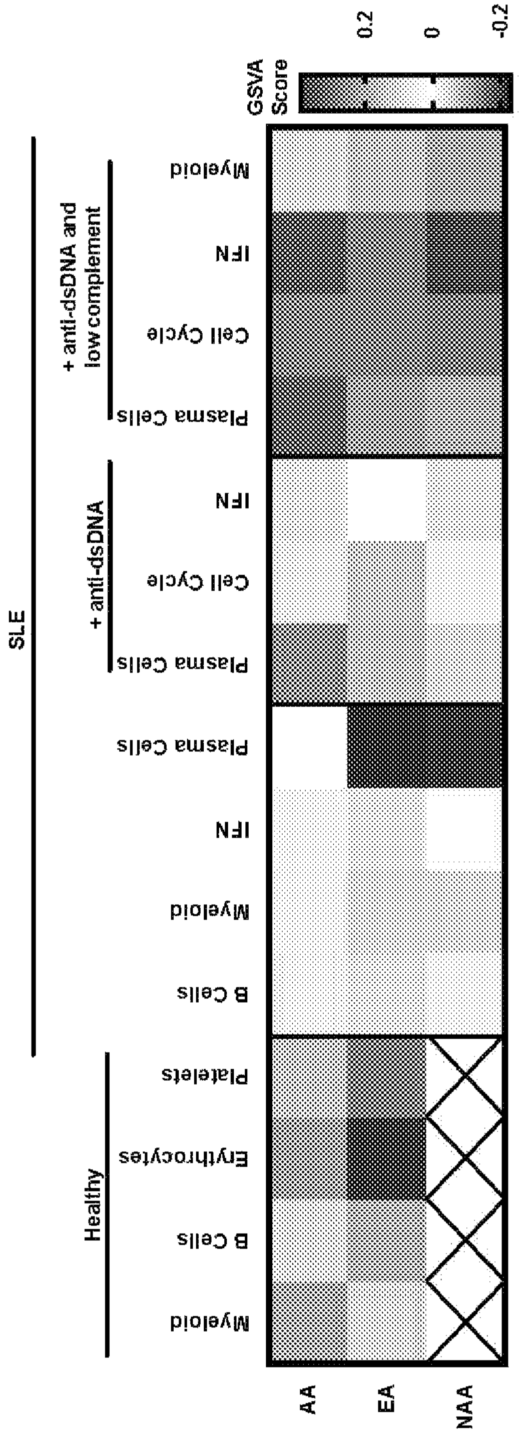
FIG. 36 shows that gene expression is affected by ancestry, SLE autoantibodies, and standard-of-care (SOC) drugs. Average difference in GSVA enrichment scores are shown for healthy subjects. Average GSVA enrichment scores are shown for lupus (SLE) patients.

FIG. 36 shows that gene expression is affected by ancestry, SLE autoantibodies, and standard-of-care (SOC) drugs. Average difference in GSVA enrichment scores are shown for healthy subjects. Average GSVA enrichment scores are shown for lupus (SLE) patients. Combinations of different ancestries, specific medications, and autoantibody production are associated with gene expression profiles (FIG. 36). Importantly, ancestry contributes unique features of gene expression, indicating differences in the molecular basis of SLE in these populations. Understanding the contributions of the gene expression signature components may permit a better interpretation of the signatures and their relationship to disease status.

Example 8: Analysis of Discoid Lupus Erythematosus (DLE) Gene Expression Reveals Dysregulation of Pathogenic Pathways Associated with Infiltrating Immune/Inflammatory Cells Discoid lupus erythematosus (DLE) is a chronic, scarring inflammatory autoimmune disease of the skin. The precise molecular pathways underlying DLE pathogenesis have not been fully delineated. To obtain a more complete view of the pathologic processes involved in DLE, a comprehensive analysis of gene expression profiles from DLE affected skin was performed.

Microarray gene expression data was obtained from skin biopsy samples of three studies (GSE81071, GSE72535, and GSE52471). Differentially expressed genes (DEGs) between DLE and control were identified by LIMMA analysis. Weighted gene co-expression network analysis (WGCNA) yielded modules of co-expressed genes. Modules correlating to clinical data were prioritized. Correlated modules were interrogated for statistical enrichment of immune and non-immune cell type specific gene signatures. Genes were functionally characterized using a curated immune-specific gene functional category database (BIG-C) and pathways elucidated using IPA®. Queries of a perturbation database (LINCS, Library of Integrated Network-Based Cellular Signatures) were used to identify drugs that could reverse the altered gene expression patterns in DLE.

For each dataset, between 7-12 WGCNA modules had significant correlations to disease. Significant WGCNA module preservation was observed between all three datasets. Non-immune cell types (fibroblasts, keratinocytes, melanocytes) and also Langerhans cells were represented in WGCNA modules negatively correlated with disease. An immune cell signature was observed in WGCNA modules positively correlated to DLE, including DCs, myeloid cells, CD4+& CD8+ T cells, NK cells, B cells as well as pre- and post-switch plasma cells (PCs). The presence of both Ig-κ and -λ as well as multiple VL genes suggests the presence of polyclonal PCs. Chemokines that mediate lymphocyte organization and/or recruitment into the skin were identified, including CCL5,7,8 and CXCL9-10,13. Cytokines (TNF, IFNγ, IFNα, IL1β, IL2, IL6, IL12, IL17, IL23, and IL27), signaling molecules (CD40L, PI3K, and mTOR) and transcription factors (NF-κB, NF-AT), as well as cellular proliferation, were evident. IPA® UPR analysis indicated that many of the expressed genes may be secondary to signaling by TNF, IFNγ, IFNα, CD40L, IL1β, IL2, IL6, IL12, IL17, IL23, and IL27. Interestingly, connectivity analysis using LINCS/CLUE identified high-priority drug targets, such as IKZF1/3 (lenalidomide, CC-220), JAK1/2 (ruxolitinib), and HDAC6 (Ricolinostat) may be viable options for therapeutic intervention.

Bioinformatic analysis of DLE gene expression has elucidated many dysregulated signaling pathways potentially involved in the pathogenesis of DLE that may be targeted by novel therapeutic strategies. Further investigation of these signatures may provide an enhanced understanding of the pathogenesis of DLE.

Example 9: Analysis of Gene Expression from Systemic Lupus Erythematosus (SLE) Synovium Reveals Unique Pathogenic Mechanisms Arthritis is a common manifestation of systemic lupus erythematosus (SLE), and the efficacy of a new lupus therapy for a given SLE patient often depends on its ability to suppress joint inflammation. Despite this, an understanding of the underlying pathogenic mechanisms driving lupus synovitis remains incomplete. Therefore, gene expression profiles of SLE synovium were interrogated to gain insight into the nature of joint inflammation in lupus arthritis.

Biopsied knee synovia from SLE and osteoarthritis (OA) patients were analyzed for differentially expressed genes (DEGs) and also by Weighted Gene Co-expression Network Analysis (WGCNA) to determine similarities and differences between gene profiles and to identify modules of highly co-expressed genes that correlated with clinical features of lupus arthritis. DEGs and correlated modules were interrogated for statistical enrichment of immune and non-immune cell type-specific signatures and validated by Gene Set Variation Analysis (GSVA). Genes were functionally characterized using BIG-C and canonical pathways and upstream regulators operative in lupus synovitis were predicted by IPA®.

DEGs upregulated in lupus arthritis revealed enrichment of numerous immune and inflammatory cell types dominated by a myeloid phentoype, whereas downregulated genes were characteristic of fibroblasts. WGCNA revealed 7 modules of co-expressed genes significantly correlated to lupus arthritis or disease activity (e.g., as indicated by SLEDAI or anti-dsDNA titer). Functional characterization of both DEGs and WGCNA modules by BIG-C analysis revealed consistent co-expression of immune signaling molecules and immune cell surface markers, pattern recognition receptors (PRRs), antigen presentation, and interferon stimulated genes. Although DEGs were predominantly enriched in myeloid cell transcripts, WGCNA also revealed enrichment of activated T cells, B cells, CD8 T, and NK cells, and plasma cells/plasmablasts, indicating an adaptive immune response in lupus arthritis. Th1, Th2, and Th17 cells were not identified by transcriptomic analysis, although IPA® analysis predicted signaling by the Th1 pathway and numerous innate immune signaling pathways were verified by GSVA. IPA® additionally predicted inflammatory cytokines TNF, CD40L, IFNα, IFNβ, IFNγ, IL27, IL1, IL12, and IL15 as active upstream regulators of the lupus arthritis gene expression profile, in addition to the PRRs IRF7, IRF3, TLR7, TICAM1, IRF4, IRF5, TLR9, TLR4, and TLR3. Analysis of chemokine receptor-ligand pairs, adhesion molecules, germinal center (GC) markers, and T follicular helper (Tfh) cell markers indicated trafficking of immune cell populations into the synovium by chemokine signaling, but not in situ generation of fully-formed GCs. GSVA confirmed activation of both myeloid and lymphoid cell types and inflammatory signaling pathways in lupus arthritis, whereas OA was characterized by tissue repair and damage.

Bioinformatic analysis of lupus arthritis revealed a pattern of immunopathogenesis in which myeloid cell-mediated inflammation dominates, leading to further recruitment of adaptive immune cells that contribute to the ongoing inflammatory synovitis.

Example 10: Transcriptomic Meta-Analysis of Lupus-Affected Tissues Reveals Shared Immune, Metabolic, and Biochemical Dysregulation Systemic lupus erythematosus (SLE) affects various organs and tissues, but whether pathologic processes in each organ are distinct or whether dysregulated molecular functions are found in common in all tissues may be unknown. Therefore, a meta-analysis of gene expression profiles in four affected SLE tissues was performed to identify commonly dysregulated pathways.

Gene expression datasets for discoid lupus erythematosus (DLE), lupus arthritis (LA), lupus nephritis (LN) glomerulus (Glom), and LN tubulointerstitium (TI) were obtained from GEO. Differentially expressed genes (DEGs) were identified by LIMMA analysis for each dataset. DEGs from each tissue were analyzed with a multi-pronged bioinformatics approach to elucidate common immune cell infiltrates and common functional categories. These findings were then utilized to form modules of co-expressed genes to determine their enrichment using Gene Set Variation Analysis (GSVA).

All tissues demonstrated the presence of immune cells with the fewest immune cell transcripts in LN TI. Analysis of bulk gene expression revealed enrichment of antigen presenting cells (APCs), monocytes, and myeloid cells in all four tissues. Notably, enrichment of B cells, plasma cells, germinal center (GC) B cells, and CD8 T cells was only detected in DLE and LA. All four tissues demonstrated upregulated immune activity, including interferon-stimulated genes, pattern recognition receptors (PRRs), and antigen presentation (MHC Class II). Pro-apoptosis genes were also found enriched in DLE, LN Glom, and LN TI. A generalized decrease in biochemical processes was found in all four tissues, and a specific decrease in both fatty acid biosynthesis and the tricarboxylic acid cycle was found in DLE and LN. Ingenuity Pathway Analysis (IPA®) further confirmed the activation of Dendritic Cell Maturation, Interferon, NFAT Regulation of Immune Response, PRRs, and TH1 signaling pathways in all four tissues. Additionally, IPA demonstrated cholesterol biosynthesis was decreased in all tissues except LA.

To confirm the aforementioned cellular infiltrates and aberrant pathways, as well as additional pathways, were operative in individual SLE tissues, GSVA was used to analyze enrichment of gene modules in patient samples. As shown in Table 18 and FIGS. 37-38, specific abnormalities were found in the majority of tissues, including enrichment of myeloid cells/monocytes, APCs, and GC B cells, whereas others were observed in some but not all tissues.

TABLE 18

Percentages of SLE tissue samples with GSVA enrichment of specific immune cell modules

| | DLE | LA | LN Glom | LN TI |
|---|---|---|---|---|
| Antigen Presenting Cell | 66.67% | 75.00% | 77.27% | 63.64% |
| Monocyte | 88.89% | 100.00% | 95.45% | 59.09% |
| Myeloid Cell | 77.78% | 100.00% | 81.82% | 68.18% |
| Germinal Center B Cell | 77.78% | 100.00% | 54.55% | 77.27% |
| Plasma Cell | 88.89% | 75.00% | 50.00% | 45.45% |

Figure 37:
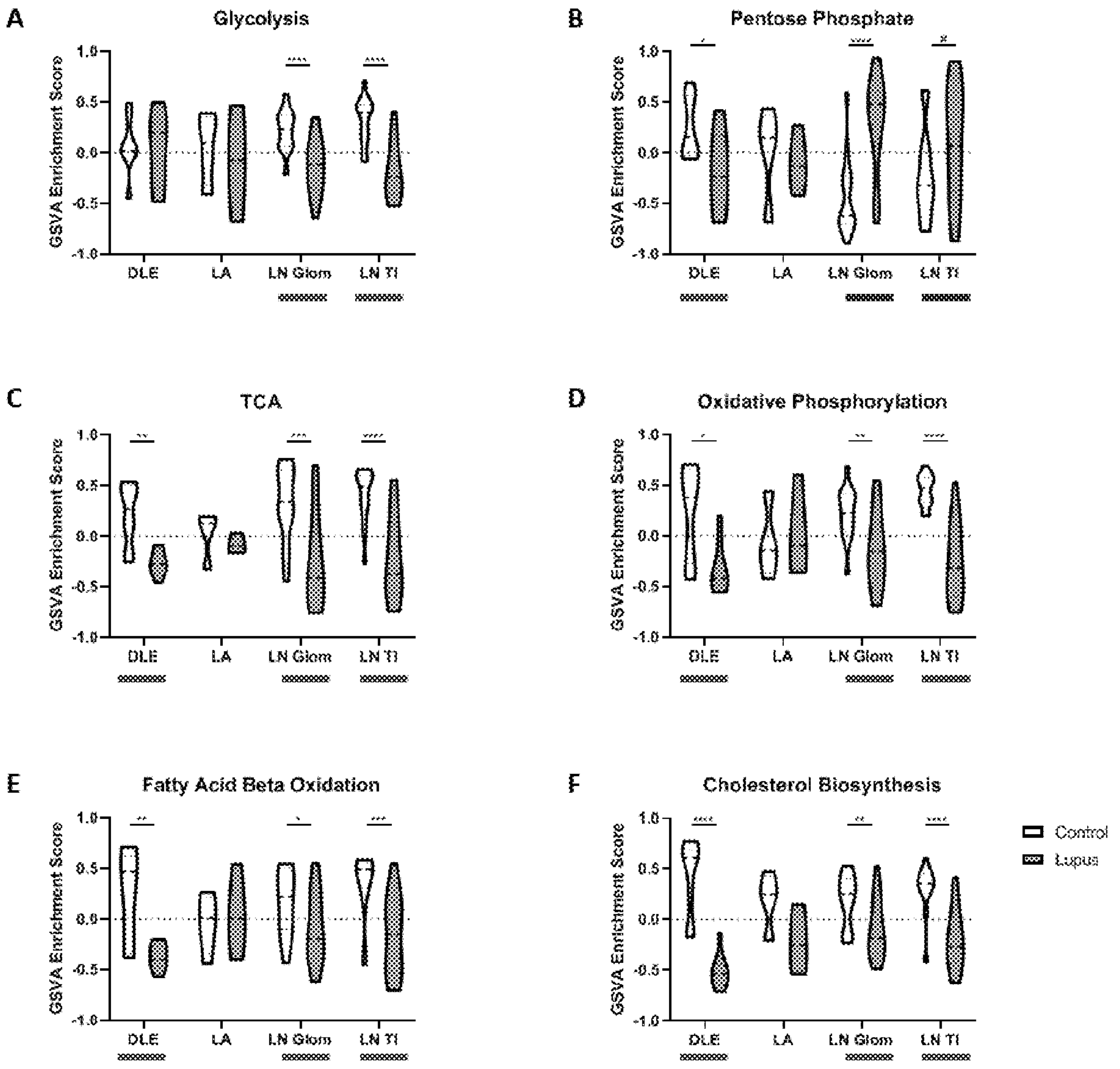
FIG. 37 contains plots showing that GSVA demonstrates metabolic dysregulation in individual SLE affected tissues. GSVA enrichment scores were calculated for (A) glycolysis, (B) pentose phosphate, (C) tricarboxylic acid cycle (TCA), (D) oxidative phosphorylation, (E) fatty acid beta oxidation, and (F) cholesterol biosynthesis modules in DLE, LA, LN Glom, and LN TI.

FIG. 37 contains plots showing that GSVA demonstrates metabolic dysregulation in individual SLE affected tissues. GSVA enrichment scores were calculated for (A) glycolysis, (B) pentose phosphate, (C) tricarboxylic acid cycle (TCA), (D) oxidative phosphorylation, (E) fatty acid beta oxidation, and (F) cholesterol biosynthesis modules in DLE, LA, LN Glom, and LN TI. Significant enrichment of tissue control to SLE affected tissue or SLE affected tissue to tissue control was determined using the Welch's t-test. The red bar represents enrichment of SLE tissue over control, and the blue bar represents enrichment of tissue control over SLE tissue. #$p<0.1$ *$p<0.05$,  $p<0.01$, * $p<0.001$, ****<0.0001.

Figures 38A, 38B, 38C:
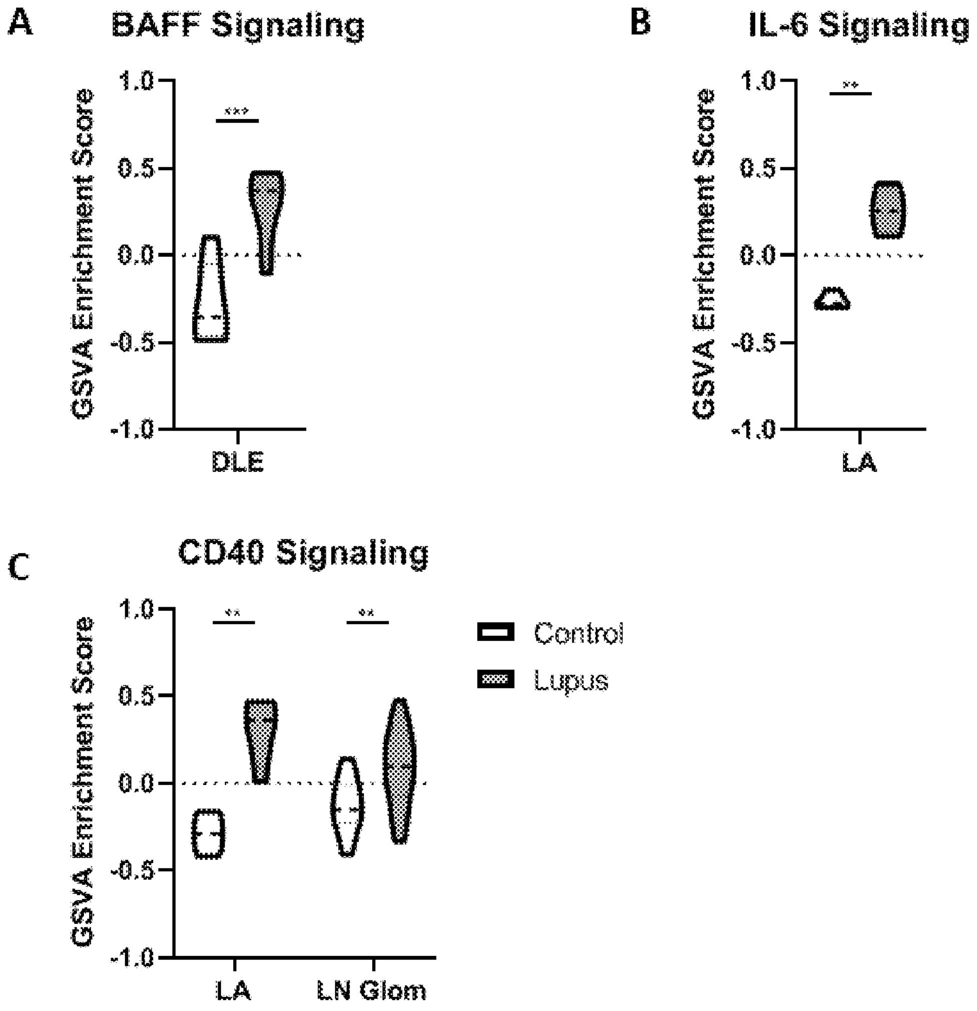
FIGS. 38A-38C contains plots showing that GSVA reveals potential pathways for therapeutic targeting in lupus affected tissues. Measures are shown for drug pathways significantly enriched in SLE affected tissue compared to control tissue as determined using the Welch's t-test for B cell activating factor (BAFF) (FIG. 38A), interleukin (IL-6) (FIG. 38B), and CD40 signaling in DLE, LA, and LN Glom (FIG. 38C).  p<0.01, * p<0.001.

FIGS. 38A-38C contains plots showing that GSVA reveals potential pathways for therapeutic targeting in lupus affected tissues. Measures are shown for drug pathways significantly enriched in SLE affected tissue compared to control tissue as determined using the Welch's t-test for B cell activating factor (BAFF) (FIG. 38A), interleukin (IL-6) (FIG. 38B), and CD40 signaling in DLE, LA, and LN Glom (FIG. 38C).  $p<0.01$, * $p<0.001$.

Figure 38D:
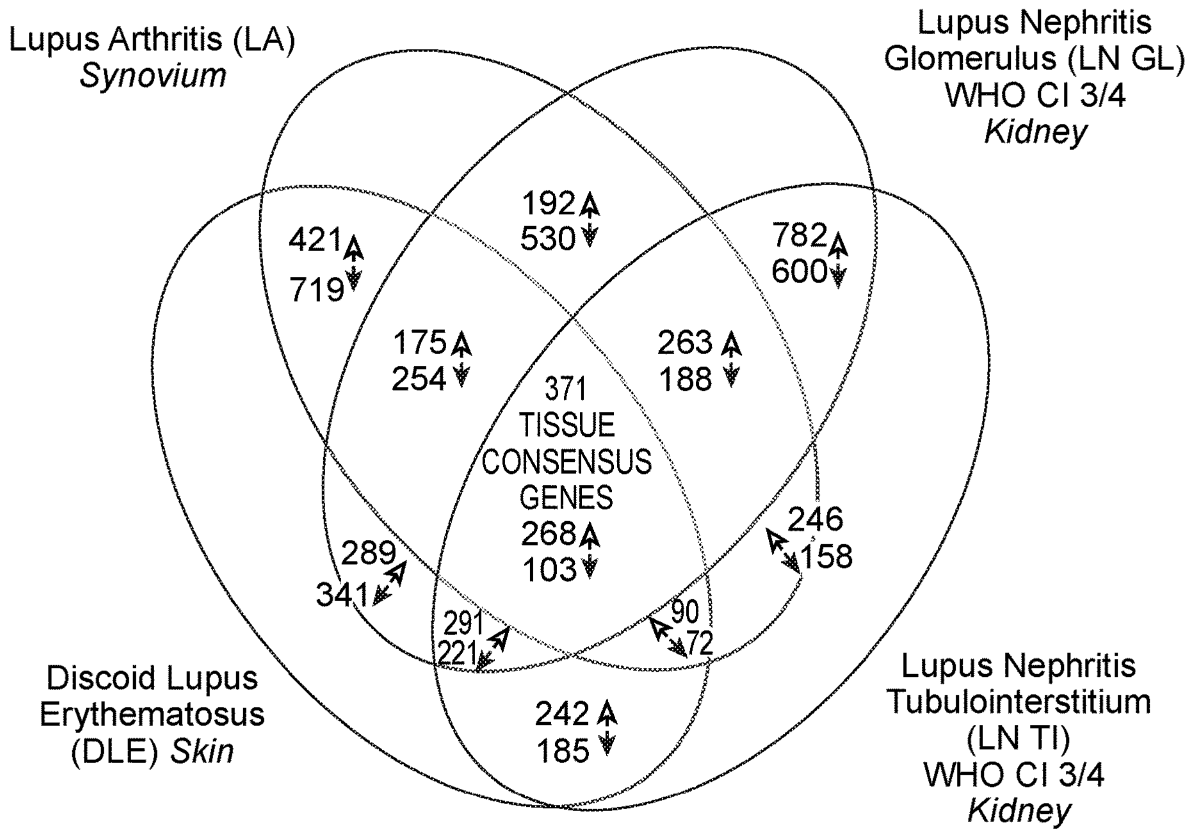
FIG. 38D shows that genes commonly dysregulated in lupus tissues identified immune processes and cellular metabolism.

FIG. 38D shows that genes commonly dysregulated in lupus tissues identified immune processes and cellular metabolism.

Figure 38E:
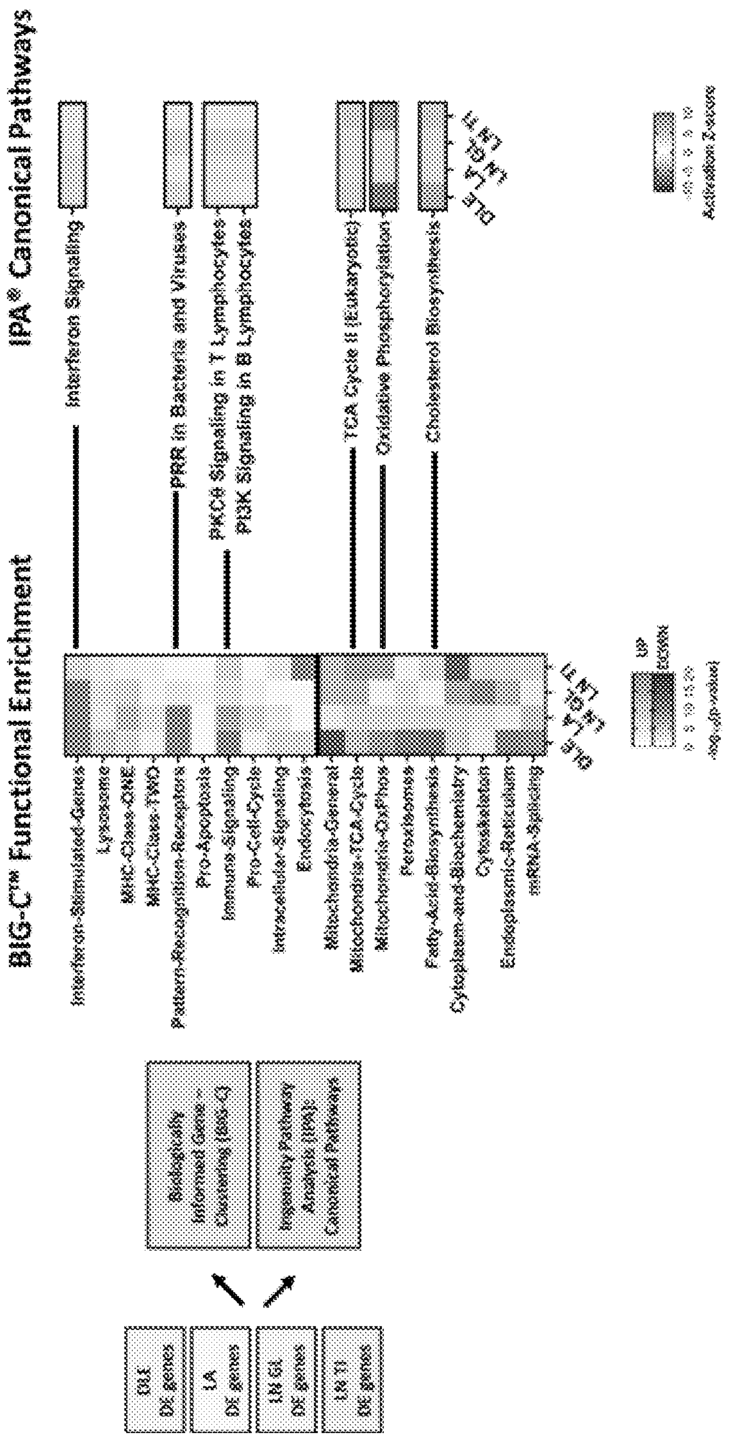
FIG. 38E shows that functional grouping and pathway analysis of DE genes expressed in lupus tissues revealed immune and metabolic abnormalities in common.

FIG. 38E shows that functional grouping and pathway analysis of DE genes expressed in lupus tissues revealed immune and metabolic abnormalities in common.

Figure 38F:
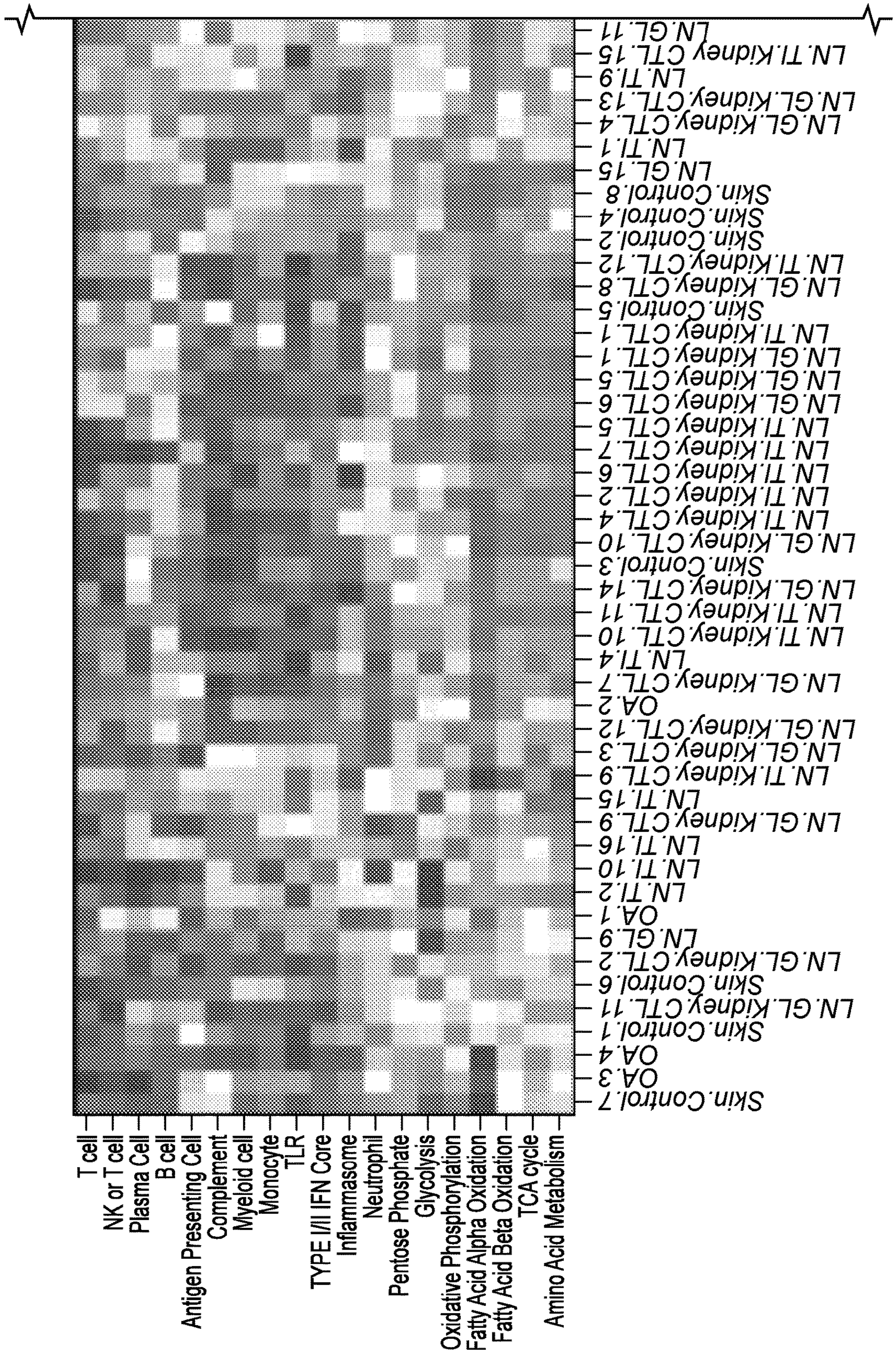
FIG. 38F shows that similar cellular and metabolic signatures were observed in lupus tissues.
Figure 38F:
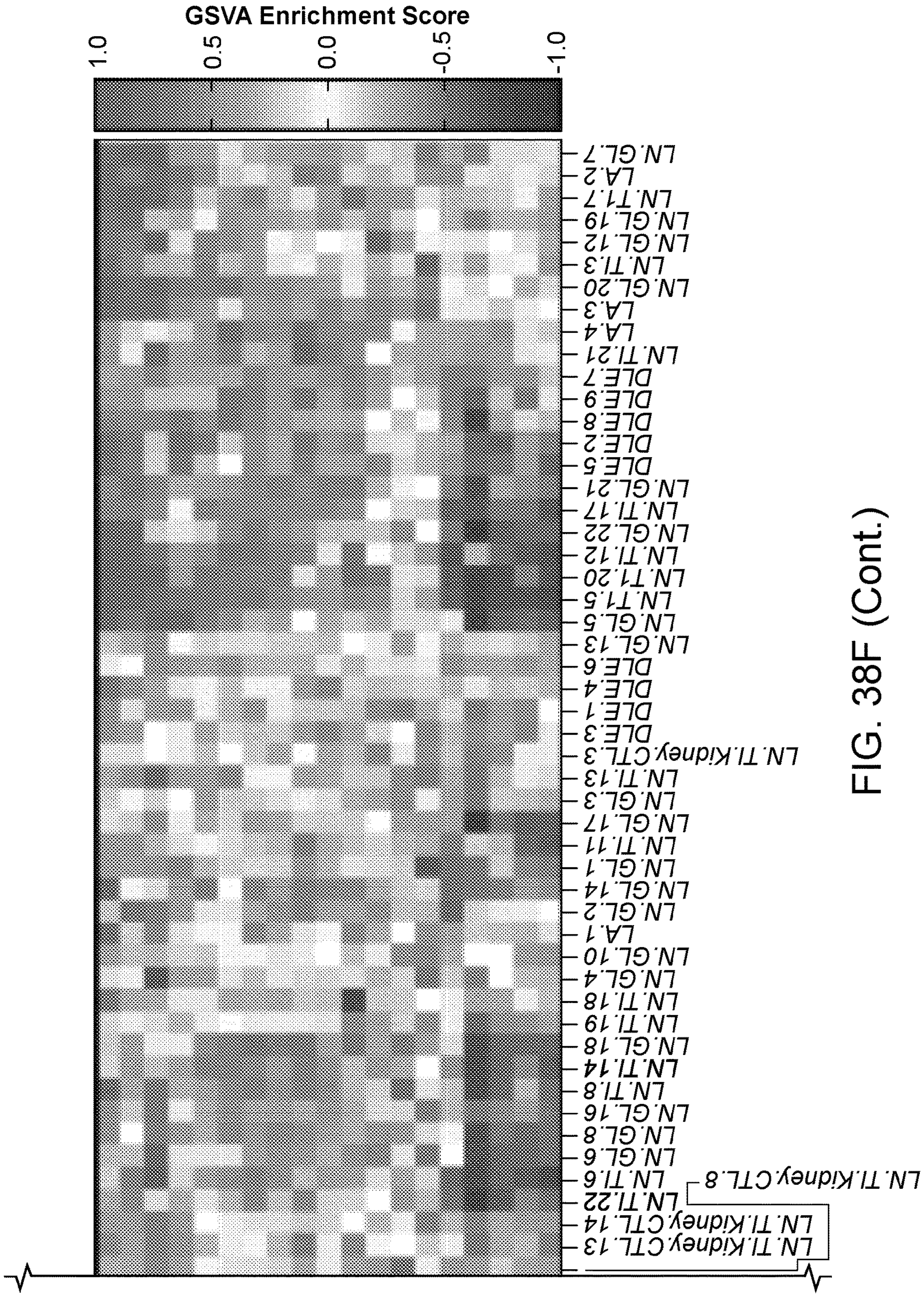

FIG. 38F shows that similar cellular and metabolic signatures were observed in lupus tissues.

Figure 38G:
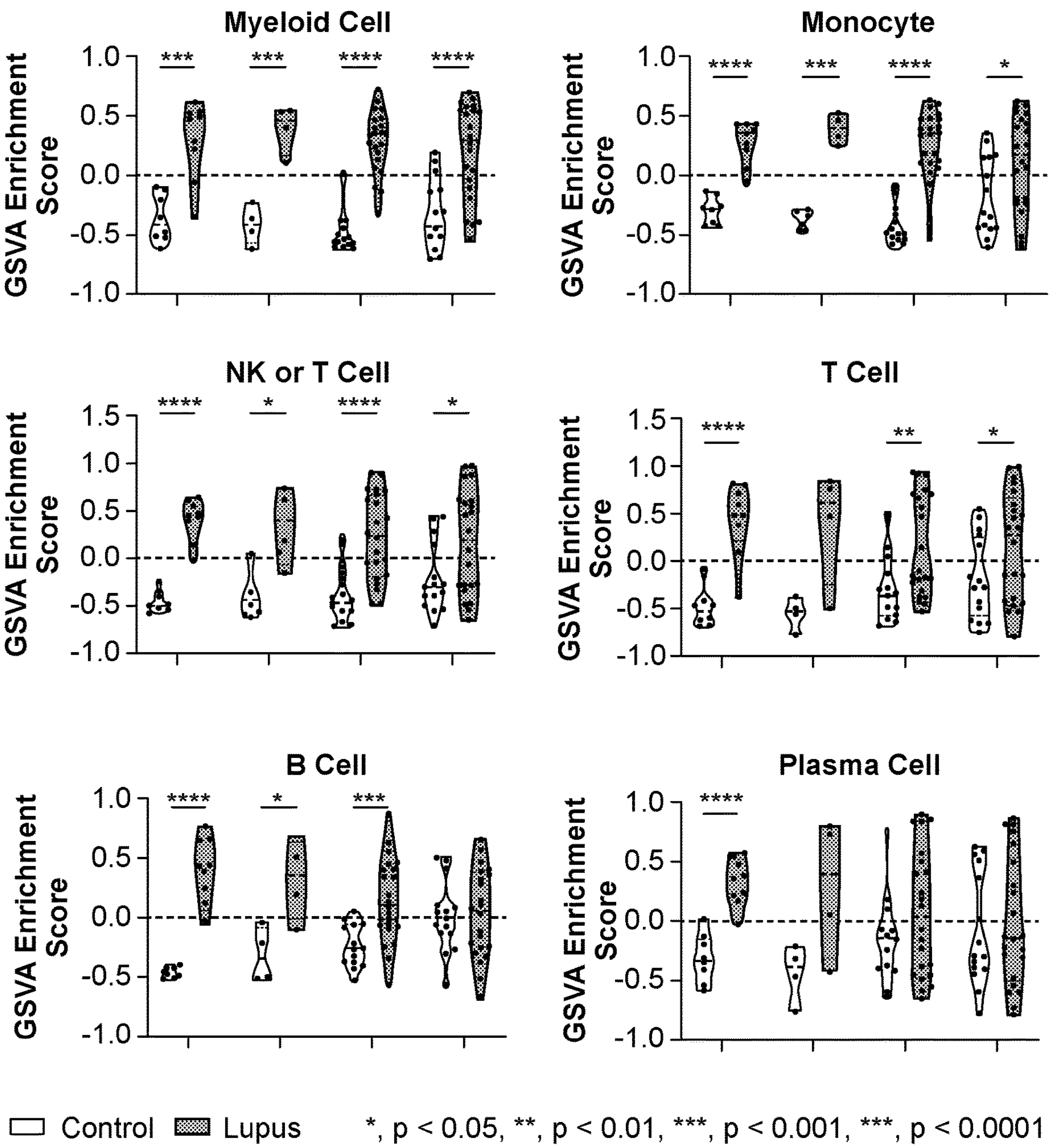
FIG. 38G shows that increased immune/inflammatory cell signatures were observed in lupus tissues.
Figure 38G:
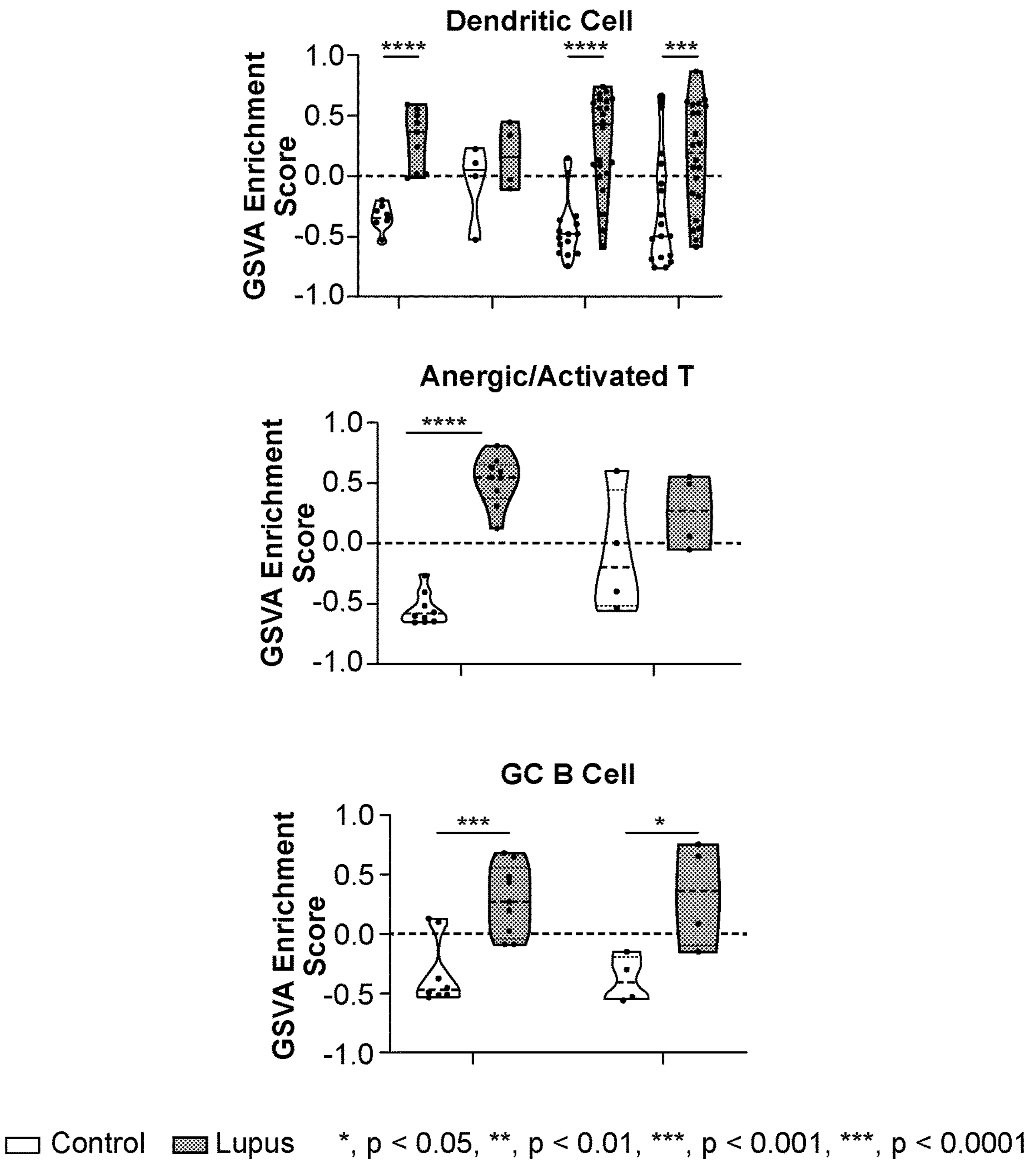

FIG. 38G shows that increased immune/inflammatory cell signatures were observed in lupus tissues.

Figure 38H:
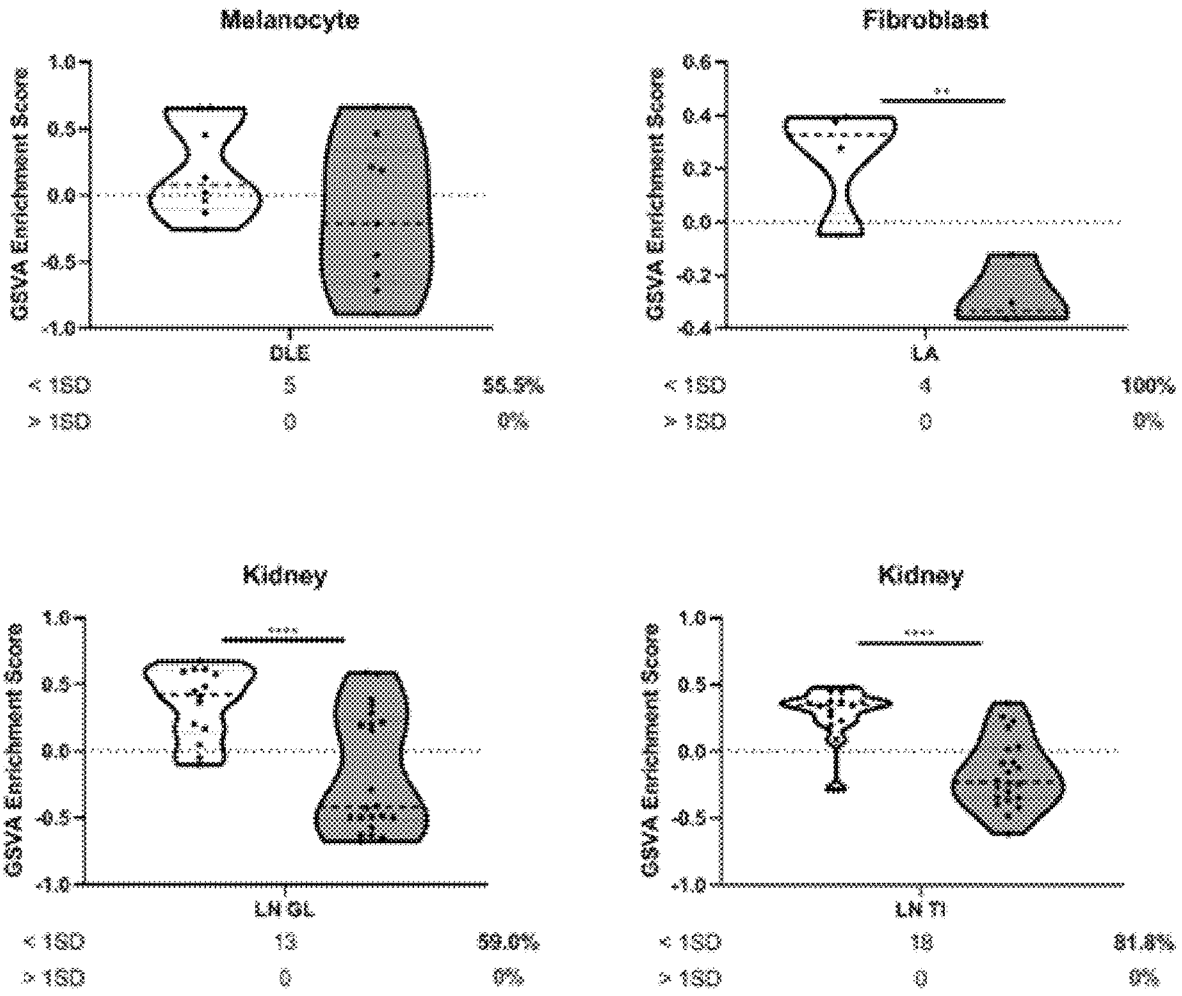
FIG. 38H shows that decreased tissue stromal cell signatures were observed in lupus tissues.

FIG. 38H shows that decreased tissue stromal cell signatures were observed in lupus tissues.

Figure 38I:
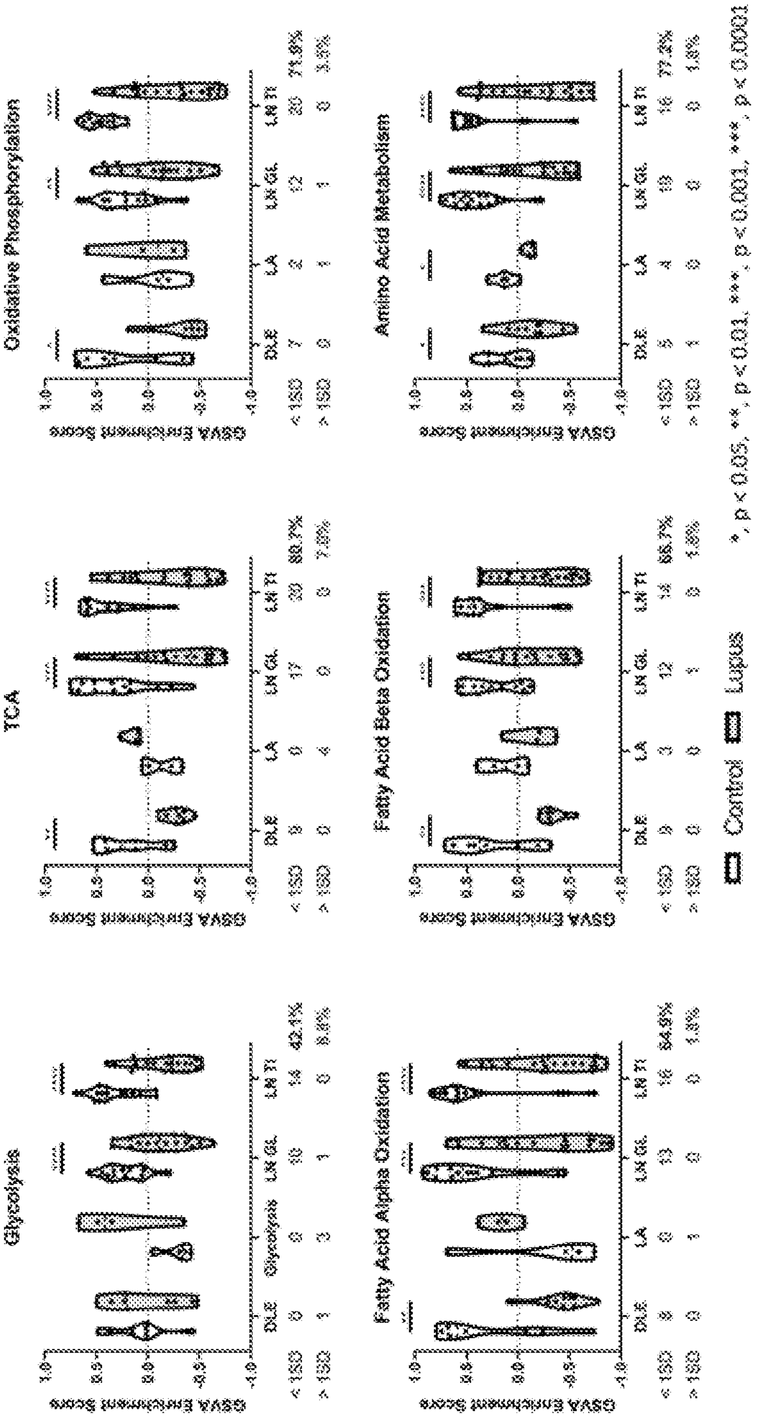
FIG. 38I shows that decreased metabolic signatures were observed in lupus tissues.

FIG. 38I shows that decreased metabolic signatures were observed in lupus tissues.

Figure 38J:
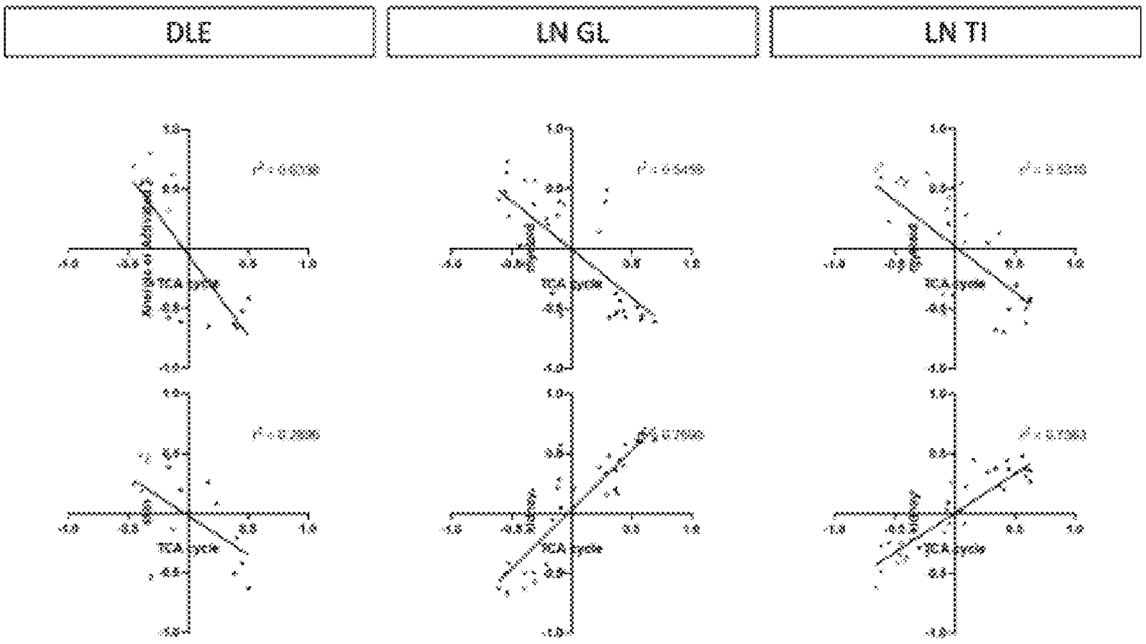
FIG. 38J contains plots showing the correlation between immune/inflammatory or tissue cell signature and metabolic signature in DLE and LN (LN GL and LN TI).

FIG. 38J contains plots showing the correlation between immune/inflammatory or tissue cell signature and metabolic signature in DLE and LN (LN GL and LN TI).

Figure 38K:
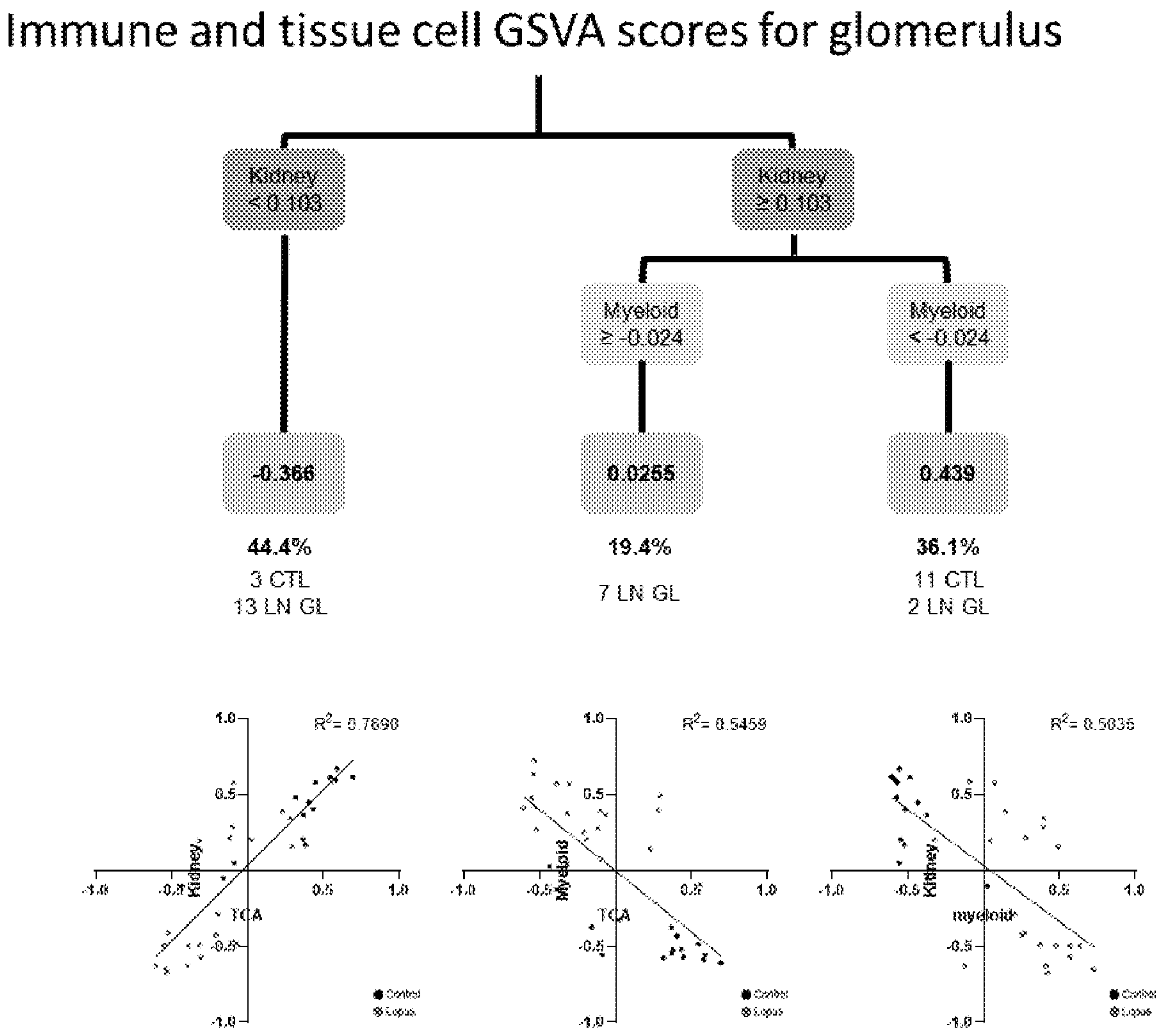
FIG. 38K-38L shows that Classification and Regression Trees (CART) analysis predicted the contributors to metabolic dysfunction.
Figure 38L:
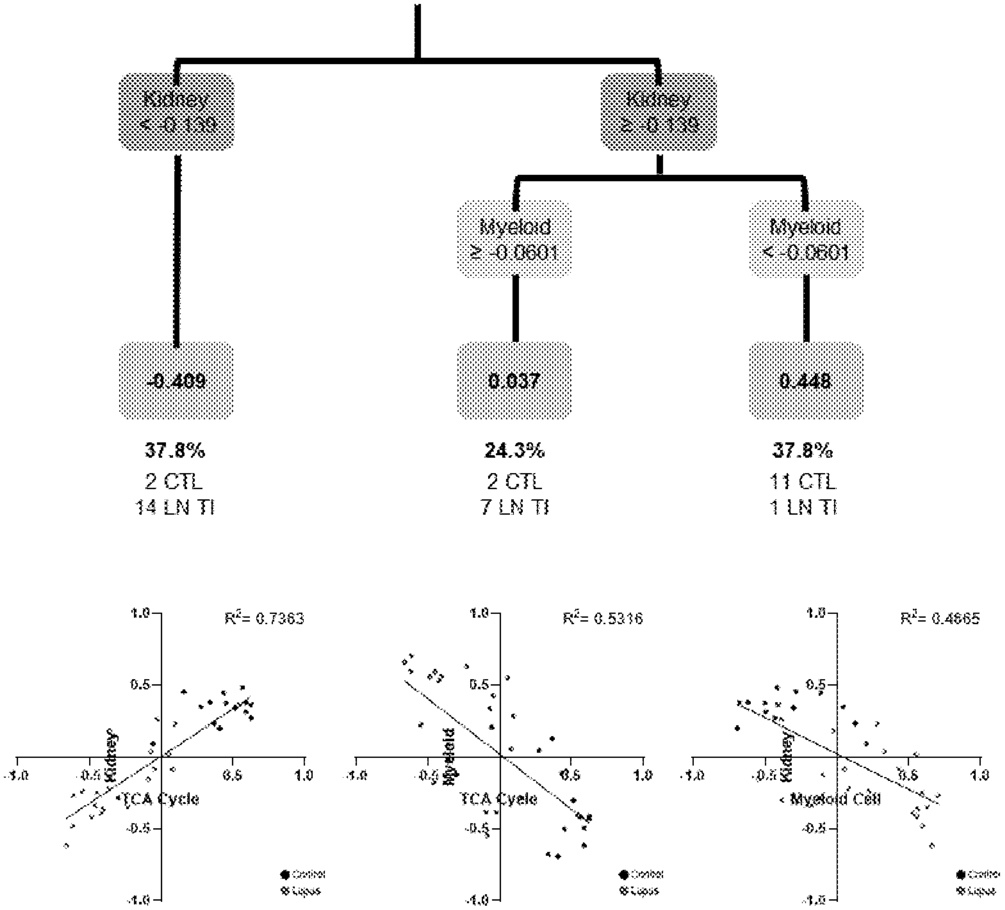

FIG. 38K-38L shows that Classification and Regression Trees (CART) analysis predicted the contributors to metabolic dysfunction.

Figure 38M:
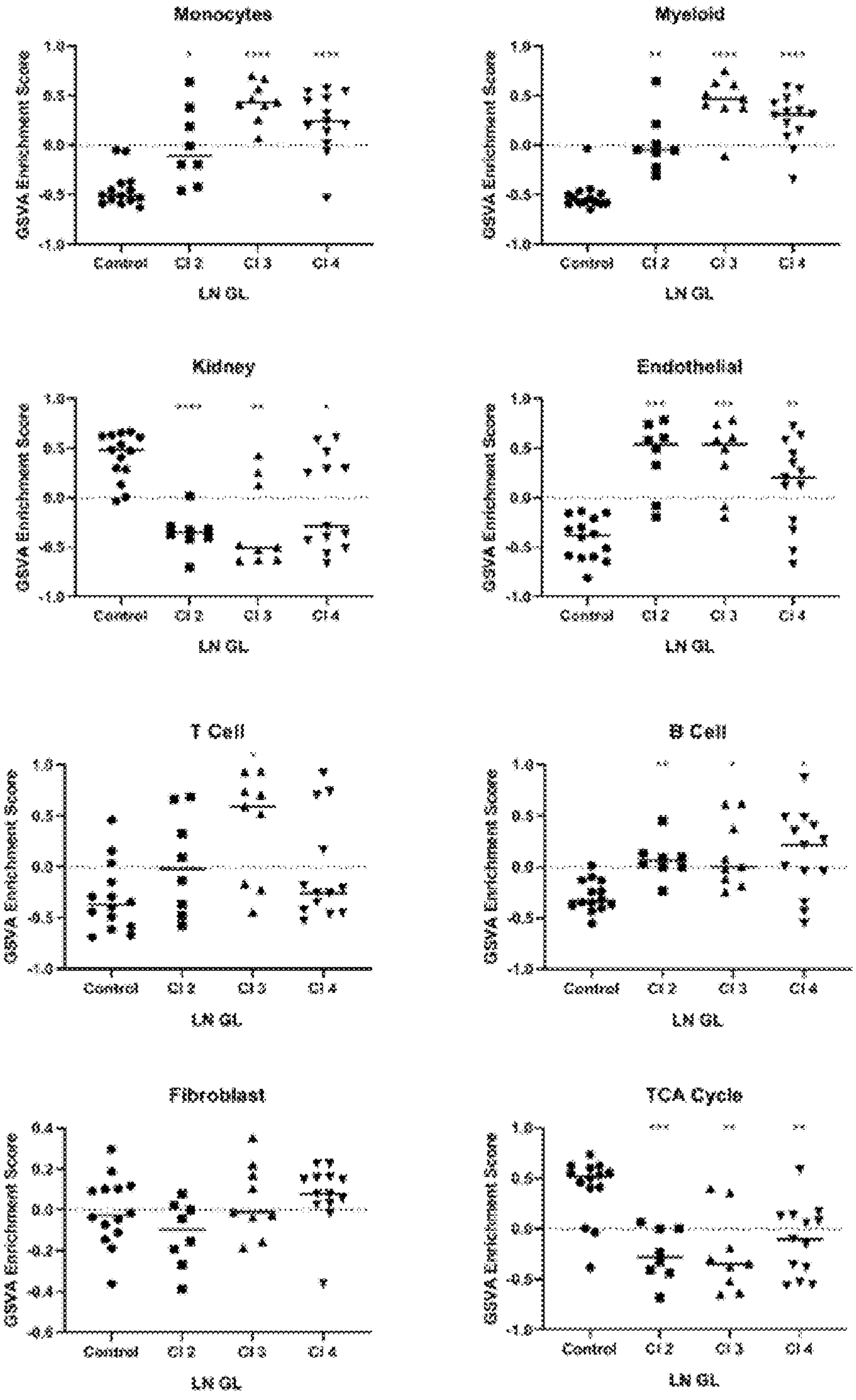
FIG. 38M shows that Class 2 LN glomerulus demonstrated similar metabolic defects, indicating dysregulation is linked to stromal cells.

FIG. 38M shows that Class 2 LN glomerulus demonstrated similar metabolic defects, indicating dysregulation is linked to stromal cells.

Figure 38N:
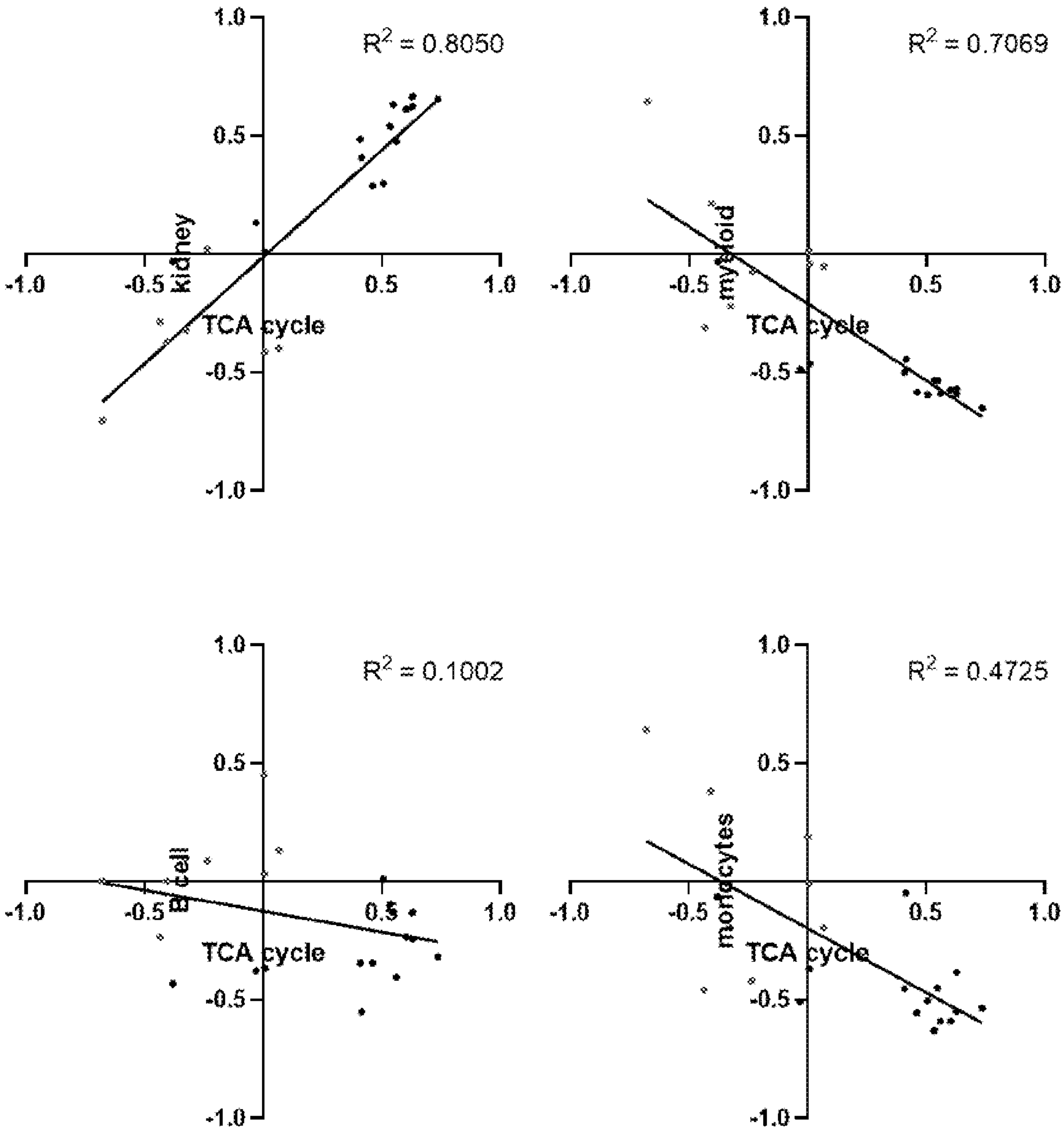
FIG. 38N contains plots showing the correlation between tissue or immune/inflammatory cell signature and metabolic signature for Class 2 LN glomerulus.

FIG. 38N contains plots showing the correlation between tissue or immune/inflammatory cell signature and metabolic signature for Class 2 LN glomerulus.

Figure 38O:
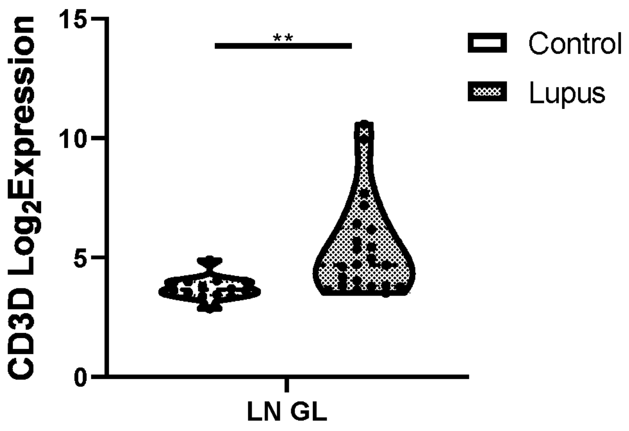
FIGS. 38O-38P contain plots showing that metabolic changes were not correlated with T Cells in LN GL.
Figure 38P:
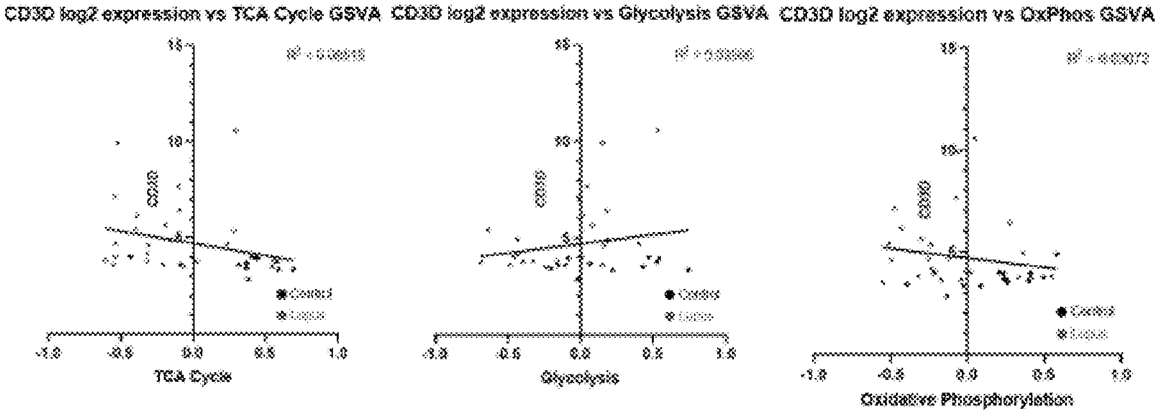

FIGS. 38O-38P contain plots showing that metabolic changes were not correlated with T Cells in LN GL.

Common cellular infiltrates and molecular pathways were found in all affected tissues, suggesting commonalities in lupus organ pathogenesis. However, certain cell types and signaling were predominant in some tissues over others and GSVA illustrated heterogeneity between patients. Together this analysis informs a tissue-specific model of lupus immunopathogenesis and metabolic dysfunction with common and unique features and highlights the importance of patient specific identification of dysfunctional pathways in lupus organ pathogenesis.

Example 11: Analysis of Lupus Nephritis (LN) Gene Expression Reveals Dysregulation of Pathogenic Pathways Activated within Infiltrating Cells Lupus nephritis (LN) is a serious complication of SLE that affects about 20-40% of all lupus patients and leads to kidney damage, end-stage renal disease, and patient mortality. Despite advances in therapy, progression to end stage renal disease may not be affected. Therefore, it is important to re-consider the pathogenic mechanisms involved in LN as a basis for development of more effective therapies. A multi-pronged approach was performed to characterize LN via bioinformatic analysis of gene expression data obtained from kidney biopsies.

Genomic expression profiling data of LN patient biopsies, microdissected into glomerulus and tubulonterstitium (TI), was sourced from GSE32591 via the GEO database. Differentially expressed genes (DEGs) detected in LN-derived samples relative to samples from healthy individuals were interrogated for cell infiltrate composition using gene set variation analysis (GSVA) against a curated database of immune and non-immune cell type signatures (I-SCOPE, T-SCOPE). Weighted gene co-expression network analysis (WGCNA) was performed to generate gene modules correlated to clinical variables. DEGs were further functionally characterized using a curated immunity-specific gene functional category database (BIG-C) and IPA signaling pathway analysis software. Queries of the perturbation database (LINCS, Library of Integrated Network-Based Cellular Signatures) were used to identify possible upstream regulators of altered gene expression patterns in LN samples as well as to identify drugs that could reverse abnormal gene expression profiles.

WGCNA produced 6 gene modules (3 glomerulus, 3 TI) positively correlated with disease stage, as measured by WHO class. These modules were enriched in signatures for several immune cell types, including granulocytes, pDC, DC, myeloid cells, CD4+/CD8+ T cells, and B cells. Additionally, the presence of both IG-κ and -λ as well as VL genes and detection of pre- and post-switch PCs as indicated by IgM, IgD, and IgG1 Ig Heavy Chain genes indicate polyclonal PC infiltration. Podocyte signatures were detected as enriched in WGCNA modules negatively correlated with WHO class. Chemokines and pathways that mediate lymphocyte proliferation, organization, and/or recruitment into lupus kidney tissue were detected as enriched via BIG-C and IPA analysis, including the cytokines TNF, IL1β, IL2, IL6, IL12, IL17, IL23, and IL27 and signaling pathways including CD40L, PI3K, NF-κB, NF-AT, and p70S6K. IPA upstream regulator analysis indicated ongoing signaling by cytokines such as TNF, IFNγ, IFNα, CD40L, IL1β, IL2, IL6, and IL17. Interestingly, connectivity analysis using LINCS elucidated high-priority drug targets such as IFNβ (PF-06823859), IL12 (Ustekinumab), and S1PR (Fingolimod) that may be suitable options for therapeutic intervention.

Bioinformatic analysis of LN gene expression highlighted several dysregulated signaling pathways that can form the targets of novel therapeutic strategies, and further elucidation of these signatures may enhance clinical surveillance and diagnosis of LN to improve patient outcomes.

Example 12: Integration of Genetic Data, Molecular Pathway Analysis, and Differential Expression to Delineate the Impact of Ancestral Differences on Lupus Systemic lupus erythematosus (SLE) is a multi-organ autoimmune disorder with a prominent genetic component. In many cases, individuals of African-Ancestry (AA) experience the disease more severely and with an increased co-morbidity burden compared to European-Ancestry (EA) populations. However, the relationship between genetics, molecular pathways, and disease severity may not have been fully delineated. AA and EA SLE-associated single nucleotide polymorphisms (SNPs) were examined and linked via expression quantitative trait loci (eQTL) across multiple tissues to genes with altered expression (E-Genes). Putative EA and AA E-Gene signatures were coupled with SLE differential expression (DE) datasets and upstream regulators to map candidate molecular pathways. Together, these genetic and gene expression analyses enable a better understanding of how the identified SNPs may contribute to aberrant immune function as well as the influence of ancestry on the genetic basis of SLE.

SLE Immunochip studies may be performed to identify SNPs significantly associated with SLE in AA (2,970 cases; 2,452 controls) and EA (6,748 cases; 11,516 controls) cohorts. eQTL mapping identified E-Genes from SLE SNPs and their ancestry-specific SNP proxies (based on linkage disequilibrium) via the GTEx database. For both ancestral groups, E-Gene lists were examined for the significant enrichment of gene ontogeny (GO) terms, canonical IPA® (Qiagen) pathways and BIG-C™ categories. Next, the gene expression profiles of predicted E-Genes were analyzed across multiple SLE DE datasets, including those from blood and multiple tissues. Differential expressed genes (DEGs) were identified and subjected to pathway analysis with IPA®, clustering using MCODE, and visualization in Cytoscape with the ClusterMaker2 plugin. Drug candidates targeting E-Genes, DEGs and upstream regulators (UPRs) were identified using CLUE, IPA®, and STITCH.

Figure 39:
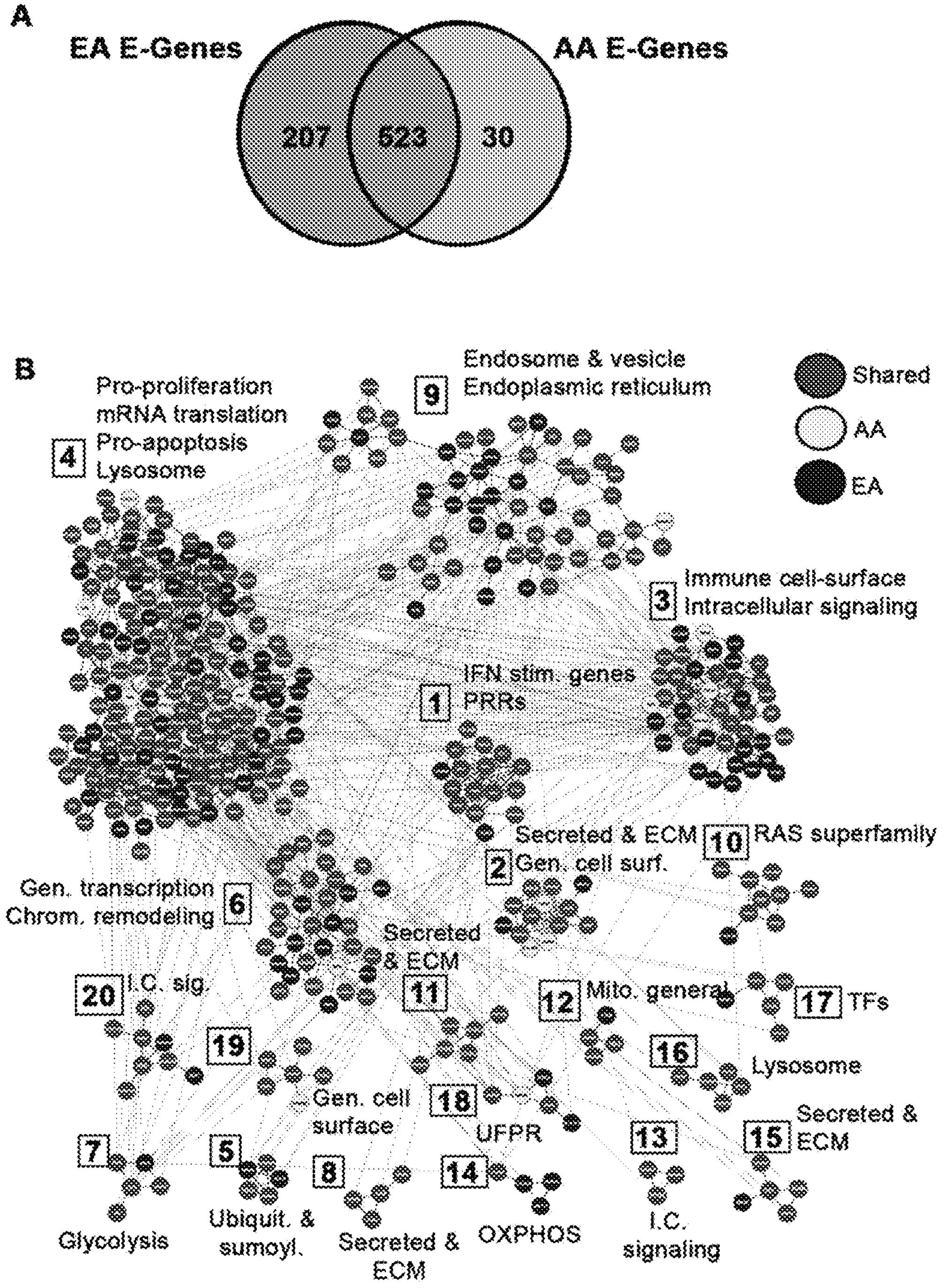
FIG. 39 contains plots showing results from mapping a total of 908 Immunochip SNPs to 252 eQTLs and coupling them to 760 E-Genes (207 in EAs, 30 in AAs, 523 shared), including (A) a Venn of E-Gene overlap and (B) a Cytoscape visualization of E-Gene PPI networks using MCODE clustering.

As shown in FIG. 39, a total of 908 Immunochip SNPs were mapped to 252 eQTLs and coupled to 760 E-Genes (207 in EAs, 30 in AAs, 523 shared). The figure shows (A) a Venn of E-Gene overlap and (B) a Cytoscape visualization of E-Gene PPI networks using MCODE clustering. Significant BIG-C functional categories for individual modules are listed. Shared E-Genes were highly enriched in interferon signaling, whereas EA E-Genes were associated with nucleotide degradation and AA E-Genes were linked to multiple biosynthesis and intracellular signaling pathways (e.g., retinol biosynthesis and AMPK signaling). Protein-protein interaction (PPI) networks of clustered EA, AA, and shared E-Genes illustrate the high degree of ancestral overlap evident within each E-Gene set. Clustering analysis of all DE E-Genes and IPA-predicted UPRs highlight disease-associated pathways that are both shared and ancestry-specific. Drug candidate comparison identified a total of 115 drugs targeting EA, AA, and shared E-Genes and their molecular pathways.

Using a bioinformatics-based approach that utilizes pathway analysis and gene expression data, ancestry-dependent and ancestry-agnostic candidate causal targets in SLE were discovered. These SLE targets may be suitable for further investigation and analysis using drug discovery tools to identify therapies with potential to impact disease processes within and across specific populations.

Example 13: E-Genes Identified Via Transancestral SNP Mapping and Gene Expression Analysis Reveal Novel Targeted Therapies for African-American and European-American SLE Patients Systemic lupus erythematosus (SLE) in African-Americans (AA) is more prevalent, more severe and associated with an increased burden of co-morbidities compared to European-American (EA) populations. Genome-wide association studies (GWAS) have linked many single nucleotide polymorphisms (SNPs) to SLE. For example, large-scale transancestral association studies of SLE may be performed to identify ancestry-dependent and independent contributions to SLE risk. Such findings may be extended to include a transancestral analysis linking SLE-associated SNPs to candidate-causal E-Genes specific to AA and EA populations and differential gene expression in these populations with the goal of matching genetic and genomic disease characteristics with available treatments unique to each ancestral group.

SNP proxies in linkage disequilibrium with SLE-associated SNPs were compared with known expression quantitative trait loci (eQTLs) contained in the GTEx (version 6) database. E-QTLs and their associated E-Genes were divided by ancestry and compared to differentially expressed (DE) genes from multiple SLE gene expression datasets. For both ancestral groups, E-Gene lists were examined for the significant enrichment of BIG-C categories and IPA (Qiagen)

Figure 40:
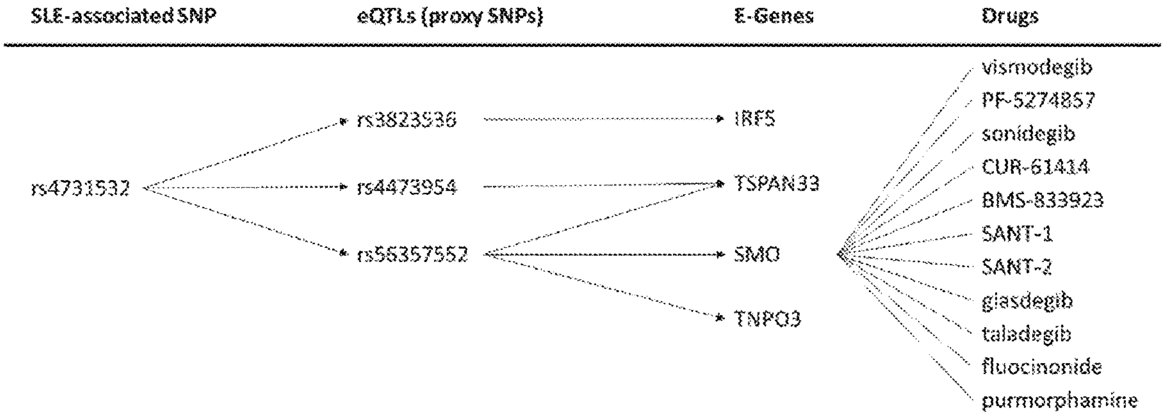
FIG. 40 shows the process of unpacking an SLE-associated SNP, in accordance with disclosed embodiments.

Canonical Pathways to predict novel upstream regulators (UPRs). For visualization and clustering analysis, STRING-generated networks of DE E-Genes were imported into Cytoscape (version 3.6.1) and partitioned with the community clustering (GLay) algorithm via the cluster-Maker2 (version 1.2.1) plugin. Finally, drug candidates targeting E-Genes, DE genes, and UPRs were identified using CLUE, REST, API, IPA, and STITCH (version 5.0; stitch.embl.de). The process of unpacking an SLE-associated SNP is shown in FIG. 40.

E-QTL and DE gene queries of GTEx were combined and newly predicted E-Genes were pooled by ancestry. Here, we identify 52 SNPs with eQTLs unique to AA ancestry, 260 SNPs unique to EA ancestry, and 1 SNP shared between AA and EA ancestries. Together, these SNPs identified a total of 891 distinct E-Genes associated with both ancestral groups. In studies comparing E-Genes to SLE DE data sets, 516 EA E-Genes were differentially expressed compared to 48 AA E-Genes. Comparison with various drug candidate databases resulted in the identification of 12 drugs targeting genes specific for AA, 77 drugs specific for EA genes, and 13 shared between EA and AA genes. Predicted EA-specific drugs include hydroxychloroquine and drugs-in-development targeting CD40LG, CXCR1 and CXCR2; whereas AA-specific drugs include HDAC inhibitors, retinoids, and drugs targeting IRAK4 and CTLA4. Drugs targeting E-Genes and/or pathways shared by EA and AA include ibrutinib, ruxolitinib, and ustekinumab.

The ancestral SNP-associated E-Genes and gene expression profiles outlined here illustrate fundamental differences in lupus molecular pathways between AA and EA. These results indicate that unique sets of drugs may be particularly effective at treating lupus within each ancestral group.

Example 14: E-Genes Identified Via Transancestral SNP Mapping and Gene Expression Analysis Reveal Novel Targeted Therapies for African-American and European-American SLE Patients Systemic lupus erythematosus (SLE) is a heterogeneous autoimmune disease that disproportionately affects subjects (e.g., women) of African-Ancestry (AA) compared to their European-Ancestral (EA) counterparts. This disparity may be further complicated by the fact that FDA-approved treatments for SLE, such as belimumab, may not provide a significant therapeutic benefit in SLE-affected AA subjects (e.g., women). Therefore, the genetic components unique to each ancestry were determined, and then these genetic targets were matched with novel drug candidates to help establish ancestry-specific therapies. To accomplish this, genetic variations or "polymorphisms" unique to each ancestral population were identified and then mapped to specific genes. Genes and their associated pathways may then be applied to multiple drug screening databases. This analysis resulted in the identification of drugs targeting genes specific for AA, EA, and genes common to both AA and EA ancestries. Together, these studies help provide a precision-medicine foundation for the establishment of patient-specific therapies and interventions for SLE.

Systemic lupus erythematosus (SLE) in African-Ancestry (AA) populations is more prevalent, more severe, and associated with an increased burden of co-morbidities compared to European-Ancestry (EA) populations. SLE is strongly influenced by genetic factors, and recent candidate gene and genome-wide association studies (GWAS) have linked many single nucleotide polymorphisms (SNPs) to SLE. Understanding the functional mechanisms of causal genetic variants underlying SLE may provide a key to identifying ancestry-specific molecular pathways and therapeutic targets relevant to disease mechanisms. Although GWAS have achieved great success in mapping disease loci, in polygenic autoimmune diseases, many GWAS findings have failed to impact clinical practice. Large-scale transancestral association studies of SLE may be performed to identify ancestry-dependent and independent contributions to SLE risk. Here, we link SLE-associated variants from diverse ancestral populations to biologically relevant genes (E-Genes) via the GTEx database. This analysis has led to the identification of 69 and 770 E-Genes specific for AA and EA respectively, with 52 E-Genes shared between AA and EA ancestries. We then applied a comprehensive systems biology approach using available bioinformatics and pathway analysis tools (e.g. IPA, STRING) to identify the genetic drivers of gene expression networks and key genes within SLE-associated biological pathways, including upstream and downstream regulators. Newly predicted E-Genes and their regulators were then coupled to SLE differential expression (DE) datasets to map candidate molecular pathways and available treatments unique to each ancestral group. Together, these genetic and gene expression analyses clarify the fundamental differences in lupus molecular pathways between ancestral populations and help identify novel drug candidates that may uniquely impact SLE in EA and AA populations.

Identification of SLE-associated SNPs, eQTLs, and E-Genes was performed as follows. A set of single nucleotide polymorphisms significantly associated with SLE in AA (2,970 cases; 2,452 controls) and EA (6,748 cases; 11,516 controls) cohorts was obtained (as described by, for example, Langefeld et al., "Transancestral mapping and genetic load in systemic lupus erythematosus," *Nature Communications,* 8:16021, Jul. 17, 2017, DOI: 10.1038/ncomms16021; which is incorporated herein by reference in its entirety). SNP proxies (raggr.usc.edu) in linkage disequilibrium (r2>0.5) with these SLE-associated SNPs were then determined, using the European (CEU) population as background for EA SNPs and the African (YRI) population for AA SNPs. Expression quantitative trait loci (eQTLs) were then identified using GTEx (version 6). These eQTLs and their associated eQTL expression genes (E-Genes) were divided into an AA group and an EA group, dependent on the ancestry of the original SLE-associated SNP from which the eQTL was obtained.

SNP genomic functional categories were obtained as follows. The Variant Effect Predictor tool available on the Ensembl genome browser 93 (www.ensembl.org) was used for SNP annotation information. SNPs within 5 kilobases (kb) upstream of transcription start sites (TSS) were considered upstream regions, and SNPs within 5 kb downstream of transcription termination sites (TTS) were considered downstream regions. The online resource tools RegulomeDB (regulomedb.org) and HaploReg (version 4.1; pubs.broadinstitute.org/mammals/haploreg/haploreg.php) were also used to identify DNA features and regulatory elements, and to assess regulatory potential.

E-Gene functional gene set analyses were performed as follows. For both ancestral groups, E-Gene lists were examined and classified using a variety of techniques, including PANTHER GO slim (Protein ANalysis THrough Evolutionary Relationships, part of the Gene Ontology (GO) reference genome project; pantherdb.org v.13.1) and statistical enrichment of BIG-C™ (Biologically Informed Gene Clustering, v. 4.3) categories. STRING (string-db.org, v. 10.5) and CytoScape (v. 3.6.1) aided genetic pathway identification and visualization, respectively. E-Genes were also compared with differential expression data gathered from SLE gene expression studies, including E-GEOD-24706, EMTAB2713, FDABMC3, GSE4588, GSE10325, GSE22098, GSE29536, GSE32591, GSE36700, GSE38351, GSE39088, GSE45291, GSE49454, GSE50772, GSE52471, GSE61635, GSE72535, GSE81071, GSE81622, GSE88884, and GSE100093. Differential expression log fold changes were determined for probes with false discovery rate (FDR) <0.2. This differential expression data was also used in conjunction with IPA® (Qiagen) to predict upstream regulators (URs) of E-Genes.

Drug candidate identification and CoLT scoring were performed as follows. Drug candidates were identified using CLUE (clue.io/repurposing), IPA, and STITCH (Search Tool for Interacting CHemicals; stitch.embl.de). Where information was available, drugs were assessed by COLTS (Combined Lupus Treatment Scoring) (as described by, for example, Grammer et al., "Drug repositioning in SLE: crowd-sourcing, literature-mining and Big Data analysis," *Lupus,* 2016 Sep. 25(10):1150-70, DOI: 10.1177/0961203316657437; which is incorporated herein by reference in its entirety) to rank potential drug candidates for repositioning in SLE. Each of these tools includes either a programmatic method of matching existing therapeutics to their targets or a list of drugs and targets for achieving the same end.

Figures 41B, 41C:
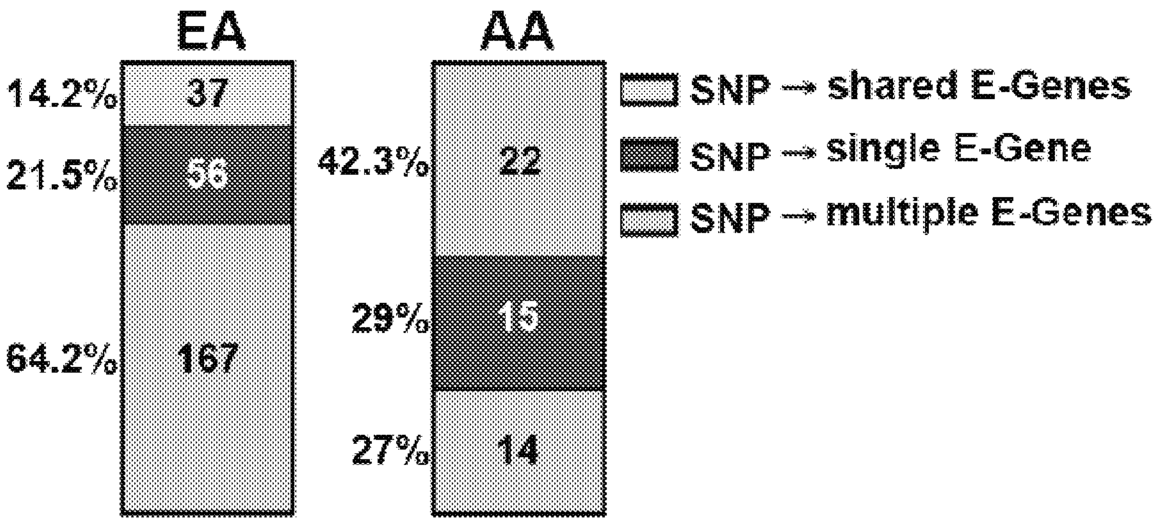
Figure 42A:
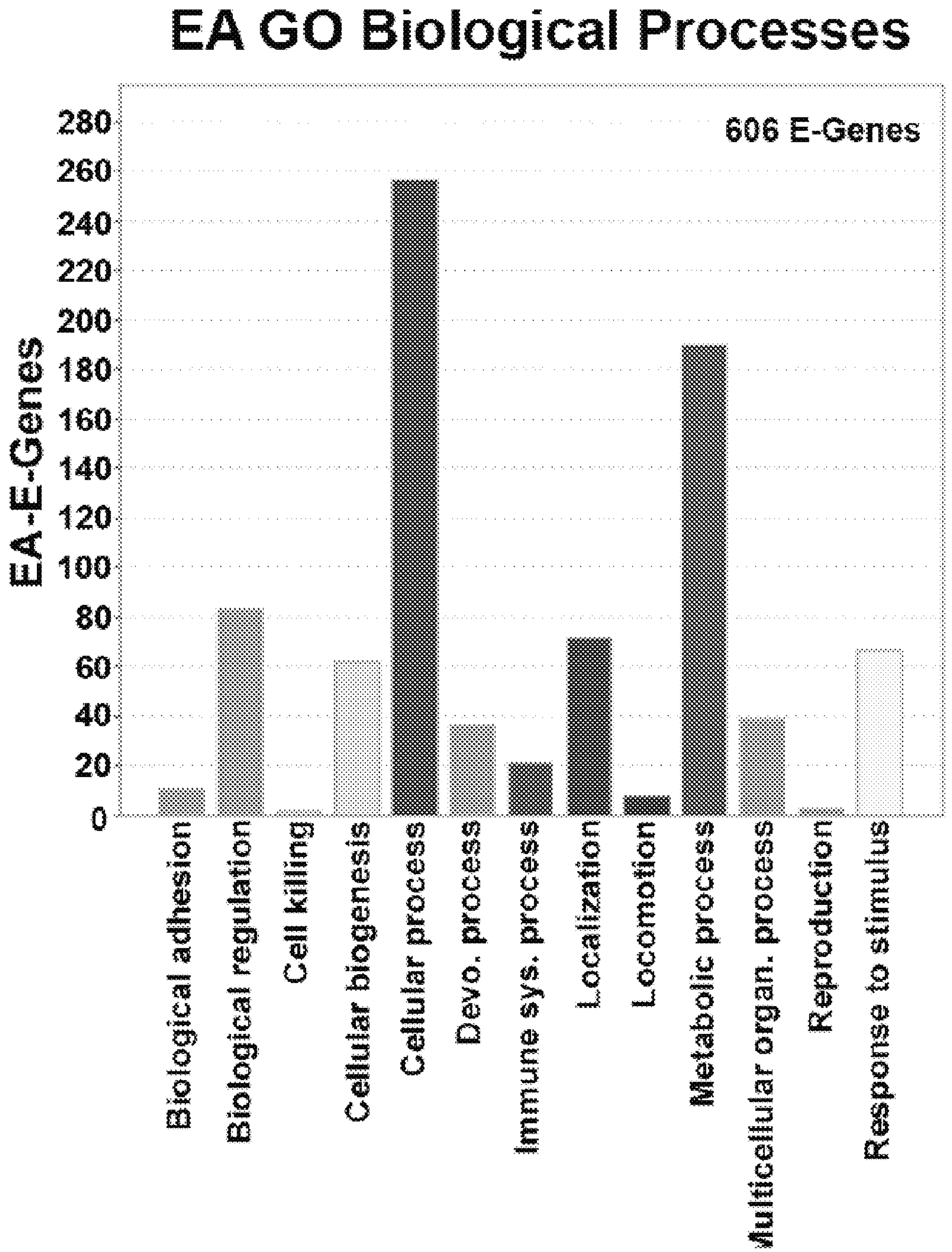
FIGS. 42A-42D show an example of E-Gene functional and pathway analysis, in accordance with disclosed embodiments. PANTHER (v.13.1) was used to classify EA and AA E-Genes according to gene ontology (GO) biological processes and pathways. The number of EA (FIG. 42A) and AA (FIG. 42B) E-Genes assigned to GO biological processes is displayed in each bar graph; GO identifiers are reported to the right of each graph. For pathway analysis, EA (FIG. 42C) and AA (FIG. 42D) E-Gene sequences were assigned to GO pathways. EA E-genes are defined by 78 pathways; several pathways of interest containing 4 or more E-Genes are labeled. AA E-Genes are defined by 15 pathways as shown in the pie chart.
Figure 42B:
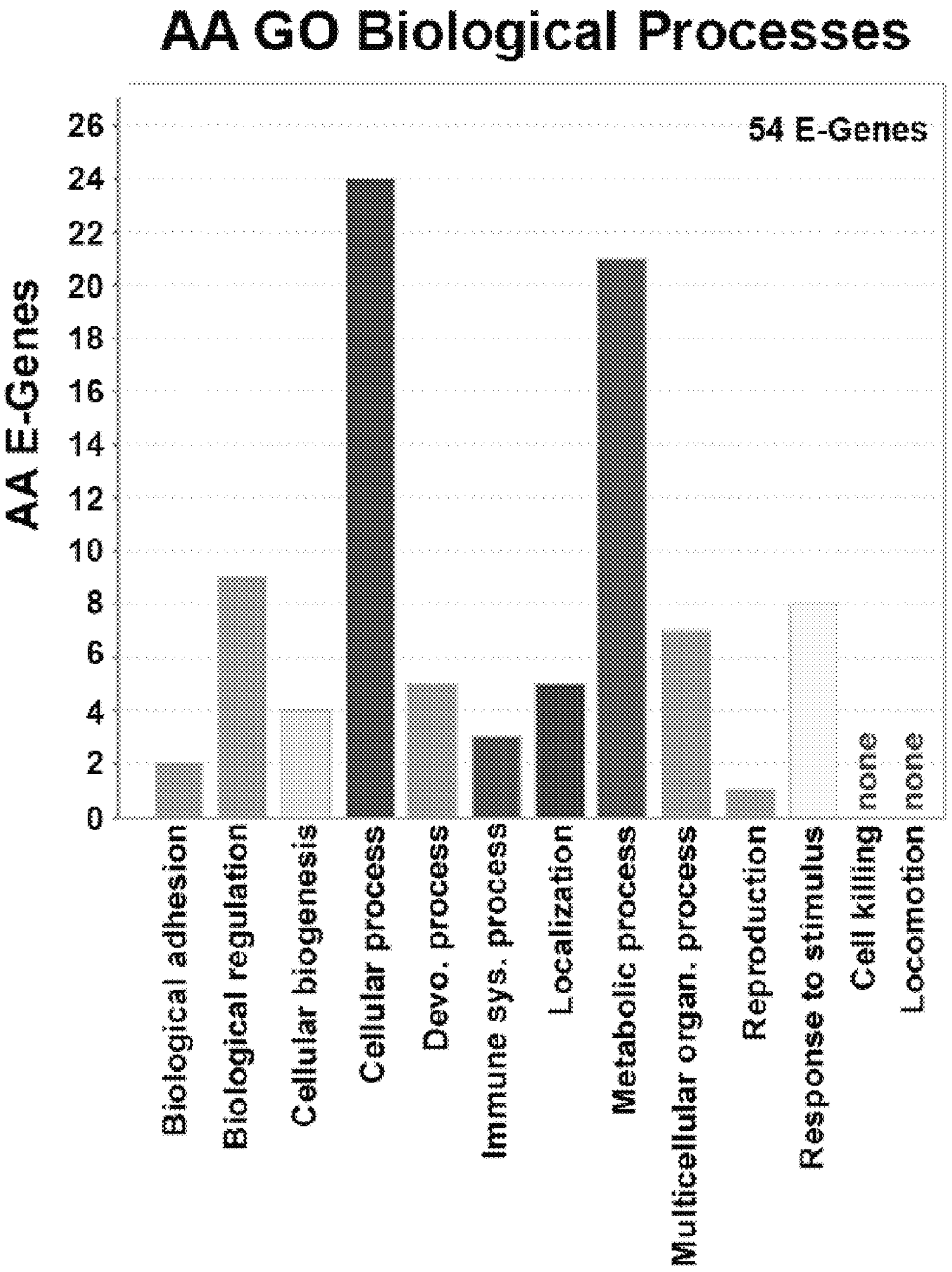
Figure 42C:
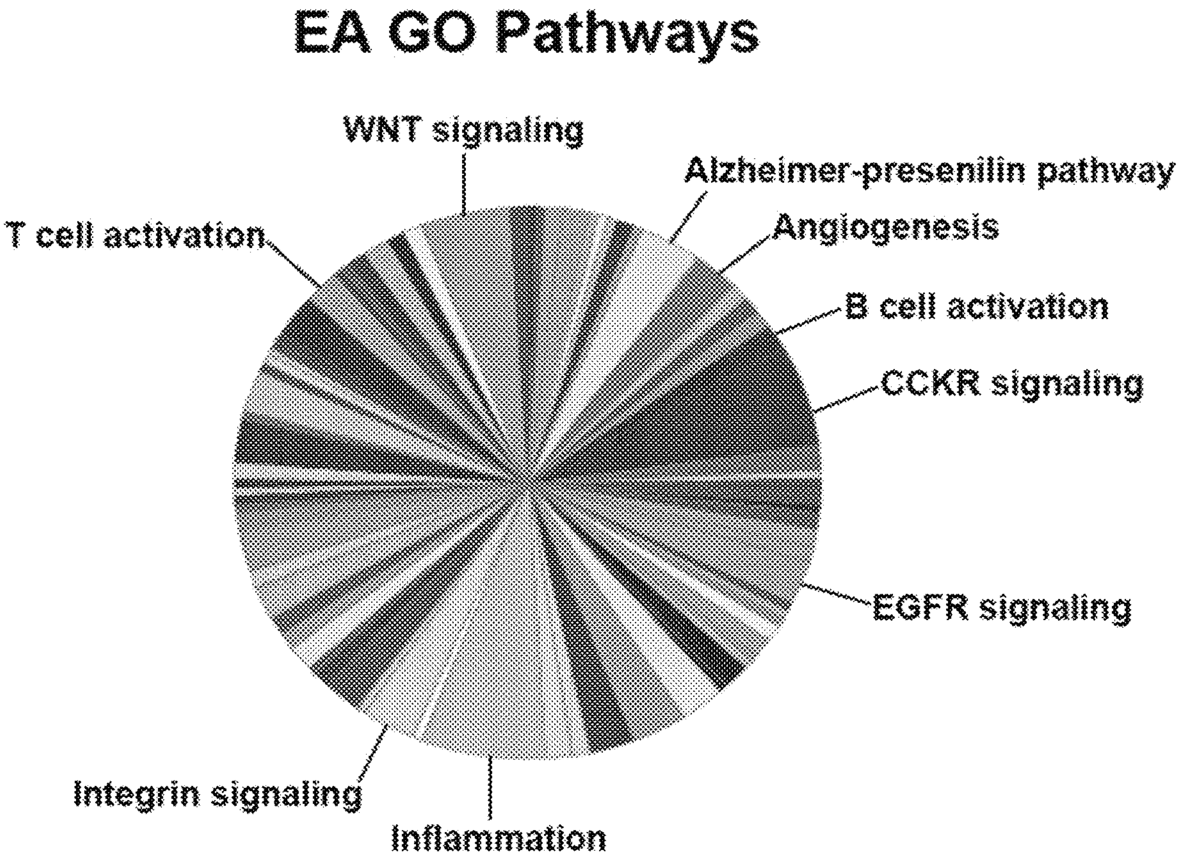
Figure 42D:
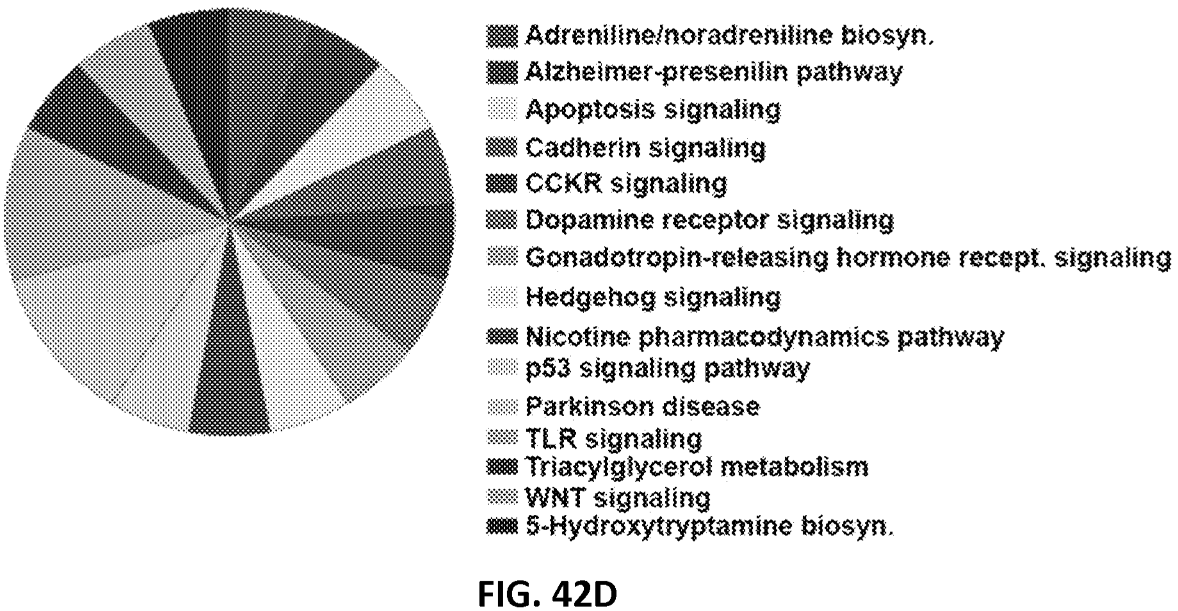

FIGS. 41A-41C show an example of mapping SNP associations to eQTLs and E-Genes, in accordance with disclosed embodiments. FIG. 41A shows a distribution of genomic functional categories for EA and AA SNP sets.

"NT-R" is defined as Non-Traditional Regulatory: intronic or intergenic SNPs exhibiting strong regulatory potential, indicated by DNAse hypersensitivity, location within protein binding sites, and evidence of epigenetic modification. "Other" non-coding regions include introns, intergenic regions, within 5 kb upstream of transcription start sites, and within 5 kb downstream of transcription termination sites. FIG. 41B shows a summary of eQTL analysis. SLE-associated SNPs identify multiple eQTLs linked to E-Genes in the GTEx database. eQTLs and their associated E-Genes were divided into European ancestry (EA) and African ancestry (AA) groups, depending on the ancestral origin of the original SLE-associated SNP. Shared E-Genes are derived from SNPs common to both EA and AA ancestries. FIG. 41C shows the number of EA and AA SNPs mapping to single E-Genes, multiple E-Genes, or shared E-Genes.

FIGS. 42A-42D show an example of E-Gene functional and pathway analysis, in accordance with disclosed embodiments. PANTHER (v.13.1) was used to classify EA and AA E-Genes according to gene ontology (GO) biological processes and pathways. The number of EA E-Genes (FIG. 42A) and AA E-Genes (FIG. 42B) assigned to GO biological processes is displayed in each bar graph; GO identifiers are reported to the right of each graph. For pathway analysis, EA E-Gene sequences (FIG. 42C) and AA E-Gene sequences (FIG. 42D) were assigned to GO pathways. EA E-Genes are defined by 78 pathways; several pathways of interest containing 4 or more E-Genes are labeled. AA E-Genes are defined by 15 pathways, as shown in the pie chart.

Figure 43A:
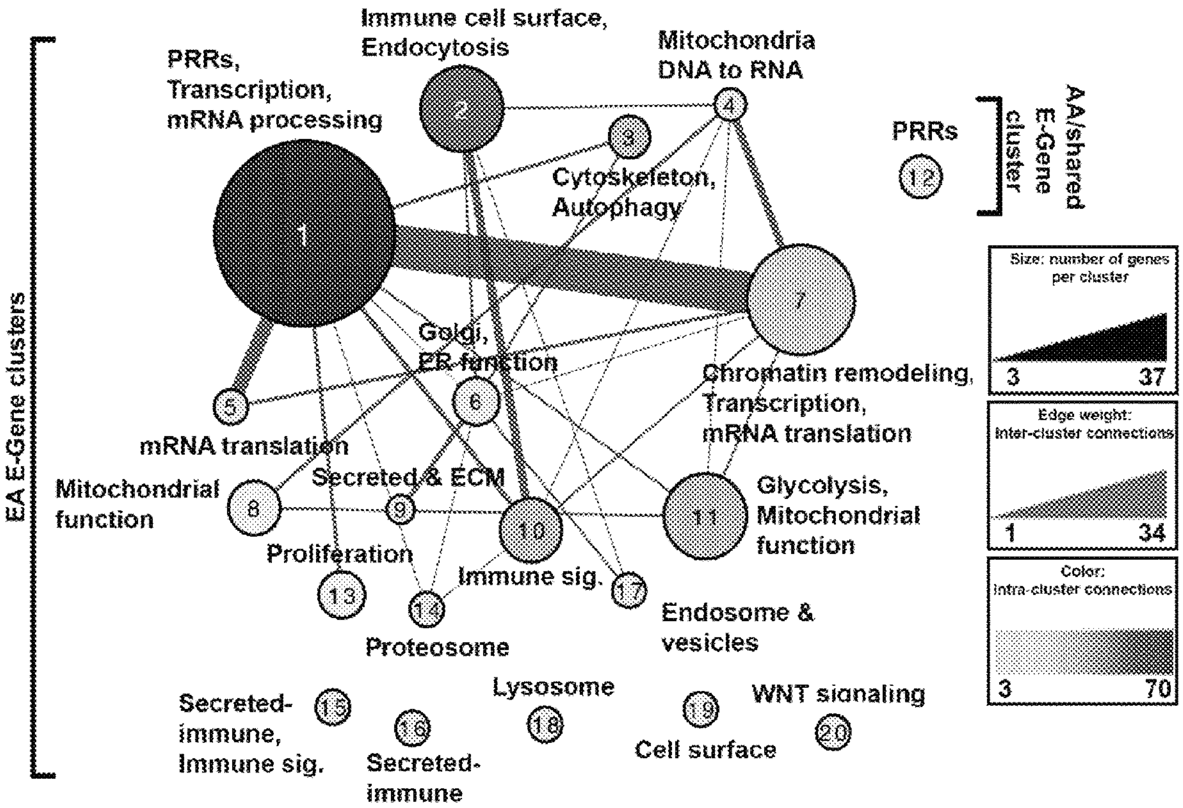
FIGS. 43A-43C show an example of generation of protein-protein interaction (PPI) networks, in accordance with disclosed embodiments. PPI networks and clusters generated were generated via CytoScape using the STRING and MCODE plugins. Networks were constructed of all EA, AA, and shared (EA+AA) E-Genes. MCODE clusters were determined by the strength of protein-protein interactions, calculated by pooling information from publicly available literature.
Figure 43B:
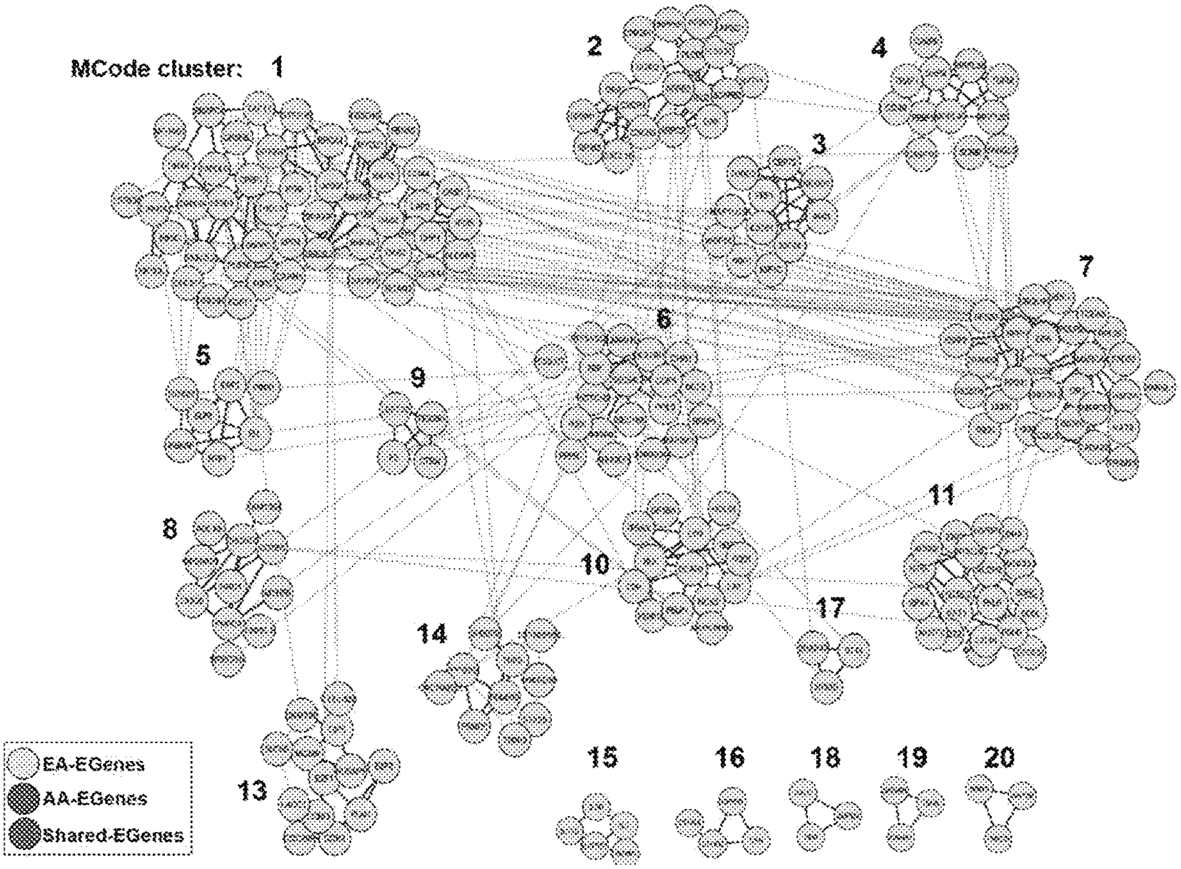
Figure 43C:
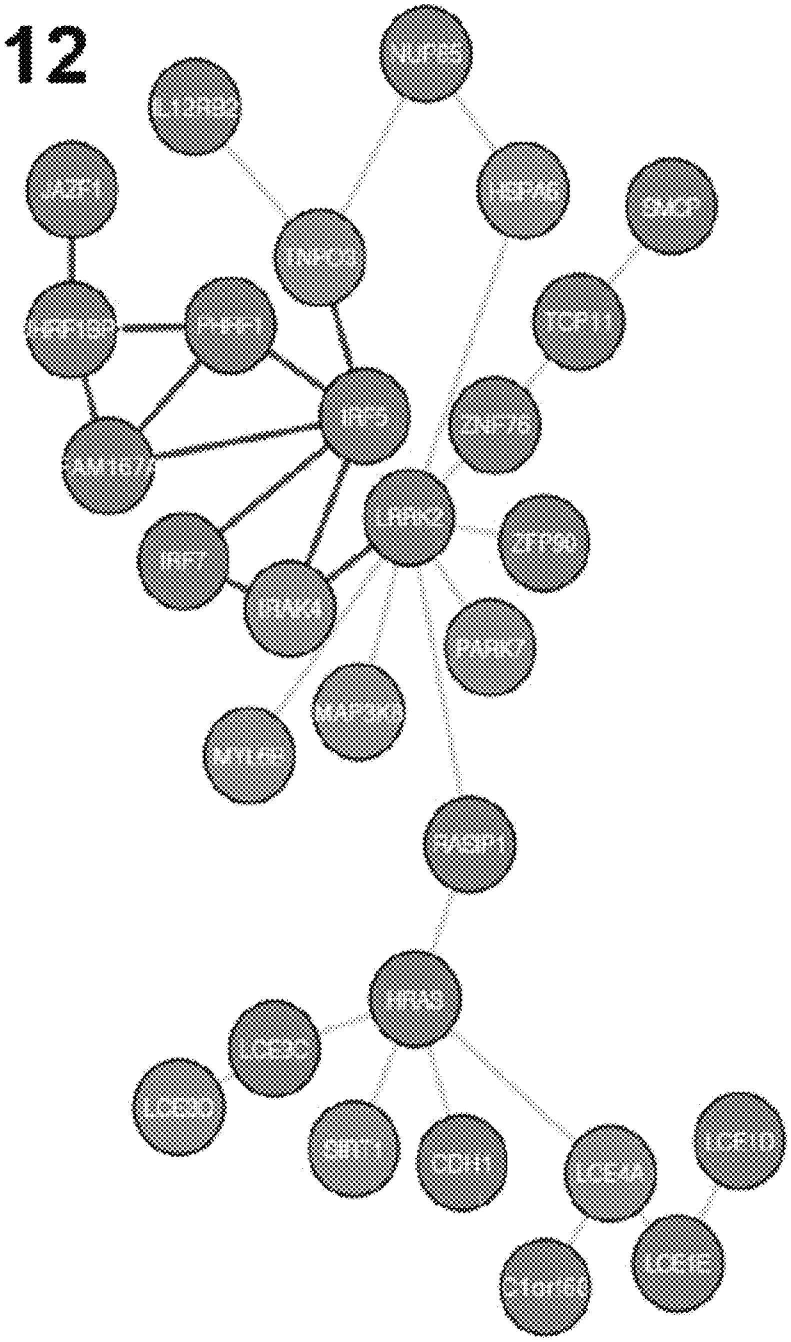
Figure 43D:
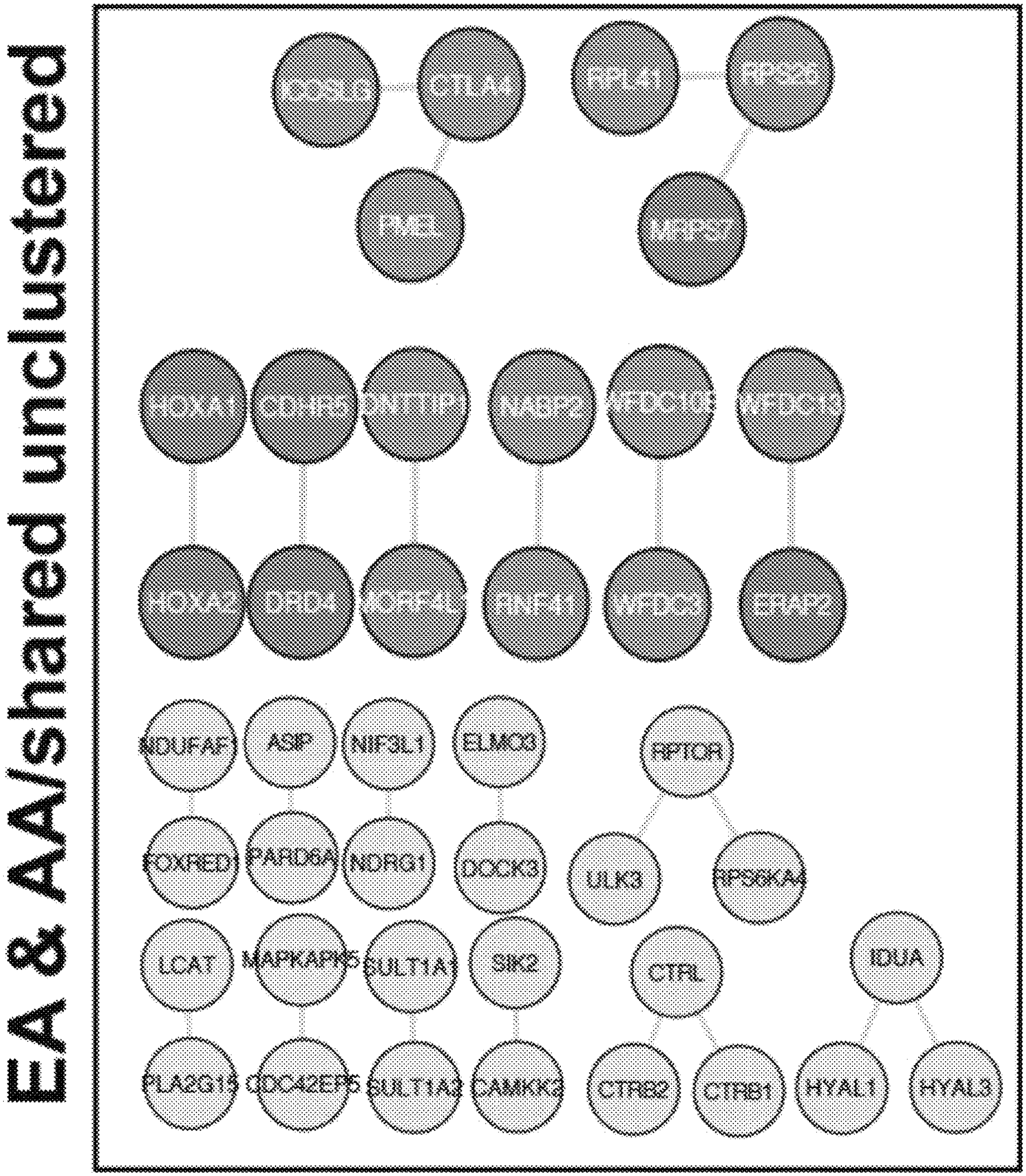
FIG. 43D shows EE, AA, and shared (EE+AA) E-Genes that were unclustered.

FIGS. 43A-43C show an example of generation of protein-protein interaction (PPI) networks, in accordance with disclosed embodiments. PPI networks and clusters were generated via CytoScape using the STRING and MCODE plugins. Networks were constructed of all EA, AA, and shared (EA+AA) E-Genes. MCODE clusters were determined by the strength of protein-protein interactions, calculated by pooling information from publicly available literature. FIG. 43A shows the cluster metastructure of each network and corresponding BIG-C™ categories, while FIGS. 43B-43C show the specific genes that make up each cluster. FIG. 43D shows EE, AA, and shared (EE+AA) E-Genes that were unclustered.

A set of examples of European-Ancestry (EA) E-Genes are shown in Table 25; a set of examples of African-Ancestry (AA) E-Genes are shown in Table 26; and a set of examples of shared E-Genes (common to both EA and AA) are shown in Table 27.

TABLE 25

European-Ancestry (EA) E-Genes by MCODE Cluster Number

| MCODE Cluster Number | Set of European-Ancestry (EA) E-Genes |
|---|---|
| 1 | SNAPC4, TAF11, GTF2H5, MFHAS1, CPSF3L, GTF2H1, BRCA1, DHX8, PAPOLG, CPSF1, PTRF, UVSSA, LRRIQ4, CIRH1A, DHX29, SF3B1, THOC5, SNAXIP, EIF3C, SNRPC, XPO4, UBE2L3, EIF3CL, SKIV2L2, PUF60, CARMI, DHCR7, HSD3B, FDFT1, FDPS, FBXO40, MYOZ1, FBXW2, ISLR2, CD44, TRIM63, LAP3, OAS1, OAS2, RNF40, CHP1, IFI35, OAS3, SLC9A3, SLC9A4, CIAPIN1, RCAN3 |
| 2 | CNKSR1, INPP5E, AP3B2, AP3D1, PLCB3, FCHO2, DGKQ, SAA1, ARRB2, SCARB2, SYT11, CXCR1, CXCR2, GPSM1, GRM2, CXCL16, ARPC2, GAK, SYNJ2 |
| 3 | CEP72, TUBG2, NEDD1, FBF1, AHI1, MAP1LC3A, IQCB1, KIF24, WDFY4, NBR1, KIF1C |
| 4 | CASP8, TRAF1, DAP3, MRPL38, TUFM, CD40, PEBP1, MRPL45, MPRL20, CASP10, SCRIB, VANGL2 |
| 5 | DDX27, EAF2, PINX1, ELP3, ELL, RTF1, IKBKAP |
| 6 | POGLUT1, ATP6V0D, LMAN1L, GOLGB1, CHN1, NSF, SEC24C, COPA, NCF2, NOTCH2, PPIL3, SEC16A, PLEK, PPP6R1, RPAP1, PPP5C, ARHGEF2, ANKRD44, MAP3K11 |
| 7 | UBQLN4, ADS1, RPS20, RPP14, EIF6, POLR2, TCEA3, RPL29, ESRP2, ZRANB3, SMARCA4, FADS2, ATC2IP, RPS11, NCSTN, ERCC6L2, DR1, H3F3A, KANSL1, DCPS, TREH, SED, CCDC1, INO80, SMARCE1, KAT8, TADA2B, TRIM24 |
| 8 | FAM136A, ADCK5, CHCHD2, COX5A, NIPSNAP1, NRD1, MYH7B, COQ9, PMPCA, GRPEL1, WBSCR16 |
| 9 | LEFTY2, TEX264, F5, CTSW |
| 10 | GP1BA, HCLS1, ITGAX, LYN, RGS1, BLK, BCAR1, LAT, CSK, NCK2, PELP1, MAPKAPK3, PDIK1 |
| 11 | HSPBP1, NT5C3L, ACSS2, NT5E, ALDH2, IMGCLL1, NT5C2, PKLR, SDHC, SDSL, GPX4, VAT1, PDHB, GFOD2, NUTF2, CD38 |
| 13 | C15orf23, OIP5, DNMT3B, SUDS3, MCM6, E2F1, NUSAP1, E2F2, LACC1, CCNO, PLAU, CDC20B, CDK3 |
| 14 | SH3BP2, CTTNBP2NL, TNKS, ANKRD65, PP2RIB, PSMB10, STK25, CACNA2D2, PSMD5, TNNI3 |
| 15 | IL6R, IL7, IL17D, IL12RB1, GZMA |
| 16 | CFHR4, CFHR3, CFHR1, CFH |
| 17 | SNAP47, STX4, STX1B |
| 18 | GALC, SMPD3, GBA |
| 19 | GPBAR1, TSHR, CRHR1 |
| 20 | WNT3, WNT2B, TMED5 |
| Un-clustered | NDUFAF1, FOXRED1, LCAT, PLA2G15, ASIP, PARD6A, MAPKAPK5, CDC42EP5, NIF3L1, NDRG1, SULTIA1, SULT1A2, ELMO3, DOCK3, SIK2, CAMKK2, RPTOR, ULK3, RPS6KA4, CTRL, CTRB2, CTRB1, IDUA, HYAL1, HYAL3 |

TABLE 26

| African-Ancestry (AA) E-Genes by MCODE Cluster Number | |
|---|---|
| MCODE Cluster Number | Set of African-Ancestry (AA) E-Genes |
| 12 | TNPO3, HSPA6, IRAK4, PARK7, MYL6B, MAP3K8, LCE3D, SIRT1, LCE4A |
| Un-clustered | ICOSLG, CTLA4, PMEL, RPL41, RPS26, DNTTIP1, MORF4L1, NABP2, RNF41, WFDC10B, WFDC3, WFDC13 |

TABLE 27

| Shared E-Genes (common to both EA and AA) by MCODE Cluster Number | |
|---|---|
| MCODE Cluster Number | Set of Shared E-Genes |
| 12 | NUP85, IL12RB2, JAZF1, UHRF1BP, PHRF1, FAM167A, IRF7, IRF5, LRRK2, ZNF76, TCP11, SMCP, ZFP90, RASIP1, HRAS, LCE3C, CDH1, C1orf68, LCE1E, LCE1D |
| Un-clustered | MRPS7, HOXA1, HOXA2, CDHR5, DRD4, ERAP2 |

Figure 44A:
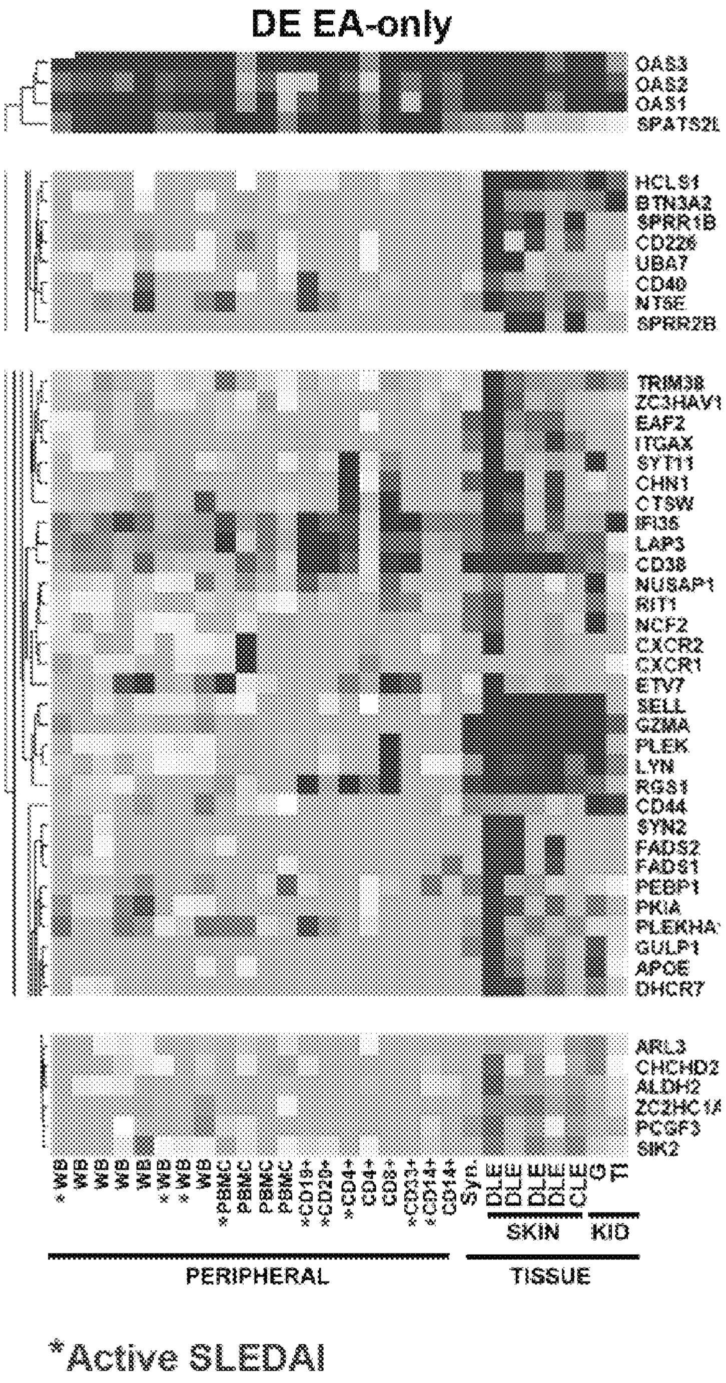
FIGS. 44A-44D show an example of a comparison of E-Genes predicted from SLE-associated SNPs with SLE differential expression datasets, in accordance with disclosed embodiments. Predicted E-Genes were matched with SLE differential expression (DE) data and organized by ancestry.
Figure 44B:
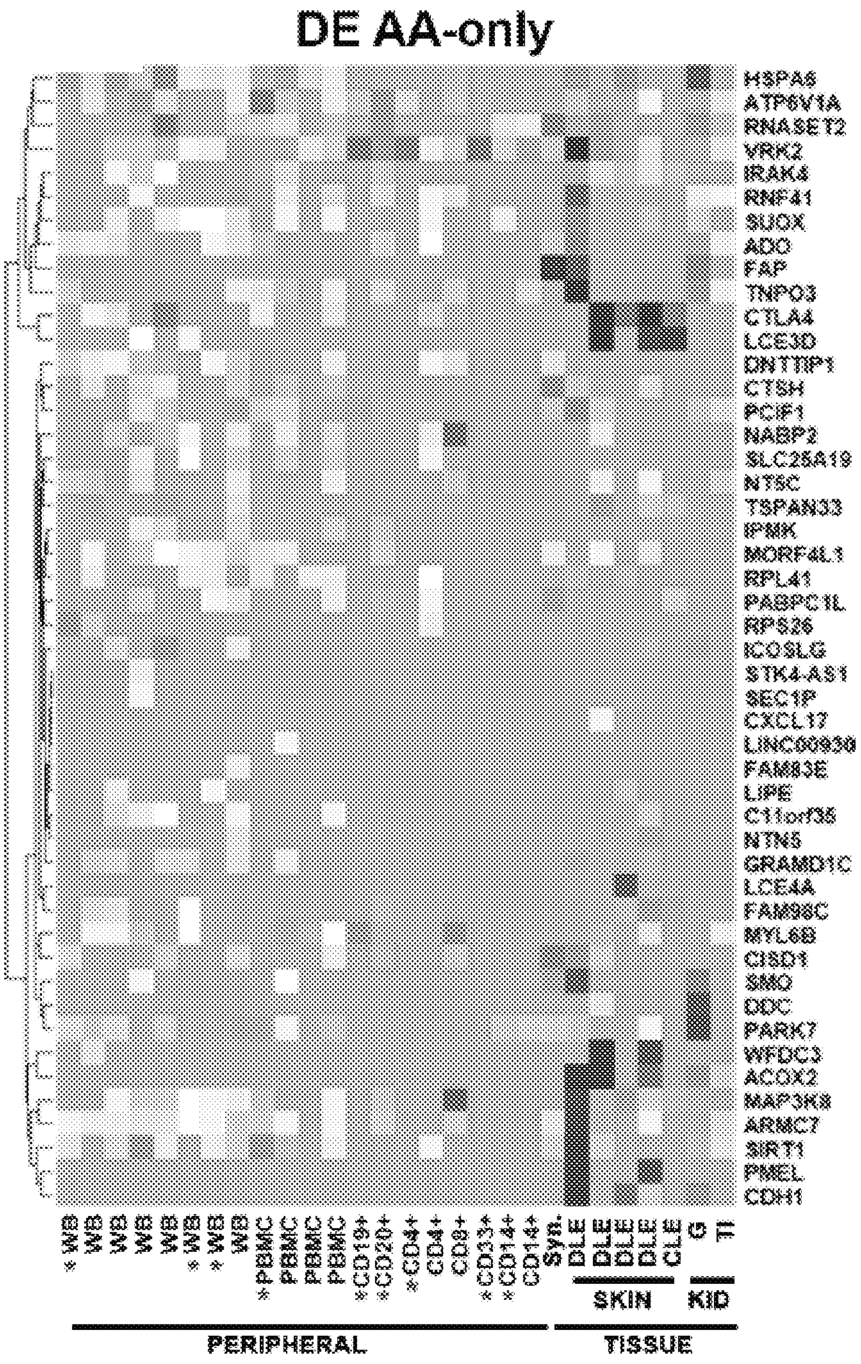
Figure 44C:
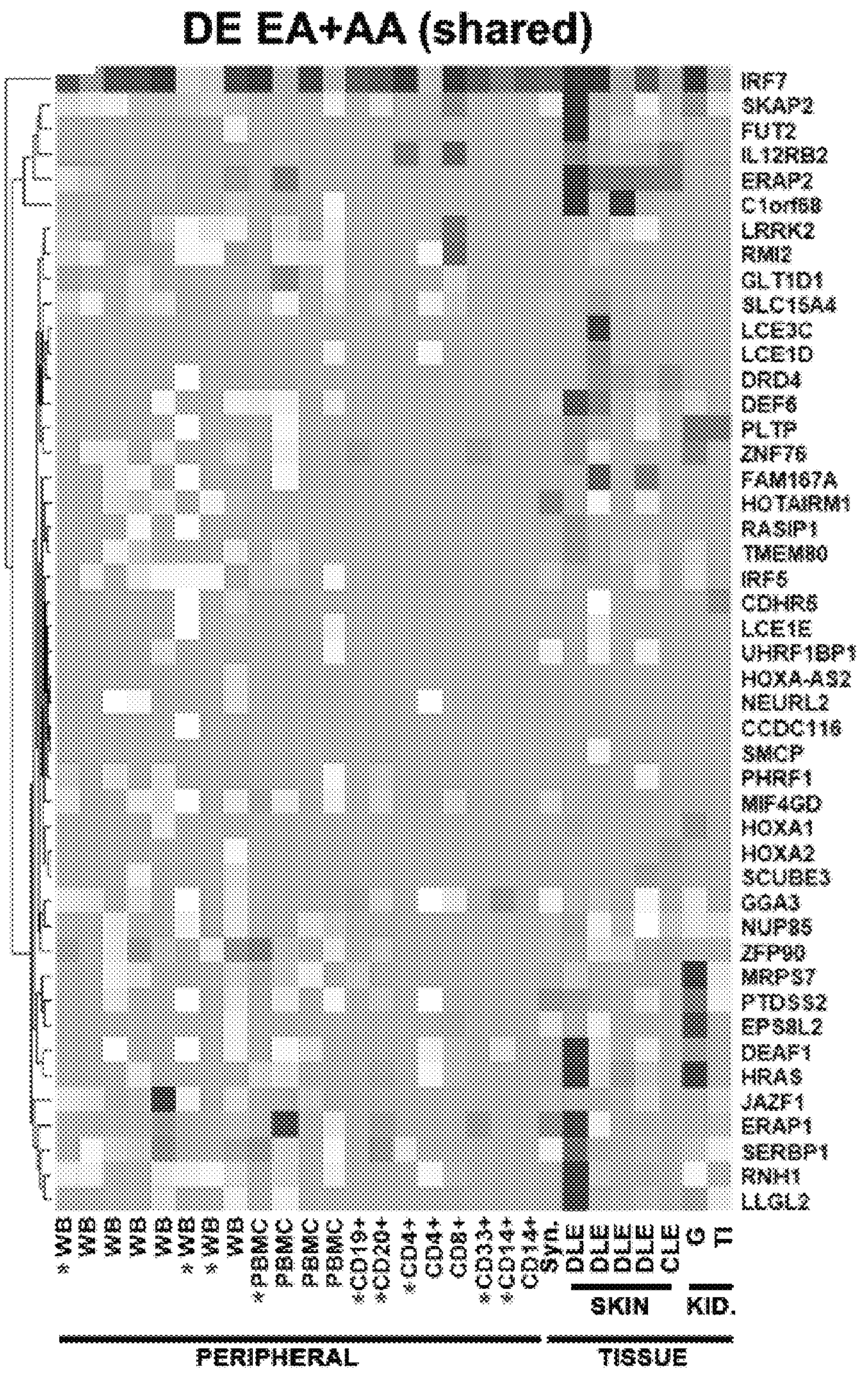
Figure 44D:
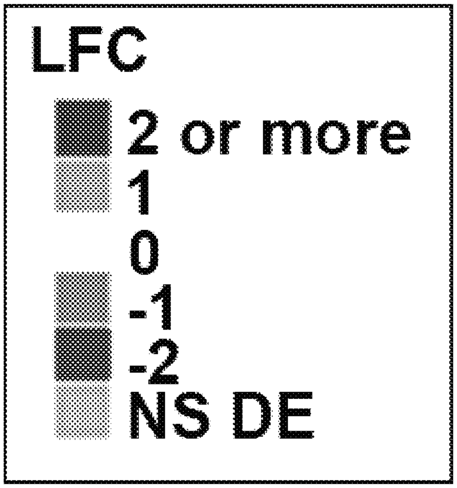

FIGS. 44A-44D show an example of a comparison of E-Genes predicted from SLE-associated SNPs with SLE differential expression datasets, in accordance with disclosed embodiments. Predicted E-Genes were matched with SLE differential expression (DE) data and organized by ancestry. FIG. 44A shows the fold-change variation of EA-only E-Genes. Due to the large number of differentially expressed (DE) EA E-Genes, a selection of the most highly upregulated and downregulated genes are presented. FIG. 44B shows AA-only DE E-Genes, and FIG. 44C shows DE E-Genes common to both the AA and EA gene sets. Color for all three heatmaps represents log fold change, as indicated by the legend underneath the central heatmap (FIG. 44D). Red asterisks indicate active SLEDAI datasets.

Figure 45:
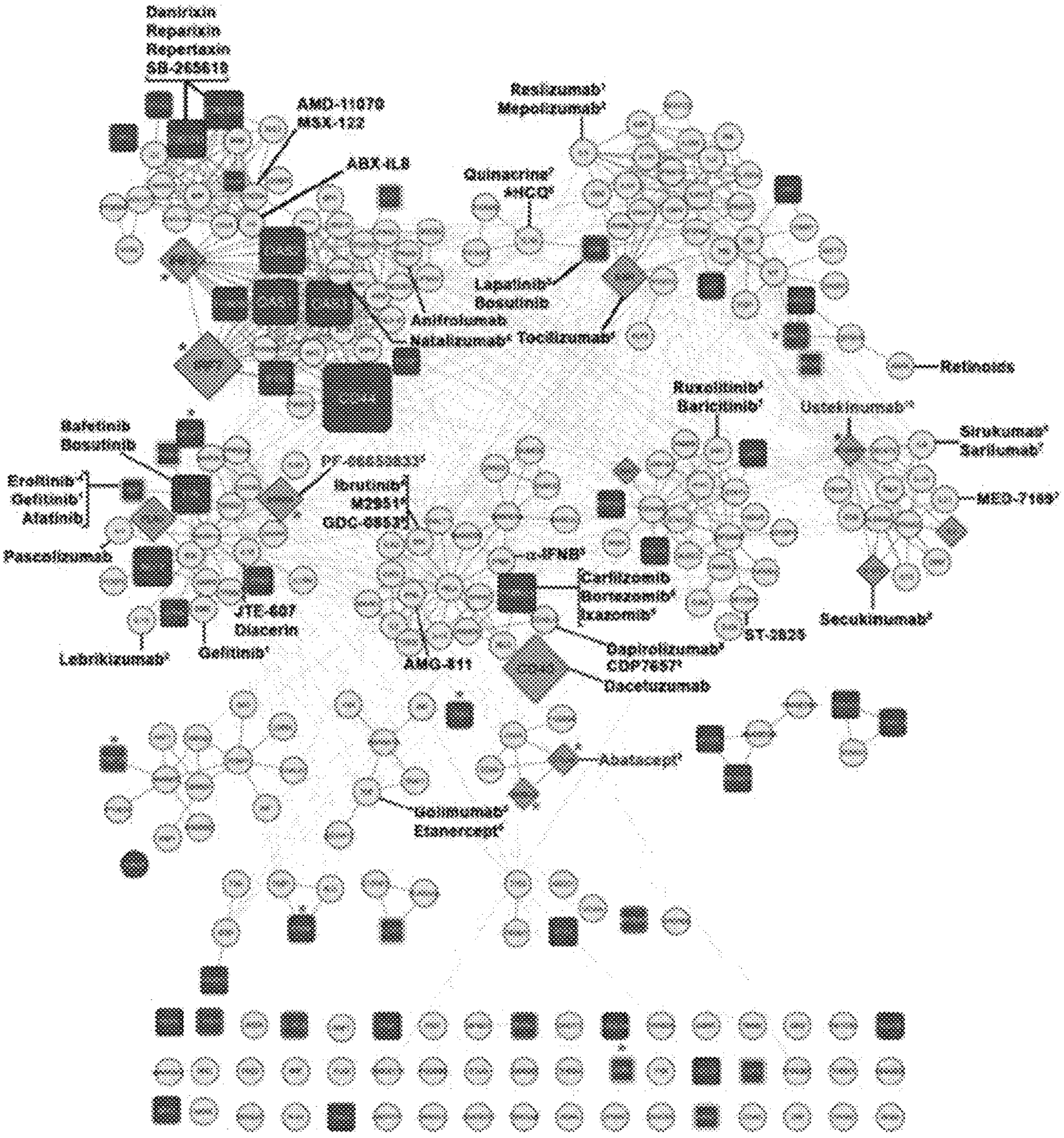
FIGS. 45-46 show an example of a comparison of E-Genes predicted from SLE-associated SNPs with SLE differential expression datasets, in accordance with disclosed embodiments. Compounds targeting EA, AA, shared tissue E-Genes and associated pathways are shown. Differentially expressed E-Genes from synovium, skin and kidney tissue datasets were first compared to immune-specific gene lists. Overlapping genes were used as input for IPA upstream regulator analysis. PPI networks and clusters were generated via CytoScape using the STRING and MCODE plugins. MCODE clusters were determined by the strength of protein-protein interactions, calculated by pooling information from publicly available literature. Select drugs acting on targets are shown. Where available, CoLT scores (−16 to +11) are depicted in superscript.
Figure 46:
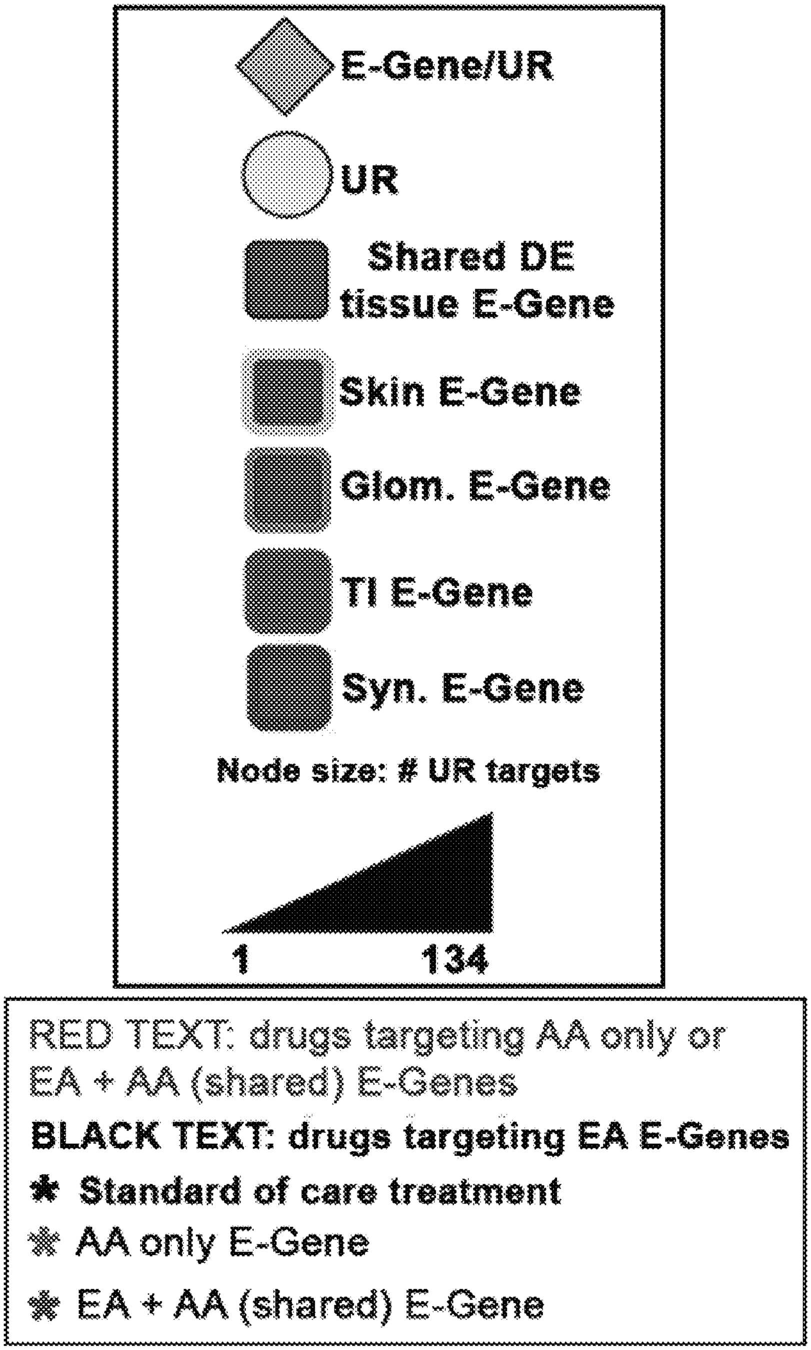

FIGS. 45-46 show an example of a comparison of E-Genes predicted from SLE-associated SNPs with SLE differential expression datasets, in accordance with disclosed embodiments. Compounds targeting EA, AA, shared tissue E-Genes and associated pathways are shown. Differentially expressed E-Genes from synovium, skin, and kidney tissue datasets were first compared to immune-specific gene lists. Overlapping genes were used as input for IPA upstream regulator analysis. PPI networks and clusters were generated via CytoScape using the STRING and MCODE plugins. MCODE clusters were determined by the strength of protein-protein interactions, calculated by pooling information from publicly available literature. Select drugs acting on targets are shown. Where available, CoLT scores (−16 to +11) are depicted in superscript.

This multi-level combined genetic and genomic bioinformatics analysis is capable of defining gene regulatory pathways which not only reflect differences in EA and AA populations, but also represent candidate pathways that may be the target of ancestry-specific therapies. Ancestral SNP-associated E-Genes and gene expression profiles illustrate fundamental differences in lupus molecular pathways between ancestral groups. In particular, different or unique sets of drugs may be particularly effective at treating lupus within each ancestral group based on these differences in lupus molecular pathways.

Example 15: Analysis of Single Nucleotide Polymorphisms Associated with Systemic Lupus Erythematosus Provides Insights into Molecular Pathways Operative in Ancestral Groups Individuals of African-Ancestry (AA) may experience systemic lupus erythematosus (SLE) more severely and with an increased co-morbidity burden compared to European-Ancestry (EA) populations. However, the relationship between genetics, molecular pathways and disease severity may not be fully delineated. A comprehensive systems biology approach was applied using bioinformatics and pathway analysis tools to identify the genetic drivers of gene expression networks and key genes within SLE-associated biological pathways. Newly predicted genes were coupled to SLE differential expression (DE) datasets to map dominant molecular pathways representative of each ancestry and available treatments unique to each ancestral group. Pathway validation was provided by gene set variation analysis (GSVA) which identified differentially enriched ancestry-specific gene signatures in SLE patients and control whole blood.

Systemic lupus erythematosus (SLE) may be a multi-organ autoimmune disorder associated with significant morbidity and mortality. SLE may be strongly influenced by genetic factors and recent candidate gene and genome wide association studies (GWAS) may identify over 90 SLE susceptibility loci. However, disease development may be complex and often unpredictable, with considerable differences noted in individuals of different ancestral groups. Some studies may show that individuals of African-Ancestry (AA) experience the disease more severely and with an increased co-morbidity burden compared to European-Ancestry (EA) populations. Moreover, there may be variability in the response of individuals of different ancestral groups to standard medications, including cyclophosphamide, mycophenylate, rituximab and belimumab. For example, belimumab, a monoclonal antibody directed to TNFSF13B may exhibit some clinical benefit in moderately active SLE, but may be reported to be less effective in treating AA populations.

Understanding the functional mechanisms of causal genetic variants underlying SLE may provide essential information to identify ancestry-specific molecular pathways and therapeutic targets relevant to disease mechanisms. Although GWAS has achieved great success in mapping disease loci in polygenic autoimmune diseases, GWAS findings may fail to impact clinical practice. Moreover, for many single nucleotide polymorphisms (SNPs), the biologic implications may not have been identified. Thus, a major challenge lies in understanding the molecular meaning of an association of a single nucleotide polymorphism (SNP) with a disease such as SLE. This process may comprise the identification of causal genes from multiple genetic candidates associated with a lead or "tagging" SNP. This analysis may be complicated by the finding that the majority of SLE-associated SNPs are located outside of protein coding regions. However, a number of approaches can be employed to deconvolute the implications of GWAS findings. For example, utilization of expression quantitative trait loci (eQTL) mapping to identify genetic variants that affect gene expression either in cis (within 1 Mb) or trans (outside of the 1 Mb window or on a different chromosome) can offer important insights into disease causing mechanisms contributing to SLE. In addition, the interactions of transcription factors (TFs) with DNA regulatory elements (e.g. promoters and enhancers) may play a critical role in determining gene expression. However, connecting distal regulatory regions, such as enhancers, with target genes may remain complex. The integration of data from functional genomics, including transcription factor chromatin immunoprecipitation sequencing (ChIP-seq), DNase-Seq, chromosome accessibility sequencing (ATAC-Seq) and chromosome conformation capture-based technologies (such as 4C, 5C, Hi-C, ChIA-PET, HiChIP and Capture Hi-C) may be used to identify variants that may disrupt transcription factor binding site (TFBS) occupancy in active regulatory regions and reliably predict altered downstream target gene expression. Together, these analyses can provide additional information on the molecular implications of GWAS results.

As a hypothesis, the use of multiple orthogonal approaches may provide novel insights into the totality of perturbations in molecular pathways predicted by GWAS results, the possible differences in pathologic mechanisms in different ancestral groups, and also identify novel therapeutic targets. To test this, SLE-associated variants were linked from diverse ancestral populations to potential biologically relevant expression genes (E-Genes) via eQTL analysis. In parallel; SNPs were queried for their potential role as regulatory variants and mapped to their downstream target genes (T-Genes). Finally, SNPs that were neither regulatory nor identified as an eQTL were assigned to the most physically proximal gene (P-Genes). Coding region SNPs associated with deleterious amino acid changes (nonsynonymous or nonsense) were annotated using functional prediction tools. This analysis yielded the identification of 1,904 potential SLE-associated genes divided by ancestry (1,156 European American (EA), 73 African American (AA), and 675 shared between ancestries). A comprehensive systems biology approach was then applied using bioinformatics and pathway analysis tools to identify the genetic drivers of gene expression networks and key genes within SLE-associated biological pathways, including upstream and downstream regulators. Predicted genes were then coupled to SLE differential expression (DE) datasets to map candidate molecular pathways and available treatments unique to each ancestral group. Together, these genetic and gene expression analyses have clarified the fundamental differences in lupus molecular pathways between ancestral populations, identified molecular pathways that are similar or differ between ancestral groups, and have helped identify novel drug candidates that may uniquely impact EA and AA SLE patients.

Figure 47A:
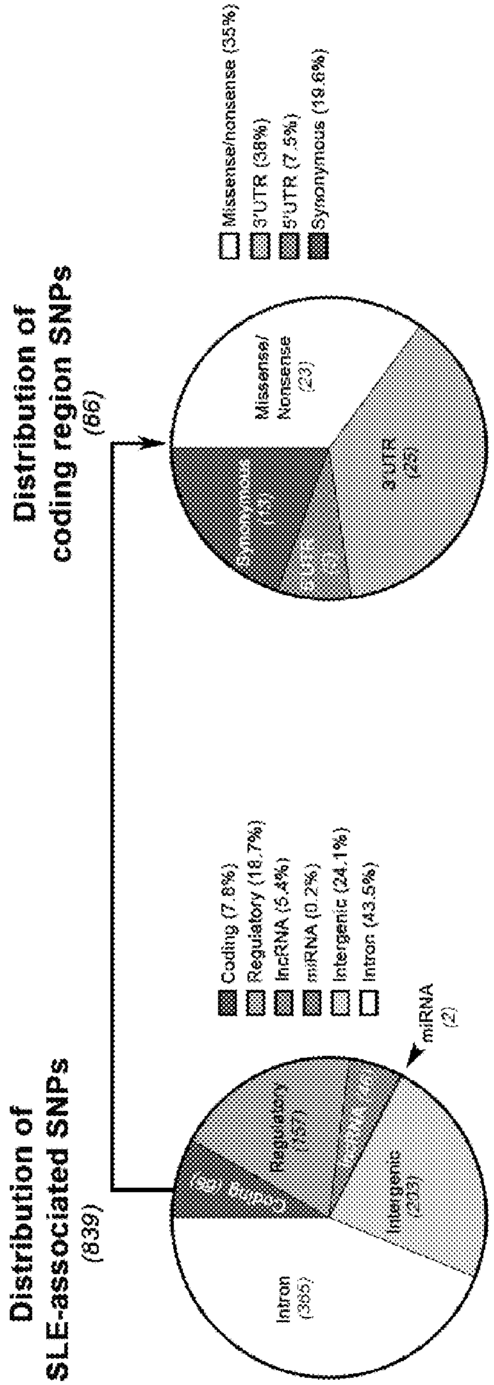
FIG. 47A-47D show results obtained by mapping the functional genes predicted by SLE-associated SNPs.

Identification of ancestry-dependent and independent SLE-associated variants and downstream target genes was performed as follows. An extensive transancestral SLE genetic association study using the Immunochip may be performed to identify 839 non-HLA, independent polymorphisms significantly associated with disease (FIG. 47A). To determine how frequently SLE-associated SNPs occur in coding and non-coding regions of the genome, the Ensembl genome browser was used to assess the distribution of genomic functional categories for all Immunochip SNPs (FIG. 47A). Approximately 26% of SNPs mapped to coding (exons, 5' UTRs, 3'UTRs) or known transcription factor binding regions (TFBS, promoters, enhancers, etc.), whereas the majority of SNPs were found in intronic or intergenic regions exhibiting little evidence of regulatory potential. Furthermore, despite the role of non-coding RNAs in the regulation of gene expression, less than 6% of SNPs mapped to regions containing long non-coding (Inc) RNAs or micro (mi) RNAs.

Figure 47B:
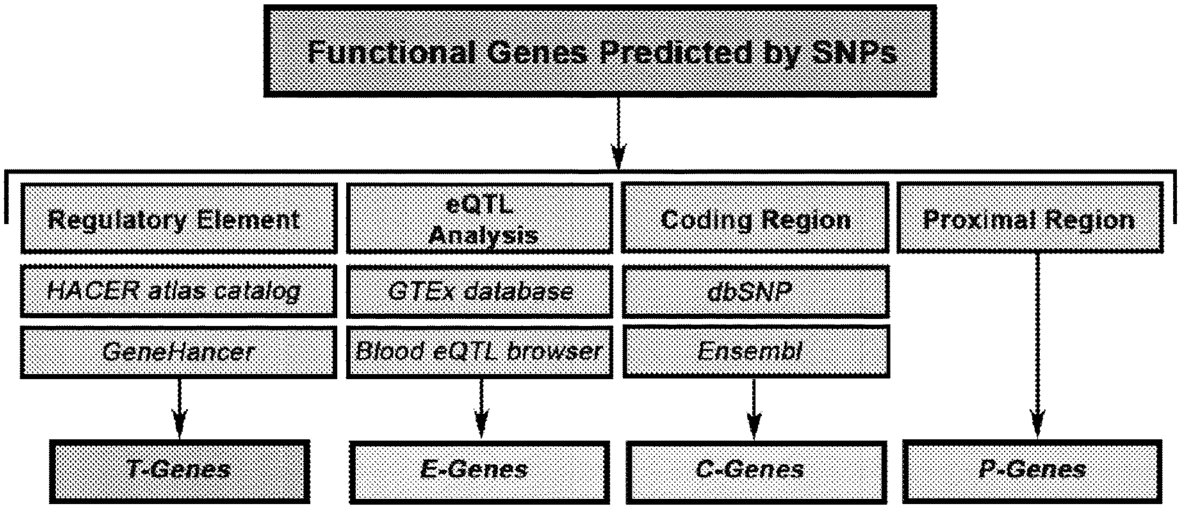

Since the function of the majority of SNPs was unaccounted for, multiple complementary bioinformatics-based approaches were performed to predict the impact of SLE-associated SNPs on downstream molecular pathways (FIG. 47B). Expression quantitative trait loci (eQTL) analysis can be used to link non-coding risk SNPs with alterations in gene expression, either in cis or trans. eQTL mapping via the GTEx and Blood eQTL browser databases, together with concurrent heterogeneity analysis to determine ancestry, identified 77 EA and 21 AA-specific eQTL linked to 207 and 30 expression genes (E-Genes) unique for EA and AA respectively. A total of 149 eQTLs were common to both ancestries and were linked to 523 shared E-Genes. As expected, the majority of predicted eQTL functioned in cis, consistent with previous studies showing that disease-associated variants typically affect gene expression levels of nearby genes. Furthermore, many eQTL identified here impact E-Gene clusters highly enriched for a common function, suggesting SNPs influencing the expression of multiple genes can help identify potential causal pathways linked to disease phenotypes within individual populations.

Figure 47C:
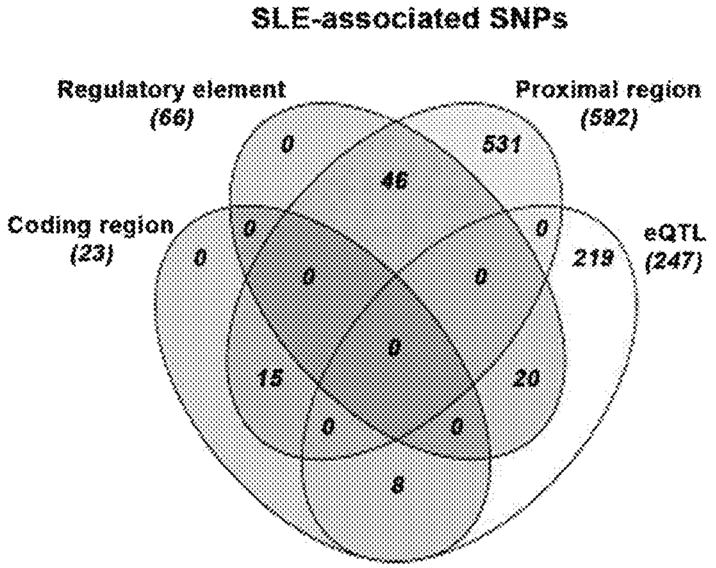
Figure 47D:
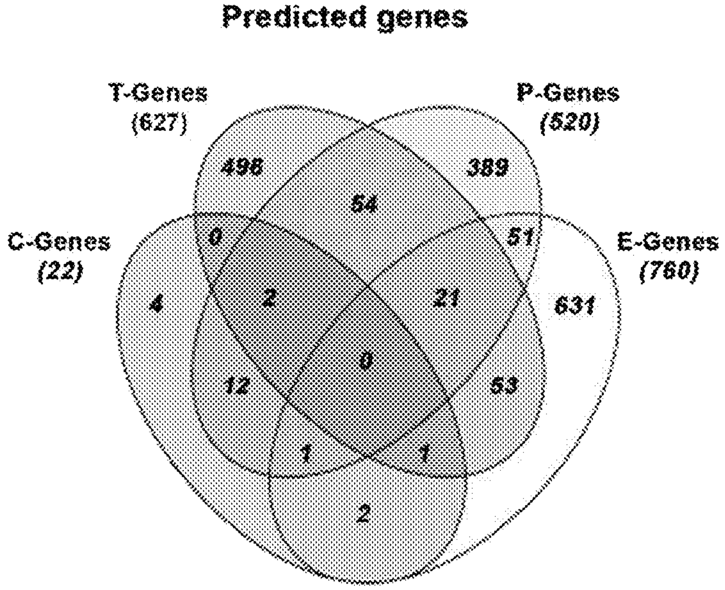

FIG. 47A-47D show results obtained by mapping the functional genes predicted by SLE-associated SNPs. FIG. 47A shows a distribution of genomic functional categories for ancestry-specific non-HLA associated SLE SNPs (Tiers 1-3). Non-coding regions include micro (mi) RNAs, long non-coding (Inc) RNAs, introns and intergenic regions. Regulatory regions include transcription factor binding sites (TFBS), promoters, enhancers, repressors, promoter flanking regions and open chromatin. Coding regions were broken down further and include 5'UTRs, 3'UTRs, synonymous and nonsynonymous (missense and nonsense) mutations. FIG. 47B shows that functional genes predicted by SNPs are derived from 4 sources including regulatory elements (T-Genes), eQTL analysis (E-Genes), coding regions (C-Genes) and proximal gene-SNP annotation (P-Genes). FIG. 47C shows a Venn diagram depicting the overlap of all SLE-associated SNPs. FIG. 47D shows a Venn diagram depicting the overlap of and all predicted E-, T-, P-, and C-Genes.

Since variants that alter or disrupt transcription factor binding may also dysregulate gene expression, SNPs were identified within distal and cis regulatory elements (e.g., enhancers and promoters). This analysis included the known regulatory regions identified above, as well as additional ones not previously related to SLE. HACER (Human ACtive Enhancers to interpret Regulatory variants; bioinfo.vanderbilt.edu/AE/HACER/) was used to analyze a catalog of active and in vivo transcribed enhancers that connects regulatory SNPs with target genes (T-Genes). Analysis with HACER identified 41 SNPs overlapping distal regulatory elements (enhancers) predicted to impact the expression of 501 downstream T-Genes. Similar to HACER, GeneHancer links variants in enhancers and promoters with target genes, revealing 25 SNPs linked to 163 T-Genes. These methods identified 472 EA, 9 AA and 143 shared T-Genes.

For variants located in coding regions, 23 SNPs (14 EA, 2 AA, 7 shared) were associated with either non-synonymous amino acid changes or premature termination, affecting 22 genes (C-Genes; 14 EA, 2 AA, and 6 shared). Functional damage scores were determined using SIFT, PolyPhen-2, and PROVEAN which predict the potential impact of amino acid substitutions on protein structure and function. Of the 23 non-synonymous SNPs, 11 were predicted to be deleterious, including the shared SLE risk variant rs2476601 (R620 W) identified to alter the protein tyrosine phosphatase PTPN22, and rs1804182, an identified AA SNP altering the plasminogen activator PLAT.

The remaining 592 SNPs that were not eQTL were assumed to regulate the closest proximal gene (P-Gene), revealing SNP associations with a further 520 P-Genes (465 EA, 34 AA and 21 shared). FIG. 47C depicts the overlap between SNPs based on source, and FIG. 47D shows the overlap between the corresponding predicted E-, T-, C- and P-Genes. No genes were shared among all four groups, and limited commonality was observed between T-, P- and E-Genes, with only 21 genes shared among the three groups. This included genes with known SLE associations (IL12RB1, PXK, BLK, CD44, IRF5, TNPO3, GSDMB, and ORMDL3) and those that have not previously been associated with SLE (ELL, GIMAP8, LRRC25, PLEK, PLTP, PPP26, SF3B1, and SIK2). Despite the overall diversity of genes observed in each list, significant overlap was observed in the number of genes shared between ancestries.

Characterization of gene signatures was performed as follows. Given the heterogeneity of genes identified by eQTL analysis, regulatory element and coding region mapping, as well as traditional annotation based on SNP-gene proximity, a more detailed analysis was performed of the potential functional genomic signatures defining the E-Gene, T-Gene, P-Gene, and C-Gene sets based on ancestry. Gene function was first examined by Biologically Informed Gene Clustering (BIG-C), a functional aggregation tool developed to understand the biological groupings of large gene lists, followed by Ingenuity Pathway Analysis (IPA). Additional analysis of gene function was determined via gene ontology (GO) annotation using the Database for Annotation, Visualization and Integrated Discovery (DAVID). Heatmap visualization of BIG-C category enrichment, IPA canonical pathways and GO terms for each set of genes is shown in FIGS. 48A-48E.

Figure 48A:
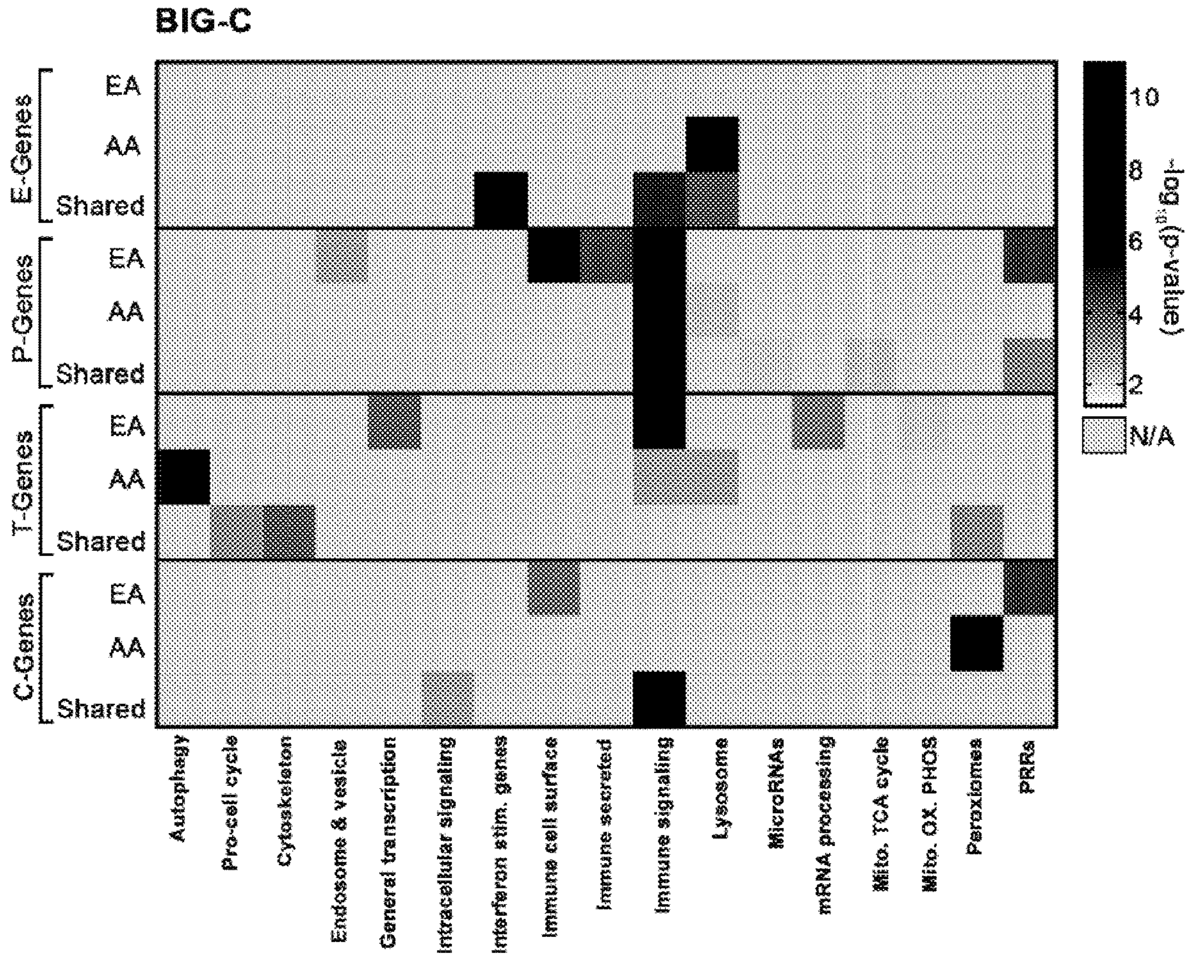
FIGS. 48A-48E show the characterization of predicted gene signatures.

FIGS. 48A-48E show the characterization of predicted gene signatures. FIG. 48A shows that ancestry-dependent and independent E-, P-, T-, and C-Genes were analyzed to determine enrichment using functional definitions from the BIG-C (Biologically Informed Gene Clustering) annotation library. Enrichment was defined as any category with an odds ratio (OR) >1 and −log 10(p-value) >1.33. FIGS. 48B-48E shows heatmap visualizations of the top five significant IPA canonical pathways for each gene list (E-, P-, T-Genes) organized by ancestry. C-Genes were analyzed together. Top pathways with −log 10(p-value) >1.33 are listed.

Figure 48B:
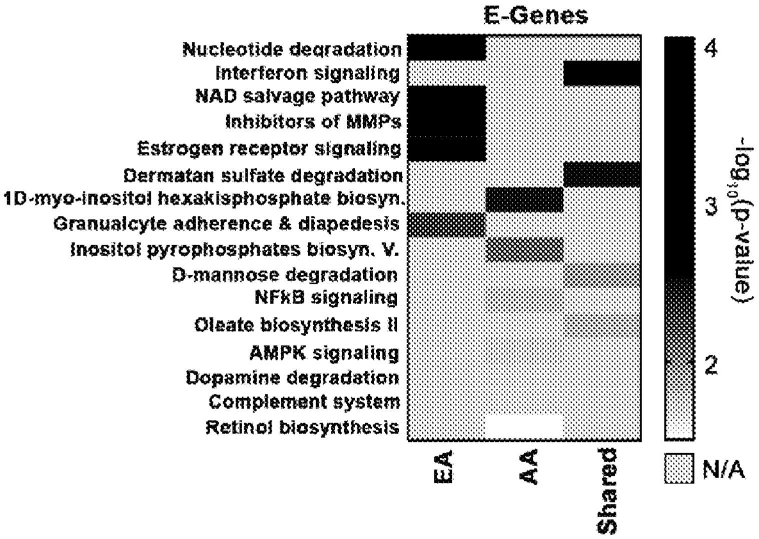
Figure 48C:
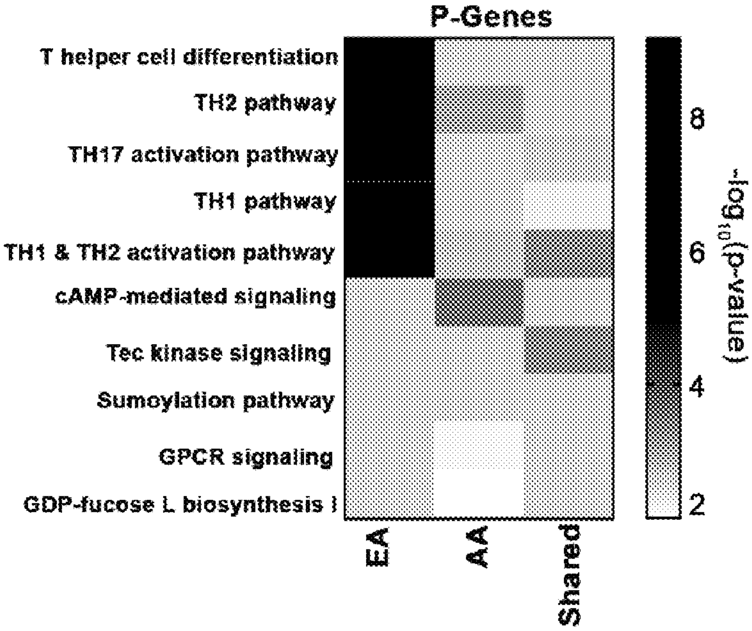
Figure 48D:
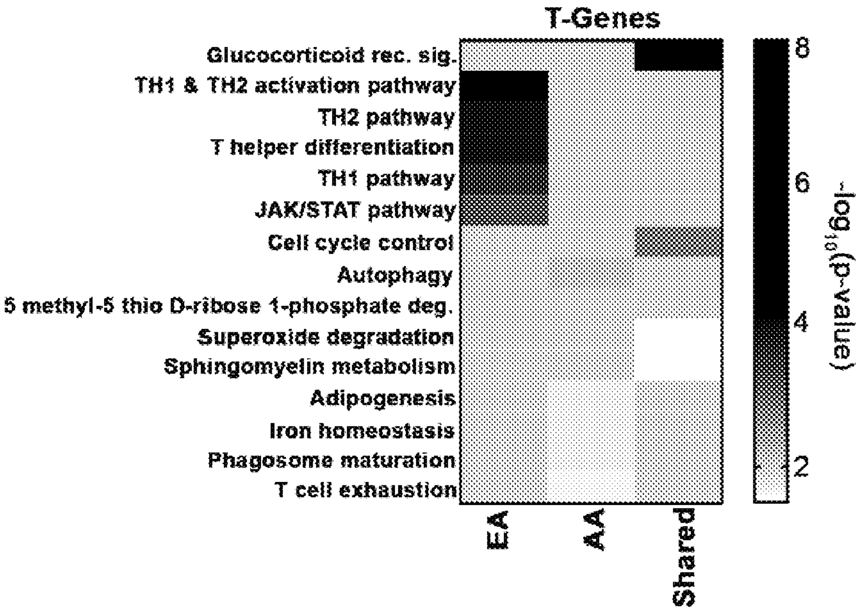
Figure 48E:
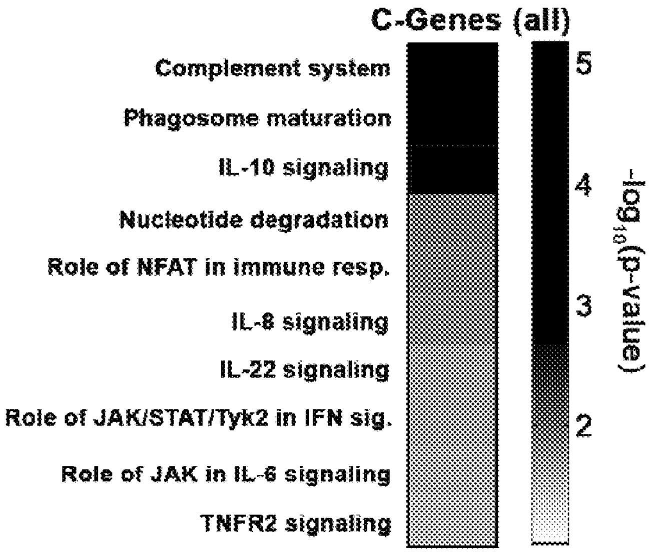

Remarkably, functional categorization remained largely consistent within each ancestry despite the derivation of genes from multiple sources. For example, analysis of all EA-associated genes revealed enrichment in processes related to leukocyte and lymphocyte migration and activation. This includes the canonical pathways for agranulocyte adherence and diapedesis and inhibitors of matrix metalloproteinases, as well as the GO term adenylate cyclase activity involved in GPCR signaling pathway (GO: 0010578) for E-Genes (FIG. 48B). EA P-Gene pathways included TH1/TH2 activation and multiple GO terms related to response to cytokine (GO: 0034097) (FIG. 48C). Similarly, T-Genes were enriched in JAK/STAT signaling, TH1/TH2 activation pathways and response to cytokine (GO: 0034097) (FIG. 48D). All C-Genes were analyzed together because of the limited number of genes available for analysis, and revealed enrichment in numerous pathways associated with cytokine signaling and immune response activation (FIG. 48E). Receptor-ligand interactions and T cell activation were also reflected in EA BIG-C categories, including immune cell surface, immune secreted, immune signaling, and pattern recognition receptors (PRRs) (FIG. 48A).

For AA-associated genes, E-, P-, and T-Genes were enriched in biological processes related to degradation, including the BIG-C category lysosome, and IPA pathways for autophagy and phagosome maturation (FIG. 48A and FIG. 48D) with additional E-Gene enrichment in peptide cross-linking (GO: 0018149) and keratinocyte differentiation (GO: 0030216). Similar to EA genes, T cell function was also observed in AA, with enrichment in T cell co-stimulation (GO: 00331295) and TH1/TH2 activation pathways for E- and P-Genes respectively (FIGS. 48B-48C).

Shared genes were distributed in a diverse range of gene categories. For example, shared E- and T-Genes were enriched in GO terms for keratinization (GO: 0031424), peptide cross-linking (GO: 0018149) and epidermis development (GO: 0008544) similar to AA genes (Supplemental FIG. 2*a, c*). Phagosome maturation is a pathway common to both AA T-Genes and C-Genes represented by the shared gene ITGAM (FIG. 48C-48D). Shared genes were also involved in processes related to leukocyte cell-cell adhesion (GO: 0007159), cellular activation (GO: 0001775) and the BIG-C category immune signaling, similar to EA genes (FIG. 48A). Furthermore, the T helper signature prevalent in both EA and AA gene sets was also observed in shared genes (FIG. 48C). Finally, shared genes contained a strong core interferon-stimulated gene signature consistent with the role of interferons in the pathogenesis of SLE (FIG. 48A-48B).

Protein interaction-based clustering of predicted genes was performed as follows. The relationship between genes was assessed systematically based on their source regardless of ancestral origin. Protein-protein interaction (PPI) networks consisting of E-, P-, T-, and C-Genes were constructed using STRING (version 10.5), visualized in Cytoscape (version 3.6.1), and clustering for E-, P-, and T-Genes was carried out using the MCODE app plugin to provide an additional level of functional annotation. The resulting networks were further simplified into metastructures defined by the number of genes in each cluster, the number of significant intra-cluster connections predicted by MCODE, and the strength of associations connecting members of different clusters to each other. This dual approach allowed a comparison of the overall topology of different gene clusters while also noting specific interactions between EA, AA, and shared genes.

FIGS. 49A-49D show that cluster metastructures were generated based on PPI networks, clustered using MCODE and visualized in CytoScape. Size indicates the number of genes per cluster, edge weight indicates the number of inter-cluster connections and color indicates the number of intra-cluster connections. FIG. 49E shows the quantitation of cluster size, intra- and intercluster connections. Error bars represent the 95% confidence interval; asterisks (*) indicate a p-value <0.05 using Welch's t-test.

Figure 49A:
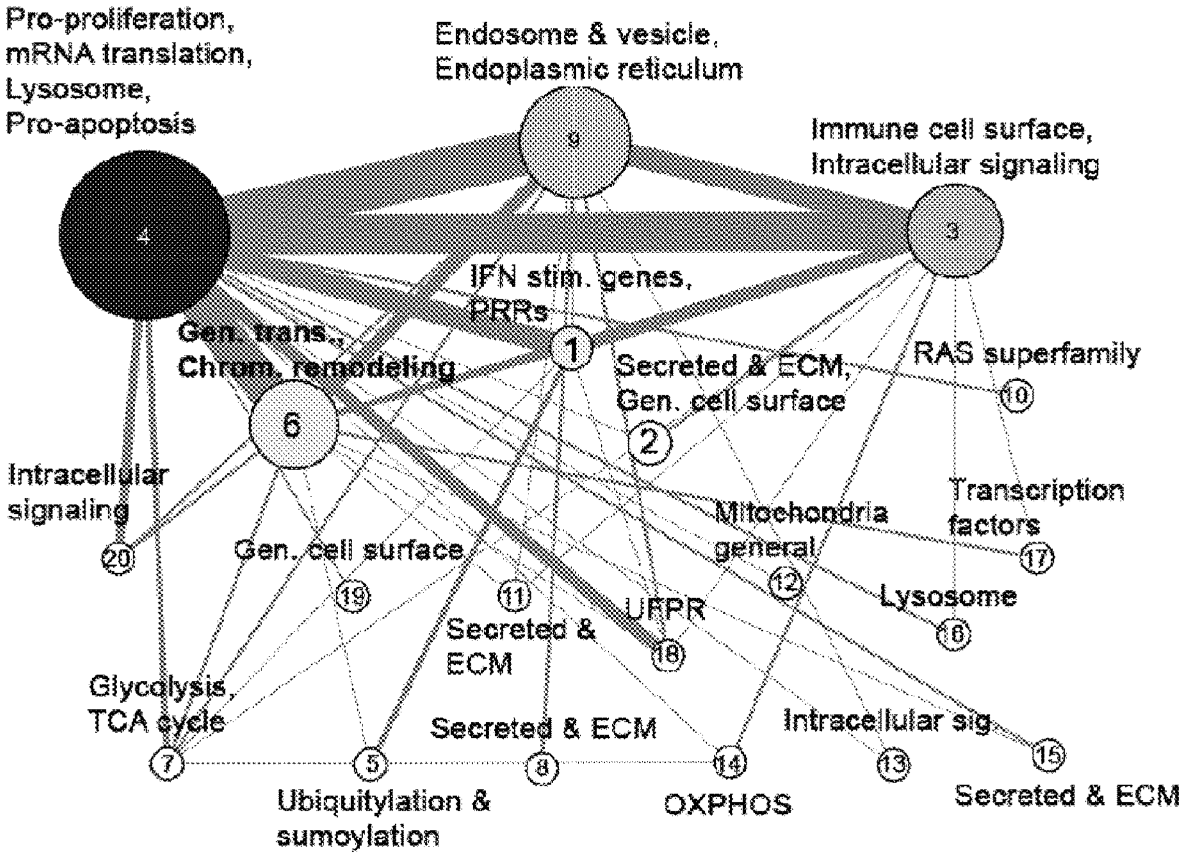
FIGS. 49A-49D show that cluster metastructures were generated based on PPI networks, clustered using MCODE and visualized in CytoScape. Size indicates the number of genes per cluster, edge weight indicates the number of inter-cluster connections and color indicates the number of intra-cluster connections.

E-Gene clusters were dominated by shared E-Genes, with ancestry-specific EA and AA E-Genes distributed throughout the network (FIG. 49A). The largest cluster of E-Genes (cluster 4) was enriched in molecules associated with proliferation, apoptosis, translation and lysosomal degradation. This cluster also contained a number of transcription factors and was highly connected to the immune function enriched cluster 3, as well as clusters 6 and 9 associated with gene regulation and endoplasmic reticulum function, respectively. The robust interferon response evident in the shared E-Gene signature was located in cluster 1, whereas cluster 2 was composed primarily of AA and shared genes involved in keratinocyte function. E-Genes related to metabolic and transcriptional function were also found in clusters 7, 12, 14 and 17. Analysis of cluster topology revealed that SLE associated E-Genes are dominated by aberrantly regulated cell cycle control, transcriptional processes and immune function (FIG. 49A).

Figure 49B:
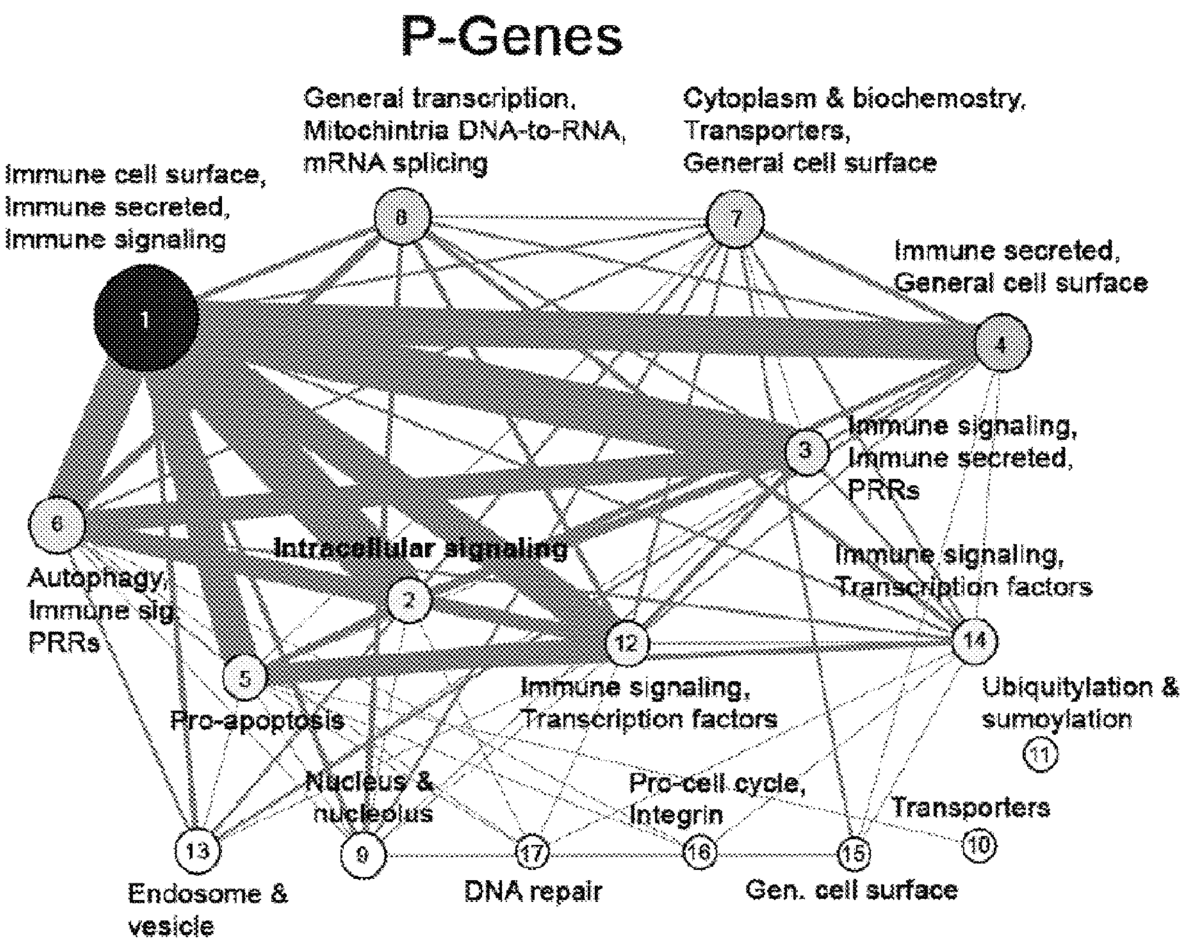
Figure 49C:
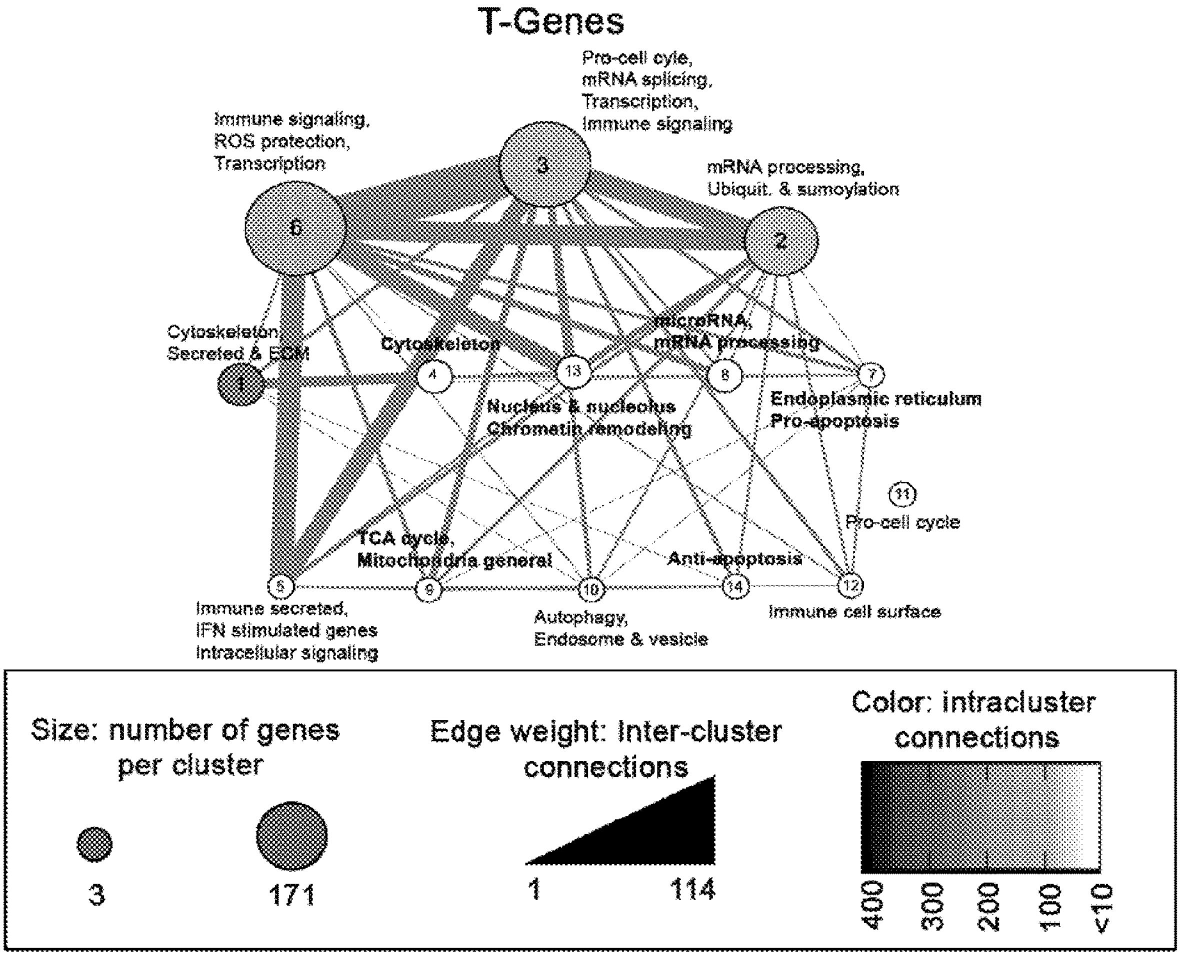

Examination of networks constructed of all P-Genes, reveals the predominance of immune function with 7 out of 10 of the largest, intraconnected clusters enriched in immune activity (FIG. 49B). For T-Genes, the largest clusters 6 and 3 were enriched in immune signaling with additional enrichment in transcriptional processes. T-Gene networks were also dominated by BIG-C categories related to mRNA splicing (cluster 3) and RNA processing (clusters 2 and 8). Clusters 1 and 4 were composed almost entirely of shared T-Genes linked to glucocorticoid signaling, including 31 keratin genes derived from rs726848 (FIG. 49C). Although MCODE clustering was not performed on C-Genes because of the small number of genes, more than half of identified C-Genes organized into a STRING network enriched in PRRs, immune signaling and immune cell surface molecules.

Figure 49D:
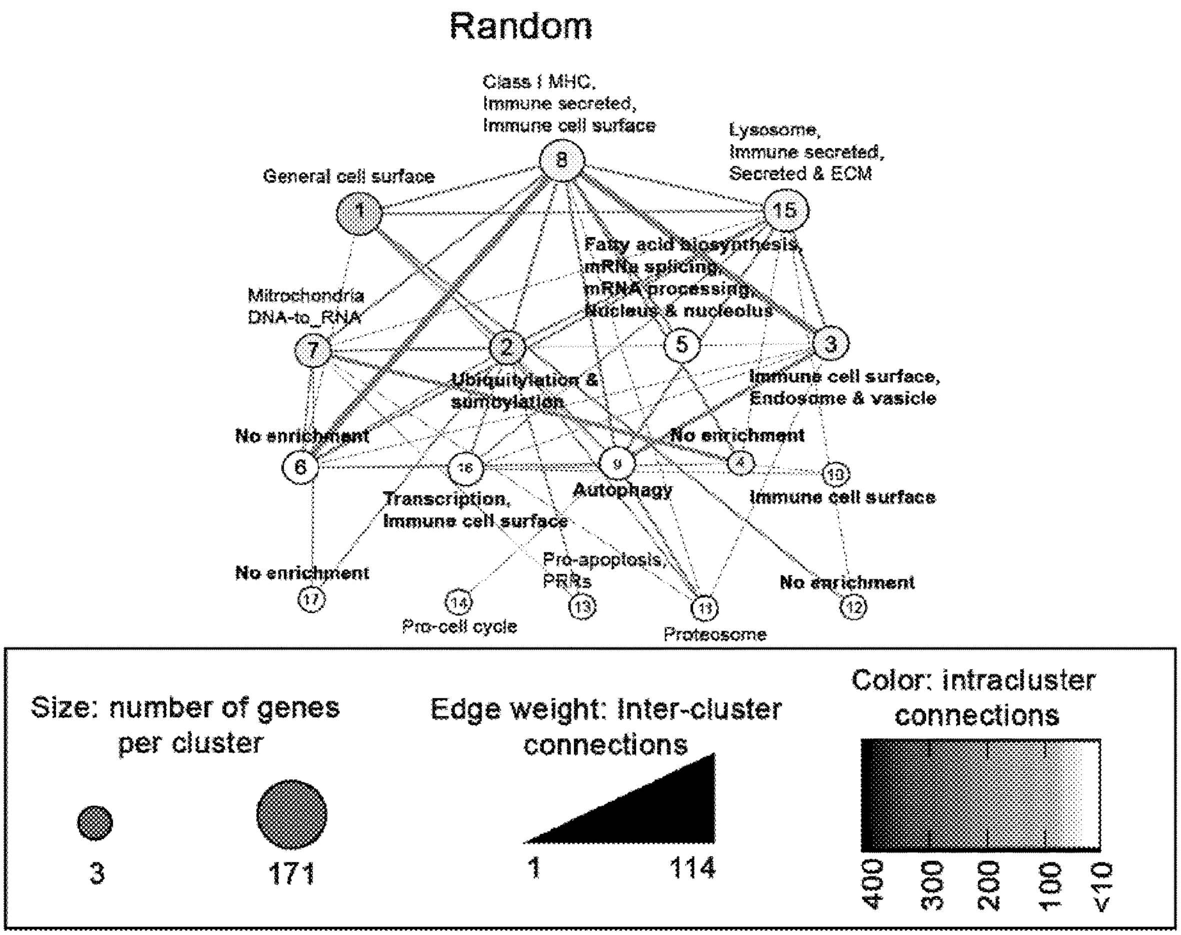
Figure 49E:
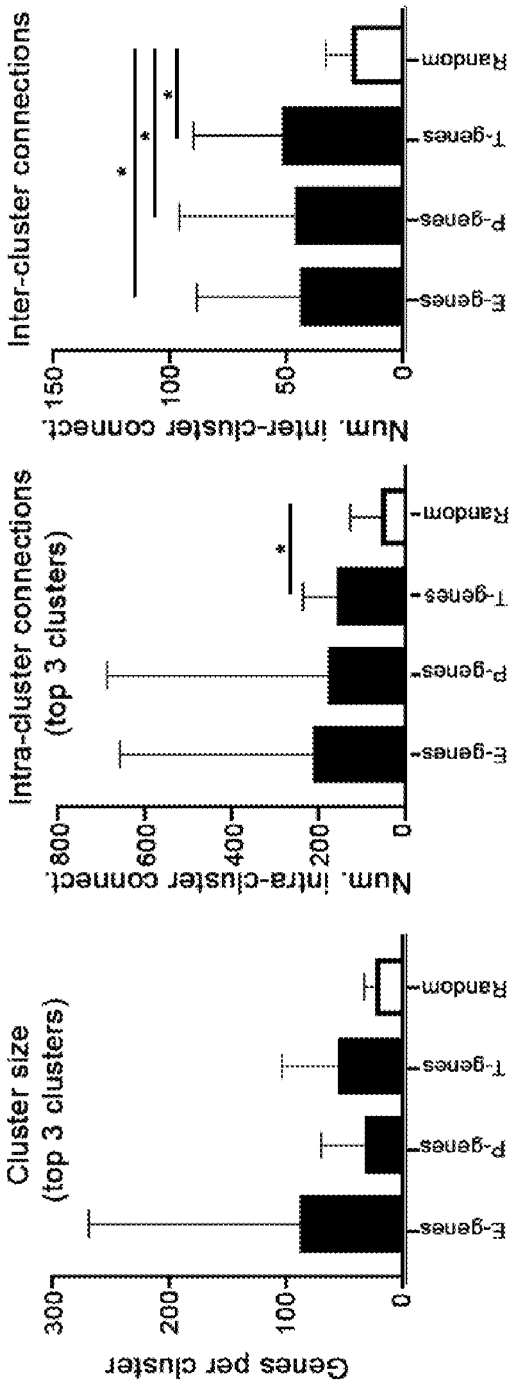
FIG. 49E shows the quantitation of cluster size, intra- and intercluster connections. Error bars represent the 95% confidence interval; asterisks (*) indicate a p-value <0.05 using Welch's t-test.

To determine whether the predicted genes (E-, T-, or P-Genes) described above represent key genes within relevant SLE biological pathways, a parallel analysis was performed examining PPI networks composed of genes derived from randomly selected Immunochip SNPs. Random SNPs analyzed by eQTL mapping identified a total of 538 random E-Genes, which were used to generate a STRING network and clustered via MCODE (FIG. 49D). Examination of metastructures revealed that random gene clusters exhibited significantly fewer intra-cluster connections and fewer inter-cluster connections, appearing as independent entities lacking robust functional relationships with neighboring clusters (FIG. 49E). Although Immunochip SNPs may be heavily biased toward immunologically relevant genes, the largest, most intraconnected random gene cluster (1) was enriched entirely in general cell surface molecules. Furthermore, composite analysis of all randomly generated E-Genes via BIG-C revealed enrichment in a single category for pro-apoptosis.

Figure 50A:
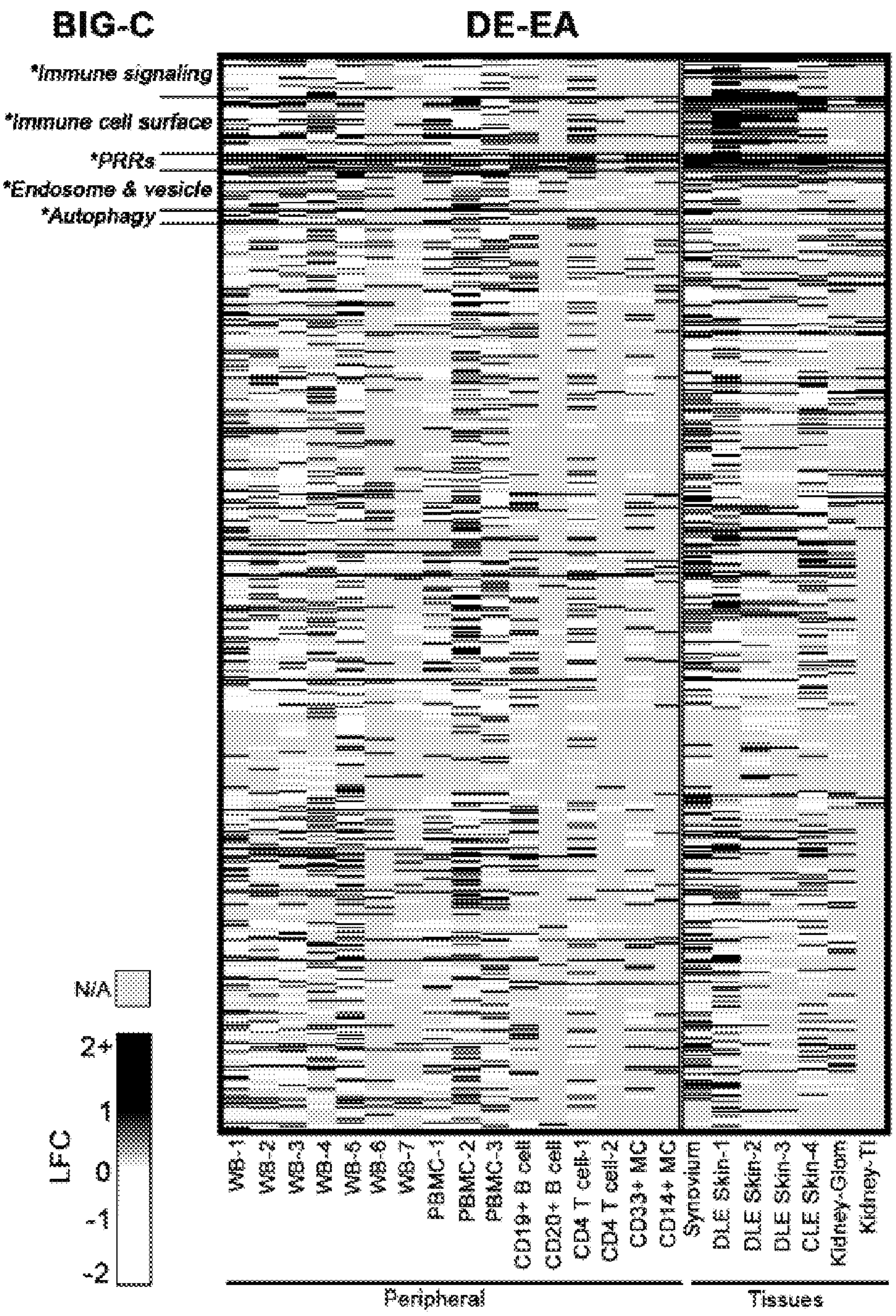
FIG. 50A-50C shows that ancestry-specific E-, P-, T-, and C-Genes were matched to differential expression (DE) SLE datasets in various tissues, including whole blood, PBMCs, B-cells, T-cells, synovium, skin and kidney.
Figure 50B:
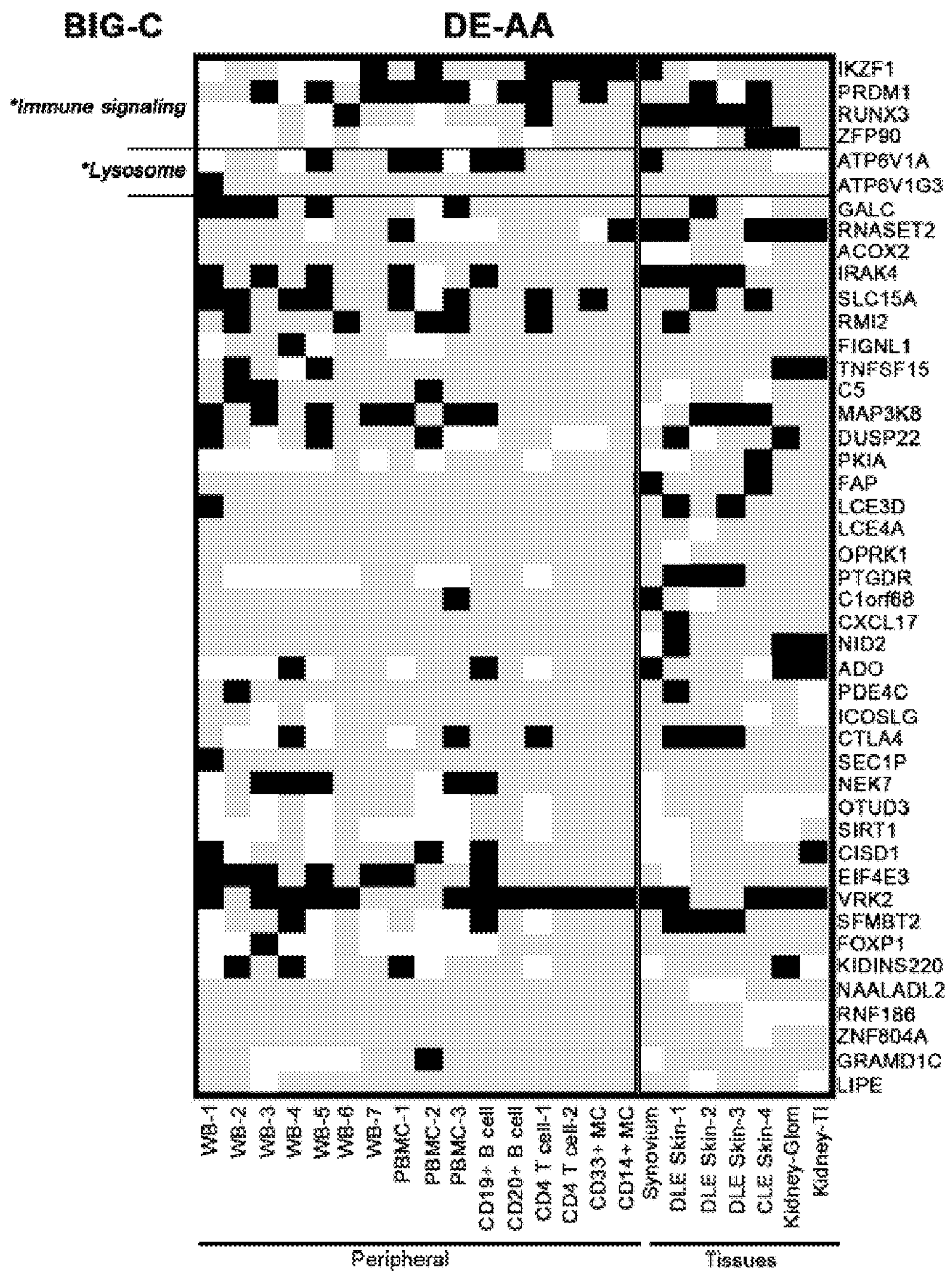
Figure 50C:
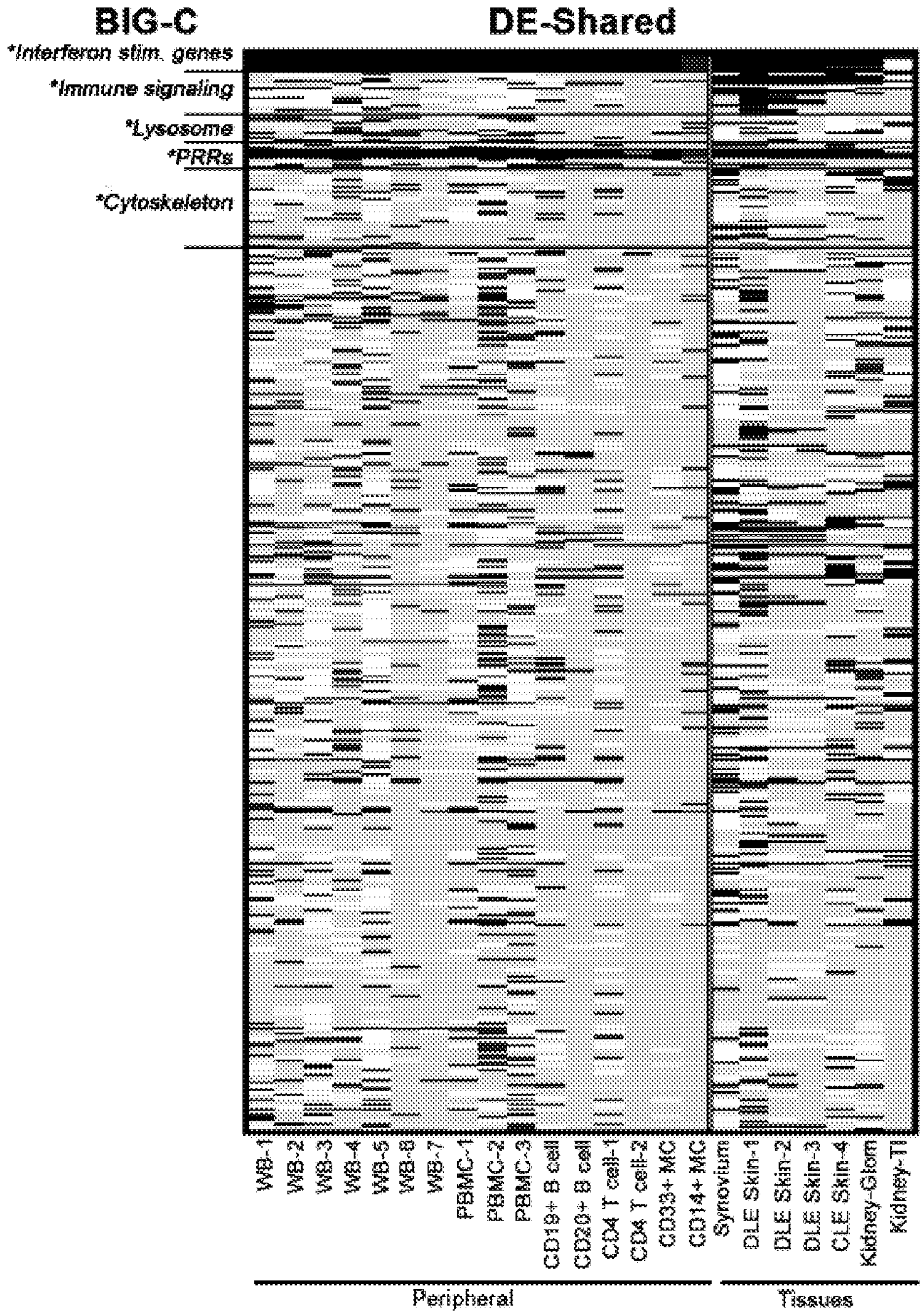

Predicted genes were observed to be linked to altered expression in SLE and were enriched in differential expression datasets as follows. Next, it was determined whether genes linked to specific populations exhibited altered expression in SLE. Ancestry-specific E-, P-, T-, and C-Genes were matched to differential expression (DE) SLE datasets in various tissues, including whole blood, PBMCs, B-cells, T-cells, synovium, skin and kidney (FIG. 50A-50C). Heatmaps depicting the log fold change for each gene were organized based on enriched BIG-C category. 743 differentially expressed EA genes were observed across all datasets enriched for immune signaling, immune cell surface, PRRs, endosome and vesicle and autophagy (FIG. 50A). For AA, 49 genes were differentially expressed exhibiting enrichment in categories related to immune signaling and lysosome. VRK2 and HSPA6 were upregulated in most blood and skin datasets, whereas both IKZF1 and RUNX3 were highly upregulated specifically in skin and synovium datasets (FIG. 50B). Of the genes shared between ancestries, 441 genes were DE, with the interferon stimulated genes (HERC5, IFI35, IFI44L, IFI6, IFIT1, MX1 and SPATSL2L), interferon regulatory factors (IRF4, IRF5 and IRF7) and PRRs (OAS1, OAS2, OAS3, SLC15A4) differentially expressed across all datasets (FIG. 50C). Further, several gene categories were observed that were consistently upregulated in tissue datasets compared to peripheral blood datasets, including genes associated with immune signaling and immune cell surface (FIG. 50C). Overall, the majority of DE predicted genes (regardless of ancestry) were observed in the tissues, including synovium, skin and kidney (FIGS. 50A-50C), with fewer DE genes observed in macrophages, T cell and B cell datasets.

Figure 51A:
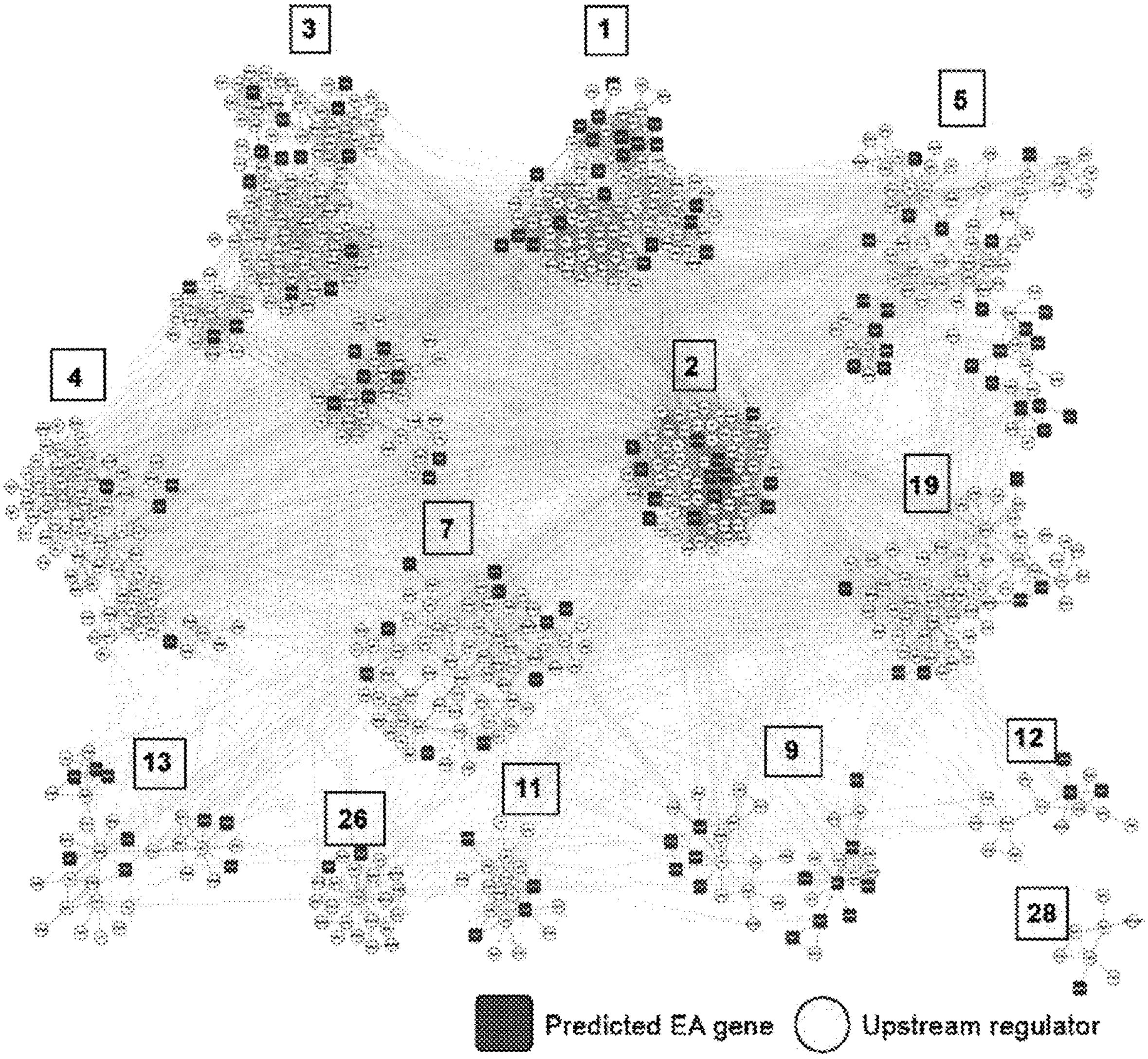

Identification of key signaling pathways was performed as follows. Ancestry-specific key signaling pathways were identified based on differentially expressed genes. To do this, IPA was employed to analyze DE EA, AA and shared gene sets to determine potential biologic upstream regulators (UPRs). Importantly, several of the resulting regulators identified by IPA were also predicted genes, and are known to play major roles in the development of SLE, including IFNG, STAT4, CD40, CTLA4, IRF5 and IRF7. Next, DE predicted genes and UPRs were used as input to build STRING-based PPI networks, visualized in CytoScape, and clustered with MCODE. Individual clusters were then analyzed by BIG-C and IPA to identify those molecules and pathways highly associated with disease. A total of 45 pathways were representative of EA DE genes and UPRs, with the largest clusters 3 and 1 heavily involved in pattern recognition receptor signaling (activation of IRFs by cytosolic PRRs and role of RIG-I in antiviral immunity) (FIG. 51A-51B). Clusters 4 and 5 revealed enrichment in lymphocyte activation and differentiation (TH differentiation pathway, TH1 and TH2 activation pathway, TH1 activation pathway), pathways that were also common to both the AA and shared gene networks. Twenty pathways were unique to EA including several involved in cellular communication (cross talk between dendritic cells and NK cells, leukotriene biosynthesis), cytokine signaling (IL6 signaling and IL17 signaling) and migration (agranulocyte adhesion and diapedesis, leukocyte extravasation, inhibition of MMPs).

Figure 52A:
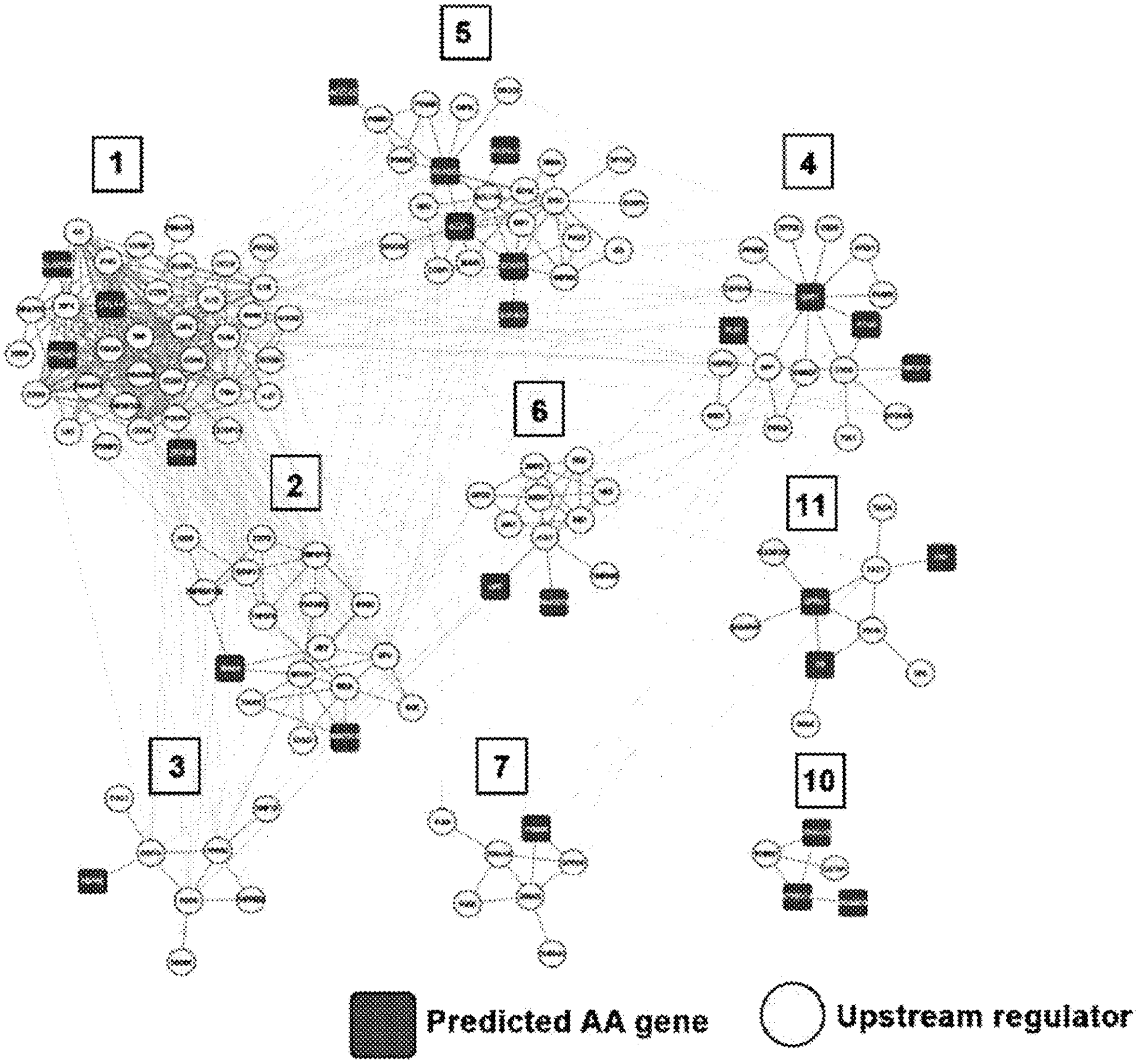

The AA network was smaller (FIG. 52A), containing fewer predicted genes and associated UPRs, yet shared multiple pathways with EA, including B cell receptor signaling, GPCR signaling, opioid signaling, phagocyte maturation and hepatic cholestasis, a pathway involved in bile acid synthesis (FIG. 52B). However, pathways unique to AA were distinct, overwhelmingly represented by processes related to degradation and cellular stress, found in clusters 5, 3 and 11 (sumoylation, ubiquitylation, neuroprotective role of THOP1 in Alzheimer's disease, unfolded protein response, ER stress pathway and the osteoarthritis (OA) pathway) as well as metabolic processes in cluster 6 (gluconeogenesis I, pentose phosphate pathway, acetyl CoA biosynthesis, glycerol-3 phosphate shuttle and insulin receptor signaling).

Figure 53A:
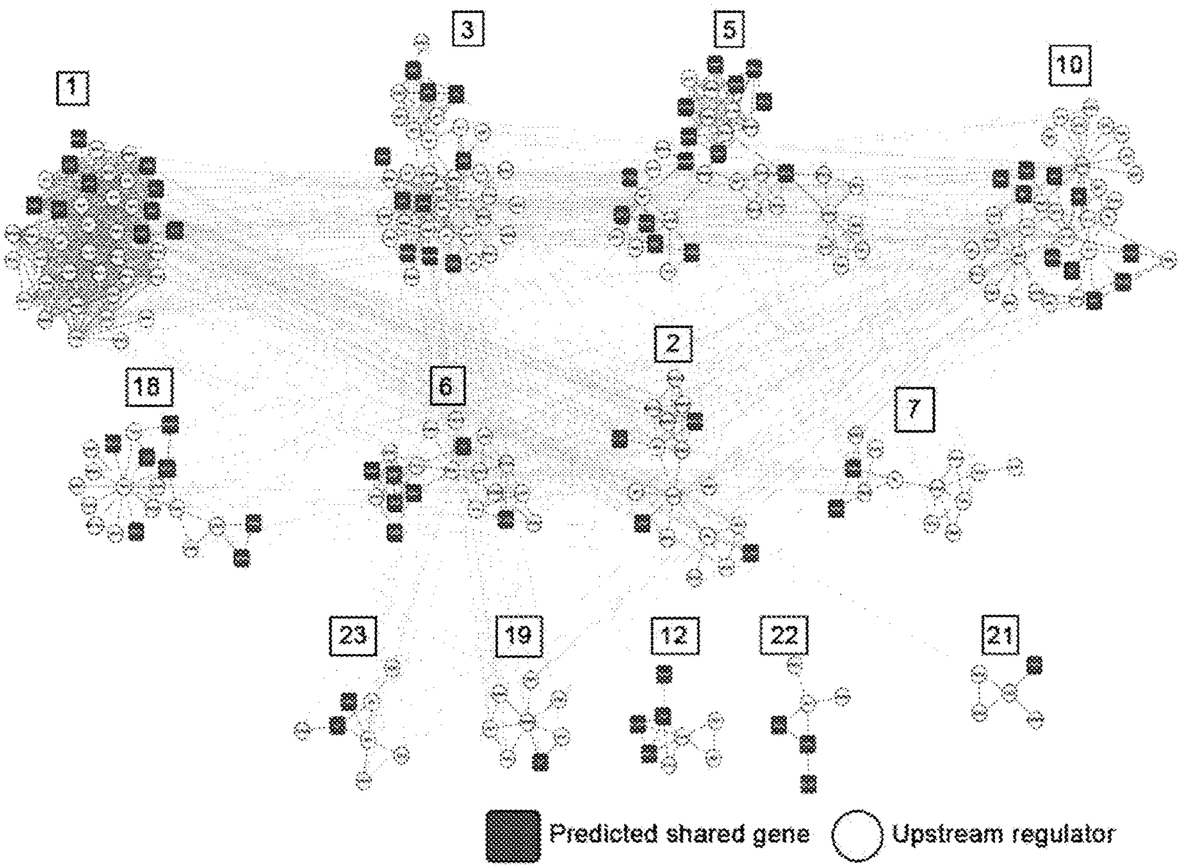
Figure 54A:
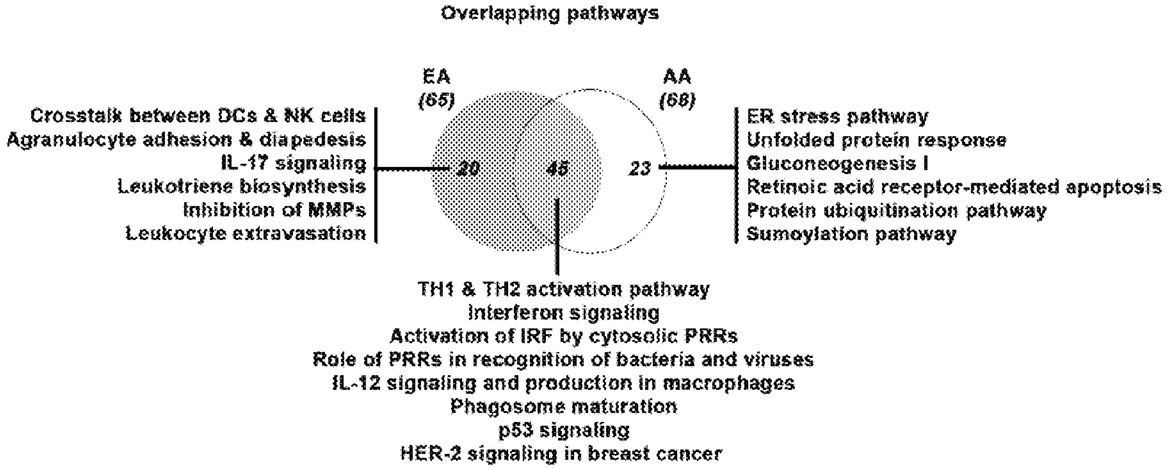
FIGS. 54A-54F depict both the unique and overlapping canonical pathways predicted by the EA and AA gene sets. Examination of pathway categories shared between EA and AA ancestral groups are those commonly associated with SLE representing aberrant immune function, altered transcriptional regulation, and abnormal cell cycle control, providing additional confirmation for the global gene expression analysis presented here (FIG. 54B).
Figure 54B:
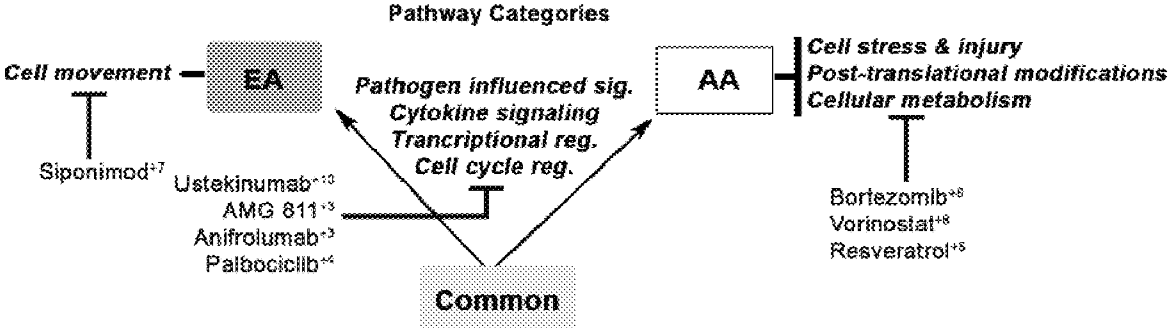

Pathways exemplified by ancestry-independent genes were a blend of both EA and AA pathways. For example, common pathways included IL12 signaling and production by macrophages, TLR signaling and activation of IRFs by cytosolic PRRs, pathways that were predicted by EA genes and UPRs, as well as PRRs in the recognition of bacteria and virus (FIGS. 53A-53B), a pathway shared with AA. FIGS. 54A-54F depicts both the unique and overlapping canonical pathways predicted by the EA and AA gene sets. Examination of pathway categories shared between EA and AA ancestral groups are those commonly associated with SLE representing aberrant immune function, altered transcriptional regulation, and abnormal cell cycle control, providing additional confirmation for the global gene expression analysis presented here (FIG. 54B). Strikingly however, several unique pathway categories were identified that are ancestry-specific, including cell movement for EA, and cell stress and injury, post-translational modification and cellular metabolism for AA.

Figure 54C:
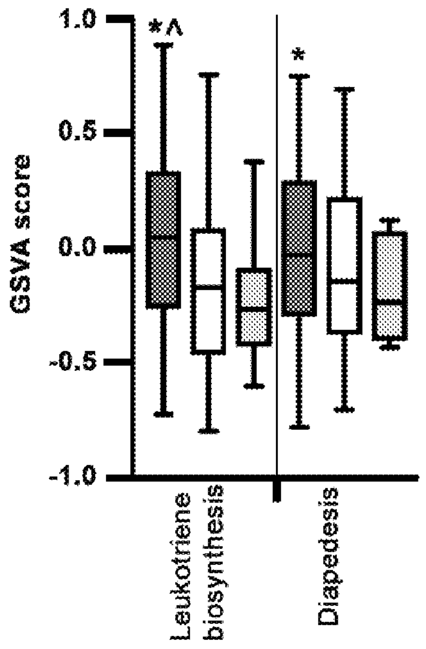
Figure 54D:
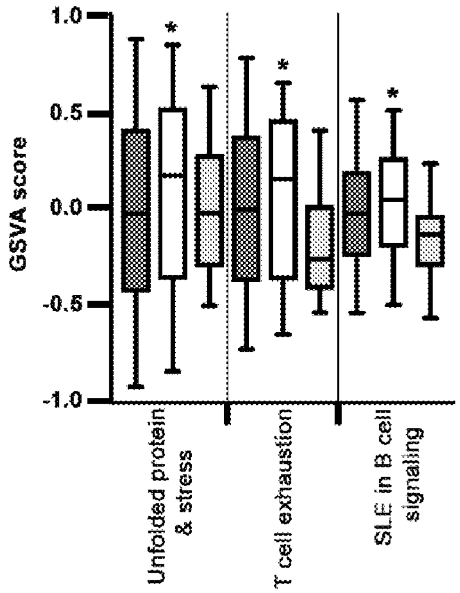

To validate these pathway predictions, gene set variation analysis (GSVA) was applied to identify differentially enriched gene signatures in SLE patients (EA and AA) and control whole blood (WB). EA and AA predicted genes were used to create a collection of signatures informed by protein-protein interaction networks and IPA canonical pathways, or were previously defined. GSVA enrichment scores using signatures for leukotriene biosynthesis and diapedesis were able to specifically separate EA SLE patients, but not AA patients, from healthy controls (FIG. 54C). Also, it was observed that the leukotriene biosynthesis signature distinguished EA patients from AA patients. In contrast, gene signatures related to cell stress pathways were significantly enriched in AA SLE compared to EA SLE patients for the unfolded protein response (UPR), and AA SLE versus healthy control the for the T cell exhaustion signature (FIG. 54D). AA SLE patients were additionally enriched in the IPA-derived signature for SLE signaling in B cells.

Figure 54E:
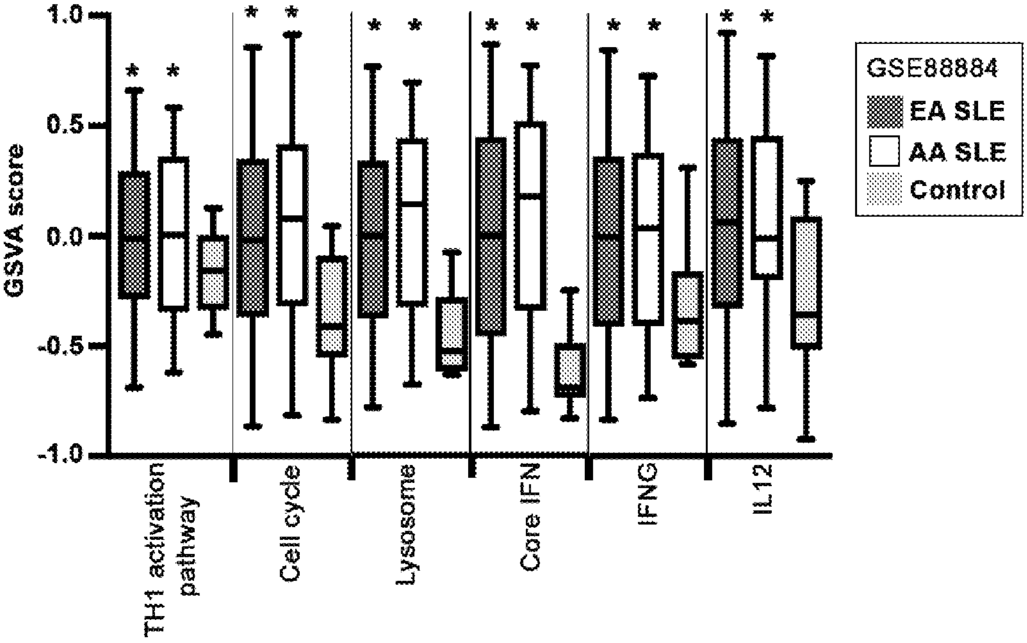
Figure 54F:
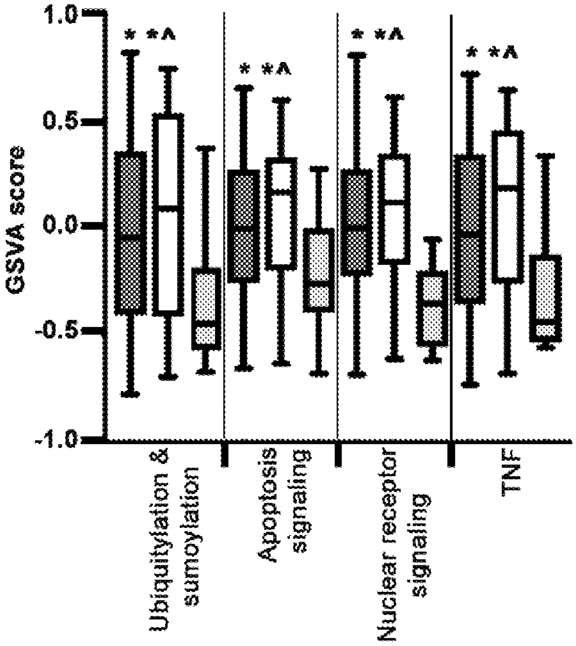

A number of signatures were able to discriminate between SLE patients and controls independent of ancestry, including signatures for TH1 activation pathway, cell cycle and lysosome (FIG. 54E). Cytokine-based signatures for core IFN, IFNG, IL12, and the IFN subtypes IFNA2, IFNB1 and IFNW gene signatures also separated EA and AA SLE patients from controls. Finally, signatures for ubiquitylation and sumoylation, apoptosis signaling, nuclear receptor signaling and TNF were sufficiently discriminatory to separate SLE individuals from controls, and furthermore exhibited significant enrichment in AA patients compared to EA patients (FIG. 54F). Gene signatures for metabolic pathways, including mitochondrial oxidative phosphorylation and glycolysis were also investigated but did not demonstrate any significant change between SLE and control or between ancestries.

Pathway analysis facilitated drug prediction as follows. Pathway identification facilitated drug prediction analysis using a number of available databases, including the Library of Integrated Network Cellular Signatures (LINCS), the Search Tool for Interacting Chemicals (STITCH; version 5.0; stitch.embl.de), as well as IPA, allowing us to identify potential drug candidates for repositioning in SLE. Canonical pathways related to T cell function are shared among ancestries, as are many predicted drugs targeting T cell activity including abatacept, theralizumab and AMG-811 (FIG. 53B). Broader analysis of common pathway categories also indicates the utility of targeting T cell signaling, as well as cytokine pathways such as IL12/23 signaling with ustekinumab and/or interferon signaling with anifrolimab (FIG. 54B). Drugs specific for EA pathways include BMS-986165, a high priority small molecular inhibitor of TYK2 (FIG. 51B), whereas therapeutic candidates targeting AA pathways include the FDA-approved proteasome inhibitor bortezomib, as well as PF-06650833, an IRAK4 specific inhibitor (FIG. 52B). Unique pathway categories identified for EA and AA suggest additional ancestry-specific interventions, such as the small molecule inhibitor of sphingosine-1-phosphate receptor 1 (S1PR1) siponimod for EA (prevents leukocyte egress), and the HDAC inhibitor vorinostat for AA, both of which have shown efficacy in autoimmune clinical trials (FIG. 54B).

SLE may be a chronic autoimmune disease with a strong genetic component. Familial aggregation studies together with GWAS may underscore the contribution of genetics to disease development. Candidate gene studies and GWAS may be performed to identify approximately 90 SLE susceptibility loci. Genetic heterogeneity between ancestral populations may also be important in SLE risk; it may be shown that patients of African descent have a higher prevalence of lupus and experience the disease more severely than those of European ancestry. Despite an improved understanding of how inherited genetic variation impacts disease risk, genetic analyses to date may fail to provide a clear path toward novel therapeutic development. This is of particular concern with respect to AA populations, where the control of disease activity remains suboptimal.

It is important to note that for the vast majority of confirmed SLE risk loci, the causal variant(s) may not have been identified. Potential target genes may be determined based on the strength of associated genetic signal and are therefore taken with inferred functional relevance. Here, a novel strategy was performed using statistical and computational analyses along with data acquired from functional genomic assays and differential gene expression studies to map the global gene expression landscape of SLE and further define the disease-associated pathways responsible for the inherent disparities influencing SLE progression.

Expression quantitative trait loci (eQTL) mapping represents a powerful, bioinformatics-driven methodology to examine the association between specific genetic variations and gene expression levels in tissues. Furthermore, eQTL impacting many genes may be particularly valuable for network modeling and disease analysis. As noted previously, eQTLs influencing the expression of several genes, support the notion that risk haplotypes may harbor multiple functional effects. Here, eQTL analysis identified 207 E-Genes specific for EA, 30 E-Genes for AA, and 523 that were shared across ancestries. While some eQTL mapped to a single causal gene, for example rs4580644 linked to CD38 and rs6131014 linked to CD40, the majority of eQTL SNPs mapped to multiple E-Genes, many of which can be found in the same functional network. This complexity is exemplified by rs4917014, a shared (EA/AA) trans-acting eQTL. Located 5' of the Ikaros family zinc finger transcription factor IKZF1, the rs4917014*T SLE risk allele is associated with the increased expression of 5 IFN-E response genes (HERC5, IFI6, IFIT1, MX1 and TNFRSF21) comprising the strong core interferon signature prevalent in the shared E-Gene set.

It may also be shown that disease-susceptibility variants frequently lie in distal regulatory enhancer elements. Indeed, nearly 20% (157) of SNPs analyzed here were located in regulatory regions, including transcription factor biding sites (TFBS), promoters, enhancers, silencers, promoter flanking regions and open chromatin. Using computational gene prediction algorithms that incorporate chromatin interaction data, regulatory SNPs were identified that changed transcription factor binding and were linked to 627 downstream targets (T-Genes). Although some regulatory SNPs also exhibit eQTL effects, we nonetheless uncovered 496 unique T-Genes enriched in a diverse array of functional categories. One major pathway identified was glucocorticoid receptor signaling, a key regulator of epidermal homeostasis, driven by rs726848 at the 17q21.2 locus. This SNP affects multiple intermediate filament keratin T-Genes, as well as the retinoic acid receptor A (RARA), potentially reflecting that fact that skin and joint involvements are among the most common clinical manifestations of SLE. This is further supported by altered expression of E-Genes within and around the late cornified envelope (LCE) locus at 1q21.3 controlling keratinocyte differentiation in both ancestries, including LCE1D, LCE1E, LCE3C, Clorf68, SPRR2G, SPRR2B, SPRR2D, SPRRIB, as well as LCE4A and LCE3D in AA E-Gene sets. Both 17q21 and 1q21-23 may be identified as chromosome regions harboring "hot spots" predisposing to SLE.

Among the loci that lead to changes in gene expression, 23 variants were identified as resulting in non-synonymous amino acid changes affecting 22 genes (C-Genes). Although C-Genes compromise a small proportion of predicted genes overall, several C-Genes, such as the R620 W PTPN22 polymorphism affecting B cell tolerance, may have been linked to SLE and other autoimmune disorders, whereas others may be novel. In the latter case, rs11539148 leads to an amino change (N2851/S) in the glutaminyl-tRNA synthetase QARS, a member of the aminoacyl-tRNA synthetase (ARS) family that plays a major role in cellular homeostasis. B cells typically exhibit high tRNA synthetase expression and increased ARS expression may be linked to a potential role for the ARS in antigen presentation. Not surprisingly, both natural and synthetic tRNA synthetase inhibitors are immunosuppressive, a property that may be exploited in the development of aminoacyl-sulfamide IBI derivatives targeting the proliferative skin disease psoriasis.

Also, traditional locus annotation was employed, mapping the identified risk SNP to the nearest, most proximal gene, resulting in 520 P-Genes (shared among EA and AA). Since computational approaches described herein are predictive, by attempting to provide a more comprehensive translation of GWAS findings, those genes and pathways that are causative and those that represent biological "noise" may be determined. To determine this, PPI networks and clustering based on interaction strength helped exclude those genes lacking strong connections to molecules within or between similarly functioning clusters. Compared to E-, T-, or P-Genes where large, highly connected clusters were observed, randomly generated genes generally formed smaller clusters, exhibited fewer intra- and inter-cluster connections and ultimately appeared as independent entities. Secondly, predicted genes were compared to SLE datasets (SLE vs. control) to determine those genes that were differentially expressed in active disease. To go beyond cataloging disease related molecules, DE genes were used as input into IPA to generate upstream and downstream regulators, which could then be combined for additional network and clustering analysis. This allowed identification of biologically relevant pathways unique to each ancestry, a strategy that revealed essential differences between EA and AA SLE, as well as many pathways that were shared.

Here, pathway-based analysis of predicted genes and their upstream regulators helps clarify the complex polygenic risk associated with SLE. Key dysregulated EA pathways centered around cell movement and cell-cell communication were observed, processes that can be related to many aspects of the disease. This can include, but is not limited to, the migration of leukocytes to sites of inflammation or damage, such as UV exposed skin, and is reflected in pathways for leukocyte extravasation and agranulocyte adhesion and diapedesis, as well as pathways for cell signaling and communication, including leukotriene biosynthesis, IL12 signaling in macrophages, IL17 signaling and cross-talk between DCs and NK cells. Remarkably, gene signatures for leukotriene biosynthesis and diapedesis were sufficiently discriminatory to separate EA SLE patients from controls, providing additional evidence for these pathways in SLE pathogenesis.

In contrast, pathways specific for AA were uniquely enriched in those associated with aberrant degradation, including sumoylation and ubiquitylation, ER stress pathway, unfolded protein response, along with osteoarthritis pathway (cell stress) and the neuroprotective role of THOP1 in Alzheimer's disease, a pathway involved in the presentation of antigen generated by the proteasome. Furthermore, GSVA enrichment scores for cell stress pathways demonstrated unique enrichment in AA SLE patients. The ubiquitin-proteasome system may play a critical role in multiple cellular functions including MHC-mediated antigen processing and presentation, and maintains homeostasis by controlling the breakdown of key proteins involved in cell cycle regulation, transcription and apoptosis. It is therefore not surprising that deregulated ubiquitylation and proteosomal processes may be observed in SLE and several additional inflammatory disorders such as type 1 diabetes, RA and psoriasis. The likely role played by these processes is also reflected in the differential enrichment of these pathways in AA SLE patients compared to both health controls and EA patients.

Given the non-linear, relapse-remitting nature of SLE, the pathways highlighted here for EA and AA may not necessarily define temporal phases of disease progression, nor are they cell-type specific. Rather, the results demonstrate that disparities in SLE may be a consequence of different types of pathways dominating within one ancestral background over another. Other pathways were ancestry independent, as is the case for the interferon signatures prevalent in the shared gene dataset and supported by the GSVA enrichment described here. By focusing on pathways instead of individual genes, this approach identifies "actionable" points of therapeutic intervention with the potential to uniquely impact EA and AA SLE patients. Thus, EA patients may derive particular benefit from treatments that prevent leukocyte or lymphocyte infiltration into tissues. This analysis highlights drugs that modulate, for example, sphingosine-1 phosphate receptor (SIPR), a pleiotropic lipid mediator involved in the regulation of a broad spectrum of cellular functions, including proliferation and survival, cytoskeletal rearrangements, cell motility, and cytoprotective effects. Siponimod, currently FDA approved for the treatment of multiple sclerosis, promotes internalization of SIPR expressed on lymphocytes preventing cell migration to sites of inflammation. Preclinical studies using a first-generation derivative, KRP-203 (fingolimod), may reveal high efficacy in preventing renal damage in lupus-prone mice, due in part, to attenuated T cell infiltration. Given its high Combined Lupus Treatment Score (CoLTS) of +7, siponimod represents a high-priority small molecule drug with potential for repurposing in SLE.

Given the dominance of proteasome and degradation in AA pathways, therapeutic intervention may include proteasome inhibitors like bortezomib (BZ). Interestingly, small-scale safety trials testing the efficacy of BZ may indicate that proteasome inhibition is clinically effective in treating refractory SLE. For example, a (male) AA patient with nephritis (WHO IV) may exhibit a reduction in SLEDAI from 10 to 2 after a single dose of BZ, indicating the possibility that BZ and/or more selective immunoproteasome may hold promise for patients who respond poorly to conventional therapies.

The study demonstrates that multilevel analysis is capable of defining gene regulatory pathways which not only reflect differences in EA and AA populations, but also represent candidate pathways that may be the target of ancestry-specific therapies. Indeed, the ancestral SNP-associated predicted genes and gene expression profiles outlined here illustrate fundamental differences in lupus molecular pathways between ancestries. The results indicate that unique sets of drugs may be particularly effective at treating lupus within each ancestral group.

Identification of SLE-associated SNPs and predicted genes was performed as follows. An SLE Immunochip study identified single nucleotide polymorphisms (SNPs) significantly associated with SLE in AA (2,970 cases; 2,452 controls) and EA (6,748 cases; 11,516 controls) cohorts. SNP proxies (raggr.usc.edu) in linkage disequilibrium (LD) (r2>0.5) with these SLE-associated SNPs were then determined, using the Central European Utah (CEU) population as background for EA SNPs and the Yoruban (YRI) population for AA SNPs. Expression quantitative trait loci (eQTLs) were then identified using GTEx version 6 (GTEXportal.org) and the Blood eQTL browser database (Westra et al) and mapped to their associated eQTL expression genes (E-Genes). In parallel, random E-Gene datasets were generated from randomly selected SLE Immunochip SNPs (Langefeld et al 2017). SNP proxies were then queried by GTEx to generate eQTLs and matched to ENSEMBL gene IDs. To find SNPs in enhancers and promoters, and their associated downstream target genes (T-Genes), the atlas of Human Active Enhancers was queried to interpret Regulatory variants (HACER, bioinfo.vanderbilt.edu/AE/HACER) and the GeneHancer database. To find structural SNPs in protein-coding genes (C-Genes), the human Ensembl genome browser (GRCh38.p12; www.ensembl.org) and dbSNP (www.ncbi.nlm.nih.gov/snp) were queried. Several additional databases were used to generate loss-of-function prediction scores, including SIFT4G (sift-dna.org/sift4g), PolyPhen-2 (genetics.bwh.harvard.edu) and PROVEAN (provean.jevi.org). All other SNPs were linked to the most proximal gene (P-Gene) or gene region. All predicted genes were divided into an AA, EA, or shared group depending on the ancestral designation of the original SLE-associated SNP.

Genomic functional categories were analyzed as follows. The Variant Effect Predictor tool available on the Ensembl genome browser 93 (www.ensembl.org) was used for annotation information to specify SNPs located within exons, untranslated regions (UTRs), introns, intergenic regions, promoters, enhancers, repressors, promoter flanking regions, open chromatin, micro RNAs, long non-coding RNAs and transcription factor binding sites (TFBS). The online resource tool HaploReg (version 4.1; pubs.broadinstitute.org/mammals/haploreg/haploreg.php) were also used to identify DNA features, regulatory elements and assess regulatory potential.

Differential expression analysis of E-Genes was performed as follows. Predicted genes were compared to multiple differential expression datasets. These datasets include the log fold changes of all genes with significant (FDR<0.2) differential expression in whole blood (WB), peripheral blood mononuclear cells (PBMC), B cells, T cells, myeloid cells, synovium, skin, kidney glomerulus (G), and kidney tubulointerstitium (TI). The FDR was selected a priori to avoid excluding false negatives from the analysis. Cohorts are SLE vs. control (CTL) unless noted otherwise. Additional cohorts include SLE synovium vs. oseteoarthritis (OA) synovium, discoid lupus erythematosus (DLE) skin vs. control skin and subacute cutaneous lupus erythematosus (CLE) skin vs. CTL skin. Datasets include GSE88884 (Illuminate 1 and 2), GSE49454, GSE22908, GSE61635, GSE29536, GSE39088, GSE50772, FDABMC3, EMTAB2713, GSE10325, GSE4588, GSE38351, GSE36700, GSE52471, GSE72535, GSE81071 and GSE32591.

Functional gene set analysis and identification of upstream regulators (UPRs) were performed as follows. For both ancestral groups, predicted gene lists were examined using Biologically Informed Gene Clustering (BIG-C; version 4.4). BIG-C is a custom functional clustering tool developed to annotate the biological meaning of large lists of genes. Genes are sorted into 54 categories based on their most likely biological function and/or cellular localization based on information from multiple online tools and databases including UniProtKB/Swiss-Prot, gene ontology (GO) Terms, MGI database, KEGG pathways, NCBI, PubMed, and the Interactome, and has been previously described (Labonte, Catalina). Enrichment of GO Biological Processes (BP) using the Database for Annotation, Visualization and Integrated Discovery (DAVID) and the Ingenuity Pathway Analysis (IPA; www.qiagenbioinformatics.com) platform provided additional genetic pathway identification. IPA upstream regulator (UPR) analysis was also used to identify potential transcription factors, cytokines, chemokines, etc. that can contribute to the observed gene expression pattern in the input dataset.

Network analysis and visualization were performed as follows. Visualization of protein-protein interaction and relationships between genes within datasets was performed using Cytoscape (version 3.6.1) software. Briefly, STRING (version 1.3.2) generated networks were imported into Cytoscape (version 3.6.1) and partitioned with MCODE via the clusterMaker2 (version 1.2.1) plugin.

Gene set variation analysis (GSVA) was performed as follows. The GSVA (V1.25.0) software package for R/Bioconductor was used. Briefly, GSVA is a non-parametric, unsupervised method for estimating the variation of pre-defined gene sets in patient and control samples of microarray expression datasets. The input for the GSVA algorithm was a gene expression matrix of log 2 microarray of expression values and a collection of pre-defined gene signatures. Enrichment scores (GSVA scores) were calculated non-parametrically using a Kolmogorov-Smirnoff (KS)-like random walk statistic and a negative value for each gene set. EA and AA predicted genes were used to create GSVA gene signatures. In the case of leukotriene biosynthesis, cell cycle, ubiquitylation and sumoylation, apoptosis signaling and nuclear receptor signaling, genes were initially identified following protein-protein interaction network construction and MCODE clustering. Cluster identity was determined by BIG-C and/or IPA canonical pathway analysis where each cluster was used as a GSVA probe. Gene signatures for diapedesis, TH1 activation pathway, unfolded protein and stress, T cell exhaustion and SLE in B cell signaling were all informed by established IPA canonical pathways. The signature for lysosome was derived from the Lysosome BIG-C category. All interferon and cytokine signatures (core IFN, IFNB1, IFNA2, IFNW, IFNG, IL12 and TNF) have been described previously (catalina). Metabolic signatures for oxidative phosphorylation and glycolysis were based on literature mining and established IPA canonical pathways. Enrichment of each signature was examined in EA and AA SLE patients and healthy control whole blood from GSE 88884. Differences between controls and SLE patient GSVA enrichment scores were determined using the Welch's t-test for unequal variances in PRISM 8.0.

Drug candidate identification and CoLTS scoring were performed as follows. Drug candidates were identified using CLUE, STITCH (version 5.0; stitch.embl.de) and IPA. Each of these tools includes either a programmatic method of matching existing therapeutics to their targets or else is a list of drugs and targets for achieving the same end. In addition to identifying drugs targeting predicted genes directly, these tools were also used to identify drugs targeting select upstream regulators. Where information was available, drugs were assessed by CoLTS to rank potential drug candidates for repositioning in SLE.

Example 16: Analysis of SNPs Associated with SLE Provides Insights into Molecular Pathways Operative in Ancestral Groups Abstract Individuals of African-Ancestry (AA) may experience systemic lupus erythematosus (SLE) more frequently, more severely and with an increased co-morbidity burden compared to European-Ancestry (EA) populations, although the mechanisms underlying elevated risk remain unclear. Here, a comprehensive systems biology approach was applied to all SNP associations detected with the Immunochip using novel bioinformatics and pathway analysis tools, and thereby 1907 ancestry-specific and trans-ancestry genetic drivers of SLE were identified. Dysregulated EA pathways centered around innate immune and myeloid cell function, whereas AA pathways suggested disease progression is driven by aberrant B cell activity accompanied by ER stress and unfolded protein response signaling. Pathway validation was provided by gene set variation analysis (GSVA), which identified differentially enriched gene signatures in SLE patients and informed ancestry-specific pharmacological targets.

Introduction

Systemic lupus erythematosus (SLE) (OMIM: 152700) may be a multi-organ autoimmune disorder associated with significant morbidity and mortality. SLE may be strongly influenced by genetic factors and recent candidate gene, Immunochip and genome wide association studies (GWAS) have identified more than 100 SLE susceptibility loci (Langefeld et al. 2017; Sun et al. 2016; Rullo and Tsao 2013; Bentham et al. 2015; Morris et al. 2016). SLE exhibits substantial clinical heterogeneity that is both unpredictable and varies in prevalence by ancestry. Specifically, individuals of African-Ancestry (AA) tend to experience the disease more severely and with an increased co-morbidity burden compared to European-Ancestry (EA) populations (Williams et al. 2016; Barnado et al. 2018; Goulielmos et al. 2018). For example, lupus nephritis and end stage renal disease (LN/ESRD) are severe complications of SLE more prevalent among AA patients. The association between LN/ESRD and APOL1 variants found in nearly 13% of the AA population within the US highlights the importance of genetic factors in ancestry-related clinical heterogeneity (Freedman et al. 2014).

Understanding the functional mechanisms of causal genetic variants underlying SLE may provide essential information to identify molecular pathways dominant in one ancestry versus another, and may help inform therapeutic targets relevant to disease mechanisms. The first step in this process is the identification of causal genes from multiple genetic candidates associated with a lead or "tagging" SNP. This analysis is complicated by the finding that the majority of SLE-associated SNPs are located outside of protein coding regions and their functional significance is unknown (Bentham et al. 2015; Langefeld et al. 2017). Nonetheless, a number of approaches can be employed to elucidate the implications of association studies. These include utilization of expression quantitative trait loci (eQTL) mapping (Schadt et al. 2003; Emilsson et al. 2008; Stranger et al. 2012) and the identification of variants impacting transcription factor binding site (TFBS) occupancy. Physical proximity of an associated polymorphism to neighboring genes is also used, but the underlying mechanism may not be clear (Cannon and Mohlke 2018).

Our hypothesis was that the use of multiple distinct approaches could provide novel insights into the totality of variation in molecular pathways identified through genetic association studies, the possible differences in pathologic mechanisms among ancestral groups, and identify novel therapeutic targets. We identified 1907 potential SLE-associated genes in one or more ancestral groups (1176 EA, 70 AA and 661 shared between ancestries). We applied a comprehensive systems biology approach to identify the predicted SLE-associated biological pathways. These implicated pathways were corroborated using connectivity mapping to differentially expressed genes (DEGs) in SLE, and the resulting set of pathways mined for candidate drug targets. Together, these genetic and gene expression analyses suggest fundamental differences in SLE risk related molecular pathways, some explicitly associated with ancestral differences. Further, these molecular pathways identified by ancestry-specific and trans-ancestry associations suggest novel drug candidates that might differentially impact EA and AA SLE patients.

Results

Figure 55:
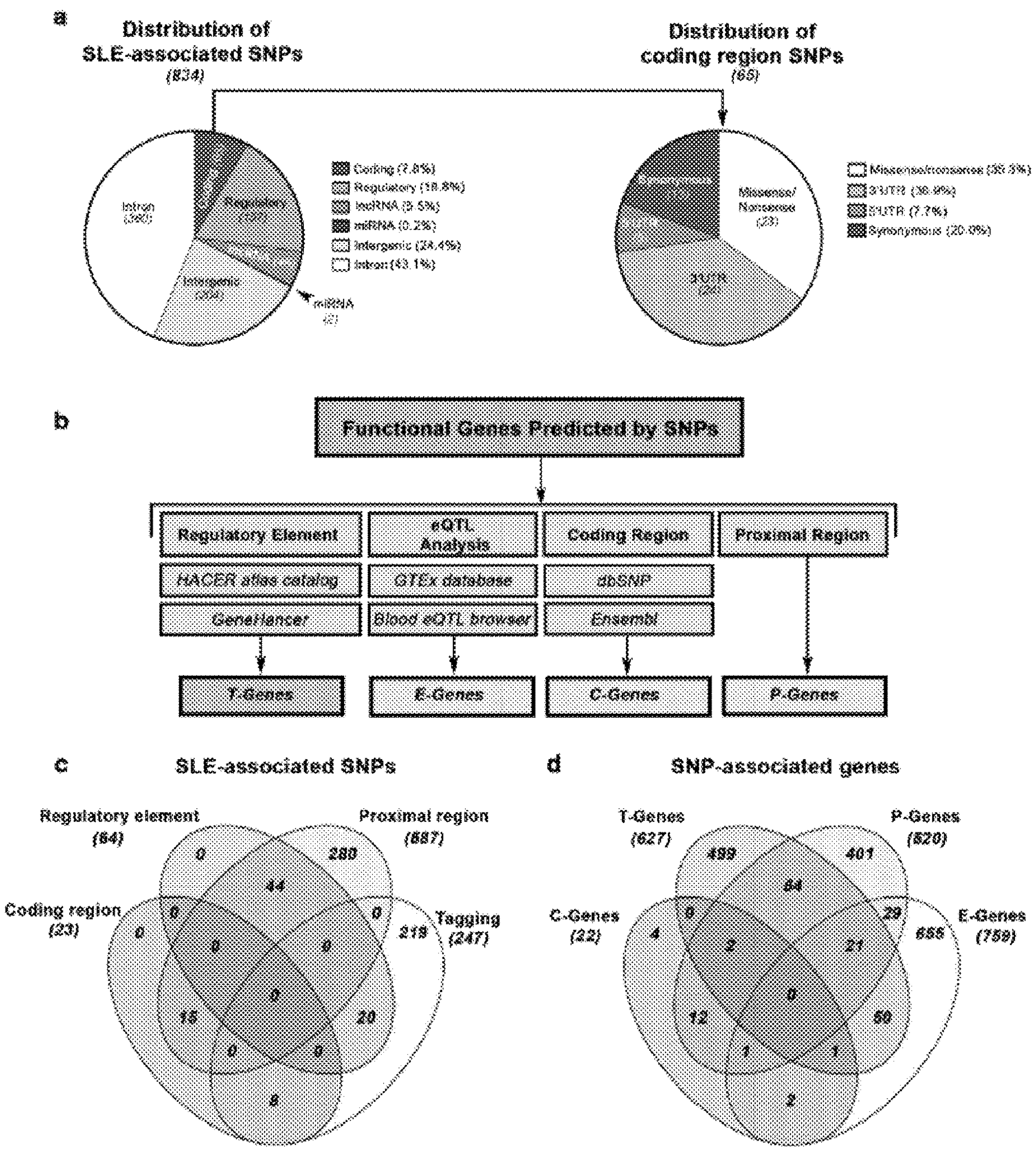
FIGS. 55A-55D show mapping the functional genes predicted by SLE-associated SNPs. (a) Distribution of genomic functional categories for all ancestry-specific non-HLA associated SLE SNPs. (b) Functional SNP-associated genes are derived from 4 sources including regulatory elements (T-Genes), eQTL analysis (E-Genes), coding regions (C-Genes) and proximal gene-SNP annotation (P-Genes). Venn diagram depicting the overlap of all SLE-associated SNPs (c) and all predicted E-, T-, P- and C-Genes (d).

Identification of ancestry-dependent and independent SLE-associated variants and downstream target genes was performed as follows. We examined the distribution (e.g., coding, non-coding) of 834 non-HLA single nucleotide polymorphisms (SNP) reported as significantly associated with SLE in a large transancestral genetic association study (Langefeld et al. 2017) (FIG. 55A). The majority of SNPs were found in intronic (43.1%) or intergenic (24.4%) regions. Approximately 26% of SLE-associated SNPs mapped to coding (7.8% exons, 5' UTRs, 3'UTRs) or known regulatory regions (18.8%; TFBS, promoters, enhancers, etc.). Despite the role of non-coding RNAs in the regulation of gene expression (Stavast and Erkeland 2019; Zhang et al. 2019), only 5.7% of SNPs mapped to regions containing long non-coding (Inc) RNAs or micro (mi) RNAs.

We used multiple bioinformatic-based approaches to identify the most plausible gene(s) affected by the SLE-SNP association (FIG. 1*b*). We first determined whether there was evidence that the SNP was a quantitative trait locus (eQTL) using the GTEx and Blood eQTL browser databases ("The Genotype-Tissue Expression (GTEx) Project" n.d.; Westra et al. 2013). The reported test of SNP-by-ancestry (i.e., heterogeneity) from the meta-analysis and ancestry-specific effect size allowed determination of whether the SNP was primarily associated in only one ancestry (e.g., AA-specific) or was a trans-ancestry association (i.e., comparable effect size across AA and EA) (Langefeld et al. 2017) (Supplementary Data 2). This study identified 78 EA and 21 AA-specific eQTLs linked to 207 and 29 expression genes (E-Genes) unique for EA and AA respectively. A total of 148 eQTL were common to both ancestries and were linked to 523 shared E-Genes (Supplementary Data 3). Interestingly, we observed that E-Genes predicted by a single SNP tended to be enriched for a common molecular function (FIG. 63).

Since variants that alter or disrupt transcription factor binding are also known to dysregulate gene expression, we next sought to identify SNPs within distal and cis regulatory elements (e.g. enhancers and promoters). To examine putative enhancer and promoter regions, we utilized GeneHancer and HACER (Human ACtive Enhancers to interpret Regulatory variants; bioinfo.vanderbilt.edu/AE/HACER/), both of which connect regulatory SNPs with transcription factors and downstream target genes (T-Genes) (Fishilevich et al. 2017; Wang et al. 2019). Together, GeneHancer and HACER identified 64 SNPs overlapping distal regulatory elements or promoters predicted to impact the expression of 627 T-Genes (475 EA, 9 AA and 143 shared) and 95 transcription factors (Supplementary Data 3 and 5). For variants located in coding regions, 23 SNPs (14 EA, 2 AA, 7 shared) were associated with either non-synonymous or nonsense changes, affecting 22 genes (C-Genes; 14 EA, 2 AA and 6 shared). Functional protein damage scores were determined using SIFT, PolyPhen-2, PROVEAN and PANTHER which predict the potential impact of amino acid substitutions on protein structure and function (Supplementary Data 6). Of the 23 non-synonymous/nonsense SNPs, 12 were predicted to be deleterious. The remaining 587 SNPs that did not identify E-, T- or C-Genes were assigned to the closest proximal gene (P-Gene). Traditional annotation identified an additional 520 P-Genes (465 EA, 34 AA and 21 shared) (Supplementary Data 3).

FIG. 55C depicts the overlap between SNPs based on discovery method, whereas FIG. 55D shows the overlap between the corresponding SNP-predicted E-, T-, C- and P-Genes. No genes were shared within all four groups, and we observed limited commonality between T-, P- and E-Genes, with only 21 genes shared among the three groups. Despite the overall diversity of genes observed in each list, significant overlap was observed in the number of genes shared between ancestries.

Figure 56:
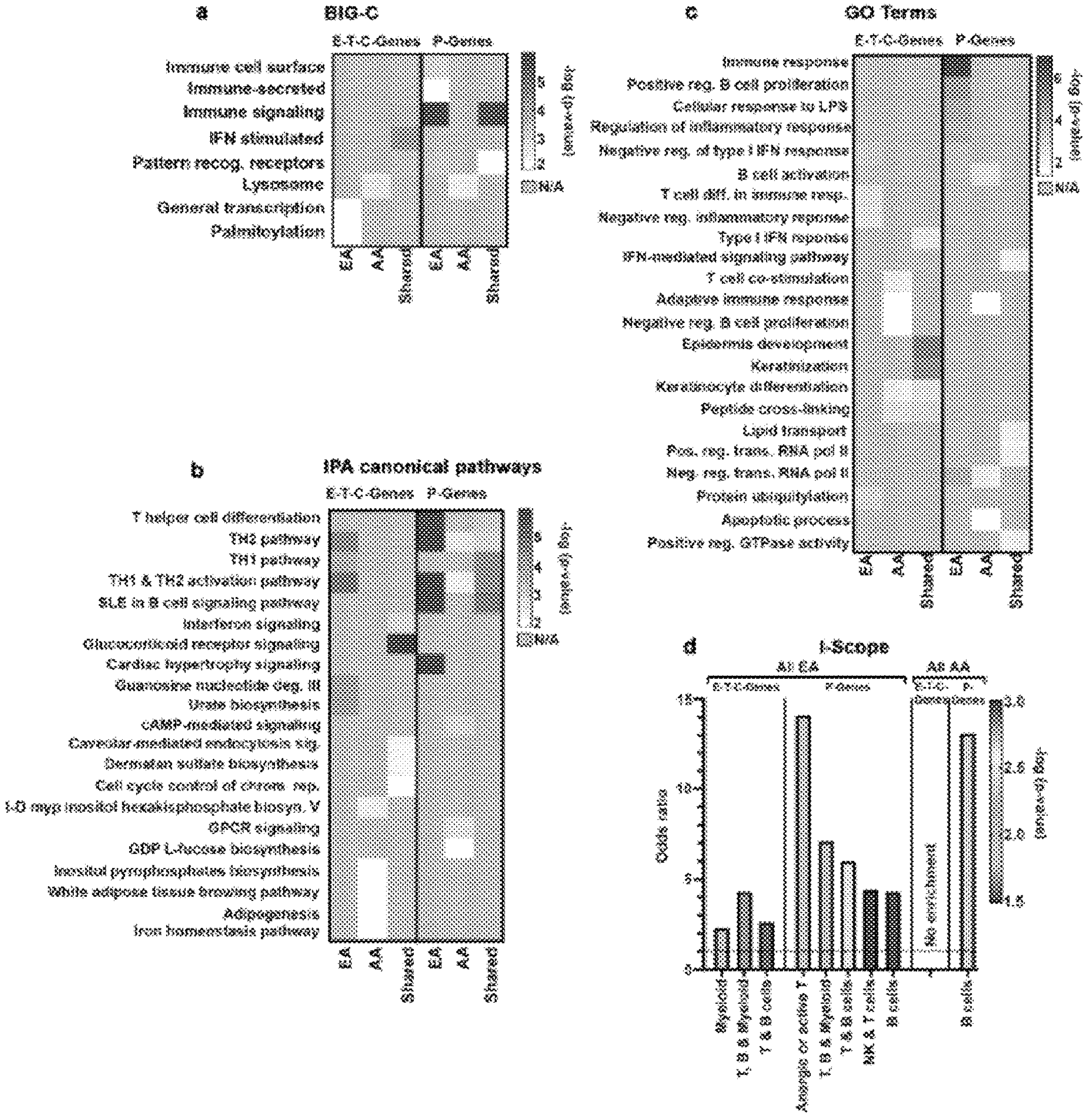
FIGS. 56A-56D show functional characterization of SNP-associated genes. (a) Ancestry-dependent and independent SNP-predicted genes were analyzed to determine enrichment using functional definitions from the BIG-C (Biologically Informed Gene Clustering) annotation library. E-T- and C-Genes were analyzed together; P-Genes were examined separately. Enrichment was defined as any category with an odds ratio (OR) >1 and −log 10(p-value) >1.33. (b-c) Heatmap visualization of the top five significant IPA canonical pathways and gene ontogeny (GO) terms for each gene list (E-T-C-Genes and P-Genes) organized by ancestry. Top pathways with −log 10(p-value) >1.33 are listed. (d) I-Scope hematopoietic cell enrichment defined as any category with an OR >1, indicated by the dotted line, and −log 10(p-value) >1.33 indicated by color scale.
Figure 64:
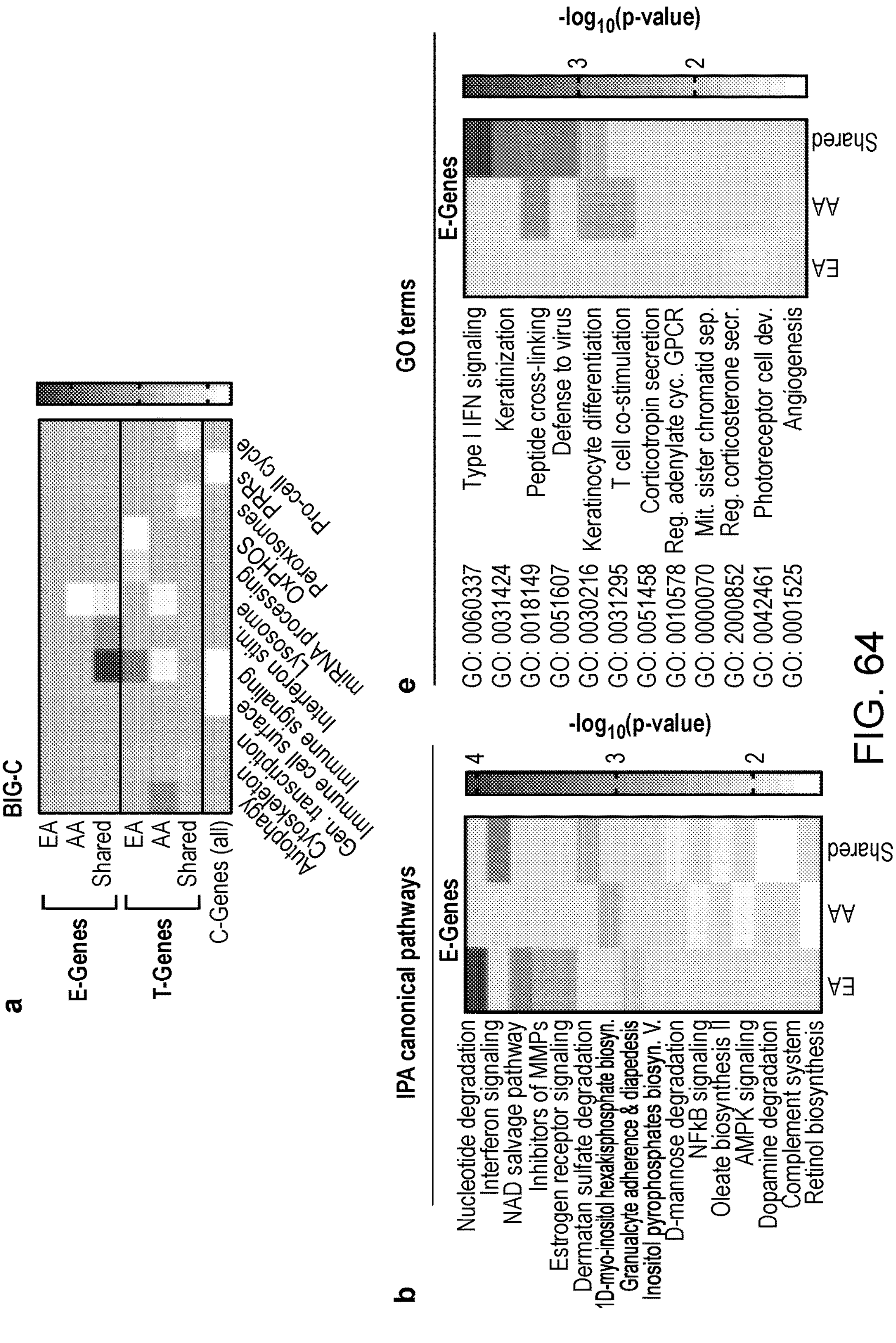
FIGS. 64A-64F show functional characterization of predicted genes. (a) Ancestry-dependent and independent E-, T- and C-Genes were independently analyzed by discovery method (source) to determine enrichment using functional definitions from the BIG-C (Biologically Informed Gene Clustering) annotation library. Enrichment was defined as any category with an odds ratio (OR) >1 and −log 10(p-value) >1.33. (b-f) Heatmap visualization of the top five significant IPA canonical pathways (b-d) and the top five significant gene ontogeny (GO) terms (d-f) for E- and T-Genes organized by ancestry. Due to the smaller number of C-Genes, this gene set was analyzed together. Top pathways with −log 10(p-value) >1.33 are listed.
Figure 64:
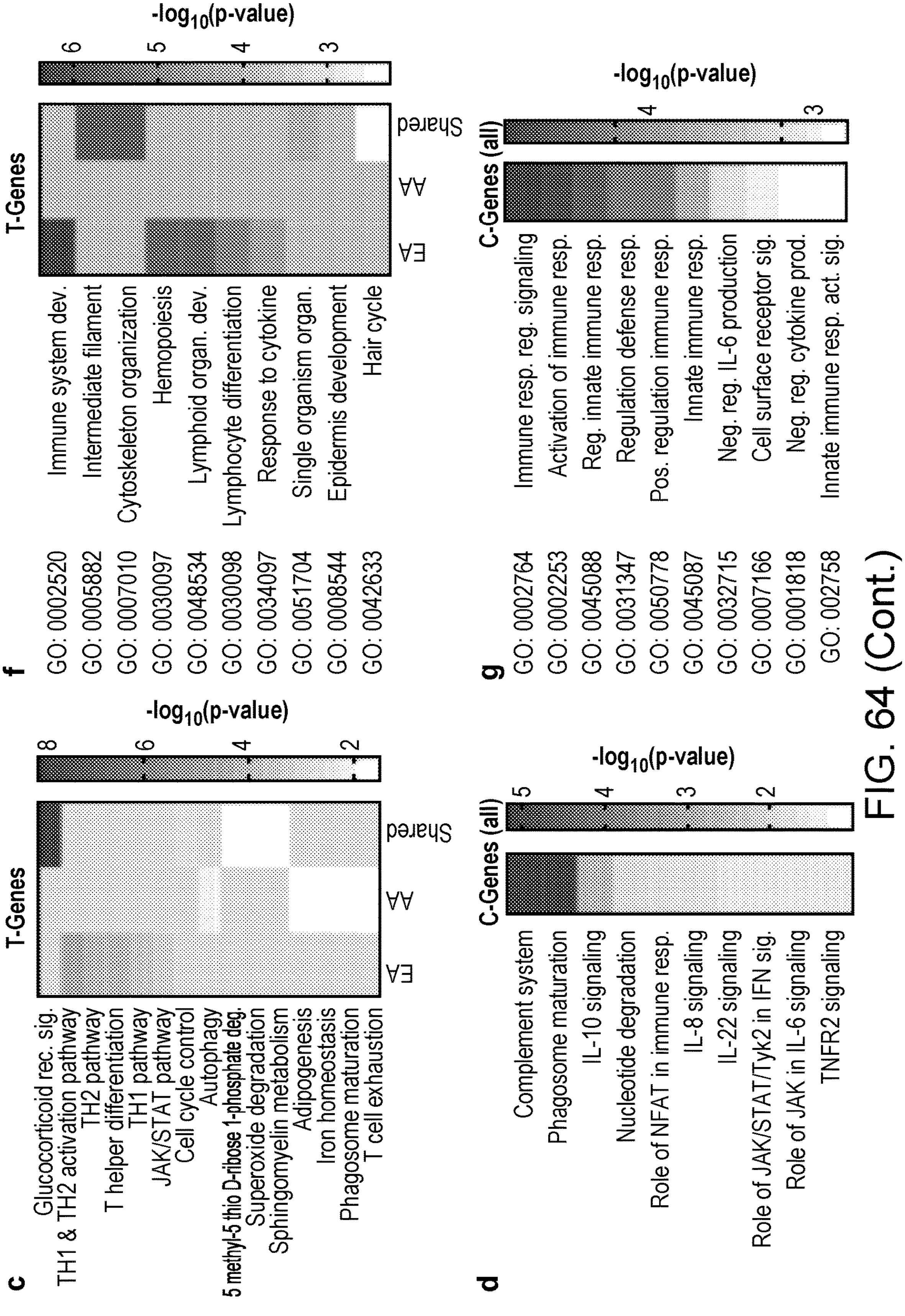

Characterization of gene signatures was performed as follows. Given the diversity of mechanisms through which SLE associated SNPs are linked to genes (e.g., eQTL, regulatory element and coding region mapping, SNP-gene proximity), we next completed a series of bioinformatic analyses using all E-, T- and C-Genes within an ancestry to determine overall biological function (FIG. 56; FIG. 64). Gene associations based on SNP-gene proximity (P-Genes) were analyzed separately to avoid overrepresentation of immune-based processes because of the design bias of the Immunochip for autoimmune and inflammatory diseases (Cortes and Brown 2011). Gene function was determined by Biologically Informed Gene Clustering (BIG-C), a functional aggregation tool developed to understand the functional groupings of large gene lists (Labonte et al. 2018; Catalina, Bachali, et al. 2019), Ingenuity Pathway Analysis (IPA) and gene ontology (GO) annotation. Heatmap visualization of BIG-C category enrichment, IPA canonical pathways and GO terms are shown in FIGS. 56A-56C. Remarkably, functional categorization remained largely consistent within each ancestry despite the derivation of genes from different association profiles and multiple bioinformatic approaches (FIG. 64). Analysis of EA genes revealed enrichment in processes related to innate immune function, including the BIG-C category for pattern recognition receptors, GO terms for the cellular response to LPS (GO: 007122), and canonical pathways for TH1 and TH2 activation pathway, JAK/STAT signaling and agranulocyte adherence and diapedesis (FIGS. 56A-56C; FIG. 64). In contrast, SNP-associated AA genes were enriched in the adaptive immune response (B cell activation (GO: 0042113) and T cell co-stimulation (GO: 0031295)), with additional enrichment in biological processes for degradation, including the BIG-C category lysosome, and IPA pathways for autophagy and phagosome maturation (FIGS. 56A-56C; FIG. 64). Shared genes were distributed in a diverse range of gene categories and contained a strong core interferon-stimulated gene signature consistent with the role of interferons in the pathogenesis of SLE (Catalina, Bachali, et al. 2019).

Finally, we used I-Scope, a clustering program that detects immune and inflammatory cell type signatures within large gene lists to identify dominant immune cell populations driving disease pathology within each ancestry (Ren et al. 2019). To analyze the full array of EA and AA genes and provide more power to these analyses, all shared genes were integrated into the EA (1675 total) and AA (725 total) gene sets. Consistent with our pathway analysis, EA exhibited strong enrichment in I-Scope categories for myeloid cells, as well as NK, T and B cells, whereas AA genes were specifically enriched in B cells (FIG. 56D). Independent analysis of shared genes on their own did not reveal enrichment in any I-Scope category.

Figure 57:
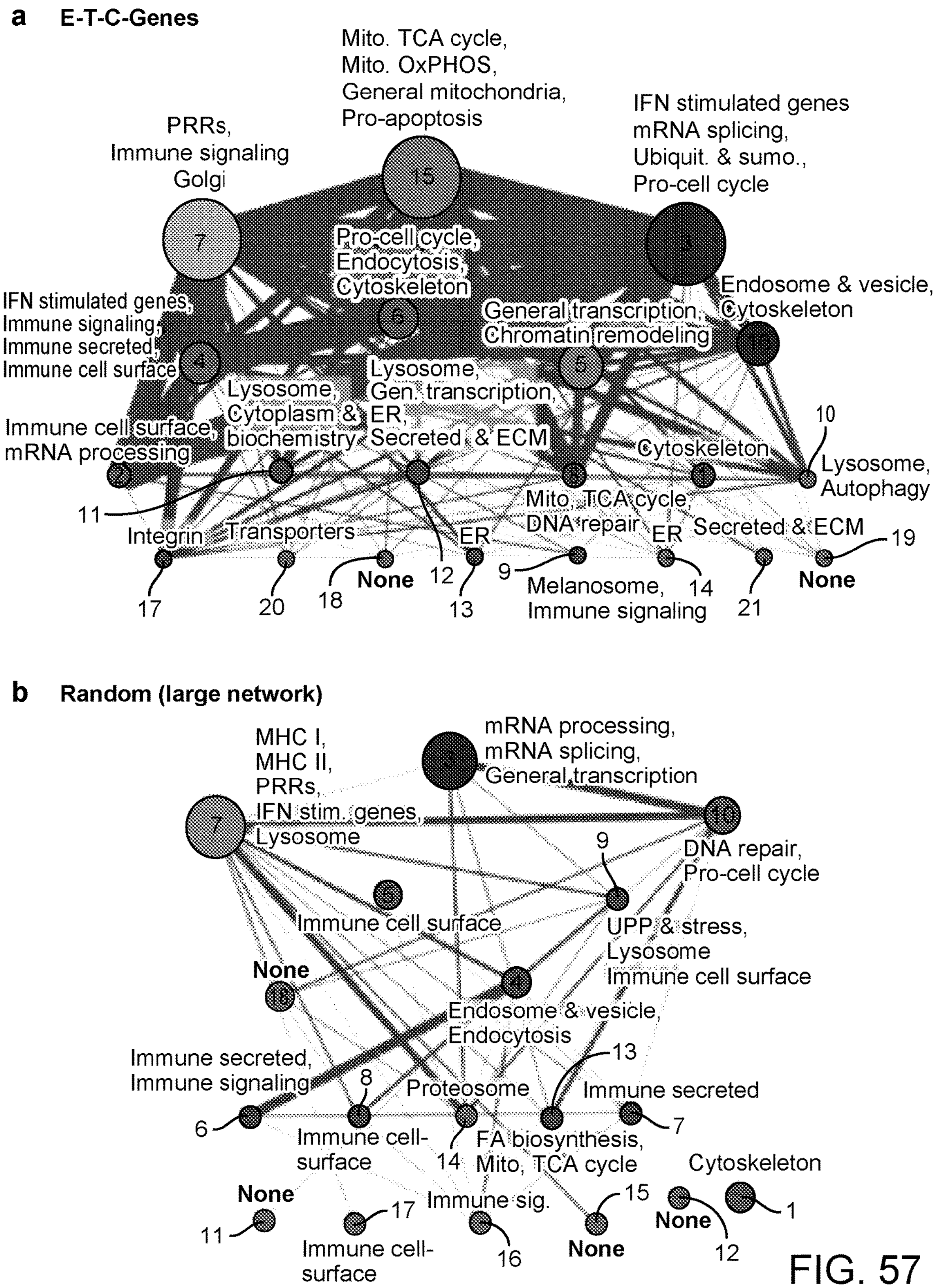
FIGS. 57A-57E show cluster metastructures for SLE-predicted and randomly generated genes. (a-d) Cluster metastructures were generated based on PPI networks, clustered using MCODE and visualized in CytoScape. Size indicates the number of genes per cluster, edge weight indicates the number of inter-cluster connections and color indicates the number of intra-cluster connections. Random gene networks (large: 1033 genes; small 538 genes) were clustered along side networks for E-T-C-Genes and P-Genes. Functional enrichment for each cluster was determined using BIG-C. (e) Quantitation of cluster size, intra-cluster connections, inter-cluster connections and the percent of genes incorporated into each network are displayed. E-T-C-Genes were compared to the large random network; P-Genes were compared to the small random network. Error bars represent the 95% confidence interval; asterisks (*) indicate a p-value <0.05 using Welch's t-test.
Figure 65:
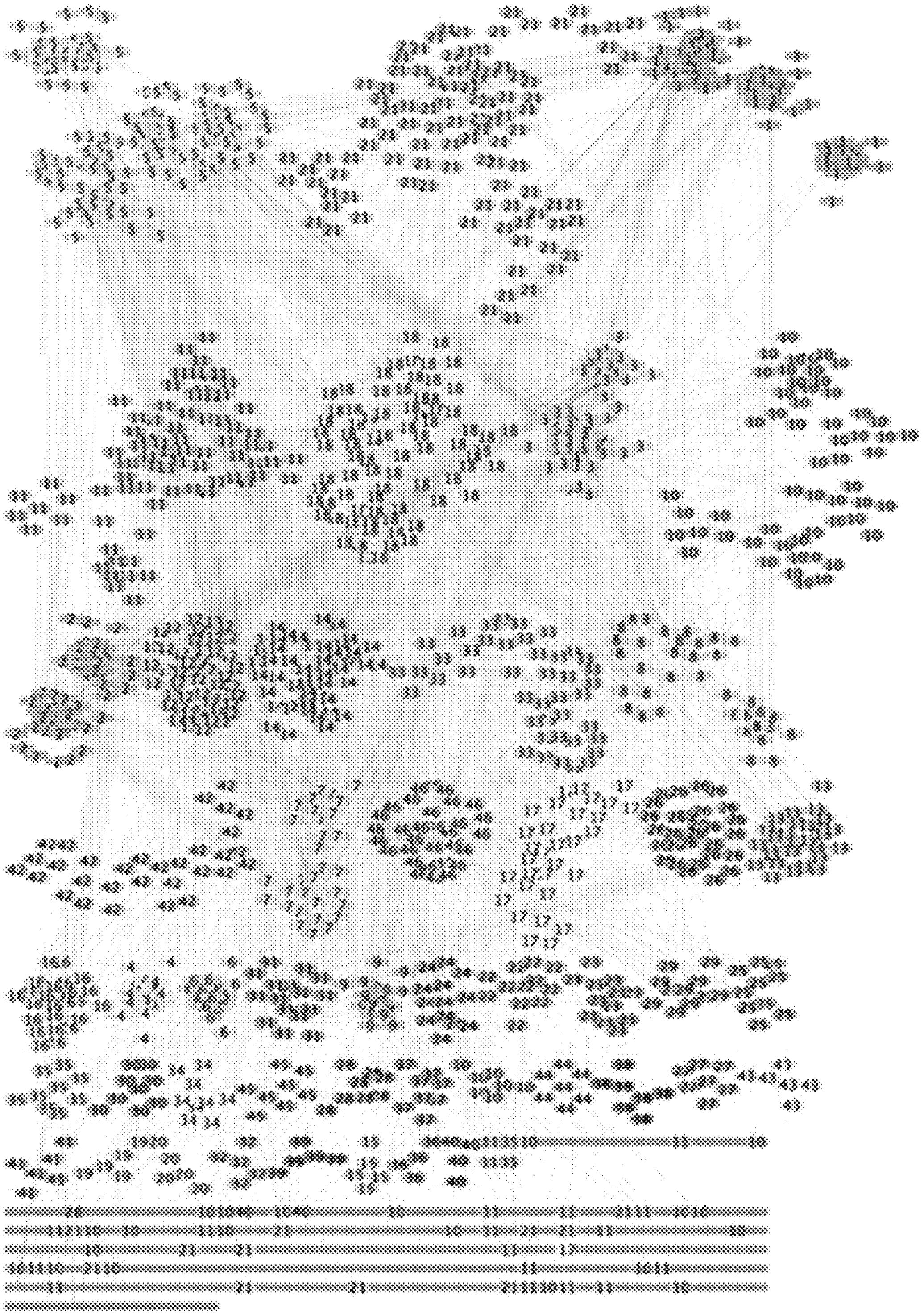
FIG. 65 shows protein-protein interaction-based clustering of predicted EA, AA and shared genes determined by source. PPIs and clusters were generated via CytoScape using the STRING and MCODE plugins. Clusters are determined by the strength of protein-protein interactions, calculated by pooling information from publicly available literature.

Protein interaction-based clustering of SNP-associated genes was performed as follows. We next sought to assess the relationship between all SNP-associations regardless of ancestral origin. Protein-protein interaction (PPI) networks consisting of E-T-C-Genes and P-Genes were constructed using STRING (version 10.5), visualized in Cytoscape (version 3.6.1) and clustered using the MCODE app plugin to provide an additional level of functional annotation. The resulting networks were further simplified into metastructures defined by the number of genes in each cluster, the number of significant intra-cluster connections predicted by MCODE, and the strength of associations connecting members of different clusters to each other. Overall, 52.7% of E-T-C-Genes (701/1330) and 53.2% of P-Genes (272/520) were incorporated into PPI networks. The majority of E-T-C-Genes coalesced into several large, multi-functional clusters, including cluster 7 which contained a mix of EA, AA and shared genes enriched in molecules associated with immune signaling and golgi function, cluster 15 dominated by metabolic processes and cluster 3 containing a robust interferon signature (FIG. 57A; FIG. 65). E-T-C-Genes were highly connected both internally (intracluster connections) and to neighboring clusters. Examination of networks constructed of all P-Genes revealed the predominance of immune function with 7 out of 10 of the largest, intraconnected clusters enriched in immune activity (FIG. 57B).

To confirm that the predicted molecular pathways derived from SNP-predicted genes were specific for SLE and not related to random chance, we carried out a parallel analysis examining PPI networks composed of genes derived from randomly selected Immunochip SNPs. Random SNPs analyzed by eQTL mapping were used to generate random E-Genes that were incorporated into STRING networks and clustered via MCODE (FIGS. 57C-57D). Given the disparity in gene numbers between the E-T-C-genes and P-Genes, 2 random networks were constructed to provide equivalent comparisons. Examination of metastructures reveals that random gene networks incorporated fewer genes overall (258/1033; 24.9% for the large network and 206/538; 38% for the small network) and exhibited significantly fewer inter-cluster connections and fewer intra-cluster connections, appearing as independent entities lacking robust functional relationships with neighboring clusters (FIG. 57E).

Figure 58:
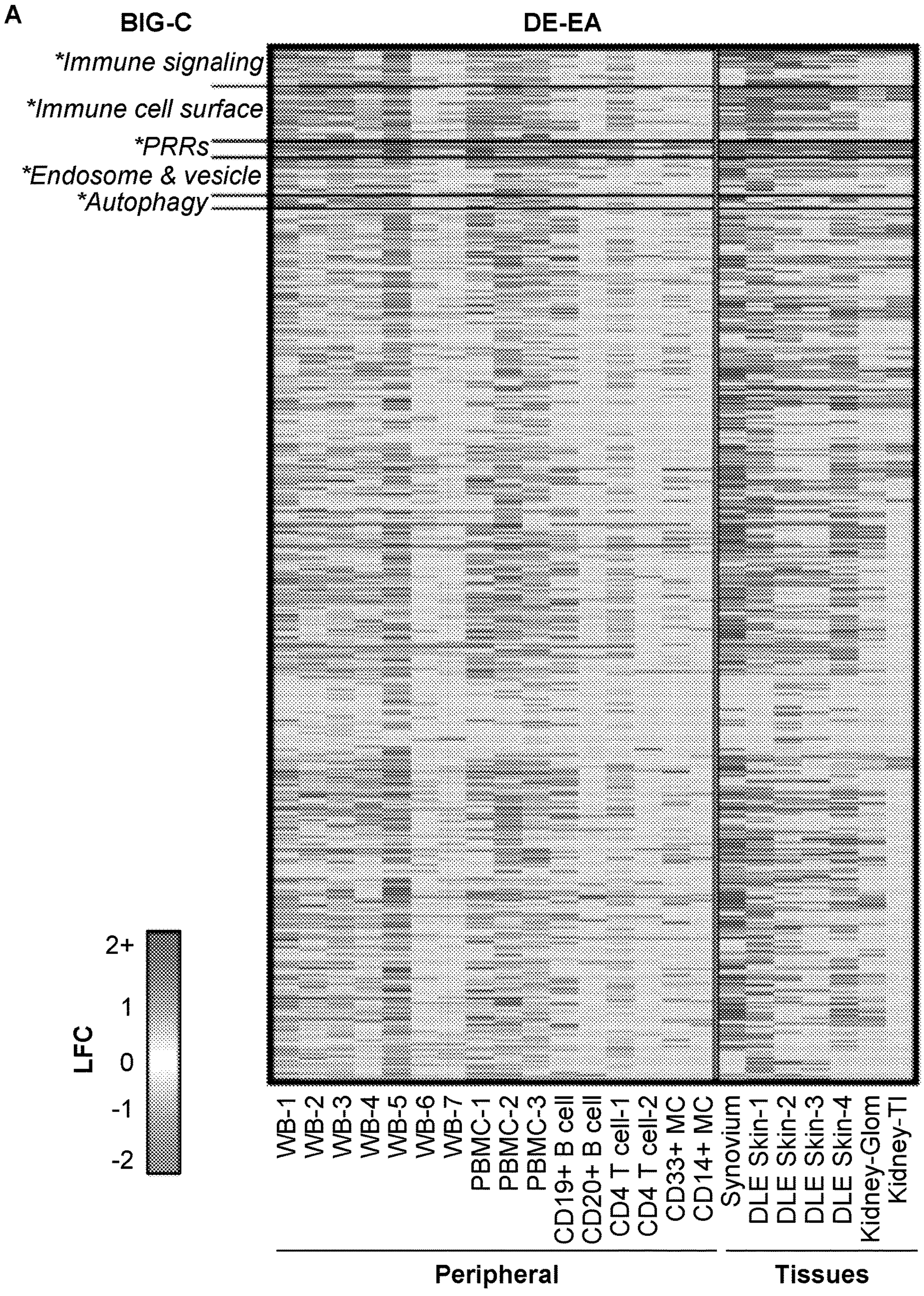
FIGS. 58A-58C show a comparison of EA, AA and shared SNP-associated genes with SLE differential expression datasets. SNP-associated genes were matched with SLE differential expression (DE) data and organized by ancestry. (a-c) shows the fold-change variation of EA, AA and shared genes. Heatmaps are organized by BIG-C category. Enriched categories indicated with an asterisk. Enrichment was defined as any category with OR >1 and −log 10(p-value) >1.33.

Predicted genes were shown to be linked to altered expression in SLE and are enriched in differential expression datasets. We next determined whether genes linked to specific populations exhibited altered expression in SLE. Ancestry-specific SNP-predicted genes were matched to DEGs in unrelated SLE datasets in various tissues, including whole blood, PBMCs, B cells, T cells, synovium, skin and kidney (Supplementary Data 8). Heatmaps depicting the log-fold change for each gene were organized based on enriched BIG-C category. We observed that of the 1176 EA SNP-predicted genes, 743 were identified as DEGs across all datasets (FIG. 58A). For the 70 AA SNP-predicted genes, 49 genes were differentially expressed (FIG. 58B). Of the 661 genes shared between ancestries, 441 genes were identified as DEGs, with the interferon stimulated genes (HERC5, IFI35, IFI44L, IFI6, IFIT1, MX1 and SPATSL2L), interferon regulatory factors (IRF4, IRF5 and IRF7) and PRRs (OAS1, OAS2, OAS3, SLC15A4) differentially expressed across all datasets (FIG. 58C).

The relationship of SNP-predicted genes and upstream regulators of gene expression profiles was determined as follows. We next sought to elucidate the relationship between ancestry-driven key signaling pathways and DEGs in greater detail. Using IPA, DEGs were used to identify potential biologic upstream regulators (UPRs) with the goal of determining whether UPRs of the altered gene expression profile in SLE were SNP-predicted genes. Overall, 141 UPRs predicted from the altered SLE gene expression profile were determined to be SNP-associated genes, including surface receptors, signaling molecules, cytokines and transcription factors, many with known roles in SLE such as IRF7, ITGAM, IFNG, IKZF1 and CD40 (Supplementary Data 12). In addition, 41 UPRs were transcription factors predicted to bind to transcription factor binding sites altered by an SLE-associated SNP, including, MYC, EZH2, NFATC1, STAT3, STAT5a, Fos, JunB and Re1A. Thus, of the 1238 UPRs inferred to influence the altered SLE gene expression profile, 181 were SNP-predicted genes.

Figure 59A:
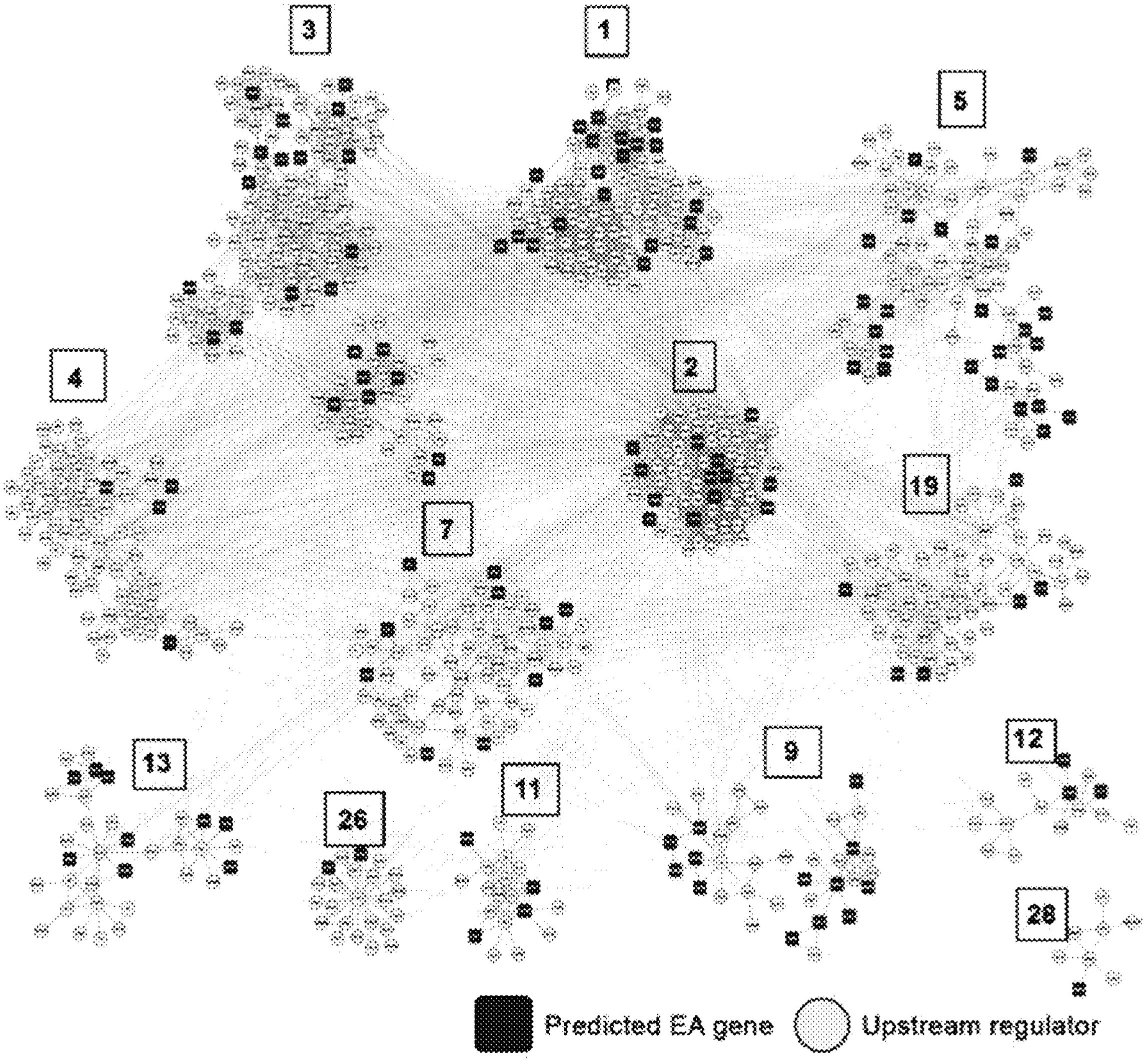

Delineation of signaling pathways identified by ancestry specific SNP-associated genes and UPRs was performed as follows. Connectivity mapping of SNP-associated genes and all UPRs inferred from SLE gene expression profiles were then used as input to build more complete PPI networks, and individual gene clusters were analyzed by BIG-C and IPA to identify those molecules and pathways highly associated with disease. A total of 45 pathways were representative of EA genes and UPRs, with the largest clusters (1 and 3) heavily involved in pattern recognition receptor signaling (FIGS. 59A-59B). Clusters 4 and 5 revealed enrichment in lymphocyte activation and differentiation pathways that were also common to both the AA and shared gene networks. Twenty pathways were unique to EA, including several involved in cellular communication, cytokine signaling and migration. The AA network was smaller (FIG. 60A), with fewer SNP-predicted genes and associated UPRs, yet contained genes critical for T cell responses such as PRDM1 and IKZF1 (FIG. 60B). Pathways unique to AA were overwhelmingly represented by processes related to degradation and cellular stress, found in clusters 5, 3 and 11, as well as metabolic processes in cluster 6.

Pathways exemplified by ancestry-independent genes were a blend of both EA and AA pathways. Common pathways included IL12 signaling and production by macrophages, TLR signaling and activation of IRFs by cytosolic PRRs (shared with EA), as well as PRRs in the recognition of bacteria and virus (FIG. 61B), a pathway shared with AA. FIG. 62A depicts both the unique and overlapping canonical pathways predicted by the EA and AA gene sets, whereas FIG. 62B shows the overall pathway categories shared between EA and AA and those that are unique to each ancestral group.

To validate our pathway predictions, Gene Set Variation Analysis (GSVA) (Hänzelmann, Castelo, and Guinney 2013) was applied to identify differentially enriched gene signatures in SLE patients (EA and AA) and control whole blood (WB) (Supplementary Data 14). All SNP-associated genes were used to create a collection of signatures informed by protein-protein interaction networks and IPA canonical pathways, or were previously defined (Supplementary Data 15) (Catalina, Bachali, et al. 2019). GSVA enrichment scores using signatures for leukotriene biosynthesis and diapedesis were able to specifically separate EA SLE patients, but not AA patients, from healthy controls (FIG. 62C). This signature also distinguished EA patients from AA patients. In contrast, gene signatures related to cell stress pathways were significantly enriched in AA SLE compared to EA SLE patients for the unfolded protein response (UPR), and AA SLE versus healthy control the for the T cell exhaustion signature (FIG. 62D). AA SLE patients were additionally enriched in the IPA-derived signature for SLE signaling in B cells.

Figure 66:
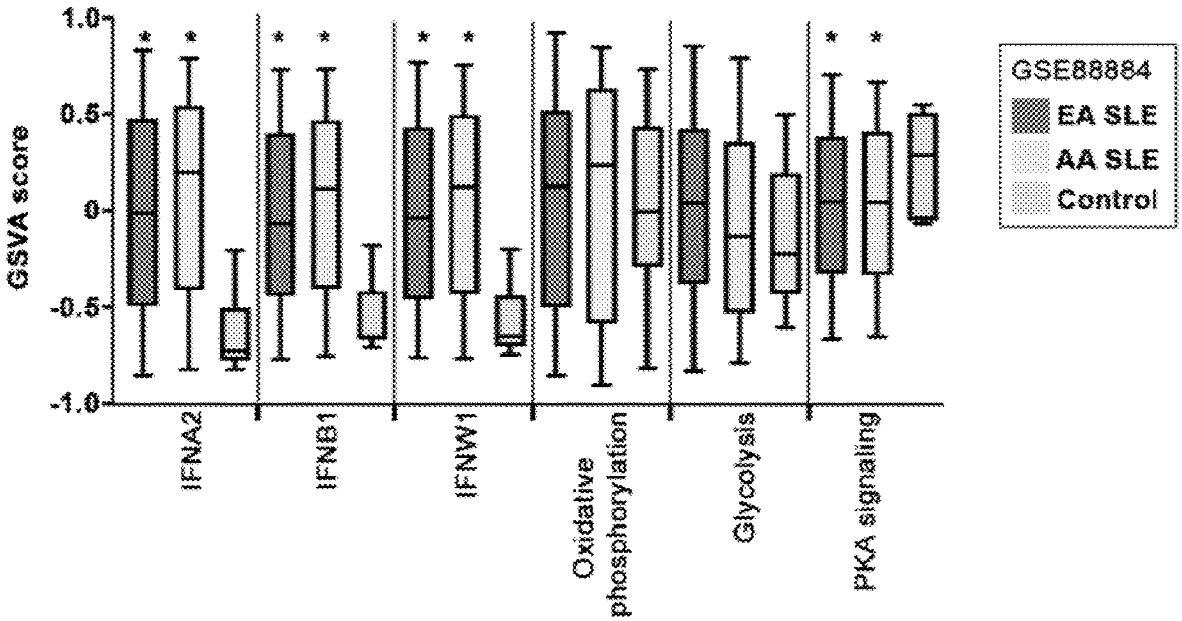
FIG. 66 shows GSVA enrichment scores for interferon and metabolic pathways. GSVA signature scores distinguishing SLE patients from healthy controls using gene modules defining IFNA2, IFNB1, IFNW1, oxidative phosphorylation, glycolysis and PKA signaling. Asterisks (*) indicate a p-value <0.05 using Welch's t-test comparing SLE to control.
Figure 67A:
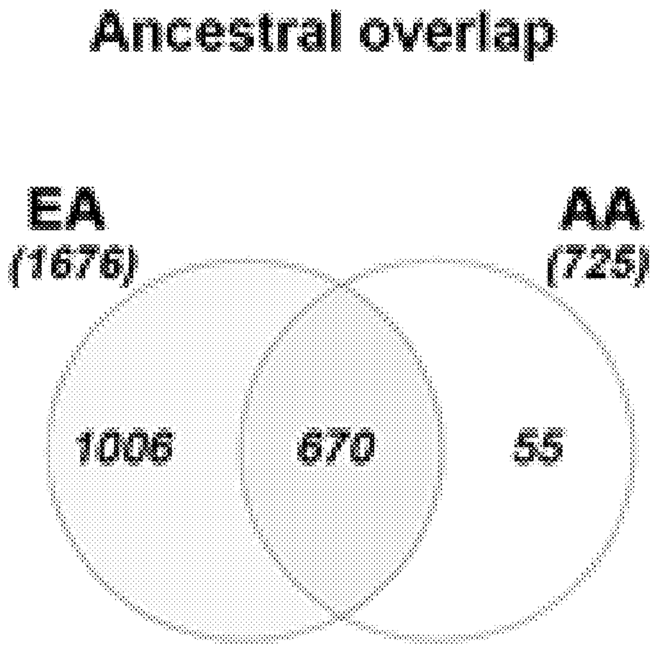
FIGS. 67A-67D show functional characterization of SNP-associated genes. (a) Venn diagram showing the overall overlap between EA and AA SNP-predicted genes. (b) Ancestry-dependent genes (1676 EA; 725 AA) were analyzed to determine enrichment using functional definitions from the BIG-C annotation library. Random genes (500) were analyzed alongside SNP-predicted genes. E-T- and C-Genes were analyzed together; P-Genes were examined separately. Enrichment was defined as any category with an odds ratio (OR) >1 and −log 10(p-value) >1.33. (c-d) Heatmap visualization of the top five significant IPA canonical pathways and gene ontogeny (GO) terms for each gene list (E-T-C-Genes and P-Genes) organized by ancestry. Top pathways with −log 10(p-value) >1.33 are listed.
Figure 67B:
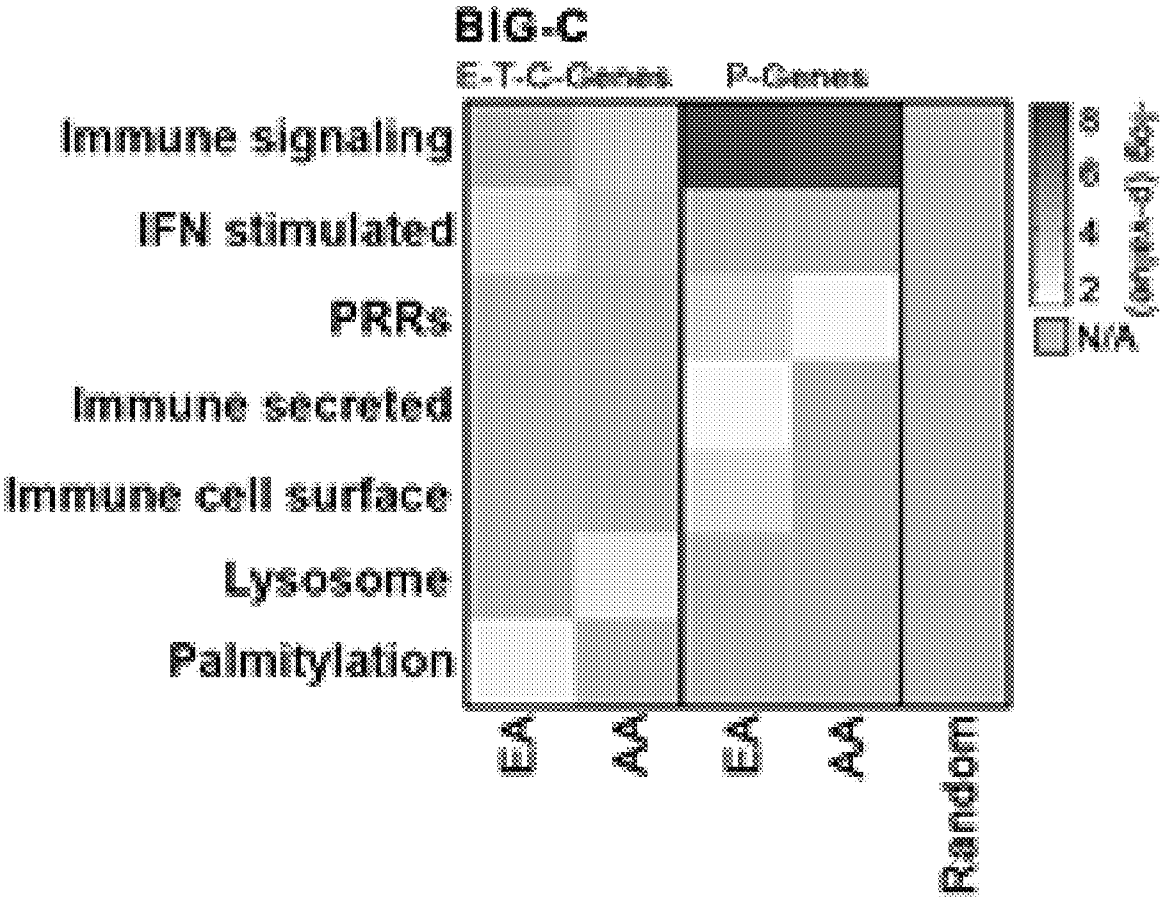
Figure 67C:
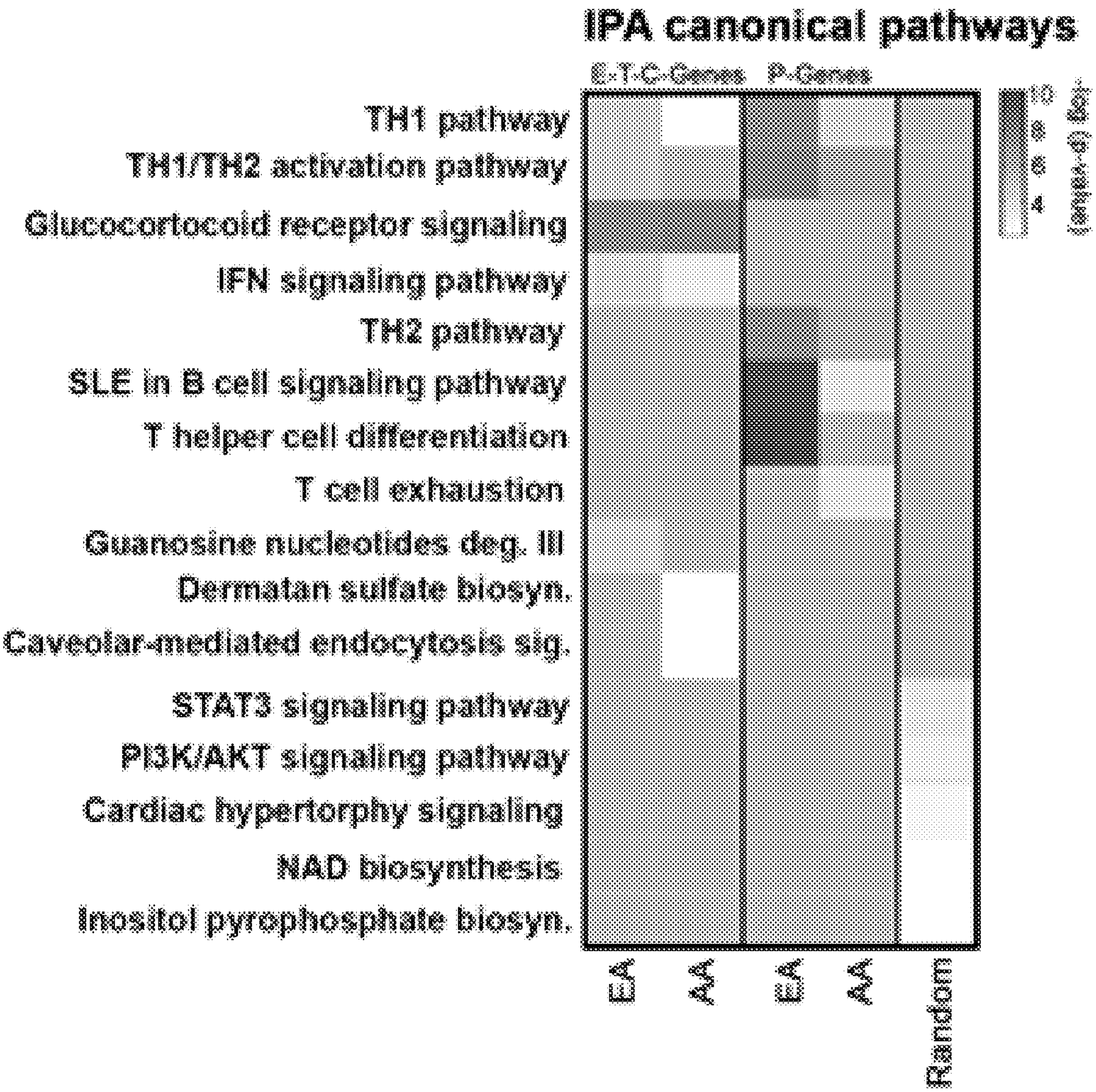
Figure 67D:
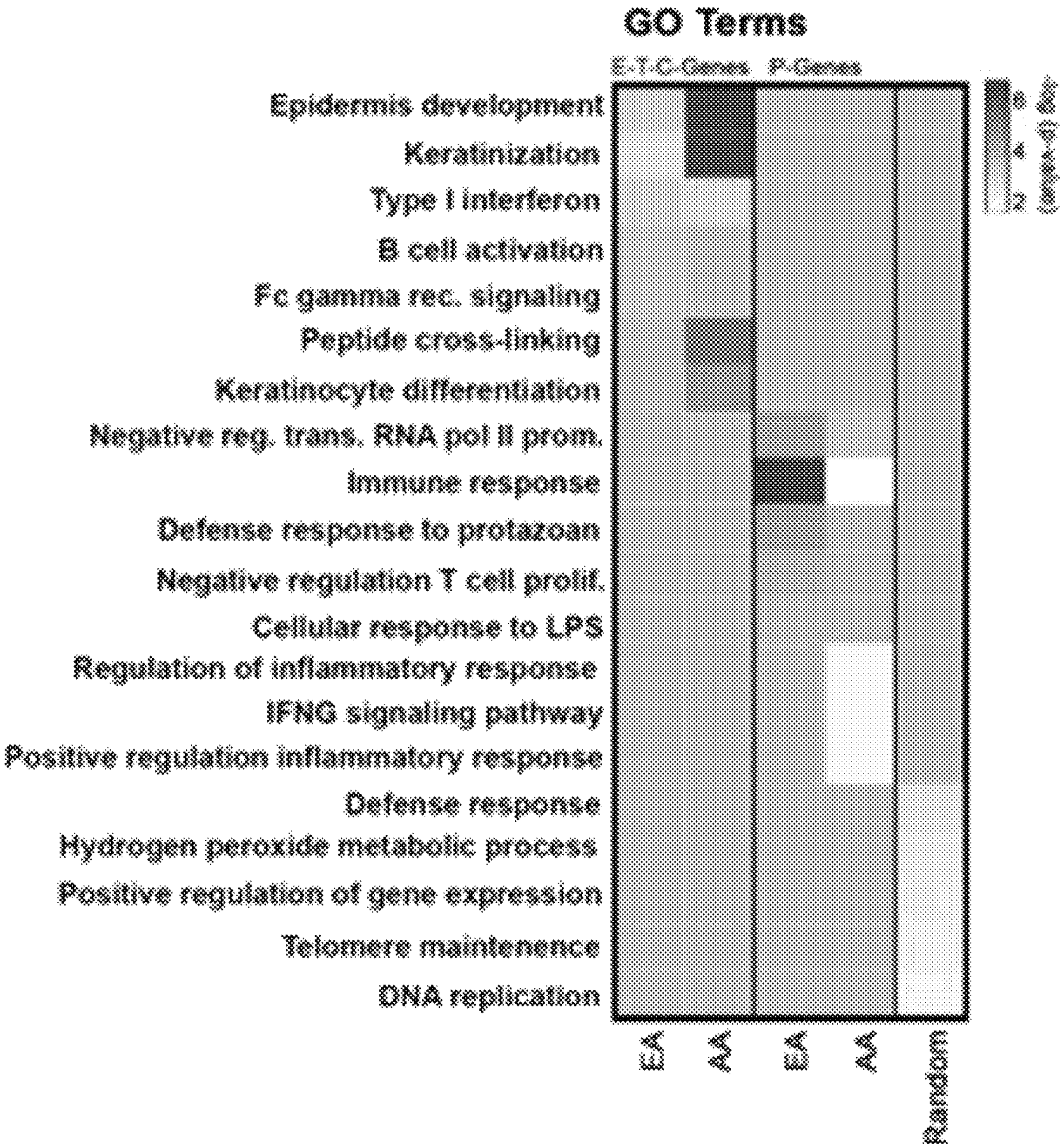

A number of signatures were able to discriminate between SLE patients and controls independent of ancestry, including signatures for TH1 activation pathway, cell cycle and lysosome (FIG. 62E). Cytokine-based signatures for core interferon (IFN), IFNG, IL12, and the IFN subtypes IFNA2, IFNB1 and IFNW gene signatures also separated SLE patients from controls (FIG. 62E; FIG. 66). Finally, signatures for ubiquitylation and sumoylation, apoptosis signaling, nuclear receptor signaling and TNF were sufficiently discriminatory to separate SLE individuals from controls, and furthermore exhibited significant enrichment in AA patients compared to EA patients (FIG. 62F). Gene signatures for metabolic pathways, including mitochondrial oxidative phosphorylation and glycolysis were also investigated but did not demonstrate any significant change between SLE and control or between ancestries. In contrast, GSVA scores for the PKA signaling gene signature were significantly lower in SLE patients compared to controls (FIG. 66).

Pathway identification facilitated drug prediction analysis, allowing us to identify potential drug candidates for repositioning in SLE. Canonical pathways related to T cell function are shared among ancestries, as are many predicted drugs targeting T cell activity including abatacept, theralizumab and AMG-811 (FIG. 61B). Broader analysis of common pathway categories also suggests the utility of targeting T cell signaling, as well as cytokine pathways such as IL12/23 signaling with ustekinumab and/or interferon signaling with anifrolimab (FIG. 62B). Drugs specific for EA pathways include BMS-986165, a small molecular inhibitor of TYK2 (FIG. 59B), whereas therapeutic candidates targeting AA pathways include the FDA-approved (for multiple myeloma) proteasome inhibitor bortezomib, as well as PF-06650833, an IRAK4 specific inhibitor (FIG. 60B). Unique pathway categories identified for EA and AA suggest additional ancestry-specific interventions, such as the small molecule inhibitor of sphingosine-1-phosphate receptor 1 (S1PR1) siponimod for EA (prevents leukocyte egress), and the HDAC inhibitor vorinostat for AA, both of which have shown efficacy in clinical trials for other autoimmune diseases (Kappos et al. 2018; Eckschlager et al. 2017) (FIG. 62B).

Discussion

SLE is a chronic autoimmune disease with a strong genetic component. Familial aggregation studies together with GWAS underscore the contribution of genetics to disease development (Alarcón-Segovia et al. 2005). Genetic heterogeneity between ancestral populations is also widely acknowledged to be important in SLE risk where patients of African descent have a higher prevalence of lupus and experience the disease more severely than those of European ancestry (Williams et al. 2016; Barnado et al. 2018). Despite improved understanding of how inherited genetic variation impacts disease risk, genetic analyses to date have failed to provide a clear path toward novel therapeutic development. This is of particular concern with respect to AA populations where the control of disease activity remains suboptimal (Lamore et al. 2012; Furie et al. 2011; Navarra et al. 2011). Here, we propose a novel strategy using statistical and computational analyses along with data acquired from functional genomic assays and differential gene expression studies to map the global gene expression landscape of SLE and further define the disease-associated pathways responsible for the inherent disparities influencing SLE progression.

Expression quantitative trait loci (eQTL) mapping represents a powerful, bioinformatics-driven methodology to examine the association between specific genetic variations and gene expression levels in tissues (Morloy et al. 2004). Here, eQTL analysis linked 247 tagging SNPs to 759 candidate causal E-Genes (77 EA, 21AA, 523 shared). Given that the majority of eQTL identified here map to multiple E-Genes (many within the same functional network), eQTL-based gene prediction may be particularly valuable for network modeling and disease analysis. Recent studies have also shown that disease-susceptibility variants frequently lie in distal regulatory enhancer elements (Corradin and Scacheri 2014). Indeed, nearly 20% (157) of SNPs analyzed here were located in known regulatory regions. Using computational gene prediction algorithms that incorporate chromatin interaction data, additional regulatory SNPs were identified that changed transcription factor binding and were linked to 627 downstream targets (T-Genes; 472 EA, 9 AA, 143 shared). Although some regulatory SNPs also exhibit eQTL effects, we nonetheless uncovered 496 unique T-Genes enriched in a diverse array of functional categories. Among the loci that lead to changes in gene expression, we identified 23 variants resulting in nonsense or non-synonymous amino acid changes affecting 22 genes (C-Genes), 12 of which were predicted to negatively impact protein function. Finally, we employed traditional locus annotation, mapping the identified risk SNP to the nearest, most proximal gene, resulting in 520 P-Genes (465 EA, 34 AA, 21 shared).

One major limitation to the current study is that all computational approaches outlined here are predictive; by attempting to provide a more comprehensive translation of GWAS findings, a major challenge remains in determining those genes that are causative and those that represent biological "noise." To address this, PPI networks and clustering based on interaction strength helped exclude those genes lacking strong connections to molecules within or between similarly functioning clusters. Compared to SNP-predicted E-, T-, C- and P-Genes where we observed large, highly connected clusters, randomly generated genes generally formed smaller clusters, exhibited fewer intra- and inter-cluster connections and ultimately appeared as independent entities. In addition, predicted genes were compared to SLE datasets (SLE vs control) to determine those genes that were differentially expressed in active disease. Importantly, we observed a high percentage of SNP-predicted genes differentially expressed across all datasets which were then used as input into IPA to generate upstream and downstream regulators and combined for further network and clustering analysis. This allowed us to identify biologically relevant pathways unique to each ancestry, a strategy that revealed essential differences between EA and AA SLE, as well as many pathways that were shared.

A second caveat to the current study is the use of the Immunochip which was constructed to cover multiple major autoimmune diseases and enable the identification of top-ranked SNPs associated with disease (Cortes and Brown 2011). However, the chip was designed for use in EA populations and is therefore less informative for other ancestral groups, especially in non-HLA associated regions. Furthermore, as chip coverage was confined to autoimmune and inflammatory diseases, SNPs affecting non-immune related processes are likely to be under-represented.

Despite these drawbacks, the pathway-based analysis of predicted genes and their upstream regulators presented here helps clarify the complex polygenic risk associated with SLE in multiple ancestries. We observed key dysregulated EA pathways centered around innate immune function and the response to inflammation, including cell movement, cytokine signaling and cell-cell communication. Remarkably, GSVA gene signatures for leukotriene biosynthesis and diapedesis were sufficiently discriminatory to separate EA SLE patients from controls, providing additional evidence for these pathways in SLE pathogenesis. Furthermore, SNP-predicted EA genes were enriched in myeloid and NK cell signatures, along with T and B cell signatures, findings that are consistent with previous reports showing increased myeloid lineage cell modules in EA patients (Banchereau et al. 2016; Catalina M, Bachali P, Yeo A, Geraci N, Petri M, Grammer A 2019).

In contrast, AA pathways included those associated with protein degradation, such as the sumoylation pathway, ubiquitylation signaling, the ER stress pathway, unfolded protein response, osteoarthritis pathway (cell stress) and the neuroprotective role of THOP1 in Alzheimer's disease, a pathway involved in the presentation of antigen generated by the proteasome. The importance of these pathways was confirmed by GSVA which demonstrated the unique enrichment of cellular stress mechanisms and B cell signaling in AA SLE patients. These observations are in line with reports showing increased B cell activation and plasma cells in AA patients (Menard et al. 2016; Banchereau et al. 2016; Catalina M, Bachali P, Yeo A, Geraci N, Petri M, Grammer A 2019). Furthermore, it is increasingly recognized that ER stress and the UPR signaling pathway in dysregulated immune responses is closely tied to aberrant B cell activity in SLE (Navid and Colbert 2017; Lam and Bhattacharya 2018).

Gene signatures representing cellular processes shared between ancestries provide further validation for our comprehensive pathway analysis. GSVA enrichment scores for the interferon response (IFN core, IFNA2, IFNB1, IFNW1 and IFNG) and inflammatory cytokines (IL-12 and TNF) exhibited the greatest difference between SLE and control, independent of ancestry. In line with this, work by Catalina et al (2019) (Catalina, Bachali, et al. 2019) showed that multiple IFN signatures are operative in an array of SLE patient samples from whole blood and tissues. Despite that metabolic abnormalities, including heightened glycolysis and mitochondrial glucose oxidation (Lightfoot, Blanco, and Kaplan 2017) have been reported in SLE, metabolic gene signatures for OXPHOS and glycolysis did not discriminate between SLE patients and controls. However, examination of protein kinase A (PKA) signaling, a pathway that participates in the regulation of immune effector functions in T cells (Wehbi and Taskén 2016) demonstrated significantly lower GSVA scores for the PKA signaling signature in both EA and AA SLE patients compared to controls. Consistent with these findings, previous reports have shown that T cells from SLE patients have a metabolic disorder of the PKA pathway characterized by markedly diminished PKA activity and dysfunctional T cell activity (Kammer, Khan, and Malemud 1994; Kammer 2002).

By focusing on pathways instead of individual genes, this approach identifies "actionable" points of therapeutic intervention with the potential to uniquely impact EA and AA SLE. Thus, EA patients may derive particular benefit from treatments that prevent leukocyte or lymphocyte infiltration into tissues highlighting drugs that modulate this process. For example, sphingosine-1 phosphate receptor (SIPR) is a pleiotropic lipid mediator involved in the regulation of many cellular functions, including proliferation, survival, and cell motility (Cartier and Hla 2019; Aoki et al. 2016). Siponimod, an FDA approved treatment for multiple sclerosis, promotes the internalization of S1PR expressed on lymphocytes preventing cell migration to sites of inflammation (Kappos et al. 2018; Faissner and Gold 2019; Gajofatto 2017). Given its high Combined Lupus Treatment Score (CoLTS) (Labonte et al. 2018; Grammer et al. 2016) of +7, siponimod represents a high priority small molecule drug with potential for repurposing in SLE.

Similarly, given the dominance of proteasome and degradation in AA pathways, therapeutic intervention may include proteasome inhibitors like bortezomib (BZ), a FDA-approved drug for mantle cell lymphoma and multiple myeloma. Despite reports of adverse events, BZ was claimed to have efficacy in treating refractory SLE in a small uncontrolled clinical trial (Alexander et al. 2015). In addition, AA SLE patients showed a better response to rituximab, an anti-CD20 inhibitor, in phase II/III clinical trials (Merrill et al. 2010), and a trend toward better response in AA patients with LN (Rovin et al. 2012), indicating the possibility that BZ (and/or more selective immunoproteasome inhibitors), and therapies targeting B cells may hold promise for AA patients who respond poorly to conventional therapies.

Methods

Identification of SLE-associated SNPs and predicted genes was performed as follows. The SLE Immunochip study (Langefeld et al. 2017) identified single nucleotide polymorphisms (SNPs) significantly associated with SLE in AA (2,970 cases; 2,452 controls) and EA (6,748 cases; 11,516 controls) cohorts. SNP proxies (http://raggr.usc.edu) in linkage disequilibrium (LD) ($r2>0.5$) with these SLE-associated SNPs were then determined, using the Central European Utah (CEU) population as background for EA SNPs and the Yoruban (YRI) population for AA SNPs. Expression quantitative trait loci (eQTLs) were then identified using GTEx version 6 (GTEXportal.org ("The Genotype-Tissue Expression (GTEx) Project" n.d.)) and the Blood eQTL browser database (Westra et al. 2013) and mapped to their associated eQTL expression genes (E-Genes). In parallel, random E-Gene datasets were generated from randomly selected SLE Immunochip SNPs using the same methodology. SNP proxies were then queried by GTEx to generate eQTLs and matched to ENSEMBL gene IDs. To find SNPs in enhancers and promoters, and their associated transcription factors and downstream target genes (T-Genes), we queried the atlas of Human Active Enhancers to interpret Regulatory variants (HACER, http://bioinfo.vanderbilt.edu/AE/HACER (Wang et al. 2019) and the GeneHancer database (Fishilevich et al. 2017). To find structural SNPs in protein-coding genes (C-Genes), we queried the human Ensembl genome browser (GRCh38.p12; www.ensembl.org) and dbSNP (www.ncbi.nlm.nih.gov/snp). Several additional databases were used to generate loss-of-function prediction scores, including SIFT4G (http://sift-dna.org/sift4g (Vaser et al. 2016; Sim et al. 2012)), PolyPhen-2 (genetics.bwh.harvard.edu (Adzhubei, Jordan, and Sunyaev 2013), PROVEAN (provean.jcvi.org (Choi et al. 2012)) and PANTHER (Mi et al. 2017). All other SNPs were linked to the most proximal gene (P-Gene) or gene region as previously detailed (Langefeld et al. 2017). For overlap studies, Venn diagrams were computed and visualized using InteractiVenn (interactivenn.net) (Heberle et al. 2015). All predicted genes were divided into an AA, EA or shared group depending on the ancestral designation of the original SLE-associated SNP.

Statistical analysis was performed as follows. The single-locus and multi-locus ancestry-specific tests of association within each ancestral group have been previously reported (Langefeld et al. 2017). Specifically, to test for an association between a SNP and case/control status separately for the AA and EA ancestries, logistic regression models were computed adjusting for population substructure using admixture factors as covariates. The Benjamini-Hochberg false discovery rate adjusted p-values (PFDR) were computed, and SNPs were considered for the subsequent analyses in this manuscript if they met a PPDR<0.05 threshold. The two ancestry-specific analyses (i.e., AA and EA) were meta-analyzed using the weighted inverse normal (weighted by sample size) method and tested for heterogeneity also as previously described (PHET) (Langefeld et al. 2017)). The following algorithm was used to classify significant associations in either ancestral group (PFDR<0.05) as shared or ancestry-specific (i.e., primarily driven by the EA or AA ancestry subpopulations). First, if the PHET>0.01 then the association was considered common (shared) across the EA and AA ancestries. If the PHET<0.01, then we considered the direction (odds ratio: OR >1, OR<1) and the ancestry-specific p-values. If PHET<0.01 and the OR was in the same direction with suggestive evidence of association (P<0.05; not FDR adjusted), then the association was considered shared. If PHET<0.01 and the OR was in the same or opposite directions without at least suggestive evidence of association in both populations (P<0.05), then the association was considered ancestry-specific and driven by the ancestry with the significant association (PFDR<0.05). Finally, if PHET<0.01 but the associations were significant and in opposite directions, the association was considered shared (noting the ancestry-specific direction of the associations). Graphpad PRISM 8.0 was used to perform mean, 95% confidence intervals and unpaired t-test with Welch's correction.

Genomic functional categories were determined as follows. The Variant Effect Predictor (VEP) tool available on the Ensembl genome browser 93 (https://www.ensembl.org) was used for annotation information to specify SNPs located within non-coding regions, including micro (mi) RNAs, long non-coding (Inc) RNAs, introns and intergenic regions. Regulatory regions include transcription factor binding sites (TFBS), promoters, enhancers, repressors, promoter flanking regions and open chromatin. Coding regions were broken down further and include 5'UTRs, 3'UTRs, synonymous and nonsynonymous (missense and nonsense) mutations. The online resource tool HaploReg (version 4.1; pubs.broadinstitute.org/mammals/haploreg/haploreg.php) (Ward and Kellis 2016) were also used to identify DNA features, regulatory elements and assess regulatory potential.

Differential expression analysis of E-Genes was performed as follows. Predicted genes were compared to multiple differential expression datasets, as summarized in Supplementary Data 8. These datasets include the log-fold changes of all genes with significant (FDR<0.2) differential expression in whole blood (WB), peripheral blood mononuclear cells (PBMC), B cells, T cells, myeloid cells, synovium, skin, kidney glomerulus (G), and kidney tubulointerstitium (TI). The FDR was selected a priori to avoid excluding false negatives from the analysis. Cohorts are SLE vs. control (CTL) unless noted otherwise. Additional cohorts include SLE synovium vs. oseteoarthritis (OA) synovium, discoid lupus erythematosus (DLE) skin vs. control skin and subacute cutaneous lupus erythematosus (CLE) skin vs. CTL skin. Datasets include GSE88884 (Illuminate 1 and 2), GSE49454, GSE22908, GSE61635, GSE29536, GSE39088, GSE50772, FDABMC3, EMTAB2713, GSE10325, GSE4588, GSE38351, GSE36700, GSE52471, GSE72535, GSE81071 and GSE32591.

Functional gene set analysis and identification of upstream regulators (UPRs) were performed as follows. For both ancestral groups, predicted gene lists were examined using Biologically Informed Gene Clustering (BIG-C; version 4.4). BIG-C is a custom functional clustering tool developed to annotate the biological meaning of large lists of genes. Genes are sorted into 54 categories based on their most likely biological function and/or cellular localization based on information from multiple online tools and databases including UniProtKB/Swiss-Prot, gene ontology (GO) Terms, MGI database, KEGG pathways, NCBI, PubMed, and the Interactome, and has been previously described (Catalina, Bachali, et al. 2019; Catalina, Owen, et al. 2019).

I-Scope is a custom clustering tool used to identify immune infiltrates in large gene datasets, and has been described previously (Ren et al. 2019). Briefly, I-Scope was created through an iterative search of more than 17,000 genes identified in more than 50 microarray datasets. These genes were researched for immune cell specific expression in 30 hematopoietic sub-categories: T cells, regulatory T cells, activated T cells, anergic cells, CD4 T cells, CD8 T cells, gamma-delta T cells, NK/NKT cells, T & B cells, B cells, activated B cells, T &B & monocytes, monocytes & B cells, MHC Class II expressing cells, monocyte dendritic cells, dendritic cells, plasmacytoid dendritic cells, Langerhans cells, myeloid cells, plasma cells, erythrocytes, neutrophils, low density granulocytes, granulocytes, platelets, and all hematopoietic stem cells.

Enrichment of GO Biological Processes (BP) using the Database for Annotation, Visualization and Integrated Discovery (DAVID; david.ncifcrf.gov) and the Ingenuity Pathway Analysis (IPA; www.qiagenbioinformatics.com) platform provided additional genetic pathway identification. IPA upstream regulator (UPR) analysis was also used to identify potential transcription factors, cytokines, chemokines, etc. that can contribute to the observed gene expression pattern in the input dataset.

Network analysis and visualization were performed as follows. Visualization of protein-protein interaction and relationships between genes within datasets was done using Cytoscape (version 3.6.1) software. Briefly, STRING (version 1.3.2) generated networks were imported into Cytoscape (version 3.6.1) and partitioned with MCODE via the clusterMaker2 (version 1.2.1) plugin.

Gene set variation analysis (GSVA). The GSVA (Hänzelmann, Castelo, and Guinney 2013) (V1.25.0) software package for R/Bioconductor and has been described previously (Labonte et al. 2018; Catalina, Bachali, et al. 2019). Briefly, GSVA is a non-parametric, unsupervised method for estimating the variation of pre-defined gene sets in patient and control samples of microarray expression datasets. The input for the GSVA algorithm was a gene expression matrix of log 2 microarray of expression values and a collection of pre-defined gene signatures. Enrichment scores (GSVA scores) were calculated non-parametrically using a Kolmogorov-Smirnoff (KS)-like random walk statistic and a negative value for each gene set. EA and AA SNP-predicted genes were used to create GSVA gene signatures (official gene symbols for each signature are listed in Supplementary Data 15). In the case of leukotriene biosynthesis, cell cycle, ubiquitylation and sumoylation, apoptosis signaling and nuclear receptor signaling and PKA signaling, genes were initially identified following protein-protein interaction network construction and MCODE clustering. Cluster identity was determined by BIG-C and/or IPA canonical pathway analysis, where each cluster was used as a GSVA probe. Gene signatures for diapedesis, TH1 activation pathway, unfolded protein and stress, T cell exhaustion and SLE in B cell signaling were all informed by established IPA canonical pathways. The signature for lysosome was derived from the Lysosome BIG-C category. All interferon and cytokine signatures (core IFN, IFNB1, IFNA2, IFNW, IFNG, IL12 and TNF) have been described previously (Catalina, Bachali, et al. 2019). Metabolic signatures for oxidative phosphorylation and glycolysis were based on literature mining and established IPA canonical pathways. Enrichment of each signature was examined in EA and AA SLE patients and healthy control whole blood from GSE 88884. Differences between controls and SLE patient GSVA enrichment scores were determined using the Welch's t-test for unequal variances in Graphpad PRISM 8.0.

Drug candidate identification and CoLT scoring were performed as follows. Drug candidates were identified using LINCS (lincsproject.org), STITCH (version 5.0; http://stitch.embl.de) and IPA. Each of these tools includes either a programmatic method of matching existing therapeutics to their targets or else is a list of drugs and targets for achieving the same end. In addition to identifying drugs targeting predicted genes directly, these tools were also used to identify drugs targeting select upstream regulators. Where information was available, drugs were assessed by CoLT scoring to rank potential drug candidates for repositioning in SLE as previously described (Grammer et al. 2016).

Data availability is as follows. All microarray datasets listed in this publication are available on the NCBI's database Gene Expression Omnibus (GEO) (www.ncbi.nlm.nih.gov/geo/).

Figure Legends

FIGS. 55A-55D. Mapping the functional genes predicted by SLE-associated SNPs. (a) Distribution of genomic functional categories for all ancestry-specific non-HLA associated SLE SNPs. (b) Functional SNP-associated genes are derived from 4 sources including regulatory elements (T-Genes), eQTL analysis (E-Genes), coding regions (C-Genes) and proximal gene-SNP annotation (P-Genes). Venn diagram depicting the overlap of all SLE-associated SNPs (c) and all predicted E-, T-, P- and C-Genes (d).

FIGS. 56A-56D. Functional characterization of SNP-associated genes. (a) Ancestry-dependent and independent SNP-predicted genes were analyzed to determine enrichment using functional definitions from the BIG-C (Biologically Informed Gene Clustering) annotation library. E-T- and C-Genes were analyzed together; P-Genes were examined separately. Enrichment was defined as any category with an odds ratio (OR) >1 and −log 10(p-value) >1.33. (b-c) Heatmap visualization of the top five significant IPA canonical pathways and gene ontogeny (GO) terms for each gene list (E-T-C-Genes and P-Genes) organized by ancestry. Top pathways with −log 10(p-value) >1.33 are listed. (d) I-Scope hematopoietic cell enrichment defined as any category with an OR >1, indicated by the dotted line, and −log 10(p-value) >1.33 indicated by color scale.

FIGS. 57A-57E. Cluster metastructures for SLE-predicted and randomly generated genes. (a-d) Cluster metastructures were generated based on PPI networks, clustered using MCODE and visualized in CytoScape. Size indicates the number of genes per cluster, edge weight indicates the number of inter-cluster connections and color indicates the number of intra-cluster connections. Random gene networks (large: 1033 genes; small 538 genes) were clustered along side networks for E-T-C-Genes and P-Genes. Functional enrichment for each cluster was determined using BIG-C. (e) Quantitation of cluster size, intra-cluster connections, inter-cluster connections and the percent of genes incorporated into each network are displayed. E-T-C-Genes were compared to the large random network; P-Genes were compared to the small random network. Error bars represent the 95% confidence interval; asterisks (*) indicate a p-value <0.05 using Welch's t-test.

FIGS. 58A-58C. Comparison of EA, AA and shared SNP-associated genes with SLE differential expression datasets. SNP-associated genes were matched with SLE differential expression (DE) data and organized by ancestry. (a-c) shows the fold-change variation of EA, AA and shared genes. Heatmaps are organized by BIG-C category. Enriched categories indicated with an asterisk. Enrichment was defined as any category with OR >1 and −log 10(p-value) >1.33.

FIGS. 59A-59B. Key pathways determined by EA genes and upstream regulators. (a) Differentially expressed EA genes and their upstream regulators (UPRs) were used to create STRING-based PPI networks. EA genes and transcription factors identified as UPRs are indicated. Clusters were generated via CytoScape using the MCODE plugin. (b) Top IPA canonical pathways representing individual clusters and enriched (OR >1, p-value <0.05) BIG-C categories are listed; heatmap depicts the −log (p-value) for significant IPA pathways. Unique pathways are indicated by asterisks. Predicted EA genes and select drugs acting on gene targets and pathways are listed. CoLT scores (−16-+11) are in superscript; # denotes FDA-approved drugs, ^ denotes drugs in development. Standard of care (SOC).

Figure 60A:
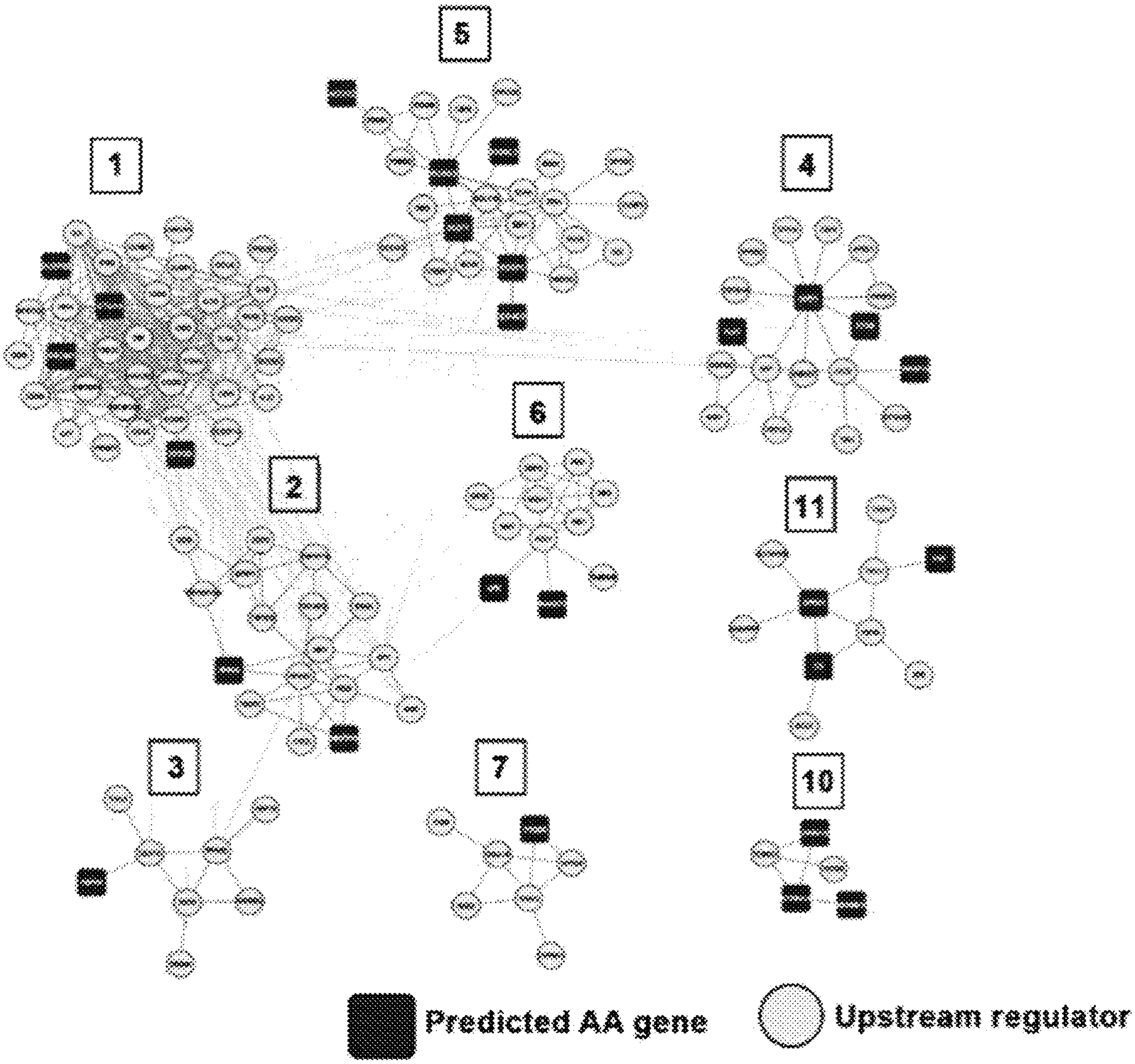
FIGS. 60A-60B show key pathways determined by AA genes and upstream regulators. (a) Differentially expressed AA genes and their upstream regulators (UPRs) were used to create STRING-based PPI networks. DE AA genes identified as UPRs are indicated. Clusters were generated via CytoScape using the MCODE plugin. (b) Top IPA canonical pathways representing individual clusters and enriched (OR >1, p-value <0.05) BIG-C categories are listed; heatmap depicts the −log (p-value) for significant IPA pathways. Unique pathways are indicated by asterisks. Predicted AA genes and select drugs acting on gene targets and pathways are listed. CoLT scores (−16-+11) are in superscript; # denotes FDA-approved drugs; ^ denotes drugs in development. Standard of care (SOC).
Figure 60B:
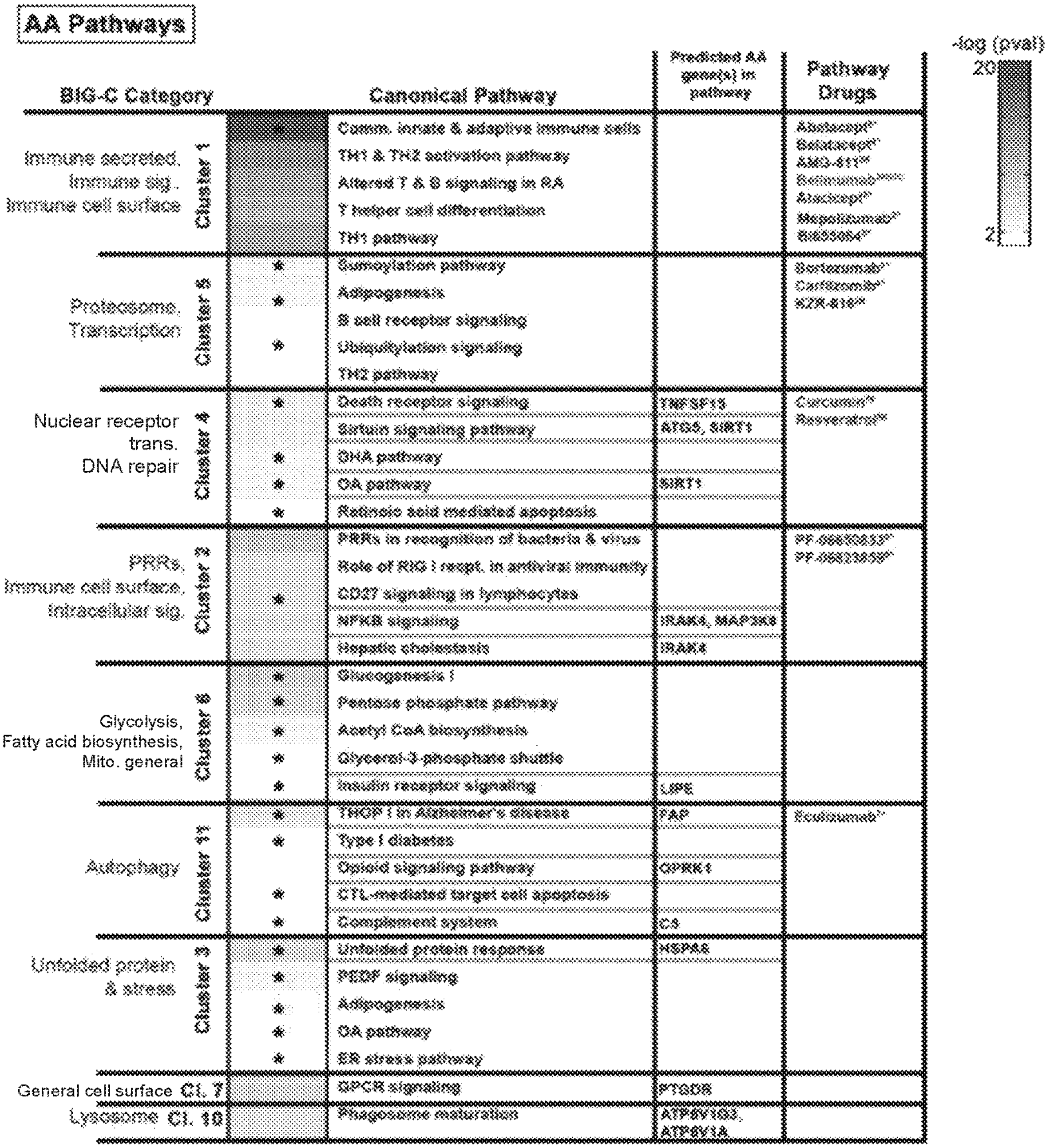

FIGS. 60A-60B. Key pathways determined by AA genes and upstream regulators. (a) Differentially expressed AA genes and their upstream regulators (UPRs) were used to create STRING-based PPI networks. DE AA genes identified as UPRs are indicated. Clusters were generated via CytoScape using the MCODE plugin. (b) Top IPA canonical pathways representing individual clusters and enriched (OR >1, p-value <0.05) BIG-C categories are listed; heatmap depicts the −log (p-value) for significant IPA pathways. Unique pathways are indicated by asterisks. Predicted AA genes and select drugs acting on gene targets and pathways are listed. CoLT scores (−16-+11) are in superscript; # denotes FDA-approved drugs; ^ denotes drugs in development. Standard of care (SOC).

Figure 61A:
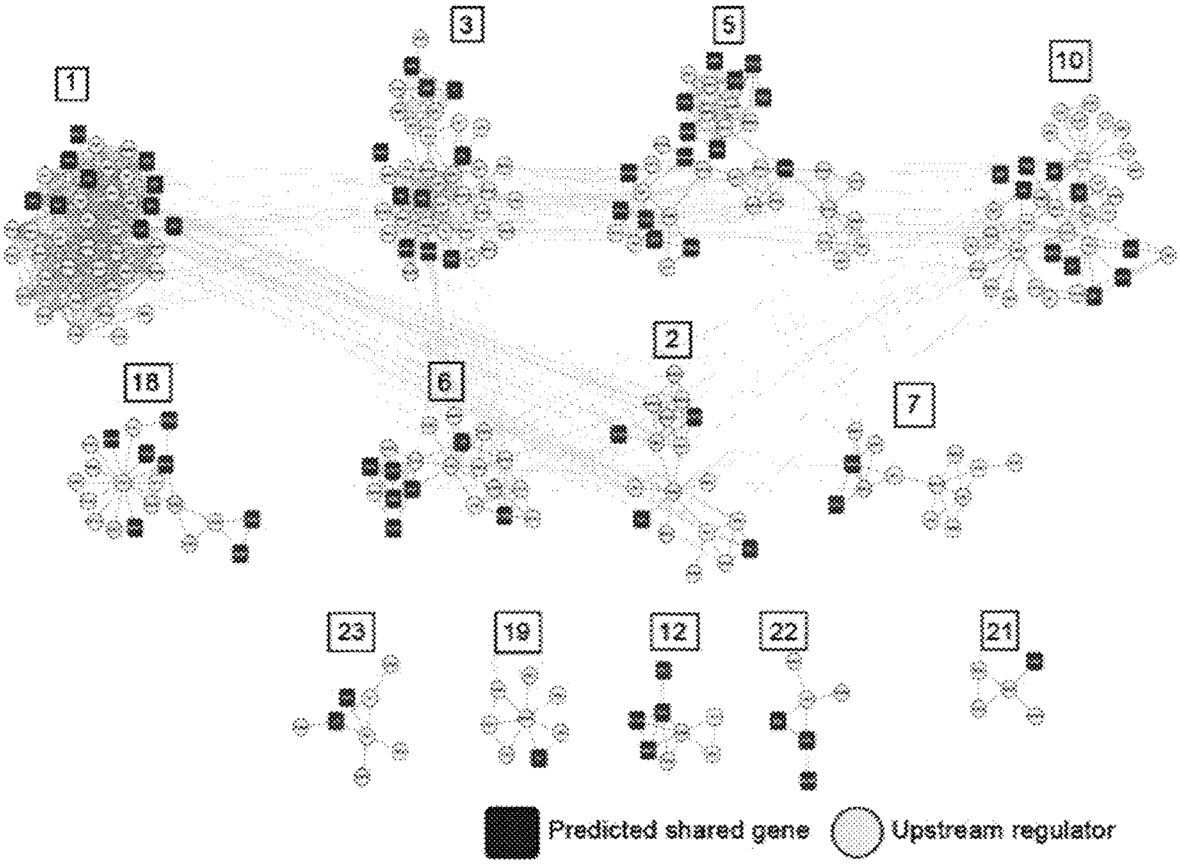

FIGS. 61A-61B. Key pathways determined by shared genes and upstream regulators. (a) Differentially expressed shared genes and their upstream regulators (UPRs) were used to create STRING-based PPI networks. DE shared genes and transcription factors identified as UPRs and indicated. Clusters were generated via CytoScape using the MCODE plugin. (b) Top IPA canonical pathways representing individual clusters and enriched (OR >1, p-value <0.05) BIG-C categories are listed; heatmap depicts the −log (p-value) for significant IPA pathways. Unique pathways are indicated by asterisks. Predicted shared genes and select drugs acting on gene targets and pathways are listed. CoLT scores (−16-+11) are in superscript; # denotes FDA-approved drugs; ^ denotes drugs in development. Standard of care (SOC).

Figure 62:
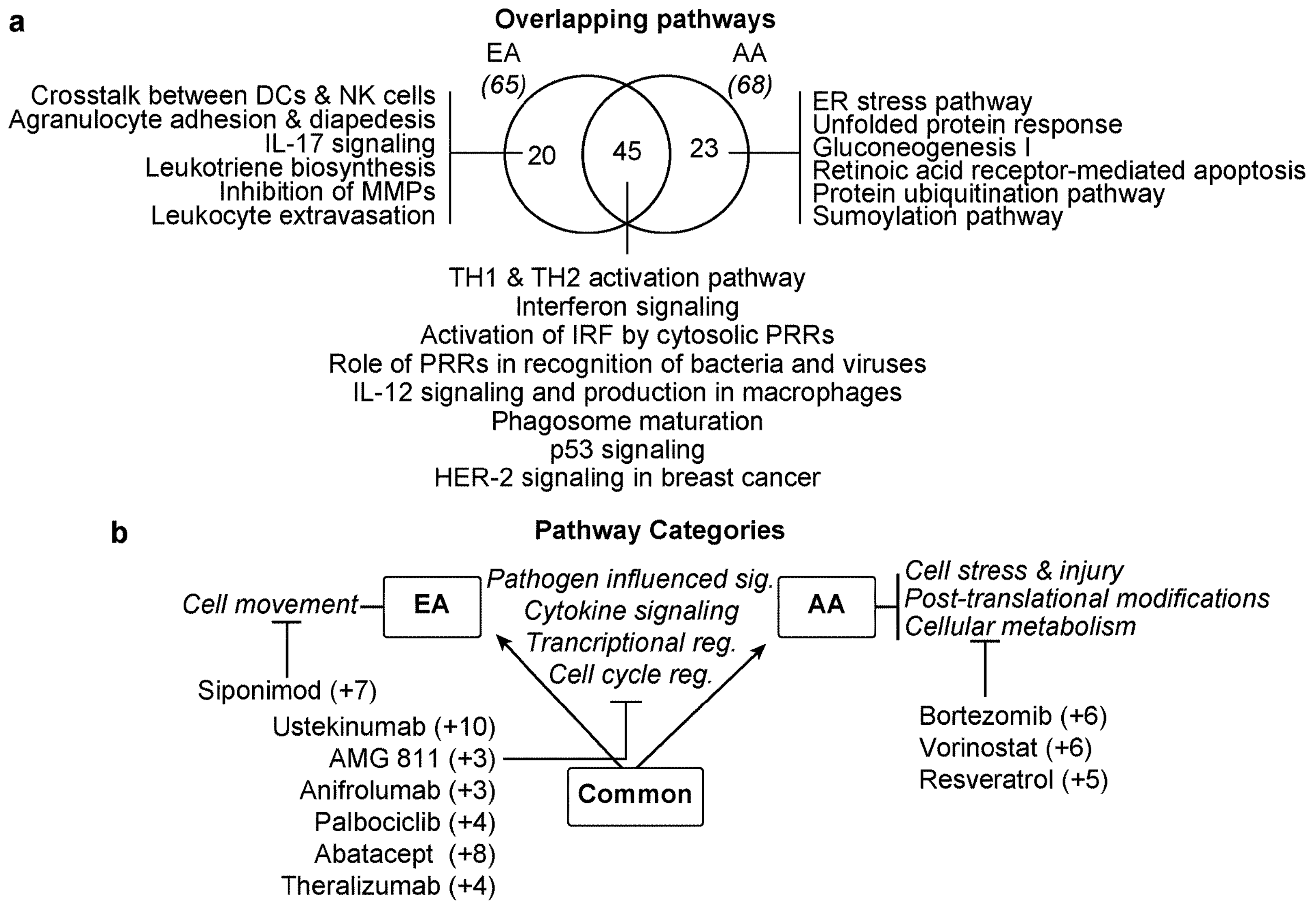
FIG. 62 shows overlapping pathways and categories defining the EA and AA gene sets. (a) Venn diagram showing the number of overlapping pathways between EA and AA genes and their UPRs. Representative IPA canonical pathways are indicated. (b) Overall pathway categories are defined; shared categories are between the arrows, EA-specific (left) and AA-specific categories (right) are indicated. Select drugs at points of intervention are noted. Superscript denotes CoLT score. (c-f) GSVA enrichment scores were calculated for ancestry-specific and independent gene signatures in patient WB (GSE 88885). (c) GSVA signature scores distinguishing EA SLE patients from AA patients and/or healthy controls, (d) signature scores distinguishing AA SLE patients from EA patients or controls, (e) signature scores separating SLE patients (EA and AA) from controls, and (f) signature scores separating SLE patients (EA and AA) from controls and that are additionally elevated in AA patients compared to EA patients. Asterisks (*) indicate a p-value <0.05 using Welch's t-test comparing SLE to control; ^ indicates a p-value <0.05 using Welch's t-test comparing EA to AA.
Figure 62:
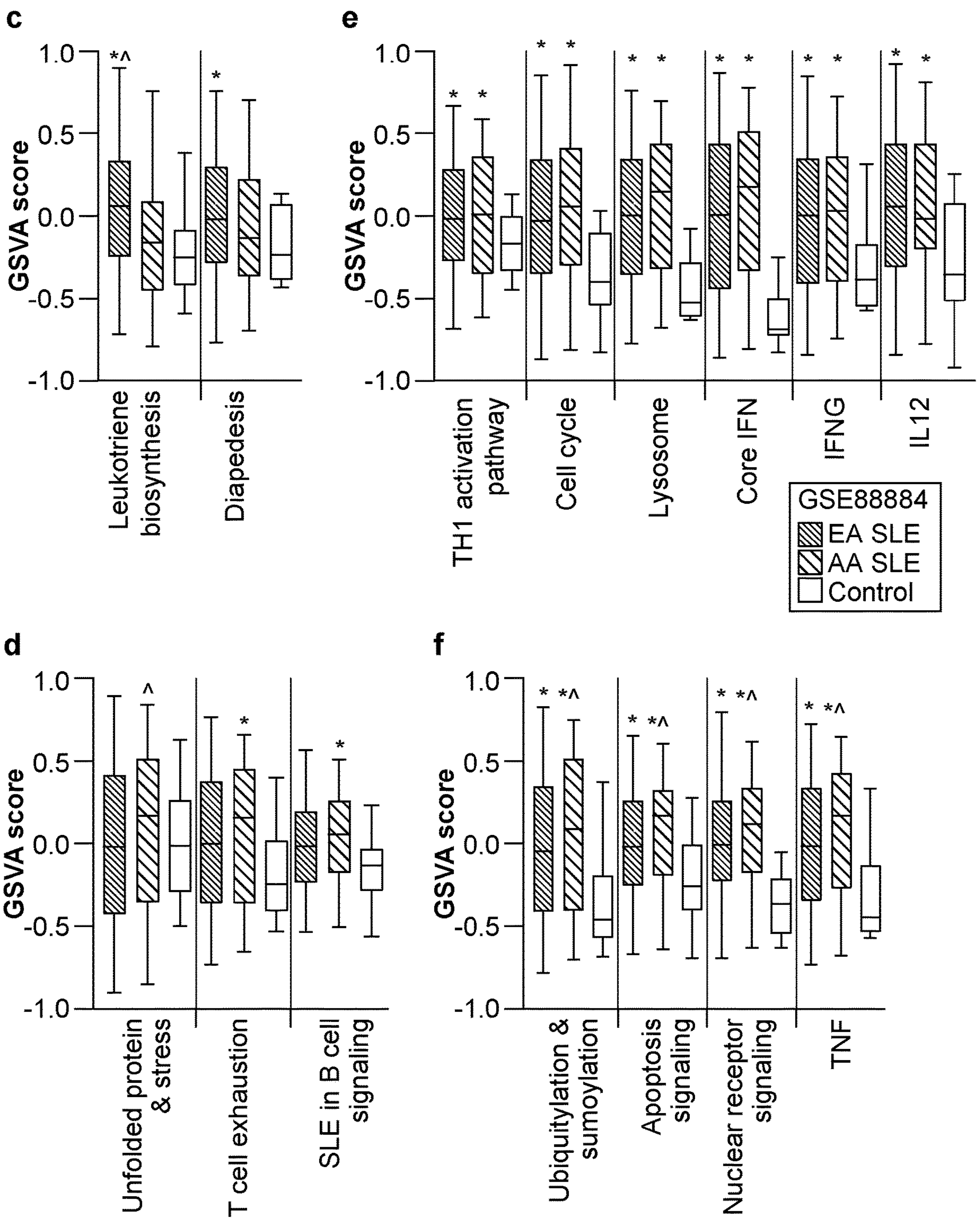

FIG. 62. Overlapping pathways and categories defining the EA and AA gene sets. (a) Venn diagram showing the number of overlapping pathways between EA and AA genes and their UPRs. Representative IPA canonical pathways are indicated. (b) Overall pathway categories are defined; shared categories are between the arrows, EA-specific (left) and AA-specific categories (right) are indicated. Select drugs at points of intervention are noted. Superscript denotes CoLT score. (c-f) GSVA enrichment scores were calculated for ancestry-specific and independent gene signatures in patient WB (GSE 88885). (c) GSVA signature scores distinguishing EA SLE patients from AA patients and/or healthy controls, (d) signature scores distinguishing AA SLE patients from EA patients or controls, (e) signature scores separating SLE patients (EA and AA) from controls, and (f) signature scores separating SLE patients (EA and AA) from controls and that are additionally elevated in AA patients compared to EA patients. Asterisks (*) indicate a p-value <0.05 using Welch's t-test comparing SLE to control; ^ indicates a p-value <0.05 using Welch's t-test comparing EA to AA.

FIG. 63. SNPs impact multiple E-Genes within a functional protein-interaction based molecular network. Protein-protein interaction networks and clusters were generated via CytoScape using the STRING and MCODE plugins. The network was constructed of SNP-predicted E-Genes; grouped E-Genes linked to one SNP are indicated with boxing.

FIGS. 64A-64F. Functional characterization of predicted genes. (a) Ancestry-dependent and independent E-, T- and C-Genes were independently analyzed by discovery method (source) to determine enrichment using functional definitions from the BIG-C (Biologically Informed Gene Clustering) annotation library. Enrichment was defined as any category with an odds ratio (OR) >1 and −log 10(p-value) >1.33. (b-f) Heatmap visualization of the top five significant IPA canonical pathways (b-d) and the top five significant gene ontogeny (GO) terms (d-f) for E- and T-Genes organized by ancestry. Due to the smaller number of C-Genes, this gene set was analyzed together. Top pathways with −log 10(p-value) >1.33 are listed.

FIG. 65. Protein-protein interaction-based clustering of predicted EA, AA and shared genes determined by source. PPIs and clusters were generated via CytoScape using the STRING and MCODE plugins. Clusters are determined by the strength of protein-protein interactions, calculated by pooling information from publicly available literature.

FIG. 66. GSVA enrichment scores for interferon and metabolic pathways. GSVA signature scores distinguishing SLE patients from healthy controls using gene modules defining IFNA2, IFNB1, IFNW1, oxidative phosphorylation, glycolysis and PKA signaling. Asterisks (*) indicate a p-value <0.05 using Welch's t-test comparing SLE to control.

FIGS. 67A-67D. Functional characterization of SNP-associated genes. (a) Venn diagram showing the overall overlap between EA and AA SNP-predicted genes. (b) Ancestry-dependent genes (1676 EA; 725 AA) were analyzed to determine enrichment using functional definitions from the BIG-C annotation library. Random genes (500) were analyzed alongside SNP-predicted genes. E-T- and C-Genes were analyzed together; P-Genes were examined separately. Enrichment was defined as any category with an odds ratio (OR) >1 and −log 10(p-value) >1.33. (c-d) Heatmap visualization of the top five significant IPA canonical pathways and gene ontogeny (GO) terms for each gene list (E-T-C-Genes and P-Genes) organized by ancestry. Top pathways with −log 10(p-value) >1.33 are listed.

REFERENCES

[Adzhubei, Ivan, Daniel M. Jordan, and Shamil R. Sunyaev. 2013. "Predicting Functional Effect of Human Missense Mutations Using PolyPhen-2." Current Protocols in Human Genetics, no. SUPPL.76. https://doi.org/10.1002/0471142905.hg0720s76.] is incorporated by reference herein in its entirety.

[Alarcón-Segovia, Donato, Marta E. Alarcón-Riquelme, Mario H. Cardiel, Francisco Caeiro, Loreto Massardo, Antonio R. Villa, and Bernardo A. Pons-Estel. 2005. "Familial Aggregation of Systemic Lupus Erythematosus, Rheumatoid Arthritis, and Other Autoimmune Diseases in 1,177 Lupus Patients from the GLADEL Cohort." Arthritis and Rheumatism 52 (4): 1138-47. https://doi.org/10.1002/art.20999.] is incorporated by reference herein in its entirety.

[Alexander, Tobias, Ramona Sarfert, Jens Klotsche, Anja A. Kühl, Andrea Rubbert-Roth, Hannes Martin Lorenz, Jürgen Rech, et al. 2015. "The Proteasome Inhibitior Bortezomib Depletes Plasma Cells and Ameliorates Clinical Manifestations of Refractory Systemic Lupus Erythematosus." Annals of the Rheumatic Diseases 74 (7): 1474-78. https://doi.org/10.1136/annrheumdis-2014-206016.] is incorporated by reference herein in its entirety.

[Aoki, Masayo, Hiroaki Aoki, Rajesh Ramanathan, Nitai C. Hait, and Kazuaki Takabe. 2016. "Sphingosine-1-Phosphate Signaling in Immune Cells and Inflammation: Roles and Therapeutic Potential." Mediators of Inflammation 2016. https://doi.org/10.1155/2016/8606878.] is incorporated by reference herein in its entirety.

[Banchereau, Romain, Seunghee Hong, Brandi Cantarel, Nicole Baldwin, Jeanine Baisch, Michelle Edens, Alma-Martina Cepika, et al. 2016. "Personalized Immunomonitoring Uncovers Molecular Networks That Stratify Lupus Patients." Cell 165 (6): 1548-50. https://doi.org/10.1016/j.cell.2016.05.057.] is incorporated by reference herein in its entirety.

[Barnado, April, Robert J Carroll, Carolyn Casey, Lee Wheless, Joshua C Denny, and Leslie J Crofford. 2018. "Phenome-Wide Association Study Identifies Marked Increased in Burden of Comorbidities in African Americans with Systemic Lupus Erythematosus." Arthritis Research & Therapy 20 (1): 69. https://doi.org/10.1186/s13075-018-1561-8.] is incorporated by reference herein in its entirety.

[Bentham, James, David L. Morris, Deborah S. Cunninghame Graham, Christopher L. Pinder, Philip Tombleson, Timothy W. Behrens, Javier Martin, et al. 2015. "Genetic Association Analyses Implicate Aberrant Regulation of Innate and Adaptive Immunity Genes in the Pathogenesis of Systemic Lupus Erythematosus." Nature Genetics. https://doi.org/10.1038/ng.3434.] is incorporated by reference herein in its entirety.

[Cannon, Maren E., and Karen L. Mohlke. 2018. "Deciphering the Emerging Complexities of Molecular Mechanisms at GWAS Loci." American Journal of Human Genetics. Cell Press. https://doi.org/10.1016/j.ajhg.2018.10.001.] is incorporated by reference herein in its entirety.

[Cartier, Andreane, and Timothy Hla. 2019. "Sphingosine 1-Phosphate: Lipid Signaling in Pathology and Therapy." Science. American Association for the Advancement of Science. https://doi.org/10.1126/science.aar5551.] is incorporated by reference herein in its entirety.

[Catalina M, Bachali P, Yeo A, Geraci N, Petri M, Grammer A, Lipsky P. 2019. "2019 ACR/ARP Annual Meeting Abstract Supplement." Arthritis & Rheumatology (Hoboken, N.J.) 71 (October): 1-5362. https://doi.org/10.1002/art.41108.] is incorporated by reference herein in its entirety.

[Catalina, Michelle D., Prathyusha Bachali, Nicholas S. Geraci, Amrie C. Grammer, and Peter E. Lipsky. 2019. "Gene Expression Analysis Delineates the Potential Roles of Multiple Interferons in Systemic Lupus Erythematosus." Communications Biology 2 (1). https://doi.org/10.1038/s42003-019-0382-x.] is incorporated by reference herein in its entirety.

[Catalina, Michelle D., Katherine A. Owen, Adam C. Labonte, Amrie C. Grammer, and Peter E. Lipsky. 2019. "The Pathogenesis of Systemic Lupus Erythematosus: Harnessing Big Data to Understand the Molecular Basis of Lupus." Journal of Autoimmunity, December, 102359. https://doi.org/10.1016/j.jaut.2019.102359.] is incorporated by reference herein in its entirety.

[Choi, Yongwook, Gregory E Sims, Sean Murphy, Jason R Miller, and Agnes P Chan. 2012. "Predicting the Functional Effect of Amino Acid Substitutions and Indels." PloS One 7 (10): e46688. https://doi.org/10.1371/journal.pone.0046688.] is incorporated by reference herein in its entirety.

[Corradin, Olivia, and Peter C. Scacheri. 2014. "Enhancer Variants: Evaluating Functions in Common Disease." Genome Medicine. BioMed Central Ltd. https://doi.org/10.1186/s13073-014-0085-3.] is incorporated by reference herein in its entirety.

[Cortes, Adrian, and Matthew A. Brown. 2011. "Promise and Pitfalls of the Immunochip." Arthritis Research and Therapy. https://doi.org/10.1186/ar3204.] is incorporated by reference herein in its entirety.

[Eckschlager, Tomas, Johana Plch, Marie Stiborova, and Jan Hrabeta. 2017. "Histone Deacetylase Inhibitors as Anticancer Drugs." International Journal of Molecular Sciences. MDPI AG. https://doi.org/10.3390/ijms18071414.] is incorporated by reference herein in its entirety.

[Emilsson, Valur, Gudmar Thorleifsson, Bin Zhang, Amy S Leonardson, Florian Zink, Jun Zhu, Sonia Carlson, et al. 2008. "Genetics of Gene Expression and Its Effect on Disease." Nature 452 (7186): 423-28. https://doi.org/10.1038/nature06758.] is incorporated by reference herein in its entirety.

[Faissner, Simon, and Ralf Gold. 2019. "Progressive Multiple Sclerosis: Latest Therapeutic Developments and Future Directions." Therapeutic Advances in Neurological Disorders. SAGE Publications Ltd. https://doi.org/10.1177/1756286419878323.] is incorporated by reference herein in its entirety.

[Fishilevich, Simon, Ron Nudel, Noa Rappaport, Rotem Hadar, Inbar Plaschkes, Tsippi Iny Stein, Naomi Rosen, et al. 2017. "GeneHancer: Genome-Wide Integration of Enhancers and Target Genes in GeneCards." Database: The Journal of Biological Databases and Curation 2017 (January). https://doi.org/10.1093/database/bax028.] is incorporated by reference herein in its entirety.

[Freedman, Barry I, Carl D Langefeld, Kelly K Andringa, Jennifer A Croker, Adrienne H Williams, Neva E Garner, Daniel J Birmingham, et al. 2014. "End-Stage Renal Disease in African Americans With Lupus Nephritis Is Associated With APOL1 Analysis and Interpretation of Data NIH Public Access." Arthritis Rheumatol 66 (2): 390-96. https://doi.org/10.1002/art.38220.] is incorporated by reference herein in its entirety.

[Furie, Richard, Michelle Petri, Omid Zamani, Ricard Cervera, Daniel J. Wallace, Dana Tegzová, Jorge Sanchez-Guerrero, et al. 2011. "A Phase III, Randomized, Placebo-Controlled Study of Belimumab, a Monoclonal Antibody That Inhibits B Lymphocyte Stimulator, in Patients with Systemic Lupus Erythematosus." Arthritis and Rheumatism 63 (12): 3918-30. https://doi.org/10.1002/art.30613.] is incorporated by reference herein in its entirety.

[Gajofatto, Alberto. 2017. "Spotlight on Siponimod and Its Potential in the Treatment of Secondary Progressive Multiple Sclerosis: The Evidence to Date." Drug Design, Development and Therapy. Dove Medical Press Ltd. https://doi.org/10.2147/DDDT.S122249.] is incorporated by reference herein in its entirety.

[Goulielmos, George N., Maria I. Zervou, Vassilis M. Vazgiourakis, Yogita Ghodke-Puranik, Alexandros Garyfallos, and Timothy B. Niewold. 2018. "The Genetics and Molecular Pathogenesis of Systemic Lupus Erythematosus (SLE) in Populations of Different Ancestry." Gene. Elsevier B. V. https://doi.org/10.1016/j.gene.2018.05.041.] is incorporated by reference herein in its entirety.

[Grammer, A. C., M. M. Ryals, S. E. Heuer, R. D. Robl, S. Madamanchi, L. S. Davis, B. Lauwerys, M. D. Catalina, and P. E. Lipsky. 2016. "Drug Repositioning in SLE: Crowd-Sourcing, Literature-Mining and Big Data Analysis." Lupus 25 (10): 1150-70. https://doi.org/10.1177/0961203316657437.] is incorporated by reference herein in its entirety.

[Hänzelmann, Sonja, Robert Castelo, and Justin Guinney. 2013. "GSVA: Gene Set Variation Analysis for Microarray and RNA-Seq Data." BMC Bioinformatics 14 (January). https://doi.org/10.1186/1471-2105-14-7.] is incorporated by reference herein in its entirety.

[Heberle, Henry, Vaz G. Meirelles, Felipe R. da Silva, Guilherme P. Telles, and Rosane Minghim. 2015. "InteractiVenn: A Web-Based Tool for the Analysis of Sets through Venn Diagrams." BMC Bioinformatics 16 (1). https://doi.org/10.1186/s12859-015-0611-3.] is incorporated by reference herein in its entirety.

[Kammer, Gary M. 2002. "Deficient Protein Kinase A in Systemic Lupus Erythematosus: A Disorder of T Lymphocyte Signal Transduction." In Annals of the New York Academy of Sciences, 968:96-105. New York Academy of Sciences. https://doi.org/10.1111/j.1749-6632.2002.tb04329.x.] is incorporated by reference herein in its entirety.

[Kammer, Gary M., Islam U. Khan, and Charles J. Malemud. 1994. "Deficient Type I Protein Kinase A Isozyme Activity in Systemic Lupus Erythematosus T Lymphocytes." Journal of Clinical Investigation 94 (1): 422-30. https://doi.org/10.1172/JCI117340.] is incorporated by reference herein in its entirety.

[Kappos, Ludwig, Amit Bar-Or, Bruce A. C. Cree, Robert J. Fox, Gavin Giovannoni, Ralf Gold, Patrick Vermersch, et al. 2018. "Siponimod versus Placebo in Secondary Progressive Multiple Sclerosis (EXPAND): A Double-Blind, Randomised, Phase 3 Study." The Lancet 391 (10127): 1263-73. https://doi.org/10.1016/S0140-6736 (18) 30475-6.] is incorporated by reference herein in its entirety.

[Labonte, Adam C, Brian Kegerreis, Nicholas S Geraci, Prathyusha Bachali, Sushma Madamanchi, Robert Robl, Michelle D Catalina, Peter E Lipsky, and Amrie C Grammer. 2018. "Identification of Alterations in Macrophage Activation Associated with Disease Activity in Systemic Lupus Erythematosus." PloS One 13 (12): e0208132. https://doi.org/10.1371/journal.pone.0208132.] is incorporated by reference herein in its entirety.

[Lam, Wing Y., and Deepta Bhattacharya. 2018. "Metabolic Links between Plasma Cell Survival, Secretion, and Stress." Trends in Immunology. Elsevier Ltd. https://doi.org/10.1016/j.it.2017.08.007.] is incorporated by reference herein in its entirety.

[Lamore, Raymond, Sapna Parmar, Khilna Patel, and Olga Hilas. 2012. "Belimumab (Benlysta): A Breakthrough Therapy for Systemic Lupus Erythematosus." P & T: A Peer-Reviewed Journal for Formulary Management 37 (4): 212-26. http://www.ncbi.nlm.nih.gov/pubmed/22593633.] is incorporated by reference herein in its entirety.

[Langefeld, Carl D., Hannah C. Ainsworth, Deborah S. Cunninghame Graham, Jennifer A. Kelly, Mary E. Comeau, Miranda C. Marion, Timothy D. Howard, et al. 2017. "Transancestral Mapping and Genetic Load in Systemic Lupus Erythematosus." Nature Communications 8 (July). https://doi.org/10.1038/ncomms16021.] is incorporated by reference herein in its entirety.

[Lightfoot, Yaima L, Luz P Blanco, and Mariana J Kaplan. 2017. "Metabolic Abnormalities and Oxidative Stress in Lupus." Current Opinion in Rheumatology 29 (5): 442-49. https://doi.org/10.1097/BOR.0000000000000413.] is incorporated by reference herein in its entirety.

[Menard, Laurence C., Sium Habte, Waldemar Gonsiorek, Deborah Lee, Dana Banas, Deborah A. Holloway, Nataly Manjarrez-Orduno, et al. 2016. "B Cells from African American Lupus Patients Exhibit an Activated Phenotype." JCI Insight 1 (9). https://doi.org/10.1172/jci.insight.87310.] is incorporated by reference herein in its entirety.

[Merrill, Joan T, C Michael Neuwelt, Daniel J Wallace, Joseph C Shanahan, Kevin M Latinis, James C Oates, Tammy O Utset, et al. 2010. "Efficacy and Safety of Rituximab in Moderately-to-Severely Active Systemic Lupus Erythematosus: The Randomized, Double-Blind, Phase II/III Systemic Lupus Erythematosus Evaluation of Rituximab Trial." Arthritis and Rheumatism 62 (1): 222-33. https://doi.org/10.1002/art.27233.] is incorporated by reference herein in its entirety.

[Mi, Huaiyu, Xiaosong Huang, Anushya Muruganujan, Haiming Tang, Caitlin Mills, Diane Kang, and Paul D. Thomas. 2017. "PANTHER Version 11: Expanded Annotation Data from Gene Ontology and Reactome Pathways, and Data Analysis Tool Enhancements." Nucleic Acids Research 45 (D1): D183-89. https://doi.org/10.1093/nar/gkw1138.] is incorporated by reference herein in its entirety.

[Morloy, Michael, Cliona M. Molony, Teresa M. Weber, James L. Devlin, Kathryn G. Ewens, Richard S. Spielman, and Vivian G. Cheung. 2004. "Genetic Analysis of Genome-Wide Variation in Human Gene Expression." Nature 430 (7001): 743-47. https://doi.org/10.1038/nature02797.] is incorporated by reference herein in its entirety.

[Morris, David L, Yujun Sheng, Yan Zhang, Yong-Fei Wang, Zhengwei Zhu, Philip Tombleson, Lingyan Chen, et al. 2016. "Genome-Wide Association Meta-Analysis in Chinese and European Individuals Identifies Ten New Loci Associated with Systemic Lupus Erythematosus." Nature Genetics 48 (8): 940-46. https://doi.org/10.1038/ng.3603.] is incorporated by reference herein in its entirety.

[Navarra, Sandra V., Renato M. Guzmán, Alberto E. Gallacher, Stephen Hall, Roger A. Levy, Renato E. Jimenez, Edmund K. M. Li, et al. 2011. "Efficacy and Safety of Belimumab in Patients with Active Systemic Lupus Erythematosus: A Randomised, Placebo-Controlled, Phase 3 Trial." The Lancet 377 (9767): 721-31. https://doi.org/10.1016/S0140-6736 (10) 61354-2.] is incorporated by reference herein in its entirety.

[Navid, Fatemeh, and Robert A. Colbert. 2017. "Causes and Consequences of Endoplasmic Reticulum Stress in Rheumatic Disease." Nature Reviews Rheumatology. Nature Publishing Group. https://doi.org/10.1038/nrrheum.2016.192.] is incorporated by reference herein in its entirety.

[Ren, Jingjing, Michelle D Catalina, Kristin Eden, Xiaofeng Liao, Kaitlin A Read, Xin Luo, Ryan P McMillan, et al. 2019. "Selective Histone Deacetylase 6 Inhibition Normalizes B Cell Activation and Germinal Center Formation in a Model of Systemic Lupus Erythematosus." Frontiers in Immunology 10 (OCT): 2512. https://doi.org/10.3389/fimmu.2019.02512.] is incorporated by reference herein in its entirety.

[Rovin, Brad H., Richard Furie, Kevin Latinis, R. John Looney, Fernando C. Fervenza, Jorge Sanchez-Guerrero, Romeo Maciuca, et al. 2012. "Efficacy and Safety of Rituximab in Patients with Active Proliferative Lupus Nephritis: The Lupus Nephritis Assessment with Rituximab Study." Arthritis and Rheumatism 64 (4): 1215-26. https://doi.org/10.1002/art.34359.] is incorporated by reference herein in its entirety.

[Rullo, Ornella Josephine, and Betty P Tsao. 2013. "Recent Insights into the Genetic Basis of Systemic Lupus Erythematosus." Annals of the Rheumatic Diseases 72 Suppl 2 (April): ii56-61. https://doi.org/10.1136/annrheumdis-2012-202351.] is incorporated by reference herein in its entirety.

[Schadt, Eric E., Stephanie A. Monks, Thomas A. Drake, Aldons J. Lusis, Nam Che, Veronica Colinayo, Thomas G. Ruff, et al. 2003. "Genetics of Gene Expression Surveyed in Maize, Mouse and Man." Nature 422 (6929): 297-302. https://doi.org/10.1038/nature01434.] is incorporated by reference herein in its entirety.

[Sim, Ngak Leng, Prateek Kumar, Jing Hu, Steven Henikoff, Georg Schneider, and Pauline C. Ng. 2012. "SIFT Web Server: Predicting Effects of Amino Acid Substitutions on Proteins." Nucleic Acids Research 40 (W1). https://doi.org/10.1093/nar/gks539.] is incorporated by reference herein in its entirety.

[Stavast, Christiaan J., and Stefan J. Erkeland. 2019. "The Non-Canonical Aspects of MicroRNAs: Many Roads to Gene Regulation." Cells 8 (11): 1465. https://doi.org/10.3390/cells8111465.] is incorporated by reference herein in its entirety.

[Stranger, Barbara E, Stephen B Montgomery, Antigone S Dimas, Leopold Parts, Oliver Stegle, Catherine E Ingle, Magda Sekowska, et al. 2012. "Patterns of Cis Regulatory Variation in Diverse Human Populations." PLOS Genetics 8 (4): e1002639. https://doi.org/10.1371/journal.pgen.1002639.] is incorporated by reference herein in its entirety.

[Sun, Celi, Julio E Molineros, Loren L Looger, Xu-Jie Zhou, Kwangwoo Kim, Yukinori Okada, Jianyang Ma, et al. 2016. "High-Density Genotyping of Immune-Related Loci Identifies New SLE Risk Variants in Individuals with Asian Ancestry." Nature Genetics 48 (3): 323-30. https://doi.org/10.1038/ng.3496.] is incorporated by reference herein in its entirety.

["The Genotype-Tissue Expression (GTEx) Project." n.d. Accessed Nov. 7, 2019. https://www.ncbi.nlm.nih.gov/pmc/articles/PMC4010069/.] is incorporated by reference herein in its entirety.

[Vaser, Robert, Swarnaseetha Adusumalli, Sim Ngak Leng, Mile Sikic, and Pauline C. Ng. 2016. "SIFT Missense Predictions for Genomes." Nature Protocols 11 (1): 1-9. https://doi.org/10.1038/nprot.2015.123.] is incorporated by reference herein in its entirety.

[Wang, Jing, Xizhen Dai, Lynne D. Berry, Joy D. Cogan, Qi Liu, and Yu Shyr. 2019. "HACER: An Atlas of Human Active Enhancers to Interpret Regulatory Variants." Nucleic Acids Research 47 (D1): D106-12. https://doi.org/10.1093/nar/gky864.] is incorporated by reference herein in its entirety.

[Ward, Lucas D., and Manolis Kellis. 2016. "HaploReg v4: Systematic Mining of Putative Causal Variants, Cell Types, Regulators and Target Genes for Human Complex Traits and Disease." Nucleic Acids Research 44 (D1): D877-81. https://doi.org/10.1093/nar/gkv1340.] is incorporated by reference herein in its entirety.

[Wehbi, Vanessa L., and Kjetil Tasken. 2016. "Molecular Mechanisms for CAMP-Mediated Immunoregulation in T Cells-Role of Anchored Protein Kinase a Signaling Units." Frontiers in Immunology. Frontiers Research Foundation. https://doi.org/10.3389/fimmu.2016.00222.] is incorporated by reference herein in its entirety.

[Westra, Harm Jan, Marjolein J. Peters, Tonu Esko, Hanieh Yaghootkar, Claudia Schurmann, Johannes Kettunen, Mark W. Christiansen, et al. 2013. "Systematic Identification of Trans EQTLs as Putative Drivers of Known Disease Associations." Nature Genetics 45 (10): 1238-43. https://doi.org/10.1038/ng.2756.] is incorporated by reference herein in its entirety.

[Williams, Edith M, Larisa Bruner, Alyssa Adkins, Caroline Vrana, Ayaba Logan, Diane Kamen, and James C Oates. 2016. "I Too, Am America: A Review of Research on Systemic Lupus Erythematosus in African-Americans." Lupus Science & Medicine 3 (1): e000144. https://doi.org/10.1136/lupus-2015-000144.] is incorporated by reference herein in its entirety.

[Zhang, Xiaopei, Wei Wang, Weidong Zhu, Jie Dong, Yingying Cheng, Zujun Yin, and Fafu Shen. 2019. "Mechanisms and Functions of Long Non-Coding RNAs at Multiple Regulatory Levels." International Journal of Molecular Sciences. MDPI AG. https://doi.org/10.3390/ijms20225573.] is incorporated by reference herein in its entirety.

Example 17: Analysis of Molecular Pathways Identified from SNPs Demonstrates Mechanistic Differences in SLE Patients of Asian and European Ancestry Systemic lupus erythematosus (SLE) may refer to a multi-organ autoimmune disorder with a prominent genetic component. Evidence may show that individuals of Asian-Ancestry (AS) experience the disease more severely, exhibiting increased renal involvement and tissue damage compared to European-Ancestry (EA) populations. In order to elucidate the mechanisms underlying elevated risk in this population, which may remain unclear, a comprehensive systems biology approach was applied, using methods and systems of the present disclosure, to all SNP associations detected with the Immunochip. This systems biology approach comprised using bioinformatics and pathway analysis tools to analyze SNP data to identify 3,450 ancestry-specific (e.g., specific to AS or EA) and trans-ancestry (e.g., not specific to AS or EA) genetic drivers of SLE. Gene associations were linked to upstream and downstream regulators using connectivity mapping, and predicted biological pathways were assessed for candidate drug targets. Pathways predicted by AS genes were determined to be enriched in processes related to tissue damage and repair, cell stress and immune cell trafficking; further, EA-associated pathways were determined to be driven by specific immune cell types, including cells of myeloid lineage, and T and B cells. To validate these findings, pathways predicted by summary genome-wide association data from Asian SLE patients were compared to those derived from AS Immunochip studies, and the results revealed remarkable similarity. Together, these analyses indicate the presence of fundamental differences in SLE-risk related molecular pathways, the majority of which are motivated by ancestral differences; further, these results indicate that novel drug candidates may be identified that differentially impact SLE patients of Asian ancestry and SLE patients of European ancestry.

Systemic lupus erythematosus (SLE) (OMIM: 152700) may be a complex autoimmune disease characterized by clinical and genetic heterogeneity. Evidence may demonstrate that individuals of Asian ancestry experience a greater burden of renal involvement, as well as elevated risk for infections and cardiovascular complications compared to their European-ancestry (EA) counterparts. In particular, lupus nephritis and end stage renal disease (LN/ESRD) may be severe complications of SLE that are more prevalent in patients of AS ancestry. While some of this variation may be accounted for by confounding environmental and/or socioeconomic factors, the mechanisms driving the differential impact of ancestry on SLE remain a key determinant of poor outcome in AS SLE.

Immunochip-based and genome-wide association (GWA) studies may reveal important ancestry-specific and trans-ancestral risk associations predisposing to disease development. For example, meta-analyses of European and Chinese GWAS data may indicate that the greater disease burden evident in East Asian populations is a consequence of altered risk variant frequencies. While such studies may enable a better understanding of the genetic architecture of SLE, they may focus on only the most significant associations and causal genes, and thereby fail to capture the totality of variation inherent in a given ancestral background. Furthermore, genetic analyses may be unable to provide a clear path toward novel therapeutic development. This is of particular concern with respect to AS patients where the control of disease activity remains suboptimal. Recognizing this need to provide a clear path toward ancestry-specific novel therapeutic development, multiple bioinformatics-driven approaches were performed, using methods and systems of the present disclosure, to identify a comprehensive list of predicted SLE-associated genes; such bioinformatics-driven approaches included eQTL mapping, the identification of functional variants in coding regions and variants impacting transcription factor binding site occupancy, and traditional annotation relying on SNP-gene proximity. Together, these approaches identified 3,450 potential SLE-associated genes in one or more ancestral groups (1,774 AS-specific genes, 1,292 EA-specific genes, and 384 genes shared between AS and EA ancestries). Connectivity mapping and network analysis were then performed to define ancestry-motivated biological pathways and inform ancestry-specific pharmacological targets. Overall, results obtained from these genetic analyses indicate fundamental differences in SLE risk-related pathways, some of which are explicitly associated with ancestral differences (e.g., among AS and EA). Further, these molecular pathways motivated by ancestry-specific and trans-ancestral associations indicate that novel drug candidates may be identified that differentially impact SLE patients of Asian ancestry and SLE patients of European ancestry.

Figure 68A:
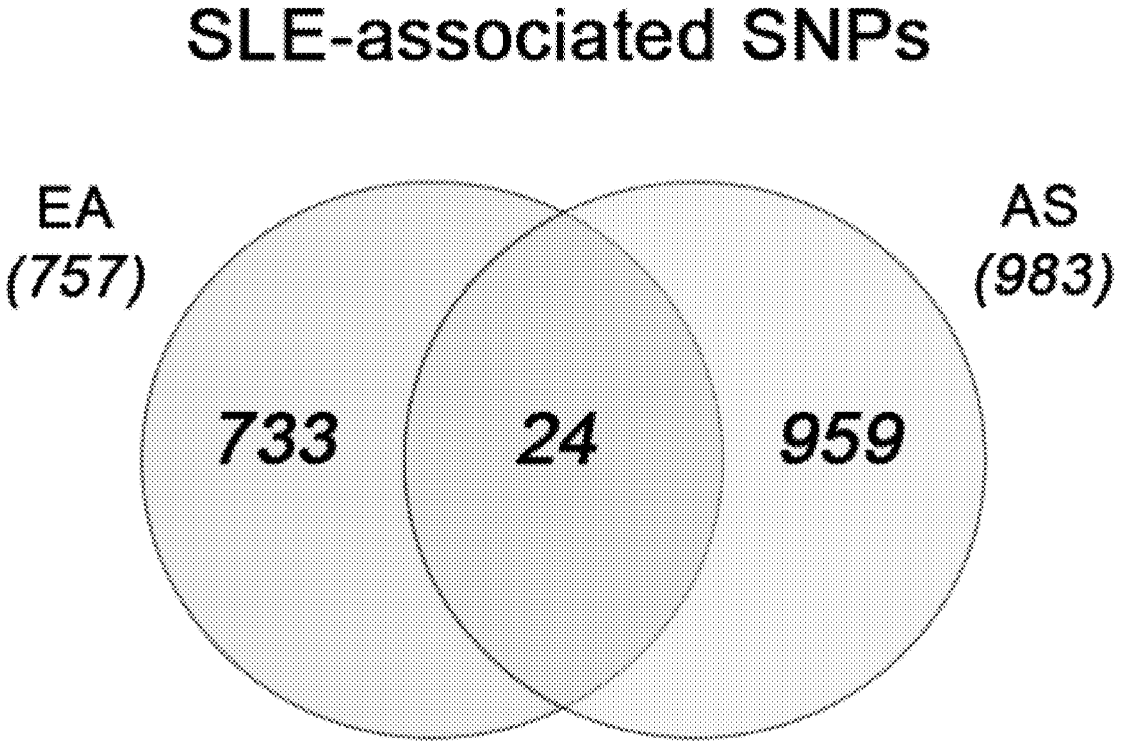
FIGS. 68A-68E show examples of results of mapping the functional genes predicted by SLE-associated SNPs, including a Venn diagram depicting the ancestral overlap of all SLE-associated Immunochip SNPs (FIG. 68A); a distribution of genomic functional categories for all EA and AS non-HLA associated SLE SNPs (FIG. 68B); functional SNP-associated genes derived from 4 sources, including eQTL analysis (E-Genes), regulatory regions (T-Genes), coding regions (C-Genes), and proximal gene-SNP annotation (P-Genes) (FIG. 68C); and Venn diagrams showing the overlap of all EA (FIG. 68D) and AS (FIG. 68E) associated E-Genes, T-Genes, C-Genes, and P-Genes.
Figure 68B:
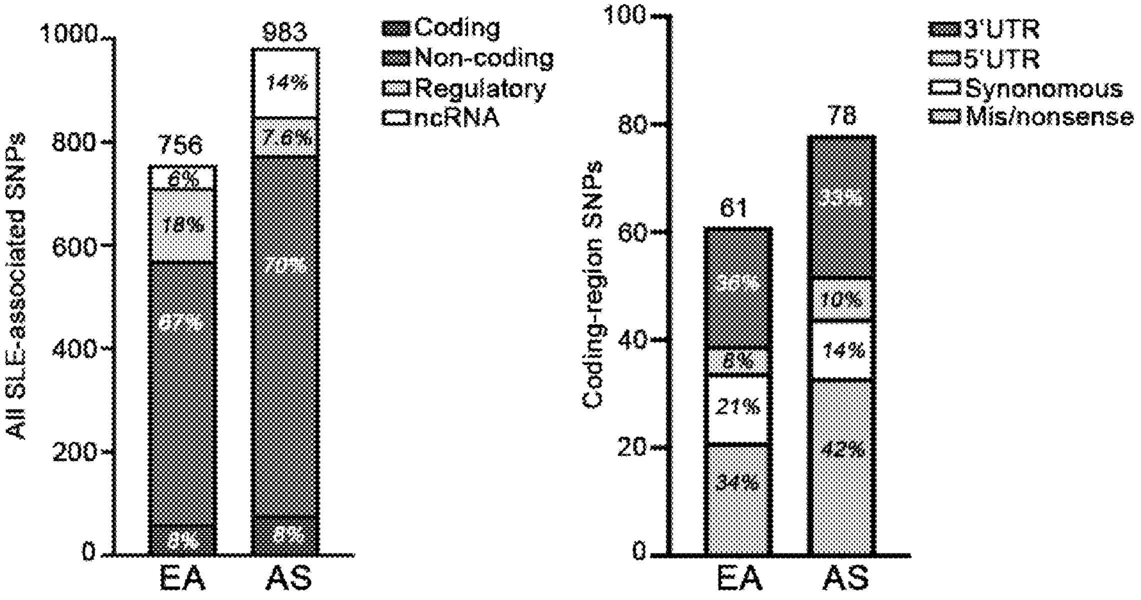

Identification of ancestry-dependent and independent SLE-associated variants and downstream target genes was performed as follows. High-density Immunochip-based association analyses may have identified 983 single-nucleotide polymorphisms (SNPs) reported as significantly associated with SLE in patients of East Asian (AS) ancestry and 757 SNPs associated with disease in European (EA) populations (FIG. 68A), as described by Langefeld et al. Of these, 24 SNPs (<1.5%) were shared between AS and EA ancestries. In both ancestries, approximately 70% of SNPs were found in non-coding regions (intergenic and intronic), with 8% of SNPs located in coding regions (3'UTRs, 5'UTRs, synonomous and missense) (FIG. 68B). AS populations had a significantly higher percentage of SNPs in non-coding RNAs (lncRNA and miRNA), whereas EA populations had more SNPs located within regulatory regions (FIG. 68B).

FIGS. 68A-68E show examples of results of mapping the functional genes predicted by SLE-associated SNPs, including a Venn diagram depicting the ancestral overlap of all SLE-associated Immunochip SNPs (FIG. 68A); a distribution of genomic functional categories for all EA and AS non-HLA associated SLE SNPs (FIG. 68B); functional SNP-associated genes derived from 4 sources, including eQTL analysis (E-Genes), regulatory regions (T-Genes), coding regions (C-Genes), and proximal gene-SNP annotation (P-Genes) (FIG. 68C); and Venn diagrams showing the overlap of all EA (FIG. 68D) and AS (FIG. 68E) associated E-Genes, T-Genes, C-Genes, and P-Genes.

Figure 68C:
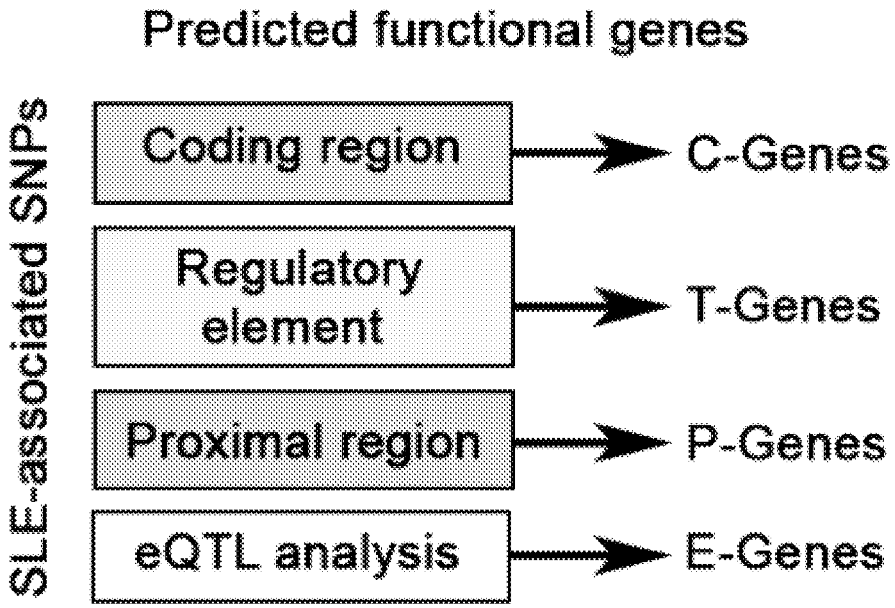
Figure 68D:
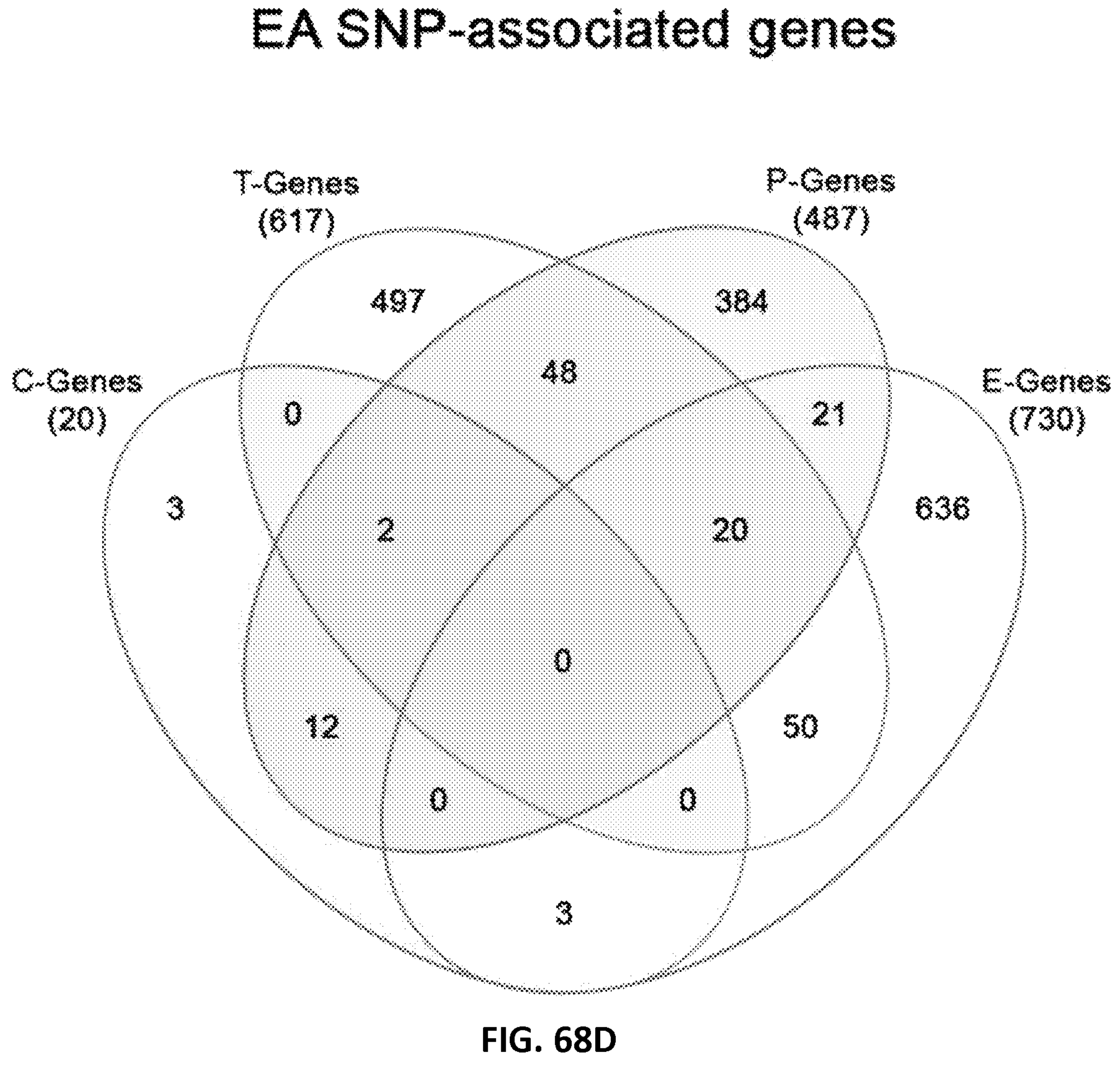
Figure 68E:
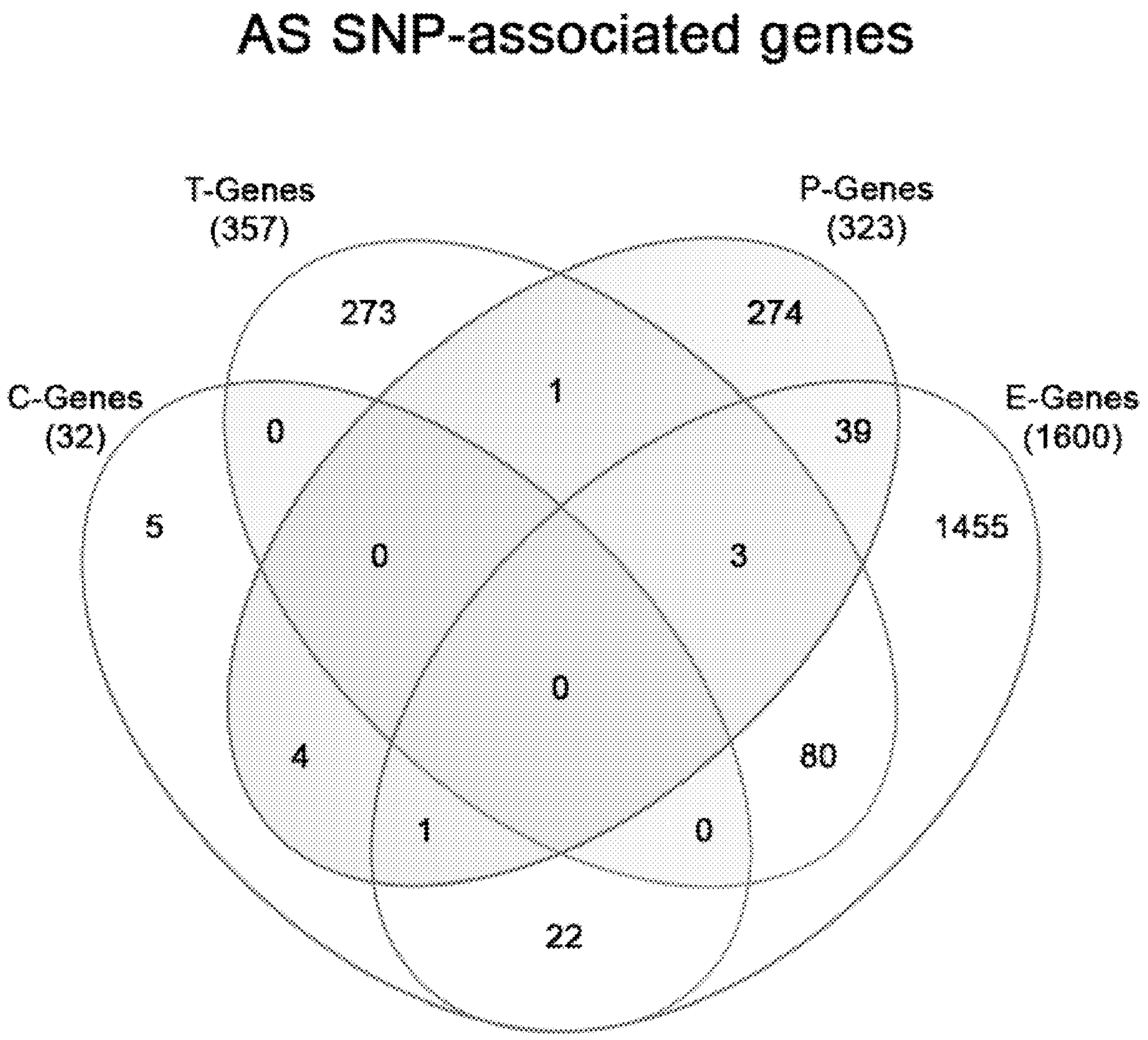

Multiple bioinformatic-based approaches were performed to identify the most plausible genes affected by the SLE-SNP association. First, as described by Owen et al 2020, it was determined whether there was evidence that the SNP was a quantitative trait locus (eQTL) using the GTEx database and Blood eQTL browser (Westra et al). This study identified 226 EA and 587 AS-specific eQTLs linked to 636 and 1455 expression genes (E-Genes) unique for EA and AS respectively (FIG. 68C-68E). Next, SNPs within distal and cis regulatory elements (e.g. enhancers and promoters) were identified. To examine putative enhancer and promoter regions, GeneHancer and HACER (Human ACtive Enhancers to interpret Regulatory variants; bioinfo.vanderbilt.edu/AE/HACER/) were used, both of which connect regulatory SNPs with downstream target genes (T-Genes) (as described by Fishilevich et al. 2017; Wang et al. 2019). Together, GeneHancer and HACER were used to identify 105 SNPs (59 EA, 46 AS) overlapping distal regulatory elements or promoters predicted to impact the expression of 974 T-Genes (617 EA, 357 AS) (FIG. 68C-68E). For variants located in coding regions, 54 SNPs (21 EA, 33 AS) were associated with either non-synonymous or nonsense changes, affecting 52 genes (C-Genes; 20 EA, 32 AS). Functional protein damage scores were determined using SIFT, PolyPhen-2, PROVEAN, and PANTHER which predict the potential impact of amino acid substitutions on protein structure and function. Of the 52 non-synonymous/nonsense SNPs, a subset of them were predicted to be deleterious. The remaining 927 SNPs that did not identify E-Genes, T-Genes, or C-Genes were assigned to the closest proximal gene (P-Gene). Traditional annotation identified an additional 810 P-Genes (487 EA, 323 AS).

Overlapping EA and AS SNP-predicted E-Genes, T-Genes, C-Genes, and P-Genes are depicted in FIG. 68D and FIG. 68E, respectively. No genes were shared within all four groups within either ancestry, and limited commonality was observed between T-Gnes, P-Genes, and E-Genes, with only 20 genes shared among the three groups in EA and 3 genes shared in AS. Despite the overall diversity of genes observed in each list, significant overlap was observed in the number of genes shared between ancestries (FIG. 69A).

Characterization of gene signatures was performed as follows. Given the diversity of mechanisms through which SLE-associated SNPs are linked to genes (e.g., eQTL, regulatory element and coding region mapping, SNP-gene proximity), a series of bioinformatic analyses were performed to determine the biological function of the 1,292 unique EA and 1,774 unique AS gene sets, as well as the 384 genes common to both ancestries. Gene function was first determined by Biologically Informed Gene Clustering (BIG-C), a functional aggregation tool developed to understand the functional groupings of large gene lists (as described by Labonte et al. 2018; Catalina, Bachali, et al. 2019), followed by analysis using Ingenuity Pathway Analysis (IPA) and gene ontology (GO) annotation. Heatmap visualization of BIG-C category enrichment (FIG. 69B), IPA canonical pathways (FIG. 69D), and GO terms (FIG. 69E) were generated.

Figure 69A:
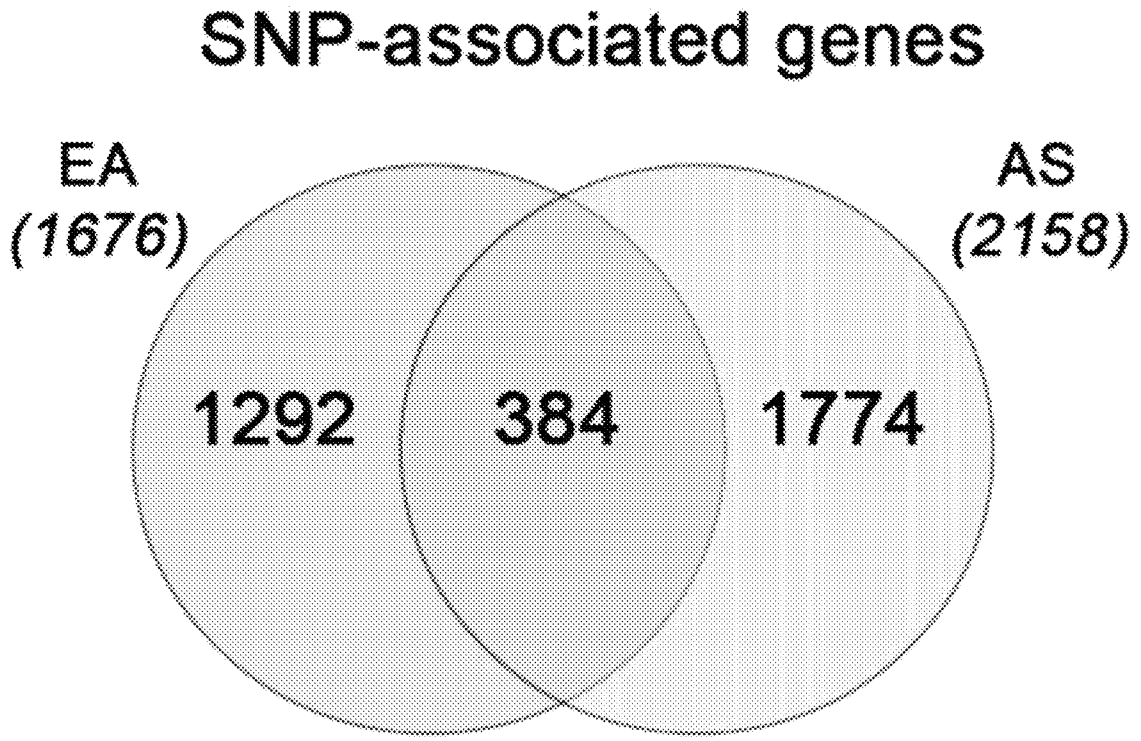
FIGS. 69A-69E show examples of results from functional characterization of SNP-associated genes, including a Venn diagram depicting the overlap between all EA- and AS-SNP associated genes (FIG. 69A); Ancestry-dependent and independent SNP-associated genes that were analyzed to determine enrichment using functional definitions from the BIG-C (Biologically Informed Gene Clustering) annotation library, where enrichment was defined as any category with an odds ratio (OR) >1 and a −log (p-value) >1.33 (FIG. 69B); a heatmap visualization of the top five significant IPA canonical pathways and gene ontogeny (GO) terms for each gene list organized by ancestry, with top pathways with −log (p-value) >1.33 listed (FIGS. 69C-69D); and I-Scope hematopoietic cell enrichment defined as any category with an OR >1, left scale; indicated by the dotted line and −log (p-value) >1.33 indicated by color scale (FIG. 69E).
Figure 69B:
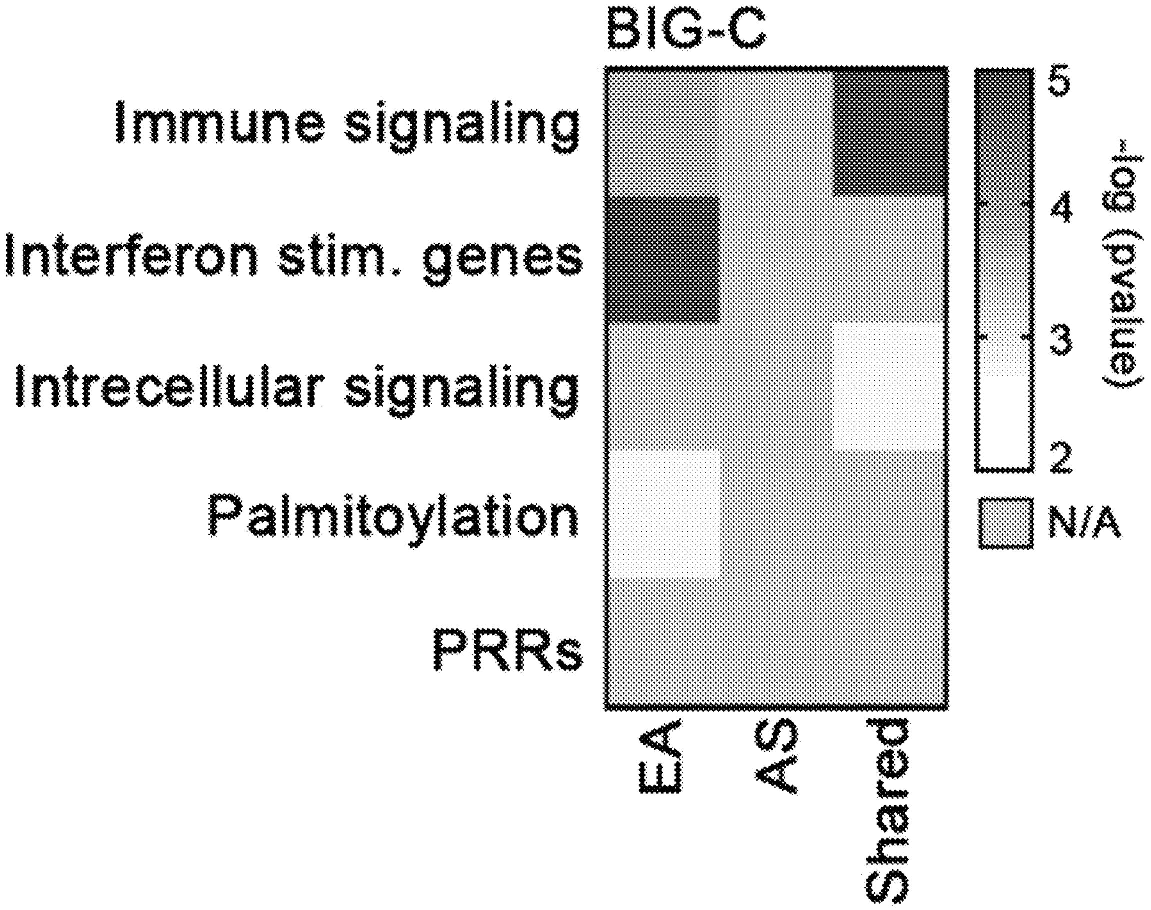
Figure 69C:
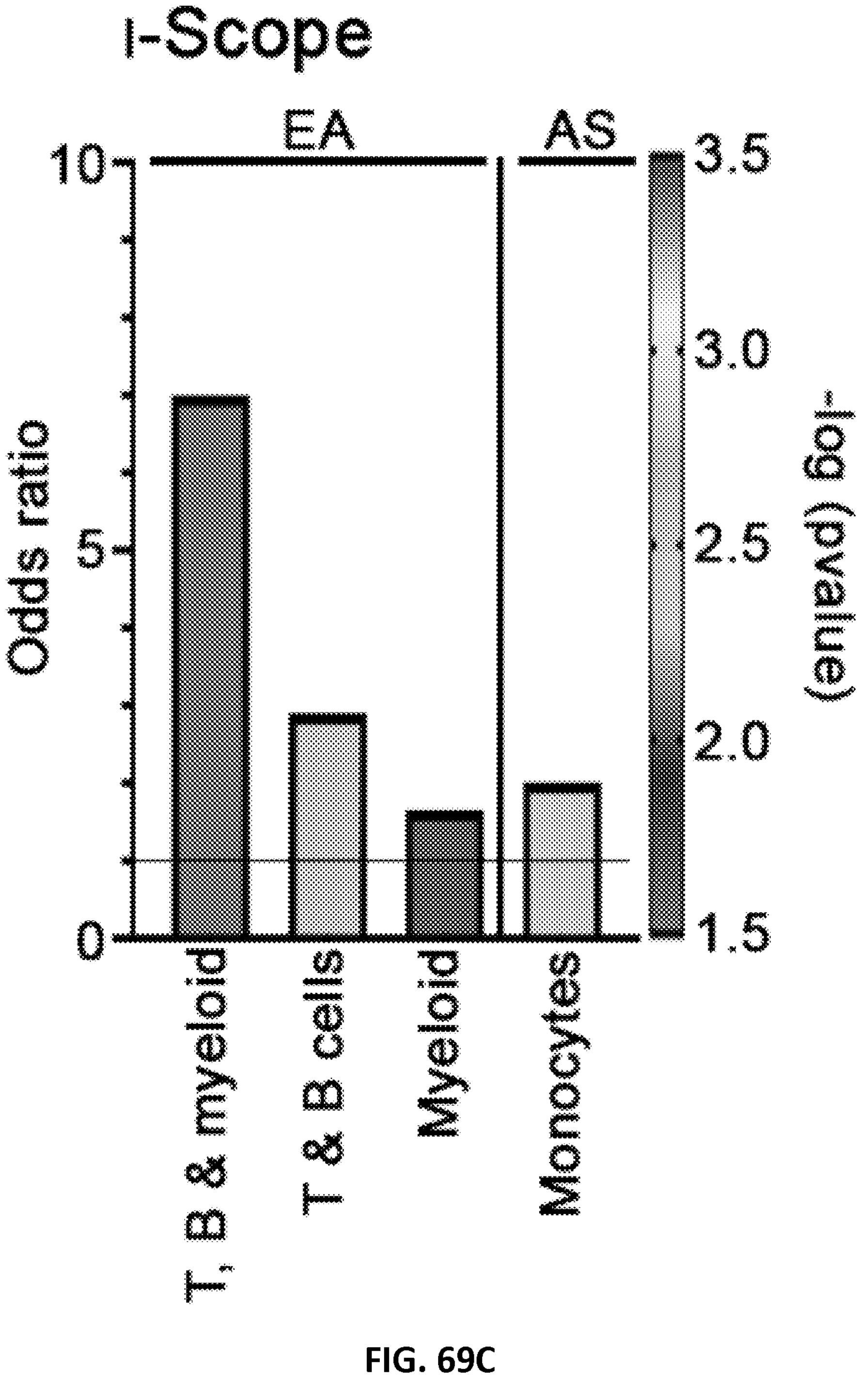
Figure 69D:
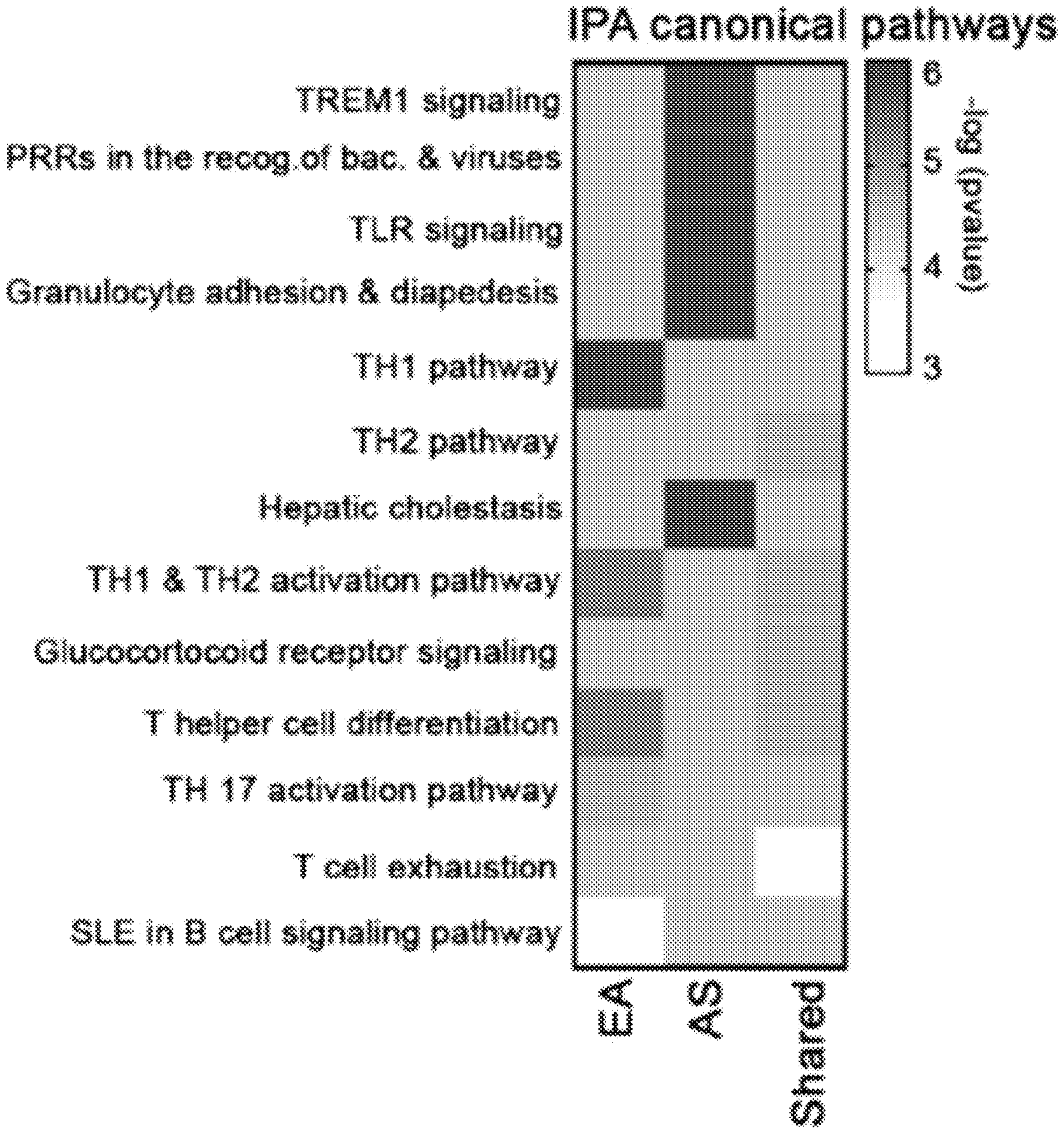
Figure 69E:
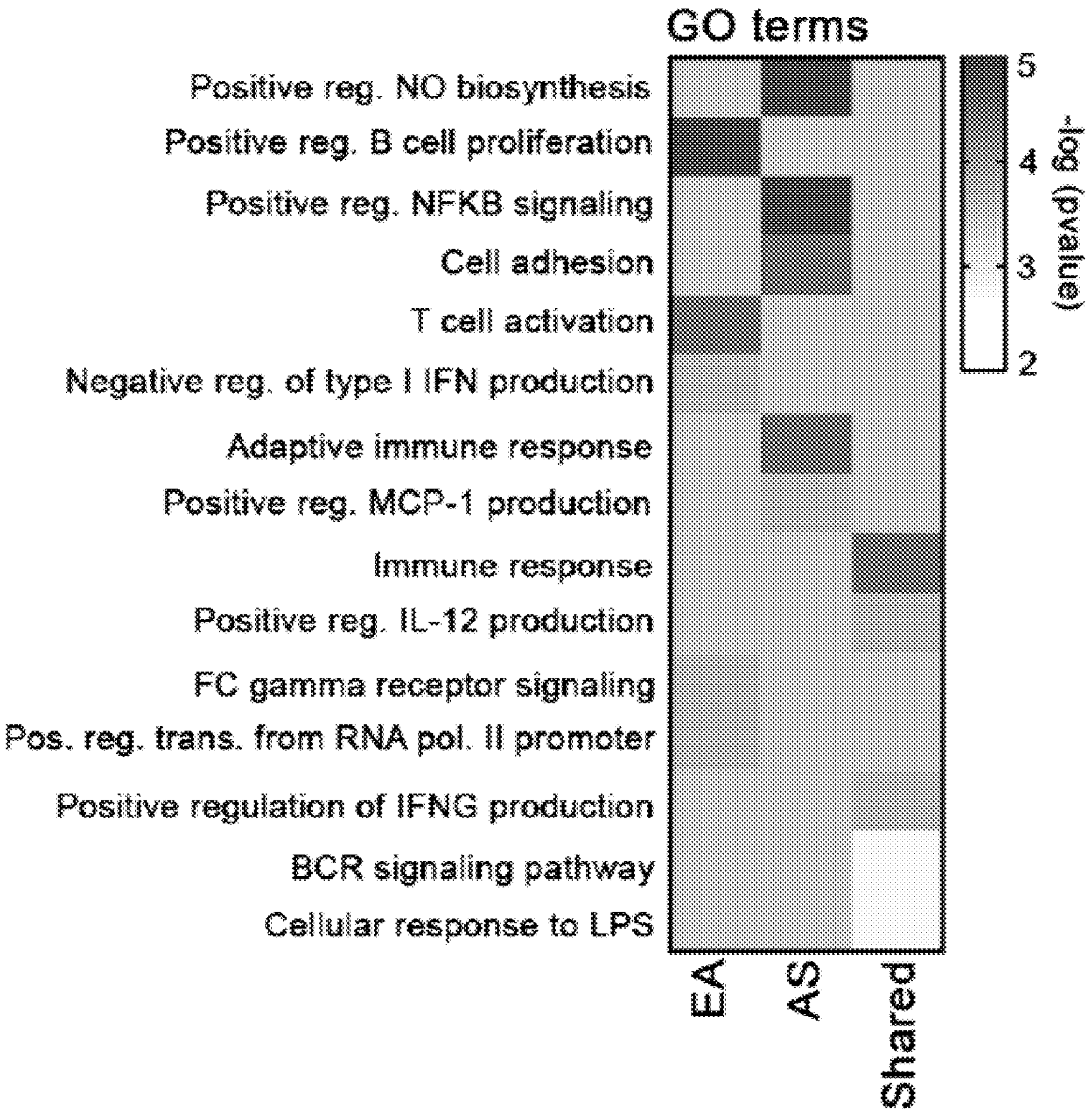

FIGS. 69A-69E show examples of results from functional characterization of SNP-associated genes, including a Venn diagram depicting the overlap between all EA- and AS-SNP associated genes (FIG. 69A); Ancestry-dependent and independent SNP-associated genes that were analyzed to determine enrichment using functional definitions from the BIG-C (Biologically Informed Gene Clustering) annotation library, where enrichment was defined as any category with an odds ratio (OR) >1 and a −log (p-value) >1.33 (FIG. 69B); a heatmap visualization of the top five significant IPA canonical pathways and gene ontogeny (GO) terms for each gene list organized by ancestry, with top pathways with −log (p-value) >1.33 listed (FIGS. 69C-69D); and I-Scope hematopoietic cell enrichment defined as any category with an OR >1, left scale; indicated by the dotted line and −log (p-value) >1.33 indicated by color scale (FIG. 69E).

Analysis of EA genes revealed enrichment in processes related to both adaptive and innate immune function, including the BIG-C category for interferon stimulated genes, canonical pathways for TH1 and TH2 activation pathway and TH17 activation pathway, and GO terms for Fc receptor signaling pathway (GO: 0038093), T cell activation (GO: 0042110) and positive regulation of B cell proliferation (GO: 0030890). SNP-associated AS genes were determined to be enriched in categories that are predominantly related to pathogen-influenced signaling, such as TLR signaling and granulocyte adhesion and diapedesis, and GO terms for positive regulation of MCP-1 production (GO: 0071639) and positive regulation of nitric oxide (NO) biosynthesis process (GO: 00445429). Shared genes were distributed in a diverse range of adaptive and innate gene categories and contained a strong core interferon-stimulated gene signature consistent with the role of interferons in the pathogenesis of SLE (FIG. 69B, FIG. 69D, FIG. 69E), as described by Catalina, Bachali, et al. 2019.

Next, analysis was performed using I-Scope, a clustering program that detects immune and inflammatory cell type signatures within large gene lists to identify dominant immune cell populations driving disease pathology within each ancestry (as described by Ren et al. 2019). To analyze the full array of EA and AS genes and provide more power to these analyses, all shared genes were integrated into the EA (1,676 total) and AS (2,158 total) gene sets. Consistent with the results of the pathway analysis, EA genes exhibited strong enrichment in I-Scope categories for myeloid cells, as well as T and B cells; further, AS genes were specifically enriched in monocytes (FIG. 69C). Independent analysis of shared genes on their own did not reveal enrichment in any I-Scope category.

Delineation of signaling pathways identified by ancestry-specific SNP-associated genes and upstream regulators was performed as follows. Ancestry-driven key signaling pathways were elucidated in greater detail. Using IPA analysis, all SNP-associated genes were used to identify potential biological upstream regulators (UPRs). Ancestry-based protein-protein interaction (PPI) networks comprising of EA-specific genes, AS-specific genes, or shared genes, and their UPRs, were constructed using STRING, visualized using Cytoscape, and clustered using MCODE to provide an additional level of functional annotation. Individual gene clusters were analyzed by BIG-C, I-Scope, and IPA to identify those molecules, cell types, and pathways highly associated with disease.

FIGS. 70A-70D show examples of key pathways motivated by EA-predicted genes (FIG. 70A) and AS-predicted genes (FIG. 70C) and upstream regulators, including cluster metastructures generated based on PPI networks, clustered using MCODE and visualized in Cytoscape, where cluster size indicates the number of genes per cluster, edge weight indicates the number of inter-cluster connections, and color indicates the number of intra-cluster connections, and functional enrichment for each cluster was determined by BIG-C; and heatmap results indicating the top five canonical EA-motivated pathways (FIG. 70B) and AS-motivated pathways (FIG. 70D), respectively, representing individual clusters (−log (p-value) >1.33), where enriched BIG-C and I-Scope categories (OR >1; p-value <0.05) are listed for each cluster, and bold text indicates categories with the highest OR and lowest p-value.

Figure 70A:
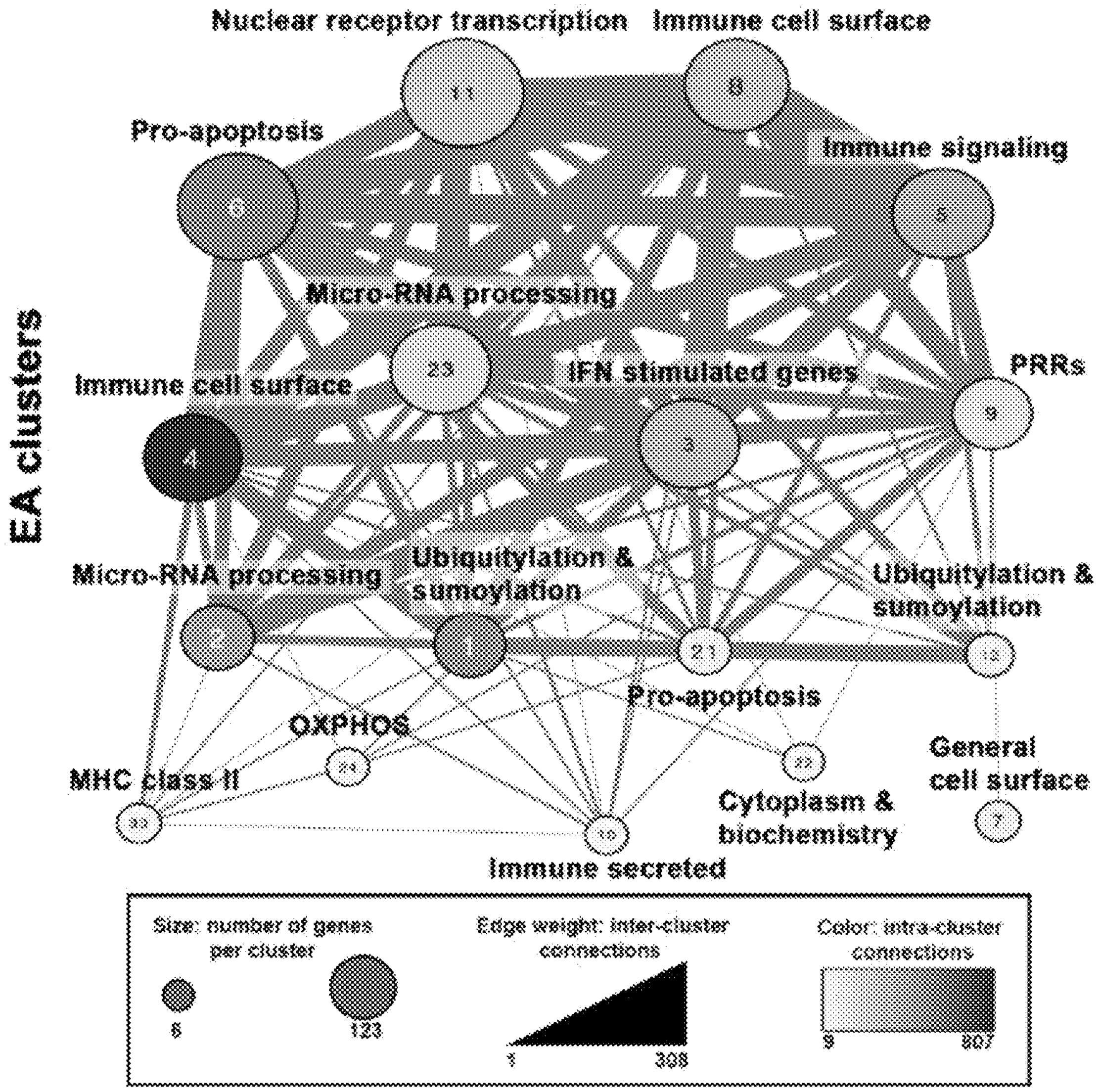
Figure 70C:
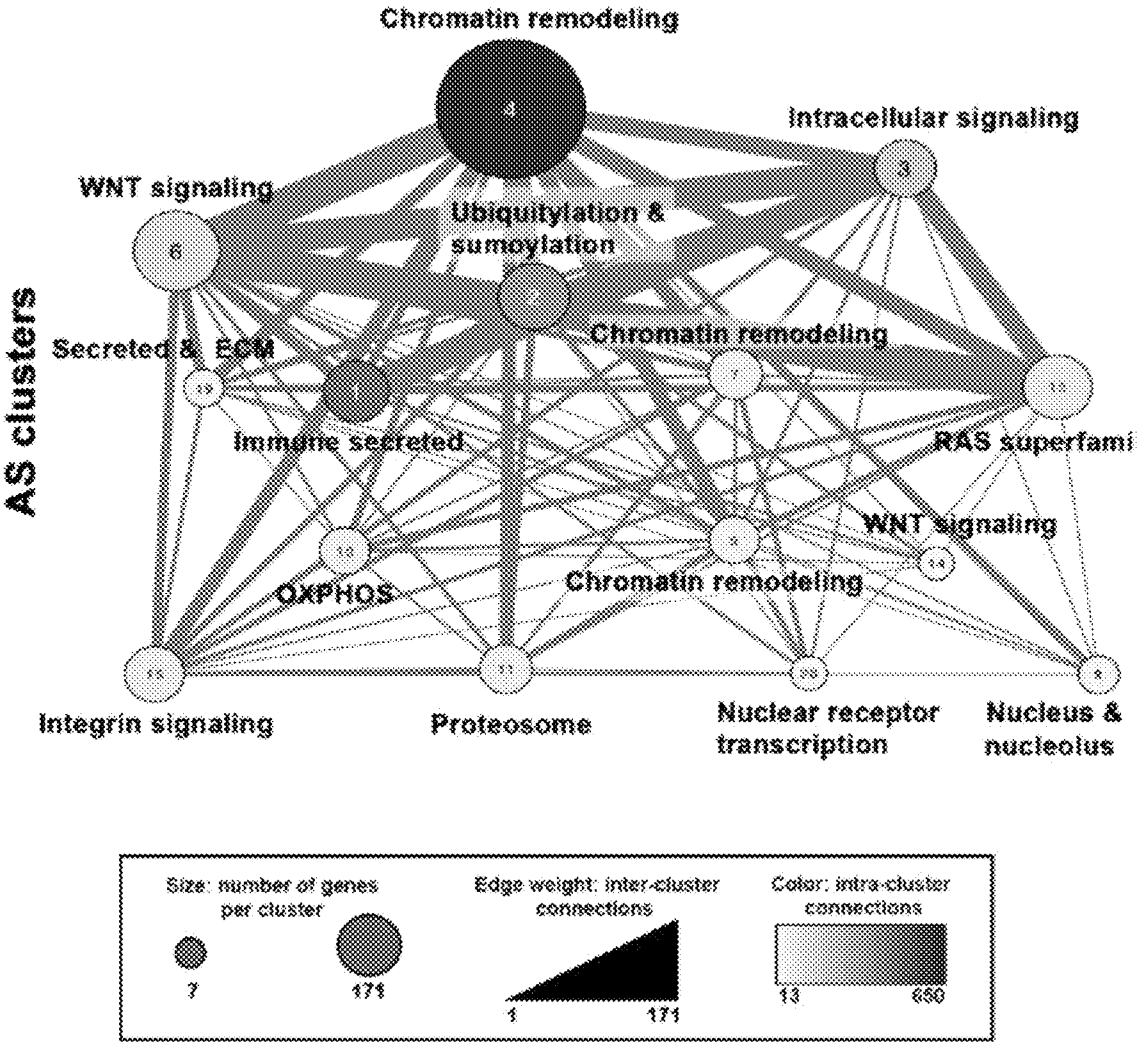

A total of 54 pathways were determined to be representative of EA genes and UPRs, with the 5 out of the 8 largest clusters (3, 4, 5, 8, and 9) enriched in BIG-C categories for immune signaling, immune cell surface, immune secreted, and pattern recognition receptors (FIGS. 70A-70B), along with multiple canonical pathways related to cytokine and TLR signaling, and I-Scope enrichment for cells of myeloid and/or lymphoid origin (FIG. 70B). Cluster 11 revealed additional enrichment in lymphocyte activation and differentiation, such as the TH1 and TH2 activation pathway that was also represented in the shared gene network.

In contrast, pathways unique to AS were represented by a diverse range of biological processes indicated by BIG-C categories for chromatin remodeling, immune secreted, and ubiquitylation and sumoylation (FIG. 70C), as well as the canonical pathways related to cell cycle and DNA repair mechanisms found in clusters 3 and 4, cellular stress found in cluster 2 and 6 and immune cell trafficking in clusters 1 and 19 (FIG. 70D).

Figure 71A:
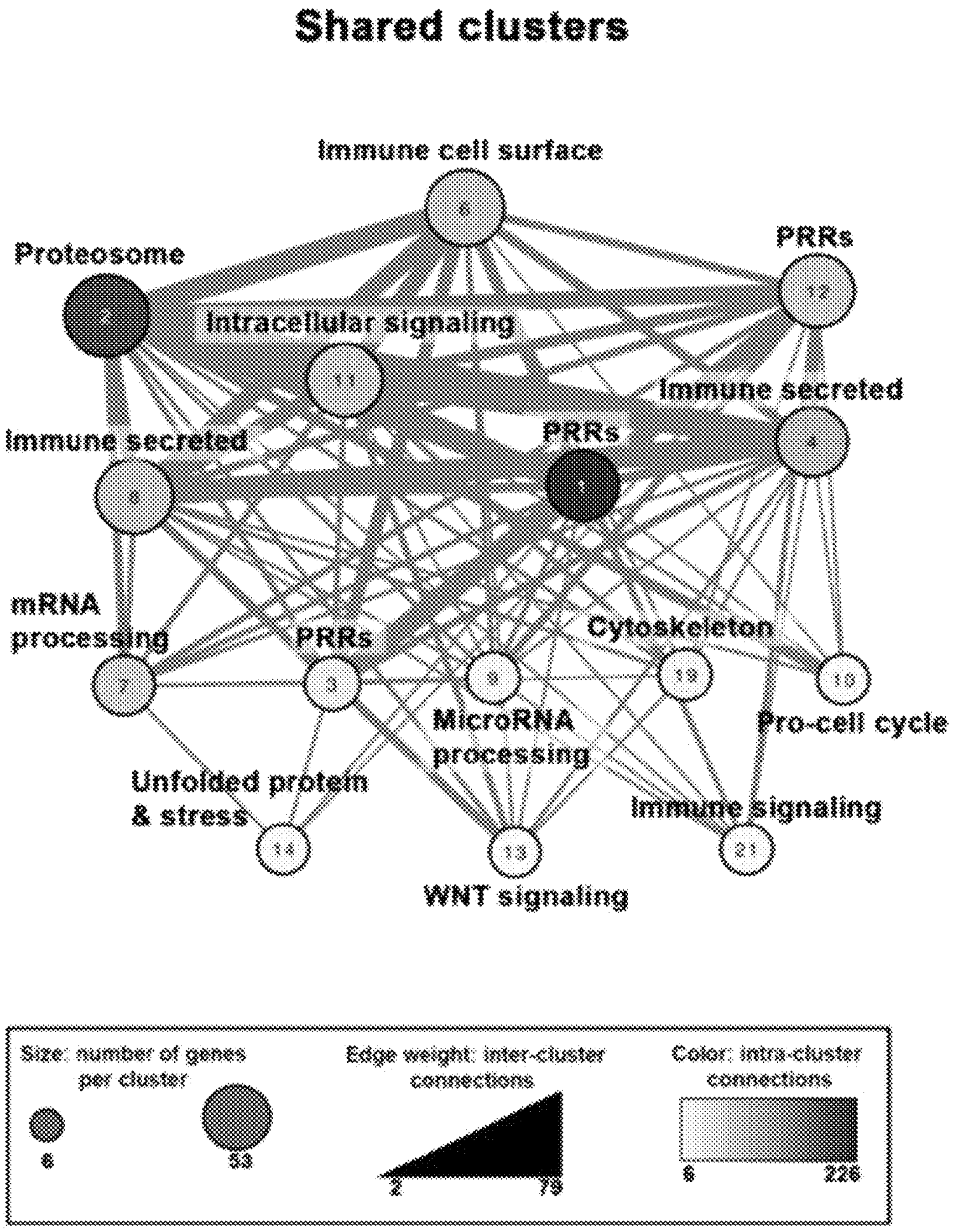
Figure 71C:
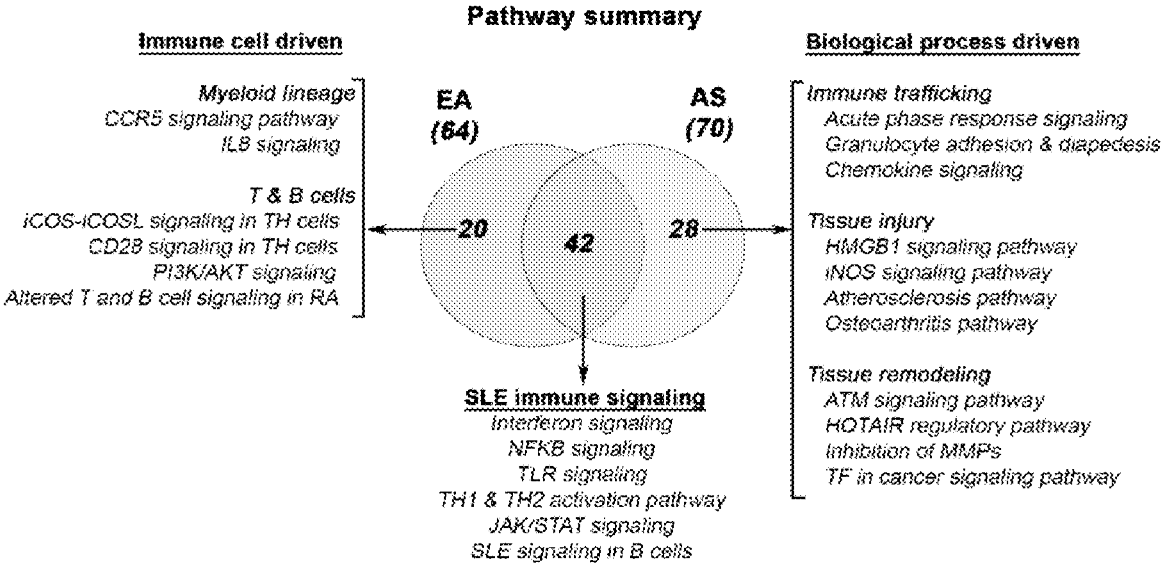

Pathways exemplified by ancestry-independent genes were a blend of both EA pathways and AS pathways. Common pathways included SLE signaling in B cells, TLR signaling as well as PRRs in the recognition of bacteria and virus (FIGS. 71A-71B). FIG. 71C depicts a selection of both the unique and overlapping canonical pathways motivated by the EA and AS gene sets. Whereas EA associated genes appear driven by specific immune cell types, including cells of myeloid lineage, and T and B cells, the AS-associated pathways are dominated by biological processes related to tissue injury, immune cell trafficking, and tissue repair.

FIGS. 71A-71C show examples of key pathways determined by shared genes and upstream regulators, including cluster metastructures generated based on PPI networks, clustered using MCODE, and visualized in Cytoscape, where cluster size indicates the number of genes per cluster, edge weight indicates the number of inter-cluster connections, and color indicates the number of intra-cluster connections, and functional enrichment for each cluster was determined by BIG-C (FIG. 71A); a heatmap indicating the top five canonical pathways representing individual clusters (−log (p-value) >1.33), where enriched BIG-C and I-Scope categories (OR >1; p-value <0.05) are listed for each cluster, and bold text indicates categories with the highest OR and lowest p-value (FIG. 71B); and a Venn diagram showing the number of overlapping pathways motivated by EA or AS predicted genes and their associated UPRs, where representative pathways are listed (FIG. 71C).

Figure 72A:
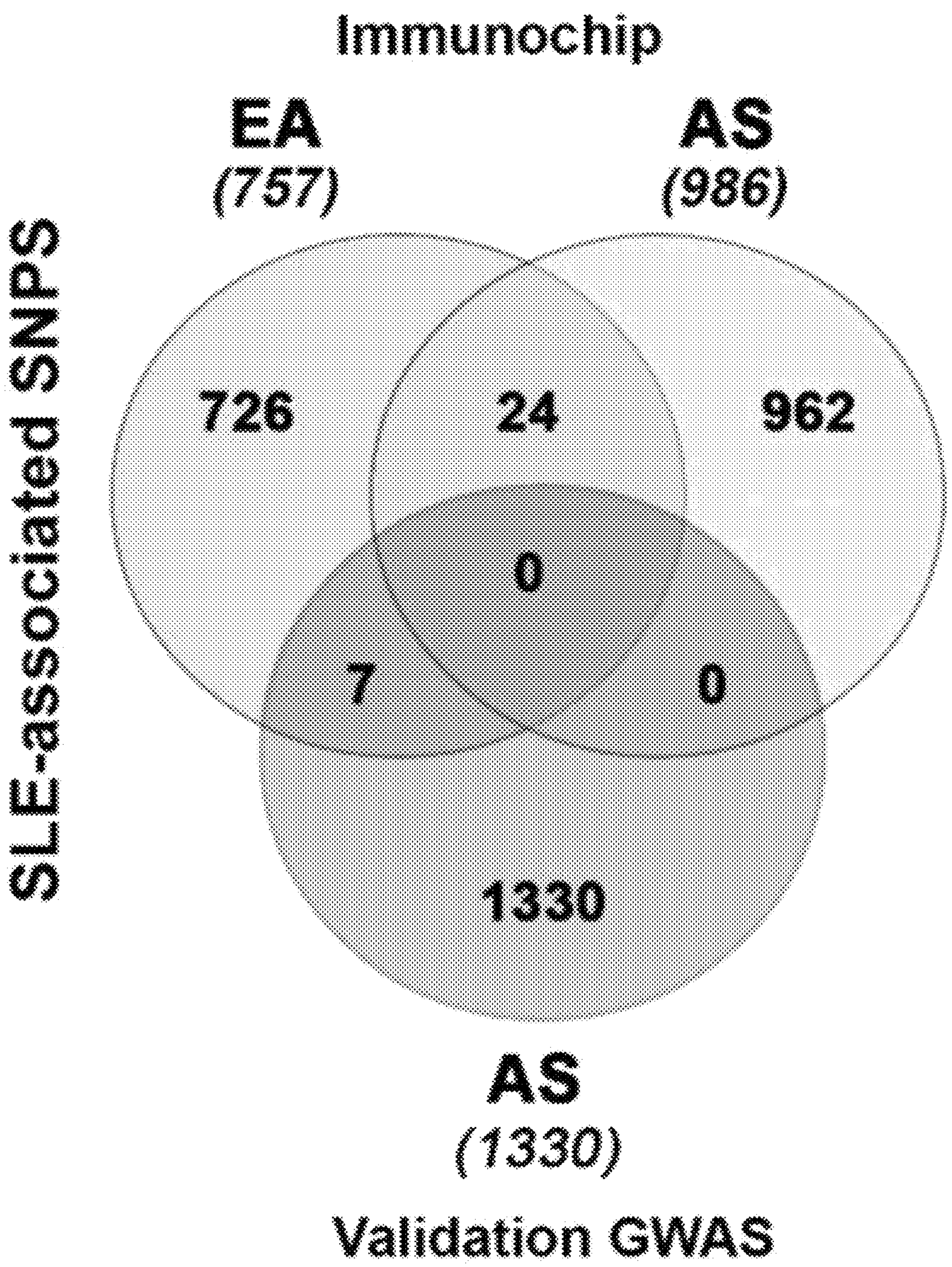
Figure 72B:
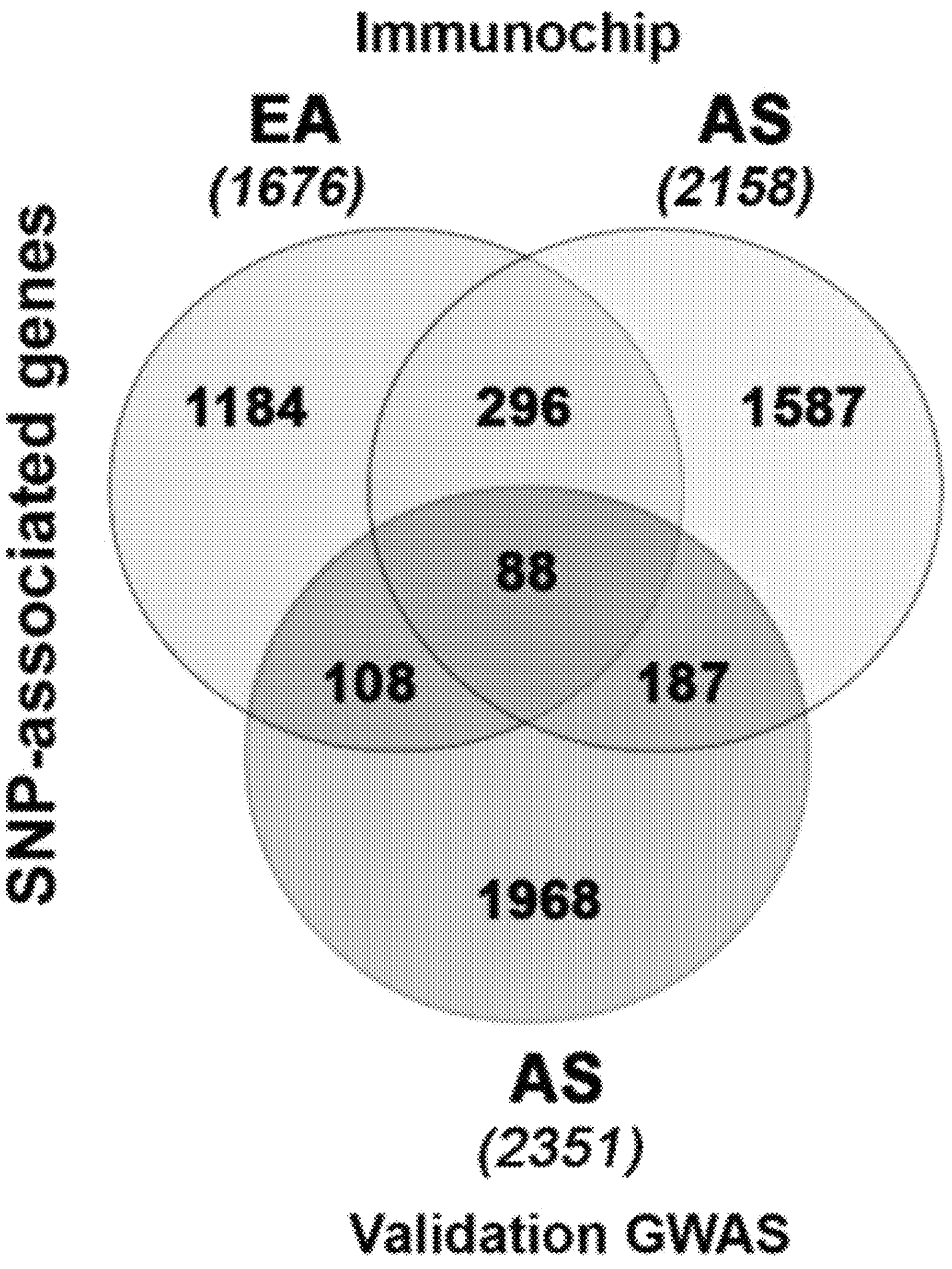
Figure 72C:
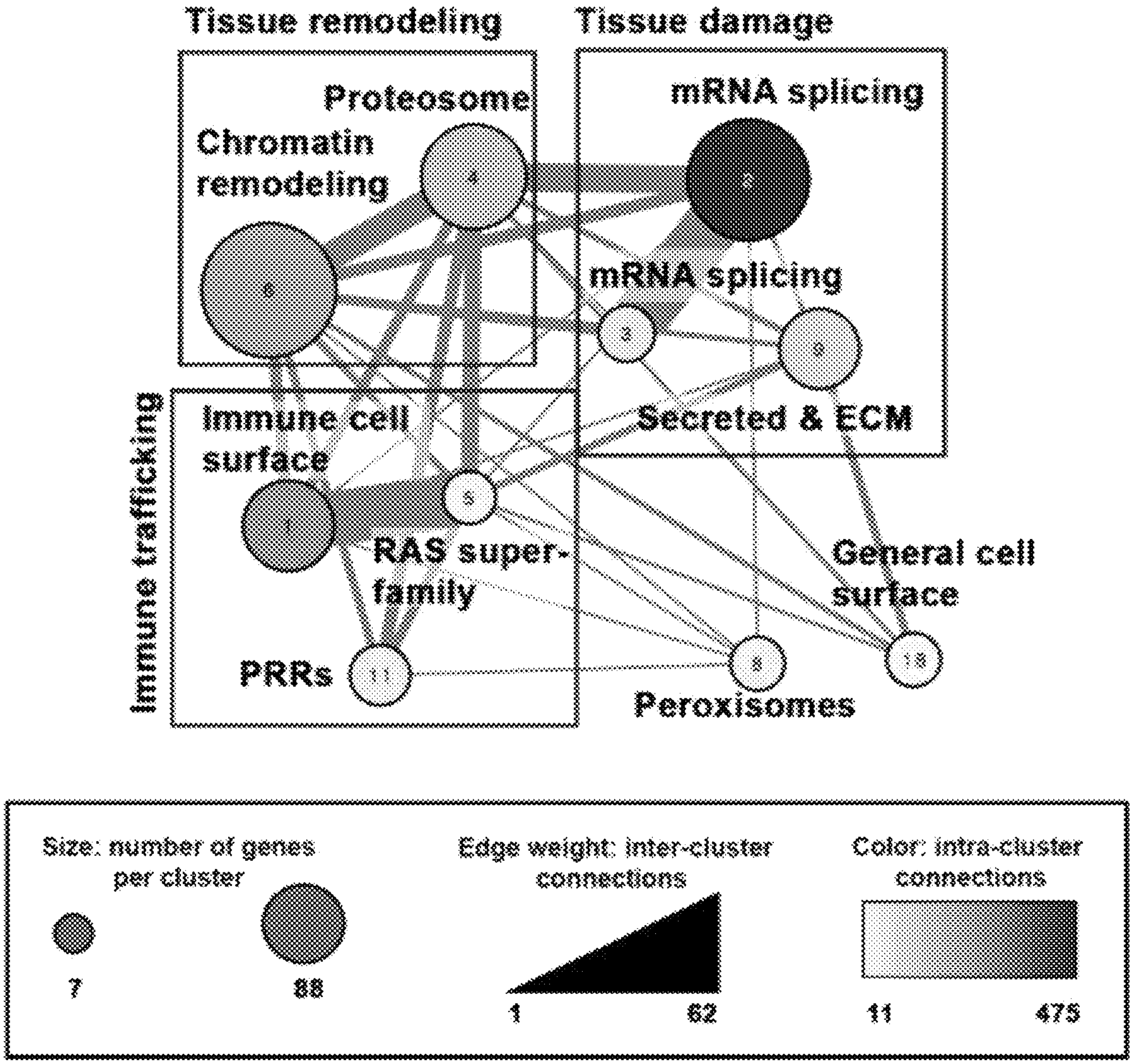

Validation of Asian pathway analysis was performed as follows. To confirm the pathway predictions, summary genome-wide association data from Asian GWA studies (as described by Morris et al; Lessard et al) were combined, and an additional 1,330 SNPs were identified as being significantly associated with SLE in patients of AS ancestry. Validation of AS GWAS SNPs was performed, and results exhibited limited commonality when compared to Immunochip SNPs, with less than 1% of EA and 0 AS Immunochip SNPs overlapping the GWAS validation set (FIG. 72A). Next, the bioinformatics-driven methodology was performed to generate a validation gene cohort composed of E-Genes, T-Genes, C-Genes, and P-Genes. Overall, 108 EA genes and 186 AS genes, representing 6.4% of EA Immunochip genes and 8.6% of AS Immunochip genes, were shared with the AS validation gene set (FIG. 72B). A total of 88 genes were shared among all three groups. The validation gene set (2,351 total) was then used as input for IPA to identify potential biological UPRs. Connectivity mapping of all validation genes and inferred UPRs were used to create PPI networks. Gene clusters were simplified into megaclusters, and functional annotation was generated by BIG-C, I-Scope, and IPA (FIGS. 72C-72D). Examination of each cluster reveals remarkable similarity to those derived from AS Immunochip-predicted genes. For example, clusters 4 and 6 shared hallmarks of tissue repair and remodeling exemplified by canonical pathways for CDK5 signaling, HIPPO signaling, ErbB2 signaling, and Protein kinase A signaling. Additionally, it was observed that clusters 2, 3, and 9 were representative of processes involved in tissue damage, cell stress, and injury, including the EIF2 pathway and Coagulation system; further, clusters 1, 5, and 11 were representative of immune function and trafficking as indicated by the role of cytokines in mediating communication between immune cells and CXCR4 signaling (FIGS. 72C-72D).

FIGS. 72A-72D show examples of Asian GWAS genes motivating similar pathways predicted by the AS Immunochip, including Venn diagrams depicting the ancestral overlap of all Immunochip and validation GWAS SNPs (FIG. 72A) and associated genes (FIG. 72B); key pathways determined by AS validation GWAS associated genes and upstream regulators, where cluster metastructures were generated based on PPI networks, clustered using MCODE, and visualized in Cytoscape, where cluster size indicates the number of genes per cluster, edge weight indicates the number of inter-cluster connections, and color indicates the number of intra-cluster connections (FIGS. 72C-72D). Functional enrichment for each cluster was determined by BIG-C (FIG. 72C). A heatmap indicates the top five canonical pathways representing individual clusters (−log (p-value) >1.33), where enriched BIG-C and I-Scope categories (OR >1; p-value <0.05) are listed for each cluster, and bold text indicates categories with the highest OR and lowest p-value (FIG. 72D).

Pathway analysis facilitated drug prediction as follows. Pathway identification facilitated drug prediction analysis, allowing the identification of potential drug candidates for repositioning in SLE. Drugs specific for EA-motivated pathways include BMS-986165, a small molecular inhibitor of TYK2 (Table 28), whereas therapeutic candidates targeting biological processes associated with AS motivated-pathways include the FDA-approved (for multiple myeloma) proteasome inhibitor bortezomib, as well as investigational drugs like the deubiquitinase inhibitor WP1130 targeting the WNT/β-catenin signaling pathway (Table 29). Unique pathway categories identified for EA and AS indicate the presence of additional ancestry-driven interventions, such as the small molecule inhibitor of complement 5A receptor (C5AR), Avacopan for AS (prevents leukocyte egress), and monoclonal anti-interferon treatments (rontalizumab, anifrolimab, PF-06823859) for EA, which may show efficacy in clinical trials for other autoimmune diseases (Table 28 and Table 29).

TABLE 28

Predicted drugs for EA-informed pathways and genes

| | |
|---|---|
| Cluster 6: Pro-apoptosis | |
| HDAC2 | Vorinostat + 6, panobinostat + 0, belinosta |
| HDAC6 | |
| IL21 | BOS-161721 + 7, NNC0114-0006 + 6 |
| IL10 | BT63 |
| IL17 | Brodalumab + 7, Ixekizumab + 8, secukinumab + 8 |
| IL21 | BOS-161721 + 7, NNC0114-0006 + 6 |
| TGFB1 | Fesolimumab |
| REL | Imatinib + 4 |
| FCGR2A | Obexelimab + 7 |
| JAK1 | Baricitinib + 7, upadacitinib + 7 |
| Cluster 11: Nuclear receptor trans. | |
| ICOS | Prezalumab + 4, Amg 570 + 5 |
| IFNG | Amg 811 + 3 |

TABLE 28-continued

| Predicted drugs for EA-informed pathways and genes | |
|---|---|
| IL12A | Ustekinumab + 10 |
| IL12B | |
| IL12RB1 | |
| IL23 | Ustekinumab + 10, guselkumab + 8 |
| TYK2 | BMS-986165 |
| Cluster 8: Immune cell surface | |
| IL4 | Dupilumab + 4 |
| LYN | Blinatumomab, dasatinib − 1, eroltinib |
| LCK | Aminogenistein, PP2, JW-7-24-1 |
| STAT3 | Cucurbitacin-I |
| Cluster 23: microRNA processing | |
| CAMK2D | KN-62 |
| CHEK1 | SA-792987 |
| MTOR | Everolimus + 3, sirolimus + 2, leflunomide + 3 |
| CDK2 | Roscovitine |
| Cluster 5: Immune signaling | |
| ERBB2 | Lapatinib0 |
| GSK3B | Kenpaullone, TWS-119 |
| CD28 | Theralizumab + 4 |
| CD80 | Belatacept + 4, Abatacept + 8 |
| CD86 | |
| IL2RA | Daclizumab + 2 |
| SYK | Fostamatinib + 2, GSK2646264 + 6 |
| JAK3 | Tofacitinib + 3 |

TABLE 28-continued

| Predicted drugs for EA-informed pathways and genes | |
|---|---|
| Cluster 3: IFN stim. genes | |
| CD40LG | Dapirolizumab pegol + 8 |
| IL2 | |
| IL5 | Reslizumab + 1, mepolizumab + 3 |
| TNF | Etanercept + 5 |
| TNFSF13B | Atacicept + 5 |
| Cluster 4: immune cell surface | |
| CCR5 | maraviroc |
| CD3 | Blinatumomab − 1 |
| Cluster 9: PRRs | |
| ROCK1 | Fasudil |
| IRAK4 | PF-06650833 + 5 |
| Cluster 2: mRNA processing | |
| IFNA1 | Rontalizumab + 4, sifalimumab + 4 |
| IFNA2 | |
| IFNA4 | |
| IFNA6 | |
| IFNA7 | |
| IFNA8 | |
| IFNAR1 | Anifrolumab + 3 |
| IFNB1 | PF-06823859 + 5 |

TABLE 29

| Predicted drugs for AS-informed pathways and genes | |
|---|---|
| Cluster 4: Chromatin remodeling | Tissue repair |
| GADD45B | palbociclib + 4 |
| P53 | ellipticine |
| TGFB1 | fesolimumab |
| ESR1 | Tamoxifen + 2, enzastaurin |
| LMTOR2 | Everolimus + 3, sirolimus + 2, leflunomide + 3 |
| NFKB1 | Quinacrine + 7, anti-TWEAK |
| RARA | AM80, tamibarotene |
| JAK2 | |
| EZH2 | |
| Cluster 6: WNT signaling | Tissue repair, fibrosis: WNT/beta catenin (WNT5A, CTNNB) WP1130, BZ, C-83 |
| AKT | Miltefosine0 |
| IL4 | Dupilumab + 4 |
| IL6R | Sarilumab + 7, tocilizumab + 8, vobarilizumab + 6 |
| IL21 | BOS-161721 + 7, NNC0114-0006 + 6 |
| JAK1 | Baricitinib + 7, filgotinib + 7, ruxolitinib + 5, solcitnib + 6, tofacitinib + 3, upadacitinib + 7 |
| PRKCB | Tamoxifen + 2, enzastaurin |
| SYK | Fostamatinib + 2, GSK2646264 + 6 |
| RHOA | Fasudil, Y27632 |
| PTK2 | PF-562271 |
| CTNNB | PRI-724 |
| CREBBP | PRI-724, CCS1477 |
| FYN | Blinatumomab, dasatinib − 1, eroltinib |
| IL10 | BT063 |
| IL13 | tralokinumab |
| FAS | APO010 |
| FGFR1 | Pazopanib − 4, dovitinib, PD-173074 |

TABLE 29-continued

| Predicted drugs for AS-informed pathways and genes | |
|---|---|
| Cluster 3: Intracellular signaling | Tissue repair |
| ITGB3 | Abciximab, cilengitide, tirofiban |
| SRC | Dasatinib, bosutinib, eroltinib |
| CCL11 | bertilimumab |
| HRAS | ISIS 2503 |
| KRAS | AZD4785, MRTX849 |
| VWF | Abciximab |
| Cluster 19: Secreted & ECM | |
| MMP2 | Marimastat, prinomastat, rebimastat, Col-3, |
| MMP9 | PD-166793, Glucosamine, GS-5745, prinomastat, rebimastat |
| MMP13 | Marimastat, prinomastat |
| STAT3 | Danvatirsen, TTI-101, golotimod |
| Cluster 1: Immune secreted | Immune trafficking: Avacopan + 7 (C5AR) |
| CCL7 | Upamostat |
| CXCL10 | MDX-1100 |
| CXCL12 | NOX-A12 |
| S1PR1 | Amiselimod + 6, siponimid + 7, cenerimod + 6, fingolimod + 5, mocravimod + 5, ozanimod + 5 |
| ADORA3 | Adenosine, tretinoin, valporic acid |
| PDE4A, PDE5A | Roflumilast + 3, dipyridamole + 4, apremolast |
| Cluster 2: Ubiq & sumoylation | |
| APOB | mipomersen |
| CSF1 | Lacnotuzumab, PD-360324 |
| IL6 | PF-04236921 + 8, siltuximab + 6, sirukumab + 6 |
| C4A/C4B/C1Q | |
| CFB | IONIS-FB-LRX |
| HSP90B1 | Cisplatin, retaspimycin |
| Cluster 7: Chromatin remodeling | |
| ICAM1 | Polydatin |
| ESR2 | Tamoxifen + 2 |
| HDAC7 | Belinostat, vorinostat + 6 |
| HDAC9 | |
| Cluster 13: RAS superfamily | |
| LYN | bafatenib |
| CD40 | BI655064 + 5 |
| IL2 | Daclizumab + 2 |
| IL3 | Talacotuzumab + 3 |
| NFATC2 | Tacrolimus + 5 |
| Cluster 5: Chromatin remodeling | |
| TNF | Infliximab + 4, golimumab + 5, etanercept + 5, certolizumab + 4, adalimumab + 4 |
| CD40LG | Dapirolizumab pegol + 8 |
| Cluster 11: Proteosome | |
| PSMA6 | Bortezomib + 6, carfilzomib + 4, ixazomib + 5 |
| PSMB9 | |
| PSMD10 | |
| Cluster 20: Nuclear receptors | |
| VDR | Ergocalciferol + 6 |

Further, Canonical pathways related to T cell function are shared among ancestries, as are many predicted drugs targeting T cell activity including abatacept, theralizumab and AMG-811. Broader analysis of common pathway categories also suggests the utility of targeting T cell signaling, as well as cytokine pathways such as IL12/23 signaling with ustekinumab.

Genomic functional categories were analyzed as follows. The Variant Effect Predictor (VEP) tool available on the Ensembl genome browser 93 (www.ensembl.org) was used for annotation information to specify SNPs located within non-coding regions, including micro (mi) RNAs, long non-coding (Inc) RNAs, introns, and intergenic regions. Regulatory regions include transcription factor binding sites (TFBS), promoters, enhancers, repressors, promoter flanking regions and open chromatin. Coding regions were broken down further and include 5'UTRs, 3'UTRs, synonymous and nonsynonymous (missense and nonsense) mutations. The online resource tool HaploReg (version 4.1; pubs.broadinstitute.org/mammals/haploreg/haploreg.php) were also used to identify DNA features, regulatory elements and assess regulatory potential.

Identification of SLE-associated SNPs and predicted genes was performed as follows. SLE Immunochip studies identified single nucleotide polymorphisms (SNPs) significantly associated with SLE in EA (6,748 cases; 11,516 controls) and AS (2,485 cases and 3,947 controls, including Korean (KR), Han Chinese (HC), and Malaysian Chinese (MC) cohorts. Expression quantitative trait loci (eQTLs) were then identified using The Genotype-Tissue Expression (GTEx) version 6 (GTEXportal.org) and the Blood eQTL browser database (as described by Westra et al. 2013), and mapped to their associated eQTL expression genes (E-Genes). To find SNPs in enhancers and promoters, and their associated transcription factors and downstream target genes (T-Genes), the atlas of Human Active Enhancers was queried to interpret Regulatory variants (HACER, bioinfo-.vanderbilt.edu/AE/HACER (as described by Wang et al. 2019), and the GeneHancer database was queried (as described by Fishilevich et al. 2017). To find structural SNPs in protein-coding genes (C-Genes), the human Ensembl genome browser (GRCh38.p12; www.ensembl.org) and dbSNP (www.ncbi.nlm.nih.gov/snp) were queried. Several additional databases were used to generate loss-of-function prediction scores, including SIFT4G (sift-dna.org/sift4g) (as described by Vaser et al. 2016; Sim et al. 2012), PolyPhen-2 (genetics.bwh.harvard.edu) (as described by Adzhubei, Jordan, and Sunyaev 2013), PROVEAN (provean.jcvi.org) (as described by Choi et al. 2012), and PANTHER (as described by Mi et al. 2017). All other SNPs were linked to the most proximal gene (P-Gene) or gene region as described by Langefeld et al. 2017. For overlap studies, Venn diagrams were computed and visualized using InteractiVenn (interactivenn.net) (as described by Heberle et al. 2015). All predicted genes were divided into an EA, AS, or shared group depending on the ancestral designation of the original SLE-associated SNP.

Functional gene set analysis and identification of upstream regulators (UPRs) were performed as follows. For both ancestral groups, predicted gene lists were examined using Biologically Informed Gene Clustering (BIG-C; version 4.4). BIG-C is a custom functional clustering tool developed to annotate the biological meaning of large lists of genes. Genes are sorted into 54 categories based on their most likely biological function and/or cellular localization based on information from multiple online tools and databases including UniProtKB/Swiss-Prot, gene ontology (GO) Terms, MGI database, KEGG pathways, NCBI, PubMed, and the Interactome (as described by Catalina, Bachali, et al. 2019; Catalina, Owen, et al. 2019).

I-Scope is a custom clustering tool used to identify immune infiltrates in large gene datasets (as described by Ren et al. 2019). Briefly, I-Scope was created through an iterative search of more than 17,000 genes identified in more than 50 microarray datasets. These genes were researched for immune cell specific expression in 30 hematopoietic sub-categories: T cells, regulatory T cells, activated T cells, anergic cells, CD4 T cells, CD8 T cells, gamma-delta T cells, NK/NKT cells, T & B cells, B cells, activated B cells, T &B & monocytes, monocytes & B cells, MHC Class II expressing cells, monocyte dendritic cells, dendritic cells, plasmacytoid dendritic cells, Langerhans cells, myeloid cells, plasma cells, erythrocytes, neutrophils, low density granulocytes, granulocytes, platelets, and all hematopoietic stem cells.

Enrichment of GO Biological Processes (BP) using the Database for Annotation, Visualization and Integrated Discovery (DAVID; david.ncifcrf.gov) and the Ingenuity Pathway Analysis (IPA; www.qiagenbioinformatics.com) platform were performed, which provided additional genetic pathway identification. IPA upstream regulator (UPR) analysis was also performed to identify potential transcription factors, cytokines, chemokines, etc. that can contribute to the observed gene expression pattern in the input dataset.

Network analysis and visualization were performed as follows. Visualization of protein-protein interaction and relationships between genes within datasets was performed using Cytoscape (version 3.6.1) software. Briefly, STRING (version 1.3.2) generated networks were imported into Cytoscape (version 3.6.1) and partitioned with MCODE via the clusterMaker2 (version 1.2.1) plugin.

Drug candidate identification and CoLT scoring were performed as follows. Drug candidates were identified using LINCS (lincsproject.org), STITCH (version 5.0; stitch.embl.de) and IPA. Each of these tools includes either a programmatic method of matching existing therapeutics to their targets or else provides a list of drugs and targets for achieving the same. In addition to identifying drugs targeting predicted genes directly, these tools were also used to identify drugs targeting select upstream regulators. Where information was available, drugs were assessed by CoLT scoring to rank potential drug candidates for repositioning in SLE (as described by Grammer et al. 2016).

Example 18: Genome-Wide Association Meta-Analysis Identifies Critical Regulators of Immune Dysfunction and Cell Stress Pathways Driving Cardiovascular Disease and Systemic Lupus Erythematosus Systemic lupus erythematosus (SLE) may be an autoimmune syndrome characterized by multi-organ inflammation and immune dysregulation, and may be highly associated with the development of cardiovascular disease (CVD). While studies exploring the association between SLE and premature CVD may demonstrate that altered immune function plays a pivotal role in the increased cardiovascular morbidity and mortality observed in SLE patients, there remains a need for identification of critical pathways in SLE and CVD pathogenesis that can be used as novel points of therapeutic interventions. Using systems and methods of the present disclosure, published genome-wide association studies (GWAS) from SLE and coronary artery disease (CAD) were used to identify 96 overlapping single-nucleotide polymorphisms (SNPs) significantly associated with both SLE and CAD. Variants were linked to 189 predicted causal genes via expression quantitative trait loci (eQTL) mapping, the identification of functional variants in coding regions and transcription factor binding sites, as well as traditional SNP-gene annotation. SLE/CAD-associated genes (e.g., genes associated with both SLE and CAD) were then used to predict biological pathways. Dysregulated pathways representative of both SLE and CAD centered around dysfunctional immune function and cell stress.

SLE may be estimated to affect nearly 1.5 million people in the United States alone. Compared to the general population, patients with SLE may have a 2- to 10-fold increased risk of CVD. For example, the relative risk for women with SLE between the ages of 35-45 may be increased by about 50-fold, and the occurrence of fatal myocardial infarction may be about 3 times greater in SLE patients. Additionally, many SLE patients who have a myocardial infarction may be relatively young, indicating an increased risk with SLE rather than chance occurrences.

The therapeutic challenge presented by SLE may be largely due to the extensive heterogeneity of the disease. In general, SLE may be associated with hyperactivity of the innate and adaptive immune system, such as T and B cell abnormalities, overproduction of autoantibodies, and disturbed cytokine balance. Heterogeneity of SLE may include differential expression of these abnormalities and clinical manifestations. Standard-of-care treatments for SLE may include glucocorticoids, non-steroidal anti-inflammatory drugs (NSAIDs), antimalarials, and immunosuppressive drugs. These drugs may only treat the symptoms of the disease and/or control the progression of the disease. Recently, drugs such as belimumab have been approved for treatment of SLE as well. Belimumab was not only the first new drug approved for SLE in decades, it also is the first biological agent used for treating SLE. Despite the moderate effectiveness, the approval of belimumab marks a shift in treatments for SLE away from symptom-relieving medicine.

While in SLE patients, mortality related to infections and active disease may have decreased, CVD-related death rates may not have improved, and the standardized mortality ratio due to CVD may have actually increased. Treatment options may remain limited, as statins may have little effect on cardiovascular outcomes in SLE populations, despite their effective preventative role in non-SLE patients. Studies exploring the association between SLE and premature CVD may demonstrate that alterations of specific immune functions play a pivotal role in the increased cardiovascular morbidity and mortality observed in SLE patients. Nonetheless, there remains a need for additional studies to identify critical pathways in SLE CVD pathogenesis that can be used as novel points of therapeutic intervention.

Genetic predispositions may be important risk factors for both SLE and CVD. A lack of a correlation between severity of SLE and development of CVD in SLE may support a hypothesis that genetic components play a role in SLE patients for developing CVD. Although Genome-Wide Association Studies (GWAS) may be successful in mapping disease loci in both autoimmune and cardiovascular disease, these results may fail to impact clinical practice. Understanding the functional mechanisms of causal genetic variants underlying SLE and CVD may provide essential information to identify shared molecular pathways and therapeutic targets relevant to disease mechanisms. Using systems and methods of the present disclosure, shared pathways underlying SLE CVD were evaluated, with a focus on identifying novel therapeutic options. Using a comprehensive bioinformatics approach, existing drugs may be matched to the molecular pathways contributing to the increased risk of CVD in SLE. By repurposing FDA-approved drugs, the process of bringing new therapeutic options to the market may be significantly expedited.

Results

Figure 73A:
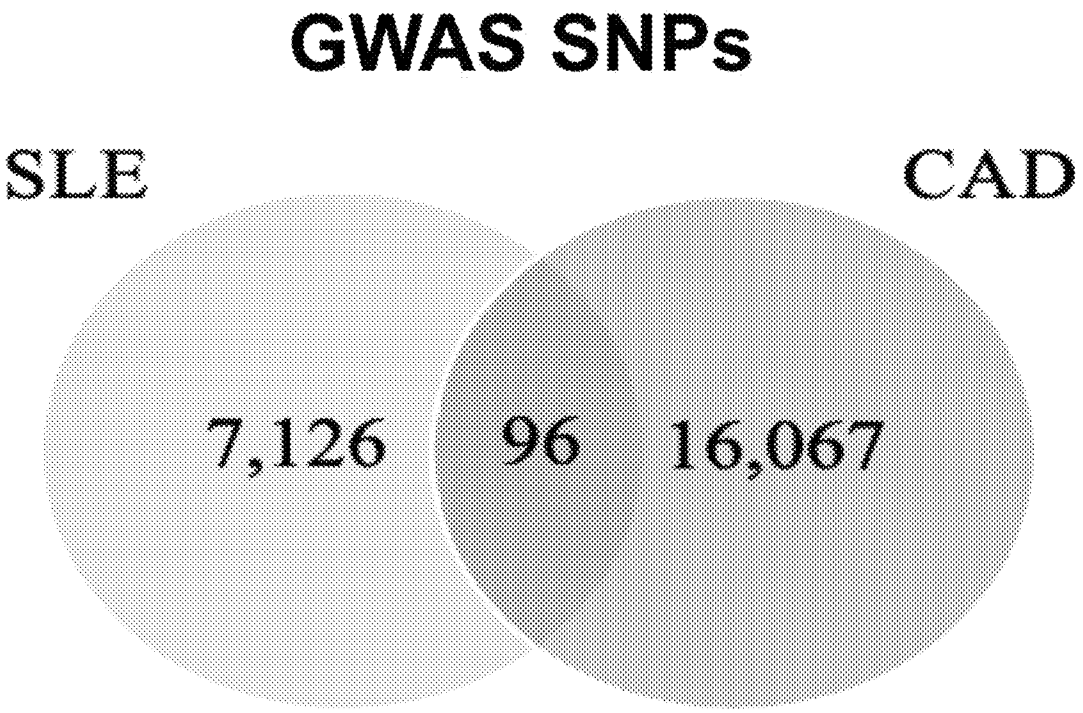
FIGS. 73A-73D show examples of identification of GWAS variants linked to CAD and SLE, including a total of 96 SNPs (e.g., the intersecting set) found to be associated with both conditions (FIG. 73A), where statistical overlap analysis was performed using Monte Carlo simulations; this overlap was determined to be highly significant (p-value <0.0001) and unlikely to be due to random chance (FIGS. 73B-73D).
Figure 73B:
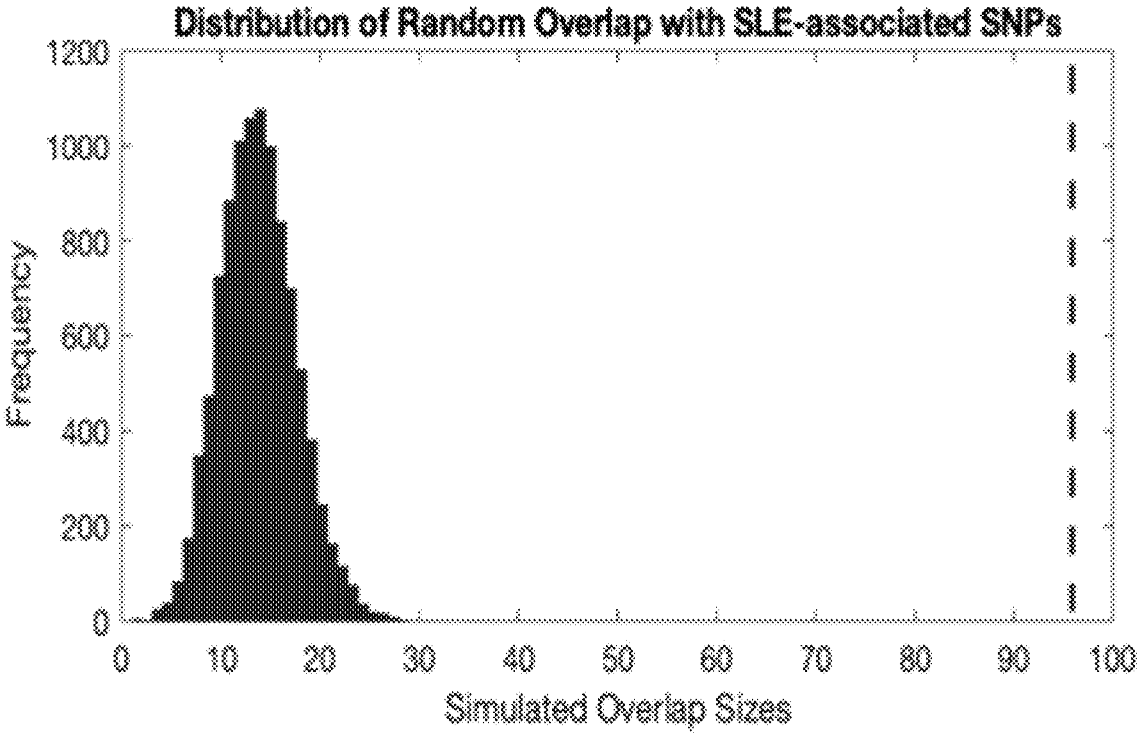
Figure 73C:
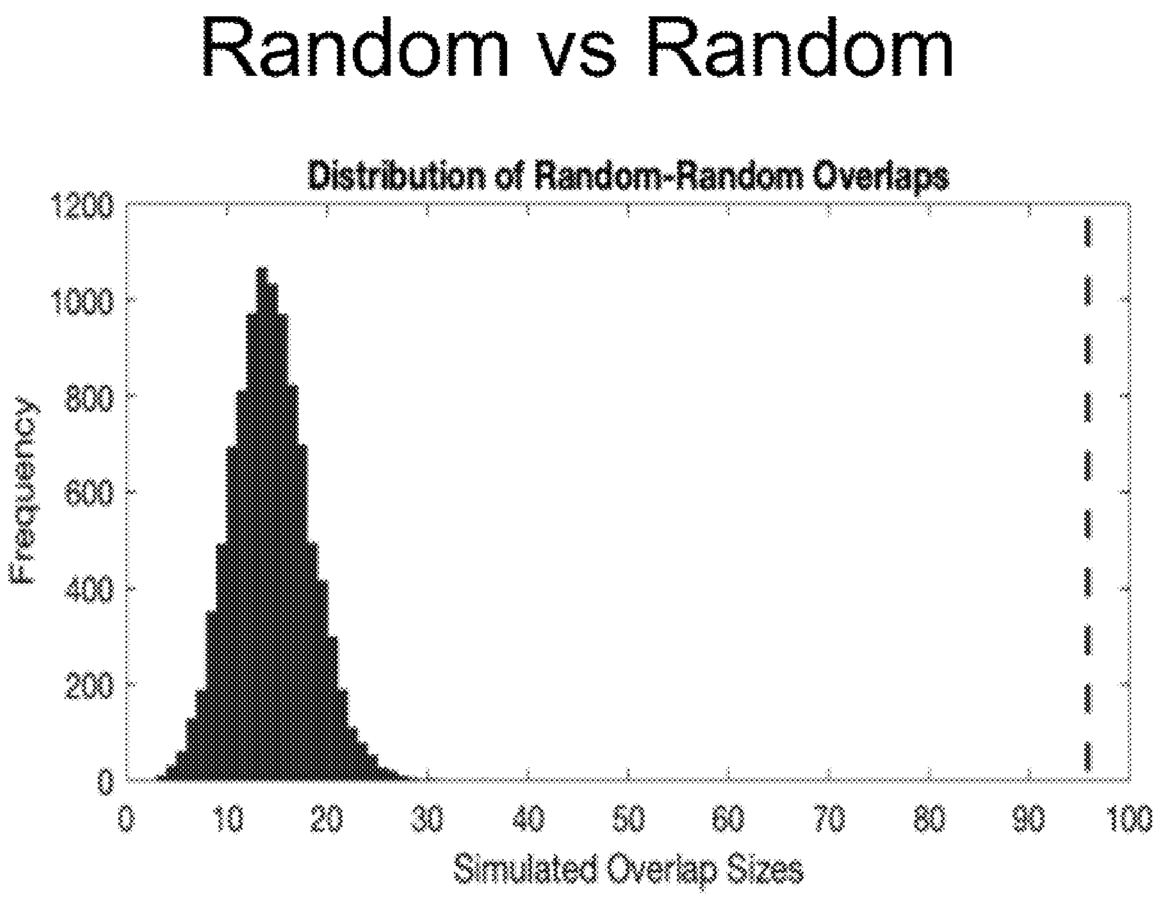
Figure 73D:
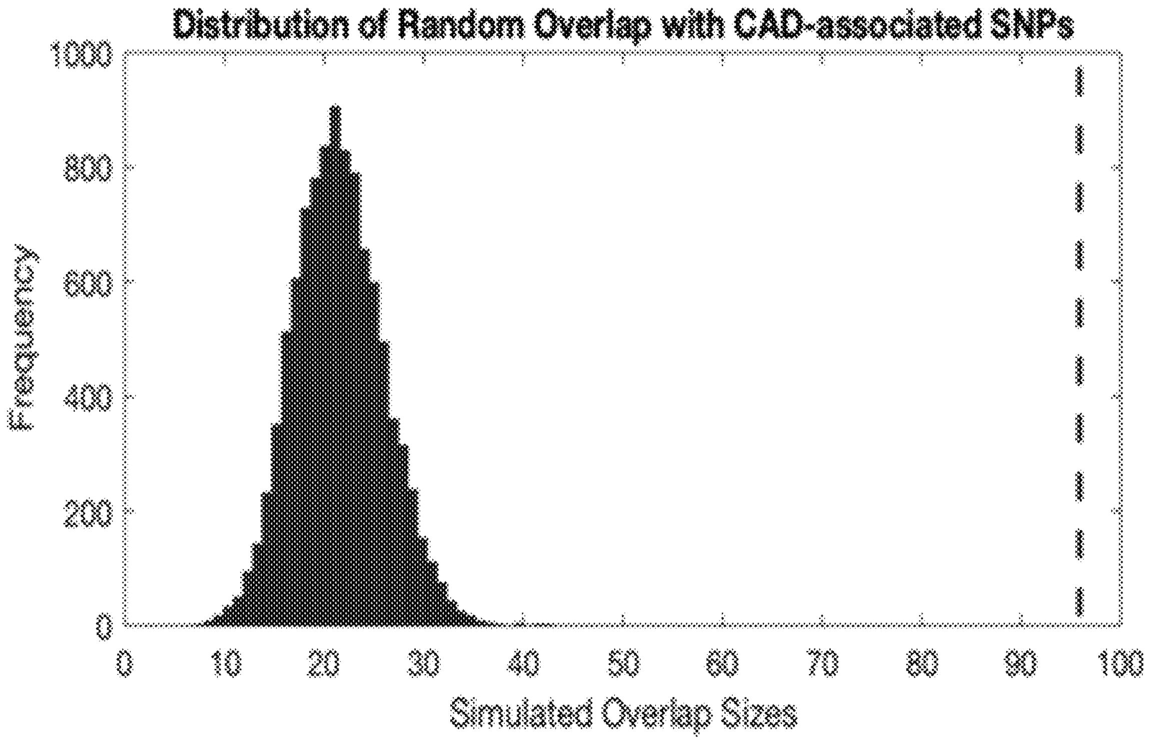
Figure 74A:
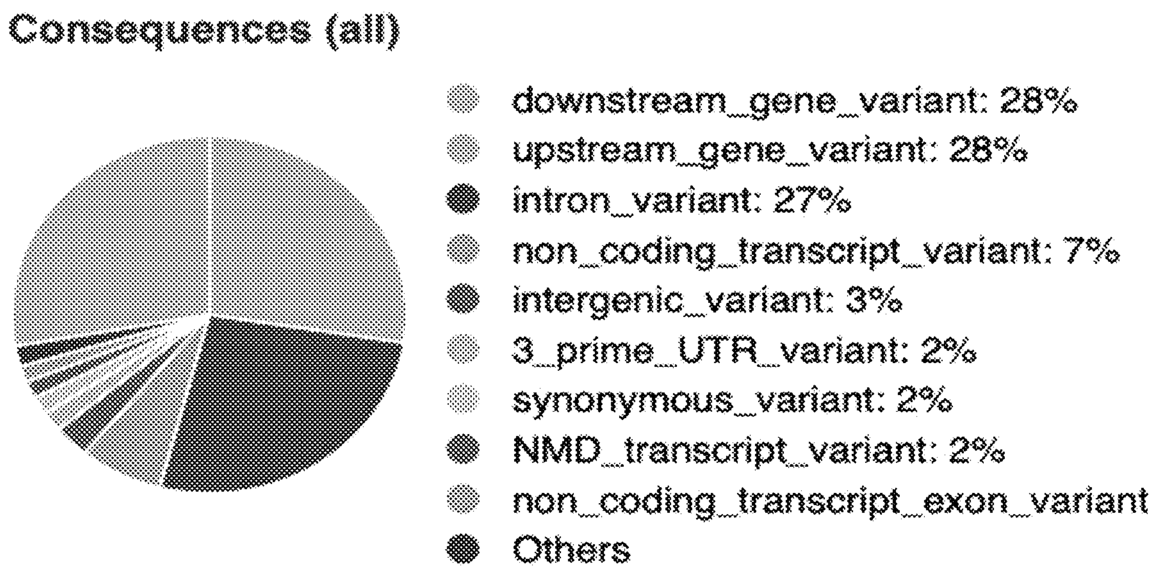
FIGS. 74A-74B show that the majority (about 80%) of the overlapping SLE/CAD SNPs were located in non-coding regions of the genome, either in introns or intergenic regions (including upstream and downstream gene variants) (FIG. 74A); approximately 7% (7) of the SNPs mapped to coding regions (FIG. 74B), while the remaining SNPs were located in regulatory regions (e.g., promoters, enhancers, and transcription factor binding sites).
Figure 74B:
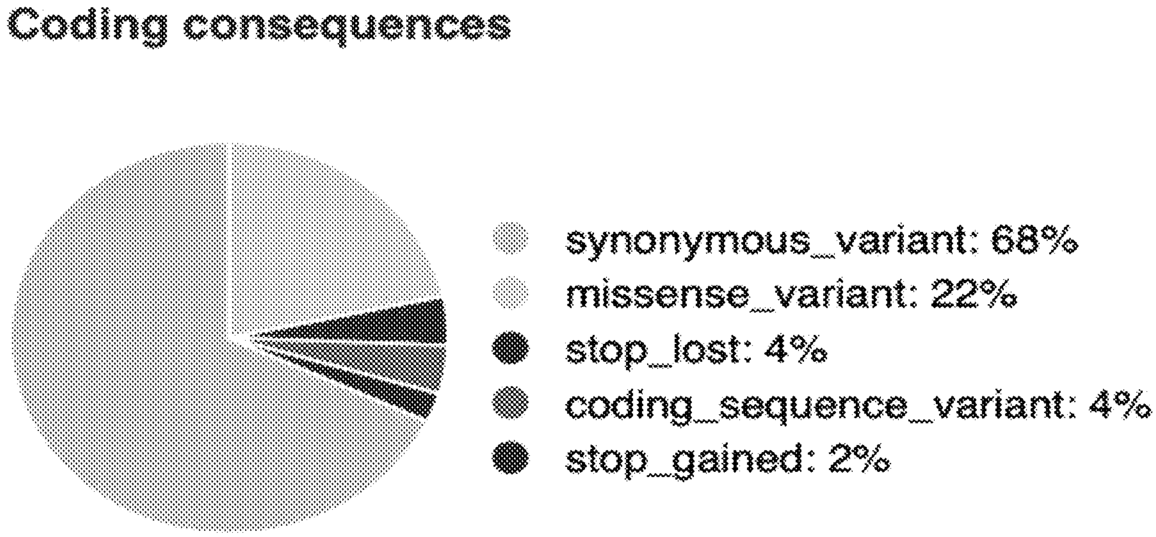

Identification of GWAS variants linked to CAD and SLE was performed as follows. Genome-Wide Association Study (GWAS) results were used to determine SNPs associated with each disease. Using a significance threshold of p-value $<10^{-6}$, a set of 7,222 SNPs was found to be significantly associated with SLE, and a set of 16,163 SNPs was found to be significantly associated with CAD. Further, a total of 96 SNPs (e.g., the intersecting set) were associated with both conditions (FIG. 73A). Statistical overlap analysis was performed using Monte Carlo simulations, and this overlap was determined to be highly significant (p-value <0.0001) and unlikely to be due to random chance (FIGS. 73B-73D). Next, the functional consequence and genomic locations of all SLE/CAD SNPs were determined, using the Ensembl Variant Effect Predictor (VEP) tool (ensembl.org). The majority (about 80%) of the overlapping SLE/CAD SNPs were located in non-coding regions of the genome, either in introns or intergenic regions (including upstream and downstream gene variants) (FIG. 74A). Approximately 7% (7) of the SNPs mapped to coding regions (FIG. 74B), while the remaining SNPs were located in regulatory regions (e.g., promoters, enhancers, and transcription factor binding sites).

Figure 75:
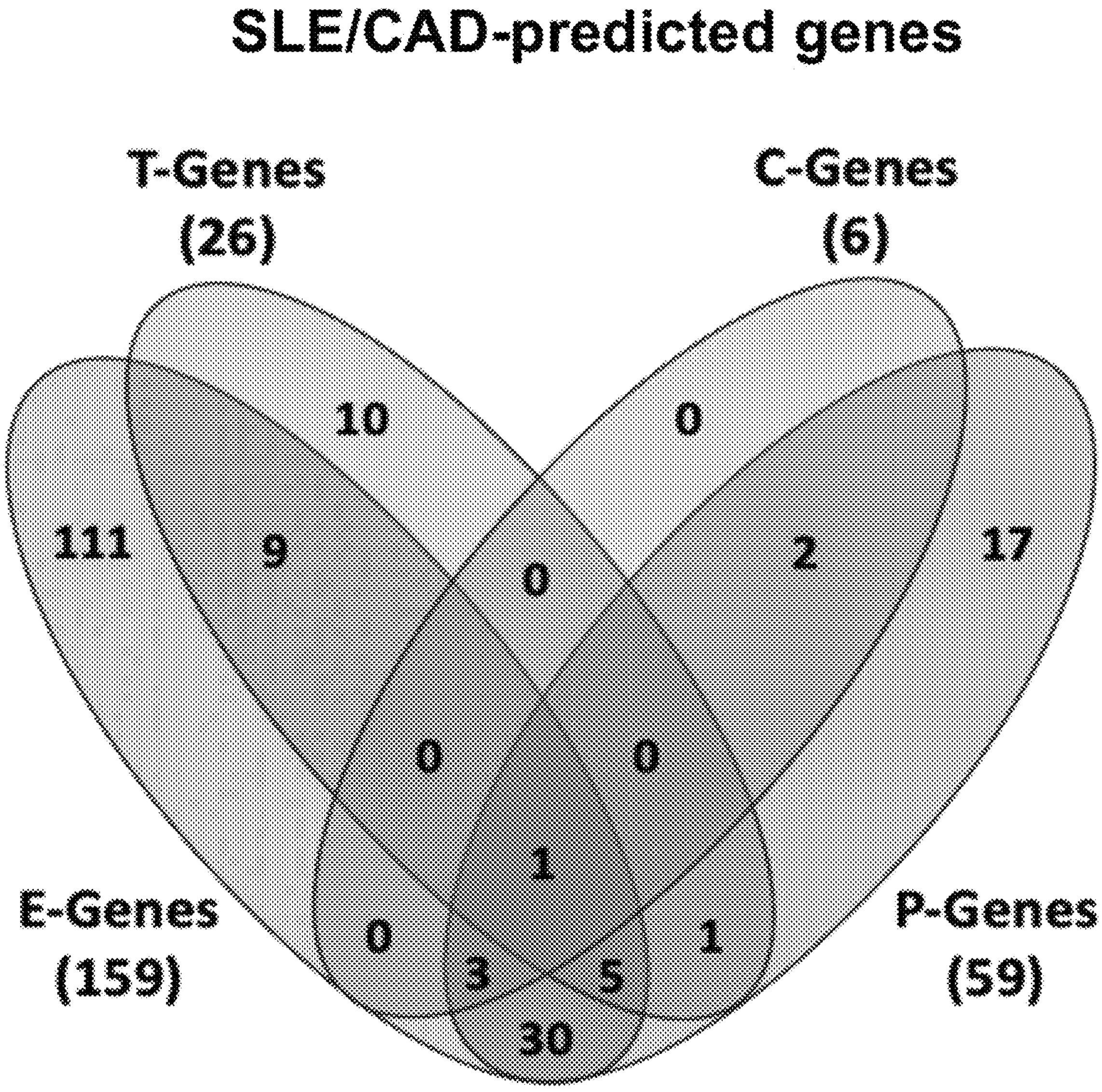
FIG. 75 depicts the overlap between the corresponding SNP-predicted E-Genes, T-Genes, C-Genes, and P-Genes. One gene, MUC22, was shared within all four groups, and limited commonality was observed between T-Genes, P-Genes, and E-Genes, with only 5 genes shared among the three groups.

SLE/CAD SNPs were used to predict downstream target genes as follows. Using multiple bioinformatic-based approaches, a set of most plausible gene(s) affected by the SLE/CAD-SNP association were identified. First, it was determined whether there was evidence that the SNP was a quantitative trait locus (eQTL) using the GTEx (version 8) database ("The Genotype-Tissue Expression (GTEx) Project" n.d.). eQTL mapping identified a total of 159 expression genes (E-Genes). Next, SNPs were identified within distal and cis regulatory elements (e.g., enhancers and promoters). To examine putative enhancer and promoter regions, HACER (Human ACtive Enhancers to interpret Regulatory variants;

bioinfo.vanderbilt.edu/AE/HACER/) was used, which connects regulatory SNPs with downstream target genes (T-Genes) (as described by Fishilevich et al. 2017; Wang et al. 2019). Using this approach, HACER was used to identify 4 SNPs overlapping distal regulatory elements or promoters that were predicted to impact the expression of 26 T-Genes. For variants located in coding regions, 7 SNPs were associated with either non-synonymous or nonsense changes, affecting 6 genes (C-Genes; Table 30). Finally, traditional annotation methods relying on SNP-gene physical proximity, such as dbSNP (www.ncbi.nlm.nih.gov/snp/), which specifies genes within 5000 base-pairs upstream and downstream of the variant, were performed to identify 59 proximal genes (P-genes). In addition, chromosomal locations obtained from dbSNP were used to perform P-Gene validation using Stanford's Genomic Regions Enrichment of Annotations Tool (GREAT) (McLean, Cory Y et al., 2010). FIG. 75 depicts the overlap between the corresponding SNP-predicted E-Genes, T-Genes, C-Genes, and P-Genes. One gene, MUC22, was shared within all four groups, and limited commonality was observed between T-Genes, P-Genes, and E-Genes, with only 5 genes shared among the three groups.

Figure 76A:
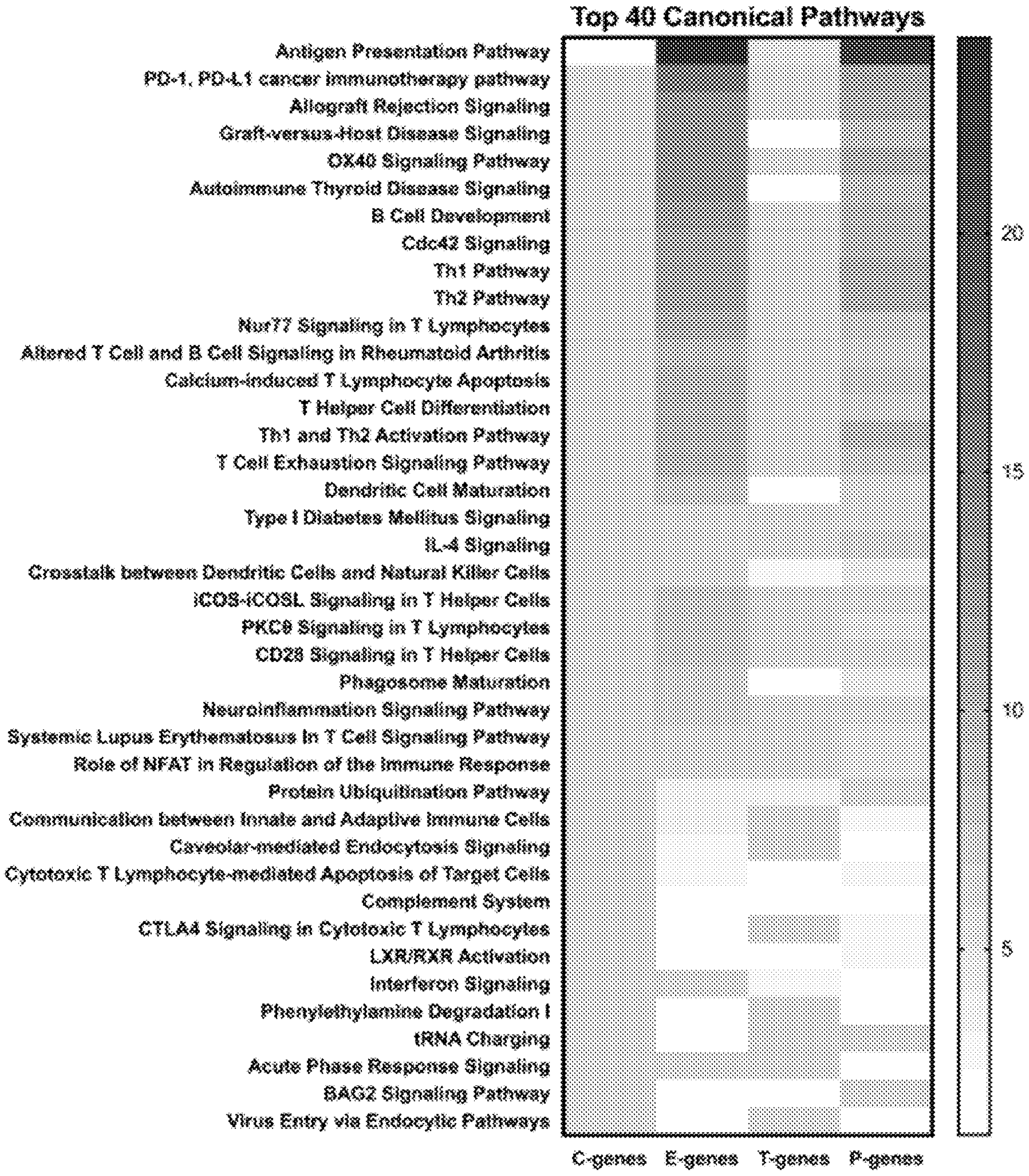
FIGS. 76A-76D show examples of characterization of the SLE/CAD gene signature, including a heatmap visualization of the top 40 IPA canonical pathways for each gene group which was generated (FIG. 76A); while many pathways were shared between the E-Gene and P-Gene sets, the antigen presentation pathway was the only pathway shared across all 4 gene sets; the dominance of immune-based processes was also reflected by EnrichR, BIG-C and I-Scope (FIGS. 76B-76D).
Figure 76B:
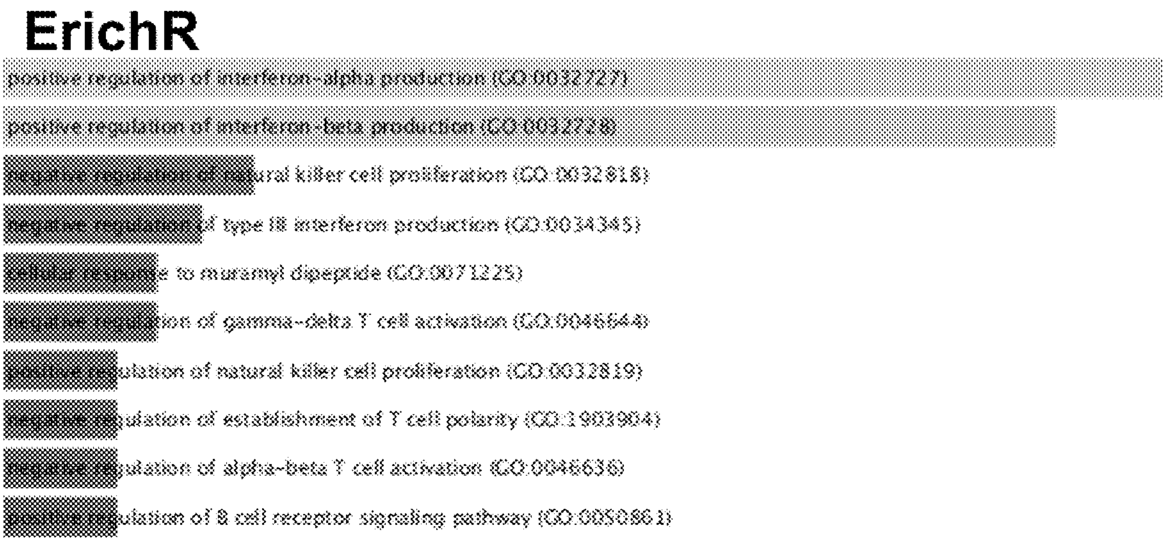
Figure 76C:
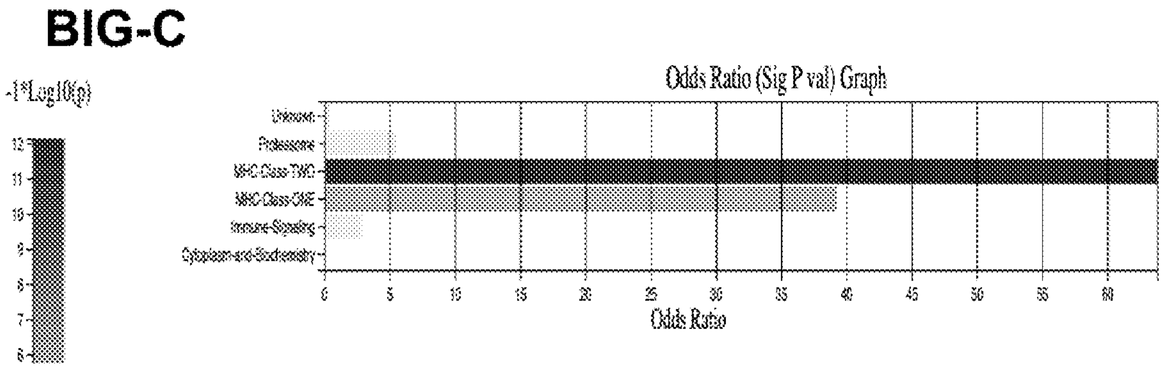
Figure 76D:
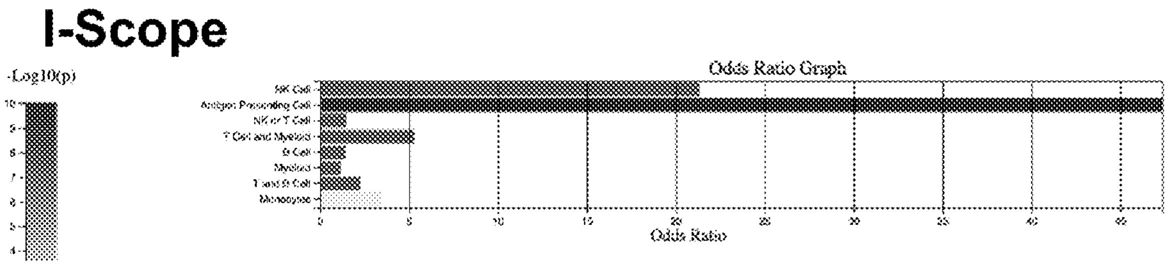

Characterization of the SLE/CAD gene signature was performed as follows. Given the diversity of mechanisms through which SLE/CAD-associated SNPs are linked to genes (e.g., eQTL, regulatory element and coding region mapping, SNP-gene proximity), a series of bioinformatic analyses were completed to examine the biological functions of E-Genes, T-Genes, C-Genes, and P-Genes, separately and collectively. Significant canonical pathways were identified using Ingenuity Pathway Analysis (IPA) and EnrichR (amp-.pharm.mssm.edu/Enrichr). Additional functional annotation was determined by Biologically Informed Gene Clustering (BIG-C), a functional aggregation tool developed to understand the functional groupings of large gene lists (Labonte et al. 2018; Catalina, Bachali, et al. 2019) and I-Scope, a clustering program that detects immune and inflammatory cell type signatures within large gene lists to identify dominant immune cell populations driving disease pathology (Ren et al. 2019). A heatmap visualization of the top 40 IPA canonical pathways for each gene group was generated, as depicted in FIG. 76A. While many pathways were shared between the E-Gene and P-Gene sets, the antigen presentation pathway was the only pathway shared across all 4 gene sets. The dominance of immune-based processes was also reflected by EnrichR, BIG-C and I-Scope (FIGS. 76B-76D).

Figure 77:
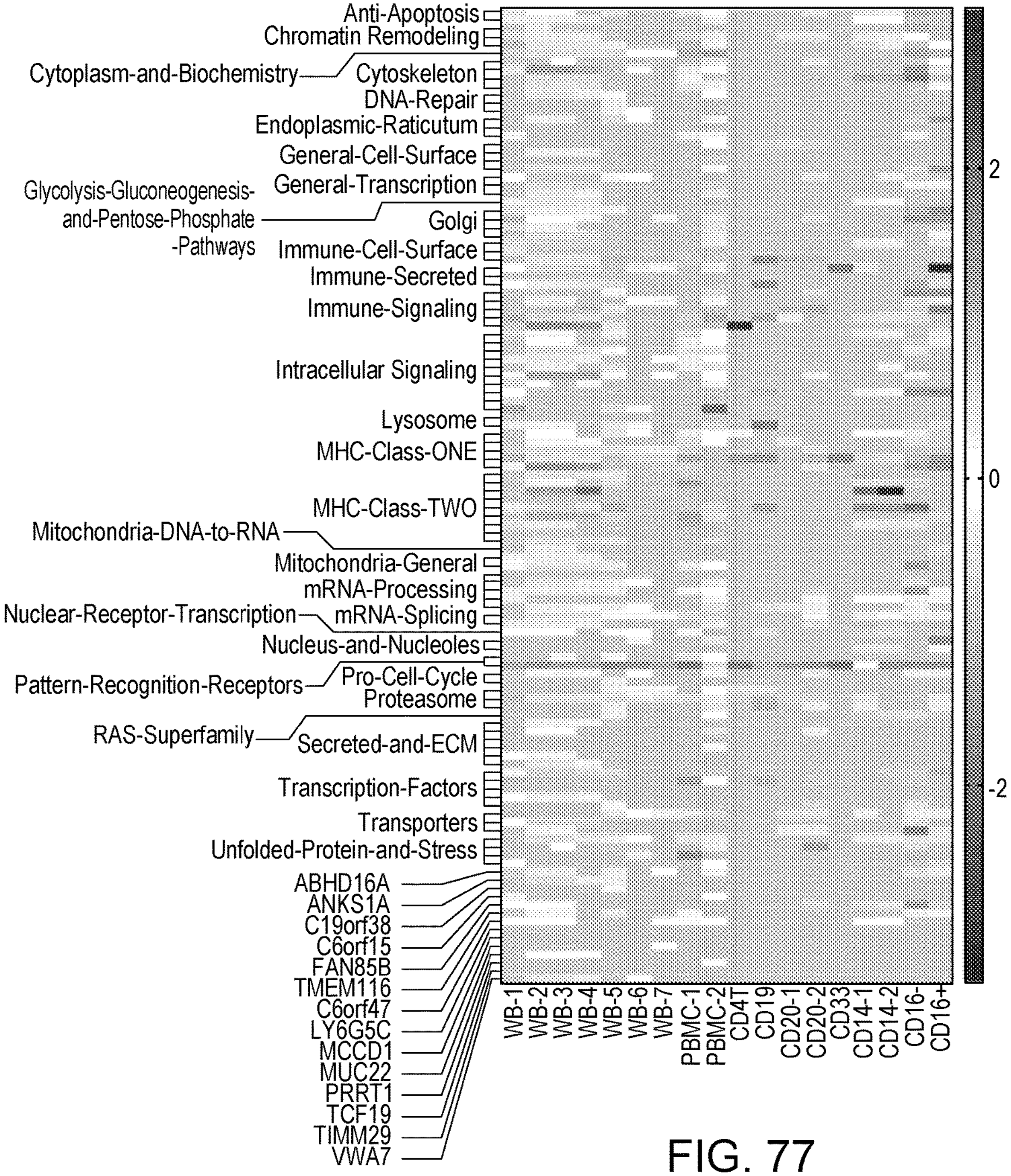
FIG. 77 shows heatmaps depicting the log-fold change for each gene were generated and organized based on enriched BIG-C category. It was observed that, of the 189 SNP-predicted genes, 118 (62%) were identified as DEGs across all datasets.

Predicted SLE/CAD genes were shown to be linked to altered expression in SLE and to be enriched in differential expression datasets as follows. Next, it was determined whether genes linked to SLE/CAD associated variants exhibited altered expression in SLE. SNP-predicted genes were matched to differentially expressed genes (DEGs) in unrelated SLE datasets in various tissues, including whole blood, PBMCs, B cells, T cells, synovium, skin, and kidney. Heatmaps depicting the log-fold change for each gene were generated and organized based on enriched BIG-C category. It was observed that, of the 189 SNP-predicted genes, 118 (62%) were identified as DEGs across all datasets (FIG. 77).

Figure 78A:
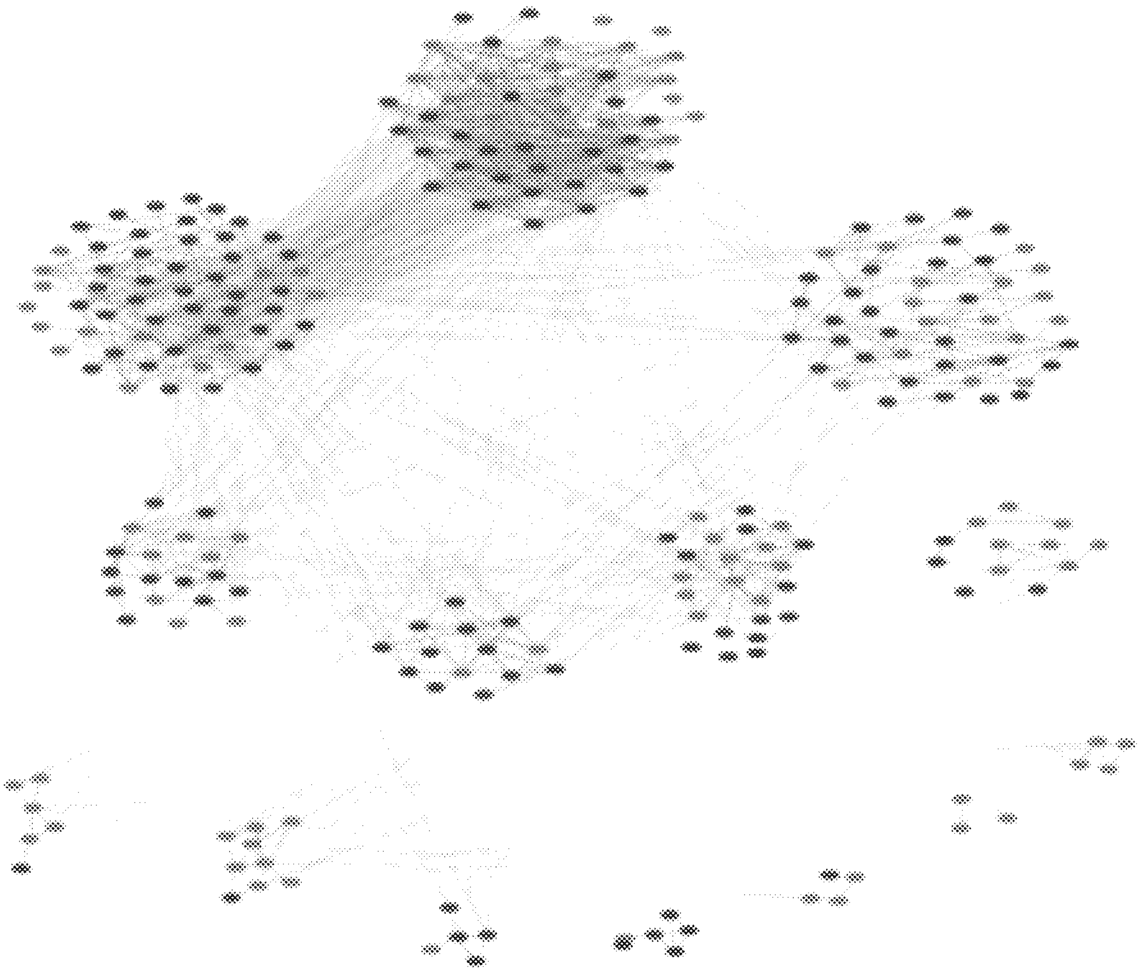
FIGS. 78A-78B show examples of delineation of signaling pathways identified by SLE/CAD SNP-associated genes and UPRs, including protein-protein interaction (PPI) networks comprising SLE/CAD DEGs and their UPRs constructed using STRING, visualized in Cytoscape, and clustered using MCODE to provide an additional level of functional annotation (FIG. 78A); the resulting networks were further simplified into meta-structures defined by the number of genes in each cluster, the number of significant intra-cluster connections predicted by MCODE, and the strength of associations connecting members of different clusters to each other (FIG. 78B).
Figure 78B:
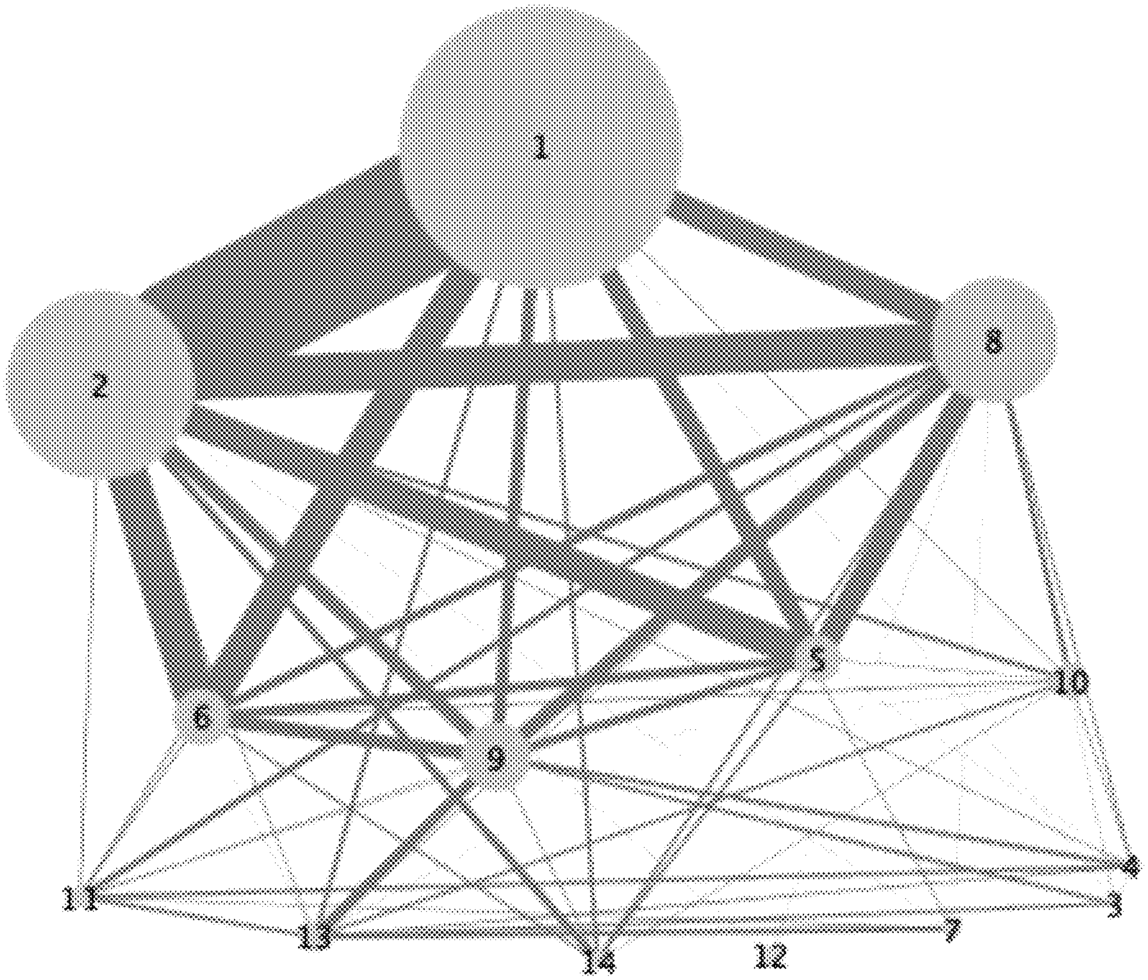

Delineation of signaling pathways were identified by SLE/CAD SNP-associated genes and UPRs as follows. SLE/CAD key signaling pathways were elucidated in greater detail. Using IPA, all differentially expressed SNP-associated genes were used to identify potential biological upstream regulators (UPRs). Protein-protein interaction (PPI) networks comprising SLE/CAD DEGs and their UPRs were constructed using STRING, visualized in Cytoscape, and clustered using MCODE to provide an additional level of functional annotation (FIG. 78A). The resulting networks were further simplified into meta-structures defined by the number of genes in each cluster, the number of significant intra-cluster connections predicted by MCODE, and the strength of associations connecting members of different clusters to each other (FIG. 78B). Finally, individual gene clusters were analyzed by BIG-C, I-Scope and IPA to identify those molecules, cell types, and pathways highly associated with disease (Table 31). Clusters 1, 2, and 8 were determined to be heavily dominated by immune-based processes, including the TH1 and TH2 activation pathway and SLE in B cell signaling pathway, whereas clusters 6 and 9 were determined to be enriched in pathways associated with acute inflammation (acute phase response signaling and complement system), and cluster 5 and 10 were determined to be enriched in pathways associated with cell stress and repair (unfolded protein response and nuclear excision repair pathway). I-Scope categories also revealed enrichment in myeloid-lineage cells and/or monocytes, which in line with the role of these cells in the development of both SLE and CAD.

Figure 79A:
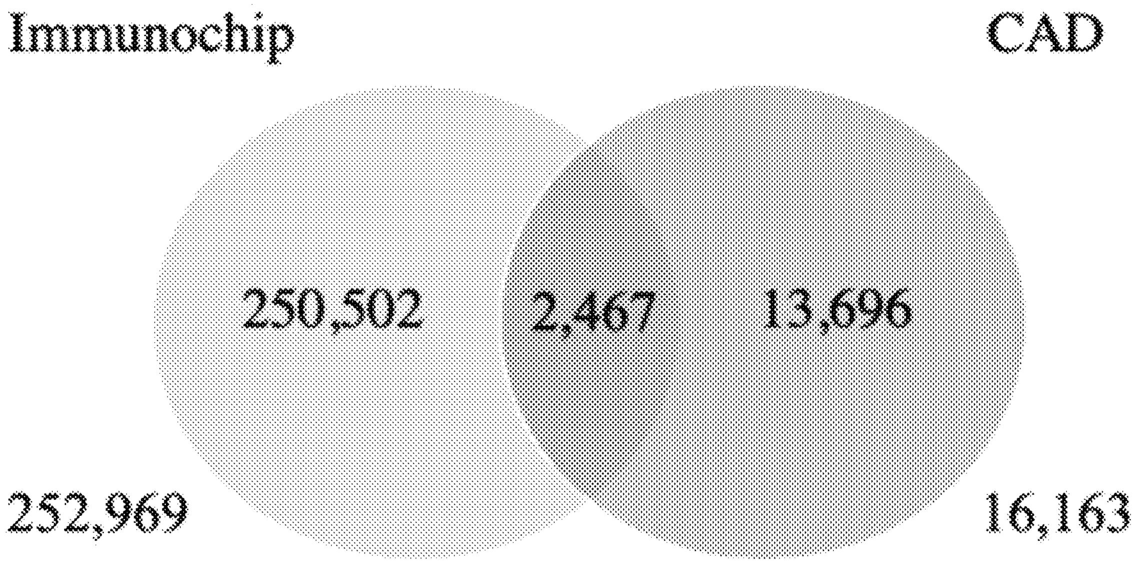
FIGS. 79A-79B show Immunochip SNPs significantly associated with CAD, including a Venn diagram of Immunochip SNPs and SNPs significantly associated with CAD (p-value <1E-6) (FIG. 79A); and histograms of the distribution of overlap sizes between the 252,969 SNPs included on the Immunochip and 10,000 random subsets of 16,163 GWAS SNPs.
Figure 79B:
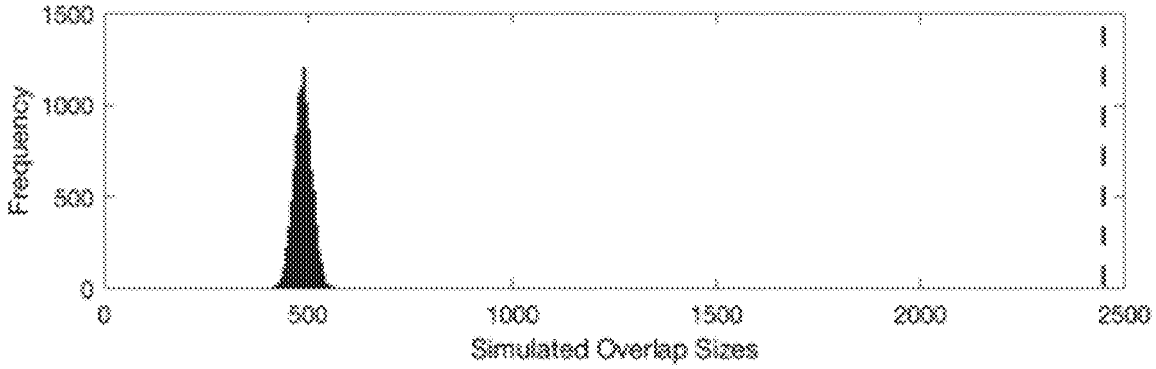

FIGS. 79A-79B show Immunochip SNPs significantly associated with CAD, including a Venn diagram of Immunochip SNPs and SNPs significantly associated with CAD (p-value <1E-6) (FIG. 79A); and histograms of the distribution of overlap sizes between the 252,969 SNPs included on the Immunochip and 10,000 random subsets of 16,163 GWAS SNPs.

Figure 80A:
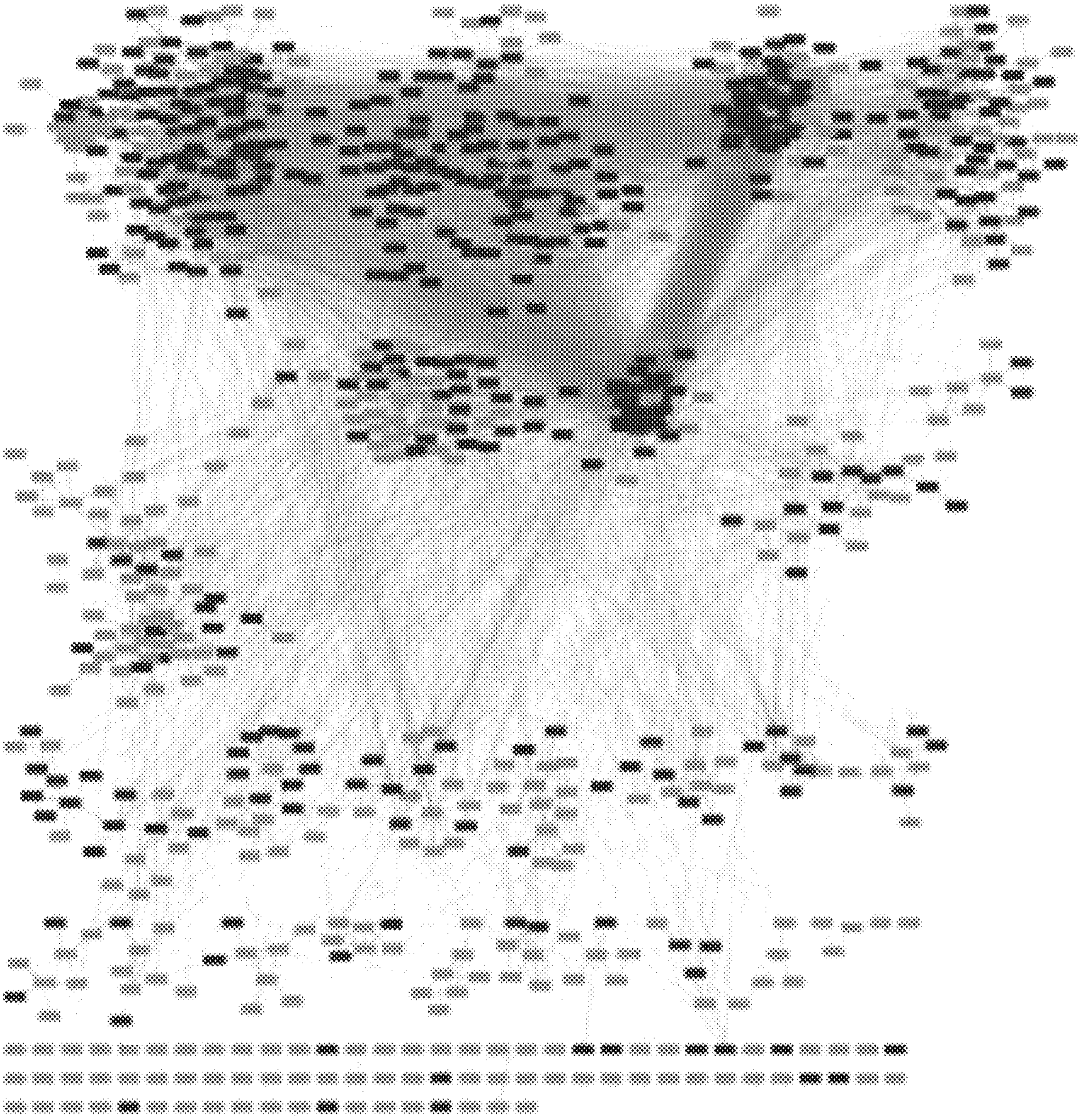
FIGS. 80A-80B show a visualization of protein interaction network and gene clusters associated with CAD and major autoimmune and inflammatory disease, including protein-protein interactions of predicted genes and their UPRs obtained with STRING, visualized with Cytoscape for visualization and clustered using MCODE (FIG. 80A), where green nodes represent SNP-predicted genes; blue nodes represent UPRs; and MCODE clusters further simplified into metaclusters where the size of each cluster represents the number of intra-cluster connections and the edge weight represents the number of inter-cluster connections (FIG. 80B).
Figure 80B:
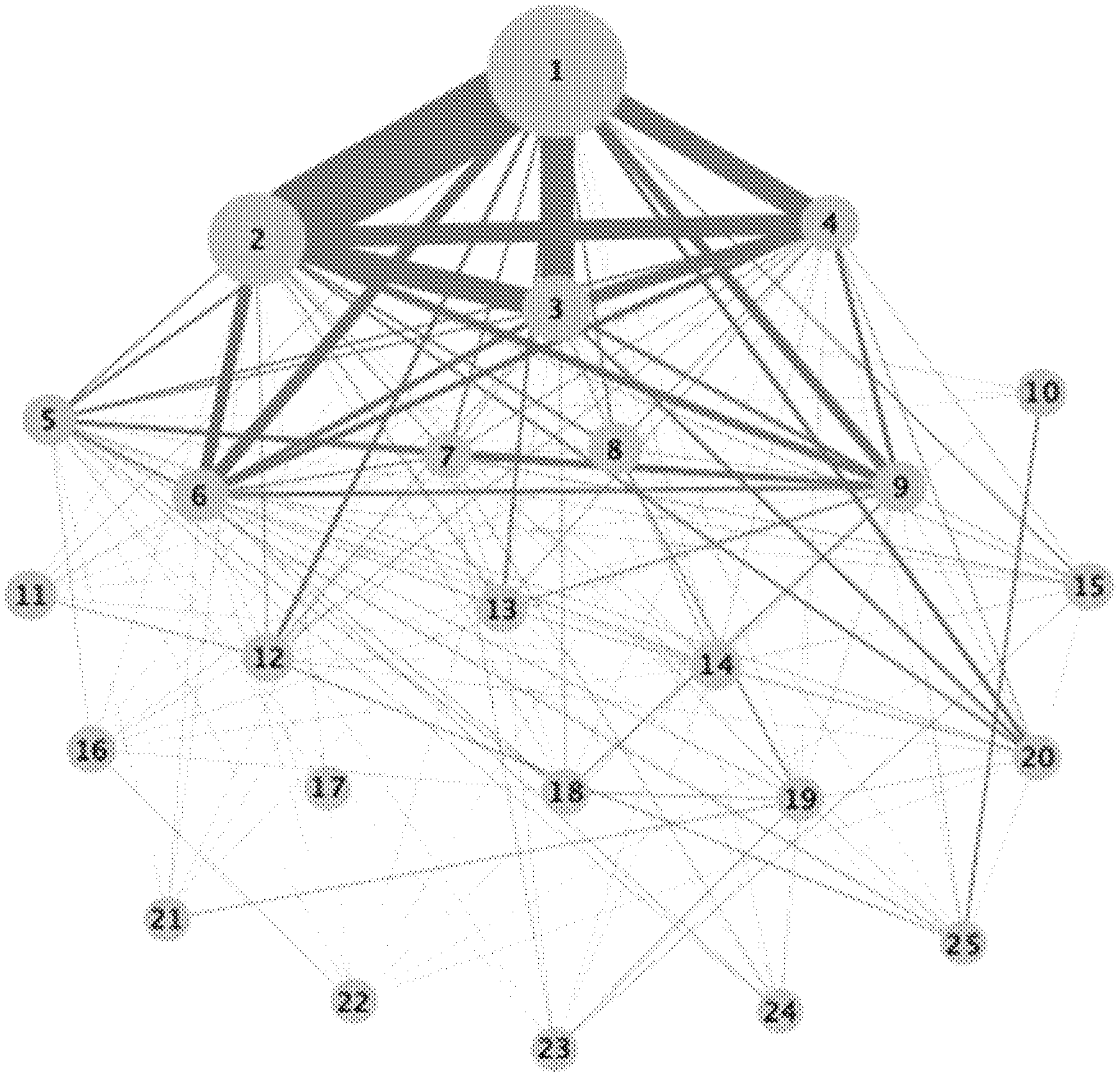

FIGS. 80A-80B show a visualization of protein interaction network and gene clusters associated with CAD and major autoimmune and inflammatory disease, including protein-protein interactions of predicted genes and their UPRs obtained with STRING, visualized with Cytoscape for visualization and clustered using MCODE (FIG. 80A), where green nodes represent SNP-predicted genes; blue nodes represent UPRs; and MCODE clusters further simplified into metaclusters where the size of each cluster represents the number of intra-cluster connections and the edge weight represents the number of inter-cluster connections (FIG. 80B).

Figure 81:
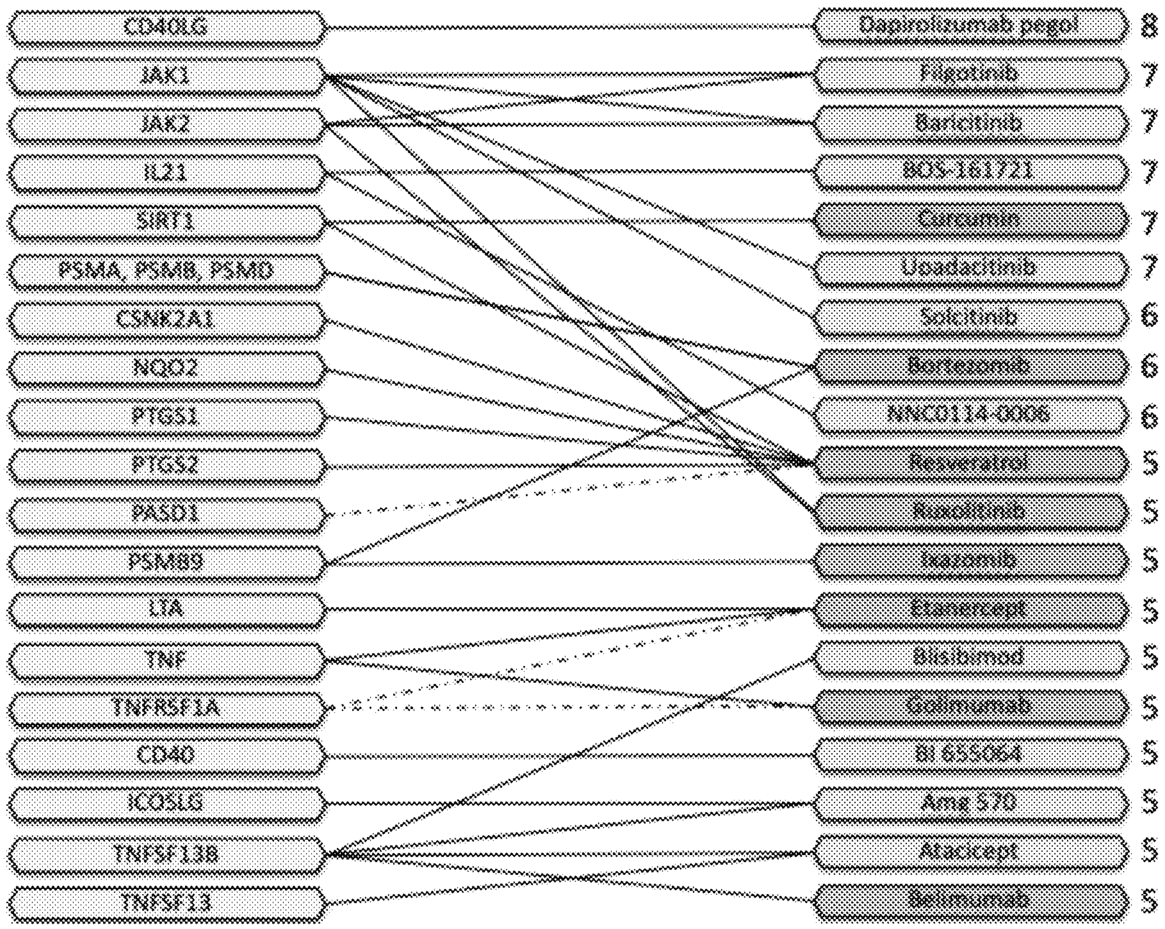
FIG. 81 shows a visualization of existing drugs targeting potential therapeutic targets within SLE/CAD gene networks. Drugs targets (left column, yellow) were identified within the molecular pathways enriched in SLE/CAD genes and matched to existing compounds (right column, green) using an in-house genomic platform, including direct targets (solid line) and indirect targets (dashed line). Identified FDA-approved drugs (bright green) and drugs in development (light green) were ranked using the Combined Lupus Treatment Scoring (CoLTs) system (numbers on far right).

FIG. 81 shows a visualization of existing drugs targeting potential therapeutic targets within SLE/CAD gene networks. Drugs targets (left column, yellow) were identified within the molecular pathways enriched in SLE/CAD genes and matched to existing compounds (right column, green) using an in-house genomic platform, including direct targets (solid line) and indirect targets (dashed line). Identified FDA-approved drugs (bright green) and drugs in development (light green) were ranked using the Combined Lupus Treatment Scoring (CoLTs) system (numbers on far right).

Methods

Genomic functional categories were determined as follows. The Variant Effect Predictor (VEP) tool available on the Ensembl genome browser 93 (www.ensembl.org) was used for annotation information to specify SNPs located within non-coding regions, including micro (mi) RNAs, long non-coding (Inc) RNAs, introns and intergenic regions. Regulatory regions included transcription factor binding sites (TFBS), promoters, enhancers, repressors, promoter flanking regions, and open chromatin. Coding regions were broken down further, and include S'UTRs, 3'UTRs, and synonymous and nonsynonymous (missense and nonsense) mutations. The online resource tool HaploReg (version 4.1; pubs.broadinstitute.org/mammals/haploreg/haploreg.php) (as described by Ward and Kellis 2016) were also used to identify DNA features and regulatory elements, and to assess regulatory potential.

Statistical analysis of overlap between SNPs associated with both SLE and CAD was performed as follows. SLE and CAD Genome-Wide Association Study (GWAS) results were used to determine a set of SNPs associated with each disease. Using a significance threshold of p-value $<10^{-6}$, a set of 7,222 significantly associated with SLE were identified, and a set of 16,163 SNPs significantly associated with CAD were identified. Of these SNPs, 96 were significantly associated with both SLE and CAD. A Monte Carlo simulation method was performed to estimate the probability of an overlap of at least 96 SNPs between two sets having 7,222 and 16,163 unrelated SNPs. Monte Carlo simulation may be performed to assess the significance of an outcome by simulating the event many times for a close approximation of the outcome probability.

The Monte Carlo simulation, which was implemented in MATLAB, comprised selecting a random subset of equivalent size to the set of significant SLE-associated or CAD-associated SNPs from all SNPs tested for in the respective study. The random subset was then intersected with the significant SNPs associated to the other disease or another random subset of that size. This was repeated 10,000 times to generate a null distribution of the number of SNPs occurring in unrelated subsets containing 7,222 and 16,163

SNPs (FIGS. 73B-73D). The null distributions were then used to estimate the probability that an overlap of 96 SNPs is obtained from intersecting random sets of 7,222 and 16,163 SNPs. The estimated probabilities were determined by calculating the percent of trials resulting in an overlap of 96 or more SNPs.

First, the likelihood of 96 SNPs overlapping the 7,222 significant SLE SNPs and 16,163 unrelated SNPs was estimated by generating random subsets of 16,163 SNPs from the over 7 million SNPs included in the CAD GWAS (FIG. 73B). Similarly, 838 SNPs were randomly selected from the Immunochip SNPs, and 6,497 SNPs were randomly selected from the GWAS SNPs. Both random subsets were then overlapped with the 16,163 CAD-associated SNPs, and the total number of unique SNPs overlapping the CAD-associated SNPs were recorded to generate a null distribution (FIG. 73D). There were 113 SNPs determined to be significantly associated with SLE by the Immunochip and GWAS results, giving a total of 7,222 SNPs. However, when 838 and 6,497 random SNPs were separately chosen, there was rarely overlap, generating a set of less than 7,335 SNPs. The simulation errs on the safer side by holding the number of SNPs identified in each study constant as opposed to the total number, thus determining the overlap of CAD-associated SNPs with over 7,222 SNPs. Finally, a third simulation was performed in which both sets of SNPs were randomly generated as previously described and overlapped (FIG. 73C).

Identification of SLE-associated SNPs and predicted genes was performed as follows. Expression quantitative trait loci (eQTLs) were identified using The Genotype-Tissue Expression (GTEx) version 68 (GTEXportal.org) and mapped to their associated eQTL expression genes (E-Genes). To find SNPs in enhancers and promoters, and their associated transcription factors and downstream target genes (T-Genes), the atlas of Human Active Enhancers was queried to interpret Regulatory variants, using HACER (bioinfo.vanderbilt.edu/AE/HACER), as described by Wang et al. 2019. To find structural SNPs in protein-coding genes (C-Genes), the human Ensembl genome browser (GRCh38.p12; ensembl.org) and dbSNP (www.ncbi.nlm-.nih.gov/snp) were queried. Additional databases were used to generate loss-of-function prediction scores, including SIFT4G (sift-dna.org/sift4g), as described by Vaser et al. 2016 and Sim et al. 2012. All other SNPs were linked to the most proximal gene (P-Gene) or gene region, as described by Langefeld et al. 2017. For overlap studies, Venn diagrams were computed and visualized using InteractiVenn (interactivenn.net), as described by Heberle et al. 2015.

Functional gene set analysis and identification of upstream regulators (UPRs) were performed as follows. Predicted genes were examined using Biologically Informed Gene Clustering (BIG-C; version 4.4). BIG-C is a custom functional clustering tool developed to annotate the biological meaning of large lists of genes. Genes are sorted into 54 categories based on their most likely biological function and/or cellular localization based on information from multiple online tools and databases, including UniProtKB/Swiss-Prot, gene ontology (GO) Terms, MGI database, KEGG pathways, NCBI, PubMed, and the Interactome. BIG-C may be described by, for example, (Catalina, Bachali, et al. 2019; Catalina, Owen, et al. 2019).

I-Scope is a custom clustering tool used to identify immune infiltrates in large gene datasets, and may be described by, for example, Ren et al. 2019. Briefly, I-Scope was created through an iterative search of more than 17,000 genes identified in more than 50 microarray datasets. These genes were researched for immune cell specific expression in 30 hematopoietic sub-categories: T cells, regulatory T cells, activated T cells, anergic cells, CD4 T cells, CD8 T cells, gamma-delta T cells, NK/NKT cells, T & B cells, B cells, activated B cells, T &B & monocytes, monocytes & B cells, MHC Class II expressing cells, monocyte dendritic cells, dendritic cells, plasmacytoid dendritic cells, Langerhans cells, myeloid cells, plasma cells, erythrocytes, neutrophils, low density granulocytes, granulocytes, platelets, and all hematopoietic stem cells.

Enrichment of GO Biological Processes (BP) using the Database for Annotation, Visualization and Integrated Discovery (DAVID; david.ncifcrf.gov) and the Ingenuity Pathway Analysis (IPA; www.qiagenbioinformatics.com) platform were performed, which provided additional genetic pathway identification. IPA upstream regulator (UPR) analysis was also performed to identify potential transcription factors, cytokines, chemokines, etc. that can contribute to the observed gene expression pattern in the input dataset.

Network analysis and visualization were performed as follows. Visualization of protein-protein interaction and relationships between genes within datasets was performed using Cytoscape (version 3.6.1) software. Briefly, STRING (version 1.3.2) generated networks were imported into Cytoscape (version 3.6.1) and partitioned with MCODE via the clusterMaker2 (version 1.2.1) plugin.

Tables

TABLE 30

Genes affected by SNPs located in coding regions (C-genes) and the predicted consequence of the SNP(s) on the encoded protein. Additional details include known gene functions as well as relevant publications or findings.

| Gene | Consequence | Notes |
|---|---|---|
| UHRF1BP1 (C6orf107) | missense | Negative regulator of cell growth, important in gut, lung, and heart development, involved in identical protein binding and histone deacetylase binding |
| TAP2 | nonsense & missense | ABC transporter, MDR/TAP subfamily are involved in multidrug resistance, involved in antigen presentation, facilitates peptide transport from the cytoplasm to the ER, mutations may be associated with ankylosing spondylitis, insulin-dependent diabetes mellitus, and celiac disease |
| IFIH1 | missense | Nucleic acid binding and hydrolase activity, encodes MDAS protein (important in innate immunity), potential inflammation regulator (multiple MDAS proteins attach to viral RNA present in the cell forming filaments and stimulating interierons) |
| MUC2Z (PBMUCL1) | missense | Within the MHC Class I locus, MUC expression contributes to the differential immune response induced by human respiratory viruses, regulated by agents associated with ocular hypertension and encode proteins translated in trabecular meshwork cells, linked to childhood asthma and Ankylosing spondylitis |
| PTPN22 | missense | Lymphoid-specific intracellular phosphatase that associates with the molecular adapter protein CBL and may be involved in regulating CBL function in the T-cell receptor signaling pathway. Variants in PTPN22 linked to several autoimmune disorders, the Arg620Trp variation likely affects |

TABLE 30-continued

Genes affected by SNPs located in coding regions (C-genes) and the predicted consequence of the SNP(s) on the encoded protein. Additional details include known gene functions as well as relevant publications or findings.

| Gene | Consequence | Notes |
|---|---|---|
| | | the activity of the PTPN22 protein, making it more difficult for the body to control inflammation and prevent the immune system from attacking its own tissues |
| AGER | synonymous | Implicated in homeostasis, development, and inflammation. Mediator of both acute and chronic vascular inflammation in atherosclerosis and complication in diabetes. AGE/RAGE signaling regulates INF-alpha expression, oxidative stress, and endothelial dysfunction in type 2 diabetes |

TABLE 31

Big-C categories, immune cell types, and canonical pathways significantly associated with genes in MCODE clusters. Significant (p-value < 0.05) Big-C categories and immune cell types were obtained using an in-house genomic platform. Top 5 canonical pathways and associated p-values were obtained from IPA variant effect analysis.

| | Big C Categories | Immuno-Scope | Top Canonical Pathways | P-value |
|---|---|---|---|---|
| Cluster 1 | MHC-Class-I | Antigen Presenting | T Helper Cell Differention | 7.11E−39 |
| | MHC-Class-I: | Cell Myloid | Th1 and Th2 Activation Pathway | 5.92E−35 |
| | Immune-Secreted | | Th1 Pathway | 5.53E−34 |
| | Pattern-Recognition | | Antigen Presentation Pathway | 1.07E−31 |
| | Receptors | | T Cell Exhaustion Signaling Pathway | 1.42E−30 |
| Cluster 2 | Intracllular-Signaling, | NK Cell | Cardiac Hyperthrophy Signaling (Enhanced) | 5.27E−12 |
| | Immune-Secreted, | Myeloid | Systemic Lupus Erythematosus in B Cell Signaling Pathway | 4.01E−11 |
| | MHC-Class I, Nuclear | | Crosstalk between Dendritic and Natural Killer Cells | 1.69E−09 |
| | Receptor-Transcription, Proteasome, | | Rate of Pattern Recognition Receptors in Recognition of Bacteria and Viruses | 2.95E−09 |
| | Pattern-Recognition-Receptors, Immune-Signaling | | HMG81 Signaling | 5.08E−09 |
| Cluster 8 | MHC-Class-I: | Antigen Presenting | Assembly of RNA Polymerase II Complex | 2.38E−06 |
| | Anti-Aporosis | Cell | Primary Immunodeficency Signaling | 1.33E−04 |
| | General-Transcription | | Estrogen Receptor Signaling | 1.55E−04 |
| | -Remodeling | | VDR/RXR Activation | 4.97E−04 |
| | DNA Repair | | Glucocorticoid Receptor Signaling | 5.15E−04 |
| Cluster 6 | Immune-Signaling | T Cell and Myeloid | Rac Signaling | 1.06E−04 |
| | | | Cdc42 Signaling | 3.46E−04 |
| | | | Acute Phase Response Signaling | 4.24E−04 |
| | | | B Cell Receptor Signaling | 4.67E−04 |
| | | | Signaling by Rho Family GTPases | 1.04E−03 |
| Cluster 9 | Nuclear Receptor | Monocytes | FXR/RXR Activation | 7.11E−12 |
| | Transcription | | LXR/RXR Activation | 2.62E−06 |
| | Secreted-and-ECM | | Complement System | 3.30E−06 |
| | Immune-Secreted | | Artherosclerosis Signaling | 1.25E−04 |
| | | | IL-12 Signaling and Production in Macrophages | 1.53E−04 |
| Cluster 5 | Unfolded-Protein-and-Stress | | BAG2 Signaling Pathway | 5.98E−06 |
| | | | Glucocorticoid Receptor Signaling | 6.71E−06 |
| | Chromatin-Remodeling | | Unfolded protein response | 1.33E−05 |
| | | | Huntington's Disease Signaling | 3.94E−05 |
| | | | Aldosterone Signaling in Epithelial Cells | 2.94E−04 |
| Cluster 10 | mRNA-Processing | | Systemic Lupus Erythematos Signaling | 6.24E−03 |
| | Proteasome | | Nucleotide Excision Repair Pathway | 1.83E−02 |
| | | | FAT10 Cancel Signaling Pathway | 2.40E−02 |
| | | | Role of BRCA1 in DNA Damage Response | 4.14E−02 |
| | | | NBR Pathway | 5.30E−02 |

REFERENCES

[Genetics Home Reference, NIH. (2019, Sep. 10). Systemic lupus erythematosus. Retrieved from https://ghr.nlm.nih-.gov/condition/systemic-lupus-erythematosus#definition.] is incorporated by reference herein in its entirety.

[Zeller, C. B., & Appenzeller, S. (2008). Cardiovascular disease in systemic lupus erythematosus: the role of traditional and lupus related risk factors. Current cardiology reviews, 4 (2), 116-122. doi: 10.2174/157340308784245775] is incorporated by reference herein in its entirety.

[Liu, Y., & Kaplan, M. J. (2018). Cardiovascular disease in systemic lupus erythematosus. Current Opinion in Rheumatology, 30 (5), 441-448. doi: 10.1097/bor.0000000000000528] is incorporated by reference herein in its entirety.

[Leonard, D., Svenungsson, E., Dahlqvist, J., Alexsson, A., Ärlestig, L., Taylor, K., . . . Rönnblom, L. (2018). Novel gene variants associated with cardiovascular disease in systemic lupus erythematosus and rheumatoid arthritis. doi: 10.1136/annrheumdis-2017-212614] is incorporated by reference herein in its entirety.

[Björnådal L, Yin L, Granath F, et al. Cardiovascular disease a hazard despite improved prognosis in patients with systemic lupus erythematosus: results from a Swedish population based study 1964-95. J Rheumatol 2004; 31:713-9.] is incorporated by reference herein in its entirety.

[Bernatsky S, Boivin J F, Joseph L, et al. Mortality in systemic lupus erythematosus. Arthritis Rheum2006; 54:2550-7. 10.1002/art.21955] is incorporated by reference herein in its entirety.

[Nasonov, E., Soloviev, S., Davidson, J. E., Lila, A., Togizbayev, G., Ivanova, R., . . . Pereira, M. H. (2015). Standard medical care of patients with systemic lupus erythematosus (SLE) in large specialised centres: data from the Russian Federation, Ukraine and Republic of Kazakhstan (ESSENCE). Lupus science & medicine, 2 (1), e000060. doi: 10.1136/lupus-2014-000060] is incorporated by reference herein in its entirety.

[Aringer M, Burkhardt H, Burmester G R et al. Current state of evidence on "off label" therapeutic options for systemic lupus erythematosus, including biological immunosuppressive agents, in Germany, Austria, and Switzerland—a consensus report. Lupus 2012; 21:386-401 doi: 10.1177/0961203311426569] is incorporated by reference herein in its entirety.

[Ciccacci C. (2018). Discovering the genetic contribution to cardiovascular diseases in patients affected by autoimmune diseases. Annals of translational medicine, 6 (Suppl 1), S44. doi: 10.21037/atm.2018.09.67] is incorporated by reference herein in its entirety.

[Alenghat F. J. (2016). The Prevalence of Atherosclerosis in Those with Inflammatory Connective Tissue Disease by Race, Age, and Traditional Risk Factors. Scientific reports, 6, 20303. doi: 10.1038/srep20303] is incorporated by reference herein in its entirety.

[Langefeld, C. D., Ainsworth, H. C., Cunninghame Graham, D. S., Kelly, J. A., Comeau, M. E., Marion, M. C., . . . Vyse, T. J. (2017). Transancestral mapping and genetic load in systemic lupus erythematosus. Nature communications, 8, 16021. doi: 10.1038/ncomms16021] is incorporated by reference herein in its entirety.

[van der Harst, P., & Verweij, N. (2018). Identification of 64 Novel Genetic Loci Provides an Expanded View on the Genetic Architecture of Coronary Artery Disease. Circulation research, 122 (3), 433-443. doi: 10.1161/CIRCRESAHA.117.312086] is incorporated by reference herein in its entirety.

[Grammer, A. C., & Lipsky, P. E. (2017). Drug repositioning strategies for the identification of novel therapies for rheumatic autoimmune inflammatory diseases. Rheumatic Disease Clinics, 43 (3), 467-480.] is incorporated by reference herein in its entirety.

[Lipsky, P. E. (2017). SP0156 How big data help us understand new and old therapy targets.] is incorporated by reference herein in its entirety.

[Shannon P, Markiel A, Ozier O, Baliga N S, Wang J T, Ramage D, Amin N, Schwikowski B, Ideker T. Cytoscape: a software environment for integrated models of biomolecular interaction networks. Genome Research 2003 November; 13 (11): 2498-504] is incorporated by reference herein in its entirety.

[Grammer, A. C., Ryals, M. M., Heuer, S. E., Robl, R. D., Madamanchi, S., Davis, L. S., . . . Lipsky, P. E. (2016). Drug repositioning in SLE: crowd-sourcing, literature-mining and Big Data analysis. Lupus, 25 (10), 1150-1170. https://doi.org/10.1177/0961203316657437] is incorporated by reference herein in its entirety.

Example 19: Molecular Pathways Identified from Single Nucleotide Polymorphisms Demonstrates Mechanistic Differences in Systemic Lupus Erythematosus Patients of Asian and European Ancestry Systemic lupus erythematosus (SLE) may refer to a multi-organ autoimmune disorder with a prominent genetic component. Individuals of Asian-Ancestry (AsA) may experience the disease more severely, exhibiting increased renal involvement and tissue damage compared to European-Ancestry (EA) populations. However, the mechanisms underlying elevated risk in this population may remain unclear. Here, a comprehensive systems biology approach was applied to all SNP associations detected with the Immunochip using novel bioinformatics and pathway analysis tools identifying 3450 ancestry-specific and trans-ancestry genetic drivers of SLE. Genetic associations were examined using connectivity mapping and gene signatures based on predicted biological pathways were used to interrogate SLE microarray datasets. AsA-dominant pathways mirror clinical findings in AsA patients reflecting elevated oxidative stress, altered metabolism and mitochondrial dysfunction, whereas EA-associated pathways were more often driven by a robust interferon response (type I and II) related to enhanced cytosolic nucleic acid receptor signaling. To validate these findings, pathways predicted by summary genome-wide association data from AsA SLE patients were compared to those derived from Immunochip studies, revealing remarkable similarity. Together, these analyses indicate fundamental differences in SLE-risk related molecular pathways, the majority of which are motivated by ancestral differences, and indicate novel drug candidates that may differentially impact Asian and European individuals with SLE.

Systemic lupus erythematosus (SLE) (OMIM: 152700) may be a complex autoimmune disease characterized by clinical and genetic heterogeneity. It may be demonstrated that individuals of Asian ancestry (AsA) experience a greater burden of renal involvement, as well as elevated risk for infections and cardiovascular complications compared to their European-ancestry (EA) counterparts. In particular, lupus nephritis and end stage renal disease (LN/ESRD) may be severe complications of SLE more prevalent in patients of AsA ancestry. Whereas some of this variation may be accounted for by confounding environmental and/or socio-economic factors, it may remain unclear why ancestry remains a key determinant of poor outcome in AsA SLE.

Figure 82A:
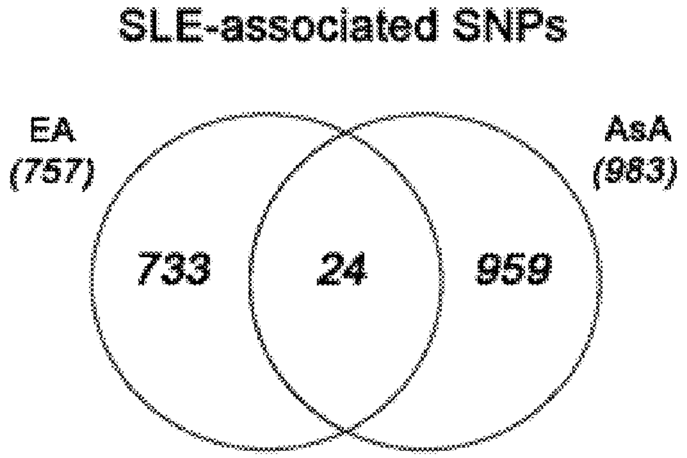
FIGS. 82A-82E show results from mapping the functional genes predicted by SLE-associated SNPs.
Figure 82B:
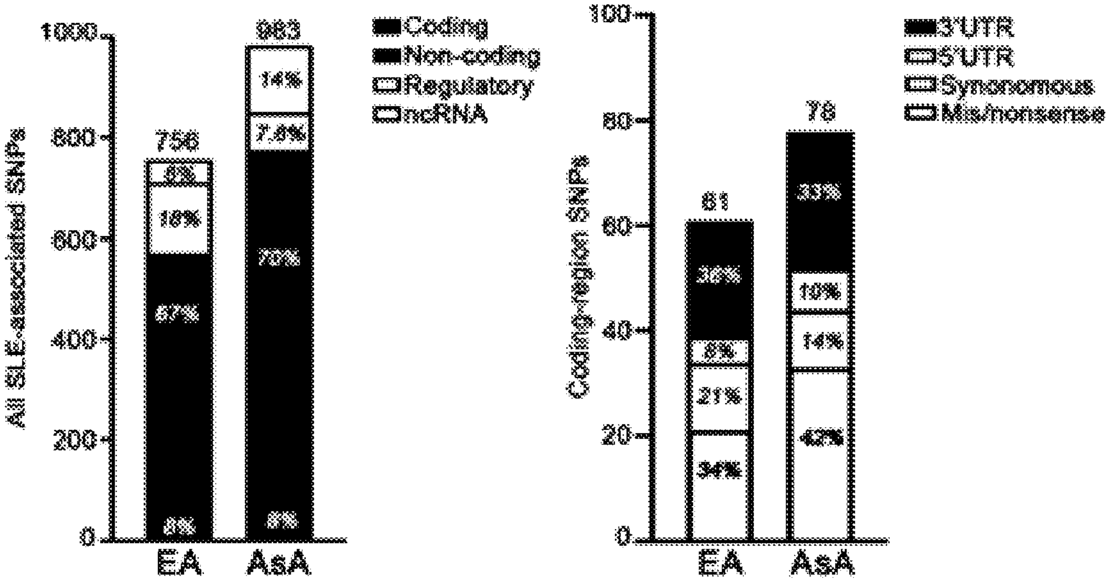

Identification of ancestry-dependent and independent SLE-associated variants and downstream target genes was performed as follows. High-density Immunochip-based association analyses were performed to identify 983 single-nucleotide polymorphisms (SNPs) as significantly associated with SLE in patients of East Asian (AsA) ancestry, and 757 SNPs associated with disease in European (EA) populations (FIG. 82A). Twenty-four SNPs (<1.5%) were shared between ancestries. In both ancestries, approximately 70% of SNPs were found in non-coding regions (intergenic and intronic), with 8% of SNPs located in coding regions (3'UTRs, 5'UTRs, synonomous and missense) (FIG. 82B). AsA populations had a significantly higher percentage of SNPs in non-coding RNAs (lncRNA and miRNA), whereas EA populations had more SNPs located within regulatory regions (FIG. 82B).

Figure 82C:
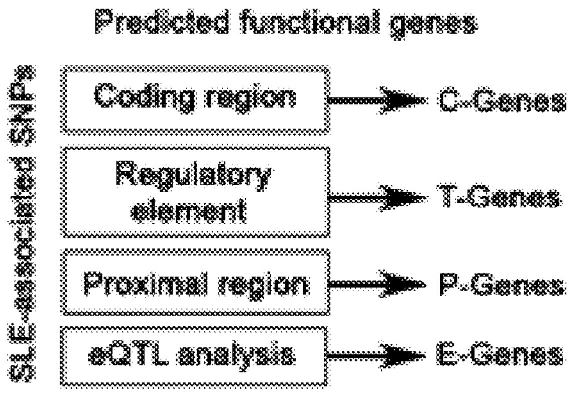
Figure 82D:
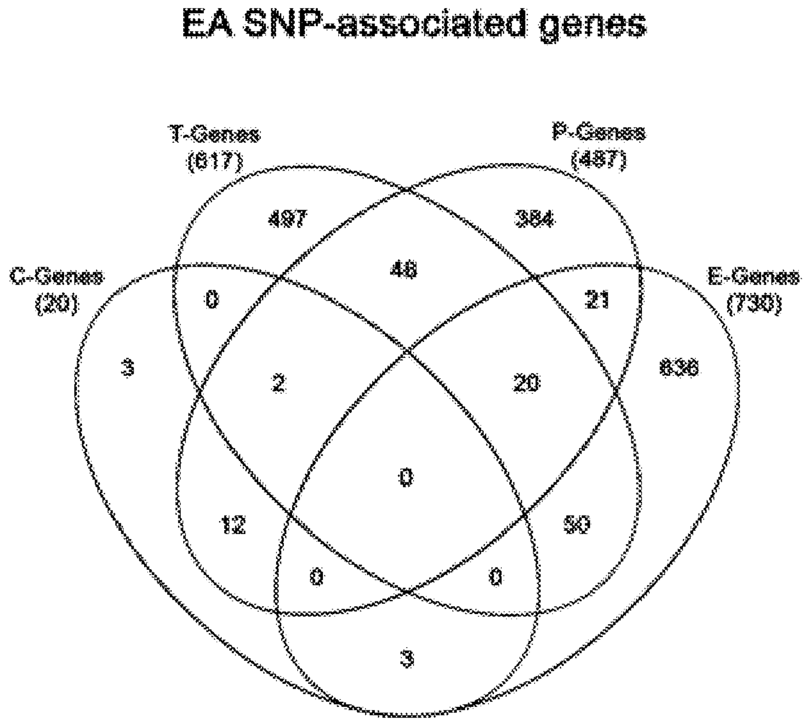
Figure 82E:
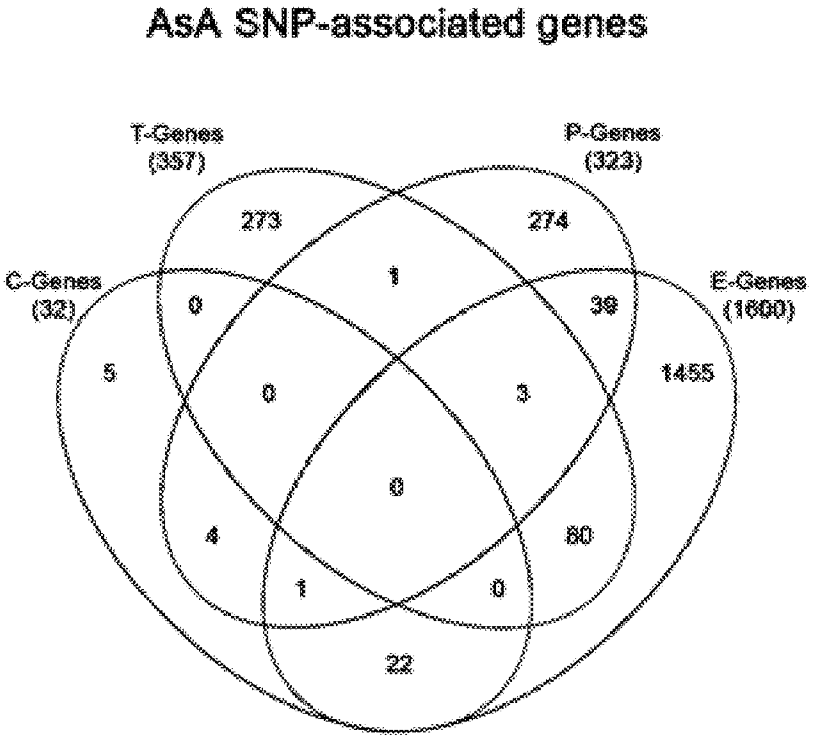

Multiple bioinformatic-based approaches were used to identify the most plausible genes affected by the SLE-SNP association. First, it was determined whether there was evidence that the SNP was a quantitative trait locus (eQTL) using the GTEx database (version 8) and the Blood eQTL browser to identify 226 EA and 587 AsA-specific eQTLs linked to 636 and 1455 expression genes (E-Genes) unique for EA and AsA respectively (FIG. 82C-82E). Next, SNPs were identified within distal and cis regulatory elements (e.g. enhancers and promoter) using the computational tools GeneHancer and HACER (Human ACtive Enhancers to interpret Regulatory variants; bioinfo.vanderbilt.edu/AE/HACER/), both of which connect regulatory SNPs with downstream target genes (T-Genes). Together, GeneHancer and HACER identified 105 SNPs (59 EA, 46 AsA) overlapping distal regulatory elements or promoters predicted to impact the expression of 974 T-Genes (617 EA, 357 AsA) (FIG. 82C-82E). For variants located in coding regions, 54 SNPs (21 EA, 33 AsA) were associated with either non-synonymous or nonsense changes, affecting 52 genes (C-Genes; 20 EA, 32 AsA). The remaining 927 SNPs that were not linked to E-, T- or C-Genes were assigned to the closest proximal gene (P-Gene), identifying an additional 810 P-Genes (487 EA, 323 AsA).

Figure 83A:
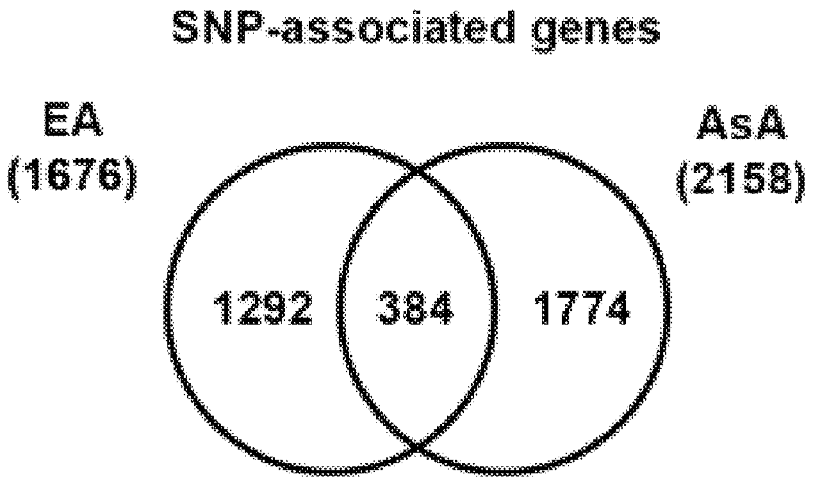
FIGS. 83A-83E show functional characterization of SNP-associated genes.

Overlapping EA and AsA SNP-predicted E-, T-, C- and P-Genes are depicted in FIGS. 82D-82E, respectively. No genes were shared within all four groups within either ancestry, and we observed limited commonality between T-, P- and E-Genes, with only 20 genes shared among the three groups in EA and 3 genes shared in AsA. Despite the overall diversity of genes observed in each list, significant overlap was observed in the number of genes shared between ancestries (FIG. 83A).

Figure 83B:
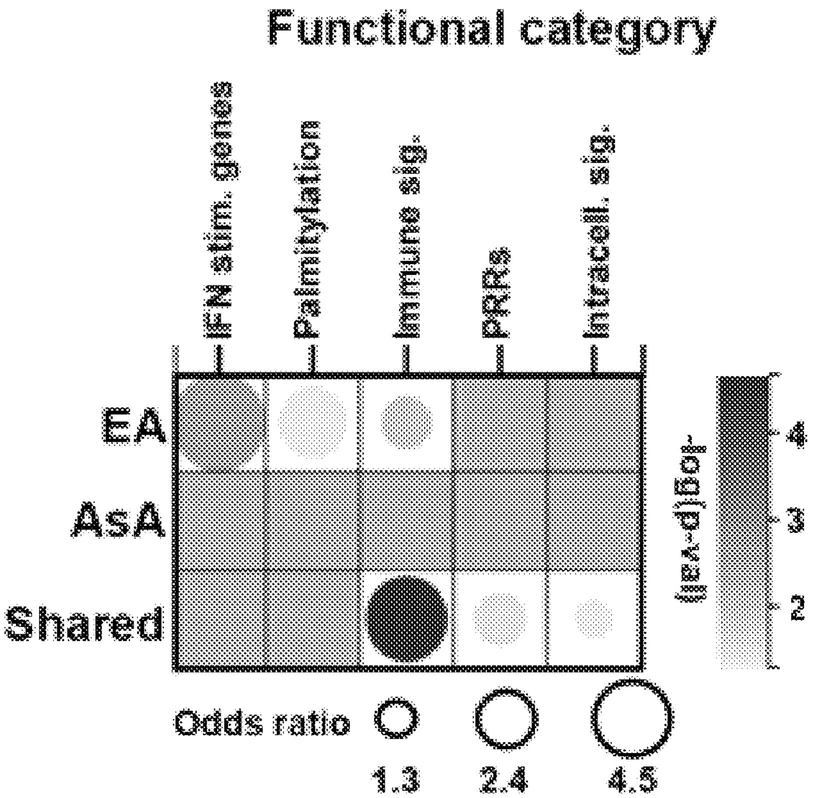
Figure 83C:
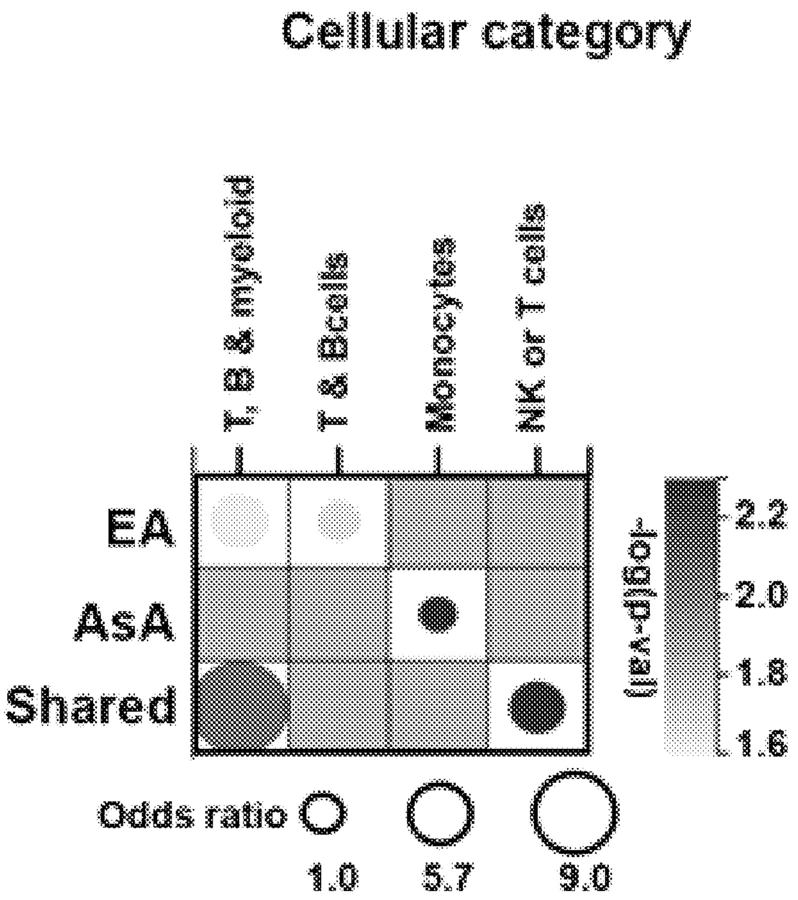
Figure 83D:
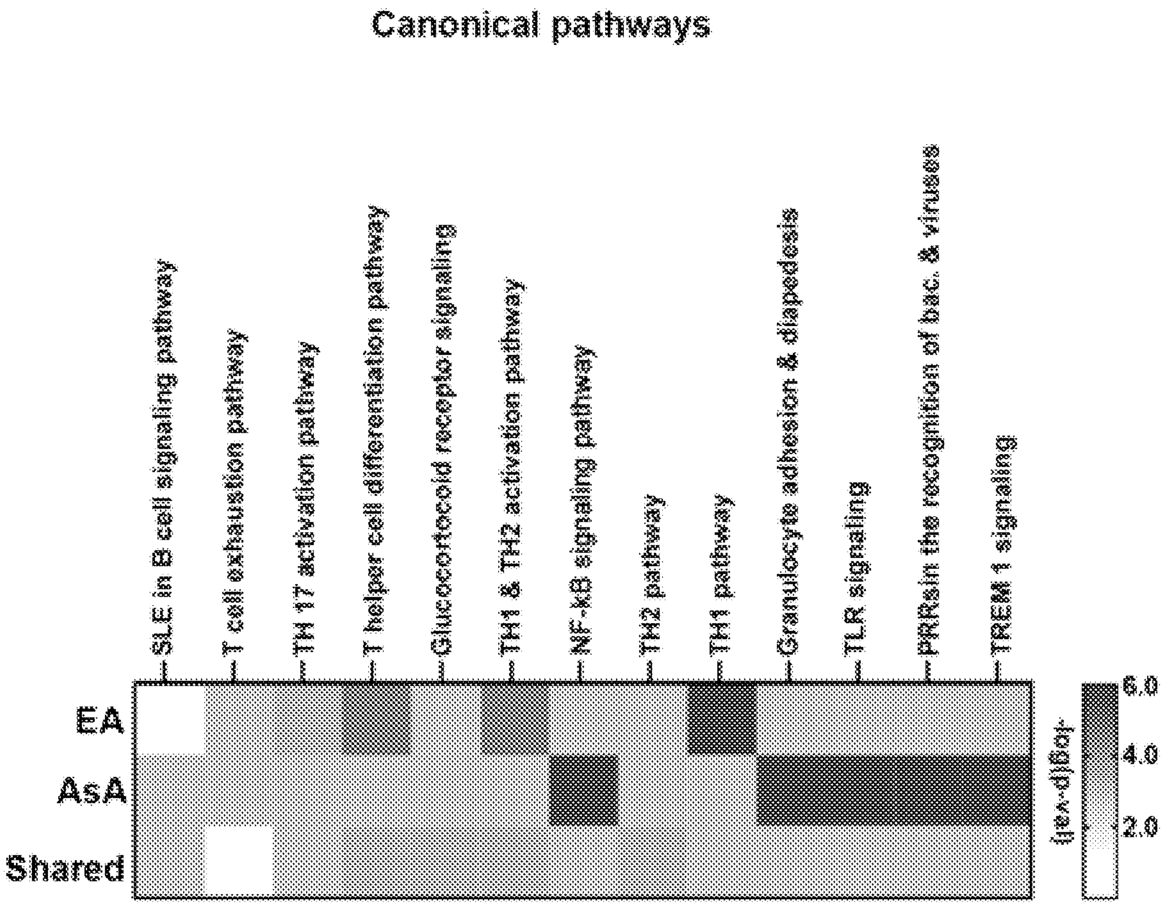
Figure 83E:
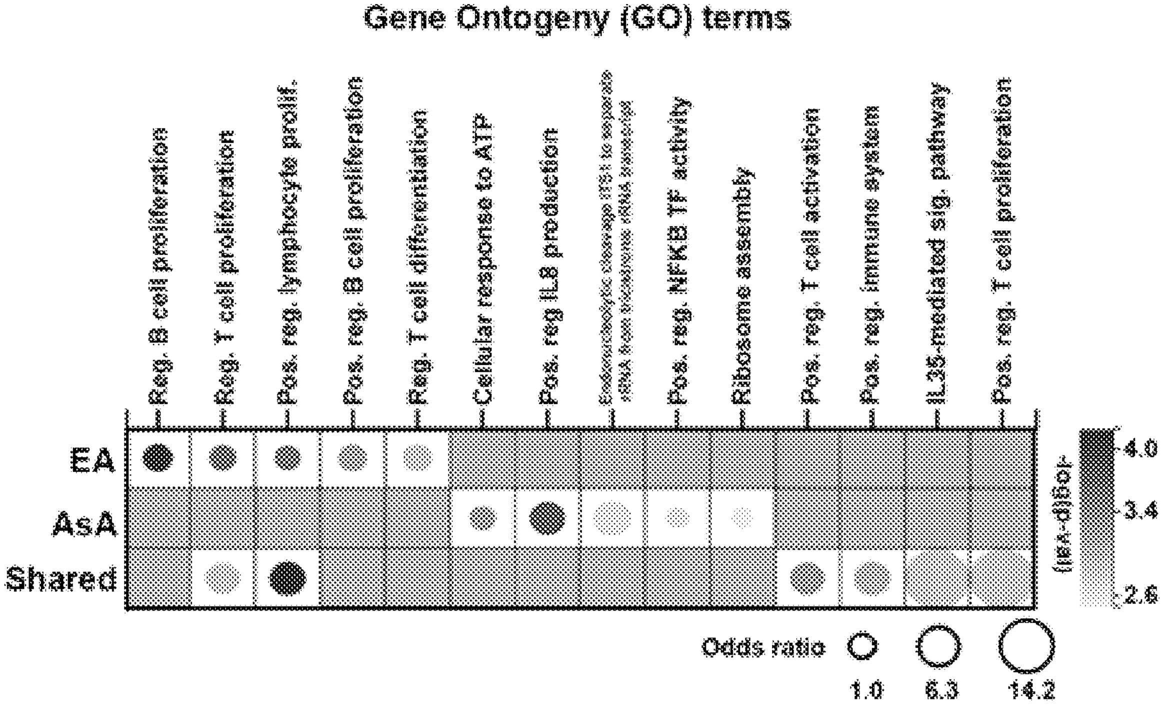

Characterization of gene signatures was performed as follows. Given the diversity of mechanisms through which SLE-associated SNPs are linked to genes (e.g., eQTL, regulatory element and coding region mapping, SNP-gene proximity), a series of bioinformatic analyses was performed to determine the biological function of the 1292 unique EA and 1774 unique AsA gene sets, as well as the 384 genes common to both ancestries. Analysis of EA genes revealed enrichment in processes related primarily to adaptive immune function, including the functional category for interferon stimulated genes, canonical pathways for TH1 and TH2 activation pathway and TH17 activation pathway, and GO terms for the regulation of B cell proliferation (GO: 0030888) and the regulation of T cell proliferation (GO: 0042129). SNP-associated AsA genes were enriched in categories related to pathogen-influenced signaling, such as TLR signaling, NFκB signaling pathway, and the positive regulation of NFκB transcription factor activity (GO: 0051092), as well as those representing more diverse biological functions such as ribosome assembly (GO: 0042255) and cellular response to ATP (GO: 0071318). Shared genes were distributed in a range of adaptive and innate gene categories (FIGS. 83B and 83D-83E).

In addition, EA and AsA gene sets were examined using a clustering program that detects immune and inflammatory cell type signatures within large gene lists to identify dominant immune cell populations driving disease pathology within each ancestry (Ren et al. 2019). Consistent with our pathway analysis, EA exhibited strong enrichment in cellular categories for myeloid cells, as well as T and B cells, whereas AsA genes were specifically enriched in monocytes (FIG. 83C). Independent analysis of shared genes on their own revealed enrichment in the T, B and myeloid, and the NK or T cell categories.

Delineation of signaling pathways identified by ancestry-specific SNP-associated genes was performed as follows. Ancestry-driven key signaling pathways were elucidated in greater detail. Ancestry-based protein-protein interaction (PPI) networks comprising EA, AsA or shared genes were constructed using STRING, visualized in Cytoscape and clustered using MCODE to provide an additional level of functional annotation. A total of 67 canonical pathways were representative of EA genes, with the largest cluster (cluster 2, 118 genes) dominated by the functional category for interferon stimulated genes (FIGS. 84A-84B), along with multiple canonical pathways related to the activation of pattern recognition receptors and downstream type I interferon signaling (FIG. 84B). Cluster 7 revealed additional enrichment in lymphocyte activation and differentiation, such as the TH1 and TH2 activation pathway that was also represented in the shared gene network, and cellular enrichment for cells of myeloid and/or lymphoid origin.

Pathways associated with AsA were represented by a diverse range of biological processes with protein metabolic functions dominating clusters 2 and 8 (FIG. 84C), whereas cluster 11 was enriched in canonical pathways for NFκB signaling and Inflammasome pathway. Interestingly, SNP-predicted AsA genes did not include a unique interferon signature, but instead coalesced into multiple small clusters associated with mitochondrial dysfunction (clusters 10 and 25) and metabolism, evident in clusters 1 and 32. (FIG. 84C). Additionally, AsA clusters were enriched in chromatin remodeling found in clusters 6 and 7, cellular stress found in clusters 1, 20 and 12, and complement activation in cluster 19. AsA cellular enrichment was dominated by monocytes, as well as neutrophils and myeloid lineage cells (FIG. 84D).

Figure 85A:
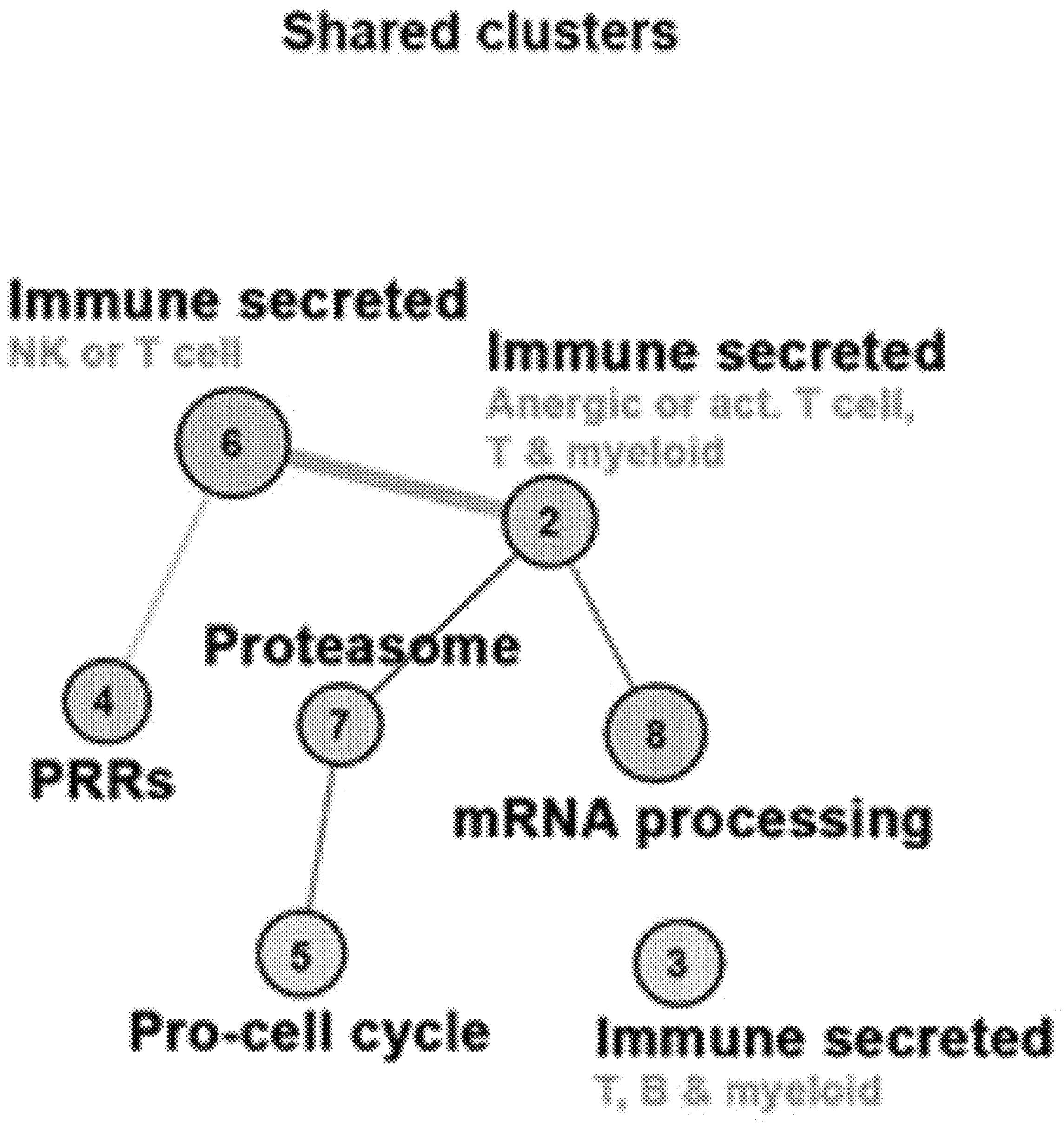

Pathways exemplified by ancestry-independent genes were a blend of both EA and AsA pathways. Common pathways included Interferon signaling, TH1 and TH2 activation pathway, TLR signaling as well as PRRs in the recognition of bacteria and virus (FIGS. 85A-85B). FIG. 85C depicts a selection of both the unique and overlapping canonical pathways motivated by the EA and AsA gene sets. Taken together, EA-associated pathways appear dominated by interferon-related signaling as well as T, B and myeloid cells, while AsA pathways are dominated by biological processes related to altered metabolism, mitochondrial dysfunction, complement activation and the cellular category for monocytes.

Figure 86:
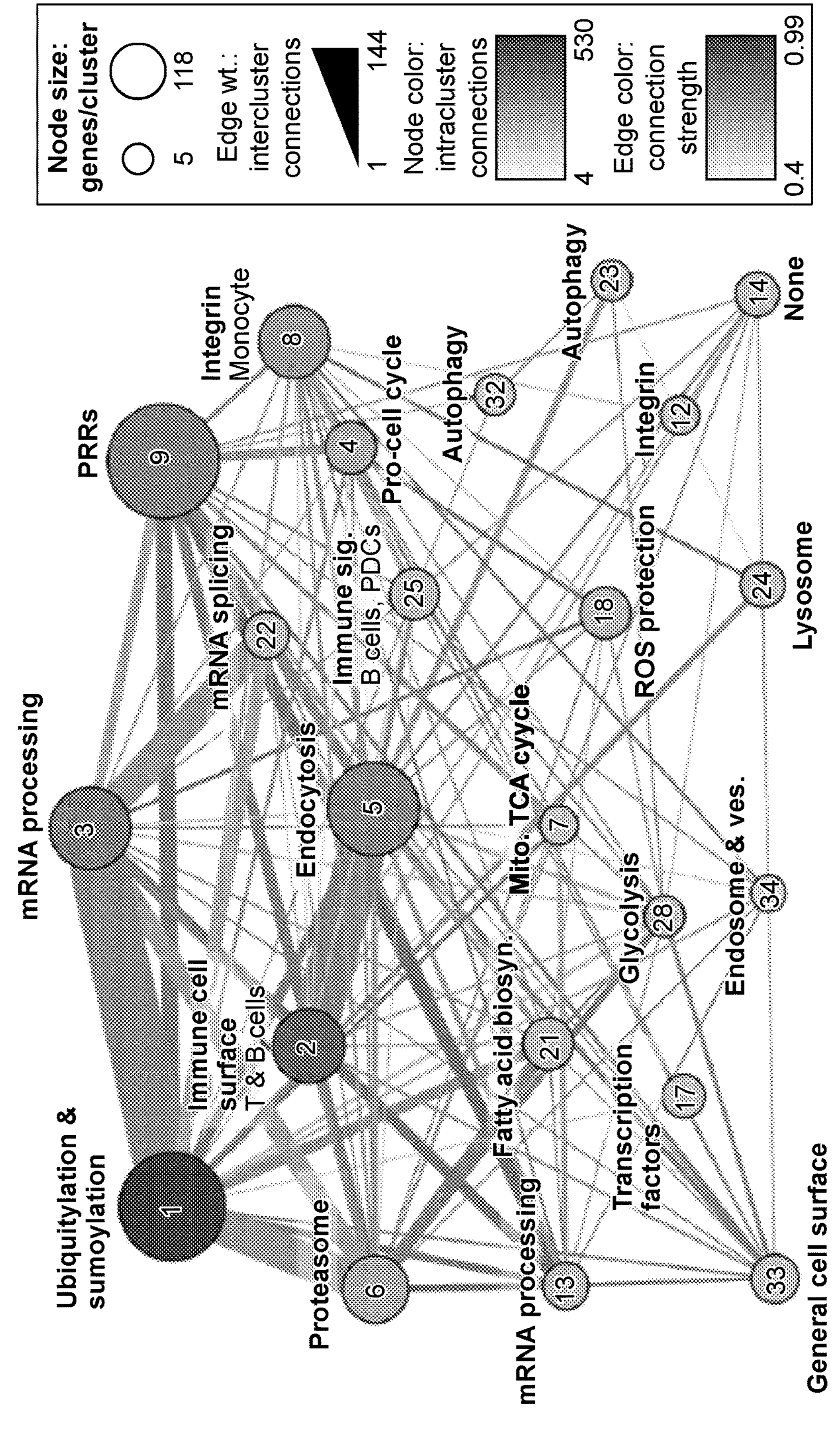
FIG. 86 shows that Asian GWAS genes identify similar pathways predicted by the AsA Immunochip. Using SNP-predicted genes from the AsA GWAS validation SNP-set, metastructures were generated based on PPI networks, clustered using MCODE and visualized in Cytoscape. Cluster size indicates the number of genes per cluster, edge weight indicates the number of inter-cluster connections and color indicates the number of intra-cluster connections. Functional enrichment for each cluster was determined by BIG-C. Heatmap indicates the top five canonical pathways representing individual clusters (−log (p-value) >1.33). Enriched BIG-C and I-Scope categories (OR >1; p-value <0.05) are listed for each cluster. Bold text indicates categories with the highest OR and lowest p-value.

Validation of Asian pathway analysis was performed as follows. To confirm our pathway predictions, summary GWAS data was combined from Asian GWA studies, identifying an additional 1351 SNPs reported as significantly associated with SLE in patients of AsA ancestry. Of these SNPs, 68% were located in non-coding regions, 6.5% were in coding regions, 2.7% were in regulatory regions and 22% were located within or proximal to non-coding RNAs. Validation AsA GWAS SNPs exhibited limited commonality when compared to Immunochip SNPs, with <1% of either EA or AsA Immunochip SNPs overlapping GWAS SNPs, and only 3 SNPs common to all 3 datasets. The same bioinformatics-driven methodology was applied to generate a validation gene cohort composed of 1321 E-Genes, 307 T-Genes, 17 C-Genes and 974 P-Genes. Overall, 108 EA and 186 AsA genes, representing 6.4% and 8.6% of EA and AsA Immunochip genes, respectively were shared with the AsA validation gene set. A total of 88 genes were shared among all three groups. Connectivity mapping of all validation genes were used to create PPI networks and clustered as described above (FIG. 86). Despite limited overlap between the Asian predicted genes in the validation set, examination of each cluster revealed remarkable functional similarity to those derived from AsA Immunochip-predicted genes. For example, clusters 1, 3, 6 and 5 share hallmarks of tissue repair and remodeling exemplified by categories for mRNA processing, pro-cell cycle and protein degradation (proteasome, lysosome, endocytosis). Additionally, smaller clusters 21, 27 and 28 were observed, which were representative of processes involved in metabolic function; further, clusters 13, 18 and 24 were observed, which were characteristic of cell stress and injury, including the Inhibition of ARE-mediated degradation pathway and Mitochondrial dysfunction canonical pathways. Cluster 9 contained a small interferon-stimulated gene signature consisting of IFI27, IFI44, and RSAD2 (FIG. 86). Cellular categories were again dominated by monocytes, T cells, NK cells, B cells and pDCs, and are consistent with findings observed with Immunochip-predicted genes.

Figure 87:
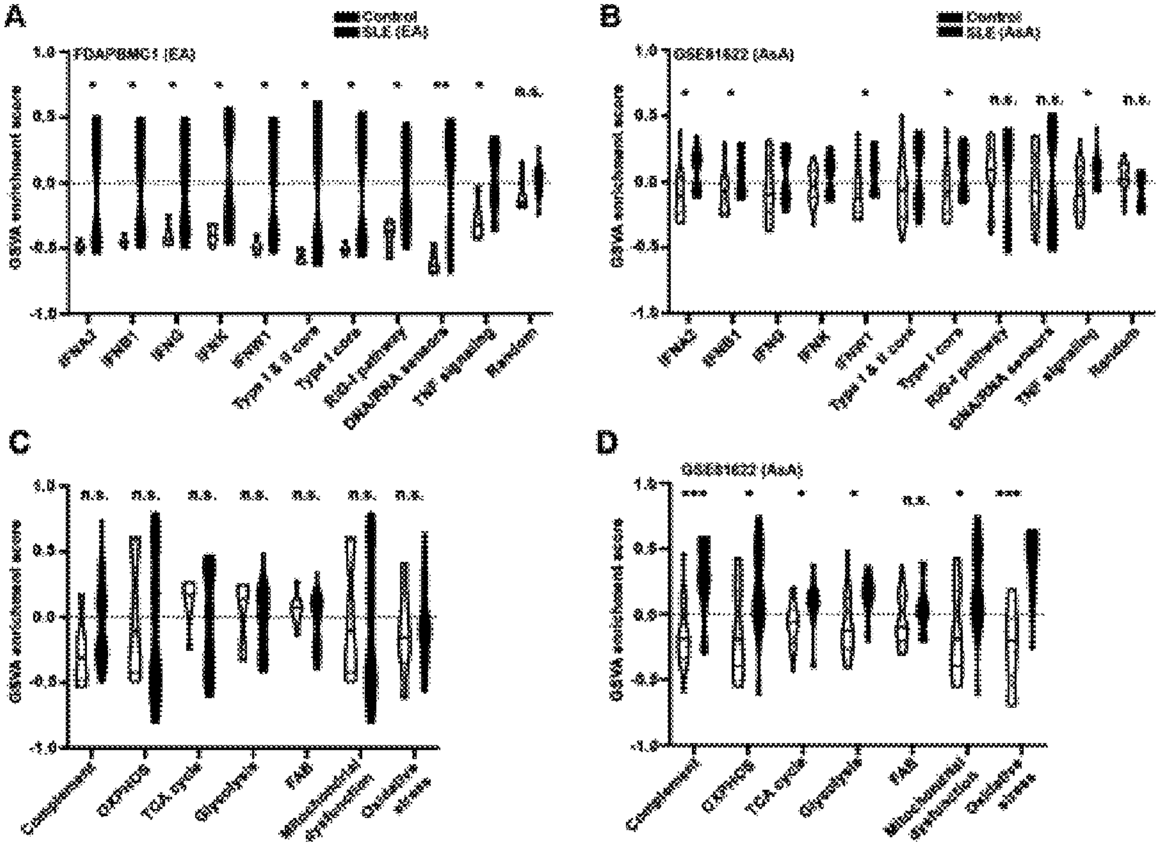
FIGS. 87A-87H show that SNP-predicted pathways inform gene signatures for GSVA analysis in patient PBMC datasets. GSVA enrichment scores were generated for PBMCs in EA and AsA SLE patients and healthy controls from FDAPBMC1 (EA-only patients) and GSE81622 (AsA-only patients). GSVA scores for type I and type II interferon-based gene signatures (FIGS. 87A-87B), metabolic gene signatures (FIGS. 87C-87D), cellular processes (FIGS. 87E-87F) and individual cell type signatures (FIGS. 87G-87H) are shown. Asterisks (*) indicate a p-value <0.05 using Welch's t-test comparing SLE to control; ^ indicates a p-value <0.05 using Welch's t-test comparing EA to AA.
Figure 87:
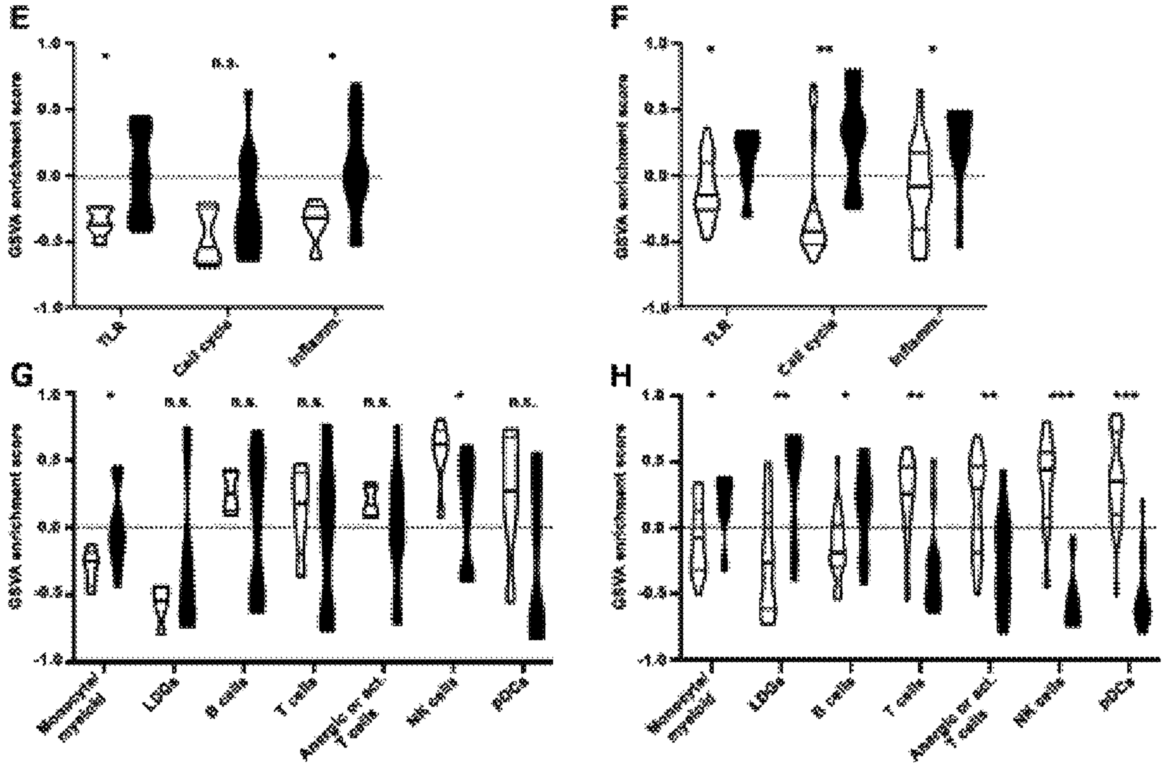

To further support our pathway predictions, Gene Set Variation Analysis (GSVA) was applied to determine the relative enrichment of gene signatures identified in peripheral blood mononuclear cell (PBMC) samples from SLE patients (EA and AsA) and controls. In FDAPBMC1, a dataset composed of EA patients, all 7 IFN gene signatures (IGS) and signatures for the RIG-I pathway and DNA/RNA sensors were strongly enriched in SLE PBMCs compared to controls (FIG. 87A). In contrast, only the signatures for IFNA2, IFNB1, IFNW1 and the Type I core were enriched in SLE PBMCs from AsA patients in GSE81622 (FIG. 87B). GSVA using a random group of genes did not separate SLE from controls in either dataset.

GSVA enrichment scores using signatures for complement activation and metabolic pathways, including mitochondrial oxidative phosphorylation (OXPHOS), the TCA cycle and glycolysis were able to separate AsA SLE patients, but not EA patients, from healthy controls (FIGS. 87C-87D). Furthermore, AsA SLE patients exhibited significant enrichment in signatures for mitochondrial dysfunction and oxidative stress. As shown in FIGS. 87D-87G, enrichment of a number of pathways and cell types in both EA and AsA SLE were noted, including TLR signaling, inflammasome, TNF signaling and monocyte/myeloid lineage cells, whereas AsA patients exhibited additional enrichment in pro-cell cycle, low density granulocytes (LDGs) and B cells. Varying degrees of T cell/NK cell lymphopenia were evident in both ancestral populations.

It was determined that correlation between inflammatory cytokine signatures and cellular processes is influenced by ancestry, as follows. To determine whether inflammatory cytokine gene signatures were related to specific hematopoietic cells, linear regression analysis was first performed between the GSVA scores for individual cell signatures, and the IFNA2 or TNF signatures from EA and AsA PBMC datasets. In both ancestries, IFNA2 and TNF gene signatures exhibited a strong, positive relationship with monocyte/myeloid lineage cells (FIG. 88A), while T cells, NK cells and pDCs displayed predominately negative correlations. Inconsistent, non-significant associations between the B cell category and GSVA enrichment scores for IFNA2 and TNF were observed in both ancestral populations. Given that oxidative stress and nucleic acid sensing are potent inducers of interferons and inflammatory cytokines, we used the same linear regression approach to examine the relationship between IFNA2 and TNF and enrichment scores for the oxidative stress, RIG-I and TNF pathways. In EA patients, GSVA scores for the RIG-I and TLR pathway signatures, but not oxidative stress, were strongly correlated with IFNA2 and TNF. In contrast, the oxidative stress signature exhibited a positive, significant correlation with both IFNA2 and TNF in AsA patients. The RIG-I pathway was also significantly correlated with IFNA2, although at a less predictive R2 value (R2=0.2) compared to its association in EA (R2=0.61). Finally the monocyte/myeloid cell signature exhibited a positive regression coefficient for the glycolysis signature in AsA, but not EA, indicating these cell may be more metabolically active in Asian ancestry patients (FIG. 88C).

SLE may be a multisystem autoimmune disorder that is heavily influenced by genetics. The incidence of SLE may vary widely across populations, with individuals of Asian, Hispanic and African ancestry demonstrating a three- to four-fold increase in disease prevalence compared to their European counterparts. The advent of candidate gene, Immunochip and genome wide association studies (GWAS) have transformed understanding of SLE genetics, however, it may remain unclear how genetic ancestry contributes to the clinical heterogeneity and variation in disease outcomes among SLE patients. Specifically, AsA patients may develop SLE at a younger age and with more severe manifestations, including lupus nephritis (LN). While increased genetic risk burden in AsA individuals may account the sustained prevalence of SLE in this population, it may not provide adequate explanation for accelerated disease progression, variation in treatment response or elevated organ damage, especially with regard to the development of LN. Our observations indicate that, in addition to higher risk load, underlying differences at the genetic level may significantly influence the dominant biological pathways operative within each ancestry. Here, results show that by identifying all of the genes implicated by GWAS and modeling them into biologic pathways, a broader, global view of the impact of genetics on SLE can be provided, as well as an indication of the disparate genetic influences manifest in patients of different ancestries.

To accomplish this, statistical and computational analyses were employed along with data acquired from functional genomic assays to map the overall gene expression landscape of SLE and further define the disease-associated pathways responsible for the inherent disparities influencing SLE progression between Asian and European ancestries. While it is important to note that many SNPs examined here may be common to both ancestral populations, differences in allele frequencies indicate some SNP associations and pathways may be more representative of one ancestry over another. Expression (e) QTL analysis identified 813 tagging SNPs associated with 2091 E-Genes (636 EA, 1455 AsA). Also, SNPs affecting gene expression were identified by modulating the activities of regulatory elements, such as enhancers and promoters. Computational gene prediction algorithms that incorporate chromatin interaction data and intergenic enhancer annotation from several hundred cell lines uncovered regulatory SNPs predicted to change transcription factor binding and were associated with 974 downstream targets (T-Genes; 617 EA, 357 AsA). In addition, long noncoding (Inc) RNAs, which are defined as a class of mRNA-like transcripts typically >200 nucleotides in length that lack protein coding potential, also contribute to the regulation of gene expression via interaction with proteins, RNA, and/or DNA. There may be an important role for lncRNAs in the differentiation, polarization and activation of both myeloid and lymphoid lineage immune cell types. In the Immunochip dataset, SNPs associated with lncRNAs were more prevalent in AsA vs EA patients, with over 50% of AsA IncSNPs exhibiting eQTL effects (compared to 17% in EA). This includes eQTLs linked to the AsA anti-sense RNA E-Genes IFNG-AS1 and IL12A-AS1, both of which are involved in the regulation of their cognate sense protein-coding genes. A high prevalence of IncSNPs was also observed in the AsA validation GWAS dataset, with 22%

(299/1350) of SNPs within or proximal to ncRNAs. Abnormal ncRNA expression may be linked to mitochondrial dysfunction-induced oxidative stress in a number of pathological conditions including SLE. Importantly, cross-talk between oxidative stress and ncRNAs may trigger and perpetuate autoimmune reactions in SLE patients (Tsai). These observations may be consistent with our pathway-based findings showing clusters of genes representative of mitochondrial dysfunction, cell stress and epigenetic remodeling. Furthermore, gene signatures for mitochondrial dysfunction and oxidative stress were exclusively enriched in PBMC from AsA patients. Finally, 23 variants were identified resulting in nonsense or non-synonymous amino acid changes affecting 22 genes (C-Genes), 12 of which were predicted to negatively impact protein function. The remaining 587 risk SNPs were mapped to the nearest, most proximal gene, resulting in 520 P-Genes (465 EA, 34 AA, 21 shared).

The pathway-based analysis of predicted genes and their upstream regulators presented here helps clarify the complex polygenic risk associated with SLE in multiple ancestries. Pathways common to both EA and AsA were centered around myeloid and lymphoid lineage signaling (e.g., TH1/TH2 activation signaling, TLR signaling and JAK/STAT signaling), along with the role of interferons in SLE. Similarly, pathways dominating EA also tended to focus on immune processes and included Role of RIG-I in antiviral innate immunity, Antigen presentation, and the SLE in T cell signaling pathway, as well as the functional category for interferon stimulated genes. GSVA analysis also confirmed the presence of gene signatures representing nucleic acid sensing (RIG-I pathway and DNA/RNA sensors) exclusively in EA patients. Cellular enrichment categories were overwhelmingly dominated by T cells, B cells and myeloid cells, and is consistent with increased myeloid gene signatures in EA ancestry independent of medication usage (e.g., SLE standard of care drugs) and auto-antibody production.

In contrast, fewer immune-based pathways motivated by AsA predicted genes were observed, as seen by the more diverse range of functional categories and pathways representative of this gene set. AsA canonical pathways were enriched in processes related to DNA damage and repair, cell stress, mitochondrial dysfunction, leukocyte migration and tissue repair. Immune cell enrichment was less varied, with monocytes the predominant cell type representative of AsA. These SNP-predicted pathways were validated in a second GWAS dataset and GSVA analysis shows that gene signatures representative of these pathways (e.g., mitochondrial dysfunction oxidative stress) were specifically enriched in AsA patients.

Both Type I interferons and inflammatory cytokine signaling (exemplified by gene signatures for IFNA2 and TNF) were enriched in EA and AsA SLE patients. Remarkably however, our results indicate that ancestral background may influence the cellular process contributing to cytokine signaling. Regression analysis revealed that IFNA2 and TNF were significantly and positively correlated with the gene signature for RIG-I pathway and TLR signaling in EA patients, whereas in AsA subjects, these cytokines correlated with the gene signature for oxidative stress.

Analyses of whether ancestry affects the clinical phenotype of SLE may be complicated by the overwhelming heterogeneity of disease manifestations, especially with respect to organ involvement. Nonetheless, many gene polymorphisms may be associated with specific phenotypes, autoantibody profiles and/or clinical outcomes in SLE. For example, Fcg receptor subtypes like FCGR3B may be significantly associated with LN among AsA patients although it may remain unclear whether there is a genetic basis for end-organ involvement based on ancestry. SLE patients of Asian descent may be at significantly higher risk for the development of lupus nephritis, whereas European genetic ancestry may be protective against renal disease. Metabolic dysfunction may be common in kidney disease and it may be shown that altered metabolic function in lupus-affected tissues (kidneys and skin) reflect damage leading to myeloid cell infiltration.

Genomic functional categories were analyzed as follows. The Variant Effect Predictor (VEP) tool available on the Ensembl genome browser 93 (www.ensembl.org) was used for annotation information to specify SNPs located within non-coding regions, including micro (mi) RNAs, long non-coding (Inc) RNAs, splice region variants, non-coding transcript exon variants, introns and intergenic regions. Regulatory regions include transcription factor binding sites (TFBS), promoters, enhancers, repressors, promoter flanking regions (PRFs) and open chromatin (OCRs). Coding regions were broken down further and include 5'UTRs, 3'UTRs, synonymous and nonsynonymous (missense and nonsense) mutations. The online resource tool HaploReg (version 4.1; pubs.broadinstitute.org/mammals/haploreg/haploreg.php) were also used to identify DNA features, regulatory elements and assess regulatory potential.

Identification of SLE-associated SNPs and predicted genes was performed as follows. SLE Immunochip studies identified single nucleotide polymorphisms (SNPs) significantly associated with SLE in EA (6748 cases; 11516 controls) and AsA (2485 cases and 3947 controls from Koreans (KR), Han Chinese (HC) and Malaysian Chinese (MC)) cohorts. Expression quantitative trait loci (eQTLs) were then identified using GTEx version 8 (GTEXportal.org ("The Genotype-Tissue Expression (GTEx) Project" n.d.)) and the Blood eQTL browser database and mapped to their associated eQTL expression genes (E-Genes). To find SNPs in enhancers and promoters, and their associated transcription factors and downstream target genes (T-Genes), the atlas of Human Active Enhancers was queried to interpret Regulatory variants (HACER, bioinfo.vanderbilt.edu/AE/HACER and the GeneHancer database. To find structural SNPs in protein-coding genes (C-Genes), the human Ensembl genome browser (GRCh38.p12; www.ensembl.org) and dbSNP (www.ncbi.nlm.nih.gov/snp) were queried. Several additional databases were used to generate loss-of-function prediction scores, including SIFT4G (sift-dna.org/sift4g) and PolyPhen-2 (genetics.bwh.harvard.edu). All other SNPs were linked to the most proximal gene (P-Gene) or gene region. For overlap studies, Venn diagrams were computed and visualized using InteractiVenn (interactivenn.net). All predicted genes were divided into an EA, AsA or shared group depending on the ancestral designation of the original SLE-associated SNP.

Functional gene set analysis and identification of upstream regulators (UPRs) were performed as follows. For both ancestral groups, predicted gene lists were examined using Biologically Informed Gene Clustering (BIG-C; version 4.4). BIG-C is a custom functional clustering tool developed to annotate the biological meaning of large lists of genes. Genes are sorted into 54 categories based on their most likely biological function and/or cellular localization based on information from multiple online tools and databases including UniProtKB/Swiss-Prot, gene ontology (GO) Terms, MGI database, KEGG pathways, NCBI, PubMed, and the Interactome.

I-Scope is a custom clustering tool used to identify immune infiltrates in large gene datasets, and has been described previously. Briefly, I-Scope was created through an iterative search of more than 17,000 genes identified in more than 50 microarray datasets. These genes were researched for immune cell specific expression in 30 hematopoietic sub-categories: T cells, regulatory T cells, activated T cells, anergic cells, CD4 T cells, CD8 T cells, gamma-delta T cells, NK/NKT cells, T & B cells, B cells, activated B cells, T &B & monocytes, monocytes & B cells, MHC Class II expressing cells, monocyte dendritic cells, dendritic cells, plasmacytoid dendritic cells, Langerhans cells, myeloid cells, plasma cells, erythrocytes, neutrophils, low density granulocytes, granulocytes, platelets, and all hematopoietic stem cells.

Enrichment of GO Biological Processes (BP) using Enrichr (maayanlab.cloud/Enrichr/) and the Ingenuity Pathway Analysis (IPA; www.qiagenbioinformatics.com) platform provided additional genetic pathway identification. IPA upstream regulator (UPR) analysis was also used to identify potential transcription factors, cytokines, chemokines, etc. that can contribute to the observed gene expression pattern in the input dataset.

Network analysis and visualization were performed as follows. Visualization of protein-protein interaction and relationships between genes within datasets was done using Cytoscape (version 3.6.1) software. Briefly, STRING (version 1.3.2) generated networks were imported into Cytoscape (version 3.6.1) and partitioned with MCODE via the clusterMaker2 (version 1.2.1) plugin.

Gene set variation analysis (GSVA) was performed as follows. The GSVA (V1.25.0) software package for R/Bioconductor and has been described previously. Briefly, GSVA is a non-parametric, unsupervised method for estimating the variation of pre-defined gene sets in patient and control samples of microarray expression datasets. The input for the GSVA algorithm was a gene expression matrix of log 2 microarray of expression values and a collection of pre-defined gene signatures. Enrichment scores (GSVA scores) were calculated non-parametrically using a Kolmogorov-Smirnoff (KS)-like random walk statistic and a negative value for each gene set. All interferon and cytokine signatures (core IFN, IFNB1, IFNA2, IFNW, IFNG and TNF) have been described previously. Metabolic signatures were based on literature mining and established IPA canonical pathways. Enrichment of each signature was examined in EA and AsA SLE patients and healthy control PBMCs from FDAPBMC1 for EA or GSE81622 for AsA. Differences between controls and SLE patient GSVA enrichment scores were determined using the Welch's t-test for unequal variances in Graphpad PRISM 8.0.

Regression models were constructed as follows. For all linear models, GSVA scores for cell type and/or pathway in each sample were used as input. Simple linear regression was performed in Graphpad PRISM 8.0

Figure legends are described as follows.

FIGS. 82A-82E show results from mapping the functional genes predicted by SLE-associated SNPs. (FIG. 82A) Venn diagram depicting the ancestral overlap of all SLE-associated Immunochip SNPs. (FIG. 82B) Distribution of genomic functional categories for all EA and AsA non-HLA associated SLE SNPs. (FIG. 82C) Functional SNP-associated genes are derived from 4 sources, including eQTL analysis (E-Genes), regulatory regions (T-Genes), coding regions (C-Genes) and proximal gene-SNP annotation (P-Genes). (FIGS. 82D-82E) Venn diagrams showing the overlap of all EA (FIG. 82D) and AsA (FIG. 82E) associated E-, T-, C- and P-Genes.

FIGS. 83A-83E show functional characterization of SNP-associated genes. (FIG. 83A) Venn diagram depicting the overlap between all EA- and AsA-SNP associated genes. (FIG. 83B) Ancestry-dependent and independent SNP-associated genes were analyzed to determine enrichment using functional definitions from the BIG-C (Biologically Informed Gene Clustering) annotation library. Enrichment was defined as any category with an odds ratio (OR) >1 and a −log (p-value) >1.33. (FIG. 83C) I-Scope hematopoietic cell enrichment is defined as any category with an OR >1, left scale; indicated by the dotted line and −log (p-value) >1.33 indicated by color scale. (FIGS. 83D-83E) Heatmap visualization of the top five significant IPA canonical pathways and gene ontogeny (GO) terms for each gene list organized by ancestry. Top pathways with −log (p-value) >1.33 are listed.

Figure 84A:
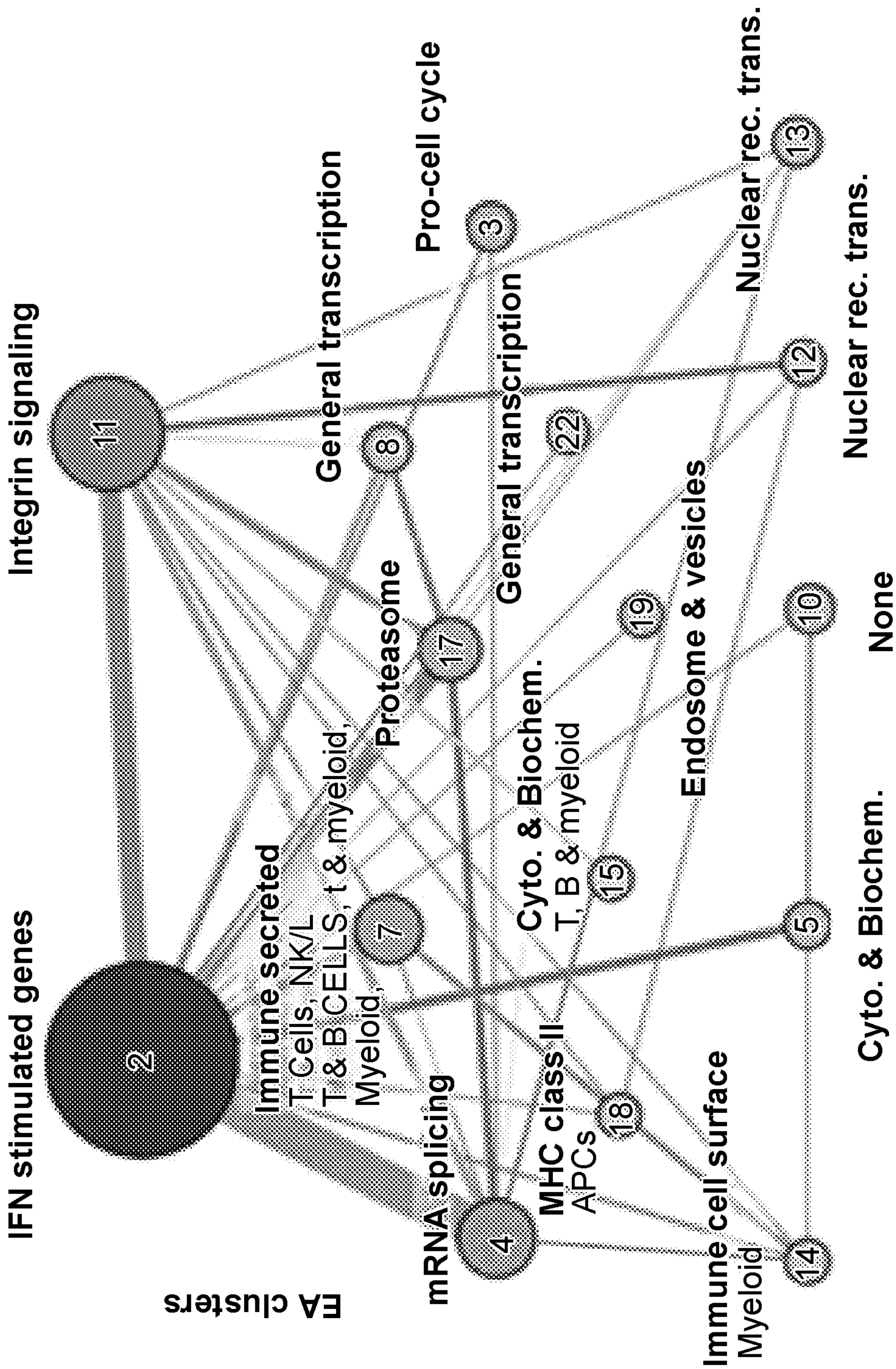
FIGS. 84A-84B show key pathways motivated by EA and AsA-predicted genes. Cluster metastructures for EA (FIG. 84A) and AsA (FIG. 84B) were generated based on PPI networks, clustered using MCODE and visualized in Cytoscape. Cluster size indicates the number of genes per cluster, edge weight indicates the number of inter-cluster connections and color indicates the number of intra-cluster connections. Functional enrichment for each cluster was determined by BIG-C. Heatmap indicates the top five canonical pathways representing individual clusters (−log (p-value) >1.33). Enriched BIG-C and I-Scope categories (OR >1; p-value <0.05) are listed for each cluster. Bold text indicates categories with the highest OR and lowest p-value.
Figure 84B:
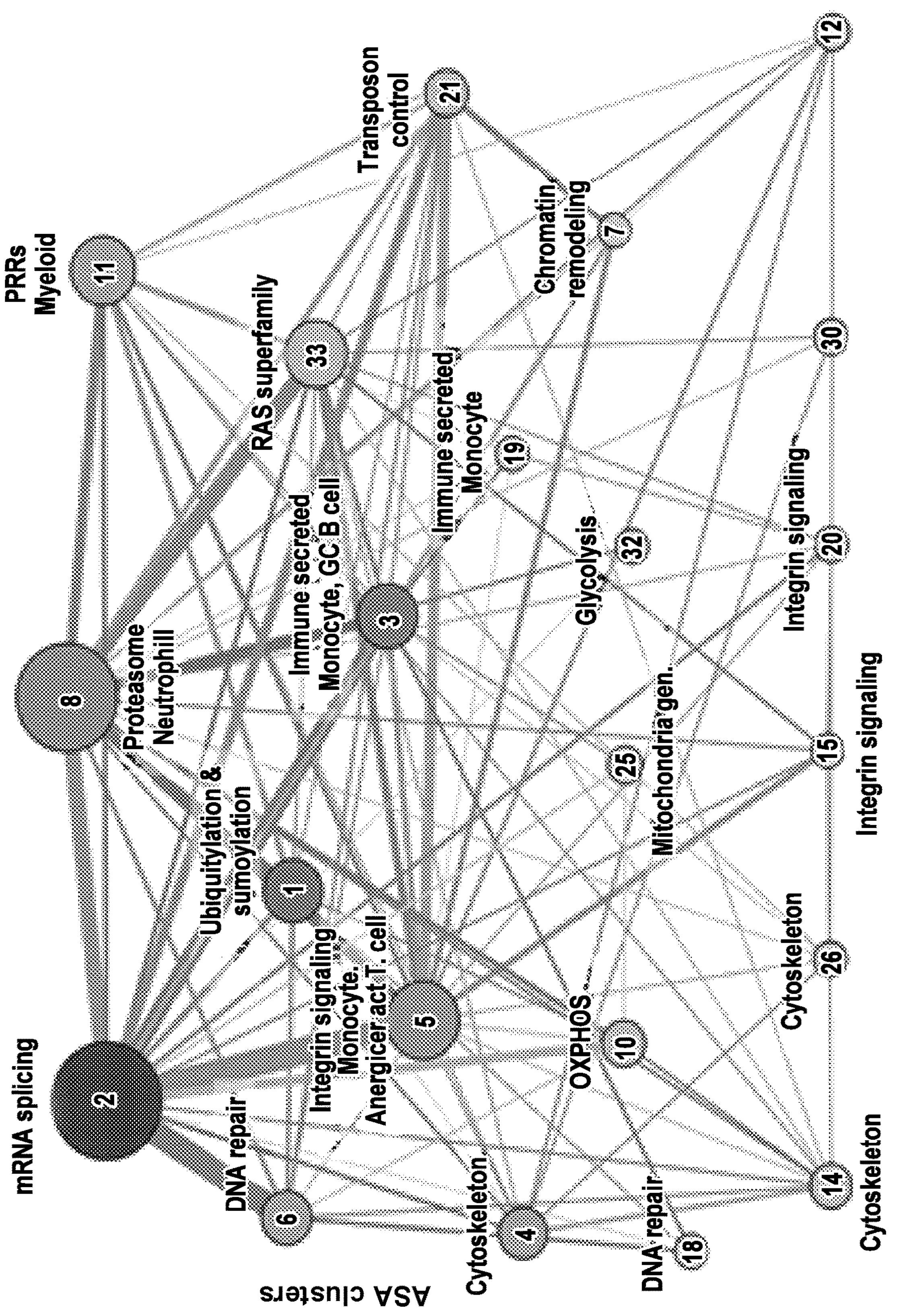

FIGS. 84A-84B show key pathways motivated by EA and AsA-predicted genes. Cluster metastructures for EA (FIG. 84A) and AsA (FIG. 84B) were generated based on PPI networks, clustered using MCODE and visualized in Cytoscape. Cluster size indicates the number of genes per cluster, edge weight indicates the number of inter-cluster connections and color indicates the number of intra-cluster connections. Functional enrichment for each cluster was determined by BIG-C. Heatmap indicates the top five canonical pathways representing individual clusters (−log (p-value) >1.33). Enriched BIG-C and I-Scope categories (OR >1; p-value <0.05) are listed for each cluster. Bold text indicates categories with the highest OR and lowest p-value.

FIGS. 85A-85C show key pathways determined by shared genes. (FIG. 85A) Cluster metastructures using the shared (EA and AsA) cohort of SNP-predicted genes were generated based on PPI networks, clustered using MCODE and visualized in Cytoscape. Cluster size indicates the number of genes per cluster, edge weight indicates the number of inter-cluster connections and color indicates the number of intra-cluster connections. Functional enrichment for each cluster was determined by BIG-C. (FIG. 85B) Heatmap indicates the top five canonical pathways representing individual clusters (−log (p-value) >1.33). Enriched BIG-C and I-Scope categories (OR >1; p-value <0.05) are listed for each cluster. Bold text indicates categories with the highest OR and lowest p-value. (FIG. 85C) Venn diagram showing the number of overlapping pathways motivated by EA or AsA predicted genes and their associated UPRs. Representative pathways are listed.

FIG. 86 shows that Asian GWAS genes identify similar pathways predicted by the AsA Immunochip. Using SNP-predicted genes from the AsA GWAS validation SNP-set, metastructures were generated based on PPI networks, clustered using MCODE and visualized in Cytoscape. Cluster size indicates the number of genes per cluster, edge weight indicates the number of inter-cluster connections and color indicates the number of intra-cluster connections. Functional enrichment for each cluster was determined by BIG-C. Heatmap indicates the top five canonical pathways representing individual clusters (−log (p-value) >1.33). Enriched BIG-C and I-Scope categories (OR >1; p-value <0.05) are listed for each cluster. Bold text indicates categories with the highest OR and lowest p-value.

FIGS. 87A-87H show that SNP-predicted pathways inform gene signatures for GSVA analysis in patient PBMC datasets. GSVA enrichment scores were generated for PBMCs in EA and AsA SLE patients and healthy controls from FDAPBMC1 (EA-only patients) and GSE81622 (AsA-only patients). GSVA scores for type I and type II interferon-based gene signatures (FIGS. 87A-87B), metabolic gene signatures (FIGS. 87C-87D), cellular processes (FIGS. 87E-87F) and individual cell type signatures (FIGS. 87G-87H) are shown. Asterisks (*) indicate a p-value <0.05 using Welch's t-test comparing SLE to control; ^ indicates a p-value <0.05 using Welch's t-test comparing EA to AA.

FIGS. 88A-88C show the use of linear regression to examine the relationship between cell types, processes and inflammatory cytokines. Linear regression analysis showing the relationship between GSVA scores for IFNA2 and TNF and individual cell types (pDCs, monocyte/myeloid, B cells, T cells and NK cells) (FIG. 88A) or cellular processes (oxidative stress, RIG-I and TLR signaling) (FIG. 88B) for FDAPBMC1 (EA) and GSE81622 (AsA). Transcripts overlapping both categories were removed. Categories with linear regression p values <0.05 are in bold; R2 predictive values are listed after the GSVA enrichment category. *Asterisks indicate significant relationship between categories. (FIG. 88C) Scatter plots showing the relationship between monocyte/myeloid GSVA scores and enrichment scores for glycolysis in EA and AsA. Blue; EA SLE patients, red, AsA SLE patients, black; healthy controls. Predictive R2 value is listed, *asterisks indicate significant relationships between categories.

Example 20: Exploring Causal Pathways from Systemic Lupus Erythematosus to Coronary Artery Disease: A Comprehensive Mendelian Randomization Study Genetic predispositions may be important risk factors for both Systemic Lupus Erythematosus (SLE) and Coronary Artery Disease (CAD). Although genetic association studies may be performed to map disease loci in both autoimmune and cardiovascular disease, these results may fail to impact clinical practice. Here, Mendelian Randomization (MR) was performed to show the causal effect of SLE-associated non-HLA variants on CAD. Interestingly, the SLE-associated HLA variants showed a strong negative causal effect on CAD and the CAD-associated HLA variants showed a strong negative causal effect on SLE, suggesting that different HLA alleles confer an increased risk for SLE or CAD independently. Additionally, genetic instruments for SLE exposure were separated by chromosome, and MR was preformed to test for chromosome-specific causal genetic estimates of SLE on CAD. Four chromosomes, chr1, chr2, chr4, and chr8, showed positive causal genetic estimates of SLE on CAD. Two chromosomes, chr6 and chr11, showed negative causal genetic estimates of SLE on CAD. Lastly, SLE-associated non-HLA variants were mapped to putative SLE genes and pathways with causal implications on CAD to better understand the pathogenesis. These results provide a comprehensive analysis of the functional mechanisms and biological processes underlying SLE patients' increased susceptibility of developing CAD.

Systemic lupus erythematosus (SLE) may affect nearly 1.5 million people in the United States alone [Reference #1]. SLE may be an autoimmune syndrome characterized by multi-organ inflammation and immune dysregulation, and may be highly associated with the development of cardiovascular disease (CVD). Compared to the general population, patients with SLE have a 2-10 fold increased risk of CVD. The relative risk for women with SLE between the ages of 35 and 45 is increased 50-fold [Reference #4] and the occurrence of fatal myocardial infarction has been reported to be 3 times greater in SLE patients [Reference #2]. Additionally, many SLE patients who have a myocardial infarction are relatively young, suggesting an increased risk with SLE rather than chance occurrences [Reference #2].

The therapeutic challenge presented by SLE may be largely due to the extensive heterogeneity of the disease. In general, SLE may be associated with hyperactivity of the innate and adaptive immune system such as T and B cell abnormalities, overproduction of autoantibodies and disturbed cytokine balance. Heterogeneity of SLE includes differential expression of these abnormalities and clinical manifestations [Reference #8]. Although mortality from infections and active disease have decreased in SLE patients, CVD-related death rates may not be improved [Reference #5] and the standardized mortality ratio due to CVD may actually increase [Reference #6]. Treatment options may remain limited, as statins may have little effect on cardiovascular outcomes in SLE populations, despite their effective preventative role in non-SLE patients. Studies exploring the association between SLE and premature CVD may demonstrate that alterations of specific immune functions play a pivotal role in the increased cardiovascular morbidity and mortality observed in SLE [Reference #3]. Nonetheless, additional studies may be performed to identify critical immune pathways in CVD pathogenesis that can be used as novel points of therapeutic intervention.

Genetic predispositions may be important risk factors for both SLE and CVD. The lack of a correlation between severity of lupus and cardiac outcomes in SLE patients [Reference #9] supports the hypothesis that genetic components play a role in lupus patients for developing CVD. Although genetic association studies may be successful in mapping disease loci in both autoimmune and cardiovascular disease, these results may fail to impact clinical practice. Understanding the functional mechanisms of causal genetic variants underlying SLE and CVD may provide essential information to identify shared molecular pathways and therapeutic targets relevant to disease mechanisms. Here, Mendelian Randomization (MR) was employed to show the causal effect of SLE-associated non-HLA variants on CAD, and these variants were mapped to putative SLE genes and pathways with causal implications on CAD. These results provide a comprehensive analysis of the functional mechanisms and biological processes underlying SLE patients' increased susceptibility of developing CAD.

SLE Immunochip study was performed as described by Langefeld, Carl D., et al. "Transancestral mapping and genetic load in systemic lupus erythematosus." (2017), which is incorporated by reference herein in its entirety.

SLE GWAS study was performed as described by Bentham J., et al. "Genetic association analyses implicate aberrant regulation of innate and adaptive immunity genes in the pathogenesis of systemic lupus erythematosus." (2015), which is incorporated by reference herein in its entirety.

CAD GWAS study was performed as described by van der Harst, Pim, and Niek Verweij. "Identification of 64 novel genetic loci provides an expanded view on the genetic architecture of coronary artery disease." (2018), which is incorporated by reference herein in its entirety.

Mendelian Randomization was performed as follows. Mendelian Randomization (MR) was used to test for causal relations between SLE and CAD using the MR-Base (www.mrbase.org) TwoSampleMR package in R (github.com/MRCIEU/TwoSampleMR).

Various sets of genetic variants used as instrumental variables and summary statistics for the exposures were manually imported into R and reformatted for MR-base compatibility using the ‘format data’ command. Data from the SLE and CAD GWAS studies are publicly available and accessible through the MR-Base software, which was used to obtain the outcome summary statistics via the ‘extract outcome data’ command. The ‘allele harmonization’ command ensures the effect estimates of the exposure and outcome are based on matching alleles, excluding SNPs with completely mismatching alleles from the MR analysis or reversing the effect and non-effect alleles along with the effect estimates when applicable. Due to the allele harmonization step, as well as some SNPs being absent from the available summary statistics, a small proportion of SNPs used as instrumental variables are absent from the final MR calculations. Up to six MR methods were performed through the TwoSampleMR package, including inverse variance weighted (IVW), weighted median, MR-Egger, MR-PRESSO (raw and outlier-corrected), and MR-RAPS, and visualized using the ‘mr scatter plot’ command.

Identification of SLE-associated SNPs and predicted genes was performed as follows. Expression quantitative trait loci (eQTLs) were identified using GTEx version 68 (GTEXportal.org) (“The Genotype-Tissue Expression (GTEx) Project” n.d.) and mapped to their associated eQTL expression genes (E-Genes). To find SNPs in enhancers and promoters, and their associated transcription factors and downstream target genes (T-Genes), the atlas of Human Active Enhancers was queried to interpret Regulatory variants (HACER, bioinfo. vanderbilt.edu/AE/HACER) (Wang et al. 2019). To find structural SNPs in protein-coding genes (C-Genes) and proximal genes within 5 kb of other SNPs (P-Genes), the human Ensembl genome browser (GRCh38.p12; www.ensembl.org) was queried.

Network analysis and visualization were performed as follows. Visualization of protein-protein interaction and relationships between genes within datasets was done using Cytoscape (version 3.6.1) software. STRING (version 1.3.2) generated networks were imported into Cytoscape (version 3.6.1) and partitioned with MCODE via the clusterMaker2 (version 1.2.1) plugin.

Functional gene set analysis and identification of upstream regulators (UPRs) were performed as follows. Predicted genes were examined using Biologically Informed Gene Clustering (BIG-C; version 4.4). BIG-C is a custom functional clustering tool developed to annotate the biological meaning of large lists of genes. Genes are sorted into 54 categories based on their most likely biological function and/or cellular localization based on information from multiple online tools and databases including UniProtKB/Swiss-Prot, gene ontology (GO) Terms, MGI database, KEGG pathways, NCBI, PubMed, and the Interactome (Catalina, Bachali, et al. 2019; Catalina, Owen, et al. 2019).

I-Scope is a custom clustering tool used to identify immune infiltrates in large gene datasets (Ren et al. 2019). I-Scope was created through an iterative search of more than 17,000 genes identified in more than 50 microarray datasets. These genes were researched for immune cell specific expression in 30 hematopoietic sub-categories: T cells, regulatory T cells, activated T cells, anergic cells, CD4 T cells, CD8 T cells, gamma-delta T cells, NK/NKT cells, T & B cells, B cells, activated B cells, T &B & monocytes, monocytes & B cells, MHC Class II expressing cells, monocyte dendritic cells, dendritic cells, plasmacytoid dendritic cells, Langerhans cells, myeloid cells, plasma cells, erythrocytes, neutrophils, low density granulocytes, granulocytes, platelets, and all hematopoietic stem cells. The Ingenuity Pathway Analysis (IPA; www.qiagenbioinformatics.com) platform and EnrichR (maayanlab.cloud/Enrichr/) web server provided additional genetic enrichment analysis.

MR estimates show a consistent positive causal effects of SLE-associated non-HLA variants on CAD. Using summary statistics from genetic association studies on SLE and CAD, Mendelian Randomization (MR) was employed to test for a causal effect of SLE on CAD. Multiple methods, including inverse variance weighted (IVW), weighted median, MR-Egger, MR-PRESSO, and MR-RAPS were performed. First, 838 non-HLA SNPs associated with SLE in a large trans-ancestral genetic association study were used as instrumental variables for SLE exposure [Reference #11]. Using summary statistics from the SLE GWAS study for the exposure and CAD UK Biobank GWAS for the outcome, four out of six MR methods resulted in a significant positive causal estimate (FIG. 89A). Using summary statistics from the SLE Immunochip study for the exposure, all six MR methods resulted in a significant positive causal estimate of SLE on CAD (FIG. 89B).

For additional validation, 970 SNPs significantly (1E-6) associated with SLE were used in both the GWAS and Immunochip studies as instrumental variables for SLE. Surprisingly, this resulted in significant negative causal estimates (FIGS. 90A-90B). Considering the consistent positive causal effects of SLE on CAD estimated using non-HLA SNPs found in other MR analyses, it was hypothesized that the HLA SNPs in this set of instrumental variables were responsible for the negative causal estimate. As such, this MR analysis was repeated without using HLA SNPs as instrumental variables. Here, HLA SNPs were filtered out in the most conservative manner, by removing all SNPs in the short-arm of chromosome 6. Consistent with our initial analysis, all MR estimates resulted in mostly significant positive causal estimates of SLE on CAD using non-HLA SNPs as instrumental variables (FIGS. 91A-91B).

Considering both sets of instrumental variables for SLE thus far have been limited to SNPs included on the Immunochip, a final set of validation analyses were performed using SLE-associated SNPs from the PhenoScanner platform (www.phenoscanner.medschl.cam.ac.uk) SNPs significantly (p-value <1E-5) associated with SLE were obtained from the database, which pools SNPs that have been reported in genotypic studies for various traits. Consistent with other results, significant negative causal estimates were predicted when using all 911 harmonized alleles from PhenoScanner as instrumental variables, but excluding the HLA SNPs resulted in significant positive causal estimates (FIGS. 92A-92B).

MR was performed to estimate various causal effects of SLE on CAD by chromosomes. Initially, to explore the hypothesis that HLA variants are predominantly responsible for the negative causal estimate of SLE on CAD, MR was performed using only the 317 out of 970 SLE-associated SNPs on chromosome 6, which contains the HLA region. Using only chromosome 6 SLE-associated SNPs as instrumental variables resulted in a strong significant and negative causal estimate (FIGS. 93A-93B). MR was also performed using SLE-associated SNPs on the other chromosomes independently, resulting in significant positive causal estimates for chromosomes 1, 2, 4, and 8 (FIGS. 94A-94D), and significant negative causal estimates for chromosomes 6 and 11 (FIGS. 93A-93B).

SLE and CAD were shown to be associated with different HLA alleles producing negative causal MR estimates. Despite no clinical evidence of a protective effect of SLE on CAD, our various MR analyses thus far have consistently indicated a strong negative causal effect of SLE-associated HLA variants on CAD. Our hypothesis explaining the negative causal effect of the SLE-associated HLA variants on CAD is that different HLA alleles significantly contribute to the genetic risk of developing SLE or CAD independently. If this hypothesis is correct, negative causal effects may be expected of SLE-associated HLA alleles on CAD as well as CAD-associated HLA alleles on SLE. Using 303 SLE-associated SNPs on the short-arm of chromosome 6 as instrumental variables for SLE exposure on CAD, three MR methods resulted in extremely significant negative causal estimates (FIG. 95A). Similarly, using 509 CAD-associated SNPs on the short-arm of chromosome 6 as instrumental variables for CAD exposure on SLE, three MR methods estimated extremely significant negative causal estimates (FIG. 95B). While MR-Egger estimated an extremely significant positive causal effect of these CAD-associated HLA variants on SLE, the estimated correlation appears to be heavily influenced by the relatively small cluster of SNPs on the mid-to-bottom left (FIG. 95B).

Identification and pathway analysis of putative SLE genes with causal implications on CAD was performed. Multiple bioinformatic-based approaches were used to identify the most plausible genes affected by the non-HLA SLE-associated SNPs determined to be causal of CAD by MR. Ensembl's Variant Effect Predictor (VEP) identified 729 proximal (P-) genes within the default setting of 5 kb upstream or downstream of variants, including 39 coding (C-) genes with one or more variants in their coding regions. The Genotype-Tissue Expression (GTEx) database identified 517 variants located in eQTLs, influencing the expression of 1,543 expression (E-) genes. Lastly, the Human Active Enhancers to Interpret Regulatory Variants (HACER) database identified 41 variants located in regulatory regions, influencing the expression of 421 target (T-) genes. In total, the 838 non-HLA SNPs were mapped to 2,336 putative SLE genes with causal implications on CAD.

Using the 2,336 putative SLE genes, protein-protein interactions were determined by the Search Tool for the Retrieval of Interacting Genes/Proteins (STRING). 1,501 out of the 2,336 putative SLE genes encode for proteins included in the STRING database and were included in the protein network. The protein interaction network was then imported into Cytoscape and clustered using MCODE to provide an additional level of function annotation. The 1,501 protein-coding genes clustered into 46 distinct clusters with 173 genes left un-clustered (FIG. 96). Finally, individual clusters were analyzed using IPA, EnrichR, and AMPEL's in-house genomic platform to characterize the pathways, cell types, and other functional or phenotypic characteristics enriched in each set of genes (FIG. 97).

REFERENCES

1. Genetics Home Reference, NIH. (2019, Sep. 10). Systemic lupus erythematosus. Retrieved from ghr.nlm.nih.gov/condition/systemic-lupus-erythematosus#definition, is incorporated by reference herein in its entirety.
2. Zeller, C. B., & Appenzeller, S. (2008). Cardiovascular disease in systemic lupus erythematosus: the role of traditional and lupus related risk factors. Current cardiology reviews, 4(2), 116-122. doi: 10.2174/157340308784245775, is incorporated by reference herein in its entirety.
3. Liu, Y., & Kaplan, M. J. (2018). Cardiovascular disease in systemic lupus erythematosus. Current Opinion in Rheumatology, 30(5), 441-448. doi: 10.1097/bor.0000000000000528, is incorporated by reference herein in its entirety.
4. Leonard, D., Svenungsson, E., Dahlqvist, J., Alexsson, A., Ärlestig, L., Taylor, K., . . . Rönnblom, L. (2018). Novel gene variants associated with cardiovascular disease in systemic lupus erythematosus and rheumatoid arthritis. doi: 10.1136/annrheumdis-2017-212614
5. Björnådal L, Yin L, Granath F, et al. Cardiovascular disease a hazard despite improved prognosis in patients with systemic lupus erythematosus: results from a Swedish population based study 1964-95. J Rheumatol 2004; 31:713-9, is incorporated by reference herein in its entirety.
6. Bernatsky S, Boivin J F, Joseph L, et al. Mortality in systemic lupus erythematosus. Arthritis Rheum2006; 54:2550-7. 10.1002/art.21955, is incorporated by reference herein in its entirety.
7. Nasonov, E., Soloviev, S., Davidson, J. E., Lila, A., Togizbayev, G., Ivanova, R., . . . Pereira, M. H. (2015). Standard medical care of patients with systemic lupus erythematosus (SLE) in large specialised centres: data from the Russian Federation, Ukraine and Republic of Kazakhstan (ESSENCE). Lupus science & medicine, 2 (1), e000060. doi: 10.1136/lupus-2014-000060, is incorporated by reference herein in its entirety.
8. Aringer M, Burkhardt H, Burmester G R et al. Current state of evidence on "off label" therapeutic options for systemic lupus erythematosus, including biological immunosuppressive agents, in Germany, Austria, and Switzerland—a consensus report. Lupus 2012; 21:386-401 doi: 10.1177/0961203311426569, is incorporated by reference herein in its entirety.
9. Ciccacci C. (2018). Discovering the genetic contribution to cardiovascular diseases in patients affected by autoimmune diseases. Annals of translational medicine, 6 (Suppl 1), S44. doi: 10.21037/atm.2018.09.67, is incorporated by reference herein in its entirety.
10. Alenghat F. J. (2016). The Prevalence of Atherosclerosis in Those with Inflammatory Connective Tissue Disease by Race, Age, and Traditional Risk Factors. Scientific reports, 6, 20303. doi: 10.1038/srep20303, is incorporated by reference herein in its entirety.
11. Langefeld, C. D., Ainsworth, H. C., Cunninghame Graham, D. S., Kelly, J. A., Comeau, M. E., Marion, M. C., . . . Vyse, T. J. (2017). Transancestral mapping and genetic load in systemic lupus erythematosus. Nature communications, 8,16021.doi: 10.1038/ncomms16021, is incorporated by reference herein in its entirety.
12. van der Harst, P., & Verweij, N. (2018). Identification of 64 Novel Genetic Loci Provides an Expanded View on the Genetic Architecture of Coronary Artery Disease. Circulation research, 122 (3), 433-443. doi: 10.1161/CIRCRESAHA.117.312086, is incorporated by reference herein in its entirety.
13. Grammer, A. C., & Lipsky, P. E. (2017). Drug repositioning strategies for the identification of novel therapies for rheumatic autoimmune inflammatory diseases. Rheumatic Disease Clinics, 43(3), 467-480, is incorporated by reference herein in its entirety.
14. Lipsky, P. E. (2017). SP0156 How big data help us understand new and old therapy targets, is incorporated by reference herein in its entirety.
15. Shannon P, Markiel A, Ozier O, Baliga N S, Wang J T, Ramage D, Amin N, Schwikowski B, Ideker T. Cytoscape: a software environment for integrated models of biomolecular interaction networks. Genome Research 2003 November; 13(11):2498-504, is incorporated by reference herein in its entirety.

16. Grammer, A. C., Ryals, M. M., Heuer, S. E., Robl, R. D., Madamanchi, S., Davis, L. S., . . . Lipsky, P. E. (2016). Drug repositioning in SLE: crowd-sourcing, literature-mining and Big Data analysis. Lupus, 25(10), 1150-1170. doi.org/10.1177/0961203316657437, is incorporated by reference herein in its entirety.

17. Marchiani, A., et al. "Curcumin and curcumin-like molecules: from spice to drugs." Current medicinal chemistry 21.2 (2014): 204-222, is incorporated by reference herein in its entirety.

18. Cleveland Clinic Cancer. (n.d.). Bortezomib. Retrieved from chemocare.com/chemothera py/drug-info/bortezomib.aspx, is incorporated by reference herein in its entirety.

Example 21: Exploring the Functional and Structural Consequences of Damaging Single Nucleotide Polymorphisms in Systemic Lupus Erythematosus Single nucleotide polymorphisms (SNPs) may account for the most common form of genetic mutations in humans and may be responsible for the majority of biological variation among individuals. While most SNPs are located in non-coding regions of the genome (introns and intergenic regions), SNPs may also be frequently found in regulatory (enhancers, promoters, transcription factor binding sites, etc.) and coding regions. In particular, SNPs causing non-synonymous mutations in protein coding regions may be evolutionarily conserved and may be significant to disease etiology because they may change the amino acid sequences and physicochemical properties of the polypeptide chains they encode. Nonsynonymous (ns) SNPs may also perturb gene regulation by modifying DNA and transcription factor function. Thus, identifying and understanding the relationship between nsSNPs and their phenotypic effects may provide novel insight into disease causing mechanisms.

Systemic lupus erythematosus (SLE) may refer to a complex autoimmune disorder strongly influenced by genetic factors. Immunochip and genome-wide association studies (GWAS) may reveal many important risk variants predisposing to SLE development, including numerous nsSNPs. For example, tyrosine-protein phosphatase non-receptor type 22 (PTPN22) is a lymphoid specific phosphatase that may control antigen receptor signal transduction in both T and B lymphocytes. The nonsynonymous variant rs2476601 (R620 W) may be associated with increased risk in SLE, as well as multiple other autoimmune diseases. PTPN22 may be expressed in most leukocytes, and studies of the coding change polymorphism may reveal a number of alterations in cellular immune system function such as effector T and Treg cell development, TLR responses and type I interferon production. However, while coding SNPs may indicate a large impact on disease pathogenesis, many studies may be focused on the genetic description of potential mutations found in correlation with disease, rather than examining the influence of nsSNPs on protein structure and function.

Although, both in vitro and in vivo experimental methodologies may improve our ability to explore the effects of nsSNPs, they may be expensive and require technical resources (e.g., personnel, animal modeling, etc.). Various computational approaches may be used for predicting the impact of mutations on protein structure and function. These methods may successfully identify structural and stability changes which occur in proteins because of mutations (Anwer et al., 2015; Sneha and Doss, 2016; Mohajer et al., 2017). Here, diverse computational methods were used, including in silico analyses and 3-dimensional protein modeling, to assess the deleterious potential of SLE nsSNPs and determine their effect on structural and functional features of SLE candidate proteins.

In silico assessment of the deleterious potential of SLE-associated nsSNPs and prioritization for further study were performed as follows. The results from transancestral SLE genetic association studies using the Immunochip (Langefeld et al., 2017; Sun et al 2016) and summary GWA studies (Morris et al. 2016; Lessard et al. 2016) were used to identify 3,104 non-HLA, independent polymorphisms significantly associated with disease in European, African and Asian ancestral populations. For variants located in coding regions, 74 SNPs were associated with either non-synonymous amino acid changes or premature termination, affecting 71 genes (Table 32). 3-dimensional structural information was available for 34 of these SNPs via the Protein Data Bank (PDB; www.rcsb.org), an online repository of biomolecular structures. Functional damage scores were determined using SIFT and PolyPhen-2, which predict the potential impact of amino acid substitutions on protein structure and function. Of the 74 nsSNPs, 13 were predicted to be deleterious. 16 SNPs were reported as SLE risk variants. This includes rs1143679 in ITGAM (Kim-Howard, Ann. Rheum. Dis. 2009) and rs1801274 in FCGR2A (Zhu Sci. Rep. 2016 (meta-analysis of FCGR variants)). All remaining SNP were either associated with other diseases or were entirely novel.

All identified nsSNPs were prioritized for further structural analysis. Of particular interested were those nsSNP-gene pairs that were associated with SLE (via GWAS) but where the accompanying amino acid change had either not been investigated or altered protein function had not been experimentally validated. The nsSNPs were also prioritized based on available 3D structural information (via PDB) and more importantly, if there was solid structural information in the SNP region (Table 33).

The missense variant rs2229524, encoding the M379→T transition in NT5E (CD73), was predicted to be benign (Table 32). While this variant may not be associated with SLE, it may be linked to aortic valve calcification and cellular drug efflux (Hellman et al., 2019; Li et al., 2010). Given that 3D structural information is available for NT5E (FIGS. 98A-98B), the potential effect of rs2229524 on NT5E structure and function was examined.

NT5E is a phosphatase expressed in multiple tissues (including kidney, lymph nodes, bone marrow and vasculature) and on macrophages, B cells, some T cell subsets and DCs. A function of this protein may be to convert extracellular AMP into adenosine (ADO). Importantly, ADO may elicit anti-inflammatory functions, maintains homeostasis, limits tissue damage and has the ability to promote would healing. Low levels of NT5E may be correlated with clinical severity in a number of autoimmune inflammatory diseases, including juvenile inflammatory arthritis, multiple sclerosis, Type 1 and 2 diabetes and rheumatoid arthritis.

To examine the impact of rs2229524 on NTSE, molecular dynamics simulations of the wild-type (WT) and M379T mutant in the open, active state were examined and show local opening and closing of the catalytic site in the WT simulation but not in the mutant simulation (FIGS. 99A-99C). Thus, despite initial predictions that this variant is benign, further examination and molecular modeling reveal the M379T mutant may cause significant molecular dysfunction. These new analyses, along with the established role of this variant in coronary artery calcification (CAC), indicate further study may be performed.

Dysfunctional NT5E and implications for SLE as described as follows. NT5E may function as an inhibitory immune checkpoint molecule where free adenosine generated by its ectonucleotidase activity inhibits cellular immune responses. Importantly, the expression of NT5E and other ecto-enzymes such as ENTPD1 may be modulated following exposure to stress, hypoxia or inflammatory cytokines. In mice, loss of NT5E leads to lupus-like symptoms, whereas in humans, dysfunctional NT5E causes CAC. In the current study, 3D molecular modeling indicates the SLE-associated variant rs2229524 reduces the functionality of NT5E. Differential gene expression examining NT5E in whole blood (WB), PBMC, T cells, B cells, kidney and skin shows NT5E is both up and down-regulated in SLE datasets depending on the cell type or tissue (FIG. 100). Given the role of NT5E in immune suppression, it was hypothesized that elevated expression of this molecule may be a compensatory mechanism to down-modulate inflammation in the presence of high ATP and/or AMP, especially in tissues susceptible to the accrual of damage (e.g., kidneys). Since the hydrolysis of AMP into adenosine may require that the enzyme cycles through open and closed conformational states, the presence of the nsSNP (and subsequent M397T transition) may compromise NT5E ectonucleotidase activity, leading to the sustained, chronic inflammation observed in SLE. To explore this further, multiple analytical approaches were performed to examine NT5E expression in specific cell types and tissues from human SLE and mouse datasets to determine the effects of dysfunctional NT5E.

NT5E was found to be enriched in tissue datasets as follows. Gene Set Variation Analysis (GSVA) (Hänzelmann, Castelo, and Guinney 2013) was first applied to determine the relative enrichment of NT5E and the related phosphatase ENTPD1 in whole blood, kidney and skin samples from SLE patients and controls. As shown in FIG. 101A, significant enrichment was observed of both genes in the kidney (glomerulus) and the skin (FIG. 101A). Next, a seven gene signature representative of NT5E ectonucleotidase activity (“nucleotidase activity signature”) was created, which was informed by ingenuity pathway analysis (IPA) canonical pathways and gene co-expression analysis (Table 34, FIG. 106). Similar to results observed with the either NT5E or ENTPD1 alone, nucleotidase activity was enriched in SLE samples from the kidney and skin (FIG. 101B).

To determine whether the NT5E nucleotidase activity gene signature was related to specific hematopoietic cell types, linear regression analysis was performed between the GSVA scores for individual cell signatures and the NT5E signature in kidney samples from SLE and control patients. NT5E activity exhibited a significant, positive relationship with many immune cell types, including monocyte/myeloid cells (R2=0.75) and GC-B cells (R2=0.56) (FIG. 5A, left panels), T cells (R2=0.23), plasma cells (R2=0.26), mesangial cells (R2=0.29), endothelial cells (R2=0.25) and granulocytes (R2=0.45; not shown), whereas podocytes and erythrocytes (FIG. 5A, right panels) along with kidney cells and platelets (not shown) displayed negative correlations with the NT5E signature.

Next, stepwise regression, which iteratively builds a model to predict a response variable based upon the smallest combination of independent variables (Zhang, 2016), was performed to analyze the relationship between cellular contributions and changes in NT5E activity (FIG. 102B). This analysis revealed that T cells and granulocytes positively contribute to the NT5E activity signature, as indicated by the positive regression coefficients. Conversely, the podocytes and platelet signatures negatively contribute to the NT5E nucleotidase activity signature.

Regression was performed to search for immune cells, as follows. It was hypothesized that in SLE, compromised NT5E ectonucleotidase activity may inhibit production of anti-inflammatory adenosine, despite the fact that NT5E is often overexpressed in inflamed tissues. Therefore, under conditions of low adenosine, it may be expected to observe an increase in immune cell infiltration. Both ATP and adenosine may play a pivotal role in neutrophil chemotaxis to inflammatory sites. At low concentrations, adenosine may act via the A1 and A3 adenosine receptor subtypes to promote neutrophil chemotaxis and phagocytosis. At higher concentrations, adenosine may act at the lower-affinity A2A and A2B receptors to inhibit neutrophil trafficking and effector functions such as oxidative burst, inflammatory mediator production, and granule release. Neutrophils may accumulate in the kidneys of patients with proliferative lupus nephritis, and this cell type along with a subset of granulocytes, called low-density granulocytes (LDG), may contribute to lupus nephritis pathogenesis.

To elucidate the relationship between neutrophils and NT5E activity in the kidney, GSVA was first performed to examine the enrichment of a three-gene neutrophil signature (FUT4, FCGR3B, and ITGAM) in the kidneys of SLE patients and controls. As shown in FIG. 103A, the neutrophil signature is significantly enriched in kidney samples from SLE patients but not health controls. Furthermore, linear regression demonstrated that the neutrophil signature was strongly and positively correlated with NT5E activity specifically in SLE patients, which is expected given the presumption of dysfunctional NT5E (and low adenosine). As an additional measure of damage, the relationship between podocytes and neutrophils was examined. In animal models, global loss of NT5E results in reduced podocytes numbers (especially in the glomerulus) that may be due to immune-driven damage (Blume et al., 2012). Similarly, patients with lupus nephritis revealed enrichment in neutrophil transcripts, whereas healthy controls were enriched in podocytes (FIG. 103B).

To further validate these results, differential expression (DE) analysis was performed on RNA-seq data from cells isolated from CD73 KO mice and WT controls (Bhalla et. al., 2020). This analysis revealed 20 upregulated and 9 down regulated DE genes (Table 35). Gene Ontology (GO) enrichment analysis was performed on both up and down regulated genes, with the significant biological processes reported based on significance level (FIG. 104). The most significant upregulated processes include B-cell differentiation, B/T-cell activation, and lymphocyte differentiation, signaling an increase in overall immune cell activity in CD73 KO mice. Meanwhile, significantly downregulated processes include pyrimidine nucleoside catabolic processes, purine/pyrimidine-containing compound catabolic processes, and purine nucleotide catabolic processes, confirming the inability of CD73 KO mice to properly synthesize adenosine and adenosine derivatives.

These results were also supported by analyses on NT5E silencing in human cells, particularly the silencing of NT5E via NT5E-siRNA in human endothelial cells (Jalkanen et. al, 2021). Performing similar analyses in NT5E-silenced cells as the above analyses in CD73 KO mice, siNT5E-treated cells were shown to have a distinct pro-inflammatory character, with upregulated immunological processes and increased expression of known inflammatory genes. Thus, in both CD73-KO mice and NT5E-silenced human endothelial cells, an increase was observed in immune cell activation and inflammation, potentially driven by a lack of adenosine production.

Together, the findings indicate that defective NT5E results in a lack of proper adenosine production, leading to overactive immune responses. The consequences of loss/reduced NT5E activity can be demonstrated experimentally, such as via CD73 KO mice and NTSE-siRNA. However, dysfunctional NT5E arising from the SLE risk SNP rs2229524 may also play a significant role in propagating inappropriate immune cell activation and predisposition for kidney damage.

Attention was also focused on three additional high-priority SNP-gene pairs, specifically rs1059702 in IRAK1, rs12619169 in IL18R1 and rs3751987 in TNFRS13B. As part of our preliminary studies examining these genes, a gene signature was created based around the affected molecule and potentially dysregulated biological processes. As described for the NT5E activity signature, these new gene signatures were informed by IPA and protein-protein interaction networks. Genes in each signature were tested for coexpression, and resulting signatures are listed in Table 36.

The enrichment of each signature was then tested using GSVA in whole blood, kidney, and skin datasets. GSVA enrichment results are summarized in Table 37 and representative violin plots examining individual signature enrichment in active, inactive and controls in the wholeblood dataset are shown in FIG. 105.

TABLE 32

Characterization of nsSNPs

| SNP | Type | Gene | Variant | SIFT | PolyPhen2 | PDB |
|---|---|---|---|---|---|---|
| rs28934585 | missense | ACADVL | P65L, P88L, P65L | Possibly deleterious | Depending | Yes |
| rs11235604 | missense | ATG16L2 | R220W, R51W, R18W | Deleterious | Probably Damaging | No |
| rs2071596 | missense? | DDX39B | P122L | Deleterious | Probably Damaging | No |
| rs5988 | missense | F13A1 | E652Q | Tolerated | Probably benign | Yes |
| rs2303007 | missense | GFPT2 | I471V | Tolerated | Probably benign | No |
| rs7742542 | missense | HBS1L | E343A | Tolerated | Probably benign | Yes |
| rs1042190 | missense | HLA-DPA1 | K142R, K9R | Tolerated | Probably benign | Yes |
| rs1573649 | start lost | HLA-DQB2 | NA | NA | — | No |
| rs2301626 | missense | ITGA3 | G840S | Tolerated | Probably benign | No |
| rs4818950 | missense | KRTAP10-10 | V158M | Tolerated | Probably benign | No |
| rs1041981 | missense | LTA | T60N | Deleterious | Probably damaging | Yes |
| rs2229094 | missense | LTA | C13R | Tolerated | Probably benign | Yes |
| rs12419635 | missense | MS4A10 | P219L | Deleterious | Possibly Damaging (low confidence) | No |
| rs1249958 | missense? | PPP1R1A | E109G | Tolerated | Probably benign | No |
| rs2305772 | missense | SIGLEC6 | P246S | Tolerated | Probably benign | No |
| rs494620 | stop gained | SLC44A4 | Y271Y, Y229Y, Y195Y | Tolerated | Probably benign | No |
| rs6781844 | missense | SLC9C1 | Q684K, Q732K | Tolerated | Probably benign | No |
| rs7097397 | missense | WDFY4 | R1816Q, R362Q | Tolerated | Probably benign | No |
| rs2230926 | missense | TNFAIP3 | F127C | Tolerated | Probably benign | Yes |
| rs7939069 | Stop gained | AGBL2 | R795del | STOP | Error | No |
| rs1990313 | missense | AKAP3 | I661T | Deleterious | Probably damaging | No |
| rs10516487 | missense | BANK1 | R61H, R31H, R46H | Tolerated | Probably benign | No |
| rs1051624 | missense | CDH17 | E739A, E525A | Tolerated | Probably benign | No |
| rs4844600 | missense | CR1 | E60D, E60E | Tolerated | Probably benign | Yes |
| rs17617 | missense | CR2 | A1062E, A1003E, A941E, A976E | Tolerated | Probably benign | No |
| rs7252175 | missense | EML2 | L334F, L388F, L187F, L187F, L165F, L12F | Deleterious | Probably damaging | No |
| rs1801274 | missense | FCGR2A | H167R, H166R | Tolerated | Probably benign | Yes |
| rs1052690 | missense | IDNK | K185T, K228T, K139T | Deleterious | Probably damaging | No |

TABLE 32-continued

Characterization of nsSNPs

| SNP | Type | Gene | Variant | SIFT | PolyPhen2 | PDB |
|---|---|---|---|---|---|---|
| rs35667974 | missense | IFIH1 | 1923V | Tolerated | Probably benign | Yes |
| rs1143679 | missense | ITGAM | R77H | Tolerated | Probably benign | No |
| rs2229524 | missense | NT5E | M379T | Error | Probably benign | Yes |
| rs10916668 | missense | OTUD3 | A333T | Tolerated | Probably benign | No |
| rs2476601 | missense | PTPN22 | W620R, W493R, W565R, W376R | Tolerated | Probably benign | No |
| rs11539148 | missense | QARS | N285S, N274S | Tolerated | Probably benign | Yes |
| rs196432 | missense | RCAN3 | R106Q, R164Q, T221T, T211T, T163T | Tolerated | Probably benign | No |
| rs1132200 | missense | TMEM39A | A487T | Tolerated | Probably benign | No |
| rs34536443 | missense | TYK2 | P1104A, P17A, P127A, P919A | Deleterious | Probably damaging | Yes |
| rs11755393 | missense | UHRF1BP1 | Q454R | Tolerated | Probably benign | No |
| rs13205210 | missense | UHRF1BP1 | M1098T | Deleterious | Probably damaging | No |
| rs1127745 | Stop gained | ACOX2 | STOP | Tolerated | — | Yes |
| rs1804182 | Stop gained | PLAT | STOP | Tolerated | — | No |
| rs1059702 | Missense | IRAK1 | F196S | Tolerated | Benign | Yes |
| rs11718350 | Missense | SPINK8 | K78N | Tolerated | Possibly damaging | No |
| rs12619169 | Missense | IL18R1 | G423R | Tolerated | Error | Yes |
| rs13306575 | Missense | NCF2 | R395W | Deleterious | Probably damaging | Yes |
| rs1545620 | Missense | MYO9B | S1011A | Tolerated | Error | Yes |
| rs161400 | Missense | CTNS | T152I | Tolerated | benign | No |
| rs1797517 | Missense | KLRF2 | V68I | Tolerated | Error | Yes |
| rs1800385 | Missense | VWF | V1565L | Tolerated | benign | Yes |
| rs2227902 | Missense | REST | E692D | Tolerated | benign | No |
| rs2231616 | Missense | TP53TG5 | R57H | Tolerated | benign | No |
| rs2240188 | Missense | OAS3 | L847L | Tolerated | Error | Yes |
| rs26506 | Missense | CAST | D24D | Tolerated | Error | No |
| rs26722 | Missense | SLC45A2 | E97K | Tolerated | Error | Yes |
| rs3213809 | Missense | ERAP1 | H417H | Tolerated | Error | Yes |
| rs34193571 | Missense | RASGRF2 | S753P | Tolerated | Error | Yes |
| rs35113423 | Missense | CCDC116 | E264K | Deleterious | Error | No |
| rs35211634 | Missense | GIF | Q23R | Tolerated | benign | Yes |
| rs3747333 | Missense | NLGN4X | L593F | Tolerated | Error | Yes |
| rs3751987 | Missense | TNFRSF13B | T234M | Deleterious | Error | Yes |
| rs4359426 | Missense | CCL22 | D2A | Tolerated | benign | No |
| rs4842838 | Missense | ADAMTSL3 | V661L | Tolerated | benign | No |
| rs6703791 | Missense | IGSF3 | Q1093R | Tolerated | benign | No |
| rs6713162 | Missense | NEB | S2912P | Tolerated | benign | Yes (SH3 domain) |
| rs6735208 | Missense | NEB | K1027N | Deleterious | probably damaging | Yes (SH3 domain) |
| rs7097397 | Missense | WDFY4 | R1816Q | Tolerated | Error | Yes |
| rs75175362 | Missense | CCDC8 | D381N | Tolerated | Error | Yes |
| rs8065080 | Missense | TRPV1 | I585V | Tolerated | benign | Yes |
| rs808119 | Missense | KAL1 | V534I | Tolerated | benign | Yes |
| rs8106673 | Missense | CEACAM18 | L160H | Tolerated | benign | No |
| rs8572 | Missense | OXA1L | A104V | Tolerated | benign | No |
| rs9282734 | Missense | IGFBP3 | H48P | Tolerated | benign | No |
| rs5744168 | nonsense | TLR5 | R392 | Error | Error | Yes |
| rs61743146 | nonsense | TMEM232 | R607 | Error | Error | No |

TABLE 33

| nsSNP Prioritization | | |
|---|---|---|
| | Gene | Function |
| First Tier priority | | |
| rs1801274 | FCGR2A | SNP reported to affect Fc region and alter affinity for IgG subclasses |
| rs2230926 | TNFAIP3 | Ub editing enzyme, negatively regulated NFKB activity |
| rs2229524 | NT5E (CD73) | 5' nucleotidase, converts extracellular nucleotides to membrane permeable nucleosides |
| rs1059702 | IRAK1 | Interleukin-1 receptor associated kinase 1. Linked to SLE anf IFNg secretion, Th1 development. |
| rs12619169 | IL18R1 | Completely novel SNP, other than showing up in a GWAS for asthma. Gene is a cytokine receptor that belongs to the interleukin 1 receptor family. |
| rs3751987 | TNFRSF13 (TACI) | The gene encodes a lymphocyte-specific member of the tumor necrosis factor (TNF) receptor superfamily. The protein induces activation of the transcription factors NFAT, AP1, and NF-kappa-B and plays a crucial role in humoral immunity by interacting with a TNF ligand. |
| Second Tier priority | | |
| rs35667974 | IFIH1 | IFN induced helicase. SNP causes loss of function. |
| rs1143679 | ITGAM (CD11b) | SNP reported in beta-propeller region, abrogates CD22-CD11b interactions. |
| rs10516487 | BANK1 | BCR signaling, SNP may interfere with BANK1-IP3R interactions |
| rs196432 | RCAN1 | Novel, may be involved in lymphocyte development |

TABLE 34

| NT5E Gene Signature | |
|---|---|
| Gene | Function |
| NT5E (CD73) | 5' nucleotidase, converts extracellular nucleotides to membrane permeable nucleosides |
| FCGR2A | Surface receptor for phagocytic cells, involved in phagocytosis and immune complex clearing |
| CCR2 | Monocyte receptor, directs monocyte infiltration and inflammatory immune response |
| CCL5 | Chemoattractant for blood monocytes, memory T-helper cells and eosinophils |
| ENTPD1 | Hydrolyzes extracellular ATP and ADP to AMP |
| CX3CR1 | Leukocyte receptor, involved in cell migration and adhesion |
| CRIP1 | LIM/double-zinc finger protein, implicated with relapse in acute myeloid leukemia |

TABLE 35

| D73 KO Differential Expression | | | | | | |
|---|---|---|---|---|---|---|
| Gene Symbol | logFC | logCPM | LR | PValue | FDR | Up/Down in KO |
| Nt5e | 2.93392792 | 6.65190324 | 138.941682 | 4.54E−32 | 1.00E−27 | Down |
| Mindy2 | 1.16720429 | 6.79143137 | 77.2307141 | 1.52E−18 | 1.68E−14 | Down |
| Cyb5r4 | 1.42231706 | 7.45290128 | 69.5015243 | 7.64E−17 | 5.62E−13 | Down |
| Rfx7 | 0.80190997 | 6.24252769 | 44.8020381 | 2.18E−11 | 1.20E−07 | Down |
| Aqp9 | 1.34428675 | 5.87004465 | 35.794229 | 2.19E−09 | 9.69E−06 | Down |
| Fos | 1.32675072 | 10.6095392 | 24.4754733 | 7.53E−07 | 0.00277102 | Down |
| Gpr137c | 0.85871726 | 5.03412176 | 23.9273221 | 1.00E−06 | 0.00315718 | Down |
| Cep162 | 1.3363575 | 3.19266053 | 23.5817013 | 1.20E−06 | 0.00330594 | Down |
| Ccdc167 | 0.74255354 | 5.88346372 | 22.9199101 | 1.69E−06 | 0.00414558 | N/A |
| Spib | −1.0492194 | 4.56241203 | 22.1179353 | 2.56E−06 | 0.0056642 | Up |
| Cd79a | −1.008401 | 3.6479948 | 21.1761222 | 4.19E−06 | 0.00841369 | Up |
| Fam129c | −1.18346 | 3.66959769 | 20.5318101 | 5.86E−06 | 0.01079669 | Up |
| Cox7a2 | 0.63000126 | 5.19877545 | 20.0297576 | 7.62E−06 | 0.0129566 | Down |
| Nuak1 | −1.4083591 | 2.00220952 | 19.8318179 | 8.46E−06 | 0.0132203 | Up |
| Col5a3 | −1.3286593 | 1.39314185 | 19.7128253 | 9.00E−06 | 0.0132203 | Up |
| Cecr2 | −1.0332256 | 4.41738364 | 19.5943577 | 9.58E−06 | 0.0132203 | Up |
| Cxxc5 | −1.0821437 | 2.10563708 | 19.2056865 | 1.17E−05 | 0.01525101 | Up |
| Enpp2 | −1.571611 | 0.56833514 | 18.9067949 | 1.37E−05 | 0.01684597 | Up |
| Klhl14 | −1.6050601 | 0.49111418 | 18.6534636 | 1.57E−05 | 0.0182265 | Up |
| Gm28635 | 4.09901499 | 1.00047131 | 18.3734365 | 1.82E−05 | 0.02005551 | N/A |

TABLE 35-continued

D73 KO Differential Expression

| Gene Symbol | logFC | logCPM | LR | PValue | FDR | Up/Down in KO |
|---|---|---|---|---|---|---|
| Dtx1 | −1.4243515 | 0.83625289 | 18.1519428 | 2.04E−05 | 0.02145575 | Up |
| Bach2 | −0.9569036 | 4.5046361 | 17.871557 | 2.36E−05 | 0.02373045 | Up |
| Cd2 | −1.338151 | 0.94731872 | 17.119907 | 3.51E−05 | 0.03370563 | Up |
| Tnfrsf13c | −1.1010475 | 1.94269226 | 16.3978816 | 5.13E−05 | 0.04725871 | Up |
| Irf4 | −0.7402956 | 4.65056391 | 16.1788043 | 5.76E−05 | 0.05092896 | Up |
| Sdc4 | −0.9968642 | 3.65135534 | 16.009754 | 6.30E−05 | 0.05354262 | Up |
| Mpp7 | 0.7126289 | 6.44116929 | 15.8291022 | 6.93E−05 | 0.05672311 | N/A |
| Gramd1c | −1.7380562 | 0.00766262 | 15.0537073 | 0.0001045 | 0.08068146 | Up |
| Krt83 | 0.74328293 | 5.17534789 | 15.0282335 | 10.00010592 | 0.08068146 | N/A |
| Cd79b | −0.9053828 | 4.10468357 | 14.7875026 | 0.00012033 | 0.08860724 | Up |
| Vpreb3 | −0.9805599 | 1.79818813 | 14.7204576 | 0.00012469 | 0.08885288 | Up |
| Tmem254b | 4.1000612 | 0.60983091 | 14.4673933 | 0.00014261 | 0.0961704 | N/A |
| Irs1 | -2.1631237 | 0.07803471 | 14.4535168 | 0.00014366 | 0.0961704 | Up |
| Scn4b | −1.6625087 | 0.21259139 | 14.3703741 | 0.00015015 | 0.09755524 | Up |

TABLE 36

Gene signatures for IRAK1, IL18R1 and TNFRSF13B

| IRAK1 signature | IL18R1 signature | TNFSF13B signature |
|---|---|---|
| IL1R1 | IL18 | TNFSF13B |
| TLR2 | IL18RAP | TNFSF13 |
| CD14 | IL37 | TRAF5 |
| IRAK3 | IL18B | TRAF6 |
| MAPK14 | STAT4 | TRAF2 |
| TLR4 | STAT3 | SDC2 |
| PELI1 | NFKB1 | CAMLG |
| PELI2 | JUN | SDC4 |
| IL1RAP | MAPK8 | TNFRSF13C |
| IL1B | SIGIRR | TNFRSF17 |
| IRAK1 | CD48 | MYD88 |
| MYD88 | IL1A | SGTA |
| TRAF6 | | CD70 |
| TOLLIP | | |
| IRF4 | | |
| IKBKG | | |
| TAB2 | | |
| PELI3 | | |
| IRF7 | | |

TABLE 37

GSVA enrichment summary using signatures for IRAK1, IL18R1 and TNFRSF13B. Summary of GSVA enrichment results using the signatures for IRAK1, IL18R1, TNFSF13B in SLE and control samples from whole blood, kidney and skin datasets. Signatures with significant (students t-test) enrichment in SLE patients are indicated by the asterisks. SLE patients in the whole blood dataset were further divided based on active vs. inactive disease.
N.s. = not significant; n.d. = not done.
For p-values, *< 0.05; < 0.01; *< 0.001

| | Wholeblood | | | | |
|---|---|---|---|---|---|
| Signature | Active | Inactive | Kidney TI | Kidney Glom | Skin |
| IRAK1 | n.s. | n.s. | ** | *** | n.s. |
| IL18R1 | n.s. | n.s. | *** | n.s. | n.s. |
| TNFSF13B | * | n.s. | n.d. | n.d. | ** |

While preferred embodiments have been shown and described herein, it will be obvious to those skilled in the art that such embodiments are provided by way of example only. Numerous variations, changes, and substitutions will now occur to those skilled in the art without departing from the scope of the disclosure. It should be understood that various alternatives to the embodiments described herein may be employed in practice. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the disclosure and that methods and structures within the scope of these claims and their equivalents be covered thereby.

What is claimed is:

1. A method for determining a disease state of a subject, the method comprising:

assaying a biological sample obtained or derived from the subject to produce a data set comprising gene expression data from a plurality of gene signatures, the assaying comprising:

performing an analysis with a microarray thereby measuring a concentration of a nucleic acid sequence from the biological sample or an amplicon thereof: or performing an RNA-Seq analysis to analyze the transcriptome of the biological sample by sequencing a complementary DNA (cDNA) synthesized from an RNA nucleic acid sequence from the biological sample or an amplicon of the cDNA; and using a computer comprising a non-transitory computer-readable storage media encoded with a computer program including instructions executable by a processor to run an application for analyzing or processing the data set to determine the disease state of the subject;

electronically outputting a report detailing the disease state of the subject;

wherein a trained machine learning classifier is used to analyze or process the data set to identify the disease state of the subject, wherein the data set comprising gene expression data comprises a quantitative measure of each of a plurality of gene signatures, wherein the plurality of gene signatures comprises transcripts of a gene selected from the group of genes listed in Tables 1-37.

2. The method of claim 1, wherein the plurality of gene signatures comprises transcripts of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 350, 400, 450, 500, 550, 600, 650, 700, 750, 800, 850, 900, 950, or 1000 genes selected from the group of genes listed in Tables 1-37.

3. The method of claim 1, further comprising determining the disease state of the subject with an accuracy of at least about 70%, a sensitivity of at least about 70%, a specificity of at least about 70%, a positive predictive value of at least about 70%, a negative predictive value of at least about 70%, an Area-Under-Curve (AUC) of at least about 0.70, or any combination thereof.

4. The method of claim 1, wherein the subject has received a diagnosis of a disease, is suspected of having the disease, is at elevated risk of having the disease or having severe complications from the disease, is asymptomatic for the disease, or any combination thereof.

5. The method of claim 4, wherein the method further comprises providing a treatment to the subject.

6. The method of claim 1, wherein the method further comprises providing a treatment to the subject in consideration of the disease state of the subject: optionally wherein the treatment comprises a drug.

7. The method of claim 6, wherein the treatment comprises a drug, wherein the drug is selected from the group consisting of: Vorinostat+6, panobinostat+0, belinosta, BOS-161721+7, NNC0114-0006+6, BT63, Brodalumab+7, Ixekizumab+8, secukinumab+8, BOS-161721+7, NNC0114-0006+6, Fesolimumab, Imatinib+4, Obexelimab+7, Baricitinib+7, upadacitinib+7, Prezalumab+4, Amg 570+5, Amg 811+3, Ustekinumab+10, Ustekinumab+10, guselkumab+8, BMS-986165, Dupilumab+4, Blinatumomab, dasatinib-1, eroltinib, Aminogenistein, PP2, JW-7-24-1, Cucurbitacin-I, KN-62, SA-792987, Everolimus+3, sirolimus+2, leflunomide+3, Roscovitine, Lapatinib0, Kenpaullone, TWS-119, Theralizumab+4, Belatacept+4, Abatacept+8, Daclizumab+2, Fostamatinib+2, GSK2646264+6, Tofacitinib+3, Dapirolizumab pegol+8, Reslizumab+1, mepolizumab+3, Etanercept+5, Atacicept+5, maraviroc, Blinatumomab-1, Fasudil, PF-06650833+5, Rontalizumab+4, sifalimumab+4, Anifrolumab+3, PF-06823859+5, palbociclib+4, ellipticine, fesolimumab, Tamoxifen+2, enzastaurin, Everolimus+3, sirolimus+2, leflunomide+3, Quinacrine+7, anti-TWEAK, AM80, tamibarotene, Miltefosine0, Dupilumab+4, Sarilumab+7, tocilizumab+8, vobarilizumab+6, BOS-161721+7, NNC0114-0006+6, Baricitinib+7, filgotinib+7, ruxolitinib+5, solcitnib+6, tofacitinib+3, upadacitinib+7, Tamoxifen+2, enzastaurin, Fostamatinib+2, GSK2646264+6, Fasudil, Y27632, PF-562271, PRI-724, PRI-724, CCS1477, Blinatumomab, dasatinib-1, eroltinib, BT063, tralokinumab, APO010, Pazopanib−4, dovitinib, PD-173074, Abciximab, cilengitide, tirofiban, Dasatinib, bosutinib, eroltinib, bertilimumab, ISIS 2503, AZD4785, MRTX849, Abciximab, Marimastat, prinomastat, rebimastat, Col-3, PD-166793, Glucosamine, GS-5745, prinomastat, rebimastat, Marimastat, prinomastat, Danvatirsen, TTI-101, golotimod, Immune secreted Immune trafficking: Avacopan+7 (C5AR), Upamostat, MDX-1100, NOX-A12, Amiselimod+6, siponimid+7, cenerimod+6, fingolimod+5, mocravimod+5, ozanimod+5, Adenosine, tretinoin, valporic acid, Roflumilast+3, dipyridamole+4, apremolast, mipomersen, Lacnotuzumab, PD-360324, PF-04236921+8, siltuximab+6, sirukumab+6, IONIS-FB-LRX, Cisplatin, retaspimycin, Polydatin, Tamoxifen+2, Belinostat, vorinostat+6, bafatenib, BI655064+5, Daclizumab+2, Talacotuzumab+3, Tacrolimus+5, Infliximab+4, golimumab+5, etanercept+5, certolizumab+4, adalimumab+4 Dapirolizumab pegol+8, Bortezomib+6, carfilzomib+4, ixazomib+5, and Ergocalciferol+6, or combinations thereof.

8. The method of claim 1, wherein the trained machine learning classifier is trained using gene expression data generated by one or more data analysis tools.

9. The method of claim 1, wherein the trained machine learning classifier is selected from the group consisting of a linear regression, a logistic regression, a Ridge regression, a Lasso regression, an elastic net (EN) regression, a support vector machine (SVM), a gradient boosted machine (GBM), a k nearest neighbors (kNN), a generalized linear model (GLM), a naive Bayes (NB) classifier, a neural network, a Random Forest (RF), a deep learning algorithm, and a combination thereof.

10. The method of claim 1, wherein (b) analyzing or processing the data set comprises comparing the data set to a reference data set.

11. The method of claim 1, wherein the biological sample is selected from the group consisting of: a blood sample, isolated peripheral blood mononuclear cells (PBMCs), a biopsy sample, and any derivative thereof.

12. The method of claim 1, further comprising monitoring the disease state of the subject, wherein the monitoring comprises assessing the disease state of the subject at a plurality of time points.

13. The method of claim 1, wherein the plurality of gene signatures comprises transcripts of single nucleotide polymorphisms (SNPs).

14. The method of claim 13, wherein the SNPs comprise ancestry-specific SNPs or nonsynonymous SNPs (nsSNPs).

15. The method of claim 1, wherein the disease state comprises a lupus condition.

16. The method of claim 15, wherein the lupus condition is systemic lupus erythematosus (SLE), discoid lupus erythematosus (DLE), or lupus nephritis (LN).

17. The method of claim 1, wherein the disease state comprises cardiovascular disease (CVD).

18. The method of claim 17, wherein the CVD comprises coronary artery disease (CAD).

19. A computer system for determining a disease state of a subject, comprising: a database that is configured to store a data set comprising gene expression data from a plurality of gene signatures, wherein the gene expression data is obtained by assaying a biological sample obtained or derived from the subject wherein the plurality of gene signatures comprises transcripts of a gene selected from the group of genes listed in Tables 1-37; and one or more computer processors operatively coupled to the database, wherein the one or more computer processors are individually or collectively programmed to: (i) computer process the data set to determine the disease state of the subject; (ii) electronically output a report indicative of the disease state of the subject.

20. A non-transitory computer readable medium comprising machine-executable code that, upon execution by one or more computer processors, implements a method for determining a disease state of a subject, the method comprising:

(a) assaying a biological sample obtained or derived from the subject to produce a data set comprising gene expression data from a plurality of gene signatures, wherein the plurality of gene signatures comprises transcripts of a gene selected from the group of genes listed in Tables 1-37;

(b) computer processing the data set to determine the disease state of the subject; and (c) electronically outputting a report indicative of the disease state of the subject.

* * * * *